US010259810B2

United States Patent
Akkari et al.

(10) Patent No.: US 10,259,810 B2
(45) Date of Patent: *Apr. 16, 2019

(54) N-SULFONYLATED PYRAZOLO[3,4-B]PYRIDIN-6-CARBOXAMIDES AND METHOD OF USE

(71) Applicants: AbbVie S.à.r.l., Luxembourg (LU); Galapagos NV, Mechelen (BE)

(72) Inventors: Rhalid Akkari, Pantin (FR); Luke Jonathan Alvey, Versailles (FR); Xavier Marie Bock, Romainville (FR); Brian S. Brown, Evanston, IL (US); Pieter Isabelle Roger Claes, Gentbrugge (BE); Marlon D. Cowart, Round Lake Beach, IL (US); Elsa De Lemos, Paris (FR); Nicolas Desroy, Massy (FR); Béranger Duthion, Paris (FR); Gregory A. Gfesser, Lindenhurst, IL (US); Romain Luc Marie Gosmini, Savigny-sur-Orge (FR); Christopher Gaëtan Housseman, Montreuil (FR); Koen Karel Jansen, Turnhout (BE); Jianguo Ji, Libertyville, IL (US); Philip R. Kym, Libertyville, IL (US); Jean-Michel Lefrancois, Le Raincy (FR); Oscar Mammoliti, Mechelen (BE); Christel Jeanne Marie Menet, Brussels (BE); Nuria Merayo Merayo, Paris (FR); Gregory John Robert Newsome, Neuilly Plaisance (FR); Adeline Marie Elise Palisse, Brussels (BE); Sachin V. Patel, Round Lake, IL (US); Matthieu Rafaël Pizzonero, Voisins le Bretonneux (FR); Anurupa Shrestha, Vernon Hills, IL (US); Elizabeth C. Swift, Highland Park, IL (US); Steven Emiel Van der Plas, Steenhuffel (BE); Xueqing Wang, Northbrook, IL (US); Ann de Blieck, Mechelen (BE)

(73) Assignees: AbbVie S.à.r.l., Luxembourg (LU); Galapagos NV, Mechelen (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/843,917

(22) Filed: Dec. 15, 2017

(65) Prior Publication Data

US 2018/0105522 A1    Apr. 19, 2018

Related U.S. Application Data

(63) Continuation of application No. 15/287,911, filed on Oct. 7, 2016, now Pat. No. 9,890,158.

(Continued)

(51) Int. Cl.
  C07D 471/04    (2006.01)
  A61K 45/06    (2006.01)
  (Continued)

(52) U.S. Cl.
  CPC .......... C07D 471/04 (2013.01); A61K 31/437 (2013.01); A61K 31/4545 (2013.01);
  (Continued)

(58) Field of Classification Search
  None
  See application file for complete search history.

(56) References Cited

U.S. PATENT DOCUMENTS 8,999,976 B2    4/2015    Binch et al.
9,890,158 B2 *  2/2018    Akkari ................ C07D 471/04
(Continued)

FOREIGN PATENT DOCUMENTS

WO    2005120497 A2    12/2005
WO    2006002421 A3    1/2006
(Continued)

OTHER PUBLICATIONS

International Search Report and Written Opinion of the International Searching Authority issued in corresponding PCT Application No. PCT/IB2016/056029, dated Jan. 19, 2017,10 pages.
(Continued)

Primary Examiner — Brian J Davis
(74) Attorney, Agent, or Firm — Quarles & Brady LLP

(57) ABSTRACT

The present invention provides for compounds of formula (I)

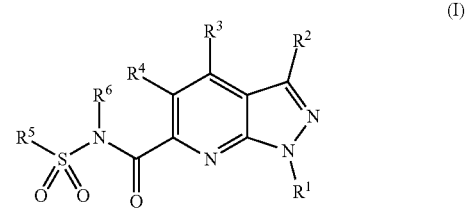

wherein $R^1$, $R^2$, $R^3$, $R^4$, $R^5$, and $R^6$ have any of the values defined in the specification, and pharmaceutically acceptable salts thereof, that are useful as agents in the treatment of diseases and conditions mediated and modulated by CFTR, including cystic fibrosis, Sjögren's syndrome, pancreatic insufficiency, chronic obstructive lung disease, and chronic obstructive airway disease. Also provided are pharmaceutical compositions comprised of one or more compounds of formula (I).

8 Claims, No Drawings

Related U.S. Application Data

(60) Provisional application No. 62/309,794, filed on Mar. 17, 2016, provisional application No. 62/239,647, filed on Oct. 9, 2015.

(51) Int. Cl.
    *A61K 31/506*     (2006.01)
    *A61K 31/4545*     (2006.01)
    *A61K 31/5377*     (2006.01)
    *A61K 31/437*     (2006.01)
    *C07D 519/00*     (2006.01)

(52) U.S. Cl.
    CPC ........ *A61K 31/506* (2013.01); *A61K 31/5377* (2013.01); *A61K 45/06* (2013.01); *C07D 519/00* (2013.01)

(56) References Cited

U.S. PATENT DOCUMENTS

| | | |
|---|---|---|
| 2009/0197911 A1 | 8/2009 | Georg et al. |
| 2015/0005275 A1 | 1/2015 | Plas et al. |
| 2015/0045327 A1 | 2/2015 | Van Der Plas et al. |
| 2016/0120841 A1 | 5/2016 | Kym et al. |
| 2016/0122331 A1 | 5/2016 | Kym et al. |

FOREIGN PATENT DOCUMENTS

| | | |
|---|---|---|
| WO | 2008147952 A1 | 4/2008 |
| WO | 2009076593 A1 | 6/2009 |
| WO | 2009074575 A3 | 8/2009 |
| WO | 2010048573 A1 | 4/2010 |
| WO | 2011113894 A1 | 9/2011 |
| WO | 2011072241 A9 | 6/2012 |
| WO | 2012048181 A4 | 6/2012 |
| WO | 2013038373 A1 | 3/2013 |
| WO | 2013038378 A1 | 3/2013 |
| WO | 2013038381 A1 | 3/2013 |
| WO | 2013038386 A1 | 3/2013 |
| WO | 2013038390 A1 | 3/2013 |
| WO | 2013043720 A1 | 3/2013 |
| WO | 2014/081820 A1 | 5/2014 |
| WO | 2014180562 A1 | 11/2014 |
| WO | 2015018823 A1 | 2/2015 |
| WO | 2015138909 A1 | 9/2015 |
| WO | 2015138934 A1 | 9/2015 |

OTHER PUBLICATIONS

P.M. Quinton, "Cystic fibrosis: a disease in electrolyte transport," FASEB, 1990. 4(10): 2709-2717.

B Kerem, et al., "Identification of the cystic fibrosis gene: genetic analysis." Science, 1989. 245(4922), 1073-108.

J.L. Bobadilla, et al. "Cystic fibrosis: a worldwide analysis of CFTR mutations—correlation with incidence data and application to screening." Hum. Mutat, 2002. 19: 575-606. doi:10.1002/humu.10041.

E.A. Pasyk, et al., "Mutant (ΔF508) Cystic Fibrosis Transmembrane Conductance Regulator Cl—Channel is Functional When Retained in Endoplasmic Reticulum of Mammalian Cells." J. Biol. Chem, 1995. 270: 12347-12350.

J.P. Morello, et al., "Pharmacological chaperones: a new twist on receptor folding." Trends Pharmacol. Sci., 2000. 21(12): 466-469. doi:10.1016/S0165-6147(00)01575-3.

B.S. Shastry, "Neurodegenerative disorders of protein aggregation." Neurochem. Int., 2001 43(1): 1-7. doi:10.1016/S0197-0186(02)00196-1.

W. Zhang, et al., "Recent advances and new perspectives in targeting CFTR for therapy of cystic fibrosis and enterotoxin-induced secretory diarrheas." Future Med. Chem., 2012. 4(3), 329-345. doi:10.4155/fmc.12.1.

\* cited by examiner

N-SULFONYLATED PYRAZOLO[3,4-B]PYRIDIN-6-CARBOXAMIDES AND METHOD OF USE

CROSS REFERENCE TO RELATED APPLICATIONS

This application is a continuation of U.S. patent application Ser. No. 15/287,911 filed on Oct. 7, 2016, which claims priority to U.S. Provisional Application No. 62/239,647, filed Oct. 9, 2015 and U.S. Provisional Application No. 62/309,794, filed Mar. 17, 2016, all of which are incorporated herein by reference for all purposes.

BACKGROUND OF THE INVENTION

Technical Field

The invention relates to compounds that are modulators of the Cystic Fibrosis Transmembrane Conductance Regulator (CFTR) protein, useful in treating diseases and conditions mediated and modulated by CFTR. Additionally, the invention relates to compositions containing compounds of the invention and processes for their preparation.

Description of Related Technology

ATP-Binding Cassette ("ABC") transporters are a family of homologous membrane transporter proteins regulating the transport of a wide variety of pharmacological agents (for example drugs, xenobiotics, anions, etc.) that bind and use cellular adenosine triphosphate (ATP) for their specific activities. Some of these transporters were found to defend malignant cancer cells against chemotherapeutic agents, acting as multidrug resistance proteins (like the MDR1-P glycoprotein, or the multidrug resistance protein, MRP 1). So far, 48 ABC transporters, grouped into 7 families based on their sequence identity and function, have been identified.

ABC transporters provide protection against harmful environmental compounds by regulating a variety of important physiological roles within the body, and therefore represent important potential drug targets for the treatment of diseases associated with transporter defects, outwards cell drug transport, and other diseases in which modulation of ABC transporter activity may be beneficial.

The cAMP/ATP-mediated anion channel, CFTR, is one member of the ABC transporter family commonly associated with diseases, which is expressed in a variety of cell types, including absorptive and secretory epithelia cells, where it regulates anion flux across the membrane, as well as the activity of other ion channels and proteins. The activity of CFTR in epithelial cells is essential for the maintenance of electrolyte transport throughout the body, including respiratory and digestive tissue (Quinton, P. M., 1990. Cystic fibrosis: a disease in electrolyte transport. FASEB J. 4, 2709-2717).

The gene encoding CFTR has been identified and sequenced (Kerem, B., Rommens, J. M., Buchanan, J. A., Markiewicz, D., Cox, T. K., Chakravarti, A., Buchwald, M., Tsui, L. C., 1989. Identification of the cystic fibrosis gene: genetic analysis. Science 245, 1073-1080). CFTR comprises about 1480 amino acids that encode a protein made up of a tandem repeat of transmembrane domains, each containing six transmembrane helices and a nucleotide binding domain. The pair of transmembrane domains is linked by a large, polar, regulatory (R)-domain with multiple phosphorylation sites that regulate channel activity and cellular trafficking.

Cystic fibrosis is (CF) caused by a defect in this gene which induces mutations in CFTR. Cystic fibrosis is the most common fatal genetic disease in humans and affects ~0.04% of white individuals (Bobadilla, J. L., Macek, M., Jr, Fine, J. P., Farrell, P. M., 2002. Cystic fibrosis: a worldwide analysis of CFTR mutations—correlation with incidence data and application to screening. Hum. Mutat. 19, 575-606. doi:10.1002/humu.10041), for example, in the United States, about one in every 2,500 infants is affected, and up to 10 million people carry a single copy of the defective gene without apparent ill effects; moreover subjects bearing a single copy of the gene exhibit increased resistance to cholera and to dehydration resulting from diarrhea. This effect might explain the relatively high frequency of the CF gene within the population.

In contrast, individuals with two copies of the CF associated gene suffer from the debilitating and fatal effects of CF, including chronic lung infections.

In cystic fibrosis patients, mutations in endogenous respiratory epithelial CFTR fail to confer chloride and bicarbonate permeability to epithelial cells in lung and other tissues, thus leading to reduced apical anion secretion and disruptions of the ion and fluid transport. This decrease in anion transport causes an enhanced mucus and pathogenic agent accumulation in the lung triggering microbial infections that ultimately cause death in CF patients.

Beyond respiratory disease, CF patients also suffer from gastrointestinal problems and pancreatic insufficiency that result in death if left untreated. Furthermore, female subjects with cystic fibrosis suffer from decreased fertility, whilst males with cystic fibrosis are infertile.

A variety of disease causing mutations have been identified through sequence analysis of the CFTR gene of CF chromosomes (Kerem, B., Rommens, J. M., Buchanan, J. A., Markiewicz, D., Cox, T. K., Chakravarti, A., Buchwald, M., Tsui, L. C., 1989. Identification of the cystic fibrosis gene: genetic analysis. Science 245, 1073-1080). ΔF508-CFTR, the most common CF mutation (present in at least 1 allele in ~90% of CF patients) and occurring in approximately 70% of the cases of cystic fibrosis, contains a single amino acid deletion of phenylalanine 508. This deletion prevents the nascent protein from folding correctly, which protein in turn cannot exit the endoplasmic reticulum (ER) and traffic to the plasma membrane, and then is rapidly degraded. As a result, the number of channels present in the membrane is far less than in cells expressing wild-type CFTR. In addition to impaired trafficking, the mutation results in defective channel gating. Indeed, even if ΔF508-CFTR is allowed to reach the cell plasma membrane by low-temperature (27° C.) rescue where it can function as a cAMP-activated chloride channel, its activity is decreased significantly compared with WT-CFTR (Pasyk, E. A., Foskett, J. K., 1995. Mutant (ΔF508) Cystic Fibrosis Transmembrane Conductance Regulator Cl⁻ Channel Is Functional When Retained in Endoplasmic Reticulum of Mammalian Cells. J. Biol. Chem. 270, 12347-12350).

Other mutations with lower incidence have also been identified that alter the channel regulation or the channel conductance. In case of the channel regulation mutants, the mutated protein is properly trafficked and localized to the plasma membrane but either cannot be activated or cannot function as a chloride channel (e.g. missense mutations located within the nucleotide binding domains), examples of these mutations are G551D, G178R, and G1349D. Mutations affecting chloride conductance have a CFTR protein that is correctly trafficked to the cell membrane but that generates reduced chloride flow (e.g. missense mutations located within the membrane-spanning domain), examples of these mutations are R117H and R334W.

In addition to cystic fibrosis, CFTR activity modulation may be beneficial for other diseases not directly caused by mutations in CFTR, such as, for example, chronic obstructive pulmonary disease (COPD), dry eye disease, and Sjogren's syndrome.

COPD is characterized by a progressive and non-reversible airflow limitation, which is due to mucus hypersecretion, bronchiolitis, and emphysema. A potential treatment of mucus hypersecretion and impaired mucociliary clearance that is common in COPD could consist in using activators of mutant or wild-type CFTR. In particular, the anion secretion increase across CFTR may facilitate fluid transport into the airway surface liquid to hydrate the mucus and optimize periciliary fluid viscosity. The resulting enhanced mucociliary clearance would help in reducing the symptoms associated with COPD.

Dry eye disease is characterized by a decrease in tear production and abnormal tear film lipid, protein and mucin profiles. Many factors may cause dry eye disease, some of which include age, arthritis, LASIK eye surgery, chemical/thermal burns, medications, allergies, and diseases, such as cystic fibrosis and Sjogrens's syndrome. Increasing anion secretion via CFTR could enhance fluid transport from the corneal endothelial cells and secretory glands surrounding the eye, and eventually improve corneal hydration, thus helping to alleviate dry eye disease associated symptoms. Sjogrens's syndrome is an autoimmune disease where the immune system harms moisture-producing glands throughout the body, including the eye, mouth, skin, respiratory tissue, liver, vagina, and gut. The ensuing symptoms, include, dry eye, mouth, and vagina, as well as lung disease. Sjogrens's syndrome is also associated with rheumatoid arthritis, systemic lupus, systemic sclerosis, and polymyositis/dermatomyositis. The cause of the disease is believed to lie in defective protein trafficking, for which treatment options are limited. As a consequence, modulation of CFTR activity may help hydrate the various organs and help alleviate the associated symptoms.

In addition to CF, the defective protein trafficking induced by the ΔF508-CFTR has been shown to be the underlying basis for a wide range of other diseases, in particular diseases where the defective functioning of the endoplasmic reticulum (ER) may either prevent the CFTR protein to exit the cell, and/or the misfolded protein is degraded (Morello, J.-P., Bouvier, M., Petaja-Repo, U. E., Bichet, D. G., 2000. Pharmacological chaperones: a new twist on receptor folding. Trends Pharmacol. Sci. 21, 466-469. doi:10.1016/S0165-6147(00)01575-3; Shastry, B. S., 2003. Neurodegenerative disorders of protein aggregation. Neurochem. Int. 43, 1-7. doi:10.1016/S0197-0186(02)00196-1; Zhang, W., Fujii, N., Naren, A. P., 2012. Recent advances and new perspectives in targeting CFTR for therapy of cystic fibrosis and enterotoxin-induced secretory diarrheas. Future Med. Chem. 4, 329-345. doi:10.4155/fmc.12.1).

A number of genetic diseases are associated with a defective ER processing equivalent to the defect observed with CFTR in CF such as glycanosis CDG type 1, hereditary emphysema (α-1-antitrypsin (PiZ variant)), congenital hyperthyroidism, osteogenesis imperfecta (Type I, II, or IV procollagen), hereditary hypofibrinogenemia (fibrinogen), ACT deficiency (α-1-antichymotrypsin), diabetes insipidus (DI), neurophyseal DI (vasopvessin hormoneN$_2$-receptor), neprogenic DI (aquaporin II), Charcot-Marie Tooth syndrome (peripheral myelin protein 22), Perlizaeus-Merzbacher disease, neurodegenerative diseases such as Alzheimer's disease (APP and presenilins), Parkinson's disease, amyotrophic lateral sclerosis, progressive supranuclear palsy, Pick's disease, several polyglutamine neurological disorders such as Huntington's disease, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (prion protein processing defect), Fabry disease (lysosomal α-galactosidase A), Straussler-Scheinker syndrome, chronic obstructive pulmonary disease (COPD), dry eye disease, and Sjogren's Syndrome.

In addition to up-regulation of the activity of CFTR, anion secretion reduction by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Regardless of the cause, excessive chloride transport is seen in all diarrhoeas, and results in dehydration, acidosis, impaired growth and death. Acute and chronic diarrhoeas remain a major medical problem worldwide, and are a significant factor in malnutrition, leading to death in children of less than five years old (5,000,000 deaths/year). Furthermore, in patients with chronic inflammatory bowel disease (IBD) and/or acquired immunodeficiency syndrome (AIDS), diarrhoea is a dangerous condition.

Accordingly, there is a need for novel compounds able to modulate CFTR. In particular, the present invention discloses compounds that may act as CFTR modulators for the treatment of cystic fibrosis. The present invention also provides methods for the preparation of these compounds, pharmaceutical compositions comprising these compounds and methods for the treatment of cystic fibrosis by administering the compounds of the invention.

SUMMARY

In one aspect the present invention provides for compounds of formula (I)

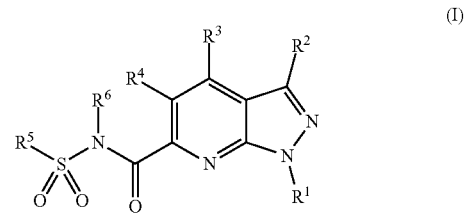

or a pharmaceutically acceptable salt thereof, wherein
$R^1$ is $G^{1A}$, $C_1$-$C_6$ haloalkyl, or $C_1$-$C_6$ alkyl; wherein the $C_1$-$C_6$ haloalkyl and the $C_1$-$C_6$ alkyl are each optionally substituted with one $G^{1A}$;
$G^{1A}$, at each occurrence, is independently phenyl, 5-6 membered monocyclic heteroaryl, 4-7 membered monocyclic heterocycle, 5-11 membered fused bicyclic heterocycle, or $C_3$-$C_6$ monocyclic cycloalkyl; wherein each $G^{1A}$ is optionally substituted with 1, 2, 3, or 4 substituents independently selected from the group consisting of $R^{1a}$ and $G^{1B}$;
$G^{1B}$, at each occurrence, is independently 4-7 membered monocyclic heterocycle which is optionally substituted with 1, 2, 3, or 4 independently selected $R^{1b}$ groups;
$R^2$ is hydrogen, $C_2$-$C_4$ alkenyl, $C_1$-$C_6$ alkyl, $C_1$-$C_6$ haloalkyl, —OR$^{2xa}$, —N(R$^{2xa}$)(R$^{2xb}$), or $G^{2A}$;

$R^{2xa}$, at each occurrence, is independently $C_1$-$C_6$ alkyl, $C_1$-$C_6$ haloalkyl, or $G^{2B}$;

$R^{2xb}$ is hydrogen, $C_1$-$C_3$ alkyl, or $C_1$-$C_3$ haloalkyl;

$G^{2A}$ and $G^{2B}$ are each independently a 4-7 membered monocyclic heterocycle or a $C_3$-$C_6$ monocyclic cycloalkyl; wherein $G^{2A}$ and $G^{2B}$ are each optionally substituted with 1, 2, or 3 independently selected $R^{2a}$ groups;

$R^3$ is $G^{3A}$, -$G^{3B}$-$L^1$-$G^{3C}$, -$G^{3B}$-$L^3$-$G^{3C}$-$G^{3E}$, —($C_1$-$C_6$ alkylenyl)-$G^{3D}$, —$OR^{3a}$, or —$N(R^{3a})(R^{3b})$;

$R^{3a}$, at each occurrence, is independently $G^{3D}$, $C_1$-$C_6$ haloalkyl, or $C_1$-$C_6$ alkyl; wherein the $C_1$-$C_6$ haloalkyl and the $C_1$-$C_6$ alkyl are each optionally substituted with one or two substituents independently selected from the group consisting of $G^{3D}$, —$OR^{3xa}$, and —$N(R^{3xb})_2$;

$R^{3xa}$ and $R^{3xb}$, at each occurrence, are each independently hydrogen, $C_1$-$C_6$ haloalkyl, $C_1$-$C_6$ alkyl, or $G^{3D}$;

$R^{3b}$ is hydrogen, $C_1$-$C_6$ alkyl, or $C_1$-$C_6$ haloalkyl;

$L^1$ is a bond, $C_1$-$C_6$ alkylenyl, ($C_1$-$C_6$ alkylenyl)$_r$-$L^2$-($C_1$-$C_6$ alkylenyl)$_s$, or O—($C_1$-$C_6$ alkylenyl)-C(O), wherein the left end of the $L^1$ moiety is attached to $G^{3B}$;

$L^2$ is O, N($R^x$), C(O), N($R^x$)C(O), or C(O)N($R^x$); wherein each $R^x$ is independently hydrogen, $C_1$-$C_6$ alkyl, or $C_1$-$C_6$ haloalkyl;

$L^3$ is a bond or $C_1$-$C_6$ alkylenyl;

r is 0 or 1;

s is 0 or 1;

$G^{3A}$, $G^{3B}$, and $G^{3C}$ and each independently $C_3$-$C_{11}$ cycloalkyl, phenyl, 5-6 membered monocyclic heteroaryl, or 4-11 membered heterocycle; wherein $G^{3A}$, $G^{3B}$, and $G^{3C}$ are each optionally substituted with 1, 2, 3, or 4 independently selected $R^e$ groups;

$G^{3D}$, at each occurrence, is independently $C_3$-$C_8$ monocyclic cycloalkyl, 4-7 membered monocyclic heterocycle, a 5-11 membered fused bicyclic heterocycle, or a 5-11 membered spiro heterocycle; wherein each $G^{3D}$ is optionally substituted with 1, 2, 3, or 4 substituents independently selected from the group consisting of $R^e$ and $G^{3E}$;

$G^{3E}$, at each occurrence, is independently $C_3$-$C_8$ monocyclic cycloalkyl or 4-7 membered monocyclic heterocycle; wherein each $G^{3E}$ is optionally substituted with 1, 2, 3, or 4 independently selected $R^e$ groups;

$R^4$ is hydrogen, $C_1$-$C_3$ alkyl, or $C_1$-$C_3$ haloalkyl;

$R^5$ is $C_1$-$C_6$ alkyl, $C_2$-$C_6$ alkenyl, $C_2$-$C_6$ alkynyl, $C_1$-$C_6$ haloalkyl, —$N(R^{5ax})(R^{5bx})$, —$OR^{5dx}$ or $G^{5A}$; wherein the $C_1$-$C_6$ alkyl and the $C_1$-$C_6$ haloalkyl are each optionally substituted with one or two substituents independently selected from the group consisting of $G^{5A}$, —CN, —$N_3$, —$OR^{5ax}$, —$S(O)_2R^{5ax}$, —$S(O)_2N(R^{5ax})(R^{5bx})$, —$N(R^{5ax})(R^{5bx})$, —$N(R^{5bx})S(O)_2R^{5ex}$, —$N(R^{5bx})C(O)R^{5cx}$, —$N(R^{5bx})C(O)N(R^{5ax})(R^{5bx})$, —$N(R^{5bx})C(O)OR^{5cx}$, —$C(O)R^{5ax}$, —$C(O)OR^{5ax}$, —$C(O)N(R^{5bx})S(O)_2R^{5cx}$, and —$C(O)N(R^{5ax})(R^{5bx})$;

$R^{5ax}$ and $R^{5bx}$, at each occurrence, are each independently hydrogen, $C_1$-$C_6$ alkyl, $C_1$-$C_6$ haloalkyl, —$OR^{5ex}$, —($C_1$-$C_6$ alkylenyl)-$OR^{5ex}$, $G^{5A}$, or —($C_1$-$C_6$ alkylenyl)-$G^{5A}$;

$R^{5cx}$, at each occurrence, is independently $C_1$-$C_6$ alkyl, $C_1$-$C_6$ haloalkyl, $G^{5A}$, or —($C_1$-$C_6$ alkylenyl)-$G^{5A}$;

$R^{5dx}$ is $C_1$-$C_6$ alkyl, or $C_1$-$C_6$ haloalkyl;

$R^{5ex}$ is hydrogen, $C_1$-$C_6$ alkyl, or $C_1$-$C_6$ haloalkyl;

$G^{5A}$, at each occurrence, is independently $C_3$-$C_{11}$ cycloalkyl, phenyl, 5-6 membered monocyclic heteroaryl, or 4-11 membered heterocycle; wherein each $G^{5A}$ is optionally substituted with 1, 2, 3, or 4 independently selected $R^{5a}$ groups;

$R^{5a}$, at each occurrence, is independently $C_1$-$C_6$ alkyl, $C_2$-$C_6$ alkenyl, $C_2$-$C_6$ alkynyl, halogen, $C_1$-$C_6$ haloalkyl, oxo, $G^{5B}$, —CN, $NO_2$, —$OR^b$, —$OC(O)R^c$, —$OC(O)N(R^d)_2$, —$SR^b$, —$S(O)_2R^b$, —$S(O)_2N(R^d)_2$, —$C(O)R^b$, —$C(O)OR^b$, —$C(O)N(R^d)_2$, —$C(O)N(R^d)$ $S(O)_2R^c$, —$N(R^d)_2$, —$N(R^d)C(O)R^c$, —$N(R^d)$ $S(O)_2R^c$, —$N(R^d)C(O)O(R^b)$, —$N(R^d)C(O)N(R^d)_2$, —$N(R^d)S(O)_2N(R^d)_2$,—($C_1$-$C_6$ alkylenyl)-CN, —($C_1$-$C_6$ alkylenyl)-$G^{5B}$,—($C_1$-$C_6$ alkylenyl)-$OR^b$, —($C_1$-$C_6$ alkylenyl)-$OC(O)R^c$, —($C_1$-$C_6$ alkylenyl)-$OC(O)N$ $(R^d)_2$, —($C_1$-$C_6$ alkylenyl)-$SR^b$, —($C_1$-$C_6$ alkylenyl)-$S(O)_2R^b$, —($C_1$-$C_6$ alkylenyl)-$S(O)_2N(R^d)_2$, —($C_1$-$C_6$ alkylenyl)-$C(O)R^b$, —($C_1$-$C_6$ alkylenyl)-$C(O)OR^b$, —($C_1$-$C_6$ alkylenyl)-$C(O)N(R^d)_2$,—($C_1$-$C_6$ alkylenyl)-$C(O)N(R^d)S(O)_2R^c$, —($C_1$-$C_6$ alkylenyl)-$N(R^d)_2$, —($C_1$-$C_6$ alkylenyl)-$N(R^d)C(O)R^c$, —($C_1$-$C_6$ alkylenyl)-$N(R^d)S(O)_2R^c$, —($C_1$-$C_6$ alkylenyl)-$N(R^d)C(O)O$ (R), —($C_1$-$C_6$ alkylenyl)-$N(R^d)C(O)N(R^d)_2$, or —($C_1$-$C_6$ alkylenyl)-$N(R^d)S(O)_2N(R^d)_2$;

$R^b$ and $R^d$, at each occurrence, are each independently hydrogen, $C_1$-$C_6$ alkyl, $C_1$-$C_6$ haloalkyl, alkoxyalkyl, $G^{5B}$, or —($C_1$-$C_6$ alkylenyl)-$G^{5B}$;

$R^c$, at each occurrence, is independently $C_1$-$C_6$ alkyl, $C_1$-$C_6$ haloalkyl, alkoxyalkyl, $G^{5B}$, or —($C_1$-$C_6$ alkylenyl)-$G^{5B}$;

$G^{5B}$, at each occurrence, is independently $C_3$-$C_6$ monocyclic cycloalkyl, phenyl, 5-6 membered monocyclic heteroaryl, or 4-7 membered monocyclic heterocycle; wherein each $G^{5B}$ is optionally substituted with 1, 2, 3, or 4 independently selected $R^{5b}$ groups;

$R^e$, at each occurrence, is independently $C_2$-$C_6$ alkenyl, $C_2$-$C_6$ alkynyl, $C_1$-$C_6$ alkyl, $C_1$-$C_6$ haloalkyl, halogen, oxo, —CN, —$N_3$, $NO_2$, —OR, —$OC(O)R^g$, —$OC(O)$ $NR^fR^h$, —$SR^f$, —$S(O)_2R^f$, —$S(O)_2NR^fR^h$, —$C(O)R^f$, —$C(O)OR^f$, —$C(O)NR^fR^h$, —$C(O)N(R^h)S(O)_2R^f$, —$N(R^f)_2$, —$N(R^h)C(O)R^h$, —$N(R^h)S(O)_2R^g$, —$N(R^h)$ $C(O)O(R^g)$, —$N(R^h)C(O)NR^fR^h$, or —$N(R^h)S(O)_2$ $NR^fR^h$; wherein the $C_1$-$C_6$ haloalkyl and the $C_1$-$C_6$ alkyl are each optionally substituted with 1 or 2 substituents independently selected from the group consisting of —CN, $NO_2$, —OR, —$OC(O)R^g$, —$OC(O)$ $NR^fR^h$, —$SR^f$, —$S(O)_2R^f$, —$S(O)_2NR^fR^h$, —$C(O)R^f$, —$C(O)OR^f$, —$C(O)NR^fR^h$, —$C(O)N(R^h)S(O)_2R^f$, —$N(R^f)_2$, —$N(R^h)C(O)R^g$, —$N(R^h)S(O)_2R^g$, —$N(R^h)$ $C(O)O(R^g)$, —$N(R^h)C(O)NR^fR^h$, and —$N(R^h)S(O)_2$ $NR^fR^h$;

$R^f$, at each occurrence, is independently hydrogen, $C_1$-$C_6$ alkyl, $C_2$-$C_6$ alkenyl, $C_2$-$C_6$ alkynyl, $C_1$-$C_6$ haloalkyl, —($C_1$-$C_6$ alkylenyl)-CN, —($C_1$-$C_6$ alkylenyl)-$OR^m$, —($C_1$-$C_6$ alkylenyl)-$OC(O)R^n$, —($C_1$-$C_6$ alkylenyl)-$OC(O)N(R^m)_2$, —($C_1$-$C_6$ alkylenyl)-$SR^m$, —($C_1$-$C_6$ alkylenyl)-$S(O)_2R^m$, —($C_1$-$C_6$ alkylenyl)-$S(O)_2$ $N(R^m)_2$,—($C_1$-$C_6$ alkylenyl)-$C(O)R^m$, —($C_1$-$C_6$ alkylenyl)-$C(O)OR^m$, —($C_1$-$C_6$ alkylenyl)-$C(O)N(R^m)_2$, —($C_1$-$C_6$ alkylenyl)-$C(O)N(R^m)S(O)_2R^n$, —($C_1$-$C_6$ alkylenyl)-$N(R^m)_2$, —($C_1$-$C_6$ alkylenyl)-$N(R^m)C(O)$ $R^n$, —($C_1$-$C_6$ alkylenyl)-$N(R^m)S(O)_2R^n$, —($C_1$-$C_6$ alkylenyl)-$N(R^m)C(O)O(R^n)$, —($C_1$-$C_6$ alkylenyl)-$N$ $(R^m)C(O)N(R^m)_2$, or —($C_1$-$C_6$ alkylenyl)-$N(R^m)$ $S(O)_2N(R^m)_2$;

$R^g$, at each occurrence, is independently $C_1$-$C_6$ alkyl, $C_2$-$C_6$ alkenyl, $C_2$-$C_6$ alkynyl, $C_1$-$C_6$ haloalkyl, —($C_1$-$C_6$ alkylenyl)-CN, —($C_1$-$C_6$ alkylenyl)-$OR^m$, —($C_1$-$C_6$ alkylenyl)-$OC(O)R^n$, —($C_1$-$C_6$ alkylenyl)-$OC(O)N$ $(R^m)_2$, —($C_1$-$C_6$ alkylenyl)-$SR^m$, —($C_1$-$C_6$ alkylenyl)-$S(O)_2R^m$, —($C_1$-$C_6$ alkylenyl)-$S(O)_2N(R^m)_2$, —($C_1$-$C_6$ alkylenyl)-$C(O)R^m$, —($C_1$-$C_6$ alkylenyl)-$C(O)OR^m$, —(C$_1$-C$_6$ alkylenyl)-C(O)N(R'")$_2$, —(C$_1$-C$_6$ alkylenyl)-C(O)N(R'")S(O)$_2$R", —(C$_1$-C$_6$ alkylenyl)-N(R'")$_2$, —(C$_1$-C$_6$ alkylenyl)-N(R'")C(O)R", —(C$_1$-C$_6$ alkylenyl)-N(R'")S(O)$_2$R", —(C$_1$-C$_6$ alkylenyl)-N(R'")C(O)O(R"), —(C$_1$-C$_6$ alkylenyl)-N(R'")C(O)N(R'")$_2$, or —(C$_1$-C$_6$ alkylenyl)-N(R'")S(O)$_2$N(R")$_2$;

R$^h$, at each occurrence, is independently hydrogen, C$_1$-C$_6$ alkyl, C$_1$-C$_6$ haloalkyl, or —(C$_1$-C$_6$ alkylenyl)-OR'";

R$^{1a}$, R$^{1b}$, R$^{2a}$, and R$^{5b}$, at each occurrence, are each independently C$_1$-C$_6$ alkyl, C$_2$-C$_6$ alkenyl, C$_2$-C$_6$ alkynyl, halogen, C$_1$-C$_6$ haloalkyl, oxo, —CN, —NO$_2$, —OR'", —OC(O)R", —OC(O)N(R'")$_2$, —SR'", —S(O)$_2$R'", —S(O)$_2$N(R'")$_2$, —C(O)R'", —C(O)OR'", —C(O)O(benzyl), —C(O)N(R'")$_2$, —C(O)N(R'")S(O)$_2$R", —N(R'")$_2$, —N(R'")(alkoxyalkyl), —N(alkoxyalkyl)$_2$, —N(R'")C(O)R", —N(R'")S(O)$_2$R", —N(R'")C(O)O(R"), —N(R'")C(O)N(R'")$_2$, —N(R'")S(O)$_2$N(R'")$_2$, —(C$_1$-C$_6$ alkylenyl)-CN, —(C$_1$-C$_6$ alkylenyl)-OR'", —(C$_1$-C$_6$ alkylenyl)-OC(O)R", —(C$_1$-C$_6$ alkylenyl)-OC(O)N(R'")$_2$, —(C$_1$-C$_6$ alkylenyl)-SR'", —(C$_1$-C$_6$ alkylenyl)-S(O)$_2$R'", —(C$_1$-C$_6$ alkylenyl)-S(O)$_2$N(R'")$_2$, —(C$_1$-C$_6$ alkylenyl)-C(O)R'", —(C$_1$-C$_6$ alkylenyl)-C(O)OR'", —(C$_1$-C$_6$ alkylenyl)-C(O)N(R'")$_2$, —(C$_1$-C$_6$ alkylenyl)-C(O)N(R'")S(O)$_2$R", —(C$_1$-C$_6$ alkylenyl)-N(R'")$_2$, —(C$_1$-C$_6$ alkylenyl)-N(R'")C(O)R", —(C$_1$-C$_6$ alkylenyl)-N(R'")S(O)$_2$R", —(C$_1$-C$_6$ alkylenyl)-N(R'")C(O)O(R), —(C$_1$-C$_6$ alkylenyl)-N(R'")C(O)N(R")$_2$, or —(C$_1$-C$_6$ alkylenyl)-N(R'")S(O)$_2$N(R")$_2$;

R'", at each occurrence, is independently hydrogen, C$_1$-C$_6$ alkyl, or C$_1$-C$_6$ haloalkyl;

R", at each occurrence, is independently C$_1$-C$_6$ alkyl or C$_1$-C$_6$ haloalkyl;

R$^6$ is hydrogen, C$_1$-C$_6$ alkyl, or C$_1$-C$_6$ haloalkyl; or

R$^5$ and R$^6$ together form a C$_1$-C$_6$ alkylenyl or —N(R$^Z$)—(C$_1$-C$_6$ alkylenyl)- wherein the N(R$^z$) is attached to the S(O)$_2$ moiety of formula (I); and R$^z$ is hydrogen, C$_1$-C$_6$ alkyl, or C$_1$-C$_6$ haloalkyl.

Another aspect of the invention relates to pharmaceutical compositions comprising a compound of the invention, and a pharmaceutical carrier. Such compositions can be administered in accordance with a method of the invention, typically as part of a therapeutic regimen for treatment or prevention of conditions and disorders related to Cystic Fibrosis Transmembrane Conductance Regulator activity. In a particular aspect, the pharmaceutical compositions may additionally comprise further therapeutically active ingredients suitable for use in combination with the compounds of the invention. In a more particular aspect, the further therapeutically active ingredient is an agent for the treatment of cystic fibrosis.

Moreover, the compounds of the invention, useful in the pharmaceutical compositions and treatment methods disclosed herein, are pharmaceutically acceptable as prepared and used.

Yet another aspect of the invention relates to a method for treating, or preventing conditions and disorders related to Cystic Fibrosis Transmembrane Conductance Regulator activity in mammals. More particularly, the method is useful for treating or preventing conditions and disorders related to cystic fibrosis, Sjögren's syndrome, pancreatic insufficiency, chronic obstructive lung disease, or chronic obstructive airway disease. Accordingly, the compounds and compositions of the invention are useful as a medicament for treating or preventing Cystic Fibrosis Transmembrane Conductance Regulator modulated disease.

The compounds, compositions comprising the compounds, methods for making the compounds, and methods for treating or preventing conditions and disorders by administering the compounds are further described herein.

In a particular aspect, the compounds of the invention are provided for use in the treatment of cystic fibrosis. In a particular aspect, the compounds of the invention are provided for use in the treatment of cystic fibrosis caused by class I, II, III, IV, V, and/or VI mutations.

The present invention also provides pharmaceutical compositions comprising a compound of the invention, and a suitable pharmaceutical carrier for use in medicine. In a particular aspect, the pharmaceutical composition is for use in the treatment of cystic fibrosis.

These and other objects of the invention are described in the following paragraphs. These objects should not be deemed to narrow the scope of the invention.

DETAILED DESCRIPTION OF THE INVENTION

Described herein are compounds of formula (I)

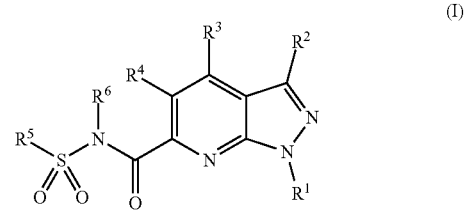

(I)

wherein R$^1$, R$^2$, R$^3$, R$^4$, R$^5$, and R$^6$, are defined above in the Summary of the Invention and below in the Detailed Description. Further, compositions comprising such compounds and methods for treating conditions and disorders using such compounds and compositions are also described.

Compounds included herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds, which can be isolated from a reaction mixture.

Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds; reference to "a pharmaceutically acceptable carrier" means a single pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "C$_2$-C$_6$ alkenyl" means an alkenyl group containing 2-6 carbon atoms. Non-limiting examples of C$_2$-C$_6$ alkenyl include buta-1,3-dienyl, ethenyl, 2-propenyl, 2-methyl-2-propenyl, 3-butenyl, 4-pentenyl, and 5-hexenyl.

The term "alkoxy" as used herein, means a $C_1$-$C_6$ alkyl group, as defined herein, appended to the parent molecular moiety through an oxygen atom. Non-limiting examples of alkoxy include methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through a $C_1$-$C_6$ alkyl group, as defined herein. Non-limiting examples of alkoxyalkyl include tert-butoxymethyl, 2-ethoxyethyl, 2-methoxyethyl, and methoxymethyl.

The term "alkyl" as used herein, means a saturated, straight or branched hydrocarbon chain radical. In some instances, the number of carbon atoms in an alkyl moiety is indicated by the prefix "$C_x$-$C_y$", wherein x is the minimum and y is the maximum number of carbon atoms in the substituent. Thus, for example, "$C_1$-$C_6$ alkyl" means an alkyl substituent containing from 1 to 6 carbon atoms and "$C_1$-$C_3$ alkyl" means an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, and 1,2,2-trimethylpropyl. The terms "alkyl," "$C_1$-$C_6$ alkyl," "$C_1$-$C_4$ alkyl," and "$C_1$-$C_3$ alkyl" used herein are unsubstituted, unless otherwise indicated.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylenyl) or of 1 to 4 carbon atoms or of 1 to 3 carbon atoms ($C_1$-$C_3$ alkylenyl) or of 2 to 6 carbon atoms ($C_2$-$C_6$ alkylenyl). Examples of $C_1$-$C_6$ alkylenyl include, but are not limited to, —$CH_2$—, —$CH_2CH_2$—, —$C(CH_3)_2$—$CH_2CH_2$—, —$C(CH_3)_2$—$CH_2CH_2$—, —$CH_2CH_2CH_2CH_2$—, and —$CH_2CH(CH_3)CH_2$—.

The term "$C_2$-$C_6$ alkynyl" as used herein, means a straight or branched chain hydrocarbon radical containing from 2 to 6 carbon atoms and containing at least one carbon-carbon triple bond. Representative examples of $C_2$-$C_6$ alkynyl include, but are not limited to, acetylenyl, 1-propynyl, 2-propynyl, 3-butynyl, 2-pentynyl, and 1-butynyl.

The term "$C_3$-$C_{11}$ cycloalkyl" as used herein, means a hydrocarbon ring radical containing 3-11 carbon atoms, zero heteroatom, and zero double bond. The $C_3$-$C_{11}$ cycloalkyl group may be a single-ring (monocyclic) or have two or more rings (polycyclic or bicyclic). Monocyclic cycloalkyl groups typically contain from 3 to 8 carbon ring atoms ($C_3$-$C_8$ monocyclic cycloalkyl), and even more typically 3-6 carbon ring atoms ($C_3$-$C_6$ monocyclic cycloalkyl). Examples of monocyclic cycloalkyls include cyclopropyl, cyclobutyl, cyclopentyl, cyclohexyl, cycloheptyl, and cyclooctyl. Polycyclic cycloalkyl groups contain two or more rings, and bicyclic cycloalkyls contain two rings. In certain embodiments, the polycyclic cycloalkyl groups contain 2 or 3 rings. The rings within the polycyclic and the bicyclic cycloalkyl groups may be in a bridged, fused, or spiro orientation, or combinations thereof. In a spirocyclic cycloalkyl, one atom is common to two different rings. An example of a spirocyclic cycloalkyl is spiro[4.5]decane. In a bridged cycloalkyl, the rings share at least two non-adjacent atoms. Examples of bridged cycloalkyls include, but are not limited to, bicyclo[2.2.2]octyl, bicyclo[3.2.1]octyl, bicyclo[3.1.1]heptyl, bicyclo[2.2.1]heptyl, bicyclo[3.2.2]nonyl, bicyclo[3.3.1]nonyl, and bicyclo[4.2.1]nonyl, tricyclo[3.3.1.0$^{3,7}$]nonyl (octahydro-2,5-methanopentalenyl or noradamantyl), tricyclo[3.3.1.1$^{3,7}$]decyl (adamantyl), and tricyclo[4.3.1.1$^{3,8}$]undecyl (homoadamantyl). In a fused ring cycloalkyl, the rings share one common bond. Examples of fused-ring cycloalkyl include, but not limited to, decalin (decahydronaphthyl) and bicyclo[2.2.0]octyl.

The term "$C_4$-$C_7$ monocyclic cycloalkenyl" as used herein, means cyclobutenyl, cyclopentenyl, cyclohexenyl, and cycloheptyl.

The term "halo" or "halogen" as used herein, means Cl, Br, I, and F.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five, or six hydrogen atoms are replaced by halogen. The term "$C_1$-$C_3$ haloalkyl" means a $C_1$-$C_3$ alkyl group, as defined herein, in which one, two, three, four, or five hydrogen atoms are replaced by halogen. Representative examples of haloalkyl include, but are not limited to, chloromethyl, 2-fluoroethyl, 2,2-difluoroethyl, fluoromethyl, 2,2,2-trifluoroethyl, trifluoromethyl, difluoromethyl, pentafluoroethyl, 2-chloro-3-fluoropentyl, trifluorobutyl, and trifluoropropyl. The terms "haloalkyl," "$C_1$-$C_6$ haloalkyl," and "$C_1$-$C_3$ haloalkyl" used herein are unsubstituted, unless otherwise indicated.

The term "4-11 membered heterocycle" as used herein, means a hydrocarbon ring radical of 4-11 carbon ring atoms wherein at least one carbon atom is replaced by a heteroatom(s) independently selected from the group consisting of O, N, and S. The 4-11 membered heterocycle ring may be a single ring (monocyclic) or have two or more rings (bicyclic or polycyclic). In certain embodiments, the monocyclic heterocycle is a four-, five-, six-, seven-, or eight-membered hydrocarbon ring wherein at least one carbon ring atom is replaced by a heteroatom(s) independently selected from the group consisting of O, N, and S. In certain embodiments, the monocyclic heterocycle is a 4-7 membered hydrocarbon ring wherein at least one carbon ring atom is replaced by a heteroatom(s). A four-membered monocyclic heterocycle contains zero or one double bond, and one heteroatom selected from the group consisting of O, N, and S. A five-membered monocyclic heterocycle contains zero or one double bond and one, two, or three heteroatoms selected from the group consisting of O, N, and S. Examples of five-membered monocyclic heterocycles include those containing in the ring: 1 O; 1 S; 1 N; 2 N; 3N; 1 S and 1 N; 1 S, and 2 N; 1 O and 1 N; or 1 O and 2 N. Non-limiting examples of 5-membered monocyclic heterocyclic groups include 1,3-dioxolanyl, tetrahydrofuranyl, dihydrofuranyl, tetrahydrothienyl, dihydrothienyl, imidazolidinyl, oxazolidinyl, imidazolinyl, imidazolidinyl, isoxazolidinyl, pyrazolidinyl, pyrazolinyl, pyrrolidinyl, 2-pyrrolinyl, 3-pyrrolinyl, thiazolinyl, and thiazolidinyl. A six-membered monocyclic heterocycle contains zero, one, or two double bonds and one, two, or three heteroatoms selected from the group consisting of O, N, and S. Examples of six-membered monocyclic heterocycles include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Examples of six-membered monocyclic heterocycles include 1,6-dihydropyridazinyl, dihydropyranyl, 1,3-dioxanyl, 1,4-dithianyl, hexahydropyrimidine, morpholinyl, piperazinyl, piperidinyl, tetrahydropyranyl, 1,2,3,6-tetrahydropyridinyl, tetrahydrothiopyranyl, thiomorpholinyl, thioxanyl, and trithianyl. Seven- and eight-membered monocyclic heterocycles contains zero, one, two, or three double bonds and one, two, or three heteroatoms selected from the group consisting of O, N, and S. Examples of monocyclic heterocycles include, but are not limited to, azetidinyl, azepanyl, aziridinyl, 1,4-diazepanyl, dihydropyranyl, 1,6-dihydropyridazinyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxazepanyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl, tetrahydrothienyl, thiadiazolinyl, thiadiazolidinyl, thiazolinyl, thiazolidinyl, thiomorpholinyl, thiopyranyl, and trithianyl. Polycyclic heterocycle groups contain two or more rings, and bicyclic heterocycles contain two rings. In certain embodiments, the polycyclic heterocycle groups contain 2 or 3 rings. The rings within the polycyclic and the bicyclic heterocycle groups may be in a bridged, fused, or spiro orientation, or combinations thereof. In a spirocyclic heterocycle, one atom is common to two different rings. Non-limiting examples of the spirocyclic heterocycle include 2-azaspiro[3.3]heptyl, 5-azaspiro[2.4]heptyl, 5-azaspiro [2.5]octyl, 2-azaspiro[3.5]nonyl, 2-azaspiro[3.4]octyl, 3-azaspiro[5.5]undecyl, 5-azaspiro[3.4]octyl, 2-oxaspiro [3.3]heptyl, 2-oxa-6-azaspiro[3.3]heptyl, 6-oxa-2-azaspiro [3.4]octyl, 6-azaspiro[3.4]octyl, 7-azaspiro[3.5]nonyl, 8-azaspiro[4.5]decyl, 1-oxa-7-azaspiro[4.4]nonyl, 1-oxa-7-azaspiro[3.5]nonyl, 1-oxa-8-azaspiro[4.5]decyl, 1-oxa-3,8-diazaspiro[4.5]decyl, 1-oxa-4,9-diazaspiro[5.5]undecyl, 3,9-diazaspiro[5.5]undecyl, 2-oxa-7-azaspiro[3.5]nonyl, 5-oxa-2-azaspiro[3.5]nonyl, 6-oxa-2-azaspiro[3.5]nonyl, 2-oxa-5,8-diazaspiro[3.5]nonyl, 7-oxa-2-azaspiro[3.5] nonyl, 8-oxa-1-azaspiro[4.5]decyl, 8-oxa-2-azaspiro[4.5]decyl, 2,7-diazaspiro[4.4]nonyl, 1,4-dioxa-8-azaspiro[4.5]decyl, 1,3,8-triazaspiro[4.5]decyl. In a fused ring heterocycle, the rings share one common bond. Examples of fused bicyclic heterocycles are a 4-6 membered monocyclic heterocycle fused to a phenyl group, or a 4-6 membered monocyclic heterocycle fused to a $C_3$-$C_6$ monocyclic cycloalkyl, or a 4-6 membered monocyclic heterocycle fused to a $C_4$-$C_7$ monocyclic cycloalkenyl, or a 4-6 membered monocyclic heterocycle fused to a 4-7 membered monocyclic heterocycle. Examples of fused bicyclic heterocycles include, but are not limited to, 1,3-benzodioxolyl, 3-azabicyclo[3.1.0]hexyl, benzopyranyl, benzothiopyranyl, indolinyl, decahydropyrrolo[3,4-b]azepinyl, 2,3-dihydrobenzofuranyl, 2,3-dihydrobenzothienyl, 2,3-dihydro-1H-indolyl, 3,4-dihydroisoquinolin-2(1H)-yl, 2,3,4,6-tetrahydro-1H-pyrido[1,2-a]pyrazin-2-yl, hexahydropyrano[3,4-b][1,4]oxazin-1 (5H)-yl, hexahydropyrrolo[3,4-c]pyrrol-2 (1H)-yl, hexahydrocyclopenta[c]pyrrol-3a(1H)-yl, hexahydro-1H-oxazolo[3,4-a]pyrazinyl, octahydropyrrolo [3,4-b][1,4]oxazinyl, octahydroimidazo[1,5-a]pyrazinyl, octahydropyrrolo[1,2-a]pyrazinyl, octahydro-1H-pyrrolo[3, 2-c]pyridinyl, and octahydropyrrolo[3,4-c]pyrrolyl. In a bridged heterocycle, the rings share at least two non-adjacent atoms. Examples of such bridged heterocycles include, but are not limited to, azabicyclo[2.2.1]heptyl (including 2-azabicyclo[2.2.1]hept-2-yl and 2-oxa-5-azabicyclo[2.2.1] heptyl), 8-azabicyclo[3.2.1]oct-8-yl, octahydro-2,5-epoxypentalene, 8-oxa-3-azabicyclo[3.2.1]octyl, hexahydro-1H-1, 4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The nitrogen and sulfur heteroatoms in the heterocycle rings may optionally be oxidized (e.g. 1,1-dioxidotetrahydrothienyl, 1,1-dioxido-1, 2-thiazolidinyl, 1,1-dioxidothiomorpholinyl) and the nitrogen atoms may optionally be quaternized.

The term "5-11 membered heteroaryl" as used herein, means a monocyclic heteroaryl and a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Examples of 5-6 membered monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a $C_3$-$C_6$ monocyclic cycloalkyl, or a monocyclic heteroaryl fused to $C_4$-$C_7$ monocyclic cycloalkenyl, or a monocyclic heteroaryl fused to a monocyclic heteroaryl, or a monocyclic heteroaryl fused to a 4-7 membered monocyclic heterocycle. Representative examples of bicyclic heteroaryl groups include, but are not limited to, benzofuranyl, benzothienyl, benzoxazolyl, benzimidazolyl, benzoxadiazolyl, phthalazinyl, 2,6-dihydropyrrolo[3,4-c]pyrazol-5(4H)-yl, 6,7-dihydro-pyrazolo[1,5-a] pyrazin-5(4H)-yl, 6,7-dihydro-1,3-benzothiazolyl, imidazo [1,2-a]pyridinyl, indazolyl, indolyl, isoindolyl, isoquinolinyl, naphthyridinyl, pyridoimidazolyl, quinolinyl, 2,4,6,7-tetrahydro-5H-pyrazolo[4,3-c]pyridin-5-yl, thiazolo [5,4-b]pyridin-2-yl, thiazolo[5,4-d]pyrimidin-2-yl, and 5,6, 7,8-tetrahydroquinolin-5-yl. The nitrogen atom in the heteroaryl rings may optionally be oxidized and may optionally be quaternized.

The phenyl, the cycloalkyls, the cycloalkenyls, the heterocycles, and the heteroaryls, including the exemplary rings, are optionally substituted unless otherwise indicated; and are attached to the parent molecular moiety through any substitutable atom contained within the ring system.

The term "heteroatom" as used herein, means a nitrogen, oxygen, and sulfur.

The term "oxo" as used herein, means a =O group.

The term "radiolabel" means a compound of the invention in which at least one of the atoms is a radioactive atom or a radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I.

A moiety is described as "substituted" when a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, then that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms. In certain embodiments, "treat," "treating," and "treatment" refer to ameliorating at least one physical parameter, which may not be discernible by the subject. In yet another embodiment, "treat", "treating", and "treatment" refer to modulating the disease or disorder, either physically (for example, stabilization of a discernible symptom), physiologically (for example, stabilization of a physical parameter), or both. In a further embodiment, "treat", "treating", and "treatment" refer to slowing the progression of the disease or disorder.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring or developing a disease or disorder.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another therapeutic agent for treatment in a particular subject or subject population. The "therapeutically effective amount" may vary depending on the compound, the disease and its severity, and the age, weight, health, etc., of the subject to be treated. For example in a human or other mammal, a therapeutically effective amount may be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, pigs, horses, dogs, cats, rabbits, rats, mice and the like. In one embodiment, the subject is a human. The terms "human," "patient," and "subject" are used interchangeably herein.

The term 'one or more' refers to one to four. In one embodiment it refers to one or three. In another embodiment it refers to one to three. In a further embodiment it refers to one to two. In yet other embodiment it refers to two. In yet other further embodiment it refers to one.

As used herein, "Class I mutation(s)" refers to mutations which interfere with protein synthesis. They result in the introduction of a premature signal of termination of translation (stop codon) in the mRNA. The truncated CFTR proteins are unstable and rapidly degraded, so, the net effect is that there is no protein at the apical membrane. In particular, Class I mutation(s) refers to p.Gly542X (G542X), W1282X, c.489+1G>T (621+1G>T), or c.579+1G>T (711+1G>T) mutation. More particularly, Class I mutation(s) refers to G542X; or W1282X mutations.

As used herein, "Class II mutation(s)" refers to mutations which affect protein maturation. These lead to the production of a CFTR protein that cannot be correctly folded and/or trafficked to its site of function on the apical membrane. In particular, Class II mutation(s) refers to p.Phe508del (F508del), p.Ile507del, or p.Asn1303Lys ($N_{1303}$K) mutations. More particularly, Class II mutation(s) refers to F508del or $N_{1303}$K mutations.

As used herein, "Class III mutation(s)" refers to mutations which alter the regulation of the CFTR channel. The mutated CFTR protein is properly trafficked and localized to the plasma membrane but cannot be activated, or it cannot function as a chloride channel. In particular, Class III mutation(s) refers to p.Gly551Asp (G551D), G551S, R553G, G1349D, S1251N, G178R, S549N mutations. More particularly, Class III mutation(s) refers to G551D, R553G, G1349D, S1251N, G178R, or S549N mutations.

As used herein, "Class IV mutation(s)" refers to mutations which affect chloride conductance. The CFTR protein is correctly trafficked to the cell membrane but generates reduced chloride flow or a "gating defect" (most are missense mutations located within the membrane-spanning domain). In particular, Class IV mutation(s) refers to p.Arg117His (R117H), R347P, or p.Arg334Trp (R334W) mutations.

As used herein, "Class V mutation(s)" refers to mutations which reduce the level of normally functioning CFTR at the apical membrane or result in a "conductance defect" (for example partially aberrant splicing mutations or inefficient trafficking missense mutations). In particular, Class V mutation(s) refers to c.1210-12T[5] (5T allele), c.S3140-26A>G (3272-26A>G), c.3850-2477C>T (3849+10 kbC>T) mutations.

As used herein, "Class VI mutation(s)" refers to mutations which decrease the stability of the CFTR which is present or which affect the regulation of other channels, resulting in inherent instability of the CFTR protein. In effect, although functional, the CFTR protein is unstable at the cell surface and it is rapidly removed and degraded by cell machinery. In particular, Class VI mutation(s) refers to Rescued F508del, 120del23, $N_{287}$Y, 4326dellTC, or 4279insA mutations. More particularly, Class VI mutation(s) refers to Rescued F508del mutations.

Compounds

Compounds of the invention have the general formula (I) as described above.

Particular values of variable groups in compounds of formula (I) are as follows. Such values may be used where appropriate with any of the other values, definitions, claims or embodiments defined hereinbefore or hereinafter.

In certain embodiments of formula (I), $R^1$ is $G^{1A}$, $C_1$-$C_6$ haloalkyl, or $C_1$-$C_6$ alkyl.

In certain embodiments of formula (I), $R^1$ is $G^{1A}$.

In certain embodiments of formula (I), $R^1$ is $G^{1A}$ wherein $G^{1A}$ is phenyl, pyrazolyl, pyridinyl, pyrimidinyl, pyrazinyl, pyridazinyl, azetidinyl, oxetanyl, tetrahydrofuranyl, pyrrolidinyl, dihydropyranyl, 1,6-dihydropyridazinyl, tetrahydropyranyl, tetrahydrothienyl, piperidinyl, cyclopropyl, cyclobutyl, cyclopentyl, or cyclohexyl.

In certain embodiments of formula (I), $R^1$ is $G^{1A}$ wherein $G^{1A}$ is phenyl, pyridinyl, tetrahydrofuranyl, tetrahydropyranyl, cyclopropyl, cyclopentyl, or cyclohexyl.

In certain embodiments of formula (I), $R^1$ is $G^{1A}$ wherein $G^{1A}$ is phenyl, pyridinyl, or cyclohexyl.

In certain embodiments of formula (I), $R^1$ is $G^{1A}$ wherein $G^{1A}$ is 4-7 membered monocyclic heterocycle. In some such embodiments, the 4-7 membered monocyclic heterocycle is tetrahydrofuranyl or tetrahydropyranyl.

In certain embodiments of formula (I), $R^1$ is $G^{1A}$ wherein $G^{1A}$ is $C_3$-$C_6$ monocyclic cycloalkyl. In some such embodiments, the $C_3$-$C_6$ monocyclic cycloalkyl is cyclohexyl. In some such embodiments, the $C_3$-$C_6$ monocyclic cycloalkyl is cyclopentyl. In some such embodiments, the $C_3$-$C_6$ monocyclic cycloalkyl is cyclopropyl.

In certain embodiments, $R^1$ is $G^{1A}$ wherein $G^{1A}$ is 5-11 membered fused bicyclic heterocycle. In some such embodiments, the 5-11 membered fused bicyclic heterocycle is 1,3-benzodioxolyl.

In certain embodiments of formula (I), $R^1$ is $G^{1A}$ wherein $G^{1A}$ is phenyl or 5-6 membered monocyclic heteroaryl. In some such embodiments, the 5-6 membered monocyclic heteroaryl is pyridinyl, pyrimidinyl, pyrazinyl, or pyridazinyl. In some such embodiments, the 5-6 membered monocyclic heteroaryl is pyridinyl or pyrimidinyl. In some such embodiments, the 5-6 membered monocyclic heteroaryl is pyridinyl.

In certain embodiments of formula (I), $R^1$ is $G^{1A}$ wherein $G^{1A}$ is phenyl.

In certain embodiments of formula (I), $R^1$ is $G^{1A}$ wherein $G^{1A}$ is 5-6 membered monocyclic heteroaryl. In some such embodiments, the 5-6 membered monocyclic heteroaryl is pyridinyl, pyrimidinyl, pyrazinyl, or pyridazinyl. In some such embodiments, the 5-6 membered monocyclic heteroaryl is pyridinyl or pyrimidinyl. In some such embodiments, the 5-6 membered monocyclic heteroaryl is pyridinyl.

In certain embodiments, $G^{1A}$, including the exemplary rings, are optionally substituted with 1, 2, 3, or 4 substituents independently selected from the group consisting of $R^{1a}$ and $G^{1B}$.

In certain embodiments, $G^{1A}$, including the exemplary rings, are optionally substituted with 1, 2, 3, or 4 independently selected $R^{1a}$.

In certain embodiments, $G^{1A}$, including the exemplary rings, are optionally substituted with 1, 2, or 3 independently selected $R^{1a}$.

In certain embodiments, $G^{1A}$, including the exemplary rings, are optionally substituted with 1 or 2 independently selected $R^{1a}$.

In certain embodiments, $G^{1A}$, including the exemplary rings, are unsubstituted.

In certain embodiments, $G^{1A}$, including the exemplary rings, are substituted with one $G^{1B}$, and said $G^{1A}$, including the exemplary rings, are optionally further substituted with 1, 2, or 3 independently selected $R^{1a}$. In some such embodiments, said $G^{1A}$, including the exemplary rings, are optionally further substituted with 1 or 2 independently selected $R^{1a}$. In some such embodiments, said $G^{1A}$, including the exemplary rings, are optionally further substituted with one $R^{1a}$. In some such embodiments, said $G^{1A}$, including the exemplary rings, are not further substituted.

In certain embodiments of formula (I), each $R^{1a}$ is independently $C_1$-$C_6$ alkyl, halogen, $C_1$-$C_6$ haloalkyl, oxo, —CN, —OR$^m$, —S(O)$_2$R$^m$, —S(O)$_2$N(R$^m$)$_2$, —C(O)R$^m$, —C(O)OR$^m$, —C(O)N(R$^m$)$_2$, —N(R$^m$)$_2$, —N(R$^m$)(alkoxyalkyl), —N(alkoxyalkyl)$_2$, or —(C$_1$-C$_6$ alkylenyl-CN).

In certain embodiments of formula (I), each $R^{1a}$ is independently $C_1$-$C_6$ alkyl, halogen, $C_1$-$C_6$ haloalkyl, —CN, —OR$^m$, —N(R$^m$)$_2$, —N(R$^m$)(alkoxyalkyl), or —N(alkoxyalkyl)$_2$.

In certain embodiments of formula (I), each $R^{1a}$ is independently $C_1$-$C_3$ alkyl, halogen, $C_1$-$C_3$ haloalkyl, —CN, —OR$^m$, or —N(R$^m$)$_2$.

In certain embodiments of formula (I), $G^{1B}$ is a 4-7 membered monocyclic heterocycle.

In certain embodiments of formula (I), $G^{1B}$ is azetidinyl, pyrrolidinyl, piperidinyl, tetrahydropyranyl, or morpholinyl.

In certain embodiments, $G^{1B}$, including the exemplary rings, are optionally substituted with 1, 2, 3, or 4 independently selected $R^{1b}$ groups.

In certain embodiments, $G^{1B}$, including the exemplary rings, are optionally substituted with 1, 2, or 3 independently selected $R^{1b}$ groups.

In certain embodiments, $G^{1B}$, including the exemplary rings, are optionally substituted with 1 or 2 independently selected $R^{1b}$.

In certain embodiments, $G^{1B}$, including the exemplary rings, are unsubstituted.

In certain embodiments of formula (I), each $R^{1b}$ is independently $C_1$-$C_3$ alkyl, halogen, $C_1$-$C_3$ haloalkyl, or —OR$^m$.

In certain embodiments of formula (I), $R^1$ is $C_1$-$C_6$ alkyl. In some such embodiments, $R^1$ is —C(CH$_3$)$_3$, —C(H)(CH$_3$)$_2$, or —CH$_2$—CH(CH$_3$)$_2$. In some such embodiments, $R^1$ is —C(H)(CH$_3$)$_2$ or —CH$_2$—CH(CH$_3$)$_2$. In some such embodiments, $R^1$ is —C(H)(CH$_3$)$_2$.

In certain embodiments of formula (I), $R^1$ is $C_1$-$C_6$ alkyl substituted with one $G^{1A}$. In some such embodiments, $G^{1A}$ is optionally substituted $C_3$-$C_6$ monocyclic cycloalkyl. In some such embodiments, $G^{1A}$ is optionally substituted cyclobutyl. In some such embodiments, $G^{1A}$ is unsubstituted cyclobutyl.

In certain embodiments of formula (I), $R^2$ is $C_1$-$C_6$ alkyl, $C_1$-$C_6$ haloalkyl, —OR$^{2xa}$, —N(R$^{2xa}$)(R$^{2xb}$), or $G^{2A}$.

In certain embodiments of formula (I), $R^2$ is $C_1$-$C_6$ alkyl, $C_1$-$C_6$ haloalkyl, —OR$^{2xa}$, or $G^{2A}$.

In certain embodiments of formula (I), $R^2$ is $C_1$-$C_6$ alkyl, $C_1$-$C_6$ haloalkyl, or $G^{2A}$.

In certain embodiments of formula (I), $R^2$ is $C_1$-$C_6$ alkyl or $G^{2A}$.

In certain embodiments of formula (I), $R^2$ is —CH$_3$, —C(H)(CH$_3$)$_2$, —C(CH$_3$)$_3$, or $G^{2A}$.

In certain embodiments of formula (I), $R^2$ is —CH$_3$, —C(H)(CH$_3$)$_2$, or $G^{2A}$.

In certain embodiments of formula (I), $R^2$ is —C(H)(CH$_3$)$_2$ or $G^{2A}$.

In certain embodiments of formula (I), $R^2$ is $C_1$-$C_6$ alkyl.

In certain embodiments of formula (I), $R^2$ is —CH$_3$, —C(H)(CH$_3$)$_2$, or —C(CH$_3$)$_3$.

In certain embodiments of formula (I), $R^2$ is —CH$_3$ or —C(H)(CH$_3$)$_2$.

In certain embodiments of formula (I), $R^2$ is $G^{2A}$.

In certain embodiments, $G^{2A}$ is a $C_3$-$C_6$ monocyclic cycloalkyl. In some such embodiments, $G^{2A}$ is cyclopropyl or cyclobutyl. In some such embodiments, $G^{2A}$ is cyclobutyl.

In certain embodiments, $G^{2A}$ is a 4-7 membered monocyclic heterocycle. In some such embodiments, $G^{2A}$ is azetidinyl, oxetanyl, pyrrolidinyl, or tetrahydrofuranyl. In some such embodiments, $G^{2A}$ is azetidinyl or oxetanyl. In some such embodiments, $G^{2A}$ is azetidinyl.

In certain embodiments, $G^{2A}$ is azetidinyl, oxetanyl, pyrrolidinyl, tetrahydrofuranyl, cyclopropyl, or cyclobutyl.

In certain embodiments, $G^{2A}$ is azetidinyl, pyrrolidinyl, cyclopropyl, or cyclobutyl.

In certain embodiments, $G^{2A}$ is azetidinyl or cyclobutyl.

In certain embodiments, $G^{2A}$ is azetidinyl.

In certain embodiments, $G^{2A}$ is cyclobutyl.

In certain embodiments of formula (I), $G^{2A}$, including the exemplary rings, are optionally substituted with 1, 2, or 3 independently selected $R^{2a}$ groups.

In certain embodiments of formula (I), $G^{2A}$, including the exemplary rings, are optionally substituted with 1 or 2 independently selected $R^{2a}$ groups.

In certain embodiments of formula (I), $G^{2A}$, including the exemplary rings, are unsubstituted.

In certain embodiments of formula (I), $R^2$ is —$OR^{2xa}$.

In certain embodiments of formula (I), $R^2$ is —$OR^{2xa}$ wherein $R^{2xa}$ is $C_1$-$C_6$ alkyl or $G^{2B}$.

In certain embodiments, $G^{2B}$ is a 4-7 membered monocyclic heterocycle.

In certain embodiments, $G^{2B}$ is azetidinyl, pyrrolidinyl, piperidinyl, oxetanyl, tetrahydrofuranyl, or tetrahydropyranyl.

In certain embodiments, $G^{2B}$ is piperidinyl, oxetanyl, or tetrahydrofuranyl.

In certain embodiments, $G^{2B}$ is oxetanyl.

In certain embodiments, $G^{2B}$ is a $C_3$-$C_6$ monocyclic cycloalkyl. In some such embodiments, the $C_3$-$C_6$ monocyclic cycloalkyl is cyclobutyl.

In certain embodiments of formula (I), $G^{2B}$, including the exemplary rings, are optionally substituted with 1, 2, or 3 independently selected $R^{2a}$ groups.

In certain embodiments of formula (I), $G^{2B}$, including the exemplary rings, are optionally substituted with 1 or 2 independently selected $R^{2a}$ groups.

In certain embodiments of formula (I), $G^{2B}$, including the exemplary rings, are unsubstituted.

In certain embodiments of formula (I), each $R^{2a}$ is independently $C_1$-$C_6$ alkyl, halogen, $C_1$-$C_6$ haloalkyl, oxo, —CN, —$OR^m$, —$C(O)R^m$, —$C(O)OR^m$, or —($C_1$-$C_6$ alkylenyl)-CN.

In certain embodiments of formula (I), each $R^{2a}$ is independently $C_1$-$C_3$ alkyl, halogen, $C_1$-$C_3$ haloalkyl, —$OR^m$, or —$C(O)OR^m$.

In certain embodiments of formula (I), $R^3$ is $G^{3A}$, -$G^{3B}$-$L^1$-$G^{3C}$, -$G^{3B}$-$L^3$-$G^{3C}$-$G^{3E}$, —($C_1$-$C_6$ alkylenyl)-$G^{3D}$, or —$OR^{3a}$.

In certain embodiments of formula (I), $R^3$ is $G^{3A}$, -$G^{3B}$-$L^1$-$G^{3C}$, or —$OR^{3a}$.

In certain embodiments of formula (I), $R^3$ is $G^{3A}$ or -$G^{3B}$-$L^1$-$G^{3C}$.

In certain embodiments of formula (I), $R^3$ is $G^{3A}$.

In certain embodiments of formula (I), $R^3$ is $G^{3A}$ wherein $G^{3A}$ is phenyl, 5-6 membered monocyclic heteroaryl, or 4-11 membered heterocycle.

In certain embodiments of formula (I), $R^3$ is $G^{3A}$ wherein $G^{3A}$ is phenyl or 5-6 membered monocyclic heteroaryl.

In certain embodiments of formula (I), $R^3$ is $G^{3A}$ wherein $G^{3A}$ is phenyl, pyrazolyl, pyrrolyl, pyridinyl, pyrimidinyl, pyridazinyl, or pyrazinyl.

In certain embodiments of formula (I), $R^3$ is $G^{3A}$ wherein $G^{3A}$ is phenyl, pyridinyl, pyrimidinyl, pyridazinyl, or pyrazinyl.

In certain embodiments of formula (I), $R^3$ is $G^{3A}$ wherein $G^{3A}$ is phenyl, pyridinyl, or pyrimidinyl.

In certain embodiments of formula (I), $R^3$ is $G^{3A}$ wherein $G^{3A}$ is phenyl.

In certain embodiments of formula (I), $R^3$ is $G^{3A}$ wherein $G^{3A}$ is pyridinyl.

In certain embodiments of formula (I), $R^3$ is $G^{3A}$ wherein $G^{3A}$ is a 4-11 membered heterocycle.

In certain embodiments of formula (I), $R^3$ is $G^{3A}$ wherein $G^{3A}$ is azetidinyl, pyrrolidinyl, piperidinyl, dihydropyranyl, piperazinyl, morpholinyl, thiomorpholinyl, tetrahydropyridinyl, azepanyl, 1,4-oxazepanyl, 1,4-diazepanyl, 2-azaspiro[3.3]heptyl, 2-oxaspiro[3.3]heptyl, 5-azaspiro[2.4]heptyl, 2-azaspiro[3.4]octyl, 5-azaspiro[2.5]octyl, 5-azaspiro[3.4]octyl, 5-oxa-2-azaspiro[3.5]nonyl, 6-oxa-2-azaspiro[3.4]octyl, 6-oxa-2-azaspiro[3.5]nonyl, 7-oxa-2-azaspiro[3.5]nonyl, 1-oxa-7-azaspiro[3.5]nonyl, 1-oxa-7-azaspiro[4.4]nonyl, 2-oxa-7-azaspiro[3.5]nonyl, 7-azaspiro[3.5]nonyl, 2,7-diazaspiro[4.4]nonyl, 2-azaspiro[3.5]nonyl, 1,3,8-triazaspiro[4.5]decyl, 8-azaspiro[4.5]decyl, 8-oxa-2-azaspiro[4.5]decyl, 1-oxa-8-azaspiro[4.5]decyl, 1-oxa-3,8-diazaspiro[4.5]decyl, 1-oxa-4,9-diazaspiro[5.5]undecyl, 1,4-dioxa-8-azaspiro[4.5]decyl, 3-azaspiro[5.5]undecyl, 3-azabicyclo[3.1.0]hexyl, 8-azabicyclo[3.2.1]octyl, octahydropyrrolo[3,4-c]pyrrolyl, hexahydro-1H-oxazolo[3,4-a]pyrazinyl, octahydropyrrolo[1,2-a]pyrazinyl, octahydroimidazo[1,5-a]pyrazinyl, octahydro-1H-pyrrolo[3,2-c]pyridinyl, decahydropyrrolo[3,4-b]azepinyl, or isoindolinyl.

In certain embodiments of formula (I), $R^3$ is $G^{3A}$ wherein $G^{3A}$ is azetidinyl, piperidinyl, piperazinyl, morpholinyl, thiomorpholinyl, 2-azaspiro[3.3]heptyl, 5-azaspiro[2.4]heptyl, 2-azaspiro[3.4]octyl, 5-azaspiro[2.5]octyl, 5-oxa-2-azaspiro[3.5]nonyl, 6-oxa-2-azaspiro[3.5]nonyl, 7-oxa-2-azaspiro[3.5]nonyl, 1-oxa-7-azaspiro[3.5]nonyl, 2-azaspiro[3.5]nonyl, 1,3,8-triazaspiro[4.5]decyl, 8-oxa-2-azaspiro[4.5]decyl, 1-oxa-8-azaspiro[4.5]decyl, 1-oxa-3,8-diazaspiro[4.5]decyl, 3-azaspiro[5.5]undecyl, 3-azabicyclo[3.1.0]hexyl, or octahydro-1H-pyrrolo[3,2-c]pyridinyl.

In certain embodiments of formula (I), $R^3$ is $G^{3A}$ is a 4-7 membered monocyclic heterocycle.

In certain embodiments of formula (I), $R^3$ is $G^{3A}$ wherein $G^{3A}$ is azetidinyl, pyrrolidinyl, piperidinyl, dihydropyranyl, piperazinyl, morpholinyl, thiomorpholinyl, tetrahydropyridinyl, azepanyl, 1,4-oxazepanyl, or 1,4-diazepanyl.

In certain embodiments of formula (I), $R^3$ is $G^{3A}$ wherein $G^{3A}$ is azetidinyl, piperidinyl, or piperazinyl.

In certain embodiments of formula (I), $R^3$ is $G^{3A}$ wherein $G^{3A}$ is piperidinyl or piperazinyl.

In certain embodiments of formula (I), $R^3$ is $G^{3A}$ wherein $G^{3A}$ is piperidinyl.

In certain embodiments, each of the aforementioned $G^{3A}$, including the exemplary rings, are optionally substituted with 1, 2, 3, or 4 independently selected $R^e$ groups.

In certain embodiments, each of the aforementioned $G^{3A}$, including the exemplary rings, are optionally substituted with 1, 2, or 3 independently selected $R^e$ groups.

In certain embodiments, each of the aforementioned $G^{3A}$, including the exemplary rings, are optionally substituted with 1 or 2 independently selected $R^e$ groups.

In certain embodiments, $G^{3A}$, including the exemplary rings, are unsubstituted.

In certain embodiments, each of the optional substituents of $G^{3A}$ is independently $C_1$-$C_6$ alkyl, $C_1$-$C_6$ haloalkyl, halogen, oxo, —CN, —$N_3$, —$OR^f$, —$S(O)_2R$, —$C(O)R^f$, —$C(O)OR^f$, —$C(O)NR^fR^h$, —$N(R)_2$, —$N(R^h)C(O)R^h$, —$N(R^h)S(O)_2R^g$, or —$N(R^h)C(O)O(R^g)$; wherein the $C_1$-$C_6$ haloalkyl and the $C_1$-$C_6$ alkyl are each optionally substituted with 1 or 2 substituents independently selected from the group consisting of —CN, —$OR^f$, —$N(R^f)_2$, —$C(O)N(R^f)_2$, and —$N(R^h)C(O)O(R^g)$.

In certain embodiments, each of the optional substituents of $G^{3A}$ is independently $C_1$-$C_6$ alkyl, $C_1$-$C_6$ haloalkyl, halogen, oxo, —CN, —$N_3$, —OR, —$S(O)_2R^f$, —C(O)OR, —$N(R)_2$, or —$N(R^h)C(O)R^h$; wherein the $C_1$-$C_6$ haloalkyl and the $C_1$-$C_6$ alkyl are each optionally substituted with 1 or 2 substituents independently selected from the group consisting of —CN, —OR, and —$N(R^f)_2$; and each $R^f$ is independently hydrogen, $C_1$-$C_6$ alkyl, $C_1$-$C_6$ haloalkyl, —($C_1$-$C_6$ alkylenyl)-OR$^m$, or —($C_1$-$C_6$ alkylenyl)-N(R$^m$)$_2$.

In certain embodiments, each of the optional substituents of G$^{3A}$ is independently $C_1$-$C_6$ alkyl, $C_1$-$C_6$ haloalkyl, halogen, —OR$^f$, or —N(R$^f$)$_2$; wherein the $C_1$-$C_6$ haloalkyl and the $C_1$-$C_6$ alkyl are each optionally substituted with 1 or 2 substituents independently selected from the group consisting of —OR$^f$ and —N(R$^f$)$_2$; and each R$^f$ is independently hydrogen, $C_1$-$C_6$ alkyl, $C_1$-$C_6$ haloalkyl, —($C_1$-$C_6$ alkylenyl)-OR$^m$, or —($C_1$-$C_6$ alkylenyl)-N(R$^m$)$_2$.

In certain embodiments of formula (I), R$^3$ is -G$^{3B}$-L$^1$-G$^{3C}$.

In certain embodiments of formula (I), G$^{3B}$ is phenyl, 5-6 membered monocyclic heteroaryl, or 4-7 membered monocyclic heterocycle.

In certain embodiments of formula (I), G$^{3B}$ is phenyl, pyridinyl, pyrazinyl, pyrimidinyl, pyridazinyl, azetidinyl, pyrrolidinyl, piperidinyl, piperazinyl, morpholinyl, 1-oxa-8-azaspiro[4.5]decyl, 3,9-diazaspiro[5.5]undecyl, octahydro-1H-pyrrolo[3,2-c]pyridinyl, or 1,4-diazepanyl.

In certain embodiments of formula (I), G$^{3B}$ is phenyl, pyridinyl, pyrazinyl, pyrimidinyl, pyridazinyl, piperidinyl, or piperazinyl.

In certain embodiments of formula (I), G$^{3B}$ is phenyl, pyridinyl, pyrimidinyl, piperidinyl, or piperazinyl.

In certain embodiments of formula (I), G$^{3B}$ is a 4-7 membered monocyclic heterocycle.

In certain embodiments of formula (I), G$^{3B}$ is azetidinyl, pyrrolidinyl, piperidinyl, piperazinyl, morpholinyl, or 1,4-diazepanyl.

In certain embodiments of formula (I), G$^{3B}$ is piperidinyl or piperazinyl.

In certain embodiments of formula (I), G$^{3B}$ is piperidinyl.

In certain embodiments of formula (I), G$^{3B}$ is piperazinyl.

In certain embodiments of formula (I), G$^{3C}$ is $C_3$-$C_6$ monocyclic cycloalkyl, phenyl, 5-6 membered monocyclic heteroaryl, or 4-7 membered monocyclic heterocycle.

In certain embodiments of formula (I), G$^{3C}$ is cyclopropyl, cyclobutyl, cyclopentyl, cyclohexyl, phenyl, pyridinyl, pyrazinyl, pyrimidinyl, pyridazinyl, azetidinyl, oxetanyl, pyrrolidinyl, tetrahydrofuranyl, oxazolidinyl, piperidinyl, piperazinyl, tetrahydropyranyl, thiomorpholinyl, 2-oxa-5,8-diazaspiro[3.5]nonyl, 2-oxa-5-azabicyclo[2.2.1]heptyl, hexahydropyrrolo[3,4-c]pyrrolyl, or morpholinyl.

In certain embodiments of formula (I), G$^{3C}$ is 4-7 membered monocyclic heterocycle.

In certain embodiments of formula (I), G$^{3C}$ is azetidinyl, oxetanyl, pyrrolidinyl, tetrahydrofuranyl, oxazolidinyl, piperidinyl, piperazinyl, tetrahydropyranyl, thiomorpholinyl, or morpholinyl.

In certain embodiments of formula (I), G$^{3C}$ is azetidinyl, pyrrolidinyl, piperidinyl, piperazinyl, tetrahydropyranyl, tetrahydropyranyl, or morpholinyl.

In certain embodiments of formula (I), G$^{3C}$ is pyrrolidinyl, piperidinyl, piperazinyl, or morpholinyl.

In certain embodiments, each of the aforementioned G$^{3B}$ and G$^{3C}$, including the exemplary rings, are optionally substituted with 1, 2, 3, or 4 independently selected R$^e$ groups.

In certain embodiments, each of the aforementioned G$^{3B}$ and G$^{3C}$, including the exemplary rings, are optionally substituted with 1, 2, or 3 independently selected R$^e$ groups.

In certain embodiments, each of the aforementioned G$^{3B}$ and G$^{3C}$, including the exemplary rings, are optionally substituted with 1 or 2 independently selected R$^e$ groups.

In certain embodiments, G$^{3B}$ and G$^{3C}$, including the exemplary rings, are unsubstituted.

In certain embodiments, each of the optional substituents of G$^{3B}$ is independently $C_1$-$C_6$ alkyl, $C_1$-$C_6$ haloalkyl, halogen, —OR$^f$, or —CN. In some such embodiments, R$^f$ is hydrogen, $C_1$-$C_3$ alkyl, or $C_1$-$C_3$ haloalkyl.

In certain embodiments, each of the optional substituents of G$^{3B}$ is independently —CH$_3$, —CH$_2$F, —CHF$_2$, —CF$_3$, or F.

In certain embodiments, each of the optional substituents of G$^{3C}$ is independently $C_1$-$C_6$ alkyl, $C_1$-$C_6$ haloalkyl, halogen, oxo, —OR$^f$, —N(R$^f$)$_2$, —C(O)OR$^f$, or —CN; wherein the $C_1$-$C_6$ alkyl is optionally substituted with one —OR$^f$.

In certain embodiments, each of the optional substituents of G$^{3C}$ is independently —CH$_3$, —CH$_2$F, —CHF$_2$, —CF$_3$, F, or —CN.

In certain embodiments, L$^1$ is a bond, $C_1$-$C_3$ alkylenyl, or ($C_1$-$C_3$ alkylenyl)$_r$-L$^2$-($C_1$-$C_3$ alkylenyl)$_s$.

In certain embodiments, L$^2$ is O, N(R$^x$), or C(O).

In certain embodiments, L$^2$ is O or N(R$^x$).

In certain embodiments of formula (I), R$^3$ is —OR$^{3a}$.

In certain embodiments of formula (I), R$^3$ is —OR$^{3a}$ wherein R$^{3a}$ is G$^{3D}$, $C_1$-$C_6$ haloalkyl, or $C_1$-$C_6$ alkyl; wherein the $C_1$-$C_6$ haloalkyl and the $C_1$-$C_6$ alkyl are each substituted with one or two substituents independently selected from the group consisting of G$^{3D}$, —OR$^{3xa}$, and —N(R$^{3xb}$)$_2$.

In certain embodiments of formula (I), R$^3$ is —OR$^{3a}$; and R$^{3a}$ is $C_1$-$C_6$ haloalkyl and $C_1$-$C_6$ alkyl; wherein the $C_1$-$C_6$ haloalkyl and the $C_1$-$C_6$ alkyl are each substituted with one G$^{3D}$.

In certain embodiments, G$^{3D}$ is oxetanyl, pyrrolidinyl, tetrahydrofuranyl, imidazolidinyl, tetrahydropyranyl, piperidinyl, piperazinyl, thiomorpholinyl, morpholinyl, 1,3-dioxolanyl, azepanyl, 1,4-diazepanyl, 1,3-dioxanyl, 1,4-dioxanyl, 8-azaspiro[4.5]decyl, cyclopropyl, cyclobutyl, cyclopentyl, or cyclohexyl.

In certain embodiments, G$^{3D}$ is a 4-7 membered monocyclic heterocycle.

In certain embodiments, G$^{3D}$ is oxetanyl, pyrrolidinyl, tetrahydrofuranyl, imidazolidinyl, tetrahydropyranyl, piperidinyl, piperazinyl, thiomorpholinyl, morpholinyl, 1,3-dioxolanyl, azepanyl, 1,4-diazepanyl, 1,3-dioxanyl, or 1,4-dioxanyl.

In certain embodiments, G$^{3D}$ is tetrahydrofuranyl, tetrahydropyranyl, piperidinyl, piperazinyl, thiomorpholinyl, morpholinyl, or 1,4-dioxanyl.

In certain embodiments, G$^{3D}$ is tetrahydropyranyl.

In certain embodiments, each of the aforementioned G$^{3D}$, including the exemplary rings, are optionally substituted with 1, 2, 3, or 4 independently substituents independently selected from the group consisting of R$^e$ and G$^{3E}$.

In certain embodiments, each of the aforementioned G$^{3D}$, including the exemplary rings, are optionally substituted with 1, 2, or 3 independently selected R$^e$ groups.

In certain embodiments, each of the aforementioned G$^{3D}$, including the exemplary rings, are optionally substituted with 1 or 2 independently selected R$^e$ groups.

In certain embodiments, each of the aforementioned G$^{3D}$, including the exemplary rings, are optionally substituted with one G$^{3E}$ and optionally with 1 or 2 independently selected R$^e$ groups. Examples of G$^{3E}$ include cyclobutyl, cyclohexyl, and tetrahydropyranyl, each of which is optionally substituted.

In certain embodiments, G$^{3D}$, including the exemplary rings, are unsubstituted. In certain embodiments, each of the R$^e$ groups of G$^{3D}$ is independently $C_1$-$C_6$ alkyl, $C_1$-$C_6$ haloalkyl, halogen, oxo, —OR$^f$, —C(O)R$^f$, —C(O)OR$^f$, or —CN.

In certain embodiments of formula (I), $R^3$ is —N($R^{3a}$)($R^{3b}$).

In certain embodiments of formula (I), $R^3$ is —N($R^{3a}$)($R^{3b}$) wherein $R^{3a}$ is $C_1$-$C_3$ haloalkyl or $C_1$-$C_3$ alkyl; wherein the $C_1$-$C_3$ haloalkyl and the $C_1$-$C_3$ alkyl are each substituted with one substituent independently selected from the group consisting of —O$R^{3xa}$ and —N($R^{3xb}$)$_2$. In some such embodiments, $R^{3xa}$ and $R^{3xb}$, at each occurrence, are each independently hydrogen, $C_1$-$C_3$ haloalkyl, or $C_1$-$C_3$ alkyl.

In certain embodiments of formula (I), $R^3$ is -$G^{3B}$-$L^3$-$G^{3C}$-$G^{3E}$. In some such embodiments, $G^{3B}$ is phenyl, 5-6 membered heteroaryl, or 4-11 membered heterocycle, $G^{3C}$ is 4-11 membered heterocycle; and $G^{3E}$ is $C_3$-$C_8$ monocyclic cycloalkyl. Examples of $G^{3B}$ are phenyl, pyridinyl, piperidinyl, and piperazinyl. In some such embodiments, $G^{3C}$ is piperidinyl or piperazinyl. In some such embodiments, $G^{3E}$ is cyclopropyl. $G^{3B}$, $G^{3C}$, and $G^{3E}$, including the exemplary rings, are each optionally substituted as described in the summary and embodiments herein above.

In certain embodiments, $R^3$ is-($C_1$-$C_6$ alkylenyl)-$G^{3D}$. In some such embodiments, $G^{3D}$ is 4-7 membered monocyclic heterocycle. In some such embodiments, $G^{3D}$ is piperidinyl, piperazinyl or morpholinyl. $G^{3D}$, including the exemplary rings are each optionally substituted as described in the Summary and embodiments herein above.

In certain embodiments of formula (I), $R^4$ is hydrogen or $C_1$-$C_3$ alkyl.

In certain embodiments of formula (I), $R^4$ is hydrogen.

In certain embodiments of formula (I), $R^5$ is $C_1$-$C_6$ alkyl, $C_2$-$C_6$ alkenyl, $C_2$-$C_6$ alkynyl, or $C_1$-$C_6$ haloalkyl; wherein the $C_1$-$C_6$ alkyl and the $C_1$-$C_6$ haloalkyl are each optionally substituted with one or two substituents independently selected from the group consisting of $G^{5A}$, —CN, —$N_3$, —O$R^{5ax}$, —S(O)$_2R^{5ax}$, —S(O)$_2$N($R^{5ax}$)($R^{5bx}$), —N($R^{5ax}$)($R^{5bx}$), —N($R^{5bx}$)S(O)$_2R^{5cx}$, —N($R^{5bx}$)C(O)$R^{5cx}$, —N($R^{5bx}$)C(O)N($R^{5ax}$)($R^{5bx}$), —N($R^{5bx}$)C(O)O$R^5C_x$, —C(O)$R^{5ax}$, —C(O)O$R^{5ax}$, —C(O)N($R^{5bx}$)S(O)$_2R^{5cx}$, and —C(O)N($R^{5ax}$)($R^{5bx}$).

In certain embodiments of formula (I), $R^5$ is $C_1$-$C_6$ alkyl or $C_1$-$C_6$ haloalkyl.

In certain embodiments of formula (I), $R^5$ is —CH$_3$, —CH$_2$CH$_3$, —CH$_2$C(H)C(CH$_3$)$_2$, —C(CH$_3$)$_3$, —CF$_3$, —CH$_2$Cl, —CH$_2$CF$_3$, or —CH$_2$CH$_2$CF$_3$.

In certain embodiments of formula (I), $R^5$ is —CH$_3$.

In certain embodiments of formula (I), $R^5$ is $C_1$-$C_6$ alkyl which is substituted with one substituent selected from the group consisting of $G^{5A}$, —CN, —$N_3$, —O$R^{5ax}$, —S(O)$_2R^{5ax}$, —S(O)$_2$N($R^{5ax}$)($R^{5bx}$), N($R^{5ax}$)($R^{5bx}$), —N($R^{5bx}$)S(O)$_2R^{5cx}$, —N($R^{5bx}$)C(O)$R^{5cx}$, —N($R^{5bx}$)C(O)N($R^{5ax}$)($R^{5bx}$), —N($R^{5bx}$)C(O)O$R^{5cx}$, —C(O)$R^{5ax}$, —C(O)O$R^{5ax}$, —C(O)N($R^{5bx}$)S(O)$_2R^{5cx}$, and —C(O)N($R^{5ax}$)($R^{5bx}$).

In certain embodiments of formula (I), $R^5$ is $C_1$-$C_6$ alkyl which is substituted with one substituent selected from the group consisting of $G^{5A}$, —CN, —$N_3$, —O$R^{5ax}$, —N($R^{5ax}$)($R^{5bx}$), —N($R^{5bx}$)C(O)$R^{5cx}$, —N($R^{5bx}$)C(O)O$R^{5cx}$, —C(O)O$R^{5ax}$, and —C(O)N($R^{5ax}$)($R^{5bx}$).

In certain embodiments of formula (I), $R^5$ is $C_1$-$C_6$ alkyl substituted with one $G^{5A}$. In some such embodiments, $G^{5A}$ is 5-6 membered monocyclic heteroaryl or a 4-11 membered heterocycle.

In certain embodiments of formula (I), $R^5$ is —N($R^{5ax}$)($R^{5bx}$). In some such embodiments, $R^{5ax}$ is hydrogen, $C_1$-$C_6$ alkyl, or $C_1$-$C_6$ haloalkyl; and $R^{5bx}$ is $C_1$-$C_6$ alkyl, $C_1$-$C_6$ haloalkyl or $G^{5A}$. In some such embodiments, $R^{5ax}$ and $R^{5bx}$ are each $C_1$-$C_6$ alkyl.

In certain embodiments of formula (I), $R^5$ is $G^{5A}$.

In certain embodiments of formula (I), $R^5$ is $G^{5A}$ wherein $G^{5A}$ is $C_3$-$C_6$ monocyclic cycloalkyl, phenyl, 5-6 membered monocyclic heteroaryl, or 4-11 membered heterocycle.

In certain embodiments, each of the aforementioned $G^{5A}$ is optionally substituted with 1, 2, 3, or 4 independently selected $R^{5a}$ groups.

In certain embodiments, $G^{5A}$ is optionally substituted with 1, 2, or 3, independently selected $R^{5a}$ groups.

In certain embodiments, $G^{5A}$ is optionally substituted with 1, or 2 independently selected $R^{5a}$ groups.

In certain embodiments, $G^{5A}$ is unsubstituted.

In certain embodiments of formula (I), $R^6$ is hydrogen.

In certain embodiments of formula (I), $R^6$ is $C_1$-$C_6$ alkyl or $C_1$-$C_6$ haloalkyl.

In certain embodiments of formula (I), $R^6$ is $C_1$-$C_6$ alkyl. In some such embodiments, $R^6$ is —CH$_3$.

In certain embodiments of formula (I), $R^5$ and $R^6$ together form a $C_1$-$C_6$ alkylenyl or —N(R)—($C_1$-$C_6$ alkylenyl)- wherein the N($R^z$) is attached to the S(O)$_2$ moiety of formula (I).

In certain embodiments of formula (I), $R^5$ and $R^6$ together form a $C_1$-$C_6$ alkylenyl.

In certain embodiments of formula (I), $R^5$ and $R^6$ together form a —N($R^z$)—($C_1$-$C_6$ alkylenyl)- wherein the N($R^z$) is attached to the S(O)$_2$ moiety of formula (I).

Various embodiments of substituents $R^1$, $R^2$, $R^3$, $R^4$, $R^5$, $R^6$, $G^{1A}$, $R^{1a}$, $G^{1B}$, $R^{1b}$, $G^{2A}$, $G^2B$, $R^{2a}$, $R^{2xa}$, $G^{3A}$, $G^{3B}$, $G^{3C}$, $R^e$, $R^f$, $L^1$, $L^2$, $R^{3a}$, $G^{3D}$, $G^{5A}$, $R^{5ax}$, and $R^{5bx}$ have been discussed above. These substituents embodiments can be combined to form various embodiments of the invention. All embodiments of present compounds, formed by combining the substituent embodiments discussed above are within the scope of Applicant's invention, and some illustrative embodiments of present compounds are provided below.

In one embodiment, the invention is directed to compounds wherein $R^1$ is $G^{1A}$, $C_1$-$C_6$ haloalkyl, or $C_1$-$C_6$ alkyl; and $R^2$ is $C_1$-$C_6$ alkyl, $C_1$-$C_6$ haloalkyl, or $G^{2A}$. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —CH$_3$. In some such embodiments, $R^5$ and $R^6$ together form a $C_1$-$C_6$ alkylenyl or —N($R^z$)—($C_1$-$C_6$ alkylenyl)- wherein the N($R^z$) is attached to the S(O)$_2$ moiety of formula (I).

In one embodiment, the invention is directed to compounds wherein $R^1$ is $G^{1A}$; and $R^2$ is $C_1$-$C_6$ alkyl or $G^{2A}$. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —CH$_3$. In some such embodiments, $R^5$ and $R^6$ together form a $C_1$-$C_6$ alkylenyl or —N($R^Z$)—($C_1$-$C_6$ alkylenyl)- wherein the N($R^z$) is attached to the S(O)$_2$ moiety of formula (I).

In one embodiment, the invention is directed to compounds wherein $R^1$ is $G^{1A}$ wherein $G^{1A}$ is phenyl or 5-6 membered monocyclic heteroaryl; and $R^2$ is $C_1$-$C_6$ alkyl or $G^{2A}$ wherein $G^{2A}$ is $C_3$-$C_6$ monocyclic cycloalkyl. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —CH$_3$. In some such embodiments, $R^5$ and $R^6$ together form a $C_1$-$C_6$ alkylenyl or —N($R^z$)—($C_1$-$C_6$ alkylenyl)- wherein the N($R^z$) is attached to the S(O)$_2$ moiety of formula (I).

In one embodiment, the invention is directed to compounds wherein $R^1$ is $G^{1A}$ wherein $G^{1A}$ is phenyl or pyridinyl; and $R^2$ is $C_1$-$C_6$ alkyl. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$. In some such embodiments, $R^5$ and $R^6$ together form a $C_1$-$C_6$ alkylenyl or —N($R^z$)—($C_1$-$C_6$ alkylenyl)- wherein the N($R^z$) is attached to the $S(O)_2$ moiety of formula (I).

In one embodiment, the invention is directed to compounds wherein $R^1$ is $G^{1A}$ wherein $G^{1A}$ is phenyl or pyridinyl; and $R^2$ is $G^{2A}$ wherein $G^{2A}$ is $C_3$-$C_6$ monocyclic cycloalkyl. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$. In some such embodiments, $R^5$ and $R^6$ together form a $C_1$-$C_6$ alkylenyl or —N($R^Z$)—($C_1$-$C_6$ alkylenyl)- wherein the N($R^z$) is attached to the $S(O)_2$ moiety of formula (I).

In one embodiment, the invention is directed to compounds wherein $R^1$ is $G^{1A}$ wherein $G^{1A}$ is phenyl or pyridinyl; and $R^2$ is $G^{2A}$ wherein $G^{2A}$ is unsubstituted cyclobutyl. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$. In some such embodiments, $R^5$ and $R^6$ together form a $C_1$-$C_6$ alkylenyl or —N($R^z$)—($C_1$-$C_6$ alkylenyl)- wherein the N($R^z$) is attached to the $S(O)_2$ moiety of formula (I).

In one embodiment, the invention is directed to compounds wherein $R^1$ is $G^{1A}$; $R^2$ is $C_1$-$C_6$ alkyl or $G^{2A}$; and $R^3$ is $G^{3A}$, -$G^{3B}$-$L^1$-$G^{3C}$, or —$OR^{3a}$. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$. In some such embodiments, $R^5$ and $R^6$ together form a $C_1$-$C_6$ alkylenyl or —N($R^z$)—($C_1$-$C_6$ alkylenyl)- wherein the N($R^z$) is attached to the $S(O)_2$ moiety of formula (I).

In one embodiment, the invention is directed to compounds wherein $R^1$ is $G^{1A}$; $R^2$ is $C_1$-$C_6$ alkyl or $G^{2A}$; and $R^5$ is $C_1$-$C_6$ alkyl or $C_1$-$C_6$ haloalkyl. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$.

In one embodiment, the invention is directed to compounds wherein $R^1$ is $G^{1A}$; $R^2$ is $C_1$-$C_6$ alkyl or $G^{2A}$; and $R^5$ is $C_1$-$C_6$ alkyl which is substituted with one substituent selected from the group consisting of $G^{5A}$, —CN, —$N_3$, —$OR^{5ax}$, —N($R^{5ax}$)($R^{5bx}$), —N($R^{5bx}$)C(O)$R^{5cx}$, —N($R^{5bx}$)C(O)O$R^{5cx}$, —C(O)O$R^{5ax}$, and —C(O)N($R^{5ax}$)($R^{5bx}$). In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$.

In one embodiment, the invention is directed to compounds wherein $R^1$ is $G^{1A}$; $R^2$ is $C_1$-$C_6$ alkyl or $G^{2A}$; and $R^5$ is —N($R^{5ax}$)($R^{5bx}$). In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$.

In one embodiment, the invention is directed to compounds wherein $R^1$ is $G^{1A}$; $R^2$ is $C_1$-$C_6$ alkyl or $G^{2A}$; and $R^5$ is $G^{5A}$. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$.

In one embodiment, the invention is directed to compounds wherein $R^1$ is $G^{1A}$; wherein $G^{1A}$ is phenyl or 5-6 membered monocyclic heteroaryl; $R^2$ is $C_1$-$C_6$ alkyl or $G^{2A}$; wherein $G^{2A}$ is a $C_3$-$C_6$ monocyclic cycloalkyl; $R^3$ is $G^{3A}$, -$G^{3B}$-$L^L$-$G^{3C}$, or —$OR^{3a}$; and $R^5$ is $C_1$-$C_6$ alkyl which is substituted with one substituent selected from the group consisting of $G^{5A}$, —CN, —$N_3$, —$OR^{5ax}$, —N($R^{5ax}$)($R^{5bx}$), —N($R^{5bx}$)C(O)$R^{5cx}$, —N($R^{5bx}$)C(O)O$R^{5cx}$, —C(O)O$R^{5ax}$, and —C(O)N($R^{5ax}$)($R^{5bx}$). In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$.

In one embodiment, the invention is directed to compounds wherein $R^1$ is $G^{1A}$; wherein $G^{1A}$ is phenyl or 5-6 membered monocyclic heteroaryl; $R^2$ is $C_1$-$C_6$ alkyl or $G^{2A}$; wherein $G^{2A}$ is a $C_3$-$C_6$ monocyclic cycloalkyl; $R^3$ is $G^{3A}$, -$G^{3B}$-$L^L$-$G^{3C}$, or —$OR^{3a}$; and $R^5$ is $C_1$-$C_6$ alkyl or $C_1$-$C_6$ haloalkyl. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$.

In one embodiment, the invention is directed to compounds wherein $R^1$ is $G^{1A}$; wherein $G^{1A}$ is phenyl or 5-6 membered monocyclic heteroaryl; $R^2$ is $C_1$-$C_6$ alkyl or $G^{2A}$; wherein $G^{2A}$ is a $C_3$-$C_6$ monocyclic cycloalkyl; $R^3$ is $G^{3A}$, -$G^{3B}$-$L^L$-$G^{3C}$, or —$OR^{3a}$; and $R^5$ is —N($R^{5ax}$)($R^{5bx}$) or —$OR^{5dx}$. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$.

In one embodiment, the invention is directed to compounds wherein $R^1$ is $G^{1A}$; wherein $G^{1A}$ is phenyl or 5-6 membered monocyclic heteroaryl; $R^2$ is $C_1$-$C_6$ alkyl or $G^{2A}$; wherein $G^{2A}$ is a $C_3$-$C_6$ monocyclic cycloalkyl; $R^3$ is $G^{3A}$, -$G^{3B}$-$L^1$-$G^{3C}$, or —$OR^{3a}$; and $R^5$ is $G^{5A}$ In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$.

In one embodiment, the invention is directed to compounds wherein $R^1$ is $G^{1A}$; wherein $G^{1A}$ is phenyl optionally substituted with 1, 2, 3, or 4 independently selected $R^{1a}$; $R^2$ is $C_1$-$C_6$ alkyl or $G^{2A}$; wherein $G^{2A}$ is unsubstituted cyclobutyl; $R^3$ is $G^{3A}$ wherein $G^{3A}$ is a 4-11 membered heterocycle; and $R^5$ is $C_1$-$C_6$ alkyl. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$.

In one embodiment, the invention is directed to compounds wherein $R^1$ is $G^{1A}$; wherein $G^{1A}$ is phenyl substituted with one $G^{1B}$, and said phenyl is optionally further substituted with 1, 2, or 3 independently selected $R^{1a}$; $R^2$ is $C_1$-$C_6$ alkyl or $G^{2A}$; wherein $G^{2A}$ is unsubstituted cyclobutyl; $R^3$ is $G^{3A}$ wherein $G^{3A}$ is a 4-11 membered heterocycle; and $R^5$ is $C_1$-$C_6$ alkyl. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$.

In one embodiment, the invention is directed to compounds wherein $R^1$ is $G^{1A}$; wherein $G^{1A}$ is phenyl optionally substituted with 1, 2, 3, or 4 independently selected $R^{1a}$; $R^2$ is $C_1$-$C_6$ alkyl or $G^{2A}$; wherein $G^{2A}$ is unsubstituted cyclobutyl; $R^3$ is -$G^{3B}$-$L^1$-$G^{3C}$; and $R^5$ is $C_1$-$C_6$ alkyl. In some such embodiments, $R^6$ is hydrogen. In some such embodiments, $R^6$ is $C_1$-$C_6$ alkyl or $C_1$-$C_6$ haloalkyl. In some such embodiments, $R^6$ is —$CH_3$.

In one embodiment, the invention is directed to compounds wherein $R^1$ is $G^{1A}$; wherein $G^{1A}$ is phenyl optionally substituted with 1, 2, 3, or 4 independently selected $R^{1a}$; $R^2$ is $C_1$-$C_6$ alkyl or $G^{2A}$; wherein $G^{2A}$ is unsubstituted cyclobutyl; $R^3$ is -$G^{3B}$-$L^1$-$G^{3C}$; $G^{3B}$ and $G^{3C}$ are 4-7 membered monocyclic heterocycle; and $R^5$ is $C_1$-$C_6$ alkyl. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$.

In one embodiment, the invention is directed to compounds wherein $R^1$ is $G^{1A}$; wherein $G^{1A}$ is phenyl substituted with one $G^{1B}$, and said phenyl is optionally further substituted with 1, 2, or 3 independently selected $R^{1a}$; $R^2$ is $C_1$-$C_6$ alkyl or $G^{2A}$; wherein $G^{2A}$ is unsubstituted cyclobutyl; $R^3$ is -$G^{3B}$-$L^L$-$G^{3C}$; $G^{3B}$ and $G^{3C}$ are 4-7 membered monocyclic heterocycle; and $R^5$ is $C_1$-$C_6$ alkyl. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$.

In one embodiment, the invention is directed to compounds wherein $R^1$ is $G^{1A}$; wherein $G^{1A}$ is phenyl optionally substituted with 1, 2, 3, or 4 independently selected $R^{1a}$; $R^2$ is $C_1$-$C_6$ alkyl or $G^{2A}$; wherein $G^{2A}$ is unsubstituted cyclobutyl; $R^3$ is —$OR^{3a}$; $R^{3a}$ is $C_1$-$C_6$ alkyl or $C_1$-$C_6$ haloalkyl wherein the $C_1$-$C_6$ alkyl and the $C_1$-$C_6$ haloalkyl are each substituted with one $G^{3D}$; $G^{3D}$ is a 4-7 membered monocyclic heterocycle; and $R^5$ is $C_1$-$C_6$ alkyl. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$.

In one embodiment, the invention is directed to compounds wherein $R^1$ is $G^{1A}$; wherein $G^{1A}$ is phenyl substituted with one $G^{1B}$, and said phenyl is optionally further substituted with 1, 2, or 3 independently selected $R^{1a}$; $R^2$ is $C_1$-$C_6$ alkyl or $G^{2A}$; wherein $G^{2A}$ is unsubstituted cyclobutyl; $R^3$ is —$OR^{3a}$; $R^{3a}$ is $C_1$-$C_6$ alkyl or $C_1$-$C_6$ haloalkyl wherein the $C_1$-$C_6$ alkyl and the $C_1$-$C_6$ haloalkyl are each substituted with one $G^{3D}$; $G^{3D}$ is a 4-7 membered monocyclic heterocycle; and $R^5$ is $C_1$-$C_6$ alkyl. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$.

In one embodiment, the invention is directed to compounds wherein $R^3$ is -$G^{3B}$-$L^3$-$G^{3C}$-$G^{3E}$; $G^{3B}$ is phenyl, 5-6 membered heteroaryl, or 4-11 membered heterocycle; each of which is optionally substituted; $G^{3C}$ is optionally substituted 4-11 membered heterocycle; and $G^{3E}$ is optionally substituted $C_3$-$C_8$ monocyclic cycloalkyl. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$. In some such embodiments, $R^5$ and $R^6$ together form a $C_1$-$C_6$ alkylenyl or —$N(R^z)$—($C_1$-$C_6$ alkylenyl)- wherein the $N(R^z)$ is attached to the $S(O)_2$ moiety of formula (I).

In one embodiment, the invention is directed to compounds wherein $R^1$ is $G^{1A}$; wherein $G^{1A}$ is phenyl, 5-6 membered monocyclic heteroaryl, or $C_3$-$C_6$ monocyclic cycloalkyl; $R^2$ is $C_1$-$C_6$ alkyl, —$OR^{2xa}$, or $G^{2A}$; wherein $G^{2A}$ is an optionally substituted $C_3$-$C_6$ monocyclic cycloalkyl; and $R^3$ is $G^{3A}$, -$G^{3B}$-$L^1$-$G^{3C}$, -$G^{3B}$-$L^3$-$G^{3C}$-$G^{3E}$, —($C_1$-$C_6$ alkylenyl)-$G^{3D}$, or —$OR^{3a}$. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$. In some such embodiments, $R^5$ and $R^6$ together form a $C_1$-$C_6$ alkylenyl or —$N(R^z)$—($C_1$-$C_6$ alkylenyl)- wherein the $N(R^z)$ is attached to the $S(O)_2$ moiety of formula (I).

In one embodiment, the invention is directed to compounds wherein $R^1$ is $G^{1A}$; wherein $G^{1A}$ is phenyl, 5-6 membered monocyclic heteroaryl, or $C_3$-$C_6$ monocyclic cycloalkyl; $R^2$ is $C_1$-$C_6$ alkyl, —$OR^{2xa}$, or $G^{2A}$; wherein $G^{2A}$ is an optionally substituted $C_3$-$C_6$ monocyclic cycloalkyl; $R^3$ is $G^{3A}$, -$G^{3B}$-$L^1$-$G^{3C}$, -$G^{3B}$-$L^3$-$G^{3C}$-$G^{3E}$, —($C_1$-$C_6$ alkylenyl)-$G^{3D}$, or —$OR^{3a}$; and $R^5$ is $C_1$-$C_6$ alkyl or $C_1$-$C_6$ haloalkyl. In some such embodiments, $R^6$ is hydrogen. In some such embodiments, $R^6$ is $C_1$-$C_6$ alkyl or $C_1$-$C_6$ haloalkyl. In some such embodiments, $R^6$ is $C_1$-$C_6$ alkyl. In some such embodiments, $R^6$ is —$CH_3$.

In one embodiment, the invention is directed to compounds wherein $R^1$ is $G^{1A}$, $C_1$-$C_6$ haloalkyl, or $C_1$-$C_6$ alkyl; wherein the $C_1$-$C_6$ haloalkyl and the $C_1$-$C_6$ alkyl are each optionally substituted with one $G^{1A}$;

$G^{1A}$, at each occurrence, is independently phenyl, 5-6 membered monocyclic heteroaryl, 4-7 membered monocyclic heterocycle, or $C_3$-$C_6$ monocyclic cycloalkyl; wherein each $G^{1A}$ is optionally substituted with 1, 2, 3, or 4 substituents independently selected from the group consisting of $R^{1a}$ and $G^{1B}$;

$G^{1B}$, at each occurrence, is independently 4-7 membered monocyclic heterocycle which is optionally substituted with 1, 2, 3, or 4 independently selected $R^{1b}$ groups;

$R^2$ is hydrogen, $C_2$-$C_4$ alkenyl, $C_1$-$C_6$ alkyl, $C_1$-$C_6$ haloalkyl, —$OR^{2xa}$, —$N(R^{2xa})(R^{2xb})$, or $G^{2A}$;

$R^{2xa}$, at each occurrence, is independently $C_1$-$C_6$ alkyl, $C_1$-$C_6$ haloalkyl, or $G^{2B}$;

$R^{2xb}$ is hydrogen, $C_1$-$C_3$ alkyl, or $C_1$-$C_3$ haloalkyl;

$G^{2A}$ and $G^{2B}$ are each independently a 4-7 membered monocyclic heterocycle or a $C_3$-$C_6$ monocyclic cycloalkyl; wherein $G^{2A}$ and $G^{2B}$ are each optionally substituted with 1, 2, or 3 independently selected $R^{2a}$ groups;

$R^3$ is $G^{3A}$, -$G^{3B}$-$L^1$-$G^{3C}$, —$OR^{3a}$, or —$N(R^{3a})(R^{3b})$;

$R^{3a}$, at each occurrence, is independently $G^{3D}$, $C_1$-$C_6$ haloalkyl, or $C_1$-$C_6$ alkyl; wherein the $C_1$-$C_6$ haloalkyl and the $C_1$-$C_6$ alkyl are each optionally substituted with one or two substituents independently selected from the group consisting of $G^{3D}$, —$OR^{3xa}$, and —$N(R^{3xb})_2$;

$R^{3xa}$ and $R^{3xb}$, at each occurrence, are each independently hydrogen, $C_1$-$C_6$ haloalkyl, $C_1$-$C_6$ alkyl, or $G^{3D}$;

$R^{3b}$ is hydrogen, $C_1$-$C_6$ alkyl, or $C_1$-$C_6$ haloalkyl;

$L^1$ is a bond, $C_1$-$C_6$ alkylenyl, ($C_1$-$C_6$ alkylenyl)$_r$-$L^2$-($C_1$-$C_6$ alkylenyl)$_s$, or O—($C_1$-$C_6$ alkylenyl)-C(O), wherein the left end of the $L^1$ moiety is attached to $G^{3B}$;

$L^2$ is O, N($R^x$), C(O), N($R^x$)C(O), or C(O)N($R^x$); wherein each $R^x$ is independently hydrogen, $C_1$-$C_6$ alkyl, or $C_1$-$C_6$ haloalkyl;

r is 0 or 1;

s is 0 or 1;

$G^{3A}$, $G^{3B}$, and $G^{3C}$ and each independently $C_3$-$C_{11}$cycloalkyl, phenyl, 5-6 membered monocyclic heteroaryl, or 4-11 membered heterocycle; wherein $G^{3A}$, $G^{3B}$, and $G^{3C}$ are each optionally substituted with 1, 2, 3, or 4 independently selected $R^e$ groups;

$G^{3D}$, at each occurrence, is independently $C_3$-$C_8$ monocyclic cycloalkyl or 4-7 membered monocyclic heterocycle; wherein each $G^{3D}$ is optionally substituted with 1, 2, 3, or 4 independently selected $R^e$ groups;

$R^4$ is hydrogen, $C_1$-$C_3$ alkyl, or $C_1$-$C_3$ haloalkyl;

$R^5$ is $C_1$-$C_6$ alkyl, $C_2$-$C_6$ alkenyl, $C_2$-$C_6$ alkynyl, $C_1$-$C_6$ haloalkyl, —$N(R^{5ax})(R^{5bx})$, or $G^{5A}$; wherein the $C_1$-$C_6$ alkyl and the $C_1$-$C_6$ haloalkyl are each optionally substituted with one or two substituents independently selected from the group consisting of $G^{5A}$, —CN, —$N_3$, —$OR^{5ax}$, —$S(O)_2R^{5ax}$, —$S(O)_2N(R^{5ax})(R^{5bx})$, —$N(R^{5ax})(R^{5bx})$, —$N(R^{5bx})S(O)_2R^{5cx}$, —$N(R^{5bx})C(O)R^{5cx}$, —$N(R^{5bx})C(O)N(R^{5ax})(R^{5bx})$, —$N(R^{5bx})C$ (O)OR$^{5cx}$, —C(O)R$^{5ax}$, —C(O)OR$^{5ax}$, —C(O)N(R$^{5bx}$)S(O)$_2$R$^{5cx}$, and —C(O)N(R$^{5ax}$)(R$^{5bx}$);

R$^{5ax}$ and R$^{5bx}$, at each occurrence, are each independently hydrogen, C$_1$-C$_6$ alkyl, C$_1$-C$_6$ haloalkyl, G$^{5A}$, or —(C$_1$-C$_6$ alkylenyl)-G$^{5A}$;

R$^{5cx}$, at each occurrence, is independently C$_1$-C$_6$ alkyl, C$_1$-C$_6$ haloalkyl, G$^{5A}$, or —(C$_1$-C$_6$ alkylenyl)-G$^{5A}$;

G$^{5A}$, at each occurrence, is independently C$_3$-C$_{11}$ cycloalkyl, phenyl, 5-6 membered monocyclic heteroaryl, or 4-11 membered heterocycle; wherein each G$^{5A}$ is optionally substituted with 1, 2, 3, or 4 independently selected R$^{5a}$ groups;

R$^{5a}$, at each occurrence, is independently C$_1$-C$_6$ alkyl, C$_2$-C$_6$ alkenyl, C$_2$-C$_6$ alkynyl, halogen, C$_1$-C$_6$ haloalkyl, oxo, G$^{5B}$, —CN, NO$_2$, —OR$^b$, —OC(O)R$^c$, —OC(O)N(R$^d$)$_2$, —SR$^b$, —S(O)$_2$R$^b$, —S(O)$_2$N(R$^d$)$_2$, —C(O)R$^b$, —C(O)OR$^b$, —C(O)N(R$^d$)$_2$, —C(O)N(R$^d$)S(O)$_2$R$^c$, —N(R$^d$)$_2$, —N(R$^d$)C(O)R$^c$, —N(R$^d$)S(O)$_2$R$^c$, —N(R$^d$)C(O)O(R$^b$), —N(R$^d$)C(O)N(R$^d$)$_2$, —N(R$^d$)S(O)$_2$N(R$^d$)$_2$, —(C$_1$-C$_6$ alkylenyl)-CN, —(C$_1$-C$_6$ alkylenyl)-G$^{5B}$, —(C$_1$-C$_6$ alkylenyl)-OR$^b$, —(C$_1$-C$_6$ alkylenyl)-OC(O)R$^c$, —(C$_1$-C$_6$ alkylenyl)-OC(O)N(R$^d$)$_2$, —(C$_1$-C$_6$ alkylenyl)-SR$^b$, —(C$_1$-C$_6$ alkylenyl)-S(O)$_2$R$^b$, —(C$_1$-C$_6$ alkylenyl)-S(O)$_2$N(R$^d$)$_2$, —(C$_1$-C$_6$ alkylenyl)-C(O)R$^b$, —(C$_1$-C$_6$ alkylenyl)-C(O)OR$^b$, —(C$_1$-C$_6$ alkylenyl)-C(O)N(R$^d$)$_2$, —(C$_1$-C$_6$ alkylenyl)-C(O)N(R$^d$)S(O)$_2$R$^c$, —(C$_1$-C$_6$ alkylenyl)-N(R$^d$)$_2$, —(C$_1$-C$_6$ alkylenyl)-N(R$^d$)C(O)R$^c$, —(C$_1$-C$_6$ alkylenyl)-N(R$^d$)S(O)$_2$R$^c$, —(C$_1$-C$_6$ alkylenyl)-N(R$^d$)C(O)O(R), —(C$_1$-C$_6$ alkylenyl)-N(R$^d$)C(O)N(R$^d$)$_2$, or —(C$_1$-C$_6$ alkylenyl)-N(R$^d$)S(O)$_2$N(R$^d$)$_2$;

R$^b$ and R$^d$, at each occurrence, are each independently hydrogen, C$_1$-C$_6$ alkyl, C$_1$-C$_6$ haloalkyl, alkoxyalkyl, G$^{5B}$, or —(C$_1$-C$_6$ alkylenyl)-G$^{5B}$;

R$^c$, at each occurrence, is independently C$_1$-C$_6$ alkyl, C$_1$-C$_6$ haloalkyl, alkoxyalkyl, G$^{5B}$, or —(C$_1$-C$_6$ alkylenyl)-G$^{5B}$;

G$^{5B}$, at each occurrence, is independently C$_3$-C$_6$ monocyclic cycloalkyl, phenyl, 5-6 membered monocyclic heteroaryl, or 4-7 membered monocyclic heterocycle; wherein each G$^{5B}$ is optionally substituted with 1, 2, 3, or 4 independently selected R$^{5b}$ groups;

R$^e$, at each occurrence, is independently C$_2$-C$_6$ alkenyl, C$_2$-C$_6$ alkynyl, C$_1$-C$_6$ alkyl, C$_1$-C$_6$ haloalkyl, halogen, oxo, —CN, —N$_3$, NO$_2$, —OR, —OC(O)R$^g$, —OC(O)NR$^f$R$^h$, —SR$^f$, —S(O)$_2$R$^f$, —S(O)$_2$NR$^f$R$^h$, —C(O)R$^f$, —C(O)OR$^f$, —C(O)NR$^f$R$^h$, —C(O)N(R$^h$)S(O)$_2$R$^f$, —N(R$^f$)$_2$, —N(R$^h$)C(O)R$^h$, —N(R$^h$)S(O)$_2$R$^g$, —N(R$^h$)C(O)O(R$^g$), —N(R$^h$)C(O)NR$^f$R$^h$, or —N(R$^h$)S(O)$_2$NR$^f$R$^h$; wherein the C$_1$-C$_6$ haloalkyl and the C$_1$-C$_6$ alkyl are each optionally substituted with 1 or 2 substituents independently selected from the group consisting of —CN, NO$_2$, —OR, —OC(O)R$^g$, —OC(O)NR$^f$R$^h$, —SR$^f$, —S(O)$_2$R$^f$, —S(O)$_2$NR$^f$R$^h$, —C(O)R$^f$, —C(O)OR$^f$, —C(O)NR$^f$R$^h$, —C(O)N(R$^h$)S(O)$_2$R$^f$, —N(R$^f$)$_2$, —N(R$^h$)C(O)R$^g$, —N(R$^h$)S(O)$_2$R$^g$, —N(R$^h$)C(O)O(R$^g$), —N(R$^h$)C(O)NR$^f$R$^h$, and —N(R$^h$)S(O)$_2$NR$^f$R$^h$;

R$^f$, at each occurrence, is independently hydrogen, C$_1$-C$_6$ alkyl, C$_2$-C$_6$ alkenyl, C$_2$-C$_6$ alkynyl, C$_1$-C$_6$ haloalkyl, —(C$_1$-C$_6$ alkylenyl)-CN, —(C$_1$-C$_6$ alkylenyl)-OR$^m$, —(C$_1$-C$_6$ alkylenyl)-OC(O)R$^n$, —(C$_1$-C$_6$ alkylenyl)-OC(O)N(R$^m$)$_2$, —(C$_1$-C$_6$ alkylenyl)-SR$^m$, —(C$_1$-C$_6$ alkylenyl)-S(O)$_2$R$^m$, —(C$_1$-C$_6$ alkylenyl)-S(O)$_2$N(R$^m$)$_2$, —(C$_1$-C$_6$ alkylenyl)-C(O)R$^m$, —(C$_1$-C$_6$ alkylenyl)-C(O)OR$^m$, —(C$_1$-C$_6$ alkylenyl)-C(O)N(R$^m$)$_2$, —(C$_1$-C$_6$ alkylenyl)-C(O)N(R$^m$)S(O)$_2$R$^n$, —(C$_1$-C$_6$ alkylenyl)-N(R$^m$)$_2$, —(C$_1$-C$_6$ alkylenyl)-N(R$^m$)C(O)R$^n$, —(C$_1$-C$_6$ alkylenyl)-N(R$^m$)S(O)$_2$R$^n$, —(C$_1$-C$_6$ alkylenyl)-N(R$^m$)C(O)O(R$^n$), —(C$_1$-C$_6$ alkylenyl)-N(R$^m$)C(O)N(R$^m$)$_2$, or —(C$_1$-C$_6$ alkylenyl)-N(R$^m$)S(O)$_2$N(R$^m$)$_2$;

R$^g$, at each occurrence, is independently C$_1$-C$_6$ alkyl, C$_2$-C$_6$ alkenyl, C$_2$-C$_6$ alkynyl, C$_1$-C$_6$ haloalkyl, —(C$_1$-C$_6$ alkylenyl)-CN, —(C$_1$-C$_6$ alkylenyl)-OR$^m$, —(C$_1$-C$_6$ alkylenyl)-OC(O)R$^n$, —(C$_1$-C$_6$ alkylenyl)-OC(O)N(R$^m$)$_2$, —(C$_1$-C$_6$ alkylenyl)-SR$^m$, —(C$_1$-C$_6$ alkylenyl)-S(O)$_2$R$^m$, —(C$_1$-C$_6$ alkylenyl)-S(O)$_2$N(R$^m$)$_2$, —(C$_1$-C$_6$ alkylenyl)-C(O)R$^m$, —(C$_1$-C$_6$ alkylenyl)-C(O)OR$^m$, —(C$_1$-C$_6$ alkylenyl)-C(O)N(R$^m$)$_2$, —(C$_1$-C$_6$ alkylenyl)-C(O)N(R$^m$)S(O)$_2$R$^n$, —(C$_1$-C$_6$ alkylenyl)-N(R$^m$)$_2$, —(C$_1$-C$_6$ alkylenyl)-N(R$^m$)C(O)R$^n$, —(C$_1$-C$_6$ alkylenyl)-N(R$^m$)S(O)$_2$R$^n$, —(C$_1$-C$_6$ alkylenyl)-N(R$^m$)C(O)O(R$^n$), —(C$_1$-C$_6$ alkylenyl)-N(R$^m$)C(O)N(R$^m$)$_2$, or —(C$_1$-C$_6$ alkylenyl)-N(R$^m$)S(O)$_2$N(R$^m$)$_2$;

R$^h$, at each occurrence, is independently hydrogen, C$_1$-C$_6$ alkyl, C$_1$-C$_6$ haloalkyl, or —(C$_1$-C$_6$ alkylenyl)-OR$^m$;

R$^{1a}$, R$^{1b}$, R$^{2a}$, and R$^{5b}$, at each occurrence, are each independently C$_1$-C$_6$ alkyl, C$_2$-C$_6$ alkenyl, C$_2$-C$_6$ alkynyl, halogen, C$_1$-C$_6$ haloalkyl, oxo, —CN, —NO$_2$, —OR$^m$, —OC(O)R$^n$, —OC(O)N(R$^m$)$_2$, —SR$^m$, —S(O)$_2$R$^m$, —S(O)$_2$N(R$^m$)$_2$, —C(O)R$^m$, —C(O)OR$^m$, —C(O)O(benzyl), —C(O)N(R$^m$)$_2$, —C(O)N(R$^m$)S(O)$_2$R$^n$, —N(R$^m$)$_2$, —N(R$^m$)(alkoxyalkyl), —N(alkoxyalkyl)$_2$, —N(R$^m$)C(O)R$^n$, —N(R$^m$)S(O)$_2$R$^n$, —N(R$^m$)C(O)O(R$^n$), —N(R$^m$)C(O)N(R$^m$)$_2$, —N(R$^m$)S(O)$_2$N(R$^m$)$_2$, —(C$_1$-C$_6$ alkylenyl)-CN, —(C$_1$-C$_6$ alkylenyl)-OR$^m$, —(C$_1$-C$_6$ alkylenyl)-OC(O)R$^n$, —(C$_1$-C$_6$ alkylenyl)-OC(O)N(R$^m$)$_2$, —(C$_1$-C$_6$ alkylenyl)-SR$^m$, —(C$_1$-C$_6$ alkylenyl)-S(O)$_2$R$^m$, —(C$_1$-C$_6$ alkylenyl)-S(O)$_2$N(R$^m$)$_2$, —(C$_1$-C$_6$ alkylenyl)-C(O)R$^m$, —(C$_1$-C$_6$ alkylenyl)-C(O)OR$^m$, —(C$_1$-C$_6$ alkylenyl)-C(O)N(R$^m$)$_2$, —(C$_1$-C$_6$ alkylenyl)-C(O)N(R$^m$)S(O)$_2$R$^n$, —(C$_1$-C$_6$ alkylenyl)-N(R$^m$)$_2$, —(C$_1$-C$_6$ alkylenyl)-N(R$^m$)C(O)R$^n$, —(C$_1$-C$_6$ alkylenyl)-N(R$^m$)S(O)$_2$R$^n$, —(C$_1$-C$_6$ alkylenyl)-N(R$^m$)C(O)O(R$^n$), —(C$_1$-C$_6$ alkylenyl)-N(R$^m$)C(O)N(R$^n$)$_2$, or —(C$_1$-C$_6$ alkylenyl)-N(R$^m$)S(O)$_2$N(R$^n$)$_2$;

R$^m$, at each occurrence, is independently hydrogen, C$_1$-C$_6$ alkyl, or C$_1$-C$_6$ haloalkyl;

R$^n$, at each occurrence, is independently C$_1$-C$_6$ alkyl or C$_1$-C$_6$ haloalkyl; and R$^6$ is hydrogen.

Exemplary compounds of formula (I) include, but are not limited to:

N-(methanesulfonyl)-3-methyl-4-[4-(morpholin-4-yl)phenyl]-1-phenyl-1H-pyrazolo[3,4-b]pyridine-6-carboxamide;

N-(benzenesulfonyl)-3-methyl-4-[4-(morpholin-4-yl)phenyl]-1-phenyl-1H-pyrazolo[3,4-b]pyridine-6-carboxamide;

3-methyl-4-[4-(morpholin-4-yl)phenyl]-1-phenyl-N-(trifluoromethanesulfonyl)-1H-pyrazolo[3,4-b]pyridine-6-carboxamide;

N-(cyclopropanesulfonyl)-3-methyl-4-[4-(morpholin-4-yl)phenyl]-1-phenyl-1H-pyrazolo[3,4-b]pyridine-6-carboxamide;

N-(ethanesulfonyl)-3-methyl-4-[4-(morpholin-4-yl)phenyl]-1-phenyl-1H-pyrazolo[3,4-b]pyridine-6-carboxamide;

N-(methanesulfonyl)-3-methyl-4-[4-(morpholin-4-yl)phenyl]-1-[3-(trifluoromethoxy)phenyl]-1H-pyrazolo[3,4-b]pyridine-6-carboxamide;

4-[4-(dimethylamino)phenyl]-N-(methanesulfonyl)-1-phenyl-3-(propan-2-yl)-1H-pyrazolo[3,4-b]pyridine-6-carboxamide;

N-(methanesulfonyl)-3-methyl-4-[4-(morpholin-4-yl)phenyl]-1-[3-(trifluoromethyl)phenyl]-1H-pyrazolo[3,4-b]pyridine-6-carboxamide;

1-cyclohexyl-4-[2-(dimethylamino)pyrimidin-5-yl]-N-(methanesulfonyl)-3-(propan-2-yl)-1H-pyrazolo[3,4-b]pyridine-6-carboxamide;

1-[3-(azetidin-1-yl)phenyl]-N-(methanesulfonyl)-4-[4-(morpholin-4-yl)phenyl]-3-(propan-2-yl)-1H-pyrazolo[3,4-b]pyridine-6-carboxamide;

1-cyclohexyl-N-(methanesulfonyl)-4-[2-(morpholin-4-yl)pyrimidin-5-yl]-3-(propan-2-yl)-1H-pyrazolo[3,4-b]pyridine-6-carboxamide;

3-tert-butyl-1-cyclopentyl-N-(methanesulfonyl)-4-[6-(morpholin-4-yl)pyridin-3-yl]-1H-pyrazolo[3,4-b]pyridine-6-carboxamide;

N-(methanesulfonyl)-3-methyl-1-phenyl-4-(piperidin-1-yl)-1H-pyrazolo[3,4-b]pyridine-6-carboxamide;

N-(methanesulfonyl)-4-(4-methoxyphenyl)-3-methyl-1-phenyl-1H-pyrazolo[3,4-b]pyridine-6-carboxamide;

N-(ethanesulfonyl)-4-(4-methoxyphenyl)-3-methyl-1-phenyl-1H-pyrazolo[3,4-b]pyridine-6-carboxamide;

N-(methanesulfonyl)-4-[4-(morpholin-4-yl)phenyl]-3-(propan-2-yl)-1-[3-(pyrrolidin-1-yl)phenyl]-1H-pyrazolo[3,4-b]pyridine-6-carboxamide;

4-[4-(dimethylamino)phenyl]-N-(methanesulfonyl)-1-(6-methoxypyridin-3-yl)-3-(propan-2-yl)-1H-pyrazolo[3,4-b]pyridine-6-carboxamide;

1-(3-chloro-4-methylphenyl)-N-(methanesulfonyl)-4-(4-methoxyphenyl)-3-methyl-1H-pyrazolo[3,4-b]pyridine-6-carboxamide;

N-(ethanesulfonyl)-3-methyl-1-phenyl-4-(piperidin-1-yl)-1H-pyrazolo[3,4-b]pyridine-6-carboxamide;

N-(methanesulfonyl)-4-[2-(morpholin-4-yl)pyrimidin-5-yl]-1-phenyl-3-(propan-2-yl)-1H-pyrazolo[3,4-b]pyridine-6-carboxamide;

1-(2,4-difluorophenyl)-N-(methanesulfonyl)-3-methyl-4-[4-(morpholin-4-yl)phenyl]-1H-pyrazolo[3,4-b]pyridine-6-carboxamide;

1-cyclohexyl-4-[6-(dimethylamino)pyridin-3-yl]-N-(methanesulfonyl)-3-(propan-2-yl)-1H-pyrazolo[3,4-b]pyridine-6-carboxamide;

1-(3,5-difluorophenyl)-N-(methanesulfonyl)-3-methyl-4-[4-(morpholin-4-yl)phenyl]-1H-pyrazolo[3,4-b]pyridine-6-carboxamide;

1-(3,5-dimethylphenyl)-N-(methanesulfonyl)-3-methyl-4-[4-(morpholin-4-yl)phenyl]-1H-pyrazolo[3,4-b]pyridine-6-carboxamide;

1-(3,4-difluorophenyl)-N-(methanesulfonyl)-3-methyl-4-[4-(morpholin-4-yl)phenyl]-1H-pyrazolo[3,4-b]pyridine-6-carboxamide;

4-[4-(dimethylamino)phenyl]-N-(methanesulfonyl)-3-methyl-1-[3-(trifluoromethyl)phenyl]-1H-pyrazolo[3,4-b]pyridine-6-carboxamide;

N-(methanesulfonyl)-4-(4-methoxyphenyl)-3-methyl-1-(3-methylphenyl)-1H-pyrazolo[3,4-b]pyridine-6-carboxamide;

N-(ethanesulfonyl)-4-(4-methoxyphenyl)-3-methyl-1-(3-methylphenyl)-1H-pyrazolo[3,4-b]pyridine-6-carboxamide;

4-[2-(dimethylamino)pyrimidin-5-yl]-N-(methanesulfonyl)-1-[3-(morpholin-4-yl)phenyl]-3-(propan-2-yl)-1H-pyrazolo[3,4-b]pyridine-6-carboxamide;

4-[2-(dimethylamino)pyrimidin-5-yl]-N-(ethanesulfonyl)-1-[3-(morpholin-4-yl)phenyl]-3-(propan-2-yl)-1H-pyrazolo[3,4-b]pyridine-6-carboxamide;

4-[6-(dimethylamino)pyridin-3-yl]-N-(methanesulfonyl)-1-[3-(morpholin-4-yl)phenyl]-3-(propan-2-yl)-1H-pyrazolo[3,4-b]pyridine-6-carboxamide;

4-[6-(dimethylamino)pyridin-3-yl]-N-(ethanesulfonyl)-1-[3-(morpholin-4-yl)phenyl]-3-(propan-2-yl)-1H-pyrazolo[3,4-b]pyridine-6-carboxamide;

4-[4-(dimethylamino)phenyl]-N-(methanesulfonyl)-3-methyl-1-phenyl-1H-pyrazolo[3,4-b]pyridine-6-carboxamide;

N-(methanesulfonyl)-4-[6-(morpholin-4-yl)pyridin-3-yl]-1-phenyl-3-(propan-2-yl)-1H-pyrazolo[3,4-b]pyridine-6-carboxamide;

N-(ethanesulfonyl)-4-[6-(morpholin-4-yl)pyridin-3-yl]-1-phenyl-3-(propan-2-yl)-1H-pyrazolo[3,4-b]pyridine-6-carboxamide;

N-(methanesulfonyl)-1-[3-(3-methoxyazetidin-1-yl)phenyl]-4-[4-(morpholin-4-yl)phenyl]-3-(propan-2-yl)-1H-pyrazolo[3,4-b]pyridine-6-carboxamide;

N-(methanesulfonyl)-3-methyl-4-[6-(morpholin-4-yl)pyridin-3-yl]-1-phenyl-1H-pyrazolo[3,4-b]pyridine-6-carboxamide;

1-(4,4-difluorocyclohexyl)-N-(methanesulfonyl)-4-[4-(morpholin-4-yl)phenyl]-3-(propan-2-yl)-1H-pyrazolo[3,4-b]pyridine-6-carboxamide;

N-(methanesulfonyl)-4-[4-(morpholin-4-yl)phenyl]-1-(oxan-3-yl)-3-(propan-2-yl)-1H-pyrazolo[3,4-b]pyridine-6-carboxamide;

N-(ethanesulfonyl)-4-[4-(morpholin-4-yl)phenyl]-1-(oxan-3-yl)-3-(propan-2-yl)-1H-pyrazolo[3,4-b]pyridine-6-carboxamide;

4-{4-[3-(dimethylamino)azetidin-1-yl]phenyl}-N-(methanesulfonyl)-3-methyl-1-phenyl-1H-pyrazolo[3,4-b]pyridine-6-carboxamide;

4-{4-[3-(dimethylamino)azetidin-1-yl]phenyl}-N-(ethanesulfonyl)-3-methyl-1-phenyl-1H-pyrazolo[3,4-b]pyridine-6-carboxamide;

1-[3-(3,3-dimethylazetidin-1-yl)phenyl]-N-(methanesulfonyl)-4-[4-(morpholin-4-yl)phenyl]-3-(propan-2-yl)-1H-pyrazolo[3,4-b]pyridine-6-carboxamide;

1-cyclohexyl-N-(methanesulfonyl)-4-[6-(morpholin-4-yl)pyridin-3-yl]-3-(propan-2-yl)-1H-pyrazolo[3,4-b]pyridine-6-carboxamide;

1-cyclohexyl-N-(ethanesulfonyl)-4-[4-(morpholin-4-yl)phenyl]-3-(propan-2-yl)-1H-pyrazolo[3,4-b]pyridine-6-carboxamide;

1-[3-(3-fluoropyrrolidin-1-yl)phenyl]-N-(methanesulfonyl)-4-[4-(morpholin-4-yl)phenyl]-3-(propan-2-yl)-1H-pyrazolo[3,4-b]pyridine-6-carboxamide;

1-cyclohexyl-N-(methanesulfonyl)-3-methyl-4-[6-(morpholin-4-yl)pyridin-3-yl]-1H-pyrazolo[3,4-b]pyridine-6-carboxamide;

1-cyclohexyl-N-(ethanesulfonyl)-3-methyl-4-[6-(morpholin-4-yl)pyridin-3-yl]-1H-pyrazolo[3,4-b]pyridine-6-carboxamide;

1-cyclohexyl-4-[2-(dimethylamino)pyrimidin-5-yl]-N-(methanesulfonyl)-3-methyl-1H-pyrazolo[3,4-b]pyridine-6-carboxamide;

1-cyclohexyl-4-[2-(dimethylamino)pyrimidin-5-yl]-N-(ethanesulfonyl)-3-methyl-1H-pyrazolo[3,4-b]pyridine-6-carboxamide;

1-cyclohexyl-N-(methanesulfonyl)-4-{6-[methyl(oxan-4-yl)amino]pyridin-3-yl}-3-(propan-2-yl)-1H-pyrazolo[3,4-b]pyridine-6-carboxamide;

methyl 3-{1-cyclohexyl-4-[2-(dimethylamino)pyrimidin-5-yl]-6-[(ethanesulfonyl)carbamoyl]-1H-pyrazolo[3,4-b]pyridin-3-yl}azetidine-1-carboxylate;

1-[3-(dimethylamino)phenyl]-N-(methanesulfonyl)-4-[6-(morpholin-4-yl)pyridin-3-yl]-3-(propan-2-yl)-1H-pyrazolo[3,4-b]pyridine-6-carboxamide;

1-[3-(dimethylamino)phenyl]-N-(ethanesulfonyl)-4-[6-(morpholin-4-yl)pyridin-3-yl]-3-(propan-2-yl)-1H-pyrazolo[3,4-b]pyridine-6-carboxamide;

1-cyclopentyl-4-[6-(dimethylamino)pyridin-3-yl]-N-(methanesulfonyl)-3-(propan-2-yl)-1H-pyrazolo[3,4-b]pyridine-6-carboxamide;

1-cyclopentyl-4-[6-(dimethylamino)pyridin-3-yl]-N-(ethanesulfonyl)-3-(propan-2-yl)-1H-pyrazolo[3,4-b]pyridine-6-carboxamide;

N-(methanesulfonyl)-3-methyl-4-[6-(morpholin-4-yl)pyridin-3-yl]-1-[3-(trifluoromethyl)phenyl]-1H-pyrazolo[3,4-b]pyridine-6-carboxamide;

N-(ethanesulfonyl)-3-methyl-4-[6-(morpholin-4-yl)pyridin-3-yl]-1-[3-(trifluoromethyl)phenyl]-1H-pyrazolo[3,4-b]pyridine-6-carboxamide;

1-[3-(dimethylamino)phenyl]-N-(methanesulfonyl)-4-[2-(morpholin-4-yl)pyrimidin-5-yl]-3-(propan-2-yl)-1H-pyrazolo[3,4-b]pyridine-6-carboxamide;

1-(2,4-difluorophenyl)-N-(methanesulfonyl)-3-methyl-4-[6-(morpholin-4-yl)pyridin-3-yl]-1H-pyrazolo[3,4-b]pyridine-6-carboxamide;

1-(2,4-difluorophenyl)-N-(ethanesulfonyl)-3-methyl-4-[6-(morpholin-4-yl)pyridin-3-yl]-1H-pyrazolo[3,4-b]pyridine-6-carboxamide;

1-[3-(dimethylamino)phenyl]-N-(ethanesulfonyl)-4-[2-(morpholin-4-yl)pyrimidin-5-yl]-3-(propan-2-yl)-1H-pyrazolo[3,4-b]pyridine-6-carboxamide;

3-cyclobutyl-N-(methanesulfonyl)-4-{6-[(2-methoxyethyl)(methyl)amino]pyridin-3-yl}-1-phenyl-1H-pyrazolo[3,4-b]pyridine-6-carboxamide;

1-cyclohexyl-4-[6-(3,3-difluoropyrrolidin-1-yl)pyridin-3-yl]-N-(methanesulfonyl)-3-(propan-2-yl)-1H-pyrazolo[3,4-b]pyridine-6-carboxamide;

1-(3-chlorophenyl)-N-(methanesulfonyl)-3-methyl-4-[4-(morpholin-4-yl)phenyl]-1H-pyrazolo[3,4-b]pyridine-6-carboxamide;

1-(3-chlorophenyl)-N-(ethanesulfonyl)-3-methyl-4-[4-(morpholin-4-yl)phenyl]-1H-pyrazolo[3,4-b]pyridine-6-carboxamide;

1-(3-fluorophenyl)-N-(methanesulfonyl)-3-methyl-4-[4-(morpholin-4-yl)phenyl]-1H-pyrazolo[3,4-b]pyridine-6-carboxamide;

N-(ethanesulfonyl)-1-(3-fluorophenyl)-3-methyl-4-[4-(morpholin-4-yl)phenyl]-1H-pyrazolo[3,4-b]pyridine-6-carboxamide;

N-(methanesulfonyl)-3-methyl-4-[4-(morpholin-4-yl)phenyl]-1-[4-(trifluoromethoxy)phenyl]-1H-pyrazolo[3,4-b]pyridine-6-carboxamide;

N-(ethanesulfonyl)-3-methyl-4-[4-(morpholin-4-yl)phenyl]-1-[4-(trifluoromethoxy)phenyl]-1H-pyrazolo[3,4-b]pyridine-6-carboxamide;

4-[6-(4-cyanopiperidin-1-yl)pyridin-3-yl]-3-cyclobutyl-N-(methanesulfonyl)-1-phenyl-1H-pyrazolo[3,4-b]pyridine-6-carboxamide;

N-(methanesulfonyl)-1-(3-methoxyphenyl)-3-methyl-4-[4-(morpholin-4-yl)phenyl]-1H-pyrazolo[3,4-b]pyridine-6-carboxamide;

N-(ethanesulfonyl)-1-(3-methoxyphenyl)-3-methyl-4-[4-(morpholin-4-yl)phenyl]-1H-pyrazolo[3,4-b]pyridine-6-carboxamide;

3-cyclobutyl-N-(methanesulfonyl)-4-{6-[methyl(oxan-4-yl)amino]pyridin-3-yl}-1-phenyl-1H-pyrazolo[3,4-b]pyridine-6-carboxamide;

3-cyclobutyl-N-(methanesulfonyl)-4-{4-[(2-methoxyethyl)(methyl)amino]phenyl}-1-phenyl-1H-pyrazolo[3,4-b]pyridine-6-carboxamide;

N-(methanesulfonyl)-1-{3-[(2-methoxyethyl)(methyl)amino]phenyl}-4-[4-(morpholin-4-yl)phenyl]-3-(propan-2-yl)-1H-pyrazolo[3,4-b]pyridine-6-carboxamide;

1-[3-(dimethylamino)phenyl]-4-[2-(dimethylamino)pyrimidin-5-yl]-N-(methanesulfonyl)-3-(propan-2-yl)-1H-pyrazolo[3,4-b]pyridine-6-carboxamide;

1-[3-(dimethylamino)phenyl]-4-[2-(dimethylamino)pyrimidin-5-yl]-N-(ethanesulfonyl)-3-(propan-2-yl)-1H-pyrazolo[3,4-b]pyridine-6-carboxamide;

4-(4-acetamidophenyl)-1-cyclohexyl-N-(methanesulfonyl)-3-(propan-2-yl)-1H-pyrazolo[3,4-b]pyridine-6-carboxamide;

4-[4-(4-cyanopiperidin-1-yl)phenyl]-1-cyclohexyl-N-(methanesulfonyl)-3-(propan-2-yl)-1H-pyrazolo[3,4-b]pyridine-6-carboxamide;

4-[4-(4-cyanopiperidin-1-yl)phenyl]-1-[3-(dimethylamino)phenyl]-N-(methanesulfonyl)-3-(propan-2-yl)-1H-pyrazolo[3,4-b]pyridine-6-carboxamide;

1-[3-(dimethylamino)phenyl]-N-(methanesulfonyl)-4-{4-[(2-methoxyethyl)(methyl)amino]phenyl}-3-(propan-2-yl)-1H-pyrazolo[3,4-b]pyridine-6-carboxamide;

4-[6-(4-cyanopiperidin-1-yl)pyridin-3-yl]-1-[3-(dimethylamino)phenyl]-N-(methanesulfonyl)-3-(propan-2-yl)-1H-pyrazolo[3,4-b]pyridine-6-carboxamide;

1-[3-(dimethylamino)phenyl]-N-(methanesulfonyl)-4-{6-[(2-methoxyethyl)(methyl)amino]pyridin-3-yl}-3-(propan-2-yl)-1H-pyrazolo[3,4-b]pyridine-6-carboxamide;

4-[6-(4-cyanopiperidin-1-yl)pyridin-3-yl]-N-(methanesulfonyl)-1-[3-(morpholin-4-yl)phenyl]-3-(propan-2-yl)-1H-pyrazolo[3,4-b]pyridine-6-carboxamide;

N-(methanesulfonyl)-4-{6-[(2-methoxyethyl)(methyl)amino]pyridin-3-yl}-1-[3-(morpholin-4-yl)phenyl]-3-(propan-2-yl)-1H-pyrazolo[3,4-b]pyridine-6-carboxamide;

N-(methanesulfonyl)-4-{6-[methyl(oxan-4-yl)amino]pyridin-3-yl}-1-[3-(morpholin-4-yl)phenyl]-3-(propan-2-yl)-1H-pyrazolo[3,4-b]pyridine-6-carboxamide;

N-(methanesulfonyl)-4-{4-[(2-methoxyethyl)(methyl)amino]phenyl}-1-[3-(morpholin-4-yl)phenyl]-3-(propan-2-yl)-1H-pyrazolo[3,4-b]pyridine-6-carboxamide;

1-[3-(dimethylamino)phenyl]-N-(methanesulfonyl)-4-{6-[methyl(oxan-4-yl)amino]pyridin-3-yl}-3-(propan-2-yl)-1H-pyrazolo[3,4-b]pyridine-6-carboxamide;

1-cyclohexyl-N-(ethanesulfonyl)-4-{6-[methyl(oxan-4-yl)amino]pyridin-3-yl}-3-(propan-2-yl)-1H-pyrazolo[3,4-b]pyridine-6-carboxamide;

1-[3-(dimethylamino)phenyl]-N-(methanesulfonyl)-4-{2-[methyl(oxan-4-yl)amino]pyrimidin-5-yl}-3-(propan-2-yl)-1H-pyrazolo[3,4-b]pyridine-6-carboxamide;

1-cyclohexyl-3-cyclopropyl-4-[6-(dimethylamino)pyridin-3-yl]-N-(ethanesulfonyl)-1H-pyrazolo[3,4-b]pyridine-6-carboxamide;

1-cyclohexyl-4-[6-(2,6-dimethylmorpholin-4-yl)pyridin-3-yl]-N-(methanesulfonyl)-3-(propan-2-yl)-1H-pyrazolo[3,4-b]pyridine-6-carboxamide;

1-cyclohexyl-4-[6-(2,2-dimethylmorpholin-4-yl)pyridin-3-yl]-N-(methanesulfonyl)-3-(propan-2-yl)-1H-pyrazolo[3,4-b]pyridine-6-carboxamide;

4-[2-(4-cyanopiperidin-1-yl)pyrimidin-5-yl]-1-[3-(dimethylamino)phenyl]-N-(methanesulfonyl)-3-(propan-2-yl)-1H-pyrazolo[3,4-b]pyridine-6-carboxamide;

1-[3-(dimethylamino)phenyl]-N-(methanesulfonyl)-4-{4-[methyl(oxan-4-yl)amino]phenyl}-3-(propan-2-yl)-1H-pyrazolo[3,4-b]pyridine-6-carboxamide;

N-(methanesulfonyl)-4-{4-[methyl(oxan-4-yl)amino]phenyl}-1-[3-(morpholin-4-yl)phenyl]-3-(propan-2-yl)-1H-pyrazolo[3,4-b]pyridine-6-carboxamide;

4-[6-(4-cyano-4-methylpiperidin-1-yl)pyridin-3-yl]-1-cyclohexyl-N-(methanesulfonyl)-3-(propan-2-yl)-1H-pyrazolo[3,4-b]pyridine-6-carboxamide;

4-[2-(4-cyanopiperidin-1-yl)pyrimidin-5-yl]-N-(methanesulfonyl)-1-[3-(morpholin-4-yl)phenyl]-3-(propan-2-yl)-1H-pyrazolo[3,4-b]pyridine-6-carboxamide;

4-{4-[3-(dimethylamino)pyrrolidin-1-yl]phenyl}-N-(methanesulfonyl)-3-methyl-1-phenyl-1H-pyrazolo[3,4-b]pyridine-6-carboxamide;

N-(methanesulfonyl)-1-(3-methylphenyl)-4-(piperidin-1-yl)-3-(propan-2-yl)-1H-pyrazolo[3,4-b]pyridine-6-carboxamide;

N-(ethanesulfonyl)-1-(3-methylphenyl)-4-(piperidin-1-yl)-3-(propan-2-yl)-1H-pyrazolo[3,4-b]pyridine-6-carboxamide;

4-[4-(4-cyanopiperidin-1-yl)phenyl]-3-cyclobutyl-1-cyclohexyl-N-(methanesulfonyl)-1H-pyrazolo[3,4-b]pyridine-6-carboxamide;

4-[6-(4-cyanopiperidin-1-yl)pyridin-3-yl]-3-cyclobutyl-1-cyclohexyl-N-(methanesulfonyl)-1H-pyrazolo[3,4-b]pyridine-6-carboxamide;

1-[3-(3-hydroxyazetidin-1-yl)phenyl]-N-(methanesulfonyl)-4-[4-(morpholin-4-yl)phenyl]-3-(propan-2-yl)-1H-pyrazolo[3,4-b]pyridine-6-carboxamide;

1-cyclohexyl-N-(methanesulfonyl)-4-[6-(3-methoxypyrrolidin-1-yl)pyridin-3-yl]-3-(propan-2-yl)-1H-pyrazolo[3,4-b]pyridine-6-carboxamide;

methyl 3-{4-(4-acetamidophenyl)-1-(3,5-difluorophenyl)-6-[(methanesulfonyl)carbamoyl]-1H-pyrazolo[3,4-b]pyridin-3-yl}azetidine-1-carboxylate;

1-cyclohexyl-4-[6-(3-fluoropiperidin-1-yl)pyridin-3-yl]-N-(methanesulfonyl)-3-(propan-2-yl)-1H-pyrazolo[3,4-b]pyridine-6-carboxamide;

N-(methanesulfonyl)-4-{4-[(2-methoxyethyl)(methyl)amino]phenyl}-3-(propan-2-yl)-1-[3-(pyrrolidin-1-yl)phenyl]-1H-pyrazolo[3,4-b]pyridine-6-carboxamide;

N-(methanesulfonyl)-4-{4-[methyl(oxan-4-yl)amino]phenyl}-3-(propan-2-yl)-1-[3-(pyrrolidin-1-yl)phenyl]-1H-pyrazolo[3,4-b]pyridine-6-carboxamide;

3-cyclobutyl-N-(methanesulfonyl)-4-{4-[methyl(oxan-4-yl)amino]phenyl}-1-[3-(pyrrolidin-1-yl)phenyl]-1H-pyrazolo[3,4-b]pyridine-6-carboxamide;

N-(ethanesulfonyl)-4-[2-(morpholin-4-yl)pyrimidin-5-yl]-1-phenyl-3-(propan-2-yl)-1H-pyrazolo[3,4-b]pyridine-6-carboxamide;

1-(2,4-difluorophenyl)-N-(ethanesulfonyl)-3-methyl-4-[4-(morpholin-4-yl)phenyl]-1H-pyrazolo[3,4-b]pyridine-6-carboxamide;

1-(3-chloro-4-methylphenyl)-N-(ethanesulfonyl)-4-(4-methoxyphenyl)-3-methyl-1H-pyrazolo[3,4-b]pyridine-6-carboxamide;

1-(3,5-dimethylphenyl)-N-(ethanesulfonyl)-3-methyl-4-[4-(morpholin-4-yl)phenyl]-1H-pyrazolo[3,4-b]pyridine-6-carboxamide;

1-(3,4-difluorophenyl)-N-(ethanesulfonyl)-3-methyl-4-[4-(morpholin-4-yl)phenyl]-1H-pyrazolo[3,4-b]pyridine-6-carboxamide;

N-(methanesulfonyl)-4-(4-methoxypiperidin-1-yl)-1-(3-methylphenyl)-3-(propan-2-yl)-1H-pyrazolo[3,4-b]pyridine-6-carboxamide;

N-(ethanesulfonyl)-4-(4-methoxypiperidin-1-yl)-1-(3-methylphenyl)-3-(propan-2-yl)-1H-pyrazolo[3,4-b]pyridine-6-carboxamide;

4-[2-(4-cyanopiperidin-1-yl)pyrimidin-5-yl]-1-cyclohexyl-N-(methanesulfonyl)-3-(propan-2-yl)-1H-pyrazolo[3,4-b]pyridine-6-carboxamide;

1-cyclohexyl-N-(methanesulfonyl)-4-{2-[(2-methoxyethyl)(methyl)amino]pyrimidin-5-yl}-3-(propan-2-yl)-1H-pyrazolo[3,4-b]pyridine-6-carboxamide;

4-{6-[bis(2-methoxyethyl)amino]pyridin-3-yl}-1-cyclohexyl-N-(methanesulfonyl)-3-(propan-2-yl)-1H-pyrazolo[3,4-b]pyridine-6-carboxamide;

1-cyclohexyl-N-(methanesulfonyl)-4-{6-[methyl(oxolan-3-yl)amino]pyridin-3-yl}-3-(propan-2-yl)-1H-pyrazolo[3,4-b]pyridine-6-carboxamide;

1-cyclohexyl-N-(methanesulfonyl)-4-{2-[methyl(oxan-4-yl)amino]pyrimidin-5-yl}-3-(propan-2-yl)-1H-pyrazolo[3,4-b]pyridine-6-carboxamide;

4-[6-(4-cyanopiperidin-1-yl)pyridin-3-yl]-N-(methanesulfonyl)-3-(propan-2-yl)-1-[3-(trifluoromethyl)phenyl]-1H-pyrazolo[3,4-b]pyridine-6-carboxamide;

1-[6-(dimethylamino)pyridin-2-yl]-N-(methanesulfonyl)-4-[4-(morpholin-4-yl)phenyl]-3-(propan-2-yl)-1H-pyrazolo[3,4-b]pyridine-6-carboxamide;

N-(methanesulfonyl)-4-[4-(morpholin-4-yl)phenyl]-3-(propan-2-yl)-1-[3-(trifluoromethoxy)phenyl]-1H-pyrazolo[3,4-b]pyridine-6-carboxamide;

1-(3,4-difluorophenyl)-N-(methanesulfonyl)-4-[4-(morpholin-4-yl)phenyl]-3-(propan-2-yl)-1H-pyrazolo[3,4-b]pyridine-6-carboxamide;

N-(methanesulfonyl)-4-[4-(morpholin-4-yl)phenyl]-1-[6-(morpholin-4-yl)pyridin-2-yl]-3-(propan-2-yl)-1H-pyrazolo[3,4-b]pyridine-6-carboxamide;

4-(2,6-difluoro-4-methoxyphenyl)-1-(3-fluoro-5-methoxyphenyl)-N-(methanesulfonyl)-3-methyl-1H-pyrazolo[3,4-b]pyridine-6-carboxamide;

4-[4-(4-cyanopiperidin-1-yl)phenyl]-1-(3,5-difluorophenyl)-N-(methanesulfonyl)-3-(propan-2-yl)-1H-pyrazolo[3,4-b]pyridine-6-carboxamide;

4-[4-(4-cyanopiperidin-1-yl)phenyl]-1-(3-fluorophenyl)-N-(methanesulfonyl)-3-(propan-2-yl)-1H-pyrazolo[3,4-b]pyridine-6-carboxamide;

N-(methanesulfonyl)-4-{4-[(2-methoxyethyl)(methyl)amino]phenyl}-3-(propan-2-yl)-1-[3-(trifluoromethyl)phenyl]-1H-pyrazolo[3,4-b]pyridine-6-carboxamide;

N-(methanesulfonyl)-4-{6-[methyl(oxan-4-yl)amino]pyridin-3-yl}-3-(propan-2-yl)-1-[3-(trifluoromethyl)phenyl]-1H-pyrazolo[3,4-b]pyridine-6-carboxamide;

1-(4-fluorophenyl)-N-(methanesulfonyl)-4-{2-[methyl(oxan-4-yl)amino]pyrimidin-5-yl}-3-(propan-2-yl)-1H-pyrazolo[3,4-b]pyridine-6-carboxamide;

4-[4-(4-cyanopiperidin-1-yl)phenyl]-N-(methanesulfonyl)-3-(propan-2-yl)-1-[3 (trifluoromethyl)phenyl]-1H-pyrazolo[3,4-b]pyridine-6-carboxamide;

N-(methanesulfonyl)-4-[4-(morpholin-4-yl)phenyl]-1-[2-(morpholin-4-yl)pyridin-4-yl]-3-(propan-2-yl)-1H-pyrazolo[3,4-b]pyridine-6-carboxamide;

N-(methanesulfonyl)-3-(1-methylcyclobutyl)-4-[4-(morpholin-4-yl)phenyl]-1-phenyl-1H-pyrazolo[3,4-b]pyridine-6-carboxamide;

N-(ethanesulfonyl)-3-(1-methylcyclobutyl)-4-[4-(morpholin-4-yl)phenyl]-1-phenyl-1H-pyrazolo[3,4-b]pyridine-6-carboxamide;

4-[2-(4-cyanopiperidin-1-yl)pyrimidin-5-yl]-1-(2,4-difluorophenyl)-N-(methanesulfonyl)-3-(propan-2-yl)-1H-pyrazolo[3,4-b]pyridine-6-carboxamide;

4-[6-(4-cyanopiperidin-1-yl)pyridin-3-yl]-1-(2,4-difluorophenyl)-N-(methanesulfonyl)-3-(propan-2-yl)-1H-pyrazolo[3,4-b]pyridine-6-carboxamide;

4-[4-(4-cyanopiperidin-1-yl)phenyl]-1-(2,4-difluorophenyl)-N-(methanesulfonyl)-3-(propan-2-yl)-1H-pyrazolo[3,4-b]pyridine-6-carboxamide;

3-cyclobutyl-N-(methanesulfonyl)-4-(4-methoxypiperidin-1-yl)-1-phenyl-1H-pyrazolo[3,4-b]pyridine-6-carboxamide;

3-cyclobutyl-N-(1,1-dioxo-1$\lambda^6$-thiolane-3-sulfonyl)-4-(4-methoxypiperidin-1-yl)-1-phenyl-1H-pyrazolo[3,4-b]pyridine-6-carboxamide;

1-[3-(dimethylamino)phenyl]-N-(methanesulfonyl)-4-[4-(methoxymethyl)piperidin-1-yl]-3-(propan-2-yl)-1H-pyrazolo[3,4-b]pyridine-6-carboxamide;

4-[6-(4-cyanopiperidin-1-yl)pyridin-3-yl]-N-(methanesulfonyl)-1-(oxan-3-yl)-3-(propan-2-yl)-1H-pyrazolo[3,4-b]pyridine-6-carboxamide;

3-cyclobutyl-N-(2-methoxyethanesulfonyl)-4-(4-methoxypiperidin-1-yl)-1-phenyl-1H-pyrazolo[3,4-b]pyridine-6-carboxamide;

3-cyclobutyl-4-(4-methoxypiperidin-1-yl)-1-phenyl-N-(3,3,3-trifluoropropane-1-sulfonyl)-1H-pyrazolo[3,4-b]pyridine-6-carboxamide;

3-cyclobutyl-N-(methanesulfonyl)-4-[4-(morpholin-4-yl)phenyl]-1-phenyl-1H-pyrazolo[3,4-b]pyridine-6-carboxamide;

4-(1,1-difluoro-5-azaspiro[2.4]heptan-5-yl)-N-(methanesulfonyl)-1-(3-methylphenyl)-3-(propan-2-yl)-1H-pyrazolo[3,4-b]pyridine-6-carboxamide;

1-cyclohexyl-N-(methanesulfonyl)-4-(4-methoxypiperidin-1-yl)-3-(propan-2-yl)-1H-pyrazolo[3,4-b]pyridine-6-carboxamide;

3-cyclobutyl-N-(methanesulfonyl)-1-phenyl-4-{4-[(propan-2-yl)oxy]piperidin-1-yl}-1H-pyrazolo[3,4-b]pyridine-6-carboxamide;

3-cyclobutyl-N-(methanesulfonyl)-1-phenyl-4-(4-propoxypiperidin-1-yl)-1H-pyrazolo[3,4-b]pyridine-6-carboxamide;

3-cyclobutyl-N-(methanesulfonyl)-4-[3-(methoxymethyl)piperidin-1-yl]-1-phenyl-1H-pyrazolo[3,4-b]pyridine-6-carboxamide;

3-cyclobutyl-N-(methanesulfonyl)-4-{4-[2-oxo-2-(pyrrolidin-1-yl)ethoxy]piperidin-1-yl}-1-phenyl-1H-pyrazolo[3,4-b]pyridine-6-carboxamide;

1-[3-(dimethylamino)phenyl]-N-(methanesulfonyl)-4-(4-methoxypiperidin-1-yl)-3-(propan-2-yl)-1H-pyrazolo[3,4-b]pyridine-6-carboxamide;

N-(methanesulfonyl)-4-[4-(methoxymethyl)piperidin-1-yl]-1-(3-methylphenyl)-3-(propan-2-yl)-1H-pyrazolo[3,4-b]pyridine-6-carboxamide;

1-[3-(dimethylamino)phenyl]-N-(methanesulfonyl)-4-(piperidin-1-yl)-3-(propan-2-yl)-1H-pyrazolo[3,4-b]pyridine-6-carboxamide;

4-[6-(4-cyanopiperidin-1-yl)pyridin-3-yl]-N-(methanesulfonyl)-3-(propan-2-yl)-1-[2-(pyrrolidin-1-yl)pyridin-4-yl]-1H-pyrazolo[3,4-b]pyridine-6-carboxamide;

3-cyclobutyl-N-(methanesulfonyl)-4-(1-oxa-7-azaspiro[3.5]nonan-7-yl)-1-phenyl-1H-pyrazolo[3,4-b]pyridine-6-carboxamide;

4-(4-cyanopiperidin-1-yl)-1-[3-(dimethylamino)phenyl]-N-(methanesulfonyl)-3-(propan-2-yl)-1H-pyrazolo[3,4-b]pyridine-6-carboxamide;

N-(methanesulfonyl)-4-[4-(2-methoxyethyl)piperidin-1-yl]-1-(3-methylphenyl)-3-(propan-2-yl)-1H-pyrazolo[3,4-b]pyridine-6-carboxamide;

N-(methanesulfonyl)-4-(3-methoxypiperidin-1-yl)-1-(3-methylphenyl)-3-(propan-2-yl)-1H-pyrazolo[3,4-b]pyridine-6-carboxamide;

N-(ethanesulfonyl)-4-(3-methoxypiperidin-1-yl)-1-(3-methylphenyl)-3-(propan-2-yl)-1H-pyrazolo[3,4-b]pyridine-6-carboxamide;

4-[4-(fluoromethyl)piperidin-1-yl]-N-(methanesulfonyl)-1-(3-methylphenyl)-3-(propan-2-yl)-1H-pyrazolo[3,4-b]pyridine-6-carboxamide;

N-(methanesulfonyl)-4-[4-(methanesulfonyl)piperidin-1-yl]-1-(3-methylphenyl)-3-(propan-2-yl)-1H-pyrazolo[3,4-b]pyridine-6-carboxamide;

N-(methanesulfonyl)-4-[4-(morpholin-4-yl)phenyl]-1-phenyl-3-[(propan-2-yl)oxy]-1H-pyrazolo[3,4-b]pyridine-6-carboxamide;

1-(4-fluorophenyl)-N-(methanesulfonyl)-4-(4-methoxypiperidin-1-yl)-3-(propan-2-yl)-1H-pyrazolo[3,4-b]pyridine-6-carboxamide;

1-(4-fluorophenyl)-N-(methanesulfonyl)-4-[4-(methoxymethyl)piperidin-1-yl]-3-(propan-2-yl)-1H-pyrazolo[3,4-b]pyridine-6-carboxamide;

4-[4-(4-cyanopiperidin-1-yl)phenyl]-N-(methanesulfonyl)-3-(propan-2-yl)-1-[2-(pyrrolidin-1-yl)pyridin-4-yl]-1H-pyrazolo[3,4-b]pyridine-6-carboxamide;

N-(methanesulfonyl)-4-[(2-methoxyethyl)(methyl)amino]-1-(3-methylphenyl)-3-(propan-2-yl)-1H-pyrazolo[3,4-b]pyridine-6-carboxamide;

N-(methanesulfonyl)-1-(3-methylphenyl)-4-(8-oxa-2-azaspiro[4.5]decan-2-yl)-3-(propan-2-yl)-1H-pyrazolo[3,4-b]pyridine-6-carboxamide;

4-(4-butoxypiperidin-1-yl)-1-(4-fluorophenyl)-N-(methanesulfonyl)-3-(propan-2-yl)-1H-pyrazolo[3,4-b]pyridine-6-carboxamide;

1-(4-fluorophenyl)-N-(methanesulfonyl)-4-(4-methoxy-4-methylpiperidin-1-yl)-3-(propan-2-yl)-1H-pyrazolo[3,4-b]pyridine-6-carboxamide;

2-[(2-{[3-cyclobutyl-4-(4-methoxypiperidin-1-yl)-1-phenyl-1H-pyrazolo[3,4-b]pyridine-6-carbonyl]sulfamoyl}ethyl)carbamoyl]benzoic acid;

1-(4-fluorophenyl)-N-(methanesulfonyl)-4-[4-(2-methylpropoxy)piperidin-1-yl]-3-(propan-2-yl)-1H-pyrazolo[3,4-b]pyridine-6-carboxamide;

3-cyclobutyl-4-(4-methoxypiperidin-1-yl)-1-phenyl-N-(2,2,2-trifluoroethanesulfonyl)-1H-pyrazolo[3,4-b]pyridine-6-carboxamide;

1-(4-fluorophenyl)-N-(methanesulfonyl)-4-(1-oxa-7-azaspiro[3.5]nonan-7-yl)-3-(propan-2-yl)-1H-pyrazolo[3,4-b]pyridine-6-carboxamide;

4-[3-(difluoromethyl)piperidin-1-yl]-1-(4-fluorophenyl)-N-(methanesulfonyl)-3-(propan-2-yl)-1H-pyrazolo[3,4-b]pyridine-6-carboxamide;

1-(4-fluorophenyl)-N-(methanesulfonyl)-4-(6-oxa-2-azaspiro[3.5]nonan-2-yl)-3-(propan-2-yl)-1H-pyrazolo[3,4-b]pyridine-6-carboxamide;

1-(4-fluorophenyl)-N-(methanesulfonyl)-4-(1-oxa-8-azaspiro[4.5]decan-8-yl)-3-(propan-2-yl)-1H-pyrazolo[3,4-b]pyridine-6-carboxamide;

3-cyclobutyl-4-(cyclohexylmethoxy)-N-(methanesulfonyl)-1-phenyl-1H-pyrazolo[3,4-b]pyridine-6-carboxamide;

3-cyclobutyl-N-(methanesulfonyl)-1-phenyl-4-(piperidin-1-yl)-1H-pyrazolo[3,4-b]pyridine-6-carboxamide;

3-cyclobutyl-N-(methanesulfonyl)-4-[4-(2-methoxyethyl)piperidin-1-yl]-1-phenyl-1H-pyrazolo[3,4-b]pyridine-6-carboxamide;

4-(2-azaspiro[3.4]octan-2-yl)-3-cyclobutyl-N-(methanesulfonyl)-1-phenyl-1H-pyrazolo[3,4-b]pyridine-6-carboxamide;

3-cyclobutyl-N-(methanesulfonyl)-4-[4-(methoxymethyl)piperidin-1-yl]-1-phenyl-1H-pyrazolo[3,4-b]pyridine-6-carboxamide;

4-(3-azabicyclo[3.1.0]hexan-3-yl)-3-cyclobutyl-N-(methanesulfonyl)-1-phenyl-1H-pyrazolo[3,4-b]pyridine-6-carboxamide;

N-(methanesulfonyl)-4-(4-methoxypiperidin-1-yl)-1-[2-(morpholin-4-yl)pyridin-4-yl]-3-(propan-2-yl)-1H-pyrazolo[3,4-b]pyridine-6-carboxamide;

N-(methanesulfonyl)-4-(4-methoxypiperidin-1-yl)-3-(propan-2-yl)-1-[2-(pyrrolidin-1-yl)pyridin-4-yl]-1H-pyrazolo[3,4-b]pyridine-6-carboxamide;

4-[6-(4-cyanopiperidin-1-yl)pyridin-3-yl]-3-cyclobutyl-N-(methanesulfonyl)-1-[2-(pyrrolidin-1-yl)pyridin-4-yl]-1H-pyrazolo[3,4-b]pyridine-6-carboxamide;

3-cyclobutyl-N-(methanesulfonyl)-4-[4-(methanesulfonyl)piperidin-1-yl]-1-phenyl-1H-pyrazolo[3,4-b]pyridine-6-carboxamide;

4-(4-cyanopiperidin-1-yl)-3-cyclobutyl-N-(methanesulfonyl)-1-phenyl-1H-pyrazolo[3,4-b]pyridine-6-carboxamide;

4-(2-azaspiro[3.5]nonan-2-yl)-3-cyclobutyl-N-(methanesulfonyl)-1-phenyl-1H-pyrazolo[3,4-b]pyridine-6-carboxamide;

3-cyclobutyl-N-(methanesulfonyl)-4-[3-(methoxymethyl)azetidin-1-yl]-1-phenyl-1H-pyrazolo[3,4-b]pyridine-6-carboxamide;

4-[6-(4-cyanopiperidin-1-yl)pyridin-3-yl]-N-(methanesulfonyl)-3-(cis-3-methoxycyclobutyl)-1-phenyl-1H-pyrazolo[3,4-b]pyridine-6-carboxamide;

4-[6-(4-cyanopiperidin-1-yl)pyridin-3-yl]-3-(3,3-difluorocyclobutyl)-N-(methanesulfonyl)-1-phenyl-1H-pyrazolo[3,4-b]pyridine-6-carboxamide;

4-[6-(4-cyanopiperidin-1-yl)pyridin-3-yl]-3-(3,3-dimethylcyclobutyl)-N-(methanesulfonyl)-1-phenyl-1H-pyrazolo[3,4-b]pyridine-6-carboxamide;

4-[6-(4-cyanopiperidin-1-yl)pyridin-3-yl]-3-(3-fluorocyclobutyl)-N-(methanesulfonyl)-1-phenyl-1H-pyrazolo[3,4-b]pyridine-6-carboxamide;

3-cyclobutyl-N-(methanesulfonyl)-4-[2-(oxan-4-yl)ethoxy]-1-phenyl-1H-pyrazolo[3,4-b]pyridine-6-carboxamide;

3-cyclobutyl-4-[(2S)-2-fluoro-2-(oxan-4-yl)ethoxy]-N-(methanesulfonyl)-1-phenyl-1H-pyrazolo[3,4-b]pyridine-6-carboxamide;

3-cyclobutyl-N-(methanesulfonyl)-4-[(oxan-4-yl)methoxy]-1-phenyl-1H-pyrazolo[3,4-b]pyridine-6-carboxamide;

4-[6-(4-cyanopiperidin-1-yl)pyridin-3-yl]-3-cyclobutyl-N-(methanesulfonyl)-1-[2-(morpholin-4-yl)pyridin-4-yl]-1H-pyrazolo[3,4-b]pyridine-6-carboxamide;

3-cyclobutyl-4-(1,1-difluoro-5-azaspiro[2.4]heptan-5-yl)-N-(methanesulfonyl)-1-phenyl-1H-pyrazolo[3,4-b]pyridine-6-carboxamide;

3-cyclobutyl-N-(methanesulfonyl)-4-(5-oxa-2-azaspiro[3.5]nonan-2-yl)-1-phenyl-1H-pyrazolo[3,4-b]pyridine-6-carboxamide;

3-cyclobutyl-N-(methanesulfonyl)-4-(7-oxa-2-azaspiro[3.5]nonan-2-yl)-1-phenyl-1H-pyrazolo[3,4-b]pyridine-6-carboxamide;

4-(5-azaspiro[2.5]octan-5-yl)-3-cyclobutyl-N-(methanesulfonyl)-1-phenyl-1H-pyrazolo[3,4-b]pyridine-6-carboxamide;

3-cyclobutyl-N-(methanesulfonyl)-4-[(2-methoxyethyl)(methyl)amino]-1-phenyl-1H-pyrazolo[3,4-b]pyridine-6-carboxamide;

3-cyclobutyl-4-(4-methoxypiperidin-1-yl)-N-(oxane-4-sulfonyl)-1-phenyl-1H-pyrazolo[3,4-b]pyridine-6-carboxamide;

benzyl 4-{[3-cyclobutyl-4-(4-methoxypiperidin-1-yl)-1-phenyl-1H-pyrazolo[3,4-b]pyridine-6-carbonyl]sulfamoyl}piperidine-1-carboxylate;

4-[6-(4-cyanopiperidin-1-yl)pyridin-3-yl]-3-(cis-3-fluorocyclobutyl)-N-(methanesulfonyl)-1-phenyl-1H-pyrazolo[3,4-b]pyridine-6-carboxamide;

4-[6-(4-cyanopiperidin-1-yl)pyridin-3-yl]-3-(trans-3-fluorocyclobutyl)-N-(methanesulfonyl)-1-phenyl-1H-pyrazolo[3,4-b]pyridine-6-carboxamide;

3-cyclobutyl-N-(methanesulfonyl)-4-[(cis-4-methoxycyclohexyl)oxy]-1-phenyl-1H-pyrazolo[3,4-b]pyridine-6-carboxamide;

3-cyclobutyl-N-(methanesulfonyl)-4-[(trans-4-methoxycyclohexyl)oxy]-1-phenyl-1H-pyrazolo[3,4-b]pyridine-6-carboxamide;

4-{4-[(benzyloxy)methyl]piperidin-1-yl}-3-cyclobutyl-N-(methanesulfonyl)-1-phenyl-1H-pyrazolo[3,4-b]pyridine-6-carboxamide;

4-(2-azaspiro[3.3]heptan-2-yl)-3-cyclobutyl-N-(methanesulfonyl)-1-phenyl-1H-pyrazolo[3,4-b]pyridine-6-carboxamide;

methyl 5-{3-cyclobutyl-6-[(methanesulfonyl)carbamoyl]-1-phenyl-1H-pyrazolo[3,4-b]pyridin-4-yl}octahydro-1H-pyrrolo[3,2-c]pyridine-11-carboxylate;

4-(1-acetyloctahydro-5H-pyrrolo[3,2-c]pyridin-5-yl)-3-cyclobutyl-N-(methanesulfonyl)-1-phenyl-1H-pyrazolo[3,4-b]pyridine-6-carboxamide;

N-(methanesulfonyl)-4-(4-methoxypiperidin-1-yl)-1-[6-(morpholin-4-yl)pyridin-2-yl]-3-(propan-2-yl)-1H-pyrazolo[3,4-b]pyridine-6-carboxamide;

1-cyclohexyl-N-(methanesulfonyl)-4-[4-(methoxymethyl)piperidin-1-yl]-3-(propan-2-yl)-1H-pyrazolo[3,4-b]pyridine-6-carboxamide;

3-cyclobutyl-4-{4-[(1S)-2-(dimethylamino)-1-fluoroethyl]piperidin-1-yl}-N-(methanesulfonyl)-1-phenyl-1H-pyrazolo[3,4-b]pyridine-6-carboxamide;

3-cyclobutyl-4-[4-(fluoromethyl)piperidin-1-yl]-N-(methanesulfonyl)-1-phenyl-1H-pyrazolo[3,4-b]pyridine-6-carboxamide;

1-(4-fluorophenyl)-N-(methanesulfonyl)-4-[4-(2-methoxypropan-2-yl)piperidin-1-yl]-3-(propan-2-yl)-1H-pyrazolo[3,4-b]pyridine-6-carboxamide;

4-(3-azaspiro[5.5]undecan-3-yl)-3-cyclobutyl-N-(methanesulfonyl)-1-phenyl-1H-pyrazolo[3,4-b]pyridine-6-carboxamide;

1-(3,4-difluorophenyl)-N-(ethanesulfonyl)-4-[4-(morpholin-4-yl)phenyl]-3-(propan-2-yl)-1H-pyrazolo[3,4-b]pyridine-6-carboxamide;

N-(ethanesulfonyl)-1-(3-fluorophenyl)-4-{6-[methyl(oxan-4-yl)amino]pyridin-3-yl}-3-(propan-2-yl)-1H-pyrazolo[3,4-b]pyridine-6-carboxamide;

N-(cyclopropanesulfonyl)-4-[4-(morpholin-4-yl)phenyl]-1-phenyl-3-[(propan-2-yl)oxy]-1H-pyrazolo[3,4-b]pyridine-6-carboxamide;

N-(2-methoxyethanesulfonyl)-4-[4-(morpholin-4-yl)phenyl]-1-phenyl-3-[(propan-2-yl)oxy]-1H-pyrazolo[3,4-b]pyridine-6-carboxamide;

4-[6-(4-cyanopiperidin-1-yl)pyridin-3-yl]-N-(methanesulfonyl)-1-[2-(morpholin-4-yl)pyridin-4-yl]-3-(propan-2-yl)-1H-pyrazolo[3,4-b]pyridine-6-carboxamide;

3-cyclobutyl-4-[4-(cyclopentyloxy)piperidin-1-yl]-N-(methanesulfonyl)-1-phenyl-1H-pyrazolo[3,4-b]pyridine-6-carboxamide;

3-cyclobutyl-4-[4-(cyclohexyloxy)piperidin-1-yl]-N-(methanesulfonyl)-1-phenyl-1H-pyrazolo[3,4-b]pyridine-6-carboxamide;

3-cyclobutyl-4-[4-(cyclopropylmethoxy)piperidin-1-yl]-N-(methanesulfonyl)-1-phenyl-1H-pyrazolo[3,4-b]pyridine-6-carboxamide;

N-(2-methoxyethanesulfonyl)-4-(4-methoxyphenyl)-3-methyl-1-(2-methylpropyl)-1H-pyrazolo[3,4-b]pyridine-6-carboxamide;

N-(2-methoxyethanesulfonyl)-4-[4-(morpholin-4-yl)phenyl]-1-(oxolan-3-yl)-3-(propan-2-yl)-1H-pyrazolo[3,4-b]pyridine-6-carboxamide;

N-(2-methoxyethanesulfonyl)-4-[4-(morpholin-4-yl)phenyl]-1-phenyl-1H-pyrazolo[3,4-b]pyridine-6-carboxamide;

N-(2-methoxyethanesulfonyl)-4-(4-methoxyphenyl)-3-methyl-1-(propan-2-yl)-1H-pyrazolo[3,4-b]pyridine-6-carboxamide;

1-cyclopropyl-N-(2-methoxyethanesulfonyl)-3-methyl-4-[4-(morpholin-4-yl)phenyl]-1H-pyrazolo[3,4-b]pyridine-6-carboxamide;

1-(4-fluorophenyl)-N-(2-methoxyethanesulfonyl)-4-[4-(methoxymethyl)piperidin-1-yl]-3-(propan-2-yl)-1H-pyrazolo[3,4-b]pyridine-6-carboxamide;

3-cyclobutyl-4-[(2R)-2-fluoro-2-(oxan-4-yl)ethoxy]-N-(methanesulfonyl)-1-phenyl-1H-pyrazolo[3,4-b]pyridine-6-carboxamide;

3-cyclobutyl-4-[(3,3-difluorocyclopentyl)methoxy]-N-(methanesulfonyl)-1-phenyl-1H-pyrazolo[3,4-b]pyridine-6-carboxamide;

1-cyclohexyl-N-(cyclopropanesulfonyl)-3-methyl-4-[4-(morpholin-4-yl)phenyl]-1H-pyrazolo[3,4-b]pyridine-6-carboxamide;

4-(4-cyanopiperidin-1-yl)-1-(4-fluorophenyl)-N-(methanesulfonyl)-3-(propan-2-yl)-1H-pyrazolo[3,4-b]pyridine-6-carboxamide;

3-cyclobutyl-N-(methanesulfonyl)-4-[4-(1-methoxyethyl)piperidin-1-yl]-1-phenyl-1H-pyrazolo[3,4-b]pyridine-6-carboxamide;

3-cyclobutyl-N-(methanesulfonyl)-1-phenyl-4-[4-(1,1,1-trifluoro-2-methoxypropan-2-yl)piperidin-1-yl]-1H-pyrazolo[3,4-b]pyridine-6-carboxamide;

3-cyclobutyl-4-[2-(1,1-dioxo-1λ$^6$,4-thiazinan-4-yl)ethoxy]-N-(methanesulfonyl)-1-phenyl-1H-pyrazolo[3,4-b]pyridine-6-carboxamide;

3-cyclobutyl-4-[4-(hydroxymethyl)piperidin-1-yl]-N-(methanesulfonyl)-1-phenyl-1H-pyrazolo[3,4-b]pyridine-6-carboxamide;

3-cyclobutyl-4-[4-(methoxymethyl)piperidin-1-yl]-N-(1-methyl-1H-pyrazole-4-sulfonyl)-1-phenyl-1H-pyrazolo[3,4-b]pyridine-6-carboxamide;

4-{6-[bis(2-methoxyethyl)amino]pyridin-3-yl}-3-cyclobutyl-N-(methanesulfonyl)-1-phenyl-1H-pyrazolo[3,4-b]pyridine-6-carboxamide;

3-cyclobutyl-N-(methanesulfonyl)-4-[4-methoxy-4-(methoxymethyl)piperidin-1-yl]-1-phenyl-1H-pyrazolo[3,4-b]pyridine-6-carboxamide;

N-(methanesulfonyl)-4-[4-(methoxymethyl)piperidin-1-yl]-1-[2-(morpholin-4-yl)pyridin-4-yl]-3-(propan-2-yl)-1H-pyrazolo[3,4-b]pyridine-6-carboxamide;

N-(2-methoxyethanesulfonyl)-4-[4-(methoxymethyl)piperidin-1-yl]-1-[2-(morpholin-4-yl)pyridin-4-yl]-3-(propan-2-yl)-1H-pyrazolo[3,4-b]pyridine-6-carboxamide;

3-cyclobutyl-N-(1,2-dimethyl-1H-imidazole-4-sulfonyl)-4-[4-(methoxymethyl)piperidin-1-yl]-1-phenyl-1H-pyrazolo[3,4-b]pyridine-6-carboxamide;

1-cyclohexyl-N-(2-methoxyethanesulfonyl)-4-[4-(methoxymethyl)piperidin-1-yl]-3-(propan-2-yl)-1H-pyrazolo[3,4-b]pyridine-6-carboxamide;

4-{6-[bis(2-methoxyethyl)amino]pyridin-3-yl}-N-(methanesulfonyl)-1-[2-(morpholin-4-yl)pyridin-4-yl]-3-(propan-2-yl)-1H-pyrazolo[3,4-b]pyridine-6-carboxamide;

3-cyclobutyl-4-[4-(methoxymethyl)piperidin-1-yl]-1-phenyl-N-(1H-pyrazole-4-sulfonyl)-1H-pyrazolo[3,4-b]pyridine-6-carboxamide;

3-cyclobutyl-N-(methanesulfonyl)-4-[(3-methyloxetan-3-yl)methoxy]-1-phenyl-1H-pyrazolo[3,4-b]pyridine-6-carboxamide;

3-cyclobutyl-4-{4-[(1,1-dioxo-1λ$^6$,4-thiazinan-4-yl)methyl]-4-methoxypiperidin-1-yl}-N-(methanesulfonyl)-1-phenyl-1H-pyrazolo[3,4-b]pyridine-6-carboxamide;

3-cyclobutyl-N-(2-methoxyethanesulfonyl)-4-[4-(methoxymethyl)piperidin-1-yl]-1-phenyl-1H-pyrazolo[3,4-b]pyridine-6-carboxamide;

4-[6-(4-cyanopiperidin-1-yl)pyridin-3-yl]-N-(methanesulfonyl)-3-(trans-3-methylcyclobutyl)-1-phenyl-1H-pyrazolo[3,4-b]pyridine-6-carboxamide;

4-[6-(4-cyanopiperidin-1-yl)pyridin-3-yl]-N-(methanesulfonyl)-1-phenyl-3-[(piperidin-4-yl)oxy]-1H-pyrazolo[3,4-b]pyridine-6-carboxamide;

tert-butyl 4-({4-[6-(4-cyanopiperidin-1-yl)pyridin-3-yl]-6-[(methanesulfonyl)carbamoyl]-1-phenyl-1H-pyrazolo[3,4-b]pyridin-3-yl}oxy)piperidine-1-carboxylate;

3-cyclobutyl-N-[2-(1,3-dioxo-1,3-dihydro-2H-isoindol-2-yl)ethanesulfonyl]-4-[4-(methoxymethyl)piperidin-1-yl]-1-phenyl-1H-pyrazolo[3,4-b]pyridine-6-carboxamide;

N-(2-aminoethanesulfonyl)-3-cyclobutyl-4-[4-(methoxymethyl)piperidin-1-yl]-1-phenyl-1H-pyrazolo[3,4-b]pyridine-6-carboxamide;

1-(cyclobutylmethyl)-N-(methanesulfonyl)-4-[4-(methoxymethyl)piperidin-1-yl]-3-(propan-2-yl)-1H-pyrazolo[3,4-b]pyridine-6-carboxamide;

1-(cyclobutylmethyl)-N-(2-methoxyethanesulfonyl)-4-[4-(methoxymethyl)piperidin-1-yl]-3-(propan-2-yl)-1H-pyrazolo[3,4-b]pyridine-6-carboxamide;

N-(methanesulfonyl)-4-[4-(methoxymethyl)piperidin-1-yl]-1-(2-methylpropyl)-3-(propan-2-yl)-1H-pyrazolo[3,4-b]pyridine-6-carboxamide;

N-(2-methoxyethanesulfonyl)-4-[4-(methoxymethyl)piperidin-1-yl]-1-(2-methylpropyl)-3-(propan-2-yl)-1H-pyrazolo[3,4-b]pyridine-6-carboxamide;

1-(4-fluorophenyl)-N-(methanesulfonyl)-3-(propan-2-yl)-4-[4-(2,2,2-trifluoroethyl)piperazin-1-yl]-1H-pyrazolo[3,4-b]pyridine-6-carboxamide;

3-cyclobutyl-4-[4-(methoxymethyl)piperidin-1-yl]-N-[2-(morpholin-4-yl)ethanesulfonyl]-1-phenyl-1H-pyrazolo[3,4-b]pyridine-6-carboxamide;

N-(methanesulfonyl)-4-[4-(methoxymethyl)piperidin-1-yl]-1-(1-methyl-6-oxo-1,6-dihydropyridazin-3-yl)-3-(propan-2-yl)-1H-pyrazolo[3,4-b]pyridine-6-carboxamide;

3-cyclobutyl-N-(2-methoxyethanesulfonyl)-4-[(3-methyloxetan-3-yl)methoxy]-1-phenyl-1H-pyrazolo[3,4-b]pyridine-6-carboxamide;

3-cyclobutyl-N-(methanesulfonyl)-1-phenyl-4-[4-(propan-2-yl)piperazin-1-yl]-1H-pyrazolo[3,4-b]pyridine-6-carboxamide;

3-cyclobutyl-N-(2-methoxyethanesulfonyl)-1-phenyl-4-[4-(propan-2-yl)piperazin-1-yl]-1H-pyrazolo[3,4-b]pyridine-6-carboxamide;

1-(4-fluorophenyl)-4-[4-(methoxymethyl)piperidin-1-yl]-N-[3-(morpholin-4-yl)propane-1-sulfonyl]-3-(propan-2-yl)-1H-pyrazolo[3,4-b]pyridine-6-carboxamide;

3-cyclobutyl-N-[2-(dimethylamino)ethanesulfonyl]-4-[4-(methoxymethyl)piperidin-1-yl]-1-phenyl-1H-pyrazolo[3,4-b]pyridine-6-carboxamide;

4-[(1-acetyl-4-fluoropiperidin-4-yl)methoxy]-3-cyclobutyl-N-(methanesulfonyl)-1-phenyl-1H-pyrazolo[3,4-b]pyridine-6-carboxamide;

4-[6-(4-cyanopiperidin-1l-yl)pyridin-3-yl]-N-(2-methoxyethanesulfonyl)-3-[(oxolan-3-yl)oxy]-1-phenyl-1H-pyrazolo[3,4-b]pyridine-6-carboxamide;

4-[6-(4-cyanopiperidin-1l-yl)pyridin-3-yl]-N-(2-methoxyethanesulfonyl)-3-(trans-3-methylcyclobutyl)-1-phenyl-1H-pyrazolo[3,4-b]pyridine-6-carboxamide;

4-[6-(4-cyanopiperidin-1l-yl)pyridin-3-yl]-N-(methanesulfonyl)-3-[(oxolan-3-yl)oxy]-1-phenyl-1H-pyrazolo[3,4-b]pyridine-6-carboxamide;

1-[3-(dimethylamino)phenyl]-N-(methanesulfonyl)-4-[(oxan-4-yl)methoxy]-3-(propan-2-yl)-1H-pyrazolo[3,4-b]pyridine-6-carboxamide;

N-(methanesulfonyl)-4-[4-(methoxymethyl)piperidin-1-yl]-1-[2-(morpholin-4-yl)pyrimidin-4-yl]-3-(propan-2-yl)-1H-pyrazolo[3,4-b]pyridine-6-carboxamide;

4-(4-cyclobutylpiperazin-1-yl)-1-(4-fluorophenyl)-N-(methanesulfonyl)-3-(propan-2-yl)-1H-pyrazolo[3,4-b]pyridine-6-carboxamide;

3-cyclobutyl-N-(methanesulfonyl)-4-[3-(morpholin-4-yl)propoxy]-1-phenyl-1H-pyrazolo[3,4-b]pyridine-6-carboxamide;

3-cyclobutyl-4-[(3,3-difluoro-1-methylcyclobutyl)methoxy]-N-(methanesulfonyl)-1-phenyl-1H-pyrazolo[3,4-b]pyridine-6-carboxamide;

3-cyclobutyl-N-(methanesulfonyl)-4-[(oxolan-2-yl)methoxy]-1-phenyl-1H-pyrazolo[3,4-b]pyridine-6-carboxamide;

1-(4-fluorophenyl)-N-(methanesulfonyl)-4-[(oxan-4-yl)methoxy]-3-(propan-2-yl)-1H-pyrazolo[3,4-b]pyridine-6-carboxamide;

1-(4-fluorophenyl)-N-(methanesulfonyl)-4-[2-(oxan-4-yl)ethoxy]-3-(propan-2-yl)-1H-pyrazolo[3,4-b]pyridine-6-carboxamide;

3-cyclobutyl-4-[4-(methoxymethyl)piperidin-1-yl]-N-(1-methyl-1H-imidazole-4-sulfonyl)-1-phenyl-1H-pyrazolo[3,4-b]pyridine-6-carboxamide;

3-cyclobutyl-N-(3,5-dimethyl-1,2-oxazole-4-sulfonyl)-4-[4-(methoxymethyl)piperidin-1-yl]-1-phenyl-1H-pyrazolo[3,4-b]pyridine-6-carboxamide;

methyl 3-({3-cyclobutyl-4-[4-(methoxymethyl)piperidin-1-yl]-1-phenyl-1H-pyrazolo[3,4-b]pyridine-6-carbonyl}sulfamoyl)propanoate;

3-({3-cyclobutyl-4-[4-(methoxymethyl)piperidin-1-yl]-1-phenyl-1H-pyrazolo[3,4-b]pyridine-6-carbonyl}sulfamoyl)propanoic acid;

N-[3-(dimethylamino)propane-1-sulfonyl]-1-(4-fluorophenyl)-4-[4-(methoxymethyl)piperidin-1-yl]-3-(propan-2-yl)-1H-pyrazolo[3,4-b]pyridine-6-carboxamide;

1-(4-fluorophenyl)-4-[4-(methoxymethyl)piperidin-1-yl]-3-(propan-2-yl)-N-[3-(pyrrolidin-1-yl)propane-1-sulfonyl]-1H-pyrazolo[3,4-b]pyridine-6-carboxamide;

1-(4-fluorophenyl)-N-(methanesulfonyl)-4-[3-(morpholin-4-yl)propoxy]-3-(propan-2-yl)-1H-pyrazolo[3,4-b]pyridine-6-carboxamide;

1-(4-fluorophenyl)-N-(methanesulfonyl)-4-[(3-methyloxetan-3-yl)methoxy]-3-(propan-2-yl)-1H-pyrazolo[3,4-b]pyridine-6-carboxamide;

3-cyclobutyl-N-(methanesulfonyl)-4-[4-(2-methoxypropan-2-yl)piperidin-1-yl]-1-phenyl-1H-pyrazolo[3,4-b]pyridine-6-carboxamide;

1-(4-fluorophenyl)-N-(methanesulfonyl)-4-[(oxolan-2-yl)methoxy]-3-(propan-2-yl)-1H-pyrazolo[3,4-b]pyridine-6-carboxamide;

4-[(1-acetylpiperidin-4-yl)methoxy]-3-cyclobutyl-N-(methanesulfonyl)-1-phenyl-1H-pyrazolo[3,4-b]pyridine-6-carboxamide;

methyl 4-[({3-cyclobutyl-6-[(methanesulfonyl)carbamoyl]-1-phenyl-1H-pyrazolo[3,4-b]pyridin-4-yl}oxy)methyl]piperidine-1-carboxylate;

3-cyclobutyl-N-[3-(dimethylamino)-3-oxopropane-1-sulfonyl]-4-[4-(methoxymethyl)piperidin-1-yl]-1-phenyl-1H-pyrazolo[3,4-b]pyridine-6-carboxamide;

4-[3-(dimethylamino)propoxy]-1-(4-fluorophenyl)-N-(methanesulfonyl)-3-(propan-2-yl)-1H-pyrazolo[3,4-b]pyridine-6-carboxamide;

4-[6-(4-cyanopiperidin-1-yl)pyridin-3-yl]-N-(methanesulfonyl)-3-[(oxetan-3-yl)oxy]-1-phenyl-1H-pyrazolo[3,4-b]pyridine-6-carboxamide;

1-(4-fluorophenyl)-N-(methanesulfonyl)-4-[(2-methoxyethyl)(methyl)amino]-3-(propan-2-yl)-1H-pyrazolo[3,4-b]pyridine-6-carboxamide;

N-[3-(azetidin-1-yl)propane-1-sulfonyl]-1-(4-fluorophenyl)-4-[4-(methoxymethyl)piperidin-1-yl]-3-(propan-2-yl)-1H-pyrazolo[3,4-b]pyridine-6-carboxamide;

3-cyclobutyl-4-[3-(dimethylamino)propoxy]-N-(methanesulfonyl)-1-phenyl-1H-pyrazolo[3,4-b]pyridine-6-carboxamide;

1-(4-fluorophenyl)-4-[4-(2-hydroxypropan-2-yl)piperidin-1-yl]-N-(methanesulfonyl)-3-(propan-2-yl)-1H-pyrazolo[3,4-b]pyridine-6-carboxamide;

1-(4-fluorophenyl)-N-(methanesulfonyl)-4-[2-(1-methylpiperidin-2-yl)ethoxy]-3-(propan-2-yl)-1H-pyrazolo[3,4-b]pyridine-6-carboxamide;

4-[(3,3-difluoro-1-methylcyclobutyl)methoxy]-1-(4-fluorophenyl)-N-(methanesulfonyl)-3-(propan-2-yl)-1H-pyrazolo[3,4-b]pyridine-6-carboxamide;

1-(4-fluorophenyl)-N-(methanesulfonyl)-4-[3-(piperidin-1-yl)propoxy]-3-(propan-2-yl)-1H-pyrazolo[3,4-b]pyridine-6-carboxamide;

4-[(1-acetyl-4-fluoropiperidin-4-yl)methoxy]-1-(4-fluorophenyl)-N-(methanesulfonyl)-3-(propan-2-yl)-1H-pyrazolo[3,4-b]pyridine-6-carboxamide;

1-(4-fluorophenyl)-N-(methanesulfonyl)-4-{2-[(oxetan-3-yl)(propan-2-yl)amino]ethoxy}-3-(propan-2-yl)-1H-pyrazolo[3,4-b]pyridine-6-carboxamide;

1-(4-fluorophenyl)-N-(methanesulfonyl)-3-(propan-2-yl)-4-{[4-(propan-2-yl)morpholin-3-yl]methoxy}-1H-pyrazolo[3,4-b]pyridine-6-carboxamide;

4-[(1,3-dimethoxypropan-2-yl)oxy]-1-(4-fluorophenyl)-N-(methanesulfonyl)-3-(propan-2-yl)-1H-pyrazolo[3,4-b]pyridine-6-carboxamide;

4-[(1,4-dioxan-2-yl)methoxy]-1-(4-fluorophenyl)-N-(methanesulfonyl)-3-(propan-2-yl)-1H-pyrazolo[3,4-b]pyridine-6-carboxamide;

1-(4-fluorophenyl)-N-(methanesulfonyl)-4-{2-[(oxetan-3-yl)oxy]ethoxy}-3-(propan-2-yl)-1H-pyrazolo[3,4-b]pyridine-6-carboxamide;

3-cyclobutyl-N-(methanesulfonyl)-1-phenyl-4-[3-(piperidin-1l-yl)propoxy]-1H-pyrazolo[3,4-b]pyridine-6-carboxamide;

3-cyclobutyl-N-(2-methoxyethanesulfonyl)-4-[(oxan-4-yl)methoxy]-1-phenyl-1H-pyrazolo[3,4-b]pyridine-6-carboxamide;

3-cyclobutyl-1-(4-fluorophenyl)-N-(methanesulfonyl)-4-[4-(methoxymethyl)piperidin-1-yl]-1H-pyrazolo[3,4-b]pyridine-6-carboxamide;

3-cyclobutyl-4-[4-(2-hydroxypropan-2-yl)piperidin-1-yl]-N-(methanesulfonyl)-1-phenyl-1H-pyrazolo[3,4-b]pyridine-6-carboxamide;

3-cyclobutyl-1-(4-fluorophenyl)-N-(methanesulfonyl)-4-[(oxan-4-yl)methoxy]-1H-pyrazolo[3,4-b]pyridine-6-carboxamide;

4-[4-(dimethylamino)piperidin-1-yl]-1-(4-fluorophenyl)-N-(methanesulfonyl)-3-(propan-2-yl)-1H-pyrazolo[3,4-b]pyridine-6-carboxamide;

1-(4-fluorophenyl)-N-(methanesulfonyl)-4-(1'-methyl[4,4'-bipiperidin]-1-yl)-3-(propan-2-yl)-1H-pyrazolo[3,4-b]pyridine-6-carboxamide;

4-[(1-acetylpiperidin-4-yl)methoxy]-1-(4-fluorophenyl)-N-(methanesulfonyl)-3-(propan-2-yl)-1H-pyrazolo[3,4-b]pyridine-6-carboxamide;

methyl 4-({[1-(4-fluorophenyl)-6-[(methanesulfonyl)carbamoyl]-3-(propan-2-yl)-1H-pyrazolo[3,4-b]pyridin-4-yl]oxy}methyl)piperidine-1-carboxylate;

3-cyclobutyl-N-(methanesulfonyl)-4-[2-(1-methylpiperidin-2-yl)ethoxy]-1-phenyl-1H-pyrazolo[3,4-b]pyridine-6-carboxamide;

3-cyclobutyl-4-[(1,3-dimethoxypropan-2-yl)oxy]-N-(methanesulfonyl)-1-phenyl-1H-pyrazolo[3,4-b]pyridine-6-carboxamide;

3-cyclobutyl-N-(methanesulfonyl)-4-{2-[(oxetan-3-yl)(propan-2-yl)amino]ethoxy}-1-phenyl-1H-pyrazolo[3,4-b]pyridine-6-carboxamide;

4-[4-(cyanomethyl)-4-hydroxypiperidin-1-yl]-3-cyclobutyl-N-(methanesulfonyl)-1-phenyl-1H-pyrazolo[3,4-b]pyridine-6-carboxamide;

4-(4-azidophenyl)-N-(3-azidopropane-1-sulfonyl)-1-[3-(dimethylamino)phenyl]-3-(propan-2-yl)-1H-pyrazolo[3,4-b]pyridine-6-carboxamide;

3-cyclobutyl-N-(methanesulfonyl)-4-[4-(morpholin-4-yl)piperidin-1-yl]-1-phenyl-1H-pyrazolo[3,4-b]pyridine-6-carboxamide;

3-cyclobutyl-N-(methanesulfonyl)-1-phenyl-4-[4-(2,2,2-trifluoroethyl)piperazin-1-yl]-1H-pyrazolo[3,4-b]pyridine-6-carboxamide;

3-cyclobutyl-N-(2-methoxyethanesulfonyl)-1-phenyl-4-[4-(2,2,2-trifluoroethyl)piperazin-1-yl]-1H-pyrazolo[3,4-b]pyridine-6-carboxamide;

3-cyclobutyl-N-(methanesulfonyl)-4-{4-[2-(morpholin-4-yl)ethyl]piperidin-1-yl}-1-phenyl-1H-pyrazolo[3,4-b]pyridine-6-carboxamide;

rac-4-[(3 aR,7aS)-1-acetyloctahydro-5H-pyrrolo[3,2-c]pyridin-5-yl]-3-cyclobutyl-N-[3-(morpholin-4-yl)propane-1-sulfonyl]-1-phenyl-1H-pyrazolo[3,4-b]pyridine-6-carboxamide;

3-cyclobutyl-N-(cyclopropanesulfonyl)-4-[(oxan-4-yl)methoxy]-1-phenyl-1H-pyrazolo[3,4-b]pyridine-6-carboxamide;

3-cyclobutyl-N-(dimethylsulfamoyl)-4-[(oxan-4-yl)methoxy]-1-phenyl-1H-pyrazolo[3,4-b]pyridine-6-carboxamide;

3-cyclobutyl-N-(ethanesulfonyl)-4-[(oxan-4-yl)methoxy]-1-phenyl-1H-pyrazolo[3,4-b]pyridine-6-carboxamide;

N-(methanesulfonyl)-1-[2-(morpholin-4-yl)pyridin-4-yl]-4-[(oxan-4-yl)methoxy]-3-(propan-2-yl)-1H-pyrazolo[3,4-b]pyridine-6-carboxamide;

ethyl 4-[1-(4-fluorophenyl)-6-[(methanesulfonyl)carbamoyl]-3-(propan-2-yl)-1H-pyrazolo[3,4-b]pyridin-4-yl]piperazine-1-carboxylate;

1-(4-fluorophenyl)-N-(methanesulfonyl)-4-(3-methyl-2-oxo-1-oxa-3,8-diazaspiro[4.5]decan-8-yl)-3-(propan-2-yl)-1H-pyrazolo[3,4-b]pyridine-6-carboxamide;

1-(4-fluorophenyl)-N-(methanesulfonyl)-3-(propan-2-yl)-4-[3-(trifluoromethyl)piperazin-1-yl]-1H-pyrazolo[3,4-b]pyridine-6-carboxamide;

1-(4-fluorophenyl)-N-(methanesulfonyl)-4-[4-(2-methoxyethyl)piperazin-1-yl]-3-(propan-2-yl)-1H-pyrazolo[3,4-b]pyridine-6-carboxamide;

4-(2,4-dioxo-1,3,8-triazaspiro[4.5]decan-8-yl)-1-(4-fluorophenyl)-N-(methanesulfonyl)-3-(propan-2-yl)-1H-pyrazolo[3,4-b]pyridine-6-carboxamide;

4-[4-(ethoxymethyl)-4-fluoropiperidin-1-yl]-1-(4-fluorophenyl)-N-(methanesulfonyl)-3-(propan-2-yl)-1H-pyrazolo[3,4-b]pyridine-6-carboxamide;

4-{4-fluoro-4-[(2-methoxyethoxy)methyl]piperidin-1-yl}-1-(4-fluorophenyl)-N-(methanesulfonyl)-3-(propan-2-yl)-1H-pyrazolo[3,4-b]pyridine-6-carboxamide;

4-[(3R,4R)-3-fluoro-4-hydroxypiperidin-1-yl]-1-(4-fluorophenyl)-N-(methanesulfonyl)-3-(propan-2-yl)-1H-pyrazolo[3,4-b]pyridine-6-carboxamide;

4-[4-fluoro-4-(methoxymethyl)piperidin-1-yl]-1-(4-fluorophenyl)-N-(methanesulfonyl)-3-(propan-2-yl)-1H-pyrazolo[3,4-b]pyridine-6-carboxamide;

4-{3-fluoro-3-[(2-methoxyethoxy)methyl]piperidin-1-yl}-1-(4-fluorophenyl)-N-(methanesulfonyl)-3-(propan-2-yl)-1H-pyrazolo[3,4-b]pyridine-6-carboxamide;

3-cyclobutyl-N-[3-(morpholin-4-yl)propane-1-sulfonyl]-4-[(oxan-4-yl)methoxy]-1-phenyl-1H-pyrazolo[3,4-b]pyridine-6-carboxamide;

4-([1,4'-bipiperidin]-1'-yl)-1-(4-fluorophenyl)-N-(methanesulfonyl)-3-(propan-2-yl)-1H-pyrazolo[3,4-b]pyridine-6-carboxamide;

3-cyclobutyl-4-[(3R)-3-(hydroxymethyl)piperidin-1-yl]-N-(methanesulfonyl)-1-phenyl-1H-pyrazolo[3,4-b]pyridine-6-carboxamide;

3-cyclobutyl-4-[(3R)-3-(hydroxymethyl)piperidin-1-yl]-N-[3-(morpholin-4-yl)propane-1-sulfonyl]-1-phenyl-1H-pyrazolo[3,4-b]pyridine-6-carboxamide;

3-cyclobutyl-4-[(oxan-4-yl)methoxy]-1-phenyl-N-[4-(pyrrolidin-1-yl)piperidine-1-sulfonyl]-1H-pyrazolo[3,4-b]pyridine-6-carboxamide;

3-cyclobutyl-N-[(2S)-2-(4-methylpiperazine-1-carbonyl)pyrrolidine-1-sulfonyl]-4-[(oxan-4-yl)methoxy]-1-phenyl-1H-pyrazolo[3,4-b]pyridine-6-carboxamide;

N-([1,4'-bipiperidine]-1'-sulfonyl)-3-cyclobutyl-4-[(oxan-4-yl)methoxy]-1-phenyl-1H-pyrazolo[3,4-b]pyridine-6-carboxamide;

3-cyclobutyl-N-[methyl(propyl)sulfamoyl]-4-[(oxan-4-yl)methoxy]-1-phenyl-1H-pyrazolo[3,4-b]pyridine-6-carboxamide;

3-cyclobutyl-N-[ethyl(propyl)sulfamoyl]-4-[(oxan-4-yl)methoxy]-1-phenyl-1H-pyrazolo[3,4-b]pyridine-6-carboxamide;

ethyl 4-[({3-cyclobutyl-4-[(oxan-4-yl)methoxy]-1-phenyl-1H-pyrazolo[3,4-b]pyridine-6-carbonyl}sulfamoyl)amino]piperidine-1-carboxylate;

N-(4-acetyl-1,4-diazepane-1-sulfonyl)-3-cyclobutyl-4-[(oxan-4-yl)methoxy]-1-phenyl-1H-pyrazolo[3,4-b]pyridine-6-carboxamide;

3-cyclobutyl-N-(morpholine-4-sulfonyl)-4-[(oxan-4-yl)methoxy]-1-phenyl-1H-pyrazolo[3,4-b]pyridine-6-carboxamide;

3-cyclobutyl-N-[4-(morpholin-4-yl)piperidine-1-sulfonyl]-4-[(oxan-4-yl)methoxy]-1-phenyl-1H-pyrazolo[3,4-b]pyridine-6-carboxamide;

3-cyclobutyl-N-[4-(4-methylpiperazine-1-carbonyl)piperidine-1-sulfonyl]-4-[(oxan-4-yl)methoxy]-1-phenyl-1H-pyrazolo[3,4-b]pyridine-6-carboxamide;

3-cyclobutyl-N-(4-methylpiperazine-1-sulfonyl)-4-[(oxan-4-yl)methoxy]-1-phenyl-1H-pyrazolo[3,4-b]pyridine-6-carboxamide;

3-cyclobutyl-N-(2-methylpropane-2-sulfonyl)-4-[(oxan-4-yl)methoxy]-1-phenyl-1H-pyrazolo[3,4-b]pyridine-6-carboxamide;

4-(4-azidophenyl)-N-(but-3-yne-1-sulfonyl)-1-[3-(dimethylamino)phenyl]-3-(propan-2-yl)-1H-pyrazolo[3,4-b]pyridine-6-carboxamide;

N-(cyanomethanesulfonyl)-3-cyclobutyl-4-[4-(methoxymethyl)piperidin-1-yl]-1-phenyl-1H-pyrazolo[3,4-b]pyridine-6-carboxamide;

4-([1,4'-bipiperidin]-1'-yl)-3-cyclobutyl-N-(methanesulfonyl)-1-phenyl-1H-pyrazolo[3,4-b]pyridine-6-carboxamide;

3-cyclobutyl-N-(2-hydroxyethanesulfonyl)-4-[4-(methoxymethyl)piperidin-1-yl]-1-phenyl-1H-pyrazolo[3,4-b]pyridine-6-carboxamide;

3-cyclobutyl-N-(3-hydroxypropane-1-sulfonyl)-4-[4-(methoxymethyl)piperidin-1-yl]-1-phenyl-1H-pyrazolo[3,4-b]pyridine-6-carboxamide;

3-cyclobutyl-4-[4-(methoxymethyl)piperidin-1-yl]-1-phenyl-N-(piperidine-4-sulfonyl)-1H-pyrazolo[3,4-b]pyridine-6-carboxamide;

3-cyclobutyl-4-[4-(methoxymethyl)piperidin-1-yl]-N-(oxolane-3-sulfonyl)-1-phenyl-1H-pyrazolo[3,4-b]pyridine-6-carboxamide;

1-(2,6-dimethylpyridin-4-yl)-N-(methanesulfonyl)-4-[4-(methoxymethyl)piperidin-1-yl]-3-(propan-2-yl)-1H-pyrazolo[3,4-b]pyridine-6-carboxamide;

3-cyclobutyl-4-(1,1-dioxo-1$\lambda^6$,4-thiazinan-4-yl)-N-(methanesulfonyl)-1-phenyl-1H-pyrazolo[3,4-b]pyridine-6-carboxamide;

3-cyclobutyl-4-[4-(methoxymethyl)piperidin-1-yl]-1-phenyl-N-[2-(1H-pyrazol-1-yl)ethanesulfonyl]-1H-pyrazolo[3,4-b]pyridine-6-carboxamide;

benzyl [2-({3-cyclobutyl-4-[4-(methoxymethyl)piperidin-1-yl]-1-phenyl-1H-pyrazolo[3,4-b]pyridine-6-carbonyl}sulfamoyl)ethyl]carbamate;

3-cyclobutyl-4-[4-(methoxymethyl)piperidin-1-yl]-N-(1-methylcyclopropane-1-sulfonyl)-1-phenyl-1H-pyrazolo[3,4-b]pyridine-6-carboxamide;

3-cyclobutyl-4-[4-(methoxymethyl)piperidin-1-yl]-N-(2-methylpropane-1-sulfonyl)-1-phenyl-1H-pyrazolo[3,4-b]pyridine-6-carboxamide;

methyl ({3-cyclobutyl-4-[4-(methoxymethyl)piperidin-1-yl]-1-phenyl-1H-pyrazolo[3,4-b]pyridine-6-carbonyl}sulfamoyl)acetate;

benzyl 3-({3-cyclobutyl-4-[4-(methoxymethyl)piperidin-1-yl]-1-phenyl-1H-pyrazolo[3,4-b]pyridine-6-carbonyl}sulfamoyl)pyrrolidine-1-carboxylate;

tert-butyl 4-[1-(4-fluorophenyl)-6-[(methanesulfonyl)carbamoyl]-3-(propan-2-yl)-1H-pyrazolo[3,4-b]pyridin-4-yl]piperidine-1-carboxylate;

3-cyclobutyl-N-(dimethylsulfamoyl)-1-(4-fluorophenyl)-4-{4-[2-(methoxymethyl)morpholin-4-yl]piperidin-1-yl}-1H-pyrazolo[3,4-b]pyridine-6-carboxamide;

3-cyclobutyl-N-(morpholine-4-sulfonyl)-1-phenyl-4-{4-[(pyrrolidin-1-yl)methyl]piperidin-1-yl}-1H-pyrazolo[3,4-b]pyridine-6-carboxamide;

3-cyclobutyl-N-(dimethylsulfamoyl)-1-(4-fluorophenyl)-4-(4-methoxy[1,4'-bipiperidin]-1'-yl)-1H-pyrazolo[3,4-b]pyridine-6-carboxamide;

3-cyclobutyl-N-(dimethylsulfamoyl)-1-(4-fluorophenyl)-4-{4-[4-(propan-2-yl)piperazin-1-yl]piperidin-1-yl})-1H-pyrazolo[3,4-b]pyridine-6-carboxamide;

3-cyclobutyl-N-(morpholine-4-sulfonyl)-4-[4-(morpholin-4-yl)piperidin-1-yl]-1-phenyl-1H-pyrazolo[3,4-b]pyridine-6-carboxamide;

N-(2-amino-2-oxoethanesulfonyl)-3-cyclobutyl-4-[4-(methoxymethyl)piperidin-1-yl]-1-phenyl-1H-pyrazolo[3,4-b]pyridine-6-carboxamide;

3-cyclobutyl-N-(methanesulfonyl)-4-[4-(methoxymethyl)piperidin-1-yl]-1-(2-methoxypyridin-4-yl)-1H-pyrazolo[3,4-b]pyridine-6-carboxamide;

N-(2-acetamidoethanesulfonyl)-3-cyclobutyl-4-[4-(methoxymethyl)piperidin-1-yl]-1-phenyl-1H-pyrazolo[3,4-b]pyridine-6-carboxamide;

3-cyclobutyl-4-[4-(methoxymethyl)piperidin-1-yl]-1-phenyl-N-(pyrrolidine-3-sulfonyl)-1H-pyrazolo[3,4-b]pyridine-6-carboxamide;

3-cyclobutyl-4-[4-(methoxymethyl)piperidin-1-yl]-1-phenyl-N-[4-(pyrrolidin-1-yl)piperidine-1-sulfonyl]-1H-pyrazolo[3,4-b]pyridine-6-carboxamide;

3-cyclobutyl-4-[4-(methoxymethyl)piperidin-1-yl]-N-[(2S)-2-(4-methylpiperazine-1-carbonyl)pyrrolidine-1-sulfonyl]-1-phenyl-1H-pyrazolo[3,4-b]pyridine-6-carboxamide;

3-cyclobutyl-4-[4-(methoxymethyl)piperidin-1-yl]-N-{4-[(2S)-2-(methoxymethyl)pyrrolidin-1-yl]piperidine-1-sulfonyl}-1-phenyl-1H-pyrazolo[3,4-b]pyridine-6-carboxamide;

3-cyclobutyl-4-[4-(methoxymethyl)piperidin-1-yl]-N-[methyl(propyl)sulfamoyl]-1-phenyl-1H-pyrazolo[3,4-b]pyridine-6-carboxamide;

3-cyclobutyl-N-[ethyl(propyl)sulfamoyl]-4-[4-(methoxymethyl)piperidin-1-yl]-1-phenyl-1H-pyrazolo[3,4-b]pyridine-6-carboxamide;

ethyl 4-[({3-cyclobutyl-4-[4-(methoxymethyl)piperidin-1-yl]-1-phenyl-1H-pyrazolo[3,4-b]pyridine-6-carbonyl}sulfamoyl)amino]piperidine-1-carboxylate;

N-(4-acetyl-1,4-diazepane-1-sulfonyl)-3-cyclobutyl-4-[4-(methoxymethyl)piperidin-1-yl]-1-phenyl-1H-pyrazolo[3,4-b]pyridine-6-carboxamide;

3-cyclobutyl-4-[4-(methoxymethyl)piperidin-1-yl]-N-{4-[(2R)-2-(methoxymethyl)pyrrolidin-1-yl]piperidine-1-sulfonyl}-1-phenyl-1H-pyrazolo[3,4-b]pyridine-6-carboxamide;

3-cyclobutyl-4-[4-(methoxymethyl)piperidin-1-yl]-N-(morpholine-4-sulfonyl)-1-phenyl-1H-pyrazolo[3,4-b]pyridine-6-carboxamide;

3-cyclobutyl-4-[4-(methoxymethyl)piperidin-1-yl]-N-[4-(morpholin-4-yl)piperidine-1-sulfonyl]-1-phenyl-1H-pyrazolo[3,4-b]pyridine-6-carboxamide;

3-cyclobutyl-4-[4-(methoxymethyl)piperidin-1-yl]-N-[4-(4-methylpiperazine-1-carbonyl)piperidine-1-sulfonyl]-1-phenyl-1H-pyrazolo[3,4-b]pyridine-6-carboxamide;

3-cyclobutyl-N-(4-fluoropiperidine-1-sulfonyl)-4-[4-(methoxymethyl)piperidin-1-yl]-1-phenyl-1H-pyrazolo[3,4-b]pyridine-6-carboxamide;

3-cyclobutyl-4-[4-(methoxymethyl)piperidin-1-yl]-N-(4-methylpiperazine-1-sulfonyl)-1-phenyl-1H-pyrazolo[3,4-b]pyridine-6-carboxamide;

3-cyclobutyl-N-(cyclopropanesulfonyl)-4-[4-(methoxymethyl)piperidin-1-yl]-1-phenyl-1H-pyrazolo[3,4-b]pyridine-6-carboxamide;

3-cyclobutyl-N-(dimethylsulfamoyl)-4-[4-(methoxymethyl)piperidin-1-yl]-1-phenyl-1H-pyrazolo[3,4-b]pyridine-6-carboxamide;

3-cyclobutyl-N-(ethanesulfonyl)-4-[4-(methoxymethyl)piperidin-1-yl]-1-phenyl-1H-pyrazolo[3,4-b]pyridine-6-carboxamide;

1-cyclohexyl-N-(methanesulfonyl)-4-{4-[(morpholin-4-yl)methyl]phenyl}-3-[(propan-2-yl)oxy]-1H-pyrazolo[3,4-b]pyridine-6-carboxamide;

1-cyclohexyl-N-(2-methoxyethanesulfonyl)-4-{4-[(morpholin-4-yl)methyl]phenyl}-3-[(propan-2-yl)oxy]-1H-pyrazolo[3,4-b]pyridine-6-carboxamide;

1-cyclohexyl-N-(dimethylsulfamoyl)-4-{4-[(morpholin-4-yl)methyl]phenyl}-3-[(propan-2-yl)oxy]-1H-pyrazolo[3,4-b]pyridine-6-carboxamide;

3-cyclobutyl-1-(4-fluorophenyl)-N-(2-methoxyethanesulfonyl)-4-[4-(morpholin-4-yl)piperidin-1-yl]-1H-pyrazolo[3,4-b]pyridine-6-carboxamide;

3-cyclobutyl-N-(dimethylsulfamoyl)-1-(4-fluorophenyl)-4-[4-(morpholin-4-yl)piperidin-1-yl]-1H-pyrazolo[3,4-b]pyridine-6-carboxamide;

3-cyclobutyl-N-(dimethylsulfamoyl)-1-(4-fluorophenyl)-4-{4-[(morpholin-4-yl)methyl]piperidin-1-yl}-1H-pyrazolo[3,4-b]pyridine-6-carboxamide;

3-cyclobutyl-1-(4-fluorophenyl)-N-(methanesulfonyl)-4-{4-[(morpholin-4-yl)methyl]piperidin-1-yl}-1H-pyrazolo[3,4-b]pyridine-6-carboxamide;

1-(4-fluorophenyl)-N-(methanesulfonyl)-4-[4-(morpholin-4-yl)piperidin-1-yl]-3-(propan-2-yl)-1H-pyrazolo[3,4-b]pyridine-6-carboxamide;

N-(dimethylsulfamoyl)-1-(4-fluorophenyl)-4-[4-(morpholin-4-yl)piperidin-1-yl]-3-(propan-2-yl)-1H-pyrazolo[3,4-b]pyridine-6-carboxamide;

N-(ethanesulfonyl)-1-(4-fluorophenyl)-4-[4-(morpholin-4-yl)piperidin-1-yl]-3-(propan-2-yl)-1H-pyrazolo[3,4-b]pyridine-6-carboxamide;

N-(cyclopropanesulfonyl)-1-(4-fluorophenyl)-4-[4-(morpholin-4-yl)piperidin-1-yl]-3-(propan-2-yl)-1H-pyrazolo[3,4-b]pyridine-6-carboxamide;

3-cyclobutyl-1-(4-fluorophenyl)-N-(2-methoxyethanesulfonyl)-4-{4-[2-(morpholin-4-yl)ethyl]piperidin-1-yl}-1H-pyrazolo[3,4-b]pyridine-6-carboxamide;

3-cyclobutyl-N-(dimethylsulfamoyl)-1-(4-fluorophenyl)-4-{4-[2-(morpholin-4-yl)ethyl]piperidin-1-yl}-1H-pyrazolo[3,4-b]pyridine-6-carboxamide;

3-cyclobutyl-N-[(1,4-dioxan-2-yl)methanesulfonyl]-4-[4-(methoxymethyl)piperidin-1-yl]-1-phenyl-1H-pyrazolo[3,4-b]pyridine-6-carboxamide;

3-cyclobutyl-1-cyclohexyl-N-(methanesulfonyl)-4-[4-(morpholin-4-yl)piperidin-1-yl]-1H-pyrazolo[3,4-b]pyridine-6-carboxamide;

3-cyclobutyl-1-cyclohexyl-N-(2-methoxyethanesulfonyl)-4-[4-(morpholin-4-yl)piperidin-1-yl]-1H-pyrazolo[3,4-b]pyridine-6-carboxamide;

3-cyclobutyl-1-cyclohexyl-N-(dimethylsulfamoyl)-4-[4-(morpholin-4-yl)piperidin-1-yl]-1H-pyrazolo[3,4-b]pyridine-6-carboxamide;

3-cyclobutyl-1-(4-fluorophenyl)-N-(methanesulfonyl)-4-[4-(morpholin-4-yl)piperidin-1-yl]-1H-pyrazolo[3,4-b]pyridine-6-carboxamide;

1-cyclohexyl-N-(methanesulfonyl)-4-[4-(4-methylpiperazine-1-carbonyl)phenyl]-3-[(propan-2-yl)oxy]-1H-pyrazolo[3,4-b]pyridine-6-carboxamide;

1-cyclohexyl-N-(dimethylsulfamoyl)-4-[4-(4-methylpiperazine-1-carbonyl)phenyl]-3-[(propan-2-yl)oxy]-1H-pyrazolo[3,4-b]pyridine-6-carboxamide;

3-cyclobutyl-1-cyclohexyl-N-(dimethylsulfamoyl)-4-{4-[(morpholin-4-yl)methyl]piperidin-1-yl}-1H-pyrazolo[3,4-b]pyridine-6-carboxamide;

3-cyclobutyl-1-cyclohexyl-N-(dimethylsulfamoyl)-4-{4-[2-(morpholin-4-yl)ethyl]piperidin-1-yl}-1H-pyrazolo[3,4-b]pyridine-6-carboxamide;

4-([1,4'-bipiperidin]-1'-yl)-3-cyclobutyl-N-(dimethylsulfamoyl)-1-phenyl-1H-pyrazolo[3,4-b]pyridine-6-carboxamide;

4-([1,4'-bipiperidin]-1'-yl)-3-cyclobutyl-N-(ethanesulfonyl)-1-phenyl-1H-pyrazolo[3,4-b]pyridine-6-carboxamide;

4-([1,4'-bipiperidin]-1'-yl)-3-cyclobutyl-N-(cyclopropanesulfonyl)-1-phenyl-1H-pyrazolo[3,4-b]pyridine-6-carboxamide;

3-cyclobutyl-1-(4-fluorophenyl)-4-[4-(morpholin-4-yl)piperidin-1-yl]-N-(oxolane-3-sulfonyl)-1H-pyrazolo[3,4-b]pyridine-6-carboxamide;

3-cyclobutyl-N-(methanesulfonyl)-4-[4-(methoxymethyl)piperidin-1-yl]-1-(2-methylpyridin-4-yl)-1H-pyrazolo[3,4-b]pyridine-6-carboxamide;

3-cyclobutyl-1-(4-fluorophenyl)-N-(methanesulfonyl)-4-{4-[2-(morpholin-4-yl)ethyl]piperidin-1-yl}-1H-pyrazolo[3,4-b]pyridine-6-carboxamide;

3-cyclobutyl-N-[methyl(propyl)sulfamoyl]-4-[4-(morpholin-4-yl)piperidin-1-yl]-1-phenyl-1H-pyrazolo[3,4-b]pyridine-6-carboxamide;

ethyl 4-[({3-cyclobutyl-4-[4-(morpholin-4-yl)piperidin-1-yl]-1-phenyl-1H-pyrazolo[3,4-b]pyridine-6-carbonyl}sulfamoyl)amino]piperidine-1-carboxylate;

3-cyclobutyl-N-(4-fluoropiperidine-1-sulfonyl)-4-[4-(morpholin-4-yl)piperidin-1-yl]-1-phenyl-1H-pyrazolo[3,4-b]pyridine-6-carboxamide;

3-cyclobutyl-N-(1-methylcyclopropane-1-sulfonyl)-4-[4-(morpholin-4-yl)piperidin-1-yl]-1-phenyl-1H-pyrazolo[3,4-b]pyridine-6-carboxamide;

3-cyclobutyl-N-(cyclopropanesulfonyl)-4-[4-(morpholin-4-yl)piperidin-1-yl]-1-phenyl-1H-pyrazolo[3,4-b]pyridine-6-carboxamide;

3-cyclobutyl-N-(ethanesulfonyl)-4-[4-(morpholin-4-yl)piperidin-1-yl]-1-phenyl-1H-pyrazolo[3,4-b]pyridine-6-carboxamide;

3-cyclobutyl-N-(2-methoxyethanesulfonyl)-4-[4-(morpholin-4-yl)piperidin-1-yl]-1-phenyl-1H-pyrazolo[3,4-b]pyridine-6-carboxamide;

3-cyclobutyl-N-{4-[(2S)-2-(methoxymethyl)pyrrolidin-1-yl]piperidine-1-sulfonyl}-4-[4-(morpholin-4-yl)piperidin-1-yl]-1-phenyl-1H-pyrazolo[3,4-b]pyridine-6-carboxamide;

3-cyclobutyl-N-(dimethylsulfamoyl)-1-(4-fluorophenyl)-4-{4-[1-(morpholin-4-yl)ethyl]piperidin-1-yl}-1H-pyrazolo[3,4-b]pyridine-6-carboxamide;

1-cyclohexyl-N-(methanesulfonyl)-4-{4-[(4-methylpiperazin-1-yl)methyl]phenyl}-3-[(propan-2-yl)oxy]-1H-pyrazolo[3,4-b]pyridine-6-carboxamide;

1-cyclohexyl-N-(dimethylsulfamoyl)-4-{4-[(4-methylpiperazin-1-yl)methyl]phenyl}-3-[(propan-2-yl)oxy]-1H-pyrazolo[3,4-b]pyridine-6-carboxamide;

1-cyclohexyl-N-(dimethylsulfamoyl)-4-{4-[(piperidin-1-yl)methyl]phenyl}-3-[(propan-2-yl)oxy]-1H-pyrazolo[3,4-b]pyridine-6-carboxamide;

1-cyclohexyl-N-(dimethylsulfamoyl)-3-[(propan-2-yl)oxy]-4-{4-[(pyrrolidin-1-yl)methyl]phenyl}-1H-pyrazolo[3,4-b]pyridine-6-carboxamide;

3-cyclobutyl-1-(4-fluorophenyl)-N-(methanesulfonyl)-4-{4-[1-(morpholin-4-yl)ethyl]piperidin-1-yl}-1H-pyrazolo[3,4-b]pyridine-6-carboxamide;

3-cyclobutyl-N-(ethanesulfonyl)-1-(4-fluorophenyl)-4-{4-[1-(morpholin-4-yl)ethyl]piperidin-1-yl}-1H-pyrazolo[3,4-b]pyridine-6-carboxamide;

3-cyclobutyl-1-(4-fluorophenyl)-N-(2-methoxyethanesulfonyl)-4-{4-[(morpholin-4-yl)methyl]piperidin-1-yl}-1H-pyrazolo[3,4-b]pyridine-6-carboxamide;

3-cyclobutyl-1-(4-fluorophenyl)-N-(2-hydroxyethanesulfonyl)-4-[4-(morpholin-4-yl)piperidin-1-yl]-1H-pyrazolo[3,4-b]pyridine-6-carboxamide;

N-(chloromethanesulfonyl)-3-cyclobutyl-4-[4-(methoxymethyl)piperidin-1-yl]-1-phenyl-1H-pyrazolo[3,4-b]pyridine-6-carboxamide;

4-([1,4'-bipiperidin]-1'-yl)-3-cyclobutyl-1-(4-fluorophenyl)-N-(methanesulfonyl)-1H-pyrazolo[3,4-b]pyridine-6-carboxamide;

4-([1,4'-bipiperidin]-1'-yl)-3-cyclobutyl-1-(4-fluorophenyl)-N-(oxolane-3-sulfonyl)-1H-pyrazolo[3,4-b]pyridine-6-carboxamide;

3-cyclobutyl-1-(4-fluorophenyl)-4-{4-[2-(morpholin-4-yl)ethyl]piperidin-1-yl}-N-(oxolane-3-sulfonyl)-1H-pyrazolo[3,4-b]pyridine-6-carboxamide;

N-([1,4'-bipiperidine]-1'-sulfonyl)-3-cyclobutyl-4-[4-(morpholin-4-yl)piperidin-1-yl]-1-phenyl-1H-pyrazolo[3,4-b]pyridine-6-carboxamide;

4-([1,4'-bipiperidin]-1'-yl)-3-cyclobutyl-N-[3-(morpholin-4-yl)propane-1-sulfonyl]-1-phenyl-1H-pyrazolo[3,4-b]pyridine-6-carboxamide;

3-cyclobutyl-N-(4-methylpiperazine-1-sulfonyl)-4-[4-(morpholin-4-yl)piperidin-1-yl]-1-phenyl-1H-pyrazolo[3,4-b]pyridine-6-carboxamide;

3-cyclobutyl-N-(dimethylsulfamoyl)-4-[4-(morpholin-4-yl)piperidin-1-yl]-1-phenyl-1H-pyrazolo[3,4-b]pyridine-6-carboxamide;

ethyl 4-{[(3-cyclobutyl-1-phenyl-4-{4-[(pyrrolidin-1-yl)methyl]piperidin-1-yl}-1H-pyrazolo[3,4-b]pyridine-6-carbonyl)sulfamoyl]amino}piperidine-1-carboxylate;

3-cyclobutyl-N-{4-[(2R)-2-(methoxymethyl)pyrrolidin-1-yl]piperidine-1-sulfonyl}-1-phenyl-4-{4-[(pyrrolidin-1-yl)methyl]piperidin-1-yl}-1H-pyrazolo[3,4-b]pyridine-6-carboxamide;

3-cyclobutyl-N-(4-fluoropiperidine-1-sulfonyl)-1-phenyl-4-{4-[(pyrrolidin-1-yl)methyl]piperidin-1-yl}-1H-pyrazolo[3,4-b]pyridine-6-carboxamide;

3-cyclobutyl-N-(4-methylpiperazine-1-sulfonyl)-1-phenyl-4-{4-[(pyrrolidin-1-yl)methyl]piperidin-1-yl}-1H-pyrazolo[3,4-b]pyridine-6-carboxamide;

3-cyclobutyl-N-(1-methylcyclopropane-1-sulfonyl)-1-phenyl-4-{4-[(pyrrolidin-1-yl)methyl]piperidin-1-yl}-1H-pyrazolo[3,4-b]pyridine-6-carboxamide;

3-cyclobutyl-N-(cyclopropanesulfonyl)-1-phenyl-4-{4-[(pyrrolidin-1-yl)methyl]piperidin-1-yl}-1H-pyrazolo[3,4-b]pyridine-6-carboxamide;

3-cyclobutyl-N-(ethanesulfonyl)-1-phenyl-4-{4-[(pyrrolidin-1-yl)methyl]piperidin-1-yl}-1H-pyrazolo[3,4-b]pyridine-6-carboxamide;

3-cyclobutyl-N-(2-methoxyethanesulfonyl)-1-phenyl-4-{4-[(pyrrolidin-1-yl)methyl]piperidin-1-yl}-1H-pyrazolo[3,4-b]pyridine-6-carboxamide;

3-cyclobutyl-N-(2-methylpropane-2-sulfonyl)-1-phenyl-4-{4-[(pyrrolidin-1-yl)methyl]piperidin-1-yl}-1H-pyrazolo[3,4-b]pyridine-6-carboxamide;

3-cyclobutyl-N-(ethanesulfonyl)-1-(4-fluorophenyl)-4-[4-(morpholin-4-yl)piperidin-1-yl]-1H-pyrazolo[3,4-b]pyridine-6-carboxamide;

3-(cyclobutyloxy)-1-cyclohexyl-4-{4-[(morpholin-4-yl)methyl]phenyl}-N-(oxolane-3-sulfonyl)-1H-pyrazolo[3,4-b]pyridine-6-carboxamide;

3-cyclobutyl-1-cyclohexyl-N-(oxolane-3-sulfonyl)-4-[4-(pyridin-4-yl)piperazin-1-yl]-1H-pyrazolo[3,4-b]pyridine-6-carboxamide;

3-cyclobutyl-1-cyclohexyl-N-(dimethylsulfamoyl)-4-[4-(pyridin-4-yl)piperazin-1-yl]-1H-pyrazolo[3,4-b]pyridine-6-carboxamide;

3-cyclobutyl-1-cyclohexyl-N-(ethanesulfonyl)-4-[4-(pyridin-4-yl)piperazin-1-yl]-1H-pyrazolo[3,4-b]pyridine-6-carboxamide;

3-cyclobutyl-1-(4-fluorophenyl)-N-[(2-methoxyethyl)(methyl)sulfamoyl]-4-[4-(morpholin-4-yl)piperidin-1-yl]-1H-pyrazolo[3,4-b]pyridine-6-carboxamide;

4-([1,4'-bipiperidin]-1'-yl)-3-cyclobutyl-N-(dimethylsulfamoyl)-1-(4-fluorophenyl)-1H-pyrazolo[3,4-b]pyridine-6-carboxamide;

3-cyclobutyl-N-(methanesulfonyl)-4-[4-(methoxymethyl)piperidin-1-yl]-1-[2-(oxan-4-yl)pyridin-4-yl]-1H-pyrazolo[3,4-b]pyridine-6-carboxamide;

3-cyclobutyl-N-(methanesulfonyl)-1-(2-methoxypyridin-4-yl)-4-[4-(morpholin-4-yl)piperidin-1-yl]-1H-pyrazolo[3,4-b]pyridine-6-carboxamide;

3-cyclobutyl-1-cyclohexyl-N-(dimethylsulfamoyl)-4-{4-[(morpholin-4-yl)methyl]phenyl}-1H-pyrazolo[3,4-b]pyridine-6-carboxamide;

3-cyclobutyl-1-cyclohexyl-N-(dimethylsulfamoyl)-4-{4-[2-(morpholin-4-yl)ethyl]phenyl}-1H-pyrazolo[3,4-b]pyridine-6-carboxamide;

N-(but-3-yne-1-sulfonyl)-3-cyclobutyl-1-(4-fluorophenyl)-4-[4-(morpholin-4-yl)piperidin-1-yl]-1H-pyrazolo[3,4-b]pyridine-6-carboxamide;

4-([1,4'-bipiperidin]-1'-yl)-3-cyclobutyl-N-(ethanesulfonyl)-1-(4-fluorophenyl)-1H-pyrazolo[3,4-b]pyridine-6-carboxamide;

3-cyclobutyl-N-(dimethylsulfamoyl)-1-(4-fluorophenyl)-4-{4-[(1R)-1-(morpholin-4-yl)ethyl]piperidin-1-yl}-1H-pyrazolo[3,4-b]pyridine-6-carboxamide;

3-cyclobutyl-N-(dimethylsulfamoyl)-1-(4-fluorophenyl)-4-{4-[(1S)-1-(morpholin-4-yl)ethyl]piperidin-1-yl}-1H-pyrazolo[3,4-b]pyridine-6-carboxamide;

3-(cyclobutyloxy)-1-cyclohexyl-N-(dimethylsulfamoyl)-4-{4-[(morpholin-4-yl)methyl]phenyl}-1H-pyrazolo[3,4-b]pyridine-6-carboxamide;

3-cyclobutyl-1-(4-fluorophenyl)-N-[methyl(propan-2-yl)sulfamoyl]-4-[4-(morpholin-4-yl)piperidin-1-yl]-1H-pyrazolo[3,4-b]pyridine-6-carboxamide;

3-cyclobutyl-N-[ethyl(methyl)sulfamoyl]-1-(4-fluorophenyl)-4-[4-(morpholin-4-yl)piperidin-1-yl]-1H-pyrazolo[3,4-b]pyridine-6-carboxamide;

3-cyclobutyl-1-(4-fluorophenyl)-N-(3-methoxyazetidine-1-sulfonyl)-4-[4-(morpholin-4-yl)piperidin-1-yl]-1H-pyrazolo[3,4-b]pyridine-6-carboxamide;

3-cyclobutyl-1-(4-fluorophenyl)-4-[4-(morpholin-4-yl)piperidin-1-yl]-N-(pyrrolidine-1-sulfonyl)-1H-pyrazolo[3,4-b]pyridine-6-carboxamide;

3-cyclobutyl-1-(4-fluorophenyl)-4-[4-(morpholin-4-yl)piperidin-1-yl]-N-(2,2,2-trifluoroethanesulfonyl)-1H-pyrazolo[3,4-b]pyridine-6-carboxamide;

3-cyclobutyl-1-(4-fluorophenyl)-N-(morpholine-4-sulfonyl)-4-[4-(morpholin-4-yl)piperidin-1-yl]-1H-pyrazolo[3,4-b]pyridine-6-carboxamide;

4-([1,4'-bipiperidin]-1'-yl)-3-cyclobutyl-1-(4-fluorophenyl)-N-(2-methoxyethanesulfonyl)-1H-pyrazolo[3,4-b]pyridine-6-carboxamide;

N-(dimethylsulfamoyl)-1-[2-(morpholin-4-yl)pyridin-4-yl]-4-[(oxan-4-yl)methoxy]-3-(propan-2-yl)-1H-pyrazolo[3,4-b]pyridine-6-carboxamide;

3-cyclobutyl-N-(methanesulfonyl)-4-[4-(morpholin-4-yl)piperidin-1-yl]-1-[2-(oxan-4-yl)pyridin-4-yl]-1H-pyrazolo[3,4-b]pyridine-6-carboxamide;

3-cyclobutyl-1-(4-fluorophenyl)-N-(2-hydroxyethanesulfonyl)-4-{4-[2-(morpholin-4-yl)ethyl]piperidin-1-yl}-1H-pyrazolo[3,4-b]pyridine-6-carboxamide;

methyl 4-(1-{3-cyclobutyl-6-[(dimethylsulfamoyl)carbamoyl]-1-(4-fluorophenyl)-1H-pyrazolo[3,4-b]pyridin-4-yl}piperidin-4-yl)piperazine-1-carboxylate;

4-[4-(4-acetylpiperazin-1-yl)piperidin-1-yl]-3-cyclobutyl-N-(dimethylsulfamoyl)-1-(4-fluorophenyl)-1H-pyrazolo[3,4-b]pyridine-6-carboxamide;

3-cyclobutyl-N-(ethanesulfonyl)-1-(4-fluorophenyl)-4-{4-[(morpholin-4-yl)methyl]piperidin-1-yl}-1H-pyrazolo[3,4-b]pyridine-6-carboxamide;

3-cyclobutyl-1-(4-fluorophenyl)-4-{4-[(morpholin-4-yl)methyl]piperidin-1-yl}-N-(oxolane-3-sulfonyl)-1H-pyrazolo[3,4-b]pyridine-6-carboxamide;

ethyl 4-[1-(4-fluorophenyl)-6-[(methanesulfonyl)carbamoyl]-3-(propan-2-yl)-1H-pyrazolo[3,4-b]pyridin-4-yl]piperidine-1-carboxylate;

ethyl 4-{6-[(dimethylsulfamoyl)carbamoyl]-1-(4-fluorophenyl)-3-(propan-2-yl)-1H-pyrazolo[3,4-b]pyridin-4-yl}piperidine-1-carboxylate;

3-cyclobutyl-N-(dimethylsulfamoyl)-1-(3-methylphenyl)-4-[4-(morpholin-4-yl)piperidin-1-yl]-1H-pyrazolo[3,4-b]pyridine-6-carboxamide;

3-cyclobutyl-N-(dimethylsulfamoyl)-1-(3-methoxyphenyl)-4-[4-(morpholin-4-yl)piperidin-1-yl]-1H-pyrazolo[3,4-b]pyridine-6-carboxamide;

3-cyclobutyl-N-(dimethylsulfamoyl)-4-[4-(morpholin-4-yl)piperidin-1-yl]-1-[4-(trifluoromethyl)phenyl]-1H-pyrazolo[3,4-b]pyridine-6-carboxamide;

3-cyclobutyl-4-[4-(ethoxymethyl)-4-fluoropiperidin-1-yl]-N-(methanesulfonyl)-1-phenyl-1H-pyrazolo[3,4-b]pyridine-6-carboxamide;

3-cyclobutyl-4-{4-fluoro-4-[(2-methoxyethoxy)methyl]piperidin-1-yl}-N-(methanesulfonyl)-1-phenyl-1H-pyrazolo[3,4-b]pyridine-6-carboxamide;

3-cyclobutyl-4-{3-fluoro-3-[(2-methoxyethoxy)methyl]piperidin-1-yl}-N-(methanesulfonyl)-1-phenyl-1H-pyrazolo[3,4-b]pyridine-6-carboxamide;

3-cyclobutyl-4-[4-fluoro-4-(methoxymethyl)piperidin-1-yl]-N-(methanesulfonyl)-1-phenyl-1H-pyrazolo[3,4-b]pyridine-6-carboxamide;

N-(4-cyanopiperidine-1-sulfonyl)-3-cyclobutyl-1-(4-fluorophenyl)-4-[4-(morpholin-4-yl)piperidin-1-yl]-1H-pyrazolo[3,4-b]pyridine-6-carboxamide;

3-cyclobutyl-1-(4-fluorophenyl)-4-[4-(morpholin-4-yl)piperidin-1-yl]-N-(oxetane-3-sulfonyl)-1H-pyrazolo[3,4-b]pyridine-6-carboxamide;

3-cyclobutyl-N-(cyclopropanesulfonyl)-1-(4-fluorophenyl)-4-[4-(morpholin-4-yl)piperidin-1-yl]-1H-pyrazolo[3,4-b]pyridine-6-carboxamide;

3-cyclobutyl-1-(4-fluorophenyl)-N-(1-methylcyclopropane-1-sulfonyl)-4-[4-(morpholin-4-yl)piperidin-1-yl]-1H-pyrazolo[3,4-b]pyridine-6-carboxamide;

3-cyclobutyl-N-(methanesulfonyl)-1-(3-methylphenyl)-4-[4-(morpholin-4-yl)piperidin-1-yl]-1H-pyrazolo[3,4-b]pyridine-6-carboxamide;

3-cyclobutyl-N-(methanesulfonyl)-4-[4-(morpholin-4-yl)piperidin-1-yl]-1-[4-(trifluoromethyl)phenyl]-1H-pyrazolo[3,4-b]pyridine-6-carboxamide;

3-cyclobutyl-N-(dimethylsulfamoyl)-1-(4-fluoro-3-methylphenyl)-4-[4-(morpholin-4-yl)piperidin-1-yl]-1H-pyrazolo[3,4-b]pyridine-6-carboxamide;

3-cyclobutyl-N-(dimethylsulfamoyl)-1-(3-fluorophenyl)-4-[4-(morpholin-4-yl)piperidin-1-yl]-1H-pyrazolo[3,4-b]pyridine-6-carboxamide;

3-cyclobutyl-N-(dimethylsulfamoyl)-4-[4-(morpholin-4-yl)piperidin-1-yl]-1-[3-(trifluoromethyl)phenyl]-1H-pyrazolo[3,4-b]pyridine-6-carboxamide;

3-cyclobutyl-1-(4-fluoro-3-methylphenyl)-N-(methanesulfonyl)-4-[4-(morpholin-4-yl)piperidin-1-yl]-1H-pyrazolo[3,4-b]pyridine-6-carboxamide;

3-cyclobutyl-1-(3-fluorophenyl)-N-(methanesulfonyl)-4-[4-(morpholin-4-yl)piperidin-1-yl]-1H-pyrazolo[3,4-b]pyridine-6-carboxamide;

3-cyclobutyl-N-(methanesulfonyl)-4-[4-(morpholin-4-yl)piperidin-1-yl]-1-[3-(trifluoromethyl)phenyl]-1H-pyrazolo[3,4-b]pyridine-6-carboxamide;

3-cyclobutyl-1-(4-fluorophenyl)-N-(methylsulfamoyl)-4-[4-(morpholin-4-yl)piperidin-1-yl]-1H-pyrazolo[3,4-b]pyridine-6-carboxamide;

3-cyclobutyl-1-(4-fluorophenyl)-N-(methanesulfonyl)-4-[(4-methylpiperazin-1-yl)methyl]-1H-pyrazolo[3,4-b]pyridine-6-carboxamide;

3-cyclobutyl-1-(4-fluorophenyl)-N-(methanesulfonyl)-4-[(morpholin-4-yl)methyl]-1H-pyrazolo[3,4-b]pyridine-6-carboxamide;

3-cyclobutyl-N-(dimethylsulfamoyl)-1-(4-fluorophenyl)-4-[(morpholin-4-yl)methyl]-1H-pyrazolo[3,4-b]pyridine-6-carboxamide;

3-cyclobutyl-N-(dimethylsulfamoyl)-1-(4-fluorophenyl)-4-{[4-(methoxymethyl)piperidin-1-yl]methyl}-1H-pyrazolo[3,4-b]pyridine-6-carboxamide;

4-(4-cyano[1,4'-bipiperidin]-1'-yl)-3-cyclobutyl-N-(dimethylsulfamoyl)-1-(4-fluorophenyl)-1H-pyrazolo[3,4-b]pyridine-6-carboxamide;

4-[4-(3-cyanoazetidin-1-yl)piperidin-1-yl]-3-cyclobutyl-N-(dimethylsulfamoyl)-1-(4-fluorophenyl)-1H-pyrazolo[3,4-b]pyridine-6-carboxamide;

3-cyclobutyl-N-(dimethylsulfamoyl)-1-(4-fluorophenyl)-4-[4-(3-methoxypyrrolidin-1-yl)piperidin-1-yl]-1H-pyrazolo[3,4-b]pyridine-6-carboxamide;

3-cyclobutyl-N-(dimethylsulfamoyl)-4-(4-fluoro[1,4'-bipiperidin]-1'-yl)-1-(4-fluorophenyl)-1H-pyrazolo[3,4-b]pyridine-6-carboxamide;

3-cyclobutyl-4-(4,4-difluoro[1,4'-bipiperidin]-1'-yl)-N-(dimethylsulfamoyl)-1-(4-fluorophenyl)-1H-pyrazolo[3,4-b]pyridine-6-carboxamide;

4-[4-(2-cyanomorpholin-4-yl)piperidin-1-yl]-3-cyclobutyl-N-(dimethylsulfamoyl)-1-(4-fluorophenyl)-1H-pyrazolo[3,4-b]pyridine-6-carboxamide;

3-cyclobutyl-N-(dimethylsulfamoyl)-1-(4-fluorophenyl)-4-{4-[methyl(oxan-4-yl)amino]piperidin-1-yl}-1H-pyrazolo[3,4-b]pyridine-6-carboxamide;

3-cyclobutyl-N-(dimethylsulfamoyl)-4-[4-(morpholin-4-yl)piperidin-1-yl]-1-{2-[(propan-2-yl)oxy]pyridin-4-yl}-1H-pyrazolo[3,4-b]pyridine-6-carboxamide;

3-cyclobutyl-N-(methanesulfonyl)-4-[4-(morpholin-4-yl)piperidin-1-yl]-1-{2-[(propan-2-yl)oxy]pyridin-4-yl}-1H-pyrazolo[3,4-b]pyridine-6-carboxamide;

3-cyclobutyl-N-(dimethylsulfamoyl)-4-[4-(methoxymethyl)piperidin-1-yl]-1-[2-(oxan-4-yl)pyridin-4-yl]-1H-pyrazolo[3,4-b]pyridine-6-carboxamide;

3-cyclobutyl-N-(dimethylsulfamoyl)-1-(4-fluorophenyl)-4-[4-(2-oxa-5-azabicyclo[2.2.1]heptan-5-yl)piperidin-1-yl]-1H-pyrazolo[3,4-b]pyridine-6-carboxamide;

3-cyclobutyl-N-(dimethylsulfamoyl)-1-(4-fluorophenyl)-4-[3-(morpholin-4-yl)-1-oxa-8-azaspiro[4.5]decan-8-yl]-1H-pyrazolo[3,4-b]pyridine-6-carboxamide;

1-cyclohexyl-N-(dimethylsulfamoyl)-3-[(propan-2-yl)oxy]-4-{4-[4-(propan-2-yl)piperazin-1-yl]phenyl}-1H-pyrazolo[3,4-b]pyridine-6-carboxamide;

3-cyclobutyl-1-cyclohexyl-N-(dimethylsulfamoyl)-4-[(2-methylpyridin-4-yl)piperazin-1-yl]-1H-pyrazolo[3,4-b]pyridine-6-carboxamide;

3-cyclobutyl-1-cyclohexyl-4-[6-(4-cyclopropylpiperazin-1-yl)pyridin-3-yl]-N-(dimethylsulfamoyl)-1H-pyrazolo[3,4-b]pyridine-6-carboxamide;

3-cyclobutyl-1-(4-fluorophenyl)-N-(3-fluoropyrrolidine-1-sulfonyl)-4-[4-(morpholin-4-yl)piperidin-1-yl]-1H-pyrazolo[3,4-b]pyridine-6-carboxamide;

3-cyclobutyl-1-(4-fluorophenyl)-N-(3-methoxypyrrolidine-1-sulfonyl)-4-[4-(morpholin-4-yl)piperidin-1-yl]-1H-pyrazolo[3,4-b]pyridine-6-carboxamide;

4-[6-(4-cyanopiperidin-1-yl)pyridin-3-yl]-3-cyclobutyl-N-(dimethylsulfamoyl)-1-phenyl-1H-pyrazolo[3,4-b]pyridine-6-carboxamide;

3-cyclobutyl-1-(4-fluorophenyl)-N-[4-(methoxymethyl)piperidine-1-sulfonyl]-4-[4-(morpholin-4-yl)piperidin-1-yl]-1H-pyrazolo[3,4-b]pyridine-6-carboxamide;

3-cyclobutyl-N-(dimethylsulfamoyl)-1-(4-fluorophenyl)-4-[4-(3-fluoropyrrolidin-1-yl)piperidin-1-yl]-1H-pyrazolo[3,4-b]pyridine-6-carboxamide;

3-cyclobutyl-1-cyclohexyl-N-(dimethylsulfamoyl)-4-{6-[4-(propan-2-yl)piperazin-1-yl]pyridin-3-yl}-1H-pyrazolo[3,4-b]pyridine-6-carboxamide;

3-cyclobutyl-1-cyclohexyl-N-(dimethylsulfamoyl)-4-{4-[1-(morpholin-4-yl)ethyl]phenyl}-1H-pyrazolo[3,4-b]pyridine-6-carboxamide;

1-cyclohexyl-4-{4-[4-(dimethylamino)piperidine-1-carbonyl]phenyl}-N-(methanesulfonyl)-3-[(propan-2-yl)oxy]-1H-pyrazolo[3,4-b]pyridine-6-carboxamide;

1-cyclohexyl-4-{4-[4-(dimethylamino)piperidine-1-carbonyl]phenyl}-N-(2-methoxyethanesulfonyl)-3-[(propan-2-yl)oxy]-1H-pyrazolo[3,4-b]pyridine-6-carboxamide;

1-cyclohexyl-4-{4-[4-(dimethylamino)piperidine-1-carbonyl]phenyl}-N-(dimethylsulfamoyl)-3-[(propan-2-yl)oxy]-1H-pyrazolo[3,4-b]pyridine-6-carboxamide;

3-cyclobutyl-1-cyclohexyl-N-(dimethylsulfamoyl)-4-{4-[4-(propan-2-yl)piperazin-1-yl]phenyl}-1H-pyrazolo[3,4-b]pyridine-6-carboxamide;

3-cyclobutyl-1-(4-fluorophenyl)-N-(methanesulfonyl)-4-(4-methoxy[1,4'-bipiperidin]-1'-yl)-1H-pyrazolo[3,4-b]pyridine-6-carboxamide;

3-cyclobutyl-4-[4-(4-cyclopropylpiperazin-1-yl)piperidin-1-yl]-N-(dimethylsulfamoyl)-1-phenyl-1H-pyrazolo[3,4-b]pyridine-6-carboxamide;

3-cyclobutyl-N-(cyclopropanesulfonyl)-4-[4-(4-cyclopropylpiperazin-1-yl)piperidin-1-yl]-1-phenyl-1H-pyrazolo[3,4-b]pyridine-6-carboxamide;

3-cyclobutyl-1-cyclohexyl-N-(dimethylsulfamoyl)-4-[6-(4-methylpiperazin-1-yl)pyridin-3-yl]-1H-pyrazolo[3,4-b]pyridine-6-carboxamide;

3-cyclobutyl-1-cyclohexyl-N-(dimethylsulfamoyl)-4-{6-[4-(2-methoxyethyl)piperazin-1-yl]pyridin-3-yl}-1H-pyrazolo[3,4-b]pyridine-6-carboxamide;

3-cyclobutyl-1-cyclohexyl-N-(dimethylsulfamoyl)-4-{4-[4-(propan-2-yl)piperazin-1-yl]piperidin-1-yl}-1H-pyrazolo[3,4-b]pyridine-6-carboxamide;

3-cyclobutyl-4-[4-(4-cyclopropylpiperazin-1-yl)piperidin-1-yl]-N-[methyl(propyl)sulfamoyl]-1-phenyl-1H-pyrazolo[3,4-b]pyridine-6-carboxamide;

3-cyclobutyl-4-[4-(4-cyclopropylpiperazin-1-yl)piperidin-1-yl]-N-(morpholine-4-sulfonyl)-1-phenyl-1H-pyrazolo[3,4-b]pyridine-6-carboxamide;

3-cyclobutyl-4-[4-(4-cyclopropylpiperazin-1-yl)piperidin-1-yl]-N-(methanesulfonyl)-1-phenyl-1H-pyrazolo[3,4-b]pyridine-6-carboxamide;

3-cyclobutyl-4-[4-(4-cyclopropylpiperazin-1-yl)piperidin-1-yl]-N-(1-methylcyclopropane-1-sulfonyl)-1-phenyl-1H-pyrazolo[3,4-b]pyridine-6-carboxamide;

3-cyclobutyl-4-[4-(4-cyclopropylpiperazin-1-yl)piperidin-1-yl]-N-(methylsulfamoyl)-1-phenyl-1H-pyrazolo[3,4-b]pyridine-6-carboxamide;

1-cyclohexyl-4-[4-(4-cyclopropylpiperazin-1-yl)phenyl]-N-(dimethylsulfamoyl)-3-[(propan-2-yl)oxy]-1H-pyrazolo[3,4-b]pyridine-6-carboxamide;

3-cyclobutyl-N-(dimethylsulfamoyl)-1-(4-fluorophenyl)-4-{4-[3-(trifluoromethyl)pyrrolidin-1-yl]piperidin-1-yl}-1H-pyrazolo[3,4-b]pyridine-6-carboxamide;

4-[4-(3-cyanopyrrolidin-1-yl)piperidin-1-yl]-3-cyclobutyl-N-(dimethylsulfamoyl)-1-(4-fluorophenyl)-1H-pyrazolo[3,4-b]pyridine-6-carboxamide;

4-(3-cyano[1,4'-bipiperidin]-1'-yl)-3-cyclobutyl-N-(dimethylsulfamoyl)-1-(4-fluorophenyl)-1H-pyrazolo[3,4-b]pyridine-6-carboxamide;

3-cyclobutyl-N-(dimethylsulfamoyl)-4-(3-fluoro[1,4'-bipiperidin]-1'-yl)-1-(4-fluorophenyl)-1H-pyrazolo[3,4-b]pyridine-6-carboxamide;

3-cyclobutyl-1-(4-fluorophenyl)-N-(methanesulfonyl)-4-{4-[3-(trifluoromethyl)pyrrolidin-1-yl]piperidin-1-yl}-1H-pyrazolo[3,4-b]pyridine-6-carboxamide;

4-[4-(3-cyanopyrrolidin-1-yl)piperidin-1-yl]-3-cyclobutyl-1-(4-fluorophenyl)-N-(methanesulfonyl)-1H-pyrazolo[3,4-b]pyridine-6-carboxamide;

4-(3-cyano[1,4'-bipiperidin]-1'-yl)-3-cyclobutyl-1-(4-fluorophenyl)-N-(methanesulfonyl)-1H-pyrazolo[3,4-b]pyridine-6-carboxamide;

3-cyclobutyl-4-(3-fluoro[1,4'-bipiperidin]-1'-yl)-1-(4-fluorophenyl)-N-(methanesulfonyl)-1H-pyrazolo[3,4-b]pyridine-6-carboxamide;

3-cyclobutyl-1-(4-fluorophenyl)-4-[4-(morpholin-4-yl)piperidin-1-yl]-N-(piperidine-1-sulfonyl)-1H-pyrazolo[3,4-b]pyridine-6-carboxamide;

3-cyclobutyl-N-(3-fluoroazetidine-1-sulfonyl)-1-(4-fluorophenyl)-4-[4-(morpholin-4-yl)piperidin-1-yl]-1H-pyrazolo[3,4-b]pyridine-6-carboxamide;

3-cyclobutyl-N-(dimethylsulfamoyl)-1-(4-fluorophenyl)-4-[4-(3-methoxyazetidin-1-yl)piperidin-1-yl]-1H-pyrazolo[3,4-b]pyridine-6-carboxamide;

3-cyclobutyl-N-(dimethylsulfamoyl)-1-(4-fluorophenyl)-4-[3-(trifluoromethyl)[1,4'-bipiperidin]-1'-yl]-1H-pyrazolo[3,4-b]pyridine-6-carboxamide;

3-cyclobutyl-N-(dimethylsulfamoyl)-1-(4-fluorophenyl)-4-(3-methoxy[1,4'-bipiperidin]-1'-yl)-1H-pyrazolo[3,4-b]pyridine-6-carboxamide;

3-cyclobutyl-4-[4-(2,2-dimethylmorpholin-4-yl)piperidin-1-yl]-N-(dimethylsulfamoyl)-1-(4-fluorophenyl)-1H-pyrazolo[3,4-b]pyridine-6-carboxamide;

N-(2-acetamidoethanesulfonyl)-3-cyclobutyl-1-(4-fluorophenyl)-4-[4-(morpholin-4-yl)piperidin-1-yl]-1H-pyrazolo[3,4-b]pyridine-6-carboxamide;

3-cyclobutyl-1-[2-(difluoromethoxy)pyridin-4-yl]-N-(dimethylsulfamoyl)-4-[4-(morpholin-4-yl)piperidin-1-yl]-1H-pyrazolo[3,4-b]pyridine-6-carboxamide;

N-(azetidine-1-sulfonyl)-3-cyclobutyl-1-(4-fluorophenyl)-4-[4-(morpholin-4-yl)piperidin-1-yl]-1H-pyrazolo[3,4-b]pyridine-6-carboxamide;

3-cyclobutyl-1-(4-fluorophenyl)-N-[(2R)-2-(methoxymethyl)pyrrolidine-1-sulfonyl]-4-[4-(morpholin-4-yl)piperidin-1-yl]-1H-pyrazolo[3,4-b]pyridine-6-carboxamide;

3-cyclobutyl-1-(4-fluorophenyl)-4-[4-(morpholin-4-yl)piperidin-1-yl]-N-[(oxan-4-yl)sulfamoyl]-1H-pyrazolo[3,4-b]pyridine-6-carboxamide;

3-cyclobutyl-1-(4-fluorophenyl)-N-[methyl(oxan-4-yl)sulfamoyl]-4-[4-(morpholin-4-yl)piperidin-1-yl]-1H-pyrazolo[3,4-b]pyridine-6-carboxamide;

3-cyclobutyl-N-(3,3-difluoroazetidine-1-sulfonyl)-1-(4-fluorophenyl)-4-[4-(morpholin-4-yl)piperidin-1-yl]-1H-pyrazolo[3,4-b]pyridine-6-carboxamide;

4-[(3S)-4-benzyl-3-methylpiperazin-1-yl]-3-cyclobutyl-1-cyclohexyl-N-(dimethylsulfamoyl)-1H-pyrazolo[3,4-b]pyridine-6-carboxamide;

4-[(3R)-4-benzyl-3-methylpiperazin-1-yl]-3-cyclobutyl-1-cyclohexyl-N-(dimethylsulfamoyl)-1H-pyrazolo[3,4-b]pyridine-6-carboxamide;

3-cyclobutyl-4-[4-(4-cyclopropylpiperazin-1-yl)piperidin-1-yl]-N-(dimethylsulfamoyl)-1-(4-fluorophenyl)-1H-pyrazolo[3,4-b]pyridine-6-carboxamide;

3-cyclobutyl-4-(9-cyclopropyl-3,9-diazaspiro[5.5]undecan-3-yl)-N-(dimethylsulfamoyl)-1-(4-fluorophenyl)-1H-pyrazolo[3,4-b]pyridine-6-carboxamide;

3-cyclobutyl-1-(4-fluorophenyl)-N-(methanesulfonyl)-4-[4-(3-methoxyazetidin-1-yl)piperidin-1-yl]-1H-pyrazolo[3,4-b]pyridine-6-carboxamide;

3-cyclobutyl-1-(4-fluorophenyl)-N-(methanesulfonyl)-4-[3-(trifluoromethyl)[1,4'-bipiperidin]-1'-yl]-1H-pyrazolo[3,4-b]pyridine-6-carboxamide;

3-cyclobutyl-1-(4-fluorophenyl)-N-(methanesulfonyl)-4-(3-methoxy[1,4'-bipiperidin]-1'-yl)-1H-pyrazolo[3,4-b]pyridine-6-carboxamide;

3-cyclobutyl-4-[4-(2,2-dimethylmorpholin-4-yl)piperidin-1-yl]-1-(4-fluorophenyl)-N-(methanesulfonyl)-1H-pyrazolo[3,4-b]pyridine-6-carboxamide;

3-cyclobutyl-N-(dimethylsulfamoyl)-1-(4-fluorophenyl)-4-{4-[(pyrrolidin-1-yl)methyl]piperidin-1-yl}-1H-pyrazolo[3,4-b]pyridine-6-carboxamide;

ethyl 4-(1-{3-cyclobutyl-6-[(dimethylsulfamoyl)carbamoyl]-1-(4-fluorophenyl)-1H-pyrazolo[3,4-b]pyridin-4-yl}piperidin-4-yl)piperazine-1-carboxylate;

3-cyclobutyl-N-(dimethylsulfamoyl)-1-(4-fluorophenyl)-4-{4-[(2-methoxyethyl)(methyl)amino]piperidin-1-yl}-1H-pyrazolo[3,4-b]pyridine-6-carboxamide;

3-cyclobutyl-1-(4-fluorophenyl)-N-(methoxysulfamoyl)-4-[4-(morpholin-4-yl)piperidin-1-yl]-1H-pyrazolo[3,4-b]pyridine-6-carboxamide;

3-cyclobutyl-4-[1-(4,4-difluorocyclohexyl)piperidin-4-yl]-1-(4-fluorophenyl)-N-(methanesulfonyl)-1H-pyrazolo[3,4-b]pyridine-6-carboxamide;

3-cyclobutyl-4-[1-(4,4-difluorocyclohexyl)piperidin-4-yl]-N-(dimethylsulfamoyl)-1-(4-fluorophenyl)-1H-pyrazolo[3,4-b]pyridine-6-carboxamide;

3-cyclobutyl-N-(dimethylsulfamoyl)-1-(4-fluorophenyl)-4-{[4-(morpholin-4-yl)piperidin-1-yl]methyl}-1H-pyrazolo[3,4-b]pyridine-6-carboxamide;

3-cyclobutyl-1-(4-fluorophenyl)-N-(methanesulfonyl)-4-{[4-(morpholin-4-yl)piperidin-1-yl]methyl}-1H-pyrazolo[3,4-b]pyridine-6-carboxamide;

1-cyclohexyl-4-{4-[(4-cyclopropylpiperazin-1-yl)methyl]phenyl}-N-(methanesulfonyl)-3-[(propan-2-yl)oxy]-1H-pyrazolo[3,4-b]pyridine-6-carboxamide;

3-cyclobutyl-N-(dimethylsulfamoyl)-1-(4-fluorophenyl)-4-[1-(propan-2-yl)piperidin-4-yl]-1H-pyrazolo[3,4-b]pyridine-6-carboxamide;

3-cyclobutyl-1-(4-fluorophenyl)-N-(methanesulfonyl)-4-[1-(oxan-4-yl)piperidin-4-yl]-1H-pyrazolo[3,4-b]pyridine-6-carboxamide;

3-cyclobutyl-1-(4-fluorophenyl)-N-(methanesulfonyl)-4-{1-[(oxan-4-yl)methyl]piperidin-4-yl}-1H-pyrazolo[3,4-b]pyridine-6-carboxamide;

3-cyclobutyl-N-(dimethylsulfamoyl)-1-(4-fluorophenyl)-4-{1-[(oxan-4-yl)methyl]piperidin-4-yl}-1H-pyrazolo[3,4-b]pyridine-6-carboxamide;

3-cyclobutyl-4-{1-[(2,5-dimethoxyoxolan-3-yl)methyl]piperidin-4-yl}-1-(4-fluorophenyl)-N-(methanesulfonyl)-1H-pyrazolo[3,4-b]pyridine-6-carboxamide;

3-cyclobutyl-1-(4-fluorophenyl)-N-(methanesulfonyl)-4-[1-(3,3,3-trifluoropropyl)piperidin-4-yl]-1H-pyrazolo[3,4-b]pyridine-6-carboxamide;

3-cyclobutyl-N-(dimethylsulfamoyl)-1-(4-fluorophenyl)-4-[1-(3,3,3-trifluoropropyl)piperidin-4-yl]-1H-pyrazolo[3,4-b]pyridine-6-carboxamide;

3-cyclobutyl-N-(dimethylsulfamoyl)-1-(4-fluorophenyl)-4-(4-hydroxy[1,4'-bipiperidin]-1'-yl)-1H-pyrazolo[3,4-b]pyridine-6-carboxamide;

methyl {3-cyclobutyl-1-(4-fluorophenyl)-4-[4-(morpholin-4-yl)piperidin-1-yl]-1H-pyrazolo[3,4-b]pyridine-6-carbonyl}sulfamate;

3-cyclobutyl-N-(dimethylsulfamoyl)-1-(4-fluorophenyl)-4-{4-[4-(2-methoxyethyl)piperazin-1-yl]piperidin-1-yl}-1H-pyrazolo[3,4-b]pyridine-6-carboxamide;

3-cyclobutyl-1-(4-fluorophenyl)-4-[4-(methoxymethyl)piperidin-1-yl]-N-[3-(morpholin-4-yl)pyrrolidine-1-sulfonyl]-1H-pyrazolo[3,4-b]pyridine-6-carboxamide;

3-cyclobutyl-N-(4-cyclopropylpiperazine-1-sulfonyl)-1-(4-fluorophenyl)-4-[4-(methoxymethyl)piperidin-1-yl]-1H-pyrazolo[3,4-b]pyridine-6-carboxamide;

3-cyclobutyl-1-(4-fluorophenyl)-N-[4-(2-methoxyethyl)piperazine-1-sulfonyl]-4-[4-(methoxymethyl)piperidin-1-yl]-1H-pyrazolo[3,4-b]pyridine-6-carboxamide;

3-cyclobutyl-1-(4-fluorophenyl)-N-(methanesulfonyl)-4-[1-(propan-2-yl)piperidin-4-yl]-1H-pyrazolo[3,4-b]pyridine-6-carboxamide;

3-cyclobutyl-N-(dimethylsulfamoyl)-1-(4-fluorophenyl)-4-[1-(oxan-4-yl)piperidin-4-yl]-1H-pyrazolo[3,4-b]pyridine-6-carboxamide;

3-cyclobutyl-4-[1-(cyclopropylmethyl)piperidin-4-yl]-N-(dimethylsulfamoyl)-1-(4-fluorophenyl)-1H-pyrazolo[3,4-b]pyridine-6-carboxamide;

3-cyclobutyl-N-(dimethylsulfamoyl)-1-(4-fluorophenyl)-4-[9-(oxetan-3-yl)-3,9-diazaspiro[5.5]undecan-3-yl]-1H-pyrazolo[3,4-b]pyridine-6-carboxamide;

3-cyclobutyl-N-(dimethylsulfamoyl)-1-(4-fluorophenyl)-4-{4-[4-(oxetan-3-yl)piperazin-1-yl]piperidin-1-yl}-1H-pyrazolo[3,4-b]pyridine-6-carboxamide;

3-cyclobutyl-4-[(1-cyclopropylpiperidin-4-yl)methoxy]-N-(dimethylsulfamoyl)-1-(4-fluorophenyl)-1H-pyrazolo[3,4-b]pyridine-6-carboxamide;

3-cyclobutyl-4-[(1-cyclobutylpiperidin-4-yl)methoxy]-N-(dimethylsulfamoyl)-1-(4-fluorophenyl)-1H-pyrazolo[3,4-b]pyridine-6-carboxamide;

3-cyclobutyl-4-[(1-cyclohexylpiperidin-4-yl)methoxy]-N-(dimethylsulfamoyl)-1-(4-fluorophenyl)-1H-pyrazolo[3,4-b]pyridine-6-carboxamide;

3-cyclobutyl-N-(dimethylsulfamoyl)-1-(4-fluorophenyl)-4-{[1-(oxan-4-yl)piperidin-4-yl]methoxy}-1H-pyrazolo[3,4-b]pyridine-6-carboxamide;

3-cyclobutyl-4-{1-[(2,5-dimethoxyoxolan-3-yl)methyl]piperidin-4-yl}-N-(dimethylsulfamoyl)-1-(4-fluorophenyl)-1H-pyrazolo[3,4-b]pyridine-6-carboxamide;

3-cyclobutyl-N-(dimethylsulfamoyl)-4-[4-(morpholin-4-yl)piperidin-1-yl]-1-{2-[(propan-2-yl)oxy]pyrimidin-4-yl}-1H-pyrazolo[3,4-b]pyridine-6-carboxamide;

3-cyclobutyl-N-(dimethylsulfamoyl)-1-(2-ethoxypyrimidin-4-yl)-4-[4-(morpholin-4-yl)piperidin-1-yl]-1H-pyrazolo[3,4-b]pyridine-6-carboxamide;

3-cyclobutyl-1-(2,2-difluoro-2H-1,3-benzodioxol-5-yl)-N-(dimethylsulfamoyl)-4-[4-(morpholin-4-yl)piperidin-1-yl]-1H-pyrazolo[3,4-b]pyridine-6-carboxamide;

3-cyclobutyl-1-(4-fluorophenyl)-N-(4-methylpiperazine-1-sulfonyl)-4-[(morpholin-4-yl)piperidin-1-yl]-1H-pyrazolo[3,4-b]pyridine-6-carboxamide;
3-cyclobutyl-N-(dimethylsulfamoyl)-1-(4-fluorophenyl)-4-[1-(propan-2-yl)octahydro-5H-pyrrolo[3,2-c]pyridin-5-yl]-1H-pyrazolo[3,4-b]pyridine-6-carboxamide;
3-cyclobutyl-4-(1-cyclobutyloctahydro-5H-pyrrolo[3,2-c]pyridin-5-yl)-N-(dimethylsulfamoyl)-1-(4-fluorophenyl)-1H-pyrazolo[3,4-b]pyridine-6-carboxamide;
3-cyclobutyl-N-(dimethylsulfamoyl)-1-(4-fluorophenyl)-4-[1-(oxetan-3-yl)octahydro-5H-pyrrolo[3,2-c]pyridin-5-yl]-1H-pyrazolo[3,4-b]pyridine-6-carboxamide;
3-cyclobutyl-N-(dimethylsulfamoyl)-1-(4-fluorophenyl)-4-[1-(oxan-4-yl)octahydro-5H-pyrrolo[3,2-c]pyridin-5-yl]-1H-pyrazolo[3,4-b]pyridine-6-carboxamide;
3-cyclobutyl-1-(4-fluorophenyl)-4-(4-methoxy[1,4'-bipiperidin]-1'-yl)-N-(methyl sulfamoyl)-1H-pyrazolo[3,4-b]pyridine-6-carboxamide;
3-cyclobutyl-1-(4-fluorophenyl)-4-(4-methoxy[1,4'-bipiperidin]-1'-yl)-N-sulfamoyl-1H-pyrazolo[3,4-b]pyridine-6-carboxamide;
1-cyclohexyl-4-[4-(hexahydropyrrolo[3,4-c]pyrrole-2(1H)-carbonyl)phenyl]-N-(methanesulfonyl)-3-[(propan-2-yl)oxy]-1H-pyrazolo[3,4-b]pyridine-6-carboxamide;
N-(azetidine-1-sulfonyl)-3-cyclobutyl-1-(4-fluorophenyl)-4-(4-methoxy[1,4'-bipiperidin]-1'-yl)-1H-pyrazolo[3,4-b]pyridine-6-carboxamide;
1-cyclohexyl-4-(4-{[3-(dimethylamino)azetidin-1-yl]methyl}phenyl)-N-(methanesulfonyl)-3-[(propan-2-yl)oxy]-1H-pyrazolo[3,4-b]pyridine-6-carboxamide;
1-cyclohexyl-N-(methanesulfonyl)-3-[(propan-2-yl)oxy]-4-(4-{[4-(propan-2-yl)piperazin-1-yl]methyl}phenyl)-1H-pyrazolo[3,4-b]pyridine-6-carboxamide;
1-cyclohexyl-N-(methanesulfonyl)-4-{4-[(4-methoxypiperidin-1-yl)methyl]phenyl}-3-[(propan-2-yl)oxy]-1H-pyrazolo[3,4-b]pyridine-6-carboxamide;
1-cyclohexyl-N-(methanesulfonyl)-4-{4-[(5-methylhexahydropyrrolo[3,4-c]pyrrol-2(1H)-yl)methyl]phenyl}-3-[(propan-2-yl)oxy]-1H-pyrazolo[3,4-b]pyridine-6-carboxamide;
1-cyclohexyl-N-(methanesulfonyl)-4-[4-(5-methylhexahydropyrrolo[3,4-c]pyrrole-2(1H)-carbonyl)phenyl]-3-[(propan-2-yl)oxy]-1H-pyrazolo[3,4-b]pyridine-6-carboxamide;
3-cyclobutyl-1-(4-fluorophenyl)-N-(methylsulfamoyl)-4-{4-[4-(propan-2-yl)piperazin-1-yl]piperidin-1-yl}-1H-pyrazolo[3,4-b]pyridine-6-carboxamide;
4-[4-(4-cyano-1-methylpiperidin-4-yl)phenyl]-1-cyclohexyl-N-(methanesulfonyl)-3-[(propan-2-yl)oxy]-1H-pyrazolo[3,4-b]pyridine-6-carboxamide;
1-cyclohexyl-4-{4-[3-(dimethylamino)azetidine-1-carbonyl]phenyl}-N-(methanesulfonyl)-3-[(propan-2-yl)oxy]-1H-pyrazolo[3,4-b]pyridine-6-carboxamide;
1-cyclohexyl-N-(methanesulfonyl)-4-{4-[(8-methyl-2-oxa-5,8-diazaspiro[3.5]nonan-5-yl)methyl]phenyl}-3-[(propan-2-yl)oxy]-1H-pyrazolo[3,4-b]pyridine-6-carboxamide;
1-cyclohexyl-4-{4-[(4-ethylpiperazin-1-yl)methyl]phenyl}-N-(methanesulfonyl)-3-[(propan-2-yl)oxy]-1H-pyrazolo[3,4-b]pyridine-6-carboxamide;
1-cyclohexyl-4-(4-{[4-(dimethylamino)piperidin-1-yl]methyl}phenyl)-N-(methanesulfonyl)-3-[(propan-2-yl)oxy]-1H-pyrazolo[3,4-b]pyridine-6-carboxamide;
1-(4-fluorophenyl)-N-(methanesulfonyl)-4-(4-methoxy[1,4'-bipiperidin]-1'-yl)-3-[(propan-2-yl)oxy]-1H-pyrazolo[3,4-b]pyridine-6-carboxamide;
3-cyclobutyl-1-(4-fluorophenyl)-N-(3-methoxyazetidine-1-sulfonyl)-4-(4-methoxy[1,4'-bipiperidin]-1'-yl)-1H-pyrazolo[3,4-b]pyridine-6-carboxamide;
3-cyclobutyl-N-(3-fluoroazetidine-1-sulfonyl)-1-(4-fluorophenyl)-4-(4-methoxy[1,4'-bipiperidin]-11'-yl)-1H-pyrazolo[3,4-b]pyridine-6-carboxamide;
3-cyclobutyl-1-(4-fluorophenyl)-4-(4-methoxy[1,4'-bipiperidin]-1'-yl)-N-(morpholine-4-sulfonyl)-1H-pyrazolo[3,4-b]pyridine-6-carboxamide;
3-cyclobutyl-N-(methanesulfonyl)-4-[4-(morpholin-4-yl)cyclohexyl]-1-phenyl-1H-pyrazolo[3,4-b]pyridine-6-carboxamide;
3-cyclobutyl-N-(dimethylsulfamoyl)-4-[4-(morpholin-4-yl)cyclohexyl]-1-phenyl-1H-pyrazolo[3,4-b]pyridine-6-carboxamide;
3-cyclobutyl-4-(4-fluoro[1,4'-bipiperidin]-1'-yl)-1-(4-fluorophenyl)-N-(methyl sulfamoyl)-1H-pyrazolo[3,4-b]pyridine-6-carboxamide;
N-(azetidine-1-sulfonyl)-3-cyclobutyl-1-(4-fluorophenyl)-4-{4-[4-(propan-2-yl)piperazin-1-yl]piperidin-1-yl}-1H-pyrazolo[3,4-b]pyridine-6-carboxamide;
3-cyclobutyl-1-[3-(difluoromethoxy)phenyl]-N-(dimethylsulfamoyl)-4-[4-(morpholin-4-yl)piperidin-1-yl]-1H-pyrazolo[3,4-b]pyridine-6-carboxamide;
3-cyclobutyl-1-(4-fluorophenyl)-N-(methanesulfonyl)-N-methyl-4-[4-(morpholin-4-yl)piperidin-1-yl]-1H-pyrazolo[3,4-b]pyridine-6-carboxamide;
3-cyclobutyl-N-(methanesulfonyl)-N-methyl-4-[4-(morpholin-4-yl)piperidin-1-yl]-1-phenyl-1H-pyrazolo[3,4-b]pyridine-6-carboxamide;
3-cyclobutyl-N-(methanesulfonyl)-4-[4-(methoxymethyl)piperidin-1-yl]-N-methyl-1-phenyl-1H-pyrazolo[3,4-b]pyridine-6-carboxamide;
3-cyclobutyl-N-(ethanesulfonyl)-N-methyl-4-[4-(morpholin-4-yl)piperidin-1-yl]-1-phenyl-1H-pyrazolo[3,4-b]pyridine-6-carboxamide;
3-cyclobutyl-N-(ethanesulfonyl)-N-methyl-1-phenyl-4-{4-[(pyrrolidin-1-yl)methyl]piperidin-1-yl}-1H-pyrazolo[3,4-b]pyridine-6-carboxamide;
2-(3-cyclobutyl-1-phenyl-4-{4-[(pyrrolidin-1-yl)methyl]piperidin-1-yl}-1H-pyrazolo[3,4-b]pyridine-6-carbonyl)-6-methyl-1$\lambda^6$,2,6-thiadiazinane-1,1-dione;
2-(3-cyclobutyl-1-phenyl-4-{4-[(pyrrolidin-1-yl)methyl]piperidin-1-yl}-1H-pyrazolo[3,4-b]pyridine-6-carbonyl)-1$\lambda^6$,2-thiazolidine-1,1-dione;
3-cyclobutyl-N-(methanesulfonyl)-N-methyl-1-phenyl-4-{4-[(pyrrolidin-1-yl)methyl]piperidin-1-yl}-1H-pyrazolo[3,4-b]pyridine-6-carboxamide;
2-(3-cyclobutyl-1-phenyl-4-{4-[(pyrrolidin-1-yl)methyl]piperidin-1-yl}-1H-pyrazolo[3,4-b]pyridine-6-carbonyl)-1$\lambda^6$,2-thiazinane-1,1-dione;
2-{3-cyclobutyl-4-[4-(morpholin-4-yl)piperidin-1-yl]-1-phenyl-1H-pyrazolo[3,4-b]pyridine-6-carbonyl}-6-methyl-$\lambda^6$,2,6-thiadiazinane-1,1-dione;
2-{3-cyclobutyl-4-[4-(morpholin-4-yl)piperidin-1-yl]-1-phenyl-1H-pyrazolo[3,4-b]pyridine-6-carbonyl}-1$\lambda^6$,2-thiazolidine-1,1-dione;
2-{3-cyclobutyl-4-[4-(morpholin-4-yl)piperidin-1-yl]-1-phenyl-1H-pyrazolo[3,4-b]pyridine-6-carbonyl}-1$\lambda^6$,2-thiazinane-1,1-dione;
2-{3-cyclobutyl-4-[4-(methoxymethyl)piperidin-1-yl]-1-phenyl-1H-pyrazolo[3,4-b]pyridine-6-carbonyl}-1$\lambda^6$,2-thiazolidine-1,1-dione;
2-{3-cyclobutyl-4-[4-(methoxymethyl)piperidin-1-yl]-1-phenyl-1H-pyrazolo[3,4-b]pyridine-6-carbonyl}-1$\lambda^6$,2-thiazinane-1,1-dione;

3-cyclobutyl-1-(4-fluorophenyl)-4-[4-(methoxymethyl)piperidin-1-yl]-N-(methylsulfamoyl)-1H-pyrazolo[3,4-b]pyridine-6-carboxamide;
3-cyclobutyl-1-(4-fluorophenyl)-N-(2-methoxyethanesulfonyl)-4-[4-(methoxymethyl)piperidin-1-yl]-1H-pyrazolo[3,4-b]pyridine-6-carboxamide;
3-cyclobutyl-1-(4-fluorophenyl)-4-[4-(methoxymethyl)piperidin-1-yl]-N-(morpholine-4-sulfonyl)-1H-pyrazolo[3,4-b]pyridine-6-carboxamide;
3-cyclobutyl-1-(4-fluorophenyl)-N-(3-hydroxypropane-1-sulfonyl)-4-[4-(methoxymethyl)piperidin-1-yl]-1H-pyrazolo[3,4-b]pyridine-6-carboxamide;
ethyl 4-[({3-cyclobutyl-1-(4-fluorophenyl)-4-[4-(methoxymethyl)piperidin-1-yl]-1H-pyrazolo[3,4-b]pyridine-6-carbonyl}sulfamoyl)amino]piperidine-1-carboxylate;
3-cyclobutyl-1-(4-fluorophenyl)-4-[4-(methoxymethyl)piperidin-1-yl]-N-[(oxetan-3-yl)sulfamoyl]-1H-pyrazolo[3,4-b]pyridine-6-carboxamide;
3-cyclobutyl-1-(4-fluorophenyl)-4-[4-(methoxymethyl)piperidin-1-yl]-N-[(oxan-4-yl)sulfamoyl]-1H-pyrazolo[3,4-b]pyridine-6-carboxamide;
3-cyclobutyl-1-(4-fluorophenyl)-4-[4-(methoxymethyl)piperidin-1-yl]-N-[4-(morpholin-4-yl)piperidine-1-sulfonyl]-1H-pyrazolo[3,4-b]pyridine-6-carboxamide;
ethyl 4-{3-cyclobutyl-1-(4-fluorophenyl)-6-[(2-methoxyethanesulfonyl)carbamoyl]-1H-pyrazolo[3,4-b]pyridin-4-yl}piperazine-1-carboxylate;
ethyl 4-{3-cyclobutyl-1-(4-fluorophenyl)-6-[(morpholine-4-sulfonyl)carbamoyl]-1H-pyrazolo[3,4-b]pyridin-4-yl}piperazine-1-carboxylate;
ethyl 4-{3-cyclobutyl-1-(4-fluorophenyl)-6-[(methanesulfonyl)carbamoyl]-1H-pyrazolo[3,4-b]pyridin-4-yl}piperazine-1-carboxylate;
ethyl 4-{3-cyclobutyl-1-(4-fluorophenyl)-6-[(methylsulfamoyl)carbamoyl]-1H-pyrazolo[3,4-b]pyridin-4-yl}piperazine-1-carboxylate;
2-methylpropyl 4-{3-cyclobutyl-1-(4-fluorophenyl)-6-[(methanesulfonyl)carbamoyl]-1H-pyrazolo[3,4-b]pyridin-4-yl}piperazine-1-carboxylate;
2-methylpropyl 4-{3-cyclobutyl-1-(4-fluorophenyl)-6-[(morpholine-4-sulfonyl)carbamoyl]-1H-pyrazolo[3,4-b]pyridin-4-yl}piperazine-1-carboxylate;
2-methylpropyl 4-{3-cyclobutyl-1-(4-fluorophenyl)-6-[(2-methoxyethanesulfonyl)carbamoyl]-1H-pyrazolo[3,4-b]pyridin-4-yl}piperazine-1-carboxylate;
2-methylpropyl 4-{3-cyclobutyl-1-(4-fluorophenyl)-6-[(methylsulfamoyl)carbamoyl]-1H-pyrazolo[3,4-b]pyridin-4-yl}piperazine-1-carboxylate;
3-cyclobutyl-1-(4-fluorophenyl)-4-(9-methyl-3,9-diazaspiro[5.5]undecan-3-yl)-N-(morpholine-4-sulfonyl)-1H-pyrazolo[3,4-b]pyridine-6-carboxamide; and
N-(2-aminopyridine-3-sulfonyl)-3-cyclobutyl-1-(4-fluorophenyl)-4-[4-(methoxymethyl)piperidin-1-yl]-1H-pyrazolo[3,4-b]pyridine-6-carboxamide.

Compounds of the invention are named by using Name 2015 naming algorithm by Advanced Chemical Development, Struct=Name naming algorithm as part of CHEMDRAW® ULTRA v. 12.0.2.1076, or Accelrys Draw 4.2.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present disclosure includes all pharmaceutically acceptable isotopically-labelled compounds of formula (I) wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) may generally be prepared by conventional techniques known to those skilled in the art or by processes analogous to those described in the accompanying Examples using an appropriate isotopically-labeled reagents in place of the non-labeled reagent previously employed.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Compounds of formula (I) may be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid, and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein refers to derivatives of the compounds of the invention which have cleavable groups. Such derivatives become, by solvolysis or under physiological conditions, the compounds of the invention which are pharmaceutically active in vivo. Prodrugs of the compounds of the invention are, within the scope of sound medical judgement, suitable for use in contact with the tissues of humans and lower animals without undue toxicity, irritation, allergic response, and the like, commensurate with a reasonable benefit/risk ratio, and effective for their intended use.

The invention contemplates compounds of formula (I) formed by synthetic means or formed by in vivo biotransformation of a prodrug.

Compounds described herein may exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Pharmaceutical Compositions

When employed as a pharmaceutical, a compound of the invention is typically administered in the form of a pharmaceutical composition. Such compositions can be prepared in a manner well known in the pharmaceutical art and comprise a therapeutically effective amount of a compound of formula (I), or a pharmaceutically acceptable salt thereof together with a pharmaceutically acceptable carrier. The phrase "pharmaceutical composition" refers to a composition suitable for administration in medical or veterinary use.

The pharmaceutical compositions that comprise a compound of formula (I), alone or in combination with further therapeutically active ingredient, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which may serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants may also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous diluents, solvents, or vehicles include water, ethanol, polyols (such as glycerol, propylene glycol, polyethylene glycol and the like), vegetable oils (such as olive oil), injectable organic esters (such as ethyl oleate), and suitable mixtures thereof. Proper fluidity may be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

In some cases, in order to prolong the effect of the drug, it may be desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release may be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations may be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In certain embodiments, solid dosage forms may contain from 1% to 95% (w/w) of a compound of formula (I). In certain embodiments, the compound of formula (I), or pharmaceutically acceptable salts thereof, may be present in the solid dosage form in a range of from 5% to 70% (w/w). In such solid dosage forms, the active compound may be mixed with at least one inert, pharmaceutically acceptable carrier, such as sodium citrate or dicalcium phosphate and/or a), fillers or extenders such as starches, lactose, sucrose, glucose, mannitol, and silicic acid; b) binders such as carboxymethylcellulose, alginates, gelatin, polyvinylpyrrolidone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form may be a capsule, tablet, cachet, or lozenge itself, or it may be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition may, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician may evaluate factors such as the circulating plasma levels of the compound, compound toxicities, and/or the progression of the disease, etc.

For administration, compounds may be administered at a rate determined by factors that may include, but are not limited to, the $LD_{50}$ of the compound, the pharmacokinetic profile of the compound, contraindicated drugs, and the side-effects of the compound at various concentrations, as applied to the mass and overall health of the subject. Administration may be accomplished via single or divided doses.

The compounds utilized in the pharmaceutical method of the invention may be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds may also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols, and fatty acid esters of sorbitan and mixtures thereof.

Besides inert diluents, the oral compositions may also include adjuvants such as wetting agents, emulsifying and suspending agents, sweetening, flavoring and perfuming agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which may be prepared by mixing the compounds with suitable non-irritating carriers or carriers such as cocoa butter, polyethylene glycol, or a suppository wax which are solid at room temperature but liquid at body temperature and therefore melt in the rectum or vaginal cavity and release the active compound.

Compounds may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes may be used. The present compositions in liposome form may contain, in addition to a compound of the invention, stabilizers, preservatives, excipients, and the like. Examples of lipids include, but are not limited to, natural and synthetic phospholipids, and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq. Dosage forms for topical administration of a compound described herein include powders, sprays, ointments, and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

A compound of the invention may also be administered in sustained release forms or from sustained release drug delivery systems.

Methods of Use

The compounds and compositions using any amount and any route of administration may be administered to a subject for the treatment or prevention of cystic fibrosis, pancreatic insufficiency, Sjögren's Syndrome (SS), chronic obstructive lung disease (COLD), or chronic obstructive airway disease (COAD).

The term "administering" refers to the method of contacting a compound with a subject. Thus, the compounds may be administered by injection, that is, intravenously, intramuscularly, intracutaneously, subcutaneously, intraduodenally, parentally, or intraperitoneally. Also, the compounds described herein may be administered by inhalation, for example, intranasally. Additionally, the compounds may be administered transdermally, topically, and via implantation. In certain embodiments, the compounds and compositions thereof may be delivered orally. The compounds may also be delivered rectally, bucally, intravaginally, ocularly, or by insufflation. CFTR-modulated disorders and conditions may be treated prophylactically, acutely, and chronically using compounds and compositions thereof, depending on the nature of the disorder or condition. Typically, the host or subject in each of these methods is human, although other mammals may also benefit from the administration of compounds and compositions thereof as set forth hereinabove.

Compounds of the invention are useful as modulators of CFTR. Thus, the compounds and compositions are particularly useful for treating or lessening the severity or progression of a disease, disorder, or a condition where hyperactivity or inactivity of CFTR is involved. Accordingly, the invention provides a method for treating cystic fibrosis, pancreatic insufficiency, Sjögren's Syndrome (SS), chronic obstructive lung disease (COLD), or chronic obstructive airway disease (COAD) in a subject, wherein the method comprises the step of administering to said subject a therapeutically effective amount of a compound of formula (I), or a pharmaceutically acceptable salt thereof, or a preferred embodiment thereof as set forth above, with or without a pharmaceutically acceptable carrier. Particularly, the method is for the treatment or prevention of cystic fibrosis. In a more particular embodiment, the cystic fibrosis is caused by a Class I, II, III, IV, V, and/or VI mutation.

One embodiment is directed to a compound of the invention or a pharmaceutically acceptable salt thereof, or pharmaceutical compositions comprising a compound of the invention for use in medicine. One embodiment is directed to a compound of the invention or a pharmaceutically acceptable salt thereof, or pharmaceutical compositions thereof, for use in the treatment of cystic fibrosis, pancreatic insufficiency, Sjögren's Syndrome (SS), chronic obstructive lung disease (COLD) or chronic obstructive airway disease (COAD). In a more particular embodiment, the present invention provides compounds of the invention or pharmaceutically acceptable salts thereof, or pharmaceutical compositions comprising thereof, for use in the treatment of cystic fibrosis. In a more particular embodiment, the cystic fibrosis is caused by a Class I, II, III, IV, V, and/or VI mutation.

One embodiment is directed to the use of a compound according to formula (I) or a pharmaceutically acceptable salt thereof in the preparation of a medicament. The medicament optionally can comprise one or more additional therapeutic agents. In some embodiments, the medicament is for use in the treatment of cystic fibrosis, pancreatic insufficiency, Sjögren's Syndrome (SS), chronic obstructive lung disease (COLD) or chronic obstructive airway disease (COAD). In a particular embodiment, the medicament is for use in the treatment of cystic fibrosis. In a more particular embodiment, the cystic fibrosis is caused by a Class I, II, III, IV, V, and/or VI mutation.

This invention also is directed to the use of a compound according to formula (I) or a pharmaceutically acceptable salt thereof in the manufacture of a medicament for the treatment of cystic fibrosis, Sjögren's syndrome, pancreatic insufficiency, chronic obstructive lung disease, and chronic obstructive airway disease. The medicament optionally can comprise one or more additional therapeutic agents. In a particular embodiment, the invention is directed to the use of a compound according to formula (I) or a pharmaceutically acceptable salt thereof in the manufacture of a medicament for the treatment of cystic fibrosis. In a more particular embodiment, the cystic fibrosis is caused by a Class I, II, III, IV, V, and/or VI mutation.

In one embodiment, the present invention provides pharmaceutical compositions comprising a compound of the invention or a pharmaceutically acceptable salt thereof, and one or more additional therapeutic agents. In a particular embodiment, the other therapeutic agent is a cystic fibrosis treatment agent. In a more particular embodiment, the cystic fibrosis is caused by a Class I, II, III, IV, V, and/or VI mutation.

The present compounds or pharmaceutically acceptable salts thereof may be administered as the sole active agent or it may be co-administered with other therapeutic agents, including other compounds or pharmaceutically acceptable salts thereof that demonstrate the same or a similar therapeutic activity and that are determined to be safe and efficacious for such combined administration. The present compounds may be co-administered to a subject. The term "co-administered" means the administration of two or more different therapeutic agents to a subject in a single pharmaceutical composition or in separate pharmaceutical compositions. Thus co-administration involves administration at the same time of a single pharmaceutical composition comprising two or more therapeutic agents or administration of two or more different compositions to the same subject at the same or different times.

The compounds of the invention or a pharmaceutically acceptable salt thereof may be co-administered with a therapeutically effective amount of one or more additional therapeutic agents to treat a CFTR mediated disease, where examples of the therapeutic agents include, but are not limited to antibiotics (for example, aminoglycosides, colistin, aztreonam, ciprofloxacin, and azithromycin), expectorants (for example, hypertonic saline, acetylcysteine, dornase alfa, and denufosol), pancreatic enzyme supplements (for example, pancreatin, and pancrelipase), epithelial sodium channel blocker (ENaC) inhibitors, CFTR modulators (for example, CFTR potentiators, CFTR correctors), and CFTR amplifiers. In one embodiment, the CFTR mediated disease is cystic fibrosis, chronic obstructive pulmonary disease (COPD), dry eye disease, pancreatic insufficiency, or Sjogren's syndrome. In one embodiment, the CFTR mediated disease is cystic fibrosis. In one embodiment, the compounds of the invention or pharmaceutically acceptable salts thereof may be co-administered with one or two CFTR modulators and one CFTR amplifier. In one embodiment, the compounds of the invention or pharmaceutically acceptable salts thereof may be co-administered with one potentiator, one or more correctors, and one CFTR amplifier. In one embodiment, the compounds of the invention or pharmaceutically acceptable salts thereof may be co-administered with one or more CFTR modulators. In one embodiment, the compounds of the invention or pharmaceutically acceptable salts thereof may be co-administered with one CFTR modulators. In one embodiment, the compounds of the invention or pharmaceutically acceptable salts thereof may be co-administered with two CFTR modulators. In one embodiment, the compounds of the invention or pharmaceutically acceptable salts thereof may be co-administered with three CFTR modulators. In one embodiment, the compounds of the invention or pharmaceutically acceptable salts thereof may be co-administered with one potentiator and one or more correctors. In one embodiment, the compounds of the invention or pharmaceutically acceptable salts thereof may be co-administered with one potentiator and one corrector. In one embodiment, the compounds of the invention or pharmaceutically acceptable salts thereof may be co-administered with one potentiator and two correctors. In one embodiment, the compounds of the invention or pharmaceutically acceptable salts thereof may be co-administered with one potentiator. In one embodiment, the compounds of the invention or pharmaceutically acceptable salts thereof may be co-administered with one or more correctors. In one embodiment, the compounds of the invention or pharmaceutically acceptable salts thereof may be co-administered with one corrector. In one embodiment, the compounds of the invention or pharmaceutically acceptable salts thereof may be co-administered with two correctors.

Examples of CFTR potentiators include, but are not limited to, Ivacaftor (VX-770), CTP-656, NVS-QBW251, FD1860293, PTI-808, GLPG2451, GLPG1837, N-(3-carbamoyl-5,5,7,7-tetramethyl-5,7-dihydro-4H-thieno[2,3-c]pyran-2-yl)-1H-pyrazole-5-carboxamide and 3-amino-N-[(2S)-2-hydroxypropyl]-5-{[4-(trifluoromethoxy)phenyl]sulfonyl}pyridine-2-carboxamide. Examples of potentiators are also disclosed in publications: WO2005120497, WO2008147952, WO2009076593, WO2010048573, WO2006002421, WO2011072241, WO2011113894, WO2013038373, WO2013038378, WO2013038381, WO2013038386, WO2013038390, WO2014180562, WO2015018823; and U.S. application Ser. Nos. 14/271,080, 14/451,619, and 15/164,317.

In one embodiment, the potentiator can be selected from the group consisting of:
Ivacaftor (VX-770, N-(2,4-di-tert-butyl-5-hydroxyphenyl)-4-oxo-1,4-dihydroquinoline-3-carboxamide);
CTP-656;
NVS-QBW251;
FD1860293;
PTI-808;
GLPG1837;
GLPG2451;
2-(2-fluorobenzamido)-5,5,7,7-tetramethyl-5,7-dihydro-4H-thieno[2,3-c]pyran-3-carboxamide;
N-(3-carbamoyl-5,5,7,7-tetramethyl-4,7-dihydro-5H-thieno[2,3-c]pyran-2-yl)-1H-pyrazole-5-carboxamide;
2-(2-hydroxybenzamido)-5,5,7,7-tetramethyl-5,7-dihydro-4H-thieno[2,3-c]pyran-3-carboxamide;
2-(1-hydroxycyclopropanecarboxamido)-5,5,7,7-tetramethyl-5,7-dihydro-4H-thieno[2,3-c]pyran-3-carboxamide;
5,5,7,7-tetramethyl-2-(2-(trifluoromethyl)benzamido)-5,7-dihydro-4H-thieno[2,3-c]pyran-3-carboxamide;
2-(2-hydroxy-2-methylpropanamido)-5,5,7,7-tetramethyl-5,7-dihydro-4H-thieno[2,3-c]pyran-3-carboxamide;
2-(1-(hydroxymethyl)cyclopropanecarboxamido)-5,5,7,7-tetramethyl-5,7-dihydro-4H-thieno[2,3-c]pyran-3-carboxamide;
2-(3-hydroxy-2,2-dimethylpropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-5-methyl-1H-pyrazole-3-carboxamide;

N-(3-carbamoyl-5,5,7,7-tetramethyl-5,7-dihydro-4H-thieno[2,3-c]pyran-2-yl)-5-cyclopropyl-1H-pyrazole-3-carboxamide;
N-(3-carbamoyl-5,5,7,7-tetramethyl-5,7-dihydro-4H-thieno[2,3-c]pyran-2-yl)-5-isopropyl-1H-pyrazole-3-carboxamide;
N-(3-carbamoyl-5,5,7,7-tetramethyl-5,7-dihydro-4H-thieno[2,3-c]pyran-2-yl)-5-(trifluoromethyl)-1H-pyrazole-3-carboxamide;
5-tert-butyl-N-(3-carbamoyl-5,5,7,7-tetramethyl-5,7-dihydro-4H-thieno[2,3-c]pyran-2-yl)-1H-pyrazole-3-carboxamide;
N-(3-carbamoyl-5,5,7,7-tetramethyl-5,7-dihydro-4H-thieno[2,3-c]pyran-2-yl)-5-ethyl-1H-pyrazole-3-carboxamide;
N-(3-carbamoyl-5,5,7,7-tetramethyl-5,7-dihydro-4H-thieno[2,3-c]pyran-2-yl)-3-ethyl-4-methyl-1H-pyrazole-5-carboxamide;
2-(2-hydroxypropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-4-chloro-1H-pyrazole-3-carboxamide;
N-(3-carbamoyl-5,5,7,7-tetramethyl-5,7-dihydro-4H-thieno[2,3-c]pyran-2-yl)-1,4,6,7-tetrahydropyrano[4,3-c]pyrazole-3-carboxamide;
4-bromo-N-(3-carbamoyl-5,5,7,7-tetramethyl-5,7-dihydro-4H-thieno[2,3-c]pyran-2-yl)-1H-pyrazole-3-carboxamide;
N-(3-carbamoyl-5,5,7,7-tetramethyl-5,7-dihydro-4H-thieno[2,3-c]pyran-2-yl)-4-chloro-5-methyl-1H-pyrazole-3-carboxamide;
N-(3-carbamoyl-5,5,7,7-tetramethyl-5,7-dihydro-4H-thieno[2,3-c]pyran-2-yl)-4-methyl-1H-pyrazole-3-carboxamide;
2-(2-hydroxy-3,3-dimethylbutanamido)-5,5,7,7-tetramethyl-5,7-dihydro-4H-thieno[2,3-c]pyran-3-carboxamide;
2-[(2-hydroxy-4-methyl-pentanoyl)amino]-5,5,7,7-tetramethyl-4H-thieno[2,3-c]pyran-3-carboxamide;
5-(2-methoxy-ethoxy)-1H-pyrazole-3-carboxylic acid (3-carbamoyl-5,5,7,7-tetramethyl-4,7-dihydro-5H-thieno[2,3-c]pyran-2-yl)-amide;
N-(3-carbamoyl-5,5,7,7-tetramethyl-4H-thieno[2,3-c]pyran-2-yl)-4-(3-methoxypropyl)-1H-pyrazole-3-carboxamide;
N-(3-carbamoyl-5,5,7,7-tetramethyl-4H-thieno[2,3-c]pyran-2-yl)-4-(2-ethoxyethyl)-1H-pyrazole-3-carboxamide;
2-[[(2S)-2-hydroxy-3,3-dimethyl-butanoyl]amino]-5,5,7,7-tetramethyl-4H-thieno[2,3-c]pyran-3-carboxamide;
2-[[(2R)-2-hydroxy-3,3-dimethyl-butanoyl]amino]-5,5,7,7-tetramethyl-4H-thieno[2,3-c]pyran-3-carboxamide;
2-[(2-hydroxy-2,3,3-trimethyl-butanoyl)amino]-5,5,7,7-tetramethyl-4H-thieno[2,3-c]pyran-3-carboxamide;
[5-[(3-carbamoyl-5,5,7,7-tetramethyl-4H-thieno[2,3-c]pyran-2-yl)carbamoyl]pyrazol-1-yl]methyl dihydrogen phosphate;
[3-[(3-carbamoyl-5,5,7,7-tetramethyl-4H-thieno[2,3-c]pyran-2-yl)carbamoyl]pyrazol-1-yl]methyl dihydrogen phosphate;
N-(3-carbamoyl-5,5,7,7-tetramethyl-4H-thieno[2,3-c]pyran-2-yl)-4-(1,4-dioxan-2-yl)-1H-pyrazole-3-carboxamide;
5,5,7,7-tetramethyl-2-[[(2S)-3,3,3-trifluoro-2-hydroxy-2-methyl-propanoyl]amino]-4H-thieno[2,3-c]pyran-3-carboxamide;
2-[[(2S)-2-hydroxypropanoyl]amino]-5,5,7,7-tetramethyl-4H-thieno[2,3-c]pyran-3-carboxamide;
3-amino-N-(2-hydroxy-2-methylpropyl)-5-{[4-(trifluoromethoxy)phenyl]sulfonyl}pyridine-2-carboxamide;
3-amino-N-[(4-hydroxy-1-methylpiperidin-4-yl)methyl]-5-{[4-(trifluoromethoxy)phenyl]sulfonyl}pyridine-2-carboxamide;
3-amino-N-(3-hydroxy-2,2-dimethylpropyl)-5-{[4-(trifluoromethoxy)phenyl]sulfonyl}pyridine-2-carboxamide;
3-amino-5-[(4-fluorophenyl)sulfonyl]-N-[(1-hydroxycyclopropyl)methyl]pyridine-2-carboxamide;
3-amino-5-[(4-fluorophenyl)sulfonyl]-N-[(2R)-3,3,3-trifluoro-2-hydroxypropyl]pyridine-2-carboxamide;
3-amino-5-[(3-fluorophenyl)sulfonyl]-N-(2-hydroxy-2-methylpropyl)pyridine-2-carboxamide;
3-amino-N-[2-(cyclopropylamino)-2-oxoethyl]-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(azetidin-1-yl)methanone;
(3-amino-5-{[4-(trifluoromethoxy)phenyl]sulfonyl}pyridin-2-yl)[3-(hydroxymethyl)azetidin-1-yl]methanone;
(3-amino-5-{[4-(trifluoromethoxy)phenyl]sulfonyl}pyridin-2-yl)(3-fluoroazetidin-1-yl)methanone;
3-amino-N-[(2R)-2-hydroxy-3-methoxypropyl]-5-{[4-(trifluoromethoxy)phenyl]sulfonyl}pyridine-2-carboxamide;
(3-amino-5-{[2-fluoro-4-(trifluoromethoxy)phenyl]sulfonyl}pyridin-2-yl)(3-hydroxyazetidin-1-yl)methanone;
(3-amino-5-{[2-(trifluoromethoxy)phenyl]sulfonyl}pyridin-2-yl)(3,3-difluoroazetidin-1-yl)methanone;
rac-3-amino-N-[(3R,4S)-4-hydroxytetrahydro-2H-pyran-3-yl]-5-{[2-(trifluoromethoxy)phenyl]sulfonyl}pyridine-2-carboxamide;
3-amino-5-[(4,4-difluoropiperidin-1-yl)sulfonyl]-N-(3,3,3-trifluoro-2-hydroxypropyl)pyridine-2-carboxamide;
(3-amino-5-{[2-(trifluoromethoxy)phenyl]sulfonyl}pyridin-2-yl)[3-hydroxy-3-(trifluoromethyl)azetidin-1-yl]methanone;
3-amino-N-(2-hydroxy-4-methylpentyl)-5-{[4-(trifluoromethoxy)phenyl]sulfonyl}pyridine-2-carboxamide;
(3-amino-5-{[4-(trifluoromethyl)phenyl]sulfonyl}pyridin-2-yl)(3-hydroxy-3-methylazetidin-1-yl)methanone;
3-amino-N-(3,3,3-trifluoro-2-hydroxypropyl)-5-{[4-(trifluoromethyl)piperidin-1-yl]sulfonyl}pyridine-2-carboxamide;
3-amino-N-[2-hydroxy-1-(4-methoxyphenyl)ethyl]-5-{[4-(trifluoromethoxy)phenyl]sulfonyl}pyridine-2-carboxamide;
3-amino-5-[(3,3-difluoroazetidin-1-yl)sulfonyl]-N-(3,3,3-trifluoro-2-hydroxypropyl)pyridine-2-carboxamide;
3-amino-5-{[2-fluoro-4-(trifluoromethyl)phenyl]sulfonyl}-N-[(2S)-2-hydroxypropyl]pyridine-2-carboxamide;
3-amino-5-{[2-fluoro-4-(trifluoromethyl)phenyl]sulfonyl}-N-[(2R)-2-hydroxy-3-methoxypropyl]pyridine-2-carboxamide;
3-amino-N-[2-oxo-2-(propan-2-ylamino)ethyl]-5-{[4-(trifluoromethyl)phenyl]sulfonyl}pyridine-2-carboxamide;
(3-amino-5-{[4-(trifluoromethyl)phenyl]sulfonyl}pyridin-2-yl)[3-hydroxy-3-(trifluoromethyl)azetidin-1-yl]methanone;
3-amino-5-{[2-fluoro-4-(trifluoromethyl)phenyl]sulfonyl}-N-[(3R)-tetrahydrofuran-3-ylmethyl]pyridine-2-carboxamide;
(3-amino-5-{[2-fluoro-4-(trifluoromethyl)phenyl]sulfonyl}pyridin-2-yl)[3-hydroxy-3-(trifluoromethyl)azetidin-1-yl]methanone;

3-amino-5-{[2-fluoro-4-(trifluoromethyl)phenyl]sulfonyl}-N-[(3S)-tetrahydrofuran-3-ylmethyl]pyridine-2-carboxamide;

3-amino-5-{[2-fluoro-4-(trifluoromethoxy)phenyl]sulfonyl}-N-[(3S)-tetrahydrofuran-3-ylmethyl]pyridine-2-carboxamide;

3-amino-N-[2-hydroxy-3-(2,2,2-trifluoroethoxy)propyl]-5-{[4-(trifluoromethyl)phenyl]sulfonyl}pyridine-2-carboxamide;

3-amino-N-(3-tert-butoxy-2-hydroxypropyl)-5-{[2-fluoro-4-(trifluoromethyl)phenyl]sulfonyl}pyridine-2-carboxamide;

[3-amino-5-(phenylsulfonyl)pyridin-2-yl][3-hydroxy-3-(trifluoromethyl)azetidin-1-yl]methanone;

{3-amino-5-[(3-fluorophenyl)sulfonyl]pyridin-2-yl}[3-hydroxy-3-(trifluoromethyl)azetidin-1-yl]methanone; and 3-amino-N-[(2S)-2-hydroxypropyl]-5-{[4-(trifluoromethoxy)phenyl]sulfonyl}pyridine-2-carboxamide.

Non-limiting examples of correctors include Lumacaftor (VX-809), 1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661), VX-983, GLPG2222, GLPG2665, GLPG2851, VX-152, VX-440, FDL169, FDL304, FD2052160, FD2035659 and PTI-801. Examples of correctors are also disclosed in U.S. application Ser. Nos. 14/925,649, 14/926,727, 15/205,512, and 62/239,475.

In one embodiment, the corrector(s) can be selected from the group consisting of:

Lumacaftor (VX-809);

1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661);

PTI-801;

VX-983;

GLPG2665;

VX-152;

VX-440;

FDL169;

FDL304;

FD2052160;

FD2035659;

3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-6-methyl-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-6-methoxy-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]cyclohexanecarboxylic acid;

3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-methoxy-3,4-dihydro-2H-chromen-2-yl]cyclohexanecarboxylic acid;

3-[(2R,4R)-4-({[1-(2,2-difluoro-1,3-benzodioxol-5-yl)cyclopropyl]carbonyl}amino)-7-fluoro-3,4-dihydro-2H-chromen-2-yl]benzoic acid;

3-({3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoyl}amino)-1-methylcyclopentanecarboxylic acid;

3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-[(2R)-2,3-dihydroxypropyl]benzamide;

3-[(2R,4R)-4-({[1-(2,2-difluoro-1,3-benzodioxol-5-yl)cyclopropyl]carbonyl}amino)-7-(2-methoxyethoxy)-3,4-dihydro-2H-chromen-2-yl]benzoic acid;

3-[(2R,4R)-7-(benzyloxy)-4-({[1-(2,2-difluoro-1,3-benzodioxol-5-yl)cyclopropyl]carbonyl}amino)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(2-fluoroethoxy)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]cyclohexanecarboxylic acid;

4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-8-fluoro-3,4-dihydro-2H-chromen-2-yl]benzoic acid;

4-[(2R,4R)-4-({[1-(2,2-difluoro-1,3-benzodioxol-5-yl)cyclopropyl]carbonyl}amino)-3,4-dihydro-2H-chromen-2-yl]benzoic acid;

4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;

rac-3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-4-[(2R,4S)-4-({[1-(2,2-difluoro-1,3-benzodioxol-5-yl)cyclopropyl]carbonyl}amino)tetrahydro-2H-pyran-2-yl]benzoic acid;

3-[(2S,4R)-4-({[1-(2,2-difluoro-1,3-benzodioxol-5-yl)cyclopropyl]carbonyl}amino)tetrahydro-2H-pyran-2-yl]benzoic acid;

3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

3-[(2S,4R,6R)-4-({[1-(2,2-difluoro-1,3-benzodioxol-5-yl)cyclopropyl]carbonyl}amino)-6-phenyltetrahydro-2H-pyran-2-yl]benzoic acid;

3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

4-[(2R,4S)-4-({[1-(2,2-difluoro-1,3-benzodioxol-5-yl)cyclopropyl]carbonyl}amino)tetrahydro-2H-pyran-2-yl]benzoic acid;

3-cyclobutyl-4-[4-(morpholin-4-yl)piperidin-1-yl]-1-phenyl-1H-pyrazolo[3,4-b]pyridine-6-carboxylic acid;

3-cyclobutyl-1-phenyl-4-{4-[(pyrrolidin-1-yl)methyl]piperidin-1-yl}-1H-pyrazolo[3,4-b]pyridine-6-carboxylic acid;

5-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyrazine-2-carboxylic acid;

6-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]pyridine-3-carboxylic acid;

trans-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;

6-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]pyridine-3-carboxylic acid;

trans-4-[(2S,4S)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid;

ethyl trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylate;

cis-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;

trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid;

1-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylic acid;

trans-4-[(2R,4R)-4-{[(5S)-2,2-difluoro-5-methyl-6,7-dihydro-2H,5H-indeno[5,6-d][1,3]dioxole-5-carbonyl]amino}-7-(trifluoromethoxy)-3,4-dihydro-2H-1-benzopyran-2-yl]cyclohexane-1-carboxylic acid;

trans-4-[(2R,4R)-4-{[(5S)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]cyclohexane-1-carboxylic acid;

trans-4-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid;

trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid; and trans-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid.

In one embodiment, the additional therapeutic agent is a CFTR amplifier. CFTR amplifiers enhance the effect of known CFTR modulators, such as potentiators and correctors. Examples of CFTR amplifiers are PTI130 and PTI-428. Examples of amplifiers are also disclosed in publications: WO2015138909 and WO2015138934.

In one embodiment, the additional therapeutic agent is a CFTR stabilizer. CFTR stabilizers enhance the stability of corrected CFTR that has been treated with a corrector, corrector/potentiator or other CFTR modulator combination(s). An example of a CFTR stabilizer is cavosonstat. Examples of stabilizers are also disclosed in publication: WO2012048181.

In one embodiment, the additional therapeutic agent is an agent that reduces the activity of the epithelial sodium channel blocker (ENaC) either directly by blocking the channel or indirectly by modulation of proteases that lead to an increase in ENaC activity (e.g., serine proteases, channel-activating proteases). Exemplary of such agents include camostat (a trypsin-like protease inhibitor), QAU145, 552-02, GS-9411, INO-4995, Aerolytic, amiloride, and VX-371. Additional agents that reduce the activity of the epithelial sodium channel blocker (ENaC) can be found, for example, in PCT Publication No. WO2009074575 and WO2013043720; and U.S. Pat. No. 8,999,976.

In one embodiment, the ENaC inhibitor is VX-371.

In one embodiment, the ENaC inhibitor is SPX-101 (S18).

In one embodiment, the present invention provides pharmaceutical compositions comprising a compound of the invention, or a pharmaceutically acceptable salt thereof, and one or more additional therapeutic agents. In a particular embodiment, the additional therapeutic agents are selected from the group consisting of CFTR modulators and CFTR amplifiers. In a further embodiment, the additional therapeutic agents are CFTR modulators. In one embodiment, the present invention provides pharmaceutical compositions comprising a compound of the invention, or a pharmaceutically acceptable salt thereof, one potentiator, and one or more additional correctors.

This invention also is directed to kits that comprise one or more compounds and/or salts of the invention, and, optionally, one or more additional therapeutic agents.

This invention also is directed to methods of use of the compounds, salts, compositions, and/or kits of the invention to, with or without one or more additional therapeutic agents, for example, modulate the Cystic Fibrosis Transmembrane Conductance Regulator (CFTR) protein, and treat a disease treatable by modulating the Cystic Fibrosis Transmembrane Conductance Regulator (CFTR) protein (including cystic fibrosis, Sjögren's syndrome, pancreatic insufficiency, chronic obstructive lung disease, and chronic obstructive airway disease).

EXAMPLES

Chemical Synthetic Procedures
General

The compounds of the invention can be better understood in connection with the following synthetic schemes and methods which illustrate a means by which the compounds may be prepared.

The compounds of this invention can be prepared by a variety of synthetic procedures. Representative procedures are shown in, but are not limited to, Schemes 1-6. In Schemes 1-6, the variables $R^1$, $R^2$, $R^3$, $R^4$, $R^5$ and $R^6$ are as described in the Summary.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be further processed in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis (3$^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

The compounds of the invention can be prepared from readily available starting materials using the following general methods and procedures. It will be appreciated that where typical or preferred process conditions (i.e. reaction temperatures, times, mole ratios of reactants, solvents, pressures, etc.) were given, other process conditions can also be used unless otherwise stated. Optimum reaction conditions may vary with the particular reactants or solvent used, but such conditions can be determined by one skilled in the art by routine optimization procedures.

The following methods are presented with details as to the preparation of a compound of the invention as defined hereinabove and the comparative examples. A compound of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 μm). Thin layer chromatography was carried out using pre-coated silica gel F-254 plates (thickness 0.25 mm). $^1$H NMR spectra were recorded on a Bruker Advance 300 NMR spectrometer (300 MHz) unless otherwise noted. Chemical shifts (δ) for $^1$H NMR spectra were reported in parts per million (ppm) relative to tetramethylsilane (δ 0.00) or the appropriate residual solvent peak, i.e. CHCl$_3$ (δ 7.27), as internal reference. Multiplicities were given as singlet (s), doublet (d), triplet (t), quartet (q), quintuplet (quin), multiplet (m) and broad (br). Electrospray MS spectra were obtained on a Waters platform LC/MS spectrometer or with Waters Acquity H-Class UPLC coupled to a Waters Mass detector 3100 spectrometer. Columns used: Waters Acquity UPLC BEH C18 1.7 μm, 2.1 mm ID×50 mm L, Waters Acquity UPLC BEH C18 1.7 μm, 2.1 mm ID×30 mm L, or Waters Xterra® MS 5 m C18, 100×4.6 mm. The methods were using either MeCN/H$_2$O gradients (H$_2$O contains either 0.1% TFA or 0.1% NH$_3$) or Methanol/H$_2$O gradients (H$_2$O contains 0.05% TFA). Microwave heating was performed with a Biotage® Initiator. Electrospray MS spectra were obtained on Waters Acquity UPLC systems coupled to Waters SQD or SQD2 mass spectrometers. Columns used: Waters Acquity UPLC BEH C18 1.7 μm, 2.1 mm ID×50 mm L or Waters Acquity UPLC BEH C18 1.7 m, 2.1 mm ID×30 mm L. The methods were using MeCN/H$_2$O gradients (both MeCN and H$_2$O contained either 0.1% formic acid or 0.05% NH$_3$).

For the compounds purified by preparative chromatography, an XSelect™ CSH Prep Guard Column, C18 19×10 mm 5 m (Waters) with an XSelect™ CSH Prep OBD Column, C18 19×100 mm 5 μm (Waters) and a gradient of 0.1% formic acid in water (A) and acetonitrile (B) at a flow rate of 20 mL/minute is used. Alternatively, an XBridge™ Prep Guard Column, C18 19×10 mm 5 m (Waters) with a XBridge™ Prep OBD Column, C18 19×100 mm 5 m (Waters) and a gradient of 0.5% NH$_3$ in water (A) and acetonitrile (B) at a flow rate of 20 mL/minute is used. After elution, the solvent was removed under vacuum to provide the product. For the compounds purified by preparative chromatography, an XBridge™ Prep Guard Column, C18 19×10 mm 5 m (Waters) with a XBridge™ Prep OBD Column, C18 30×100 mm 5 μm (Waters) and a gradient of 0.1% formic acid in water (A) and acetonitrile (B) at a flow rate of 50 mL/minute were used. Alternatively, a gradient of 0.1% DEA in water (A) and acetonitrile (B) at a flow rate of 50 mL/minute was used on the same references of guard column and column. After elution, the solvent was removed under vacuum to provide the dry product.

Alternatively, compounds were purified by automated reversed phase HPLC, using a Phenomenex® Luna® C8(2), 5 μm, 100 Å, 50×30 mm, with a SecurityGuard™ 15×30 mm guard column, and a gradient of acetonitrile (A) and 0.1% trifluoroacetic acid in water (B), at a flow rate of 40 mL/min (0-1.0 minute 10% A, 1.0-9.0 minutes linear gradient 10-100% A, 9.0-9.5 minutes 100% A, 9.5-10.0 minutes linear gradient 100-10% A). After elution, solvent was removed under vacuum to provide the pure product.

Racemic mixtures were separated on an Agilent HP1100 system with UV detection. Column used: Chiralpak® IA (10×250 mm, 5 μm). Solvents used: iPrOH and tBME. Enantiomeric purity was determined on an Agilent HP1100 system with UV detection. Column used: Chiralpak IA (4.6×250 mm, 5 μm). Solvents used: iPrOH and tBME.

List of abbreviations used in the experimental section:

| Abbreviation | Definition |
|---|---|
| Bn | benzyl |
| Boc | tert-butoxycarbonyl |
| Et | ethyl |
| Me | methyl |
| Ph | phenyl |
| Pr | propyl |
| Tf | trifluoromethanesulfonyl |
| OTf | trifluormethanesulfonate |
| DCM | dichloromethane |
| MeCN | acetonitrile |
| DMA | N,N-dimethylacetamide |
| DMF | N,N-dimethylformamide |
| AcOH or HOAc | acetic acid |
| eq or equiv | equivalents |
| TFA | trifluoroacetic acid |
| THF | tetrahydrofuran |
| NMR | nuclear magnetic resonance |
| DMSO | dimethyl sulfoxide |
| LC/MS or LCMS | liquid chromatography-mass spectrometry |
| EtOAc | ethyl acetate |
| EtOH | ethanol |
| MeOH | methanol |
| tBuOH or t-BuOH | tert-butanol |
| tBME or MTBE | tert-butyl methyl ether |
| s | singlet |
| br s | broad singlet |
| d | duplet |
| dd | double duplet |
| m | multiplet |
| min | minute |
| h | hours |
| mL | milliliter |
| µL | microliter |
| g | gram |
| mg | milligram |
| kg | kilogram |
| atm | atmosphere |
| w/w | weight/weight |
| RT | room(ambient) temperature |
| $NEt_3$ | triethylamine |
| BOP | (benzotriazol-yloxy)tris(dimethylamino)phosphonium hexafluorophosphate |
| DIPEA | diisopropylethylamine |
| DMAP | dimethylaminopyridine |
| EDC | N-ethyl-N'-(3-dimethylaminopropyl)carbodiimide |
| mmol | millimoles |
| HPLC | high pressure liquid chromatography |
| MS | mass spectrum |
| NMR | nuclear magnetic resonance |
| TLC | thin layer chromatography |
| NMP | N-methylpyrrolidone |
| ppm | parts per million |
| psi | pounds per square inch |
| $Pd(OAc)_2$ | palladium(II) acetate |
| Xantphos | 4,5-bis(diphenylphosphino)-9,9-dimethylxanthene |
| SM | starting material |
| Cpd | compound |
| Int | intermediate |
| MW | molecular weight |
| Mes | molecular weight measured |
| NA | not active |
| $Pd(dppf)Cl_2$ | [1,1'-bis(diphenylphosphino)ferrocene]dichloropalladium(II) |
| $Pd(dppf)Cl_2 \cdot CH_2Cl_2$ or $Pd(dppf)Cl_2 \cdot DCM$ | [1,1'-bis(diphenylphosphino)ferrocene]dichloropalladium(II) complex with dichloromethane |
| µm | micrometer |
| iPrOH | iso-propanol |
| DBU | 1,8-diazabicycloundec-7-ene |
| DPPA | diphenylphosphoryl azide |
| LiHMDS | lithium hexamethyldisilazide or lithium bis(trimethylsilyl)amide |
| rac-BINAP | rac-1,1'-binaphthyl-2,2'-diamine |

-continued

List of abbreviations used in the experimental section:

| Abbreviation | Definition |
|---|---|
| TfOH | trifluoromethanesulfonic acid |
| $Tf_2O$ | trifluoromethanesulfonic anhydride |
| XPhos | 2-dicyclohexylphosphino-2',4',6'-triisopropylbiphenyl |
| XPhos Pd G1 | (2-dicyclohexylphosphino-2',4',6'-triisopropyl-1,1'-biphenyl)[2-(2-aminoethyl)phenyl)]palladium(II) chloride |
| $K_2CO_3$ | potassium carbonate |
| $MgSO_4$ | magnesium sulfate |
| $NaHCO_3$ | sodium hydrogencarbonate or sodium bicarbonate |
| $Na_2CO_3$ | sodium carbonate |
| $Na_2SO_4$ | sodium sulfate |
| CO | carbon monoxide |
| NaCl | sodium chloride |
| NaH | sodium hydride |
| LiOH | lithium hydroxide |
| $Pd(amphos)Cl_2$ | bis(di-tert-butyl(4-dimethylaminophenyl)phosphine)dichloropalladium(II) |
| SPhos | 2-dicyclohexylphosphino-2',6'-dimethoxybiphenyl |

Synthetic Preparation of the Compounds of the Invention

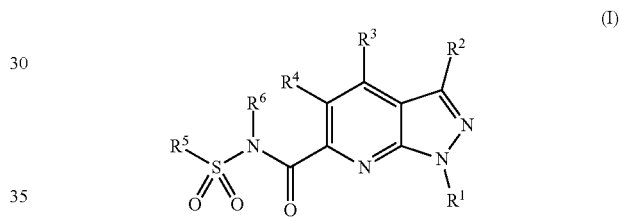

(I)

General Synthetic Routes

The compounds of the invention and the comparative examples can be produced according to the following schemes.

Scheme 1: General synthetic access to aminopyrazoles

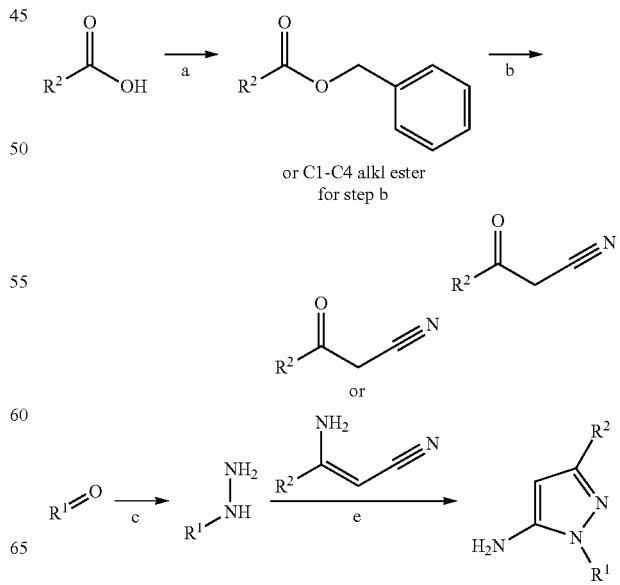

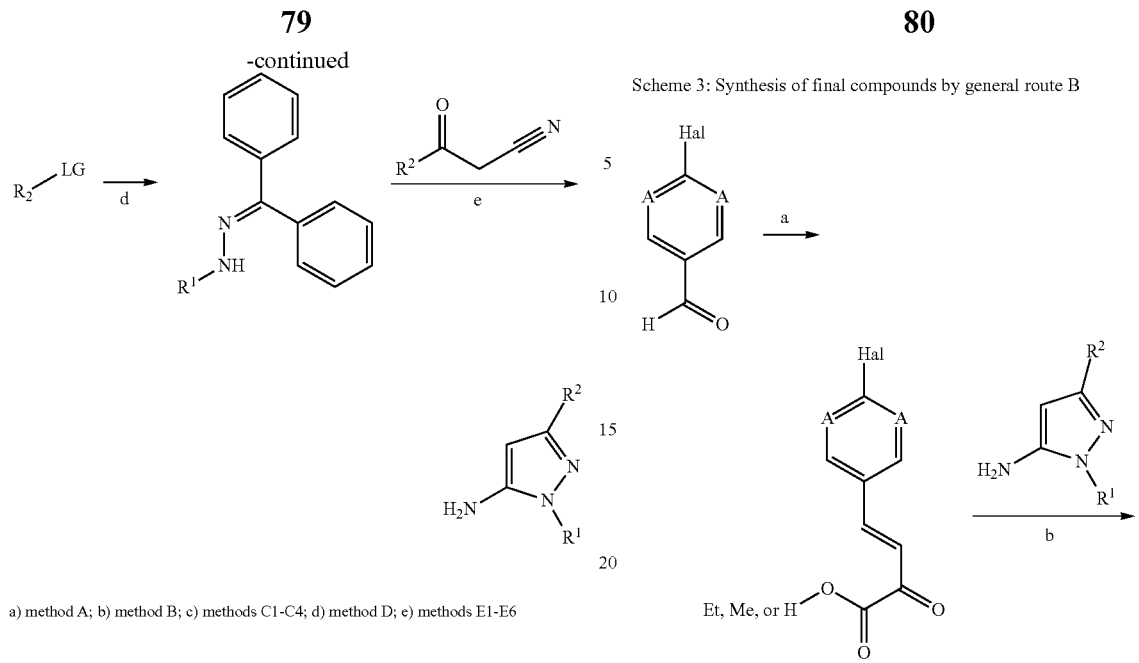
Scheme 3: Synthesis of final compounds by general route B
a) method A; b) method B; c) methods C1-C4; d) method D; e) methods E1-E6
Scheme 2: Synthesis of final compounds by general route A
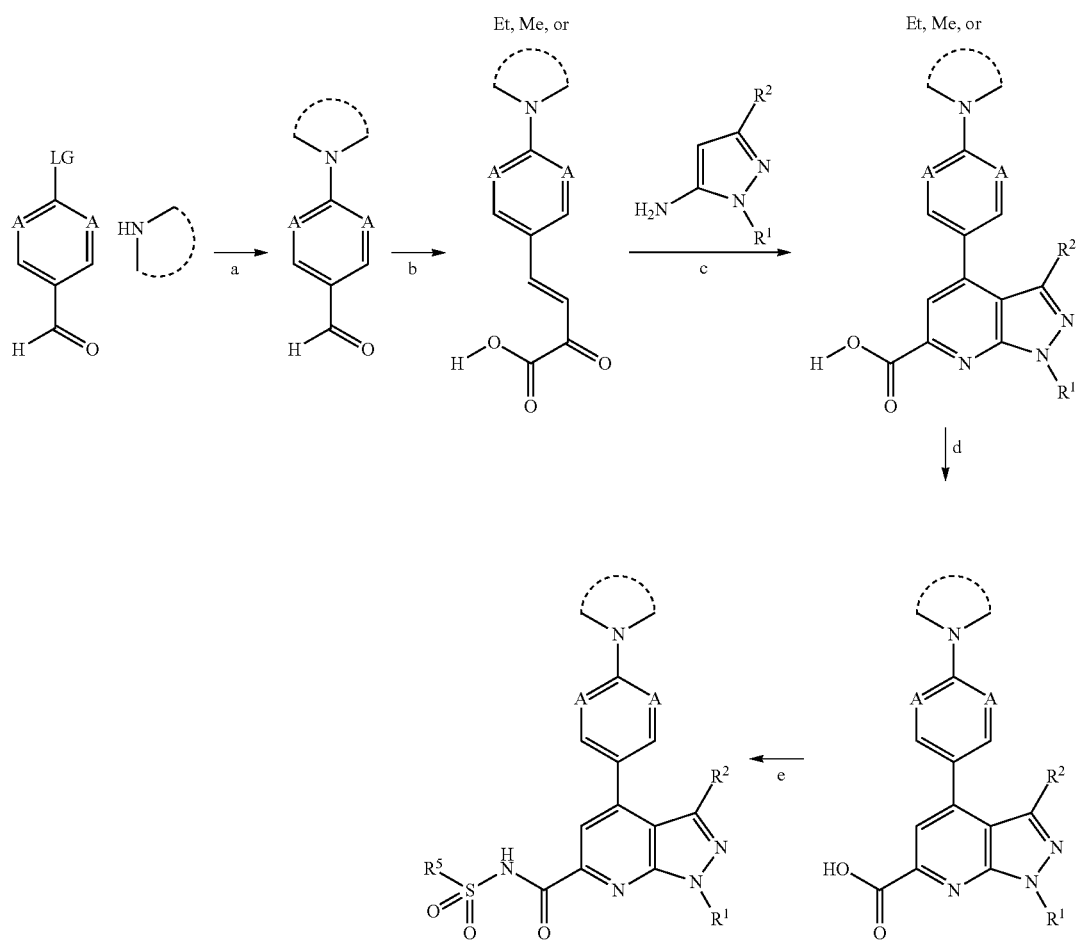
LG = F, Cl, Br
A = CH or N
a) method F; b) methods G1-G2; c) methods I1, J2; d) method J1; e) methods Y1-Y10

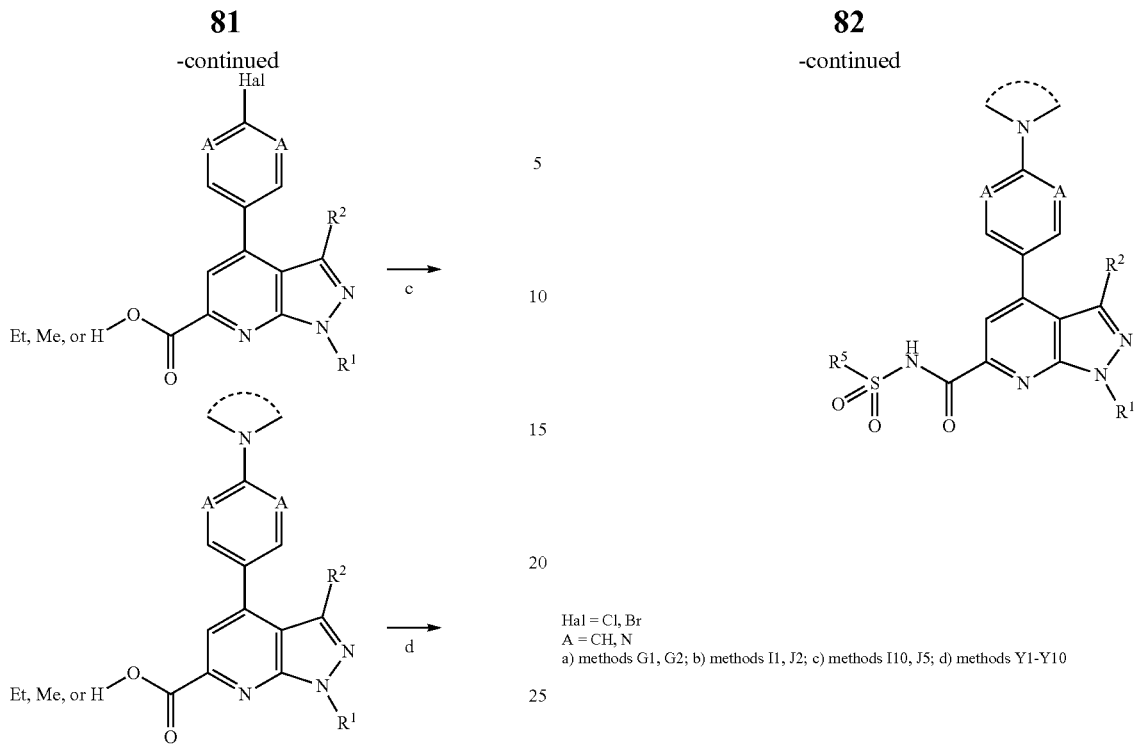
Hal = Cl, Br
A = CH, N
a) methods G1, G2; b) methods I1, J2; c) methods I10, J5; d) methods Y1-Y10
Scheme 4: Synthesis of final compounds by general route C
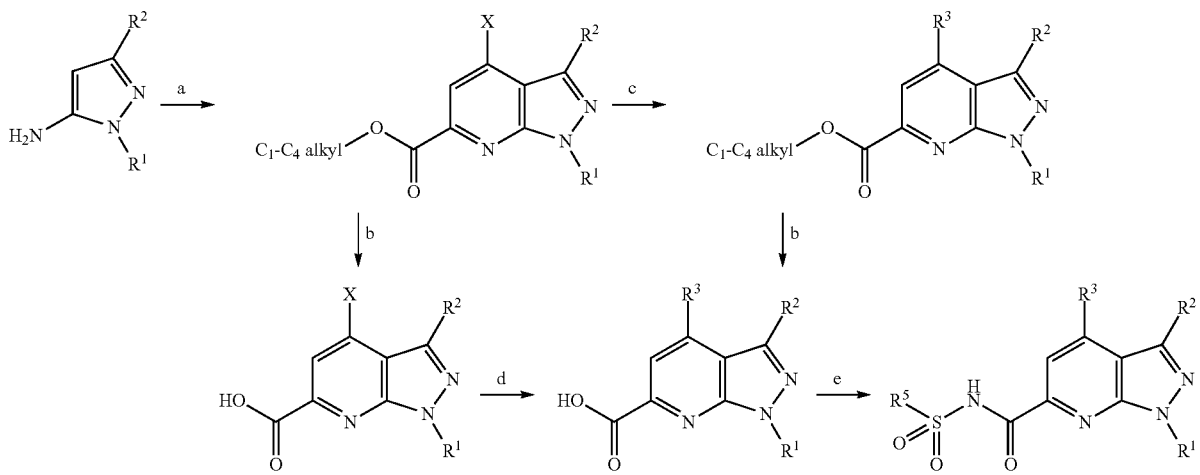
X = Cl, Br, OTf, OH
a) methods H1-H3, Specific examples HP12 and HP14; b) method J1, J1A; c) methods I2, I3, I14, J13, J14; d) methods J3, J4, J10; e) methods Y1-Y10
Scheme 5: Synthesis of final compounds by general route D
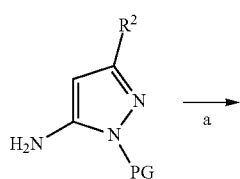

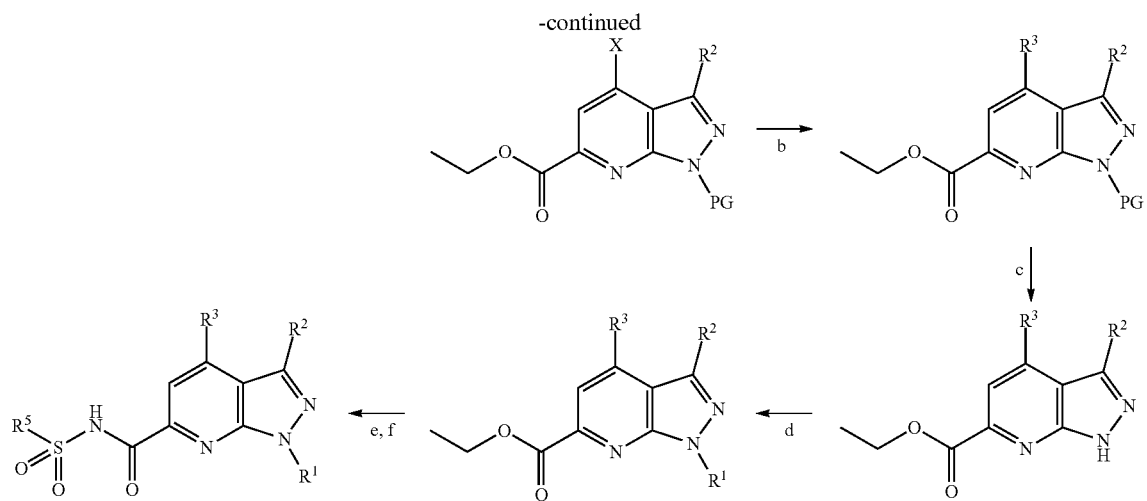

PG = protecting group (i.e., dimethoxybenzyl)
X = Cl, Br, OTf
a) method H3 and Specific example HP14; b) methods I2, I3, I14; c) method I15;
d) methods I4-I7, I16; e) method J1, J1A; f) methods Y1-Y10

Scheme 6: Synthesis of final compounds by general route E.

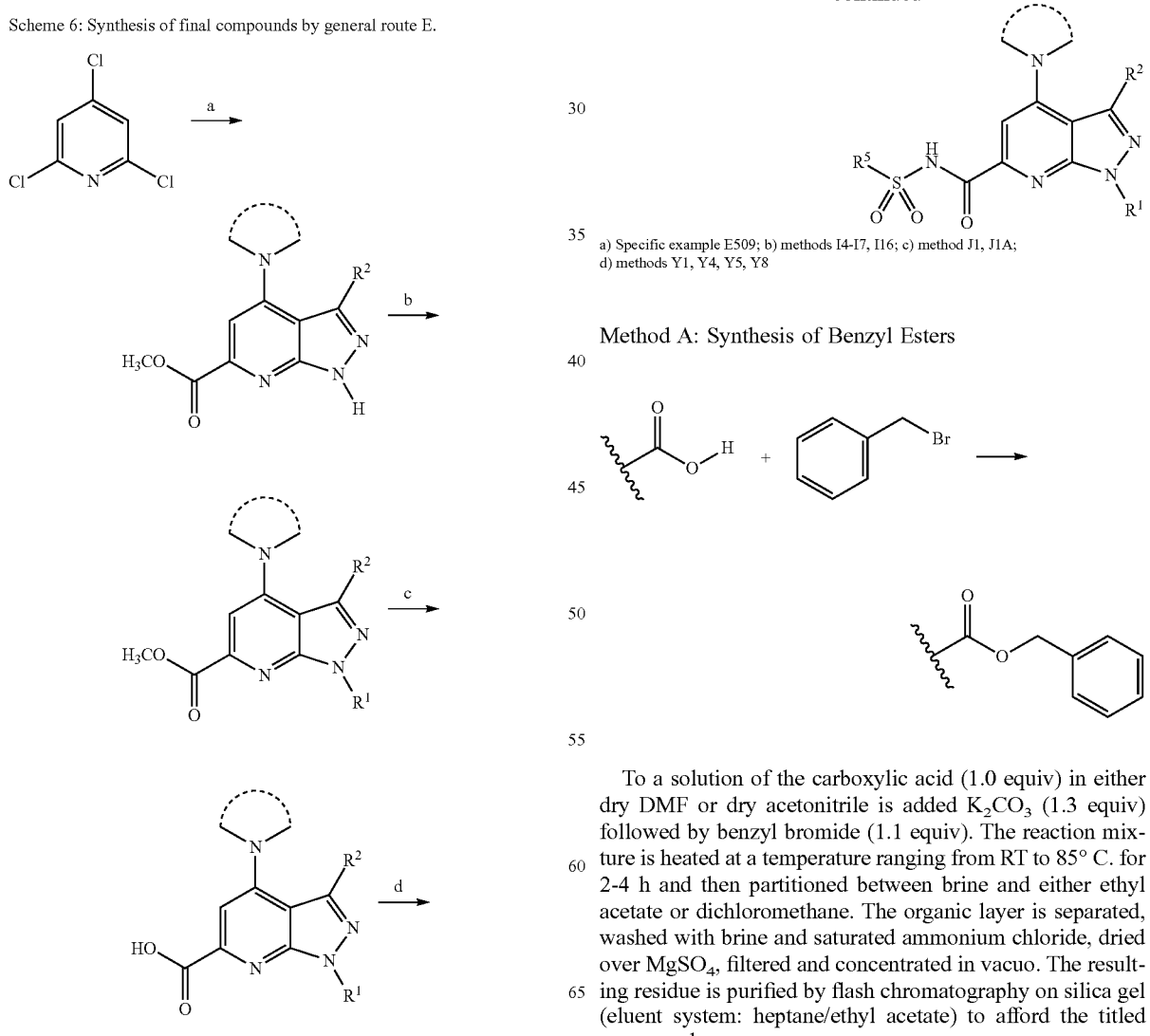

a) Specific example E509; b) methods I4-I7, I16; c) method J1, J1A;
d) methods Y1, Y4, Y5, Y8

Method A: Synthesis of Benzyl Esters

To a solution of the carboxylic acid (1.0 equiv) in either dry DMF or dry acetonitrile is added $K_2CO_3$ (1.3 equiv) followed by benzyl bromide (1.1 equiv). The reaction mixture is heated at a temperature ranging from RT to 85° C. for 2-4 h and then partitioned between brine and either ethyl acetate or dichloromethane. The organic layer is separated, washed with brine and saturated ammonium chloride, dried over $MgSO_4$, filtered and concentrated in vacuo. The resulting residue is purified by flash chromatography on silica gel (eluent system: heptane/ethyl acetate) to afford the titled compound.

Illustrative Synthesis of Intermediate BE01:
1-Methyl-cyclobutanecarboxylic Acid Benzyl Ester

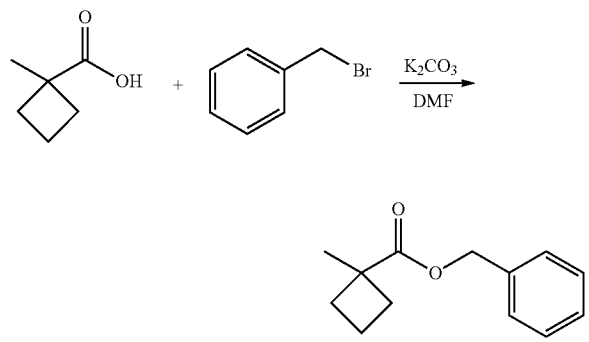

To a solution of 1-methylcyclobutanecarboxylic acid (CAS: 32936-76-8, 0.5 g, 4.38 mmol, 1.0 equiv) in dry DMF was added $K_2CO_3$ (0.787 g, 5.69 mmol, 1.3 equiv) followed by benzyl bromide (CAS: 100-39-0, 0.57 mL, 4.82 mmol, 1.1 equiv). The reaction mixture was stirred at RT for 2.5 h and then diluted with ethyl acetate and brine. The organic layer was separated, washed with a saturated solution of ammonium chloride and brine, dried over $MgSO_4$, filtered and concentrated in vacuo. The resulting residue was purified by flash chromatography on silica gel (eluent system: heptane/ethyl acetate gradient from 100/0 to 90/10) to afford the titled compound.

Method B: Cyanoketone Formation

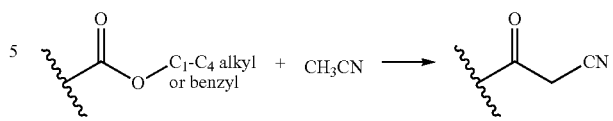

A flame-dried round bottom flask is cooled down to RT under nitrogen. A solution of 1 M LiHMDS in THF (1.5 equiv) is introduced into the flask, and then it is cooled down to −78° C. (acetone/dry ice bath). Dry MeCN (from 1.5 to 1.7 equiv) is then added dropwise under nitrogen, and the reaction mixture is stirred for 30 min at −78° C. At this point a solution of ester (1.0 equiv) in dry THF is added dropwise, and then the reaction mixture is stirred at −78° C. for 1-2 h. The reaction mixture is quenched with cold $H_2O$, partitioned between ethyl acetate (or diethyl ether) and $H_2O$. The organic layer is separated, and the aqueous layer is extracted with ethyl acetate (or diethyl ether). The aqueous fraction is then acidified to pH=1 with 2 N HCl and extracted with ethyl acetate (or diethyl ether). The combined organic layers are then washed with brine, dried over $MgSO_4$, filtered and concentrated in vacuo to afford the titled compound which is used as such or purified by flash chromatography on silica gel.

TABLE I

List of benzyl esters

| Int. | Structure | Name | SM | method | MW |
|---|---|---|---|---|---|
| BE01 | 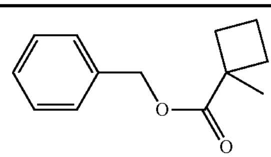 | 1-Methyl-cyclobutanecarboxylic acid benzyl ester | 32936-76-8 | A, Specific example | 204 |
| BE02 | 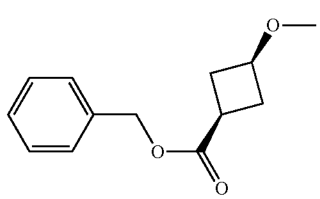 [SMILES: CO[C@H]1C[C@@H](C(=O)OCc2ccccc2)C1] | 3-Methoxy-cyclobutanecarboxylic acid benzyl ester | 552849-35-1 | A | 220 |
| BE03 | 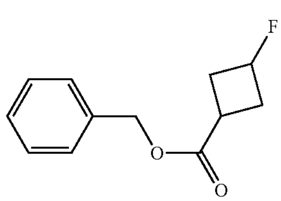 [SMILES: O=C(OCc1ccccc1)C1CC(F)C1] | 3-Fluoro-cyclobutanecarboxylic acid benzyl ester | 122665-96-7 | A | 208 |
| BE04 | 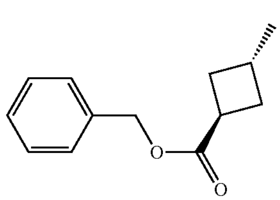 | 3-Methyl-cyclobutanecarboxylic acid benzyl ester | 87863-09-0 | A | 204 |

Illustrative Synthesis of CK01:
Cyclobutyl-3-oxo-propionitrile

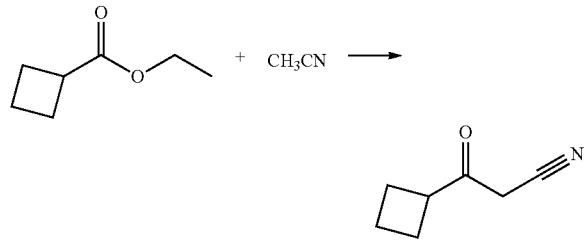

A 1 L 4 neck round bottom flask was equipped with 2 dropping funnels and a septum on top of the apparatus. The whole system was flame-dried (heat gun) for 10 minutes under vacuum and then cooled down to RT under a positive stream of nitrogen (balloon). A low-temperature thermometer was adapted under a positive stream of nitrogen, then a 1 N LiHMDS solution in THF (468.0 mL, 468.0 mmol, 1.5 equiv) was cannulated into the flask using a positive stream of nitrogen. The solution was cooled down to −78° C. (dry ice/acetone cooling bath) as confirmed with the thermometer. Dry MeCN (24.4 mL, 468.0 mmol, 1.5 equiv) was added via syringe into the first dropping funnel, and then added dropwise (over 20 min) into the reaction mixture. After the end of the addition, the mixture was stirred at −78° C. for 1 h. At this point, cyclobutanecarboxylic acid ethyl ester (CAS: 14924-53-9, 43.1 mL, 312.1 mmol, 1.0 equiv) as a solution in dry THF (106 mL) was introduced into the second dropping funnel. This solution was slowly added over 2 h into the reaction mixture at −78° C. The mixture was stirred at −78° C. for 2 h. The reaction mixture was poured into 300 mL of cold water, stirred for 30 min and allowed to warm to RT. The mixture was then partitioned between ethyl acetate and H₂O. The organic layer was separated, and the aqueous layer was extracted with ethyl acetate (3×300 mL). The combined organic phases were discarded. The aqueous layer was then acidified with 100 mL of 2 N HCl, then extracted with ethyl acetate (3×300 mL), washed with 50 mL of brine, dried over MgSO₄, filtered and concentrated in vacuo to afford the titled compound which was used without further purification.

TABLE II

| | List of cyanoketones | | | | | |
|---|---|---|---|---|---|---|
| Int. | Structure | Name | SM | method | MW | Mes |
| 29509-06-6 | | 4-Methyl-3-oxo-pentanenitrile | | | 111 | |
| 29509-06-6 | | 4-Methyl-3-oxo-pentanenitrile | | | 111 | |
| CK01, 118431-89-3 | | 3-Cyclobutyl-3-oxo-propionitrile | 14924-53-9 | B, Specific example | 123 | |
| 59997-51-2 | | 4,4-Dimethyl-3-oxo-pentanenitrile | | | 125 | |

TABLE II-continued

List of cyanoketones

| Int. | Structure | Name | SM | method | MW | Mes |
|---|---|---|---|---|---|---|
| 887594-13-0 | 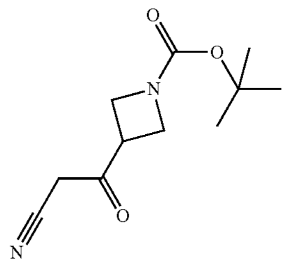 [SMILES: CC(C)(C)OC(=O)N1CC(C(=O)CC#N)C1] | 3-(2-Cyano-acetyl)-azetidine-1-carboxylic acid tert-butyl ester | | | 224 | |
| 118431-88-2 | 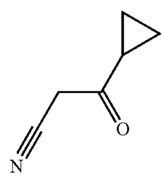 | 3-Cyclopropyl-3-oxo-propionitrile | | | 109 | |
| CK02 | 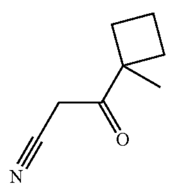 | 3-(1-Methyl-cyclobutyl)-3-oxo-propionitrile | BE01 | B | 137 | 138 |
| CK03 | 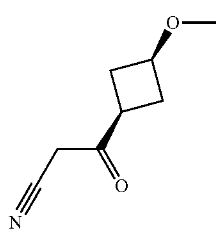 | 3-(cis-3-Methoxy-cyclobutyl)-3-oxo-propionitrile | BE02 | B | 153 | |
| 29509-06-6 | 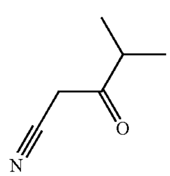 | 4-Methyl-3-oxo-pentanenitrile | | | 111 | |
| 1234616-26-2 | 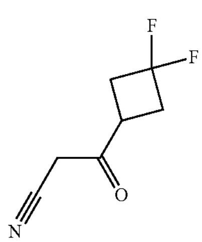 [SMILES: N#CCC(=O)C1CC(F)(F)C1] | 3-(3,3-Difluoro-cyclobutyl)-3-oxo-propionitrile | | | 159 | |
| CK04 | 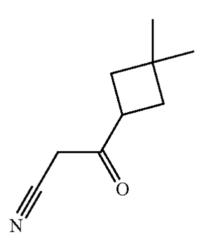 | 3-(3,3-Dimethyl-cyclobutyl)-3-oxo-propionitrile | 3854-83-9 | B | 151 | |

TABLE II-continued

List of cyanoketones

| Int. | Structure | Name | SM | method | MW | Mes |
|---|---|---|---|---|---|---|
| CK05 | 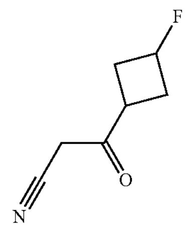 | 3-(3-Fluoro-cyclobutyl)-3-oxo-propionitrile | BE03 | B | 141 | |
| CK06 | 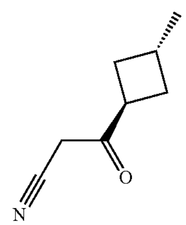 | 3-(trans-3-Methyl-cyclobutyl)-3-oxo-propionitrile | BE04 | B | 137 | |

Method C: Hydrazine Formation

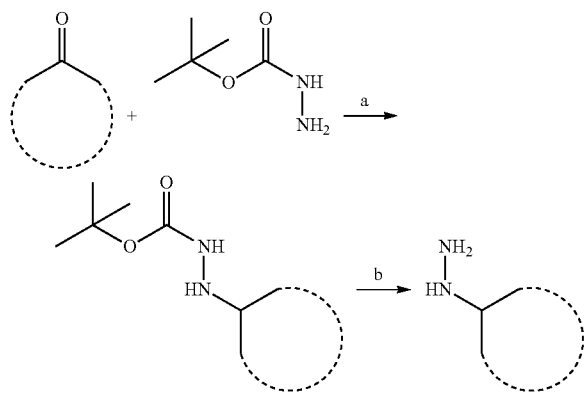

a) methods C1, C2; b) methods C3, C4

Method C1: Reductive Amination

To a solution of ketone (1 equiv) and tert-butyl carbazate (CAS: 870-46-2, 1.0 equiv) in anhydrous dichloromethane at 0° C. is added acetic acid (2.0 equiv) and sodium triacetoxyborohydride (CAS: 56553-60-7, 3.0 equiv). The reaction mixture is warmed up to RT and stirred for 1 h to several days (up to 8). The reaction mixture is then basified with a solution of 2 M sodium hydroxide and a saturated solution of sodium hydrogencarbonate. The two phases are separated, and the aqueous phase is extracted with dichloromethane. The combined organic phases are washed with a saturated solution of sodium hydrogencarbonate and brine, dried over MgSO$_4$, filtered and concentrated in vacuo to afford the tert-butoxy carbonyl hydrazine which is used as such or purified by flash chromatography on silica gel.

Method C2: Reductive Amination

To the ketone (1 equiv) in anhydrous methanol at RT is added tert-butyl carbazate (CAS: 870-46-2, 1.0 equiv). The reaction mixture is stirred for 20 minutes at RT, then acetic acid (3.0 equiv) and sodium cyanoborohydride (CAS: 25895-60-7, 1.5 equiv) are added. The reaction mixture is stirred at RT for 1 h to several days (up to 8). The reaction mixture is then basified with a solution of 2 M sodium hydroxide and a saturated solution of sodium hydrogencarbonate. The two phases are separated, and the aqueous phase is extracted with dichloromethane. The combined organic phases are washed with a saturated solution of sodium hydrogencarbonate and brine, dried over MgSO$_4$, filtered and concentrated in vacuo to afford the tert-butoxy carbonyl hydrazine which is used as such or purified by flash chromatography on silica gel.

Method C3: Tert-Butoxy Carbonyl-Deprotection

To a solution of a tert-butoxy carbonyl hydrazine intermediate from Methods C1 or C2 in anhydrous dichloromethane at RT is added 4 M HCl in dioxane (20 equiv). The reaction mixture is stirred at RT until the reaction is finished. The solids are collected by filtration, washed twice with diethyl ether, and dried in vacuo to afford the hydrazine which is used as such.

Method C4: Tert-Butoxy Carbonyl-Deprotection

A tert-butoxy carbonyl hydrazine intermediate from Methods C1 or C2 is stirred at RT in a 1:1 mixture of dichloromethane and trifluoroacetic acid until the reaction is finished. The reaction mixture is concentrated in vacuo. The residue is taken up three times with toluene and concentrated in vacuo to afford the hydrazine which is used as such.

Illustrative Synthesis of H01:
(Tetrahydro-pyran-3-yl)-hydrazine Di-hydrochloride Salt

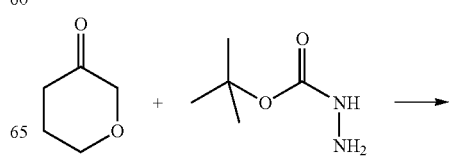

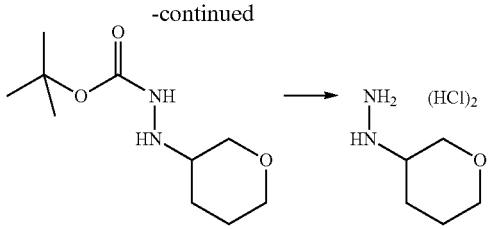

Step 1: Tert-butyl N-(tetrahydropyran-3-ylamino)carbamate

To a solution of dihydro-2H-pyran-3(4H)-one (CAS: 23462-75-1, 0.6 g, 5.99 mmol, 1.0 equiv) and tert-butyl carbazate (CAS: 870-46-2, 0.792 g, 5.99 mmol, 1.0 equiv) in anhydrous dichloromethane (20 mL) at 0° C. was added acetic acid (0.685 mL, 11.98 mmol, 2.0 equiv) and sodium triacetoxyborohydride (CAS: 56553-60-7, 3.81 g, 17.97 mmol, 3.0 equiv). The reaction mixture was warmed up to RT and stirred for 24 h. The reaction mixture was then basified with a solution of 2 M sodium hydroxide (45 mL) and a saturated solution of sodium hydrogencarbonate (30 mL). The two phases were separated, and the aqueous phase was extracted with dichloromethane. The combined organic phases were washed with a saturated solution of sodium hydrogencarbonate and brine, dried over $MgSO_4$, filtered and concentrated in vacuo. The resulting residue was purified by flash chromatography on silica gel (eluent system: heptane/ethyl acetate 70/30) to afford tert-butyl 2-(oxan-3-yl)hydrazine-1-carboxylate.

Step 2: (Tetrahydro-pyran-3-yl)-hydrazine Di-hydrochloride Salt

To a solution of tert-butyl 2-(oxan-3-yl)hydrazine-1-carboxylate from Step 1 (0.534 g, 2.46 mmol, 1 equiv) in anhydrous dichloromethane (1.74 mL) at RT was added 4 M HCl in dioxane (12.34 mL, 49.38 mmol, 20 equiv). The reaction mixture was stirred at RT overnight, and then the solid was collected by filtration. The solid was washed twice with diethyl ether and dried in vacuo to afford the titled compound, H01.

Illustrative Synthesis of H02: 4,4-Difluoro-cyclohexyl)-hydrazine Bis(trifluoroacetate)

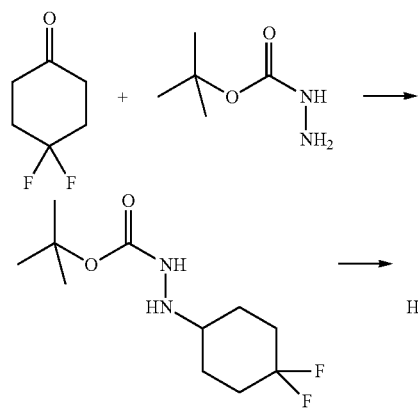

Step 1: Tert-butyl N-[(4,4-difluorocyclohexyl) amino]carbamate

To 4,4-difluorocyclohexanone (CAS: 22515-18-0, 0.4 g, 2.98 mmol, 1.0 equiv) in anhydrous methanol (8.5 mL) at RT was added tert-butyl carbazate (CAS: 870-46-2, 0.394 g, 2.98 mmol, 1.0 equiv). The reaction mixture was stirred for 20 minutes at RT, and then acetic acid (0.51 mL, 8.95 mmol, 3.0 equiv) and sodium cyanoborohydride (CAS: 25895-60-7, 0.281 g, 4.47 mmol, 1.5 equiv) were added. The reaction mixture was stirred at RT overnight. The reaction mixture was then basified with a solution of 2 M sodium hydroxide (22 mL) and a saturated solution of sodium hydrogencarbonate (15 mL). The two phases were separated, and the aqueous phase was extracted with dichloromethane. The combined organic phases were washed with a saturated solution of sodium hydrogencarbonate and brine, dried over $MgSO_4$, filtered and concentrated in vacuo. The resulting residue was purified by flash chromatography on silica gel (eluent system: heptane/ethyl acetate gradient from 100/0 to 50/50) to afford tert-butyl 2-(4,4-difluorocyclohexyl)hydrazine-1-carboxylate.

Step 2: 4,4-Difluoro-cyclohexyl)-hydrazine Bis(trifluoroacetate)

The tert-butyl 2-(4,4-difluorocyclohexyl)hydrazine-1-carboxylate intermediate from Step 1 (0.2 g, 0.8 mmol, 1 equiv) was stirred at RT in a 1:1 mixture of dichloromethane (0.65 mL) and trifluoroacetic acid (0.65 mL) for 1.5 h. The reaction mixture was concentrated in vacuo. The residue was taken up three times with toluene and concentrated in vacuo to afford the titled compound, H02.

Synthesis of H04: (2,4-Dimethoxy-benzyl)-hydrazine Di-hydrochloride Salt

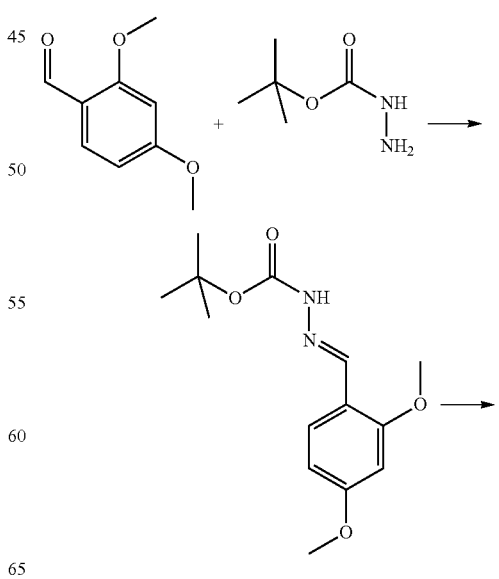

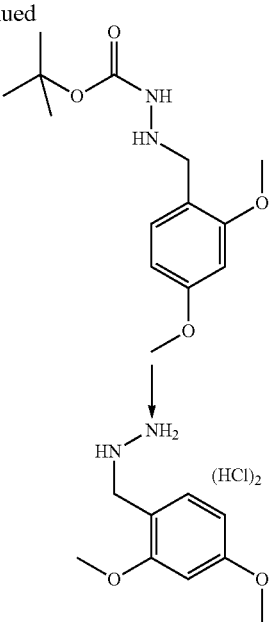

Step 1: Tert-butyl N-[(E)-(2,4-dimethoxyphenyl) methyleneamino]carbamate

To 2,4-dimethoxybenzaldehyde (CAS: 613-45-6, 37.82 g, 228 mmol, 1.0 equiv) in methanol at RT was added tert-butyl carbazate (CAS: 870-46-2, 30.08 g, 228 mmol, 1.0 equiv) and MgSO$_4$ (18.9 g). The reaction mixture was stirred at RT overnight. The reaction mixture was filtered through a pad of diatomaceous earth. The solids were washed with dichloromethane, and the filtrate was concentrated in vacuo. The residue was taken up in diethyl ether (120 mL) and stirred at RT. The resulting slurry was filtered. The solid was washed three times with diethyl ether and dried in vacuo to afford tert-butyl 2-[(2,4-dimethoxyphenyl)methylidene]hydrazine-1-carboxylate.

Step 2: Tert-butyl N-[(2,4-dimethoxyphenyl)methylamino]carbamate

A 2-L round bottom flask under nitrogen atmosphere was charged with methanol (1.3 L), 10% palladium on carbon (13.6 g), and tert-butyl 2-[(2,4-dimethoxyphenyl)methylidene]hydrazine-1-carboxylate from Step 1 (68.41 g, 228 mmol, 1 equiv). The reaction mixture was placed under vacuum then filled with hydrogen and kept under a hydrogen atmosphere (balloon). The reaction mixture was stirred at RT for 5 h. The reaction mixture was filtered through a pad of diatomaceous earth. The solids were washed with methanol, and the filtrate was concentrated in vacuo. The resulting residue was purified by flash chromatography on silica gel (eluent system: heptane/ethyl acetate, gradient from 50/50 to 40/60) to afford tert-butyl 2-[(2,4-dimethoxyphenyl)methyl] hydrazine-1-carboxylate.

Step 3: (2,4-Dimethoxy-benzyl)-hydrazine Di-hydrochloride Salt

A 2-L round bottom flask was charged with tert-butyl 2-[(2,4-dimethoxyphenyl)methyl]hydrazine-1-carboxylate from Step 2 (59.8 g, 211 mmol, 1.0 equiv), then a solution of 4 M HCl in dioxane (600 mL, 2400 mmol, 11.35 equiv) was added. The reaction mixture was stirred at RT overnight. The reaction mixture was filtered. The solid was washed three times with diethyl ether and dried in vacuo to afford the titled compound, H04.

TABLE III

| | | List of Hydrazines | | | | |
|---|---|---|---|---|---|---|
| Int. | Structure | Name | SM | method | MW | Mes |
| H01 | (HCl)$_2$ HN–NH$_2$ (tetrahydropyran) | (Tetrahydro-pyran-3-yl)-hydrazine di-hydrochloride salt | 23462-75-1 | C1, C3 Specific example | 116 | |
| H02 | (TFA)$_2$ HN–NH$_2$ (4,4-difluorocyclohexyl) | (4,4-Difluoro-cyclohexyl)-hydrazine di-trifluoroacetic acid salt | 22515-18-0 | C2, C4 Specific example | 150 | |

TABLE III-continued

List of Hydrazines

| Int. | Structure | Name | SM | method | MW | Mes |
|---|---|---|---|---|---|---|
| H03 | (HCl)$_2$, HN(NH$_2$)-tetrahydrofuran-3-yl | (Tetrahydro-furan-3-yl)-hydrazine di-hydrochloride salt | 22929-52-8 | C2, C3 | 102 | |
| H04 | (HCl)$_2$, HN(NH$_2$)-CH$_2$-(2,4-dimethoxyphenyl) | (2,4-Dimethoxy-benzyl)-hydrazine di-hydrochloride salt | 613-45-6 | Specific example | 182 | 183 |

Method D: Aryl Hydrazones Formation

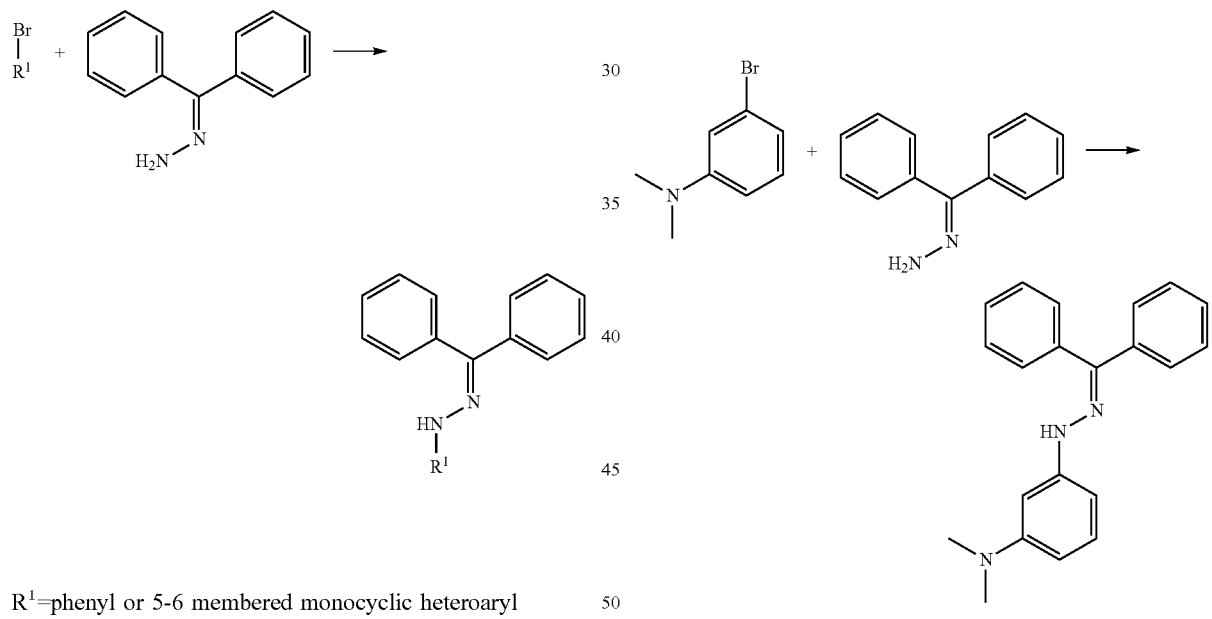

R$^1$=phenyl or 5-6 membered monocyclic heteroaryl

An aryl bromide (1.05 equiv), benzophenone hydrazone (CAS: 5350-57-2, 1.0 equiv) and rac-BINAP (CAS: 98327-87-8, 0.06 equiv) are introduced in a round bottom flask at RT and suspended in anhydrous toluene. The slurry is purged with argon (bubbling). Then palladium(II) acetate (CAS: 3375-31-3, 0.02 equiv) and sodium tert-butoxide (CAS: 865-48-5, 1.3 equiv) are added, and the resulting slurry is purged with argon again. The reaction mixture is heated at 100° C. until the reaction is finished. The reaction mixture is cooled down to RT and filtered through a pad of diatomaceous earth. Solids were washed with ethyl acetate, and the filtrate is concentrated in vacuo. The titled compound is obtained from the crude filtrate either by precipitation from a suitable solvent or by purification by flash chromatography on silica gel (eluent system: heptane/ethyl acetate).

Illustrative Synthesis of ArH01: [3-(N'-Benzhydrylidene-hydrazino)-phenyl]-dimethyl-amine 3-Bromo-N,N-dimethylaniline (CAS: 16518-62-0, 18.55 mL, 130 mmol, 1.05 equiv), benzophenone hydrazone (CAS: 5350-57-2, 24.29 g, 124 mmol, 1.0 equiv) and rac-BINAP (CAS: 98327-87-8, 4.62 g, 7.43 mmol, 0.06 equiv) were combined in a round bottom flask at RT and suspended in anhydrous toluene (80 mL). The slurry was purged with argon (bubbling), and then palladium(II) acetate (CAS: 3375-31-3, 0.556 g, 2.48 mmol, 0.02 equiv) and sodium tert-butoxide (CAS: 865-48-5, 15.46 g, 161 mmol, 1.3 equiv) were added. The resulting slurry was purged with argon again, and the reaction mixture was heated at 100° C. for 1.5 h. The reaction mixture was cooled down to RT and filtered through a pad of diatomaceous earth. The solids were washed with ethyl acetate, and the filtrate was concentrated in vacuo. The residue was taken up in diethyl ether, and stirred at RT. The resulting slurry was filtered. The collected solid was washed twice with diethyl ether and dried in vacuo to afford the titled compound.

TABLE IV

| | List of Arylhydrazones | | | | | |
|---|---|---|---|---|---|---|
| Int. | Structure | Name | SM | method | MW | Mes |
| ArH01 | | [3-(N'-Benzhydrylidene-hydrazino)-phenyl]-dimethyl-amine | 16518-62-0 | D Specific example | 315 | 316 |
| ArH02 | | N-Benzhydrylidene-N'-(3-morpholin-4-yl-phenyl)-hydrazine | 197846-82-5 | D | 357 | 358 |
| ArH03 | | N-Benzhydrylidene-N'-(3-fluoro-5-methoxy-phenyl)-hydrazine | 29578-39-0 | D | 320 | 321 |
| ArH04 | | N-Benzhydrylidene-N'-(6-fluoro-pyridin-2-yl)-hydrazine | 144100-07-2 | D | 291 | 292 |

TABLE IV-continued

List of Arylhydrazones

| Int. | Structure | Name | SM | method | MW | Mes |
|---|---|---|---|---|---|---|
| ArH05 | 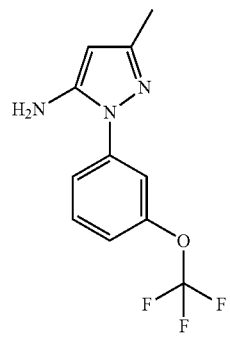 | N-Benzhydrylidene-N'-(2-chloro-pyridin-4-yl)-hydrazine | 73583-37-6 | D | 308 | 309 |

Methods E1-E7: Synthesis of Aminopyrazoles

Method E1: Cyclization of Hydrazines with 3-aminocrotononitrile

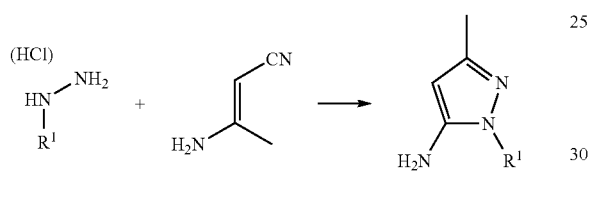

3-Aminocrotononitrile (CAS: 1118-61-2, 1.1 equiv), the hydrazine hydrochloride (1.0 equiv) and few drops of 1 N HCl solution are heated in EtOH at reflux until the reaction is finished. The reaction mixture is cooled down to RT and then is diluted with a saturated solution of sodium hydrogencarbonate. The aqueous phase is extracted with dichloromethane. The combined organic phases are filtered through a phase separator and concentrated under vacuum to afford the aminopyrazole which is used as such.

Illustrative Synthesis of AMP01: (5-Methyl-2-(3-trifluoromethoxy-phenyl)-2H-pyrazol-3-ylamine

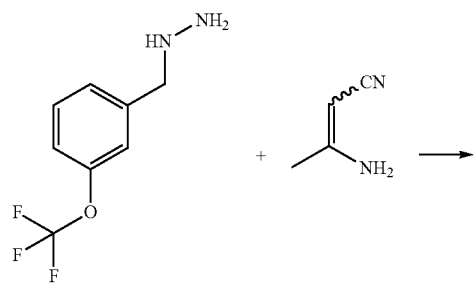

-continued

3-Aminocrotononitrile (CAS: 1118-61-2, 0.5 g, 6.09 mmol, 1.1 eq;), 3-(trifluoromethoxy)phenylhydrazine hydrochloride (1.27 g, 5.54 mmol, 1.0 equiv) and two drops of 1 N HCl solution were heated in EtOH (1.5 mL) at reflux overnight. The reaction mixture was diluted with a saturated solution of sodium hydrogencarbonate, and the aqueous phase was extracted with dichloromethane. The combined organic phases were filtered through a phase separator and concentrated under vacuum to afford the titled compound which was used as such.

Method E2: Cyclization of Hydrochloride Salts of Hydrazines with Cyano Ketones

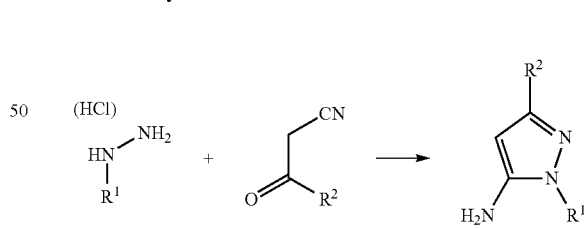

n = 1 or 2

A round bottom flask is charged with the cyanoketone (from 1.0 to 1.5 equiv), the hydrazine hydrochloride or dihydrochloride (1 equiv) and EtOH. This mixture is stirred at a temperature ranging from RT to refluxing ethanol until the reaction is finished. Then the reaction mixture is concentrated in vacuo to afford a crude mixture which is used as such or undergoes one of the following processes:

Either the crude mixture is taken up in a suitable solvent. The resulting slurry is filtered, and the solids are washed with the same solvent and dried in vacuo to afford the aminopyrazole as its hydrochloride salt which is used as such or is taken up in either ethyl acetate or dichloromethane and basified with a saturated solution of either potassium carbonate or sodium hydrogencarbonate. The two phases are separated, and the aqueous phase is extracted with either ethyl acetate or dichloromethane. The combined organic phases are washed with brine, dried over MgSO$_4$, filtered and concentrated in vacuo to afford the aminopyrazole as its free base which is used as such or further purified by flash chromatography on silica gel.

Or alternatively this crude mixture is partitioned between water and either ethyl acetate or dichloromethane. The two phases are separated, and the aqueous phase is washed with either ethyl acetate or dichloromethane, basified with a saturated solution of sodium hydrogencarbonate and extracted with either ethyl acetate or dichloromethane. The combined organic phases are washed with brine, dried over MgSO$_4$, filtered and concentrated in vacuo to afford the aminopyrazole as its free base which is used as such or further purified by flash chromatography on silica gel.

Illustrative Synthesis of AMP29:
5-Cyclobutyl-2-phenyl-2H-pyrazol-3-ylamine

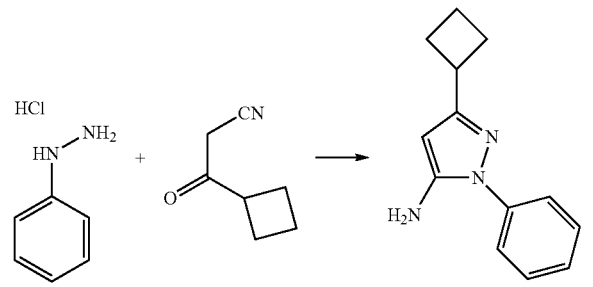 [SMILES: NNc1ccccc1 ; Cl ; N#CCC(=O)C1CCC1 ; Nc1cc(C2CCC2)nn1-c1ccccc1]

A round bottom flask was charged with 3-cyclobutyl-3-oxo-propionitrile (CK01, 19.6 g, 159 mmol, 1.1 equiv), phenylhydrazine hydrochloride (CAS: 59-88-1, 20.92 g, 145 mmol, 1.0 equiv) and EtOH (210 mL). The reaction mixture was stirred at reflux for 1 h. Then the reaction mixture was concentrated in vacuo to afford a crude mixture which was taken up in diethyl ether. The resulting slurry was filtered, and the solid was washed with diethyl ether and dried in vacuo to afford the titled compound as its hydrochloride salt which was taken up in dichloromethane and basified with a saturated solution of sodium hydrogencarbonate. The two phases were separated, and the aqueous phase was extracted with dichloromethane. The combined organic phases were washed with brine, dried over MgSO$_4$, filtered and concentrated in vacuo to afford the titled compound as its free base.

Illustrative Synthesis of AMP 35:
5-Cyclobutyl-2-cyclohexyl-2H-pyrazol-3-ylamine

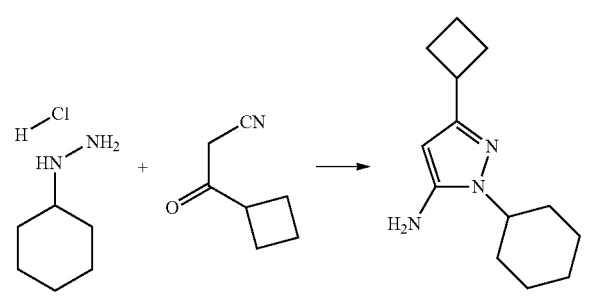

A round bottom flask was charged with 3-cyclobutyl-3-oxo-propionitrile (CK01, [118431-89-3], 20.4 g, 166 mmol), cyclohexylhydrazine hydrochloride ([24214-73-1], 25 g, 166 mmol) and EtOH (200 mL). The reaction mixture was refluxed overnight and cooled down to RT. Next, the mixture was concentrated and water (150 mL) was added. The pH was modified till pH=7 with a saturated K$_2$CO$_3$ solution. Subsequently, the aqueous phase was extracted with DCM. The obtained organic phase was dried and concentrated to give a yellow solid. Trituration with MTBE gave the titled compound.

Illustrative Synthesis of AMP93:
3-cyclobutyl-1-(4-fluorophenyl)-1H-pyrazol-5-amine

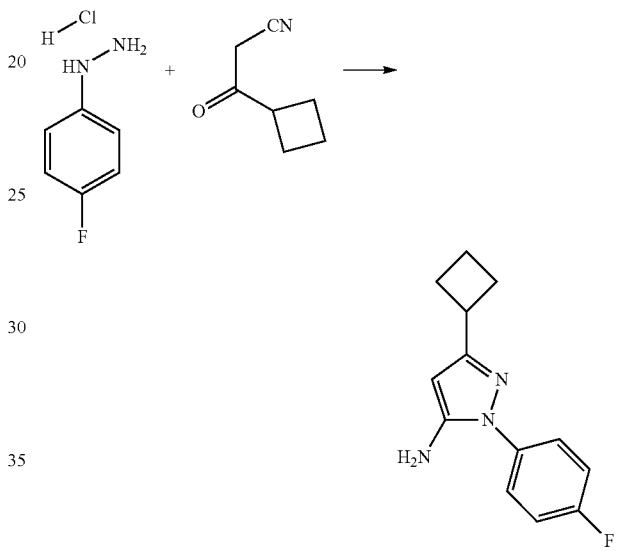

A round bottom flask was charged with 3-cyclobutyl-3-oxo-propionitrile (CK01, 10 g, 81.4 mmol), 4-fluorophenyl-hydrazine hydrochloride ([823-85-8], 12 g, 74 mmol) and EtOH (35 mL). The reaction mixture was refluxed for 2 hours and cooled down to RT. Half of the solvent was removed in vacuo. The mixture was vigorously stirred and diisopropyl ether (350 mL) was added. The stirring was continued for 1 hour, and the formed precipitate was filtered, washed with diisopropyl ether and dried at 40° C. under reduced pressure to give the titled compound.

Illustrative Synthesis of AMP94:
1-tert-butyl-3-cyclobutyl-1H-pyrazol-5-amine

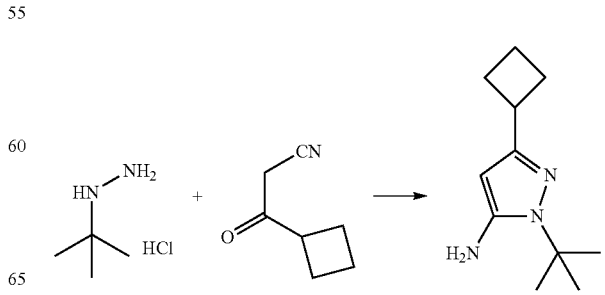

A round bottom flask was charged with 3-cyclobutyl-3-oxo-propionitrile (CK01, 12.3 g, 0.1 mol), tert-butylhydrazine hydrochloride ([7400-27-3], 13.5 g, 0.11 mol) and EtOH (150 mL). The reaction mixture was refluxed for 20 hours and cooled down to RT. Half of the solvent was removed by concentration in vacuo, and the mixture was cooled in an ice bath. The formed precipitate was collected by filtration and washed successively with diethyl ether and n-pentane. The filtrate was allowed to stand for 1 hour, and the formed precipitate was again collected by filtration and washed with diethyl ether and n-pentane. The combined solids were stirred in ethyl acetate and a saturated solution of $NaHCO_3$. The organic phase was dried over sodium sulfate, filtered and evaporated under reduced pressure to give the titled compound.

Method E3: Cyclization of Cyano Ketones with Hydrazines Either as Free Base, Hydrochloride or TFA Salt, in the Presence of an Organic Base

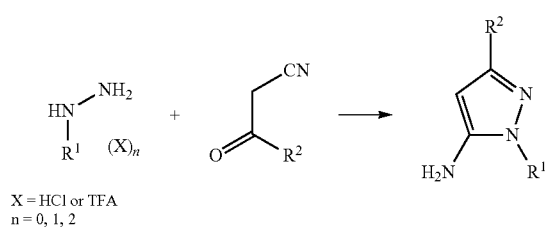

X = HCl or TFA
n = 0, 1, 2

To the hydrazine either as free base or as a hydrochloride or a trifluoroacetic acid mono or di-salt (1 equiv) and the cyanoketone (from 1.0 to 1.5 equiv) in ethanol or toluene at RT is added DIPEA (from 0 to 2.0 equiv). Then the reaction mixture is heated at reflux until the reaction is finished. The reaction mixture is concentrated in vacuo to afford a crude mixture which is used as such or purified by flash chromatography on silica gel to afford the aminopyrazole as its free base.

Illustrative Synthesis of AMP26:
2-Cyclopentyl-5-isopropyl-2H-pyrazol-3-ylamine

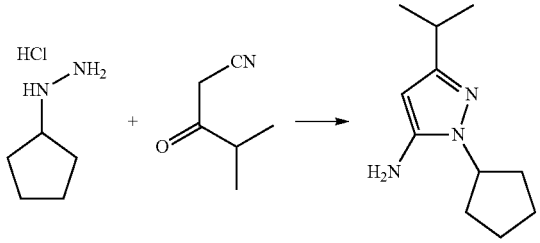

To cyclopentylhydrazine hydrochloride (CAS: 24214-72-0, 0.35 g, 2.56 mmol, 1.0 equiv) and 4-methyl-3-oxo-pentanenitrile (CAS: 29509-06-6, 0.33 mL, 2.82 mmol, 1.1 equiv) in toluene (12.8 mL) at RT was added DIPEA (0.82 mL, 5.12 mmol, 2.0 equiv). Then the reaction mixture was heated at reflux for 1.5 h. The reaction mixture was cooled down to RT and concentrated in vacuo to afford a crude mixture which was purified by flash chromatography on silica gel (eluent system: heptane/ethyl acetate gradient from 100/0 to 30/70) to afford the titled compound.

Method E4: Cyclization of Arylhydrazones with Cyanoketones

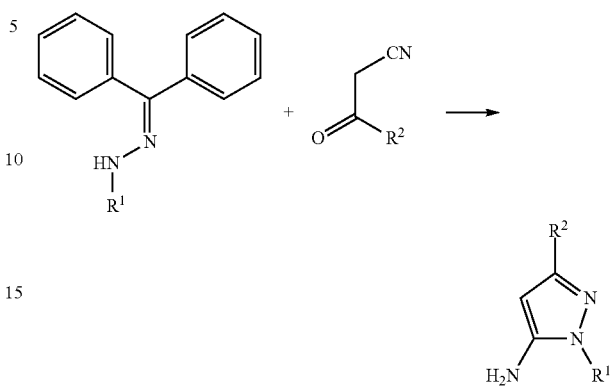

To the arylhydrazone (1 equiv) and the cyanoketone (from 1.0 to 2 equiv) in ethanol at RT is added an aqueous solution of 2 M HCl or 12 M HCl (5 equiv). Then the reaction mixture is heated at reflux until the reaction is finished. Then the reaction mixture is cooled down to RT and undergoes one of the following processes.

The reaction mixture is concentrated to dryness in vacuo to afford a crude mixture. The aminopyrazole is obtained from this crude mixture by precipitation from a suitable solvent to afford the aminopyrazole as its hydrochloride salt and used as such.

Ethanol from the reaction mixture is removed in vacuo. The resulting aqueous residue is diluted with an aqueous solution of 2 M HCl, washed with dichloromethane, then basified with a saturated solution of sodium hydrogencarbonate and extracted with dichloromethane. The combined organic phases are washed with brine, dried over $MgSO_4$, filtered and concentrated in vacuo to afford the aminopyrazole as a free base which is used as such or further purified by flash chromatography on silica gel.

Illustrative Synthesis of AMP06: 2-(3-Dimethyl-amino-phenyl)-5-isopropyl-2H-pyrazol-3-ylamine

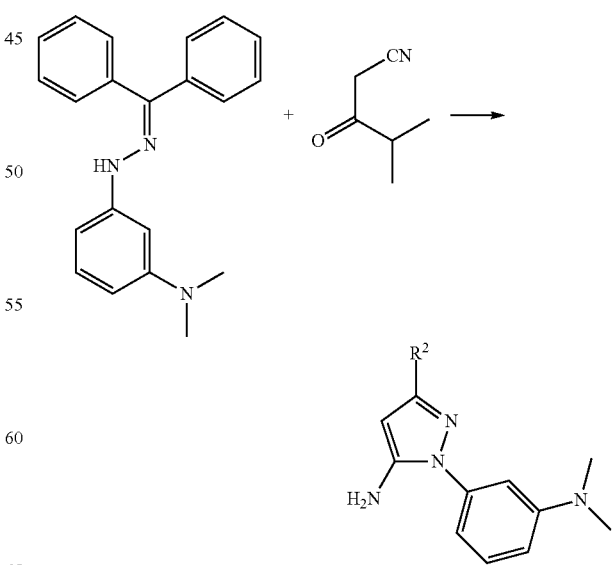

To [3-(N'-benzhydrylidene-hydrazino)-phenyl]-dimethylamine (ArH01, 25.57 g, 81 mmol, 1 equiv) and 4-methyl- 3-oxo-pentanenitrile (CAS: 29509-06-6, 10.57 mL, 89.2 mmol, 1.1 equiv) in ethanol (255 mL) at RT was added an aqueous solution of 2 M HCl (203 mL, 405 mmol, 5 equiv). Then the reaction mixture was heated at reflux overnight. The reaction mixture was cooled down to RT, and ethanol from the reaction mixture was removed in vacuo. The resulting aqueous residue was diluted with an aqueous solution of 2 M HCl, washed with dichloromethane, then basified with a saturated solution of sodium hydrogencarbonate and extracted twice with dichloromethane. The combined organic phases were washed with brine, dried over MgSO$_4$, filtered and concentrated in vacuo to afford the titled compound which was used as such.

Method E5: SNAr on 2-(2-chloro-pyridin-4-yl)-yl-2H-pyrazol-3-ylamine Intermediates

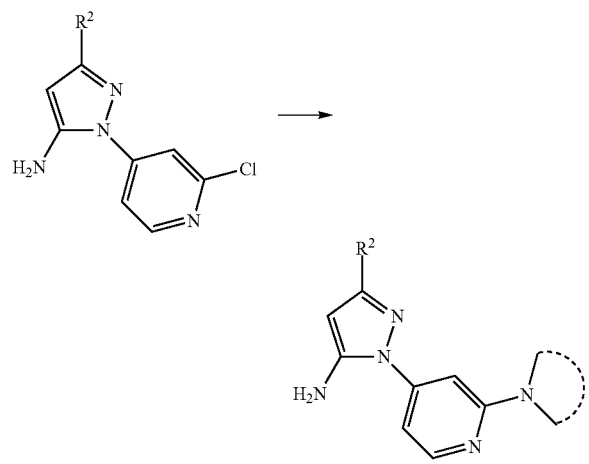

A sealed tube is charged with the 2-(2-chloro-pyridin-4-yl)-yl-2H-pyrazol-3-ylamine intermediate (1 equiv), the amine (from 10 to 15 equiv), DIPEA (3 equiv) and DMA. This mixture is heated at a temperature ranging from 130° C. to 160° C. until the reaction is finished. Then the reaction mixture is cooled down to RT and partitioned between ethyl acetate and water. The two phases are separated and the aqueous phase is extracted with ethyl acetate. The combined organic phases are washed with water and brine, dried over MgSO$_4$, filtered and concentrated in vacuo. The substituted aminopyrazole is obtained from the crude mixture either by precipitation or by purification by flash chromatography on silica gel.

Illustrative Synthesis of AMP22: 5-Isopropyl-2-(2-pyrrolidin-1-yl-pyridin-4-yl)-2H-pyrazol-3-ylamine

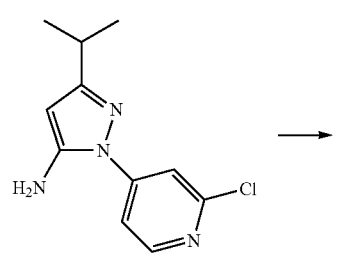

-continued

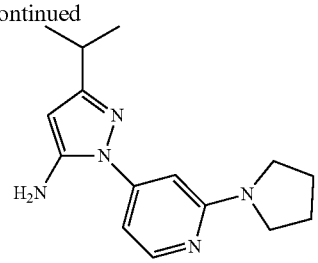

A sealed tube was charged with 2-(2-chloro-pyridin-4-yl)-yl-2H-pyrazol-3-ylamine intermediate (AMP20, 1.2 g, 5.07 mmol, 1 equiv), pyrrolidine (CAS: 123-75-1, 4 mL, 50.7 mmol, 10 equiv), DIPEA (2.6 mL, 15.2 mmol, 3 equiv) and DMA (10 mL). This mixture was heated at 130° C. for 2 h. Then the reaction mixture was cooled down to RT, and additional pyrrolidine (CAS: 123-75-1, 1 mL, 12.67 mmol, 2.5 equiv) was introduced, and the reaction mixture was heated at 130° C. for 30 minutes. Then the reaction mixture was cooled down to RT and partitioned between ethyl acetate and water. The two phases were separated, and the aqueous phase was extracted twice with ethyl acetate. The combined organic phases were washed with water (three times) and brine, dried over MgSO$_4$, filtered and concentrated in vacuo. The crude mixture was purified by flash chromatography on silica gel (eluent system: dichloromethane/methanol gradient from 100/0 to 97/3) to afford the titled compound.

Method E6: Buchwald Coupling

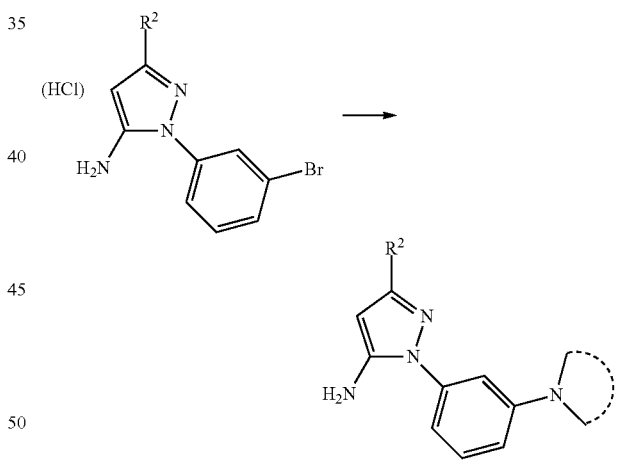

To the 2-(3-bromo-phenyl)-2H-pyrazol-3-ylamine hydrochloride salt intermediate (1 equiv) in anhydrous THF at RT under a nitrogen atmosphere is added the amine (1.2 equiv), a solution of 1 N LiHMDS in THF (5 equiv) and XPhos Pd G1 (CAS 1028206-56-5, 0.1 equiv). The reaction mixture is stirred at RT until the reaction is finished. The reaction mixture is hydrolyzed with a saturated solution of ammonium chloride and diluted with dichloromethane. The two phases are separated, and the aqueous phase is extracted with dichloromethane. The combined organic phases are washed with brine, dried over MgSO$_4$, filtered and concentrated in vacuo. The substituted aminopyrazole is obtained from the crude mixture by purification with flash chromatography on silica gel (eluent system: heptane/ethyl acetate).

109

Illustrative Synthesis of AMP11: 5-Isopropyl-2-(3-pyrrolidin-1-yl-phenyl)-2H-pyrazol-3-ylamine

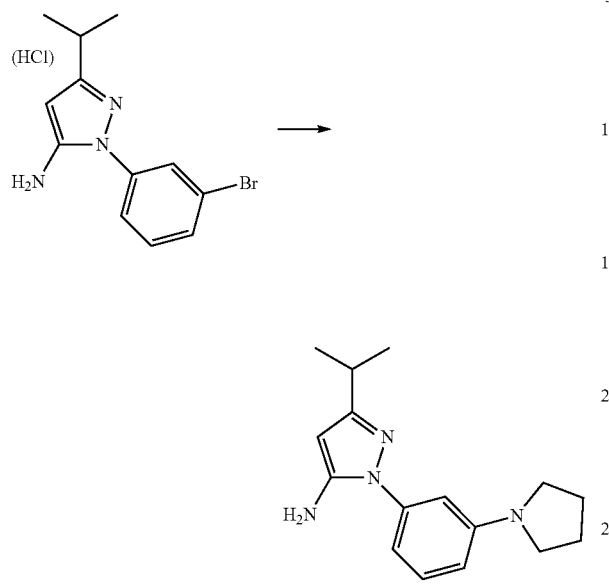

To 2-(3-bromo-phenyl)-5-isopropyl-2H-pyrazol-3-ylamine hydrochloride salt (AMP05, 0.5 g, 1.58 mmol, 1 equiv) in anhydrous THF (5 mL) at RT under nitrogen atmosphere was added pyrrolidine (CAS: 123-75-1, 0.16 mL, 1.9 mmol, 1.2 equiv), a solution of 1 N LiHMDS in THF (8 mL, 8 mmol, 5 equiv) and XPhos Pd G1 (CAS 1028206-56-5, 0.117 g, 0.16 mmol, 0.1 equiv). The reaction mixture was stirred at RT for 5 h. The reaction mixture was treated with a saturated solution of ammonium chloride and diluted with dichloromethane. The two phases were separated, and the aqueous phase was extracted with dichloromethane. The combined organic phases were washed with brine, dried over MgSO₄, filtered and concentrated in vacuo. The crude mixture was purified by flash chromatography on silica gel (eluent system: heptane/ethyl acetate gradient from 100/0 to 65/35) to afford the titled compound.

Method E7: O-Alkylation of 5-aminopyrazol-3-ol Analogues

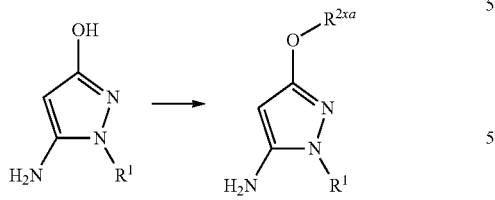

A suspension of 5-aminopyrazol-3-ol derivative (1 equiv), cesium carbonate (1.2 equiv) and 2-bromopropane (1 equiv) in N-methylpyrrolidine is stirred at RT for 20 to 72 hours. The reaction mixture is diluted with DCM and washed with water. The organic phase is dried over sodium sulfate, filtered and concentrated under reduced pressure. The O-alkylated product is purified by flash column chromatography on silica gel.

110

Illustrative Synthesis of AMP96: 1-(4-fluorophenyl)-3-[(propan-2-yl)oxy]-1H-pyrazol-5-amine

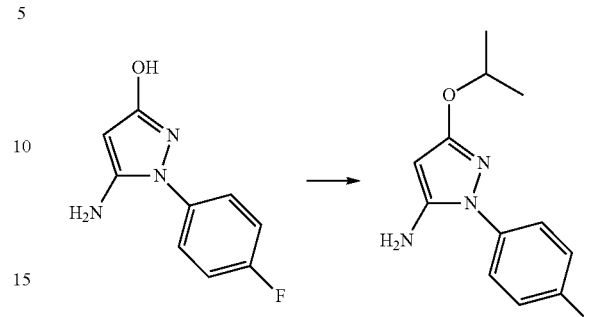

A suspension of 5-amino-1-(4-fluorophenyl)-1H-pyrazol-3-ol ([1247169-18-1], 800 mg, 4.14 mmol), cesium carbonate (2.15 g, 4.97 mmol) and 2-bromopropane (516 µL, 4.14 mmol) in N-methylpyrrolidine (8 mL) was stirred at RT for 20 hours. The reaction mixture was diluted with DCM and washed with water. The organic phase was dried over sodium sulfate, filtered and concentrated under reduced pressure. The residue was purified by flash column chromatography on silica gel eluting with ethyl acetate/n-heptane to yield the titled compound.

Synthesis of Intermediates AMP18 and AMP19: [6-(5-Amino-3-isopropyl-pyrazol-1-yl)-pyridin-2-yl]-dimethyl-amine and 5-Isopropyl-2-(6-morpholin-4-yl-pyridin-2-yl)-2H-pyrazol-3-ylamine

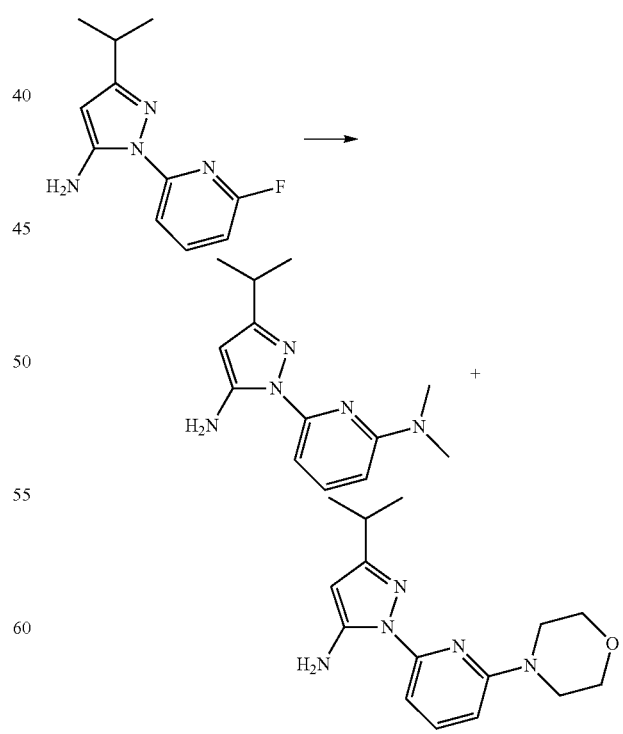

A sealed tube was charged with 2-(6-fluoro-pyridin-2-yl)-5-isopropyl-2H-pyrazol-3-ylamine (AMP17, 0.2 g, 0.91 mmol, 1 equiv), morpholine (CAS: 110-91-8, 0.12 mL, 1.37 mmol, 1.5 equiv), DIPEA (0.19 mL, 1.09 mmol, 1.2 equiv) and DMF (2 mL). This mixture was heated at 100° C. overnight. Then the reaction mixture was cooled down to RT and partitioned between ethyl acetate and water. The two phases were separated, and the aqueous phase was extracted with ethyl acetate. The combined organic phases were washed with water (three times) and brine, dried over MgSO$_4$, filtered and concentrated in vacuo. The crude mixture was purified by flash chromatography on silica gel (eluent system: heptane/ethyl acetate gradient from 100/0 to 60/40) to afford the two titled compounds.

TABLE V

List of aminopyrazoles

| Int. | Structure | Name | SM | method | MW | Mes |
|---|---|---|---|---|---|---|
| 70373-98-7 | 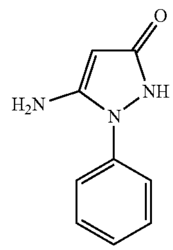 | 5-Amino-1-phenyl-1,2-dihydro-pyrazol-3-one | | | 175 | |
| 826-85-7 | 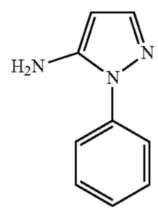 [SMILES: Nc1ccnn1-c1ccccc1] | 2-Phenyl-2H-pyrazol-3-ylamine | | | 159 | |
| 1131-18-6 | 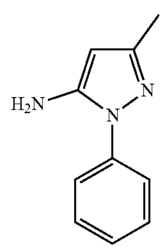 | 5-Methyl-2-phenyl-2H-pyrazol-3-ylamine | | | 173 | |
| 345-07-3 | 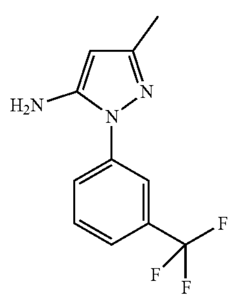 [SMILES: Cc1cc(N)n(-c2cccc(C(F)(F)F)c2)n1] | 5-Methyl-2-(3-trifluoromethyl-phenyl)-2H-pyrazol-3-ylamine | | | 241 | |
| 866472-29-9 | 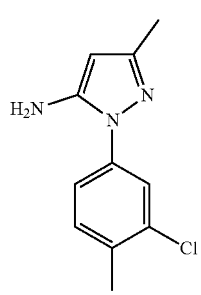 | 2-(3-Chloro-4-methyl-phenyl)-5-methyl-2H-pyrazol-3-ylamine | | | 221 | |

TABLE V-continued

List of aminopyrazoles

| Int. | Structure | Name | SM | method | MW | Mes |
|---|---|---|---|---|---|---|
| 380569-79-9 | 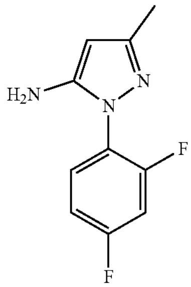 | 2-(2,4-Difluorophenyl)-5-methyl-2H-pyrazol-3-ylamine | | | 209 | |
| 1232796-65-4 | 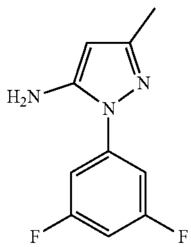 | 2-(3,5-Difluorophenyl)-5-methyl-2H-pyrazol-3-ylamine | | | 209 | |
| 890010-89-6 | 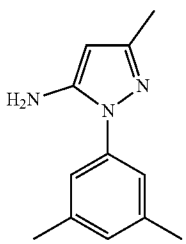 | 2-(3,5-Dimethylphenyl)-5-methyl-2H-pyrazol-3-ylamine | | | 201 | |
| 92721-83-0 | 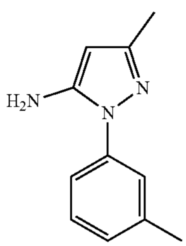 | 5-Methyl-2-m-tolyl-2H-pyrazol-3-ylamine | | | 187 | |
| 56547-82-1 | 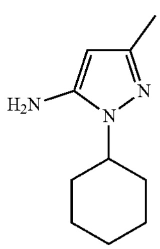 | 2-Cyclohexyl-5-methyl-2H-pyrazol-3-ylamine | | | 179 | |
| 40401-41-0 | 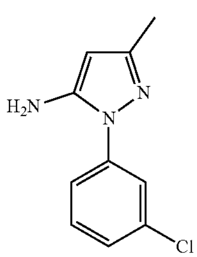 | 2-(3-Chlorophenyl)-5-methyl-2H-pyrazol-3-ylamine | | | 207 | |

TABLE V-continued

List of aminopyrazoles

| Int. | Structure | Name | SM | method | MW | Mes |
|---|---|---|---|---|---|---|
| 105438-45-7 | 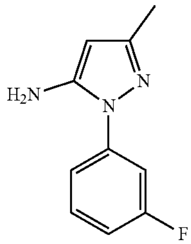 | 2-(3-Fluoro-phenyl)-5-methyl-2H-pyrazol-3-ylamine | | | 191 | |
| 497141-59-0 | 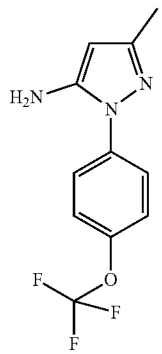 | 5-Methyl-2-(4-trifluoromethoxy-phenyl)-2H-pyrazol-3-ylamine | | | 257 | |
| 92721-94-3 | 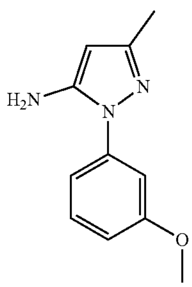 | 2-(3-Methoxy-phenyl)-5-methyl-2H-pyrazol-3-ylamine | | | 203 | |
| 3524-36-5 | 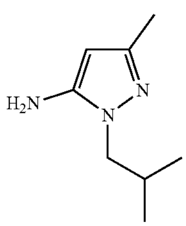 | 2-Isobutyl-5-methyl-2H-pyrazol-3-ylamine | | | 153 | |
| 1124-16-9 | 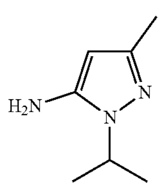 | 2-Isopropyl-5-methyl-2H-pyrazol-3-yL amine | | | 139 | |
| 436088-86-7 | 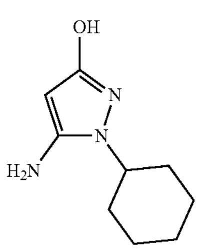 [SMILES: Nc1cc(O)nn1C1CCCCC1] | 5-Amino-1-cyclohexyl-1H-pyrazol-3-ol | | | 181 | |

TABLE V-continued

| | List of aminopyrazoles | | | | | |
|---|---|---|---|---|---|---|
| Int. | Structure | Name | SM | method | MW | Mes |
| 1247169-18-1 | | 5-Amino-1-(4-fluorophenyl)-1H-pyrazol-3-ol | | | 193 | |
| AMP01 | | 5-Methyl-2-(3-trifluoromethoxy-phenyl)-2H-pyrazol-3-ylamine | 133115-55-6, 1118-61-2 | E1 Specific example | 257 | 258 |
| AMP02 | | 2-(3,4-Difluoro-phenyl)-5-methyl-2H-pyrazol-3-ylamine | 161886-22-2, 1118-22-2 | E1 | 209 | 210 |
| AMP03 | | 2-(3-Fluoro-5-methoxy-phenyl)-5-methyl-2H-pyrazol-3-ylamine | ArH03, 1118-61-2 | E4 | 221 | 222 |
| AMP04 | | 5-Isopropyl-2-phenyl-2H-pyrazol-3-ylamine | 100-63-0, 29509-06-6 | E3 | 201 | 202 |

TABLE V-continued

List of aminopyrazoles

| Int. | Structure | Name | SM | method | MW | Mes |
|---|---|---|---|---|---|---|
| AMP05 | 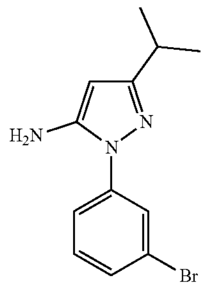 [SMILES: CC(C)c1cc(N)n(-c2cccc(Br)c2)n1] | 2-(3-Bromo-phenyl)-5-isopropyl-2H-pyrazol-3-ylamine | 27246-81-7, 29509-06-6 | E2 | 280 | 281 |
| AMP06 | 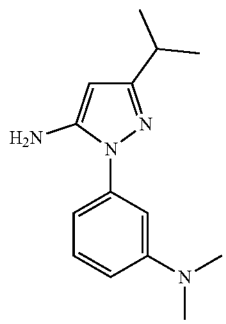 [SMILES: CC(C)c1cc(N)n(-c2cccc(N(C)C)c2)n1] | 2-(3-Dimethylamino-phenyl)-5-isopropyl-2H-pyrazol-3-ylamine | ArH01, 29509-06-6 | E4 Specific example | 244 | 245 |
| AMP07 | 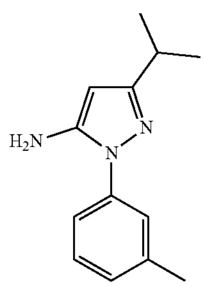 [SMILES: Cc1cccc(-n2nc(C(C)C)cc2N)c1] | 5-Isopropyl-2-m-tolyl-2H-pyrazol-3-ylamine | 637-04-7, 29509-06-6 | E2 | 215 | 216 |
| AMP08 | 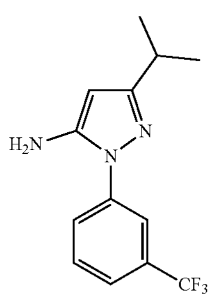 [SMILES: CC(C)c1cc(N)n(-c2cccc(C(F)(F)F)c2)n1] | 5-Isopropyl-2-(3-trifluoromethyl-phenyl)-2H-pyrazol-3-ylamine | 368-78-5, 29509-06-6 | E3 | 269 | 270 |
| AMP09 | 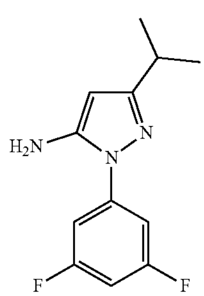 [SMILES: CC(C)c1cc(N)n(-c2cc(F)cc(F)c2)n1] | 2-(3,5-Difluoro-phenyl)-5-isopropyl-2H-pyrazol-3-ylamine | 134993-88-7, 29509-06-6 | E2 | 237 | 238 |

TABLE V-continued

List of aminopyrazoles

| Int. | Structure | Name | SM | method | MW | Mes |
|---|---|---|---|---|---|---|
| AMP10 | 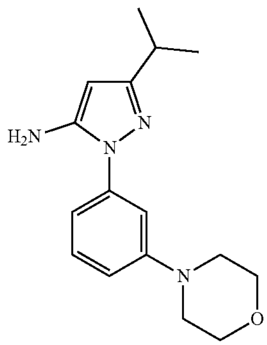 [SMILES: CC(C)c1cc(N)n(-c2cccc(N3CCOCC3)c2)n1] | 5-Isopropyl-2-(3-morpholin-4-yl-phenyl)-2H-pyrazol-3-ylamine | ArH02, 29509-06-6 | E4 | 286 | 287 |
| AMP11 | 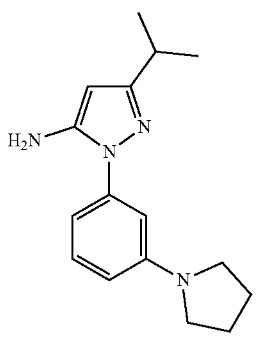 [SMILES: CC(C)c1cc(N)n(-c2cccc(N3CCCC3)c2)n1] | 5-Isopropyl-2-(3-pyrrolidin-1-yl-phenyl)-2H-pyrazol-3-ylamine | AMP05 | E6 Specific example | 270 | 271 |
| AMP12 | 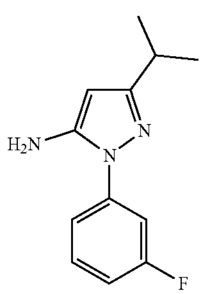 [SMILES: CC(C)c1cc(N)n(-c2cccc(F)c2)n1] | 2-(3-Fluoro-phenyl)-5-isopropyl-2H-pyrazol-3-ylamine | 502496-27-7, 2950906-6 | E2 | 219 | 220 |
| AMP13 | 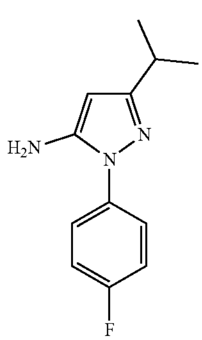 [SMILES: CC(C)c1cc(N)n(-c2ccc(F)cc2)n1] | 2-(4-Fluoro-phenyl)-5-isopropyl-2H-pyrazol-3-ylamine | 823-85-8, 29509-06-6 | E2 | 219 | 220 |

TABLE V-continued

List of aminopyrazoles

| Int. | Structure | Name | SM | method | MW | Mes |
|---|---|---|---|---|---|---|
| AMP14 | 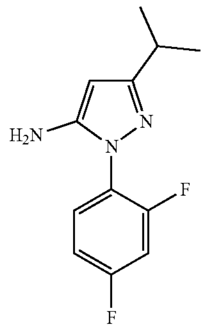 [SMILES: CC(C)c1cc(N)n(-c2ccc(F)cc2F)n1] | 2-(2,4-Difluoro-phenyl)-5-isopropyl-2H-pyrazol-3-ylamine | 51523-79-6, 29509-06-6 | E2 | 237 | 238 |
| AMP15 | 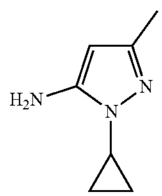 | 2-Cyclopropyl-5-methyl-2H-pyrazol-3-ylamine | 213764-25-1, 1118-61-2 | E1 | 137 | 138 |
| AMP16 | 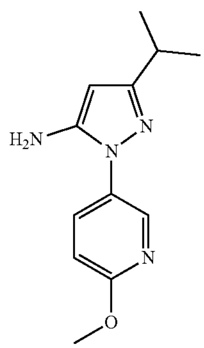 [SMILES: COc1ccc(-n2nc(C(C)C)cc2N)cn1] | 5-Isopropyl-2-(6-methoxy-pyridin-3-yl)-2H-pyrazol-3-ylamine | 179543-88-5, 29509-06-6 | E2 | 232 | 233 |
| AMP17 | 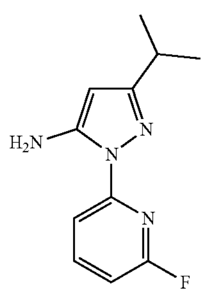 [SMILES: CC(C)c1cc(N)n(-c2cccc(F)n2)n1] | 2-(6-Fluoro-pyridin-2-yl)-5-isopropyl-2H-pyrazol-3-ylamine | ArH04, 29509-06-6 | E4 | 220 | 221 |
| AMP18 | 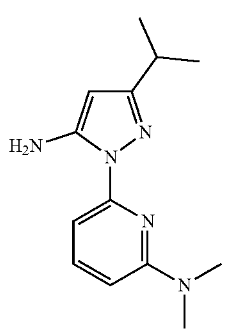 [SMILES: CC(C)c1cc(N)n(-c2cccc(N(C)C)n2)n1] | [6-(5-Amino-3-isopropyl-pyrazol-1-yl)-pyridin-2-yl]-dimethyl-amine | AMP17 | Specific example | 245 | 246 |

TABLE V-continued

List of aminopyrazoles

| Int. | Structure | Name | SM | method | MW | Mes |
|---|---|---|---|---|---|---|
| AMP19 | 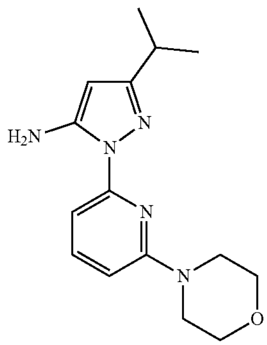 [SMILES: CC(C)c1cc(N)n(-c2cccc(N3CCOCC3)n2)n1] | 5-Isopropyl-2-(6-morpholin-4-yl-pyridin-2-yl)-2H-pyrazol-3-ylamine | AMP17 | Specific example | 287 | 288 |
| AMP20 | 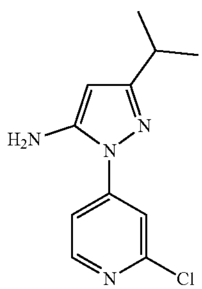 [SMILES: CC(C)c1cc(N)n(-c2ccnc(Cl)c2)n1] | 2-(2-Chloro-pyridin-4-yl)-5-isopropyl-2H-pyrazol-3-ylamine | ArH05, 29509-06-6 | E4 | 237 | 238 |
| AMP21 | 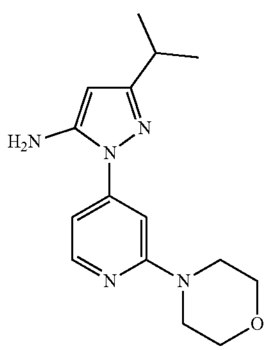 [SMILES: CC(C)c1cc(N)n(-c2ccnc(N3CCOCC3)c2)n1] | 5-Isopropyl-2-(2-morpholin-4-yl-pyridin-4-yl)-2H-pyrazol-3-ylamine | AMP20 | E5 | 287 | 288 |
| AMP22 | 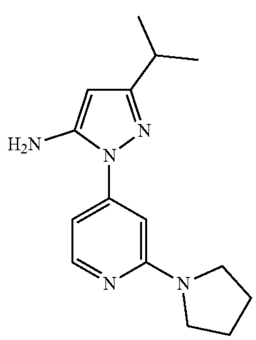 [SMILES: CC(C)c1cc(N)n(-c2ccnc(N3CCCC3)c2)n1] | 5-Isopropyl-2-(2-pyrrolidin-1-yl-pyridin-4-yl)-2H-pyrazol-3-ylamine | AMP20 | E5 Specific example | 271 | 272 |

TABLE V-continued

| | List of aminopyrazoles | | | | | |
|---|---|---|---|---|---|---|
| Int. | Structure | Name | SM | method | MW | Mes |
| AMP23 | | 2-Cyclohexyl-5-isopropyl-2H-pyrazol-3-ylamine | 30929-57-8, 29509-06-6 | E2 | 207 | 208 |
| AMP24 | | 2-(4,4-Difluoro-cyclohexyl)-5-isopropyl-2H-pyrazol-3-ylamine | H02, 29509-06-6 | E3 | 243 | 244 |
| AMP25 | | 5-Isopropyl-2-(tetrahydro-pyran-3-yl)-2H-pyrazol-3-ylamine | H01, 29509-06-6 | E3 | 209 | 210 |
| AMP26 | | 2-Cyclopentyl-5-isopropyl-2H-pyrazol-3-ylamine | 24214-72-0, 29509-06-6 | E3 Specific example | 193 | 194 |
| AMP27 | | 5-Isopropyl-2-(tetrahydro-furan-3-yl)-2H-pyrazol-3-ylamine | H03, 29509-06-6 | E3 | 195 | 196 |

TABLE V-continued

List of aminopyrazoles

| Int. | Structure | Name | SM | method | MW | Mes |
|---|---|---|---|---|---|---|
| AMP28 | 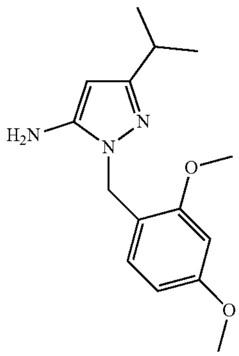 [SMILES: COc1ccc(Cn2nc(C(C)C)cc2N)c(OC)c1] | 2-(2,4-Dimethoxy-benzyl)-5-isopropyl-2H-pyrazol-3-ylamine | H04, 29509-06-6 | E2 | 275 | 276 |
| AMP29 | 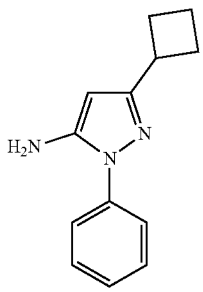 [SMILES: Nc1cc(C2CCC2)nn1-c1ccccc1] | 5-Cyclobutyl-2-phenyl-2H-pyrazol-3-ylamine | 59-88-1, CK01 | E2 Specific example | 213 | 214 |
| AMP30 | 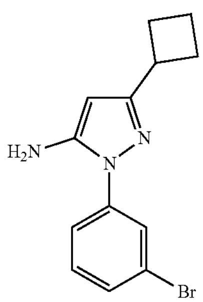 [SMILES: Nc1cc(C2CCC2)nn1-c1cccc(Br)c1] | 2-(3-Bromo-phenyl)-5-cyclobutyl-2H-pyrazol-3-ylamine | 27246-81-7, CK01 | E3 | 292 | 293 |
| AMP31 | 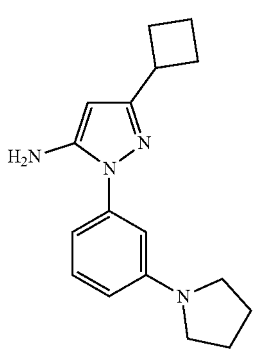 [SMILES: Nc1cc(C2CCC2)nn1-c1cccc(N2CCCC2)c1] | 5-Cyclobutyl-2-(3-pyrrolidin-1-yl-phenyl)-2H-pyrazol-3-ylamine | AMP30 | E6 | 282 | 283 |

TABLE V-continued

List of aminopyrazoles

| Int. | Structure | Name | SM | method | MW | Mes |
|---|---|---|---|---|---|---|
| AMP32 | 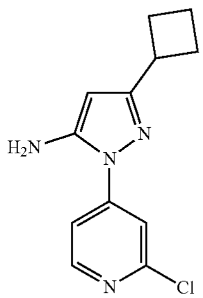 [SMILES: Nc1cc(C2CCC2)nn1-c1ccnc(Cl)c1] | 2-(2-Chloro-pyridin-4-yl)-5-cyclobutyl-2H-pyrazol-3-ylamine | 700811-29-6, CK01 | E3 | 248 | 249 |
| AMP33 | 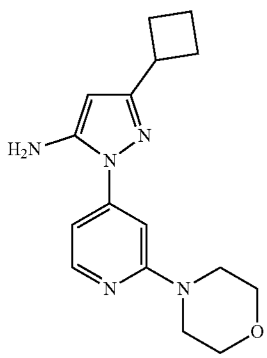 [SMILES: Nc1cc(C2CCC2)nn1-c1ccnc(N2CCOCC2)c1] | 5-Cyclobutyl-2-(2-morpholin-4-yl-pyridin-4-yl)-2H-pyrazol-3-ylamine | AMP32 | E5 | 299 | 300 |
| AMP34 | 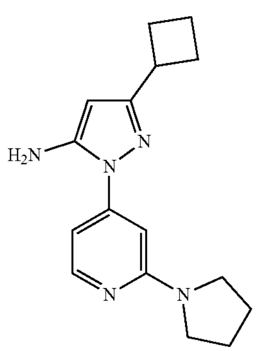 [SMILES: Nc1cc(C2CCC2)nn1-c1ccnc(N2CCCC2)c1] | 5-Cyclobutyl-2-(2-pyrrolidin-1-yl-pyridin-4-yl)-2H-pyrazol-3-ylamine | AMP32 | E5 | 283 | 284 |
| AMP35 | 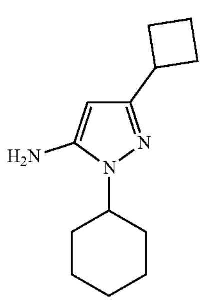 [SMILES: Nc1cc(C2CCC2)nn1C1CCCCC1] | 5-Cyclobutyl-2-cyclohexyl-2H-pyrazol-3-ylamine | 30929-57-8, CK01 | E2, Specific Example | 219 | 220 |

TABLE V-continued

List of aminopyrazoles

| Int. | Structure | Name | SM | method | MW | Mes |
|---|---|---|---|---|---|---|
| AMP36 | 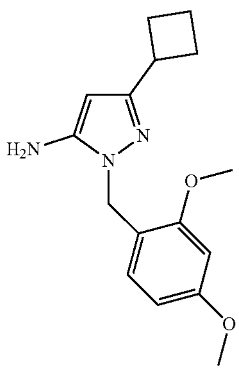 [SMILES: COc1ccc(Cn2nc(C3CCC3)cc2N)c(OC)c1] | 5-Cyclobutyl-2-(2,4-dimethoxy-benzyl)-2H-pyrazol-3-ylamine | H04, CK01 | E2 | 287 | 288 |
| AMP37 | 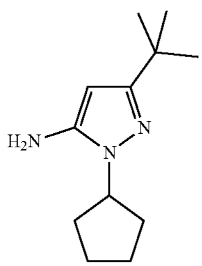 | 5-tert-Butyl-2-cyclopentyl-2H-pyrazol-3-ylamine | 24214-72-0, 599917-51-2 | E2 | 207 | 208 |
| AMP38 | 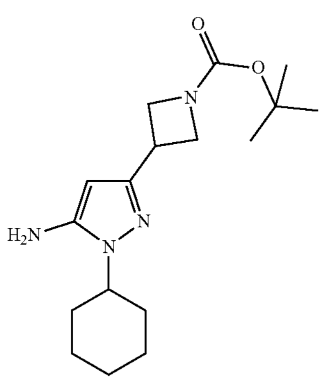 [SMILES: CC(C)(C)OC(=O)N1CC(c2cc(N)n(C3CCCCC3)n2)C1] | 3-(5-Amino-1-cyclohexyl-1H-pyrazol-3-yl)-azetidine-1-carboxylic acid tert-butyl ester | 30929-57-8, 887594-13-0 | E2 | 320 | 321 |
| AMP39 | 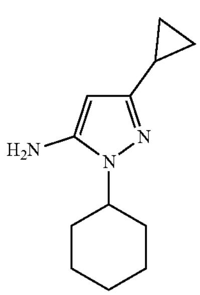 [SMILES: Nc1cc(C2CC2)nn1C1CCCCC1] | 2-Cyclohexyl-5-cyclopropyl-2H-pyrazol-3-ylamine | 30929-57-8, 118431-88-2 | E2 | 205 | 206 |

TABLE V-continued

List of aminopyrazoles

| Int. | Structure | Name | SM | method | MW | Mes |
|---|---|---|---|---|---|---|
| AMP40 | 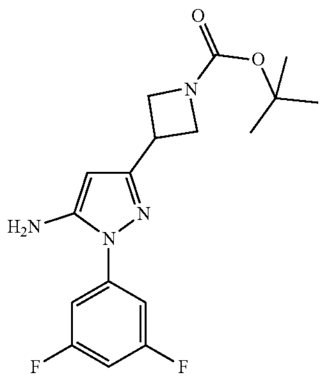 [SMILES: CC(C)(C)OC(=O)N1CC(c2cc(N)n(-c3cc(F)cc(F)c3)n2)C1] | 3-[5-Amino-1-(3,5-difluoro-phenyl)-1H-pyrazol-3-yl]-azetidine-1-carboxylic acid tert-butyl ester | 134993-88-7, 887594-13-0 | E2 | 350 | 295[1] |
| AMP41 | 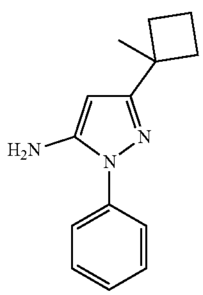 [SMILES: CC1(c2cc(N)n(-c3ccccc3)n2)CCC1] | 5-(1-Methyl-cyclobutyl)-2-phenyl-2H-pyrazol-3-ylamine | 100-63-0, CK02 | E3 | 227 | 228 |
| AMP42 | 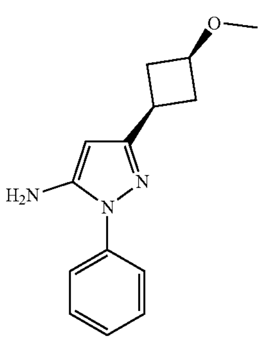 [SMILES: CO[C@H]1C[C@@H](c2cc(N)n(-c3ccccc3)n2)C1] | 5-(3-Methoxy-cyclobutyl)-2-phenyl-2H-pyrazol-3-ylamine | 59-88-1, CK03 | E2 | 243 | |
| AMP43 | 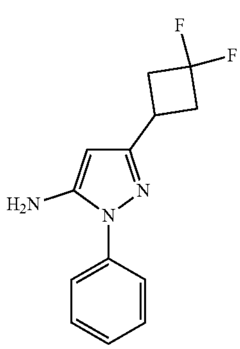 [SMILES: Nc1cc(C2CC(F)(F)C2)nn1-c1ccccc1] | 5-(3,3-Difluoro-cyclobutyl)-2-phenyl-2H-pyrazol-3-ylamine | 59-88-1, 1234616-26-2 | E2 | 249 | |

TABLE V-continued
List of aminopyrazoles
| Int. | Structure | Name | SM | method | MW | Mes |
|---|---|---|---|---|---|---|
| AMP44 | 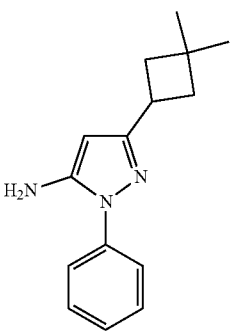 [SMILES: CC1(C)CC(c2cc(N)n(-c3ccccc3)n2)C1] | 5-(3,3-Dimethyl-cyclobutyl)-2-phenyl-2H-pyrazol-3-ylamine | 59-88-1, CK04 | E2 | 241 | |
| AMP45 | 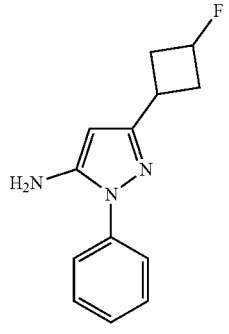 [SMILES: Nc1cc(C2CC(F)C2)nn1-c1ccccc1] | 5-(3-Fluoro-cyclobutyl)-2-phenyl-2H-pyrazol-3-ylamine | 59-88-1, CK05 | E2 | 231 | |
| AMP46 | 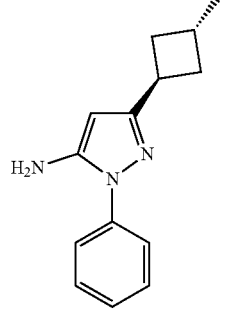 | 5-(trans-3-Methyl-cyclobutyl)-2-phenyl-2H-pyrazol-3-ylamine | 59-88-1, CK06 | E2 | 227.31 | |
| AMP93 | 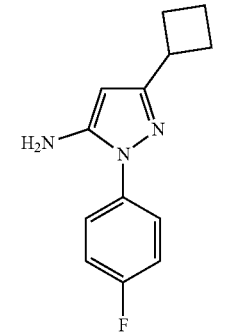 [SMILES: Nc1cc(C2CCC2)nn1-c1ccc(F)cc1] | 3-Cyclobutyl-1-(4-fluorophenyl)-1H-pyrazol-5-amine | 823-85-8, CK01 | Specific example | 231 | 232 |

TABLE V-continued

List of aminopyrazoles

| Int. | Structure | Name | SM | method | MW | Mes |
|---|---|---|---|---|---|---|
| AMP94 | 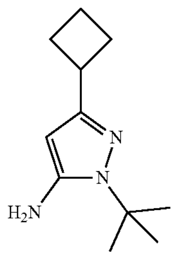 | 1-tert-Butyl-3-cyclobutyl-1H-pyrazol-5-amine | 7400-27-3, 118431-89-3 | Specific example | 193 | 194 |
| AMP95 | 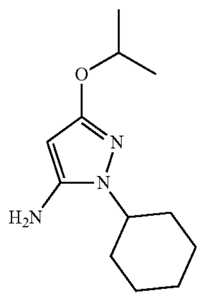 [SMILES: CC(C)Oc1cc(N)n(C2CCCCC2)n1] | 1-Cyclohexyl-3-[(propan-2-yl)oxy]-1H-pyrazol-5-amine | 436088-86-7 | E7 | 223 | 224 |
| AMP96 | 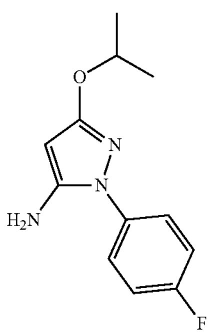 [SMILES: CC(C)Oc1cc(N)n(-c2ccc(F)cc2)n1] | 1-(4-Fluorophenyl)-3-[(propan-2-yl)oxy]-1H-pyrazol-5-amine | 1247169-18-1 | E7, Specific example | 235 | 236 |

[1](M-tBu + H)⁺

Method F: Synthesis of Aldehydes by SN—Ar

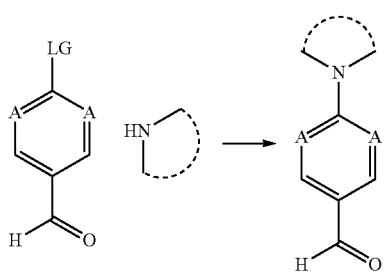

A is either CH or N
LG is F, Cl, or Br

A solution of the aldehyde (1 equiv), the amine (1.3 to 2 equiv) and the base (DIPEA or $K_2CO_3$) (2 equiv) is prepared in acetonitrile, DMSO or DMA. This mixture is heated under thermal conditions or under microwave irradiations at a temperature ranging from 85° C. to 150° C. The reaction is worked up either by filtration of the base when needed or by diluting the reaction mixture with ethyl acetate or DCM and washing the organic phase with water and brine. In all cases, the organic phase is concentrated under reduced pressure, and the crude residue is used as such or purified either by flash column chromatography or precipitation to give the titled compound.

Illustrative Synthesis of ALD02: 5'-Formyl-3,4,5,6-tetrahydro-2H-[1,2']bipyridinyl-4-carbonitrile

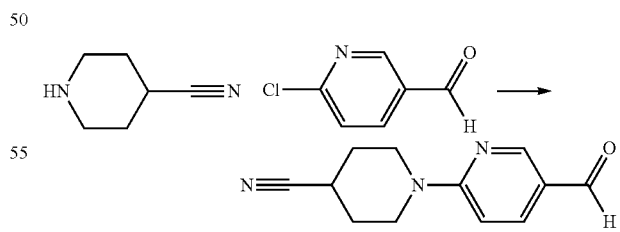

A solution of 2-chloropyridine-5-carboxaldehyde (CAS: 23100-12-1, 25.1 g, 177.4 mmol), 4-cyanopiperidine (CAS: 4395-98-6, 25.4 g, 230.6 mmol) and DIPEA (62 mL, 354.7 mmol) in acetonitrile (250 mL) was refluxed for 20 hours. The reaction mixture was cooled to RT, and the mixture was concentrated under reduced pressure. The residue was dissolved in DCM (500 mL) and washed successively with a saturated aqueous solution of $Na_2CO_3$ (250 mL) and brine (250 mL). The organic phase was stirred for 2 minutes with 10 g of silica gel, dried over sodium sulfate, filtered and concentrated under reduced pressure. The resulting mixture was dissolved in DCM (150 mL) and poured into a stirring solution of diisopropyl ether (1.5 L). The mixture was stirred vigorously for 4 hours. The precipitate was collected by filtration, washed with diisopropyl ether, and dried at 40° C. under reduced pressure to give the titled compound.

TABLE VI

List of aldehydes

| Int. | Structure | Name | SM | method | MW | Mes |
|---|---|---|---|---|---|---|
| ALD01 | 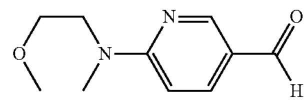 | 6-[(2-Methoxy-ethyl)-methyl-amino]-pyridine-3-carbaldehyde | 23100-12-1 | F | 194 | 195 |
| ALD02 | 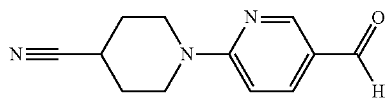 [SMILES: N#CC1CCN(c2ccc(C=O)cn2)CC1] | 5'-Formyl-3,4,5,6-tetrahydro-2H-[1,2']bipyridinyl 4-carbonitrile | 23100-12-1 | F, Specific example | 215 | 216 |
| ALD03 | 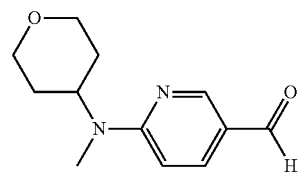 [SMILES: CN(c1ccc(C=O)cn1)C1CCOCC1] | 6-[Methyl-(tetrahydro-pyran-4-yl)-amino]-pyridine-3-carbaldehyde | 23100-12-1 | F | 220 | 221 |
| ALD04 | 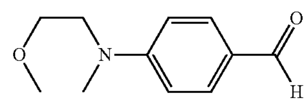 | 4-[(2-Methoxy-ethyl)-methyl-amino]-benzaldehyde | 459-57-4 | F | 193 | 194 |
| ALD05 | 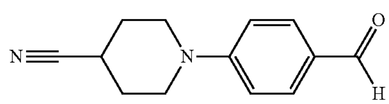 [SMILES: N#CC1CCN(c2ccc(C=O)cc2)CC1] | 1-(4-Formyl-phenyl)-piperidine-4-carbonitrile | 459-57-4 | F | 214 | 215 |
| ALD06 | 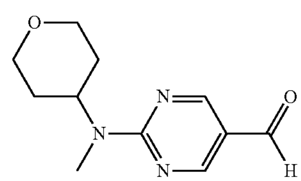 [SMILES: CN(c1ncc(C=O)cn1)C1CCOCC1] | 2-[Methyl-(tetrahydro-pyran-4-yl)-amino]-pyrimidine-5-carbaldehyde | 933702-55-7 | F | 221 | 222 |
| ALD07 | 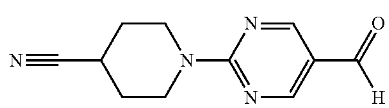 [SMILES: N#CC1CCN(c2ncc(C=O)cn2)CC1] | 1-(5-Formyl-pyrimidin-2-yl)-piperidine-4-carbonitrile | 933702-55-7 | F | 216 | 217 |
| ALD08 | 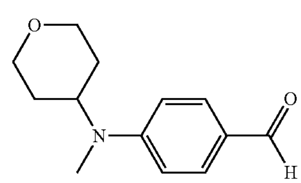 [SMILES: CN(c1ccc(C=O)cc1)C1CCOCC1] | 4-[Methyl-(tetrahydro-pyran-4-yl)-amino]-benzaldehyde | 459-57-4 | F | 219 | 220 |
| ALD09 | 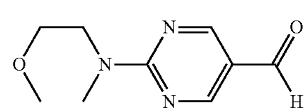 | 2-[(2-Methoxy-ethyl)-methyl-amino]-pyrimidine-5-carbaldehyde | 933702-55-7 | F | 195 | 196 |
| ALD10 | 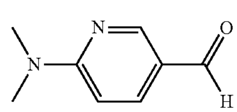 | 6-Dimethylamino-pyridine-3-carbaldehyde | 23100-12-1 | F | 150 | 151 |
| ALD11 1204-86-0 | 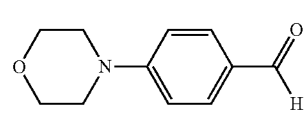 [SMILES: O=Cc1ccc(N2CCOCC2)cc1] | 4-Morpholino-benzaldehyde | | | | 191 |

TABLE VI-continued

List of aldehydes

| Int. | Structure | Name | SM | method | MW | Mes |
|---|---|---|---|---|---|---|
| ALD12 | 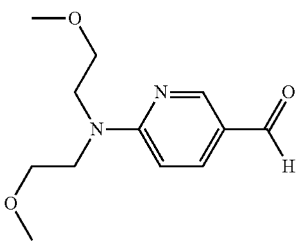 [SMILES: COCCN(CCOC)c1ccc(C=O)cn1] | 6-[bis(2-methoxyethyl)amino]pyridine-3-carbaldehyde | 23100-12-1 | F | 238 | 239 |

Methods G1-G3: Synthesis of Alkylidene Pyruvate

Method G1: Synthesis of Alkylidene Pyruvate

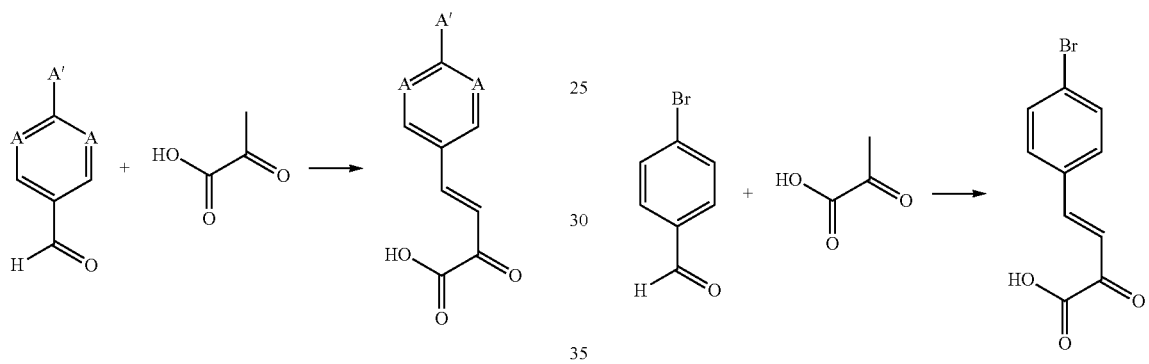

A is either N or CH

A' is either $R^e$ or $L^1$-$G^{3C}$ as described in the Summary

A solution of potassium hydroxide (from 1.5 to 2 equiv) in water is added dropwise at 0° C. to a solution of aldehyde (1 equiv) and pyruvic acid (CAS 127-17-3, from 1 eq to 1.5 equiv) in methanol. The reaction is warmed up to RT and then heated at 40° C. for 1 h to several days. Then the reaction mixture undergoes one of the following processes:

Either the formed precipitate is collected by filtration, suspended in an aqueous acidic solution, collected by filtration again, and dried in vacuo to give the titled compound.

Or alternatively, methanol is removed in vacuo, and the resulting suspension is filtered. The solid is taken up in water and either ethyl acetate or dichloromethane and acidified to pH=3-5 with either acetic acid or an aqueous solution of 2 M HCl. The two phases are separated, and the aqueous phase is extracted with either ethyl acetate or dichloromethane. The combined organic phases are washed with water and brine, dried over MgSO₄, filtered and concentrated in vacuo to afford the titled compound which is used as such or further purified by precipitation.

Illustrative Synthesis of ALP19: (E)-4-(4-Bromophenyl)-2-oxo-but-3-enoic Acid

A solution of potassium hydroxide (6.9 g, 121.6 mmol) in water (45 mL) was added at 0° C. to a stirring solution of 4-bromobenzaldehyde (CAS 1122-91-4, 15 g, 81.1 mmol) and pyruvic acid (CAS 127-17-3, 5.7 mL, 81.1 mmol) in methanol (105 mL) over a 5 minutes period. The reaction mixture was then heated at 40° C. for 4 hours, cooled down to RT and poured into ice/water (300 mL). The precipitate was stirred for 10 minutes, collected by filtration, washed with water and n-heptane, and air dried for 1 hour. The solid was suspended in aqueous 2 N HCl and stirred for 10 minutes. The precipitate was collected by filtration and dried at 40° C. under reduced pressure to afford the titled compound.

Method G2: Synthesis of Alkylidene Pyruvate

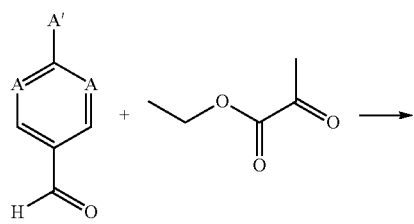

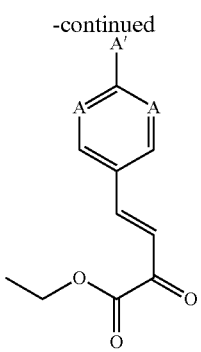

A is either N or CH
A' is either $R^e$ or $L^1$-$G^{3C}$ as described in the Summary Triflic acid (CAS 1493-13-6, from 1.35 eq to 2.5 equiv) is added dropwise to a solution of aldehyde (1 equiv), triethyl orthoformate (CAS 122-51-0, from 1.1 eq to 1.3 equiv) and ethyl pyruvate (CAS 617-35-6, from 1.5 to 3.5 equiv) in chloroform. The solution is refluxed for 30 minutes to 24 h. The reaction mixture is cooled down to RT, diluted with dichloromethane, basified with a saturated aqueous solution of $Na_2CO_3$ or $NaHCO_3$. The two phases are separated, and the aqueous phase is extracted with dichloromethane. The combined organic phases are dried over sodium sulfate, filtered and concentrated under reduced pressure. This crude mixture is purified either by flash chromatography on silica gel or by precipitation to afford the titled compound.

Illustrative Synthesis of ALP09: Ethyl (E)-4-[6-(4-cyano-1-piperidyl)-3-pyridyl]-2-oxo-but-3-enoate

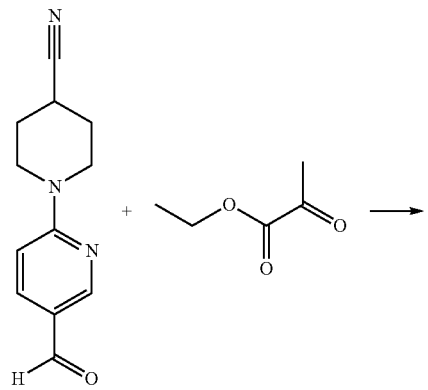

Triflic acid (CAS 1493-13-6, 26.7 mL, 301 mmol) was added dropwise to a solution of intermediate ALD02 (32.4 g, 150.5 mmol), triethyl orthoformate (CAS 122-51-0, 32.6 g, 195.7 mmol) and ethyl pyruvate (CAS 617-35-6, 41.7 mL, 376.3 mmol) in chloroform (180 mL). The solution was refluxed for 30 minutes and then cooled to RT. The reaction mixture was diluted with DCM (500 mL) and washed successively with a saturated aqueous solution of $Na_2CO_3$ (400 mL) and brine (400 mL). The organic phase was dried over sodium sulfate, filtered and concentrated under reduced pressure. The crude sample was purified by flash column chromatography on silica gel eluting with a gradient of n-heptane/ethyl acetate to yield the titled compound.

Method G3: Synthesis of Alkylidene Pyruvate

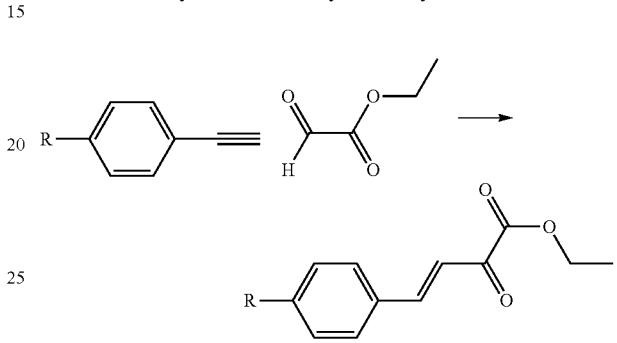

In a round bottom flask, under a nitrogen atmosphere, a suspension of 4-ethynylbenzene derivative (1 equiv.), 50% ethyl glyoxalate in toluene (2 equiv), morpholine ([110-91-8], 2 equiv), copper(I) bromide ([7787-70-4], 0.5 equiv) in dioxane is heated to 85° C. for 3 to 20 hours. The reaction mixture is cooled to RT, and the solvent was evaporated under reduced pressure. The residue is suspended in a mixture of DCM or DCM/2-propanol (95/5) and is washed twice with water. The organic phase is dried over sodium sulfate, filtered and concentrated under reduced pressure. The crude sample is purified by flash chromatography eluting with ethyl acetate/n-heptane/DCM.

Illustrative Synthesis of ALP36: Ethyl 4-(4-formylphenyl)-2-oxobut-3-enoate

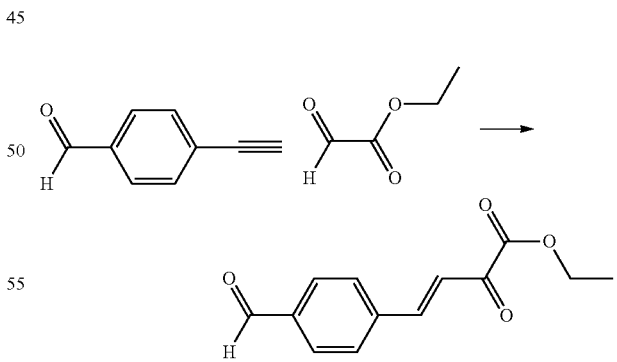

In a round bottom flask, under a nitrogen atmosphere, a suspension of 4-ethynylbenzaldehyde ([63697-96-1], 5 g, 38.4 mmol), 50% ethyl glyoxalate in toluene ([924-44-7], 15.7 mL, 15.7 g, 76.8 mmol), morpholine ([110-91-8], 6.7 mL, 76.8 mmol), copper(I) bromide ([7787-70-4], 2.8 g, 19.2 mmol) in dioxane (50 mL) was heated to 85° C. for 3 hours. The reaction mixture was cooled to RT, and the volatiles were removed under reduced pressure. The residue was suspended in a mixture of DCM/2-propanol (200 mL, 95/5) and washed twice with water (50 mL). The organic phase was dried over sodium sulfate, filtered and concentrated under reduced pressure. The residue was purified by flash chromatography eluting with ethyl acetate/n-heptane to yield the titled compound.

Synthesis of ALP38: 4-Cyano-4-[4-((E)-3-ethoxy-carbonyl-3-oxo-propenyl)-phenyl]-piperidine-1-carboxylic Acid Tert-butyl Ester

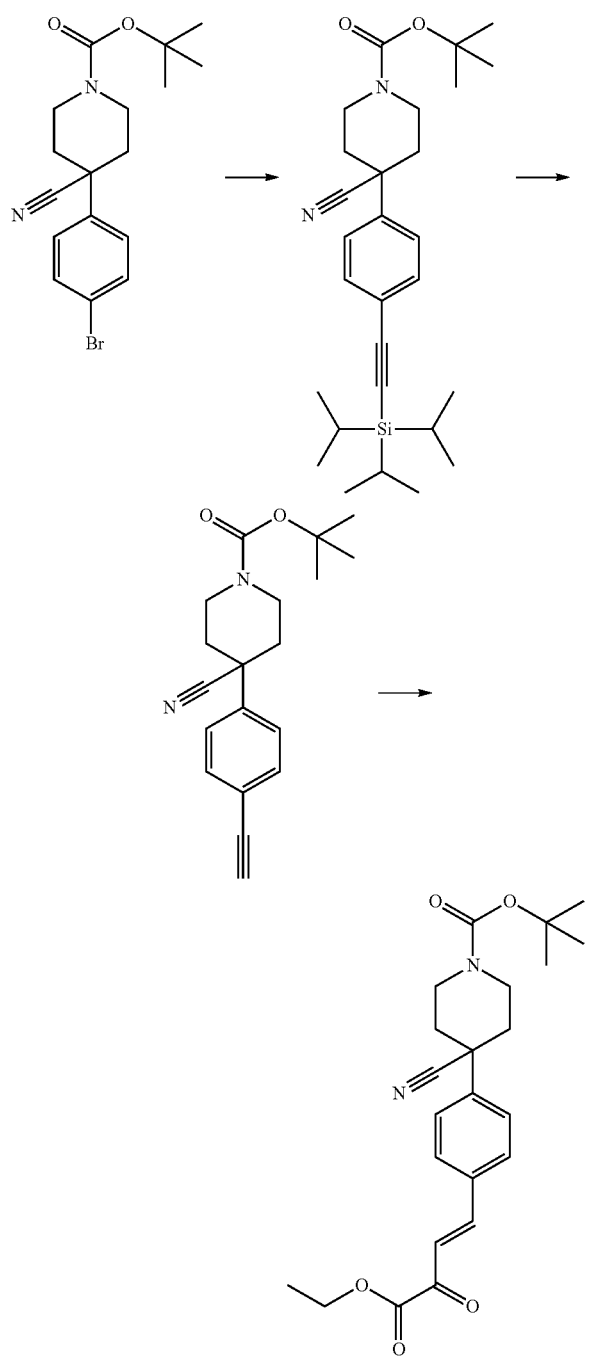

Step 1: 4-Cyano-4-{4-[(triisopropylsilanyl)-ethynyl]-phenyl}-piperidine-1-carboxylic Acid Tert-butyl Ester Nitrogen was bubbled for 5 minutes through a suspension of tert-butyl 4-(4-bromophenyl)-4-cyanopiperidine-1-carboxylate ([847615-14-9], 547 mg, 1.5 mmol), tetrakis(triphenylphosphine)palladium(0) ([14221-01-3], 90 mg, 77 µmol), copper(I) iodide ([7681-65-4], 8 mg, 42 µmol), lithium chloride ([7447-41-8], 8 mg, 189 µmol), and (triisopropylsilyl)acetylene ([89343-06-6], 670 µL, 3 mmol) in triethylamine (8 mL). The tube was sealed and heated at 100° C. for 6 hours. The mixture was then concentrated under reduced pressure, and the residue was partitioned between ethyl acetate and water. The organic phase was dried over sodium sulfate, filtered and concentrated in vacuo. The residue was purified by flash column chromatography eluting with ethyl acetate/n-heptane to give the titled compound.

Step 2: 4-Cyano-4-(4-ethynyl-phenyl)-piperidine-1-carboxylic Acid Tert-butyl Ester The compound from Step 1 (700 mg, 1.5 mmol) was dissolved in anhydrous THF (10 mL) and 1 M tetra-n-butylammonium fluoride in THF (1.7 mL, 1.7 mmol) was added. The reaction mixture was stirred at RT for 2 hours and then concentrated under reduced pressure. The residue was partitioned between ethyl acetate and water. The organic phase was dried over sodium sulfate, filtered and concentrated in vacuo. The residue was purified by flash column chromatography eluting with ethyl acetate/n-heptane to give the titled compound.

Step 3: 4-Cyano-4-[4-((E)-3-ethoxycarbonyl-3-oxo-propenyl)-phenyl]-piperidine-1-carboxylic Acid Tert-butyl Ester In a round bottom flask, under a nitrogen atmosphere, a suspension of the compound from Step 2 (270 mg, 0.58 mmol), 50% ethyl glyoxalate in toluene ([924-44-7], 232 µL, 1.16 mmol), morpholine ([110-91-8], 101 µL, 1.16 mmol), and copper(I) bromide ([7787-70-4], 42 mg, 0.29 mmol) in dioxane (5 mL) was heated to 85° C. for 20 hours. The reaction mixture was cooled down to RT and 50% ethyl glyoxalate in toluene ([924-44-7], 232 µL, 1.16 mmol), morpholine ([110-91-8], 101 µL, 1.16 mmol), and copper(I) bromide ([7787-70-4], 42 mg, 0.29 mmol) were added again, and the sealed tube was heated at 100° C. for 1 hour. The reaction mixture was cooled to RT and concentrated under reduced pressure. The residue was suspended in DCM (20 mL) and washed with water (15 mL). The organic phase was dried over sodium sulfate, filtered and concentrated under reduced pressure. The residue was purified by flash chromatography eluting with ethyl acetate/n-heptane to yield the titled compound.

TABLE VII

List of alkylidene pyruvates

| Int. | Structure | Name | SM | method | MW | Mes |
|---|---|---|---|---|---|---|
| ALP01 | 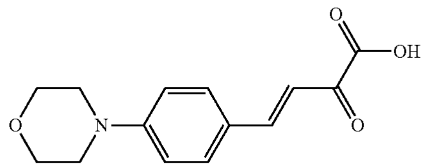 [SMILES: O=C(O)C(=O)/C=C/c1ccc(N2CCOCC2)cc1] | (E)-4-(4-morpholino-phenyl)-2-oxo-but-3-enoic acid | 1204-86-0 | G1 | 261 | 262 |
| ALP02 | 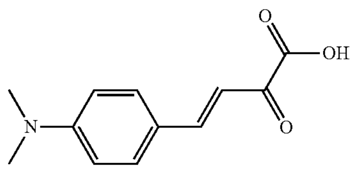 [SMILES: CN(C)c1ccc(/C=C/C(=O)C(=O)O)cc1] | (E)-4-[4-(dimethylamino)phenyl]-2-oxo-but-3-enoic acid | 100-10-7 | G1 | 219 | 220 |
| ALP03 | 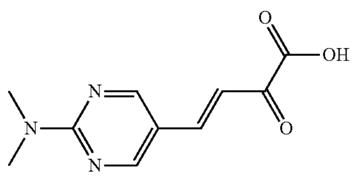 [SMILES: CN(C)c1ncc(/C=C/C(=O)C(=O)O)cn1] | (E)-4-[2-(dimethylamino)pyrimidin-5-yl]-2-oxo-but-3-enoic acid | 55551-49-0 | G1 | 221 | 222 |
| ALP04 | 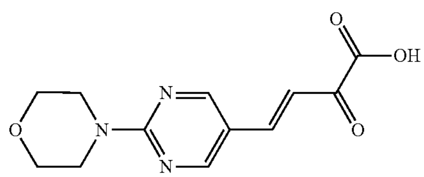 [SMILES: O=C(O)C(=O)/C=C/c1cnc(N2CCOCC2)nc1] | (E)-4-[2-morpholino-pyrimidin-5-yl]-2-oxo-but-3-enoic acid | 842974-69-0 | G1 | 263 | 264 |
| ALP05 | 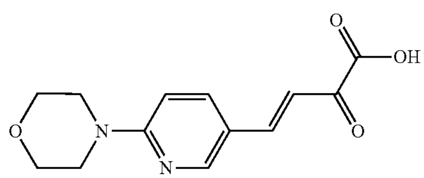 [SMILES: O=C(O)C(=O)/C=C/c1ccc(N2CCOCC2)nc1] | (E)-4-(6-morpholino-3-pyridyl)-2-oxo-but-3-enoic acid | 173282-60-5 | G1 | 262 | 263 |
| ALP06 | 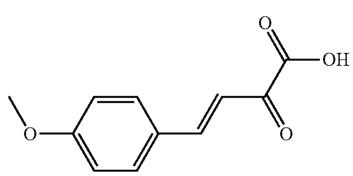 | (E)-4-(4-methoxyphenyl)-2-oxo-but-3-enoic acid | 123-11-5 | G1 | 206 | 207 |
| ALP07 | 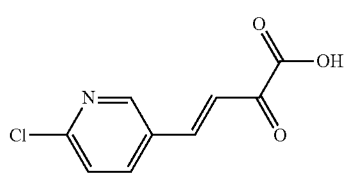 [SMILES: O=C(O)C(=O)/C=C/c1ccc(Cl)nc1] | (E)-4-(6-Chloro-pyridin-3-yl)-2-oxo-but-3-enoic acid | 23100-12-1 | G1 | 211-213 | 212-214 |
| ALP08 | 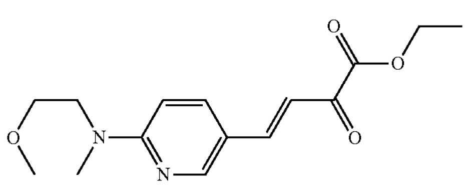 [SMILES: CCOC(=O)C(=O)/C=C/c1ccc(N(C)CCOC)nc1] | ethyl (E)-4-[6-[2-methoxyethyl(methyl)amino]-3-pyridyl]-2-oxo-but-3-enoate | ALD01 | G2 | 291 | 292 |

TABLE VII-continued

List of alkylidene pyruvates

| Int. | Structure | Name | SM | method | MW | Mes |
|---|---|---|---|---|---|---|
| ALP09 | 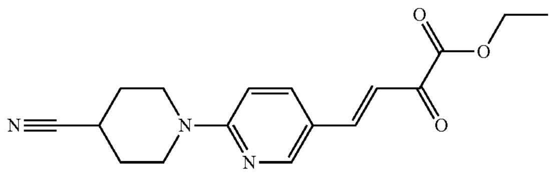 [SMILES: CCOC(=O)C(=O)/C=C/c1ccc(N2CCC(C#N)CC2)nc1] | ethyl (E)-4-[6-(4-cyano-1-piperidyl)-3-pyridyl]-2-oxo-but-3-enoate | ALD02 | G2, Specific example | 313 | 314 |
| ALP10 | 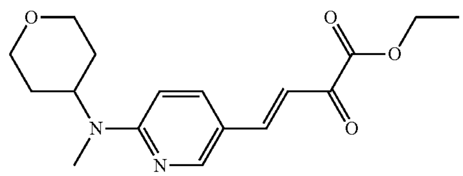 [SMILES: CCOC(=O)C(=O)/C=C/c1ccc(N(C)C2CCOCC2)nc1] | ethyl (E)-4-[6-[methyl(tetra-hydropyran-4-yl)amino]-3-pyridyl]-2-oxo-but-3-enoate | ALD03 | G2 | 318 | 319 |
| ALP11 | 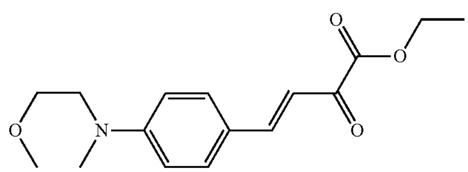 [SMILES: CCOC(=O)C(=O)/C=C/c1ccc(N(C)CCOC)cc1] | ethyl (E)-4-[4-[2-methoxyethyl(methyl)amino]phenyl]-2-oxo-but-3-enoate | ALD04 | G2 | 291 | 292 |
| ALP12 | 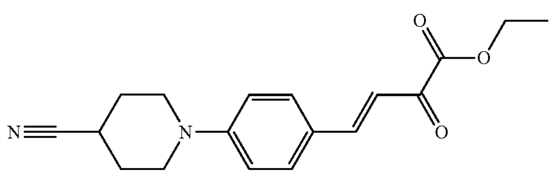 [SMILES: CCOC(=O)C(=O)/C=C/c1ccc(N2CCC(C#N)CC2)cc1] | ethyl (E)-4-[4-(4-cyano-1-piperidyl)phenyl]-2-oxo-but-3-enoate | ALD05 | G2 | 312 | 313 |
| ALP13 | 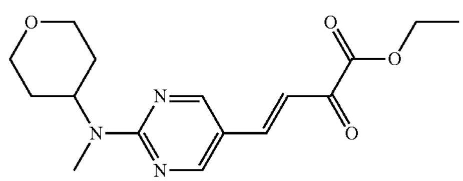 [SMILES: CCOC(=O)C(=O)/C=C/c1cnc(N(C)C2CCOCC2)nc1] | ethyl (E)-4-[2-[methyl(tetra-hydropyran-4-yl)amino]pyrimidin-5-yl]-2-oxo-but-3-enoate | ALD06 | G2 | 319 | 320 |
| ALP14 | 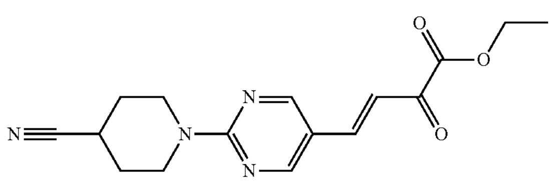 [SMILES: CCOC(=O)C(=O)/C=C/c1cnc(N2CCC(C#N)CC2)nc1] | ethyl (E)-4-[2-(4-cyano-1-piperidyl)pyrimidin-5-yl]-2-oxo-but-3-enoate | ALD07 | G2 | 314 | 315 |
| ALP15 | 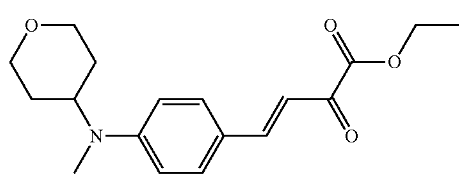 [SMILES: CCOC(=O)C(=O)/C=C/c1ccc(N(C)C2CCOCC2)cc1] | ethyl (E)-4-[4-[methyl(tetra-hydropyran-4-yl)amino]phenyl]-2-oxo-but-3-enoate | ALD08 | G2 | 317 | 318 |
| ALP16 | 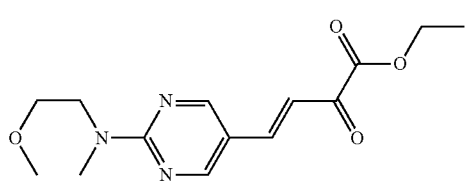 [SMILES: CCOC(=O)C(=O)/C=C/c1cnc(N(C)CCOC)nc1] | ethyl (E)-4-[2-[2-methoxyethyl(methyl)amino]pyrimidin-5-yl]-2-oxo-but-3-enoate | ALD09 | G2 | 293 | 294 |

TABLE VII-continued

List of alkylidene pyruvates

| Int. | Structure | Name | SM | method | MW | Mes |
|---|---|---|---|---|---|---|
| ALP17 | 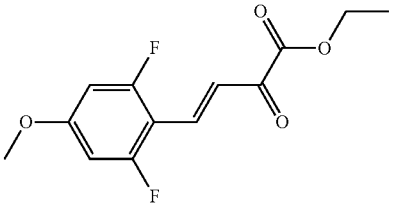 [SMILES: CCOC(=O)C(=O)/C=C/c1c(F)cc(OC)cc1F] | ethyl (E)-4-(2,6-difluoro-4-methoxy-phenyl)-2-oxo-but-3-enoate | 256417-10-4 | G2 | 270 | 271 |
| ALP18 | 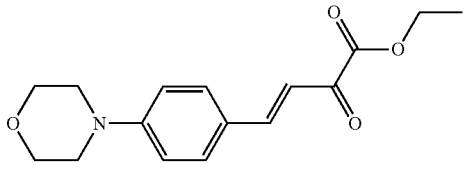 [SMILES: CCOC(=O)C(=O)/C=C/c1ccc(N2CCOCC2)cc1] | (E)-4-(4-Morpholin-4-yl-phenyl)-2-oxo-but-3-enoic acid ethyl ester | ALD11, 1204-86-0 | G2 | 289 | 290 |
| ALP19 | 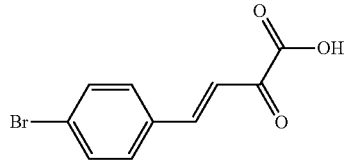 [SMILES: O=C(O)C(=O)/C=C/c1ccc(Br)cc1] | (E)-4-(4-Bromo-phenyl)-2-oxo-but-3-enoic acid | 1122-91-4 | G1, Specific example | 254-256 | 255-257 |
| ALP20 | 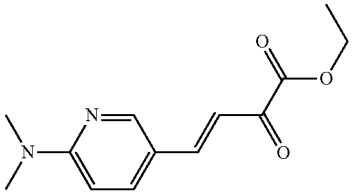 [SMILES: CCOC(=O)C(=O)/C=C/c1ccc(N(C)C)nc1] | (E)-4-(6-Dimethylamino-pyridin-3-yl)-2-oxo-but-3-enoic acid ethyl ester | ALD10 | G2 | 248 | 249 |
| ALP21 | 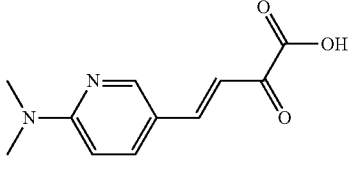 | (E)-4-(6-Dimethylamino-pyridin-3-yl)-2-oxo-but-3-enoic acid | ALD10 | G1 | 220 | 221 |
| ALP22 | 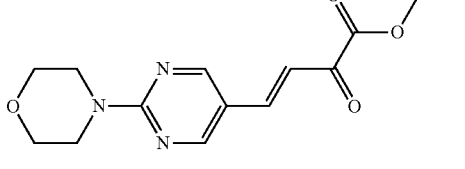 | (E)-4-(2-Morpholin-4-yl-pyrimidin-5-yl)-2-oxo-but-3-enoic acid ethyl ester | 842974-69-0 | G2 | 291 | 292 |
| ALP23 | 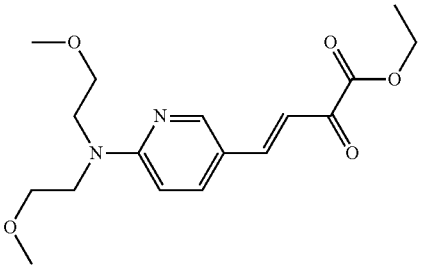 [SMILES: CCOC(=O)C(=O)/C=C/c1ccc(N(CCOC)CCOC)nc1] | (E)-4-{6-[Bis-(2-methoxy-ethyl)-amino]-pyridin-3-yl}-2-oxo-but-3-enoic acid ethyl ester | ALD12 | G2 | 336 | 337 |

TABLE VII-continued

List of alkylidene pyruvates

| Int. | Structure | Name | SM | method | MW | Mes |
|---|---|---|---|---|---|---|
| ALP24 | 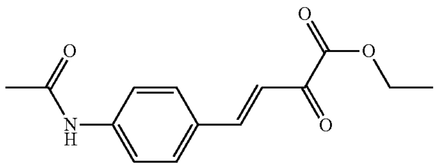 [SMILES: CCOC(=O)C(=O)/C=C/c1ccc(NC(C)=O)cc1] | (E)-4-(4-Acetylamino-phenyl)-2-oxo-but-3-enoic acid ethyl ester | 122-85-0 | G2 | 261 | 262 |
| ALP25 | 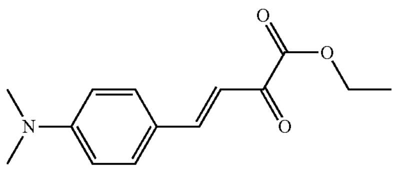 [SMILES: CCOC(=O)C(=O)/C=C/c1ccc(N(C)C)cc1] | (E)-4-(4-Dimethylamino-phenyl)-2-oxo-but-3-enoic acid ethyl ester | 100-10-7 | G2 | 247 | 248 |
| ALP26 | 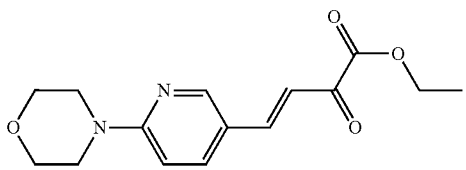 [SMILES: CCOC(=O)C(=O)/C=C/c1ccc(N2CCOCC2)nc1] | (E)-4-(6-Morpholin-4-yl-pyridin-3-yl)-2-oxo-but-3-enoic acid ethyl ester | 173282-60-5 | G2 | 290 | 291 |
| ALP36 | 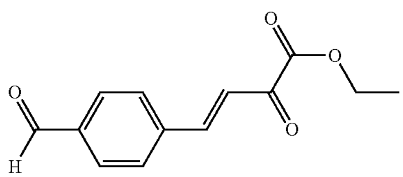 [SMILES: CCOC(=O)C(=O)/C=C/c1ccc(C=O)cc1] | ethyl 4-(4-formylphenyl)-2-oxobut-3-enoate | 63697-96-1 | G3, Specific example | 232 | |
| ALP38 | 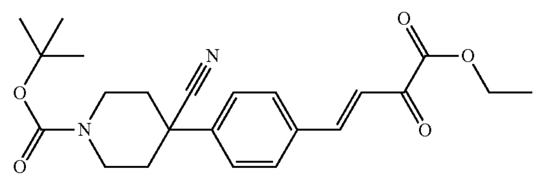 [SMILES: CCOC(=O)C(=O)/C=C/c1ccc(C2(C#N)CCN(C(=O)OC(C)(C)C)CC2)cc1] | 4-Cyano-4-[4-((E)-3-ethoxycarbonyl-3-oxo-propenyl)-phenyl]-piperidine-1-carboxylic acid tert-butyl ester | 847615-14-9 | Specific example | 412 | NA |

Methods H1-H3: Synthesis of Halogenated Pyrazolopyridine

Method H1: Synthesis of Halogenated Pyrazolopyridine (Route 1)

Illustrative Synthesis of HP01: Ethyl 4-chloro-3-isopropyl-1-(m-tolyl)pyrazolo[3,4-b]pyridine-6-carboxylate

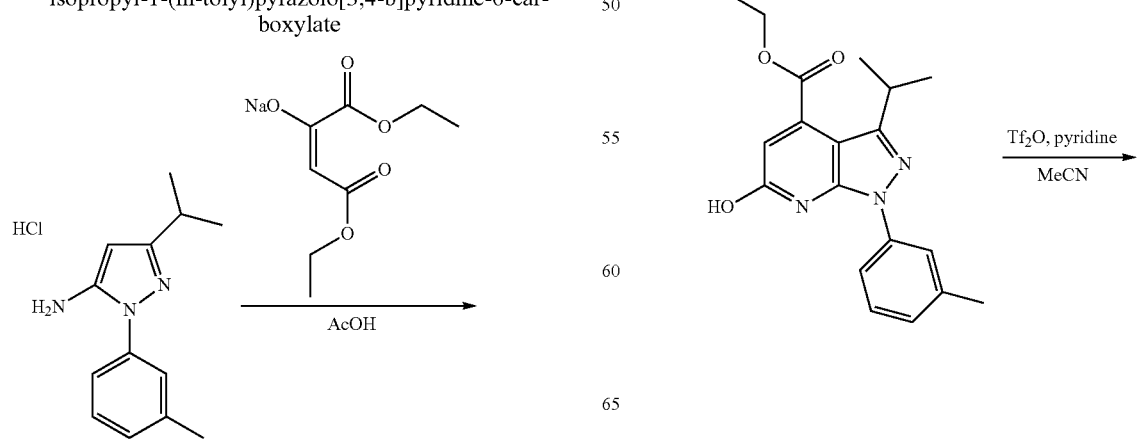

-continued

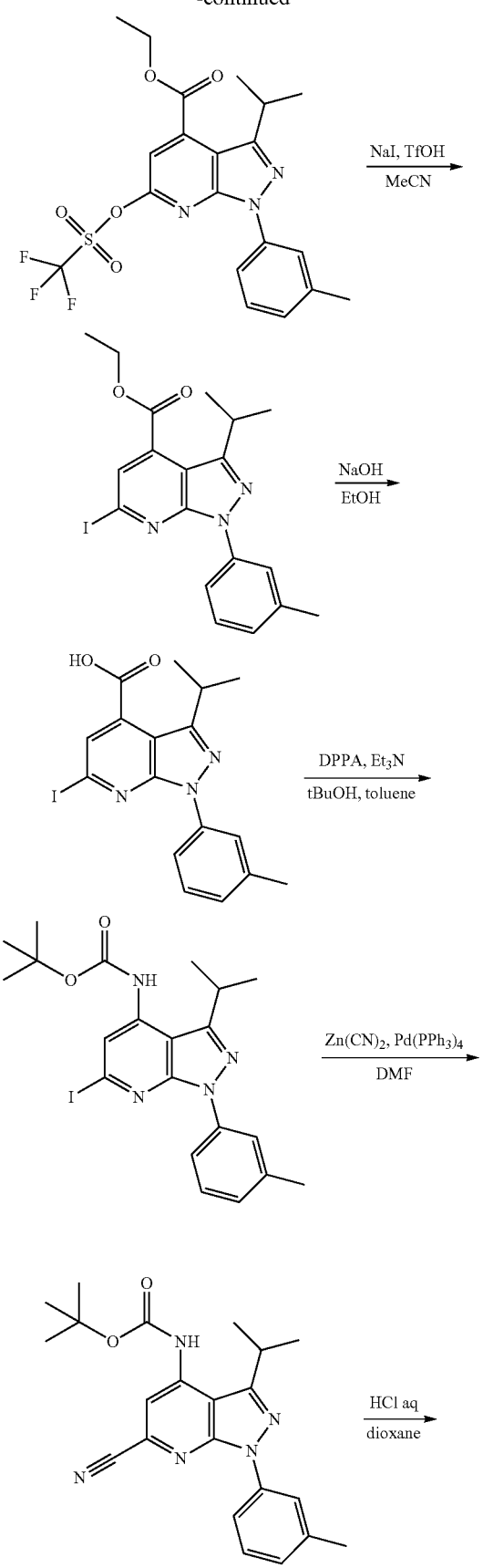

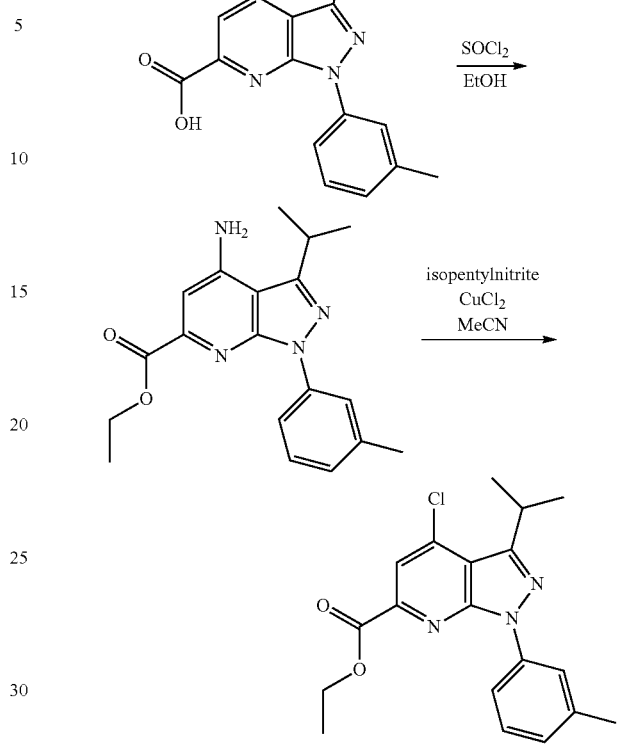

Step 1: 6-Hydroxy-3-isopropyl-1-m-tolyl-1H-pyrazolo[3,4-b]pyridine-4-carboxylic Acid Ethyl Ester 5-Isopropyl-2-m-tolyl-2H-pyrazol-3-ylamine hydrochloride (AMP07, 14.97 g, 59.7 mmol) was dissolved in AcOH (100 mL). Diethyloxalacetate sodium salt (CAS: 40876-98-0, 15 g, 71.6 mmol, 1.2 equiv) was added, and the reaction mixture was refluxed overnight. The reaction mixture was cooled down to RT, poured into water (400 mL) and diluted with ethyl acetate. The two phases were separated, and the aqueous phase was extracted with ethyl acetate. The combined organic layers were concentrated in vacuo, and the resulting residue was taken up twice with cyclohexane (2×200 mL) and concentrated in vacuo again. The residue was suspended in a mixture of ethanol/water (100 mL/20 mL), and the resulting precipitate was collected by filtration and washed with heptane. The solid was dried under vacuum to provide the titled compound.

Step 2: 3-Isopropyl-1-m-tolyl-6-trifluoromethanesulfonyloxy-1H-pyrazolo[3,4-b]pyridine-4-carboxylic Acid Ethyl Ester 6-Hydroxy-3-isopropyl-1-m-tolyl-1H-pyrazolo[3,4-b]pyridine-4-carboxylic acid ethyl ester (14.25 g, 42 mmol) was suspended in acetonitrile under nitrogen atmosphere. Pyridine (3.8 mL, 46.2 mmol, 1.1 equiv) was added. The reaction mixture was cooled to 0° C., and trifluoromethanesulfonic anhydride (CAS 358-23-6, 7.8 mL, 46.2 mmol, 1.1 equiv) was added dropwise over 20 min. The reaction mixture was then warmed up to RT over 20 min. Water was added (200 mL), and the suspension was filtered. The solid was washed successively with water and ethanol (40 mL) and then dried in vacuo to afford the titled compound.

Step 3: 6-Iodo-3-isopropyl-1-m-tolyl-1H-pyrazolo[3,4-b]pyridine-4-carboxylic Acid Ethyl Ester 3-Isopropyl-1-m-tolyl-6-trifluoromethanesulfonyloxy-1H-pyrazolo[3,4-b]pyridine-4-carboxylic acid ethyl ester (13.0 g, 27.6 mmol) was suspended in acetonitrile. Sodium iodide (20.7 g, 138 mmol, 5 equiv) was added. The reaction mixture was cooled to 0° C., trifluoromethanesulfonic acid (5.4 mL, 60.7 mmol, 2.2 equiv) was added dropwise. The reaction mixture was stirred at RT overnight. At this point, the reaction was not complete and additional trifluoromethanesulfonic acid (2 mL, 22.6 mmol, 0.8 equiv) was added and stirring was continued for 1 hour. Water was added to the reaction mixture, and the suspension was filtered. The solid was washed with ethanol (10 mL) and dried in vacuo to afford the titled compound.

Step 4: 6-Iodo-3-isopropyl-1-m-tolyl-1H-pyrazolo[3,4-b]pyridine-4-carboxylic Acid 6-Iodo-3-isopropyl-1-m-tolyl-1H-pyrazolo[3,4-b]pyridine-4-carboxylic acid ethyl ester (8.73 g, 4.63 mmol) was suspended in ethanol (10 mL). An aqueous solution of 2 M sodium hydroxide (10 mL, 20 mmol, 4.3 equiv) was added, and the reaction mixture was stirred at 70° C. until complete conversion. Then the reaction mixture was cooled down to 0° C., and an aqueous solution of 2 M HCl was added until pH<2 was reached. The resulting suspension was filtered, and the solid was dried in vacuo to afford the titled compound.

Step 5: (6-Iodo-3-isopropyl-1-m-tolyl-1H-pyrazolo[3,4-b]pyridin-4-yl)-carbamic Acid Tert-butyl Ester 6-Iodo-3-isopropyl-1-m-tolyl-1H-pyrazolo[3,4-b]pyridine-4-carboxylic acid (8.12 g, 19.3 mmol) was suspended in toluene (43 mL). tert-Butanol (3.1 mL, 32.6 mmol, 2.0 equiv), triethylamine (4.54 mL, 32.6 mmol, 2.0 equiv) and diphenylphosphoryl azide (CAS 26386-88-9, 5 mL, 23.1 mmol, 1.2 equiv) were successively added. The reaction mixture was refluxed for 30 minutes. The reaction mixture was cooled to RT and partitioned between ethyl acetate and water. The aqueous phase was further extracted with ethyl acetate. The combined organic phases were washed with brine, dried over $Na_2SO_4$, filtered and concentrated in vacuo. The residue was suspended in ethanol. The resulting precipitate was collected by filtration, washed with ethanol and dried under vacuum to provide the titled compound.

Step 6: (6-Cyano-3-isopropyl-1-m-tolyl-1H-pyrazolo[3,4-b]pyridin-4-yl)-carbamic Acid Tert-butyl Ester (6-Iodo-3-isopropyl-1-m-tolyl-1H-pyrazolo[3,4-b]pyridin-4-yl)-carbamic acid tert-butyl ester (7.56 g, 15.4 mmol) was solubilized in dry dimethylformamide (20 mL) in a sealed vial. Zinc cyanide (CAS 557-21-1, 1.1 g, 9.2 mmol, 0.6 equiv) was added, and the reaction mixture was degassed with argon (bubbling) for 5 minutes. Tetrakis(triphenylphosphine)palladium(0) (CAS 14221-01-3, 0.9 g, 0.77 mmol, 0.05 equiv) was added, and the reaction mixture was degassed again with argon (bubbling) for 5 minutes. The vial was sealed, and the reaction mixture was stirred at 110° C. for 2 hour. The reaction mixture was cooled down to room temperature and diluted with water and ethyl acetate. The aqueous phase was further extracted with ethyl acetate. The combined organic phases were washed with brine, dried over $Na_2SO_4$, filtered and concentrated to a volume of 10 mL. Ethanol (10 mL) was added, and the suspension was stirred at 0° C. for 10 min. The resulting precipitate was collected by filtration, washed with ethanol and dried under vacuum to provide the titled compound.

Step 7: 4-Amino-3-isopropyl-1-m-tolyl-1H-pyrazolo[3,4-b]pyridine-6-carboxylic Acid Hydrochloride Salt (6-Cyano-3-isopropyl-1-m-tolyl-1H-pyrazolo[3,4-b]pyridin-4-yl)-carbamic acid tert-butyl ester (4.8 g, 12.26 mmol) was suspended in 6 M HCl (50 mL). The reaction mixture was refluxed for 24 h. The reaction mixture was cooled to 0° C., and the obtained suspension was filtered. The solid was washed with diisopropyl ether and dried in vacuo to yield the titled compound.

Step 8: 4-Amino-3-isopropyl-1-m-tolyl-1H-pyrazolo[3,4-b]pyridine-6-carboxylic Acid Ethyl Ester 4-Amino-3-isopropyl-1-m-tolyl-1H-pyrazolo[3,4-b]pyridine-6-carboxylic acid hydrochloride salt (4.23 g, 12.26 mmol) was solubilized in ethanol (150 mL). Thionyl chloride (CAS 7719-09-7, 1.34 mL, 18.39 mmol, 1.5 equiv) was carefully added. The reaction mixture was refluxed for 24 hours. The reaction mixture was cooled down to RT and concentrated in vacuo. The residue was taken up in ethanol (85 mL) and thionyl chloride (CAS 7719-09-7, 2.32 mL, 31.86 mmol, 2.6 equiv) was carefully added at RT. The mixture was refluxed for 6 hours. The reaction mixture was cooled down to RT and concentrated in vacuo. The crude mixture was diluted with ethyl acetate, basified with a saturated solution of sodium hydrogencarbonate. This mixture was filtered through a pad of Celpure® P65. Solids were washed with ethyl acetate. The two phases of the filtrate were separated, and the aqueous fraction was further extracted with ethyl acetate. The combined organic phases were washed with brine, dried over $MgSO_4$, filtered and concentrated in vacuo. The residue was purified by flash chromatography on silica gel (eluent system: heptane/ethyl acetate gradient from 95/5 to 80/20) to afford the titled compound.

Step 9: 4-Chloro-3-isopropyl-1-m-tolyl-1H-pyrazolo[3,4-b]pyridine-6-carboxylic Acid Ethyl Ester Copper (II) chloride (CAS 7447-39-4, 1.045 g, 7.77 mmol, 1.0 equiv) was suspended in acetonitrile (33 mL). Isopentylnitrite (CAS 110-46-3, 1.57 mL, 11.65 mmol, 1.5 equiv) was added, and the reaction mixture was stirred at RT for 30 minutes. 4-Amino-3-isopropyl-1-m-tolyl-1H-pyrazolo[3,4-b]pyridine-6-carboxylic acid ethyl ester (2.63 g, 7.77 mmol, 1.0 equiv) was added. The reaction mixture was stirred at 75° C. for 2.5 h. The reaction mixture was cooled down to 0° C., and the resulting suspension was filtered. The solid was washed with cold acetonitrile and dried in vacuo to afford the titled compound. The filtrate was concentrated in vacuo and purified by flash chromatography on silica gel (eluent system: heptane/ethyl acetate gradient from 100/0 to 98/2) to provide additional titled compound.

Method H1': Alternative Conditions for Chlorination Route 1 Step 9

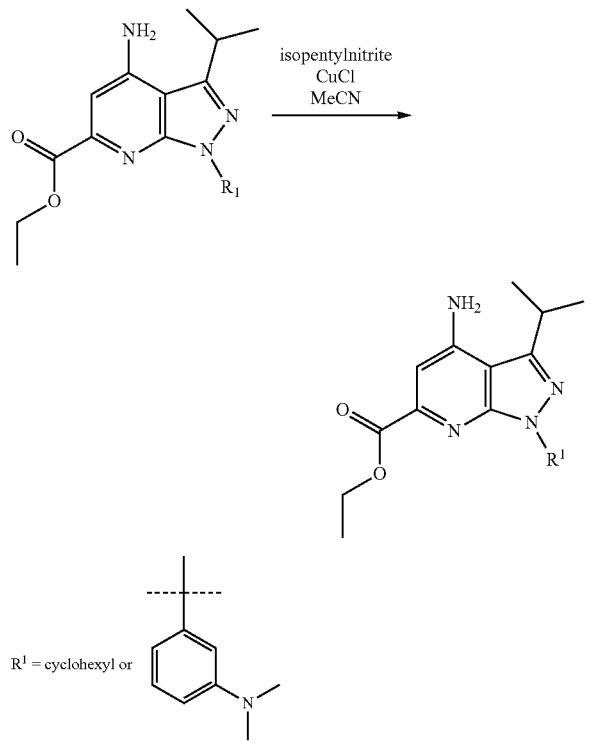

R¹ = cyclohexyl or

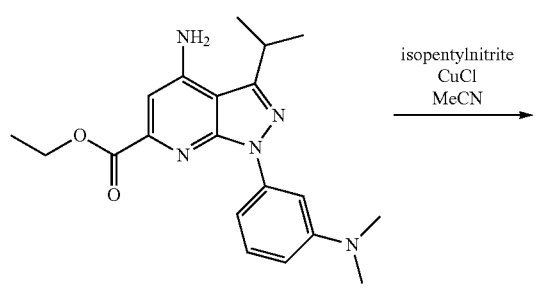

To the 4-amino intermediate (1 equiv) in acetonitrile at RT is added isopentylnitrite (CAS 110-46-3, from 3 to 6 eq) followed by copper(I) chloride (CAS 7758-89-6, from 3 to 6 equiv), and the reaction mixture is stirred at RT for 1 h to 24 h. The reaction mixture is diluted with dichloromethane and with a saturated solution of sodium hydrogencarbonate. The two phases are separated, and the aqueous phase is extracted with dichloromethane. The combined organic phases are washed with brine, dried over MgSO₄, filtered and concentrated in vacuo. The resulting residue is purified by flash chromatography on silica gel to afford the titled compound.

Illustrative Synthesis of HP03: Ethyl 4-chloro-1-[3-(dimethylamino)phenyl]-3-isopropyl-pyrazolo[3,4-b]pyridine-6-carboxylate

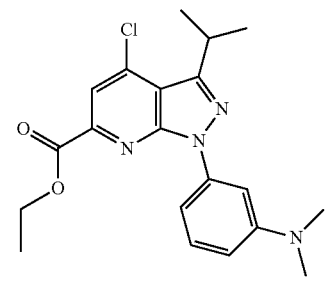

To 4-amino-1-(3-dimethylamino-phenyl)-3-isopropyl-1H-pyrazolo[3,4-b]pyridine-6-carboxylic acid ethyl ester (1 g, 2.74 mmol, 1 equiv) in acetonitrile (10 mL) at RT was added isopentylnitrite (CAS 110-46-3, 1.1 mL, 8.21 mmol, 3 equiv) followed by copper(I) chloride (CAS 7758-89-6, 0.82 g, 8.21 mmol, 3 equiv), and the reaction mixture was stirred at RT for 1 h. The reaction mixture was diluted with dichloromethane and with a saturated solution of sodium hydrogencarbonate. The two phases were separated, and the aqueous phase was extracted with dichloromethane. The combined organic phases were washed with brine, dried over MgSO₄, filtered and concentrated in vacuo. The resulting residue was purified by flash chromatography on silica gel (eluent system: heptane/ethyl acetate gradient from 100/0 to 90/10) to afford the titled compound.

Synthesis of HP13: Ethyl 4-chloro-3-methyl-1-phenyl-pyrazolo[3,4-b]pyridine-6-carboxylate

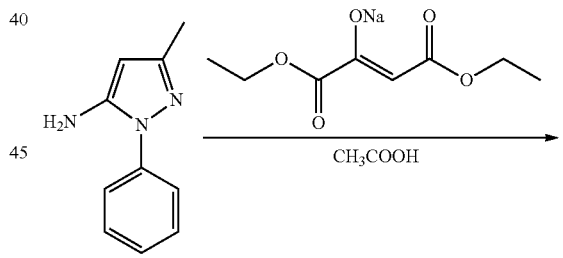

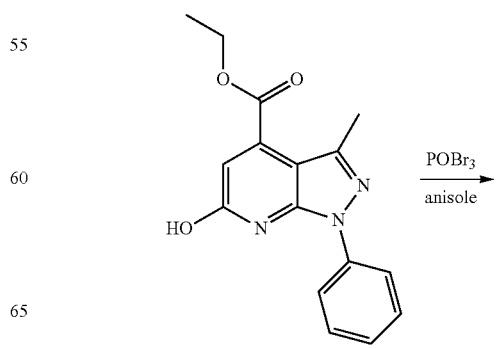

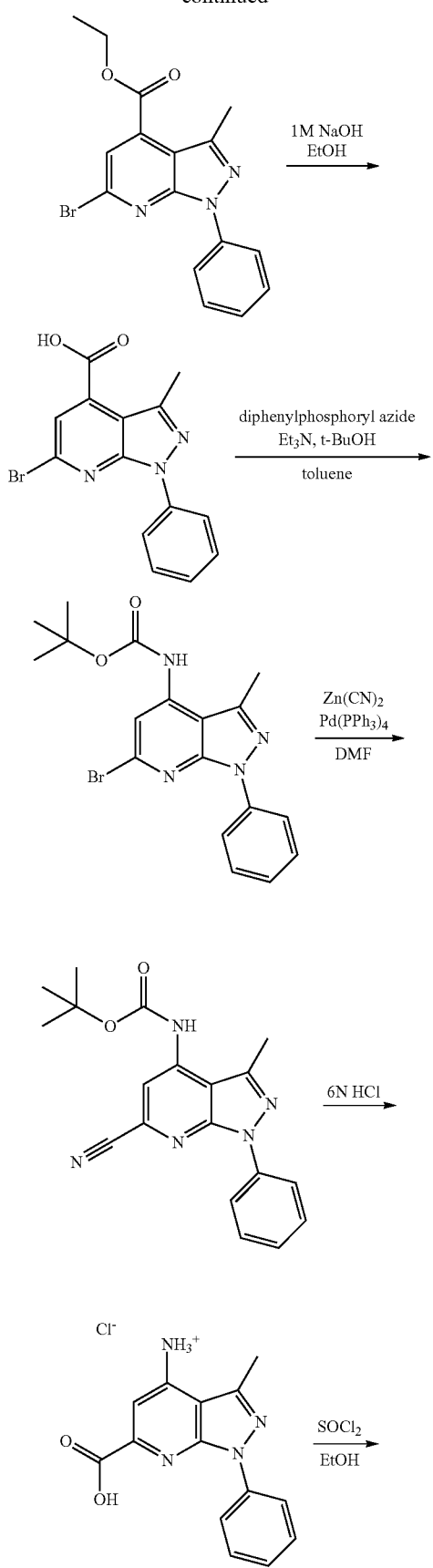

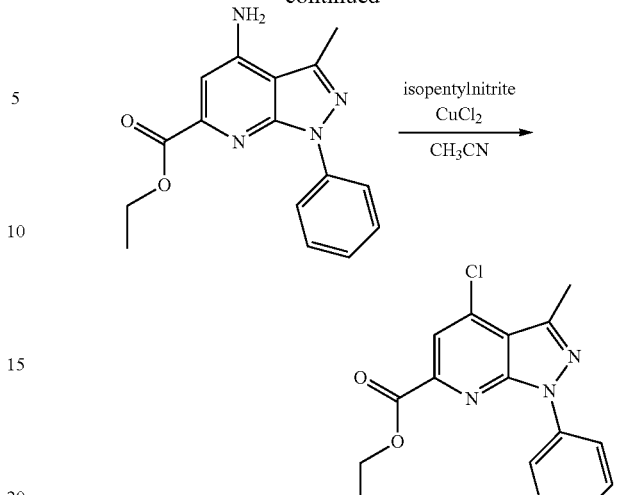

Step 1: 6-Hydroxy-3-methyl-1-phenyl-1H-pyrazolo[3,4-b]pyridine-4-carboxylic Acid Ethyl Ester 5-Amino-3-methyl-1-phenylpyrazole (CAS: 1131-18-6, 6.83 g, 39.4 mmol) was dissolved in AcOH (70 mL). Diethyloxalacetate sodium salt (CAS: 40876-98-0, 9.12 g, 44.4 mmol, 1.1 equiv) was added, and the reaction mixture was refluxed until complete conversion. The reaction mixture was concentrated in vacuo, and the residue was taken up in cyclohexane (2×100 mL) and concentrated in vacuo again. The residue was suspended in a mixture of MeOH/water (150 mL/100 mL). The resulting precipitate was collected by filtration and washed with heptane. The solid was dried under vacuum to provide the titled compound.

Step 2: 6-Bromo-3-methyl-1-phenyl-1H-pyrazolo[3,4-b]pyridine-4-carboxylic Acid Ethyl Ester 6-Hydroxy-3-methyl-1-phenyl-1H-pyrazolo[3,4-b]pyridine-4-carboxylic acid ethyl ester (7.27 g, 24.5 mmol) was solubilized in anisole (30 mL). Phosphorous(V) oxybromide (CAS 7789-59-5, 8.23 g, 29.3 mmol, 1.2 equiv) was added, and the reaction mixture was refluxed at 140° C. for 1 h. The reaction mixture was cooled down to room temperature and basified with a saturated solution of sodium hydrogencarbonate. The reaction mixture was extracted twice with ethyl acetate, and the combined organic phases were washed with brine, dried over $Na_2SO_4$, filtered and concentrated in vacuo. The residue was purified by filtration on a pad of silica gel (200 g), heptane/EtOAc 100/0 to 90/10) to give the titled compound.

Step 3: 6-Bromo-3-methyl-1-phenyl-1H-pyrazolo[3,4-b]pyridine-4-carboxylic Acid 6-Bromo-3-methyl-1-phenyl-1H-pyrazolo[3,4-b]pyridine-4-carboxylic acid ethyl ester (3.90 g, 10.8 mmol) was suspended in ethanol (20 mL). An aqueous solution of 1 M sodium hydroxide (20 mL, 20 mmol, 1.9 equiv) was added, and the reaction mixture was stirred at 70° C. for 30 min. The reaction mixture was then concentrated in vacuo. The residue was acidified with an aqueous solution of 2 M HCl and extracted with ethyl acetate. The organic phase was dried over Na₂SO₄, filtered and concentrated in vacuo to yield the titled compound.

Step 4: (6-Bromo-3-methyl-1-phenyl-1H-pyrazolo [3,4-b]pyridin-4-yl)-carbamic Acid Tert-butyl Ester 6-Bromo-3-methyl-1-phenyl-1H-pyrazolo[3,4-b]pyridine-4-carboxylic acid (3.50 g, 10.4 mmol) was suspended in toluene (35 mL). tert-Butanol (2 mL, 21.6 mmol, 2.1 equiv), triethylamine (4.4 mL, 31.2 mmol, 3.0 equiv) and diphenylphosphoryl azide (CAS 26386-88-9, 3.2 mL, 14.8 mmol, 1.4 equiv) were successively added. The reaction mixture was refluxed for 1.5 h. The reaction mixture was cooled down to RT and concentrated in vacuo, then partitioned between ethyl acetate and water. The aqueous phase was further extracted with ethyl acetate. The combined organic phases were washed with brine, dried over Na₂SO₄, filtered and concentrated in vacuo. The residue was purified by filtration on a pad of silica gel (200 g, heptane/EtOAc 100/0 to 90/10) to give the titled compound.

Step 5: (6-Cyano-3-methyl-1-phenyl-1H-pyrazolo[3, 4-b]pyridin-4-yl)-carbamic Acid Tert-butyl Ester (6-Bromo-3-methyl-1-phenyl-1H-pyrazolo[3,4-b]pyridin-4-yl)-carbamic acid tert-butyl ester (4.16 g, 10.3 mmol) was solubilized in dry dimethylformamide (20 mL) in a sealed vial. Zinc cyanide (CAS 557-21-1, 0.727 g, 6.2 mmol, 0.6 equiv) was added, and the reaction mixture was degassed with argon for 5 minutes. Tetrakis(triphenylphosphine) palladium(0) (CAS 14221-01-3, 0.595 g, 0.5 mmol, 0.05 equiv) was added, and the vial was sealed. The reaction mixture was stirred at 100° C. for 1 hour. The reaction was not complete. Additional tetrakis(triphenylphosphine)palladium(0) (CAS 14221-01-3, 0.595 g, 0.5 mmol, 0.05 equiv) and zinc cyanide (CAS 14221-01-3, 0.485 g, 4.1 mmol, 0.4 equiv) were added at RT, and the vial was sealed again. The reaction mixture was stirred at 100° C. for one hour and cooled down to room temperature. Water was added to the reaction mixture and precipitation occurred. The suspension was filtered, and the cake was washed with water. The solid residue was taken up with dichloromethane and with an aqueous solution of 0.5 M NaOH. The organic phase was separated, dried over Na₂SO₄, filtered and concentrated. The residue was purified by filtration on a pad of silica gel (150 g, heptane/EtOAc 100/0 to 60/40) to give the titled compound mixed with (6-cyano-3-methyl-1-phenyl-1H-pyrazolo[3,4-b]pyridin-4-yl)-carbonitrile. The mixture was engaged in the next step without further purification.

Step 6: 4-Amino-3-methyl-1-phenyl-1H-pyrazolo[3, 4-b]pyridine-6-carboxylic Acid Hydrochloride Salt A mixture of (6-cyano-3-methyl-1-phenyl-1H-pyrazolo [3,4-b]pyridin-4-yl)-carbamic acid tert-butyl ester and (6-cyano-3-methyl-1-phenyl-1H-pyrazolo[3,4-b]pyridin-4-yl)-carbonitrile (3.5 g) was suspended in 6 M HCl (50 mL). The reaction mixture was refluxed for 18 h. The reaction mixture was cooled to 0° C. and the obtained suspension was filtered. The solid was washed with an aqueous solution of 0.1 M HCl. The filtrate was concentrated in vacuo and precipitation occurred. The solid was also collected by filtration. The combined solids were dried in vacuo to yield the titled compound.

Step 7: 4-Amino-3-methyl-1-phenyl-1H-pyrazolo[3, 4-b]pyridine-6-carboxylic Acid Ethyl Ester 4-Amino-3-methyl-1-phenyl-1H-pyrazolo[3,4-b]pyridine-6-carboxylic acid hydrochloride salt (2.03 g, 7.6 mmol) was solubilized in ethanol (40 mL). Thionyl chloride (CAS 7719-09-7, 1.16 mL, 15.9 mmol, 2.1 equiv) was carefully added. The reaction mixture was refluxed for 24 hours. The reaction mixture was concentrated in vacuo and partitioned between ethyl acetate and aqueous saturated NaHCO₃. The aqueous phase was further extracted with ethyl acetate. The combined organic phases were dried over Na₂SO₄, filtered and concentrated in vacuo to give the titled compound.

Step 8: 4-Chloro-3-methyl-1-phenyl-1H-pyrazolo[3, 4-b]pyridine-6-carboxylic Acid Ethyl Ester Copper (II) chloride (CAS 7447-39-4, 0.908 g, 6.75 mmol, 1.0 equiv) was added to acetonitrile (50 mL). Isopentylnitrite (CAS 110-46-3, 1.4 mL, 10.1 mmol, 1.5 equiv) was added, and the reaction mixture was stirred at 75° C. for 5 minutes. 4-Amino-3-methyl-1-phenyl-1H-pyrazolo[3,4-b] pyridine-6-carboxylic acid ethyl ester (2.0 g, 6.75 mmol, 1.0 equiv) dissolved in acetonitrile (50 mL) was added. The reaction mixture was stirred at 75° C. for 2.5 h. The reaction mixture was cooled down and concentrated in vacuo. Water was added to the residue, and the mixture was extracted with ethyl acetate. Copper salts prevented clean extraction. The suspension was filtered through diatomaceous earth. The organic phase was dried over Na₂SO₄, filtered and concentrated. The residue was suspended in ethanol (10 mL) and filtered. The solid was dried in vacuo to give the titled compound. The copper salts on the diatomaceous earth were washed with dichloromethane. The filtrate was concentrated to provide additional titled compound.

Method H2: Synthesis of Halogenated Pyrazolopyridine (Route 2)

Illustrative Synthesis of HP02: Methyl 4-chloro-3-cyclobutyl-1-phenyl-pyrazolo[3,4-b]pyridine-6-carboxylate

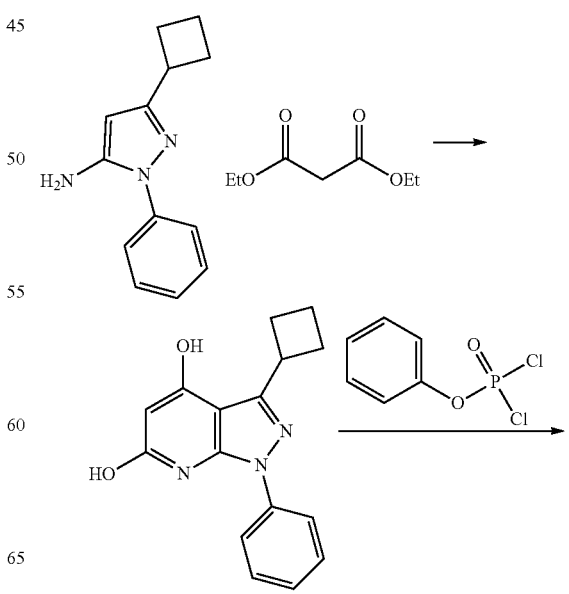

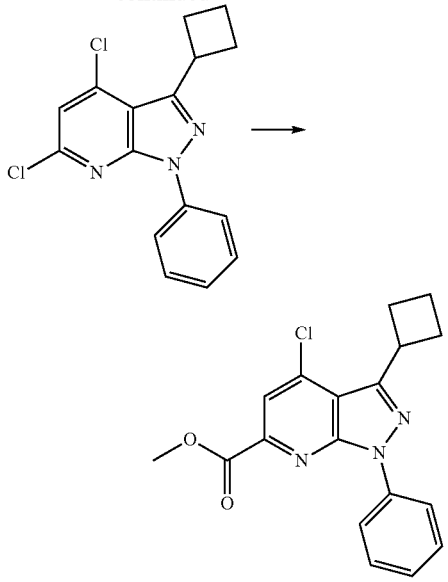

Step 1: 3-cyclobutyl-1-phenyl-pyrazolo[3,4-b]pyridine-4,6-diol

To a mixture of 3-cyclobutyl-1-phenyl-1H-pyrazol-5-amine (AMP29, 74.0 g, 347 mmol) in oxydibenzene (450.0 g, 2.64 mol) was added diethyl malonate (CAS 105-53-3, 139.0 g, 867 mmol). The system was heated at 130-150° C. for 40 h. By this time solid had precipitated and heating was stopped. Two more reactions were set up as described above. All three reaction mixtures were combined. The combined mixture was cooled to below 40° C. and diluted with about 1.8 L of diethyl ether, and the resulting suspension was stirred for 2 h and then filtered. The collected solids were rinsed with diethyl ether (1 L). The solids were dried on the filter to give the titled compound. $^1$H NMR (400 MHz, DMSO-$d_6$) δ ppm 11.28 (s, 1H), 8.18 (d, J=7.9 Hz, 2H), 7.58-7.39 (m, 2H), 7.21 (t, J=7.1 Hz, 1H), 5.85 (s, 1H), 3.88 (quin, J=8.4 Hz, 1H), 2.44-2.22 (m, 4H), 2.07-1.78 (m, 2H).

Step 2: 4,6-dichloro-3-cyclobutyl-1-phenyl-pyrazolo[3,4-b]pyridine

A mixture of 3-cyclobutyl-1-phenyl-pyrazolo[3,4-b]pyridine-4,6-diol (60.0 g, 213 mmol) in phenyl dichlorophosphate (CAS 770-12-7, 135 g, 640 mmol) was stirred at 170° C. for 15 h. Two more reactions were set up as described above. All three reaction mixtures were combined and poured into ice water (5 L) keeping the internal temperature <10° C. The mixture was neutralized with concentrated NH$_4$OH (500 mL) to pH 6-7, then the suspension was stirred for 2 h. As the pH increased and with continued stirring, the semi-solid suspension becomes a flowing solid. The solid was collected by filtration. The wet solid was dissolved in dichloromethane (3 L) and filtered through a short path of silica gel (2 kg), eluting with dichloromethane (15 L). The filtrate was concentrated to a solid which was triturated with acetonitrile (1.5 L) and and collected by filtration to give the titled compound. $^1$H NMR (400 MHz, DMSO-$d_6$) δ ppm 8.20 (d, J=7.9 Hz, 2H), 7.51 (t, J=7.5 Hz, 2H), 7.35-7.27 (m, 1H), 7.16 (s, 1H), 4.15 (quin, J=8.4 Hz, 1H), 2.63-2.41 (m, 4H), 2.20-2.07 (m, 1H), 2.00 (s, 1H).

Step 3: Methyl 4-chloro-3-cyclobutyl-1-phenyl-pyrazolo[3,4-b]pyridine-6-carboxylate To a mixture of 4,6-dichloro-3-cyclobutyl-1-phenyl-1H-pyrazolo[3,4-b]pyridine (50.0 g, 157 mmol) in methanol (700 mL) was added triethylamine (31.8 g, 314 mmol) and Pd(dppf)Cl$_2$.DCM (CAS 95464-05-4, 6.4 g, 7.86 mmol). The system was heated at 60° C. under CO (30 psi) for 40 h. Two more reactions were set up as described above. All three reaction mixtures were combined and concentrated to give a semisolid which was dissolved in dichloromethane (3 L) and filtered through a 2 kg plug of silica gel. After concentration, about 130 g of solid was obtained. This solid was taken up in 1.3 L of ethyl acetate with heating. This solution was stirred at room temperature. Solids came out over a couple of minutes, and then 1.3 L of hexane was added in a thin stream via addition funnel with stirring for 2 hours. The solids were collected by filtration to give the titled compound. $^1$H NMR (400 MHz, CDCl$_3$) δ ppm 8.38-8.27 (m, 2H), 7.95 (s, 1H), 7.53 (t, J=7.9 Hz, 2H), 7.35-7.27 (m, 1H), 4.21 (q, J=8.6 Hz, 1H), 4.08-4.03 (m, 1H), 2.66-2.40 (m, 4H), 2.22-1.93 (m, 2H).

Illustrative Synthesis of HP19: Methyl 4-chloro-3-cyclobutyl-1-(4-fluorophenyl)-1H-pyrazolo[3,4-b]pyridine-6-carboxylate

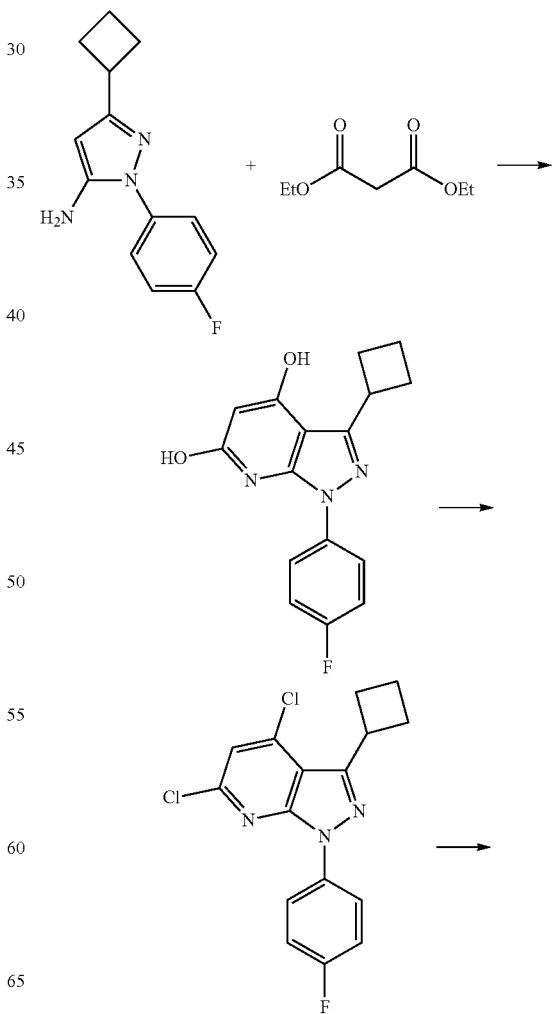

-continued

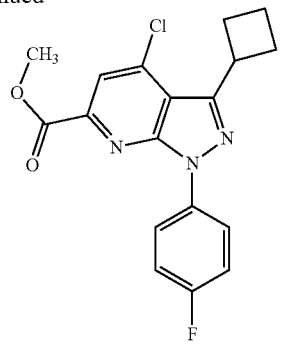

Step 1: 3-Cyclobutyl-1-(4-fluorophenyl)-1H-pyrazolo[3,4-b]pyridine-4,6-diol

A mixture of 3-cyclobutyl-1-(4-fluorophenyl)-1H-pyrazol-5-amine (AMP93, 5 g, 18.6 mmol) and diethyl malonate ([105-53-3], 8.5 mL, 55.8 mmol) was heated at 100° C. for 30 minutes and then at 170° C. for 3 hours. The reaction mixture was cooled down to RT and dissolved in dichloromethane (60 mL). The resultant solution was poured into a stirred solution of n-heptane (700 mL). The precipitate was collected by filtration, washed with n-heptane and dried at 40° C. under reduced pressure to give the titled compound.

Step 2: 4,6-Dichloro-3-cyclobutyl-1-(4-fluorophenyl)-1H-pyrazolo[3,4-b]pyridine A three-neck round-bottom flask equipped with a Dean-Stark apparatus was charged with phenyl dichlorophosphate ([770-12-7], 854 g, 4.05 mol). 3-Cyclobutyl-1-(4-fluorophenyl)-1H-pyrazolo[3,4-b]pyridine-4,6-diol (404 g, 1.35 mol) was added in portions over a period of 5 minutes. The temperature was increased to 170° C. over a period of 1 hour, and the stirring at 170° C. was continued for 21 hours. The reaction mixture was cooled down to 50° C. and added slowly to a stirred aqueous 4 N NaOH (5 L) keeping the temperature below 20° C. The suspension was stirred for 1 hour at 10-15° C., and then cold water (3 L) was added. The precipitate was collected by filtration, washed with water and dried at 40° C. under reduced pressure to give the titled compound.

Step 3: Methyl 4-chloro-3-cyclobutyl-1-(4-fluorophenyl)-1H-pyrazolo[3,4-b]pyridine-6-carboxylate A pressured vessel was charged with 4,6-dichloro-3-cyclobutyl-1-(4-fluorophenyl)-1H-pyrazolo[3,4-b]pyridine (5 g, 14.9 mmol), Pd(dppf)Cl$_2$.DCM (CAS 95464-05-4, 218 mg, 0.3 mmol), and sodium acetate (1.8 g, 22.3 mmol) in dioxane/methanol (1:1, 25 mL). The system was loaded with CO (4 bars) and heated at 40° C. for 2 hours. The vessel was cooled to RT, and the conversion was monitored by LCMS. The reaction vessel was charged again with CO (4 bars) and heated at 40° C. The sequence was repeated until full conversion was observed. The crude mixture was concentrated under reduced pressure and purified by flash column chromatography eluting with a mixture of n-heptane/dichloromethane (90/10 to 30/70) to give the titled compound.

Illustrative Synthesis of HP25: Methyl 4-chloro-3-cyclobutyl-1-cyclohexyl-1H-pyrazolo[3,4-b]pyridine-6-carboxylate

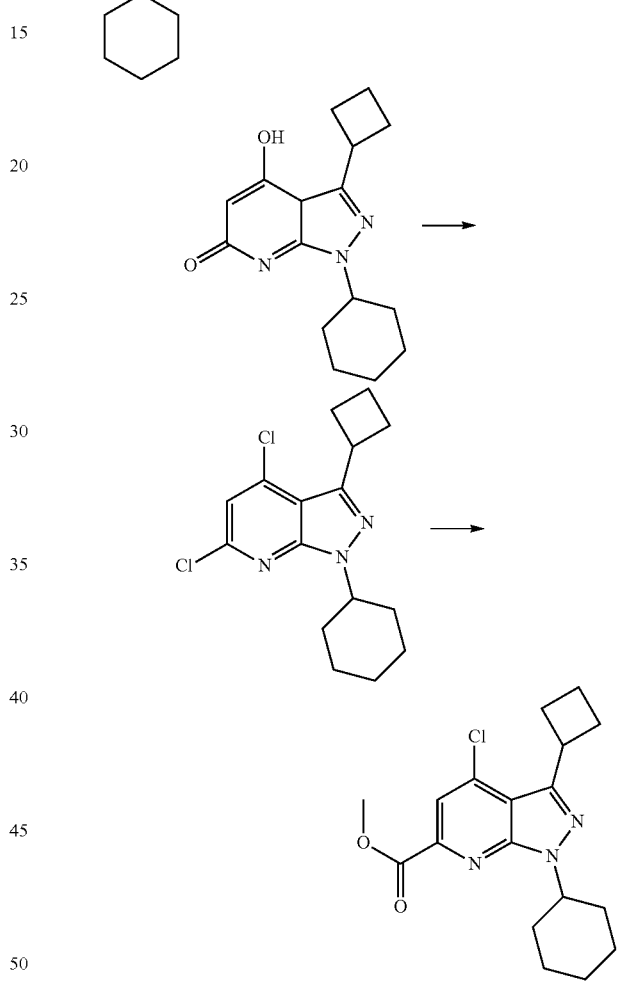

Step 1: 3-cyclobutyl-1-cyclohexyl-4-hydroxy-3aH-pyrazolo[3,4-b]pyridin-6-one A mixture of 5-cyclobutyl-2-cyclohexyl-2H-pyrazol-3-ylamine (AMP35, 10 g, 45.7 mmol) and diethyl malonate ([105-53-3], 27.7 mL, 183 mmol) in diphenylether (50 mL) was heated at 130° C. over approximately 60 hours. The reaction mixture was cooled down to RT and quenched with 0.5 M NaOH solution (100 mL, 50 mmol). Extraction with EtOAc gave an aqueous phase that was acidified with a 12 M HCl solution (4.3 mL, 51.6 mmol) giving rise to a suspension. This suspension was extracted with EtOAc. The obtained organic layer was dried and concentrated to give the titled compound that was used as such.

Step 2: 4,6-dichloro-3-cyclobutyl-1-cyclohexyl-pyrazolo[3,4-b]pyridine

The 3-cyclobutyl-1-cyclohexyl-4-hydroxy-3 aH-pyrazolo [3,4-b]pyridin-6-one (5.15 g, 17.9 mmol) was suspended in phenyl dichlorophosphate ([770-12-7], 8.01 mL, 53.8 mmol). The mixture was heated at 130° C. overnight. Next, the mixture was diluted in DCM and poured into ice water. After increasing the pH till 7-8 with a 20% $NH_4OH$ solution, the biphasic mixture was stirred for 30 minutes. Subsequently, the organic phase was separated, dried and concentrated to give a residue. This residue was purified by chromatography using a petroleum ether/EtOAc gradient (100/0 to 90/10). This resulted in the titled compound that was used as such.

Step 3: Methyl 4-chloro-3-cyclobutyl-1-cyclohexyl-1H-pyrazolo[3,4-b]pyridine-6-carboxylate In a Parr apparatus, 4,6-dichloro-3-cyclobutyl-1-cyclohexyl-pyrazolo[3,4-b]pyridine (2.17 g, 6.72 mmol) was dissolved in MeOH (50 mL) together with $Pd(dppf)Cl_2.DCM$ (CAS 95464-05-4, 275 mg, 0.33 mmol) and triethylamine (1.87 mL, 13.4 mmol). The system was loaded with CO (5 bar) and heated at 45° C. for 18 hours. After cooling down the mixture till RT, the mixture was concentrated, and the obtained residue was purified by chromatography using a petroleum ether/EtOAc gradient (100/0 till 95/5). This yielded the titled compound.

Method H3: Synthesis of Halogenated or Sulfonylated Pyrazolopyridine (Route 3)

Step 1: Diethyl But-2-Enedioate

To a suspension of aminopyrazole (1 equiv) in ethanol (150 mL) is added diethyl acetylenedicarboxylate (1.1 equiv). The reaction mixture is stirred at room temperature for 4 hours. The reaction mixture is concentrated. The crude residue is purified by silica gel column chromatography (heptane/EtOAc 100/0 to 70/30) to give the titled compound.

Step 2: Pyrazolopyridine Formation

The diethyl but-2-enedioate is heated under air atmosphere at 190-195° C. for one hour. The reaction mixture is cooled to room temperature and is partitioned between dichloromethane and water. The aqueous phase is separated and extracted two times with dichloromethane. The combined organic phases were dried, filtered and concentrated in vacuo. The crude residue can be purified by silica gel column chromatography to provide the pyrazolopyridine.

Step 3: Chlorination

A solution of the above pyrazolopyridine (1 equiv) in phosphorus(V) oxychloride (32 equiv) was stirred at 115° C. for 1 h. The reaction mixture is then cooled to room temperature and concentrated in vacuo. The residue is dissolved in ethyl acetate, and the reaction mixture is added dropwise to a solution of saturated of sodium hydrogencarbonate till total neutralization of phosphorus(V) oxychloride (pH 8). The aqueous phase is separated and extracted two times with ethyl acetate. The combined organic phases are

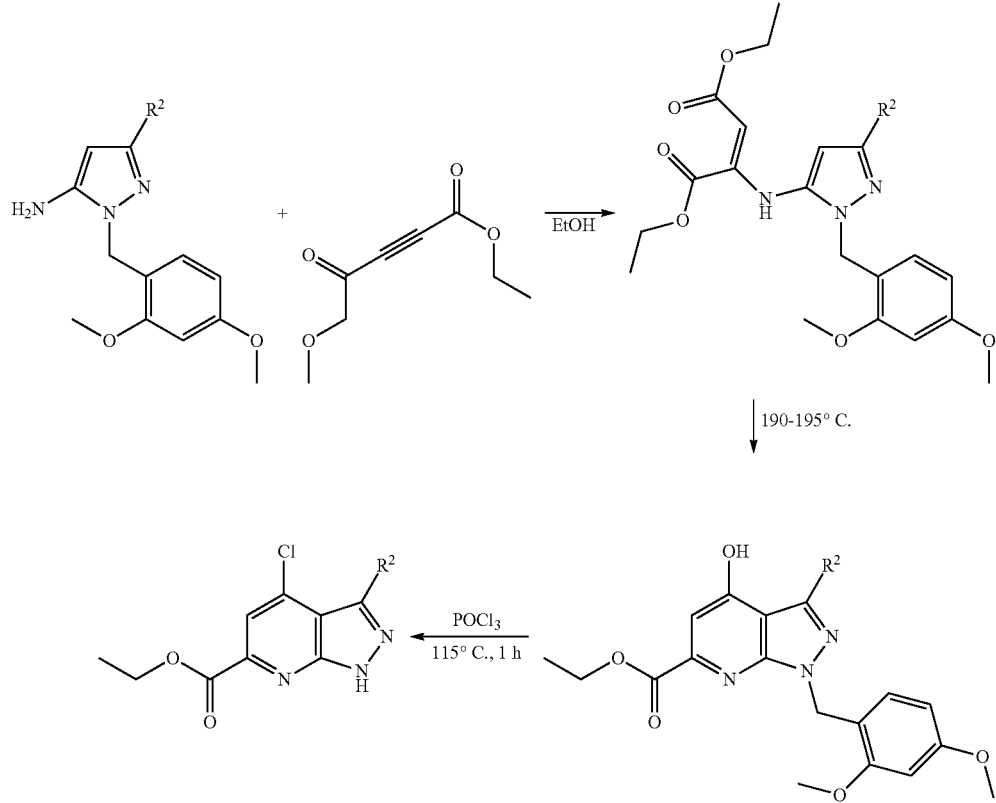

Illustrative Synthesis of HP08: 4-Chloro-3-isopropyl-1H-pyrazolo[3,4-b]pyridine-6-carboxylic Acid Ethyl Ester

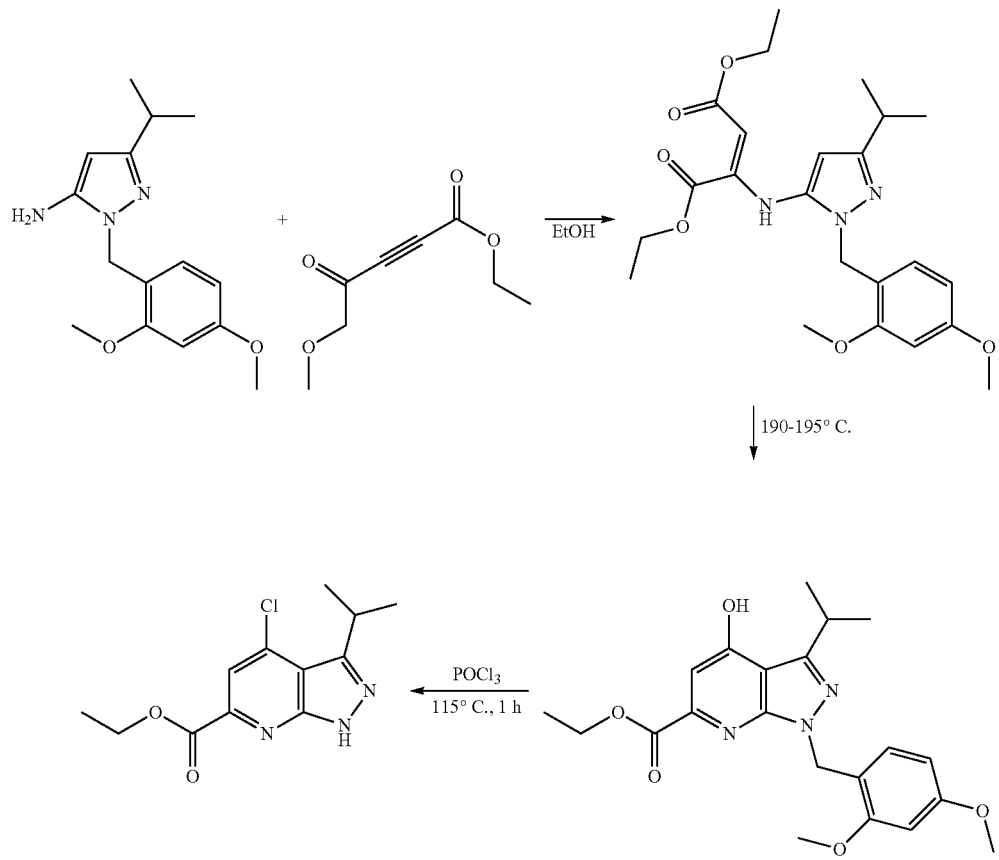

Step 1: 2-[2-(2,4-Dimethoxy-benzyl)-5-isopropyl-2H-pyrazol-3-ylamino]-but-2-enedioic Acid Diethyl Ester To a suspension of 2-(2,4-dimethoxy-benzyl)-5-isopropyl-2H-pyrazol-3-ylamine (AMP28, 18.14 g, 65.88 mmol) in ethanol (150 mL) was added diethyl acetylenedicarboxylate (CAS: 762-21-0, 11.60 mL, 72.47 mmol). The reaction mixture was stirred at room temperature for 4 hours. The reaction mixture was concentrated. The crude residue was purified by silica gel column chromatography (heptane/EtOAc 100/0 to 70/30) to give the titled compound.

Step 2: Compound HP06: 1-(2,4-Dimethoxy-benzyl)-4-hydroxy-3-isopropyl-1H-pyrazolo[3,4-b]pyridine-6-carboxylic Acid Ethyl Ester 2-[2-(2,4-Dimethoxy-benzyl)-5-isopropyl-2H-pyrazol-3-ylamino]-but-2-enedioic acid diethyl ester (13.46 g, 30.21 mmol) was heated under air atmosphere at 190-195° C. for one hour. The reaction mixture cooled to room temperature and was partitioned between dichloromethane and water. The aqueous phase was separated and extracted two times with dichloromethane. The combined organic phases were dried over MgSO$_4$, filtered and concentrated in vacuo. The crude residue was purified by silica gel column chromatography (heptane/EtOAc 100/0 to 60/40) to provide the titled compound.

Step 3: Compound HP08: 4-Chloro-3-isopropyl-1H-pyrazolo[3,4-b]pyridine-6-carboxylic Acid Ethyl Ester A solution of 1-(2,4-dimethoxy-benzyl)-4-hydroxy-3-isopropyl-1H-pyrazolo[3,4-b]pyridine-6-carboxylic acid ethyl ester (HP06, 4.02 g, 10.06 mmol) in phosphorus(V) oxychloride (CAS 100025-87-3, 30 mL, 322 mmol) was stirred at 115° C. for 1 h. The reaction mixture was then cooled to room temperature and concentrated in vacuo. The residue was dissolved in ethyl acetate, and the reaction mixture was added dropwise to a solution of saturated of sodium hydrogencarbonate till total neutralization of phosphorus(V) oxychloride (pH 8). The aqueous phase was separated and extracted two times with ethyl acetate. The combined organic phases were washed with brine, dried over MgSO$_4$, filtered and concentrated in vacuo. The crude residue was purified by silica gel column chromatography (heptane/EtOAc 100/0 to 75/25) to provide the titled compound.

Illustrative Synthesis of HP20: Ethyl 1-tert-butyl-3-cyclobutyl-4-[(trifluoromethanesulfonyl)oxy]-1H-pyrazolo[3,4-b]pyridine-6-carboxylate

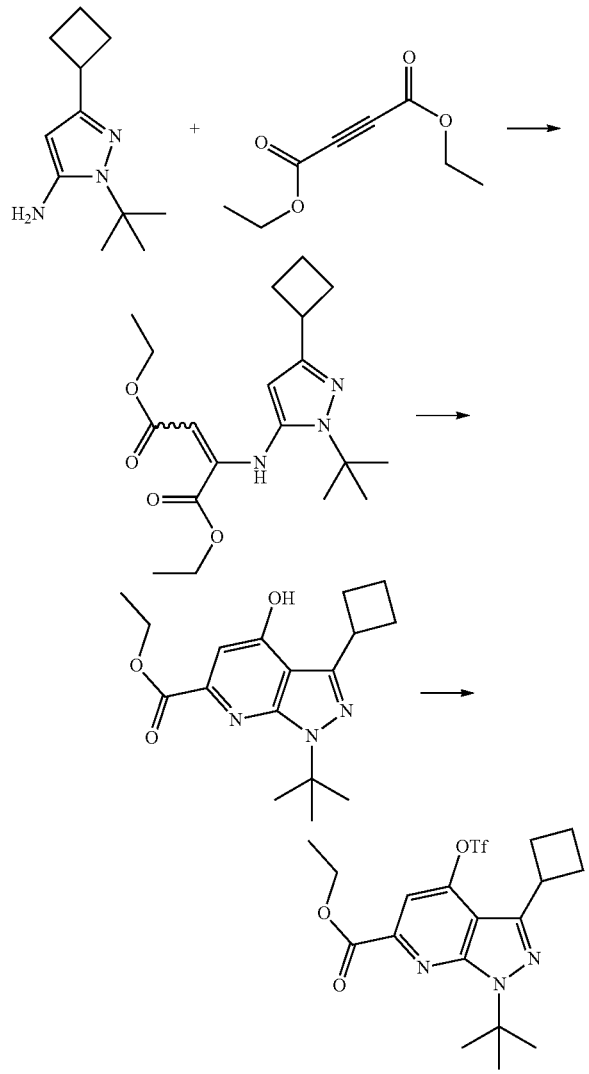

Step 1: Diethyl 2-[(1-tert-butyl-3-cyclobutyl-1H-pyrazol-5-yl)amino]but-2-enedioate In an amber round bottom flask, diethyl acetylenedicarboxylate ([762-21-0], 14.8 mL, 87 mmol) was added to a suspension of AMP94 (15.2 g, 78.8 mmol) in ethanol (200 mL). The reaction mixture was stirred at room temperature for 20 hours, and the mixture was concentrated in vacuo. The crude residue was purified by silica gel column chromatography (heptane/dichloromethane 100/0 to 0/100) to give the titled compound.

Step 2: Ethyl 1-tert-butyl-3-cyclobutyl-4-hydroxy-1H-pyrazolo[3,4-b]pyridine-6-carboxylate In a sealed tube, a suspension of diethyl 2-[(1-tert-butyl-3-cyclobutyl-1H-pyrazol-5-yl)amino]but-2-enedioate (5 g, 13.8 mmol) in Dowtherm® A (5 mL) was heated at 185-190° C. for 24 hours. The reaction mixture was cooled to room temperature and was partitioned between n-heptane and acetonitrile. The acetonitrile phase was separated and evaporated under reduced pressure. The crude sample was purified by silica gel column chromatography (dichloromethane/n-heptane) to give the titled compound.

Step 3: Ethyl 1-tert-butyl-3-cyclobutyl-4-[(trifluoromethanesulfonyl)oxy]-1H-pyrazolo[3,4-b]pyridine-6-carboxylate Trifluoromethanesulfonic anhydride ([358-23-6], 1.9 mL, 11.3 mmol) was added dropwise to a solution of ethyl 1-tert-butyl-3-cyclobutyl-4-hydroxy-1H-pyrazolo[3,4-b]pyridine-6-carboxylate (2.5 g, 7.89 mmol) and pyridine (1.9 mL, 23.5 mmol) in acetonitrile (80 mL), maintaining the temperature around 20-25° C. The reaction mixture was stirred at RT for 20 hours. Then solid sodium hydrogencarbonate and few milliliters of water were added, and the reaction mixture was concentrated in vacuo. The residue was taken up in dichloromethane and water. The two phases were separated, and the aqueous phase was again extracted with dichloromethane. The combined organic phases were washed with brine, dried over MgSO$_4$, filtered and concentrated under reduced pressure. The resulting residue was purified by silica gel chromatography (n-heptane/ethyl acetate) to yield the titled compound.

Synthesis of HP12: Methyl 4-chloro-1-cyclohexyl-3-isopropyl-pyrazolo[3,4-b]pyridine-6-carboxylate

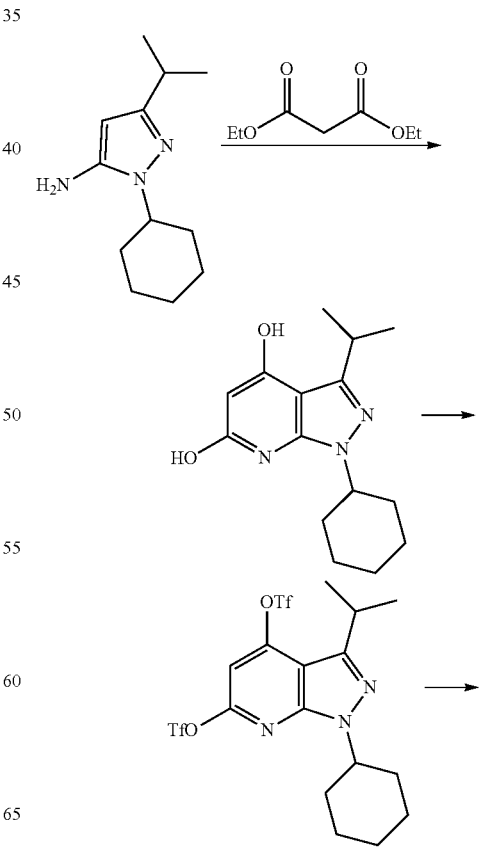

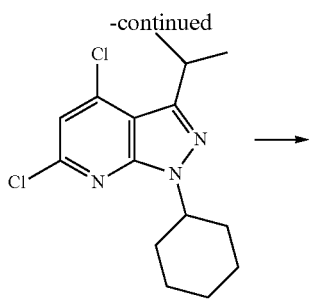

Step 4: HP12: Methyl 4-chloro-1-cyclohexyl-3-isopropyl-pyrazolo[3,4-b]pyridine-6-carboxylate Triethylamine (1.9 mL, 13.6 mmol, 2.0 equiv) and Pd(dppf)Cl$_2$ (CAS: 72287-26-4, 100 mg, 0.14 mmol, 0.02 equiv) were added to a solution of 4,6-dichloro-1-cyclohexyl-3-isopropyl-pyrazolo[3,4-b]pyridine (2.13 g, 6.82 mmol) in methanol (55 mL). The system was filled at RT with CO (40 psi) and heated at 100° C. for 1 hour. The reaction mixture was cooled down to RT and concentrated in vacuo. The residue was purified by chromatography on silica gel (heptane/ethyl acetate 100/0 to 90/10) to yield the titled compound.

Synthesis of HP14: Ethyl 3-cyclobutyl-1-[(2,4-dimethoxyphenyl)methyl]-4-(trifluoromethylsulfonyloxy)pyrazolo[3,4-b]pyridine-6-carboxylate

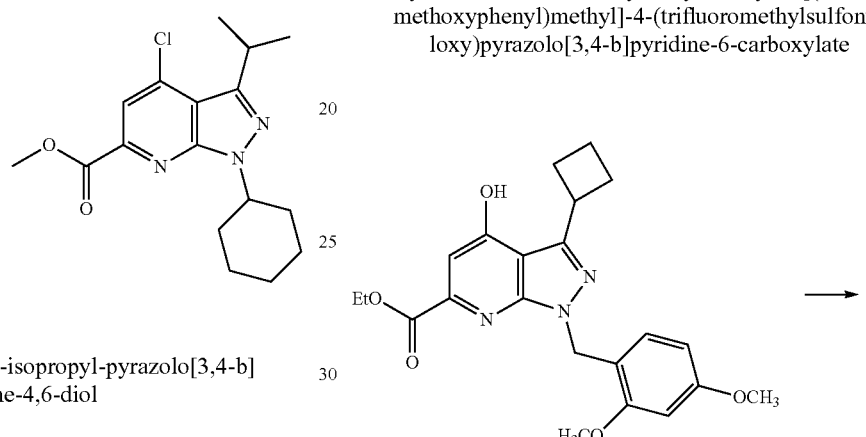

Step 1: 1-cyclohexyl-3-isopropyl-pyrazolo[3,4-b]pyridine-4,6-diol

A mixture of AMP23 (5.0 g, 24.1 mmol) and diethylmalonate (CAS 105-53, 37.36 mL, 48.2 mmol, 2.0 equiv) was stirred at 190° C. for 2 hours. The reaction mixture was then cooled to RT, and diethyl ether was added. The obtained suspension was filtered; the solid was washed with pentane, and dried in vacuo to give the titled compound.

Step 2: [1-cyclohexyl-3-isopropyl-6-(trifuoromethylsulfonyloxy)pyrazolo[3,4-b]pyridin-4-yl]trifluoromethanesulfonate Trifluoromethanesulfonic anhydride (CAS 358-23-6, 6.26 mL, 37.2 mmol, 1.75 equiv) was added dropwise at 0° C. to a solution of 1-cyclohexyl-3-isopropyl-pyrazolo[3,4-b]pyridine-4,6-diol (5.85 g, 21.2 mmol) and pyridine (4.3 mL, 53.1 mmol, 2.5 equiv) in acetonitrile (145 mL). The reaction mixture was stirred at RT for 16 hours. Dichloromethane and water were added to the reaction mixture. The two phases were separated, and the organic phase was washed with water and brine, dried over MgSO$_4$, filtered and concentrated in vacuo. The residue was taken up in toluene and concentrated again in vacuo to give the titled compound.

Step 3: 4,6-dichloro-1-cyclohexyl-3-isopropyl-pyrazolo[3,4-b]pyridine

A mixture of [1-cyclohexyl-3-isopropyl-6-(trifluoromethylsulfonyloxy)pyrazolo[3,4-b]pyridin-4-yl]trifluoromethanesulfonate (10.86 g, 20.1 mmol) and 4 N HCl in dioxane (50 mL, 200 mmol, 10 equiv) was stirred at 100° C. for 16 hours in a sealed tube. The reaction mixture was cooled to RT and concentrated in vacuo. The residue was purified by chromatography on silica gel (heptane/dichloromethane 100/0 to 80/20) to yield the titled compound.

Trifluoromethanesulfonic anhydride (CAS 358-23-6, 92 HL, 0.56 mmol, 1.45 equiv) was added dropwise at RT to a solution of HP15 (160 mg, 0.39 mmol, 1 equiv) and pyridine (46 µL, 0.58 mmol, 1.5 equiv) in acetonitrile (4 mL). The reaction mixture was stirred at RT for 3 h. Then solid sodium hydrogencarbonate and few milliliters of water were added, and the reaction mixture was concentrated in vacuo. The residue was taken up in dichloromethane and water. The two phases were separated, and the aqueous phase was extracted with dichloromethane. The combined organic phases were washed with brine, dried over MgSO$_4$, filtered and concentrated in vacuo. The resulting residue was purified by flash chromatography on silica gel (eluent system: heptane/dichloromethane gradient from 100/0 to 0/100) to yield the titled compound.

TABLE VIII

| Int. | Structure | Name | SM | method | MW | Mes |
|---|---|---|---|---|---|---|
| HP01 | 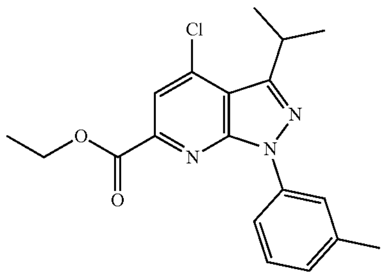 [SMILES: CCOC(=O)c1cc(Cl)c2c(C(C)C)nn(-c3cccc(C)c3)c2n1] | ethyl 4-chloro-3-isopropyl-1-(m-tolyl)pyrazolo[3,4-b]pyridine-6-carboxylate | AMP07 | H1 Specific example | 357-359 | 358-360 |
| HP02 | 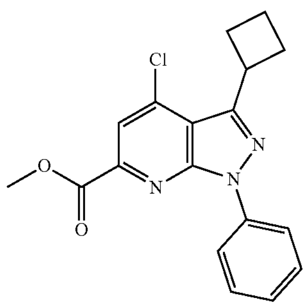 [SMILES: COC(=O)c1cc(Cl)c2c(C3CCC3)nn(-c3ccccc3)c2n1] | methyl 4-chloro-3-cyclobutyl-1-phenyl-pyrazolo[3,4-b]pyridine-6-carboxylate | AMP29 | H2 Specific example | 341-343 | 342-344 |
| HP03 | 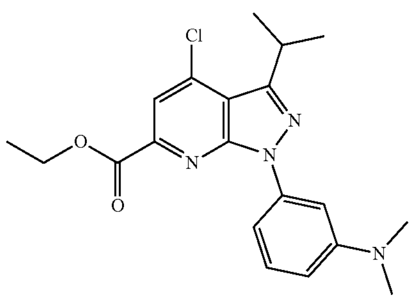 [SMILES: CCOC(=O)c1cc(Cl)c2c(C(C)C)nn(-c3cccc(N(C)C)c3)c2n1] | ethyl 4-chloro-1-[3-(dimethylamino)phenyl]-3-isopropyl-pyrazolo[3,4-b]pyridine-6-carboxylate | AMP06 | H1(steps 1 to 8) and H1' (step 9) Specific example | 386-388 | 387-389 |
| HP04 | 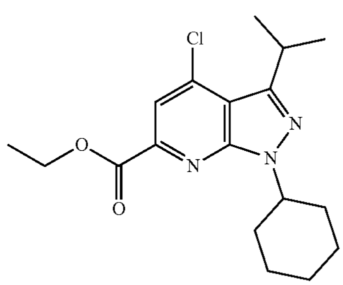 [SMILES: CCOC(=O)c1cc(Cl)c2c(C(C)C)nn(C3CCCCC3)c2n1] | ethyl 4-chloro-1-cyclohexyl-3-isopropyl-pyrazolo[3,4-b]pyridine-6-carboxylate | AMP23 | H1(steps 1 to 8) and H1' (step 9) | 349-351 | 350-352 |
| HP05 | 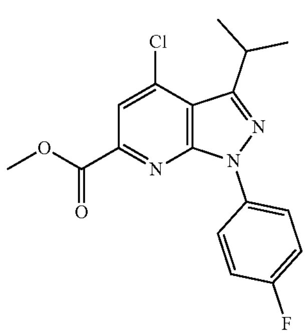 [SMILES: COC(=O)c1cc(Cl)c2c(C(C)C)nn(-c3ccc(F)cc3)c2n1] | methyl 4-chloro-1-(4-fluorophenyl)-3-isopropyl-pyrazolo[3,4-b]pyridine-6-carboxylate | AMP13 | H2 | 347-349 | 348-350 |

TABLE VIII-continued

List of halogenated pyrazolopyridine

| Int. | Structure | Name | SM | method | MW | Mes |
|---|---|---|---|---|---|---|
| HP06 | 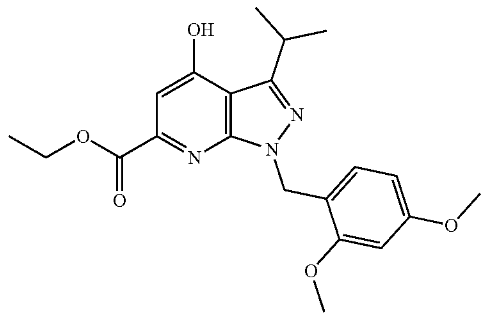 [SMILES: CCOC(=O)c1cc(O)c2c(C(C)C)nn(Cc3ccc(OC)cc3OC)c2n1] | ethyl 1-[(2,4-dimethoxyphenyl)methyl]-4-hydroxy-3-isopropyl-pyrazolo[3,4-b]pyridine-6-carboxylate | AMP28 | H3 (steps 1 & 2 only) | 399 | 400 |
| HP07 | 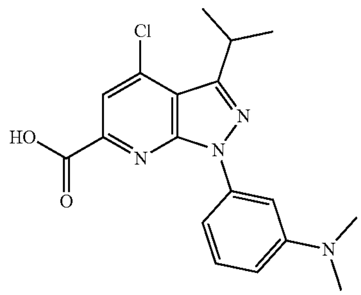 [SMILES: CC(C)c1nn(-c2cccc(N(C)C)c2)c2nc(C(=O)O)cc(Cl)c12] | 4-chloro-1-[3-(dimethylamino)phenyl]-3-isopropyl-pyrazolo[3,4-6]pyridine-6-carboxylic acid | HP03 | J1 | 358-360 | 359-361 |
| HP08 | 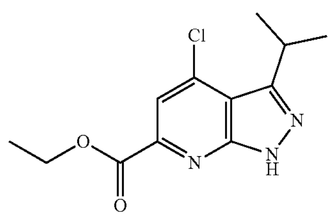 [SMILES: CCOC(=O)c1cc(Cl)c2c(C(C)C)n[nH]c2n1] | ethyl 4-chloro-3-isopropyl-1H-pyrazolo[3,4-£]pyridine-6-carboxylate | AMP28 | H3 Specific example | 267-269 | 268-270 |
| HP09 | 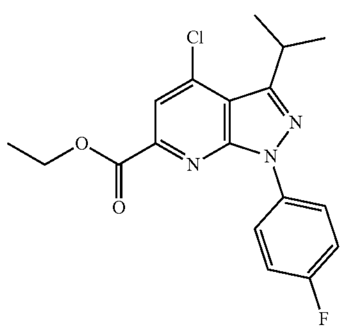 [SMILES: CCOC(=O)c1cc(Cl)c2c(C(C)C)nn(-c3ccc(F)cc3)c2n1] | ethyl 4-chloro-1-(4-fluorophenyl)-3-isopropyl-pyrazolo[3,4-b]pyridine-6-carboxylate | HP08, 1765-93-1 | I4 | 361-363 | 362-364 |
| HP10 | 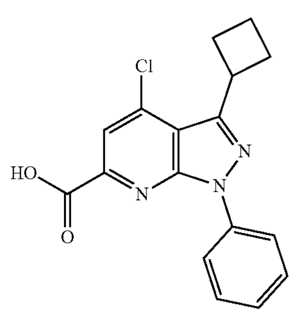 [SMILES: O=C(O)c1cc(Cl)c2c(C3CCC3)nn(-c3ccccc3)c2n1] | 4-chloro-3-cyclobutyl-1-phenyl-pyrazolo[3,4-b]pyridine-6-carboxylic acid | HP02 | J1 | 327-329 | 328-330 |

TABLE VIII-continued

List of halogenated pyrazolopyridine

| Int. | Structure | Name | SM | method | MW | Mes |
|---|---|---|---|---|---|---|
| HP11 | 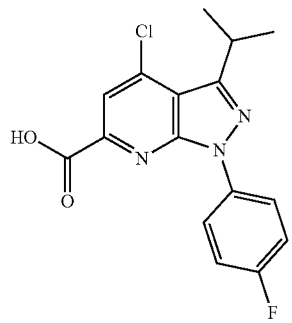 [SMILES: CC(C)c1nn(-c2ccc(F)cc2)c2nc(C(=O)O)cc(Cl)c12] | 4-chloro-1-(4-fluorophenyl)-3-isopropyl-pyrazolo[3,4-b]pyridine-6-carboxylic acid | HP05 | J1 | 333-335 | 334-336 |
| HP12 | 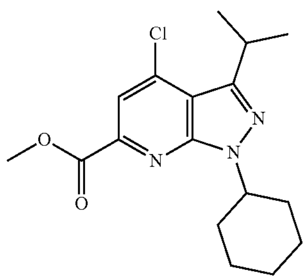 [SMILES: COC(=O)c1cc(Cl)c2c(C(C)C)nn(C3CCCCC3)c2n1] | methyl 4-chloro-1-cyclohexyl-3-isopropyl-pyrazolo[3,4-b]pyridine-6-carboxylate | AMP23 | Specific example | 335-337 | 336-338 |
| HP13 | 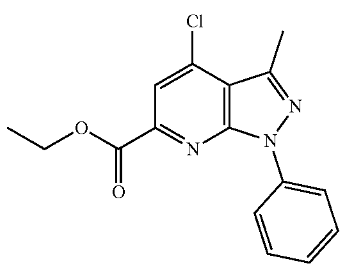 [SMILES: CCOC(=O)c1cc(Cl)c2c(C)nn(-c3ccccc3)c2n1] | ethyl 4-chloro-3-methyl-1-phenyl-pyrazolo[3,4-b]pyridine-6-carboxylate | 1131-18-6 | Specific example | 315-317 | 316-318 |
| HP14 | 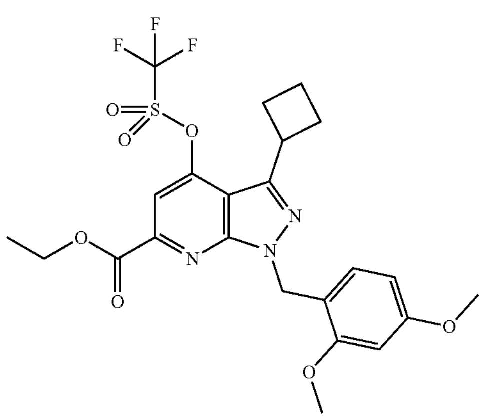 [SMILES: CCOC(=O)c1cc(OS(=O)(=O)C(F)(F)F)c2c(C3CCC3)nn(Cc3ccc(OC)cc3OC)c2n1] | ethyl 3-cyclobutyl-1-[(2,4-dimethoxyphenyl)methyl]-4-(trifluoromethyl-sulfonyloxy)pyrazolo[3,4-b]pyridine-6-carboxylate | HP15 | Specific example | 543 | 544 |

TABLE VIII-continued

List of halogenated pyrazolopyridine

| Int. | Structure | Name | SM | method | MW | Mes |
|------|-----------|------|----|----|-----|-----|
| HP15 | 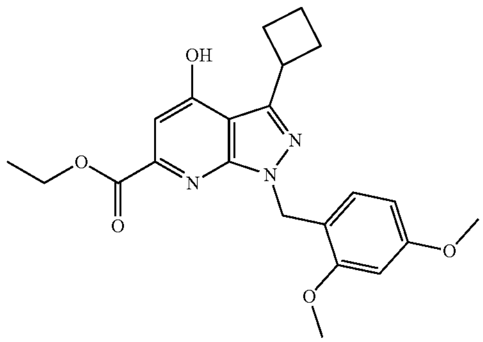 [SMILES: CCOC(=O)c1cc(O)c2c(C3CCC3)nn(Cc3ccc(OC)cc3OC)c2n1] | ethyl 3-cyclobutyl-1-[(2,4-dimethoxyphenyl)methyl]-4-hydroxy-pyrazolo[3,4-b]pyridine-6-carboxylate | AMP36 | H3 (steps 1 & 2 only)[1] | 411 | 412 |
| HP16 | 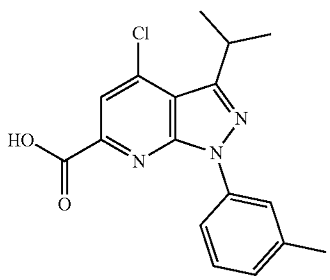 [SMILES: Cc1cccc(-n2nc(C(C)C)c3c(Cl)cc(C(=O)O)nc32)c1] | 4-chloro-3-isopropyl-1-(m-tolyl)pyrazolo[3,4-6]pyridine-6-carboxylic acid | HP01 | J1 | 329-331 | 330-332 |
| HP19 | 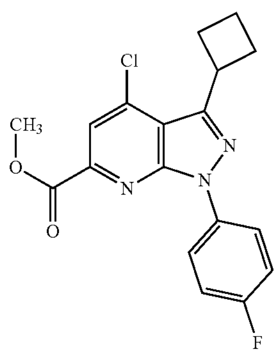 [SMILES: COC(=O)c1cc(Cl)c2c(C3CCC3)nn(-c3ccc(F)cc3)c2n1] | methyl 4-chloro-3-cyclobutyl-1-(4-fluorophenyl)-1H-pyrazolo[3,4-b]pyridine-6-carboxylate | AMP93 | Specific example | 359-361 | 360-362 |
| HP20 | 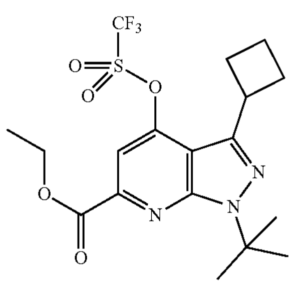 [SMILES: CCOC(=O)c1cc(OS(=O)(=O)C(F)(F)F)c2c(C3CCC3)nn(C(C)(C)C)c2n1] | ethyl 1-tert-butyl-3-cyclobutyl-4-[(trifluoromethanesulfonyl)oxy]-1H-pyrazolo[3,4-b]pyridine-6-carboxylate | AMP94 | Specific example | 449 | 450 |
| HP25 | 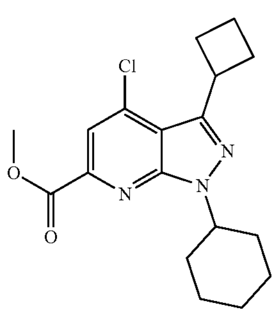 [SMILES: COC(=O)c1cc(Cl)c2c(C3CCC3)nn(C3CCCCC3)c2n1] | methyl 4-chloro-3-cyclobutyl-1-cyclohexyl-1H-pyrazolo[3,4-b]pyridine-6-carboxylate | AMP35 | Specific example | 347 | 348 |

TABLE VIII-continued

List of halogenated pyrazolopyridine

| Int. | Structure | Name | SM | method | MW | Mes |
|---|---|---|---|---|---|---|
| HP26 | 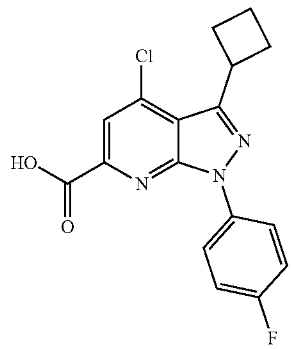 [SMILES: O=C(O)c1cc(Cl)c2c(C3CCC3)nn(-c3ccc(F)cc3)c2n1] | 4-chloro-3-cyclobutyl-1-(4-fluorophenyl)-1H-pyrazolo[3,4-b]pyridine-6-carboxylic acid | AMP19 | J1 | 345 | 346 |

[1]Step 2 performed in Dowtherm ™ at 160° C. for 48 h.

Method I1-I34: Synthesis of Esters
Method I1: Cyclization of Alkylidene Pyruvates and Aminopyrazoles

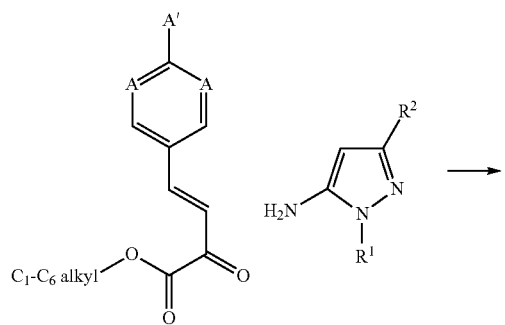

A is either N or CH
A' is either $R^e$ or $L^1$-$G^{3C}$ as described in the Summary The alkylidene pyruvate (1 to 1.5 equiv) and the aminopyrazole (1 to 1.5 equiv) in acetic acid or DMF are stirred under air at temperatures ranging from RT to reflux for 1 h to several days. Alternatively, the reaction mixture is heated under microwave irradiation at 150° C. for 20 minutes to 2 h followed either by stirring under air in an opened flask at temperatures ranging from RT to 90° C. for 1 h to several days or by removal of the solvent in vacuo, dilution of the residue in ethanol and stirring at reflux for 1 h to several days. Then volatiles are removed in vacuo to afford the titled compound which is used as such or alternatively worked up by dilution with an organic solvent, washed successively with a basic aqueous solution and brine, dried over sodium sulfate, filtered and concentrated in vacuo and used as such or further purified either by precipitation, by preparative HPLC or by flash chromatography on silica gel.

Alternatively, the alkylidene pyruvate (1 equiv) and the aminopyrazole (1 equiv) in N-methylpyrrolidone can be heated at 80 to 100° C. over 8 to 24 hours. Next, the reaction mixture is cooled down to room temperature and a base such as $Cs_2CO_3$ (2-6 equiv) is added. The resulting mixture is stirred open to the air until full oxidation is observed.

Illustrative Synthesis of E018: 4-(4-Cyano-3,4,5,6-tetrahydro-2H-[1,2']bipyridinyl-5'-yl)-3-cyclobutyl-1-phenyl-1H-pyrazolo[3,4-b]pyridine-6-carboxylic Acid Ethyl Ester

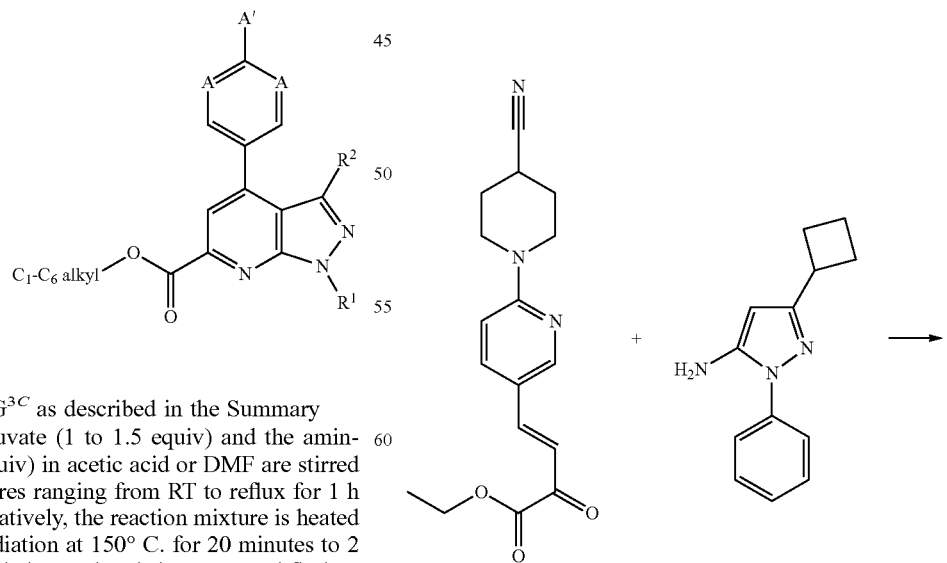

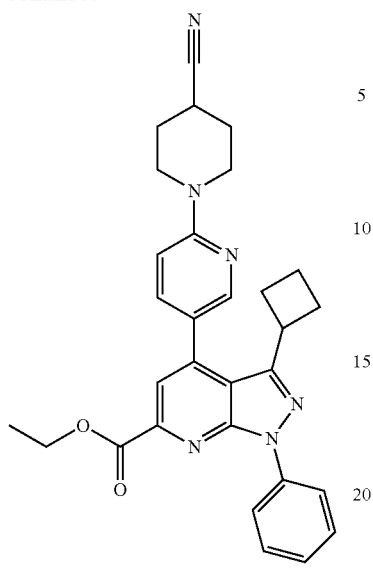

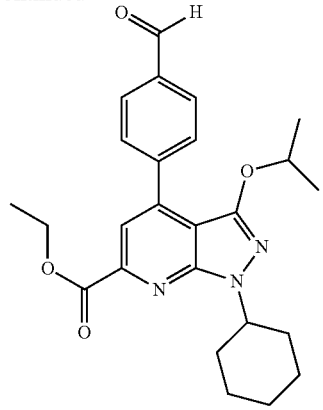

A solution of ALP36 (116 mg, 0.5 mmol) and AMP95 (112 mg, 0.5 mmol) in N-methylpyrrolidine (2 mL) was heated at 100° C. for 20 hours in a sealed tube. The volatiles were removed in vacuo, and the residue was purified by flash chromatography on silica gel eluted with ethyl acetate/n-heptane (0/1 to 1/0) to give the titled compound.

Illustrative Synthesis of E503: Methyl 4-(4-bromophenyl)-1-cyclohexyl-3-hydroxy-1H-pyrazolo[3,4-b]pyridine-6-carboxylate The alkylidene pyruvate ALP09 (47.1 g, 150.5 mmol) and the aminopyrazole AMP29 (30 g, 140.7 mmol) were dissolved in acetic acid (240 mL) in an opened round bottom flask equipped with a condenser. The solution was heated at 80° C. for 40 hours and then left cooling down to RT. The mixture was concentrated under reduced pressure, and the crude residue was diluted with DCM (400 mL). The organic phase was washed successively with a saturated aqueous solution of Na₂CO₃ and a saturated aqueous solution of NaCl, dried over sodium sulfate, filtered and concentrated in vacuo. The crude sample was purified by flash column chromatography eluting with dichloromethane/ethyl acetate. The solid was stirred for 10 minutes in methanol, filtered and dried at 40° C. under reduced pressure to give the titled compound.

Illustrative Synthesis of E425: Ethyl 1-cyclohexyl-4-(4-formylphenyl)-3-[(propan-2-yl)oxy]-1H-pyrazolo[3,4-b]pyridine-6-carboxylate

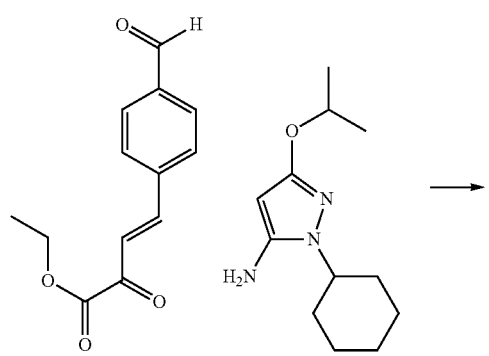

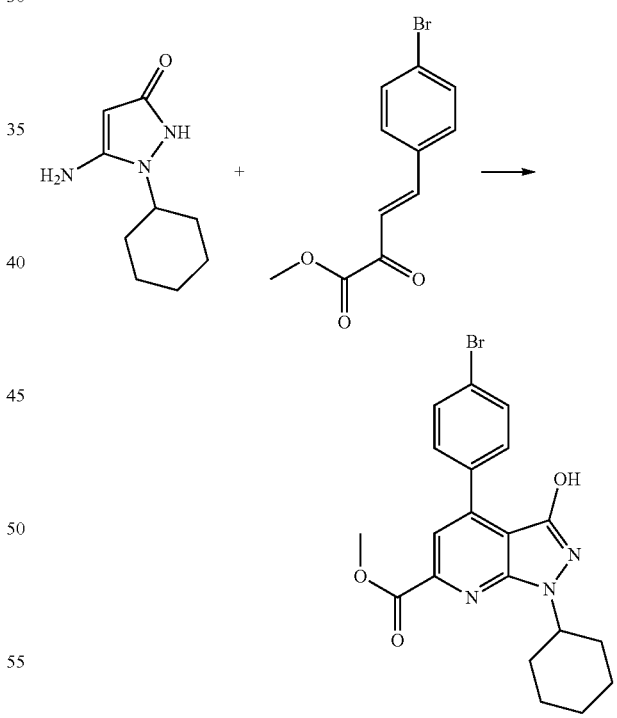

5-Amino-1-cyclohexyl-1H-pyrazol-3-ol ([436088-86-7], 5.54 g, 30.5 mmol,) and (E)-methyl-4-(4-bromophenyl)-2-oxobut-3-enoate ([608128-34-3], 8.22 g, 30.5 mmol,) in NMP (60 mL,) were heated overnight at 90° C. Next, the reaction mixture was cooled down to room temperature and Cs₂CO₃ (30 g, 91.6 mmol) was added. The resulting mixture was stirred open to the air until full oxidation to the titled compound was observed. The obtained solution was used as such for alkylation.

Method I2: Suzuki Coupling

Illustrative Synthesis of E197 and E198: Methyl 4-(1-tert-butoxycarbonyl-4-piperidyl)-1-(4-fluorophenyl)-3-isopropyl-pyrazolo[3,4-b]pyridine-6-carboxylate and Methyl 4-(1-tert-butoxycarbonyl-3,6-dihydro-2H-pyridin-4-yl)-1-(4-fluorophenyl)-3-isopropyl-pyrazolo[3,4-b]pyridine-6-carboxylate

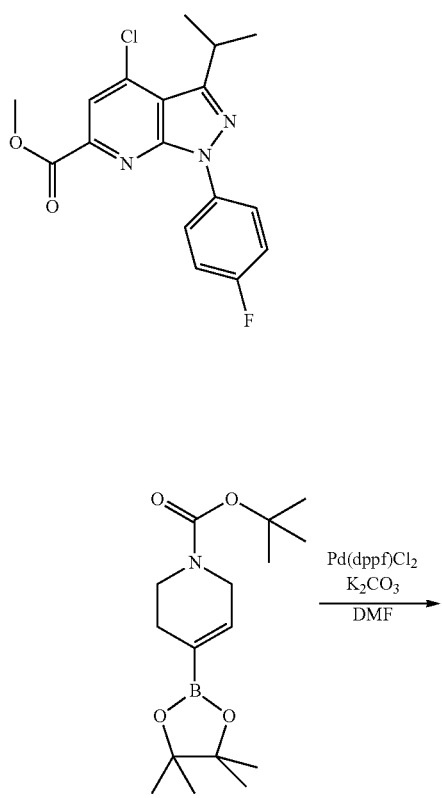

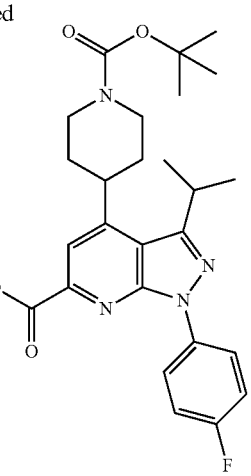

Step 1: Methyl 4-(1-tert-butoxycarbonyl-3,6-dihydro-2H-pyridin-4-yl)-1-(4-fluorophenyl)-3-isopropyl-pyrazolo[3,4-b]pyridine-6-carboxylate E198

A suspension of methyl 4-chloro-1-(4-fluorophenyl)-3-isopropyl-pyrazolo[3,4-b]pyridine-6-carboxylate (HP05, 2.0 g, 5.75 mmol, 1.0 equiv), tert-butyl 4-(4,4,5,5-tetramethyl-1,3,2-dioxaborolan-2-yl)-3,6-dihydro-2H-pyridine-1-carboxylate (CAS 286961-14-6, 3.6 g, 11.5 mmol, 2.0 equiv), K₂CO₃ (2.4 g, 17.25 mmol, 3.0 equiv) and Pd(dppf)Cl₂ (CAS: 72287-26-4, 939 mg, 1.15 mmol, 0.2 equiv) in anhydrous DMF (15 mL) was degassed with nitrogen at room temperature for 2 minutes. The reaction mixture was heated at reflux overnight. The mixture was cooled to RT, and the mixture was poured into 150 mL of water and diluted with ethyl acetate. The two phases were separated, and the aqueous phase was extracted with ethyl acetate. The combined organic layers were washed with brine, dried over MgSO₄, filtered and concentrated. The crude residue was purified by silica gel chromatography (heptane/ethyl acetate: 100/0 to 80/20) to give E198.

Step 2: Methyl 4-(1-tert-butoxycarbonyl-4-piperidyl)-1-(4-fluorophenyl)-3-isopropyl-pyrazolo[3,4-b] pyridine-6-carboxylate A suspension of E198 (2.44 g, 4.93 mmol, 1.0 equiv) and platinum(IV) oxide (CAS 1314-15-4, 1.2 g) in AcOH was stirred at RT under hydrogen atmosphere (balloon) overnight. Then the reaction mixture was filtered over Celpure® P65. Solids were washed with ethyl acetate, and the filtrate was concentrated in vacuo. The crude residue was purified by silica gel chromatography (heptane/ethyl acetate: 100/0 to 80/20) to give the title compound.

Method I3: Nucleophilic Substitutions of Amines

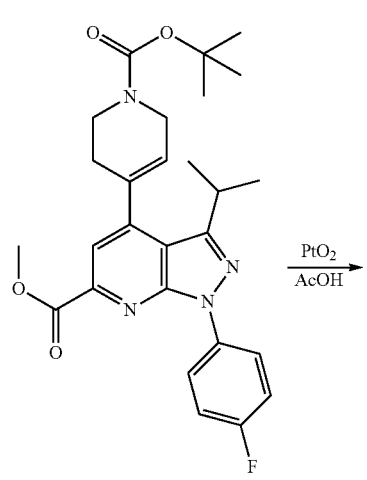

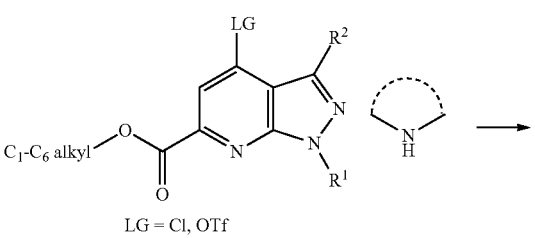

-continued

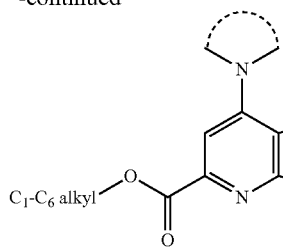

A mixture of the chloride or triflate pyrazolopyridine intermediate (1.0 equiv), the amine as free base or hydrochloride salt (from 1 to 10 equiv) and DIPEA (from 1 to 15 equiv) in anhydrous acetonitrile and DMSO in a sealed tube or a round bottom flask is heated at a temperature ranging from 50 to 130° C. for 1 h to several days (up to 8 days). The reaction mixture is cooled to RT, and volatiles are removed in vacuo. The resulting residue is either purified by precipitation or by flash chromatography on silica gel to afford the titled compound or alternatively partitioned between either dichloromethane or ethyl acetate and water. The two phases are then separated, and the aqueous phase is extracted with either ethyl acetate or dichloromethane. The combined organic phases are washed with brine, dried over MgSO$_4$, filtered and concentrated in vacuo and the resulting crude mixture is either used as such or purified by flash chromatography on silica gel to afford the titled compound.

Illustrative Synthesis of E092: Methyl 1-(4-fluorophenyl)-3-isopropyl-4-[4-(methoxymethyl)-1-piperidyl]pyrazolo[3,4-b]pyridine-6-carboxylate A mixture of HP05 (6.71 g, 19.29 mmol, 1.0 equiv), 4-(methoxymethyl)piperidine hydrochloride (CAS 916317-00-5, 6.39 g, 38.58 mmol, 2 equiv) and DIPEA (10.1 mL, 57.88 mmol, 3 equiv) in anhydrous DMSO (65 mL) was heated at 100° C. for 20 h. The reaction mixture was cooled to RT, partitioned between ethyl acetate (300 mL) and a mixture of water and a saturated solution of NaCl 1:1 (300 mL). The two phases were separated, and the aqueous phase was extracted with ethyl acetate (150 mL). The combined organic phases were washed with brine, dried over MgSO$_4$, filtered and concentrated in vacuo. The crude mixture was purified by flash chromatography on silica gel eluting with n-heptane/ethyl acetate to afford the titled compound.

Illustrative Synthesis of E356: Methyl 3-cyclobutyl-1-(4-fluorophenyl)-4-[4-(4-methoxy-1-piperidyl)-1-piperidyl]pyrazolo[3,4-b]pyridine-6-carboxylate

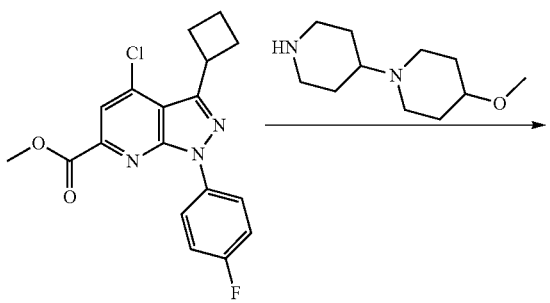

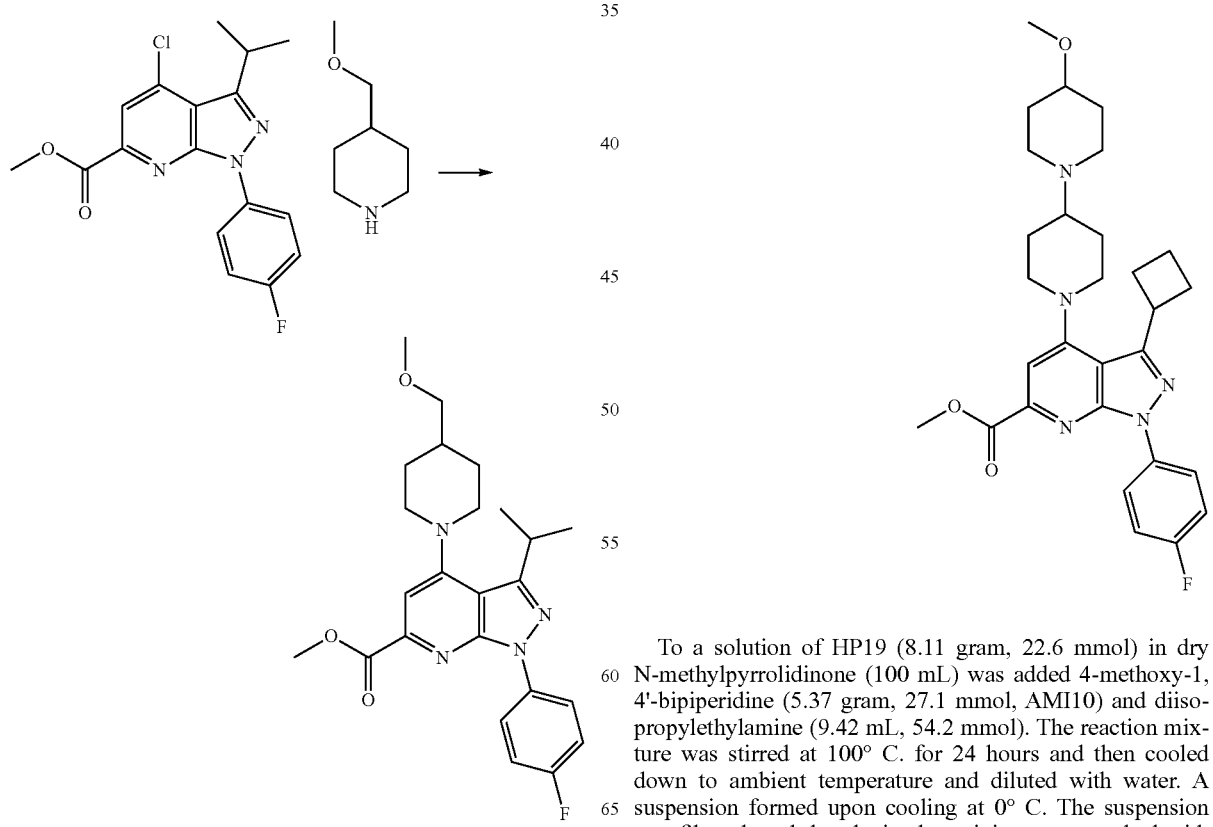

To a solution of HP19 (8.11 gram, 22.6 mmol) in dry N-methylpyrrolidinone (100 mL) was added 4-methoxy-1,4'-bipiperidine (5.37 gram, 27.1 mmol, AMI10) and diisopropylethylamine (9.42 mL, 54.2 mmol). The reaction mixture was stirred at 100° C. for 24 hours and then cooled down to ambient temperature and diluted with water. A suspension formed upon cooling at 0° C. The suspension was filtered, and the obtained precipitate was washed with water. After drying, the titled compound was obtained.

195

Illustrative Synthesis of E357: Methyl 3-cyclobutyl-1-phenyl-4-{4-[(pyrrolidin-1-yl)methyl]piperidin-1-yl}-1H-pyrazolo[3,4-b]pyridine-6-carboxylate

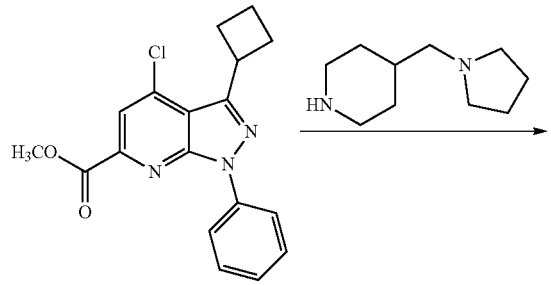

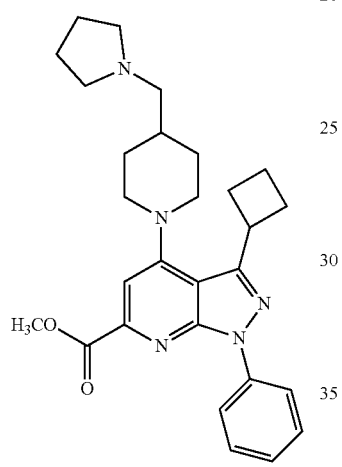

Methyl 4-chloro-3-cyclobutyl-1-phenyl-pyrazolo[3,4-b]pyridine-6-carboxylate (15 g, 43.9 mmol, HP02) and 4-(pyrrolidin-1-ylmethyl)piperidine (13.29 g, 79 mmol) were dissolved in a mixture of N-ethyl-N-isopropylpropan-2-amine (45.9 mL, 263 mmol) and N-methylpyrrolidinone (90 mL). The resulting solution was heated at 100° C. under nitrogen for two hours. After diluting with water (200 mL), the mixture was extracted with tert-butyl methyl ether (3×150 mL). The combined organic fractions were washed with 1 M aqueous NaOH (2×100 mL), water (2×50 mL), and saturated aqueous sodium chloride, then dried over sodium sulfate and concentrated under vacuum to approximately 100 mL followed by the addition of heptanes (200 mL). Volatiles were removed under vacuum, and the resulting thick slurry was stirred overnight at room temperature. The solid was collected by filtration, and then dried to constant weight under vacuum to give 18.39 g of the titled compound. $^1$H NMR (400 MHz, CDCl$_3$) δ ppm 8.39-8.31 (m, 2H), 7.51 (dd, J=8.6, 7.4 Hz, 2H), 7.40 (s, 1H), 7.31-7.23 (m, 1H), 4.00 (m, 4H), 3.70-3.57 (m, 2H), 2.89 (td, J=12.2, 2.4 Hz, 2H), 2.63 (dq, J=11.7, 9.2 Hz, 2H), 2.56-2.49 (m, 4H), 2.47-2.38 (m, 4H), 2.05 (m, 4H), 1.86-1.78 (m, 4H), 1.73 (m, 1H), 1.53 (qd, J=12.1, 3.7 Hz, 2H); LC/MS (APCI) m/z 474.6 (M+H)$^+$.

196

Method I4: Chan-Lam Coupling

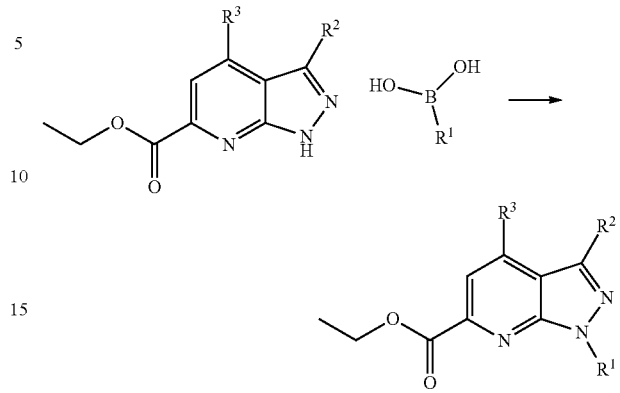

To a solution of ethyl 1H-pyrazolo[3,4-b]pyridine-6-carboxylate intermediate (1.0 equiv) in dichloromethane at RT is added the aryl boronic acid (2.0 to 3.0 equiv), copper(II) acetate (CAS 142-71-2, 1.5 equiv) and pyridine (4.0 equiv). The reaction mixture is stirred at room temperature under air for 1 h to 48 h. Then the reaction mixture is filtered on a pad of diatomaceous earth. Solids are washed with dichloromethane, and the filtrate is concentrated in vacuo. The resulting residue is purified by flash chromatography on silica gel to afford the titled compound.

Illustrative Synthesis of E111: Ethyl 1-(2-fluoro-4-pyridyl)-3-isopropyl-4-(4-methoxy-1-piperidyl)pyrazolo[3,4-b]pyridine-6-carboxylate

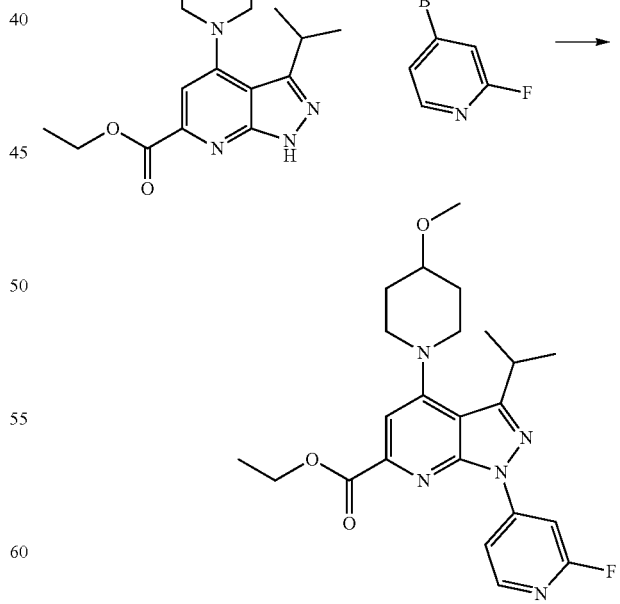

To a solution of ethyl 3-isopropyl-4-(4-methoxy-1-piperidyl)-1H-pyrazolo[3,4-b]pyridine-6-carboxylate E109 (70 mg, 0.20 mmol, 1.0 equiv) in dichloromethane (2 mL) at RT was added (2-fluoropyridin-4-yl)boronic acid (CAS:

401815-98-3, 56 mg, 0.40 mmol, 2.0 equiv), copper(II) acetate (CAS 142-71-2, 54 mg, 0.30 mmol, 1.5 equiv) and pyridine (64 µL, 0.80 mmol, 4.0 equiv). The reaction mixture was stirred at room temperature under air overnight. The reaction mixture was filtered on a pad of diatomaceous earth. Solids were washed with dichloromethane, and the filtrate was concentrated in vacuo. The resulting residue was purified by flash chromatography on silica gel (eluent system: heptane/ethyl acetate: 100/0 to 70/30) to give the titled compound.

Method I5: Nucleophilic Substitution

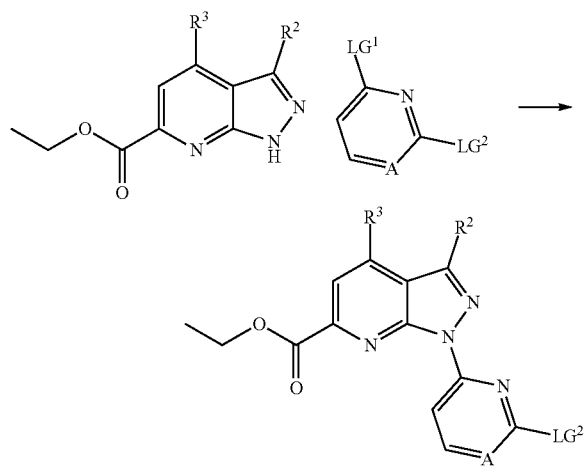

$R^2$ is isopropyl or cyclobutyl
A is CH or N
$LG^1$ and $LG^2$ are independently F, Cl or Br To a solution of ethyl 3-substituted-1H-pyrazolo[3,4-b]pyridine-6-carboxylate intermediate (1.0 equiv) in anhydrous DMF or THF under nitrogen atmosphere at 0° C. is added sodium hydride (60% in mineral oil, from 1.2 equiv to 1.5 equiv), and the mixture is stirred 5 minutes at 0° C. Then, an aromatic halide (2.0 equiv) is added, and the reaction mixture is warmed up to RT and stirred overnight. The reaction mixture is partitioned between water and ethyl acetate and acidified to pH 5 with AcOH. The two phases are separated. The organic phase is washed with brine, dried over MgSO$_4$, filtered and concentrated in vacuo to afford the titled compound which is used as such or purified by flash chromatography on silica gel.

Illustrative Synthesis of E133: Ethyl 1-(6-bromo-2-pyridyl)-3-isopropyl-4-(4-methoxy-1-piperidyl)pyrazolo[3,4-b]pyridine-6-carboxylate

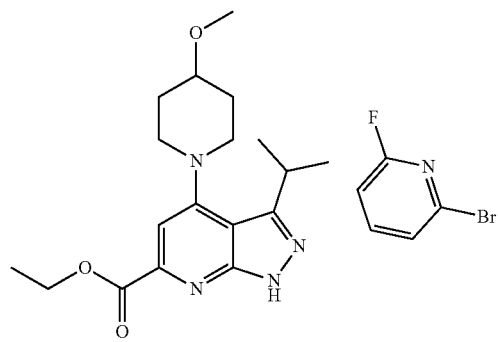

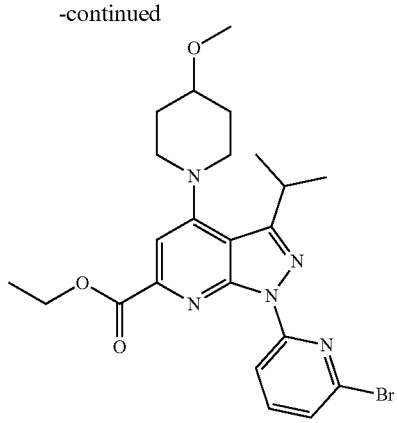

To a solution of ethyl 3-isopropyl-4-(4-methoxy-1-piperidyl)-1H-pyrazolo[3,4-b]pyridine-6-carboxylate E109 (245 mg, 0.71 mmol, 1.0 equiv) in anhydrous DMF (3 mL) under nitrogen atmosphere at 0° C. was added sodium hydride (60% in mineral oil, 34 mg, 0.85 mmol, 1.2 equiv), and the mixture was stirred 5 minutes at 0° C. then 2-bromo-6-fluoropyridine (CAS 144100-07-2, 250 mg, 1.42 mmol, 2.0 equiv) was added, and the reaction mixture was warmed up to RT and stirred overnight. The reaction mixture was partitioned between water and ethyl acetate and acidified to pH 5 with AcOH. The two phases were separated. The organic phase was washed with brine, dried over MgSO$_4$, filtered and concentrated in vacuo to afford the titled compound which was used as such.

Method I6: Alkylation

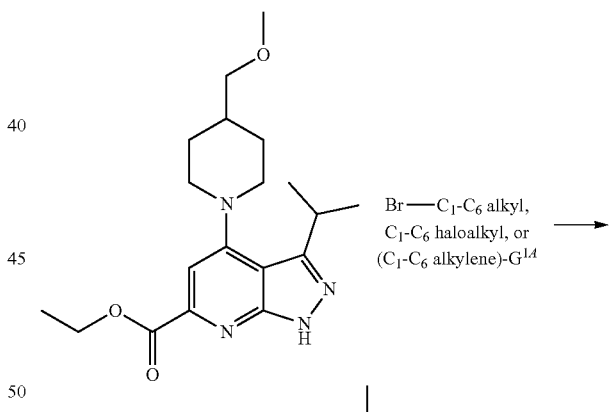

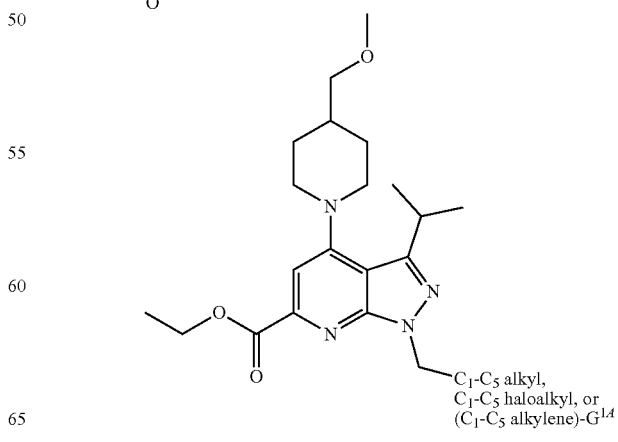

To a suspension of ethyl 3-isopropyl-4-[4-(methoxymethyl)-1-piperidyl]-1H-pyrazolo[3,4-b]pyridine-6-carboxylate E148 (1.0 equiv) in anhydrous DMF under nitrogen atmosphere is added potassium carbonate (1.2 equiv), then alkyl bromide (1.1 equiv). The reaction mixture is stirred at room temperature overnight. Then cesium carbonate (1.2 equiv) and potassium iodide (0.1 equiv) are added, and the reaction mixture is stirred at room temperature for 24 h. The mixture is partitioned between water and ethyl acetate. The aqueous phase is extracted with ethyl acetate. The combined organic phases are washed with brine, dried over MgSO$_4$, filtered and concentrated in vacuo. The crude mixture is purified by flash chromatography on silica gel to afford the titled compound.

Illustrative Synthesis of E154: Ethyl 1-(cyclobutylmethyl)-3-isopropyl-4-[4-(methoxymethyl)-1-piperidyl]pyrazolo[3,4-b]pyridine-6-carboxylate

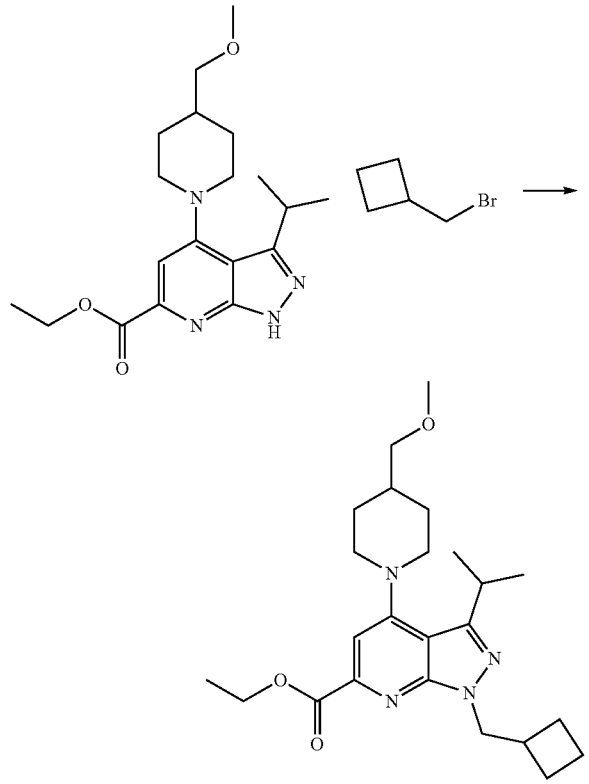

To a suspension of ethyl 3-isopropyl-4-[4-(methoxymethyl)-1-piperidyl]-1H-pyrazolo[3,4-b]pyridine-6-carboxylate E148 (100 mg, 0.28 mmol, 1.0 equiv) in anhydrous DMF (2 mL) under nitrogen atmosphere was added potassium carbonate (47 mg, 0.34 mmol, 1.2 equiv) and then (bromomethyl)cyclobutane (CAS: 17247-58-4, 35 µL, 0.31 mmol, 1.1 equiv). The reaction mixture was stirred at room temperature overnight. Then cesium carbonate (111 mg, 0.34 mmol, 1.2 equiv) and potassium iodide (5 mg, 0.028 mmol, 0.1 equiv) were added, and the reaction mixture was stirred at room temperature for 24 h. The mixture was partitioned between water and ethyl acetate. The aqueous phase was extracted with ethyl acetate. The combined organic phases were washed with brine, dried over MgSO$_4$, filtered and concentrated in vacuo. The crude mixture was purified by flash chromatography on silica gel (eluent system: heptane/ethyl acetate gradient from 100/0 to 75/25) to afford the titled compound.

Method I7: Cross-Coupling to Pyrazole

Illustrative Synthesis of E157: Ethyl 3-isopropyl-4-[4-(methoxymethyl)-1-piperidyl]-1-(1-methyl-6-oxopyridazin-3-yl)pyrazolo[3,4-b]pyridine-6-carboxylate

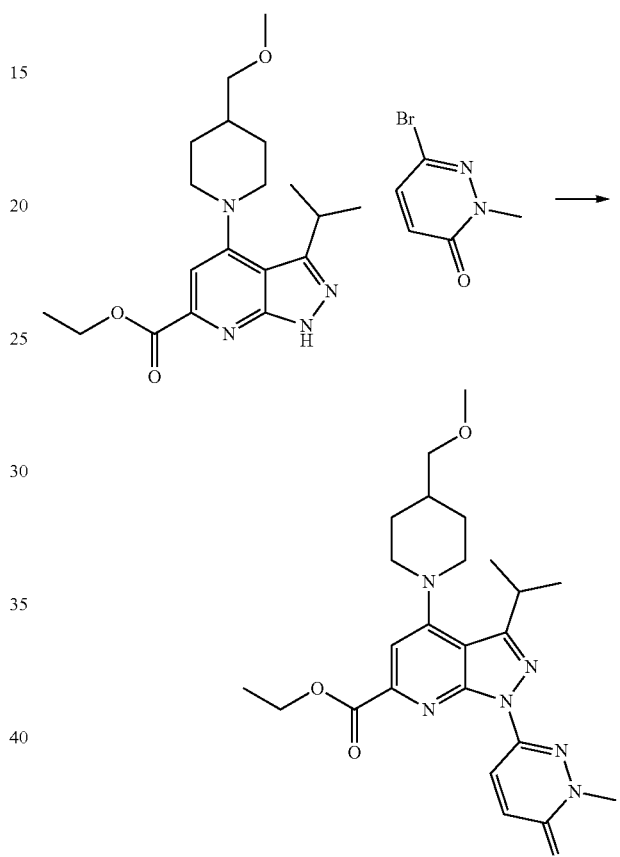

A suspension of ethyl 3-isopropyl-4-[4-(methoxymethyl)-1-piperidyl]-1H-pyrazolo[3,4-b]pyridine-6-carboxylate E148 (100 mg, 0.28 mmol, 1.0 equiv) in anhydrous toluene (1 mL) was degassed with nitrogen (bubbling) at room temperature for 5 minutes. Then to this suspension was added 6-bromo-2-methyl-pyridazin-3-one (CAS 1123169-25-4, 58 mg, 0.31 mmol, 1.1 equiv), cesium carbonate (365 mg, 1.12 mmol, 4.0 equiv), Xantphos (CAS 161265-03-8, 16 mg, 0.028 mmol, 0.1 equiv), and palladium(II) acetate (CAS 3375-31-3, 3 mg, 0.014 mmol, 0.05 equiv). The mixture was purged again with nitrogen at RT for 10 minutes, and then the mixture was stirred at reflux overnight. The reaction mixture was cooled down and concentrated in vacuo. The residue was partitioned between water and ethyl acetate. The aqueous phase was extracted with ethyl acetate. The combined organic phases were washed with brine, dried over MgSO$_4$, filtered and concentrated in vacuo. The crude mixture was purified by flash chromatography on silica gel (eluent system: heptane/ethyl acetate gradient from 100/0 to 0/100) to afford the titled compound.

Illustrative Synthesis of E510: Methyl 3-cyclobutyl-1-[3-(difluoromethoxy)phenyl]-4-[4-(morpholin-4-yl)piperidin-1-yl]-1H-pyrazolo[3,4-b]pyridine-6-carboxylate Method I8: Buchwald Coupling

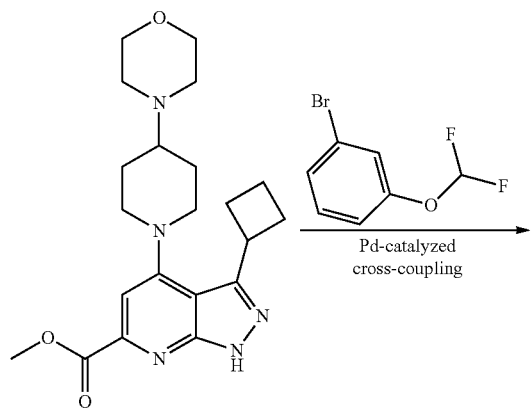

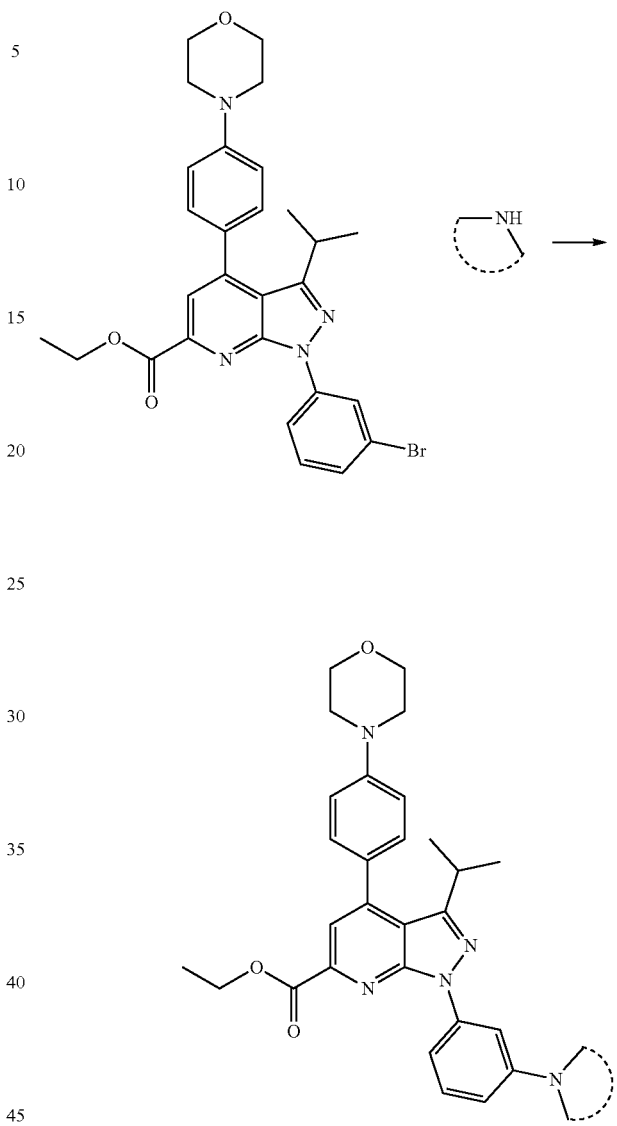

A nitrogen-purged mixture of tris(dibenzylideneacetone)dipalladium(0) (0.0193 g, 0.021 mmol), and di-tert-butyl(2',4',6'-triisopropyl-3,4,5,6-tetramethyl-[1,1'-biphenyl]-2-yl)phosphine (0.0251 g, 0.052 mmol) in toluene (2.2 mL) was stirred for 20 minutes and then added to an nitrogen-purged mixture of methyl 3-cyclobutyl-4-[4-(morpholin-4-yl)piperidin-1-yl]-1H-pyrazolo[3,4-b]pyridine-6-carboxylate (0.1760 g, 0.441 mmol, E509), 1-bromo-3-(difluoromethoxy)benzene (0.1179 g, 0.529 mmol), and Cs$_2$CO$_3$ (0.2143 g, 0.658 mmol). The mixture was heated to 70° C. overnight, diluted with water, extracted with DCM (3×8 mL), dried (Na$_2$SO$_4$), and concentrated. The residue was chromatographed on silica (30-60% EtOAc/DCM to 4% MeOH/DCM) and re-chromatographed (2.5-4% iPrOH/DCM) to give the titled compound. $^1$H NMR (400 MHz, DMSO-d$_6$) δ ppm 8.28-8.16 (m, 2H), 7.58 (t, J=8.2 Hz, 1H), 7.51-7.03 (m, 3H), 3.95 (dq, J=18.1, 9.8, 8.5 Hz, 1H), 3.88 (s, 3H), 3.63-3.48 (m, 6H), 2.91 (t, J=11.9 Hz, 2H), 2.53-2.48 (m, 4H), 2.46-2.28 (m, 2H), 2.12-1.88 (m, 4H), 1.63 (td, J=13.1, 12.6, 6.4 Hz, 2H).

A suspension of ethyl 1-(3-bromophenyl)-3-isopropyl-4-(4-morpholinophenyl)pyrazolo[3,4-b]pyridine-6-carboxylate E001 (1.0 equiv), XPhos Pd G1 (CAS 1028206-56-5, 0.1 equiv) and sodium tert-butoxide (CAS: 865-48-5, 1.3 equiv) in anhydrous toluene is degassed with argon (bubbling) at room temperature for 15 minutes. Amine (1.3 equiv) is added, and the mixture is purged with argon at RT for 2 minutes. The reaction mixture is stirred at 100° C. for 30 minutes to 24 h. The reaction mixture is concentrated in vacuo, and the residue is partitioned between water and dichloromethane and filtered on a pad of Celpure P65®. Solids were washed with dichloromethane and water, and the two phases of the filtrate are separated. The aqueous layer is extracted with dichloromethane. The combined organic phases are washed with brine, dried over MgSO$_4$, filtered and concentrated in vacuo. The titled compound is obtained from the crude mixture either by precipitation or by purification by flash chromatography on silica gel.

Illustrative Synthesis of E002: Ethyl 1-[3-(azetidin-1-yl)phenyl]-3-isopropyl-4-(4-morpholinophenyl)pyrazolo[3,4-b]pyridine-6-carboxylate

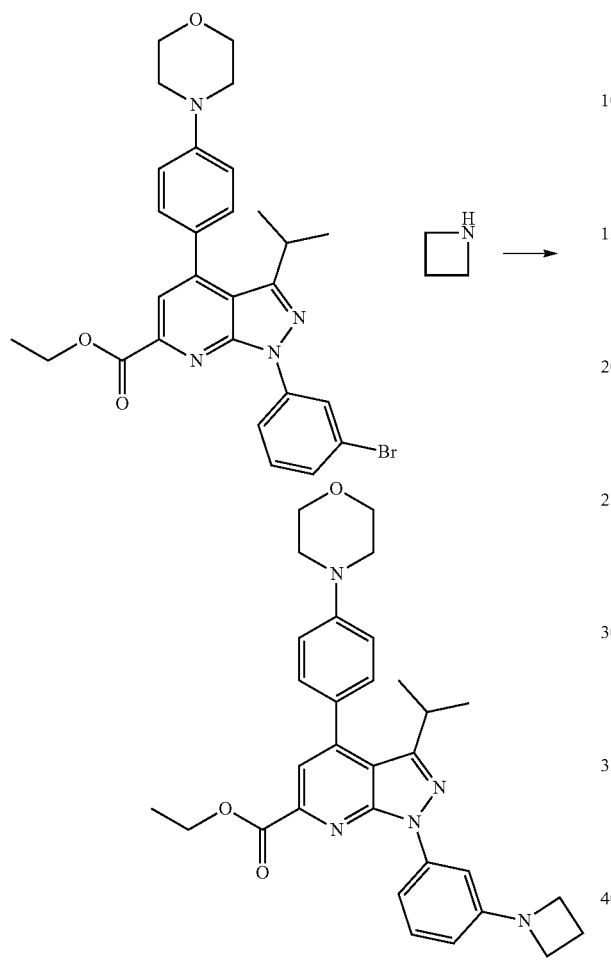

A suspension of ethyl 1-(3-bromophenyl)-3-isopropyl-4-(4-morpholinophenyl)pyrazolo[3,4-b]pyridine-6-carboxylate E001 (60 mg, 0.115 mmol, 1.0 equiv), XPhos Pd G1 (CAS 1028206-56-5, 9 mg, 0.011 mmol, 0.1 equiv), and sodium tert-butoxide (CAS: 865-48-5, 14 mg, 0.149 mmol, 1.3 equiv) in anhydrous toluene (1.2 mL) was degassed with argon (bubbling) at room temperature for 15 minutes. Azetidine (13 µL, 0.149 mmol, 1.3 equiv) was added, and the mixture was purged with argon at RT for 2 minutes. The reaction mixture was stirred at 100° C. for 1 hour. The reaction mixture was concentrated in vacuo; the residue was partitioned between water and dichloromethane, and then was filtered on a pad of Celpure P65®. Solids were washed with dichloromethane and water, and the two phases of the filtrate were separated. The aqueous layer was extracted with dichloromethane. The combined organic phases were washed with brine, dried over MgSO$_4$, filtered and concentrated in vacuo. The residue was purified by flash chromatography on silica gel (eluent system: dichloromethane/methanol gradient from 100/0 to 90/10). The obtained solid was suspended in ethanol, filtered, washed with diethyl ether and dried in vacuo to afford the titled compound.

Method I9: Esterification

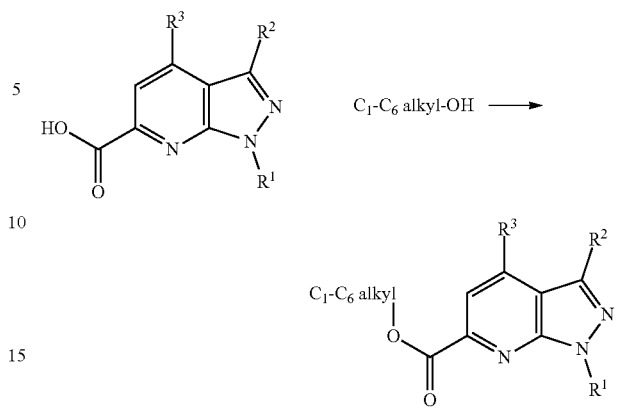

To the acid (1 equiv) in either ethanol or methanol at RT is added concentrated sulfuric acid (catalytic amount). The reaction mixture is refluxed for 1 h to several days (up to 8 days). Then the reaction mixture is cooled down to RT. The resulting suspension is filtered; the solid is washed with either ethanol or methanol and then dried in vacuo. The crude solid is purified by flash chromatography on silica gel (eluent system: heptane/ethyl acetate) to give the titled compound.

Alternatively, if no suspension is formed when cooling down the reaction mixture, the solvent is removed in vacuo. The resulting residue is taken up in dichloromethane and basified with a saturated solution of NaHCO$_3$. The two phases are separated, and the aqueous phase is extracted with dichloromethane. The combined organic phases are washed with brine, dried over MgSO$_4$, filtered and concentrated in vacuo to afford the titled compound which is used as such or further purified by flash chromatography on silica gel.

Illustrative Synthesis of E001 ethyl 1-(3-bromophenyl)-3-isopropyl-4-(4-morpholinophenyl)pyrazolo[3,4-b]pyridine-6-carboxylate

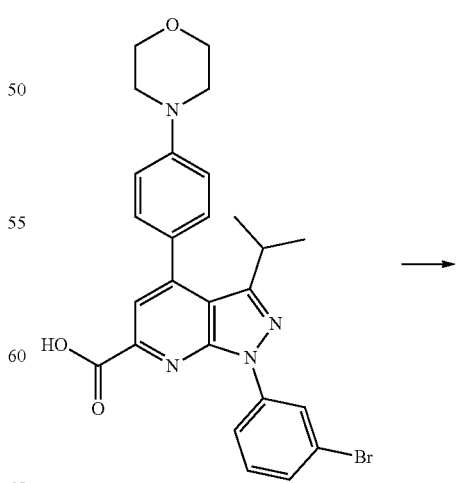

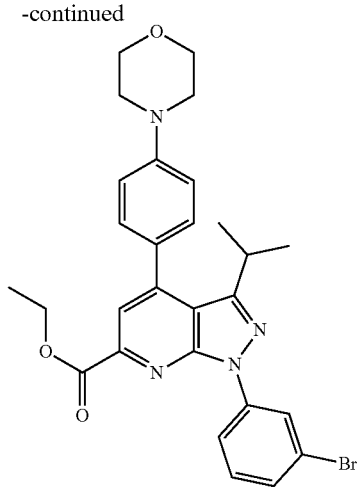

Concentrated sulfuric acid (0.23 mL) was added to a suspension of A242 (2.56 g, 4.9 mmol) in absolute ethanol (64 mL) at RT. The reaction mixture was refluxed for 5 hours. The reaction mixture was cooled down to RT, and the obtained suspension was filtered. The cake was washed with ethanol and dried in vacuo. The solid residue was purified by chromatography on silica gel (heptane/ethyl acetate 100/0 to 70/30) to give the titled compound.

Method I10: Buchwald Coupling on the Aryl Linker

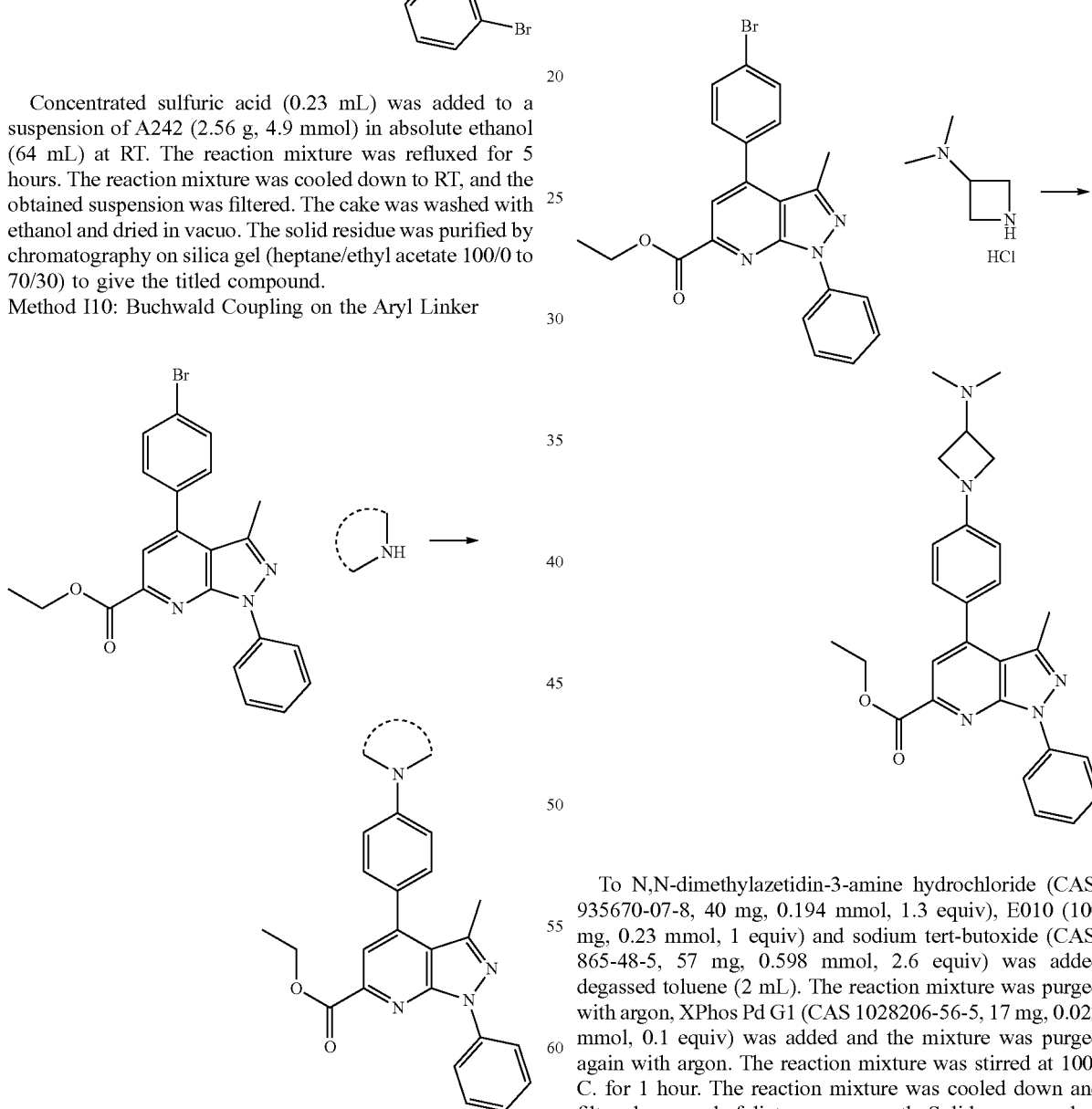

To the amine (from 1.3 to 2 equiv), E010 (1 equiv) and sodium tert-butoxide (CAS: 865-48-5, from 1.3 to 3 equiv) is added degassed anhydrous toluene. The reaction mixture is purged with argon, XPhos Pd G1 (CAS 1028206-56-5, 0.1 equiv) is added, and the mixture is purged again with argon. The reaction mixture is stirred at a temperature ranging from 90° C. to 110° C. for 1 h to 24 h. The reaction mixture is cooled down and filtered on a pad of diatomaceous earth. Solids are washed with organic solvents, and the combined filtrates are concentrated in vacuo. The resulting residue is purified by flash chromatography on silica gel to afford the titled compound.

Illustrative Synthesis of E011: Ethyl 4-[4-[3-(dimethylamino)azetidin-1-yl]phenyl]-3-methyl-1-phenyl-pyrazolo[3,4-b]pyridine-6-carboxylate To N,N-dimethylazetidin-3-amine hydrochloride (CAS: 935670-07-8, 40 mg, 0.194 mmol, 1.3 equiv), E010 (100 mg, 0.23 mmol, 1 equiv) and sodium tert-butoxide (CAS: 865-48-5, 57 mg, 0.598 mmol, 2.6 equiv) was added degassed toluene (2 mL). The reaction mixture was purged with argon, XPhos Pd G1 (CAS 1028206-56-5, 17 mg, 0.023 mmol, 0.1 equiv) was added and the mixture was purged again with argon. The reaction mixture was stirred at 100° C. for 1 hour. The reaction mixture was cooled down and filtered on a pad of diatomaceous earth. Solids were washed with toluene, ethyl acetate and dichloromethane, and the combined filtrates were concentrated in vacuo. The residue was purified by flash chromatography on silica gel (dichloromethane/methanol 98/2) to afford the titled compound.

207

Method I11: Acylation of Amine

Synthesis of E176: Methyl 4-[(1-acetyl-4-piperidyl)methoxy]-1-(4-fluorophenyl)-3-isopropyl-pyrazolo[3,4-b]pyridine-6-carboxylate

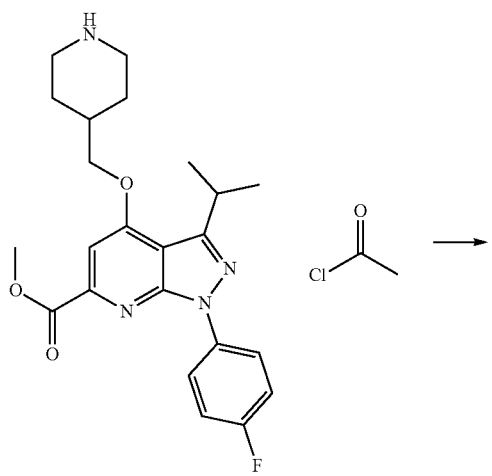

208

Synthesis of E178: Methyl 1-(4-fluorophenyl)-3-isopropyl-4-[(1-methoxycarbonyl-4-piperidyl)methoxy]pyrazolo[3,4-b]pyridine-6-carboxylate

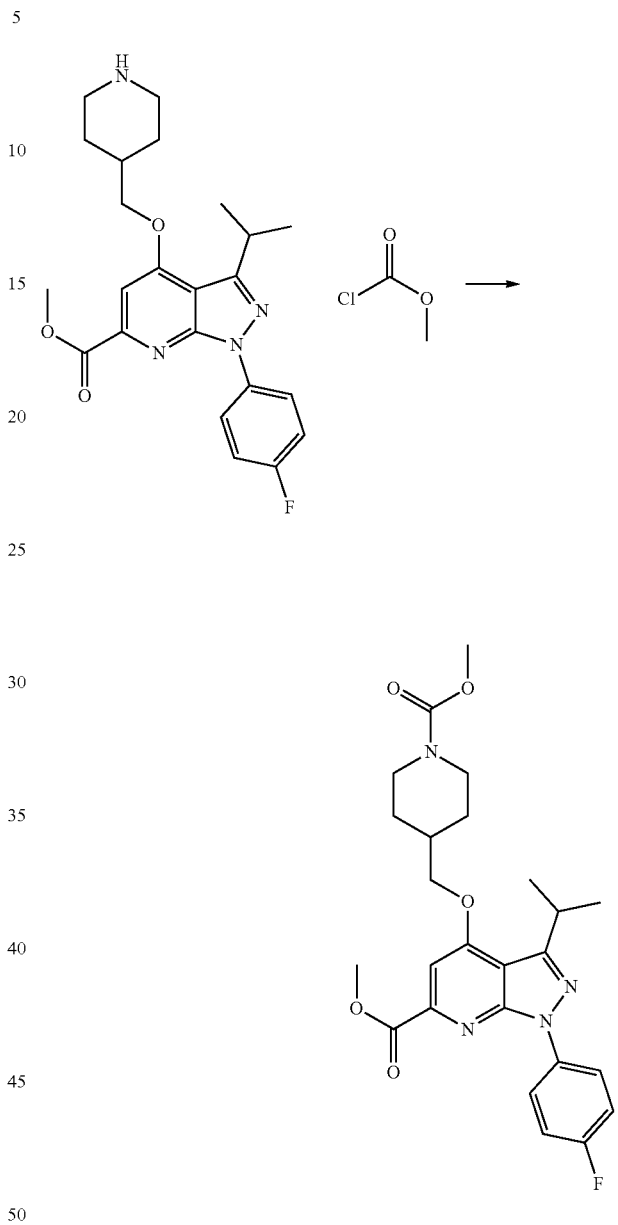

To E177 (0.1 g, 0.23 mmol, 1 equiv) in anhydrous dichloromethane (2 mL) at RT was added acetyl chloride (CAS 75-36-5, 19 µL, 0.28 mmol, 1.2 equiv) followed by triethylamine (47 µL, 0.345 mmol, 1.5 equiv). The reaction mixture was stirred at RT for 2 h. The reaction mixture was diluted with dichloromethane and water. The two phases were separated, and the aqueous phase was extracted with dichloromethane. The combined organic phases were washed with brine, dried over $MgSO_4$, filtered and concentrated in vacuo. The resulting residue was purified by flash chromatography on silica gel (eluent system: heptane/ethyl acetate gradient from 100/0 to 0/100) to afford the titled compound.

To E177 (0.1 g, 0.23 mmol, 1 equiv) in anhydrous dichloromethane (2 mL) at RT was added methyl chloroformate (CAS: 79-22-1, 19 µL, 0.28 mmol, 1.2 equiv) followed by triethylamine (47 µL, 0.345 mmol, 1.5 equiv). The reaction mixture was stirred at RT for 2 h. The reaction mixture was diluted with dichloromethane and water. The two phases were separated, and the aqueous phase was extracted with dichloromethane. The combined organic phases were washed with brine, dried over $MgSO_4$, filtered and concentrated in vacuo. The resulting residue was purified by flash chromatography on silica gel (eluent system: heptane/ethyl acetate gradient from 100/0 to 50/50) to afford the titled compound.

209

Synthesis of E042: Ethyl 4-(4-acetamidophenyl)-1-(3,5-difluorophenyl)-3-(1-methoxycarbonylazetidin-3-yl)pyrazolo[3,4-b]pyridine-6-carboxylate

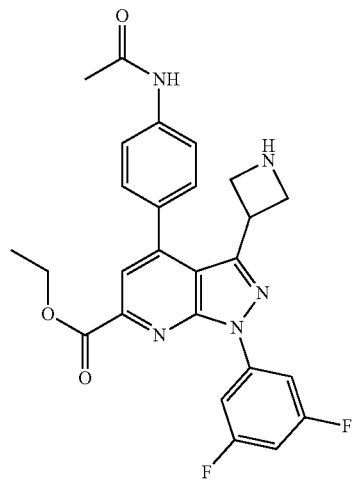 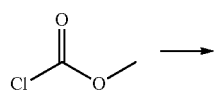 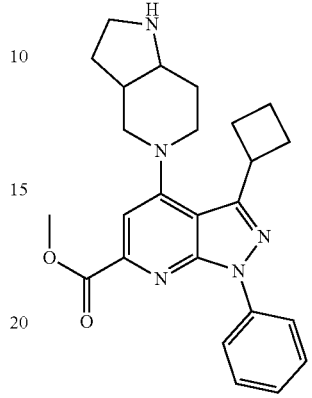

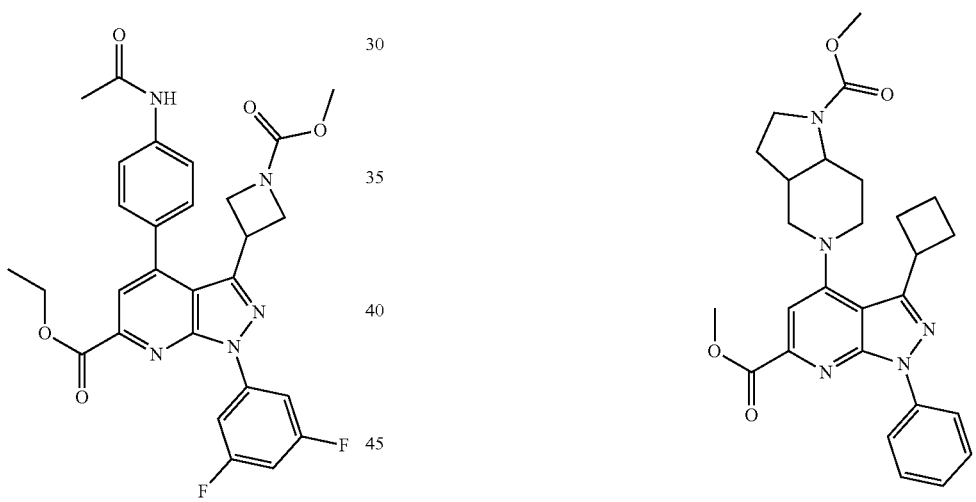

210

Synthesis of E129: Methyl 3-cyclobutyl-4-(1-methoxycarbonyl-3,3a,4,6,7,7a-hexahydro-2H-pyrrolo[3,2-c]pyridin-5-yl)-1-phenyl-pyrazolo[3,4-b]pyridine-6-carboxylate Diisopropylethylamine (0.045 mL, 0.26 mmol, 2.0 equiv) and 4-(dimethylamino)pyridine (CAS 1122-58-3, 3 mg, 0.026, 0.2 equiv) were added to a solution of E043 (65 mg, 0.13 mmol, 1 equiv) in dichloromethane (1 mL) at RT. The reaction mixture was cooled to 0° C. and methyl chloroformate (CAS: 79-22-1, 0.010 mL, 0.13 mmol, 1.0 equiv) was added. The reaction mixture was stirred at RT for 45 min then partitioned between dichloromethane and water. The organic phase was separated, washed with water, dried over MgSO₄, filtered and concentrated. The residue was purified by silica gel chromatography (DCM/MeOH: 100/0 to 93/7) to give the titled compound.

To E130 (31 mg, 0.073 mmol, 1 equiv) in anhydrous dichloromethane (0.5 mL) at 0° C. was added triethylamine (31 μL, 0.219 mmol, 3 equiv) followed by methyl chloroformate (CAS: 79-22-1, 7 μL, 0.088 mmol, 1.2 equiv). The reaction mixture was stirred at RT for 1.5 h. The reaction mixture was diluted with dichloromethane and water. The two phases were separated, and the aqueous phase was extracted with dichloromethane. The combined organic phases were washed with brine, dried over MgSO₄, filtered and concentrated in vacuo. The resulting residue was purified by flash chromatography on silica gel (eluent system: dichloromethane/methanol, gradient from 100/0 to 98/2) to afford the titled compound.

211

Synthesis of E132: Methyl 4-(1-acetyl-3,3a,4,6,7,7a-hexahydro-2H-pyrrolo[3,2-c]pyridin-5-yl)-3-cyclobutyl-1-phenyl-pyrazolo[3,4-b]pyridine-6-carboxylate

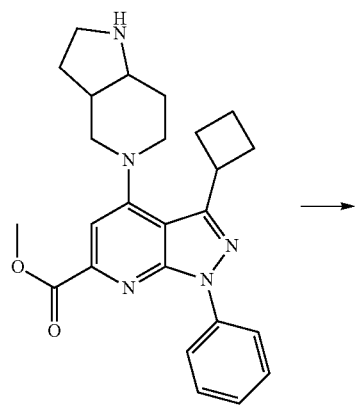

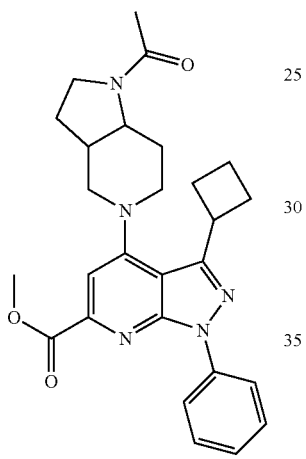

To E130 (31 mg, 0.073 mmol, 1 equiv) in anhydrous dichloromethane (2 mL) at 0° C. was added (31 µL, 0.219 mmol, 3 equiv) followed by acetyl chloride (CAS 75-36-5, 5 µL, 0.088 mmol, 1.2 equiv). The reaction mixture was stirred at RT for 1.5 h. The reaction mixture was diluted with dichloromethane and water. The two phases were separated, and the aqueous phase was extracted with dichloromethane. The combined organic phases were washed with brine, dried over MgSO₄, filtered and concentrated in vacuo. The resulting residue was purified by flash chromatography on silica gel (eluent system: dichloromethane/methanol, gradient from 100/0 to 96/4) to afford the titled compound.

Method I12: Nucleophilic Substitution

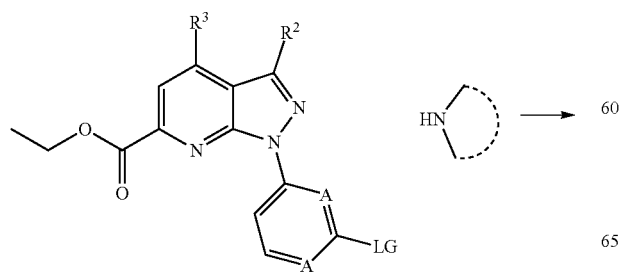

212

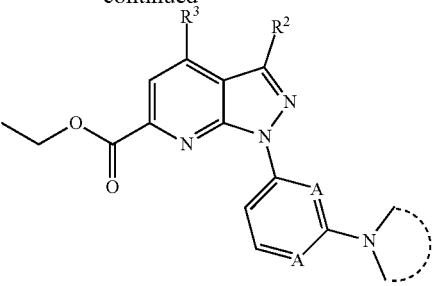

LG = F, Cl
A = CH, N

To a solution of the intermediate ester (1.0 equiv) in anhydrous DMSO, are added the amine (from 2.0 to 3.0 equiv) and $K_2CO_3$ (3.0 equiv). The reaction mixture is stirred at 100° C. overnight. The reaction mixture is cooled down to RT, poured into water and extracted with ethyl acetate. The combined organic layers are washed with brine, dried over MgSO₄, filtered and concentrated in vacuo. The resulting residue is purified by silica gel chromatography to afford the titled compound.

Illustrative Synthesis of E110: Ethyl 3-isopropyl-4-(4-methoxy-1-piperidyl)-1-(2-pyrrolidin-1-yl-4-pyridyl)pyrazolo[3,4-b]pyridine-6-carboxylate

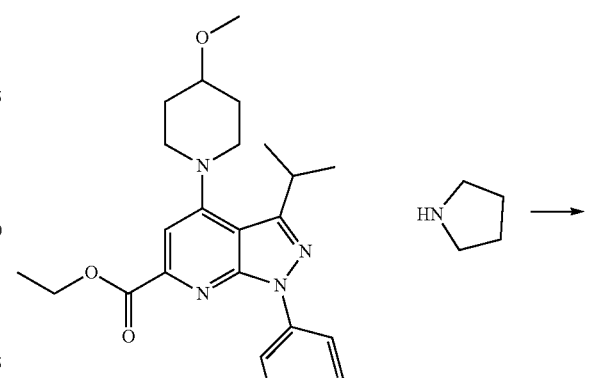

To a solution of ethyl 1-(2-fluoro-4-pyridyl)-3-isopropyl-4-(4-methoxy-1-piperidyl)pyrazolo[3,4-b]pyridine-6-carboxylate E111 (50 mg, 0.11 mmol, 1.0 equiv) in anhydrous DMSO (1 mL), were added pyrrolidine (18 µL, 0.22 mmol, 2.0 equiv) and K₂CO₃ (46 mg, 0.33 mmol, 3.0 equiv). The reaction mixture was stirred at 100° C. overnight. The reaction mixture was cooled down to RT, poured into water and extracted with ethyl acetate. The combined organic layers were washed with brine, dried over MgSO₄, filtered and concentrated in vacuo. The crude residue was purified by silica gel chromatography (heptane/ethyl acetate: 100/0 to 40/60) to afford the titled compound.

Method I13: O-Alkylation of the Pyrazole titled compound which is used as such or purified by flash chromatography on silica gel.

Illustrative Synthesis of E152: Ethyl 3-[(1-tert-butoxycarbonyl-4-piperidyl)oxy]-4-[6-(4-cyano-1-piperidyl)-3-pyridyl]-1-phenyl-pyrazolo[3,4-b]pyridine-6-carboxylate

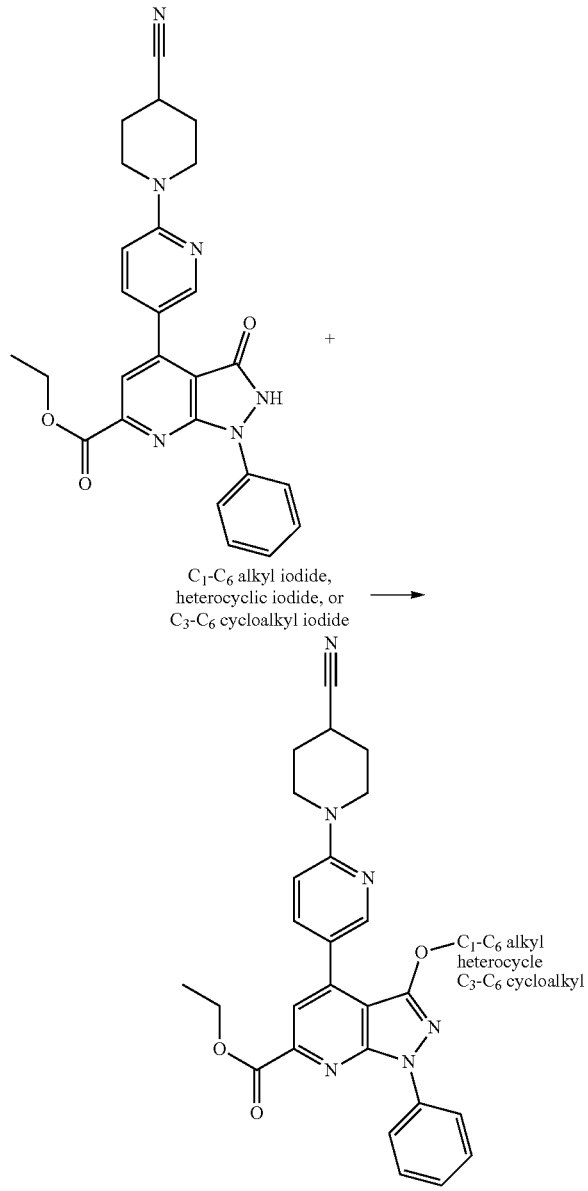

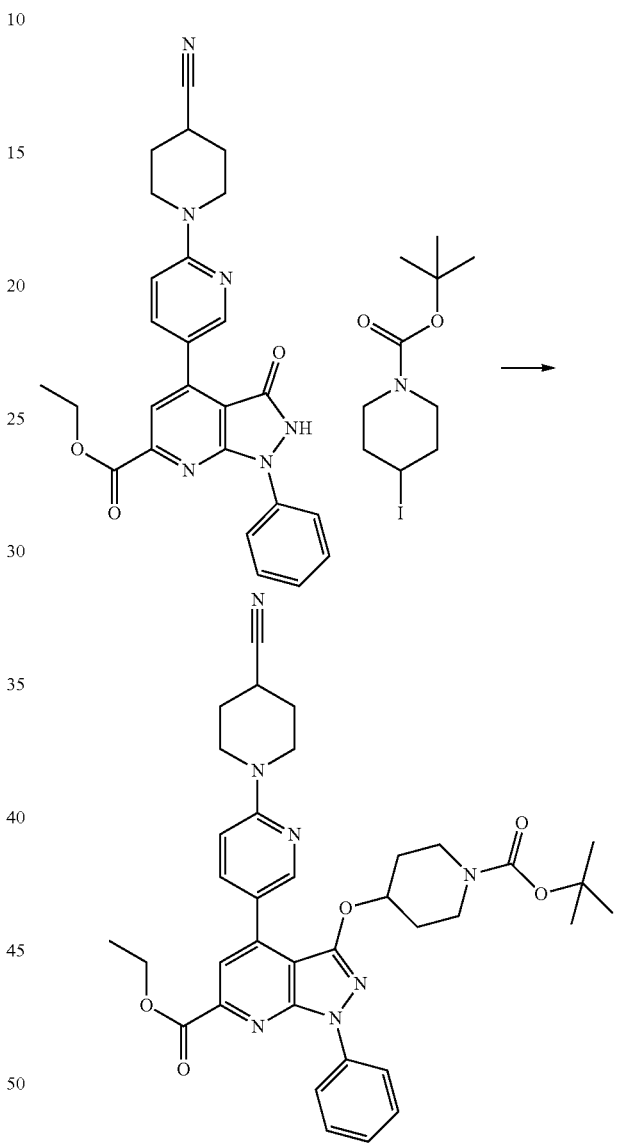

Intermediate E153 (1.0 equiv), the alkyl iodide (from 3 to 5.7 equiv) and cesium carbonate (from 3 to 5.7 equiv) are charged in a sealed vial. NMP is added, and the vial is sealed. The reaction mixture is stirred at 130° C. for 1 hour. The reaction mixture is cooled down to RT and partitioned between water and ethyl acetate. The phases are separated, and the aqueous phase is extracted with ethyl acetate. The combined organic phases are washed with brine, dried over MgSO₄, filtered and concentrated in vacuo to afford the Intermediate E153 (110 mg, 0.23 mmol), N-Boc-4-iodopiperidine (CAS: 301673-14-3, 410 mg, 1.32 mmol, 5.7 equiv) and cesium carbonate (430 mg, 1.32 mmol, 5.7 equiv) were charged in a sealed vial. NMP (2.9 mL) was added, and the vial was sealed. The reaction mixture was stirred at 130° C. for 1 hour. The reaction mixture was cooled down to RT and partitioned between water and ethyl acetate. The phases were separated, and the aqueous phase was extracted with ethyl acetate. The combined organic phases were washed with brine, dried over MgSO₄, filtered and concentrated in vacuo. The residue was purified by silica gel chromatography (heptane/ethyl acetate: gradient from 100/0 to 2:1) to give the titled compound.

Method I14: Mitsunobu Reaction

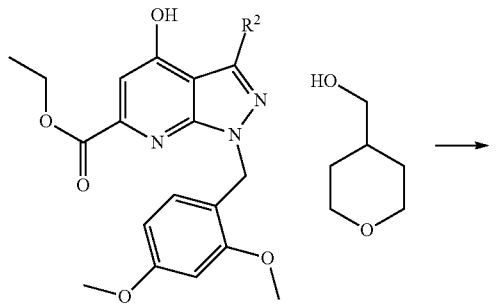

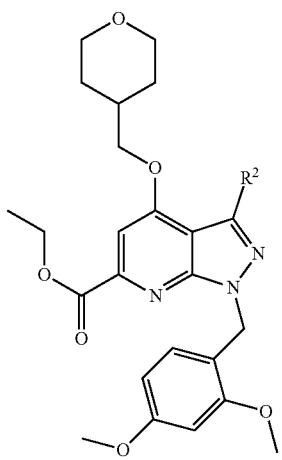

Diisopropyl azodicarboxylate (CAS: 2446-83-5, 0.606 mL, 3.075 mmol, 1.5 equiv) is added dropwise to a stirred solution of the intermediate phenol HP (1 equiv), tetrahydropyran-4-methanol (CAS: 14774-37-9, from 1.5 to 2.0 equiv) and triphenylphosphine (CAS: 603-35-0, 1.5 equiv) in tetrahydrofuran under nitrogen atmosphere. The reaction mixture is stirred at RT for 1 to 3 h. The solvent is removed under reduced pressure, and the resulting crude sample is purified by flash column chromatography on silica gel (eluent system: heptane/ethyl acetate) to yield the titled compound.

Illustrative Synthesis of E183 ethyl 1-[(2,4-dimethoxyphenyl)methyl]-3-isopropyl-4-(tetrahydropyran-4-ylmethoxy)pyrazolo[3,4-b]pyridine-6-carboxylate

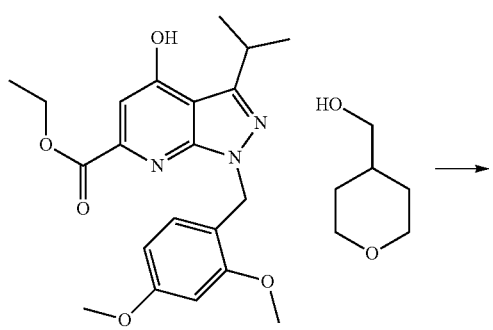

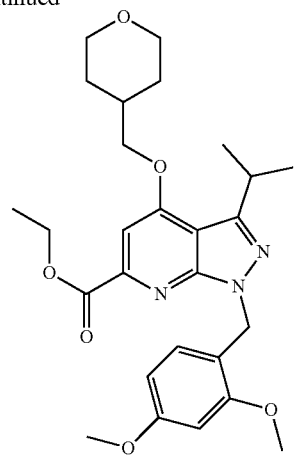

Diisopropyl azodicarboxylate (CAS: 2446-83-5, 0.606 mL, 3.075 mmol, 1.5 equiv) was added dropwise to a stirred solution of HP06 (820 mg, 2.05 mmol), tetrahydropyran-4-methanol (CAS: 14774-37-9, 477 mg, 4.1 mmol, 2.0 equiv) and triphenylphosphine (CAS: 603-35-0, 806 mg, 3.075 mmol, 1.5 equiv) in tetrahydrofuran (20 mL) under nitrogen atmosphere. The reaction mixture was stirred at RT for 1 hour. The volatiles were removed under reduced pressure, and the crude sample was purified by flash column chromatography on silica gel eluting with n-heptane/ethyl acetate from 90/10 to 1/1 to yield the titled compound.

Method I15: Dimethoxybenzyl Group Removal

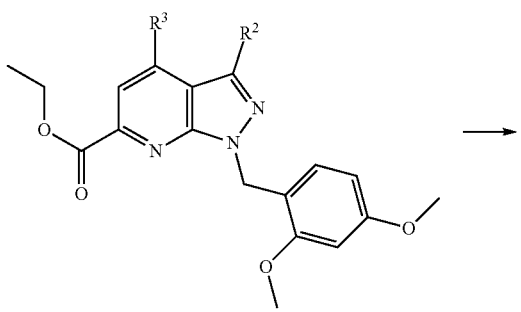

Trifluoroacetic acid or a mixture of dichloromethane and trifluoroacetic acid is added to the (2,4-dimethoxyphenyl)methyl]pyrazolo[3,4-b]pyridine compound. The reaction mixture is stirred at RT for several hours. Then the titled compound is isolated by precipitation in diethyl ether directly from the reaction mixture or after removal of volatiles and is used as such or is taken up in dichloromethane and basified with a saturated solution of sodium hydrogencarbonate. The phases are separated and the aqueous phase is extracted with dichloromethane. The combined organic phases are washed with brine, dried over MgSO$_4$, filtered and concentrated in vacuo to afford the titled compound which is used as such or further purified by silica gel chromatography.

Alternatively the reaction mixture is concentrated in vacuo. The residue is taken up in dichloromethane and basified with a saturated solution of sodium hydrogencarbonate. The phases are separated and the aqueous phase is extracted with dichloromethane. The combined organic phases are washed with brine, dried over MgSO$_4$, filtered and concentrated in vacuo which was used as such or purified by precipitation or by flash chromatography on silica gel.

Illustrative Synthesis of compound E055: Ethyl 3-isopropyl-4-(4-morpholinophenyl)-1H-pyrazolo[3,4-b]pyridine-6-carboxylate

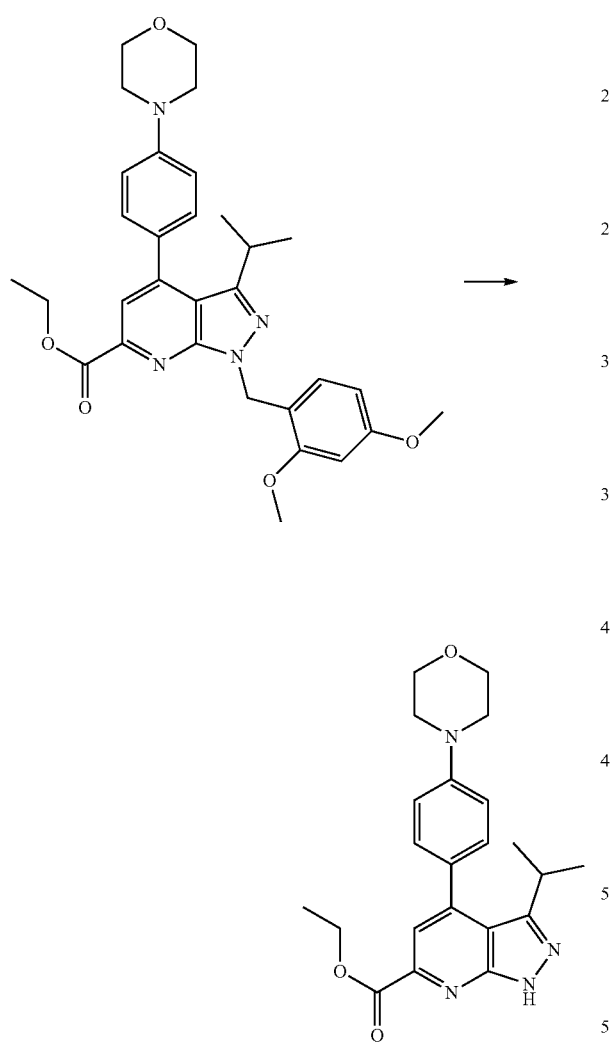

Trifluoroacetic acid (4.24 mL, 55.4 mmol, 71 equiv) was added to compound E056 (424 mg, 0.78 mmol). The reaction mixture was stirred at RT for 3 hours. Diethyl ether (20 mL) was added to the reaction mixture which was vigorously stirred for 5 minutes. The resulting suspension was filtered, and the cake was washed with diethyl ether. The solid was partitioned between dichloromethane and a saturated solution of sodium hydrogencarbonate and vigorously stirred. The suspension was filtered, and the solids were washed with dichloromethane. The two phases of the filtrate were separated, and the aqueous phase was extracted with dichloromethane. The combined organic phases were dried over MgSO$_4$, filtered and concentrated in vacuo to yield the titled compound which was used without further purification.

Method I16: Ullmann Coupling

Synthesis of E171: Ethyl 3-cyclobutyl-1-(4-fluorophenyl)-4-(tetrahydropyran-4-ylmethoxy)pyrazolo[3,4-b]pyridine-6-carboxylate

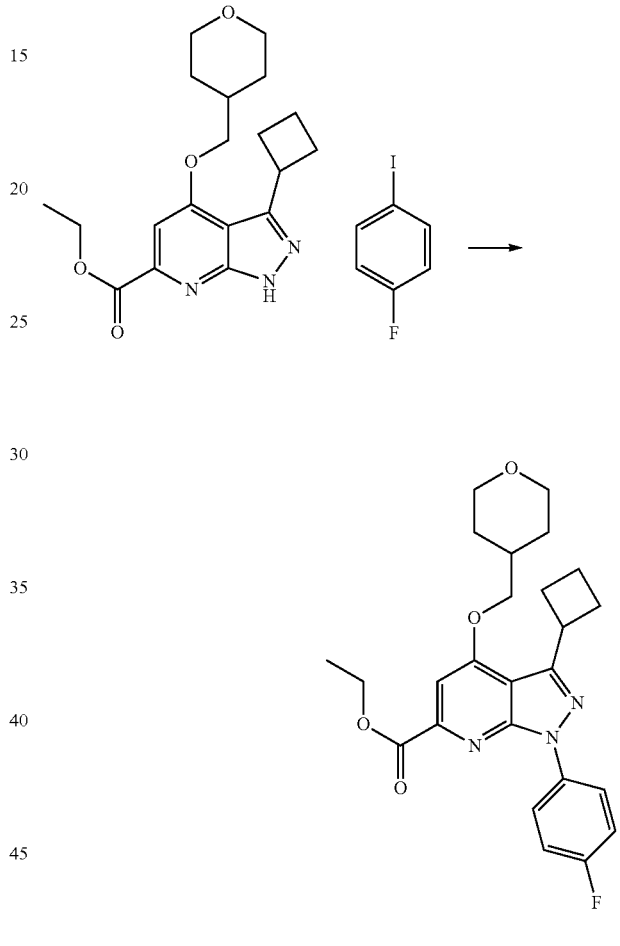

A degassed solution of trans-N,N'-dimethyl-1,2-cyclohexane (CAS: 67579-81-1, 0.002 mL, 0.01 mmol, 0.15 equiv) and 1-fluoro-4-iodobenzene (CAS: 352-34-1, 0.007 mL, 0.06 mmol, 0.7 equiv) in toluene (2 mL) was added to a mixture of E172 (30 mg, 0.08 mmol), K$_3$PO$_4$ (35 mg, 0.167 mmol, 2.0 equiv) and CuI (1 mg, 0.005 mmol, 0.07 equiv). The vial was sealed and the reaction mixture was stirred at 110° C. for 16 hours. The reaction mixture was cooled down to RT and partitioned between water and ethyl acetate. The organic phase was separated, dried over MgSO$_4$, filtered and concentrated in vacuo. The residue was purified by silica gel chromatography (dichloromethane/heptane/ethyl acetate: 100/0/0 to 0/70/30) to give the titled compound.

Method I17: O-Alkylation of Pyrazole

Synthesis of Compound E090: Isopropyl 3-isopropoxy-4-(4-morpholinophenyl)-1-phenyl-pyrazolo[3,4-b]pyridine-6-carboxylate

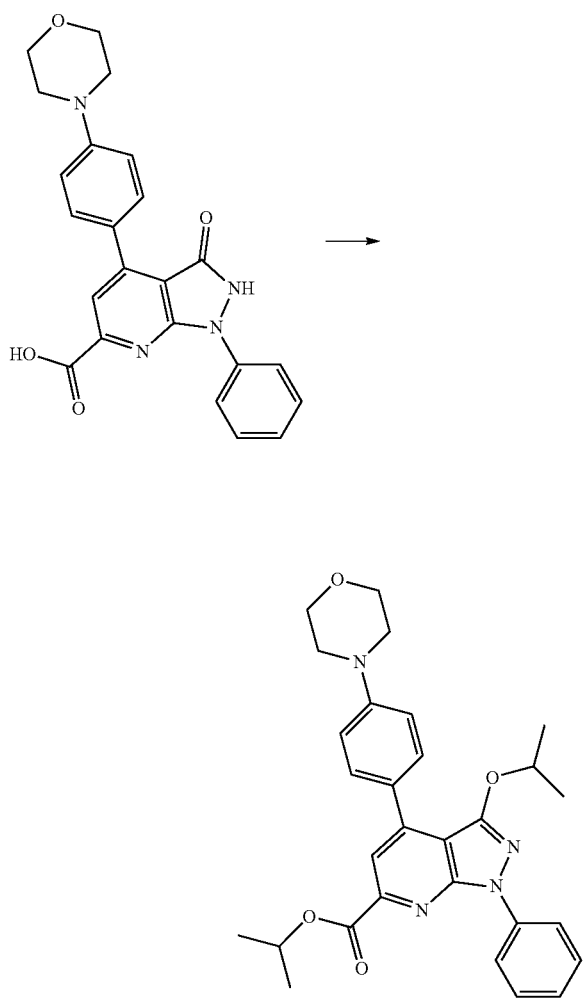

To a solution of A256 (330 mg, 0.79 mmol) and 2-iodopropane (CAS 75-30-9, 0.19 mL, 1.90 mmol, 2.4 equiv) in anhydrous NMP (4 mL) was added cesium carbonate (775 mg, 2.38 mmol, 3.0 equiv), and the reaction mixture was stirred at 130° C. for 16 hours. The reaction mixture was cooled down to RT and partitioned between dichloromethane and a saturated solution of sodium hydrogencarbonate. The organic phase was separated, washed with brine, dried over MgSO₄, filtered and concentrated in vacuo. The residue was purified by silica gel chromatography (petroleum ether/ethyl acetate: 80/20 to 70/30) to give the titled compound.

Synthesis of Intermediate E504: Methyl 4-(4-bromophenyl)-1-cyclohexyl-3-[(propan-2-yl)oxy]-1H-pyrazolo[3,4-b]pyridine-6-carboxylate

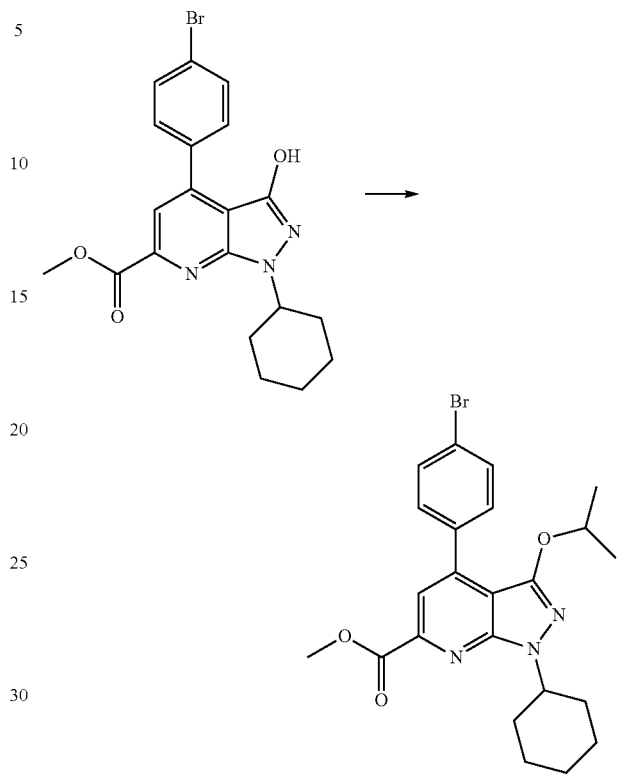

To a solution containing methyl 4-(4-bromophenyl)-1-cyclohexyl-3-hydroxy-1H-pyrazolo[3,4-b]pyridine-6-carboxylate (30.5 mmol, E503) was added isopropyl bromide ([75-26-3], 5.73 mL, 61.1 mmol) and cesium carbonate (2.70 g, 8.28 mmol), and the resulting mixture stirred under N₂ at 60° C. for 1 hour. The mixture was diluted with water and extracted with ethyl acetate. The organic phase was washed with brine (2×) and concentrated. The obtained residue was purified by column chromatography using a petroleum ether/EtOAc gradient (95/5 till 90/10) to afford the titled compound.

Synthesis of Intermediate E505: Methyl 4-(4-bromophenyl)-3-(cyclobutyloxy)-1-cyclohexyl-1H-pyrazolo[3,4-b]pyridine-6-carboxylate

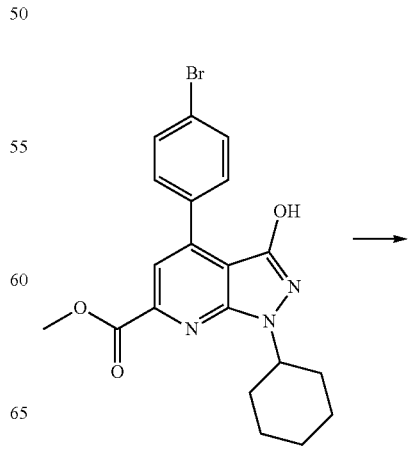

221

-continued

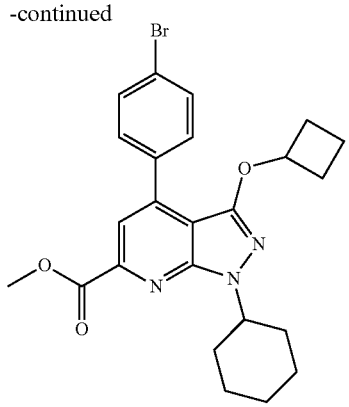

To a solution containing methyl 4-(4-bromophenyl)-1-cyclohexyl-3-hydroxy-1H-pyrazolo[3,4-b]pyridine-6-carboxylate (5.52 mmol, E503) was added cyclobutyl bromide ([4399-47-7], 1.04 mL, 11.0 mmol) and cesium carbonate (5.40 g, 11.0 mmol), and the resulting mixture stirred under $N_2$ at 60° C. for 1 hour. The mixture was diluted with water and extracted with ethyl acetate. The organic phase was washed with brine (2×) and concentrated. The obtained residue was purified by column chromatography using a petroleum ether/EtOAc gradient (95/5 till 90/10) to afford the titled compound.

Method I18: General Method for Reductive Amination

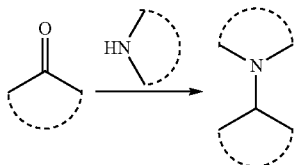

A suspension of ketone (1 eq), amine (1.5 to 3 eq) and triethylamine (1 to 2 eq) in dichloromethane is stirred at RT for 5 minutes. Acetic acid (1 to 2 eq) is added, and the stirring at RT is continued for 30 minutes. Sodium triacetoxyborohydride (1 to 3 eq) is then added, and the stirring is continued for 20 hours. The reaction mixture is diluted with dichloromethane and washed with a saturated aqueous solution of $NaHCO_3$. The organic phase is separated, dried over sodium sulfate and concentrated under reduced pressure. The crude sample is used as such or purified by flash column chromatography.

222

Illustrative Synthesis of E354: Methyl 3-cyclobutyl-1-(4-fluorophenyl)-4-{4-[2-(methoxymethyl)morpholin-4-yl]piperidin-1-yl}-1H-pyrazolo[3,4-b]pyridine-6-carboxylate

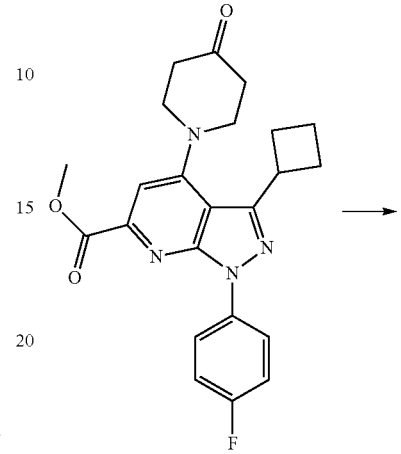

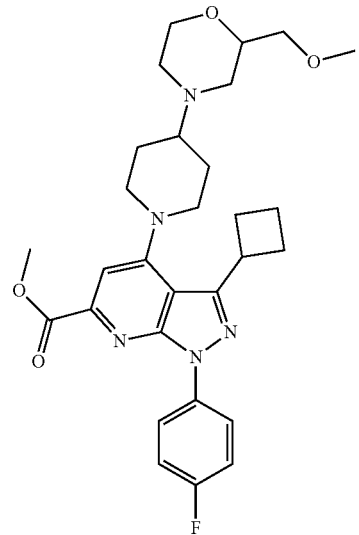

A suspension of E353 (0.1 g, 0.24 mmol), 2-(methoxymethyl)morpholine ([156121-15-2], 63 mg, 0.47 mmol) and triethylamine (33 μL, 0.24 mmol) in dichloromethane (2 mL) was stirred at RT for 5 minutes. Acetic acid (21 μL, 0.35 mmol) was added, and the stirring at RT was continued for 30 minutes. Sodium triacetoxyborohydride (76 mg, 0.35 mmol) was then added, and the stirring was continued for 20 hours. The reaction mixture was diluted with dichloromethane (3 mL) and washed with a saturated aqueous solution of $NaHCO_3$ (2 mL). The organic phase was separated using a phase separator and concentrated in vacuo to give the titled compound.

Method I19: General Method for the Reductive Removal of Benzyloxycarbonyl

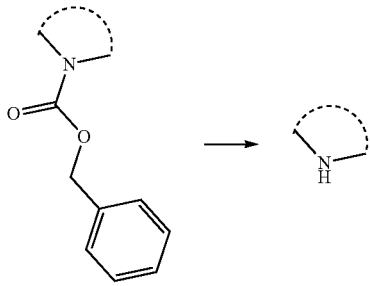

A solution of the benzyloxycarbonyl-protected amine (1 eq) in methanol is flushed with $N_2$. Next, 10% Pd/C (0.1 eq) is added and the mixture is put under hydrogen pressure with a balloon. After stirring overnight at ambient temperature, the mixture is filtered through diatomaceous earth, and the filtrate is concentrated. The residue is used as such or purified by flash column chromatography.

Method I23: General Method for Oxidation

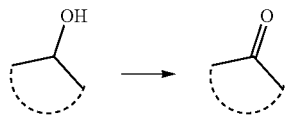

Dess Martin's periodinane (1 to 2 eq) is added at RT to a stirred solution of alcohol (1 eq) in dichloromethane. After 0.5 to 2 hours, the reaction mixture is diluted with dichloromethane. A solution of 20% $Na_2S_2O_3$ in water and a saturated aqueous solution of $NaHCO_3$ (1:1) is added and the stirring is continued for 30 minutes. The organic phase is separated, dried over sodium sulfate, filtered and concentrated under reduced pressure to give the titled compound. The compound can be used as such or purified by flash column chromatography.

Synthesis of Compound E353: Methyl 3-cyclobutyl-1-(4-fluorophenyl)-4-(4-oxopiperidin-1-yl)-1H-pyrazolo[3,4-b]pyridine-6-carboxylate

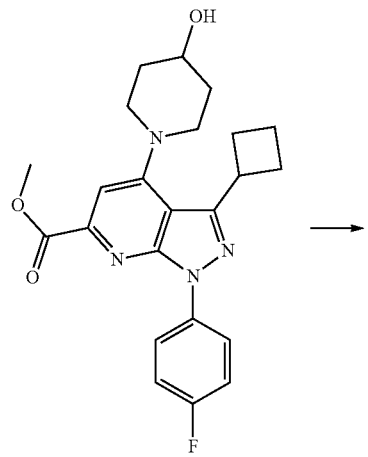

-continued

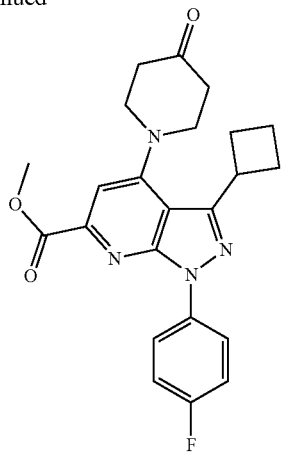

Dess-Martin periodinane (4 g, 9.4 mmol) was added at RT to a stirred solution of E352 (3.6 g, 8.6 mmol) in dichloromethane (40 mL). After 30 minutes, the reaction mixture was diluted with dichloromethane (50 mL). A solution of 20% aqueous $Na_2S_2O_3$ 20% and a saturated aqueous solution of $NaHCO_3$ (1:1, 50 mL) were added, and the stirring was continued for 30 minutes. The organic phase was separated, dried over sodium sulfate, filtered and concentrated under reduced pressure to give the titled compound.

Method I24: Coupling of Amines

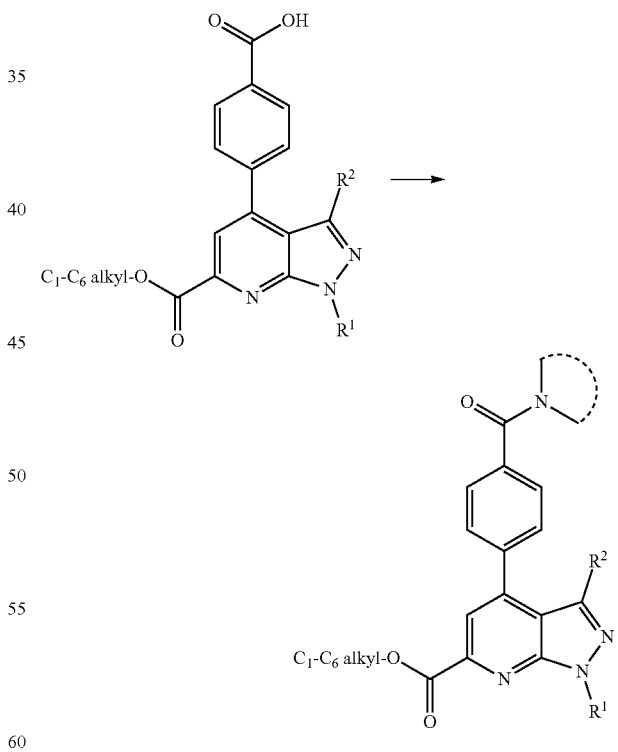

EDC.HCl ([25952-538], 1.2 equiv) is added at RT to a stirring solution of carboxylic acid (1 equiv), amine (4 equiv) and 4-(dimethylamino) pyridine ([1122-58-3], 2 equiv) in dichloromethane. The reaction mixture is stirred at RT for 20 hours. The solvent is evaporated under reduced pressure. The residue is purified flash column chromatography eluting with ethyl acetate/n-heptane and/or DCM/MeOH to yield the desired compound.

Illustrative Synthesis of E439: Ethyl 4-{4-[5-(tert-butoxycarbonyl)hexahydropyrrolo[3,4-c]pyrrole-2(1H)-carbonyl]phenyl}-1-cyclohexyl-3-[(propan-2-yl)oxy]-1H-pyrazolo[3,4-b]pyridine-6-carboxylate

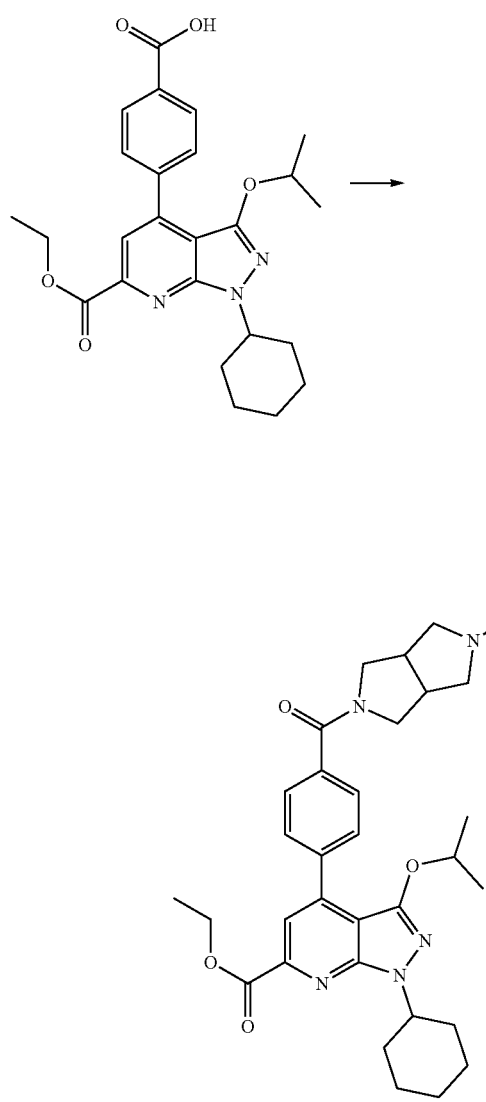

EDC.HCl ([25952-538], 18 mg, 74 µmol) was added at RT to a stirred solution of E438 (30 mg, 62 µmol), tert-butyl hexahydropyrrolo[3,4-c]pyrrole-2(1H)-carboxylate ([141449-85-6], 52 mg, 248 µmol) and 4-(dimethylamino)pyridine ([1122-58-3], 17 mg, 124 µmol) in dichloromethane (5 mL). The reaction mixture was stirred at RT for 20 hours. The mixture was concentrated under reduced pressure. The residue was purified by flash column chromatography eluting with ethyl acetate/n-heptane to yield the titled compound.

Illustrative Synthesis of E441: Ethyl 1-cyclohexyl-4-{4-[3-(dimethylamino)azetidine-1-carbonyl]phenyl}-3-[(propan-2-yl)oxy]-1H-pyrazolo[3,4-b]pyridine-6-carboxylate

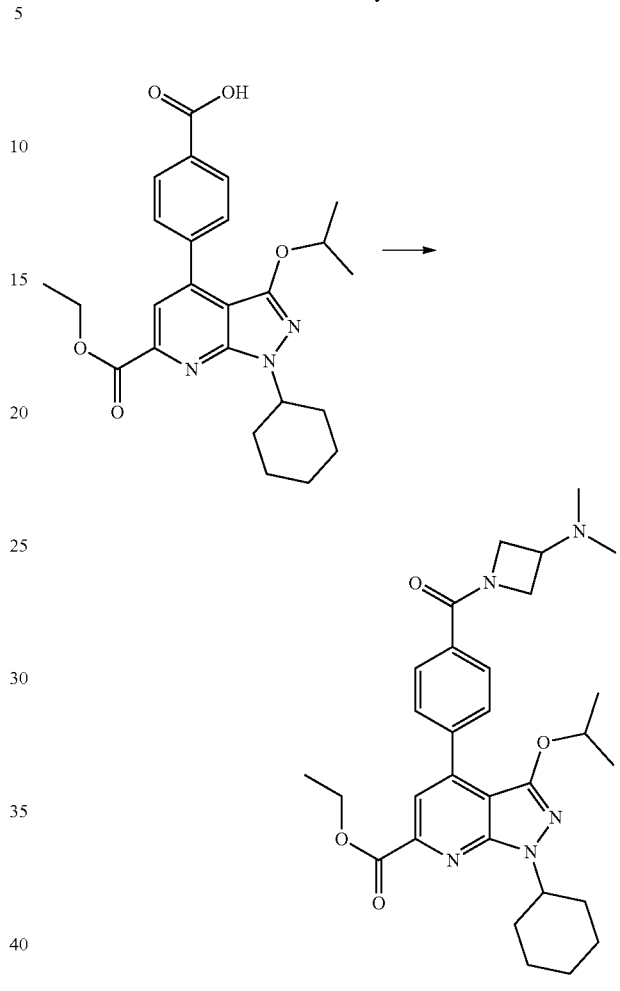

EDC.HCl ([25952-538], 24 mg, 125 µmol) was added at RT to a stirred solution of E438 (40 mg, 89 µmol), N,N-dimethylazetidin-3-amine hydrochloride ([935670-07-8], 49 mg, 358 µmol), triethylamine (50 µL, 358 µmol) and 4-(dimethylamino)pyridine ([1122-58-3], 24 mg, 196 µmol) in dichloromethane (15 mL). The reaction mixture was stirred at RT for 20 hours. The mixture was concentrated under reduced pressure. The residue was purified by flash column chromatography eluting with ethyl acetate/DCM/MeOH (100/0/0 to 0/90/10) to yield the titled compound.

Method I25: Tert-Butoxycarbonyl (Boc) Deprotection

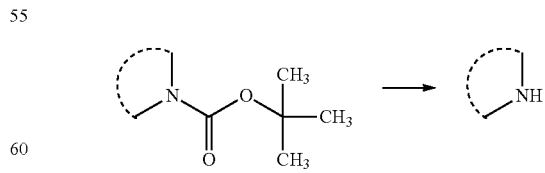

To a solution of the Boc-protected amine (1 eq) in dichloromethane at 0° C., TFA (76-05-1, 5-20 eq) is added. The resulting mixture is stirred at room temperature until deprotection is complete. The mixture can be worked up by diluting the reaction mixture with DCM followed by washing with a saturated aqueous NaHCO₃ solution. The organic fraction is dried over sodium sulfate, filtered, and concentrated under reduced pressure to give the titled compound. Alternatively, the reaction mixture can be concentrated under reduced pressure, and the crude titled compound can be used as such without further purification.

Illustrative Synthesis of Compound E043: Ethyl 4-(4-acetamidophenyl)-3-(azetidin-3-yl)-1-(3,5-difluorophenyl)pyrazolo[3,4-b]pyridine-6-carboxylate Illustrative Synthesis of Compound E130: Methyl 4-(1,2,3,3a,4,6,7,7a-octahydropyrrolo[3,2-c]pyridin-5-yl)-3-cyclobutyl-1-phenyl-pyrazolo[3,4-b]pyridine-6-carboxylate

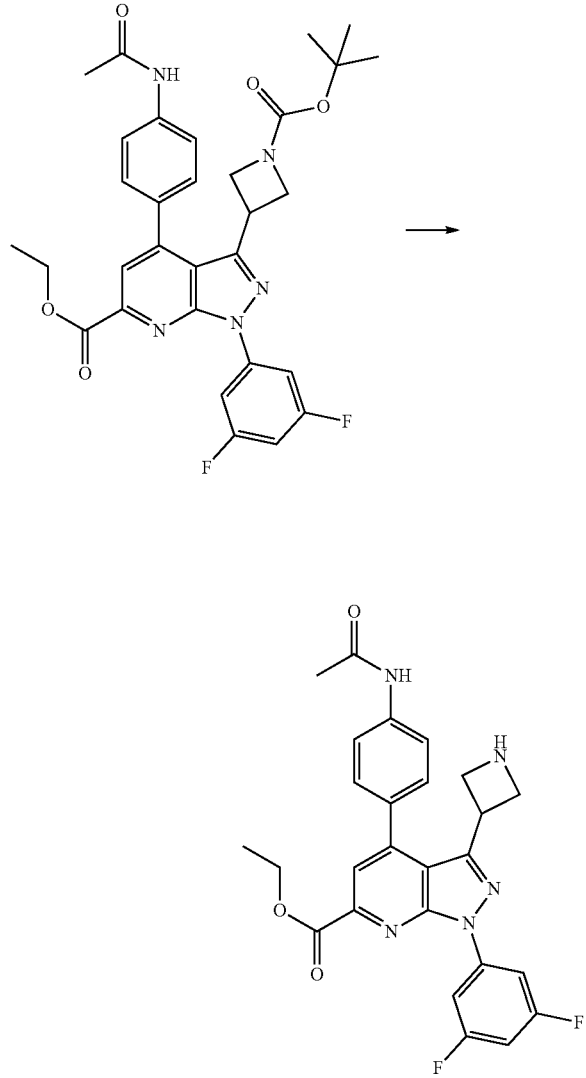

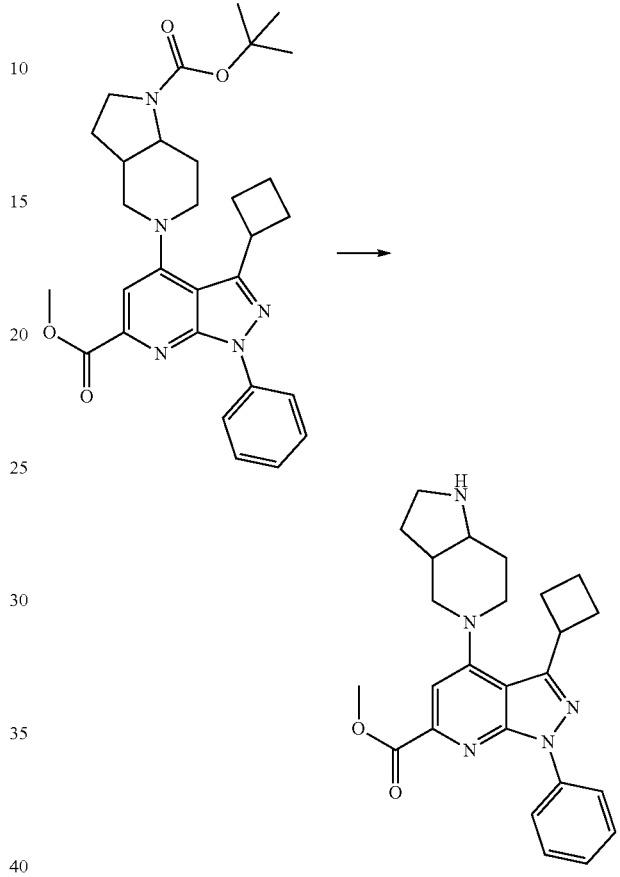

A solution of 4 M HCl in dioxane (0.245 mL, 0.98 mmol, 4.0 equiv) was added at RT to a solution of E131 (130 mg, 0.24 mmol) in dioxane (2.0 mL). The reaction mixture was stirred at RT for 16 hours. Additional 4 M HCl in dioxane (0.1 mL, 0.4 mmol, 1.7 equiv) was added, and the reaction mixture was stirred at RT for 48 hours. The reaction mixture was concentrated in vacuo and partitioned between dichloromethane and a saturated solution of sodium hydrogencarbonate. The organic phase was separated, dried over Na₂SO₄, filtered and concentrated in vacuo to give the titled compound.

Method I26: Reductive Amination to Install a Cyclopropyl Group

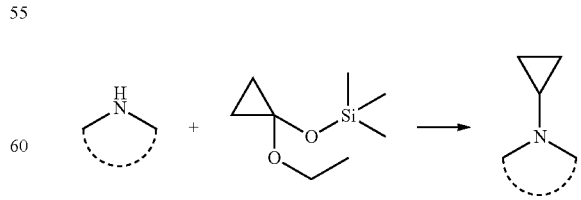

Trifluoroacetic acid (1.0 mL, 13.0 mmol, 33 equiv) was added at 0° C. to a solution of E044 (230 mg, 0.39 mmol) in dichloromethane (5.0 mL). The reaction mixture was stirred at RT for 1 hour. The reaction mixture was partitioned between dichloromethane and a saturated solution of sodium hydrogencarbonate. The organic phase was separated, dried over Na₂SO₄, filtered and concentrated to give the titled compound.

The amine (1 eq) is mixed with (1-ethoxycyclopropoxy)trimethylsilane ([27374-25-0], 2 eq), AcOH (1.6 eq) and NaBH₃CN (1.5 eq) in a mixture of THF/MeOH (1/1). The resulting mixture is stirred overnight at 50° C. After cooling the mixture down to room temperature, the reaction is quenched by the addition of water. Next, 1 M NaOH solution is added, and the mixture is stirred for another 15 minutes. After dilution with DCM, the organic layer is separated, dried and concentrated to give the titled compound.

Illustrative Synthesis of Compound E465: Methyl 3-cyclobutyl-4-[4-(4-cyclopropylpiperazin-1-yl)piperidin-1-yl]-1-(4-fluorophenyl)-1H-pyrazolo[3,4-b]pyridine-6-carboxylate

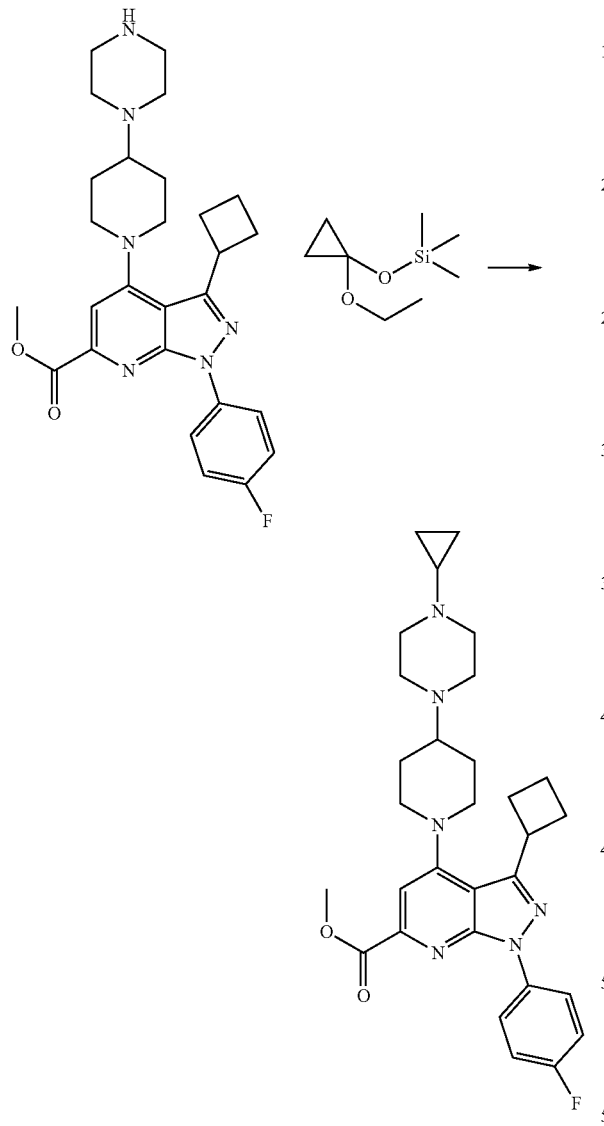

Methyl 3-cyclobutyl-1-(4-fluorophenyl)-4-[4-(piperazin-1-yl)piperidin-1-yl]-1H-pyrazolo[3,4-b]pyridine-6-carboxylate (200 mg, 0.41 mmol, E498) was mixed with (1-ethoxycyclopropoxy)trimethylsilane ([27374-25-0], 163 µL, 0.81 mmol), AcOH (26 µL, 0.65 mmol) and sodium cyanoborohydride ([25895-60-7], 38 mg, 0.61 mmol) in a mixture of THF/MeOH (1/1, 1 mL). The resulting mixture was stirred overnight at 50° C. After cooling the mixture down to room temperature, the reaction was quenched by the addition of water. Next, 1 M NaOH solution was added, and the mixture was stirred for another 15 minutes. After dilution with DCM, the organic layer was separated, dried and concentrated to give the titled compound.

Method I27: Alkylation Amine

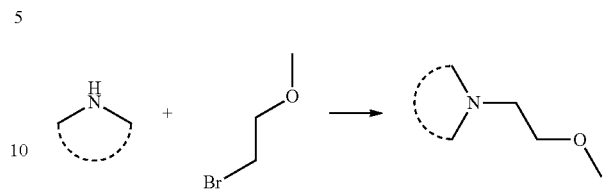

The amine (1 eq) is mixed with 1-bromo-2-methoxyethane ([6482-24-2], 1.1 eq) and $K_2CO_3$ (2 eq) in MeCN. The resulting mixture is heated at reflux overnight at 50° C. After cooling down, the mixture is used as such in the next step.

Method I28: Amino-Carbonylation

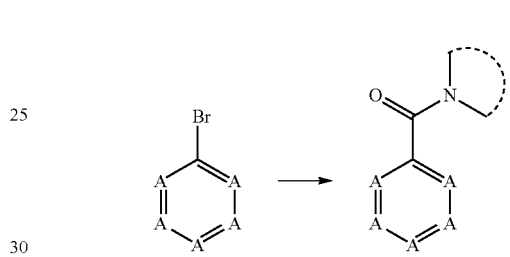

A is CH or N

In a Parr reactor, the arylbromide (1 eq) is mixed with an amine (2 eq), $Et_3N$ (4 eq) and Xantphos Pd G3 (0.03 eq) in dioxane. A CO pressure of 5 bars is applied and the mixture is heated at 100° C. overnight. Concentration gives a residue that is re-dissolved in DCM. Extraction with water gives an organic phase that is concentrated to give a residue that is used as such in the next step.

Illustrative Synthesis of Compound E474: Methyl 1-cyclohexyl-4-[4-(4-methylpiperazine-1-carbonyl)phenyl]-3-[(propan-2-yl)oxy]-1H-pyrazolo[3,4-b]pyridine-6-carboxylate

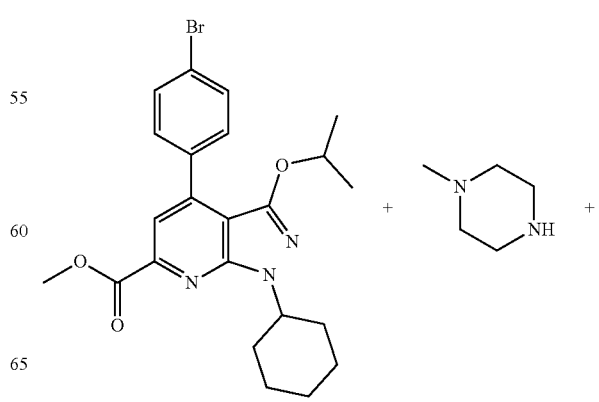

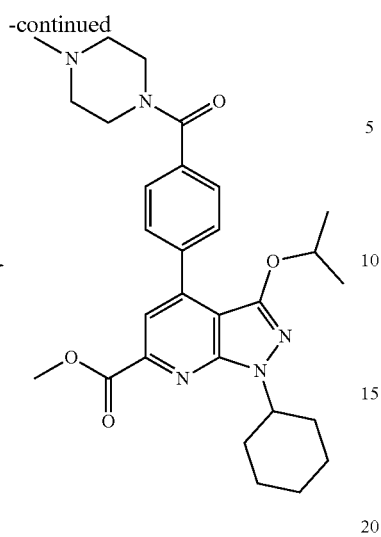

A Parr reactor was loaded with E504 (0.50 mmol, 250 mg), 1-methylpiperazine dihydrochloride ([34352-59-5], 1.0 mmol, 173 mg) and [(4,5-bis(diphenylphosphino)-9,9-dimethylxanthene)-2-(2'-amino-1,1'-biphenyl)]palladium(II) methanesulfonate] (0.015 mmol, 14 mg). The reactor was evacuated and back-filled with $N_2$, $Et_3N$ (4.0 equiv, 2.0 mmol, 279 μL) and 1,4-dioxane (dry, 8 mL/mmol, 4 mL) were added, and the reaction mixture was heated to 100° C. under a CO atmosphere (5 bar) overnight. The reaction mixture was concentrated in vacuo, and the residue was partitioned between $H_2O$ and dichloromethane. The organic phase was dried and concentrated in vacuo to give the titled compound which was used as such in the next step.

Method I29: Alternative Buchwald Coupling on the Aryl Linker

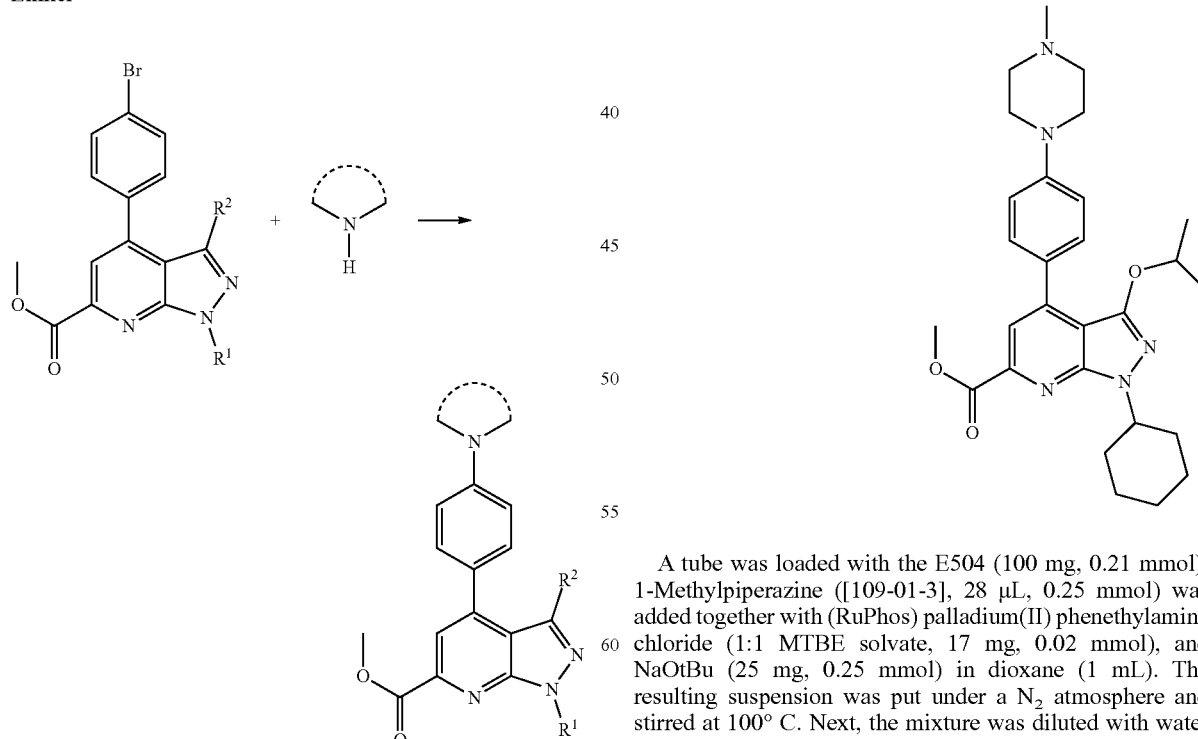

A tube is loaded with the arylbromide (1 eq). The amine (1.2 eq) is added together with (RuPhos) palladium(II) phenethylamine chloride (1:1 MTBE solvate, 0.1 eq), NaOtBu (1.2 eq) in dioxane. The resulting suspension is put under a $N_2$ atmosphere and stirred at 100° C. Next, the mixture is diluted with water and acidified with a 1 N citric acid solution till pH 3-4. Extraction with DCM gives the crude product that is either used as such or purified by chromatography. During this method, it is possible that partial hydrolysis of the ester to the corresponding acid occurs.

Illustrative Synthesis of Compound E502: Methyl 1-cyclohexyl-4-[4-(4-methylpiperazin-1-yl)phenyl]-3-[(propan-2-yl)oxy]-1H-pyrazolo[3,4-b]pyridine-6-carboxylate

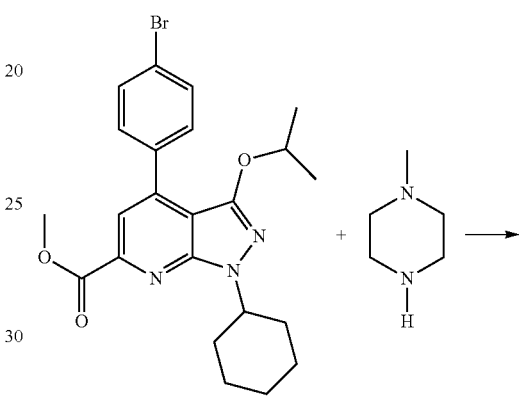

A tube was loaded with the E504 (100 mg, 0.21 mmol). 1-Methylpiperazine ([109-01-3], 28 μL, 0.25 mmol) was added together with (RuPhos) palladium(II) phenethylamine chloride (1:1 MTBE solvate, 17 mg, 0.02 mmol), and NaOtBu (25 mg, 0.25 mmol) in dioxane (1 mL). The resulting suspension was put under a $N_2$ atmosphere and stirred at 100° C. Next, the mixture was diluted with water and acidified with a 1 N citric acid solution till pH 3-4. Extraction with DCM gave the titled compound that was used as such. Partial hydrolysis of the ester to the corresponding acid was observed.

Method I30: Alternative Reductive Amination

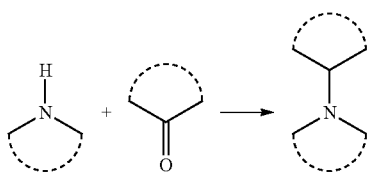

A solution of the amine (1 eq), the ketone (2 eq) and AcOH (1.5 eq) in DCM is cooled to 0° C. Next, sodium triacetoxyborohydride ([56553-60-7], 2 eq) is added portionwise, and the reaction is stirred overnight at ambient temperature. Subsequently, the mixture is diluted with saturated NaHCO$_3$ solution and extracted with DCM. The organic phase is concentrated to give the alkylated amine that is used as such or purified by chromatography.

Illustrative Example of Compound E469: Methyl 3-cyclobutyl-1-(4-fluorophenyl)-4-[9-(oxetan-3-yl)-3,9-diazaspiro[5.5]undecan-3-yl]-1H-pyrazolo[3,4-b]pyridine-6-carboxylate

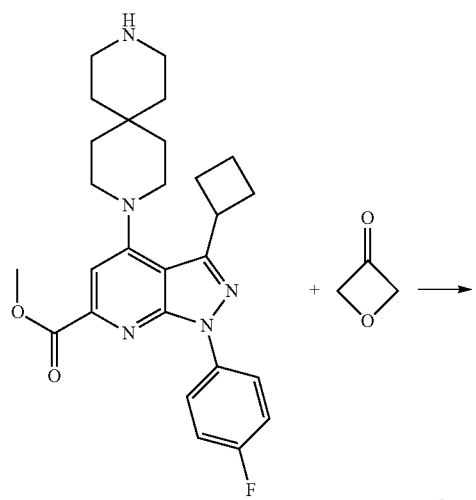

A solution of the methyl 3-cyclobutyl-4-(3,9-diazaspiro[5.5]undecan-3-yl)-1-(4-fluorophenyl)-1H-pyrazolo[3,4-b]pyridine-6-carboxylate (200 mg, 0.42 mmol, E500), 3-oxetanone ([6704-31-0], 54 µL, 0.84 mmol) and AcOH (36 µL) in DCM (3 mL) was cooled at 0° C. Next, sodium triacetoxyborohydride ([56553-60-7], 178 mg, 0.84 mmol) was added portion wise and the reaction was stirred overnight at ambient temperature. Subsequently, the mixture was diluted with sat. NaHCO$_3$ solution and extracted with DCM. The organic phase was evaporated to give the titled compound.

Method I31: Carbamate Synthesis

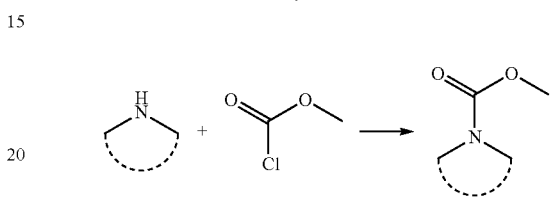

To a solution of the amine (1 eq) in DCM is added trimethylamine (2 eq) and then methyl chloroformate ([79-22-1], 2 eq). The mixture is stirred at RT overnight. Next, the reaction mixture is diluted with saturated NaHCO$_3$ solution and extracted with DCM. After concentration, the carbamate is obtained that is used as such or purified by chromatography.

Illustrative Example of Compound E486: Methyl 3-cyclobutyl-1-(4-fluorophenyl)-4-{4-[4-(methoxycarbonyl)piperazin-1-yl]piperidin-1-yl}-1H-pyrazolo[3,4-b]pyridine-6-carboxylate

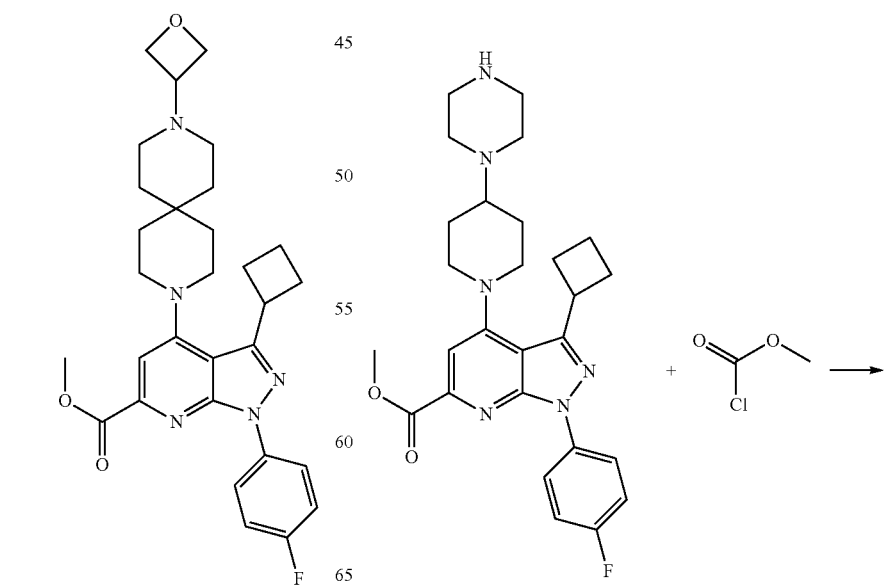

Illustrative Example of Compound E487: Methyl 4-[4-(4-acetylpiperazin-1-yl)piperidin-1-yl]-3-cyclobutyl-1-(4-fluorophenyl)-1H-pyrazolo[3,4-b]pyridine-6-carboxylate

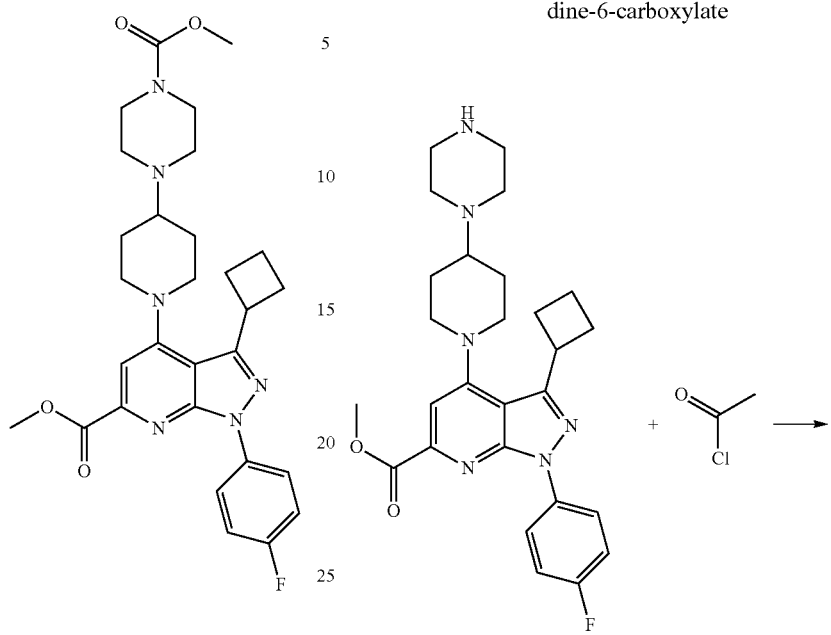

To a solution of the E498 (118 mg, 0.239 mmol) in DCM (1 mL) was added triethylamine (67 μL, 0.478 mmol) and then methyl chloroformate (37 μL, 0.478 mmol). The mixture was stirred at RT overnight. Next, the reaction mixture was diluted with saturated NaHCO₃ solution and extracted with DCM. After concentration, the titled compound was obtained that was used as such.

Method I32: Amide Synthesis Using Acetyl Chloride

To a solution of the amine (1 eq) in DCM is added trimethylamine (2 eq) and then acetyl chloride ([75-36-5], 2 eq). The mixture is stirred at RT overnight. Next, the reaction mixture is diluted with saturated NaHCO₃ solution extracted with DCM. After concentration, the amide is obtained that is used as such or purified by chromatography.

To a solution of the E498 (118 mg, 0.239 mmol) in DCM (1 mL) was added triethylamine (67 μL, 0.478 mmol) and then acetyl chloride ([75-36-5], 0.478 mmol). The mixture was stirred at RT overnight. Next, the reaction was diluted with saturated NaHCO₃ solution and extracted with DCM. After concentration, the titled compound was obtained that was used as such.

Method I34: Reductive Amination on Aldehydes

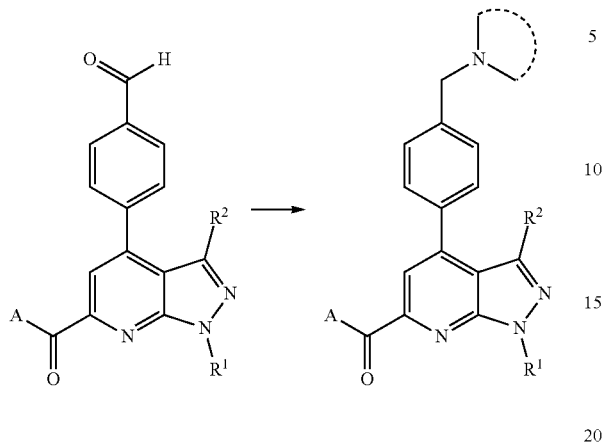

A is —O—$C_1$-$C_6$ alkyl or —NHS(O)$_2$R$^5$

A suspension of amine hydrochloride or free base (1 to 2 equiv) and triethylamine (from 1 to 2 equiv) in 1,2-dichloroethane is stirred at RT for 10 minutes. Aldehyde (1 equiv), sodium triacetoxyborohydride (2 equiv), and acetic acid (0.6 to 4 equiv) are successively added, and the stirring at RT is continued for 20 hours. Starting reagents can be added until full conversion is observed. The reaction mixture is diluted with DCM, washed with a saturated aqueous solution of NaHCO$_3$ and/or a saturated aqueous solution of NH$_4$Cl and a phosphate buffer (pH 6.2). The organic phase is dried over sodium sulfate and concentrated under reduced pressure. The residue is used as such or purified by flash column chromatography to yield the reductively aminated compound.

Illustrative Synthesis of E426: Ethyl 1-cyclohexyl-4-(4-{[3-(dimethylamino)azetidin-1-yl]methyl}phenyl)-3-[(propan-2-yl)oxy]-1H-pyrazolo[3,4-b]pyridine-6-carboxylate

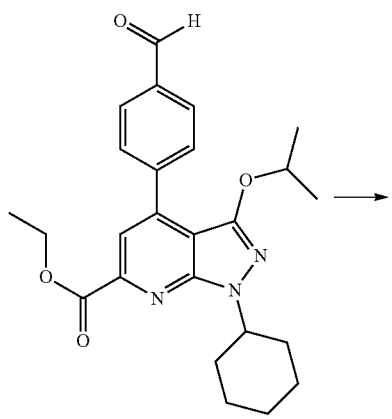

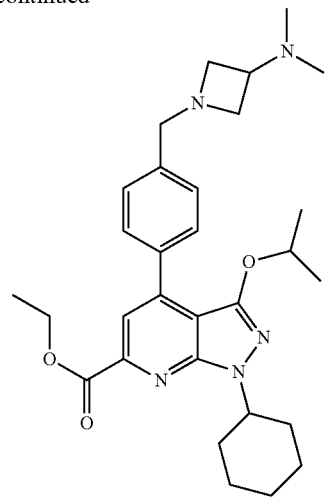

A suspension of 3-(dimethylamino)azetidine dihydrochloride ([124668-49-1], 17 mg, 124 µmol) and triethylamine (35 µL, 248 µmol) in 1,2-dichloroethane (2 mL) was stirred at RT for 10 minutes. Aldehyde E425 (54 mg, 124 µmol), sodium triacetoxyborohydride (53 mg, 248 mol), and acetic acid (29 µL, 496 µmol) were successively added, and the stirring at RT was continued for 20 hours. The reaction mixture was diluted with DCM and washed with a saturated aqueous solution of NaHCO$_3$. The organic phase was separated, dried over sodium sulfate and concentrated under reduced pressure. The residue was used as such or purified by flash column chromatography eluted with ethyl acetate/n-heptane to yield the titled compound.

Synthesis of E199: Methyl 4-(4-azidophenyl)-1-[3-(dimethylamino)phenyl]-3-isopropyl-pyrazolo[3,4-b]pyridine-6-carboxylate

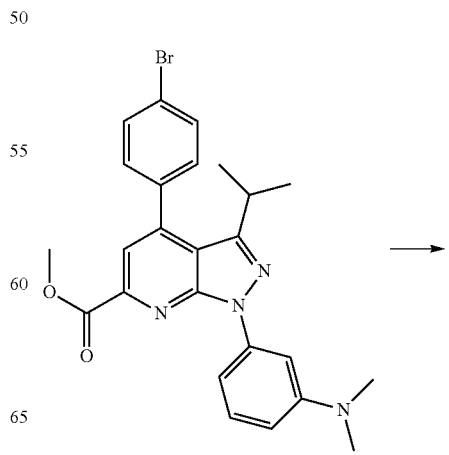

-continued

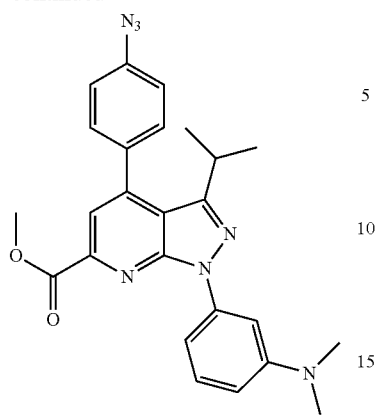

Intermediate E074 (0.5 g, 1.013 mmol, 1.0 equiv) and sodium azide (CAS 26628-22-8, 132 mg, 2.026 mmol, 2 equiv) were put in a sealed vial. A 2:1 mixture of ethanol and water (2 mL) was added, and the vial was purged with nitrogen. Then copper(I) iodide (CAS 7681-65-4, 20 mg, 0.101 mmol, 0.1 equiv), sodium ascorbate (CAS 134-03-2, 11 mg, 0.051 mmol, 0.05 equiv) and N,N-dimethylethylenediamine (CAS 110-70-3, 45 µL, 0.405 mmol, 0.2 equiv) were added, and the vial was sealed. The reaction mixture was heated under microwave irradiation at 80° C. for 45 minutes. Volatiles were removed in vacuo. The resulting aqueous residue was diluted with ethyl acetate. The two phases were separated, and the aqueous phase was extracted with ethyl acetate. The combined organic phases were washed with brine, dried over MgSO$_4$, filtered and concentrated in vacuo to afford the titled compound which was used as such.

Synthesis of E390: Ethyl 3-cyclobutyl-1-[2-(3,6-dihydro-2H-pyran-4-yl)pyridin-4-yl]-4-[4-(methoxymethyl)piperidin-1-yl]-1H-pyrazolo[3,4-b]pyridine-6-carboxylate and E391: Ethyl 3-cyclobutyl-4-[4-(methoxymethyl)piperidin-1-yl]-1-[2-(oxan-4-yl)pyridin-4-yl]-1H-pyrazolo[3,4-b]pyridine-6-carboxylate

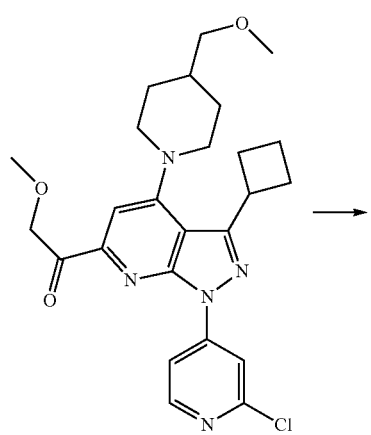

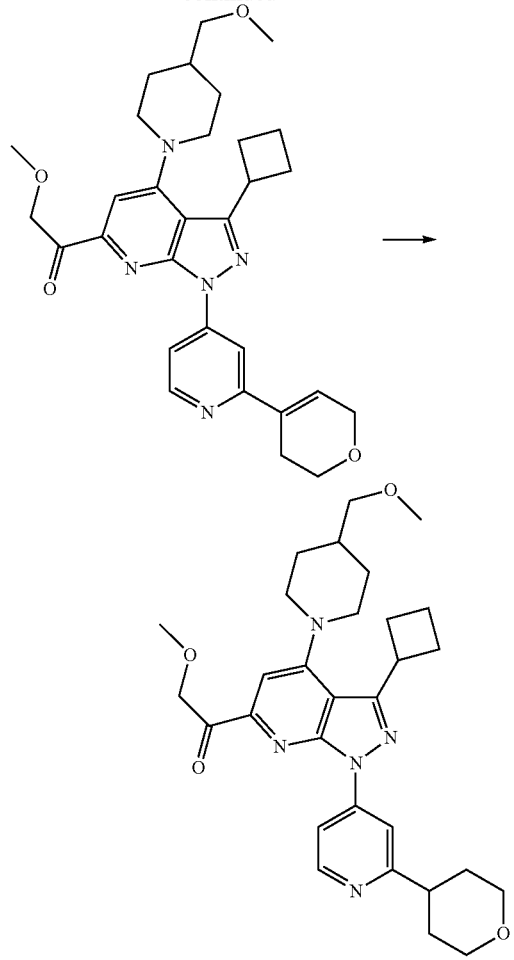

Step 1: E390: Ethyl 3-cyclobutyl-1-[2-(3,6-dihydro-2H-pyran-4-yl)pyridin-4-yl]-4-[4-(methoxymethyl)piperidin-1-yl]-1H-pyrazolo[3,4-b]pyridine-6-carboxylate In a sealed tube, a suspension of E389 (110 mg, 0.23 mmol), 3,6-dihydro-2H-pyran-4-boronic pinacol ester (72 mg, 0.34 mmol), K$_3$PO$_4$ (146 mg, 0.69 mmol) and Pd(Amphos)Cl$_2$ ([887919-35-9], 16 mg, 23 µmol) in dioxane (3 mL) and water (0.5 mL) was degassed with N$_2$ at room temperature for 2 minutes. The reaction mixture was heated at 100° C. for 3 hours. The mixture was cooled to RT and then concentrated under reduced pressure. The crude sample was purified by flash column chromatography eluted with ethyl acetate/n-heptane to give the titled compound E390.

Step 2: E391: Ethyl 3-cyclobutyl-4-[4-(methoxymethyl)piperidin-1-yl]-1-[2-(oxan-4-yl)pyridin-4-yl]-1H-pyrazolo[3,4-b]pyridine-6-carboxylate A suspension of E390 (60 mg, 0.11 mmol) and palladium hydroxide on carbon (20 mg) in ethanol was hydrogenated for 6 hours. The reaction mixture was filtered over Celpure® and washed with ethyl acetate. The filtrate was concentrated in vacuo, and the residue was purified by silica gel chromatography eluted with ethyl acetate/n-heptane to give the titled compound E391.

Synthesis of E393: Ethyl 3-cyclobutyl-4-[4-(morpholin-4-yl)piperidin-1-yl]-1H-pyrazolo[3,4-b]pyridine-6-carboxylate

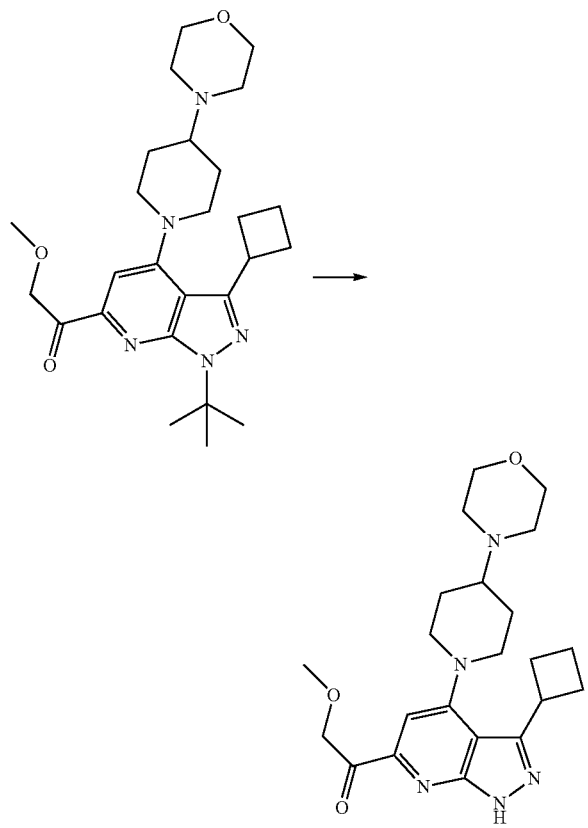

Trifluoromethanesulfonic acid (860 µL, 10 mmol) was added dropwise at RT to a solution of E392 (1 g, 2 mmol) in dichloromethane (10 mL). The reaction mixture was stirred for 4 hours and poured into a mixture of saturated aqueous NaHCO₃ and water (1:1, 10 mL). The aqueous phase was extracted twice with dichloromethane/isopropanol (95/5, 20 mL). The combined organic phases were combined, dried over sodium sulfate, filtered and concentrated under reduced pressure to give the titled compound as a colorless solid.

Synthesis of E402: Ethyl 3-cyclobutyl-1-(2-hydroxypyridin-4-yl)-4-[4-(morpholin-4-yl)piperidin-1-yl]-1H-pyrazolo[3,4-b]pyridine-6-carboxylate

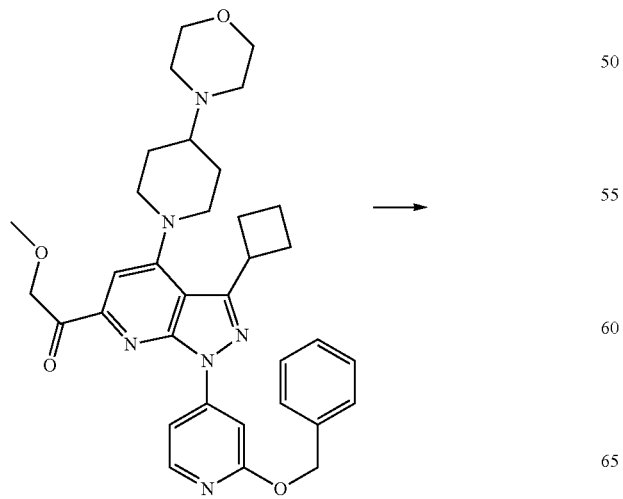

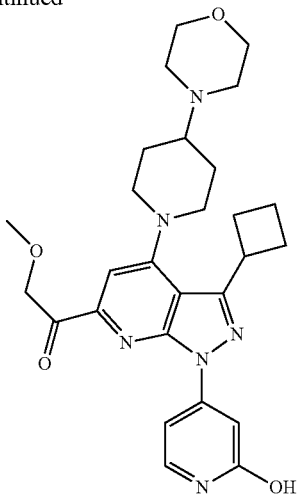

A suspension of E401 (75 mg, 0.12 mmol) and palladium hydroxide on carbon (10 mg) in THF was hydrogenated for 20 hours. The reaction mixture was filtered over Celpure® that was washed with dichloromethane/methanol. The filtrate was concentrated in vacuo to give the titled compound E402.

Synthesis of E407: Ethyl 3-cyclobutyl-4-[4-(morpholin-4-yl)piperidin-1-yl]-1-[2-(oxan-4-yl)pyridin-4-yl]-1H-pyrazolo[3,4-b]pyridine-6-carboxylate

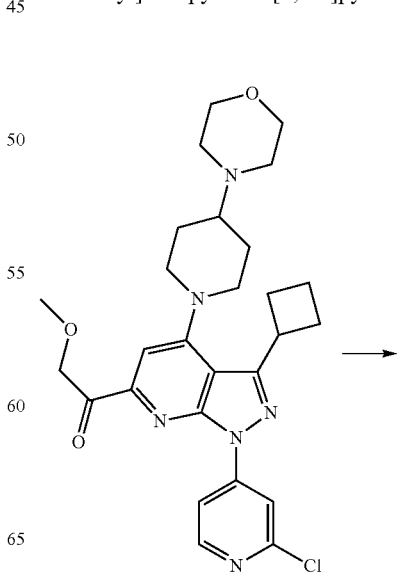

-continued

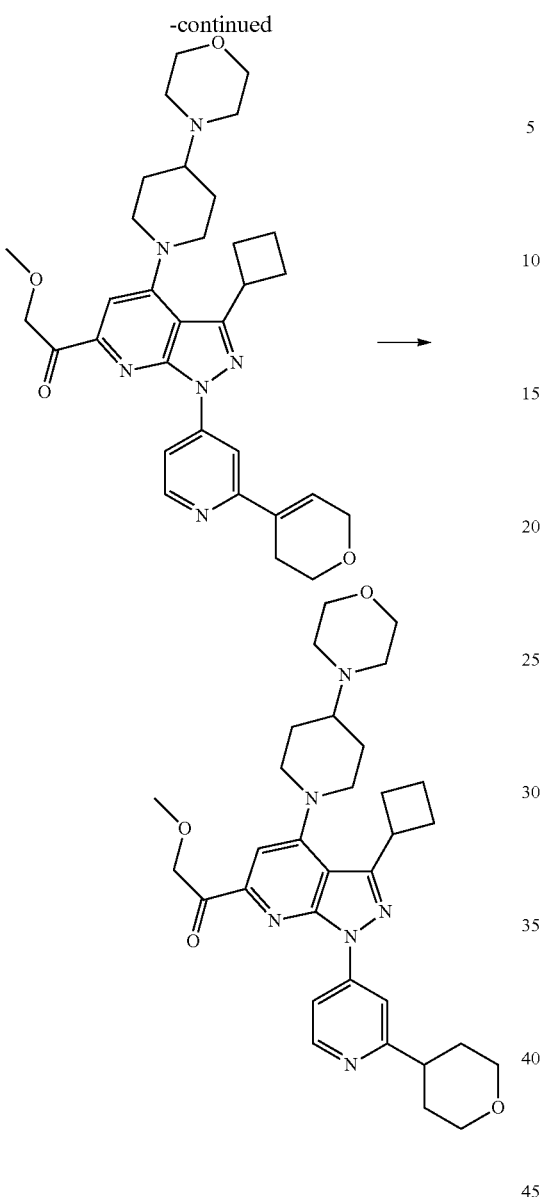

Step 1: Ethyl 3-cyclobutyl-1-[2-(3,6-dihydro-2H-pyran-4-yl)pyridin-4-yl]-4-[4-(morpholin-4-yl)piperidin-1-yl]-1H-pyrazolo[3,4-b]pyridine-6-carboxylate In a sealed tube, a suspension of E406 (110 mg, 0.21 mmol), 3,6-dihydro-2H-pyran-4-boronic pinacol ester (72 mg, 0.34 mmol), K₃PO₄ (146 mg, 0.69 mmol) and Pd(Amphos)Cl₂ ([887919-35-9], 16 mg, 23 µmol) in dioxane (3 mL) and water (0.5 mL) was degassed with N₂ at room temperature for 2 minutes. The reaction mixture was heated at 100° C. for 20 hours. The mixture was cooled to RT, and the mixture was concentrated under reduced pressure. The crude sample was purified by flash column chromatography eluted with ethyl acetate/n-heptane to give the titled compound.

Step 2: Ethyl 3-cyclobutyl-4-[4-(morpholin-4-yl)piperidin-1-yl]-1-[2-(oxan-4-yl)pyridin-4-yl]-1H-pyrazolo[3,4-b]pyridine-6-carboxylate A suspension of ethyl 3-cyclobutyl-1-[2-(3,6-dihydro-2H-pyran-4-yl)pyridin-4-yl]-4-[4-(morpholin-4-yl)piperidin-1-yl]-1H-pyrazolo[3,4-b]pyridine-6-carboxylate (54 mg, 0.94 mmol) and palladium hydroxide on carbon (15 mg) in ethanol/THF (1:1, 10 mL) was hydrogenated for 6 hours. The reaction mixture was filtered over Celpure® that was washed with ethyl acetate, and the filtrate was concentrated in vacuo. The residue was purified by silica gel chromatography eluted with ethyl acetate/n-heptane to give the titled compound, E407.

Synthesis of E413: Methyl 3-cyclobutyl-1-(4-fluorophenyl)-4-(piperidin-4-yl)-1H-pyrazolo[3,4-b]pyridine-6-carboxylate

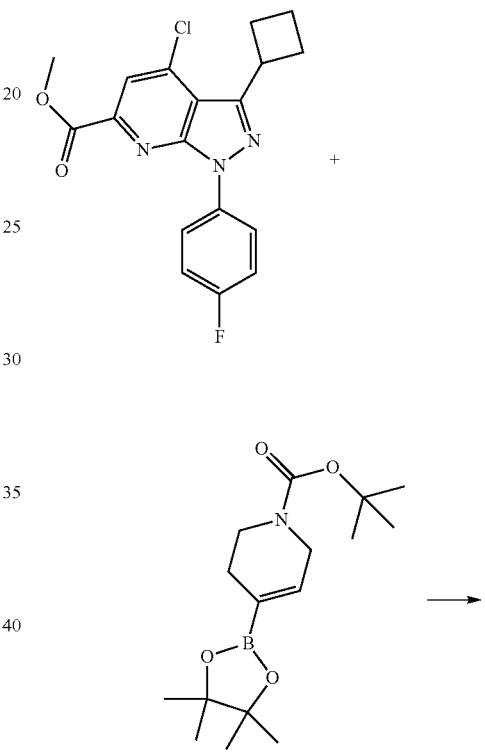

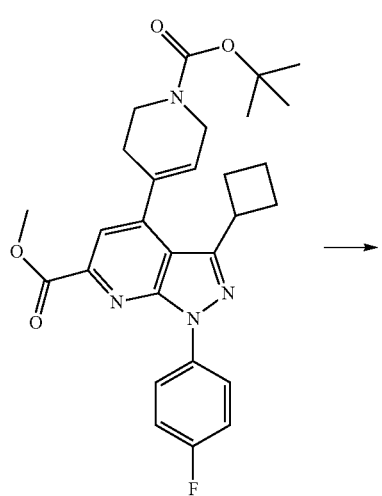

-continued

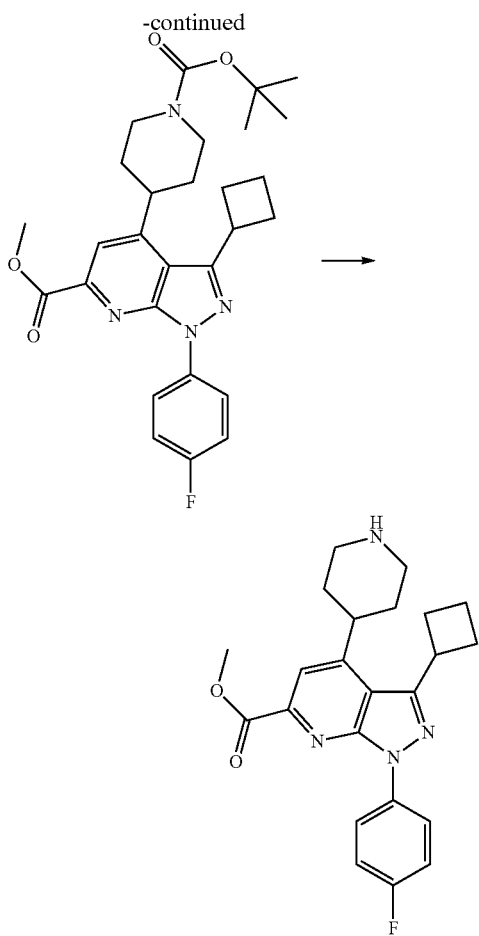

Step 1: Methyl 4-[1-(tert-butoxycarbonyl)-1,2,3,6-tetrahydropyridin-4-yl]-3-cyclobutyl-1-(4-fluorophenyl)-1H-pyrazolo[3,4-b]pyridine-6-carboxylate A suspension of methyl 4-chloro-3-cyclobutyl-1-(4-fluorophenyl)-1H-pyrazolo[3,4-b]pyridine-6-carboxylate (HP19, 2.0 g, 5.75 mmol, 1.0 equiv), tert-butyl 4-(4,4,5,5-tetramethyl-1,3,2-dioxaborolan-2-yl)-3,6-dihydro-2H-pyridine-1-carboxylate (CAS 286961-14-6, 3.6 g, 11.5 mmol, 2.0 equiv), $K_2CO_3$ (2.4 g, 17.25 mmol, 3.0 equiv) and Pd(dppf)Cl$_2$ (CAS: 72287-26-4, 939 mg, 1.15 mmol, 0.2 equiv) in anhydrous DMF (15 mL) was degassed with nitrogen at room temperature for 2 minutes. The reaction mixture was refluxed for 20 hours. The mixture was cooled to RT, poured into 150 mL of iced water and diluted with ethyl acetate. The two phases were separated, and the aqueous phase was extracted again with ethyl acetate. The combined organic layers were washed with brine, dried over sodium sulfate, filtered and concentrated. The crude residue was purified by silica gel chromatography (heptane/ethyl acetate: 100/0 to 80/20) to give the titled compound.

Step 2: Methyl 4-[1-(tert-butoxycarbonyl)piperidin-4-yl]-3-cyclobutyl-1-(4-fluorophenyl)-1H-pyrazolo[3,4-b]pyridine-6-carboxylate A suspension of compound from Step 1 (2.44 g, 4.93 mmol, 1.0 equiv) and platinum (IV) oxide (CAS 1314-15-4, 1.2 g) in acetic acid (240 mL) was stirred at RT under a hydrogen atmosphere (balloon) for 20 hours. The reaction mixture was filtered over Celpure® P65. Solids were washed with ethyl acetate, and the filtrate was concentrated in vacuo. The crude residue was purified by silica gel chromatography (heptane/ethyl acetate: 100/0 to 80/20) to give the title compound.

Step 3: Methyl 3-cyclobutyl-1-(4-fluorophenyl)-4-(piperidin-4-yl)-1H-pyrazolo[3,4-b]pyridine-6-carboxylate Methyl 4-[1-(tert-butoxycarbonyl)piperidin-4-yl]-3-cyclobutyl-1-(4-fluorophenyl)-1H-pyrazolo[3,4-b]pyridine-6-carboxylate (2.75 g, 5.4 mmol, 1 equiv) was dissolved in 4 M HCl in dioxane (40 mL, 162.2 mmol, 30 equiv), and the solution was stirred at RT for 2 hours. The solvent was concentrated under reduced pressure. The residue was dissolved in a minimum of methanol and poured into diethyl ether (500 mL). The precipitate was filtered, washed with diethyl ether and dried at 40° C. under reduced pressure to give the titled compound, E413.

Synthesis of E430: Methyl 3-cyclobutyl-4-(1,4-dioxaspiro[4.5]dec-7-en-8-yl)-1-phenyl-1H-pyrazolo[3,4-b]pyridine-6-carboxylate

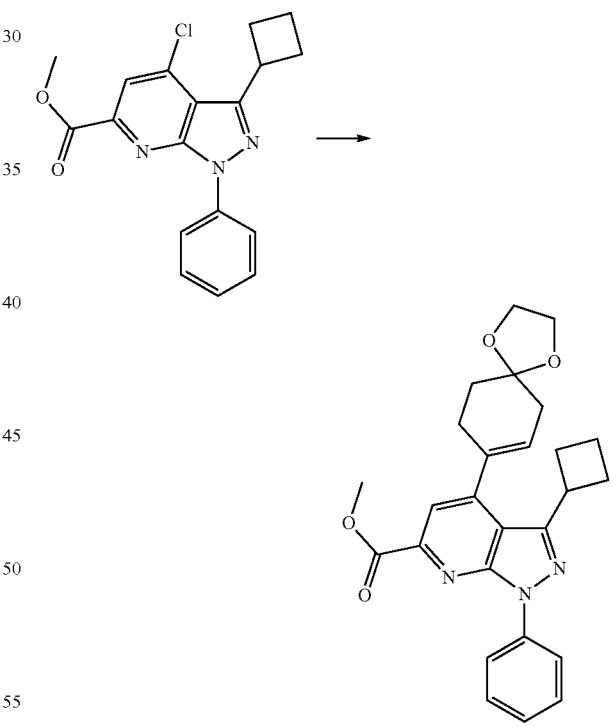

In a sealed tube, a suspension of HP02 (1 g, 2.92 mmol), 1,4-dioxa-spiro[4,5]dec-7-en-8-boronic acid, pinacol ester ([680596-79-6], 1.01 g, 3.8 mmol), $K_3PO_4$ (1.86 g, 8.77 mmol), Pd(OAc)$_2$ ([3375-31-3], 330 mg, 0.14 mmol), and SPhos ([657408-07-6], 150 mg, 0.365 mmol) in toluene (22 mL) and water (6 mL) was degassed with $N_2$ at room temperature for 5 minutes. The reaction mixture was stirred at RT for 2 hours. Additional Pd(OAc)$_2$ ([3375-31-3], 330 mg, 0.14 mmol) and SPhos ([657408-07-6], 150 mg, 0.365 mmol) were added. The stirring at RT was continued for 20 hours. Pd(OAc)₂ ([3375-31-3], 165 mg, 0.07 mmol) and SPhos ([657408-07-6], 75 mg, 0.18 mmol) were again added, and the reaction mixture was heated at 100° C. for 1 hour. The reaction mixture was cooled to RT, diluted with ethyl acetate and filtered. The filtrate was washed successively with water and a saturated aqueous solution of NaCl. The organic phase was separated, dried over sodium sulfate, filtered and concentrated under reduced pressure. The crude residue was purified by flash column chromatography on silica gel eluting with ethyl acetate/n-heptane to give the titled compound.

Synthesis of E431: Methyl 3-cyclobutyl-4-(1,4-dioxaspiro[4.5]decan-8-yl)-1-phenyl-1H-pyrazolo[3,4-b]pyridine-6-carboxylate

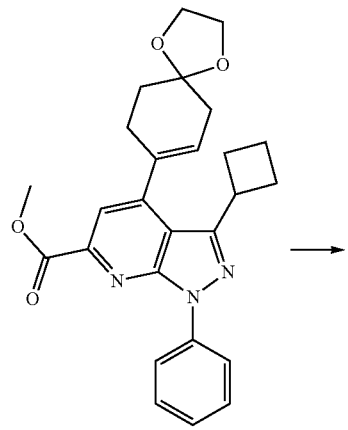

A suspension of E430 (823 mg, 1.85 mmol) and palladium hydroxide on carbon ([12135-22-7], 280 mg) in THF/MeOH (25 mL, 2/1) was hydrogenated for 20 hours. The reaction mixture was filtered over Celpure® which was washed with DCM. The filtrate was concentrated in vacuo. The residue was purified by silica gel chromatography eluting with ethyl acetate/n-heptane to give the titled compound E431.

Synthesis of E432: Methyl 3-cyclobutyl-1-[(3E,5Z)-hepta-1,3,5-trien-4-yl]-4-(4-oxocyclohexyl)-1H-pyrazolo[3,4-b]pyridine-6-carboxylate

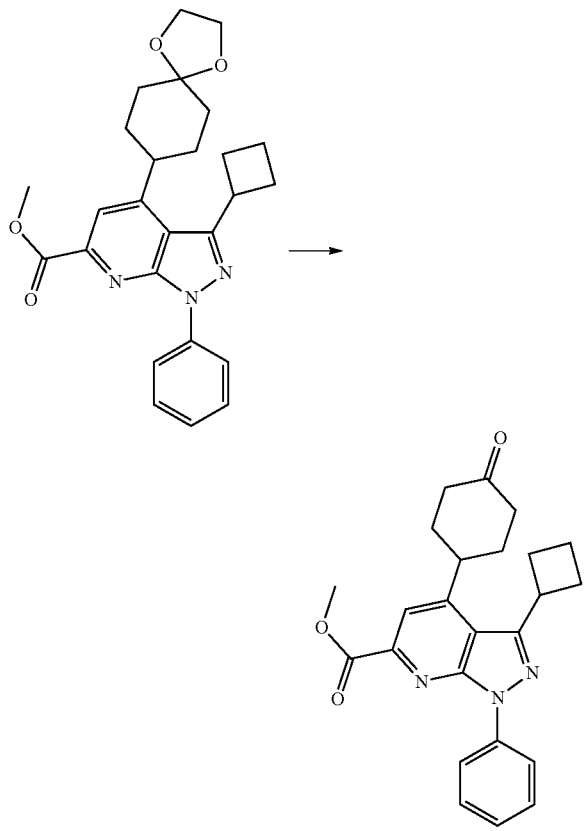

The ester, E431 (732 mg, 1.64 mmol), was dissolved in DCM and TFA (2.2 mL, 3 volumes) was added dropwise at RT. The solution was stirred for 48 hours and then diluted with DCM. The mixture was washed with a saturated aqueous solution of NaHCO₃. The organic phase was separated, dried over sodium sulfate, filtered and concentrated in vacuo. The residue was purified by silica gel chromatography eluting with ethyl acetate/n-heptane to give the titled compound E432.

Synthesis of E438: 4-{1-cyclohexyl-6-(ethoxycarbonyl)-3-[(propan-2-yl)oxy]-1H-pyrazolo[3,4-b]pyridin-4-yl}benzoic Acid

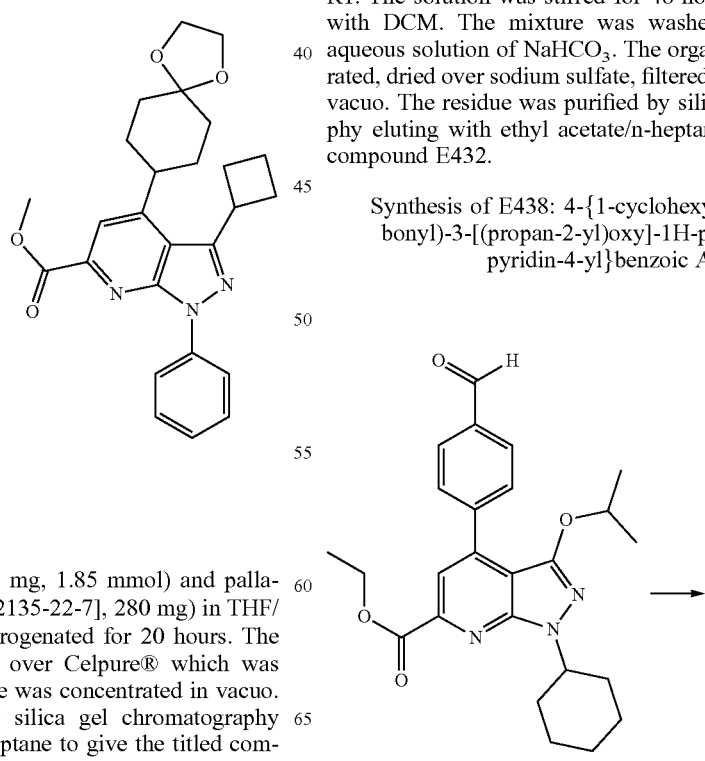

-continued

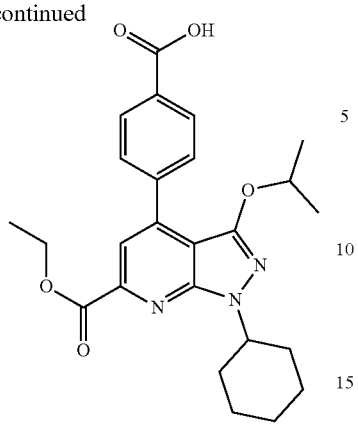

A mixture of aldehyde E425 (27 mg, 62 µmol), sulfamic acid ([226-18-8], 17 mg, 168 µmol), and sodium chlorite ([7758-19-2], 17 mg, 188 µmol) in THF/water (3.3 mL, 10/1) was stirred at RT for 1 hour. The reaction mixture was diluted with DCM (20 mL) and washed with water (20 mL). The organic phase was dried over sodium sulfate, filtered and evaporated under reduced pressure. The titled compound was used as such in the next step.

Synthesis of E444: Ethyl 1-cyclohexyl-4-{4-[(8-methyl-2-oxa-5,8-diazaspiro[3.5]nonan-5-yl)methyl]phenyl}-3-[(propan-2-yl)oxy]-1H-pyrazolo[3,4-b]pyridine-6-carboxylate

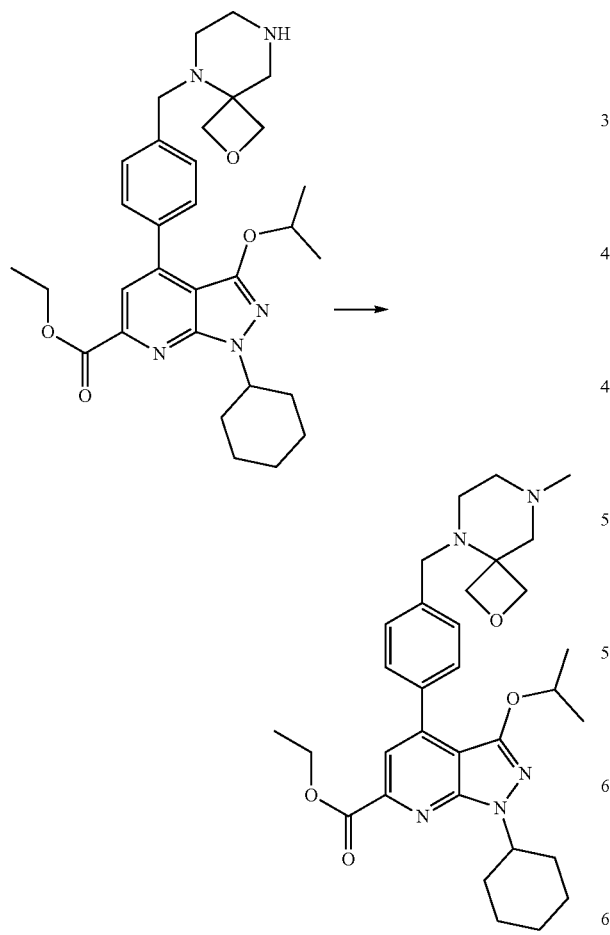

Iodomethane (3 µL, 48 µmol) was added at RT to a stirred suspension of E443 (22 mg, 40 µmol) and cesium carbonate (33 mg, 100 µmol) in DMF (2 mL). The reaction mixture was stirred for 20 hours. The reaction mixture was partitioned between water and ethyl acetate. The organic phase was dried over sodium sulfate, filtered and concentrated under reduced pressure. The residue was purified by flash column chromatography eluting with ethyl acetate/DCM/MeOH (100/0/0 to 0/90/10) to give the titled compound.

Synthesis of E445: Ethyl 4-[4-(4-cyano-1-methylpiperidin-4-yl)phenyl]-1-cyclohexyl-3-[(propan-2-yl)oxy]-1H-pyrazolo[3,4-b]pyridine-6-carboxylate

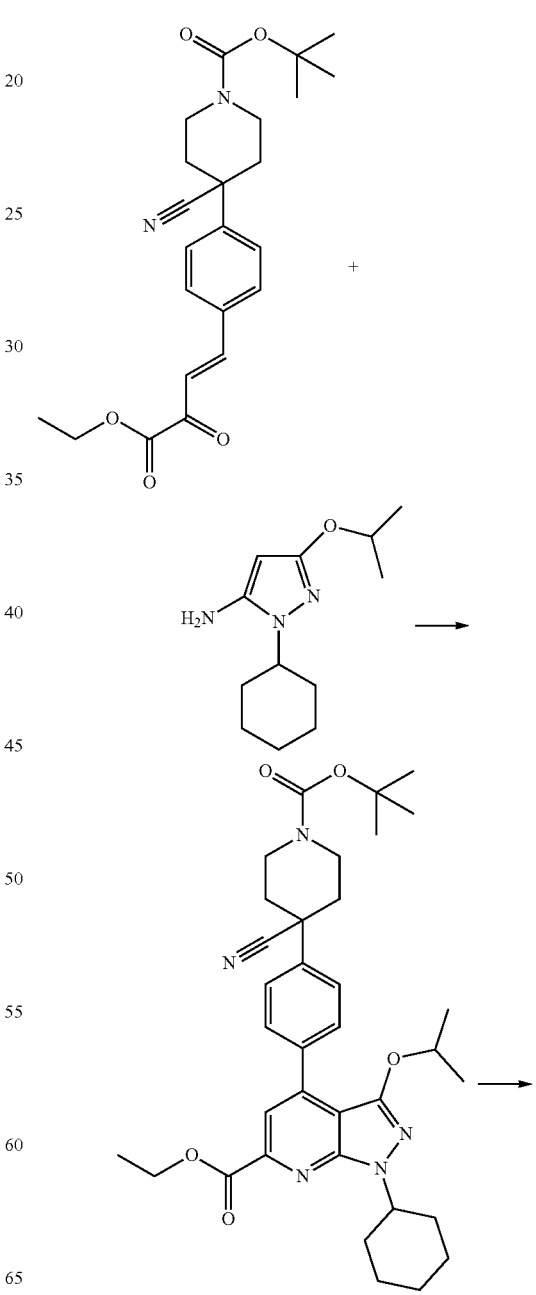

251

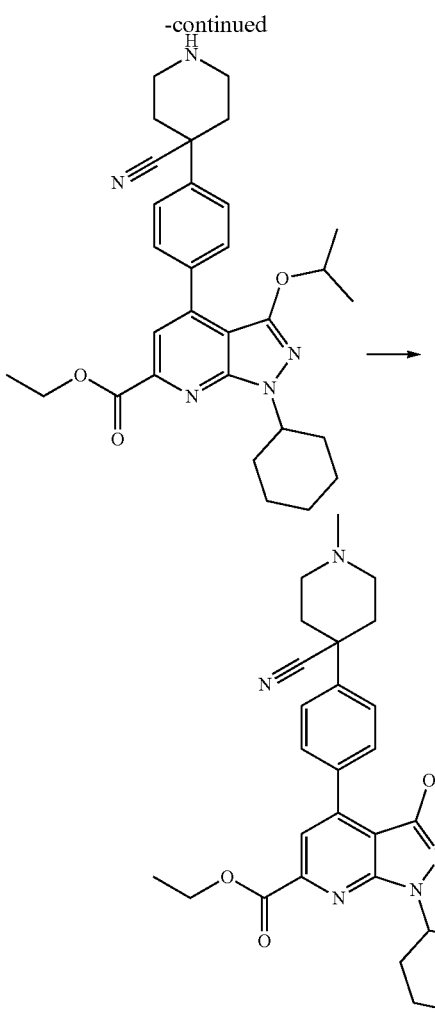

Step 1: Ethyl 4-{4-[1-(tert-butoxycarbonyl)-4-cyanopiperidin-4-yl]phenyl}-1-cyclohexyl-3-[(propan-2-yl)oxy]-1H-pyrazolo[3,4-b]pyridine-6-carboxylate A solution of ALP38 (305 mg, 0.74 mmol) and AMP95 (575 mg, 0.77 mmol) in N-methylpyrrolidine (4 mL) was heated at 110° C. for 24 hours in an opened vessel. The reaction mixture was cooled to RT, and the mixture was concentrated in vacuo. The residue was partitioned between ethyl acetate and water. The organic phase was separated, dried over sodium sulfate, filtered and concentrated under reduced pressure. The residue was purified by flash chromatography on silica gel eluting with ethyl acetate/n-heptane to give the titled compound.

Step 2: Ethyl 4-[4-(4-cyanopiperidin-4-yl)phenyl]-1-cyclohexyl-3-[(propan-2-yl)oxy]-1H-pyrazolo[3,4-b]pyridine-6-carboxylate Trifluoroacetic acid (1 mL) was added to a solution of the tert-butoxycarbonyl protected compound from Step 1 (230 mg, 0.37 mmol) in DCM (10 mL). The solution was stirred at RT for 2 hours. The reaction mixture was diluted with toluene (5 mL) and then concentrated under reduced pressure. The residue was partitioned between ethyl acetate, water, and a phosphate buffer solution (pH 6.2). The organic

252 phase was dried over sodium sulfate, filtered and concentrated in vacuo. The residue was purified by flash column chromatography on silica gel eluting with ethyl acetate/n-heptane to give the titled compound.

Step 3: Ethyl 4-[4-(4-cyano-1-methylpiperidin-4-yl)phenyl]-1-cyclohexyl-3-[(propan-2-yl)oxy]-1H-pyrazolo[3,4-b]pyridine-6-carboxylate Iodomethane (2 μL, 32 μmol) was added at RT to a stirred suspension of the compound from Step 2 (15 mg, 29 μmol) and cesium carbonate (33 mg, 100 μmol) in DMF (2 mL). The reaction mixture was stirred for 2 hours. The reaction mixture was partitioned between water and DCM. The organic phase was dried over sodium sulfate, filtered and concentrated under reduced pressure. The residue was purified by flash column chromatography eluting with ethyl acetate/DCM/MeOH (100/0/0 to 0/90/10) to give the titled compound.

Synthesis of E509: Methyl 3-cyclobutyl-4-[4-(morpholin-4-yl)piperidin-1-yl]-1H-pyrazolo[3,4-b]pyridine-6-carboxylate

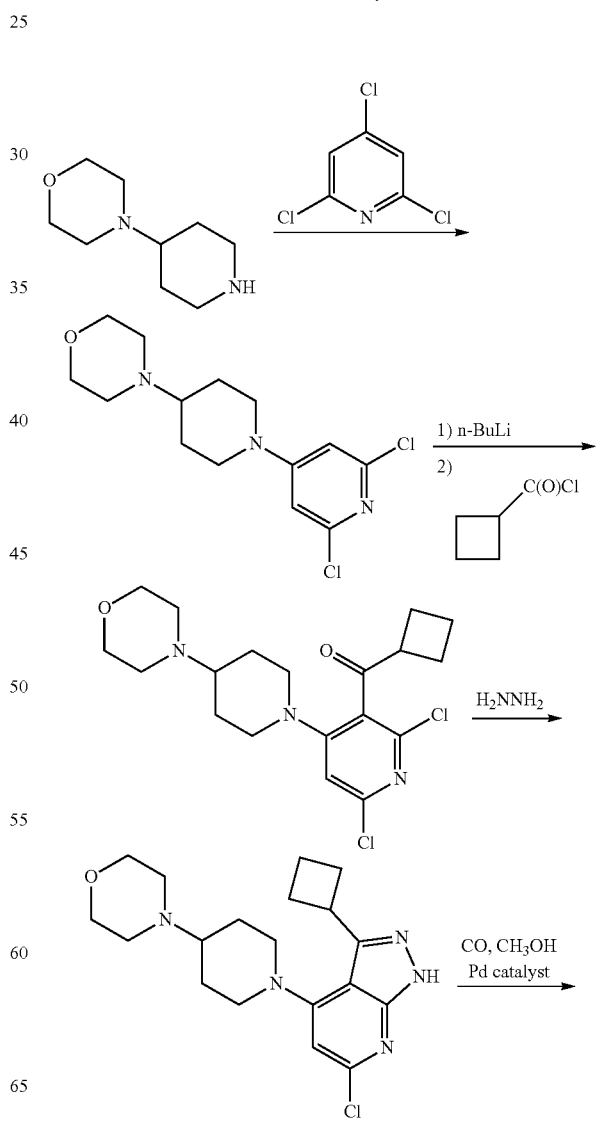

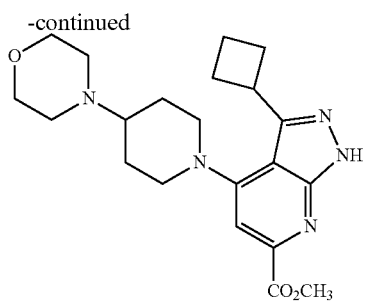

Step 1: 4-[1-(2,6-dichloropyridin-4-yl)piperidin-4-yl]morpholine

N-Ethyl-N-isopropylpropan-2-amine (22.91 mL, 132 mmol) was added to a suspension of 2,4,6-trichloropyridine (12 g, 65.8 mmol) and 4-(piperidin-4-yl)morpholine (13.44 g, 79 mmol) in acetonitrile (120 mL). The reaction mixture was heated to 60° C. and stirred for 16 hours. Upon cooling to room temperature, the precipitate was collected by filtration. The crude solid was then precipitated from EtOAc to give the titled compound. $^1$H NMR (400 MHz, CDCl$_3$) δ ppm 6.59 (s, 2H), 3.89-3.79 (m, 2H), 3.77-3.69 (m, 4H), 2.96 (ddd, J=13.3, 11.8, 2.8 Hz, 2H), 2.60-2.52 (m, 4H), 2.45 (tt, J=10.8, 3.7 Hz, 1H), 1.95 (ddd, J=12.9, 3.9, 1.9 Hz, 2H), 1.61-1.48 (m, 2H); MS (APCI+) m/z 316.2 (M+H)$^+$.

Step 2: Cyclobutyl{2,6-dichloro-4-[4-(morpholin-4-yl)piperidin-1-yl]pyridin-3-yl}methanone n-Butyllithium (19.2 mL, 26.9 mmol) was added in 5 mL portions to a stirred solution of 4-[1-(2,6-dichloropyridin-4-yl)piperidin-4-yl]morpholine (7.95 g, 25.1 mmol) in THF (160 mL) at −78° C. After stirring at this temperature for 1.5 hours, cyclobutanecarbonyl chloride (1.42 g, 11.9 mmol) was added rapidly, and the reaction mixture was stirred for 10 minutes. To obtain higher conversion, sequential additions of n-butyllithium and cyclobutanecarbonyl chloride were performed in the same manner. Addition 1: n-butyllithium (13.0 mL, 18.2 mmol) and cyclobutanecarbonyl chloride (0.97 g, 8.1 mmol); Addition 2: n-butyllithium (9.2 mL, 12.9 mmol) and cyclobutanecarbonyl chloride (0.68 g, 5.6 mmol); Addition 3: n-butyllithium (6.9 mL, 9.7 mmol) and cyclobutanecarbonyl chloride (0.51 g, 4.2 mmol); Addition 4: n-butyllithium (5.7 mL, 8.0 mmol) and cyclobutanecarbonyl chloride (0.41 g, 3.4 mmol). Upon completion of the last addition, the excess n-butyl lithium was quenched with water (200 mL), and the mixture was extracted with ethyl acetate (3×100 mL). The combined organic fractions were washed with brine (100 mL), dried over sodium sulfate, and concentrated in vacuo. The residue was purified by column chromatography (0-5% 95/5 MeOH/30% aqueous NH$_3$ in DCM) to give the titled compound. $^1$H NMR (400 MHz, CDCl$_3$) δ ppm 6.76 (s, 1H), 3.80-3.65 (m, 5H), 3.50-3.40 (m, 2H), 2.98-2.76 (m, 2H), 2.62-2.50 (m, 4H), 2.50-2.37 (m, 2H), 2.29 (tt, J=11.0, 3.8 Hz, 1H), 2.22-2.08 (m, 2H), 2.08-1.93 (m, 2H), 1.93-1.83 (m, 2H), 1.52 (dddd, J=14.8, 12.8, 7.5, 3.8 Hz, 2H); MS (APCI+) m/z 398.2 (M+H)$^+$.

Step 3: 6-chloro-3-cyclobutyl-4-[4-(morpholin-4-yl)piperidin-1-yl]-1H-pyrazolo[3,4-b]pyridine Hydrazine (35% in water, 3.10 mL, 33.9 mmol) was added to cyclobutyl{2,6-dichloro-4-[4-(morpholin-4-yl)piperidin-1-yl]pyridin-3-yl}methanone (4.5 g, 11.30 mmol) in EtOH (32 mL). The reaction mixture was heated to reflux for 14 hours. Upon cooling to −5° C., the precipitate was isolated by filtration. The filter cake was rinsed with cold EtOH to give the titled compound. $^1$H NMR (400 MHz, CDCl$_3$) δ ppm 10.21 (br s, 1H), 6.45 (s, 1H), 3.94-3.76 (m, 5H), 3.63 (d, J=12.4 Hz, 2H), 2.84 (td, J=12.4, 2.3 Hz, 2H), 2.71-2.59 (m, 4H), 2.58-2.44 (m, 2H), 2.44-2.31 (m, 3H), 2.14-1.97 (m, 4H), 1.85-1.70 (m, 2H); MS (APCI+) m/z 376.2 (M+H)$^+$.

Step 4: Methyl 3-cyclobutyl-4-(4-morpholinopiperidin-1-yl)-1H-pyrazolo[3,4-b]pyridine-6-carboxylate Into a 600 mL Parr reactor was charged 6-chloro-3-cyclobutyl-4-[4-(morpholin-4-yl)piperidin-1-yl]-1H-pyrazolo[3,4-b]pyridine (3.4 g, 9.05 mmol), followed by THF (170 mL) and MeOH (170 mL). 1,1'-Bis(diphenylphosphino)ferrocene-palladium (II) dichloride dichloromethane complex (0.739 g, 0.905 mmol), and triethylamine (2.52 mL, 18.09 mmol) were added to give a suspension. The reaction vessel was purged with argon followed by CO, pressurized to 100 psig with CO, and heated to 80° C. After 8 hours, the reaction mixture was cooled to room temperature, diluted with CH$_2$Cl$_2$ (800 mL), and filtered. The filtrate was concentrated in vacuo, and the residue was dissolved in CH$_2$Cl$_2$ (800 mL). The organic mixture was washed with saturated aqueous NaHCO$_3$ (300 mL), dried over Na$_2$SO$_4$, filtered, and concentrated in vacuo. The crude residue was slurried in EtOAc to give the titled compound. $^1$H NMR (400 MHz, CDCl$_3$) δ ppm 10.98 (br s, 1H), 7.37 (s, 1H), 4.08 (s, 3H), 3.96 (p, J=8.4 Hz, 1H), 3.83-3.76 (m, 4H), 3.70 (d, J=12.3 Hz, 2H), 2.92 (t, J=11.8 Hz, 2H), 2.66 (t, J=4.7 Hz, 4H), 2.55 (dq, J=11.3, 9.0 Hz, 2H), 2.44-2.31 (m, 3H), 2.15-2.00 (m, 4H), 1.88-1.74 (m, 2H); MS (APCI+) m/z 400.3 (M+H)$^+$.

Synthesis of E511: Methyl 1-(4-fluorophenyl)-4-(4-methoxy[1,4'-bipiperidin]-1'-yl)-3-[(propan-2-yl)oxy]-1H-pyrazolo[3,4-b]pyridine-6-carboxylate

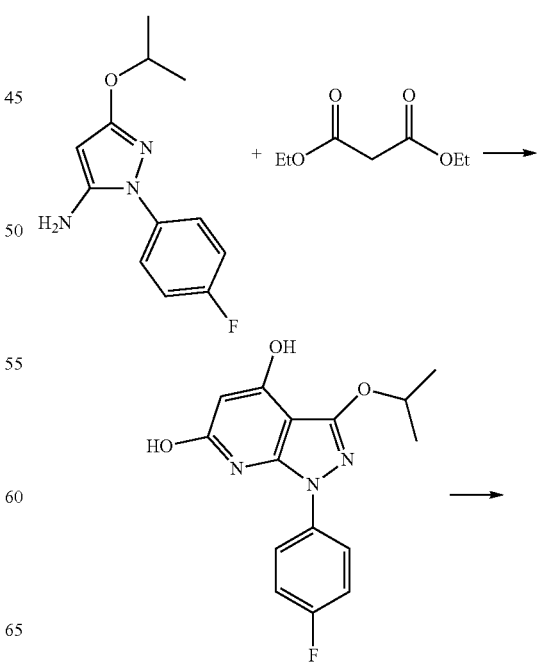

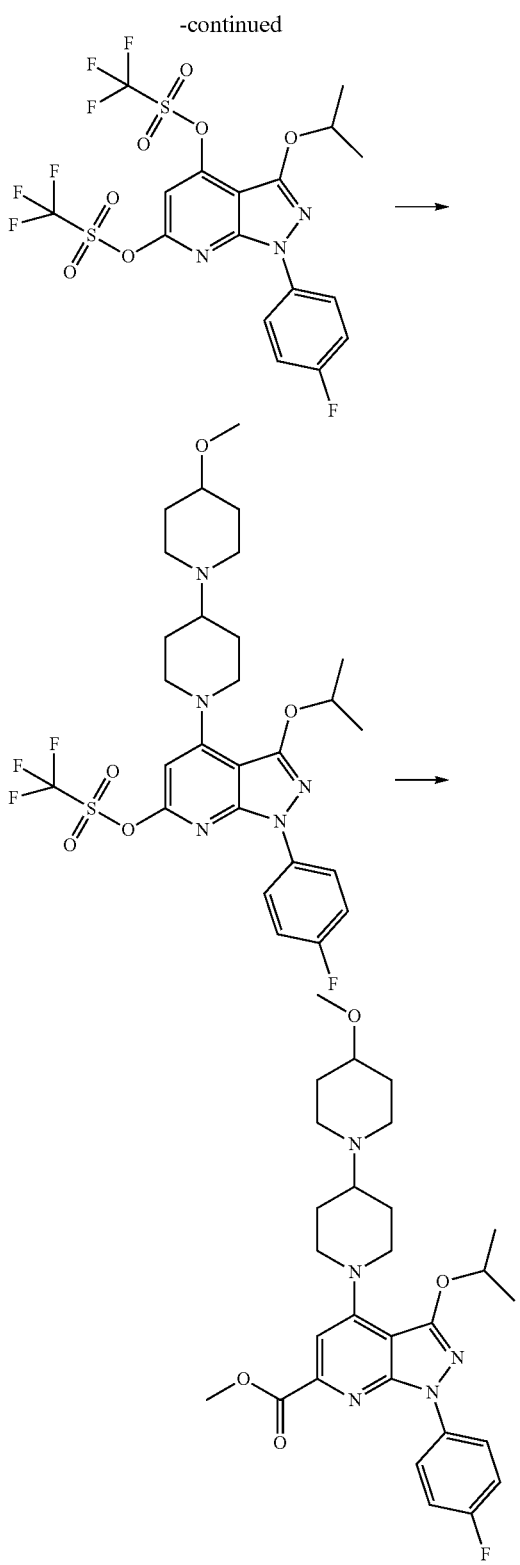

Step 1: 1-(4-fluorophenyl)-3-[(propan-2-yl)oxy]-1H-pyrazolo[3,4-b]pyridine-4,6-diol In a sealed tube, a suspension of AMP96 (215 mg, 0.91 mmol) and diethyl malonate ([105-53-3], 418 µL, 2.75 mmol) in Dowtherm® A was heated at 200° C. 4 hours. The reaction mixture was cooled down to 70-80° C. and poured onto a stirring solution of n-heptane (200 mL). The precipitate was collected by filtration, washed with n-heptane and dried at 40° C. under reduced pressure to give the titled compound.

Step 2: 1-(4-fluorophenyl)-3-[(propan-2-yl)oxy]-1H-pyrazolo[3,4-b]pyridine-4,6-diyl Bis(trifluoromethanesulfonate)

Trifluoromethanesulfonic anhydride ([358-23-6], 302 µL, 1.8 mmol) was added dropwise to a solution of 1-(4-fluorophenyl)-3-[(propan-2-yl)oxy]-1H-pyrazolo[3,4-b]pyridine-4,6-diol (270 mg, 0.9 mmol, Step 1) and pyridine (220 µL, 2.25 mmol) in acetonitrile (5 mL), maintaining the temperature around 20-25° C. The reaction mixture was stirred at RT for 20 hours. The reaction mixture was diluted with DCM and extracted twice with a saturated aqueous solution of NaHCO$_3$. The organic phase was separated, dried over MgSO$_4$, filtered and concentrated under reduced pressure. The resulting residue was purified by silica gel chromatography (n-heptane/ethyl acetate, 1/0 to 0/1) to yield the titled compound.

Step 3: 1-(4-fluorophenyl)-4-(4-methoxy[1,4'-bipiperidin]-1'-yl)-3-[(propan-2-yl)oxy]-1H-pyrazolo[3,4-b]pyridin-6-yl Trifluoromethanesulfonate A mixture of 1-(4-fluorophenyl)-3-[(propan-2-yl)oxy]-1H-pyrazolo[3,4-b]pyridine-4,6-diyl bis(trifluoromethanesulfonate) (29 mg, 50 µmol, Step 2), 4-methoxy-1-piperidin-4-ylpiperidine hydrochloride ([930603-98-8], 14 mg, 50 µmol) and DIPEA (35 µL, 200 µmol) in anhydrous DMSO (1 mL) was heated at 100° C. for 2 hours. The reaction mixture was cooled to RT and partitioned between ethyl acetate (50 mL) and water (30 mL). The organic phase was separated, dried over MgSO$_4$, filtered and concentrated in vacuo. The crude mixture was purified by flash chromatography on silica gel eluting with n-heptane/ethyl acetate (1/0 to 0/1) and ethyl acetate/(DCM/MeOH, 9/1) (1/0 to 0/1) to afford the titled compound.

Step 4: Methyl 1-(4-fluorophenyl)-4-(4-methoxy[1,4'-bipiperidin]-1'-yl)-3-[(propan-2-yl)oxy]-1H-pyrazolo[3,4-b]pyridine-6-carboxylate A pressured vessel was charged with 1-(4-fluorophenyl)-4-(4-methoxy[1,4'-bipiperidin]-1'-yl)-3-[(propan-2-yl)oxy]-1H-pyrazolo[3,4-b]pyridin-6-yl trifluoromethanesulfonate (145 mg, 240 µmol, Step 3), Pd(dppf)Cl$_2$.DCM ([95464-05-4], 4 mg, 4.8 µmol), and triethylamine (66 µL, 500 µmol) in MeOH (5 mL). The system was loaded with CO (6 bars) and heated at 100° C. for 1 hour. The vessel was cooled down to RT, and the mixture was concentrated under reduced pressure. The residue was purified by flash column chromatography eluting with a mixture of ethyl acetate/(DCM/MeOH, 9/1) (1/0 to 0/1) to give the titled compound.

257
Synthesis of AMI01:
4-(methoxymethyl)piperidin-4-ol Hydrochloride

258
Synthesis of AMI02: 4-[(1,1-dioxo-1,4-thiazinan-4-yl)methyl]piperidin-4-ol Hydrochloride

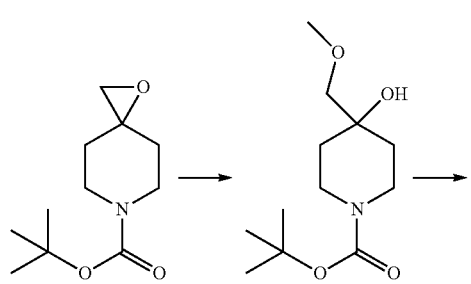

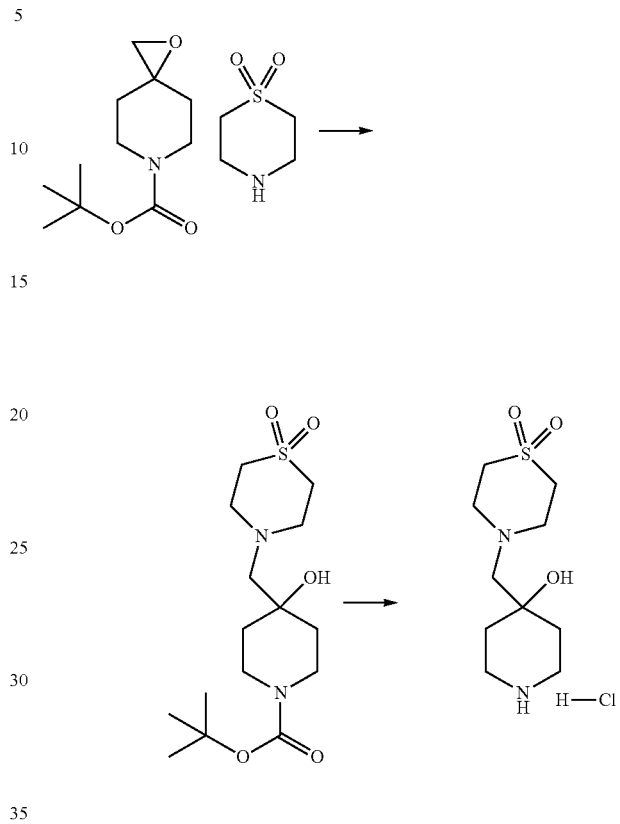

Step 1:
4-Hydroxy-4-methoxymethyl-piperidine-1-carboxylic Acid Tert-butyl Ester A suspension of tert-butyl 1-oxa-6-azaspiro[2.5]octane-6-carboxylate (CAS: 147804-30-6, 200 mg, 0.94 mmol) and sodium methoxide (61 mg, 1.13 mmol) in methanol (2 mL) was placed in a sealed tube and was heated at 100° C. for 20 hours. The reaction mixture was cooled to RT, acidified with acetic acid to pH 5-6, diluted with DCM and washed with water. The organic phase was separated using a phase separator and concentrated in vacuo. The titled compound was used as such in the next step without any further purification.

Step 2: 4-Methoxymethyl-piperidin-4-ol Hydrochloride

4-Hydroxy-4-methoxymethyl-piperidine-1-carboxylic acid tert-butyl ester (206 mg, 0.84 mmol) was dissolved in dioxane (2 mL). 4 M HCl in dioxane (1.05 mL, 4.2 mmol) was added, and the solution was stirred at RT for 20 hours. The volatiles were removed under reduced pressure. The titled compound was used as such in the next step without any further purification.

Step 1: Tert-butyl 4-[(1,1-dioxo-1,4-thiazinan-4-yl)methyl]-4-hydroxy-piperidine-1-carboxylate A solution of tert-butyl 1-oxa-6-azaspiro[2.5]octane-6-carboxylate (CAS: 147804-30-6, 150 mg, 0.7 mmol) and thiomorpholine 1,1-dioxide (CAS: 39093-93-1, 380 mg, 2.8 mmol) in ethanol (2 mL) was placed in a sealed tube and was heated at 75° C. for 20 hours. The reaction mixture was cooled to RT, diluted with DCM and washed with water. The organic phase was separated using a phase separator and concentrated in vacuo. The titled compound was obtained by flash column chromatography eluting with DCM/MeOH.

Step 2: 4-[(1,1-dioxo-1,4-thiazinan-4-yl)methyl] piperidin-4-ol Hydrochloride tert-Butyl 4-[(1,1-dioxo-1,4-thiazinan-4-yl)methyl]-4-hydroxy-piperidine-1-carboxylate (215 mg, 0.62 mmol) was dissolved in dioxane (2 mL). 4 M HCl in dioxane (0.89 mL, 3.6 mmol) was added, and the solution was stirred at RT for 20 hours. The volatiles were removed under reduced pressure. The titled compound was used as such in the next step without any further purification.

Synthesis of AMI03: (2S)-2-fluoro-N,N-dimethyl-2-(4-piperidyl)ethanamine Hydrochloride

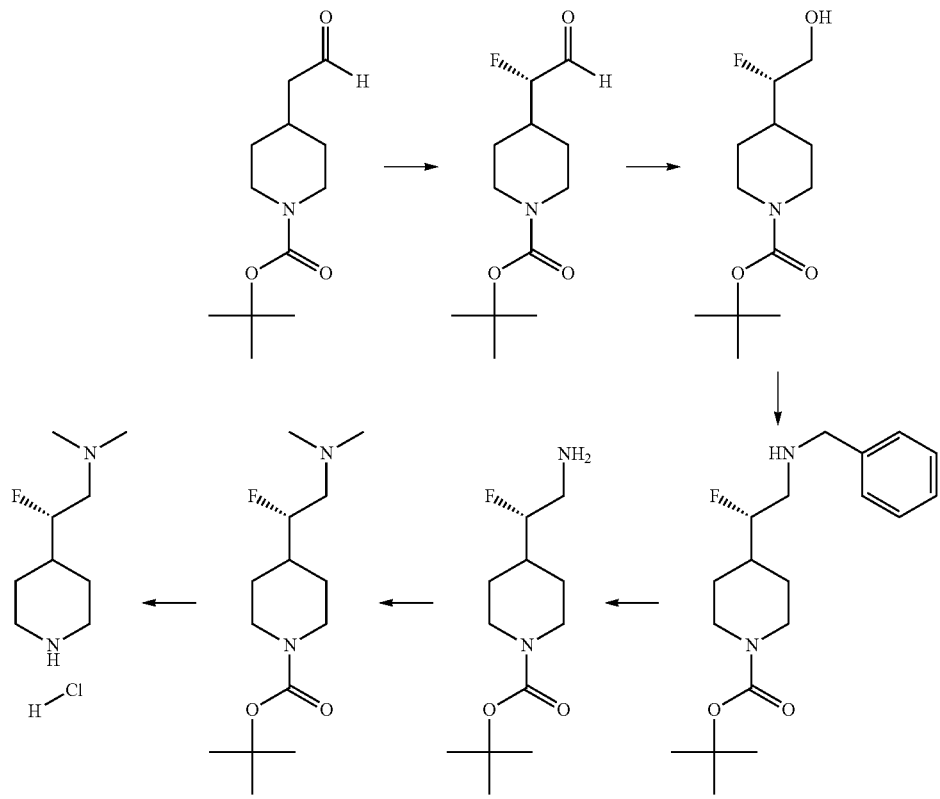

Step 1: (S)-tert-butyl 4-(1-fluoro-2-oxoethyl)piperidine-1-carboxylate

To a suspension of N-fluoro-N-(phenylsulfonyl)benzenesulfonamide ((CAS 133745-75-2, 347 g, 1100 mmol) and (5R)-(+)-2,2,3-trimethyl-5-benzyl-4-imidazolidinone dichloroacetic acid (CAS 857303-87-8, 76 g, 220 mmol) in THF and isopropyl alcohol at −20° C. was added a solution of tert-butyl 4-(2-oxoethyl)piperidine-1-carboxylate (250 g, 1100 mmol, CAS: 142374-19-4) in THF. The mixture was stirred at 10° C. for 16 h, diluted with hexane at −78° C. and filtered through silica, washed with hexane, then with saturated aqueous $NaHCO_3$, dried, filtered, and concentrated to give (S)-tert-butyl 4-(1-fluoro-2-oxoethyl)piperidine-1-carboxylate.

Step 2: (S)-tert-butyl 4-(1-fluoro-2-hydroxyethyl)piperidine-1-carboxylate

A solution of (S)-tert-butyl 4-(1-fluoro-2-oxoethyl)piperidine-1-carboxylate (10 g, 40.8 mmol) in dichloromethane (280 mL) and ethanol (220 mL) was stirred at 10° C. Then, sodium borohydride (CAS 16940-66-2, 4.0 g, 105.7 mmol, 2.6 equiv) was added. The mixture was stirred at 10° C. for 1 hour, was diluted with water and extracted with dichloromethane. The organic layer was dried, filtered and concentrated, and the residue was purified by chromatography on silica gel (petroleum ether:ethyl acetate) to give (S)-tert-butyl 4-(1-fluoro-2-hydroxyethyl)piperidine-1-carboxylate.

Step 3: (S)-tert-butyl 4-(2-(benzylamino)-1-fluoroethyl)piperidine-1-carboxylate Trifluoromethanesulfonic anhydride (CAS 358-23-6, 5.70 g, 20.22 mmol, 1.0 equiv) was added to a solution of (S)-tert-butyl 4-(1-fluoro-2-hydroxyethyl)piperidine-1-carboxylate (5 g, 20.22 mmol) and 2,6-dimethylpyridine (CAS 108-48-5, 2.166 g, 20.22 mmol, 1.0 equiv) in dichloromethane at 0° C. The mixture was stirred at 0° C. for 0.5 h. A separated round bottom flask was charged with benzylamine (2.166 g, 20.22 mmol, 1.0 equiv) in dichloromethane at 0° C. The solution of the triflate was then added slowly at 0° C. The reaction mixture was stirred at 25° C. for 12 hours, quenched with a saturated aqueous solution of sodium hydrogencarbonate, and extracted with dichloromethane. The organic fraction was concentrated. The residue was purified on silica gel chromatography, eluting with acetone/dichloromethane to give (S)-tert-butyl 4-(2-(benzylamino)-1-fluoroethyl)piperidine-1-carboxylate.

Step 4: (S)-tert-butyl 4-(2-amino-1-fluoroethyl)piperidine-1-carboxylate

To a solution of (S)-tert-butyl 4-(2-(benzylamino)-1-fluoroethyl)piperidine-1-carboxylate (4.5 g, 13.38 mmol) in methanol was added Pd/C, then the solution was stirred at 35° C. under hydrogen atmosphere (45 psi) for 12 hours. The mixture was filtered and concentrated to give (S)-tert-butyl 4-(2-amino-1-fluoroethyl)piperidine-1-carboxylate.

Step 5: (S)-tert-butyl 4-(2-(dimethylamino)-1-fluoroethyl)piperidine-1-carboxylate To a mixture of (S)-tert-butyl 4-(2-amino-1-fluoroethyl)piperidine-1-carboxylate (3.0 g, 12.18 mmol) in methanol was added paraformaldehyde (CAS 30525-89-4, 1.828 g, 60.9 mmol, 5.0 equiv) followed by three drops of acetic acid. The reaction mixture stirred for 1 hour. Then sodium cyanoborohydride (CAS 25895-60-7, 1.148 g, 18.27 mmol, 1.5 equiv) was added, and the mixture was stirred for 12 hours. The reaction mixture was filtered and concentrated, and the residue was purified by column chromatography on silica gel (DCM/MeOH) to afford (S)-tert-butyl 4-(2-(dimethylamino)-1-fluoroethyl)piperidine-1-carboxylate

Step 6: (S)-2-fluoro-N,N-dimethyl-2-(piperidin-4-yl)ethanamine hydrochloride To a solution of (S)-tert-butyl 4-(2-(dimethylamino)-1-fluoroethyl)piperidine-1-carboxylate (2 g, 7.29 mmol) in MeOH was added 4 N hydrogen chloride in methanol (10 mL, 40 mmol, 5.5 equiv), and the mixture was stirred at RT for 2 hours. Then the solution was concentrated to give (S)-2-fluoro-N,N-dimethyl-2-(piperidin-4-yl)ethanamine hydrochloride.

Synthesis of AMI04:
4-(ethoxymethyl)-4-fluoro-piperidine

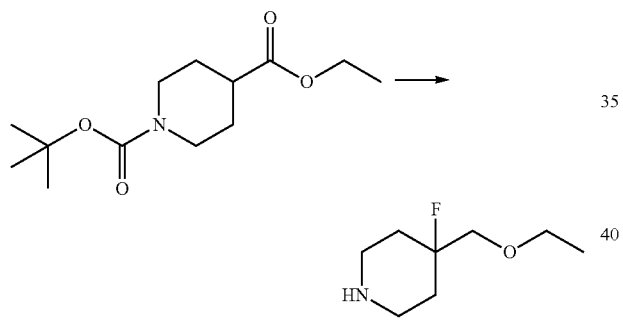

Step 1: 1-tert-butyl 4-ethyl 4-fluoropiperidine-1,4-dicarboxylate

In a 100 mL round-bottomed flask was combined 1-tert-butyl 4-ethyl piperidine-1,4-dicarboxylate (1 g, 3.89 mmol) and THF (10 mL). The solution was cooled to −78° C., and sodium hexamethyldisilazide (6 mL of 1 M THF solution, 6.00 mmol) was added slowly via syringe. After 60 min, N-fluoro-N-(phenylsulfonyl)benzenesulfonamide (2 g, 6.34 mmol) in THF (3 mL) was added. After 2 h, dichloromethane/water (1:1, 40 mL) was added. The aqueous layer was extracted with dichloromethane, and the combined organic fractions were dried over $Na_2SO_4$, filtered, and concentrated in vacuo.

Step 2: Tert-butyl 4-fluoro-4-(hydroxymethyl)piperidine-1-carboxylate

A solution of 1-tert-butyl 4-ethyl 4-fluoropiperidine-1,4-dicarboxylate (1.5 g, 5.45 mmol) in THF (5 mL) was cooled to 0° C., and then 1 M $LiAlH_4$ in THF (3.81 mL, 3.81 mmol) was added dropwise. The reaction mixture was warmed up to RT and stirred for 2 h. Water (0.9 mL) was added to the reaction mixture dropwise followed by 2 N NaOH (0.3 mL). The mixture was stirred for another 30 minutes, and then solid removed by filtration through diatomaceous earth and washed with EtOAc. The filtrate was washed with brine, dried over $Na_2SO_4$, and concentrated from acetonitrile under vacuum several time to remove the water to afford tert-butyl 4-fluoro-4-(hydroxymethyl)piperidine-1-carboxylate.

Step 3: Tert-butyl 4-(ethoxymethyl)-4-fluoropiperidine-1-carboxylate tert-Butyl 4-fluoro-4-(hydroxymethyl)piperidine-1-carboxylate (30 g, 129 mmol) was first treated with sodium hydride (6.17 g, 154 mmol) DMF (500 mL), and then iodoethane (24.07 g, 154 mmol) was added at room temperature. The reaction mixture was stirred at 25° C. for 12 h. The mixture was washed with $H_2O$ and extracted with EtOAc, and then the combined organic phases were washed with $H_2O$, and brine. The organic fraction was dried $Na_2SO_4$, filtered and concentrated to give tert-butyl 4-(ethoxymethyl)-4-fluoropiperidine-1-carboxylate (26.9 g, 103 mmol, 80% purity).

Step 4: 4-(ethoxymethyl)-4-fluoro-piperidine

A mixture of tert-butyl 4-(ethoxymethyl)-4-fluoropiperidine-1-carboxylate 26.9 g, 103 mmol) in ethyl acetate (200 mL) was made acidic by addition of HCl in ethyl acetate solution at 0° C. Then the mixture was allowed to warm to 15° C. and stirred at 15° C. for 3 h. The reaction mixture was concentrated under vacuum to yield 4-(ethoxymethyl)-4-fluoropiperidine as a hydrochloride salt (15.27 g, 95 mmol, 92% yield).

Synthesis of AMI05:
4-fluoro-4-(2-methoxyethoxymethyl)piperidine

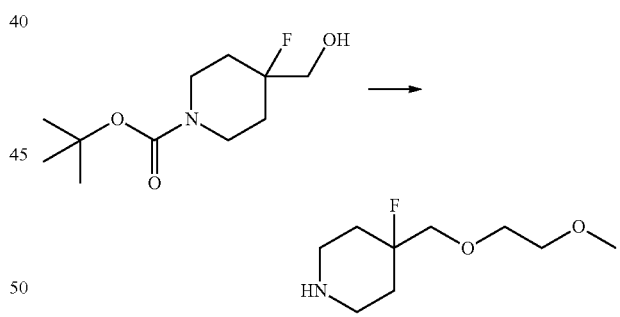

Step 1: Tert-butyl 4-fluoro-4-((2-methoxyethoxy)methyl)piperidine-1-carboxylate To a mixture of tert-butyl 4-fluoro-4-(hydroxymethyl) piperidine-1-carboxylate (30 g, 129 mmol, prepared as described in the synthesis of AMI04) in DMF (400 mL) was added sodium hydride (6.43 g, 161 mmol) at 0° C. After 15 minutes, 1-bromo-2-methoxyethane (35.7 g, 257 mmol) was added at 0° C., and the mixture was stirred at 25° C. for 12 h. The mixture was quenched with 200 mL of aqueous $NH_4Cl$ at 5° C. The organic layer was separated, washed with water and brine, dried over $Na_2SO_4$, and concentrated. After column chromatography on silica gel (petroleum ether/EtOAc=10:1 to petroleum ether/EtOAc=2:1), tert-butyl 4-fluoro-4-((2-methoxyethoxy)methyl)piperidine-1-carboxylate (20.5 g, 70.4 mmol, 54.% yield) was obtained.

Step 2: 4-fluoro-4-(2-methoxyethoxymethyl)piperidine

A solution of tert-butyl 4-fluoro-4-((2-methoxyethoxy)methyl)piperidine-1-carboxylate (20 g, 68.6 mmol) in 200 mL EtOAc was made acidic with HCl in EtOAc at room temperature. After TLC on silica gel (petroleum ether/EtOAc=1:1) showed that the reaction was complete, the mixture was concentrated to afford the titled compound as a hydrochloride salt (15 g, 65.9 mmol, 96% yield).

Synthesis of AMI07:
4-fluoro-4-(methoxymethyl)piperidine

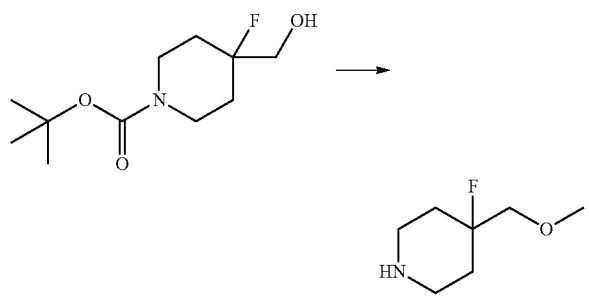

Step 1: Tert-butyl 4-fluoro-4-(methoxymethyl)piperidine-1-carboxylate

To a mixture of tert-butyl 4-fluoro-4-(hydroxymethyl)piperidine-1-carboxylate (30 g, 129 mmol, prepared as described in the synthesis of AMI04) and NaH (3.09 g, 129 mmol) in THF (500 mL) was added iodomethane (41.9 g, 295 mmol) at room temperature, and then the mixture was stirred at 25° C. for 12 h, The reaction mixture was diluted with water and extracted with EtOAc. The combined organic phases were washed with water and brine. The organic fraction was dried over $Na_2SO_4$, filtered, and concentrated under vacuum. The residue was purified on a silica gel column eluted with petroleum ether/EtOAc=2:1 to give tert-butyl 4-fluoro-4-(methoxymethyl)piperidine-1-carboxylate (25 g, 101 mmol, 79% yield).

Step 2: 4-fluoro-4-(methoxymethyl)piperidine

A mixture of tert-butyl 4-fluoro-4-(methoxymethyl)piperidine-1-carboxylate (25 g, 101 mmol) in EtOAc (300 mL) was made acidic with HCl in EtOAc at 0° C., and the mixture was allowed to warm to 15° C. and stirred at 15° C. for 3 h. The reaction mixture was concentrated under vacuum to yield the titled compound as a hydrochloride salt (13 g, 70.8 mmol, 70.0% yield).

Synthesis of AMI08:
3-fluoro-3-(2-methoxyethoxymethyl)piperidine

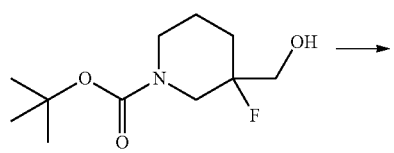

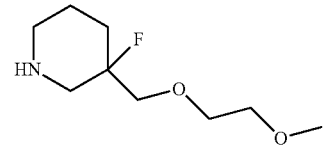

Step 1: Tert-butyl 3-fluoro-3-((2-methoxyethoxy)methyl)piperidine-1-carboxylate

To a mixture of tert-butyl 3-fluoro-3-(hydroxymethyl)piperidine-1-carboxylate (25 g, 107 mmol) in THF (300 mL) was added NaH (2.57 g, 107 mmol) at 0° C. After 15 minutes, 1-bromo-2-methoxyethane (29.8 g, 214 mmol) was added at 0° C. The mixture was stirred at 25° C. for 12 h, and then the reaction was quenched by the addition of saturated aqueous $NH_4Cl$ and extracted with EtOAc. The combined organic phases were washed with water and brine, dried over $Na_2SO_4$, filtered and concentrated in vacuum. The residue was added to a silica gel column eluted with hexanes:ethyl acetate (2:1) to give tert-butyl 3-fluoro-3-((2-methoxyethoxy)methyl)piperidine-1-carboxylate (22 g, 76 mmol, 70.5% yield).

Step 2: 3-fluoro-3-(2-methoxyethoxymethyl)piperidine

A mixture of tert-butyl 3-fluoro-3-((2-methoxyethoxy)methyl)piperidine-1-carboxylate (25 g, 86 mmol) in EtOAc (200 mL) was made acidic with HCl in EtOAc at 0° C. The mixture was allowed to warm to 15° C. and stirred at 15° C. for 3 h. The reaction mixture was concentrated under vacuum to the titled compound as a hydrochloride salt (15 g, 65.9 mmol, 77% yield).

Synthesis of AMI09:
2-(4-hydroxy-4-piperidyl)acetonitrile Hydrochloride

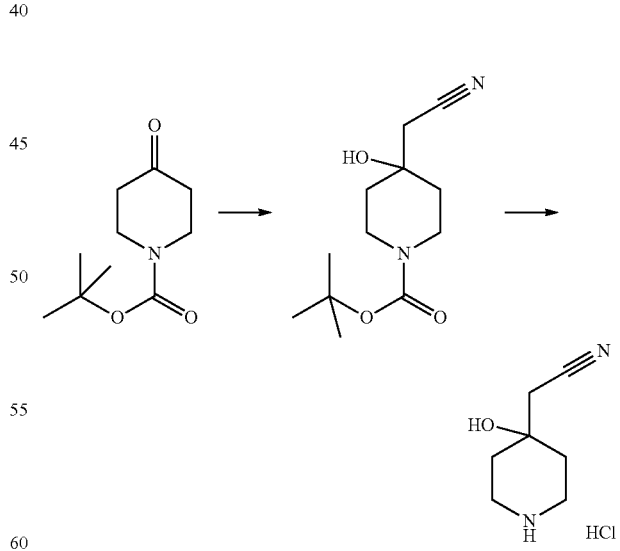

Step 1: Tert-butyl 4-(cyanomethyl)-4-hydroxy-piperidine-1-carboxylate

A flame-dried round bottom flask was cooled down to RT under argon. A solution of 1 M LiHMDS in THF (1.51 mL, 3.02 mmol, 2.0 equiv) was introduced into the flask and cooled down to −78° C. (acetone/dry ice bath). Dry MeCN (157 µL, 3.02 mmol, 2.0 equiv) in anhydrous THF (5 mL) was then added dropwise under argon, and the reaction mixture was stirred for 45 minutes at −78° C. At this point, a solution of 1-(tert-butoxycarbonyl)-4-piperidone (300 mg, 1.51 mmol, 1.0 equiv) in dry THF (5 mL) was added dropwise, and the reaction mixture was stirred at −78° C. for 1 h. The reaction mixture was quenched with an aqueous saturated solution of ammonium chloride and diluted with ethyl acetate. The two phases were separated, and the aqueous phase was extracted with ethyl acetate. The combined organic layers were washed with brine, dried over MgSO$_4$, filtered and concentrated in vacuo to afford tert-butyl 4-(cyanomethyl)-4-hydroxypiperidine-1-carboxylate which was used as such in the next step.

Step 2: 2-(4-hydroxy-4-piperidyl)acetonitrile Hydrochloride tert-Butyl 4-(cyanomethyl)-4-hydroxypiperidine-1-carboxylate (226 mg, 0.94 mmol, 1 equiv) was dissolved in dioxane (2.5 mL). 4 M HCl in dioxane (1.41 mL, 1.88 mmol, 6 equiv) was added, and the solution was stirred at RT for 5 days. The reaction mixture was concentrated under reduced pressure. The titled compound was used as such without any further purification.

Synthesis of AMI10: 4-methoxy-1,4'-bipiperidine

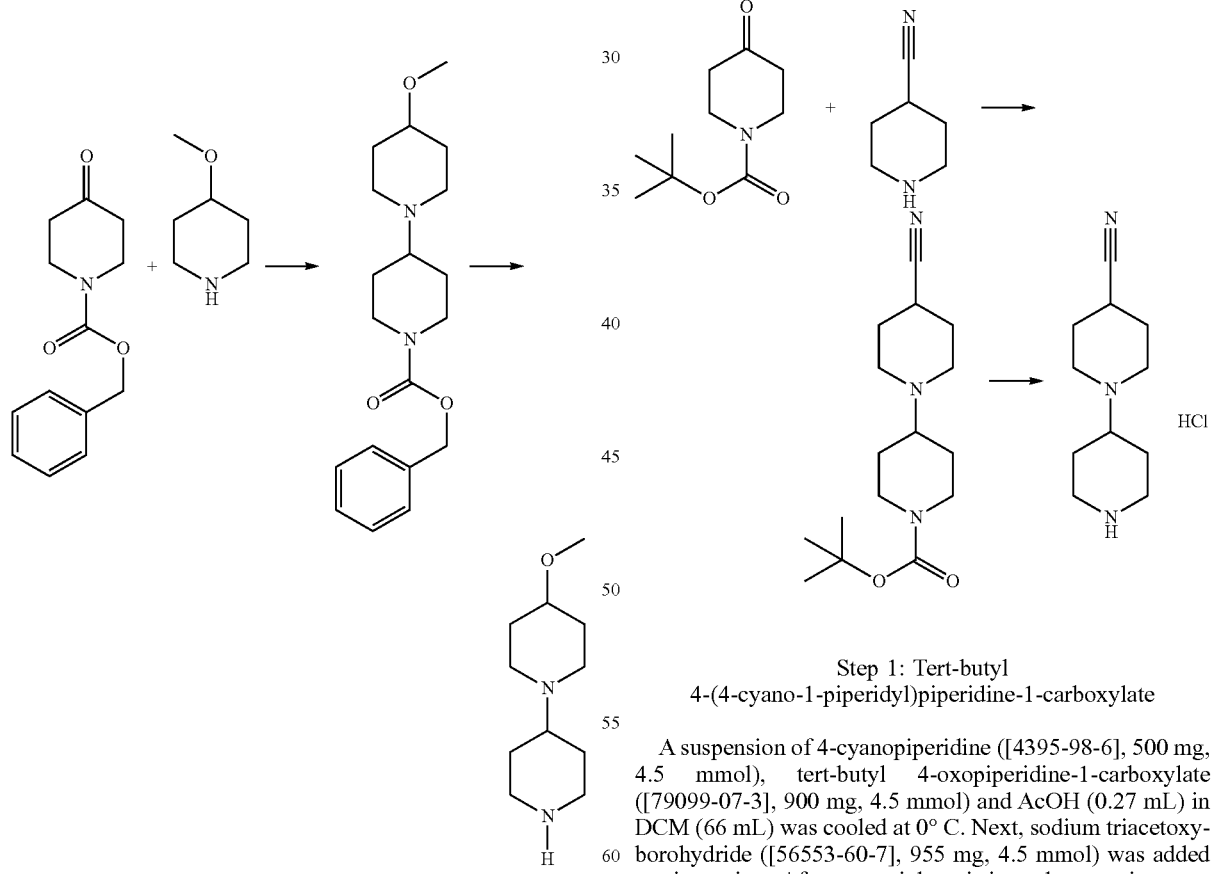

Step 1: Benzyl 4-methoxy-[1,4'-bipiperidine]-1'-carboxylate

To a solution of benzyl 4-oxopiperidine-1-carboxylate ([19099-93-5], 40 gram, 171 mmol) and 4-methoxypiperidine ([4045-24-3], 24.6 gram) in dichloromethane (800 mL) was added acetic acid (10.8 mL, 189 mmol) and sodium triacetoxyborohydride (54.5 gram, 257 mmol). The mixture was stirred at 0° C. for 120 minutes. Next, the mixture was washed with a saturated aqueous K$_2$CO$_3$ solution. The organic phase was separated and concentrated to give a residue that was purified by chromatography on silica gel using a gradient elution with CH$_2$Cl$_2$ to CH$_2$Cl$_2$/CH$_3$OH (100/0 to 97/2.5) to give the titled compound.

Step 2: 4-methoxy-1,4'-bipiperidine

Benzyl 4-methoxy-[1,4'-bipiperidine]-1'-carboxylate (23 gram, 69 mmol) was dissolved in CH$_3$OH (350 mL). The solution was flushed with N$_2$ and 10% Pd/C (7.3 gram, 6.9 mmol) was added. After applying a balloon with H$_2$, the mixture was stirred at ambient temperature overnight. Next, the mixture was filtered through diatomaceous earth, and the resulting filtrate was concentrated to give the titled compound.

Synthesis of AMI11:
1-piperidin-1-ium-4-ylpiperidine-4-carbonitrile Chloride

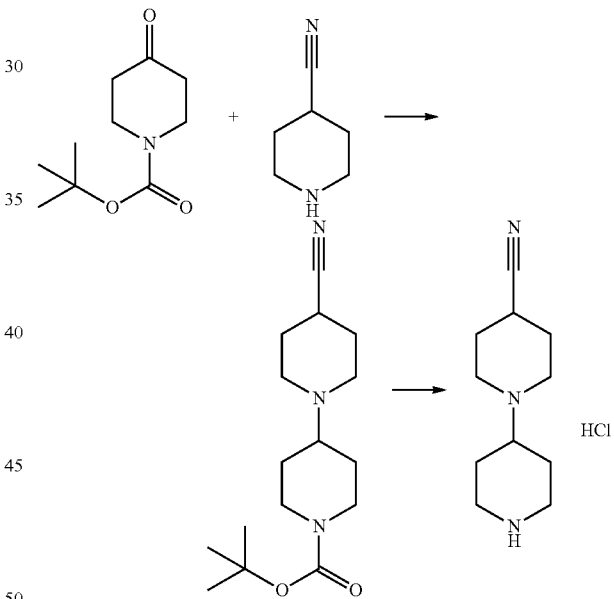

Step 1: Tert-butyl 4-(4-cyano-1-piperidyl)piperidine-1-carboxylate

A suspension of 4-cyanopiperidine ([4395-98-6], 500 mg, 4.5 mmol), tert-butyl 4-oxopiperidine-1-carboxylate ([79099-07-3], 900 mg, 4.5 mmol) and AcOH (0.27 mL) in DCM (66 mL) was cooled at 0° C. Next, sodium triacetoxyborohydride ([56553-60-7], 955 mg, 4.5 mmol) was added portion wise. After overnight stirring, the reaction was diluted with 60 mL of water together with a 1 N citric acid solution to bring down the pH till 3-4. The organic layer was separated and discarded. Next, the aqueous layer was brought to neutral pH with a saturated aqueous NaHCO$_3$ solution. After extraction with DCM, the organic phase was concentrated to give the titled compound.

Step 2:
1-piperidin-1-ium-4-ylpiperidine-4-carbonitrile Chloride tert-Butyl 4-(4-cyano-1-piperidyl)piperidine-1-carboxylate (662 mg, 2.26 mmol) was dissolved in DCM and trifluoroacetic acid ([76-05-1], 0.93 mL) was added. After overnight stirring, the mixture was concentrated to dryness. The obtained residue was suspended in 4 N HCl in dioxane. The addition of ethanol gave a suspension which was filtered to give the titled compound as a precipitate.

Synthesis of ALC02:
(2R)-2-fluoro-2-tetrahydropyran-4-yl-ethanol

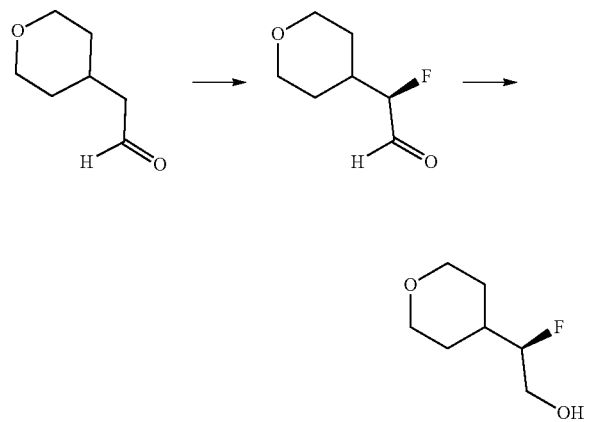

Step 1:
(2R)-2-fluoro-2-tetrahydropyran-4-yl-acetaldehyde

To a mixture of (R)-5-benzyl-2,2,3-trimethylimidazolidin-4-one dichloroacetic acid salt (CAS 857303-87-8, 2.71 g, 7.80 mmol, 0.2 equiv) and N-fluoro-N-(phenylsulfonyl)benzenesulfonamide (CAS 133745-75-2, 12.30 g, 39 mmol, 1.0 equiv) in THF (200 mL) and isopropyl alcohol (25 mL) was slowly added at −20° C. a solution 2-(tetrahydro-2H-pyran-4-yl)acetaldehyde (5 g, 39 mmol, CAS 65626-23-5) in THF (25 mL). The mixture was stirred at −20° C. for 12 hours, then diluted with hexane (800 mL) cooled to −78° C. and filtered through silica, washed with hexane. The filtrate was concentrated to give (R)-2-fluoro-2-(tetrahydro-2H-pyran-4-yl)acetaldehyde.

Step 2:
(2R)-2-fluoro-2-tetrahydropyran-4-yl-ethanol

To a solution of (R)-2-fluoro-2-(tetrahydro-2H-pyran-4-yl)acetaldehyde (4 g, 27.4 mmol) in dichloromethane (48 mL) and ethanol (40 mL) was added sodium borohydride (CAS 16940-66-2, 2.59 g, 68.4 mmol, 2.5 equiv). The mixture was stirred at 25° C. for 12 hours, then diluted with water and extracted with dichloromethane. The organic layer was dried, filtered, concentrated and purified by chromatography (petroleum ether, ethylate) to give (2R)-2-fluoro-2-tetrahydropyran-4-yl-ethanol.

Synthesis of ALC03: 1-[4-fluoro-4-(hydroxymethyl)-1-piperidyl]ethanone

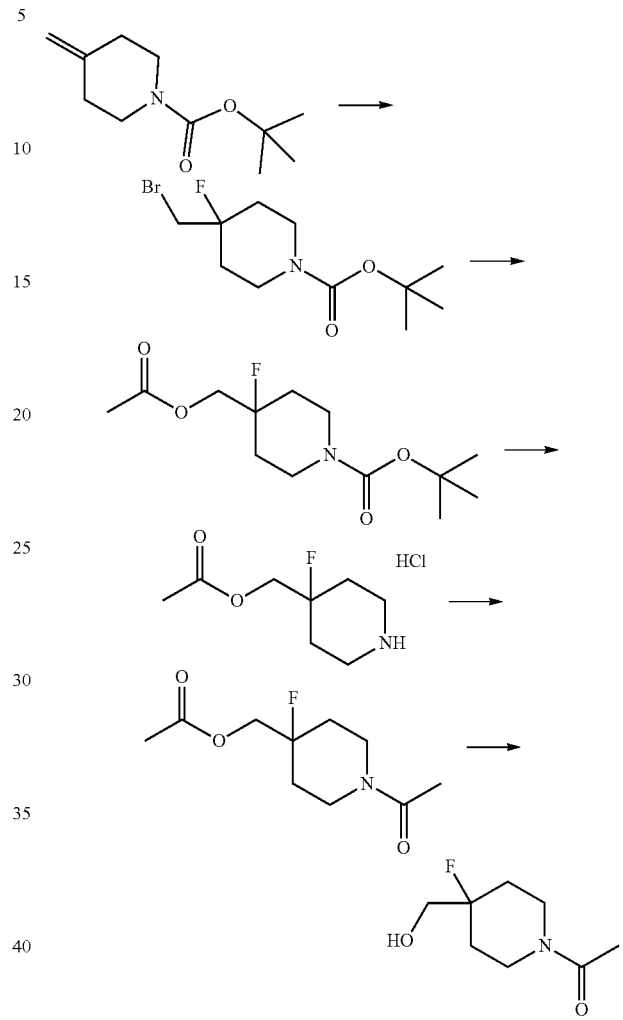

Step 1: Tert-butyl 4-(bromomethyl)-4-fluoropiperidine-1-carboxylate

To a mixture of tert-butyl 4-methylenepiperidine-1-carboxylate (159635-49-1, 50 g, 253 mmol) and triethylamine trihydrofluoride (102 g, 634 mmol) in dichloromethane (1 L) was added 1-bromopyrrolidine-2,5-dione (67.7 g, 380 mmol) at 0° C. After 15 min, stirring was continued at 20° C. for 3 h. Then the mixture was poured into ice-water, neutralized with aqueous 28% ammonia and extracted with dichloromethane. The combined extracts were washed with ~0.1 N HCl and with 5% aqueous sodium hydrogencarbonate solution, dried with sodium sulfate, filtered and concentrated. The residue was purified by column chromatography to provide tert-butyl 4-(bromomethyl)-4-fluoropiperidine-1-carboxylate (60.1 g, 203 mmol, 80% yield).

Step 2: Tert-butyl 4-(acetoxymethyl)-4-fluoropiperidine-1-carboxylate

To a mixture of tert-butyl 4-(bromomethyl)-4-fluoropiperidine-1-carboxylate (50 g, 169 mmol) and potassium iodide (7.01 g, 42.2 mmol) in dimethyl formamide (1.5 L) was added potassium acetate (249 g, 2532 mmol) at room temperature. The mixture was stirred at 120-140° C. for 12 h, then cooled, diluted with water, and extracted with ethyl acetate. The combined organic phases were washed with water and brine. The organic layer was dried over Na$_2$SO$_4$, filtered, and concentrated in vacuo. The residue was purified by chromatography on a silica gel column eluted with hexanes:ethyl acetate to give tert-butyl 4-(acetoxymethyl)-4-fluoropiperidine-1-carboxylate (42 g, 153 mmol, 90% yield).

Step 3: (4-fluoropiperidin-4-yl)methyl Acetate Hydrochloride

To a mixture of tert-butyl 4-(acetoxymethyl)-4-fluoropiperidine-1-carboxylate (50 g, 182 mmol) in ethyl acetate (400 mL) was added a solution of HCl (1 L) at 0° C. The mixture was allowed to warm to 15° C. and stirred at 15° C. overnight. The reaction mixture was concentrated under vacuum, and the residue washed with dichloromethane. Then the precipitate was collected by filtration to obtain (4-fluoropiperidin-4-yl)methyl acetate hydrochloride (33 g, 156 mmol, 86% yield).

Step 4: (1-acetyl-4-fluoropiperidin-4-yl)methyl Acetate

To a solution of (4-fluoropiperidin-4-yl)methyl acetate hydrochloride (30 g, 142 mmol) and triethylamine (59.3 mL, 425 mmol) in dichloromethane (300 mL) was added acetyl chloride (16.69 g, 213 mmol) at 0° C. The mixture was stirred overnight at 20° C., then diluted with dichloromethane and washed with water. The dichloromethane layer was concentrated to give crude (1-acetyl-4-fluoropiperidin-4-yl)methyl acetate (21 g, 97 mmol, 68.2% yield).

Step 5: 1-[4-fluoro-4-(hydroxymethyl)-1-piperidyl]ethanone (1-Acetyl-4-fluoropiperidin-4-yl)methyl acetate (30.8 g, 142 mmol) was dissolved in 3:1 THF:water (400 mL) at 0° C., and then lithium hydroxide (6.80 g, 284 mmol) was added in one portion. The reaction mixture was stirred for 1 hour at 0° C. The mixture was poured into ethyl acetate and water, shaken, and the layers separated. The aqueous layer was extracted with ethyl acetate. The ethyl acetate extracts were combined, dried over Na$_2$SO$_4$, and concentrated under reduced pressure. The residue was titrated with CH$_2$Cl$_2$ and cyclohexane to afford 1-[4-fluoro-4-(hydroxymethyl)-1-piperidyl]ethanone (19 g, 108 mmol, 76% yield). Alternatively, 1-[4-fluoro-4-(hydroxymethyl)-1-piperidyl]ethanone is available by treatment of commercially available (4-fluoropiperidin-4-yl)methanol (CAS: 949100-11-2) with acetic anhydride.

Synthesis of ALC04: 2-[isopropyl(oxetan-3-yl)amino]ethanol

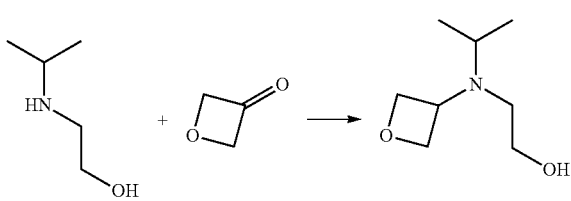

2-[Isopropyl(oxetan-3-yl)amino]ethanol is available by the reaction of (isopropylamino)ethanol (CAS: 109-56-8) with 1 equivalent of 3-oxetanone (CAS: 6704-31-0) in a solvent such as isopropanol or THF with a reducing agent such as sodium borohydride or sodium triacetoxyborohydride, followed by distillation.

Synthesis of ALC05: 2-(oxetan-3-yloxy)ethanol

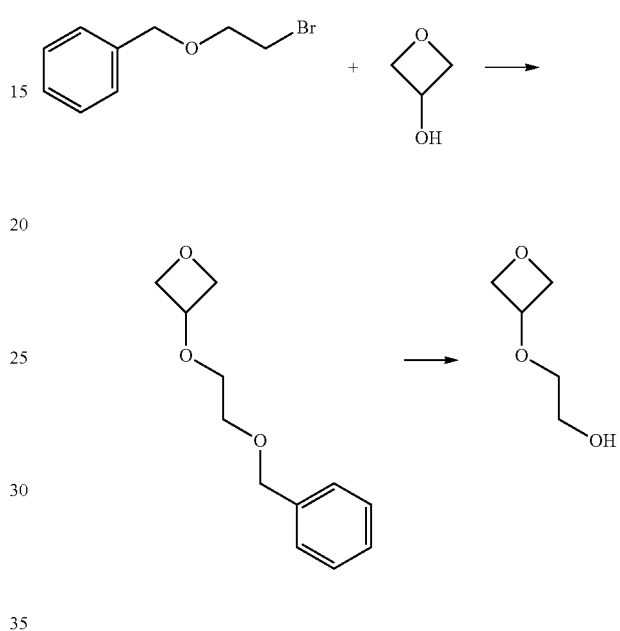

Step 1: 3-(2-benzyloxyethoxy)oxetane 1.0 M Lithium bis(trimethylsilyl)amide in THF (31.1 mL, 31.1 mmol, 1.2 equiv) was added dropwise at RT to a solution of oxetan-3-ol (1.92 g, 25.9 mmol) and ((2-bromoethoxy)methyl)benzene (6.13 g, 28.5 mmol, 1.1 equiv) in dioxane (15 mL). The mixture was stirred at ambient temperature for 2 hours. DMF (20 mL) was added along with sodium iodide, and the reaction mixture was stirred at ambient temperature overnight, then stirred at 70° C. for 20 hours. The reaction mixture was concentrated under reduced pressure, and the residue was partitioned between ethyl acetate and aqueous citric acid. The organic layer was washed twice with brine, then dried over MgSO$_4$, filtered and concentrated. The residue was purified by column chromatography on silica gel (dichloromethane and ethyl acetate) to give 3-(2-(benzyloxy)ethoxy)oxetane.

Step 2: 2-(oxetan-3-yloxy)ethanol

To a solution of 3-(2-(benzyloxy)ethoxy)oxetane (1.40 g, 6.72 mmol) in THF (28 mL) was added 20% palladium hydroxide on carbon (0.178 g, 0.645 mmol) in a 50 mL pressure bottle, and the mixture was stirred for 4 h under a hydrogen atmosphere. The reaction mixture was filtered free of catalyst and solids, and the filtrate was concentrated under reduced pressure. The residue was purified by silica gel chromatography eluting with a mixture of ethyl acetate and dichloromethane to give the titled compound.

Synthesis of Intermediate BF01: Potassium Trifluorido{[4-(methoxymethyl)piperidin-1-yl]methyl}borate

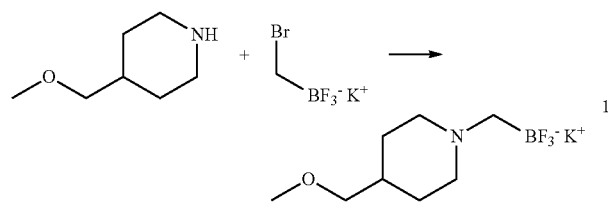

4-(Methoxymethyl)piperidine hydrochloride ([916317-00-5], 1.0 g, 6.03 mmol,), potassium bromomethyl trifluoroborate (1.21 g, 6.03 mmol), $KHCO_3$ (1.2 g, 12.1 mmol) and KI (100 mg, 0.6 mmol) were stirred under $N_2$ in dry THF (8 mL) at 80° C. for 4 hours. The reaction mixture was cooled to room temperature and concentrated in vacuo. The residue was suspended in dry acetone and filtered. The filtrate was treated with diethyl ether, and the resulting precipitate was collected by filtration and dried to afford the titled compound, which was used as such in the next step.

TABLE IX

| | | List of amines | | | | |
|---|---|---|---|---|---|---|
| Int. | Structure | Name | SM | method | MW | Mes |
| AMI01 | | 4-(methoxymethyl)piperidin-4-ol hydrochloride | 147804-30-6 | Specific example | 181 | |
| AMI02 | | 4-[(1,1-dioxo-1,4-thiazinan-4-yl)methyl]piperidin-4-ol hydrochloride | 147804-30-6 | Specific example | 284 | |
| AMI03 | | (2S)-2-fluoro-N,N-dimethyl-2-(4-piperidyl)ethanamine hydrochloride | 142374-19-4 | Specific example | 210 | |
| AMI04 | | 4-(ethoxymethyl)-4-fluoro-piperidine | 142851-03-4 | Specific example | 161 | |

US 10,259,810 B2

TABLE IX-continued

List of amines

| Int. | Structure | Name | SM | method | MW | Mes |
|---|---|---|---|---|---|---|
| AMI05 | 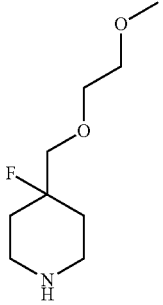 | 4-fluoro-4-(2-methoxyethoxy methyl)piperidine | 614730-97-1 | Specific example | 191 | |
| AMI06 955082-95-8 or 955028-84-9 (HCl salt) | 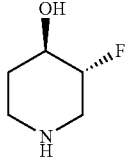 | (3R,4R)-3-fluoropiperidin-4-ol | | | 119 | |
| AMI07 | 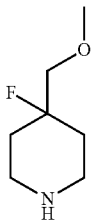 | 4-fluoro-4-(methoxymethyl) piperidine | 614730-97-1 | Specific example | 147 | |
| AMI08 | 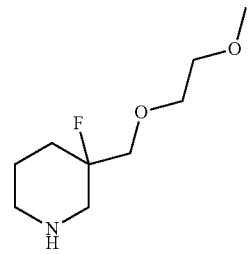 | 3-fluoro-3-(2-methoxyethoxy methyl)piperidine | 1209781-11-2 | Specific example | 191 | |
| AMI09 | 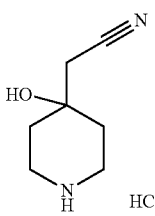 | 2-(4-hydroxy-4-piperidyl) acetonitrile hydrochloride | 79099-07-3 | Specific example | 140 | |
| AMI10 | 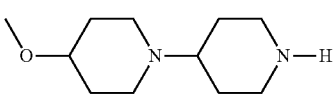 | 4-methoxy-1,4'-bipiperidine | 19099-93-5 and 4045-24-3 | Specific example | 198 | |
| AMI11 | 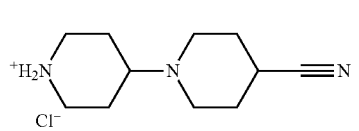 [SMILES: N#CC1CCN(C2CC[NH2+]CC2)CC1 ; [Cl-]] | 1-piperidin-1-ium-4-ylpiperidine-4-carbonitrile chloride | 79099-07-3 and 4395-98-6 | Specific example | 249 | |

TABLE X

| Int. | Structure | Name | SM | method | MW | Mes |
|---|---|---|---|---|---|---|
| ALC01 | 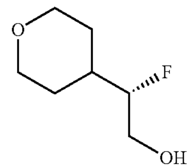 | (2S)-2-fluoro-2-2-tetrahydro-pyran-4-yl-ethanol | | Analogous to ALC02 | 148 | |
| ALC02 | 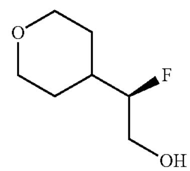 | (2R)-2-fluoro-2-tetrahydropyran-4-yl-ethanol | 65626-23-5 | Specific example | 148 | |
| ALC03 | 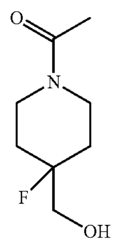 | 1-[4-fluoro-4-(hydroxymethyl)-1-piperidyl]ethanone | 159635-49-1 | Specific example | 175 | |
| ALC04 | 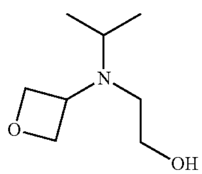 | 2-[isopropyl(oxetan-3-yl)amino]ethanol | | Specific example | 159 | |
| ALC05 | 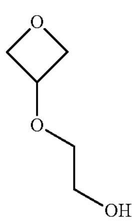 | 2-(oxetan-3-yloxy)ethanol | | Specific example | 118 | |
| ALC06 | 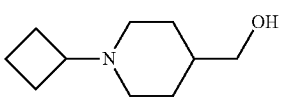 [SMILES: OCC1CCN(C2CCC2)CC1] | (1-cyclobutyl-4-piperidyl)methanol | 6457-49-4 and 1191-95-3 | 118 | 169 | 170 |
| ALC07 | 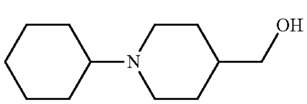 [SMILES: OCC1CCN(C2CCCCC2)CC1] | (1-cyclohexyl-4-piperidyl)methanol | 6457-49-4 and 108-94-1 | 118 | 197 | 198 |
| ALC08 | 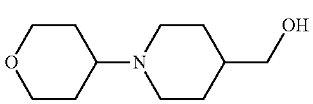 | (1-tetrahydro-pyran-4-yl-4-piperidyl)methanol | 6457-49-4 and 29943-42-8 | 118 | 199 | 200 |
| ALC09 | 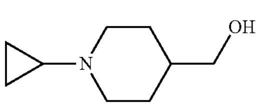 [SMILES: OCC1CCN(C2CC2)CC1] | (1-cyclopropyl-4-piperidyl)methanol | 6457-49-4 and 27374-25-0 | 126 | 155 | 156 |

TABLE XI

List of BF₃ salts

| Int. | Structure | Name | SM | method | MW | Mes |
|---|---|---|---|---|---|---|
| BF01 | 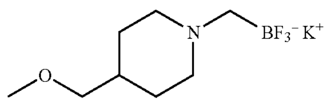 | potassium trifluorido{[4-(methoxymethyl)piperidin-1-yl]methyl}borate | 916317-00-5 and 888711-44-2 | Specific example | 249 | NA |

TABLE XII

List of esters

| Int. | Structure | Name | SM | method | MW | Mes |
|---|---|---|---|---|---|---|
| E001 | 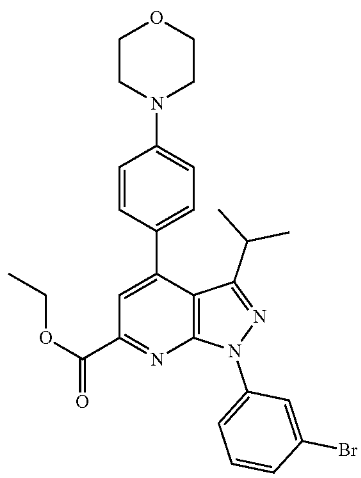 [SMILES: CCOC(=O)c1cc(-c2ccc(N3CCOCC3)cc2)c2c(C(C)C)nn(-c3cccc(Br)c3)c2n1] | ethyl 1-(3-bromophenyl)-3-isopropyl-4-(4-morpholinophenyl)pyrazolo[3,4-b]pyridine-6-carboxylate | A242 | I9, Specific example | 548-550 | 549-551 |
| E002 | 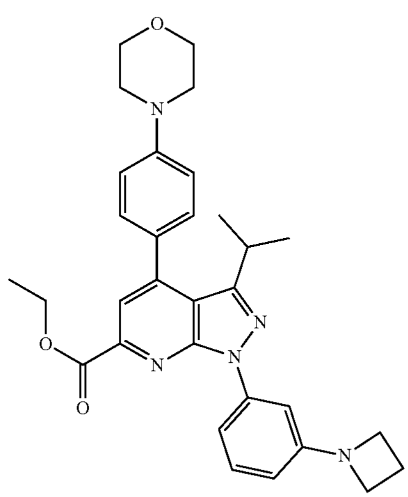 [SMILES: CCOC(=O)c1cc(-c2ccc(N3CCOCC3)cc2)c2c(C(C)C)nn(-c3cccc(N4CCC4)c3)c2n1] | ethyl 1-[3-(azetidin-1-yl)phenyl]-3-isopropyl-4-(4-morpholinophenyl)pyrazolo[3,4-b]pyridine-6-carboxylate | E001, 935670-07-8 | I8, Specific example | 525 | 526 |

TABLE XII-continued

List of esters

| Int. | Structure | Name | SM | method | MW | Mes |
|---|---|---|---|---|---|---|
| E003 | 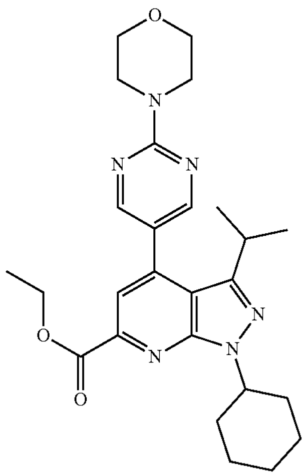 [SMILES: CCOC(=O)c1cc(-c2cnc(N3CCOCC3)nc2)c2c(C(C)C)nn(C3CCCCC3)c2n1] | ethyl 1-cyclohexyl-3-isopropyl-4-(2-morpholinopyrimidin-5-yl)pyrazolo[3,4-b]pyridine-6-carboxylate | ALP22, AMP23 | I1 | 478 | 479 |
| E004 | 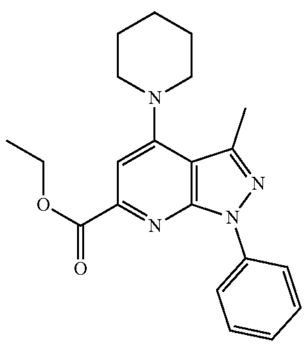 [SMILES: CCOC(=O)c1cc(N2CCCCC2)c2c(C)nn(-c3ccccc3)c2n1] | ethyl 3-methyl-1-phenyl-4-(1-piperidyl)pyrazolo[3,4-b]pyridine-6-carboxylate | HP13, 98-77-1 | I3 | 364 | 365 |
| E005 | 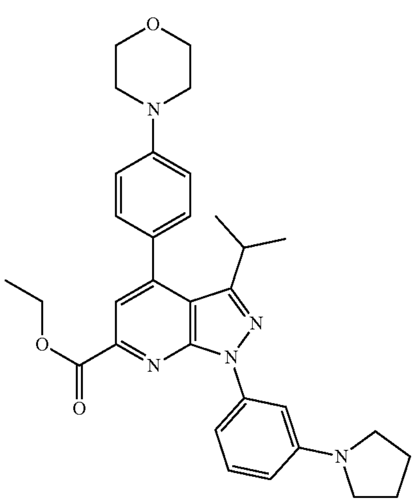 [SMILES: CCOC(=O)c1cc(-c2ccc(N3CCOCC3)cc2)c2c(C(C)C)nn(-c3cccc(N4CCCC4)c3)c2n1] | ethyl 3-isopropyl-4-(4-morpholinophenyl)-1-(3-pyrrolidin-1-ylphenyl)pyrazolo[3,4-b]pyridine-6-carboxylate | E001 | I8 | 539 | 540 |

TABLE XII-continued

List of esters

| Int. | Structure | Name | SM | method | MW | Mes |
|---|---|---|---|---|---|---|
| E006 | 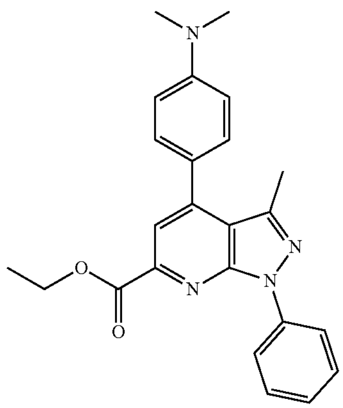 [SMILES: CCOC(=O)c1cc(-c2ccc(N(C)C)cc2)c2c(C)nn(-c3ccccc3)c2n1] | ethyl 4-[4-(dimethylamino)phenyl]-3-methyl-1-phenyl-pyrazolo[3,4-b]pyridine-6-carboxylate | ALP25, 1131-18-6 | I1 | 400 | 401 |
| E007 | 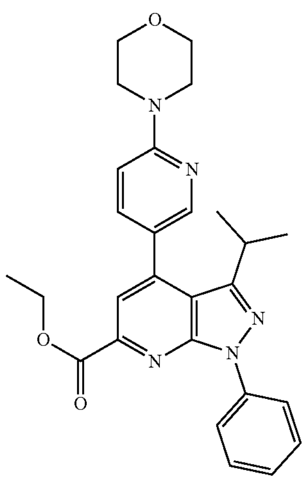 [SMILES: CCOC(=O)c1cc(-c2ccc(N3CCOCC3)nc2)c2c(C(C)C)nn(-c3ccccc3)c2n1] | ethyl 3-isopropyl-4-(6-morpholino-3-pyridyl)-1-phenyl-pyrazolo[3,4-b]pyridine-6-carboxylate | ALP26, AMP04 | I1 | 471 | 472 |
| E008 | 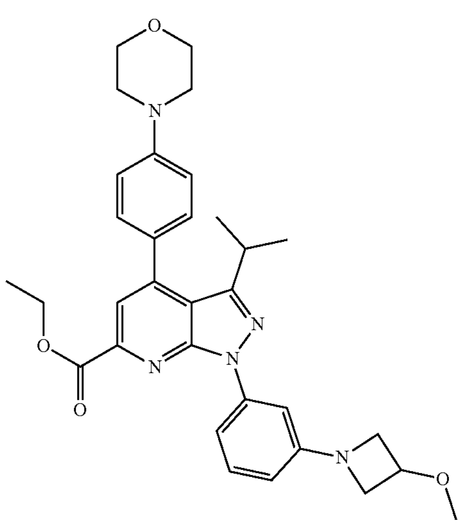 [SMILES: CCOC(=O)c1cc(-c2ccc(N3CCOCC3)cc2)c2c(C(C)C)nn(-c3cccc(N4CC(OC)C4)c3)c2n1] | ethyl 3-isopropyl-1-[3-(3-methoxyazetidin-1-yl)phenyl]-4-(4-morpholinophenyl)pyrazolo[3,4-b]pyridine-6-carboxylate | E001, 110925-17-2 | I8, Specific example | 555 | 556 |

TABLE XII-continued

List of esters

| Int. | Structure | Name | SM | method | MW | Mes |
|---|---|---|---|---|---|---|
| E009 | 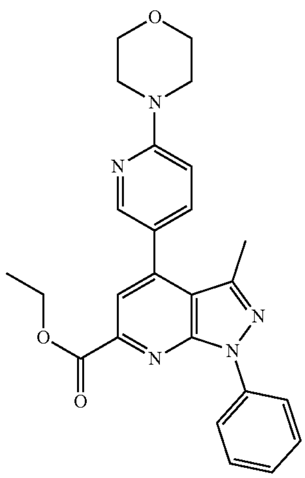 [SMILES: CCOC(=O)c1cc(-c2ccc(N3CCOCC3)nc2)c2c(C)nn(-c3ccccc3)c2n1] | ethyl 3-methyl-4-(6-morpholino-3-pyridyl)-1-phenyl-pyrazolo[3,4-b]pyridine-6-carboxylate | ALP26, 1131-18-6 | I1 | 443 | 444 |
| E010 | 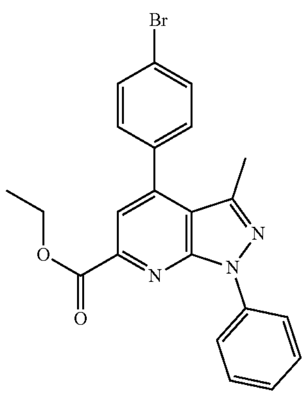 [SMILES: CCOC(=O)c1cc(-c2ccc(Br)cc2)c2c(C)nn(-c3ccccc3)c2n1] | ethyl 4-(4-bromophenyl)-3-methyl-1-phenyl-pyrazolo[3,4-b]pyridine-6-carboxylate | A246 | I9 | 435-437 | 436-438 |
| E011 | 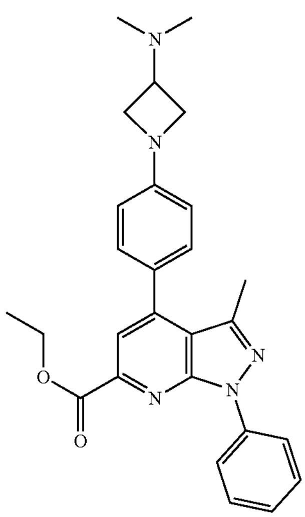 [SMILES: CCOC(=O)c1cc(-c2ccc(N3CC(N(C)C)C3)cc2)c2c(C)nn(-c3ccccc3)c2n1] | ethyl 4-[4-[3-(dimethylamino)azetidin-1-yl]phenyl]-3-methyl-1-phenyl-pyrazolo[3,4-b]pyridine-6-carboxylate | E010, 138022-85-2 | I10 Specific example | 455 | 456 |

TABLE XII-continued

List of esters

| Int. | Structure | Name | SM | method | MW | Mes |
|------|-----------|------|----|--------|----|----|
| E012 | 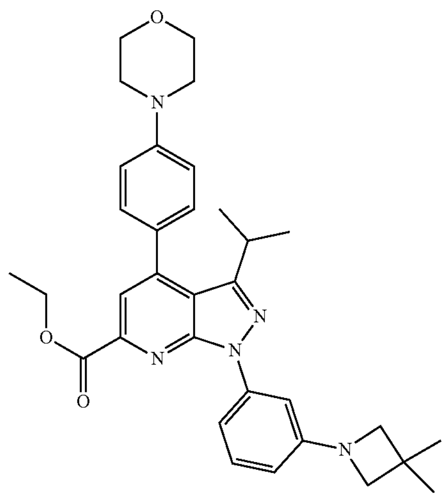 [SMILES: CCOC(=O)c1cc(-c2ccc(N3CCOCC3)cc2)c2c(C(C)C)nn(-c3cccc(N4CC(C)(C)C4)c3)c2n1] | ethyl 1-[3-(3,3-dimethylazetidin-1-yl)phenyl]-3-isopropyl-4-(4-morpholinophenyl)pyrazolo[3,4-b]pyridine-6-carboxylate | E001, 19816-92-3 | I8 | 553 | 554 |
| E013 | 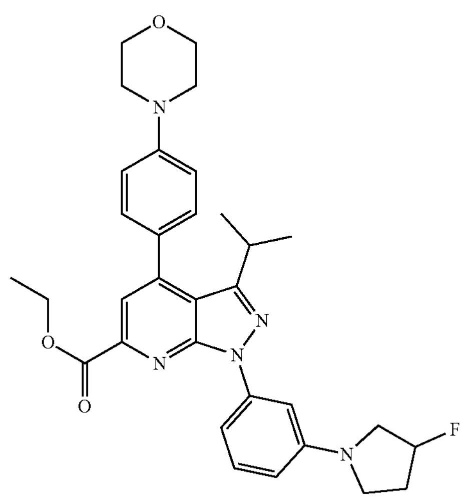 [SMILES: CCOC(=O)c1cc(-c2ccc(N3CCOCC3)cc2)c2c(C(C)C)nn(-c3cccc(N4CCC(F)C4)c3)c2n1] | ethyl 1-[3-(3-fluoropyrrolidin-1-yl)phenyl]-3-isopropyl-4-(4-morpholinophenyl)pyrazolo[3,4-b]pyridine-6-carboxylate | E001-116574-74-4 | I8 | 553 | 558 |
| E014 | 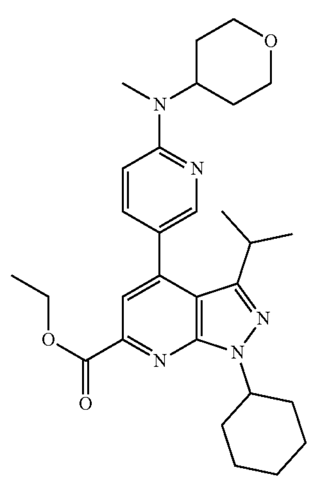 [SMILES: CCOC(=O)c1cc(-c2ccc(N(C)C3CCOCC3)nc2)c2c(C(C)C)nn(C3CCCCC3)c2n1] | ethyl 1-cyclohexyl-3-isopropyl-4-[6-[methyl(tetrahydropyran-4-yl)amino]-3-pyridyl]pyrazolo[3,4-b]pyridine-6-carboxylate | ALP10, AMP23 | I1 | 505 | 506 |

TABLE XII-continued

List of esters

| Int. | Structure | Name | SM | method | MW | Mes |
|---|---|---|---|---|---|---|
| E015 | 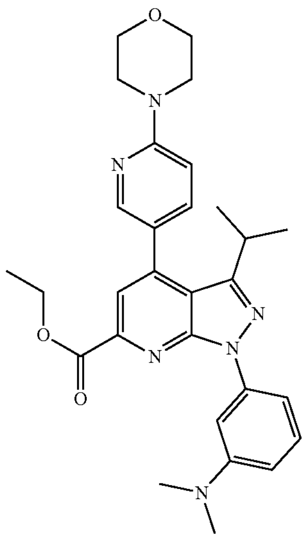 [SMILES: CCOC(=O)c1cc(-c2ccc(N3CCOCC3)nc2)c2c(C(C)C)nn(-c3cccc(N(C)C)c3)c2n1] | ethyl 1-[3-(dimethylamino)phenyl]-3-isopropyl-4-(6-morpholino-3-pyridyl)pyrazolo[3,4-b]pyridine-6-carboxylate | ALP26, AMP06 | I1 | 514 | 515 |
| E016 | 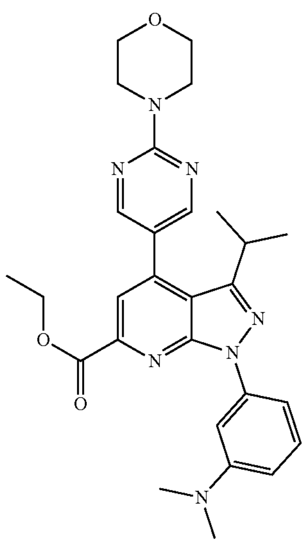 [SMILES: CCOC(=O)c1cc(-c2cnc(N3CCOCC3)nc2)c2c(C(C)C)nn(-c3cccc(N(C)C)c3)c2n1] | ethyl 1-[3-(dimethylamino)phenyl]-3-isopropyl-4-(2-morpholinopyrimidin-5-yl)pyrazolo[3,4-b]pyridine-6-carboxylate | ALP22, AMP06 | I1 | 515 | 516 |
| E017 | 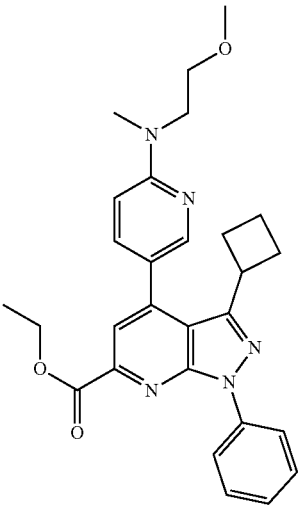 [SMILES: CCOC(=O)c1cc(-c2ccc(N(C)CCOC)nc2)c2c(C3CCC3)nn(-c3ccccc3)c2n1] | ethyl 3-cyclobutyl-4-[6-[2-methoxyethyl(methyl)amino]-3-pyridyl]-1-phenyl-pyrazolo[3,4-b]pyridine-6-carboxylate | ALP08, AMP29 | I1 | 485 | 486 |

TABLE XII-continued

List of esters

| Int. | Structure | Name | SM | method | MW | Mes |
|---|---|---|---|---|---|---|
| E018 | 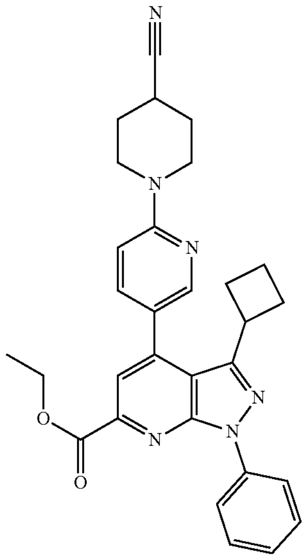 [SMILES: CCOC(=O)c1cc(-c2ccc(N3CCC(C#N)CC3)nc2)c2c(C3CCC3)nn(-c3ccccc3)c2n1] | ethyl 4-[6-(4-cyano-1-piperidyl)-3-pyridyl]-3-cyclobutyl-1-phenyl-pyrazolo[3,4-b]pyridine-6-carboxylate | ALP09, AMP29 | I1 | 506 | 507 |
| E019 | 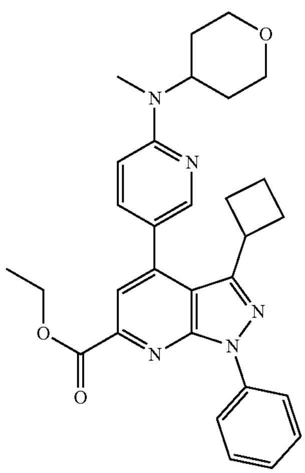 [SMILES: CCOC(=O)c1cc(-c2ccc(N(C)C3CCOCC3)nc2)c2c(C3CCC3)nn(-c3ccccc3)c2n1] | ethyl 3-cyclobutyl-4-[6-[methyl(tetrahydropyran-4-yl)amino]-3-pyridyl]-1-phenyl-pyrazolo[3,4-b]pyridine-6-carboxylate | ALP10, AMP29 | I1 | 511 | 512 |
| E020 | 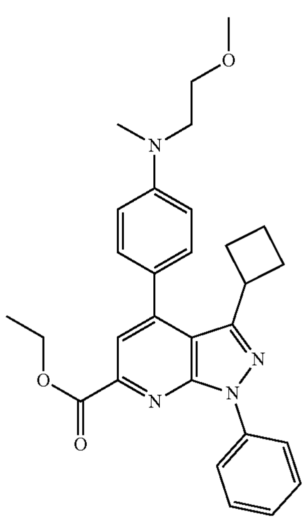 [SMILES: CCOC(=O)c1cc(-c2ccc(N(C)CCOC)cc2)c2c(C3CCC3)nn(-c3ccccc3)c2n1] | ethyl 3-cyclobutyl-4-[4-[2-methoxyethyl(methyl)amino]phenyl]-1-phenyl-pyrazolo[3,4-b]pyridine-6-carboxylate | ALP11, AMP29 | I1 | 484 | 485 |

TABLE XII-continued

List of esters

| Int. | Structure | Name | SM | method | MW | Mes |
|---|---|---|---|---|---|---|
| E021 | 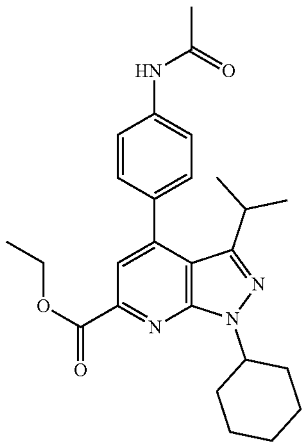 [SMILES: CCOC(=O)c1cc(-c2ccc(NC(C)=O)cc2)c2c(C(C)C)nn(C3CCCCC3)c2n1] | ethyl 4-(4-acetamidophenyl)-1-cyclohexyl-3-isopropyl-pyrazolo[3,4-b]pyridine-6-carboxylate | ALP24, AMP23 | I1 | 448 | 449 |
| E022 | 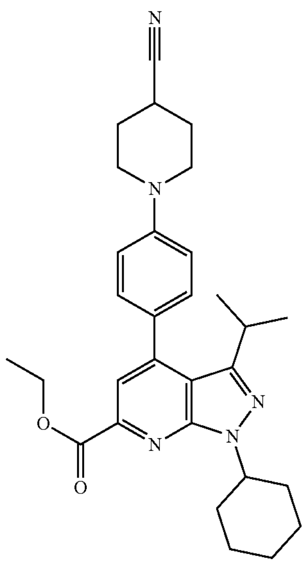 [SMILES: CCOC(=O)c1cc(-c2ccc(N3CCC(C#N)CC3)cc2)c2c(C(C)C)nn(C3CCCCC3)c2n1] | ethyl 4-[4-(4-cyano-1-piperidyl)phenyl]-1-cyclohexyl-3-isopropyl-pyrazolo[3,4-b]pyridine-6-carboxylate | ALP12, AMP23 | I1 | 499 | 500 |
| E023 | 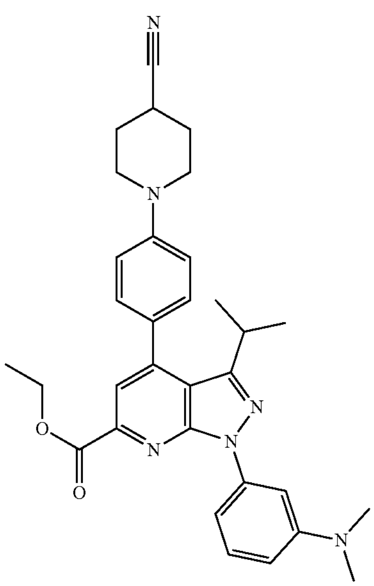 [SMILES: CCOC(=O)c1cc(-c2ccc(N3CCC(C#N)CC3)cc2)c2c(C(C)C)nn(-c3cccc(N(C)C)c3)c2n1] | ethyl 4-[4-(4-cyano-1-piperidyl)phenyl]-1-[3-(dimethylamino)phenyl]-3-isopropyl-pyrazolo[3,4-b]pyridine-6-carboxylate | ALP12, AMP06 | I1 | 536 | 537 |

TABLE XII-continued
List of esters
| Int. | Structure | Name | SM | method | MW | Mes |
|---|---|---|---|---|---|---|
| E024 | 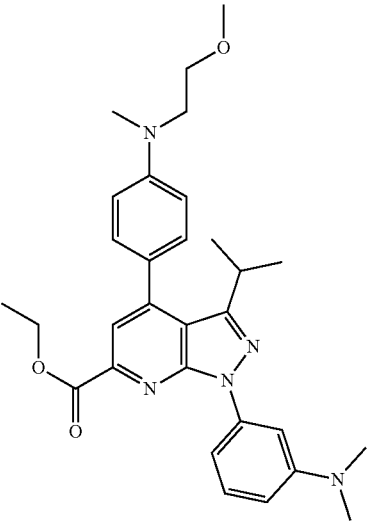 [SMILES: CCOC(=O)c1cc(-c2ccc(N(C)CCOC)cc2)c2c(C(C)C)nn(-c3cccc(N(C)C)c3)c2n1] | ethyl 1-[3-(dimethylamino)phenyl]-3-isopropyl-4-[4-[2-methoxyethyl(methyl)amino]phenyl]pyrazolo[3,4-b]pyridine-6-carboxylate | ALP11, AMP06 | I1 | 515 | 516 |
| E025 | 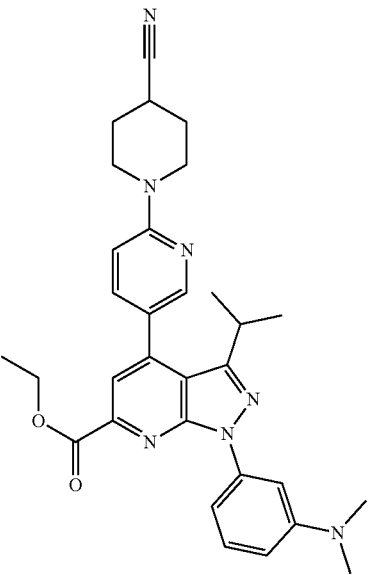 [SMILES: CCOC(=O)c1cc(-c2ccc(N3CCC(C#N)CC3)nc2)c2c(C(C)C)nn(-c3cccc(N(C)C)c3)c2n1] | ethyl 4-[6-(4-cyano-1-piperidyl)-3-pyridyl]-1-[3-(dimethylamino)phenyl]-3-isopropyl-pyrazolo[3,4-b]pyridine-6-carboxylate | ALP09, AMP06 | I1 | 537 | 538 |

TABLE XII-continued
| | | List of esters | | | | |
|---|---|---|---|---|---|---|
| Int. | Structure | Name | SM | method | MW | Mes |
| E026 | 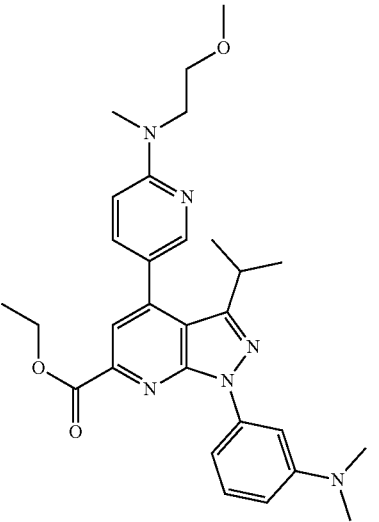 [SMILES: CCOC(=O)c1cc(-c2ccc(N(C)CCOC)nc2)c2c(C(C)C)nn(-c3cccc(N(C)C)c3)c2n1] | ethyl 1-[3-(dimethylamino)phenyl]-3-isopropyl-4-[6-[2-methoxyethyl(methyl)amino]-3-pyridyl]pyrazolo[3,4-b]pyridine-6-carboxylate | ALP08, AMP06 | I1 | 516 | 517 |
| E027 | 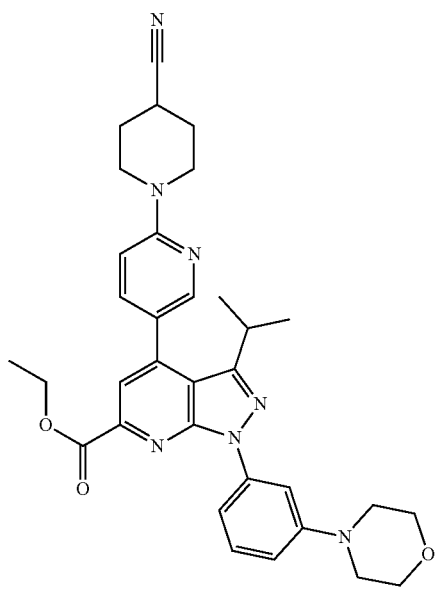 [SMILES: CCOC(=O)c1cc(-c2ccc(N3CCC(C#N)CC3)nc2)c2c(C(C)C)nn(-c3cccc(N4CCOCC4)c3)c2n1] | ethyl 4-[6-(4-cyano-1-piperidyl)-3-pyridyl]-3-isopropyl-1-(3-morpholinophenyl)pyrazolo[3,4-b]pyridine-6-carboxylate | ALP09, AMP10 | I1 | 579 | 580 |

TABLE XII-continued

List of esters

| Int. | Structure | Name | SM | method | MW | Mes |
|---|---|---|---|---|---|---|
| E028 | 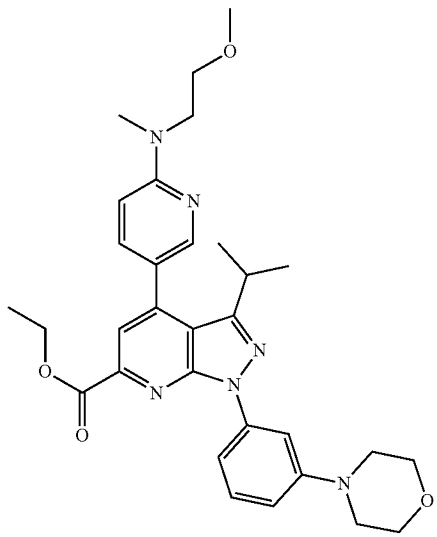 [SMILES: CCOC(=O)c1cc(-c2ccc(N(C)CCOC)nc2)c2c(C(C)C)nn(-c3cccc(N4CCOCC4)c3)c2n1] | ethyl 3-isopropyl-4-[6-[2-methoxyethyl(methyl)amino]-3-pyridyl]-1-(3-morpholinophenyl)pyrazolo[3,4-b]pyridine-6-carboxylate | ALP08, AMP10 | I1 | 558 | 559 |
| E029 | 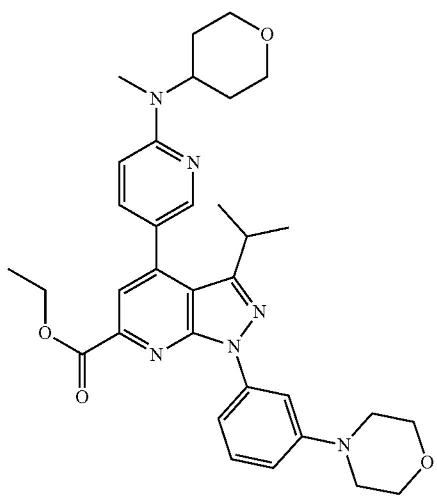 [SMILES: CCOC(=O)c1cc(-c2ccc(N(C)C3CCOCC3)nc2)c2c(C(C)C)nn(-c3cccc(N4CCOCC4)c3)c2n1] | ethyl 3-isopropyl-4-[6-[methyl(tetrahydropyran-4-yl)amino]-3-pyridyl]-1-(3-morpholinophenyl)pyrazolo[3,4-b]pyridine-6-carboxylate | ALP10, AMP10 | I1 | 584 | 585 |
| E030 | 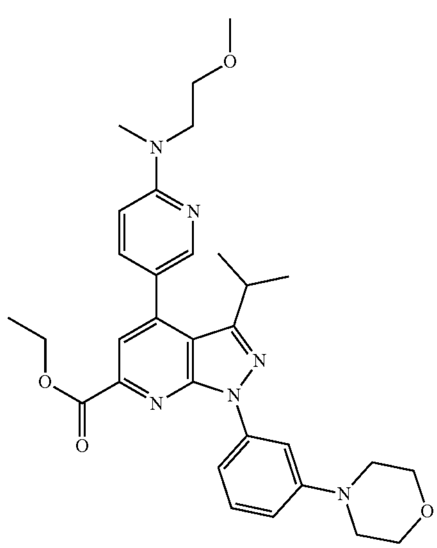 [SMILES: CCOC(=O)c1cc(-c2ccc(N(C)CCOC)nc2)c2c(C(C)C)nn(-c3cccc(N4CCOCC4)c3)c2n1] | ethyl 3-isopropyl-4-[4-[2-methoxyethyl(methyl)amino]phenyl]-1-(3-morpholinophenyl)pyrazolo[3,4-b]pyridine-6-carboxylate | ALP11, AMP10 | I1 | 557 | 558 |

TABLE XII-continued

List of esters

| Int. | Structure | Name | SM | method | MW | Mes |
|---|---|---|---|---|---|---|
| E031 | 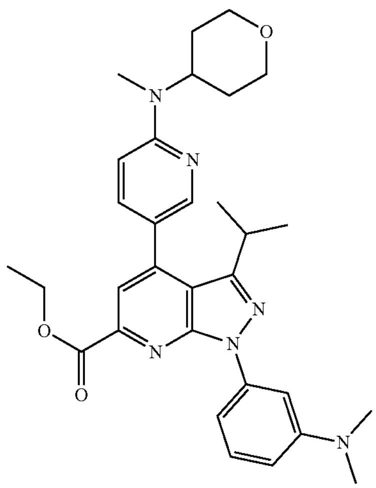 [SMILES: CCOC(=O)c1cc(-c2ccc(N(C)C3CCOCC3)nc2)c2c(C(C)C)nn(-c3cccc(N(C)C)c3)c2n1] | ethyl 1-[3-(dimethylamino)phenyl]-3-isopropyl-4-[6-[methyl(tetrahydropyran-4-yl)amino]-3-pyridyl]pyrazolo[3,4-b]pyridine-6-carboxylate | ALP10, AMP06 | I1 | 542 | 543 |
| E032 | 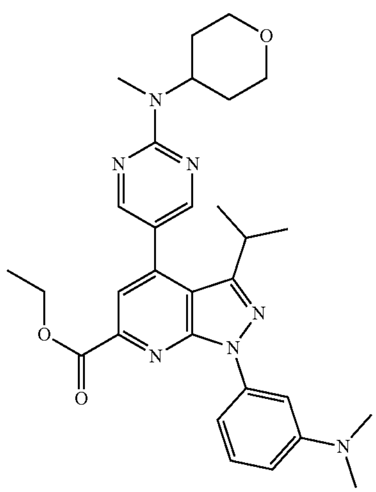 [SMILES: CCOC(=O)c1cc(-c2cnc(N(C)C3CCOCC3)nc2)c2c(C(C)C)nn(-c3cccc(N(C)C)c3)c2n1] | ethyl 1-[3-(dimethylamino)phenyl]-3-isopropyl-4-[2-[methyl(tetrahydropyran-4-yl)amino]pyrimidin-5-yl]pyrazolo[3,4-b]pyridine-6-carboxylate | ALP13, AMP06 | I1 | 543 | 544 |
| E033 | 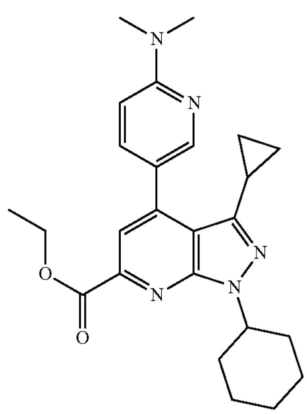 [SMILES: CCOC(=O)c1cc(-c2ccc(N(C)C)nc2)c2c(C3CC3)nn(C3CCCCC3)c2n1] | ethyl 1-cyclohexyl-3-cyclopropyl-4-[6-(dimethylamino)-3-pyridyl]pyrazolo[3,4-b]pyridine-6-carboxylate | ALP20, AMP39 | I1 | 433 | 434 |

TABLE XII-continued

List of esters

| Int. | Structure | Name | SM | method | MW | Mes |
|---|---|---|---|---|---|---|
| E034 | 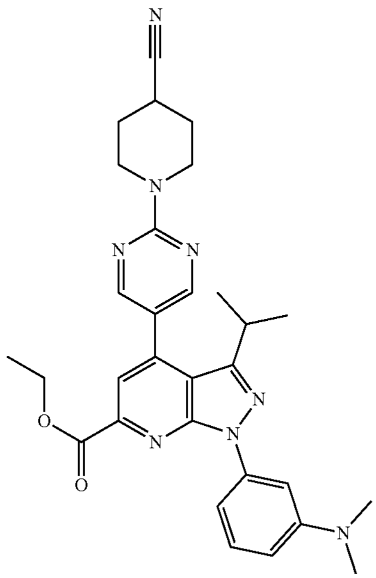 [SMILES: CCOC(=O)c1cc(-c2cnc(N3CCC(C#N)CC3)nc2)c2c(C(C)C)nn(-c3cccc(N(C)C)c3)c2n1] | ethyl 4-[2-(4-cyano-1-piperidyl)pyrimidin-5-yl]-1-[3-(dimethylamino)phenyl]-3-isopropyl-pyrazolo[3,4-b]pyridine-6-carboxylate | ALP14, AMP06 | I1 | 538 | 539 |
| E035 | 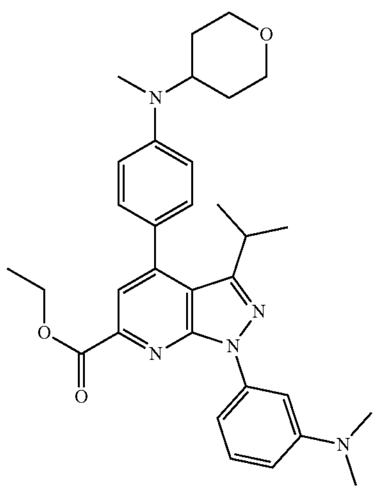 [SMILES: CCOC(=O)c1cc(-c2ccc(N(C)C3CCOCC3)cc2)c2c(C(C)C)nn(-c3cccc(N(C)C)c3)c2n1] | ethyl 1-[3-(dimethylamino)phenyl]-3-isopropyl-4-[4-[methyl(tetrahydro-pyran-4-yl)amino]phenyl]pyrazolo[3,4-b]pyridine-6-carboxylate | ALP15, AMP06 | I1 | 541 | 542 |
| E036 | 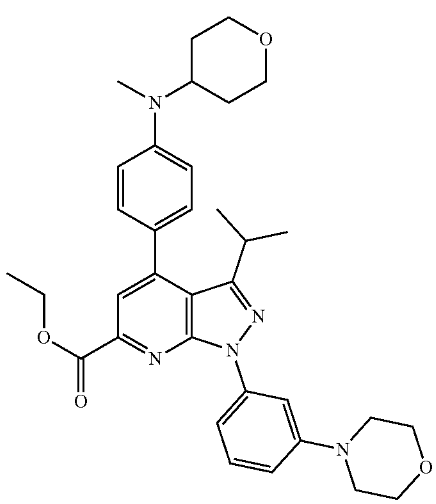 [SMILES: CCOC(=O)c1cc(-c2ccc(N(C)C3CCOCC3)cc2)c2c(C(C)C)nn(-c3cccc(N4CCOCC4)c3)c2n1] | ethyl 3-isopropyl-4-[4-[methyl(tetrahydro-pyran-4-yl)amino]phenyl]-1-(3-morpholinophenyl)pyrazolo[3,4-b]pyridine-6-carboxylate | ALP15, AMP10 | I1 | 583 | 584 |

TABLE XII-continued

List of esters

| Int. | Structure | Name | SM | method | MW | Mes |
|---|---|---|---|---|---|---|
| E037 | 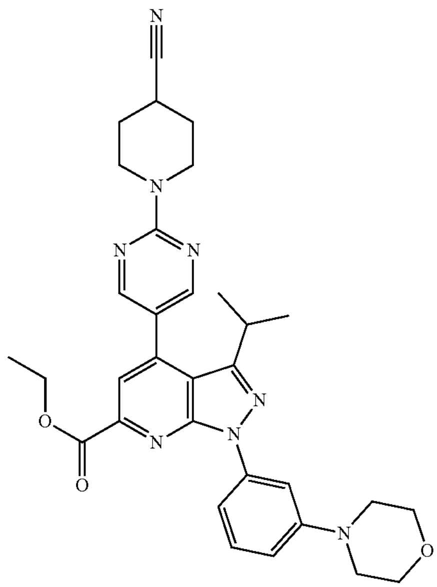 [SMILES: CCOC(=O)c1cc(-c2cnc(N3CCC(C#N)CC3)nc2)c2c(C(C)C)nn(-c3cccc(N4CCOCC4)c3)c2n1] | ethyl 4-[2-(4-cyano-1-piperidyl)pyrimidin-5-yl]-3-isopropyl-1-(3-morpholinophenyl)pyrazolo[3,4-6]pyridine-6-carboxylate | ALP14, AMP10 | I1 | 580 | 581 |
| E038 | 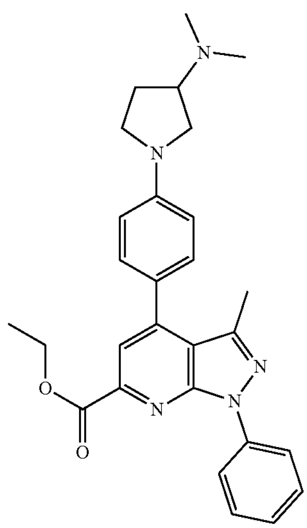 [SMILES: CCOC(=O)c1cc(-c2ccc(N3CCC(N(C)C)C3)cc2)c2c(C)nn(-c3ccccc3)c2n1] | ethyl 4-[4-[3-(dimethylamino)pyrrolidin-1-yl]phenyl]-3-methyl-1-phenyl-pyrazolo[3,4-b]pyridine-6-carboxylate | E010, 69478-75-7 | I10 | 469 | 470 |
| E039 | 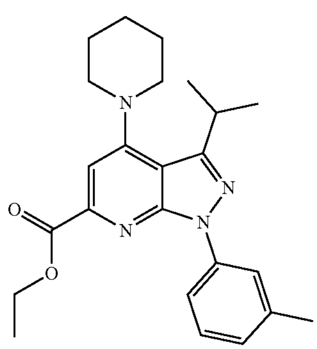 [SMILES: CCOC(=O)c1cc(N2CCCCC2)c2c(C(C)C)nn(-c3cccc(C)c3)c2n1] | ethyl 3-isopropyl-1-(m-tolyl)-4-(1-piperidyl)pyrazolo[3,4-b]pyridine-6-carboxylate | Hp01, 98-77-1 | I3 | 406 | 407 |

TABLE XII-continued
List of esters
| Int. | Structure | Name | SM | method | MW | Mes |
|---|---|---|---|---|---|---|
| E040 | 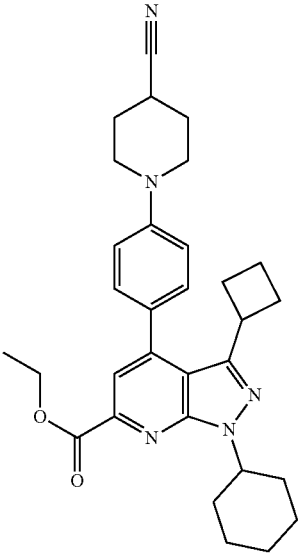 [SMILES: CCOC(=O)c1cc(-c2ccc(N3CCC(C#N)CC3)cc2)c2c(C3CCC3)nn(C3CCCCC3)c2n1] | ethyl 4-[4-(4-cyano-1-piperidyl)phenyl]-3-cyclobutyl-1-cyclohexyl-pyrazolo[3,4-b]pyridine-6-carboxylate | ALP12, AMP35 | I1 | 511 | 512 |
| E041 | 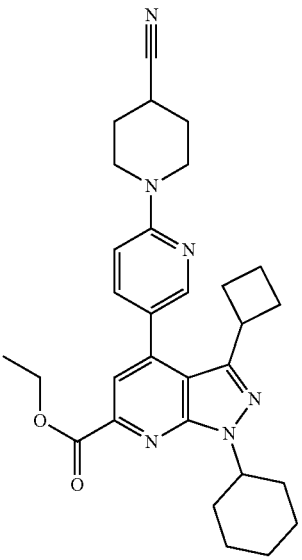 [SMILES: CCOC(=O)c1cc(-c2ccc(N3CCC(C#N)CC3)nc2)c2c(C3CCC3)nn(C3CCCCC3)c2n1] | ethyl 4-[6-(4-cyano-1-piperidyl)-3-pyridyl]-3-cyclobutyl-1-cyclohexyl-pyrazolo[3,4-b]pyridine-6-carboxylate | ALP09, AMP35 | I1 | 512 | 513 |

TABLE XII-continued

List of esters

| Int. | Structure | Name | SM | method | MW | Mes |
|---|---|---|---|---|---|---|
| E042 | 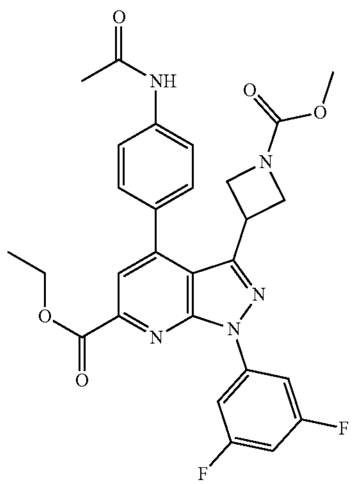 [SMILES: CCOC(=O)c1cc(-c2ccc(NC(C)=O)cc2)c2c(C3CN(C(=O)OC)C3)nn(-c3cc(F)cc(F)c3)c2n1] | ethyl 4-(4-acetamidophenyl)-1-(3,5-difluorophenyl)-3-(1-methoxycarbonyl-azetidin-3-yl)pyrazolo[3,4-b]pyridine-6-carboxylate | E043 | I11 Specific example | 549 | 550 |
| E043 | 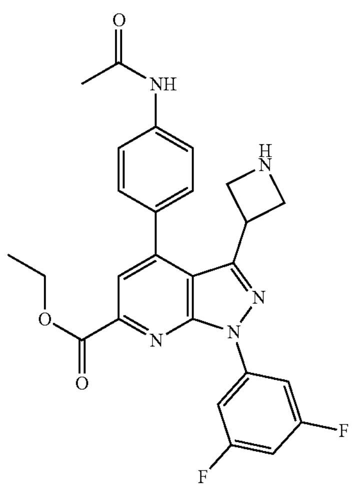 [SMILES: CCOC(=O)c1cc(-c2ccc(NC(C)=O)cc2)c2c(C3CNC3)nn(-c3cc(F)cc(F)c3)c2n1] | ethyl 4-(4-acetamidophenyl)-3-(azetidin-3-yl)-1-(3,5-difluorophenyl)pyrazolo[3,4-b]pyridine-6-carboxylate | E044 | Specific example | 491 | 492 |
| E044 | 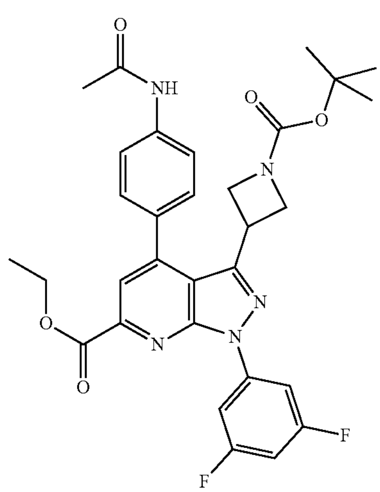 [SMILES: CCOC(=O)c1cc(-c2ccc(NC(C)=O)cc2)c2c(C3CN(C(=O)OC(C)(C)C)C3)nn(-c3cc(F)cc(F)c3)c2n1] | ethyl 4-(4-acetamidophenyl)-3-(1-tert-butoxycarbonylazetidin-3-yl)-1-(3,5-difluorophenyl)pyrazolo[3,4-b]pyridine-6-carboxylate | ALP24, AMP40 | I1 | 591 | 592 |

TABLE XII-continued

List of esters

| Int. | Structure | Name | SM | method | MW | Mes |
|---|---|---|---|---|---|---|
| E045 | 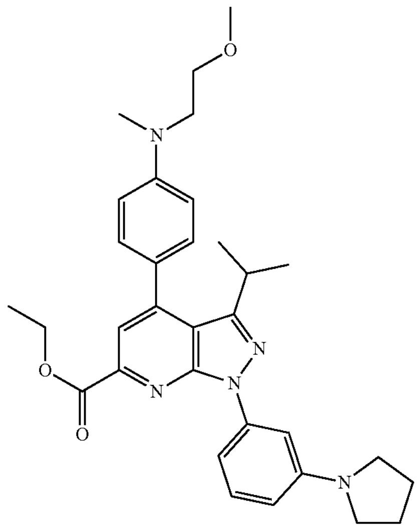 [SMILES: CCOC(=O)c1cc(-c2ccc(N(C)CCOC)cc2)c2c(C(C)C)nn(-c3cccc(N4CCCC4)c3)c2n1] | ethyl 3-isopropyl-4-[4-[2-methoxyethyl(methyl)amino]phenyl]-1-(3-pyrrolidin-1-ylphenyl)pyrazolo[3,4-b]pyridine-6-carboxylate | ALP11, AMP11 | I1 | 541 | 542 |
| E046 | 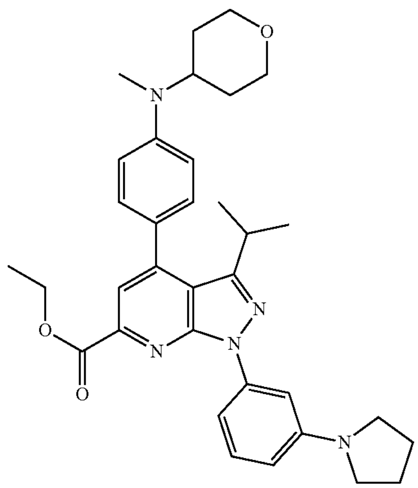 [SMILES: CCOC(=O)c1cc(-c2ccc(N(C)C3CCOCC3)cc2)c2c(C(C)C)nn(-c3cccc(N4CCCC4)c3)c2n1] | ethyl 3-isopropyl-4-[4-[methyl(tetrahydropyran-4-yl)amino]phenyl]-1-(3-pyrrolidin-1-ylphenyl)pyrazolo[3,4-6]pyridine-6-carboxylate | ALP15, AMP11 | I1 | 567 | 568 |
| E047 | 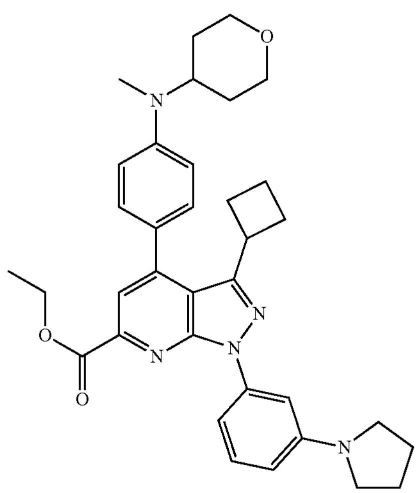 [SMILES: CCOC(=O)c1cc(-c2ccc(N(C)C3CCOCC3)cc2)c2c(C3CCC3)nn(-c3cccc(N4CCCC4)c3)c2n1] | ethyl 3-cyclobutyl-4-[4-[methyl(tetrahydropyran-4-yl)amino]phenyl]-1-(3-pyrrolidin-1-ylphenyl)pyrazolo[3,4-b]pyridine-6-carboxylate | ALP15, AMP31 | I1 | 580 | 581 |

TABLE XII-continued

List of esters

| Int. | Structure | Name | SM | method | MW | Mes |
|---|---|---|---|---|---|---|
| E048 | 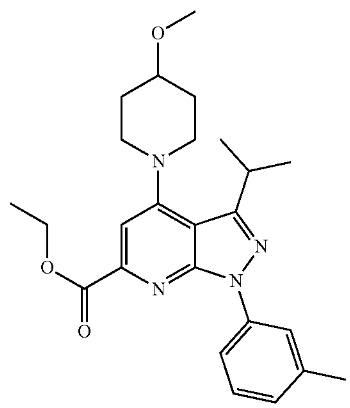 [SMILES: CCOC(=O)c1cc(N2CCC(OC)CC2)c2c(C(C)C)nn(-c3cccc(C)c3)c2n1] | ethyl 3-isopropyl-4-(4-methoxy-1-piperidyl)-1-(m-tolyl)pyrazolo[3,4-b]pyridine-6-carboxylate | HP01, 4045-24-3 | I3 | 436 | 437 |
| E049 | 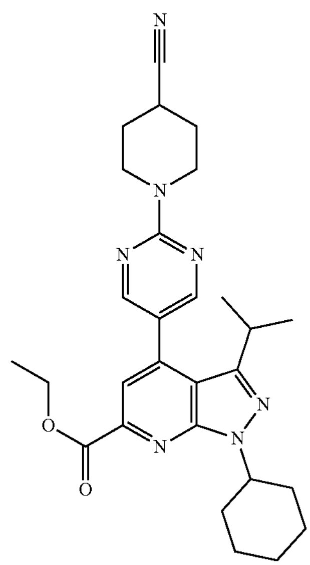 | ethyl 4-[2-(4-cyano-1-piperidyl)pyrimidin-5-yl]-1-cyclohexyl-3-isopropyl-pyrazolo[3,4-b]pyridine-6-carboxylate | ALP14, AMP23 | I1 | 501 | 502 |
| E050 | 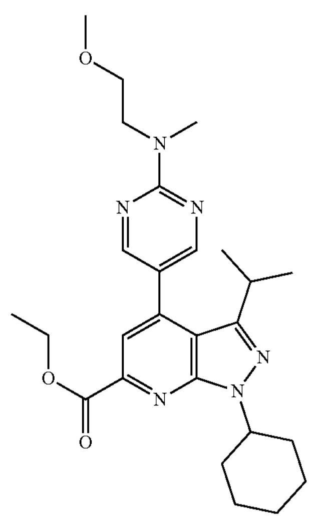 [SMILES: CCOC(=O)c1cc(-c2cnc(N(C)CCOC)nc2)c2c(C(C)C)nn(C3CCCCC3)c2n1] | ethyl 1-cyclohexyl-3-isopropyl-4-[2-[2-methoxyethyl(methyl)amino]pyrimidin-5-yl]pyrazolo[3,4-b]pyridine-6-carboxylate | ALP16, AMP23 | I1 | 480 | 481 |

TABLE XII-continued

List of esters

| Int. | Structure | Name | SM | method | MW | Mes |
|---|---|---|---|---|---|---|
| E051 | 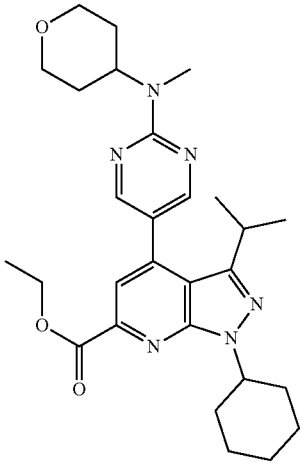 [SMILES: CCOC(=O)c1cc(-c2cnc(N(C)C3CCOCC3)nc2)c2c(C(C)C)nn(C3CCCCC3)c2n1] | ethyl 1-cyclohexyl-3-isopropyl-4-[2-[methyl(tetrahydropyran-4-yl)amino]pyrimidin-5-yl]pyrazolo[3,4-b]pyridine-6-carboxylate | ALP13, AMP23 | I1 | 506 | 507 |
| E052 | 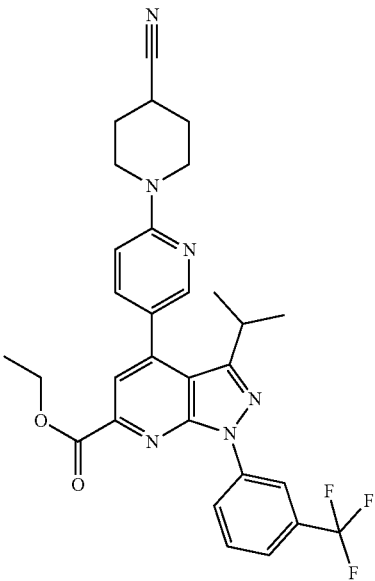 [SMILES: CCOC(=O)c1cc(-c2ccc(N3CCC(C#N)CC3)nc2)c2c(C(C)C)nn(-c3cccc(C(F)(F)F)c3)c2n1] | ethyl 4-[6-(4-cyano-1-piperidyl)-3-pyridyl]-3-isopropyl-1-[3-(trifluoromethyl)phenyl]pyrazolo[3,4-b]pyridine-6-carboxylate | ALP09, AMP08 | I1 | 562 | 563 |
| E053 | 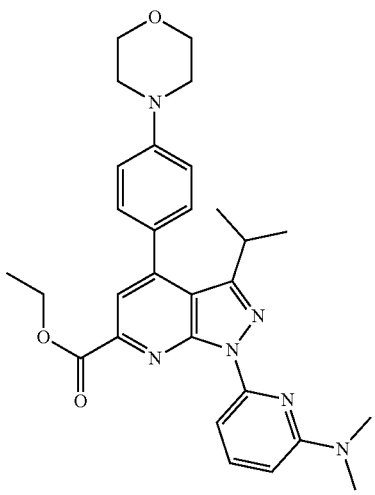 [SMILES: CCOC(=O)c1cc(-c2ccc(N3CCOCC3)cc2)c2c(C(C)C)nn(-c3cccc(N(C)C)n3)c2n1] | ethyl 1-[6-(dimethylamino)-2-pyridyl]-3-isopropyl-4-(4-morpholinophenyl)pyrazolo[3,4-b]pyridine-6-carboxylate | ALP18, AMP18 | I1 | 514 | 515 |

TABLE XII-continued

List of esters

| Int. | Structure | Name | SM | method | MW | Mes |
|---|---|---|---|---|---|---|
| E054 | 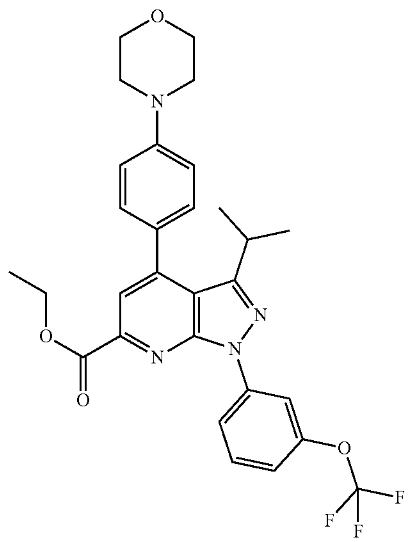 [SMILES: CCOC(=O)c1cc(-c2ccc(N3CCOCC3)cc2)c2c(C(C)C)nn(-c3cccc(OC(F)(F)F)c3)c2n1] | ethyl 3-isopropyl-4-(4-morpholinophenyl)-1-[3-(trifluoromethoxy)phenyl]pyrazolo[3,4-b]pyridine-6-carboxylate | E055, 179113-90-7 | I4 | 554 | 555 |
| E055 | 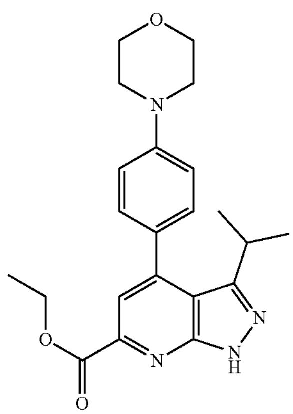 [SMILES: CCOC(=O)c1cc(-c2ccc(N3CCOCC3)cc2)c2c(C(C)C)n[nH]c2n1] | ethyl 3-isopropyl-4-(4-morpholinophenyl)-1H-pyrazolo[3,4-b]pyridine-6-carboxylate | E056 | I15, Specific example | 394 | 395 |
| E056 | 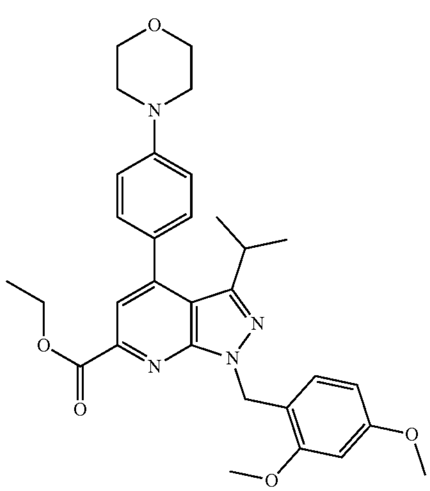 [SMILES: CCOC(=O)c1cc(-c2ccc(N3CCOCC3)cc2)c2c(C(C)C)nn(Cc3ccc(OC)cc3OC)c2n1] | ethyl 1-[(2,4-dimethoxyphenyl)methyl]-3-isopropyl-4-(4-morpholinophenyl)pyrazolo[3,4-b]pyridine-6-carboxylate | ALP18, AMP28 | I1 | 544 | 545 |

TABLE XII-continued

List of esters

| Int. | Structure | Name | SM | method | MW | Mes |
|---|---|---|---|---|---|---|
| E057 | 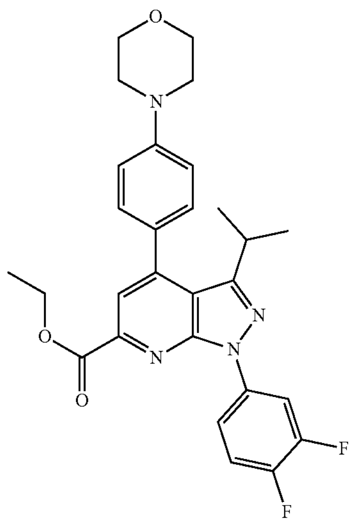 [SMILES: CCOC(=O)c1cc(-c2ccc(N3CCOCC3)cc2)c2c(C(C)C)nn(-c3ccc(F)c(F)c3)c2n1] | ethyl 1-(3,4-difluorophenyl)-3-isopropyl-4-(4-morpholinophenyl)pyrazolo[3,4-b]pyridine-6-carboxylate | E055 | I4 | 506 | 507 |
| E058 | 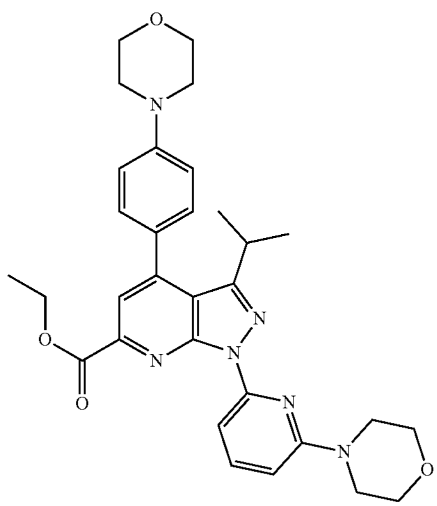 [SMILES: CCOC(=O)c1cc(-c2ccc(N3CCOCC3)cc2)c2c(C(C)C)nn(-c3cccc(N4CCOCC4)n3)c2n1] | ethyl 3-isopropyl-4-(4-morpholinophenyl)-1-(6-morpholino-2-pyridyl)pyrazolo[3,4-b]pyridine-6-carboxylate | ALP18, AMP19 | I1 | 556 | 557 |
| E059 | 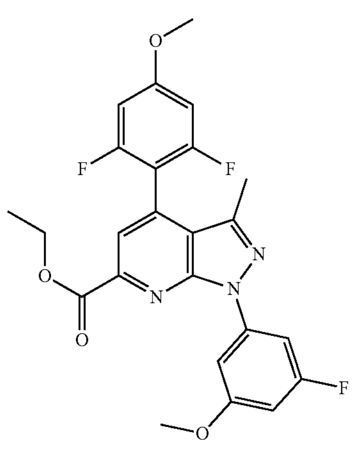 [SMILES: CCOC(=O)c1cc(-c2c(F)cc(OC)cc2F)c2c(C)nn(-c3cc(F)cc(OC)c3)c2n1] | ethyl 4-(2,6-difluoro-4-methoxy-phenyl)-1-(3-fluoro-5-methoxy-phenyl)-3-methyl-pyrazolo[3,4-b]pyridine-6-carboxylate | ALP17, AMP03 | I1 | 471 | 472 |

TABLE XII-continued
List of esters
| Int. | Structure | Name | SM | method | MW | Mes |
|---|---|---|---|---|---|---|
| E060 | 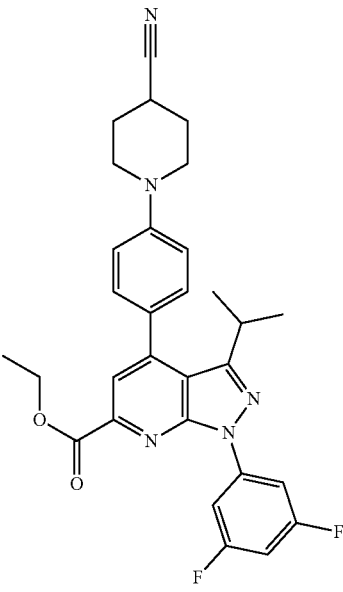 [SMILES: CCOC(=O)c1cc(-c2ccc(N3CCC(C#N)CC3)cc2)c2c(C(C)C)nn(-c3cc(F)cc(F)c3)c2n1] | ethyl 4-[4-(4-cyano-1-piperidyl)phenyl]-1-(3,5-difluorophenyl)-3-isopropyl-pyrazolo[3,4-b]pyridine-6-carboxylate | ALP12, AMP09 | I1 | 529 | 530 |
| E061 | 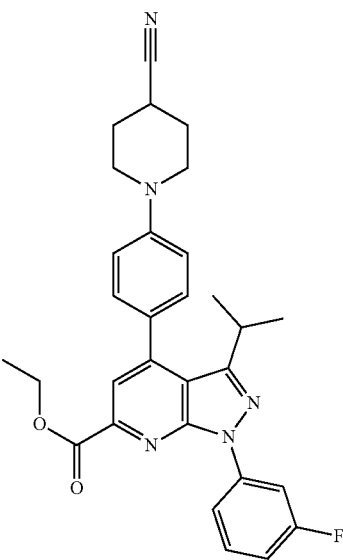 [SMILES: CCOC(=O)c1cc(-c2ccc(N3CCC(C#N)CC3)cc2)c2c(C(C)C)nn(-c3cccc(F)c3)c2n1] | ethyl 4-[4-(4-cyano-1-piperidyl)phenyl]-1-(3-fluorophenyl)-3-isopropyl-pyrazolo[3,4-b]pyridine-6-carboxylate | ALP12, AMP12 | I1 | 511 | 512 |

TABLE XII-continued

List of esters

| Int. | Structure | Name | SM | method | MW | Mes |
|------|-----------|------|-----|--------|-----|-----|
| E062 | 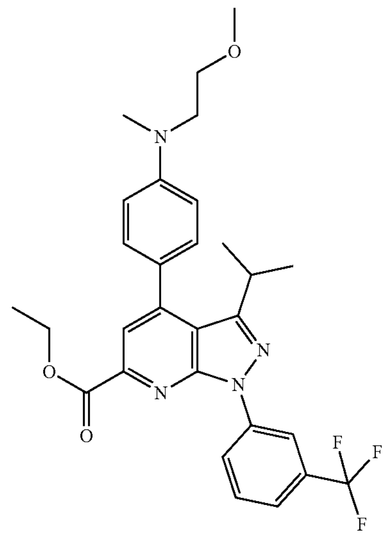 [SMILES: CCOC(=O)c1cc(-c2ccc(N(C)CCOC)cc2)c2c(C(C)C)nn(-c3cccc(C(F)(F)F)c3)c2n1] | ethyl 3-isopropyl-4-[4-[2-methoxyethyl(methyl)amino]phenyl]-1-[3-(trifluoromethyl)phenyl]pyrazolo[3,4-b]pyridine-6-carboxylate | ALP11, AMP08 | I1 | 540 | 541 |
| E063 | 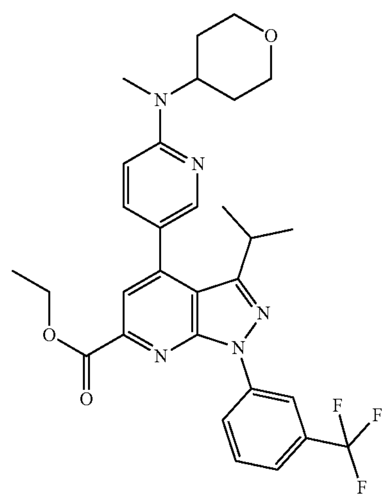 [SMILES: CCOC(=O)c1cc(-c2ccc(N(C)C3CCOCC3)nc2)c2c(C(C)C)nn(-c3cccc(C(F)(F)F)c3)c2n1] | ethyl 3-isopropyl-4-[6-[methyl(tetrahydropyran-4-yl)amino]-3-pyridyl]-1-[3-(trifluoromethyl)phenyl]pyrazolo[3,4-b]pyridine-6-carboxylate | ALP10, AMP08 | I1 | 567 | 568 |
| E064 | 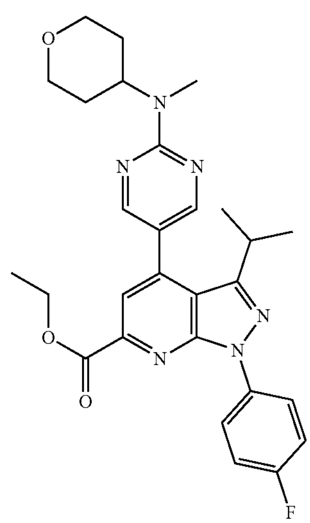 [SMILES: CCOC(=O)c1cc(-c2cnc(N(C)C3CCOCC3)nc2)c2c(C(C)C)nn(-c3ccc(F)cc3)c2n1] | ethyl 1-(4-fluorophenyl)-3-isopropyl-4-[2-[methyl(tetrahydropyran-4-yl)amino]pyrimidin-5-yl]pyrazolo[3,4-b]pyridine-6-carboxylate | ALP13, AMP13 | I1 | 518 | 519 |

TABLE XII-continued

List of esters

| Int. | Structure | Name | SM | method | MW | Mes |
|---|---|---|---|---|---|---|
| E065 | 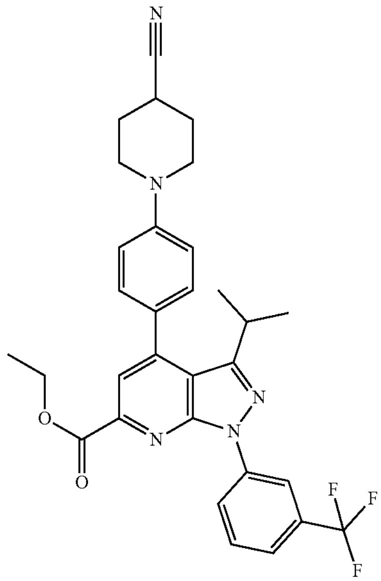 [SMILES: CCOC(=O)c1cc(-c2ccc(N3CCC(C#N)CC3)cc2)c2c(C(C)C)nn(-c3cccc(C(F)(F)F)c3)c2n1] | ethyl 4-[4-(4-cyano-1-piperidyl)phenyl]-3-isopropyl-1-[3-(trifluoromethyl)phenyl]pyrazolo[3,4-b]pyridine-6-carboxylate | ALP12, AMP08 | I1 | 561 | 562 |
| E066 | 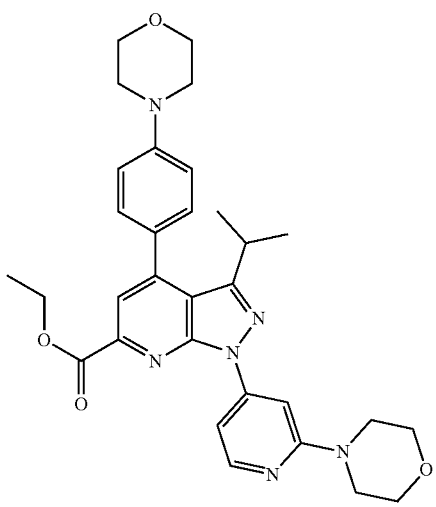 [SMILES: CCOC(=O)c1cc(-c2ccc(N3CCOCC3)cc2)c2c(C(C)C)nn(-c3ccnc(N4CCOCC4)c3)c2n1] | ethyl 3-isopropyl-4-(4-morpholinophenyl)-1-(2-morpholino-4-pyridyl)pyrazolo[3,4-b]pyridine-6-carboxylate | ALP18, AMP21 | I1 | 556 | 557 |
| E067 | 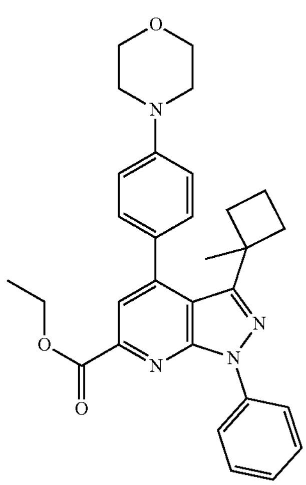 [SMILES: CCOC(=O)c1cc(-c2ccc(N3CCOCC3)cc2)c2c(C3(C)CCC3)nn(-c3ccccc3)c2n1] | ethyl 3-(1-methylcyclobutyl)-4-(4-morpholinophenyl)-1-phenyl-pyrazolo[3,4-b]pyridine-6-carboxylate | ALP18, AMP41 | I1 | 496 | 497 |

TABLE XII-continued
List of esters
| Int. | Structure | Name | SM | method | MW | Mes |
|---|---|---|---|---|---|---|
| E068 | 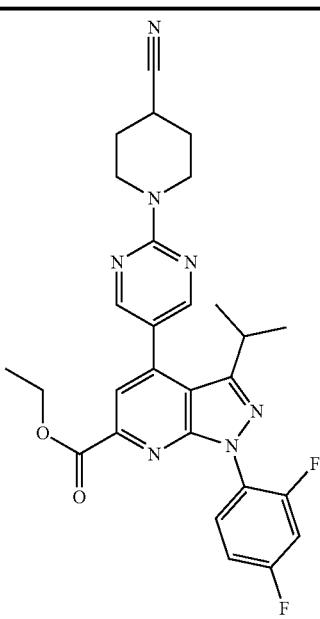 | ethyl 4-[2-(4-cyano-1-piperidyl)pyrimidin-5-yl]-1-(2,4-difluorophenyl)-3-isopropyl-pyrazolo[3,4-b]pyridine-6-carboxylate | ALP14, AMP14 | I1 | 531 | 532 |
| E069 | 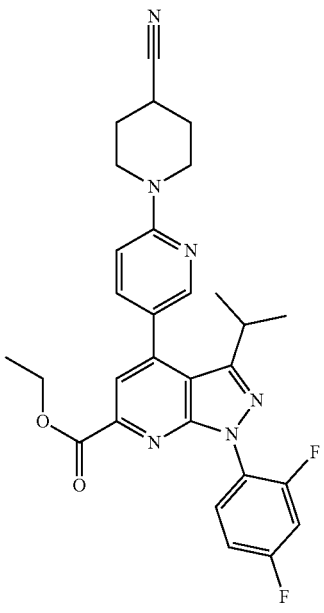 [SMILES: CCOC(=O)c1cc(-c2ccc(N3CCC(C#N)CC3)nc2)c2c(C(C)C)nn(-c3ccc(F)cc3F)c2n1] | ethyl 4-[6-(4-cyano-1-piperidyl)-3-pyridyl]-1-(2,4-difluorophenyl)-3-isopropyl-pyrazolo[3,4-b]pyridine-6-carboxylate | ALP09, AMP14 | I1 | 530 | 531 |

TABLE XII-continued

List of esters

| Int. | Structure | Name | SM | method | MW | Mes |
|---|---|---|---|---|---|---|
| E070 | 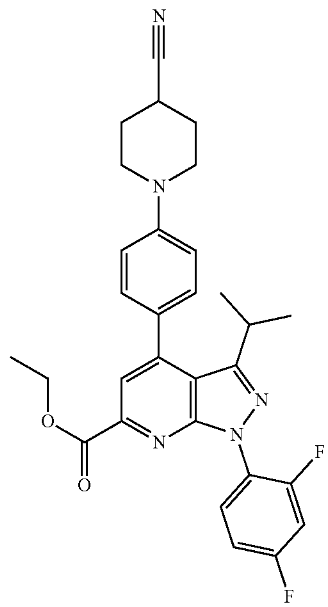 [SMILES: CCOC(=O)c1cc(-c2ccc(N3CCC(C#N)CC3)cc2)c2c(C(C)C)nn(-c3ccc(F)cc3F)c2n1] | ethyl 4-[4-(4-cyano-1-piperidyl)phenyl]-1-(2,4-difluorophenyl)-3-isopropyl-pyrazolo[3,4-b]pyridine-6-carboxylate | ALP12, AMP14 | I1 | 529 | 530 |
| E071 | 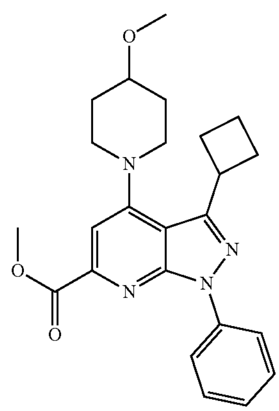 [SMILES: COC(=O)c1cc(N2CCC(OC)CC2)c2c(C3CCC3)nn(-c3ccccc3)c2n1] | methyl 3-cyclobutyl-4-(4-methoxy-1-piperidyl)-1-phenyl-pyrazolo[3,4-b]pyridine-6-carboxylate | HP02 | I3 | 420 | 421 |
| E072 | 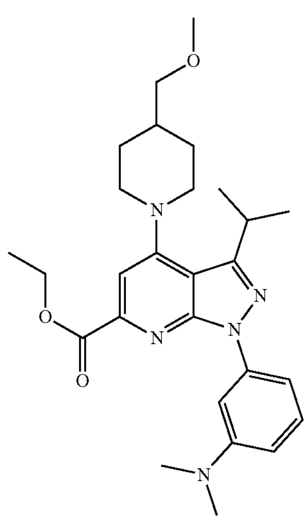 [SMILES: CCOC(=O)c1cc(N2CCC(COC)CC2)c2c(C(C)C)nn(-c3cccc(N(C)C)c3)c2n1] | ethyl 1-[3-(dimethylamino)phenyl]-3-isopropyl-4-[4-(methoxymethyl)-1-piperidyl]pyrazolo[3,4-b]pyridine-6-carboxylate | HP03 | I3 | 479 | 480 |

TABLE XII-continued

List of esters

| Int. | Structure | Name | SM | method | MW | Mes |
|---|---|---|---|---|---|---|
| E073 | 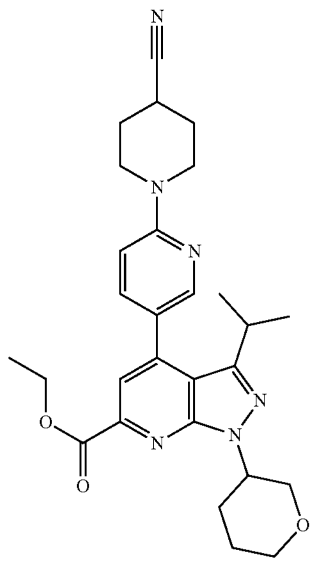 [SMILES: CCOC(=O)c1cc(-c2ccc(N3CCC(C#N)CC3)nc2)c2c(C(C)C)nn(C3CCCOC3)c2n1] | ethyl 4-[6-(4-cyano-1-piperidyl)-3-pyridyl]-3-isopropyl-1-tetrahydropyran-3-yl-pyrazolo[3,4-b]pyridine-6-carboxylate | ALP09, AMP25 | I1 | 502 | 503 |
| E074 | 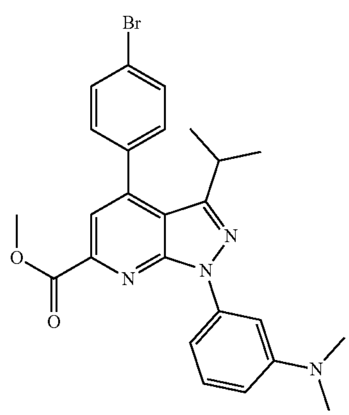 [SMILES: COC(=O)c1cc(-c2ccc(Br)cc2)c2c(C(C)C)nn(-c3cccc(N(C)C)c3)c2n1] | methyl 4-(4-bromophenyl)-1-[3-(dimethylamino)phenyl]-3-isopropyl-pyrazolo[3,4-b]pyridine-6-carboxylate | 308128-34-3, AMP06 | I1 | 492-494 | 493-495 |
| E075 | 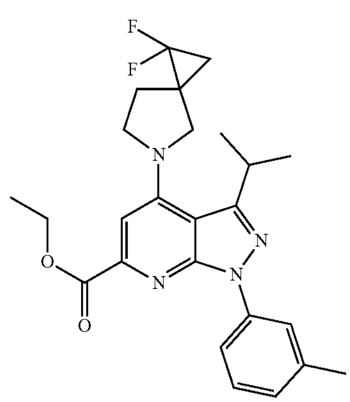 [SMILES: CCOC(=O)c1cc(N2CCC3(C2)CC3(F)F)c2c(C(C)C)nn(-c3cccc(C)c3)c2n1] | ethyl 4-(2,2-difluoro-5-azaspiro[2.4]heptan-5-yl)-3-isopropyl-1-(m-tolyl)pyrazolo[3,4-b]pyridine-6-carboxylate | HP01 | I3 | 454 | 455 |

TABLE XII-continued
List of esters
| Int. | Structure | Name | SM | method | MW | Mes |
|---|---|---|---|---|---|---|
| E076 | 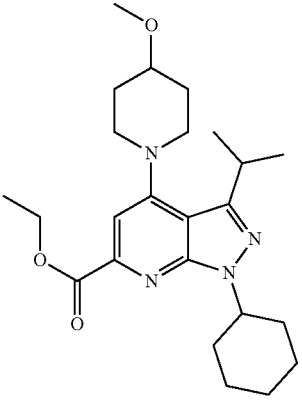 [SMILES: CCOC(=O)c1cc(N2CCC(OC)CC2)c2c(C(C)C)nn(C3CCCCC3)c2n1] | ethyl 1-cyclohexyl-3-isopropyl-4-(4-methoxy-1-piperidyl)pyrazolo[3,4-b]pyridine-6-carboxylate | HP04 | I3 | 428 | 429 |
| E077 | 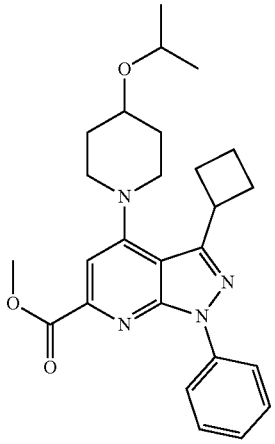 [SMILES: COC(=O)c1cc(N2CCC(OC(C)C)CC2)c2c(C3CCC3)nn(-c3ccccc3)c2n1] | methyl 3-cyclobutyl-4-(4-isopropoxy-1-piperidyl)-1-phenyl-pyrazolo[3,4-b]pyridine-6-carboxylate | HP02 | I3 | 448 | 449 |
| E078 | 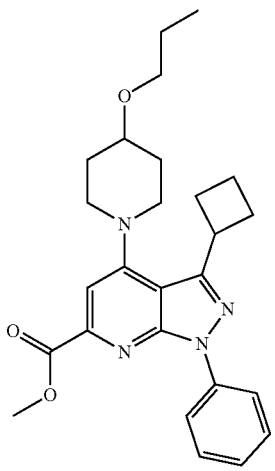 [SMILES: CCCOC1CCN(c2cc(C(=O)OC)nc3c2c(C2CCC2)nn3-c2ccccc2)CC1] | methyl 3-cyclobutyl-1-phenyl-4-(4-propoxy-1-piperidyl)pyrazolo[3,4-b]pyridine-6-carboxylate | HP02 | I3 | 448 | 449 |

TABLE XII-continued
List of esters
| Int. | Structure | Name | SM | method | MW | Mes |
|---|---|---|---|---|---|---|
| E079 | 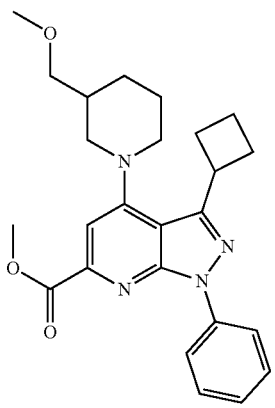 [SMILES: COCC1CCCN(c2cc(C(=O)OC)nc3c2c(C2CCC2)nn3-c2ccccc2)C1] | methyl 3-cyclobutyl-4-[3-(methoxymethyl)-1-piperidyl]-1-phenyl-pyrazolo[3,4-b]pyridine-6-carboxylate | HP02 | I3 | 434 | 435 |
| E080 | 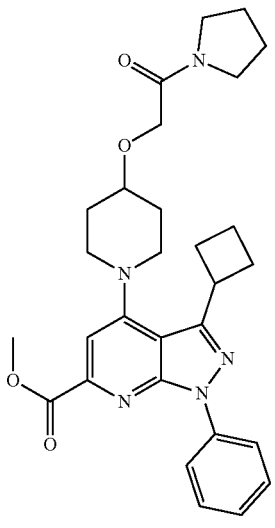 [SMILES: COC(=O)c1cc(N2CCC(OCC(=O)N3CCCC3)CC2)c2c(C3CCC3)nn(-c3ccccc3)c2n1] | methyl 3-cyclobutyl-4-[4-(2-oxo-2-pyrrolidin-1-yl-ethoxy)-1-piperidyl]-1-phenyl-pyrazolo[3,4-b]pyridine-6-carboxylate | HP02 | I3 | 517 | 518 |
| E081 | 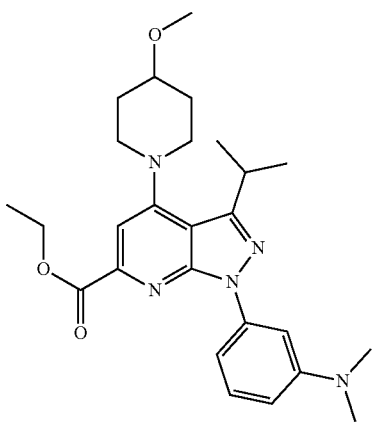 [SMILES: CCOC(=O)c1cc(N2CCC(OC)CC2)c2c(C(C)C)nn(-c3cccc(N(C)C)c3)c2n1] | ethyl 1-[3-(dimethylamino)phenyl]-3-isopropyl-4-(4-methoxy-1-piperidyl)pyrazolo[3,4-6]pyridine-6-carboxylate | HP03 | I3 | 465 | 466 |

TABLE XII-continued

List of esters

| Int. | Structure | Name | SM | method | MW | Mes |
|------|-----------|------|-----|--------|-----|-----|
| E082 | 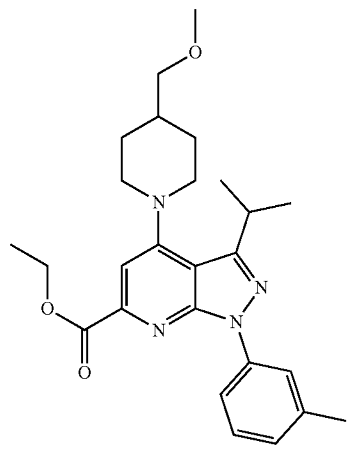 [SMILES: CCOC(=O)c1cc(N2CCC(COC)CC2)c2c(C(C)C)nn(-c3cccc(C)c3)c2n1] | ethyl 3-isopropyl-4-[4-(methoxymethyl)-1-piperidyl]-1-(m-tolyl)pyrazolo[3,4-b]pyridine-6-carboxylate | HP01 | I3 | 450 | 451 |
| E083 | 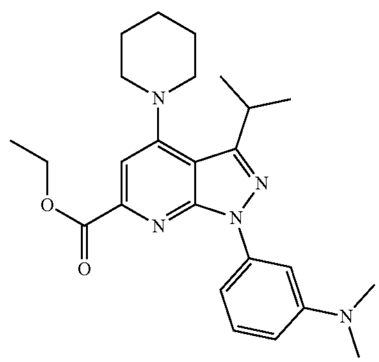 [SMILES: CCOC(=O)c1cc(N2CCCCC2)c2c(C(C)C)nn(-c3cccc(N(C)C)c3)c2n1] | ethyl 1-[3-(dimethylamino)phenyl]-3-isopropyl-4-(1-piperidyl)pyrazolo[3,4-b]pyridine-6-carboxylate | HP03 | I3 | 435 | 436 |
| E084 | 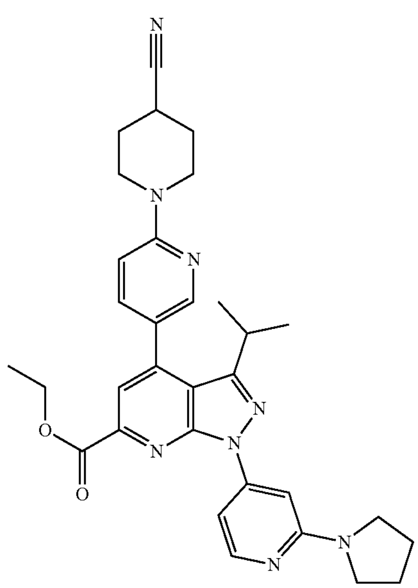 [SMILES: CCOC(=O)c1cc(-c2ccc(N3CCC(C#N)CC3)nc2)c2c(C(C)C)nn(-c3ccnc(N4CCCC4)c3)c2n1] | ethyl 4-[6-(4-cyano-1-piperidyl)-3-pyridyl]-3-isopropyl-1-(2-pyrrolidin-1-yl-4-pyridyl)pyrazolo[3,4-b]pyridine-6-carboxylate | ALP09, AMP22 | I1 | 564 | 565 |

TABLE XII-continued

List of esters

| Int. | Structure | Name | SM | method | MW | Mes |
|---|---|---|---|---|---|---|
| E085 | 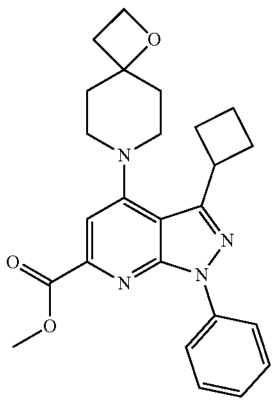 [SMILES: COC(=O)c1cc(N2CCC3(CCO3)CC2)c2c(C3CCC3)nn(-c3ccccc3)c2n1] | methyl 3-cyclobutyl-4-(1-oxa-7-azaspiro[3.5]nonan-7-yl)-1-phenyl-pyrazolo[3,4-b]pyridine-6-carboxylate | HP02 | I3 | 432 | 433 |
| E086 | 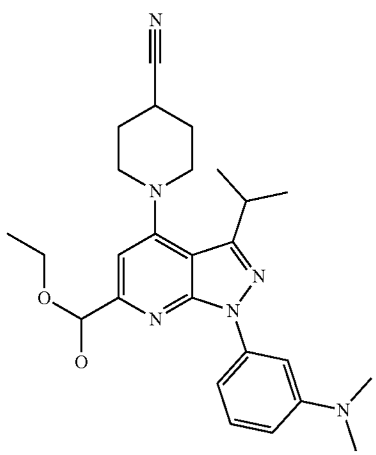 [SMILES: CCOC(O)c1cc(N2CCC(C#N)CC2)c2c(C(C)C)nn(-c3cccc(N(C)C)c3)c2n1] | ethyl 4-(4-cyano-1-piperidyl)-1-[3-(dimethylamino)phenyl]-3-isopropyl-pyrazolo[3,4-b]pyridine-6-carboxylate | HP03 | I3 | 460 | 461 |
| E087 | 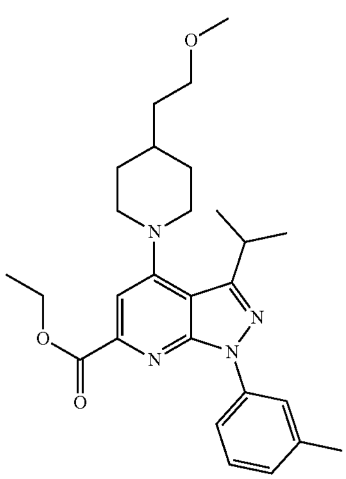 [SMILES: CCOC(=O)c1cc(N2CCC(CCOC)CC2)c2c(C(C)C)nn(-c3cccc(C)c3)c2n1] | ethyl 3-isopropyl-4-[4-(2-methoxyethyl)-1-piperidyl]-1-(m-tolyl)pyrazolo[3,4-b]pyridine-6-carboxylate | HP01 | I3 | 464 | 465 |

TABLE XII-continued

List of esters

| Int. | Structure | Name | SM | method | MW | Mes |
|---|---|---|---|---|---|---|
| E088 | 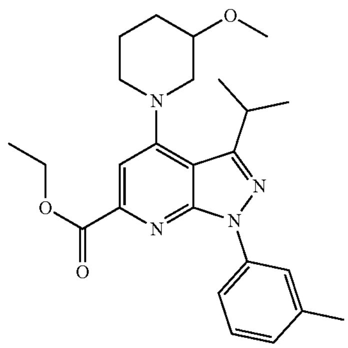 [SMILES: CCOC(=O)c1cc(N2CCCC(OC)C2)c2c(C(C)C)nn(-c3cccc(C)c3)c2n1] | ethyl 3-isopropyl-4-(3-methoxy-1-piperidyl)-1-(m-tolyl)pyrazolo[3,4-b]pyridine-6-carboxylate | HP01 | I3 | 436 | 437 |
| E089 | 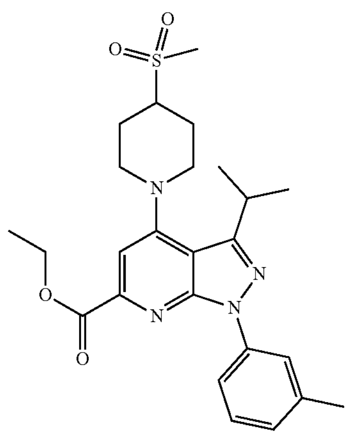 [SMILES: CCOC(=O)c1cc(N2CCC(S(C)(=O)=O)CC2)c2c(C(C)C)nn(-c3cccc(C)c3)c2n1] | ethyl 3-isopropyl-4-(4-methylsulfonyl-1-piperidyl)-1-(m-tolyl)pyrazolo[3,4-b]pyridine-6-carboxylate | HP01 | I3 | 484 | 485 |
| E090 | 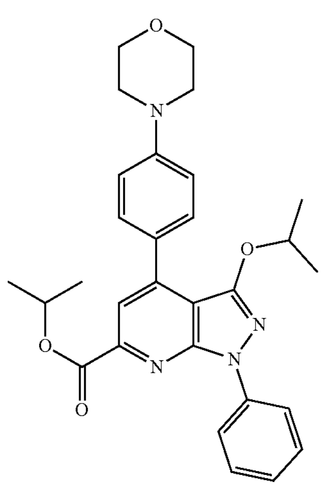 [SMILES: CC(C)OC(=O)c1cc(-c2ccc(N3CCOCC3)cc2)c2c(OC(C)C)nn(-c3ccccc3)c2n1] | isopropyl 3-isopropoxy-4-(4-morpholinophenyl)-1-phenyl-pyrazolo[3,4-b]pyridine-6-carboxylate | A256 | I17, Specific example | 500 | 501 |

TABLE XII-continued

| | | List of esters | | | | |
|---|---|---|---|---|---|---|
| Int. | Structure | Name | SM | method | MW | Mes |
| E091 | | methyl 1-(4-fluorophenyl)-3-isopropyl-4-(4-methoxy-1-piperidyl)pyrazolo[3,4-b]pyridine-6-carboxylate | HP05 | I3 | 426 | 427 |
| E092 | | methyl 1-(4-fluorophenyl)-3-isopropyl-4-[4-(methoxymethyl)-1-piperidyl]pyrazolo[3,4-b]pyridine-6-carboxylate | HP05 | I3, Specific example | 440 | 441 |
| E093 | | ethyl 4-[4-(4-cyano-1-piperidyl)phenyl]-3-isopropyl-1-(2-pyrrolidin-1-yl-4-pyridyl)pyrazolo[3,4-b]pyridine-6-carboxylate | ALP12, AMP22 | I1 | 563 | 564 |

TABLE XII-continued

List of esters

| Int. | Structure | Name | SM | method | MW | Mes |
|---|---|---|---|---|---|---|
| E094 | 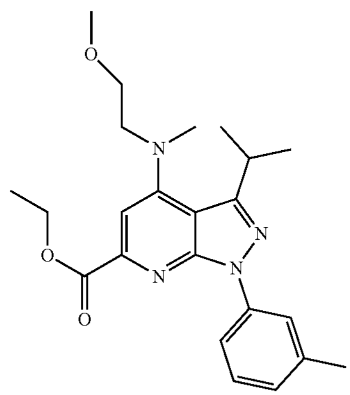 [SMILES: CCOC(=O)c1cc(N(C)CCOC)c2c(C(C)C)nn(-c3cccc(C)c3)c2n1] | ethyl 3-isopropyl-4-[2-methoxyethyl(methyl)amino]-1-(m-tolyl)pyrazolo[3,4-b]pyridine-6-carboxylate | HP01 | I1 | 410 | 411 |
| E095 | 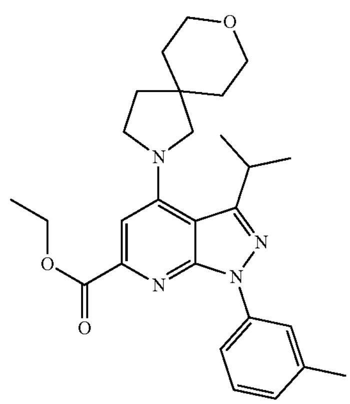 [SMILES: CCOC(=O)c1cc(N2CCC3(CCOCC3)C2)c2c(C(C)C)nn(-c3cccc(C)c3)c2n1] | ethyl 3-isopropyl-1-(m-tolyl)-4-(8-oxa-2-azaspiro[4.5]decan-2-yl)pyrazolo[3,4-b]pyridine-6-carboxylate | HP01 | I3 | 462 | 463 |
| E096 | 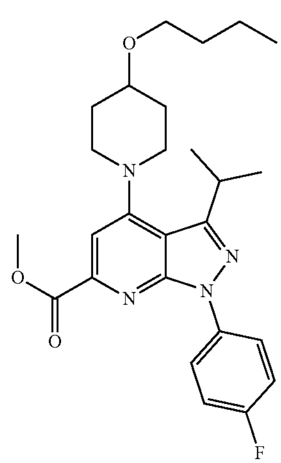 [SMILES: CCCCOC1CCN(c2cc(C(=O)OC)nc3c2c(C(C)C)nn3-c2ccc(F)cc2)CC1] | methyl 4-(4-butoxy-1-piperidyl)-1-(4-fluorophenyl)-3-isopropyl-pyrazolo[3,4-b]pyridine-6-carboxylate | HP05 | I3 | 468 | 467 |

TABLE XII-continued

List of esters

| Int. | Structure | Name | SM | method | MW | Mes |
|---|---|---|---|---|---|---|
| E097 | 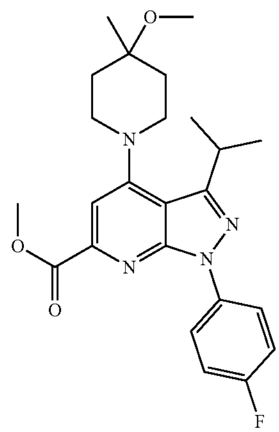 [SMILES: COC(=O)c1cc(N2CCC(C)(OC)CC2)c2c(C(C)C)nn(-c3ccc(F)cc3)c2n1] | methyl 1-(4-fluorophenyl)-3-isopropyl-4-(4-methoxy-4-methyl-1-piperidyl)pyrazolo[3,4-b]pyridine-6-carboxylate | HP05 | I3 | 440 | 441 |
| E098 | 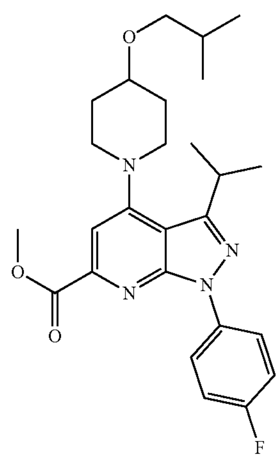 [SMILES: COC(=O)c1cc(N2CCC(OCC(C)C)CC2)c2c(C(C)C)nn(-c3ccc(F)cc3)c2n1] | methyl 1-(4-fluorophenyl)-4-(4-isobutoxy-1-piperidyl)-3-isopropyl-pyrazolo[3,4-b]pyridine-6-carboxylate | HP05 | I3 | 468 | 469 |
| E099 | 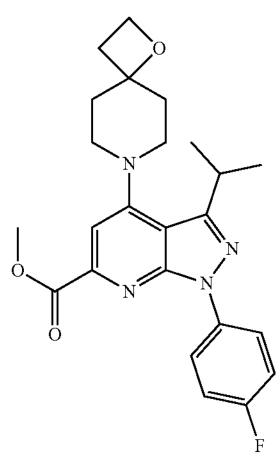 [SMILES: COC(=O)c1cc(N2CCC3(CCO3)CC2)c2c(C(C)C)nn(-c3ccc(F)cc3)c2n1] | methyl 1-(4-fluorophenyl)-3-isopropyl-4-(1-oxa-7-azaspiro[3.5]nonan-7-yl)pyrazolo[3,4-b]pyridine-6-carboxylate | HP05 | I3 | 438 | 439 |

TABLE XII-continued

List of esters

| Int. | Structure | Name | SM | method | MW | Mes |
|---|---|---|---|---|---|---|
| E100 | 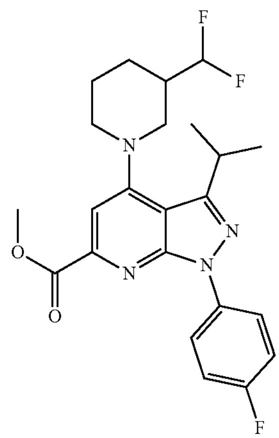 [SMILES: COC(=O)c1cc(N2CCCC(C(F)F)C2)c2c(C(C)C)nn(-c3ccc(F)cc3)c2n1] | methyl 4-[3-(difluoromethyl)-1-piperidyl]-1-(4-fluorophenyl)-3-isopropyl-pyrazolo[3,4-b]pyridine-6-carboxylate | HP05 | I3 | 446 | 447 |
| E101 | 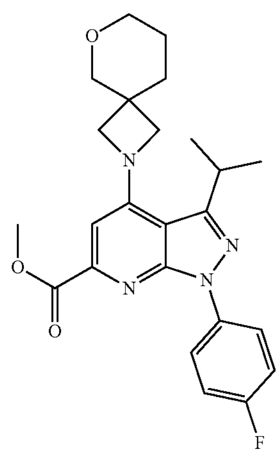 [SMILES: COC(=O)c1cc(N2CC3(CCCOC3)C2)c2c(C(C)C)nn(-c3ccc(F)cc3)c2n1] | methyl 1-(4-fluorophenyl)-3-isopropyl-4-(6-oxa-2-azaspiro[3.5]nonan-2-yl)pyrazolo[3,4-b]pyridine-6-carboxylate | HP05 | I3 | 438 | 439 |
| E102 | 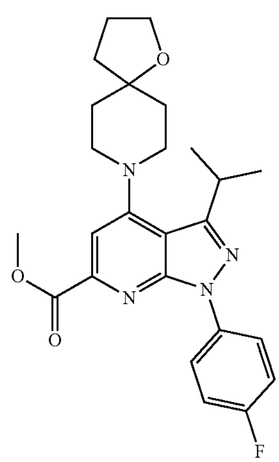 [SMILES: COC(=O)c1cc(N2CCC3(CCCO3)CC2)c2c(C(C)C)nn(-c3ccc(F)cc3)c2n1] | methyl 1-(4-fluorophenyl)-3-isopropyl-4-(1-oxa-8-azaspiro[4.5]decan-8-yl)pyrazolo[3,4-b]pyridine-6-carboxylate | HP05 | I3 | 452 | 453 |

TABLE XII-continued

List of esters

| Int. | Structure | Name | SM | method | MW | Mes |
|------|-----------|------|-----|--------|-----|-----|
| E103 | 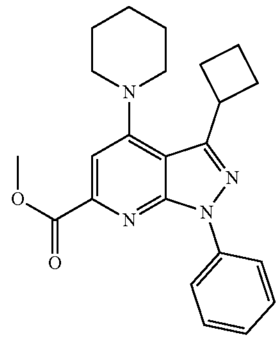 [SMILES: COC(=O)c1cc(N2CCCCC2)c2c(C3CCC3)nn(-c3ccccc3)c2n1] | methyl 3-cyclobutyl-1-phenyl-4-(1-piperidyl)pyrazolo[3,4-b]pyridine-6-carboxylate | HP02 | I3 | 390 | 391 |
| E104 | 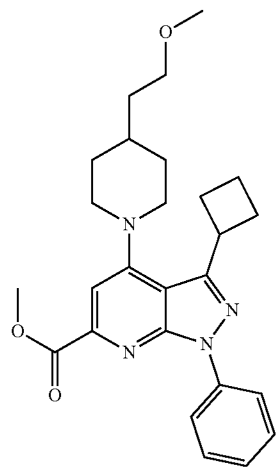 [SMILES: COCCC1CCN(c2cc(C(=O)OC)nc3c2c(C2CCC2)nn3-c2ccccc2)CC1] | methyl 3-cyclobutyl-4-[4-(2-methoxyethyl)-1-piperidyl]-1-phenyl-pyrazolo[3,4-b]pyridine-6-carboxylate | HP02 | I3 | 448 | 449 |
| E105 | 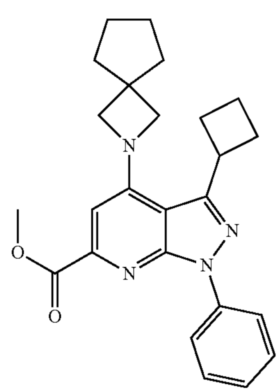 [SMILES: COC(=O)c1cc(N2CC3(CCCC3)C2)c2c(C3CCC3)nn(-c3ccccc3)c2n1] | methyl 4-(2-azaspiro[3.4]octan-2-yl)-3-cyclobutyl-1-phenyl-pyrazolo[3,4-b]pyridine-6-carboxylate | HP02 | I3 | 416 | 417 |

TABLE XII-continued

List of esters

| Int. | Structure | Name | SM | method | MW | Mes |
|---|---|---|---|---|---|---|
| E106 | 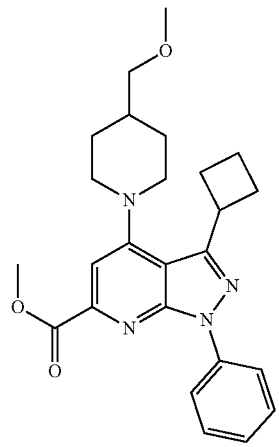 [SMILES: COCC1CCN(c2cc(C(=O)OC)nc3c2c(C2CCC2)nn3-c2ccccc2)CC1] | methyl 3-cyclobutyl-4-[4-(methoxymethyl)-1-piperidyl]-1-phenyl-pyrazolo[3,4-b]pyridine-6-carboxylate | HP02 | I3 | 434 | 435 |
| E107 | 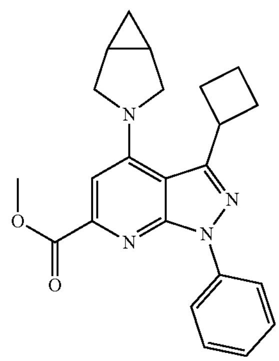 [SMILES: COC(=O)c1cc(N2CC3CC3C2)c2c(C3CCC3)nn(-c3ccccc3)c2n1] | methyl 4-(3-azabicyclo[3.1.0]hexan-3-yl)-3-cyclobutyl-1-phenyl-pyrazolo[3,4-b]pyridine-6-carboxylate | HP02 | I3 | 388 | 389 |
| E108 | 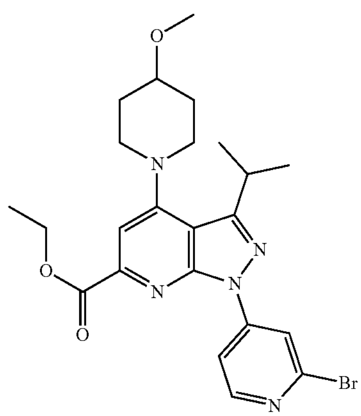 [SMILES: CCOC(=O)c1cc(N2CCC(OC)CC2)c2c(C(C)C)nn(-c3ccnc(Br)c3)c2n1] | ethyl 1-(2-bromo-4-pyridyl)-3-isopropyl-4-(4-methoxy-1-piperidyl)pyrazolo[3,4-b]pyridine-6-carboxylate | HP09 | I4 | 501-503 | 502-504 |
| E109 | 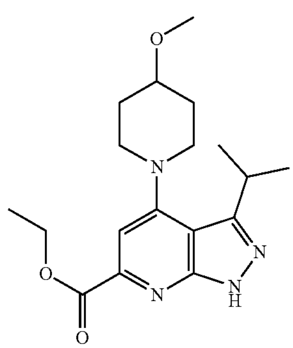 [SMILES: CCOC(=O)c1cc(N2CCC(OC)CC2)c2c(C(C)C)n[nH]c2n1] | ethyl 3-isopropyl-4-(4-methoxy-1-piperidyl)-1H-pyrazolo[3,4-b]pyridine-6-carboxylate | HP08 | I3 | 346 | 347 |

TABLE XII-continued

List of esters

| Int. | Structure | Name | SM | method | MW | Mes |
|---|---|---|---|---|---|---|
| E110 | 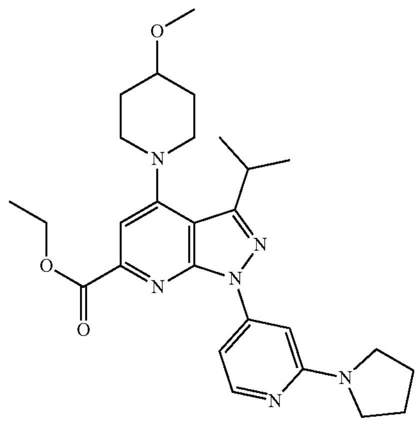 [SMILES: CCOC(=O)c1cc(N2CCC(OC)CC2)c2c(C(C)C)nn(-c3ccnc(N4CCCC4)c3)c2n1] | ethyl 3-isopropyl-4-(4-methoxy-1-piperidyl)-1-(2-pyrrolidin-1-yl-4-pyridyl)pyrazolo[3,4-b]pyridine-6-carboxylate | E111 | I12, Specific example | 492 | 493 |
| E111 | 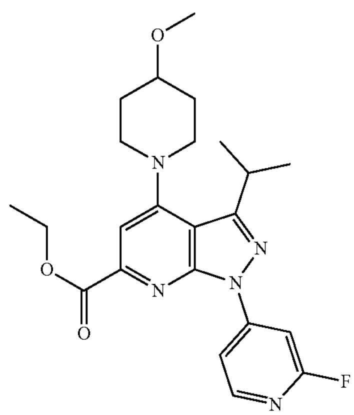 [SMILES: CCOC(=O)c1cc(N2CCC(OC)CC2)c2c(C(C)C)nn(-c3ccnc(F)c3)c2n1] | ethyl 1-(2-fluoro-4-pyridyl)-3-isopropyl-4-(4-methoxy-1-piperidyl)pyrazolo[3,4-b]pyridine-6-carboxylate | E109 | I4, Specific example | 441 | 442 |
| E112 | 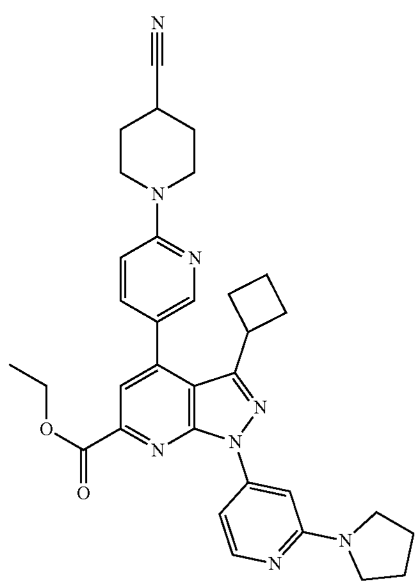 [SMILES: CCOC(=O)c1cc(-c2ccc(N3CCC(C#N)CC3)nc2)c2c(C3CCC3)nn(-c3ccnc(N4CCCC4)c3)c2n1] | ethyl 4-[6-(4-cyano-1-piperidyl)-3-pyridyl]-3-cyclobutyl-1-(2-pyrrolidin-1-yl-4-pyridyl)pyrazolo[3,4-b]pyridine-6-carboxylate | ALP09, AMP34 | I1 | 576 | 577 |

TABLE XII-continued

List of esters

| Int. | Structure | Name | SM | method | MW | Mes |
|---|---|---|---|---|---|---|
| E113 | 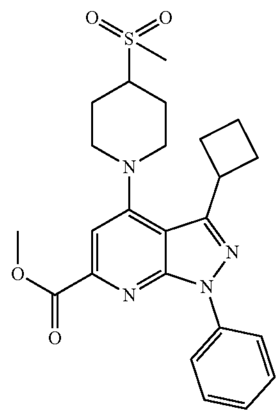 [SMILES: COC(=O)c1cc(N2CCC(S(C)(=O)=O)CC2)c2c(C3CCC3)nn(-c3ccccc3)c2n1] | methyl 3-cyclobutyl-4-(4-methylsulfonyl-1-piperidyl)-1-phenyl-pyrazolo[3,4-b]pyridine-6-carboxylate | HP02 | I3 | 468 | 469 |
| E114 | 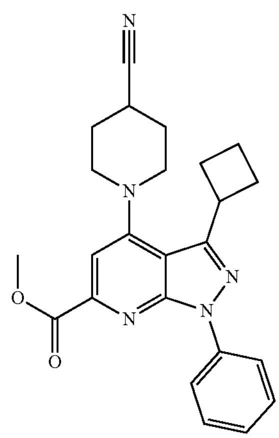 [SMILES: COC(=O)c1cc(N2CCC(C#N)CC2)c2c(C3CCC3)nn(-c3ccccc3)c2n1] | methyl 4-(4-cyano-1-piperidyl)-3-cyclobutyl-1-phenyl-pyrazolo[3,4-b]pyridine-6-carboxylate | HP02 | I3 | 415 | 416 |
| E115 | 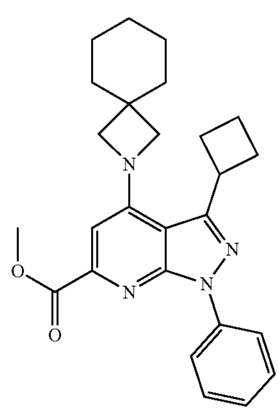 [SMILES: COC(=O)c1cc(N2CC3(CCCCC3)C2)c2c(C3CCC3)nn(-c3ccccc3)c2n1] | methyl 4-(2-azaspiro[3.5]nonan-2-yl)-3-cyclobutyl-1-phenyl-pyrazolo[3,4-b]pyridine-6-carboxylate | HP02 | I3 | 430 | 431 |

TABLE XII-continued

List of esters

| Int. | Structure | Name | SM | method | MW | Mes |
|---|---|---|---|---|---|---|
| E116 | 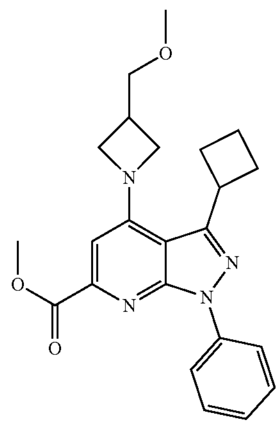 [SMILES: COCC1CN(c2cc(C(=O)OC)nc3c2c(C2CCC2)nn3-c2ccccc2)C1] | methyl 3-cyclobutyl-4-[3-(methoxymethyl)azetidin-1-yl]-1-phenyl-pyrazolo[3,4-b]pyridine-6-carboxylate | HP02 | I3 | 406 | 407 |
| E117 | 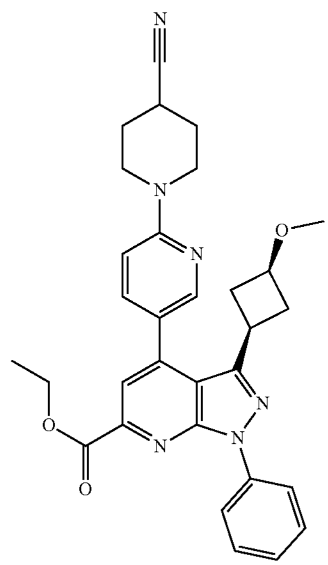 [SMILES: CCOC(=O)c1cc(-c2ccc(N3CCC(C#N)CC3)nc2)c2c(n1)n(-c1ccccc1)nc2[C@H]1C[C@@H](OC)C1] | ethyl 4-[6-(4-cyano-1-piperidyl)-3-pyridyl]-3-(3-methoxycyclobutyl)-1-phenyl-pyrazolo[3,4-b]pyridine-6-carboxylate | ALP09, AMP42 | I1 | 536 | 537 |
| E118 | 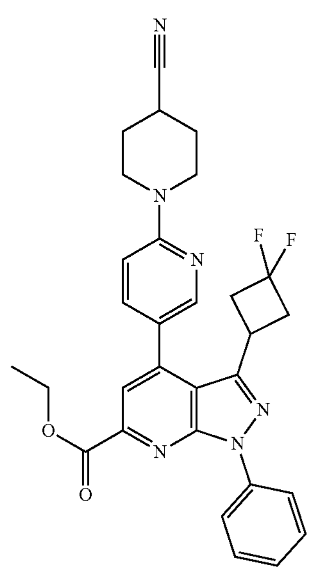 [SMILES: CCOC(=O)c1cc(-c2ccc(N3CCC(C#N)CC3)nc2)c2c(C3CC(F)(F)C3)nn(-c3ccccc3)c2n1] | ethyl 4-[6-(4-cyano-1-piperidyl)-3-pyridyl]-3-(3,3-difluorocyclobutyl)-1-phenyl-pyrazolo[3,4-6]pyridine-6-carboxylate | ALP09, AMP43 | I1 | 542 | 543 |

TABLE XII-continued
List of esters
| Int. | Structure | Name | SM | method | MW | Mes |
|---|---|---|---|---|---|---|
| E119 | 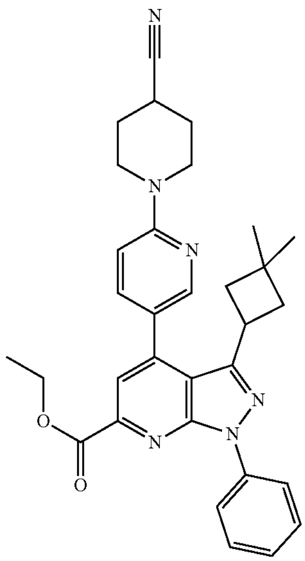 [SMILES: CCOC(=O)c1cc(-c2ccc(N3CCC(C#N)CC3)nc2)c2c(C3CC(C)(C)C3)nn(-c3ccccc3)c2n1] | ethyl 4-[6-(4-cyano-1-piperidyl)-3-pyridyl]-3-(3,3-dimethylcyclobutyl)-1-phenyl-pyrazolo[3,4-b]pyridine-6-carboxylate | ALP09, AMP44 | I1 | 534 | 535 |
| E120 | 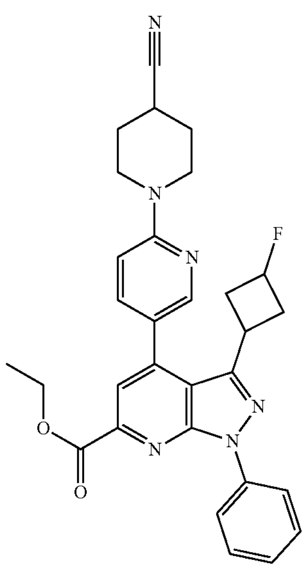 [SMILES: CCOC(=O)c1cc(-c2ccc(N3CCC(C#N)CC3)nc2)c2c(C3CC(F)C3)nn(-c3ccccc3)c2n1] | ethyl 4-[6-(4-cyano-1-piperidyl)-3-pyridyl]-3-(3-fluorocyclobutyl)-1-phenyl-pyrazolo[3,4-b]pyridine-6-carboxylate | ALP09, AMP45 | I1 | 524 | 525 |

TABLE XII-continued

List of esters

| Int. | Structure | Name | SM | method | MW | Mes |
|---|---|---|---|---|---|---|
| E121 | 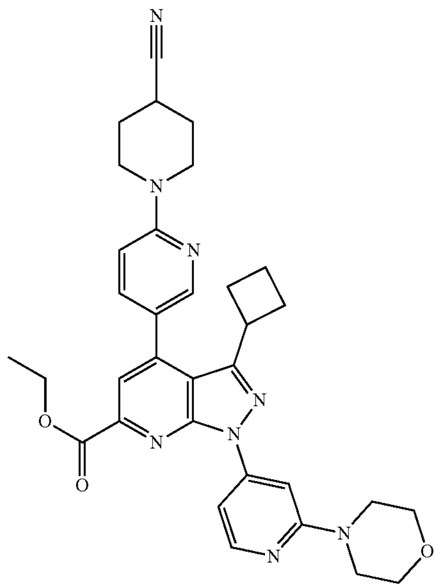 [SMILES: CCOC(=O)c1cc(-c2ccc(N3CCC(C#N)CC3)nc2)c2c(C3CCC3)nn(-c3ccnc(N4CCOCC4)c3)c2n1] | ethyl 4-[6-(4-cyano-1-piperidyl)-3-pyridyl]-3-cyclobutyl-1-(2-morpholino-4-pyridyl)pyrazolo[3,4-b]pyridine-6-carboxylate | ALP09, AMP33 | I1 | 592 | 593 |
| E122 | 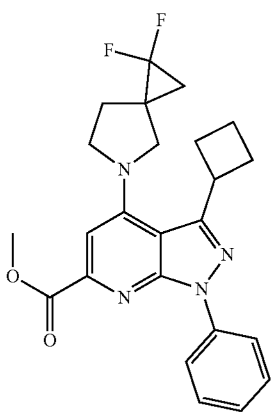 [SMILES: COC(=O)c1cc(N2CCC3(C2)CC3(F)F)c2c(C3CCC3)nn(-c3ccccc3)c2n1] | methyl 3-cyclobutyl-4-(2,2-difluoro-5-azaspiro[2.4]heptan-5-yl)-1-phenyl-pyrazolo[3,4-b]pyridine-6-carboxylate | HP02 | I3 | 438 | 439 |
| E123 | 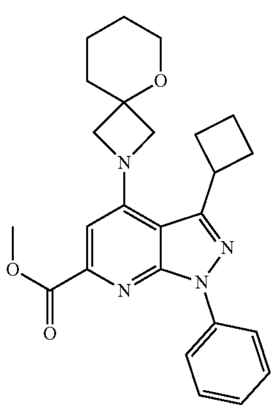 | methyl 3-cyclobutyl-4-(5-oxa-2-azaspiro[3.5]nonan-2-yl)-1-phenyl-pyrazolo[3,4-b]pyridine-6-carboxylate | HP02 | I3 | 432 | 433 |

TABLE XII-continued

| Int. | Structure | Name | SM | method | MW | Mes |
|---|---|---|---|---|---|---|
| E124 | 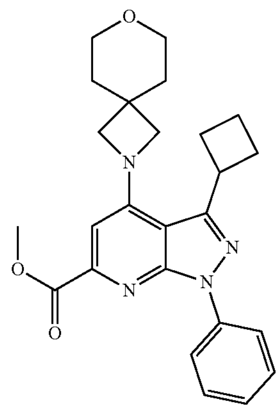 [SMILES: COC(=O)c1cc(N2CC3(CCOCC3)C2)c2c(C3CCC3)nn(-c3ccccc3)c2n1] | methyl 3-cyclobutyl-4-(7-oxa-2-azaspiro[3.5]nonan-2-yl)-1-phenyl-pyrazolo[3,4-b]pyridine-6-carboxylate | HP02 | I3 | 432 | 433 |
| E125 | 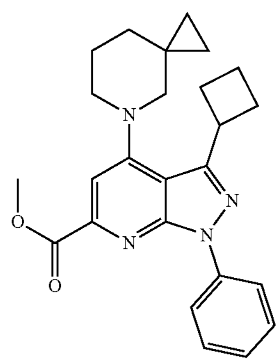 [SMILES: COC(=O)c1cc(N2CCCC3(CC3)C2)c2c(C3CCC3)nn(-c3ccccc3)c2n1] | methyl 4-(5-azaspiro[2.5]octan-5-yl)-3-cyclobutyl-1-phenyl-pyrazolo[3,4-b]pyridine-6-carboxylate | HP02 | I3 | 416 | 417 |
| E126 | 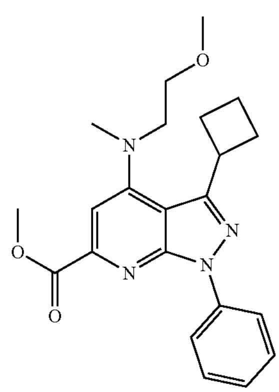 [SMILES: COCCN(C)c1cc(C(=O)OC)nc2c1c(C1CCC1)nn2-c1ccccc1] | methyl 3-cyclobutyl-4-[2-methoxyethyl(methyl)amino]-1-phenyl-pyrazolo[3,4-b]pyridine-6-carboxylate | HP02 | I3 | 394 | 395 |

TABLE XII-continued

List of esters

| Int. | Structure | Name | SM | method | MW | Mes |
|------|-----------|------|-----|--------|-----|-----|
| E127 | 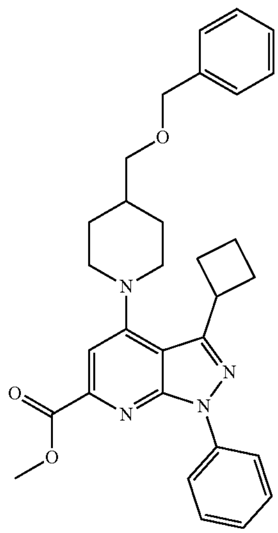 [SMILES: COC(=O)c1cc(N2CCC(COCc3ccccc3)CC2)c2c(C3CCC3)nn(-c3ccccc3)c2n1] | methyl 4-[4-(benzyloxymethyl)-1-piperidyl]-3-cyclobutyl-1-phenyl-pyrazolo[3,4-b]pyridine-6-carboxylate | HP02 | I3 | 510 | 511 |
| E128 | 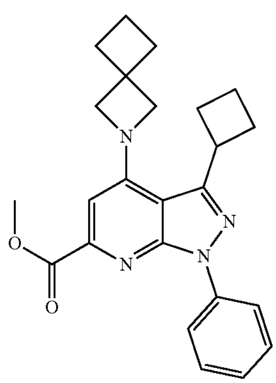 [SMILES: COC(=O)c1cc(N2CC3(CCC3)C2)c2c(C3CCC3)nn(-c3ccccc3)c2n1] | methyl 4-(2-azaspiro[3.3]heptan-2-yl)-3-cyclobutyl-1-phenyl-pyrazolo[3,4-b]pyridine-6-carboxylate | HP02 | I3 | 402 | 403 |
| E129 | 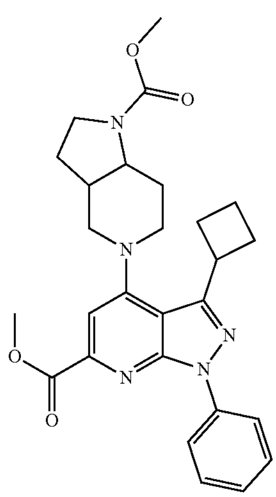 [SMILES: COC(=O)c1cc(N2CCC3C(CCN3C(=O)OC)C2)c2c(C3CCC3)nn(-c3ccccc3)c2n1] | methyl 3-cyclobutyl-4-(1-methoxycarbonyl-3,3a,4,6,7,7a-hexahydro-2H-pyrrolo[3,2-c]pyridin-5-yl)-1-phenyl-pyrazolo[3,4-b]pyridine-6-carboxylate | E130 | I11, Specific example | 489 | 490 |

TABLE XII-continued

| | | List of esters | | | | |
|---|---|---|---|---|---|---|
| Int. | Structure | Name | SM | method | MW | Mes |
| E130 | | methyl 4-(1,2,3,3a,4,6,7,7a-octahydropyrrolo[3,2-c]pyridin-5-yl)-3-cyclobutyl-1-phenyl-pyrazolo[3,4-b]pyridine-6-carboxylate | E131 | Specific example | 431 | 432 |
| E131 | | methyl 4-(1-tert-butoxycarbonyl-3,3a,4,6,7,7a-hexahydro-2H-pyrrolo[3,2-c]pyridin-5-yl)-3-cyclobutyl-1-phenyl-pyrazolo[3,4-6]pyridine-6-carboxylate | HP02 | I3 | 531 | 532 |
| E132 | | methyl 4-(1-acetyl-3,3a,4,6,7,7a-hexahydro-2H-pyrrolo[3,2-c]pyridin-5-yl)-3-cyclobutyl-1-phenyl-pyrazolo[3,4-b]pyridine-6-carboxylate | E130 | I11, Specific exampl | 473 | 474 |

TABLE XII-continued

| | | List of esters | | | | |
|---|---|---|---|---|---|---|
| Int. | Structure | Name | SM | method | MW | Mes |
| E133 | | ethyl 1-(6-bromo-2-pyridyl)-3-isopropyl-4-(4-methoxy-1-piperidyl)pyrazolo[3,4-b]pyridine-6-carboxylate | E109 | I5, Specific example | 501-503 | 502-504 |
| E134 | | methyl 1-cyclohexyl-4-[4-(hydroxymethyl)-1-piperidyl]-3-isopropyl-pyrazolo[3,4-b]pyridine-6-carboxylate | HP12 | I3 | 414 | 415 |
| E135 | | methyl 3-cyclobutyl-4-[4-[(1S)-2-(dimethylamino)-1-fluoro-ethyl]-1-piperidyl]-1-phenyl-pyrazolo[3,4-b]pyridine-6-carboxylate | HP02, AMI03 | I3 | 479 | 480 |

TABLE XII-continued

List of esters

| Int. | Structure | Name | SM | method | MW | Mes |
|---|---|---|---|---|---|---|
| E136 | 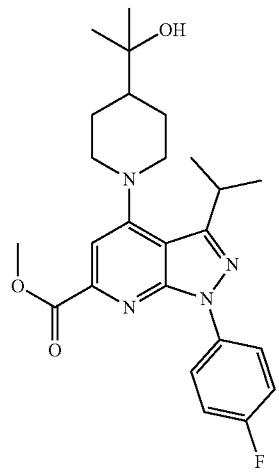 [SMILES: COC(=O)c1cc(N2CCC(C(C)(C)O)CC2)c2c(C(C)C)nn(-c3ccc(F)cc3)c2n1] | methyl 1-(4-fluorophenyl)-4-[4-(1-hydroxy-1-methyl-ethyl)-1-piperidyl]-3-isopropyl-pyrazolo[3,4-b]pyridine-6-carboxylate | HP05 | I3 | 454 | 455 |
| E137 | 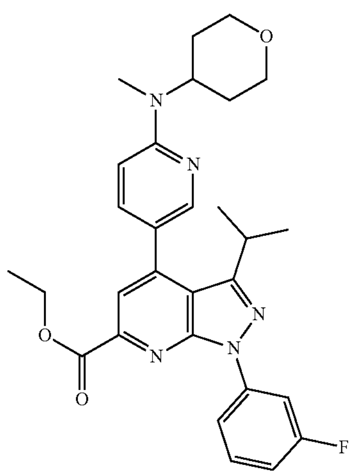 [SMILES: CCOC(=O)c1cc(-c2ccc(N(C)C3CCOCC3)nc2)c2c(C(C)C)nn(-c3cccc(F)c3)c2n1] | ethyl 1-(3-fluorophenyl)-3-isopropyl-4-[6-[methyl(tetrahydropyran-4-yl)amino]-3-pyridyl]pyrazolo[3,4-b]pyridine-6-carboxylate | ALP10, AMP12 | I1 | 517 | 518 |
| E138 | 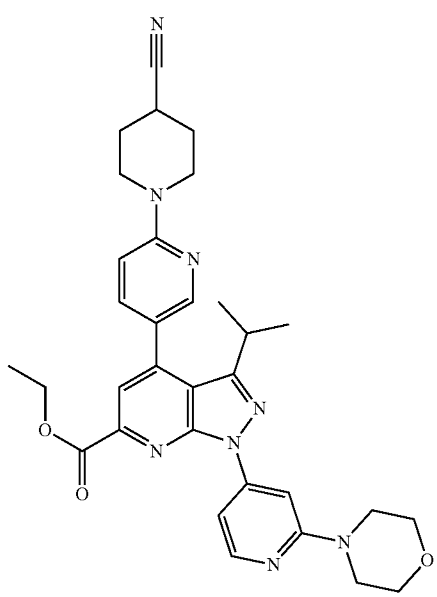 | ethyl 4-[6-(4-cyano-1-piperidyl)-3-pyridyl]-3-isopropyl-1-(2-morpholino-4-pyridyl)pyrazolo[3,4-b]pyridine-6-carboxylate | ALP09, AMP21 | I1 | 580 | 581 |

TABLE XII-continued

List of esters

| Int. | Structure | Name | SM | method | MW | Mes |
|---|---|---|---|---|---|---|
| E139 | 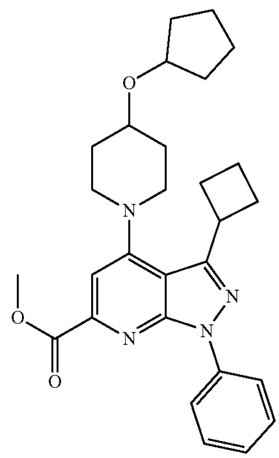 [SMILES: COC(=O)c1cc(N2CCC(OC3CCCC3)CC2)c2c(C3CCC3)nn(-c3ccccc3)c2n1] | methyl 3-cyclobutyl-4-[4-(cyclopentoxy)-1-piperidyl]-1-phenyl-pyrazolo[3,4-b]pyridine-6-carboxylate | HP02 | I3 | 474 | 475 |
| E140 | 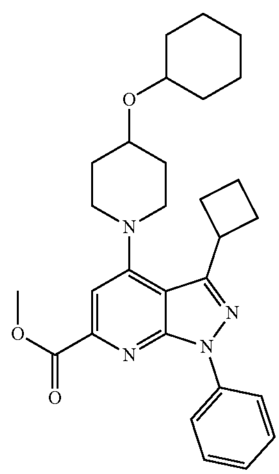 [SMILES: COC(=O)c1cc(N2CCC(OC3CCCCC3)CC2)c2c(C3CCC3)nn(-c3ccccc3)c2n1] | methyl 3-cyclobutyl-4-[4-(cyclohexoxy)-1-piperidyl]-1-phenyl-pyrazolo[3,4-b]pyridine-6-carboxylate | HP02 | I3 | 488 | 489 |
| E141 | 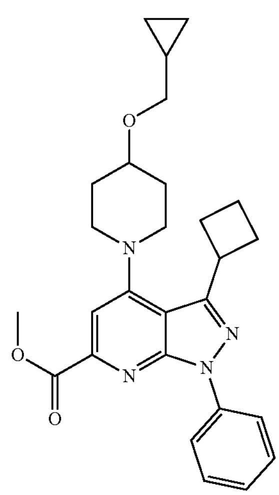 [SMILES: COC(=O)c1cc(N2CCC(OCC3CC3)CC2)c2c(C3CCC3)nn(-c3ccccc3)c2n1] | methyl 3-cyclobutyl-4-[4-(cyclopropylmethoxy)-1-piperidyl]-1-phenyl-pyrazolo[3,4-b]pyridine-6-carboxylate | HP02 | I3 | 460 | 461 |

TABLE XII-continued

List of esters

| Int. | Structure | Name | SM | method | MW | Mes |
|---|---|---|---|---|---|---|
| E142 | 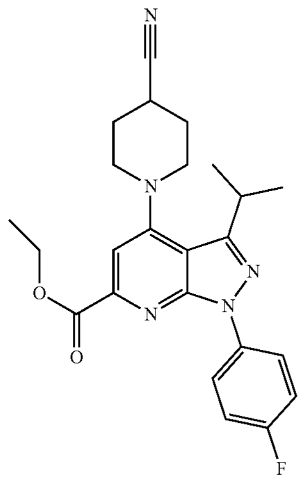 [SMILES: CCOC(=O)c1cc(N2CCC(C#N)CC2)c2c(C(C)C)nn(-c3ccc(F)cc3)c2n1] | ethyl 4-(4-cyano-1-piperidyl)-1-(4-fluorophenyl)-3-isopropyl-pyrazolo[3,4-b]pyridine-6-carboxylate | HP09 | I3 | 435 | 436 |
| E143 | 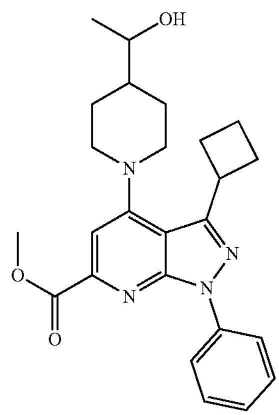 [SMILES: COC(=O)c1cc(N2CCC(C(C)O)CC2)c2c(C3CCC3)nn(-c3ccccc3)c2n1] | methyl 3-cyclobutyl-4-[4-(1-hydroxyethyl)-1-piperidyl]-1-phenyl-pyrazolo[3,4-b]pyridine-6-carboxylate | HP02 | I3 | 434 | 435 |
| E144 | 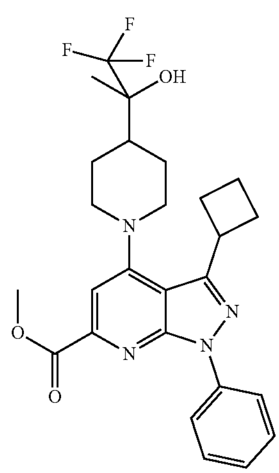 [SMILES: COC(=O)c1cc(N2CCC(C(C)(O)C(F)(F)F)CC2)c2c(C3CCC3)nn(-c3ccccc3)c2n1] | methyl 3-cyclobutyl-1-phenyl-4-[4-(2,2,2-trifluoro-1-hydroxy-1-methyl-ethyl)-1-piperidyl]pyrazolo[3,4-b]pyridine-6-carboxylate | HP02 | I3 | 502 | 503 |

TABLE XII-continued

List of esters

| Int. | Structure | Name | SM | method | MW | Mes |
|---|---|---|---|---|---|---|
| E145 | 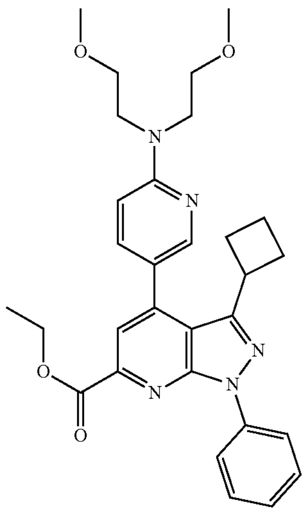 [SMILES: CCOC(=O)c1cc(-c2ccc(N(CCOC)CCOC)nc2)c2c(C3CCC3)nn(-c3ccccc3)c2n1] | ethyl 4-[6-[bis(2-methoxyethyl)amino]-3-pyridyl]-3-cyclobutyl-1-phenyl-pyrazolo[3,4-b]pyridine-6-carboxylate | ALP23, AMP29 | I1 | 529 | 530 |
| E146 | 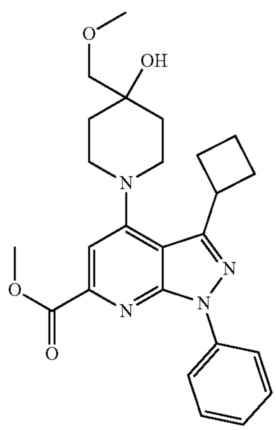 [SMILES: COCC1(O)CCN(c2cc(C(=O)OC)nc3c2c(C2CCC2)nn3-c2ccccc2)CC1] | methyl 3-cyclobutyl-4-[4-hydroxy-4-(methoxymethyl)-1-piperidyl]-1-phenyl-pyrazolo[3,4-b]pyridine-6-carboxylate | HP02, AMI01 | I3 | 450 | 451 |
| E147 | 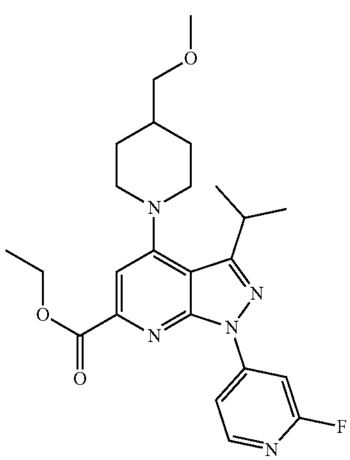 [SMILES: CCOC(=O)c1cc(N2CCC(COC)CC2)c2c(C(C)C)nn(-c3ccnc(F)c3)c2n1] | ethyl 1-(2-fluoro-4-pyridyl)-3-isopropyl-4-[4-(methoxymethyl)-1-piperidyl]pyrazolo[3,4-b]pyridine-6-carboxylate | E148 | I4 | 455 | 456 |

TABLE XII-continued

List of esters

| Int. | Structure | Name | SM | method | MW | Mes |
|---|---|---|---|---|---|---|
| E148 | 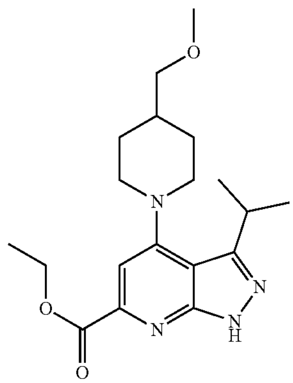 [SMILES: CCOC(=O)c1cc(N2CCC(COC)CC2)c2c(C(C)C)n[nH]c2n1] | ethyl 3-isopropyl-4-[4-(methoxymethyl)-1-piperidyl]-1H-pyrazolo[3,4-b]pyridine-6-carboxylate | HP08 | I3 | 360 | 361 |
| E149 | 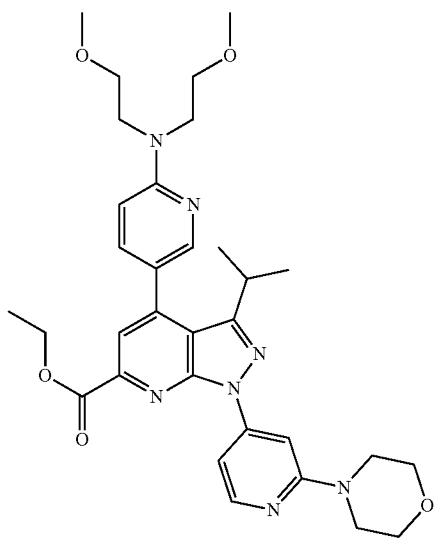 [SMILES: CCOC(=O)c1cc(-c2ccc(N(CCOC)CCOC)nc2)c2c(C(C)C)nn(-c3ccnc(N4CCOCC4)c3)c2n1] | ethyl 4-[6-[bis(2-methoxyethyl)amino]-3-pyridyl]-3-isopropyl-1-(2-morpholino-4-pyridyl)pyrazolo[3,4-b]pyridine-6-carboxylate | ALP23, AMP21 | I1 | 603 | 604 |
| E150 | 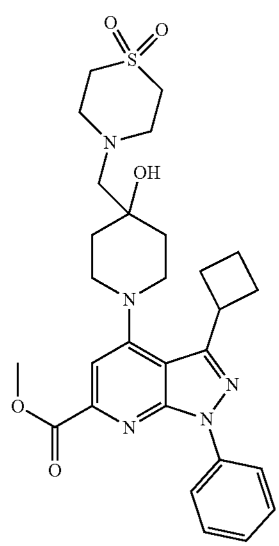 [SMILES: COC(=O)c1cc(N2CCC(O)(CN3CCS(=O)(=O)CC3)CC2)c2c(C3CCC3)nn(-c3ccccc3)c2n1] | methyl 3-cyclobutyl-4-[4-[(1,1-dioxo-1,4-thiazinan-4-yl)methyl]-4-hydroxy-1-piperidyl]-1-phenyl-pyrazolo[3,4-b]pyridine-6-carboxylate | HP02, AMI02 | I3 | 553 | 554 |

TABLE XII-continued
List of esters
| Int. | Structure | Name | SM | method | MW | Mes |
|---|---|---|---|---|---|---|
| E151 | 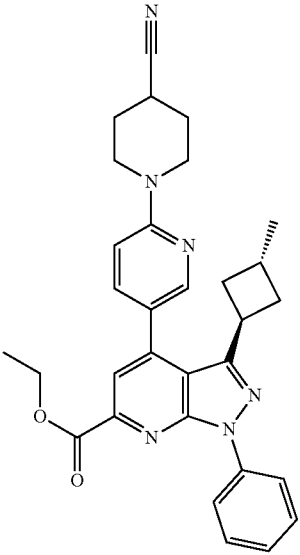 [SMILES: CCOC(=O)c1cc(-c2ccc(N3CCC(C#N)CC3)nc2)c2c(n1)n(-c1ccccc1)nc2[C@H]1C[C@H](C)C1] | ethyl 4-[6-(4-cyano-1-piperidyl)-3-pyridyl]-3-(3-methylcyclobutyl)-1-phenyl-pyrazolo[3,4-b]pyridine-6-carboxylate | ALP09, AMP46 | I1 | 520 | 521 |
| E152 | 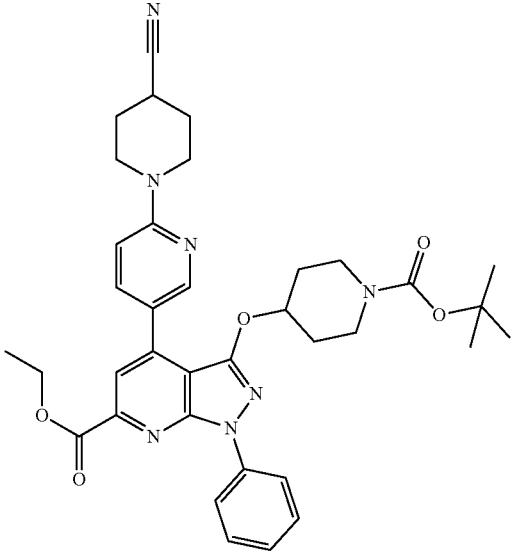 [SMILES: CCOC(=O)c1cc(-c2ccc(N3CCC(C#N)CC3)nc2)c2c(OC3CCN(C(=O)OC(C)(C)C)CC3)nn(-c3ccccc3)c2n1] | ethyl 3-[(1-tert-butoxycarbonyl-4-piperidyl)oxy]-4-[6-(4-cyano-1-piperidyl)-3-pyridyl]-1-phenyl-pyrazolo[3,4-b]pyridine-6-carboxylate | E153 | I13, Specific example | 651 | |

TABLE XII-continued

List of esters

| Int. | Structure | Name | SM | method | MW | Mes |
|---|---|---|---|---|---|---|
| E153 | 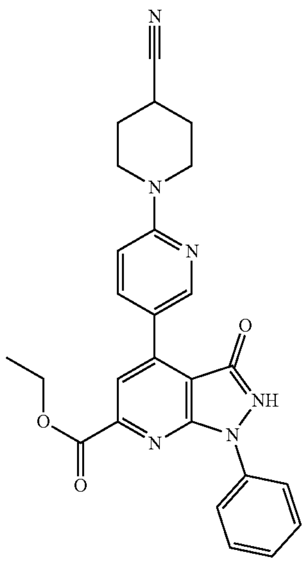 | ethyl 4-[6-(4-cyano1-1-piperidyl)-3-pyridyl]-3-oxo-1-phenyl-2H-pyrazolo[3,4-b]pyridine-6-carboxylate | ALP09, 70373-98-7 | I1 | 468 | 469 |
| E154 | 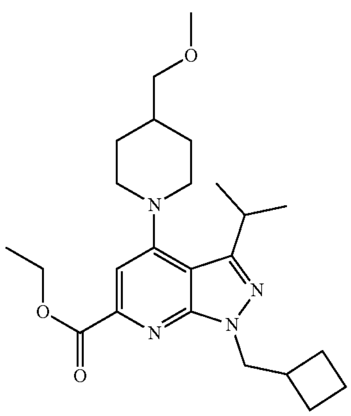 [SMILES: CCOC(=O)c1cc(N2CCC(COC)CC2)c2c(C(C)C)nn(CC3CCC3)c2n1] | ethyl 1-(cyclobutylmethyl)-3-isopropyl-4-[4-(methoxymethyl)-1-piperidyl]pyrazolo[3,4-b]pyridine-6-carboxylate | E148 | I6, Specific example | 428 | 429 |
| E155 | 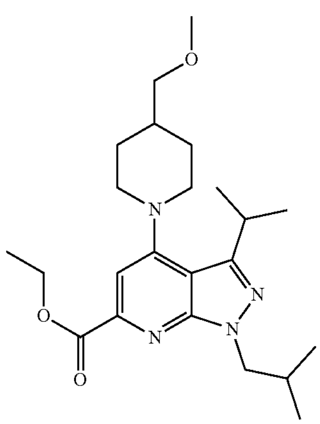 [SMILES: CCOC(=O)c1cc(N2CCC(COC)CC2)c2c(C(C)C)nn(CC(C)C)c2n1] | ethyl 1-isobutyl-3-isopropyl-4-[4-(methoxymethyl)-1-piperidyl]pyrazolo[3,4-b]pyridine-6-carboxylate | E148 | I6 | 416 | 417 |

TABLE XII-continued

List of esters

| Int. | Structure | Name | SM | method | MW | Mes |
|---|---|---|---|---|---|---|
| E156 | 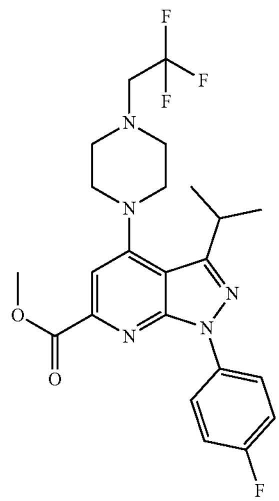 [SMILES: COC(=O)c1cc(N2CCN(CC(F)(F)F)CC2)c2c(C(C)C)nn(-c3ccc(F)cc3)c2n1] | methyl 1-(4-fluorophenyl)-3-isopropyl-4-[4-(2,2,2-trifluoroethyl)piperazin-1-yl]pyrazolo[3,4-b]pyridine-6-carboxylate | HP05 | I3 | 479 | 480 |
| E157 | 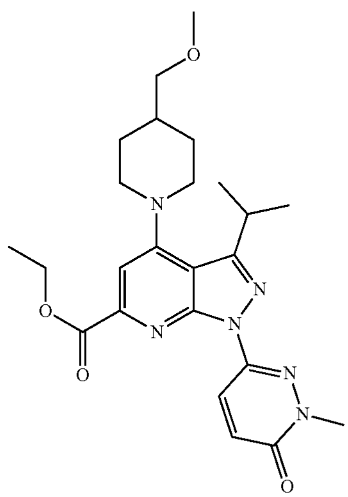 [SMILES: CCOC(=O)c1cc(N2CCC(COC)CC2)c2c(C(C)C)nn(-c3ccc(=O)n(C)n3)c2n1] | ethyl 3-isopropyl-4-[4-(methoxymethyl)-1-piperidyl]-1-(1-methyl-6-oxo-pyridazin-3-yl)pyrazolo[3,4-b]pyridine-6-carboxylate | E148 | I7 | 468 | 469 |
| E158 | 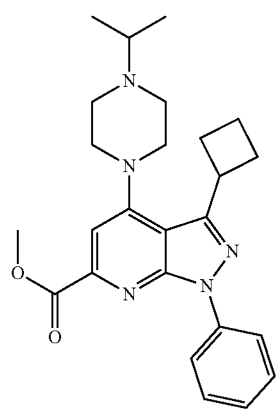 [SMILES: COC(=O)c1cc(N2CCN(C(C)C)CC2)c2c(C3CCC3)nn(-c3ccccc3)c2n1] | methyl 3-cyclobutyl-4-(4-isopropylpiperazin-1-yl)-1-phenyl-pyrazolo[3,4-6]pyridine-6-carboxylate | HP02 | I3 | 433 | 434 |

TABLE XII-continued

List of esters

| Int. | Structure | Name | SM | method | MW | Mes |
|---|---|---|---|---|---|---|
| E159 | 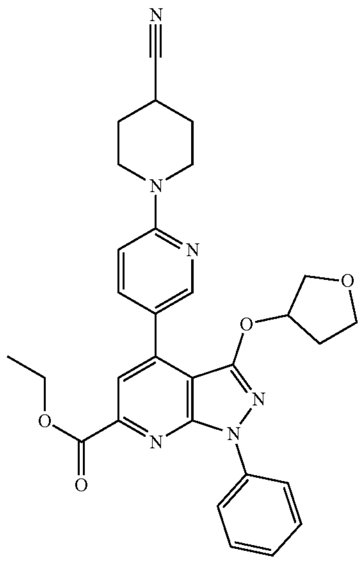 [SMILES: CCOC(=O)c1cc(-c2ccc(N3CCC(C#N)CC3)nc2)c2c(OC3CCOC3)nn(-c3ccccc3)c2n1] | ethyl 4-[6-(4-cyano-1-piperidyl)-3-pyridyl]-1-phenyl-3-tetrahydrofuran-3-yloxy-pyrazolo[3,4-b]pyridine-6-carboxylate | E153 | I13 | 538 | 539 |
| E160 | 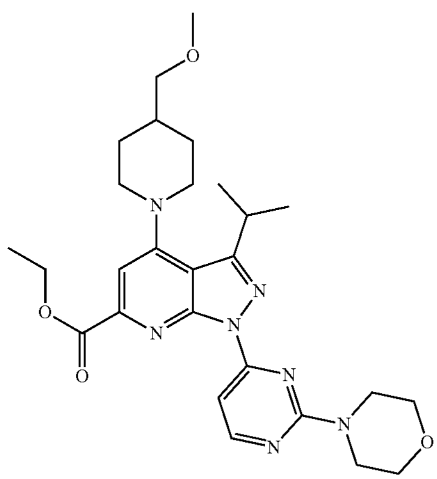 [SMILES: CCOC(=O)c1cc(N2CCC(COC)CC2)c2c(C(C)C)nn(-c3ccnc(N4CCOCC4)n3)c2n1] | ethyl 3-isopropyl-4-[4-(methoxymethyl)-1-piperidyl]-1-(2-morpholinopyrimidin-4-yl)pyrazolo[3,4-b]pyridine-6-carboxylate | E161 | I12 | 523 | 524 |
| E161 | 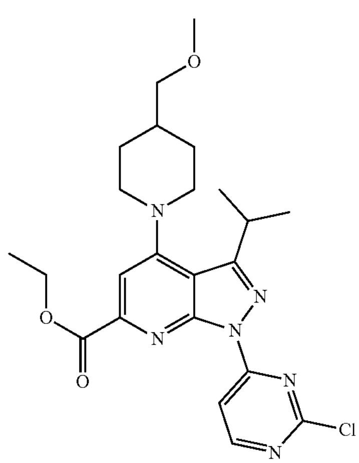 [SMILES: CCOC(=O)c1cc(N2CCC(COC)CC2)c2c(C(C)C)nn(-c3ccnc(Cl)n3)c2n1] | ethyl 1-(2-chloropyrimidin-4-yl)-3-isopropyl-4-[4-(methoxymethyl)-1-piperidyl]pyrazolo[3,4-b]pyridine-6-carboxylate | E148 | I5 | 472-474 | 476-475 |

… TABLE XII-continued

List of esters

| Int. | Structure | Name | SM | method | MW | Mes |
|---|---|---|---|---|---|---|
| E162 | 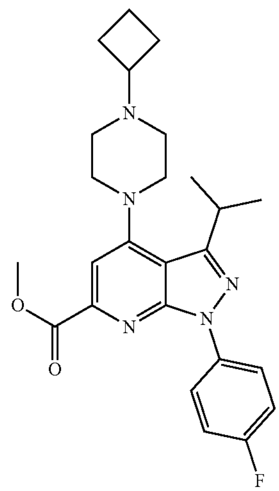 [SMILES: COC(=O)c1cc(N2CCN(C3CCC3)CC2)c2c(C(C)C)nn(-c3ccc(F)cc3)c2n1] | methyl 4-(4-cyclobutylpiperazin-1-yl)-1-(4-fluorophenyl)-3-isopropyl-pyrazolo[3,4-b]pyridine-6-carboxylate | HP05 | I3 | 451 | 452 |
| E163 | 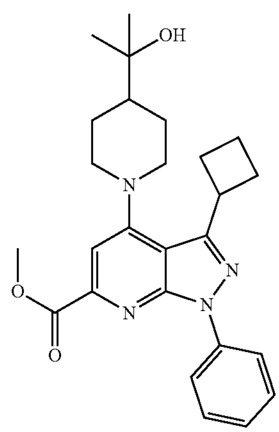 [SMILES: COC(=O)c1cc(N2CCC(C(C)(C)O)CC2)c2c(C3CCC3)nn(-c3ccccc3)c2n1] | methyl 3-cyclobutyl-4-[4-(1-hydroxy-1-methyl-ethyl)-1-piperidyl]-1-phenyl-pyrazolo[3,4-b]pyridine-6-carboxylate | HP02 | I3 | 448 | 449 |
| E164 | 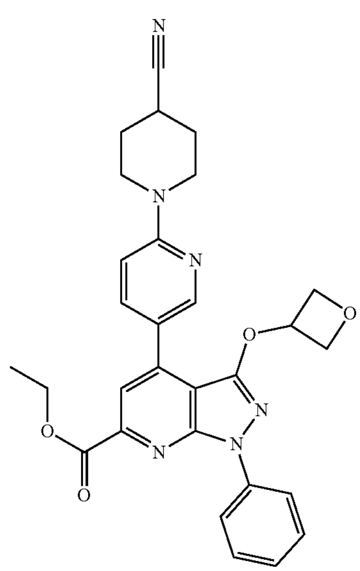 [SMILES: CCOC(=O)c1cc(-c2ccc(N3CCC(C#N)CC3)nc2)c2c(OC3COC3)nn(-c3ccccc3)c2n1] | ethyl 4-[6-(4-cyano-1-piperidyl)-3-pyridyl]-3-(oxetan-3-yloxy)-1-phenyl-pyrazolo[3,4-b]pyridine-6-carboxylate | E153 | I13 | 524 | 525 |

TABLE XII-continued

| | | List of esters | | | | |
|---|---|---|---|---|---|---|
| Int. | Structure | Name | SM | method | MW | Mes |
| E165 | | methyl 1-(4-fluorophenyl)-3-isopropyl-4-[2-methoxyethyl(methyl)amino]pyrazolo[3,4-b]pyridine-6-carboxylate | HP05 | I3 | 400 | 401 |
| E166 | | methyl 1-(4-fluorophenyl)-4-[4-(1-hydroxy-1-methyl-ethyl)-1-piperidyl]-3-isopropyl-pyrazolo[3,4-b]pyridine-6-carboxylate | HP05 | I3 | 454 | 455 |
| E167 | | ethyl 3-cyclobutyl-1-(4-fluorophenyl)-4-[4-(methoxymethyl)-1-piperidyl]pyrazolo[3,4-6]pyridine-6-carboxylate | E168 | I4 | 466 | 467 |

TABLE XII-continued
List of esters
| Int. | Structure | Name | SM | method | MW | Mes |
|---|---|---|---|---|---|---|
| E168 | 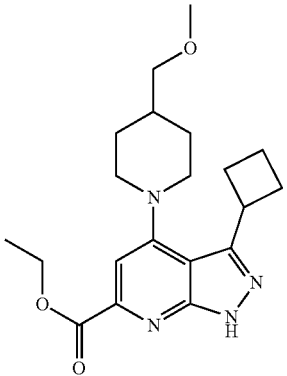 [SMILES: CCOC(=O)c1cc(N2CCC(COC)CC2)c2c(C3CCC3)n[nH]c2n1] | ethyl 3-cyclobutyl-4-[4-(methoxymethyl)-1-piperidyl]-1H-pyrazolo[3,4-b]pyridine-6-carboxylate | E169 | I15 | 372 | 373 |
| E169 | 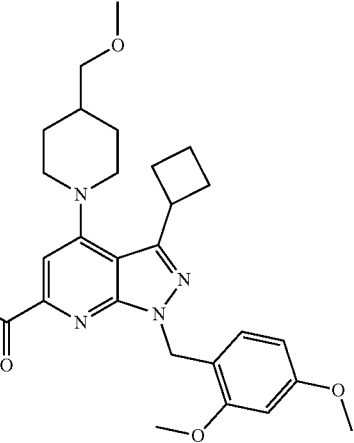 | ethyl 3-cyclobutyl-1-[(2,4-dimethoxyphenyl)methyl]-4-[4-(methoxymethyl)-1-piperidyl]pyrazolo[3,4-b]pyridine-6-carboxylate | HP14 | I3 | 522 | 523 |
| E170 | 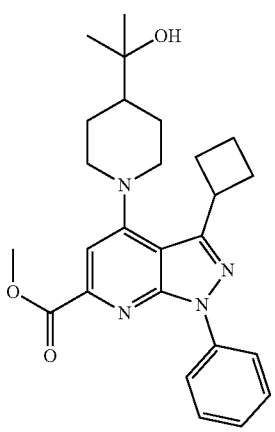 | methyl 3-cyclobutyl-4-[4-(1-hydroxy-1-methyl-ethyl)-1-piperidyl]-1-phenyl-pyrazolo[3,4-b]pyridine-6-carboxylate | HP02 | I3 | 448 | 449 |

TABLE XII-continued

List of esters

| Int. | Structure | Name | SM | method | MW | Mes |
|---|---|---|---|---|---|---|
| E171 | 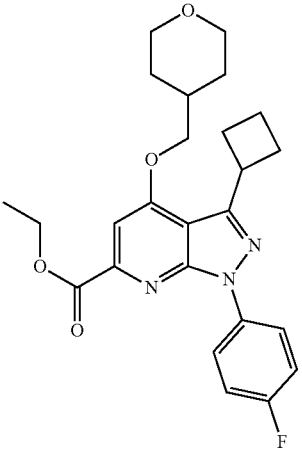 [SMILES: CCOC(=O)c1cc(OCC2CCOCC2)c2c(C3CCC3)nn(-c3ccc(F)cc3)c2n1] | ethyl 3-cyclobutyl-1-(4-fluorophenyl)-4-(tetrahydropyran-4-ylmethoxy)pyrazolo[3,4-b]pyridine-6-carboxylate | E172 | I16, Specific example | 453 | 454 |
| E172 | 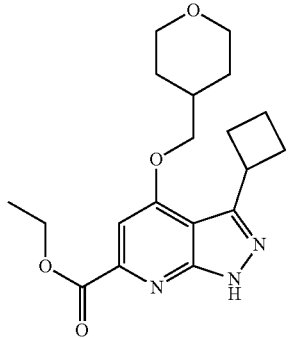 [SMILES: CCOC(=O)c1cc(OCC2CCOCC2)c2c(C3CCC3)n[nH]c2n1] | ethyl 3-cyclobutyl-4-(tetrahydropyran-4-ylmethoxy)-1H-pyrazolo[3,4-b]pyridine-6-carboxylate | E173 | I15 | 359 | 360 |
| E173 | 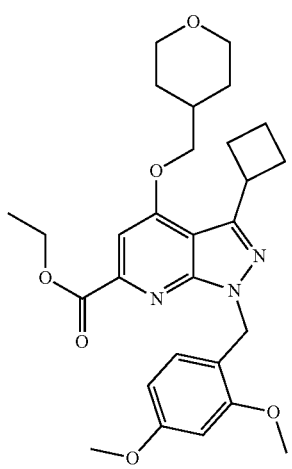 [SMILES: CCOC(=O)c1cc(OCC2CCOCC2)c2c(C3CCC3)nn(Cc3ccc(OC)cc3OC)c2n1] | ethyl 3-cyclobutyl-1-[(2,4-dimethoxyphenyl)methyl]-4-(tetrahydropyran-4-ylmethoxy)pyrazolo[3,4-b]pyridine-6-carboxylate | HP15 | I14 | 509 | 510 |

TABLE XII-continued

List of esters

| Int. | Structure | Name | SM | method | MW | Mes |
|---|---|---|---|---|---|---|
| E174 | 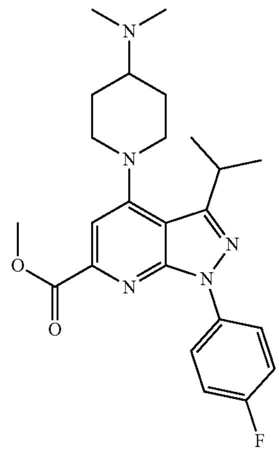 [SMILES: COC(=O)c1cc(N2CCC(N(C)C)CC2)c2c(C(C)C)nn(-c3ccc(F)cc3)c2n1] | methyl 4-[4-(dimethylamino)-1-piperidyl]-1-(4-fluorophenyl)-3-isopropyl-pyrazolo[3,4-b]pyridine-6-carboxylate | HP05 | I3 | 439 | 440 |
| E175 | 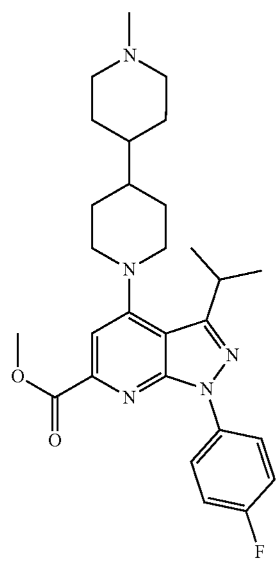 [SMILES: COC(=O)c1cc(N2CCC(C3CCN(C)CC3)CC2)c2c(C(C)C)nn(-c3ccc(F)cc3)c2n1] | methyl 1-(4-fluorophenyl)-3-isopropyl-4-[4-(1-methyl-4-piperidyl)-1-piperidyl]pyrazolo[3,4-b]pyridine-6-carboxylate | HP05 | I3 | 493 | 494 |
| E176 | 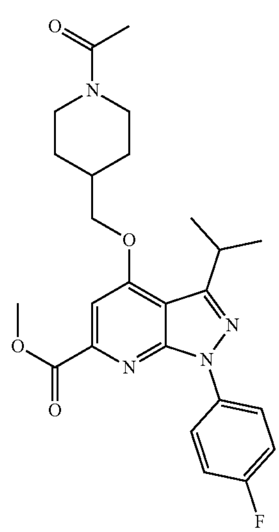 [SMILES: COC(=O)c1cc(OCC2CCN(C(C)=O)CC2)c2c(C(C)C)nn(-c3ccc(F)cc3)c2n1] | methyl 4-[(1-acetyl-4-piperidyl)methoxy]-1-(4-fluorophenyl)-3-isopropyl-pyrazolo[3,4-b]pyridine-6-carboxylate | E177 | I11, Specific example | 468 | 469 |

TABLE XII-continued

| | | List of esters | | | | |
|---|---|---|---|---|---|---|
| Int. | Structure | Name | SM | method | MW | Mes |
| E177 | | methyl 1-(4-fluorophenyl)-3-isopropyl-4-(4-piperidylmethoxy)pyrazolo[3,4-b]pyridine-6-carboxylate | A263 | I9 | 426 | 427 |
| E178 | | methyl 1-(4-fluorophenyl)-3-isopropyl-4-[(1-methoxycarbonyl-4-piperidyl)methoxy]pyrazolo[3,4-b]pyridine-6-carboxylate | E177 | I11, Specific example | 484 | 485 |
| E179 | | methyl 4-[4-(cyanomethyl)-4-hydroxy-1-piperidyl]-3-cyclobutyl-1-phenyl-pyrazolo[3,4-b]pyridine-6-carboxylate | HP02, AMI09 | I3 | 445 | 446 |

TABLE XII-continued

List of esters

| Int. | Structure | Name | SM | method | MW | Mes |
|---|---|---|---|---|---|---|
| E180 | 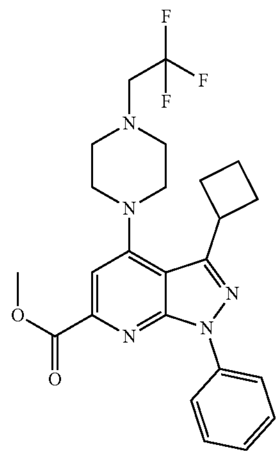 [SMILES: COC(=O)c1cc(N2CCN(CC(F)(F)F)CC2)c2c(C3CCC3)nn(-c3ccccc3)c2n1] | methyl 3-cyclobutyl-1-phenyl-4-[4-(2,2,2-trifluoroethyl)piperazin-1-yl]pyrazolo[3,4-b]pyridine-6-carboxylate | HP02 | I3 | 473 | 474 |
| E181 | 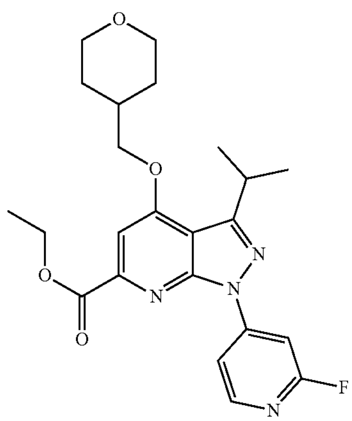 [SMILES: CCOC(=O)c1cc(OCC2CCOCC2)c2c(C(C)C)nn(-c3ccnc(F)c3)c2n1] | ethyl 1-(2-fluoro-4-pyridyl)-3-isopropyl-4-(tetrahydropyran-4-ylmethoxy)pyrazolo[3,4-b]pyridine-6-carboxylate | E182 | I4 | 442 | 443 |
| E182 | 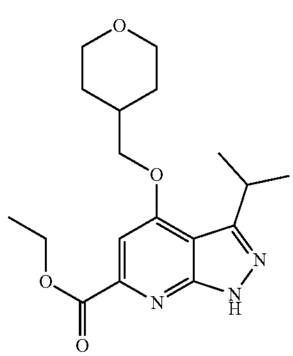 [SMILES: CCOC(=O)c1cc(OCC2CCOCC2)c2c(C(C)C)n[nH]c2n1] | ethyl 3-isopropyl-4-(tetrahydropyran-4-ylmethoxy)-1H-pyrazolo[3,4-b]pyridine-6-carboxylate | E183 | I15 | 347 | 348 |

TABLE XII-continued

List of esters

| Int. | Structure | Name | SM | method | MW | Mes |
|---|---|---|---|---|---|---|
| E183 | 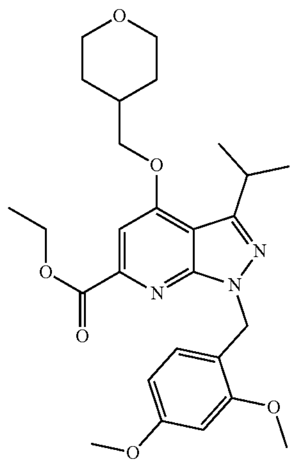 [SMILES: CCOC(=O)c1cc(OCC2CCOCC2)c2c(C(C)C)nn(Cc3ccc(OC)cc3OC)c2n1] | ethyl 1-[(2,4-dimethoxyphenyl)methyl]-3-isopropyl-4-(tetrahydropyran-4-ylmethoxy)pyrazolo[3,4-b]pyridine-6-carboxylate | HP06 | I14, Specific example | 497 | 498 |
| E184 | 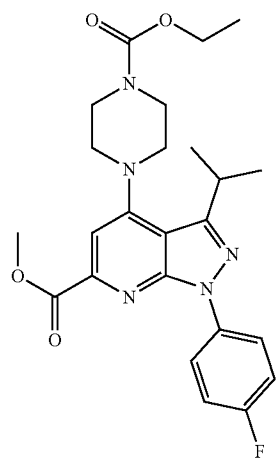 [SMILES: CCOC(=O)N1CCN(c2cc(C(=O)OC)nc3c2c(C(C)C)nn3-c2ccc(F)cc2)CC1] | methyl 4-(4-ethoxycarbonylpiperazin-1-yl)-1-(4-fluorophenyl)-3-isopropyl-pyrazolo[3,4-b]pyridine-6-carboxylate | HP05 | I3 | 469 | 470 |
| E185 | 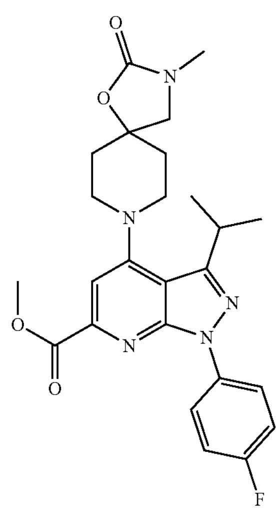 [SMILES: COC(=O)c1cc(N2CCC3(CC2)CN(C)C(=O)O3)c2c(C(C)C)nn(-c3ccc(F)cc3)c2n1] | methyl 1-(4-fluorophenyl)-3-isopropyl-4-(3-methyl-2-oxo-1-oxa-3,8-diazaspiro[4.5]decan-8-yl)pyrazolo[3,4-b]pyridine-6-carboxylate | HP05 | I3 | 481 | 482 |

TABLE XII-continued

List of esters

| Int. | Structure | Name | SM | method | MW | Mes |
|---|---|---|---|---|---|---|
| E186 | 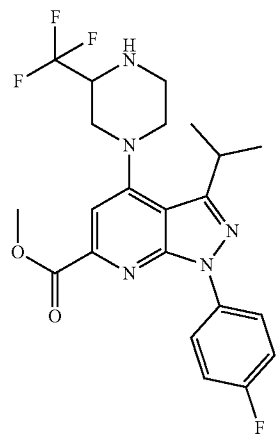 [SMILES: COC(=O)c1cc(N2CCNC(C(F)(F)F)C2)c2c(C(C)C)nn(-c3ccc(F)cc3)c2n1] | methyl 1-(4-fluorophenyl)-3-isopropyl-4-[3-(trifluoromethyl)piperazin-1-yl]pyrazolo[3,4-b]pyridine-6-carboxylate | HP05 | I3 | 465 | 466 |
| E187 | 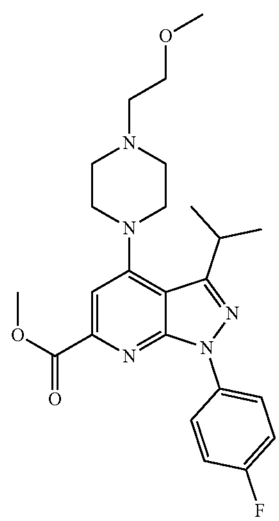 [SMILES: COCCN1CCN(c2cc(C(=O)OC)nc3c2c(C(C)C)nn3-c2ccc(F)cc2)CC1] | methyl 1-(4-fluorophenyl)-3-isopropyl-4-[4-(2-methoxyethyl)piperazin-1-yl]pyrazolo[3,4-b]pyridine-6-carboxylate | HP05 | I3 | 455 | 456 |
| E188 | 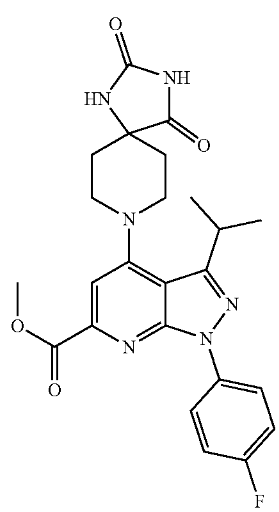 [SMILES: COC(=O)c1cc(N2CCC3(CC2)NC(=O)NC3=O)c2c(C(C)C)nn(-c3ccc(F)cc3)c2n1] | methyl 4-(2,4-dioxo-1,3,8-triazaspiro[4.5]decan-8-yl)-1-(4-fluorophenyl)-3-isopropyl-pyrazolo[3,4-b]pyridine-6-carboxylate | HP05 | I3 | 480 | 481 |

TABLE XII-continued

List of esters

| Int. | Structure | Name | SM | method | MW | Mes |
|---|---|---|---|---|---|---|
| E189 | 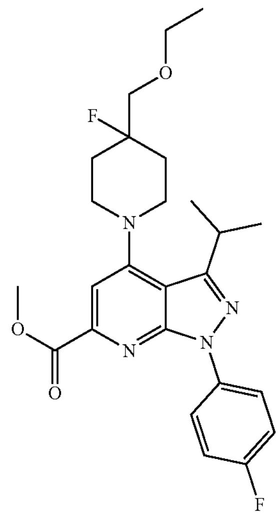 [SMILES: CCOCC1(F)CCN(c2cc(C(=O)OC)nc3c2c(C(C)C)nn3-c2ccc(F)cc2)CC1] | methyl 4-[4-(ethoxymethyl)-4-fluoro-1-piperidyl]-1-(4-fluorophenyl)-3-isopropyl-pyrazolo[3,4-b]pyridine-6-carboxylate | HP05, AMI04 | I3 | 472 | 473 |
| E190 | 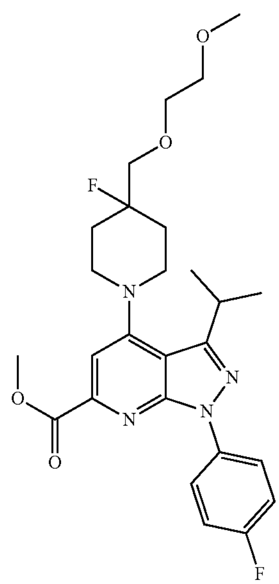 [SMILES: COCCOCC1(F)CCN(c2cc(C(=O)OC)nc3c2c(C(C)C)nn3-c2ccc(F)cc2)CC1] | methyl 4-[4-fluoro-4-(2-methoxyethoxymethyl)-1-piperidyl]-1-(4-fluorophenyl)-3-isopropyl-pyrazolo[3,4-b]pyridine-6-carboxylate | HP05, AMI05 | I3 | 502 | 503 |
| E191 | 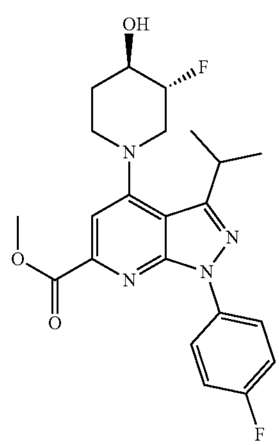 [SMILES: COC(=O)c1cc(N2CC[C@@H](O)[C@H](F)C2)c2c(C(C)C)nn(-c3ccc(F)cc3)c2n1] | methyl 4-[(3R,4R)-3-fluoro-4-hydroxy-1-piperidyl]-1-(4-fluorophenyl)-3-isopropyl-pyrazolo[3,4-b]pyridine-6-carboxylate | HP05, AMI06 | I3 | 430 | 431 |

TABLE XII-continued

List of esters

| Int. | Structure | Name | SM | method | MW | Mes |
|---|---|---|---|---|---|---|
| E192 | 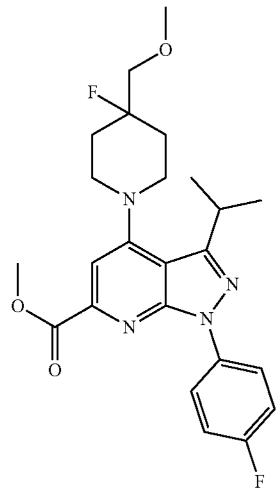 [SMILES: COCC1(F)CCN(c2cc(C(=O)OC)nc3c2c(C(C)C)nn3-c2ccc(F)cc2)CC1] | methyl 4-[4-fluoro-4-(methoxymethyl)-1-piperidyl]-1-(4-fluorophenyl)-3-isopropyl-pyrazolo[3,4-b]pyridine-6-carboxylate | HP05, AMI07 | I3 | 458 | 459 |
| E193 | 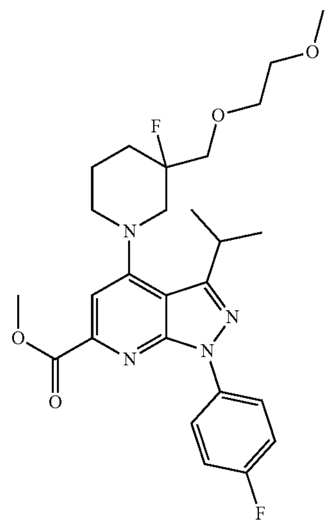 [SMILES: COCCOCC1(F)CCCN(c2cc(C(=O)OC)nc3c2c(C(C)C)nn3-c2ccc(F)cc2)C1] | methyl 4-[3-fluoro-3-(2-methoxyethoxymethyl)-1-piperidyl]-1-(4-fluorophenyl)-3-isopropyl-pyrazolo[3,4-b]pyridine-6-carboxylate | HP05, AMI08 | I3 | 502 | 503 |
| E194 | 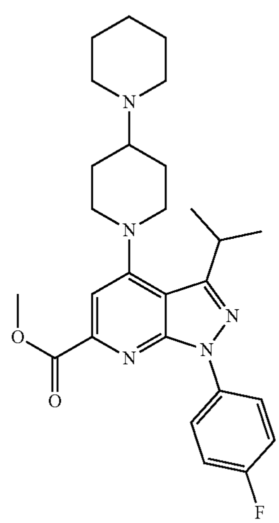 [SMILES: COC(=O)c1cc(N2CCC(N3CCCCC3)CC2)c2c(C(C)C)nn(-c3ccc(F)cc3)c2n1] | methyl 1-(4-fluorophenyl)-3-isopropyl-4-[4-(1-piperidyl)-1-piperidyl]pyrazolo[3,4-b]pyridine-6-carboxylate | HP05 | I3 | 479 | 480 |

TABLE XII-continued

List of esters

| Int. | Structure | Name | SM | method | MW | Mes |
|---|---|---|---|---|---|---|
| E195 | 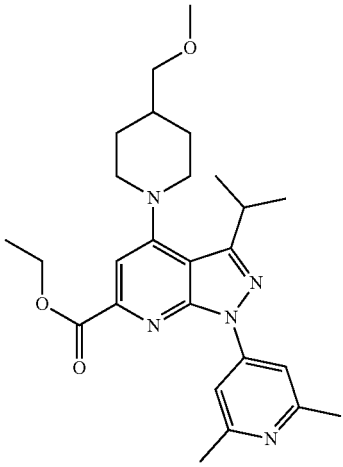 [SMILES: CCOC(=O)c1cc(N2CCC(COC)CC2)c2c(C(C)C)nn(-c3cc(C)nc(C)c3)c2n1] | ethyl 1-(2,6-dimethyl-4-pyridyl)-3-isopropyl-4-[4-(methoxymethyl)-1-piperidyl]pyrazolo[3,4-b]pyridine-6-carboxylate | E148 | I4 | 465 | 466 |
| E196 | 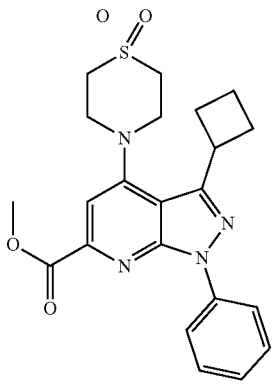 | methyl 3-cyclobutyl-4-(1,1-dioxo-1,4-thiazinan-4-yl)-1-phenyl-pyrazolo[3,4-b]pyridine-6-carboxylate | HP02 | I3 | 440 | 441 |
| E197 | 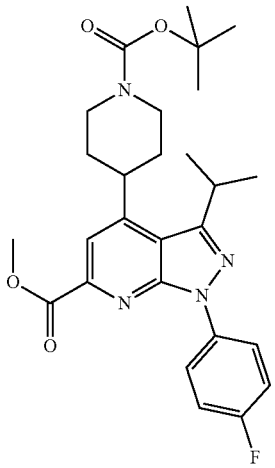 [SMILES: COC(=O)c1cc(C2CCN(C(=O)OC(C)(C)C)CC2)c2c(C(C)C)nn(-c3ccc(F)cc3)c2n1] | methyl 4-(1-tert-butoxycarbonyl-4-piperidyl)-1-(4-fluorophenyl)-3-isopropyl-pyrazolo[3,4-b]pyridine-6-carboxylate | E198 | Specific example | 496 | 497 |

TABLE XII-continued

| | | List of esters | | | | |
|---|---|---|---|---|---|---|
| Int. | Structure | Name | SM | method | MW | Mes |
| E198 | | methyl 4-(1-tert-butoxycarbonyl-3,6-dihydro-2H-pyridin-4-yl)-1-(4-fluorophenyl)-3-isopropyl-pyrazolo[3,4-b]pyridine-6-carboxylate | HP05 | I2, Specific example | 494 | 495 |
| E199 | | methyl 4-(4-azidophenyl)-1-[3-(dimethylamino)phenyl]-3-isopropyl-pyrazolo[3,4-b]pyridine-6-carboxylate | E074 | Specific example | 455 | 456 |
| E352 | | methyl 3-cyclobutyl-1-(4-fluorophenyl)-4-(4-hydroxypiperidin-1-yl)-1H-pyrazolo[3,4-b]pyridine-6-carboxylate | HP19 | I3 | 424 | 425 |

TABLE XII-continued

List of esters

| Int. | Structure | Name | SM | method | MW | Mes |
|---|---|---|---|---|---|---|
| E353 | 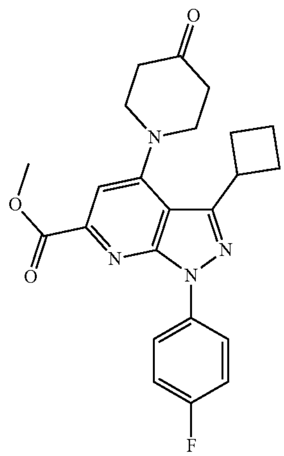 [SMILES: COC(=O)c1cc(N2CCC(=O)CC2)c2c(C3CCC3)nn(-c3ccc(F)cc3)c2n1] | methyl 3-cyclobutyl-1-(4-fluorophenyl)-4-(4-oxopiperidin-1-yl)-1H-pyrazolo[3,4-b]pyridine-6-carboxylate | E352 | Specific example | 422 | 423 |
| E354 | 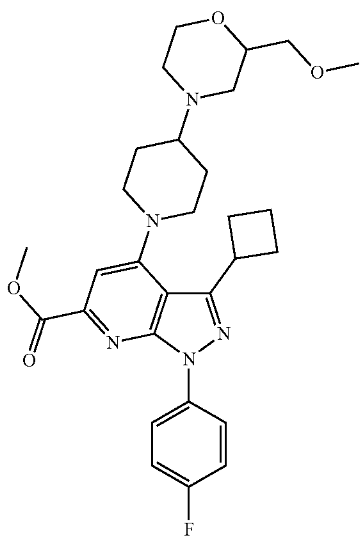 [SMILES: COCC1CN(C2CCN(c3cc(C(=O)OC)nc4c3c(C3CCC3)nn4-c3ccc(F)cc3)CC2)CCO1] | methyl 3-cyclobutyl-1-(4-fluorophenyl)-4-{4-[2-(methoxymethyl)morpholin-4-yl]piperidin-1-yl}-1H-pyrazolo[3,4-b]pyridine-6-carboxylate | E353 | Specific example | 537 | 538 |
| E355 | 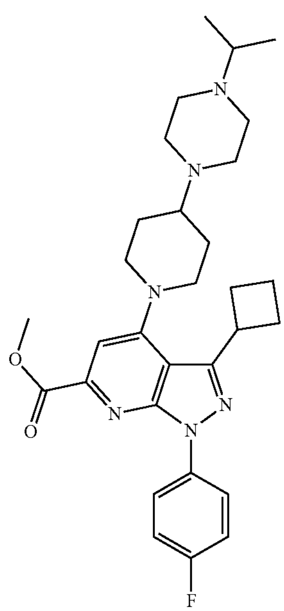 [SMILES: COC(=O)c1cc(N2CCC(N3CCN(C(C)C)CC3)CC2)c2c(C3CCC3)nn(-c3ccc(F)cc3)c2n1] | methyl 3-cyclobutyl-1-(4-fluorophenyl)-4-[4-(4-isopropylpiperazin-1-yl)-1-piperidyl]pyrazolo[3,4-b]pyridine-6-carboxylate | HP19, 202991-78-4 | I3 | 534 | 535 |

TABLE XII-continued

List of esters

| Int. | Structure | Name | SM | method | MW | Mes |
|---|---|---|---|---|---|---|
| E356 | 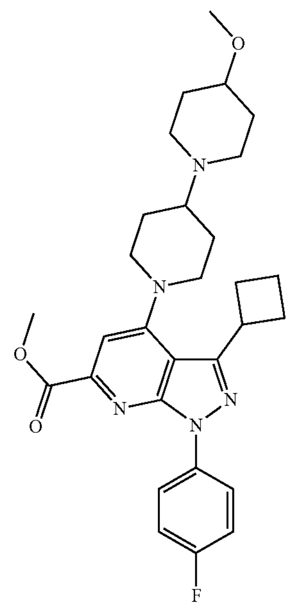 [SMILES: COC(=O)c1cc(N2CCC(N3CCC(OC)CC3)CC2)c2c(C3CCC3)nn(-c3ccc(F)cc3)c2n1] | methyl 3-cyclobutyl-1-(4-fluorophenyl)-4-[4-(4-methoxy-1-piperidyl)-1-piperidyl]pyrazolo[3,4-b]pyridine-6-carboxylate | HP19, AMI10 | I3, Specific example | 522 | 523 |
| E357 | 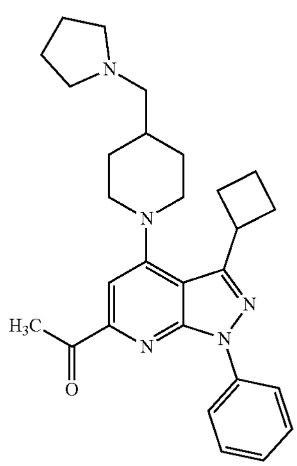 [SMILES: CC(=O)c1cc(N2CCC(CN3CCCC3)CC2)c2c(C3CCC3)nn(-c3ccccc3)c2n1] | methyl 3-cyclobutyl-1-phenyl-4-{4-[(pyrrolidin-1-yl)methyl]piperidin-1-yl}-1H-pyrazolo[3,4-b]pyridine-6-carboxylate | HP02, 683772-11-4 | I3, Specific example | 473 | 474 |

TABLE XII-continued
List of esters
| Int. | Structure | Name | SM | method | MW | Mes |
|---|---|---|---|---|---|---|
| E358 | 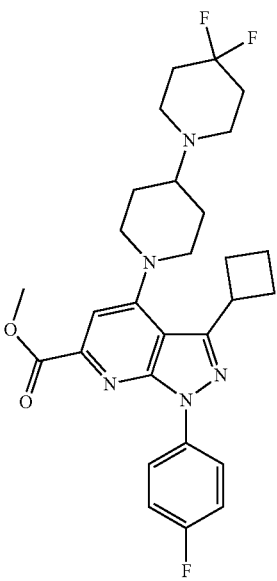 [SMILES: COC(=O)c1cc(N2CCC(N3CCC(F)(F)CC3)CC2)c2c(C3CCC3)nn(-c3ccc(F)cc3)c2n1] | methyl 3-cyclobutyl-4-(4,4-difluoro[1,4'-bipiperidin]-1'-yl)-1-(4-fluorophenyl)-1H-pyrazolo[3,4-b]pyridine-6-carboxylate | E353 | I18 | 527 | 528 |
| E359 | 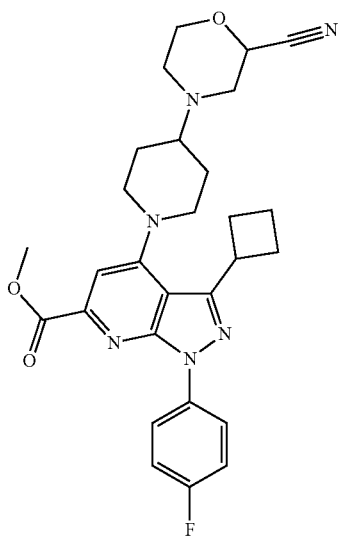 [SMILES: COC(=O)c1cc(N2CCC(N3CCOC(C#N)C3)CC2)c2c(C3CCC3)nn(-c3ccc(F)cc3)c2n1] | methyl 4-[4-(2-cyanomorpholin-4-yl)piperidin-1-yl]-3-cyclobutyl-1-(4-fluorophenyl)-1H-pyrazolo[3,4-b]pyridine-6-carboxylate | E353 | I18 | 518 | 519 |

TABLE XII-continued
List of esters
| Int. | Structure | Name | SM | method | MW | Mes |
|---|---|---|---|---|---|---|
| E360 | 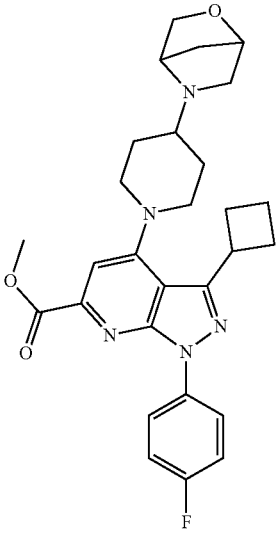 [SMILES: COC(=O)c1cc(N2CCC(N3CC4CC3CO4)CC2)c2c(C3CCC3)nn(-c3ccc(F)cc3)c2n1] | methyl 3-cyclobutyl-1-(4-fluorophenyl)-4-[4-(2-oxa-5-azabicyclo[2.2.1]heptan-5-yl)piperidin-1-yl]-1H-pyrazolo[3,4-b]pyridine-6-carboxylate | E353 | I18 | 505 | 506 |
| E361 | 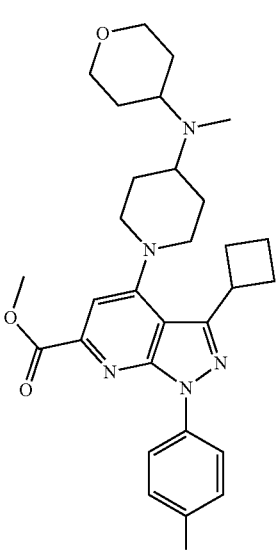 | methyl 3-cyclobutyl-1-(4-fluorophenyl)-4-{4-[methyl(oxan-4-yl)amino]piperidin-1-yl}-1H-pyrazolo[3,4-b]pyridine-6-carboxylate | E353 | I18 | 521 | 522 |

TABLE XII-continued
List of esters
| Int. | Structure | Name | SM | method | MW | Mes |
|------|-----------|------|----|--------|----|-----|
| E362 | 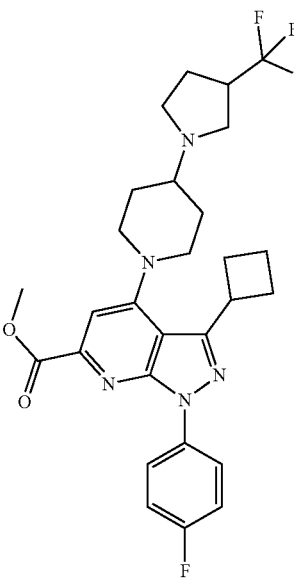 | methyl 3-cyclobutyl-1-(4-fluorophenyl)-4-{4-[3-(trifluoromethyl)pyrrolidin-1-yl]piperidin-1-yl}-1H-pyrazolo[3,4-b]pyridine-6-carboxylate | E353 | I18 | 545 | 546 |
| E363 | 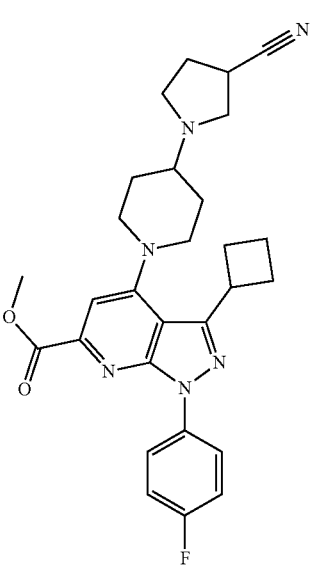 [SMILES: COC(=O)c1cc(N2CCC(N3CCC(C#N)C3)CC2)c2c(C3CCC3)nn(-c3ccc(F)cc3)c2n1] | methyl 4-[4-(3-cyanopyrrolidin-1-yl)piperidin-1-yl]-3-cyclobutyl-1-(4-fluorophenyl)-1H-pyrazolo[3,4-b]pyridine-6-carboxylate | E353 | I18 | 502 | 503 |

TABLE XII-continued
List of esters
| Int. | Structure | Name | SM | method | MW | Mes |
|---|---|---|---|---|---|---|
| E364 | 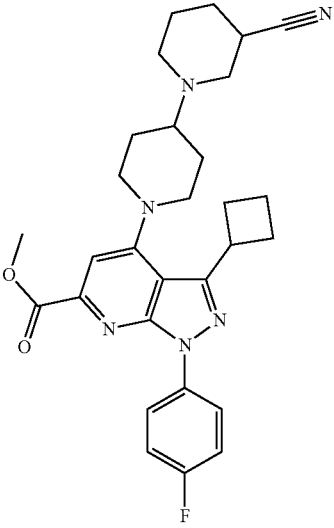 [SMILES: COC(=O)c1cc(N2CCC(N3CCCC(C#N)C3)CC2)c2c(C3CCC3)nn(-c3ccc(F)cc3)c2n1] | methyl 4-(3-cyano[1,4'-bipiperidin]-1'-yl)-3-cyclobutyl-1-(4-fluorophenyl)-1H-pyrazolo[3,4-b]pyridine-6-carboxylate | E353 | I18 | 516 | 517 |
| E365 | 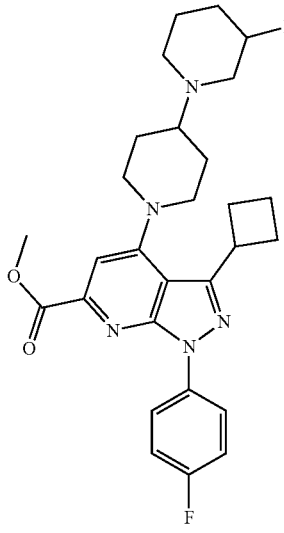 | methyl 3-cyclobutyl-4-(3-fluoro[1,4'-bipiperidin]-1'-yl)-1-(4-fluorophenyl)-1H-pyrazolo[3,4-b]pyridine-6-carboxylate | E353 | I18 | 509 | 510 |

TABLE XII-continued

List of esters

| Int. | Structure | Name | SM | method | MW | Mes |
|---|---|---|---|---|---|---|
| E366 | 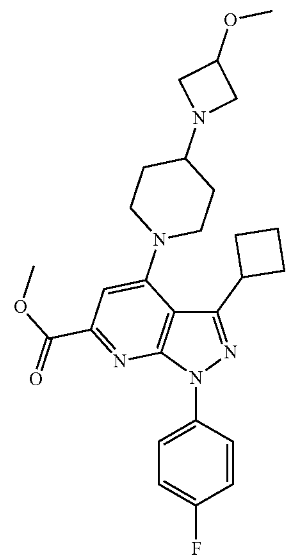 [SMILES: COC(=O)c1cc(N2CCC(N3CC(OC)C3)CC2)c2c(C3CCC3)nn(-c3ccc(F)cc3)c2n1] | methyl 3-cyclobutyl-1-(4-fluorophenyl)-4-[4-(3-methoxyazetidin-1-yl)piperidin-1-yl]-1H-pyrazolo[3,4-b]pyridine-6-carboxylate | E353 | I18 | 493 | 494 |
| E367 | 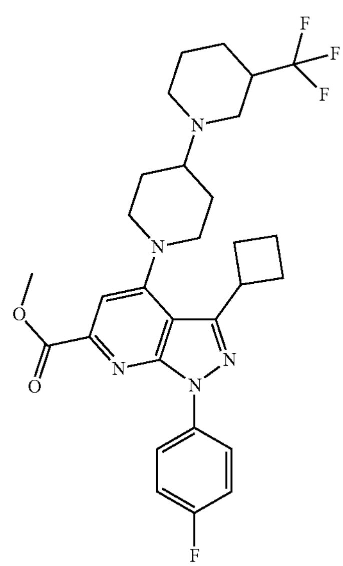 [SMILES: COC(=O)c1cc(N2CCC(N3CCCC(C(F)(F)F)C3)CC2)c2c(C3CCC3)nn(-c3ccc(F)cc3)c2n1] | methyl 3-cyclobutyl-1-(4-fluorophenyl)-4-[3-(trifluoromethyl)[1,4'-bipiperidin]-1'-yl]-1H-pyrazolo[3,4-b]pyridine-6-carboxylate | E353 | I18 | 559 | 560 |

TABLE XII-continued
List of esters
| Int. | Structure | Name | SM | method | MW | Mes |
|---|---|---|---|---|---|---|
| E368 | 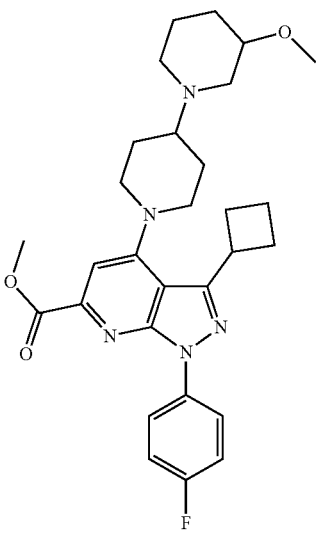 [SMILES: COC(=O)c1cc(N2CCC(N3CCCC(OC)C3)CC2)c2c(C3CCC3)nn(-c3ccc(F)cc3)c2n1] | methyl 3-cyclobutyl-1-(4-fluorophenyl)-4-(3-methoxy[1,4'-bipiperidin]-1'-yl)-1H-pyrazolo[3,4-b]pyridine-6-carboxylate | E353 | I18 | 521 | 522 |
| E369 | 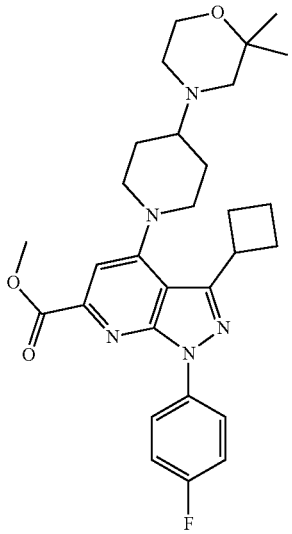 [SMILES: COC(=O)c1cc(N2CCC(N3CCOC(C)(C)C3)CC2)c2c(C3CCC3)nn(-c3ccc(F)cc3)c2n1] | methyl 3-cyclobutyl-4-[4-(2,2-dimethylmorpholin-4-yl)piperidin-1-yl]-1-(4-fluorophenyl)-1H-pyrazolo[3,4-b]pyridine-6-carboxylate | E353 | I18 | 521 | 522 |

TABLE XII-continued
List of esters
| Int. | Structure | Name | SM | method | MW | Mes |
|---|---|---|---|---|---|---|
| E370 | 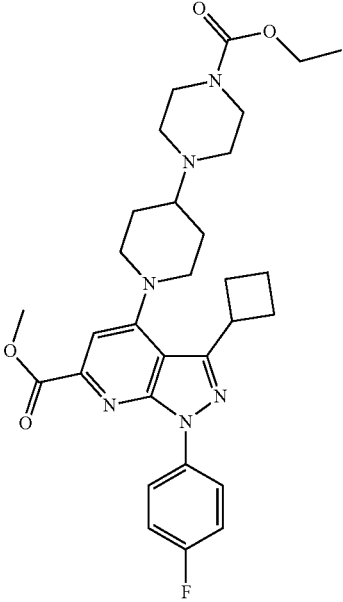 [SMILES: CCOC(=O)N1CCN(C2CCN(c3cc(C(=O)OC)nc4c3c(C3CCC3)nn4-c3ccc(F)cc3)CC2)CC1] | methyl 3-cyclobutyl-4-{4-[4-(ethoxycarbonyl)piperazin-1-yl]piperidin-1-yl}-1-(4-fluorophenyl)-1H-pyrazolo[3,4-b]pyridine-6-carboxylate | E353 | I18 | 564 | 565 |
| E371 | 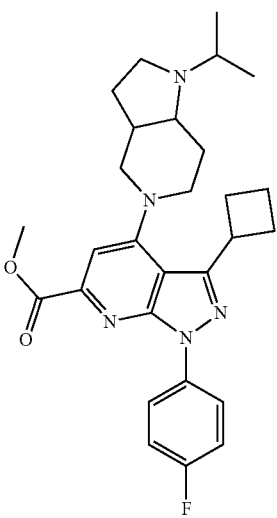 [SMILES: COC(=O)c1cc(N2CCC3C(CCN3C(C)C)C2)c2c(C3CCC3)nn(-c3ccc(F)cc3)c2n1] | methyl 3-cyclobutyl-1-(4-fluorophenyl)-4-[1-(propan-2-yl)octahydro-5H-pyrrolo[3,2-c]pyridin-5-yl]-1H-pyrazolo[3,4-b]pyridine-6-carboxylate | E514 | I33 | 491 | 492 |

TABLE XII-continued

List of esters

| Int. | Structure | Name | SM | method | MW | Mes |
|---|---|---|---|---|---|---|
| E372 | 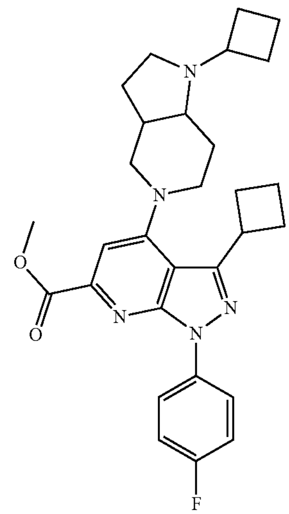 [SMILES: COC(=O)c1cc(N2CCC3C(CCN3C3CCC3)C2)c2c(C3CCC3)nn(-c3ccc(F)cc3)c2n1] | methyl 3-cyclobutyl-4-(1-cyclobutyloctahydro-5H-pyrrolo[3,2-c]pyridin-5-yl)-1-(4-fluorophenyl)-1H-pyrazolo[3,4-b]pyridine-6-carboxylate | E514 | I33 | 503 | 504 |
| E373 | 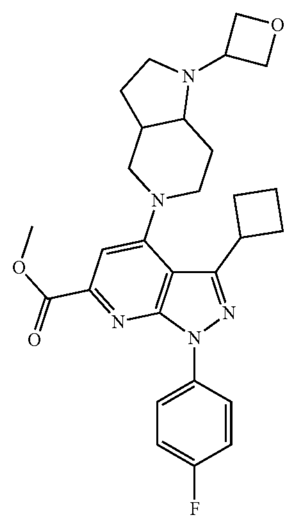 [SMILES: COC(=O)c1cc(N2CCC3C(CCN3C3COC3)C2)c2c(C3CCC3)nn(-c3ccc(F)cc3)c2n1] | methyl 3-cyclobutyl-1-(4-fluorophenyl)-4-[1-(oxetan-3-yl)octahydro-5H-pyrrolo[3,2-c]pyridin-5-yl]-1H-pyrazolo[3,4-b]pyridine-6-carboxylate | E514 | I33 | 505 | 506 |
| E374 | 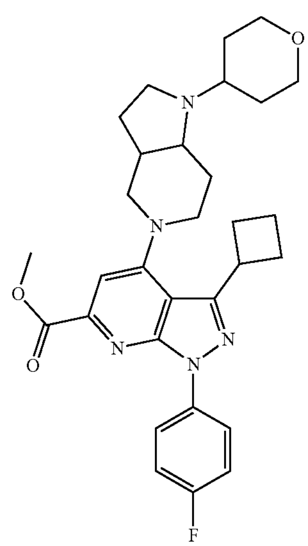 [SMILES: COC(=O)c1cc(N2CCC3C(CCN3C3CCOCC3)C2)c2c(C3CCC3)nn(-c3ccc(F)cc3)c2n1] | methyl 3-cyclobutyl-1-(4-fluorophenyl)-4-[1-(oxan-4-yl)octahydro-5H-pyrrolo[3,2-c]pyridin-5-yl]-1H-pyrazolo[3,4-b]pyridine-6-carboxylate | E514 | I33 | 533 | 534 |

TABLE XII-continued

List of esters

| Int. | Structure | Name | SM | method | MW | Mes |
|---|---|---|---|---|---|---|
| E375 | 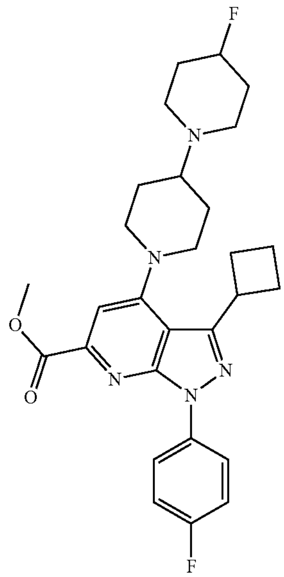 [SMILES: COC(=O)c1cc(N2CCC(N3CCC(F)CC3)CC2)c2c(C3CCC3)nn(-c3ccc(F)cc3)c2n1] | methyl 3-cyclobutyl-4-(4-fluoro[1,4'-bipiperidin]-1'-yl)-1-(4-fluorophenyl)-1H-pyrazolo[3,4-b]pyridine-6-carboxylate | E353 | I18 | 509 | 510 |
| E376 | 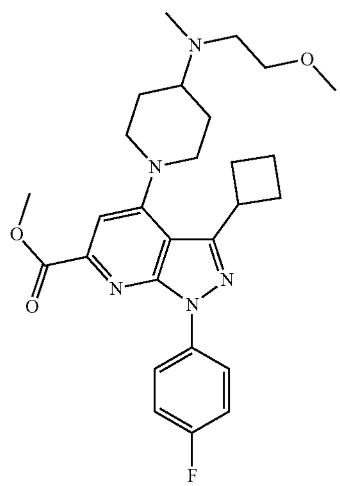 [SMILES: COCCN(C)C1CCN(c2cc(C(=O)OC)nc3c2c(C2CCC2)nn3-c2ccc(F)cc2)CC1] | methyl 3-cyclobutyl-1-(4-fluorophenyl)-4-{4-[(2-methoxyethyl)(methyl)amino]piperidin-1-yl}-1H-pyrazolo[3,4-b]pyridine-6-carboxylate | E353 | I18 | 495 | 496 |
| E377 | 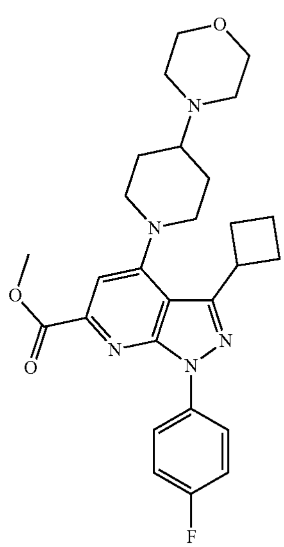 [SMILES: COC(=O)c1cc(N2CCC(N3CCOCC3)CC2)c2c(C3CCC3)nn(-c3ccc(F)cc3)c2n1] | methyl 3-cyclobutyl-1-(4-fluorophenyl)-4-[4-(morpholin-4-yl)piperidin-1-yl]-1H-pyrazolo[3,4-b]pyridine-6-carboxylate | HP19 | I3 | 493 | 494 |

TABLE XII-continued

List of esters

| Int. | Structure | Name | SM | method | MW | Mes |
|---|---|---|---|---|---|---|
| E378 | 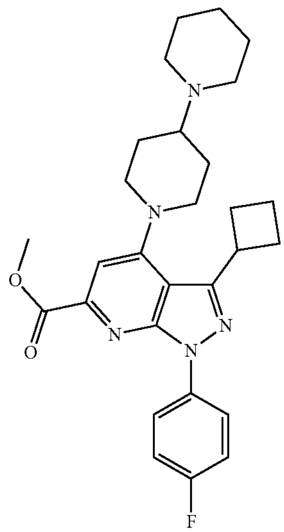 [SMILES: COC(=O)c1cc(N2CCC(N3CCCCC3)CC2)c2c(C3CCC3)nn(-c3ccc(F)cc3)c2n1] | methyl 4-([1,4'-bipiperidin]-1'-yl)-3-cyclobutyl-1-(4-fluorophenyl)-1H-pyrazolo[3,4-b]pyridine-6-carboxylate | HP19 | I3 | 491 | 492 |
| E379 | 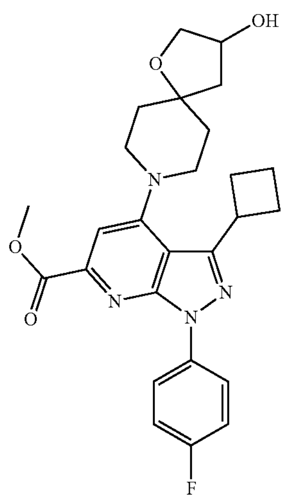 [SMILES: COC(=O)c1cc(N2CCC3(CC2)CC(O)CO3)c2c(C3CCC3)nn(-c3ccc(F)cc3)c2n1] | methyl 3-cyclobutyl-1-(4-fluorophenyl)-4-(3-hydroxy-1-oxa-8-azaspiro[4.5]decan-8-yl)-1H-pyrazolo[3,4-b]pyridine-6-carboxylate | HP19 | I3 | 480 | 481 |
| E380 | 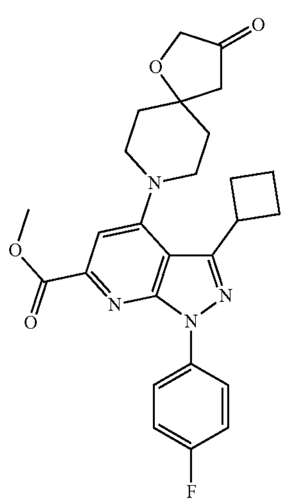 [SMILES: COC(=O)c1cc(N2CCC3(CC2)CC(=O)CO3)c2c(C3CCC3)nn(-c3ccc(F)cc3)c2n1] | methyl 3-cyclobutyl-1-(4-fluorophenyl)-4-(3-oxo-1-oxa-8-azaspiro[4.5]decan-8-yl)-1H-pyrazolo[3,4-b]pyridine-6-carboxylate | E379 | I23 | 478 | 479 |

//  
TABLE XII-continued

List of esters

| Int. | Structure | Name | SM | method | MW | Mes |
|---|---|---|---|---|---|---|
| E381 | 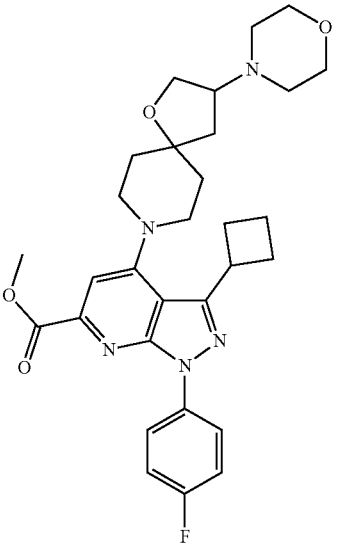 [SMILES: COC(=O)c1cc(N2CCC3(CC2)CC(N2CCOCC2)CO3)c2c(C3CCC3)nn(-c3ccc(F)cc3)c2n1] | methyl 3-cyclobutyl-1-(4-fluorophenyl)-4-[3-(morpholin-4-yl)-1-oxa-8-azaspiro[4.5]decan-8-yl]-1H-pyrazolo[3,4-b]pyridine-6-carboxylate | E380 | I18 | 533 | 534 |
| E382 | 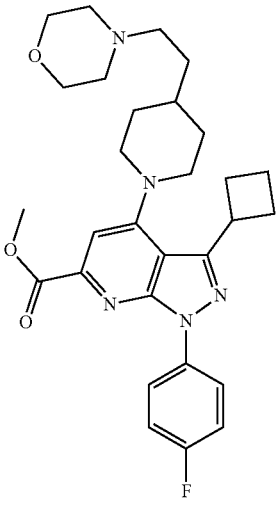 [SMILES: COC(=O)c1cc(N2CCC(CCN3CCOCC3)CC2)c2c(C3CCC3)nn(-c3ccc(F)cc3)c2n1] | methyl 3-cyclobutyl-1-(4-fluorophenyl)-4-{4-[2-(morpholin-4-yl)ethyl]piperidin-1-yl}-1H-pyrazolo[3,4-b]pyridine-6-carboxylate | HP19 | I3 | 521 | 522 |
| E383 | 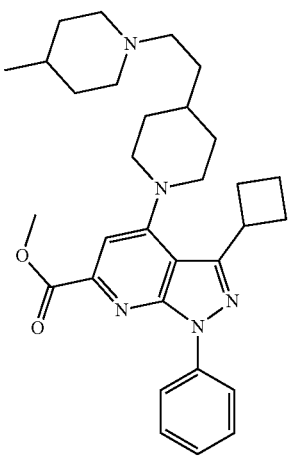 [SMILES: COC(=O)c1cc(N2CCC(CCN3CCC(C)CC3)CC2)c2c(C3CCC3)nn(-c3ccccc3)c2n1] | methyl 3-cyclobutyl-4-{4-[2-(4-methylpiperidin-1-yl)ethyl]piperidin-1-yl}-1-phenyl-1H-pyrazolo[3,4-b]pyridine-6-carboxylate | HP02 | I3 | 515 | 516 |

TABLE XII-continued
| Int. | Structure | Name | SM | method | MW | Mes |
|---|---|---|---|---|---|---|
| E384 | 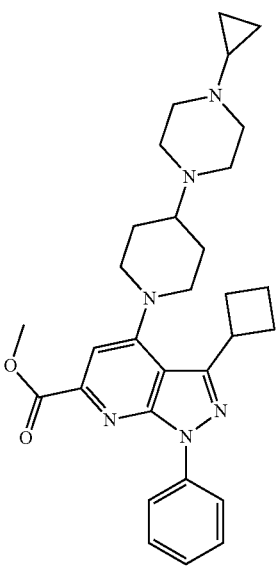 [SMILES: COC(=O)c1cc(N2CCC(N3CCN(C4CC4)CC3)CC2)c2c(C3CCC3)nn(-c3ccccc3)c2n1] | methyl 3-cyclobutyl-4-[4-(4-cyclopropylpiperazin-1-yl)piperidin-1-yl]-1-phenyl-1H-pyrazolo[3,4-b]pyridine-6-carboxylate | HP02 | I3 | 514 | 515 |
| E385 | 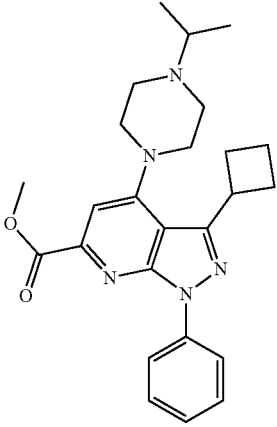 [SMILES: COC(=O)c1cc(N2CCN(C(C)C)CC2)c2c(C3CCC3)nn(-c3ccccc3)c2n1] | methyl 3-cyclobutyl-1-phenyl-4-[4-(propan-2-yl)piperazin-1-yl]-1H-pyrazolo[3,4-b]pyridine-6-carboxylate | HP02 | I3 | 433 | 434 |
| E388 | 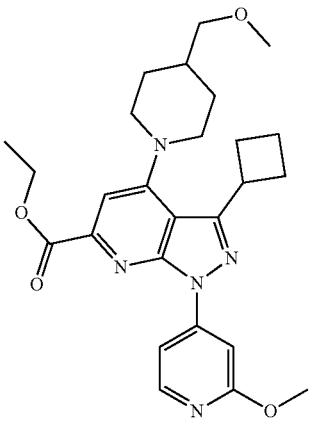 [SMILES: CCOC(=O)c1cc(N2CCC(COC)CC2)c2c(C3CCC3)nn(-c3ccnc(OC)c3)c2n1] | ethyl 3-cyclobutyl-4-[4-(methoxymethyl)piperidin-1-yl]-1-(2-methoxypyridin-4-yl)-1H-pyrazolo[3,4-b]pyridine-6-carboxylate | E168 | I4 | 479 | 480 |

TABLE XII-continued

List of esters

| Int. | Structure | Name | SM | method | MW | Mes |
|---|---|---|---|---|---|---|
| E389 | 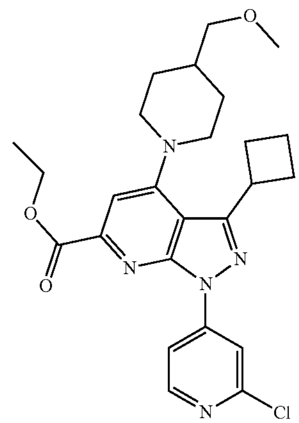 [SMILES: CCOC(=O)c1cc(N2CCC(COC)CC2)c2c(C3CCC3)nn(-c3ccnc(Cl)c3)c2n1] | ethyl 1-(2-chloropyridin-4-yl)-3-cyclobutyl-4-[4-(methoxymethyl)piperidin-1-yl]-1H-pyrazolo[3,4-b]pyridine-6-carboxylate | E-168 | I4 | 484-486 | 485-487 |
| E390 | 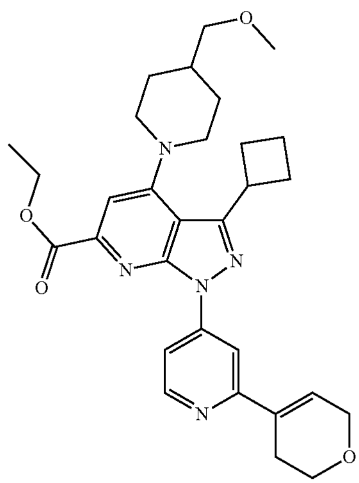 [SMILES: CCOC(=O)c1cc(N2CCC(COC)CC2)c2c(C3CCC3)nn(-c3ccnc(C4=CCOCC4)c3)c2n1] | ethyl 3-cyclobutyl-1-[2-(3,6-dihydro-2H-pyran-4-yl)pyridin-4-yl]-4-[4-(methoxymethyl)piperidin-1-yl]-1H-pyrazolo[3,4-b]pyridine-6-carboxylate | E389 | Specific example | 531 | 532 |
| E391 | 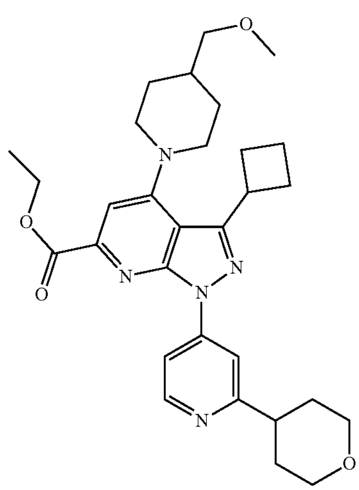 [SMILES: CCOC(=O)c1cc(N2CCC(COC)CC2)c2c(C3CCC3)nn(-c3ccnc(C4CCOCC4)c3)c2n1] | ethyl 3-cyclobutyl-4-[4-(methoxymethyl)piperidin-1-yl]-1-[2-(oxan-4-yl)pyridin-4-yl]-1H-pyrazolo[3,4-b]pyridine-6-carboxylate | E390 | Specific example | 533 | 534 |

TABLE XII-continued

List of esters

| Int. | Structure | Name | SM | method | MW | Mes |
|---|---|---|---|---|---|---|
| E392 | 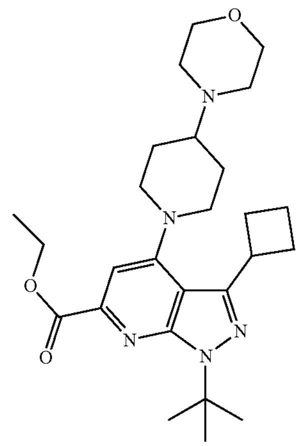 [SMILES: CCOC(=O)c1cc(N2CCC(N3CCOCC3)CC2)c2c(C3CCC3)nn(C(C)(C)C)c2n1] | ethyl 1-tert-butyl-3-cyclobutyl-4-[4-(morpholin-4-yl)piperidin-1-yl]-1H-pyrazolo[3,4-b]pyridine-6-carboxylate | HP20 | I3 | 469 | 470 |
| E393 | 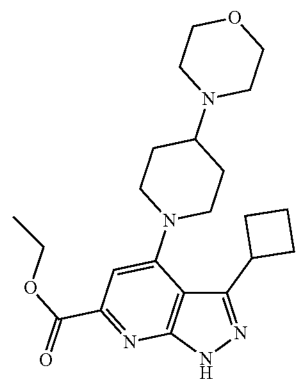 [SMILES: CCOC(=O)c1cc(N2CCC(N3CCOCC3)CC2)c2c(C3CCC3)n[nH]c2n1] | ethyl 3-cyclobutyl-4-[4-(morpholin-4-yl)piperidin-1-yl]-1H-pyrazolo[3,4-b]pyridine-6-carboxylate | E392 | Specific example | 413 | 414 |
| E394 | 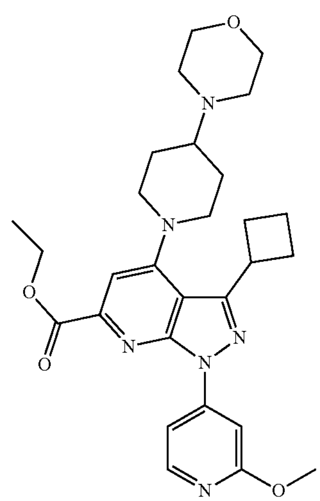 [SMILES: CCOC(=O)c1cc(N2CCC(N3CCOCC3)CC2)c2c(C3CCC3)nn(-c3ccnc(OC)c3)c2n1] | ethyl 3-cyclobutyl-1-(2-methoxypyridin-4-yl)-4-[4-(morpholin-4-yl)piperidin-1-yl]-1H-pyrazolo[3,4-b]pyridine-6-carboxylate | E393 | I4 | 520 | 521 |

TABLE XII-continued

List of esters

| Int. | Structure | Name | SM | method | MW | Mes |
|---|---|---|---|---|---|---|
| E395 | 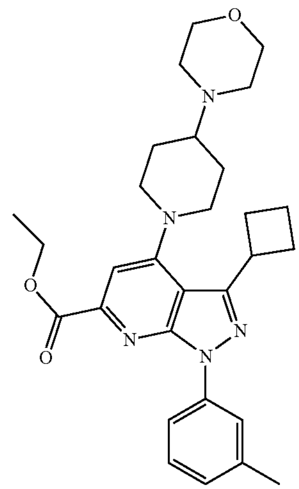 [SMILES: CCOC(=O)c1cc(N2CCC(N3CCOCC3)CC2)c2c(C3CCC3)nn(-c3cccc(C)c3)c2n1] | ethyl 3-cyclobutyl-1-(3-methylphenyl)-4-[4-(morpholin-4-yl)piperidin-1-yl]-1H-pyrazolo[3,4-b]pyridine-6-carboxylate | E393 | I4 | 503 | 504 |
| E396 | 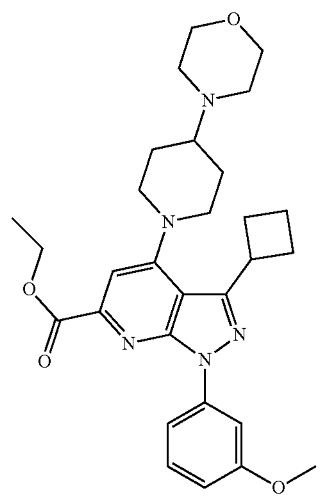 [SMILES: CCOC(=O)c1cc(N2CCC(N3CCOCC3)CC2)c2c(C3CCC3)nn(-c3cccc(OC)c3)c2n1] | ethyl 3-cyclobutyl-1-(3-methoxyphenyl)-4-[4-(morpholin-4-yl)piperidin-1-yl]-1H-pyrazolo[3,4-b]pyridine-6-carboxylate | E393 | I4 | 519 | 520 |
| E397 | 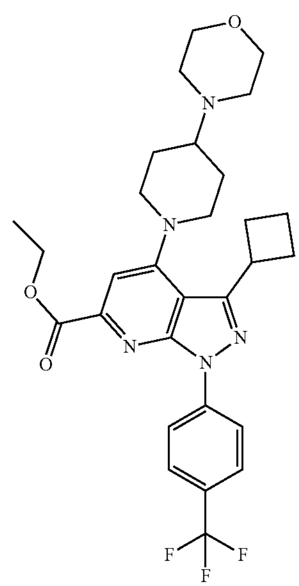 [SMILES: CCOC(=O)c1cc(N2CCC(N3CCOCC3)CC2)c2c(C3CCC3)nn(-c3ccc(C(F)(F)F)cc3)c2n1] | ethyl 3-cyclobutyl-4-[4-(morpholin-4-yl)piperidin-1-yl]-1-[4-(trifluoromethyl)phenyl]-1H-pyrazolo[3,4-b]pyridine-6-carboxylate | E393 | I4 | 557 | 558 |

TABLE XII-continued

List of esters

| Int. | Structure | Name | SM | method | MW | Mes |
|---|---|---|---|---|---|---|
| E398 | 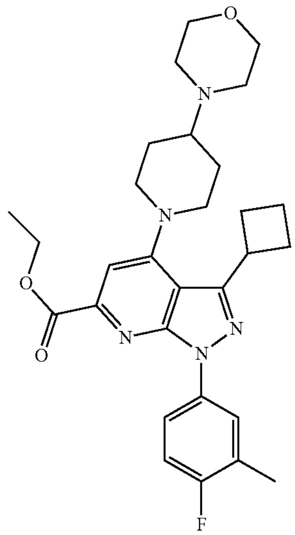 [SMILES: CCOC(=O)c1cc(N2CCC(N3CCOCC3)CC2)c2c(C3CCC3)nn(-c3ccc(F)c(C)c3)c2n1] | ethyl 3-cyclobutyl-1-(4-fluoro-3-methylphenyl)-4-[4-(morpholin-4-yl)piperidin-1-yl]-1H-pyrazolo[3,4-b]pyridine-6-carboxylate | E393 | I4 | 521 | 522 |
| E399 | 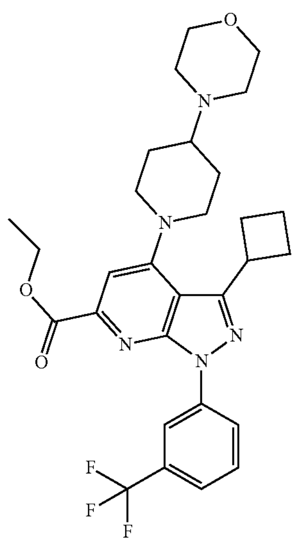 [SMILES: CCOC(=O)c1cc(N2CCC(N3CCOCC3)CC2)c2c(C3CCC3)nn(-c3cccc(C(F)(F)F)c3)c2n1] | ethyl 3-cyclobutyl-4-[4-(morpholin-4-yl)piperidin-1-yl]-1-[3-(trifluoromethyl)phenyl]-1H-pyrazolo[3,4-b]pyridine-6-carboxylate | E393 | I4 | 557 | 558 |
| E400 | 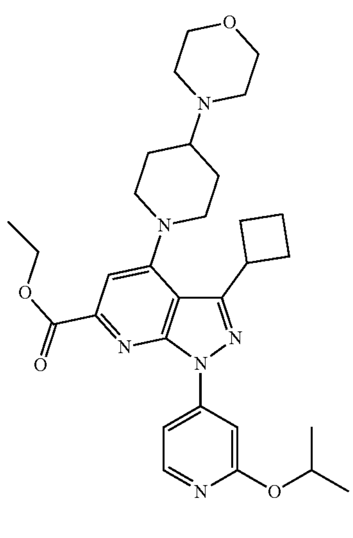 [SMILES: CCOC(=O)c1cc(N2CCC(N3CCOCC3)CC2)c2c(C3CCC3)nn(-c3ccnc(OC(C)C)c3)c2n1] | ethyl 3-cyclobutyl-4-[4-(morpholin-4-yl)piperidin-1-yl]-1-{2-[(propan-2-yl)oxy]pyridin-4-yl}-1H-pyrazolo[3,4-b]pyridine-6-carboxylate | E393 | I4 | 548 | 549 |

TABLE XII-continued

List of esters

| Int. | Structure | Name | SM | method | MW | Mes |
|---|---|---|---|---|---|---|
| E401 | 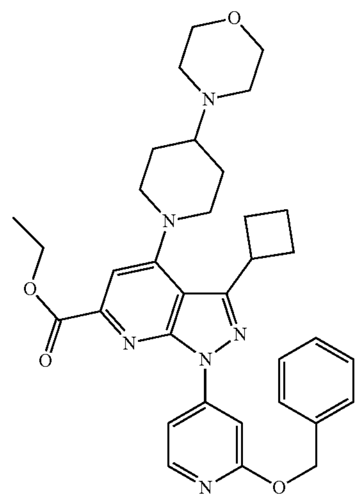 [SMILES: CCOC(=O)c1cc(N2CCC(N3CCOCC3)CC2)c2c(C3CCC3)nn(-c3ccnc(OCc4ccccc4)c3)c2n1] | ethyl 1-[2-(benzyloxy)pyridin-4-yl]-3-cyclobutyl-4-[4-(morpholin-4-yl)piperidin-1-yl]-1H-pyrazolo[3,4-b]pyridine-6-carboxylate | E393 | I4 | 596 | 597 |
| E402 | 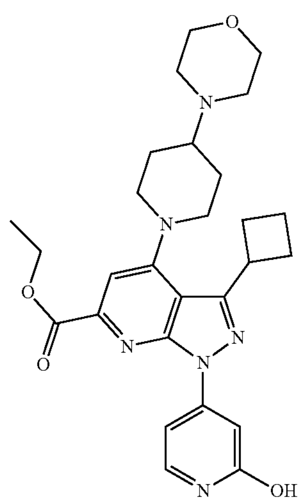 [SMILES: CCOC(=O)c1cc(N2CCC(N3CCOCC3)CC2)c2c(C3CCC3)nn(-c3ccnc(O)c3)c2n1] | ethyl 3-cyclobutyl-1-(2-hydroxypyridin-4-yl)-4-[4-(morpholin-4-yl)piperidin-1-yl]-1H-pyrazolo[3,4-b]pyridine-6-carboxylate | E401 | Specific example | 506 | 507 |
| E403 | 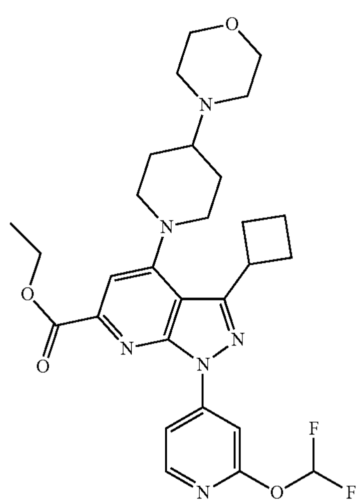 [SMILES: CCOC(=O)c1cc(N2CCC(N3CCOCC3)CC2)c2c(C3CCC3)nn(-c3ccnc(OC(F)F)c3)c2n1] | ethyl 3-cyclobutyl-1-[2-(difluoromethoxy)pyridin-4-yl]-4-[4-(morpholin-4-yl)piperidin-1-yl]-1H-pyrazolo[3,4-b]pyridine-6-carboxylate | E393 | I4 | 556 | 557 |

TABLE XII-continued

List of esters

| Int. | Structure | Name | SM | method | MW | Mes |
|---|---|---|---|---|---|---|
| E404 | 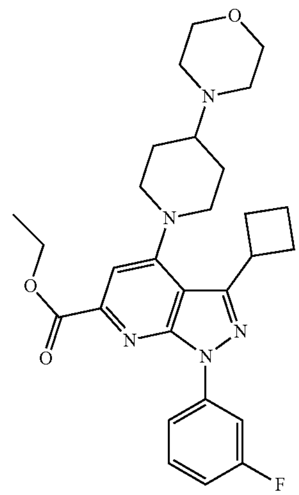 [SMILES: CCOC(=O)c1cc(N2CCC(N3CCOCC3)CC2)c2c(C3CCC3)nn(-c3cccc(F)c3)c2n1] | ethyl 3-cyclobutyl-1-(3-fluorophenyl)-4-[4-(morpholin-4-yl)piperidin-1-yl]-1H-pyrazolo[3,4-b]pyridine-6-carboxylate | E393 | I4 | 507 | 508 |
| E405 | 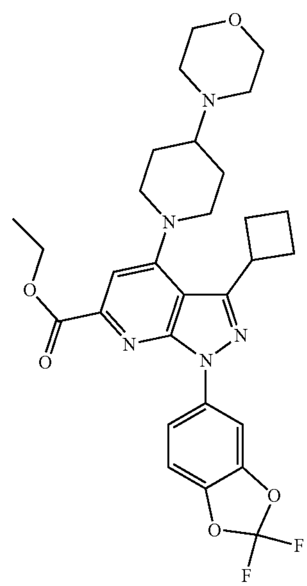 [SMILES: CCOC(=O)c1cc(N2CCC(N3CCOCC3)CC2)c2c(C3CCC3)nn(-c3ccc4c(c3)OC(F)(F)O4)c2n1] | ethyl 3-cyclobutyl-1-(2,2-difluoro-2H-1,3-benzodioxol-5-yl)-4-[4-(morpholin-4-yl)piperidin-1-yl]-1H-pyrazolo[3,4-b]pyridine-6-carboxylate | E393 | I4 | 569 | 570 |
| E406 | 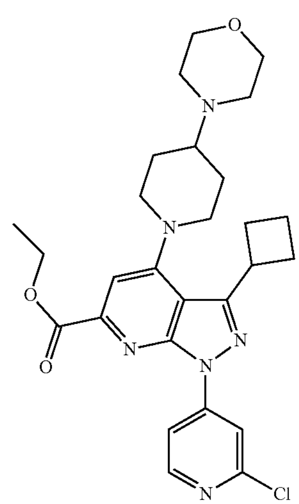 [SMILES: CCOC(=O)c1cc(N2CCC(N3CCOCC3)CC2)c2c(C3CCC3)nn(-c3ccnc(Cl)c3)c2n1] | ethyl 1-(2-chloropyridin-4-yl)-3-cyclobutyl-4-[4-(morpholin-4-yl)piperidin-1-yl]-1H-pyrazolo[3,4-b]pyridine-6-carboxylate | E393 | I4 | 525-527 | 526-528 |

TABLE XII-continued

List of esters

| Int. | Structure | Name | SM | method | MW | Mes |
|------|-----------|------|----|--------|----|-----|
| E407 | 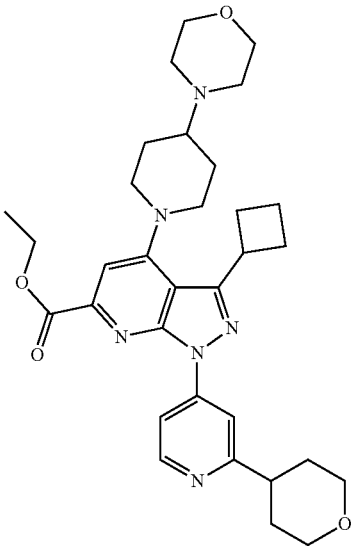 [SMILES: CCOC(=O)c1cc(N2CCC(N3CCOCC3)CC2)c2c(C3CCC3)nn(-c3ccnc(C4CCOCC4)c3)c2n1] | ethyl 3-cyclobutyl-4-[4-(morpholin-4-yl)piperidin-1-yl]-1-[2-(oxan-4-yl)pyridin-4-yl]-1H-pyrazolo[3,4-b]pyridine-6-carboxylate | E406 | Specific example | 574 | 575 |
| E408 | 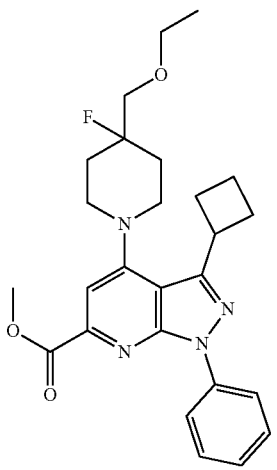 [SMILES: CCOCC1(F)CCN(c2cc(C(=O)OC)nc3c2c(C2CCC2)nn3-c2ccccc2)CC1] | methyl 3-cyclobutyl-4-[4-(ethoxymethyl)-4-fluoropiperidin-1-yl]-1-phenyl-1H-pyrazolo[3,4-b]pyridine-6-carboxylate | HP02, AMI04 | I3 | 466 | 467 |
| E409 | 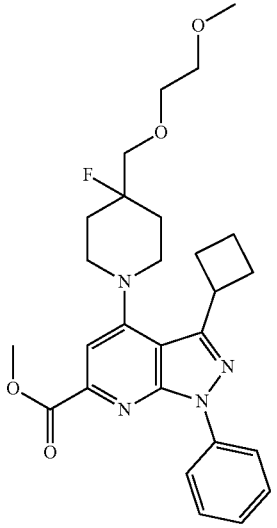 [SMILES: COCCOCC1(F)CCN(c2cc(C(=O)OC)nc3c2c(C2CCC2)nn3-c2ccccc2)CC1] | methyl 3-cyclobutyl-4-{4-fluoro-4-[(2-methoxyethoxy)methyl]piperidin-1-yl}-1-phenyl-1H-pyrazolo[3,4-b]pyridine-6-carboxylate | HP02, AMI05 | I3 | 496 | 497 |

TABLE XII-continued

List of esters

| Int. | Structure | Name | SM | method | MW | Mes |
|---|---|---|---|---|---|---|
| E410 | 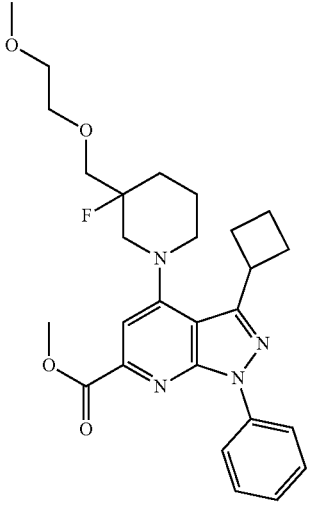 [SMILES: COCCOCC1(F)CCCN(c2cc(C(=O)OC)nc3c2c(C2CCC2)nn3-c2ccccc2)C1] | methyl 3-cyclobutyl-4-{3-fluoro-3-[(2-methoxyethoxy)methyl]piperidin-1-yl}-1-phenyl-1H-pyrazolo[3,4-b]pyridine-6-carboxylate | HP02, AMI08 | I3 | 496 | 497 |
| E411 | 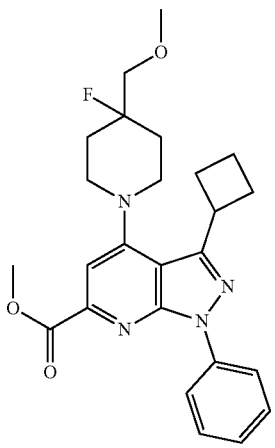 [SMILES: COCC1(F)CCN(c2cc(C(=O)OC)nc3c2c(C2CCC2)nn3-c2ccccc2)CC1] | methyl 3-cyclobutyl-4-[4-fluoro-4-(methoxymethyl)piperidin-1-yl]-1-phenyl-1H-pyrazolo[3,4-b]pyridine-6-carboxylate | HP02, AMI07 | I3 | 452 | 453 |
| E412 | 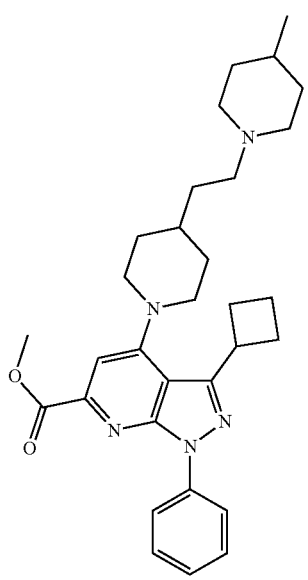 [SMILES: COC(=O)c1cc(N2CCC(CCN3CCC(C)CC3)CC2)c2c(C3CCC3)nn(-c3ccccc3)c2n1] | methyl 3-cyclobutyl-4-{4-[2-(4-methylpiperidin-1-yl)ethyl]piperidin-1-yl}-1-phenyl-1H-pyrazolo[3,4-b]pyridine-6-carboxylate | HP02 | I3 | 515 | 516 |

TABLE XII-continued

List of esters

| Int. | Structure | Name | SM | method | MW | Mes |
|---|---|---|---|---|---|---|
| E413 | 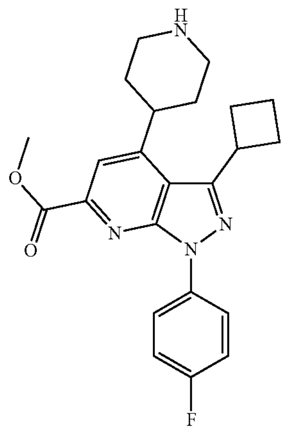 [SMILES: COC(=O)c1cc(C2CCNCC2)c2c(C3CCC3)nn(-c3ccc(F)cc3)c2n1] | methyl 3-cyclobutyl-1-(4-fluorophenyl)-4-(piperidin-4-yl)-1H-pyrazolo[3,4-b]pyridine-6-carboxylate | HP19 | Specific example | 408 | 409 |
| E414 | 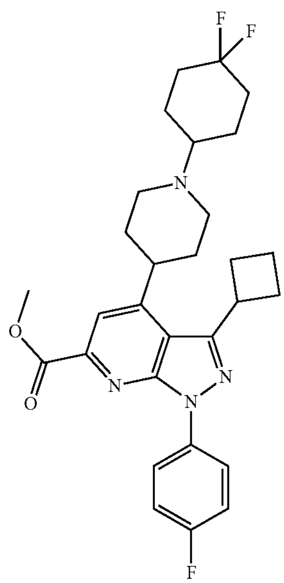 [SMILES: COC(=O)c1cc(C2CCN(C3CCC(F)(F)CC3)CC2)c2c(C3CCC3)nn(-c3ccc(F)cc3)c2n1] | methyl 3-cyclobutyl-4-[1-(4,4-difluorocyclohexyl)piperidin-4-yl]-1-(4-fluorophenyl)-1H-pyrazolo[3,4-b]pyridine-6-carboxylate | E413 | I18 | 526 | 527 |
| E415 | 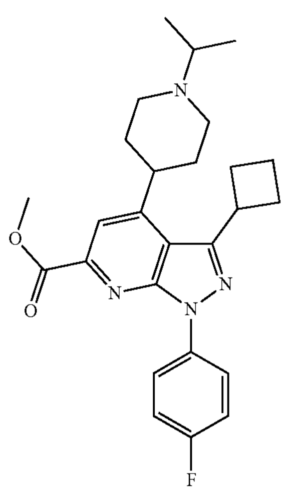 [SMILES: COC(=O)c1cc(C2CCN(C(C)C)CC2)c2c(C3CCC3)nn(-c3ccc(F)cc3)c2n1] | methyl 3-cyclobutyl-1-(4-fluorophenyl)-4-[1-(propan-2-yl)piperidin-4-yl]-1H-pyrazolo[3,4-b]pyridine-6-carboxylate | E413 | I18 | 450 | 451 |

TABLE XII-continued

List of esters

| Int. | Structure | Name | SM | method | MW | Mes |
|---|---|---|---|---|---|---|
| E416 | 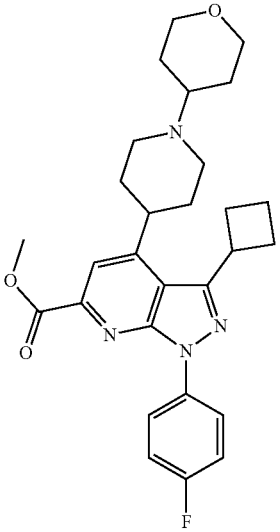 [SMILES: COC(=O)c1cc(C2CCN(C3CCOCC3)CC2)c2c(C3CCC3)nn(-c3ccc(F)cc3)c2n1] | methyl 3-cyclobutyl-1-(4-fluorophenyl)-4-[1-(oxan-4-yl)piperidin-4-yl]-1H-pyrazolo[3,4-b]pyridine-6-carboxylate | E413 | I18 | 492 | 493 |
| E417 | 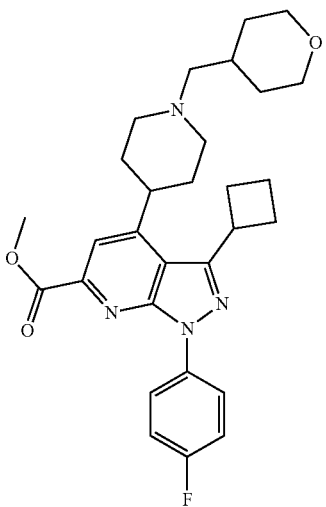 [SMILES: COC(=O)c1cc(C2CCN(CC3CCOCC3)CC2)c2c(C3CCC3)nn(-c3ccc(F)cc3)c2n1] | methyl 3-cyclobutyl-1-(4-fluorophenyl)-4-{1-[(oxan-4-yl)methyl]piperidin-4-yl}-1H-pyrazolo[3,4-b]pyridine-6-carboxylate | E413 | I18 | 506 | 507 |
| E418 | 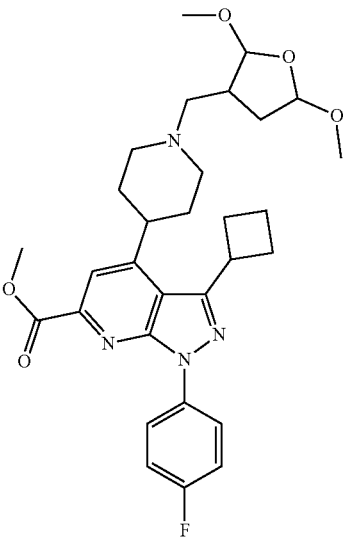 [SMILES: COC(=O)c1cc(C2CCN(CC3CC(OC)OC3OC)CC2)c2c(C3CCC3)nn(-c3ccc(F)cc3)c2n1] | methyl 3-cyclobutyl-4-{1-[(2,5-dimethoxyoxolan-3-yl)methyl]piperidin-4-yl}-1-(4-fluorophenyl)-1H-pyrazolo[3,4-b]pyridine-6-carboxylate | E413 | I18 | 552 | 553 |

TABLE XII-continued

List of esters

| Int. | Structure | Name | SM | method | MW | Mes |
|---|---|---|---|---|---|---|
| E419 | 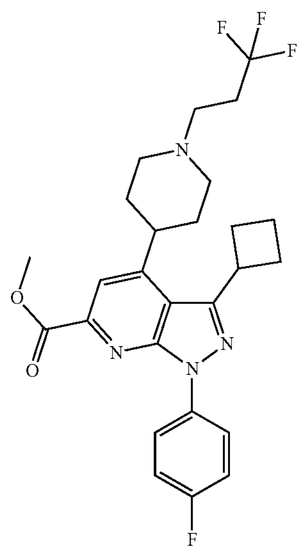 [SMILES: COC(=O)c1cc(C2CCN(CCC(F)(F)F)CC2)c2c(C3CCC3)nn(-c3ccc(F)cc3)c2n1] | methyl 3-cyclobutyl-1-(4-fluorophenyl)-4-[1-(3,3,3-trifluoropropyl)piperidin-4-yl]-1H-pyrazolo[3,4-b]pyridine-6-carboxylate | E413 | I18 | 504 | 505 |
| E421 | 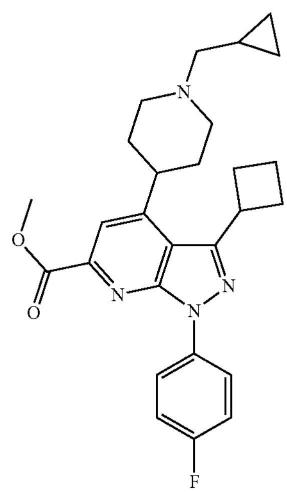 [SMILES: COC(=O)c1cc(C2CCN(CC3CC3)CC2)c2c(C3CCC3)nn(-c3ccc(F)cc3)c2n1] | methyl 3-cyclobutyl-4-[1-(cyclopropylmethyl)piperidin-4-yl]-1-(4-fluorophenyl)-1H-pyrazolo[3,4-b]pyridine-6-carboxylate | E413 | I18 | 462 | 463 |
| E422 | 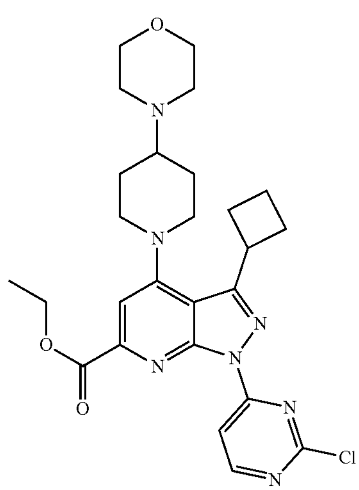 [SMILES: CCOC(=O)c1cc(N2CCC(N3CCOCC3)CC2)c2c(C3CCC3)nn(-c3ccnc(Cl)n3)c2n1] | ethyl 1-(2-chloropyrimidin-4-yl)-3-cyclobutyl-4-[4-(morpholin-4-yl)piperidin-1-yl]-1H-pyrazolo[3,4-b]pyridine-6-carboxylate | E393 | I5 | 525 | 526 |

TABLE XII-continued

List of esters

| Int. | Structure | Name | SM | method | MW | Mes |
|---|---|---|---|---|---|---|
| E424 | 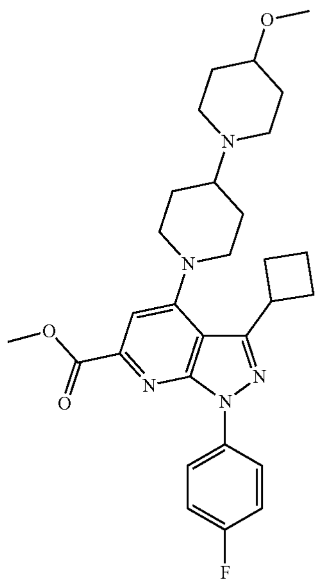 [SMILES: COC(=O)c1cc(N2CCC(N3CCC(OC)CC3)CC2)c2c(C3CCC3)nn(-c3ccc(F)cc3)c2n1] | methyl 3-cyclobutyl-1-(4-fluorophenyl)-4-(4-methoxy[1,4'-bipiperidin]-1'-yl)-1H-pyrazolo[3,4-b]pyridine-6-carboxylate | HP19 | I3 | 521 | 522 |
| E425 | 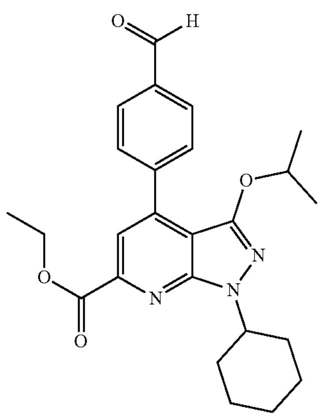 [SMILES: CCOC(=O)c1cc(-c2ccc(C=O)cc2)c2c(OC(C)C)nn(C3CCCCC3)c2n1] | ethyl 1-cyclohexyl-4-(4-formylphenyl)-3-[(propan-2-yl)oxy]-1H-pyrazolo[3,4-b]pyridine-6-carboxylate | ALP36, AMP95 | Specific example | 435 | 436 |
| E426 | 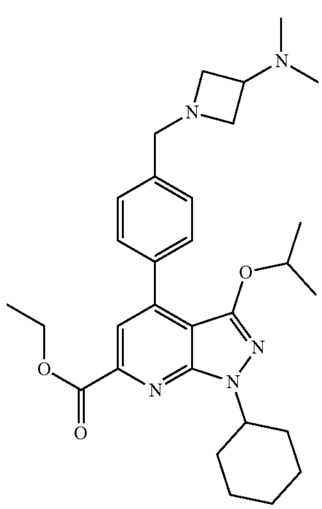 [SMILES: CCOC(=O)c1cc(-c2ccc(CN3CC(N(C)C)C3)cc2)c2c(OC(C)C)nn(C3CCCCC3)c2n1] | ethyl 1-cyclohexyl-4-(4-{[3-(dimethylamino)azetidin-1-yl]methyl}phenyl)-3-[(propan-2-yl)oxy]-1H-pyrazolo[3,4-b]pyridine-6-carboxylate | E425 | I34, Specific example | 519 | 520 |

467
468
TABLE XII-continued
List of esters
| Int. | Structure | Name | SM | method | MW | Mes |
|---|---|---|---|---|---|---|
| E427 | 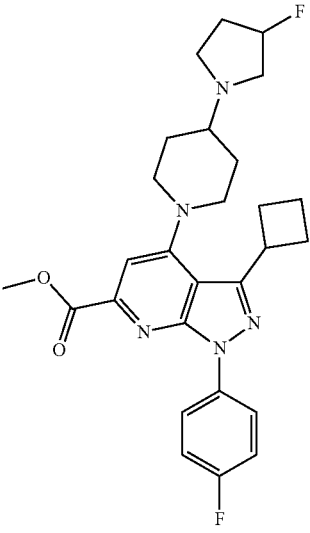 [SMILES: COC(=O)c1cc(N2CCC(N3CCC(F)C3)CC2)c2c(C3CCC3)nn(-c3ccc(F)cc3)c2n1] | methyl 3-cyclobutyl-1-(4-fluorophenyl)-4-[4-(3-fluoropyrrolidin-1-yl)piperidin-1-yl]-1H-pyrazolo[3,4-b]pyridine-6-carboxylate | E353 | I18 | 495 | 496 |
| E428 | 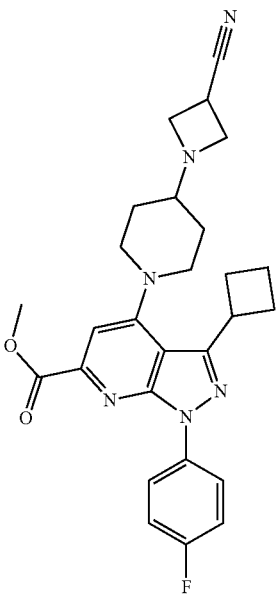 [SMILES: COC(=O)c1cc(N2CCC(N3CC(C#N)C3)CC2)c2c(C3CCC3)nn(-c3ccc(F)cc3)c2n1] | methyl 4-[4-(3-cyanoazetidin-1-yl)piperidin-1-yl]-3-cyclobutyl-1-(4-fluorophenyl)-1H-pyrazolo[3,4-b]pyridine-6-carboxylate | E353 | I18 | 488 | 489 |

TABLE XII-continued

List of esters

| Int. | Structure | Name | SM | method | MW | Mes |
|---|---|---|---|---|---|---|
| E429 | 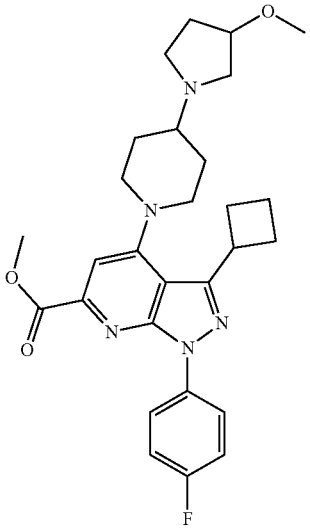 [SMILES: COC(=O)c1cc(N2CCC(N3CCC(OC)C3)CC2)c2c(C3CCC3)nn(-c3ccc(F)cc3)c2n1] | methyl 3-cyclobutyl-1-(4-fluorophenyl)-4-[4-(3-methoxypyrrolidin-1-yl)piperidin-1-yl]-1H-pyrazolo[3,4-b]pyridine-6-carboxylate | E353 | I18 | 507 | 508 |
| E430 | 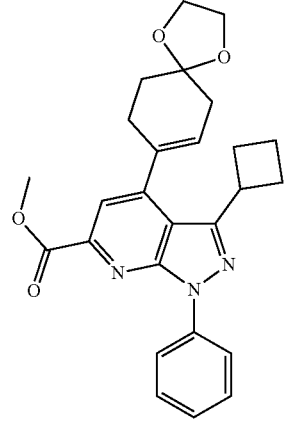 [SMILES: COC(=O)c1cc(C2=CCC3(CC2)OCCO3)c2c(C3CCC3)nn(-c3ccccc3)c2n1] | methyl 3-cyclobutyl-4-(1,4-dioxaspiro[4.5]dec-7-en-8-yl)-1-phenyl-1H-pyrazolo[3,4-b]pyridine-6-carboxylate | HP02 | Specific example | 445 | 446 |
| E431 | 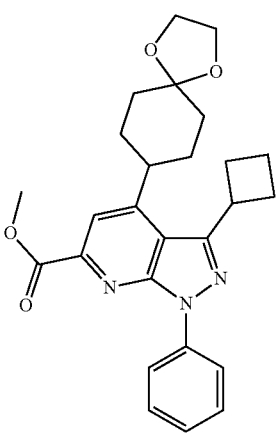 [SMILES: COC(=O)c1cc(C2CCC3(CC2)OCCO3)c2c(C3CCC3)nn(-c3ccccc3)c2n1] | methyl 3-cyclobutyl-4-(1,4-dioxaspiro[4.5]decan-8-yl)-1-phenyl-1H-pyrazolo[3,4-b]pyridine-6-carboxylate | E430 | Specific example | 447 | 448 |

TABLE XII-continued

List of esters

| Int. | Structure | Name | SM | method | MW | Mes |
|---|---|---|---|---|---|---|
| E432 | 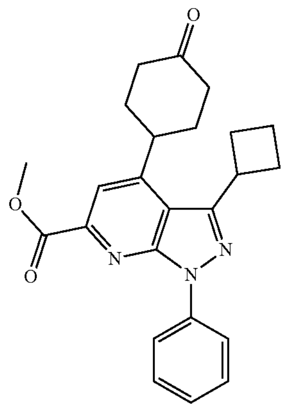 [SMILES: COC(=O)c1cc(C2CCC(=O)CC2)c2c(C3CCC3)nn(-c3ccccc3)c2n1] | methyl 3-cyclobutyl-4-(4-oxocyclohexyl)-1-phenyl-1H-pyrazolo[3,4-b]pyridine-6-carboxylate | E431 | Specific example | 403 | 404 |
| E433 | 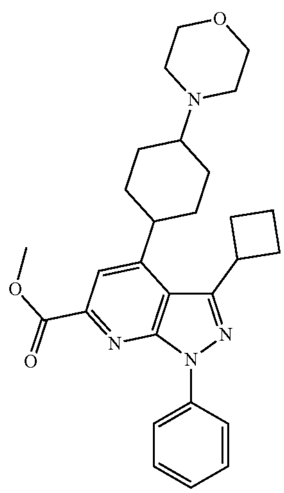 [SMILES: COC(=O)c1cc(C2CCC(N3CCOCC3)CC2)c2c(C3CCC3)nn(-c3ccccc3)c2n1] | methyl 3-cyclobutyl-4-[4-(morpholin-4-yl)cyclohexyl]-1-phenyl-1H-pyrazolo[3,4-b]pyridine-6-carboxylate | E432 | I18 | 474 | 475 |
| E434 | 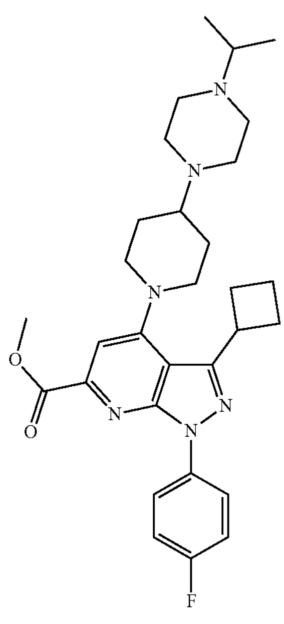 [SMILES: COC(=O)c1cc(N2CCC(N3CCN(C(C)C)CC3)CC2)c2c(C3CCC3)nn(-c3ccc(F)cc3)c2n1] | methyl 3-cyclobutyl-1-(4-fluorophenyl)-4-{4-[4-(propan-2-yl)piperazin-1-yl]piperidin-1-yl}-1H-pyrazolo[3,4-b]pyridine-6-carboxylate | E353 | I18 | 534 | 535 |

TABLE XII-continued

List of esters

| Int. | Structure | Name | SM | method | MW | Mes |
|---|---|---|---|---|---|---|
| E435 | 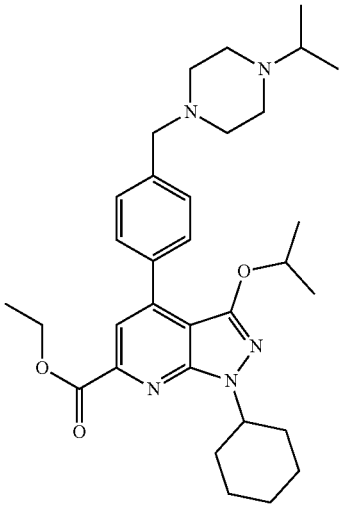 [SMILES: CCOC(=O)c1cc(-c2ccc(CN3CCN(C(C)C)CC3)cc2)c2c(OC(C)C)nn(C3CCCCC3)c2n1] | ethyl 1-cyclohexyl-3-[(propan-2-yl)oxy]-4-(4-{[4-(propan-2-yl)piperazin-1-yl]methyl}phenyl)-1H-pyrazolo[3,4-b]pyridine-6-carboxylate | E425 | I34 | 547 | 548 |
| E436 | 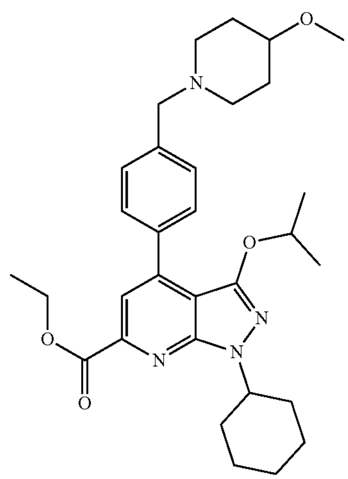 [SMILES: CCOC(=O)c1cc(-c2ccc(CN3CCC(OC)CC3)cc2)c2c(OC(C)C)nn(C3CCCCC3)c2n1] | ethyl 1-cyclohexyl-4-(4-[(4-methoxypiperidin-1-yl)methyl]phenyl}-3-[(propan-2-yl)oxy]-1H-pyrazolo[3,4-b]pyridine-6-carboxylate | E425 | I34 | 534 | 535 |
| E437 | 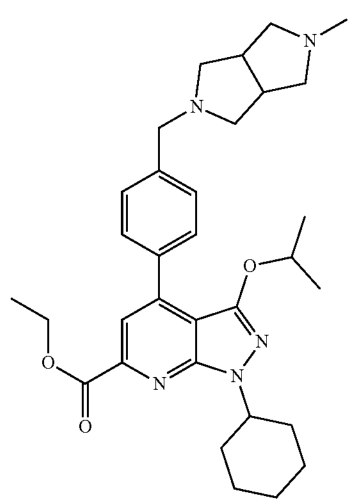 [SMILES: CCOC(=O)c1cc(-c2ccc(CN3CC4CN(C)CC4C3)cc2)c2c(OC(C)C)nn(C3CCCCC3)c2n1] | ethyl 1-cyclohexyl-4-{4-[(5-methylhexahydropyrrolo[3,4-c]pyrrol-2(1H)-yl)methyl]phenyl}-3-[(propan-2-yl)oxy]-1H-pyrazolo[3,4-b]pyridine-6-carboxylate | E425 | I34 | 545 | 546 |

TABLE XII-continued

| | | List of esters | | | | |
|---|---|---|---|---|---|---|
| Int. | Structure | Name | SM | method | MW | Mes |
| E438 | | 4-{1-cyclohexyl-6-(ethoxycarbonyl)-3-[(propan-2-yl)oxy]-1H-pyrazolo[3,4-b]pyridin-4-yl}benzoic acid | E425 | Specific example | 451 | 452 |
| E439 | | ethyl 4-{4-[5-(tert-butoxycarbonyl)hexahydropyrrolo[3,4-c]pyrrole-2(1H)-carbonyl]phenyl}-1-cyclohexyl-3-[(propan-2-yl)oxy]-1H-pyrazolo[3,4-b]pyridine-6-carboxylate | E438 | I24, Specific example | 645 | 646 |
| E440 | | ethyl 1-cyclohexyl-4-[4-(5-methylhexahydropyrrolo[3,4-c]pyrrole-2(1H)-carbonyl)phenyl]-3-[(propan-2-yl)oxy]-1H-pyrazolo[3,4-b]pyridine-6-carboxylate | E438 | I24 | 559 | 560 |

TABLE XII-continued

| | | List of esters | | | | |
|---|---|---|---|---|---|---|
| Int. | Structure | Name | SM | method | MW | Mes |
| E441 | 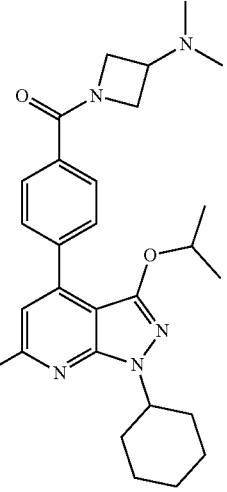 | ethyl 1-cyclohexyl-4-{4-[3-(dimethylamino)azetidine-1-carbonyl]phenyl}-3-[(propan-2-yl)oxy]-1H-pyrazolo[3,4-b]pyridine-6-carboxylate | E438 | I24, Specific example | 533 | 534 |
| E442 | 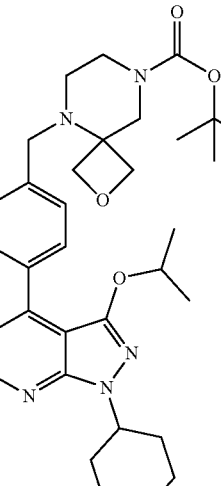 | ethyl 4-(4-{[8-(tert-butoxycarbonyl)-2-oxa-5,8-diazaspiro[3.5]nonan-5-yl]methyl}phenyl)-1-cyclohexyl-3-[(propan-2-yl)oxy]-1H-pyrazolo[3,4-b]pyridine-6-carboxylate | E425 | I34 | 647 | 648 |
| E443 | 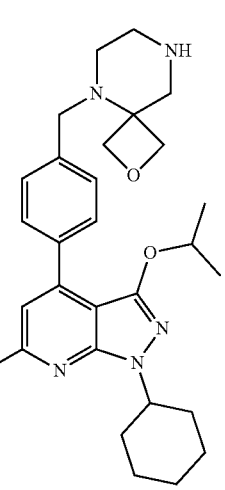 | ethyl 1-cyclohexyl-4-{4-[(2-oxa-5,8-diazaspiro[3.5]nonan-5-yl)methyl]phenyl}-3-[(propan-2-yl)oxy]-1H-pyrazolo[3,4-b]pyridine-6-carboxylate | E442 | I25 | 547 | 548 |

TABLE XII-continued

List of esters

| Int. | Structure | Name | SM | method | MW | Mes |
|---|---|---|---|---|---|---|
| E444 | 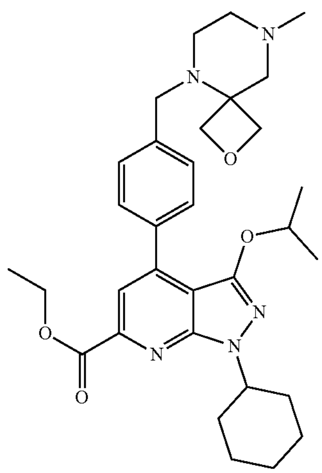 [SMILES: CCOC(=O)c1cc(-c2ccc(CN3CCN(C)CC34COC4)cc2)c2c(OC(C)C)nn(C3CCCCC3)c2n1] | ethyl 1-cyclohexyl-4-(4-[(8-methyl-2-oxa-5,8-diazaspiro[3.5]nonan-5-yl)methyl]phenyl}-3-[(propan-2-yl)oxy]-1H-pyrazolo[3,4-b]pyridine-6-carboxylate | E443 | Specific example | 561 | 562 |
| E445 | 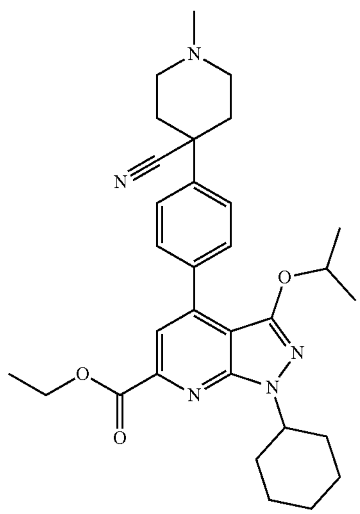 [SMILES: CCOC(=O)c1cc(-c2ccc(C3(C#N)CCN(C)CC3)cc2)c2c(OC(C)C)nn(C3CCCCC3)c2n1] | ethyl 4-[4-(4-cyano-1-methylpiperidin-4-yl)phenyl]-1-cyclohexyl-3-[(propan-2-yl)oxy]-1H-pyrazolo[3,4-b]pyridine-6-carboxylate | ALP38, AMP95 | Specific example | 529 | 530 |
| E460 | 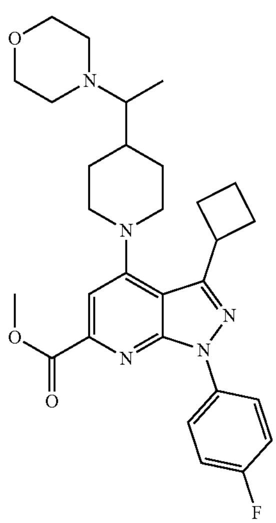 [SMILES: COC(=O)c1cc(N2CCC(C(C)N3CCOCC3)CC2)c2c(C3CCC3)nn(-c3ccc(F)cc3)c2n1] | methyl 3-cyclobutyl-1-(4-fluorophenyl)-4-{4-[1-(morpholin-4-yl)ethyl]piperidin-1-yl}-1H-pyrazolo[3,4-b]pyridine-6-carboxylate | HP19, 436852-25-4 | I3 | 521 | 522 |

TABLE XII-continued

List of esters

| Int. | Structure | Name | SM | method | MW | Mes |
|---|---|---|---|---|---|---|
| E461 | 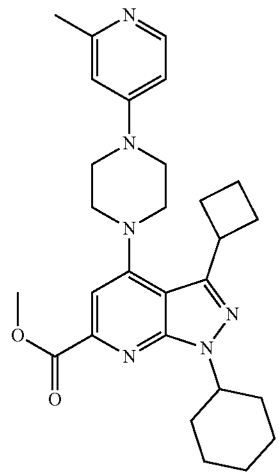 [SMILES: COC(=O)c1cc(N2CCN(c3ccnc(C)c3)CC2)c2c(C3CCC3)nn(C3CCCCC3)c2n1] | methyl 3-cyclobutyl-1-cyclohexyl-4-[4-(2-methylpyridin-4-yl)piperazin-1-yl]-1H-pyrazolo[3,4-b]pyridine-6-carboxylate | HP25, 98010-38-9 | I3 | 488 | 489 |
| E462 | 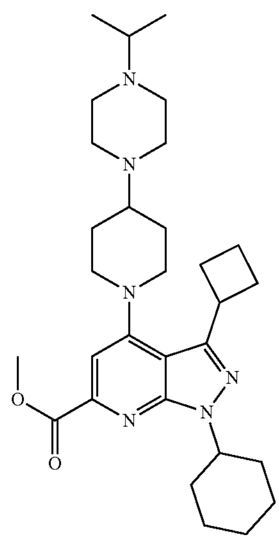 [SMILES: COC(=O)c1cc(N2CCC(N3CCN(C(C)C)CC3)CC2)c2c(C3CCC3)nn(C3CCCCC3)c2n1] | methyl 3-cyclobutyl-1-cyclohexyl-4-{4-[4-(propan-2-yl)piperazin-1-yl]piperidin-1-yl}-1H-pyrazolo[3,4-b]pyridine-6-carboxylate | HP25, 202991, 202991-78-4 | I3 | 522 | 523 |
| E463 | 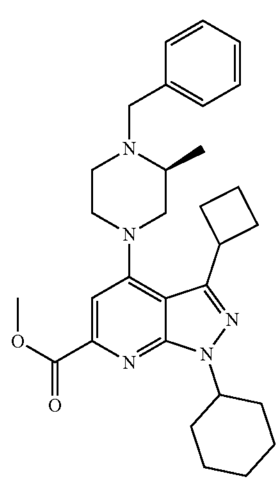 [SMILES: COC(=O)c1cc(N2CCN(Cc3ccccc3)[C@@H](C)C2)c2c(C3CCC3)nn(C3CCCCC3)c2n1] | methyl 4-[(3,S)-4-benzyl-3-methylpiperazin-1-yl]-3-cyclobutyl-1-cyclohexyl-1H-pyrazolo[3,4-b]pyridine-6-carboxylate | HP25, 511254-95-57 | I3 | 501 | 502 |

TABLE XII-continued
List of esters
| Int. | Structure | Name | SM | method | MW | Mes |
|---|---|---|---|---|---|---|
| E464 | 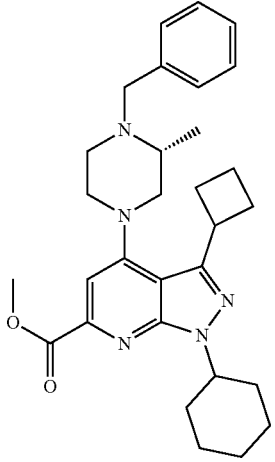 [SMILES: COC(=O)c1cc(N2CCN(Cc3ccccc3)[C@H](C)C2)c2c(C3CCC3)nn(C3CCCCC3)c2n1] | methyl 4-[(3R)-4-benzyl-3-methylpiperazin-1-yl]-3-cyclobutyl-1-cyclohexyl-1H-pyrazolo[3,4-b]pyridine-6-carboxylate | HP25, 1588480-39-0 | I3 | 501 | 502 |
| E465 | 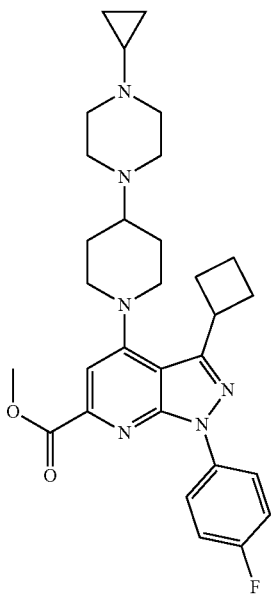 [SMILES: COC(=O)c1cc(N2CCC(N3CCN(C4CC4)CC3)CC2)c2c(C3CCC3)nn(-c3ccc(F)cc3)c2n1] | methyl 3-cyclobutyl-4-[4-(4-cyclopropylpiperazin-1-yl)piperidin-1-yl]-1-(4-fluorophenyl)-1H-pyrazolo[3,4-b]pyridine-6-carboxylate | E498 | I26, Specific example | 517 | 518 |

TABLE XII-continued
List of esters
| Int. | Structure | Name | SM | method | MW | Mes |
|---|---|---|---|---|---|---|
| E466 | 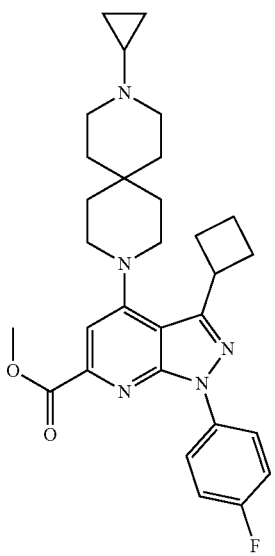 [SMILES: COC(=O)c1cc(N2CCC3(CC2)CCN(C2CC2)CC3)c2c(C3CCC3)nn(-c3ccc(F)cc3)c2n1] | methyl 3-cyclobutyl-4-(9-cyclopropyl-3,9-diazaspiro[5.5]undecan-3-yl)-1-(4-fluorophenyl)-1H-pyrazolo[3,4-b]pyridine-6-carboxylate | E500 | I26 | 517 | 518 |
| E467 | 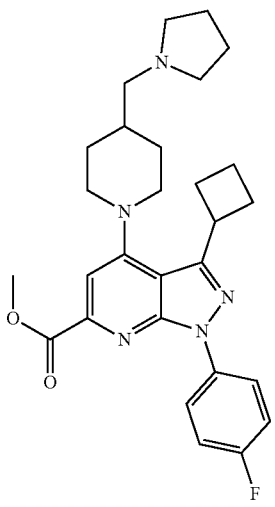 [SMILES: COC(=O)c1cc(N2CCC(CN3CCCC3)CC2)c2c(C3CCC3)nn(-c3ccc(F)cc3)c2n1] | methyl 3-cyclobutyl-1-(4-fluorophenyl)-4-{4-[(pyrrolidin-1-yl)methyl]piperidin-1-yl}-1H-pyrazolo[3,4-b]pyridine-6-carboxylate | HP19, 683772-11-5 | I3 | 491 | 492 |

TABLE XII-continued
List of esters
| Int. | Structure | Name | SM | method | MW | Mes |
|---|---|---|---|---|---|---|
| E468 | 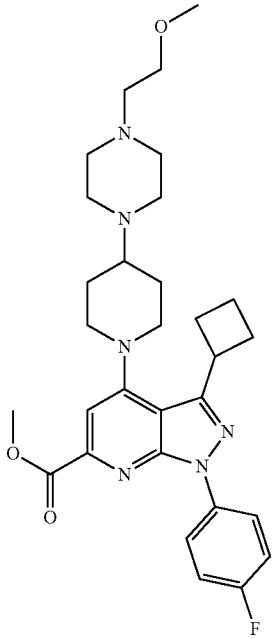 [SMILES: COCCN1CCN(C2CCN(c3cc(C(=O)OC)nc4c3c(C3CCC3)nn4-c3ccc(F)cc3)CC2)CC1] | methyl 3-cyclobutyl-1-(4-fluorophenyl)-4-{4-[4-(2-methoxyethyl)piperazin-1-yl]piperidin-1-yl}-1H-pyrazolo[3,4-b]pyridine-6-carboxylate | E498, 6482-24-2 | I27 | 550 | 551 |
| E469 | 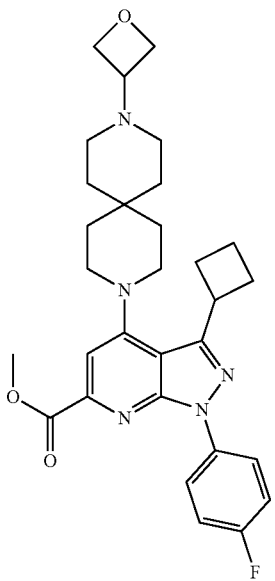 [SMILES: COC(=O)c1cc(N2CCC3(CC2)CCN(C2COC2)CC3)c2c(C3CCC3)nn(-c3ccc(F)cc3)c2n1] | methyl 3-cyclobutyl-1-(4-fluorophenyl)-4-[9-(oxetan-3-yl)-3,9-diazaspiro[5.5]undecan-3-yl]-1H-pyrazolo[3,4-b]pyridine-6-carboxylate | E500, 6704-31-0 | I30, Specific example | 533 | 534 |

TABLE XII-continued

List of esters

| Int. | Structure | Name | SM | method | MW | Mes |
|---|---|---|---|---|---|---|
| E470 | 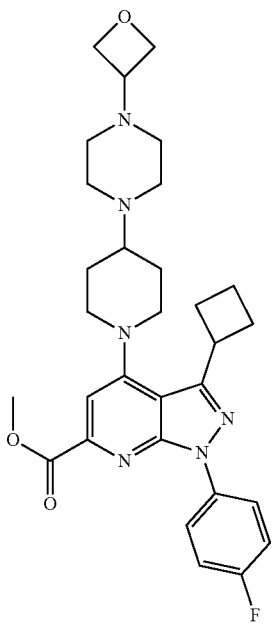 [SMILES: COC(=O)c1cc(N2CCC(N3CCN(C4COC4)CC3)CC2)c2c(C3CCC3)nn(-c3ccc(F)cc3)c2n1] | methyl 3-cyclobutyl-1-(4-fluorophenyl)-4-{4-[4-(oxetan-3-yl)piperazin-1-yl]piperidin-1-yl}-1H-pyrazolo[3,4-b]pyridine-6-carboxylate | E498, 6704-31-0 | I30 | 548 | 549 |
| E471 | 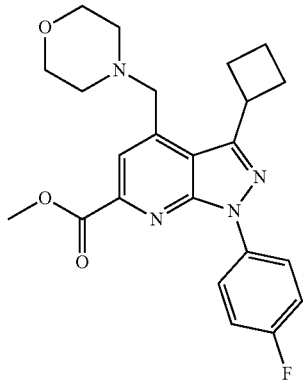 [SMILES: COC(=O)c1cc(CN2CCOCC2)c2c(C3CCC3)nn(-c3ccc(F)cc3)c2n1] | methyl 3-cyclobutyl-1-(4-fluorophenyl)-4-[(morpholin-4-yl)methyl]-1H-pyrazolo[3,4-b]pyridine-6-carboxylate | HP19, 936329-94-1 | J13 | 424 | 425 |
| E472 | 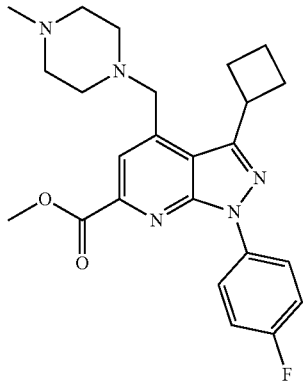 [SMILES: COC(=O)c1cc(CN2CCN(C)CC2)c2c(C3CCC3)nn(-c3ccc(F)cc3)c2n1] | methyl 3-cyclobutyl-1-(4-fluorophenyl)-4-[(4-methylpiperazin-1-yl)methyl]-1H-pyrazolo[3,4-b]pyridine-6-carboxylate | HP19, 1015484-22-6 | J13 | 438 | 439 |

TABLE XII-continued

| Int. | Structure | Name | SM | method | MW | Mes |
|---|---|---|---|---|---|---|
| E473 | 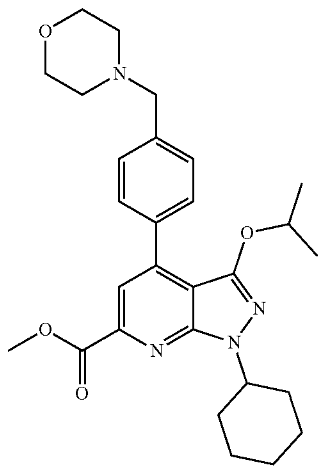 [SMILES: COC(=O)c1cc(-c2ccc(CN3CCOCC3)cc2)c2c(OC(C)C)nn(C3CCCCC3)c2n1] | methyl 1-cyclohexyl-4-{4-[(morpholin-4-yl)methyl]phenyl}-3-[(propan-2-yl)oxy]-1H-pyrazolo[3,4-b]pyridine-6-carboxylate | E504, 1268340-94-8 | J13 | 493 | 493 |
| E474 | 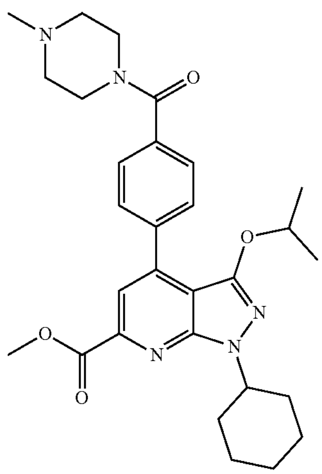 [SMILES: COC(=O)c1cc(-c2ccc(C(=O)N3CCN(C)CC3)cc2)c2c(OC(C)C)nn(C3CCCCC3)c2n1] | methyl 1-cyclohexyl-4-[4-(4-methylpiperazine-1-carbonyl)phenyl]-3-[(propan-2-yl)oxy]-1H-pyrazolo[3,4-b]pyridine-6-carboxylate | E504, 34352-59-5 | I28, Specific example | 519 | 520 |
| E475 | 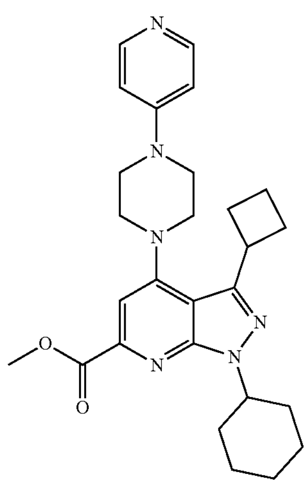 [SMILES: COC(=O)c1cc(N2CCN(c3ccncc3)CC2)c2c(C3CCC3)nn(C3CCCCC3)c2n1] | methyl 3-cyclobutyl-1-cyclohexyl-4-[4-(pyridin-4-yl)piperazin-1-yl]-1H-pyrazolo[3,4-b]pyridine-6-carboxylate | HP25, 1008-91-9 | I3 | 474 | 475 |

TABLE XII-continued

List of esters

| Int. | Structure | Name | SM | method | MW | Mes |
|---|---|---|---|---|---|---|
| E476 | 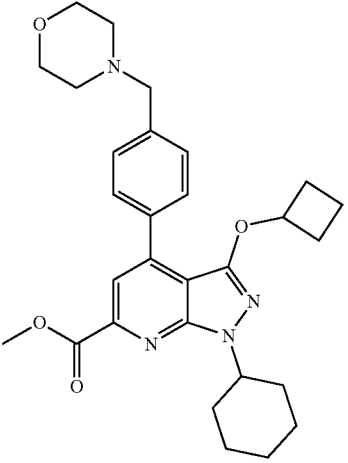 [SMILES: COC(=O)c1cc(-c2ccc(CN3CCOCC3)cc2)c2c(OC3CCC3)nn(C3CCCCC3)c2n1] | methyl 3-(cyclobutyloxy)-1-cyclohexyl-4-{4-[(morpholin-4-yl)methyl]phenyl}-1H-pyrazolo[3,4-b]pyridine-6-carboxylate | E505, 1268340-94-8 | J13 | 504 | 505 |
| E477 | 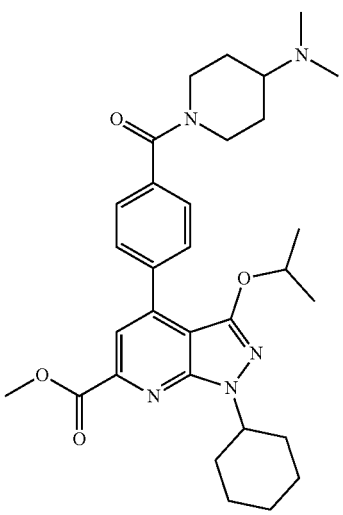 | methyl 1-cyclohexyl-4-{4-[4-(dimethylamino)piperidine-1-carbonyl]phenyl}-3-[(propan-2-yl)oxy]-1H-pyrazolo[3,4-b]pyridine-6-carboxylate | E504-4318-42-7 | I28 | 548 | 549 |
| E478 | 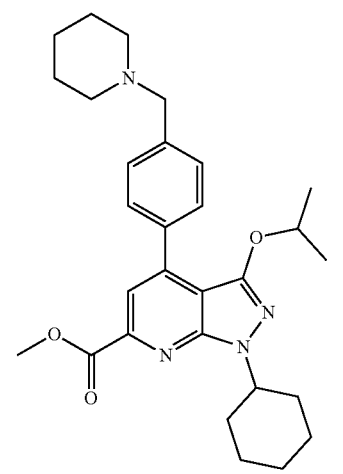 [SMILES: COC(=O)c1cc(-c2ccc(CN3CCCCC3)cc2)c2c(OC(C)C)nn(C3CCCCC3)c2n1] | methyl 1-cyclohexyl-4-{4-[(piperidin-1-yl)methyl]phenyl}-3-[(propan-2-yl)oxy]-1H-pyrazolo[3,4-b]pyridine-6-carboxylate | E504, 1268340-93-7 | J13 | 491 | 492 |

TABLE XII-continued

List of esters

| Int. | Structure | Name | SM | method | MW | Mes |
|---|---|---|---|---|---|---|
| E479 | 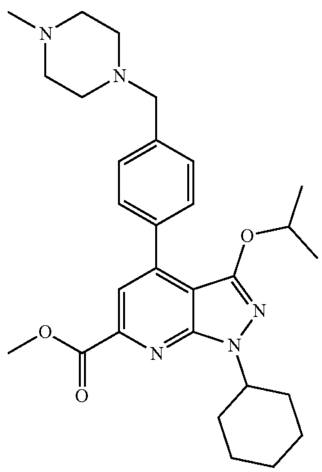 [SMILES: COC(=O)c1cc(-c2ccc(CN3CCN(C)CC3)cc2)c2c(OC(C)C)nn(C3CCCCC3)c2n1] | methyl 1-cyclohexyl-4-{4-[(4-methylpiperazin-1-yl)methyl]phenyl}-3-[(propan-2-yl)oxy]-1H-pyrazolo[3,4-b]pyridine-6-carboxylate | E504, 1015484-22-6 | J13 | 506 | 507 |
| E480 | 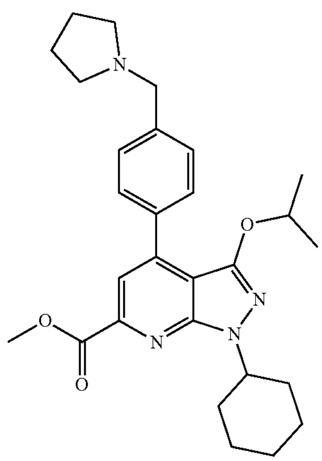 [SMILES: COC(=O)c1cc(-c2ccc(CN3CCCC3)cc2)c2c(OC(C)C)nn(C3CCCCC3)c2n1] | methyl 1-cyclohexyl-3-[(propan-2-yl)oxy]-4-{4-[(pyrrolidin-1-yl)methyl]phenyl}-1H-pyrazolo[3,4-b]pyridine-6-carboxylate | E504, 888711-53-3 | J13 | 477 | 477 |
| E481 | 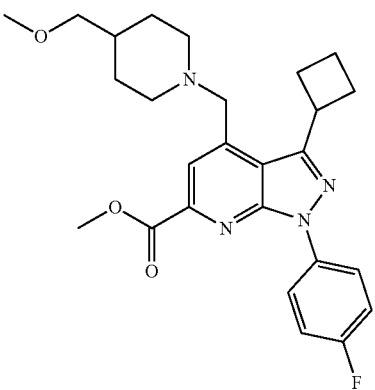 [SMILES: COCC1CCN(Cc2cc(C(=O)OC)nc3c2c(C2CCC2)nn3-c2ccc(F)cc2)CC1] | methyl 3-cyclobutyl-1-(4-fluorophenyl)-4-{[4-(methoxymethyl)piperidin-1-yl]methyl}-1H-pyrazolo[3,4-b]pyridine-6-carboxylate | HP19, BF01 | J13 | 466 | 467 |

TABLE XII-continued

List of esters

| Int. | Structure | Name | SM | method | MW | Mes |
|---|---|---|---|---|---|---|
| E482 | 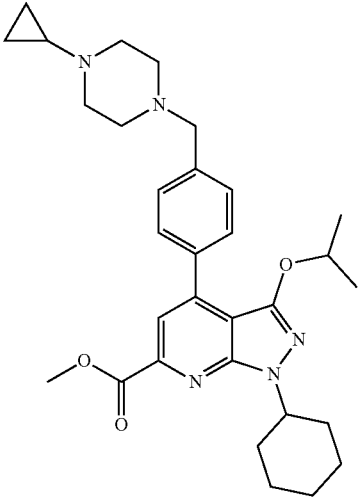 [SMILES: COC(=O)c1cc(-c2ccc(CN3CCN(C4CC4)CC3)cc2)c2c(OC(C)C)nn(C3CCCCC3)c2n1] | methyl 1-cyclohexyl-4-{4-[(4-cyclopropylpiperazin-1-yl)methyl]phenyl}-3-[(propan-2-yl)oxy]-1H-pyrazolo[3,4-b]pyridine-6-carboxylate | E494 | I26 | 531 | 532 |
| E483 | 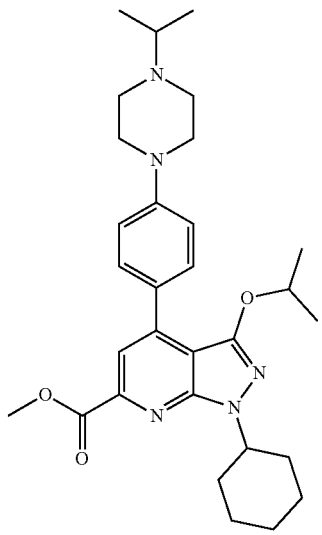 [SMILES: COC(=O)c1cc(-c2ccc(N3CCN(C(C)C)CC3)cc2)c2c(OC(C)C)nn(C3CCCCC3)c2n1] | methyl 1-cyclohexyl-3-[(propan-2-yl)oxy]-4-{4-[4-(propan-2-yl)piperazin-1-yl]phenyl}-1H-pyrazolo[3,4-b]pyridine-6-carboxylate | E504, 4318-42-7 | I29 | 519 | 520 |
| E484 | 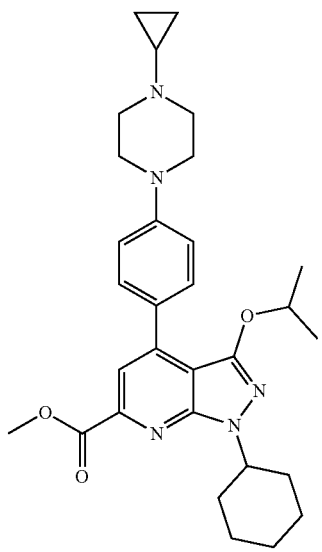 [SMILES: COC(=O)c1cc(-c2ccc(N3CCN(C4CC4)CC3)cc2)c2c(OC(C)C)nn(C3CCCCC3)c2n1] | methyl 1-cyclohexyl-4-[4-(4-cyclopropylpiperazin-1-yl)phenyl]-3-[(propan-2-yl)oxy]-1H-pyrazolo[3,4-b]pyridine-6-carboxylate | E504, 20327-23-5 | I29 | 517 | 518 |

TABLE XII-continued
List of esters
| Int. | Structure | Name | SM | method | MW | Mes |
|------|-----------|------|----|--------|----|----|
| E485 | 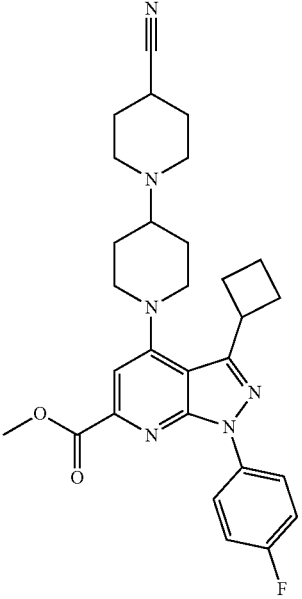 [SMILES: COC(=O)c1cc(N2CCC(N3CCC(C#N)CC3)CC2)c2c(C3CCC3)nn(-c3ccc(F)cc3)c2n1] | methyl 4-(4-cyano[1,4'-bipiperidin]-1'-yl)-3-cyclobutyl-1-(4-fluorophenyl)-1H-pyrazolo[3,4-b]pyridine-6-carboxylate | HP19, AMI11 | I3 | 516 | 517 |
| E486 | 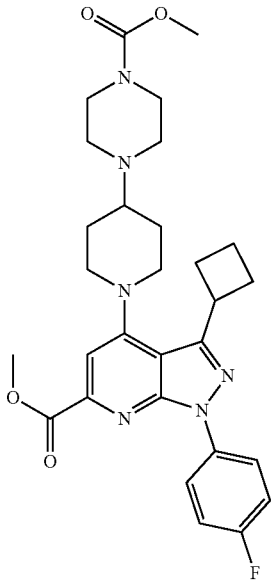 [SMILES: COC(=O)c1cc(N2CCC(N3CCN(C(=O)OC)CC3)CC2)c2c(C3CCC3)nn(-c3ccc(F)cc3)c2n1] | methyl 3-cyclobutyl-1-(4-fluorophenyl)-4-{4-[4-(methoxycarbonyl)piperazin-1-yl]piperidin-1-yl}-1H-pyrazolo[3,4-b]pyridine-6-carboxylate | E498 | I31, Specific example | 550 | 551 |

TABLE XII-continued

List of esters

| Int. | Structure | Name | SM | method | MW | Mes |
|---|---|---|---|---|---|---|
| E487 | 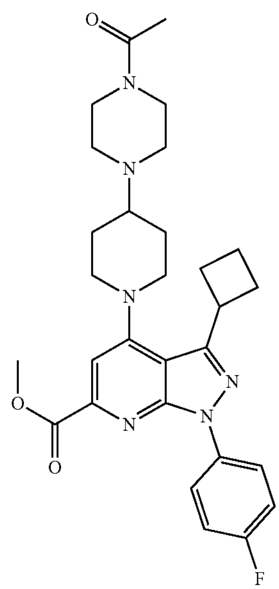 [SMILES: COC(=O)c1cc(N2CCC(N3CCN(C(C)=O)CC3)CC2)c2c(C3CCC3)nn(-c3ccc(F)cc3)c2n1] | methyl 4-[4-(4-acetylpiperazin-1-yl)piperidin-1-yl]-3-cyclobutyl-1-(4-fluorophenyl)-1H-pyrazolo[3,4-b]pyridine-6-carboxylate | E498 | I32, Specific example | 534 | 535 |
| E488 | 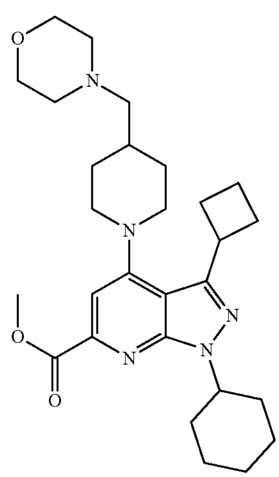 [SMILES: COC(=O)c1cc(N2CCC(CN3CCOCC3)CC2)c2c(C3CCC3)nn(C3CCCCC3)c2n1] | methyl 3-cyclobutyl-1-cyclohexyl-4-{4-[(morpholin-4-yl)methyl]piperidin-1-yl}-1H-pyrazolo[3,4-b]pyridine-6-carboxylate | HP25, 81310-62-5 | I3 | 495 | 496 |
| E489 | 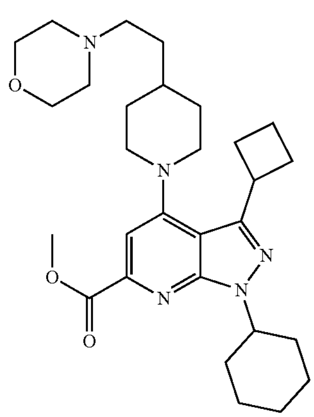 [SMILES: COC(=O)c1cc(N2CCC(CCN3CCOCC3)CC2)c2c(C3CCC3)nn(C3CCCCC3)c2n1] | methyl 3-cyclobutyl-1-cyclohexyl-4-{4-[2-(morpholin-4-yl)ethyl]piperidin-1-yl}-1H-pyrazolo[3,4-b]pyridine-6-carboxylate | HP25, 500357-64-2 | I3 | 509 | 510 |

TABLE XII-continued

List of esters

| Int. | Structure | Name | SM | method | MW | Mes |
|---|---|---|---|---|---|---|
| E490 | 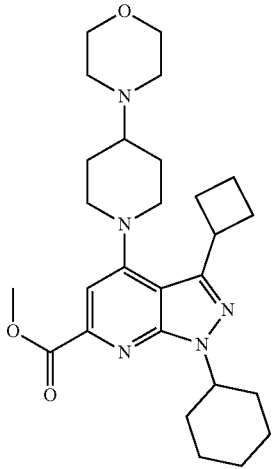 [SMILES: COC(=O)c1cc(N2CCC(N3CCOCC3)CC2)c2c(C3CCC3)nn(C3CCCCC3)c2n1] | methyl 3-cyclobutyl-1-cyclohexyl-4-[4-(morpholin-4-yl)piperidin-1-yl]-1H-pyrazolo[3,4-b]pyridine-6-carboxylate | HP25, 53617-35-9 | I3 | 481 | 482 |
| E491 | 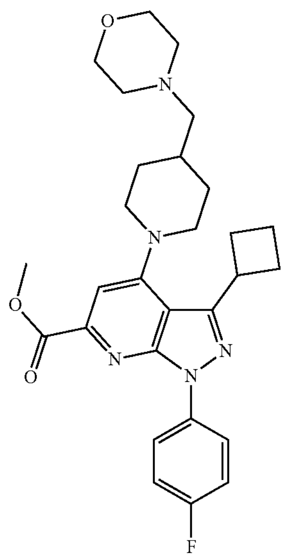 [SMILES: COC(=O)c1cc(N2CCC(CN3CCOCC3)CC2)c2c(C3CCC3)nn(-c3ccc(F)cc3)c2n1] | methyl 3-cyclobutyl-1-(4-fluorophenyl)-4-{4-[(morpholin-4-yl)methyl]piperidin-1-yl}-1H-pyrazolo[3,4-b]pyridine-6-carboxylate | HP19, 202991-78-4 | I3 | 507 | 508 |
| E492 | 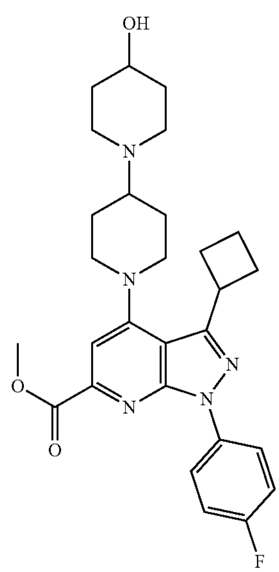 [SMILES: COC(=O)c1cc(N2CCC(N3CCC(O)CC3)CC2)c2c(C3CCC3)nn(-c3ccc(F)cc3)c2n1] | methyl 3-cyclobutyl-1-(4-fluorophenyl)-4-(4-hydroxy[1,4'-bipiperidin]-1'-yl)-1H-pyrazolo[3,4-b]pyridine-6-carboxylate | HP19, 202991-78-4 | I3 | 507 | 508 |

TABLE XII-continued

List of esters

| Int. | Structure | Name | SM | method | MW | Mes |
|------|-----------|------|----|--------|----|----|
| E493 | 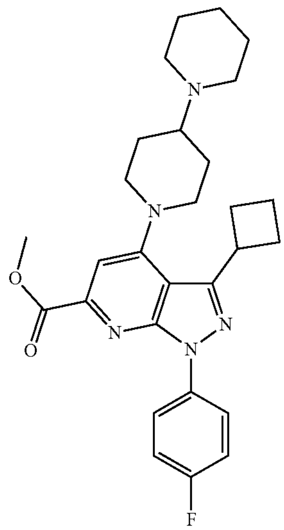 [SMILES: COC(=O)c1cc(N2CCC(N3CCCCC3)CC2)c2c(C3CCC3)nn(-c3ccc(F)cc3)c2n1] | methyl 4-([1,4'-bipiperidin]-1'-yl)-3-cyclobutyl-1-(4-fluorophenyl)-1H-pyrazolo[3,4-b]pyridine-6-carboxylate | HP19, 202991-78-4 | I3 | 491 | 492 |
| E494 | 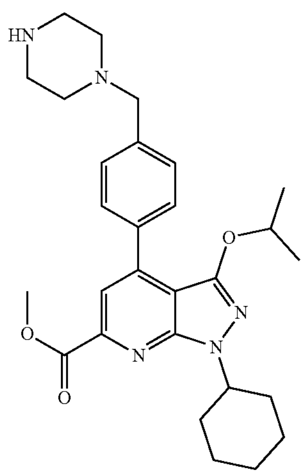 [SMILES: COC(=O)c1cc(-c2ccc(CN3CCNCC3)cc2)c2c(OC(C)C)nn(C3CCCCC3)c2n1] | methyl 1-cyclohexyl-4-{4-[(piperazin-1-yl)methyl]phenyl}-3-[(propan-2-yl)oxy]-1H-pyrazolo[3,4-b]pyridine-6-carboxylate | E495 | I25 | 491 | 492 |
| E495 | 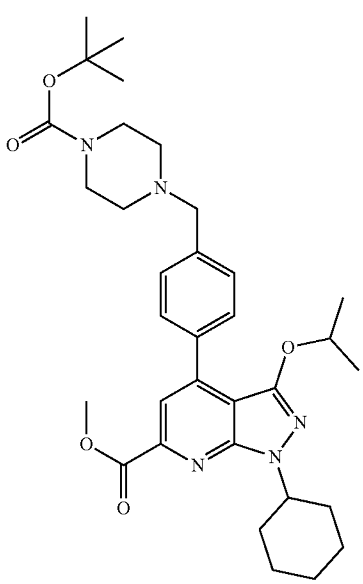 [SMILES: COC(=O)c1cc(-c2ccc(CN3CCN(C(=O)OC(C)(C)C)CC3)cc2)c2c(OC(C)C)nn(C3CCCCC3)c2n1] | methyl 4-(4-{[4-(tert-butoxycarbonyl)piperazin-1-yl]methyl}phenyl)-1-cyclohexyl-3-[(propan-2-yl)oxy]-1H-pyrazolo[3,4-b]pyridine-6-carboxylate | E504, 936329-97-4 | J13 | 591 | 592 |

TABLE XII-continued
| | | List of esters | | | | |
|---|---|---|---|---|---|---|
| Int. | Structure | Name | SM | method | MW | Mes |
| E498 | 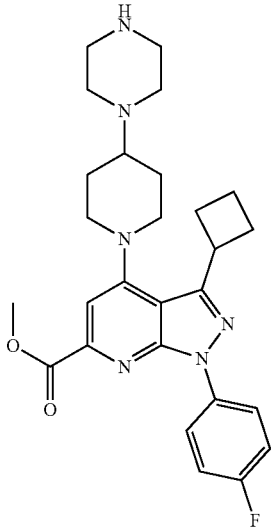 [SMILES: COC(=O)c1cc(N2CCC(N3CCNCC3)CC2)c2c(C3CCC3)nn(-c3ccc(F)cc3)c2n1] | methyl 3-cyclobutyl-1-(4-fluorophenyl)-4-[4-(piperazin-1-yl)piperidin-1-yl]-1H-pyrazolo[3,4-6]pyridine-6-carboxylate | E499 | I25 | 492 | 493 |
| E499 | 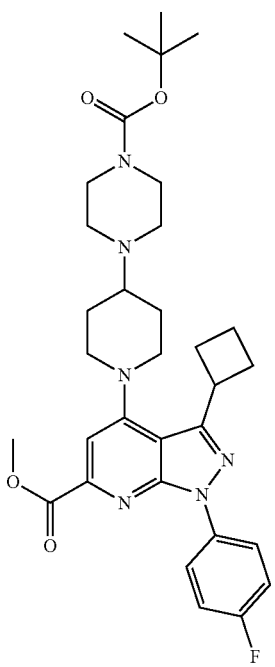 [SMILES: COC(=O)c1cc(N2CCC(N3CCN(C(=O)OC(C)(C)C)CC3)CC2)c2c(C3CCC3)nn(-c3ccc(F)cc3)c2n1] | methyl 4-{4-[4-(tert-butoxycarbonyl)piperazin-1-yl]piperidin-1-yl}-3-cyclobutyl-1-(4-fluorophenyl)-1H-pyrazolo[3,4-b]pyridine-6-carboxylate | HP19, 205059-24-1 | I3 | 592 | 593 |

TABLE XII-continued

List of esters

| Int. | Structure | Name | SM | method | MW | Mes |
|---|---|---|---|---|---|---|
| E500 | 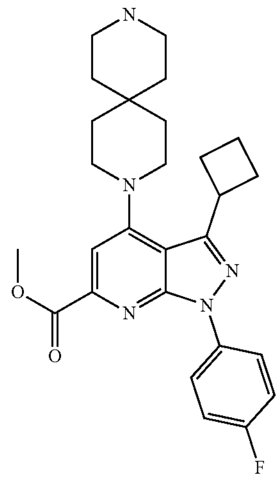 [SMILES: COC(=O)c1cc(N2CCC3(CCNCC3)CC2)c2c(C3CCC3)nn(-c3ccc(F)cc3)c2n1] | methyl 3-cyclobutyl-4-(3,9-diazaspiro[5.5]undecan-3-yl)-1-(4-fluorophenyl)-1H-pyrazolo[3,4-b]pyridine-6-carboxylate | E501 | I25 | 477 | 478 |
| E501 | 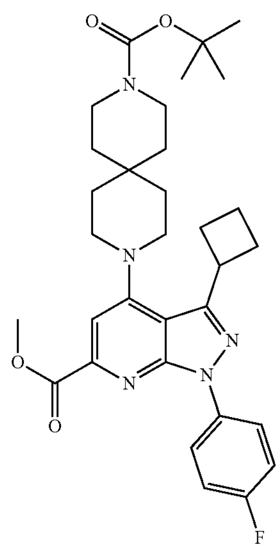 [SMILES: COC(=O)c1cc(N2CCC3(CCN(C(=O)OC(C)(C)C)CC3)CC2)c2c(C3CCC3)nn(-c3ccc(F)cc3)c2n1] | tert-butyl 9-[3-cyclobutyl-1-(4-fluorophenyl)-6-(methoxycarbonyl)-1H-pyrazolo[3,4-b]pyridin-4-yl]-3,9-diazaspiro[5.5]undecane-3-carboxylate | HP19 173405-78-2 | I3 | 577 | 578 |
| E502 | 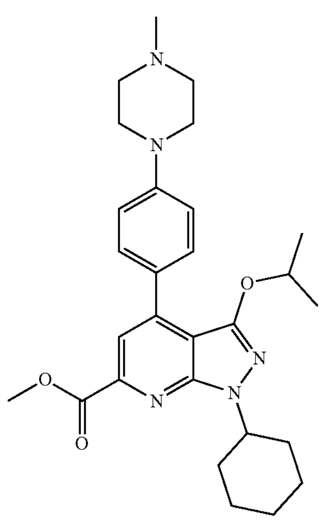 [SMILES: COC(=O)c1cc(-c2ccc(N3CCN(C)CC3)cc2)c2c(OC(C)C)nn(C3CCCCC3)c2n1] | methyl 1-cyclohexyl-4-[4-(4-methylpiperazin-1-yl)phenyl]-3-[(propan-2-yl)oxy]-1H-pyrazolo[3,4-b]pyridine-6-carboxylate | E504, 109-01-3 | I29, Specific example | 491 | 492 |

TABLE XII-continued

List of esters

| Int. | Structure | Name | SM | method | MW | Mes |
|---|---|---|---|---|---|---|
| E503 | 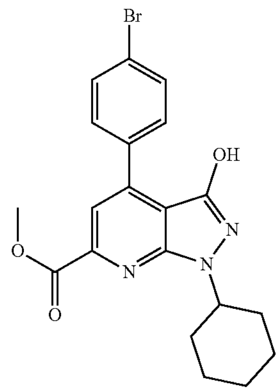 [SMILES: COC(=O)c1cc(-c2ccc(Br)cc2)c2c(O)nn(C3CCCCC3)c2n1] | methyl 4-(4-bromophenyl)-1-cyclohexyl-3-hydroxy-1H-pyrazolo[3,4-b]pyridine-6-carboxylate | 436088-86-7 and 608128-34-3 | I1, Specific example | 430 | 431 |
| E504 | 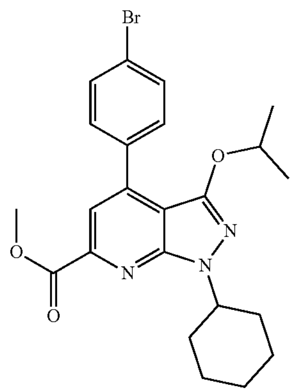 [SMILES: COC(=O)c1cc(-c2ccc(Br)cc2)c2c(OC(C)C)nn(C3CCCCC3)c2n1] | methyl 4-(4-bromophenyl)-1-cyclohexyl-3-[(propan-2-yl)oxy]-1H-pyrazolo[3,4-b]pyridine-6-carboxylate | E503 | I17, Specific example | 472 | 472 |
| E505 | 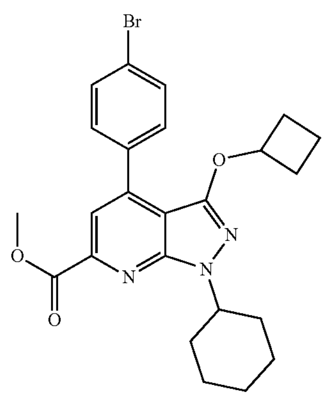 [SMILES: COC(=O)c1cc(-c2ccc(Br)cc2)c2c(OC3CCC3)nn(C3CCCCC3)c2n1] | methyl 4-(4-bromophenyl)-3-(cyclobutyloxy)-1-cyclohexyl-1H-pyrazolo[3,4-b]pyridine-6-carboxylate | E503 | I17, Specific example | 504 | 505 |
| E509 | 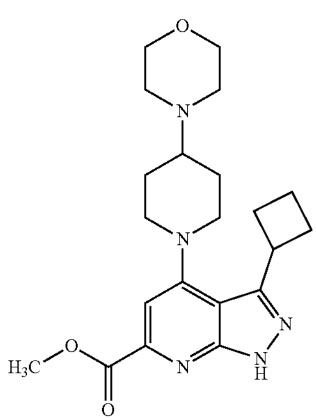 [SMILES: COC(=O)c1cc(N2CCC(N3CCOCC3)CC2)c2c(C3CCC3)n[nH]c2n1] | methyl 3-cyclobutyl-4-[4-(morpholin-4-yl)piperidin-1-yl]-1H-pyrazolo[3,4-b]pyridine-6-carboxylate | 53617-35-9, 16063-69-7, 5006-22-4, 301-01-2, 630-08-0 | Specific example | 399 | 400 |

TABLE XII-continued
List of esters
| Int. | Structure | Name | SM | method | MW | Mes |
|---|---|---|---|---|---|---|
| E510 | 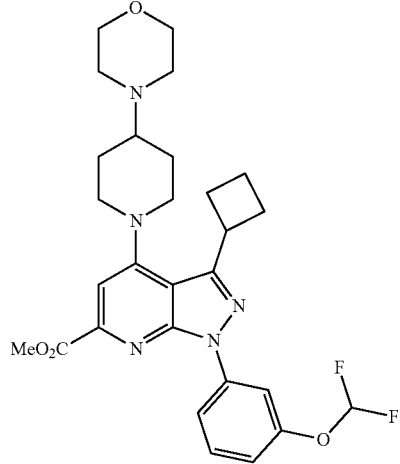 [SMILES: COC(=O)c1cc(N2CCC(N3CCOCC3)CC2)c2c(C3CCC3)nn(-c3cccc(OC(F)F)c3)c2n1] | methyl 3-cyclobutyl-1-[3-(difluoromethoxy)phenyl]-4-[4-(morpholin-4-yl)piperidin-1-yl]-1H-pyrazolo[3,4-b]pyridine-6-carboxylate | E509 | I7, Specific example | 541 | 542 |
| E511 | 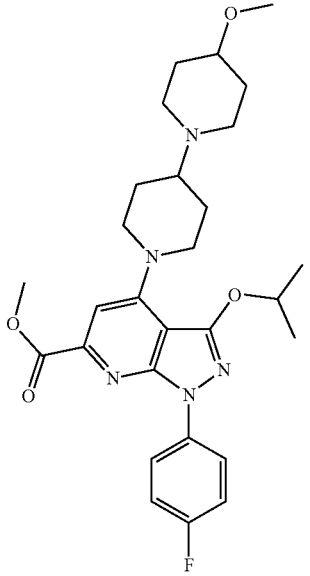 [SMILES: COC(=O)c1cc(N2CCC(N3CCC(OC)CC3)CC2)c2c(OC(C)C)nn(-c3ccc(F)cc3)c2n1] | methyl 1-(4-fluorophenyl)-4-(4-methoxy[1,4'-bipiperidin]-1'-yl)-3-[(propan-2-yl)oxy]-1H-pyrazolo[3,4-b]pyridine-6-carboxylate | AMP96 | Specific example | 525 | 526 |

TABLE XII-continued

List of esters

| Int. | Structure | Name | SM | method | MW | Mes |
|------|-----------|------|-----|--------|-----|-----|
| E513 | 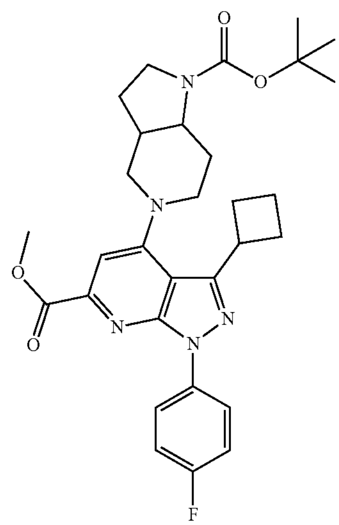 [SMILES: COC(=O)c1cc(N2CCC3C(CCN3C(=O)OC(C)(C)C)C2)c2c(C3CCC3)nn(-c3ccc(F)cc3)c2n1] | methyl 4-[1-(tert-butoxycarbonyl)octahydro-5H-pyrrolo[3,2-c]pyridin-5-yl]-3-cyclobutyl-1-(4-fluorophenyl)-1H-pyrazolo[3,4-b]pyridine-6-carboxylatee | HP19 | I3 | 549 | 550 |
| E514 | 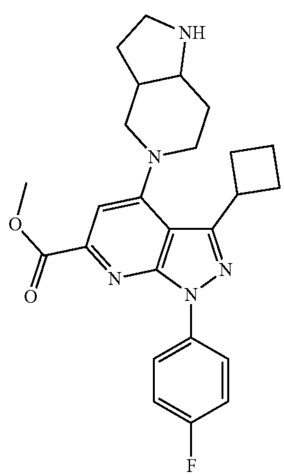 [SMILES: COC(=O)c1cc(N2CCC3NCCC3C2)c2c(C3CCC3)nn(-c3ccc(F)cc3)c2n1] | methyl 3-cyclobutyl-1-(4-fluorophenyl)-4-(octahydro-5H-pyrrolo[3,2-c]pyridin-5-yl)-1H-pyrazolo[3,4-b]pyridine-6-carboxylate | E513 | I21A | 449 | 450 |
| E515 | 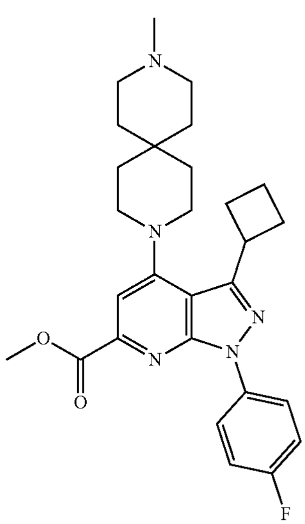 [SMILES: COC(=O)c1cc(N2CCC3(CCN(C)CC3)CC2)c2c(C3CCC3)nn(-c3ccc(F)cc3)c2n1] | methyl 3-cyclobutyl-1-(4-fluorophenyl)-4-(9-methyl-3,9-diazaspiro[5.5]undecan-3-yl)-1H-pyrazolo[3,4-b]pyridine-6-carboxylate | HP19, 13323-45-0 | I3 | 491 | 492 |

TABLE XII-continued

List of esters

| Int. | Structure | Name | SM | method | MW | Mes |
|---|---|---|---|---|---|---|
| E516 | 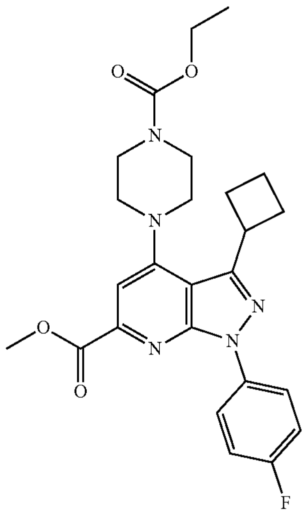 [SMILES: CCOC(=O)N1CCN(c2cc(C(=O)OC)nc3c2c(C2CCC2)nn3-c2ccc(F)cc2)CC1] | methyl 3-cyclobutyl-4-[4-(ethoxycarbonyl)piperazin-1-yl]-1-(4-fluorophenyl)-1H-pyrazolo[3,4-b]pyridine-6-carboxylate | HP19, 120-43-4 | I3 | 481 | 482 |
| E517 | 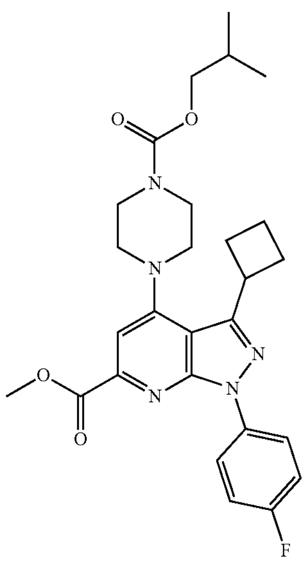 [SMILES: COC(=O)c1cc(N2CCN(C(=O)OCC(C)C)CC2)c2c(C3CCC3)nn(-c3ccc(F)cc3)c2n1] | methyl 3-cyclobutyl-1-(4-fluorophenyl)-4-(4-{[(2-methylpropoxy)carbonyl]piperazin-1-yl}-1H-pyrazolo[3,4-b]pyridine-6-carboxylate | HP19, 23672-96-0 | I3 | 509 | 510 |

Method J1: Synthesis of Carboxylic Acids by Saponification of Ester

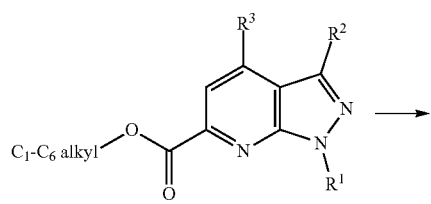

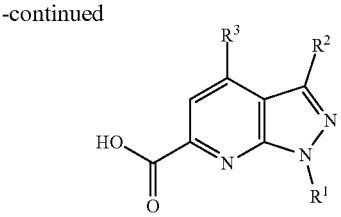

To the intermediate ester (1 equiv) in THF or in a mixture of THF/methanol or in dioxane/water or in THF/methanol/water at RT is added either aqueous 1 to 2 N sodium hydroxide or lithium hydroxide monohydrate (from 1 to 5 equiv). The reaction mixture is stirred at a temperature ranging from RT to 60° C. for 20 minutes to several days (up to 8 days). The volatiles are removed under reduced pressure, and the resulting mixture is acidified with either aqueous 2-6 N HCl or acetic acid. If a filterable suspension is obtained, the precipitate is collected by filtration, washed with water and dried in vacuo to afford the titled compound which is used as such or further purified either by preparative HPLC or flash chromatography on silica gel. In other cases, the mixture is partitioned between water and either dichloromethane or ethyl acetate. The two phases are separated, and the aqueous phase is optionally neutralized and then extracted either with dichloromethane or ethyl acetate. The combined organic phases are washed with brine, dried over MgSO₄, filtered and concentrated in vacuo to afford the titled compound which is used as such or further purified either by preparative HPLC or flash chromatography on silica gel.

Illustrative Synthesis of Intermediate A056: 4-(4-Cyano-3,4,5,6-tetrahydro-2H-[1,2']bipyridinyl-5'-yl)-3-cyclobutyl-1-phenyl-1H-pyrazolo[3,4-b]pyridine-6-carboxylic Acid

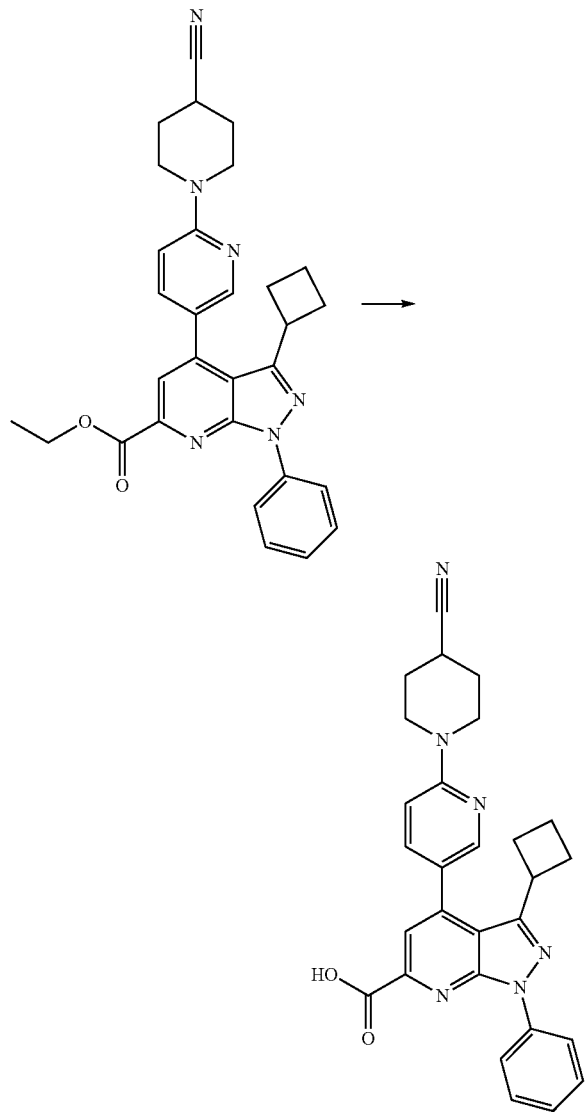

Intermediate E018 (30.7 g, 60.3 mmol) was dissolved in a mixture of THF/methanol (1/1; 1 L) and 2 N sodium hydroxide (109 mL, 218 mmol) in water was added at RT. The solution was stirred for 1 hour. The volatiles were removed under reduced pressure, and the resulting mixture was diluted with water (300 mL). The aqueous phase was acidified with aqueous 2 N HCl (110 mL), and the precipitate was filtered, washed with water and dried at 40° C. under reduced pressure to give the titled compound.

Illustrative Synthesis of Intermediate A285: 3-cyclobutyl-1-phenyl-4-{4-[(pyrrolidin-1-yl)methyl]piperidin-1-yl}-1H-pyrazolo[3,4-b]pyridine-6-carboxylic Acid

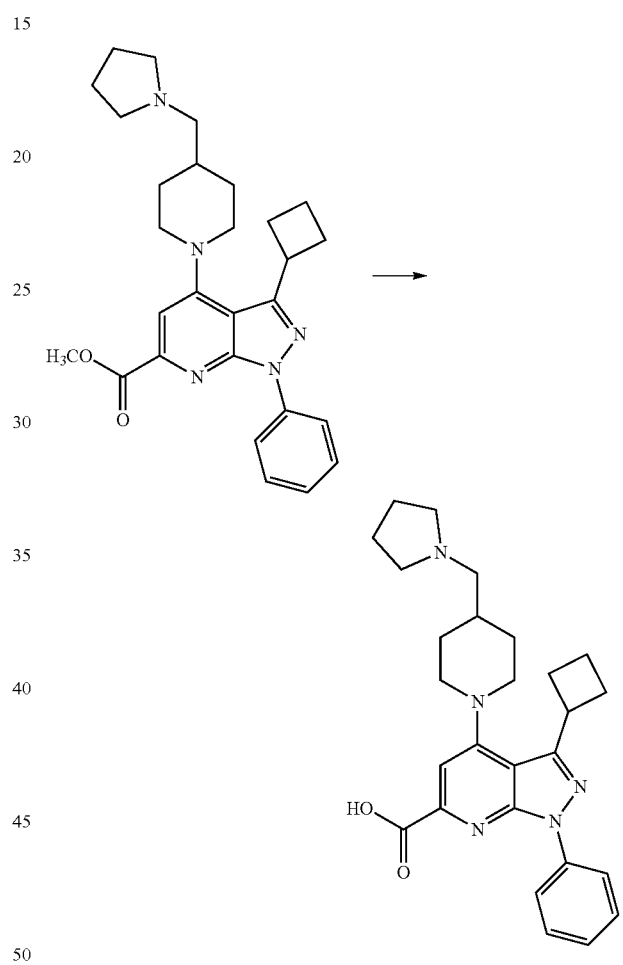

Methyl 3-cyclobutyl-1-phenyl-4-{4-[(pyrrolidin-1-yl)methyl]piperidin-1-yl})-1H-pyrazolo[3,4-b]pyridine-6-carboxylate (18.39 g, 38.8 mmol, E357) was dissolved in a mixture of tetrahydrofuran (100 mL), methanol (50 mL), and water (100 mL). To this mixture was added lithium hydroxide hydrate (4.89 g, 116 mmol). The resulting suspension was heated at 50° C. for 30 minutes. The reaction mixture was cooled to room temperature and neutralized with 6 M aqueous HCl (6 mL) to a pH of 7. To this was then added water in 10 mL portions. After a total of 200 mL of water had been added, a solid formed. The solid was collected by filtration and dried to constant weight in a vacuum oven at 50° C. over 72 hours to give 14.98 g of the titled compound. ¹H NMR (400 MHz, pyridine-d₅) δ ppm 8.89 (d, J=8.0 Hz, 2H), 7.84 (s, 1H), 7.52 (t, J=7.9 Hz, 2H), 7.25 (t, J=7.5 Hz, 1H), 4.14 (p, J=8.4 Hz, 1H), 3.56 (dd, J=12.2, 3.7 Hz, 2H), 2.86-2.67 (m, 4H), 2.63 (br s, 4H), 2.53-2.42 (m, 4H), 2.10-1.98 (m, 4H), 1.83-1.68 (m, 5H), 1.63-1.48 (m, 2H); MS (ESI+) m/z 460.2 (M+H)+.

Method J1A: Synthesis of Carboxylic Acids by Saponification of Ester

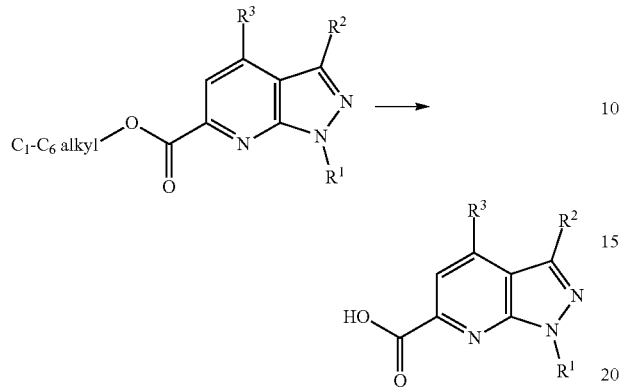

To the ester intermediate (1 equiv) in THF or ethanol or methanol or a mixture of the cited solvents at RT is added either aqueous 1 N or 2 N sodium hydroxide 1 (from 1 to 10 equiv). The reaction mixture is stirred at RT until complete conversion is observed. Sodium hydroxide can be added to allow the full conversion of the starting ester. The volatiles are removed under reduced pressure, and the resulting mixture is acidified with either aqueous 1 N or 2 N HCl. If a filterable suspension is obtained, the precipitate is collected by filtration, washed with water and dried in vacuo to afford the titled compound which is used as such or further purified either by preparative HPLC or flash chromatography on silica gel. In other cases, the mixture is partitioned between a phosphate buffer (pH 6.2) and either dichloromethane or chloroform or a mixture of dichloromethane/isopropanol. The organic phases are separated, dried over MgSO4, filtered and concentrated in vacuo to afford the titled compound which is used as such or further purified either by preparative HPLC or flash chromatography on silica gel.

Illustrative Synthesis of A318a: 3-cyclobutyl-1-(3-methylphenyl)-4-[4-(morpholin-4-yl)piperidin-1-yl]-1H-pyrazolo[3,4-b]pyridine-6-carboxylic Acid

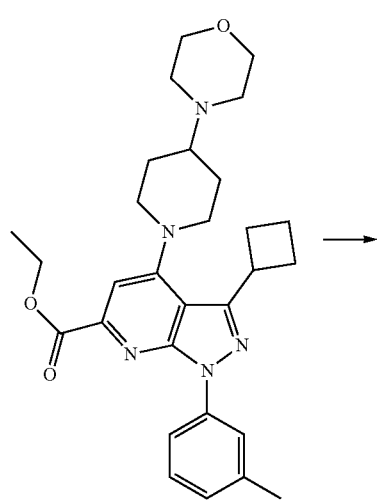

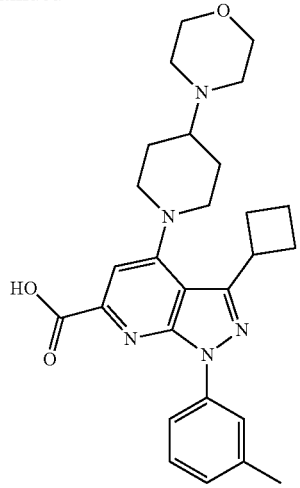

Ester E395 (40 mg, 80 µmol) was dissolved in a mixture of THF/ethanol (1/1; 6 mL) and 1 N sodium hydroxide (0.5 mL, 500 µmol) in water was added at RT. The solution was stirred for 4 hours. Aqueous 1 N HCl (0.5 mL, 500 µmol) and a phosphate buffer were added (pH 6.2). The solvent was partially removed under reduced pressure, and the resulting mixture was extracted twice with chloroform. The combined organic phases were dried over magnesium sulfate, filtered and evaporated under reduced pressure to give the titled compound.

Method J2: Synthesis of Acids

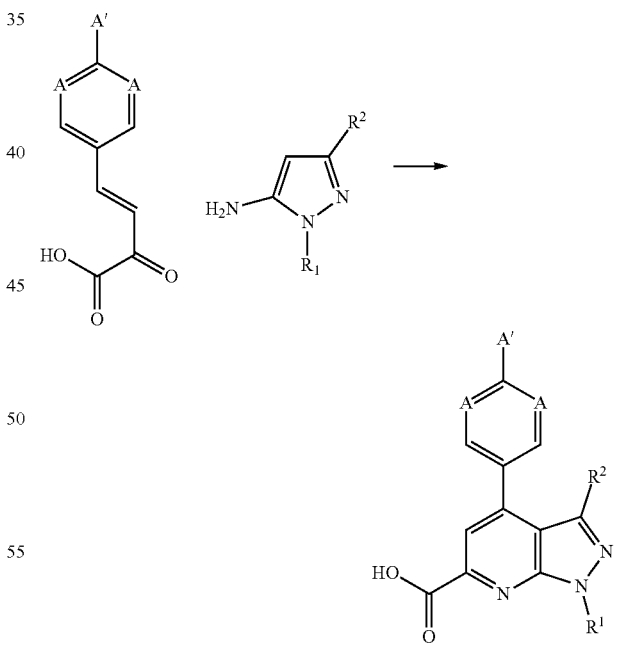

A is either N or CH
A' is either $R^e$ or $L^1$-$G^{3C}$ as described in the Summary The alkylidene pyruvate (1 to 1.5 equiv) and the aminopyrazole (1 to 1.5 equiv) in acetic acid are stirred under air at temperatures ranging from RT to reflux for 1 h to several days. Alternatively, the alkylidene pyruvate (1 to 1.5 equiv) and the aminopyrazole (1 to 1.5 equiv) in DMF or acetic acid are heated under microwave irradiation at 150° C. for 20 minutes to 2 h followed by stirring under air in an opened flask at temperatures ranging from RT to 90° C. for 1 h to several days with or without dilution of the reaction mixture with a large amount of ethanol or methanol. Then the reaction mixture is filtered, and the solid is washed with solvents, and dried in vacuo to afford the titled compound which is used as such or purified by precipitation, by preparative HPLC or by flash chromatography on silica gel. Alternatively, the reaction mixture is concentrated in vacuo to afford a crude mixture which is used as such or further purified either by precipitation, by preparative HPLC or by flash chromatography on silica gel.

Illustrative Synthesis of Intermediate A002: 3-methyl-4-(4-morpholinophenyl)-1-phenyl-pyrazolo[3,4-b]pyridine-6-carboxylic Acid

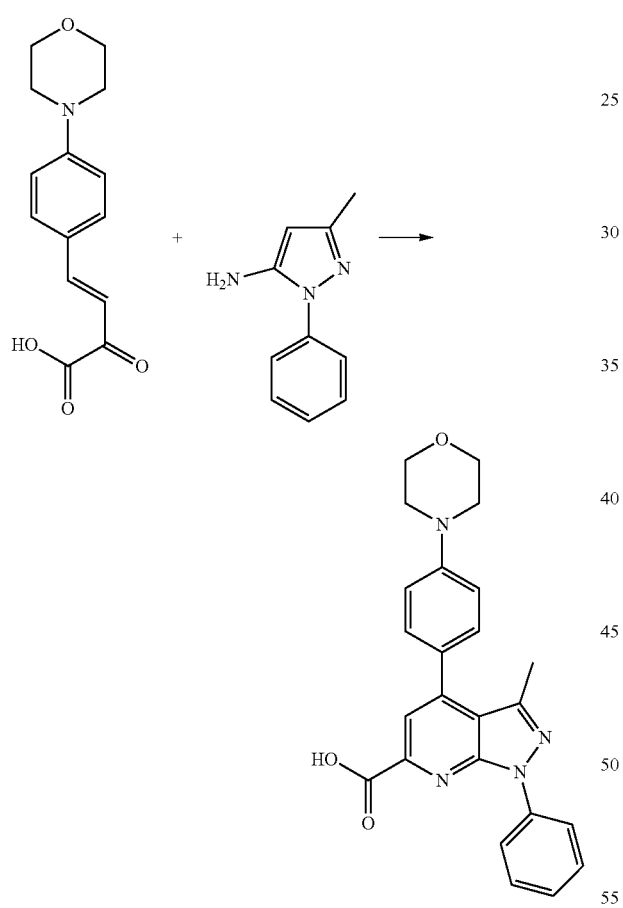

ALP01 (261 mg, 1 mmol, 1 equiv) and 3-methyl-1-phenyl-1H-pyrazol-5-amine (CAS 1131-18-6, 173 mg, 1 mmol, 1 equiv) were introduced in a sealed tube. DMF (2 mL) was added, and the vial was sealed. The reaction mixture was heated under microwave irradiation at 150° C. for 1 h. Then after cooling down to RT, the vial was opened, diluted with a large amount of ethanol, and stirred vigorously under air at RT overnight. The resulting suspension was filtered. The solid was washed with ethanol, and dried in vacuo to afford the titled compound.

Method J3: Nucleophilic Substitution on the Central Core with Alcohols

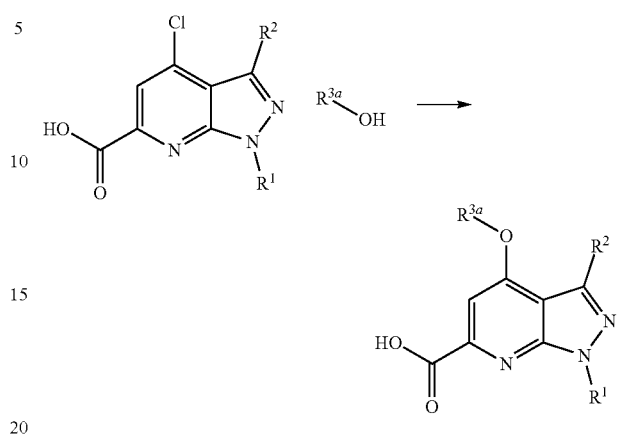

To a solution of alcohol (3.0 equiv) in anhydrous THF under nitrogen atmosphere at RT is added 60% sodium hydride in mineral oil (6.0 equiv), and the mixture is stirred at room temperature for 30 minutes. Then the aryl chloride intermediate HP (1.0 equiv) is added, the reaction mixture is stirred at room temperature for 5 minutes, and then heated at reflux for 1 h to 24 h. The reaction mixture is cooled to 0° C., diluted with heptane, quenched with water and acidified with 2 N HCl (6.0 equiv). Volatiles are removed in vacuo. The resulting aqueous residue is filtered, and the solid is washed with water and with a mixture heptane/Et$_2$O 1/1, and dried in vacuo to afford the titled compound which is used as such or purified by silica gel chromatography. Alternatively, the aqueous residue is diluted with dichloromethane. The two phases are separated and the aqueous phase is extracted with dichloromethane. The combined organic phases are washed with brine, dried over MgSO$_4$, filtered and concentrated in vacuo to afford the titled compound which is used as such or purified by silica gel chromatography.

Alternatively, to a solution of alcohol (2.0 equiv) in anhydrous DMF is added 1 M potassium tert-butoxide (3-4 equiv), and the mixture is stirred at room temperature for several minutes. Then the aryl chloride intermediate HP (1.0 equiv) is added, and then the reaction mixture is heated at 40-60° C. for 1 h to 24 h. After cooling to ambient temperature, the product can be precipitated from an appropriate solvent or purified chromatographically.

Illustrative Synthesis of Intermediate A148: 3-cyclobutyl-1-phenyl-4-(tetrahydropyran-4-ylmethoxy)pyrazolo[3,4-b]pyridine-6-carboxylic Acid

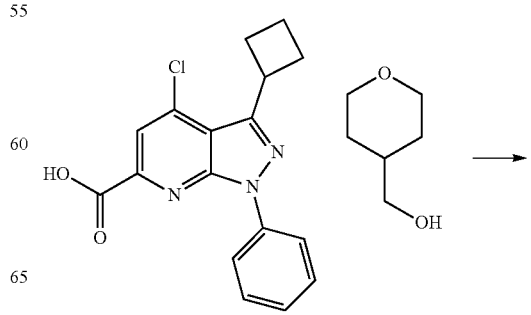

525
-continued

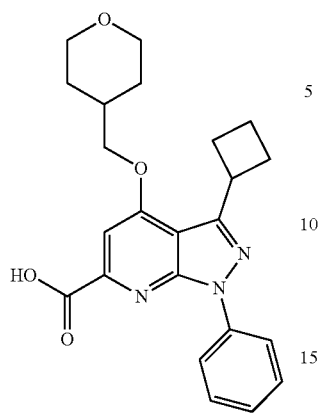

To a solution of tetrahydropyran-4-ylmethanol (CAS: 14774-37-9, 54 mg, 0.457 mmol, 3.0 equiv) in anhydrous THF (1 mL) under nitrogen atmosphere was added 60% sodium hydride in mineral oil (37 mg, 0.915 mmol, 6.0 equiv), and the mixture was stirred at room temperature for 30 minutes. HP10 (50 mg, 0.152 mmol, 1.0 equiv) was added; the reaction mixture was stirred at room temperature for 5 minutes and then heated at reflux for 3 hours. The reaction mixture was cooled to 0° C., diluted with heptane (1 mL), quenched with water (1 mL) and acidified with 2 N HCl (0.46 mL, 6.0 equiv). Volatiles were removed in vacuo. The resulting aqueous suspension was diluted with a mixture heptane/Et$_2$O: 1/1 (1 mL) and filtered. The solid was washed with water and with a mixture heptane/Et$_2$O 1/1 and dried in vacuo. The crude solid was purified by silica gel chromatography (eluent system: DCM/(DCM/MeOH/AcOH/H$_2$O: 90/10/1/1) gradient from 100/0 to 90/10) to give the titled compound.

Illustrative Synthesis of Intermediate A173: 3-cyclobutyl-4-(3-morpholinopropoxy)-1-phenyl-pyrazolo[3,4-b]pyridine-6-carboxylic Acid

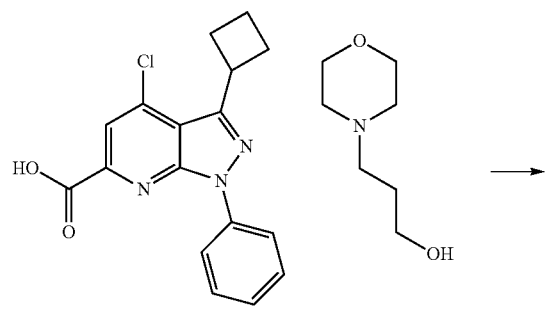

526
-continued

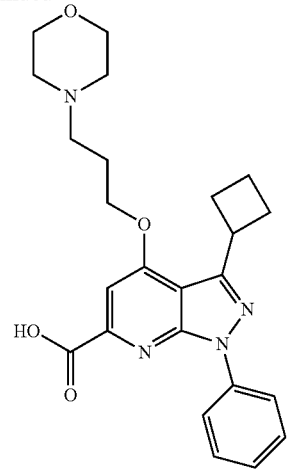

3-Morpholinopropan-1-ol (73 mg, 0.50 mmol) was dissolved into anhydrous DMF (830 µL), treated with 1 M KOtBu in THF (830 µL, 0.83 mmol), stirred three minutes, treated further with intermediate HP10 (82 mg, 0.25 mmol), and heated at 50° C. for about an hour. More DMF (570 µL) was added and heating was continued overnight. The mixture was brought to room temperature, diluted with MeCN and filtered with a MeCN rinse. The collected solids were mixed with acetic acid into DMSO, and diluted with water to precipitate solids which were collected by filtration, rinsed with water and dried under vacuum to give the titled compound (65 mg). $^1$H NMR (400 MHz, DMSO-d$_6$) δ ppm 8.38-8.28 (m, 2H), 7.61-7.52 (m, 2H), 7.41 (s, 1H), 7.36-7.29 (m, 1H), 4.43-4.34 (m, 2H), 4.08-3.98 (m, 1H), 3.62-3.58 (m, 4H), 2.57-2.35 (m, 10H), 2.15-1.89 (m, 4H).

Method J4: Buchwald Coupling on the Central Core

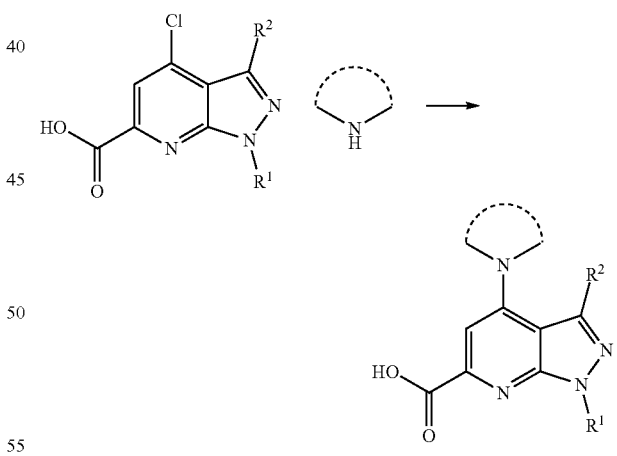

To a degassed solution of the aryl chloride intermediate HP (1.0 equiv) and the amine as free base or hydrochloride salt (1.5 equiv) in anhydrous THF at RT under nitrogen atmosphere in a sealed vial is added XPhos Pd G1 (CAS 1028206-56-5, 0.1 equiv) followed by 1 N LiHMDS in THF (from 3 to 5 equiv). The reaction mixture is purged with nitrogen and the vial is sealed. The reaction mixture is stirred at 100° C. for 1 h to 24 h. Then the reaction mixture is cooled down and volatiles are removed in vacuo. The resulting residue is taken up in dichloromethane and water and acidified with acetic acid. The two phases are separated and Illustrative Synthesis of Intermediate A216: 3-cyclobutyl-4-[4-(fluoromethyl)-1-piperidyl]-1-phenyl-pyrazolo[3,4-b]pyridine-6-carboxylic Acid

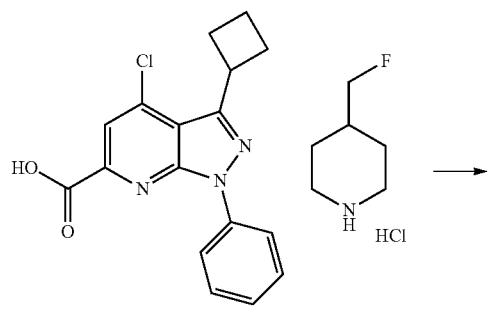

To a degassed solution of HP10 (64 mg, 0.194 mmol, 1.0 equiv) and 4-(fluoromethyl)piperidine hydrochloride (CAS 259143-04-9, 45 mg, 0.292 mmol, 1.5 equiv) in anhydrous THF (2 mL) at RT under nitrogen atmosphere in a sealed vial was added XPhos Pd G1 (CAS 1028206-56-5, 14 mg, 0.019 mmol, 0.1 equiv) followed by 1 N LiHMDS in THF (0.97 mL, 0.97 mmol, 5.0 equiv). The reaction mixture was purged with nitrogen, and the vial was sealed. The reaction mixture was stirred at 100° C. overnight. Then the reaction mixture was cooled down and volatiles were removed in vacuo. The resulting residue was taken up in dichloromethane and water and acidified with acetic acid. The two phases were separated, and the aqueous phase was extracted with dichloromethane. The combined organic layers were washed with brine, dried over MgSO$_4$, filtered and concentrated in vacuo. The resulting residue was purified by flash chromatography on silica gel (eluent system: dichloromethane/methanol gradient from 100/0 to 95/5) to afford the titled compound.

Method J5: Buchwald Coupling on the Aryl Linker

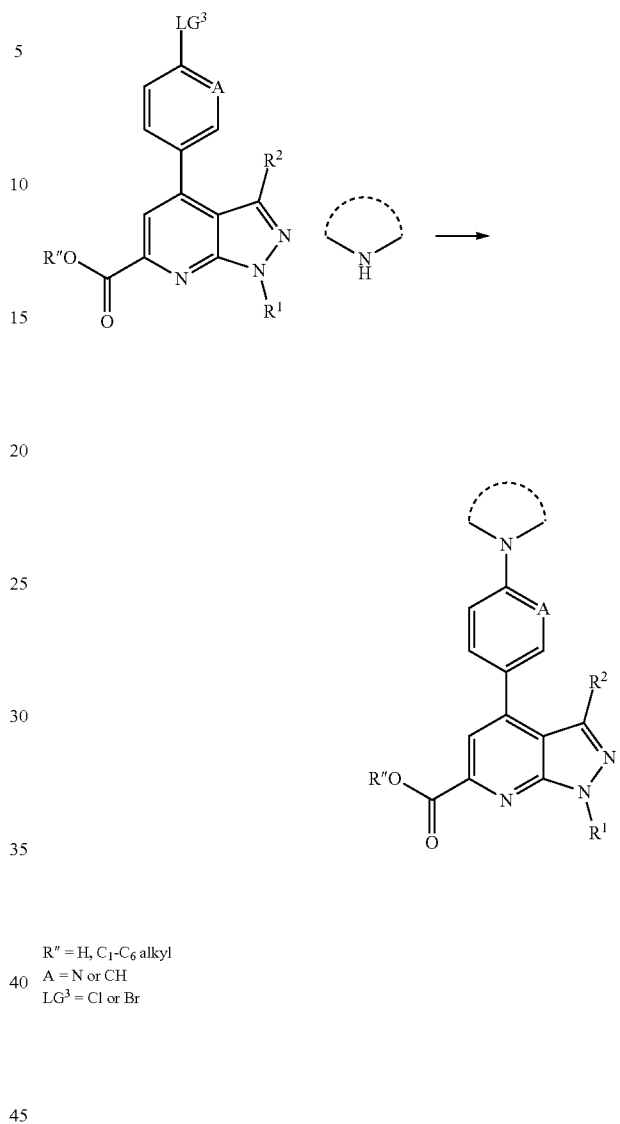

R″ = H, C$_1$-C$_6$ alkyl
A = N or CH
LG$^3$ = Cl or Br

To a degassed solution of pyridyl chloride (1.0 equiv) and amine (1.5 equiv) in anhydrous THF at RT under nitrogen atmosphere is added 1 N LiHMDS in THF (from 3 to 4.5 equiv) followed by XPhos Pd G1 (CAS 1028206-56-5, 0.1 equiv). The reaction mixture is stirred at room temperature for 1 h to 24 h. The mixture is quenched with acetic acid and diluted with water and dichloromethane. The organic layer is separated, washed with water and brine, dried over MgSO$_4$, filtered and concentrated in vacuo to afford the titled compound which is used as such or further purified by preparative HPLC or by flash chromatography on silica gel. The cross-coupling reaction can be performed on either a carboxylic acid or ester. In some instances, an ester starting material is concomitantly hydrolyzed to the corresponding carboxylic acid product under the reaction conditions.

529

Illustrative Synthesis of Intermediate A065: 1-cyclohexyl-4-[6-(2,6-dimethylmorpholin-4-yl)-3-pyridyl]-3-isopropyl-pyrazolo[3,4-b]pyridine-6-carboxylic Acid

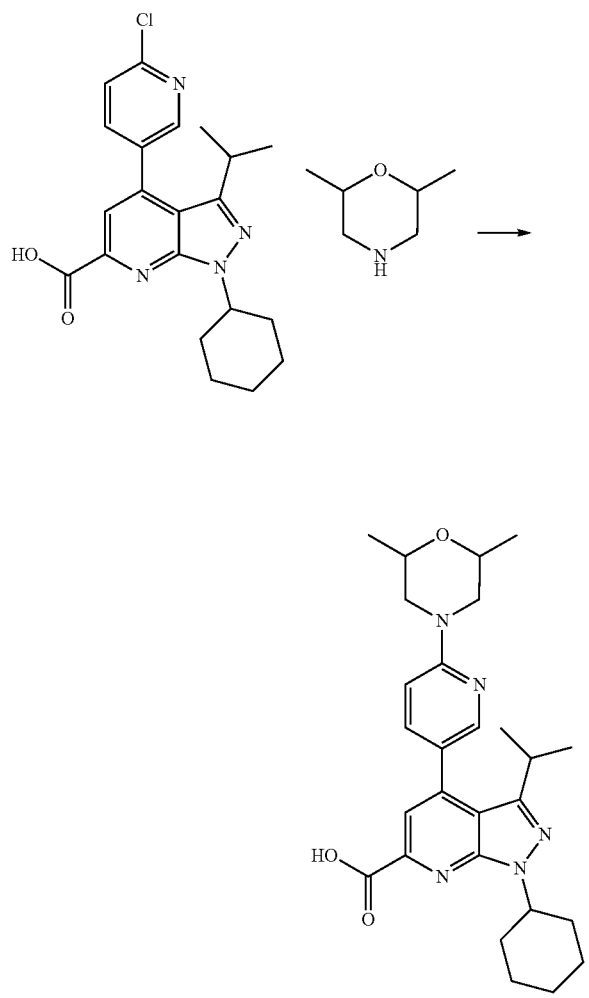

To a degassed solution of A250 (75 mg, 0.188 mmol, 1.0 equiv) and 2,6-dimethylmorpholine (CAS 141-91-3, 32 µL, 0.26 mmol, 1.5 equiv) in anhydrous THF (0.7 mL) at RT under nitrogen atmosphere was added 1 N LiHMDS in THF (765 µL, 0.765 mmol, 4.5 equiv) followed by XPhos Pd G1 (CAS 1028206-56-5, 12.5 mg, 0.017 mmol, 0.1 equiv). The reaction mixture was stirred at room temperature for 1 h. The mixture was quenched with AcOH and diluted with water and dichloromethane. The organic layer was separated, washed with water and brine, dried over MgSO₄, filtered and concentrated in vacuo. The resulting residue was purified by silica gel chromatography (eluent system: dichloromethane/methanol, gradient from 100/0 to 95/5) to afford the titled compound.

530

Method J6: Nucleophilic Substitution on the $R^1$ Part

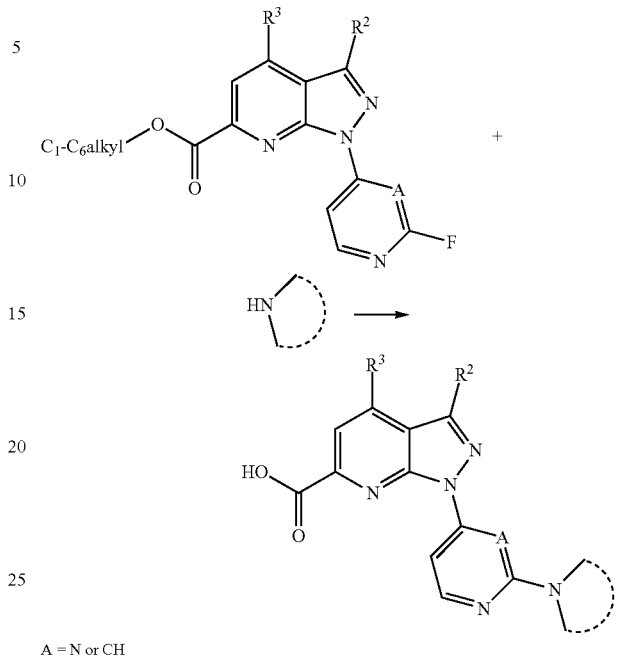

A = N or CH

To the intermediate fluoropyridine (1.0 equiv) in anhydrous DMSO is added the amine (from 2.0 to 10.0 equiv) and K₂CO₃ (from 3.0 to 10 equiv). The reaction mixture is stirred at 100° C. overnight. If the reaction is not complete, additional amine (from 2.0 to 10 equiv) and K₂CO₃ (from 0 to 10 equiv) are added, and the reaction mixture is stirred at 100° C. until the reaction is finished. Then the reaction mixture is cooled down to RT, diluted with water and extracted with ethyl acetate. The combined organic layers are washed with brine, dried over MgSO₄, filtered and concentrated in vacuo to afford the titled compound which is used as such or purified by flash chromatography on silica gel.

Illustrative Synthesis of Intermediate A179: 3-isopropyl-4-[4-(methoxymethyl)-1-piperidyl]-1-(2-morpholino-4-pyridyl)pyrazolo[3,4-b]pyridine-6-carboxylic Acid

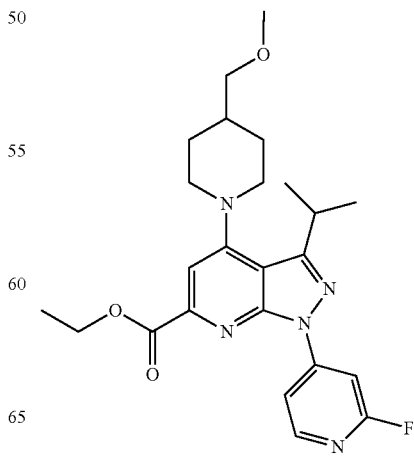

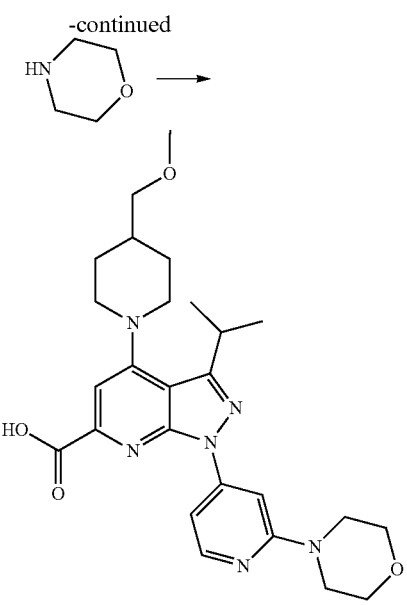

To E147 (144 mg, 0.32 mmol, 1.0 equiv) in anhydrous DMSO (1.5 mL) was added morpholine (56 µL, 0.64 mmol, 2.0 equiv) and $K_2CO_3$ (133 mg, 0.96 mmol, 3.0 equiv). The reaction mixture was stirred at 100° C. overnight. Additional morpholine (56 µL, 0.64 mmol, 2.0 equiv) and $K_2CO_3$ (133 mg, 0.96 mmol, 3.0 equiv) were added, and the reaction mixture was stirred at 100° C. for 24 h. Then additional morpholine (56 µL, 0.64 mmol, 2.0 equiv) was added again, and the reaction mixture was stirred at 100° C. for 5 days. Then the reaction mixture was cooled down to RT, diluted with water and extracted with ethyl acetate. The combined organic layers were washed with brine, dried over $MgSO_4$, filtered and concentrated in vacuo. The resulting residue was purified by silica gel chromatography (eluent system: dichloromethane/methanol, gradient 100/0 to 95/5 with 0.1% AcOH) to afford the titled compound.

Method J7: Buchwald Coupling on the Phenyl or Heteroaryl Halogen

To a degassed solution of the aromatic bromide intermediate (1.0 equiv) and the amine as free base or hydrochloride salt (from 1.5 to 2 equiv) in anhydrous THF at RT under nitrogen atmosphere in a sealed vial is added XPhos Pd G1 (CAS 1028206-56-5, 0.1 equiv) followed by 1 N LiHMDS in THF (from 3 to 5 equiv). The reaction mixture is purged with nitrogen, and the vial is sealed. The reaction mixture is stirred at a temperature ranging from RT to 100° C. for 1 h to 3 h. If the reaction is not complete, additional amine (from 1.0 to 3.0 equiv), LiHMDS (from 1.5 to 6.0 equiv) and XPhos Pd G1 (CAS 1028206-56-5, from 0.05 to 0.2 equiv) are added at RT. The reaction mixture is purged again with nitrogen and the vial is sealed. The reaction mixture is stirred at a temperature ranging from RT to 100° C. for 1 h to 3 h. Then the reaction mixture is cooled down and volatiles are removed in vacuo. The resulting residue is taken up in dichloromethane and water and acidified with acetic acid. The two phases are separated, and the aqueous phase is extracted with dichloromethane. The combined organic layers are washed with brine, dried over $MgSO_4$, filtered and concentrated in vacuo. The resulting residue is purified by flash chromatography on silica gel to afford the titled compound.

Illustrative Synthesis of Intermediate A212: 3-isopropyl-4-(4-methoxy-1-piperidyl)-1-(2-morpholino-4-pyridyl)pyrazolo[3,4-b]pyridine-6-carboxylic Acid

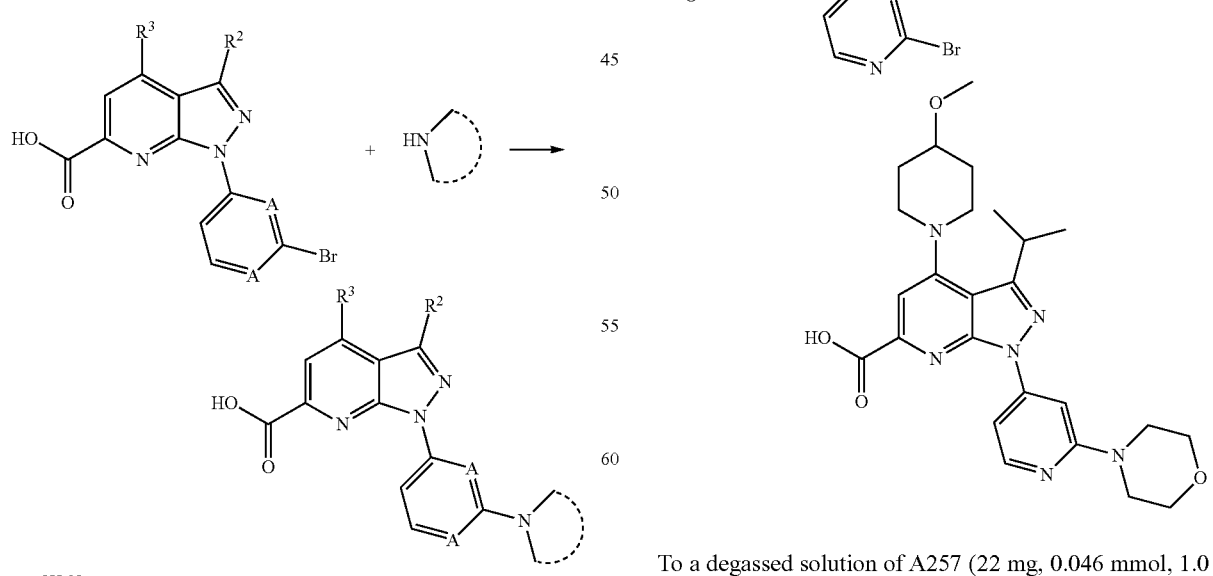

To a degassed solution of A257 (22 mg, 0.046 mmol, 1.0 equiv) and morpholine (6 µL, 0.069 mmol, 1.5 equiv) in anhydrous THF (1 mL) at RT under nitrogen atmosphere in a sealed vial was added XPhos Pd G1 (CAS 1028206-56-5, 3 mg, 0.0046 mmol, 0.1 equiv) followed by 1 N LiHMDS in THF (138 μL, 0.138 mmol, 3.0 equiv). The reaction mixture was purged with nitrogen, and the vial was sealed. The reaction mixture was stirred at 100° C. for 1.5 h. Additional morpholine (12 μL, 0.138 mmol, 3.0 equiv), 1 N LiHMDS in THF (276 μL, 0.276 mmol, 6.0 equiv) and XPhos Pd G1 (CAS 1028206-56-5, 6 mg, 0.0092 mmol, 0.2 equiv) were added at RT. The reaction mixture was purged again with nitrogen, and the vial was sealed. The reaction mixture was stirred at 100° C. for 1 h. Then the reaction mixture was cooled down and volatiles were removed in vacuo. The resulting residue was taken up in dichloromethane and water and acidified with acetic acid. The two phases were separated, and the aqueous phase was extracted with dichloromethane. The combined organic layers were washed with brine, dried over MgSO₄, filtered and concentrated in vacuo. The resulting residue was purified by flash chromatography on silica gel (eluent system dichloromethane/methanol gradient from 100/0 to 90/10 with 0.1% AcOH) to afford the titled compound.

Method J8: Tandem Methylation and Saponification

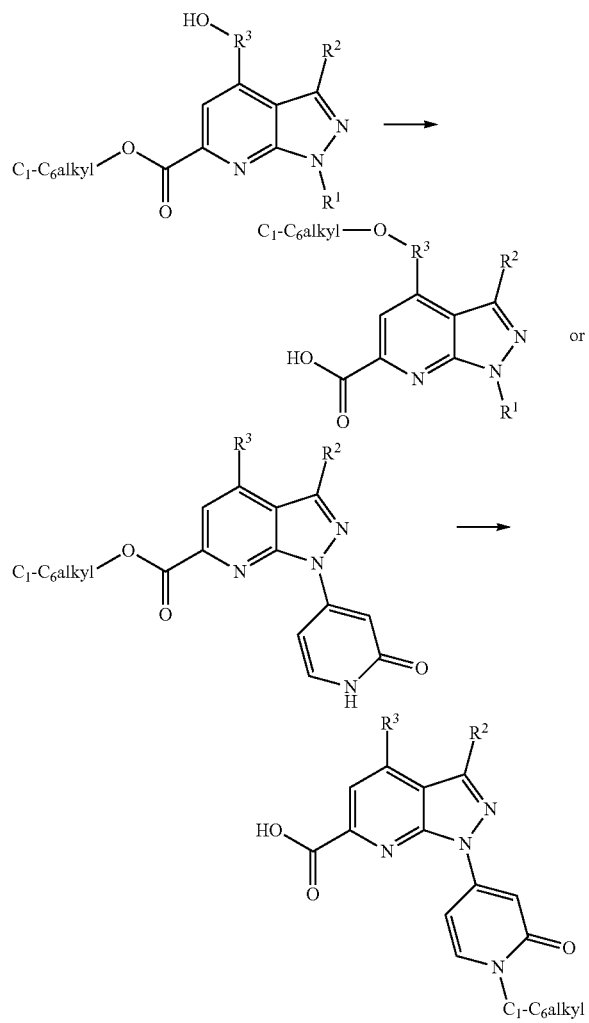

60% NaH in mineral oil (6.0 equiv) is added to a solution of an ester/alcohol or a 2-oxo-1,2-dihydropyridin-4-yl/ester (1 equiv) in THF. The reaction mixture is stirred at RT for 5 minutes, and a C₁-C₆ alkyl halide (6.0 equiv) was added. The reaction mixture was stirred at RT for 1-24 hours and then concentrated. The residue was purified by silica gel chromatography to give the ether/carboxylic acid or the 1-methyl-2-oxo-1,2-dihydropyridin-4-yl/carboxylic acid.

Illustrative Synthesis of Intermediate A62: 1-cyclohexyl-3-isopropyl-4-[4-(methoxymethyl)-1-piperidyl]pyrazolo[3,4-b]pyridine-6-carboxylic Acid

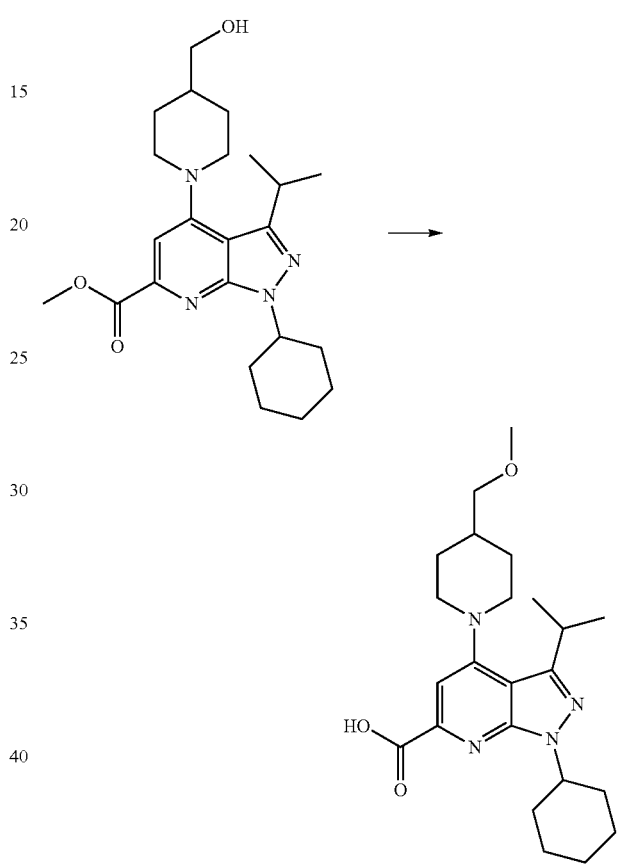

60% NaH in mineral oil (24 mg, 0.60 mmol, 6.0 equiv) was added to a solution of E134 (42 mg, 0.10 mmol) in THF (1 mL). The reaction mixture was stirred at RT for 5 minutes, and methyl iodide (0.037 mL, 0.60 mmol, 6.0 equiv) was added. The reaction mixture was stirred at RT for 16 hours and then concentrated. The residue was purified by silica gel chromatography (DCM/MeOH: 100/0 to 90/10) to give the titled compound.

Method J9: Amide or Carbamate Formation from an Amine

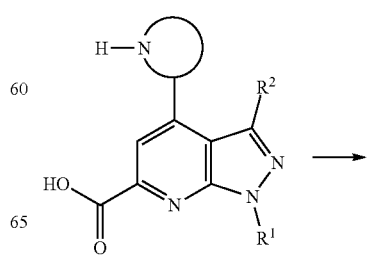

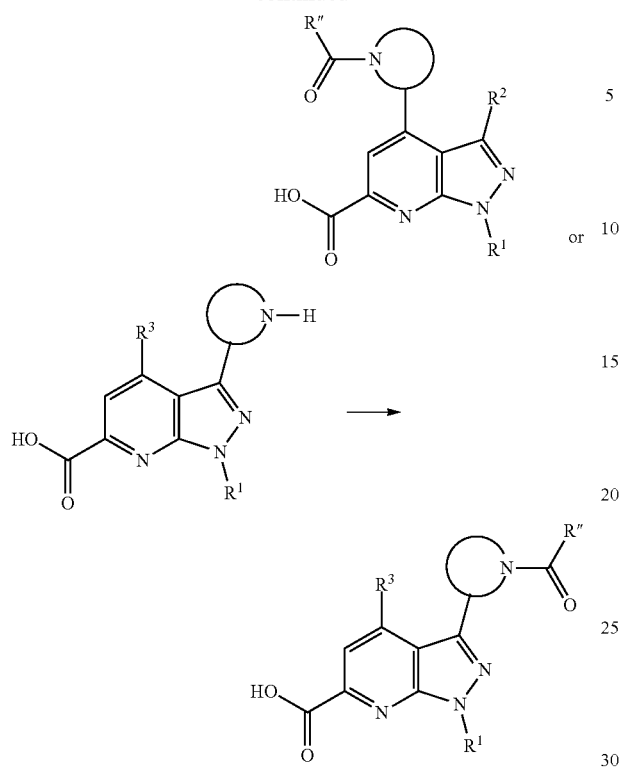

R'' = C₁-C₆ alkyl or O-C₁-C₆ alkyl

A heterocyclic amine at either the $R^2$ or $R^3$ positions can be reacted with an acid chloride or chloroformate dissolved is solvents such as dichloromethane, tetrahydrofuran or DMF at 0° C. to ambient temperature over 0.5-4 hours in the presence a tertiary amine base or an inorganic carbonate base. The reaction mixture is extractively worked up and/or purified chromatographically either by flash chromatography or by preparative HPLC.

Illustrative Synthesis of Intermediate A225: 4-[(1-acetyl-4-piperidyl)methoxy]-3-cyclobutyl-1-phenyl-pyrazolo[3,4-b]pyridine-6-carboxylic Acid To A261 as a trifluoroacetic acid salt (0.43 g, 0.83 mmol, 1 equiv) in anhydrous dichloromethane (10 mL) at 0° C. was added triethyl amine (0.69 mL, 4.98 mmol, 6 equiv) followed by acetyl chloride (CAS 75-36-5, 119 µL, 1.66 mmol, 2 equiv). The reaction mixture was stirred at RT for 1 h. The reaction mixture was diluted with dichloromethane and water. The two phases were separated, and the aqueous phase was extracted with dichloromethane. The combined organic phases were washed with brine, dried over MgSO₄, filtered and concentrated in vacuo. The resulting residue was purified by flash chromatography on silica gel (eluent system: dichloromethane/methanol gradient from 100/0 to 95/5) to afford the titled compound.

Illustrative Synthesis of Intermediate A237: 3-cyclobutyl-4-[(1-methoxycarbonyl-4-piperidyl)methoxy]-1-phenyl-pyrazolo[3,4-b]pyridine-6-carboxylic Acid

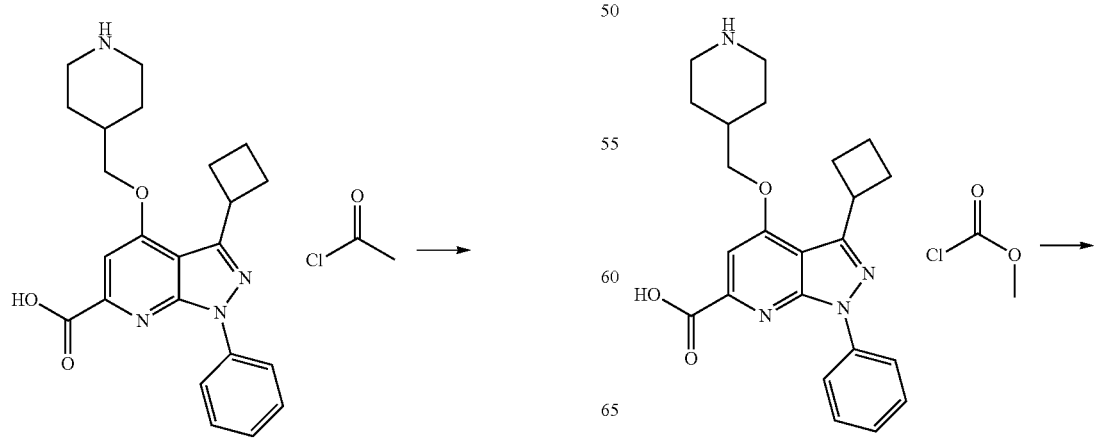

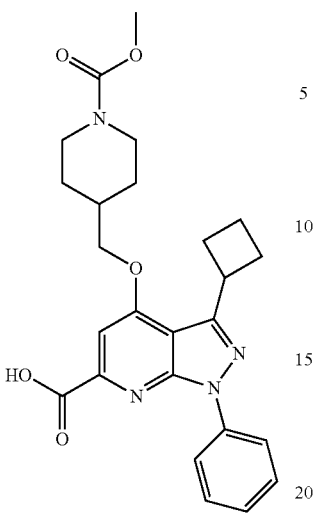

To A261 as a trifluoroacetic acid salt (0.43 g, 0.83 mmol, 1 equiv) in anhydrous dichloromethane (10 mL) at 0° C. was added triethylamine (0.69 mL, 4.98 mmol, 6 equiv) followed by methyl chloroformate (CAS: 79-22-1, 128 µL, 1.66 mmol, 2 equiv). The reaction mixture was stirred at RT for 1 h. The reaction mixture was diluted with dichloromethane and water. The two phases were separated, and the aqueous phase was extracted with dichloromethane. The combined organic phases were washed with brine, dried over MgSO$_4$, filtered and concentrated in vacuo. The resulting residue was taken up in a mixture of THF (1.5 mL), methanol (1.5 mL) and aqueous 2 M sodium hydroxide (0.17 mL) and stirred at RT for 1.5 h. The mixture was concentrated in vacuo. The residue was diluted with ethyl acetate and water and acidified with 1 M HCl (0.34 mL). The two phases were separated, and the aqueous phase was extracted with ethyl acetate. The combined organic phases were washed with brine, dried over MgSO$_4$, filtered and concentrated in vacuo to afford the titled compound which was used as such.

Illustrative Synthesis of Intermediate A249: 1-cyclohexyl-4-[2-(dimethylamino)pyrimidin-5-yl]-3-(1-methoxycarbonylazetidin-3-yl)pyrazolo[3,4-b]pyridine-6-carboxylic Acid

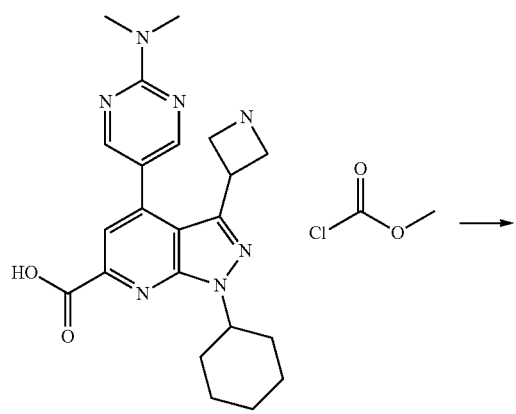

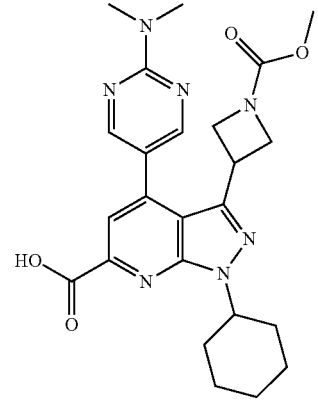

Diisopropylethylamine (0.55 mL, 3.12 mmol, 6.0 equiv) and DMAP (13 mg, 0.104 mmol, 0.2 equiv) were added to a solution of A248 (220 mg, 0.52 mmol, 1 equiv) in dichloromethane (2 mL). The mixture was cooled to 0° C. and methyl chloroformate (CAS: 79-22-1, 81 µL, 0.104 mmol, 2.0 equiv) was added. The reaction mixture was warmed up to RT and stirred for 1.5 h. The reaction mixture was partitioned between dichloromethane and water. The two phases were separated, and the aqueous phase was extracted with dichloromethane. The combined organic phase were dried over MgSO$_4$, filtered and concentrated in vacuo. The residue was purified by preparative HPLC to afford the titled compound.

Method J10: Nucleophilic Substitution on the Central Core with Amines

LG = Cl, OTf

A mixture of the chloride or triflate intermediate HP (1.0 equiv), the amine as free base or hydrochloride salt (from 1 to 10 equiv) and DIPEA (from 1 to 15 equiv) in anhydrous acetonitrile and DMSO or N,N-dimethylacetamide in a sealed tube or a round bottom flask is heated at a temperature ranging from 50 to 130° C. for 1 h to several days (up to 8 days). The reaction mixture is cooled to RT. The resulting residue is either purified by precipitation or by flash chromatography on silica gel to afford the titled compound or alternatively partitioned between either dichloromethane or ethyl acetate and water. The two phases are then separated, and the aqueous phase is extracted with either ethyl acetate or dichloromethane. The combined organic phases are dried, filtered and concentrated in vacuo, and the resulting crude mixture is either used as such or purified by flash chromatography on silica gel to afford the titled compound.

Alternatively, a mixture of the chloride or triflate intermediate HP (1.0 equiv), the amine as free base or hydrochloride salt (from 1 to 10 equiv) and triethylamine (from 1 to 15 equiv) in N,N-dimethylacetamide is heated with microwave irradiation at a temperature ranging from 130 to 150° C. for 5 to 20 min. DBU (1 equiv) was added, and the reaction mixture is again heated with microwave irradiation for 1 to 4 hours at 130 to 150° C. Upon cooling, solids are collected and then precipitated from a solvent such as acetonitrile.

Illustrative Synthesis of Intermediate A081: 3-cyclobutyl-1-phenyl-4-[4-(1-piperidyl)-1-piperidyl]pyrazolo[3,4-b]pyridine-6-carboxylic Acid

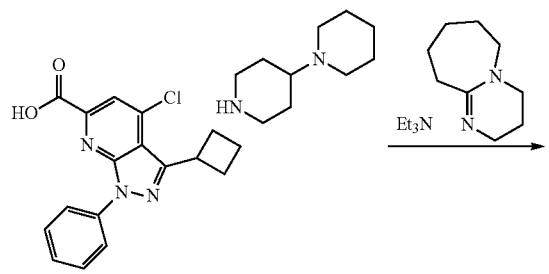

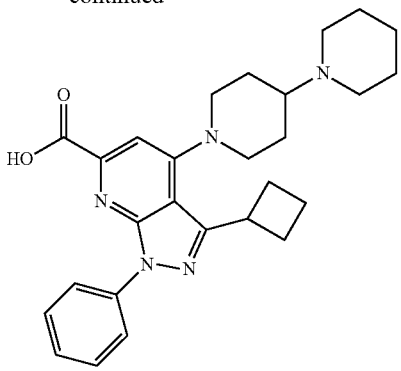

A suspension of intermediate HP10 (328 mg, 1.0 mmol), 1,4'-bipiperidine (253 mg, 1.50 mmol) and triethylamine (350 µL, 2.5 mmol) in anhydrous DMA (800 µL) was heated in a Biotage® Initiator microwave synthesizer at 150° C. for fifteen minutes. DBU (180 µL, 1.2 mmol) was added, and the reaction mixture was heated with microwave irradiation at 150° C. for one hour and 45 minutes, brought to room temperature, diluted with water (8 mL) and washed with 1:2 EtOAc/MTBE. The aqueous phase was acidified with 3 M aqueous citric acid (400 µL) to precipitate the product, which was collected by filtration, washed with water and dried under vacuum to give the titled compound (423 mg). $^1$H NMR (400 MHz, DMSO-$d_6$, 120° C.) δ ppm 8.32 (d, J=8.1 Hz, 2H), 7.54-7.48 (m, 2H), 7.32-7.26 (m, 2H), 4.02 (p, J=8.1 Hz, 1H), 3.63-3.58 (m, 2H), 3.00-2.91 (m, 2H), 2.63-2.57 (m, 4H), 2.56-2.41 (m, 5H), 2.16-1.91 (m, 4H), 1.82-1.69 (m, 2H), 1.60-1.51 (m, 4H), 1.48-1.39 (m, 2H).

Illustrative Synthesis of Intermediate A268: 3-cyclobutyl-4-(4-morpholino-1-piperidyl)-1-phenylpyrazolo[3,4-b]pyridine-6-carboxylic Acid

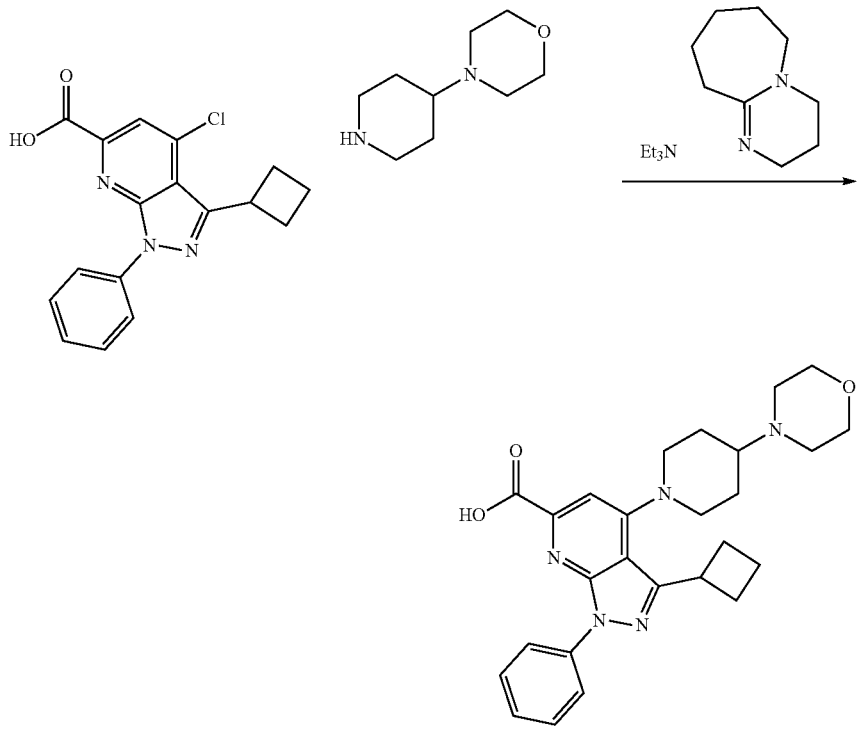

A suspension of intermediate HP10 (230 mg, 0.70 mmol), 4-(piperidin-4-yl)morpholine (177 mg, 1.05 mmol) and triethylamine (245 µL, 1.76 mmol) in anhydrous DMA (600 µL) was heated in a Biotage® Initiator microwave synthesizer at 140° C. for five minutes. DBU (105 µL, 0.70 mmol) was added, and the reaction mixture was heated with microwave irradiation at 140° C. for three hours, brought to room temperature and filtered through a C18 column (MeOH/H$_2$O). The filtrate was concentrated, and the residual solids were washed with EtOAc, boiled in MeCN and allowed to cool to room temperature. The solid was collected by filtration, rinsed with acetonitrile and dried under vacuum to give the titled compound (305 mg). $^1$H NMR (400 MHz, DMSO-d$_6$, 90° C.) δ ppm 8.34-8.30 (m, 2H), 7.54-7.48 (m, 2H), 7.30-7.25 (m, 2H), 4.00 (p, J=8.1 Hz, 1H), 3.62-3.58 (m, 4H), 3.56-3.53 (m, 2H), 2.97-2.89 (m, 1H), 2.76-2.68 (m, 1H), 2.56-2.51 (m, 4H), 2.45-2.41 (m, 3H), 2.11-1.94 (m, 4H), 1.85-1.77 (m, 1H), 1.74-1.63 (m, 2H), 1.55-1.44 (m, 1H).

Illustrative Synthesis of Intermediate A270: 3-cyclobutyl-4-[4-(2-morpholinoethyl)-1-piperidyl]-1-phenyl-pyrazolo[3,4-b]pyridine-6-carboxylic Acid Illustrative Synthesis of Intermediate A284: 3-cyclobutyl-4-[(3R)-3-(hydroxymethyl)-1-piperidyl]-1-phenyl-pyrazolo[3,4-b]pyridine-6-carboxylic Acid

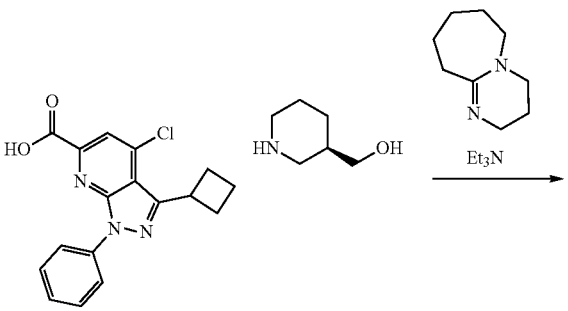

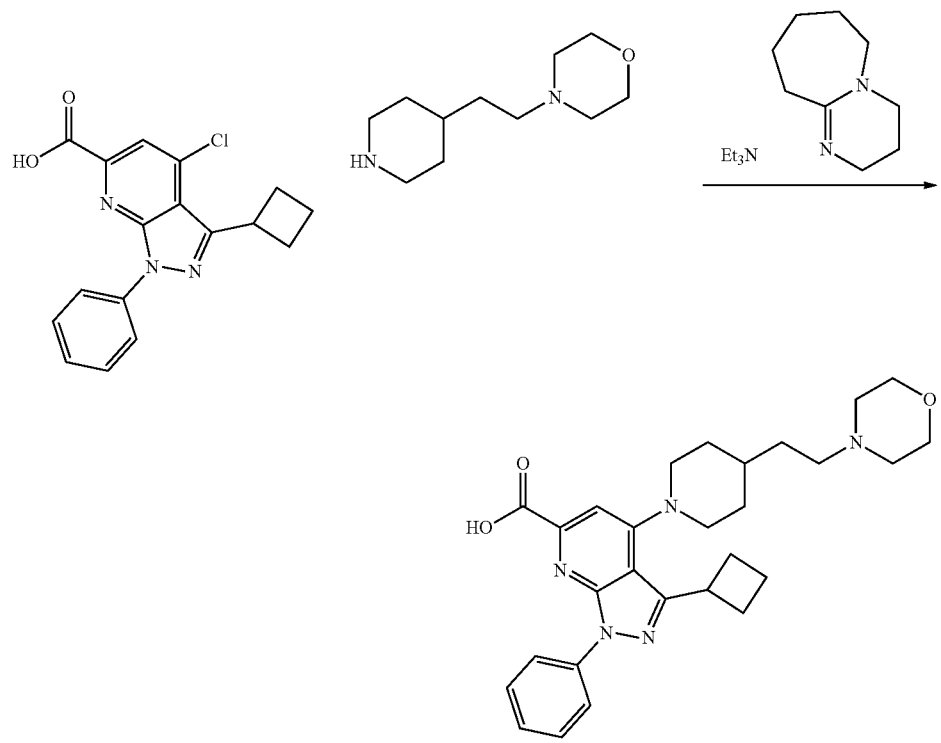

A suspension of intermediate HP10 (164 mg, 0.50 mmol), 4-(2-(piperidin-4-yl)ethyl)morpholine (149 mg, 0.75 mmol) and triethylamine (175 µL, 1.26 mmol) in anhydrous DMA (400 µL) was heated in a Biotage® Initiator microwave synthesizer at 150° C. for fifteen minutes. DBU (90 µL, 0.60 mmol) was added, and the reaction mixture was heated by microwave irradiation at 150° C. for one hour, brought to room temperature, diluted with water (8 mL) and concentrated. The residue was slurried in acetonitrile and the solids were collected by filtration to give the titled compound (155 mg).

-continued

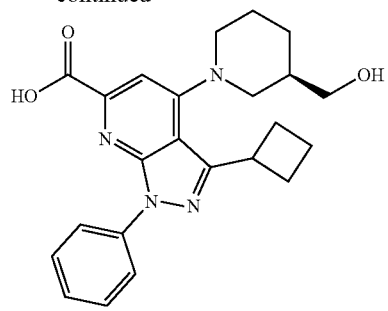

A suspension of 4-chloro-3-cyclobutyl-1-phenyl-pyrazolo[3,4-b]pyridine-6-carboxylic acid (HP10, 164 mg, 0.50 mmol), (R)-piperidin-3-ylmethanol (86 mg, 0.75 mmol) and triethylamine (175 µL, 1.26 mmol) in anhydrous DMA (400 µL) was heated in a microwave reactor at 150° C. for fifteen minutes. DBU (90 µL, 0.60 mmol) was added, and the reaction mixture was heated in the reactor at 150° C. for one hour, brought to room temperature, diluted with water (8 mL), concentrated, and purified by preparative HPLC on a Waters® T3 column (30 mm×100 mm) with a 20 to 100% gradient of acetonitrile in 10 mM aqueous ammonium acetate to give the titled compound (156 mg). $^1$H NMR (400 MHz, CD$_2$Cl$_2$) δ ppm 7.84 (d, J=8.1 Hz, 2H), 7.21-7.13 (m, 3H), 6.92 (t, J=7.4 Hz, 1H), 3.81 (tt, J=8.5, 8.4 Hz, 1H), 3.54-3.46 (m, 1H), 3.43-3.20 (m, 3H), 2.57-2.24 (m, 6H), 2.04-1.88 (m, 2H), 1.84-1.71 (m, 1H), 1.63-1.49 (m, 3H), 0.95-0.79 (m, 1H).

Illustrative Synthesis of Intermediate A408: 1-(4-fluorophenyl)-4-[4-(morpholin-4-yl)piperidin-1-yl]-3-(propan-2-yl)-1H-pyrazolo[3,4-b]pyridine-6-carboxylic Acid A suspension of the 4-chloro-1-(4-fluorophenyl)-3-isopropyl-pyrazolo[3,4-b]pyridine-6-carboxylic acid (267 mg, 0.80 mmol, HP11), 4-morpholinopiperidine (204 mg, 1.2 mmol) and triethylamine (280 µL, 2.0 mmol) in anhydrous DMA (700 µL) was heated in a microwave reactor at 150° C. for fifteen minutes. DBU (145 µL, 0.96 mmol) was added, and the reaction mixture was heated at 150° C. two hours, brought to room temperature, diluted with water (7 mL) and washed twice with 1:2 EtOAc/MTBE. The aqueous phase was acidified with aqueous citric acid to pH 5, and the solids were collected by filtration, washed with water and dried under vacuum to give the titled compound.

Illustrative Synthesis of Compound A413: 3-cyclobutyl-4-[4-(hydroxymethyl)piperidin-1-yl]-1-phenyl-1H-pyrazolo[3,4-b]pyridine-6-carboxylic Acid

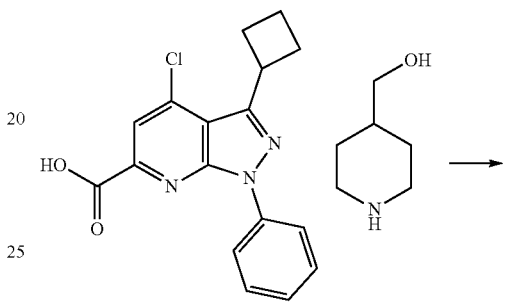

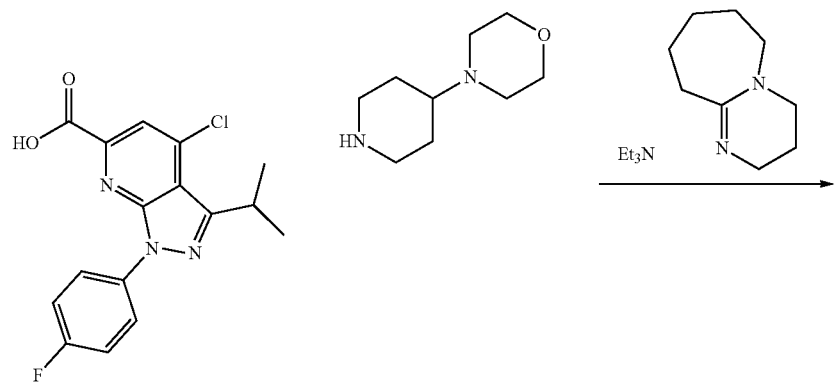

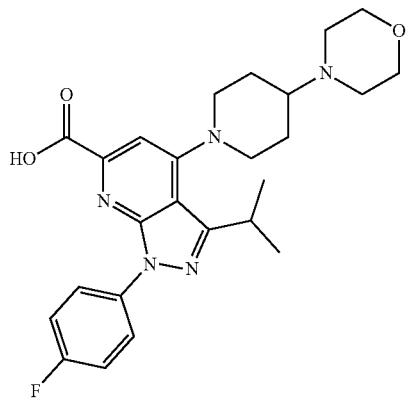

545
-continued

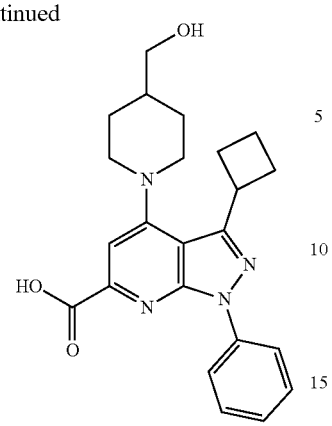

To a solution of HP10 (0.502 g, 1.532 mmol) and 4-piperidinemethanol (0.441 g, 3.83 mmol) in N,N-dimethylacetamide (DMA, 1.5 mL) was added diisopropylethylamine (1.5 mL, 8.59 mmol), and the reaction mixture was then stirred at 150° C. for 12 hours. The reaction mixture was then partitioned between dichloromethane and 1 N HCl. The organic fraction was separated, dried over anhydrous sodium sulfate, filtered, and concentrated under vacuum. The residue was purified on silica gel, eluting with a gradient of 0-5% MeOH/DCM to give the titled compound. $^1$H NMR (400 MHz, DMSO-$d_6$) δ ppm 1.41 (qd, J=12.2, 3.7 Hz, 2H), 1.60 (dtdd, J=13.2, 10.0, 6.2, 3.6 Hz, 1H), 1.83 (dd, J=13.3, 3.4 Hz, 2H), 1.87-2.12 (m, 3H), 2.36 (dtd, J=11.8, 8.5, 3.1 Hz, 2H), 2.51 (dd, J=9.3, 2.3 Hz, 1H), 2.76-2.96 (m, 2H), 3.54 (dd, J=9.4, 6.2 Hz, 2H), 3.94 (p, J=8.4 Hz, 1H), 4.55 (s, 1H), 7.24-7.33 (m, 2H), 7.47-7.58 (m, 2H), 8.30 (d, J=8.0 Hz, 2H).

Method J11: Tandem Nucleophilic Substitution/Saponification

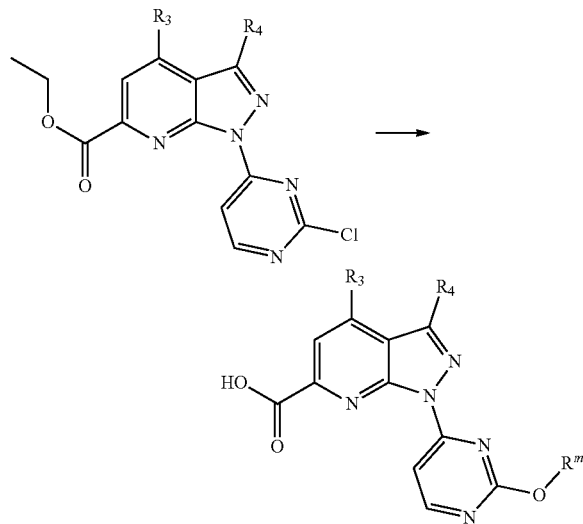

R$^m$: isopropyl, ethyl

The intermediate ester (1 equiv) is suspended in a mixture of appropriate alcohol for the nucleophilic substitution and THF. 1 N NaOH (from 17 to 19 equiv) is added, and the reaction mixture is stirred at RT or 50° C. until full conversion is observed. 1 N HCl (2 equiv) and a phosphate buffer solution (pH 6.2) are added. The mixture is concentrated under reduced pressure, and the crude residue is partitioned between water and dichloromethane. The organic phase is dried over sodium sulfate, filtered and concentrated under reduced pressure to give the titled compound.

Illustrative Synthesis of A343: 3-cyclobutyl-1-(2-ethoxypyrimidin-4-yl)-4-[4-(morpholin-4-yl)piperidin-1-yl]-1H-pyrazolo[3,4-b]pyridine-6-carboxylic Acid

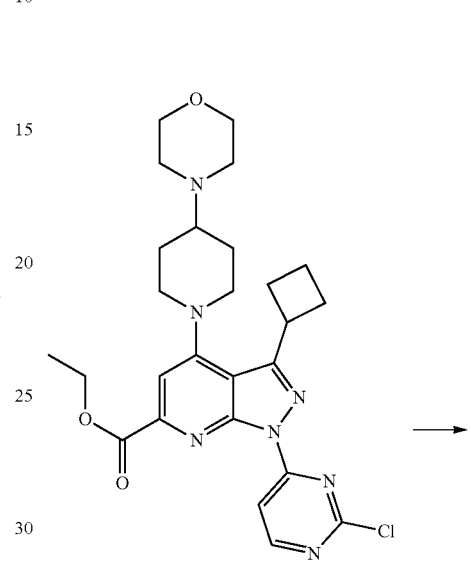

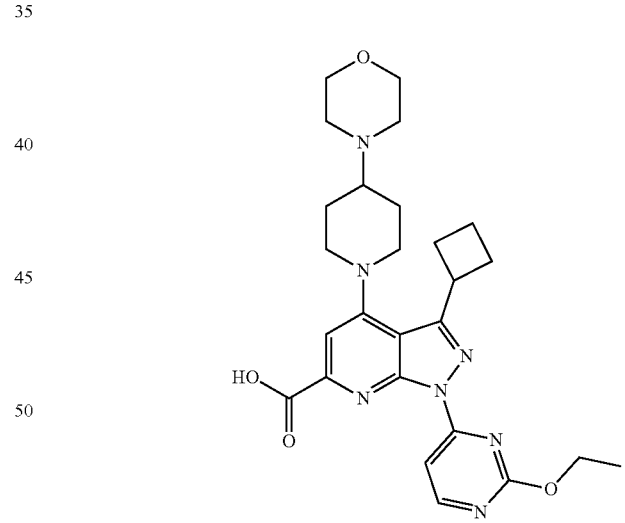

The intermediate ester E422 (30 mg, 57 µmol) was suspended in a mixture of ethanol (8 mL) and THF (3 mL). 1 N NaOH (1 mL, 1 mmol) was added, and the reaction mixture was stirred at RT for 2 hours. 1N HCl (1 mL, 1 mmol) and a phosphate buffer solution (pH 6.2, 5 mL) were added. The mixture was concentrated under reduced pressure, and the crude residue was partitioned between water and dichloromethane. The organic phase was dried over sodium sulfate, filtered and concentrated under reduced pressure to give the titled compound, A343.

Method I12: S<sub>N</sub>Ar on Fluoropyridine

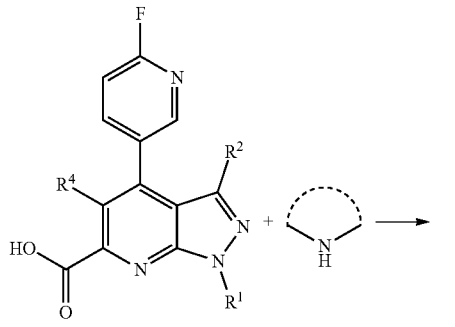

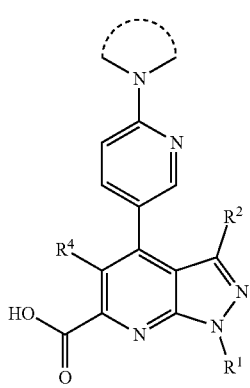

The (6-fluoro-pyridin-3-yl)-1H-pyrazolo[3,4-b]pyridine-6-carboxylic acid (1 eq) is heated together with the amine (1.05 eq) and DIPEA (1.25 eq) in NMP at 100° C. for 18 hours. Mixture is diluted with EtOAc and water. Isolation of the organic layer and subsequent concentration yields the desired product.

Illustrative Synthesis of Compound A405: 3-Cyclobutyl-1-cyclohexyl-4-[6-(4-cyclopropyl-piperazin-1-yl)-pyridin-3-yl]-1H-pyrazolo[3,4-b]pyridine-6-carboxylic Acid

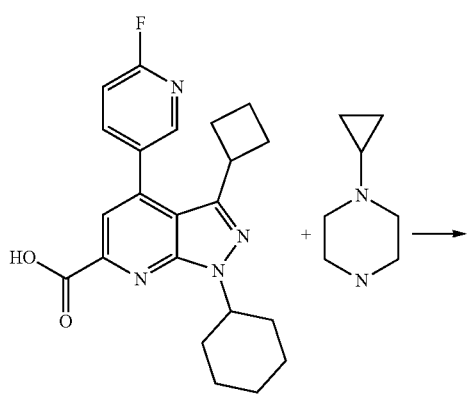

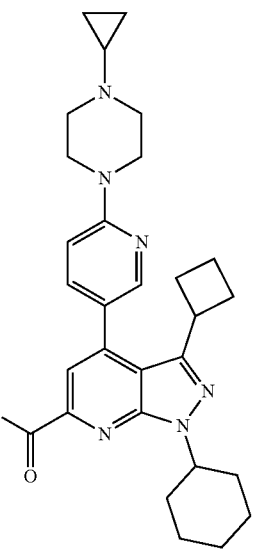

3-Cyclobutyl-1-cyclohexyl-4-(6-fluoro-pyridin-3-yl)-1H-pyrazolo[3,4-b]pyridine-6-carboxylic acid (200 mg, 0.51 mmol) was heated together with 1-cyclopropylpiperazine ([20327-23-5], 64 µL, 0.53 mmol) and DIPEA (110 µL, 0.64 mmol) in NMP (2 mL) at 100° C. for 18 hours. The mixture was diluted with EtOAc and water. Isolation of the organic layer and subsequent concentration yielded the titled compound.

Method J13: Suzuki with Alkyl-BF₃ Salts

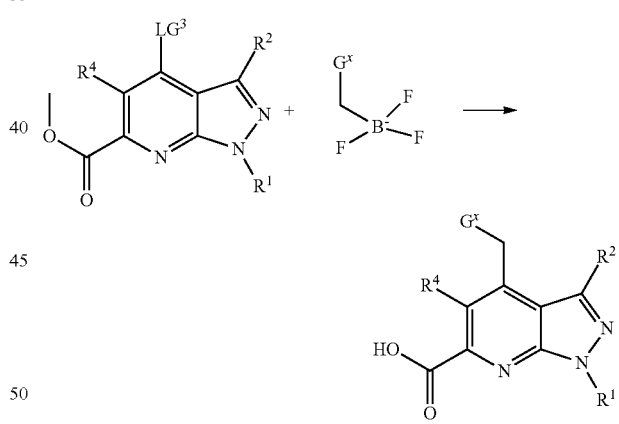

LG³ is a leaving group suitable for the coupling reaction
G<sup>x</sup> is -G<sup>3B</sup> or -G<sup>3B</sup>-L¹-G<sup>3C</sup>

The aryl halide (1 eq) is mixed together with the alkyl-BF3 salt (1.5 eq), Pd(dppf)Cl₂.DCM (CAS 95464-05-4, 0.05 eq) and Cs₂CO₃ (3 eq) in a mixture of THF/H₂O (10/1). The mixture is put under N₂ atmosphere and heated at 80° C. overnight.

If the method is performed on an ester, the ester can be subsequently hydrolyzed to the acid by the addition of LiOH (2 eq) and heating at 50° C. The titled compound is isolated by acidifying with citric acid till pH=6 and extraction with EtOAc. Concentration, possibly followed by chromatographic purification, gives the titled compound.

549

Illustrative Synthesis of Compound A361: 3-Cyclobutyl-1-(4-fluoro-phenyl)-4-(4-morpholin-4-yl-piperidin-1-ylmethyl)-1H-pyrazolo[3,4-b]pyridine-6-carboxylic Acid

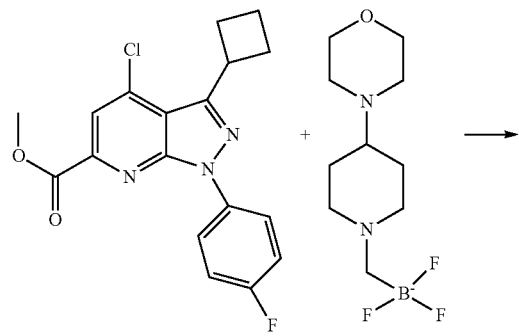

HP19 (352 mg, 0.98 mmol) was mixed together with the potassium trifluorido{[4-(morpholin-4-yl)piperidin-1-yl]methyl}borate (426 mg, 1.47 mmol), Pd(dppf)Cl$_2$.DCM (CAS 95464-05-4, 40 mg, 0.05 mmol) and Cs$_2$CO$_3$ (959 mg, 2.94 mmol) in a mixture of THF/H$_2$O (10/1, 5 mL). The mixture was put under a N$_2$ atmosphere and heated at 80° C. overnight. Next, LiOH (82 mg, 2 mmol) was added, and the mixture was heated at 50° C. The titled compound was isolated by acidifying with citric acid till pH=6 and extraction with EtOAc. Concentration, followed by automated preparative chromatographic purification, gave the titled compound.

Method I14: Suzuki and Subsequent Hydrolysis

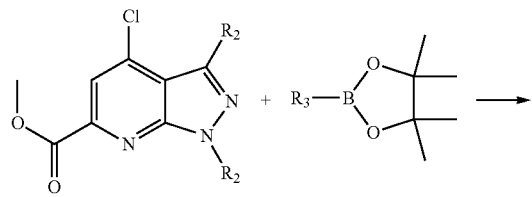

550

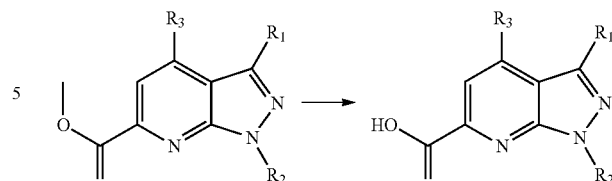

The arylchloride (1 eq) is mixed with the boronic ester (or acid) (1.5 eq), Pd(dppf)Cl$_2$.DCM (CAS 95464-05-4, 0.1 eq) and DIPEA (3 eq) in a mixture of water/dioxane (1/2). The resulting mixture is stirred at 120° C. for 18 hours. Next, LiOH (2 eq) is added, and the mixture is heated at 40° C. After acidifying with 2 M HCl solution, extraction with EtOAc gives an organic phase that is concentrated to give the titled compound.

Illustrative Synthesis of Compound A365: 3-cyclobutyl-1-cyclohexyl-4-{4-[2-(morpholin-4-yl)ethyl]phenyl}-1H-pyrazolo[3,4-b]pyridine-6-carboxylic Acid

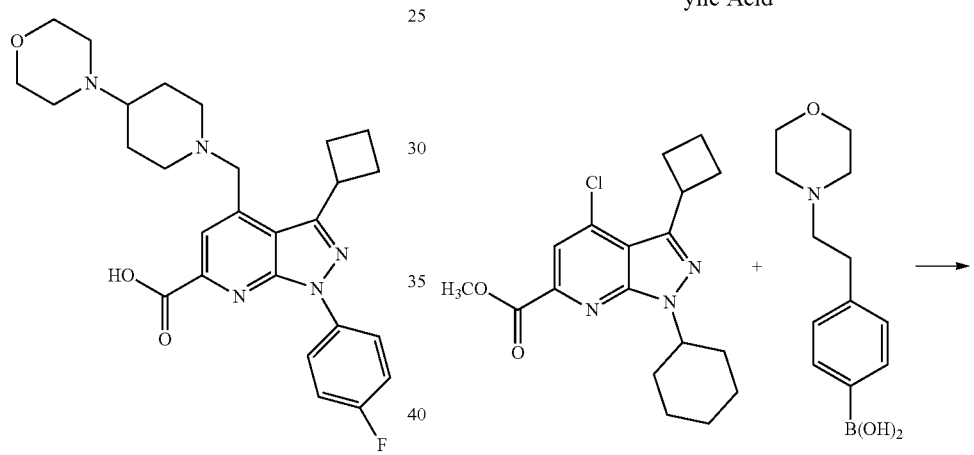

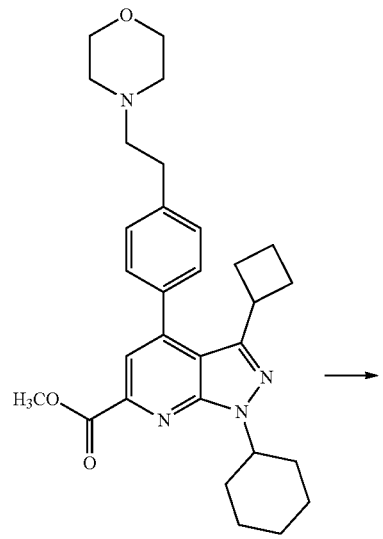

551
-continued

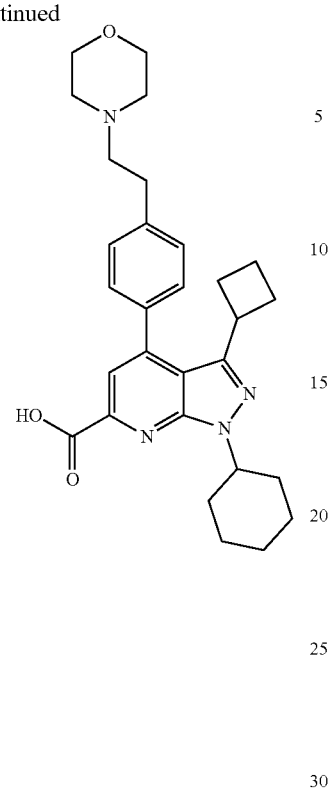

Intermediate HP25 (140 mg, 0.40 mmol), 4-(2-morpholinoethyl)phenylboronic acid (142 mg, 0.60 mmol, CAS#1150114-55-8), Pd(dppf)₂Cl₂ (33 mg, 0.04 mmol) and DIPEA (211 μL, 1.20 mmol) were heated at 120° C. in a mixture of water and dioxane (3 mL, 1:2 water/dioxane). After overnight stirring, LiOH (34 mg, 0.81 mmol) was added, and the resulting mixture was stirred at 40° C. until the hydrolysis was finished. Next, the mixture was diluted with EtOAc and water. After separation, the aqueous phase was acidified with 2 N HCl and subsequently extracted with DCM. The resulting organic phase was dried and concentrated to give the titled compound.

Synthesis of A271: 4-[(3aR,7aS)-1-acetyl-3,3a,4,6,7,7a-hexahydro-2H-pyrrolo[3,2-c]pyridin-5-yl]-3-cyclobutyl-1-phenyl-pyrazolo[3,4-b]pyridine-6-carboxylic Acid

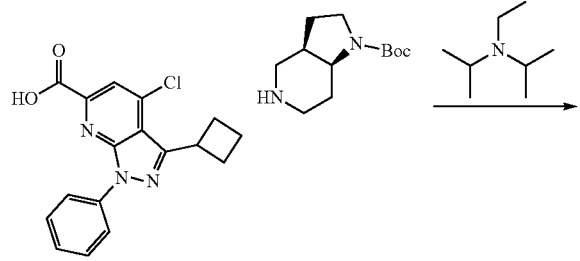

552
-continued

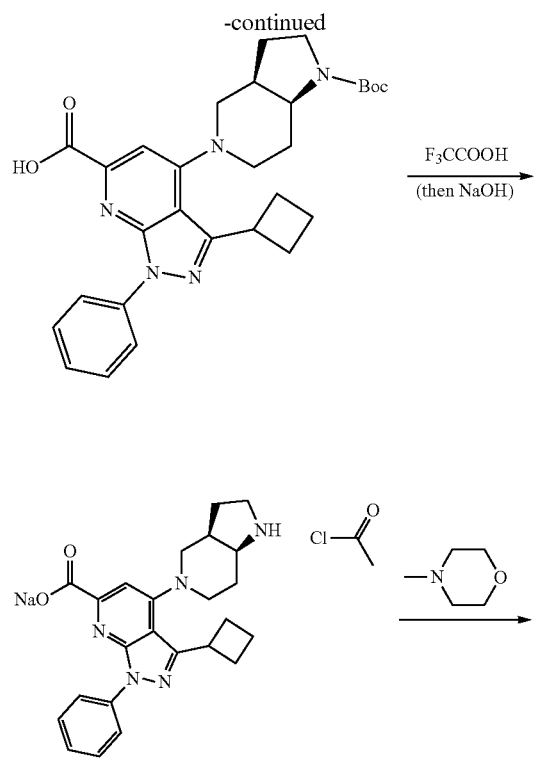

Step 1: Rac-4-[(3aR,7aS)-1-(tert-butoxycarbonyl) octahydro-5H-pyrrolo[3,2-c]pyridin-5-yl]-3-cyclobutyl-1-phenyl-1H-pyrazolo[3,4-b]pyridine-6-carboxylic Acid Intermediate HP10 (164 mg, 0.50 mmol), the tert-butyl rac-(3aR,7aS)-octahydro-1H-pyrrolo[3,2-c]pyridine-1-carboxylate (181 mg, 0.80 mmol, CAS#848410-13-9) and diisopropylethylamine (175 μL, 1.0 mmol) were heated in DMSO (350 μL) at 120° C. for a day, brought to room temperature, and partitioned between EtOAc and 2:1 water/brine (600 μL). The aqueous phase was separated and extracted thrice with EtOAc, and the combined organic phases were acidified with TFA, concentrated and chromatographed on silica (0.1% TFA in 1:1 EtOAc/heptane) to give the titled compound (274 mg). ¹H NMR (501 MHz, methanol-d₄) δ ppm 1.50 (s, 9H), 1.94-2.27 (m, 6H), 2.42-2.51 (m, 2H), 2.52-2.66 (m, 3H), 2.95-3.06 (m, 1H), 3.37-3.58 (m, 5H), 3.94-4.00 (m, 1H), 4.02-4.07 (m, 1H), 7.31-7.35 (m, 1H), 7.44 (s, 1H), 7.50-7.55 (m, 2H), 8.24-8.28 (m, 2H).

Step 2: Sodium Rac-3-cyclobutyl-4-[(3aR,7aS)-octahydro-5H-pyrrolo[3,2-c]pyridin-5-yl]-1-phenyl-1H-pyrazolo[3,4-b]pyridine-6-carboxylate rac-4-[(3aR,7aS)-1-(tert-Butoxycarbonyl)octahydro-5H-pyrrolo[3,2-c]pyridin-5-yl]-3-cyclobutyl-1-phenyl-1H-pyrazolo[3,4-b]pyridine-6-carboxylic acid (1.00 g, <1.9 mmol) was dissolved into anhydrous $CH_2Cl_2$ (8.0 mL), treated with TFA (2.0 mL), stirred at room temperature for two hours and then concentrated. The residue was redissolved into $CH_2Cl_2$, treated with aqueous $K_2HPO_4$ and basified to pH 11+ with aqueous NaOH. Brine was added, and the mixture was extracted with 10% $MeOH/CH_2Cl_2$. The separated organic phase was dried ($Na_2SO_4$), passed through a short column of $Na_2SO_4$ and concentrated to give the titled compound (452 mg). $^1$H NMR (500 MHz, methanol-$d_4$) δ ppm 1.69-1.77 (m, 1H), 1.98-2.21 (m, 5H), 2.40-2.66 (m, 6H), 2.94-3.01 (m, 2H), 3.15-3.3 (m, 3H), 3.32-3.36 (m, 1H), 4.07-4.15 (m, 1H), 7.24-7.28 (m, 1H), 7.38 (s, 1H), 7.47-7.51 (m, 2H), 8.35-8.38 (m, 2H); MS (ESI) m/z 418 $(M+H)^+$.

Step 3: 4-[(3aR,7aS)-1-acetyl-3,3a,4,6,7,7a-hexahydro-2H-pyrrolo[3,2-c]pyridin-5-yl]-3-cyclobutyl-1-phenyl-pyrazolo[3,4-b]pyridine-6-carboxylic Acid Sodium rac-3-cyclobutyl-4-[(3 aR,7aS)-octahydro-5H-pyrrolo[3,2-c]pyridin-5-yl]-1-phenyl-1H-pyrazolo[3,4-b]pyridine-6-carboxylate (209 mg, 0.50 mmol) and N-methylmorpholine (220 μL, 2.0 mmol) were suspended in DMF (2.5 mL) and chilled with a water ice bath. A solution of acetyl chloride (50 μL, 0.70 mmol) in dichloromethane (500 μL) was added dropwise, and the mixture was stirred for two minutes before the bath was removed. The cloudy solution was stirred another thirty minutes at room temperature before being diluted with EtOAc and placed directly on silica for chromatography (EtOAc, then 0 to 20% MeOH/MeCN, then 0.1% TFA/19.9% MeOH/80% MeCN) to give rac-4-[(3aR,7aS)-1-acetyloctahydro-5H-pyrrolo[3,2-c]pyridin-5-yl]-3-cyclobutyl-1-phenyl-1H-pyrazolo[3,4-b]pyridine-6-carboxylic acid (236 mg).

The racemate was then subjected to preparative supercritical fluid chromatography set to maintain a maximum back pressure of 100 MPa using a Chiralcel® OJ-H (21×250 mm) column with the sample at a concentration of 10 mg/mL in methanol using 35% methanol in $CO_2$ at a flow rate of 45 mL/minute to provide both enantiomers separately. The first enantiomer eluted (retention time=5.4 minutes), and the second enantiomer eluted (retention time=7.4 minutes) as the titled compound (stereochemistry arbitrarily assigned). $^1$H NMR (400 MHz, DMSO-$d_6$, 120° C.) δ ppm 1.98 (s, 3H), 1.88-2.22 (m, 6H), 2.40-2.59 (m, 4H), 2.98-3.07 (m, 1H), 3.15-3.19 (m, 1H), 3.31-3.61 (m, 4H), 3.78-3.83 (m, 1H), 3.99-4.13 (m, 2H), 7.27-7.32 (m, 1H), 7.34 (s, 1H), 7.49-7.55 (m, 2H), 8.29-8.35 (m, 2H).

Synthesis of A222: 4-(4-morpholinophenyl)-1-phenyl-pyrazolo[3,4-b]pyridine-6-carboxylic Acid

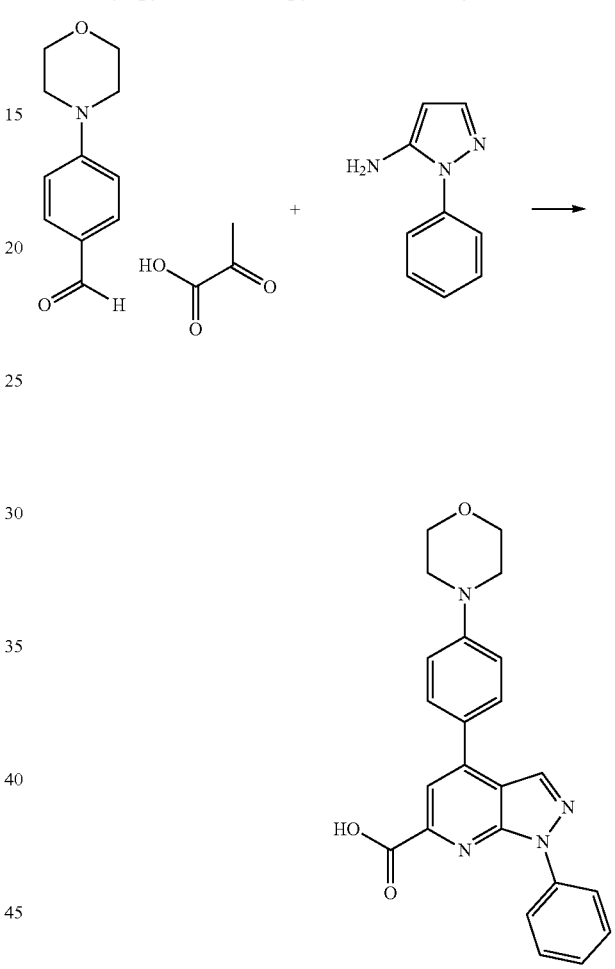

4-(4-Morpholinyl)benzaldehyde (CAS 1204-86-0, 241 mg, 1.26 mmol, 1 equiv), pyruvic acid (CAS 127-17-3, 88 μL, 1.26 mmol, 1 equiv) and 5-amino-1-phenylpyrazole (CAS 826-85-7, 200 mg, 1.26 mmol, 1 equiv) were combined in a sealed tube. Acetic acid (5 mL) was added, and the vial was sealed. The reaction mixture was heated under microwave irradiation at 160° C. for 20 min. The reaction mixture was cooled down and concentrated in vacuo. The resulting residue was purified by preparative HPLC to afford the tiled compound.

TABLE XIII

List of acids

| Int. | Structure | Name | SM | method | MW | Mes |
|---|---|---|---|---|---|---|
| A001 | 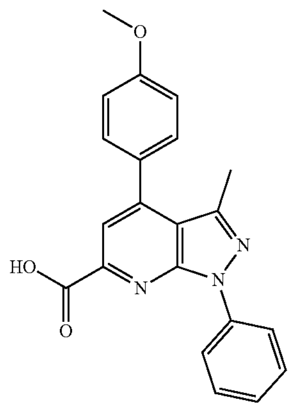 [SMILES: COc1ccc(-c2cc(C(=O)O)nc3c2c(C)nn3-c2ccccc2)cc1] | 4-(4-methoxyphenyl)-3-methyl-1-phenyl-pyrazolo[3,4-b]pyridine-6-carboxylic acid | — | 926282-55-5 | — | — |
| A002 | 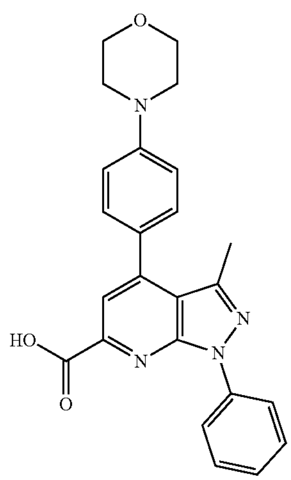 [SMILES: Cc1nn(-c2ccccc2)c2nc(C(=O)O)cc(-c3ccc(N4CCOCC4)cc3)c12] | 3-methyl-4-(4-morpholinophenyl)-1-phenyl-pyrazolo[3,4-b]pyridine-6-carboxylic acid | ALP01, 1131-18-6 | J2 Specific example | 414 | 415 |
| A003 | 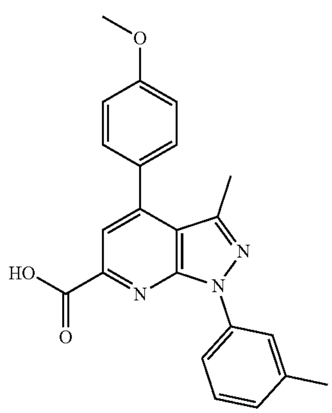 [SMILES: COc1ccc(-c2cc(C(=O)O)nc3c2c(C)nn3-c2cccc(C)c2)cc1] | 4-(4-methoxyphenyl)-3-methyl-1-(m-tolyl)pyrazolo[3,4-b]pyridine-6-carboxylic acid | ALP06, 92721-83-0 | J2 | 373 | 374 |

TABLE XIII-continued
List of acids
| Int. | Structure | Name | SM | method | MW | Mes |
|---|---|---|---|---|---|---|
| A004 | 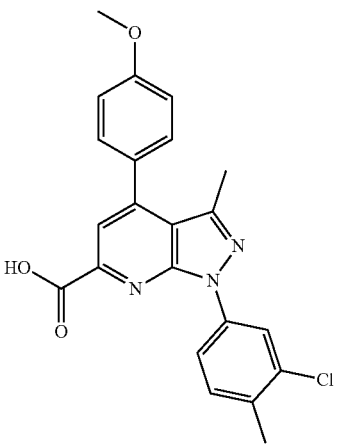 [SMILES: COc1ccc(-c2cc(C(=O)O)nc3c2c(C)nn3-c2ccc(C)c(Cl)c2)cc1] | 1-(3-chloro-4-methyl-phenyl)-4-(4-methoxyphenyl)-3-methyl-pyrazolo[3,4-b]pyridine-6-carboxylic acid | ALP06, 866472-29-9 | J2 | 407 | 408 |
| A005 | 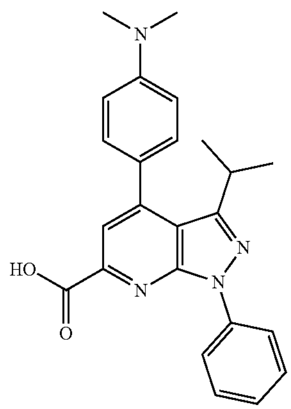 [SMILES: CC(C)c1nn(-c2ccccc2)c2nc(C(=O)O)cc(-c3ccc(N(C)C)cc3)c12] | 4-[4-(dimethylamino)phenyl]-3-isopropyl-1-phenyl-pyrazolo[3,4-b]pyridine-6-carboxylic acid | ALP02, AMP04 | J2 | 400 | 401 |
| A006 | 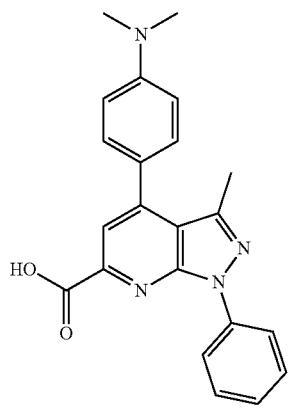 [SMILES: Cc1nn(-c2ccccc2)c2nc(C(=O)O)cc(-c3ccc(N(C)C)cc3)c12] | 4-(4-dimethylamino-phenyl)-3-methyl-1-phenyl-pyrazolo[3,4-b]pyridine-6-carboxylic acid | E006 | J1 | 372 | 373 |

TABLE XIII-continued

List of acids

| Int. | Structure | Name | SM | method | MW | Mes |
|------|-----------|------|-----|--------|-----|-----|
| A007 | 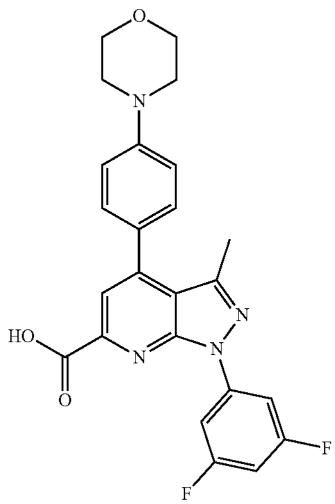 [SMILES: Cc1nn(-c2cc(F)cc(F)c2)c2nc(C(=O)O)cc(-c3ccc(N4CCOCC4)cc3)c12] | 1-(3,5-difluorophenyl)-3-methyl-4-(4-morpholinophenyl)pyrazolo[3,4-b]pyridine-6-carboxylic acid | ALP01, 1232796-65-4 | J2 | 450 | 451 |
| A008 | 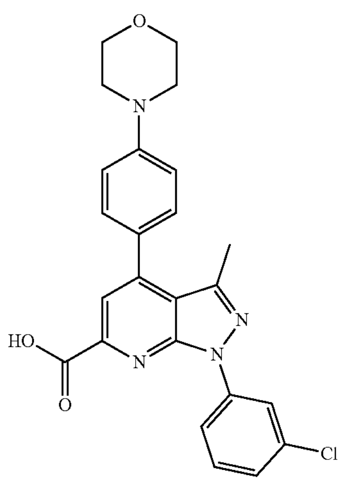 [SMILES: Cc1nn(-c2cccc(Cl)c2)c2nc(C(=O)O)cc(-c3ccc(N4CCOCC4)cc3)c12] | 1-(3-chlorophenyl)-3-methyl-4-(4-morpholinophenyl)pyrazolo[3,4-b]pyridine-6-carboxylic acid | ALP01, 40401-41-0 | J2 | 448 | 449 |
| A009 | 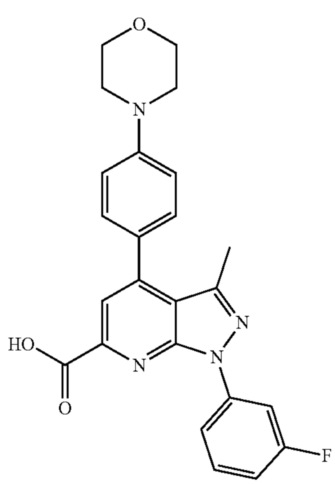 [SMILES: Cc1nn(-c2cccc(F)c2)c2nc(C(=O)O)cc(-c3ccc(N4CCOCC4)cc3)c12] | 1-(3-fluorophenyl)-3-methyl-4-(4-morpholinophenyl)pyrazolo[3,4-d]pyridine-6-carboxylic acid | ALP01, 105438-45-7 | J2 | 432 | 433 |

TABLE XIII-continued

List of acids

| Int. | Structure | Name | SM | method | MW | Mes |
|------|-----------|------|-----|--------|-----|-----|
| A010 | 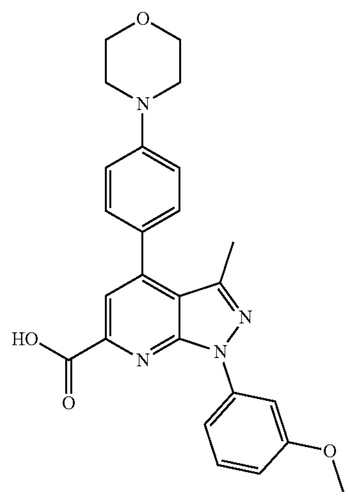 [SMILES: COc1cccc(-n2nc(C)c3c(-c4ccc(N5CCOCC5)cc4)cc(C(=O)O)nc32)c1] | 1-(3-methoxyphenyl)-3-methyl-4-(4-morpholinophenyl)pyrazolo[3,4-b]pyridine-6-carboxylic acid | ALP01, 92721-94-3 | J2 | 444 | 445 |
| A011 | 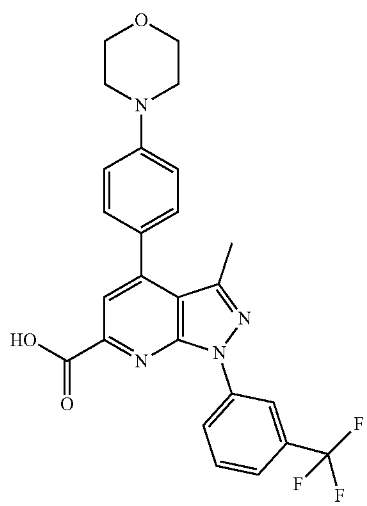 [SMILES: Cc1nn(-c2cccc(C(F)(F)F)c2)c2nc(C(=O)O)cc(-c3ccc(N4CCOCC4)cc3)c12] | 3-methyl-4-(4-morpholinophenyl)-1-[3-(trifluoromethyl)phenyl]pyrazolo[3,4-b]pyridine-6-carboxylic acid | ALP01, 345-07-3 | J2 | 482 | 483 |
| A012 | 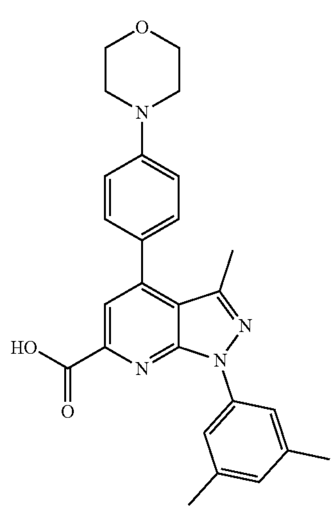 [SMILES: Cc1cc(C)cc(-n2nc(C)c3c(-c4ccc(N5CCOCC5)cc4)cc(C(=O)O)nc32)c1] | 1-(3,5-dimethylphenyl)-3-methyl-4-(4-morpholinophenyl)pyrazolo[3,4-b]pyridine-6-carboxylic acid | ALP01, 890010-89-6 | J2 | 442 | 443 |

TABLE XIII-continued

List of acids

| Int. | Structure | Name | SM | method | MW | Mes |
|---|---|---|---|---|---|---|
| A013 | 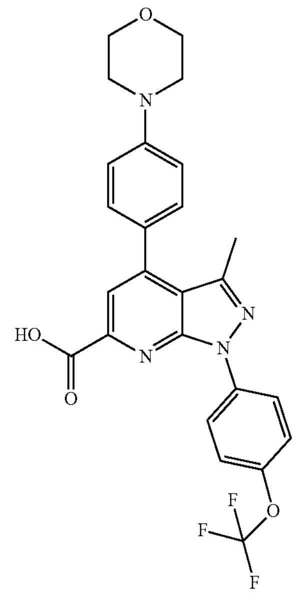 [SMILES: Cc1nn(-c2ccc(OC(F)(F)F)cc2)c2nc(C(=O)O)cc(-c3ccc(N4CCOCC4)cc3)c12] | 3-methyl-4-(4-morpholinophenyl)-1-[4-(trifluoromethoxy)phenyl]pyrazolo[3,4-b]pyridine-6-carboxylic acid | ALP01, 497141-59-0 | J2 | 414 | 415 |
| A014 | 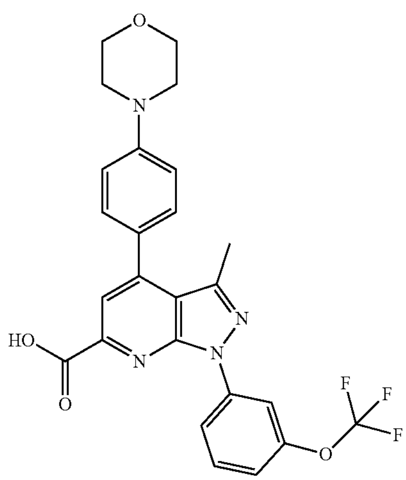 [SMILES: Cc1nn(-c2cccc(OC(F)(F)F)c2)c2nc(C(=O)O)cc(-c3ccc(N4CCOCC4)cc3)c12] | 3-methyl-4-(4-morpholinophenyl)-1-[3-(trifluoromethoxy)phenyl]pyrazolo[3,4-b]pyridine-6-carboxylic acid | ALP01, AMP01 | J2 | 498 | 499 |
| A015 | 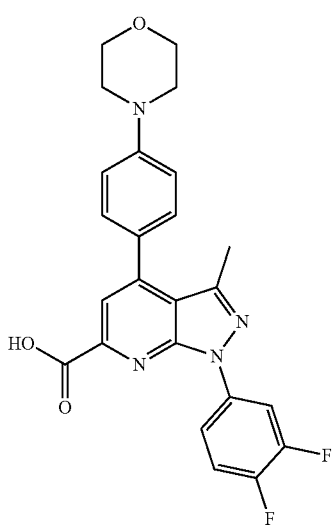 [SMILES: Cc1nn(-c2ccc(F)c(F)c2)c2nc(C(=O)O)cc(-c3ccc(N4CCOCC4)cc3)c12] | 1-(3,4-difluorophenyl)-3-methyl-4-(4-morpholinophenyl)pyrazolo[3,4-b]pyridine-6-carboxylic acid | ALP01, AMP02 | J2 | 450 | 451 |

TABLE XIII-continued

List of acids

| Int. | Structure | Name | SM | method | MW | Mes |
|---|---|---|---|---|---|---|
| A016 | 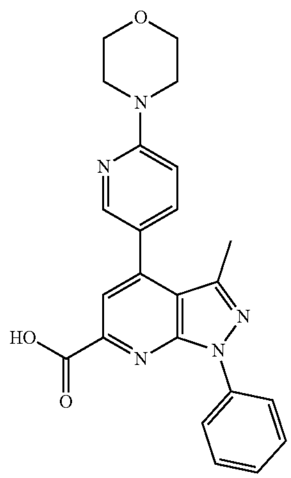 [SMILES: Cc1nn(-c2ccccc2)c2nc(C(=O)O)cc(-c3ccc(N4CCOCC4)nc3)c12] | 3-methyl-4-(6-morpholino-3-pyridyl)-1-phenyl-pyrazolo[3,4-b]pyridine-6-carboxylic acid | E009 | J1 | 415 | 416 |
| A017 | 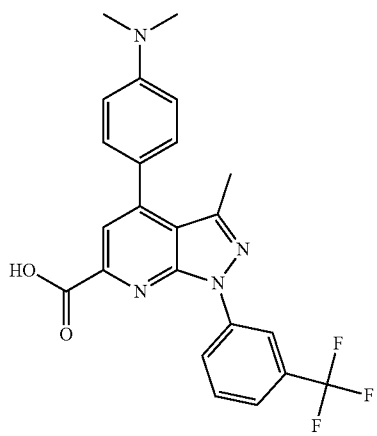 [SMILES: Cc1nn(-c2cccc(C(F)(F)F)c2)c2nc(C(=O)O)cc(-c3ccc(N(C)C)cc3)c12] | 4-(4-dimethylamino-phenyl)-3-methyl-1-[3-(trifluoromethyl)phenyl]pyrazolo[3,4-b]pyridine-6-carboxylic acid | ALP02, 345-07-3 | J2 | 440 | 441 |
| A018 | 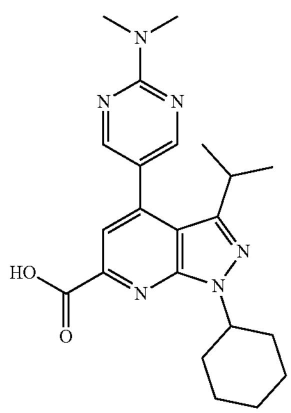 [SMILES: CC(C)c1nn(C2CCCCC2)c2nc(C(=O)O)cc(-c3cnc(N(C)C)nc3)c12] | cyclohexyl-4-[2-(dimethylamino)pyrimidin-5-yl]-3-isopropyl-pyrazolo[3,4-b]pyridine-6-carboxylic acid | ALP03, AMP23 | J2 | 408 | 409 |

TABLE XIII-continued

List of acids

| Int. | Structure | Name | SM | method | MW | Mes |
|---|---|---|---|---|---|---|
| A019 | 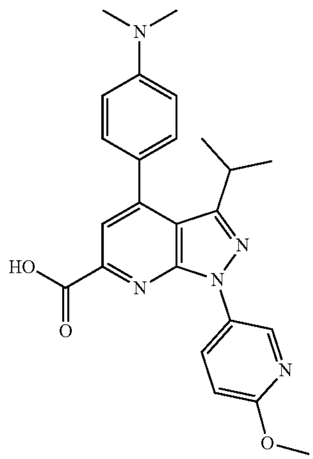 [SMILES: COc1ccc(-n2nc(C(C)C)c3c(-c4ccc(N(C)C)cc4)cc(C(=O)O)nc32)cn1] | 4-[4-(dimethylamino)phenyl]-3-isopropyl-1-(6-methoxy-3-pyridyl)pyrazolo[3,4-b]pyridine-6-carboxylic acid | ALP02, AMP16 | J2 | 431 | 432 |
| A020 | 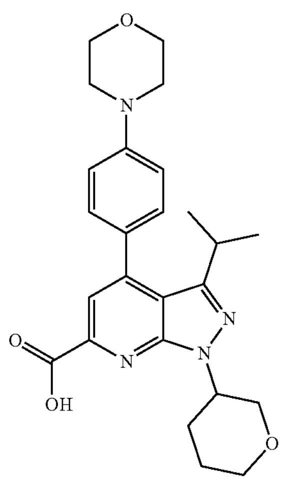 [SMILES: CC(C)c1nn(C2CCCOC2)c2nc(C(=O)O)cc(-c3ccc(N4CCOCC4)cc3)c12] | 3-isopropyl-4-(4-morpholinophenyl)-1-tetrahydropyran-3-yl-pyrazolo[3,4-b]pyridine-6-carboxylic acid | ALP01, AMP25 | J2 | 450 | 451 |
| A021 | 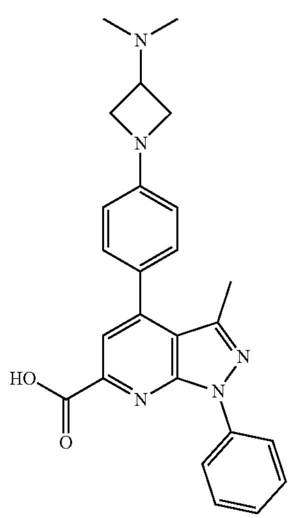 [SMILES: Cc1nn(-c2ccccc2)c2nc(C(=O)O)cc(-c3ccc(N4CC(N(C)C)C4)cc3)c12] | 4-[4-[3-(dimethylamino)azetidin-1-yl]phenyl]-3-methyl-1-phenyl-pyrazolo[3,4-b]pyridine-6-carboxylic acid | E011 | J1 | 427 | 428 |

TABLE XIII-continued

List of acids

| Int. | Structure | Name | SM | method | MW | Mes |
|---|---|---|---|---|---|---|
| A022 | 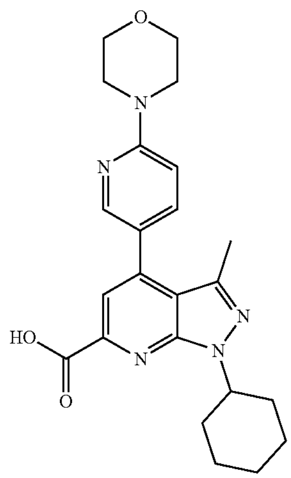 [SMILES: Cc1nn(C2CCCCC2)c2nc(C(=O)O)cc(-c3ccc(N4CCOCC4)nc3)c12] | 1-cyclohexyl-3-methyl-4-(6-morpholino-3-pyridyl)pyrazolo[3,4-b]pyridine-6-carboxylic acid | ALP05, 56547-82-1 | J2 | 421 | 422 |
| A023 | 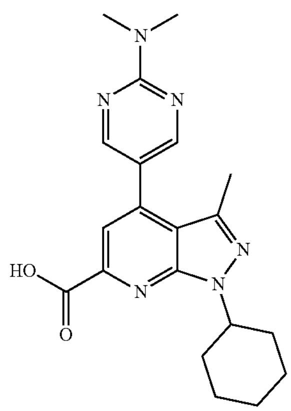 [SMILES: Cc1nn(C2CCCCC2)c2nc(C(=O)O)cc(-c3cnc(N(C)C)nc3)c12] | 1-cyclohexyl-4-[2-(dimethylamino)pyrimidin-5-yl]-3-methyl-pyrazolo[3,4-b]pyridine-6-carboxylic acid | ALP03, 56547-82-1 | J2 | 380 | 381 |
| A024 | 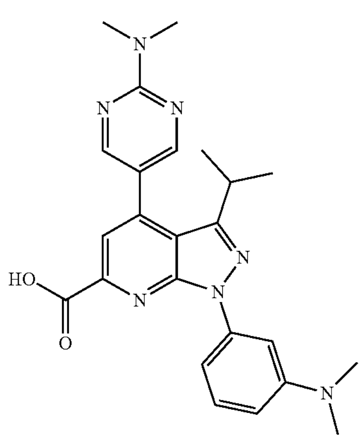 [SMILES: CC(C)c1nn(-c2cccc(N(C)C)c2)c2nc(C(=O)O)cc(-c3cnc(N(C)C)nc3)c12] | 1-[3-(dimethylamino)phenyl]-4-[2-(dimethylamino)pyrimidin-5-yl]-3-isopropyl-pyrazolo[3,4-b]pyridine-6-carboxylic acid | ALP03, AMP06 | J2 | 445 | 446 |

TABLE XIII-continued

List of acids

| Int. | Structure | Name | SM | method | MW | Mes |
|---|---|---|---|---|---|---|
| A025 | 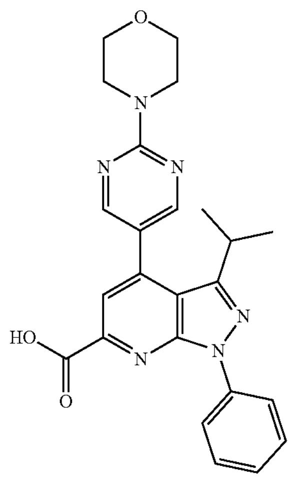 [SMILES: CC(C)c1nn(-c2ccccc2)c2nc(C(=O)O)cc(-c3cnc(N4CCOCC4)nc3)c12] | 3-isopropyl-4-(2-morpholinopyrimidin-5-yl)-1-phenyl-pyrazolo[3,4-b]pyridine-6-carboxylic acid | ALP04, AMP04 | J2 | 444 | 445 |
| A026 | 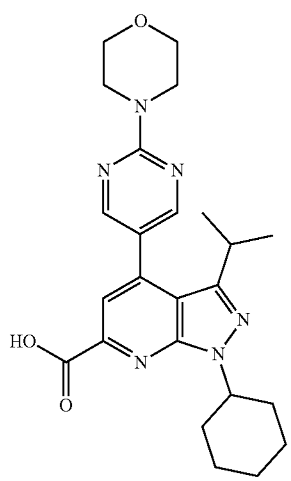 [SMILES: CC(C)c1nn(C2CCCCC2)c2nc(C(=O)O)cc(-c3cnc(N4CCOCC4)nc3)c12] | 3-isopropyl-4-(2-morpholinopyrimidin-5-yl)-1-phenyl-pyrazolo[3,4-b]pyridine-6-carboxylic acid | E003 | J1 | 450 | 451 |
| A027 | 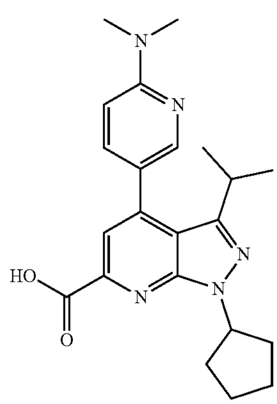 [SMILES: CC(C)c1nn(C2CCCC2)c2nc(C(=O)O)cc(-c3ccc(N(C)C)nc3)c12] | 1-cyclopentyl-4-[6-(dimethylamino)-3-pyridyl]-3-isopropyl-pyrazolo[3,4-b]pyridine-6-carboxylic acid | ALP21, AMP26 | J2 | 393 | 394 |

TABLE XIII-continued

List of acids

| Int. | Structure | Name | SM | method | MW | Mes |
|---|---|---|---|---|---|---|
| A028 | 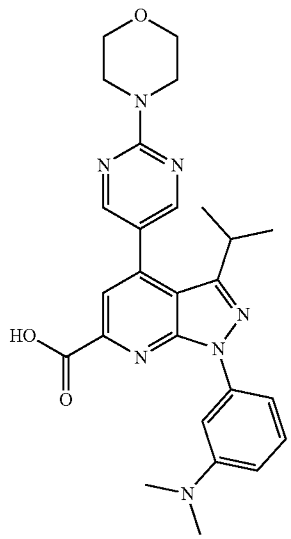 [SMILES: CC(C)c1nn(-c2cccc(N(C)C)c2)c2nc(C(=O)O)cc(-c3cnc(N4CCOCC4)nc3)c12] | 1-[3-(dimethylamino)phenyl]-3-isopropyl-4-(2-morpholinopyrimidin-5-yl)pyrazolo[3,4-b]pyridine-6-carboxylic acid | E016 | J1 | 487 | 488 |
| A029 | 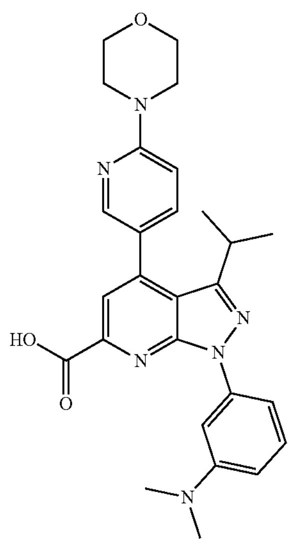 [SMILES: CC(C)c1nn(-c2cccc(N(C)C)c2)c2nc(C(=O)O)cc(-c3ccc(N4CCOCC4)nc3)c12] | 1-[3-(dimethylamino)phenyl]-3-isopropyl-4-(6-morpholino-3-pyridyl)pyrazolo[3,4-b]pyridine-6-carboxylic acid | E015 | J1 | 486 | 487 |
| A030 | 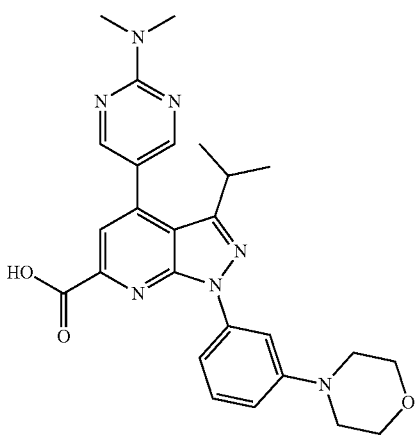 [SMILES: CC(C)c1nn(-c2cccc(N3CCOCC3)c2)c2nc(C(=O)O)cc(-c3cnc(N(C)C)nc3)c12] | 4-[2-(dimethylamino)pyrimidin-5-yl]-3-isopropyl-1-(3-morpholinophenyl)pyrazolo[3,4-b]pyridine-6-carboxylic acid | ALP03, AMP10 | J2 | 487 | 488 |

TABLE XIII-continued

List of acids

| Int. | Structure | Name | SM | method | MW | Mes |
|---|---|---|---|---|---|---|
| A031 | 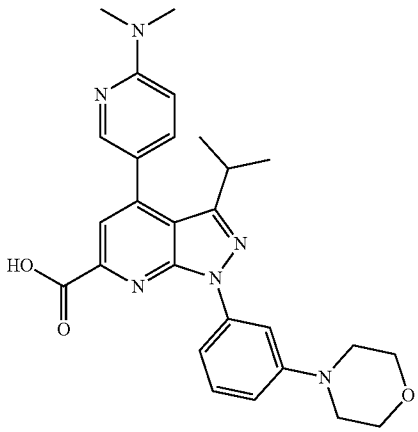 [SMILES: CC(C)c1nn(-c2cccc(N3CCOCC3)c2)c2nc(C(=O)O)cc(-c3ccc(N(C)C)nc3)c12] | 4-[6-(dimethylamino)-3-pyridyl]-3-isopropyl-1-(3-morpholinophenyl)pyrazolo[3,4-b]pyridine-6-carboxylic acid | ALP21, AMP10 | J2 | 486 | 487 |
| A032 | 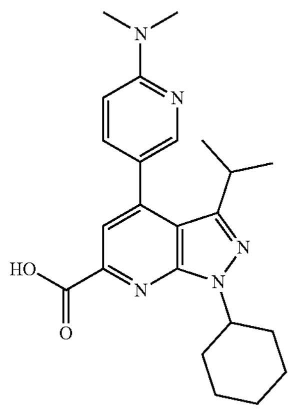 [SMILES: CC(C)c1nn(C2CCCCC2)c2nc(C(=O)O)cc(-c3ccc(N(C)C)nc3)c12] | 1-cyclohexyl-4-[6-(dimethylamino)-3-pyridyl]-3-isopropyl-pyrazolo[3,4-b]pyridine-6-carboxylic acid | ALP21, AMP23 | J2 | 407 | 408 |
| A033 | 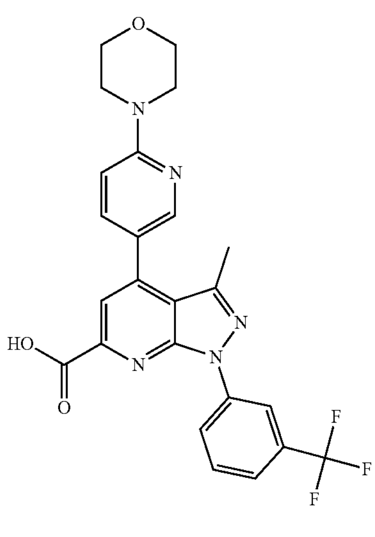 [SMILES: Cc1nn(-c2cccc(C(F)(F)F)c2)c2nc(C(=O)O)cc(-c3ccc(N4CCOCC4)nc3)c12] | 3-methyl-4-(6-morpholino-3-pyridyl)-1-[3-(trifluoromethyl)phenyl]pyrazolo[3,4-b]pyridine-6-carboxylic acid | ALP05, 345-07-3 | J2 | 483 | 484 |

TABLE XIII-continued

| | | List of acids | | | | |
|---|---|---|---|---|---|---|
| Int. | Structure | Name | SM | method | MW | Mes |
| A034 | | 1-(2,4-difluorophenyl)-3-methyl-4-(6-morpholino-3-pyridyl)pyrazolo[3,4-b]pyridine-6-carboxylic acid | ALP05, 380569-79-9 | J2 | 451 | 452 |
| A035 | | 1-(2,4-difluorophenyl)-3-methyl-4-(4-morpholinophenyl)pyrazolo[3,4-b]pyridine-6-carboxylic acid | ALP01, 380569-79-9 | J2 | 450 | 451 |
| A036 | | 3-methyl-1-phenyl-4-(1-piperidyl)pyrazolo[3,4-b]pyridine-6-carboxylic acid | E004 | J1 | 336 | 337 |

TABLE XIII-continued
| Int. | Structure | Name | SM | method | MW | Mes |
|------|-----------|------|-----|--------|-----|-----|
| A037 | 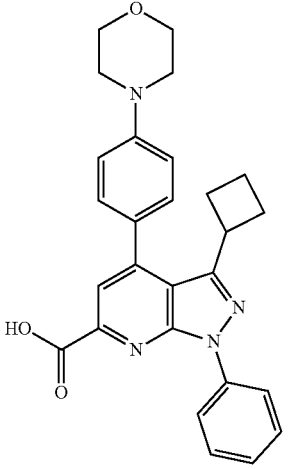 [SMILES: O=C(O)c1cc(-c2ccc(N3CCOCC3)cc2)c2c(C3CCC3)nn(-c3ccccc3)c2n1] | 3-cyclobutyl-4-(4-morpholinophenyl)-1-phenyl-pyrazolo[3,4-b]pyridine-6-carboxylic acid | ALP01, AMP29 | J2 | 454 | 455 |
| A038 | 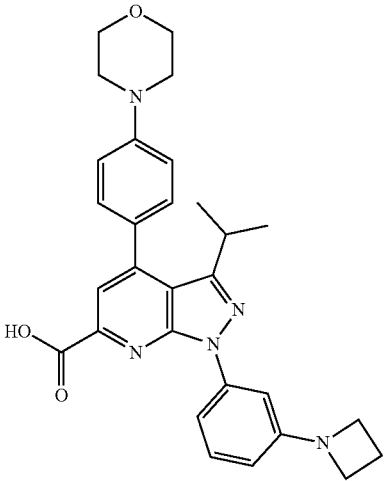 [SMILES: CC(C)c1nn(-c2cccc(N3CCC3)c2)c2nc(C(=O)O)cc(-c3ccc(N4CCOCC4)cc3)c12] | 1-[3-(azetidin-1-yl)phenyl]-3-isopropyl-4-(4-morpholinophenyl)pyrazolo[3,4-b]pyridine-6-carboxylic acid | E002 | J1 | 497 | 498 |
| A039 | 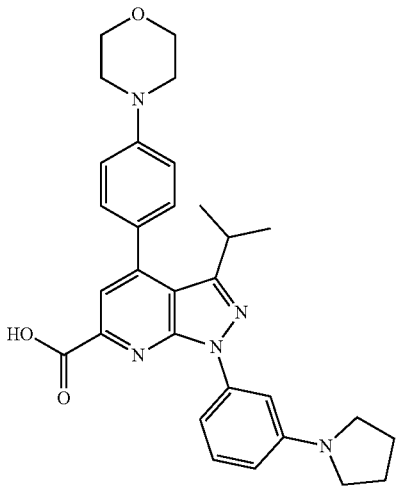 [SMILES: CC(C)c1nn(-c2cccc(N3CCCC3)c2)c2nc(C(=O)O)cc(-c3ccc(N4CCOCC4)cc3)c12] | 3-isopropyl-4-(4-morpholinophenyl)-1-(3-pyrrolidin-1-ylphenyl)pyrazolo[3,4-b]pyridine-6-carboxylic acid | E005 | J1 | 511 | 512 |

TABLE XIII-continued

List of acids

| Int. | Structure | Name | SM | method | MW | Mes |
|---|---|---|---|---|---|---|
| A040 | 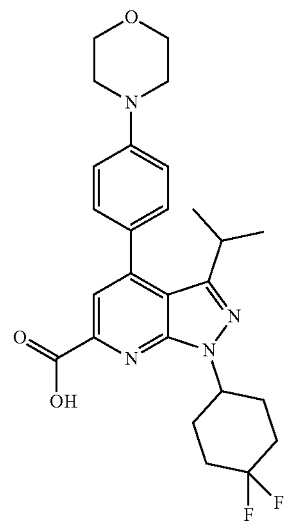 [SMILES: CC(C)c1nn(C2CCC(F)(F)CC2)c2nc(C(=O)O)cc(-c3ccc(N4CCOCC4)cc3)c12] | 1-(4,4-difluorocyclohexyl)-3-isopropyl-4-(4-morpholinophenyl)pyrazolo[3,4-b]pyridine-6-carboxylic acid | ALP01, AMP24 | J2 | 484 | 485 |
| A041 | 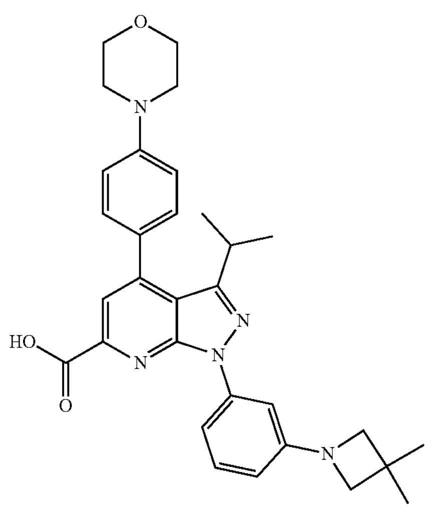 [SMILES: CC(C)c1nn(-c2cccc(N3CC(C)(C)C3)c2)c2nc(C(=O)O)cc(-c3ccc(N4CCOCC4)cc3)c12] | 1-[3-(3,3-dimethylazetidin-1-yl)phenyl]-3-isopropyl-4-(4-morpholinophenyl)pyrazolo[3,4-b]pyridine-6-carboxylic acid | E012 | J1 | 525 | 526 |
| A042 | 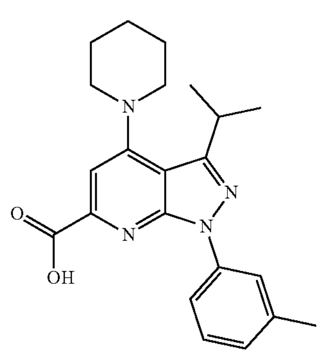 [SMILES: Cc1cccc(-n2nc(C(C)C)c3c(N4CCCCC4)cc(C(=O)O)nc32)c1] | 3-isopropyl-1-(m-tolyl)-4-(1-piperidyl)pyrazolo[3,4-b]pyridine-6-carboxylic acid | E039 | J1 | 378 | 379 |

TABLE XIII-continued

List of acids

| Int. | Structure | Name | SM | method | MW | Mes |
|------|-----------|------|----|--------|----|----|
| A043 | 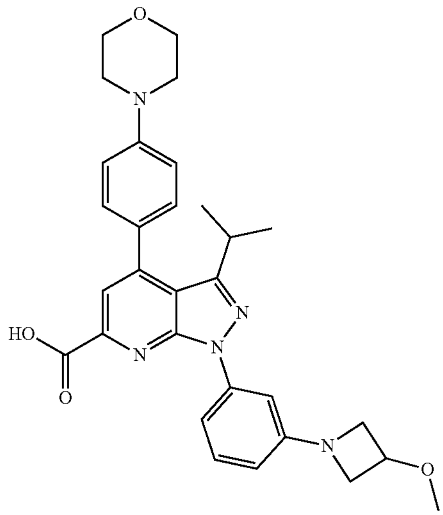 [SMILES: COC1CN(c2cccc(-n3nc(C(C)C)c4c(-c5ccc(N6CCOCC6)cc5)cc(C(=O)O)nc43)c2)C1] | 3-isopropyl-1-[3-(3-methoxyazetidin-1-yl)phenyl]-4-(4-morpholinophenyl)pyrazolo[3,4-b]pyridine-6-carboxylic acid | E008 | J1 | 527 | 528 |
| A044 | 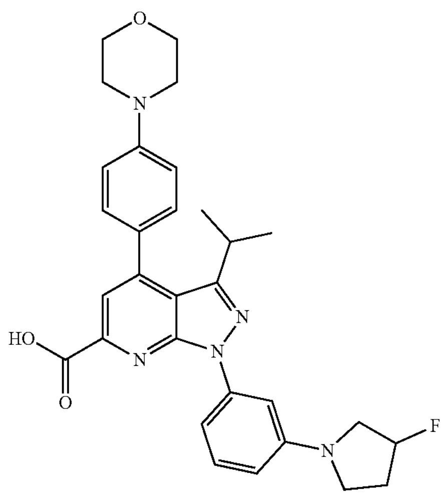 [SMILES: CC(C)c1nn(-c2cccc(N3CCC(F)C3)c2)c2nc(C(=O)O)cc(-c3ccc(N4CCOCC4)cc3)c12] | 1-[3-(3-fluoropyrrolidin-1-yl)phenyl]-3-isopropyl-4-(4-morpholinophenyl)pyrazolo[3,4-b]pyridine-6-carboxylic acid | E013 | J1 | 529 | 530 |
| A045 | 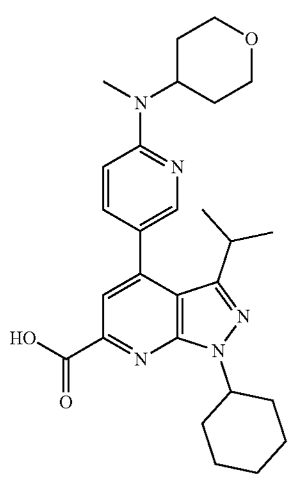 [SMILES: CC(C)c1nn(C2CCCCC2)c2nc(C(=O)O)cc(-c3ccc(N(C)C4CCOCC4)nc3)c12] | 1-cyclohexyl-3-isopropyl-4-[6-[methyl(tetrahydropyran-4-yl)amino]-3-pyridyl]pyrazolo[3,4-b]pyridine-6-carboxylic acid | E014 | J1 | 477 | 478 |

TABLE XIII-continued

List of acids

| Int. | Structure | Name | SM | method | MW | Mes |
|---|---|---|---|---|---|---|
| A046 | 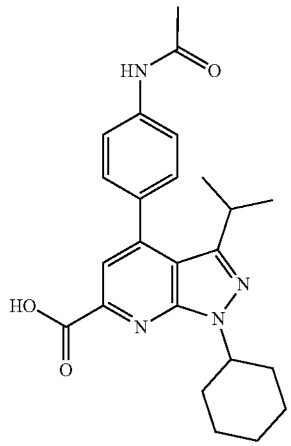 [SMILES: CC(=O)Nc1ccc(-c2cc(C(=O)O)nc3c2c(C(C)C)nn3C2CCCCC2)cc1] | 4-(4-acetamidophenyl)-1-cyclohexyl-3-isopropyl-pyrazolo[3,4-b]pyridine-6-carboxylic acid | E021 | J1 | 420 | 421 |
| A047 | 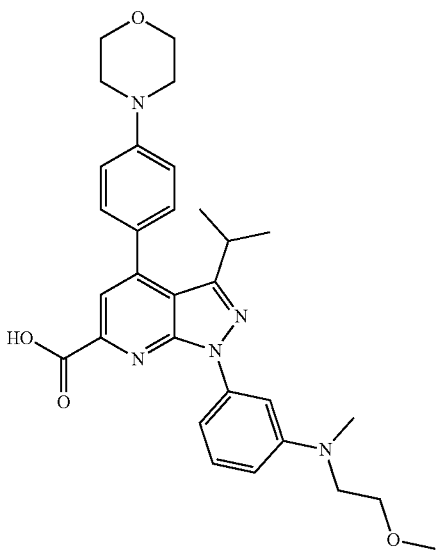 [SMILES: COCCN(C)c1cccc(-n2nc(C(C)C)c3c(-c4ccc(N5CCOCC5)cc4)cc(C(=O)O)nc32)c1] | 3-isopropyl-1-[3-[2-methoxyethyl(methyl)amino]phenyl]-4-(4-morpholinophenyl)pyrazolo[3,4-b]pyridine-6-carboxylic acid | A242 | J7 | 529 | 530 |
| A048 | 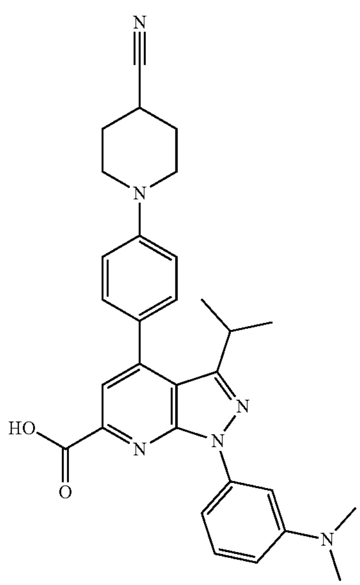 [SMILES: CC(C)c1nn(-c2cccc(N(C)C)c2)c2nc(C(=O)O)cc(-c3ccc(N4CCC(C#N)CC4)cc3)c12] | 4-[4-(4-cyano-1-piperidyl)phenyl]-1-[3-(dimethylamino)phenyl]-3-isopropyl-pyrazolo[3,4-b]pyridine-6-carboxylic acid | E023 | J1 | 508 | 509 |

TABLE XIII-continued
| | | List of acids | | | | |
|---|---|---|---|---|---|---|
| Int. | Structure | Name | SM | method | MW | Mes |
| A049 | 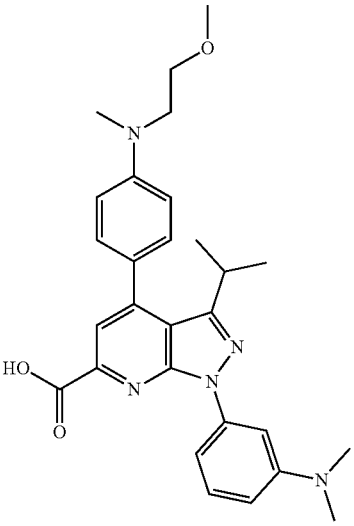 [SMILES: COCCN(C)c1ccc(-c2cc(C(=O)O)nc3c2c(C(C)C)nn3-c2cccc(N(C)C)c2)cc1] | 1-[3-(dimethylamino)phenyl]-3-isopropyl-4-[4-[2-methoxyethyl(methyl)amino]phenyl]pyrazolo[3,4-b]pyridine-6-carboxylic acid | E024 | J1 | 487 | 488 |
| A050 | 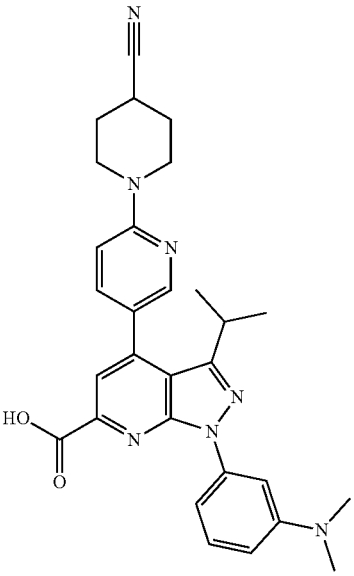 [SMILES: CC(C)c1nn(-c2cccc(N(C)C)c2)c2nc(C(=O)O)cc(-c3ccc(N4CCC(C#N)CC4)nc3)c12] | 4-[6-(4-cyano-1-piperidyl)-3-pyridyl]-1-[3-(dimethylamino)phenyl]-3-isopropyl-pyrazolo[3,4-b]pyridine-6-carboxylic acid | E025 | J1 | 509 | 510 |

TABLE XIII-continued
List of acids
| Int. | Structure | Name | SM | method | MW | Mes |
|------|-----------|------|-----|--------|-----|-----|
| A051 | 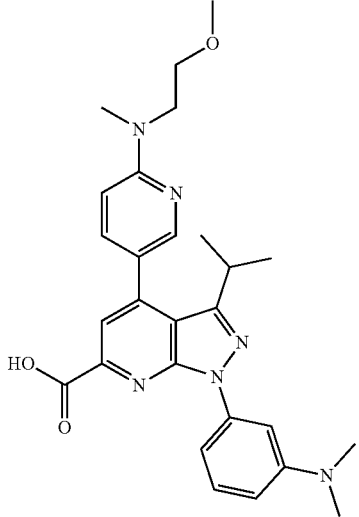 [SMILES: COCCN(C)c1ccc(-c2cc(C(=O)O)nc3c2c(C(C)C)nn3-c2cccc(N(C)C)c2)cn1] | 1-[3-(dimethylamino)phenyl]-3-isopropyl-4-[6-[2-methoxyethyl(methyl)amino]-3-pyridyl]pyrazolo[3,4-b]pyridine-6-carboxylic acid | E026 | J1 | 488 | 489 |
| A052 | 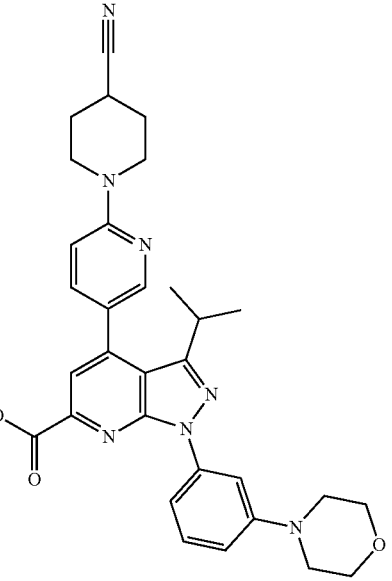 | 4-[6-(4-cyano-1-piperidyl)-3-pyridyl]-3-isopropyl-1-(3-morpholinophenyl)pyrazolo[3,4-b]pyridine-6-carboxylic acid | E027 | J1 | 551 | 552 |

TABLE XIII-continued

List of acids

| Int. | Structure | Name | SM | method | MW | Mes |
|---|---|---|---|---|---|---|
| A053 | 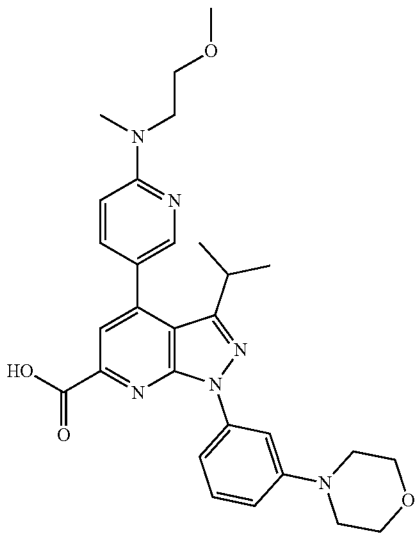 [SMILES: COCCN(C)c1ccc(-c2cc(C(=O)O)nc3c2c(C(C)C)nn3-c2cccc(N3CCOCC3)c2)cn1] | 3-isopropyl-4-[6-[2-methoxyethyl(methyl)amino]-3-pyridyl]-1-(3-morpholinophenyl)pyrazolo[3,4-b]pyridine-6-carboxylic acid | E028 | J1 | 530 | 531 |
| A054 | 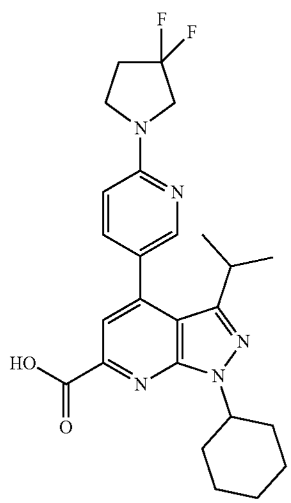 [SMILES: CC(C)c1nn(C2CCCCC2)c2nc(C(=O)O)cc(-c3ccc(N4CCC(F)(F)C4)nc3)c12] | 1-cyclohexyl-4-[6-(3,3-difluoropyrrolidin-1-yl)-3-pyridyl]-3-isopropyl-pyrazolo[3,4-b]pyridine-6-carboxylic acid | A250 | J5 | 469 | 470 |
| A055 | 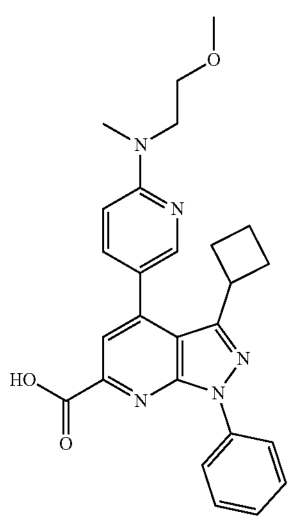 [SMILES: COCCN(C)c1ccc(-c2cc(C(=O)O)nc3c2c(C2CCC2)nn3-c2ccccc2)cn1] | 3-cyclobutyl-4-[6-[2-methoxyethyl(methyl)amino]-3-pyridyl]-1-phenyl-pyrazolo[3,4-b]pyridine-6-carboxylic acid | E017 | J1 | 457 | 458 |

TABLE XIII-continued

List of acids

| Int. | Structure | Name | SM | method | MW | Mes |
|---|---|---|---|---|---|---|
| A056 | 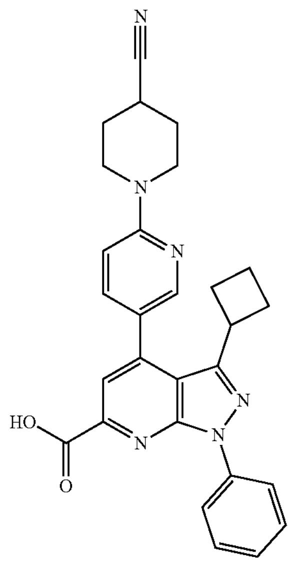 [SMILES: N#CC1CCN(c2ccc(-c3cc(C(=O)O)nc4c3c(C3CCC3)nn4-c3ccccc3)cn2)CC1] | 4-[6-(4-cyano-1-piperidyl)-3-pyridyl]-3-cyclobutyl-1-phenyl-pyrazolo[3,4-b]pyridine-6-carboxylic acid | E018 | J1 Specific example | 478 | 479 |
| A057 | 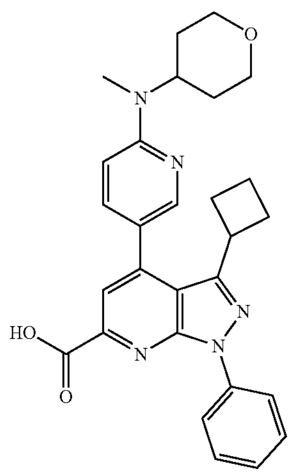 [SMILES: CN(c1ccc(-c2cc(C(=O)O)nc3c2c(C2CCC2)nn3-c2ccccc2)cn1)C1CCOCC1] | 3-cyclobutyl-4-[6-[methyl(tetrahydro-pyran-4-yl)amino]-3-pyridyl]-1-phenyl-pyrazolo[3,4-b]pyridine-6-carboxylic acid | E019 | J1 | 483 | 484 |
| A058 | 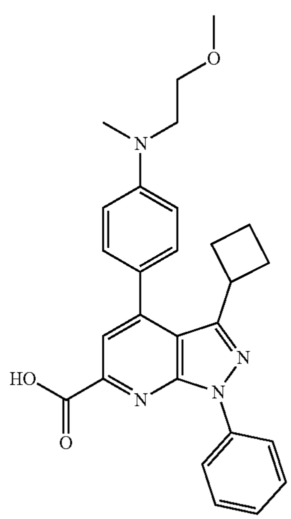 [SMILES: COCCN(C)c1ccc(-c2cc(C(=O)O)nc3c2c(C2CCC2)nn3-c2ccccc2)cc1] | 3-cyclobutyl-4-[4-[2-methoxyethyl(methyl)amino]phenyl]-1-phenyl-pyrazolo[3,4-b]pyridine-6-carboxylic acid | E020 | J1 | 456 | 457 |

TABLE XIII-continued

List of acids

| Int. | Structure | Name | SM | method | MW | Mes |
|---|---|---|---|---|---|---|
| A059 | 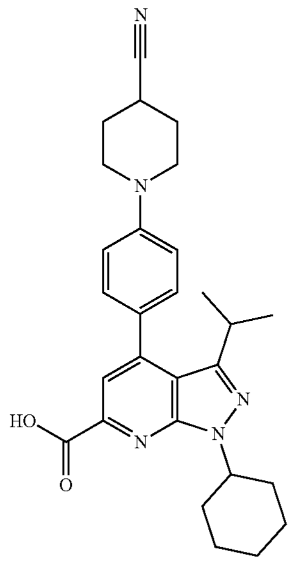 [SMILES: CC(C)c1nn(C2CCCCC2)c2nc(C(=O)O)cc(-c3ccc(N4CCC(C#N)CC4)cc3)c12] | 4-[4-(4-cyano-1-piperidyl)phenyl]-1-cyclohexyl-3-isopropyl-pyrazolo[3,4-b]pyridine-6-carboxylic acid | E022 | J1 | 471 | 472 |
| A060 | 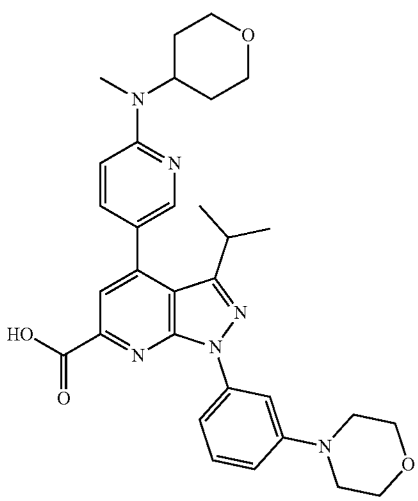 [SMILES: CC(C)c1nn(-c2cccc(N3CCOCC3)c2)c2nc(C(=O)O)cc(-c3ccc(N(C)C4CCOCC4)nc3)c12] | 3-isopropyl-4-[6-[methyl(tetrahydro-pyran-4-yl)amino]-3-pyridyl]-1-(3-morpholinophenyl)pyrazolo[3,4-b]pyridine-6-carboxylic acid | E029 | J1 | 556 | 557 |
| A061 | 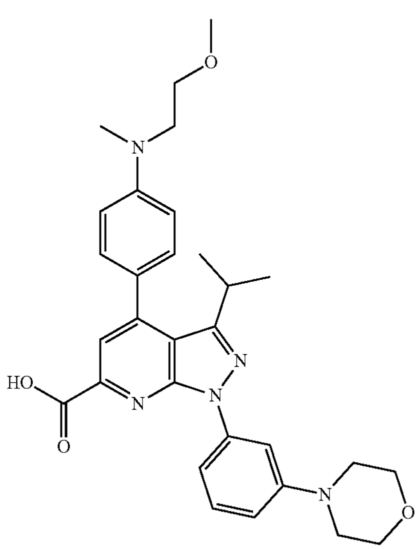 [SMILES: COCCN(C)c1ccc(-c2cc(C(=O)O)nc3c2c(C(C)C)nn3-c2cccc(N3CCOCC3)c2)cc1] | 3-isopropyl-4-[4-[2-methoxyethyl(methyl)amino]phenyl]-1-(3-morpholinophenyl)pyrazolo[3,4-b]pyridine-6-carboxylic acid | E030 | J1 | 529 | 530 |

TABLE XIII-continued

List of acids

| Int. | Structure | Name | SM | method | MW | Mes |
|---|---|---|---|---|---|---|
| A062 | 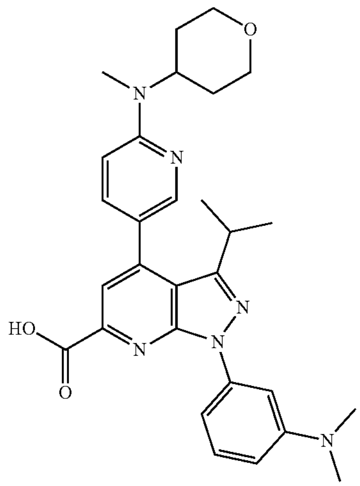 [SMILES: CC(C)c1nn(-c2cccc(N(C)C)c2)c2nc(C(=O)O)cc(-c3ccc(N(C)C4CCOCC4)nc3)c12] | 1-[3-(dimethylamino)phenyl]-3-isopropyl-4-[6-[methyl(tetrahydro-pyran-4-yl)amino]-3-pyridyl]pyrazolo[3,4-b]pyridine-6-carboxylic acid | E031 | J1 | 514 | 515 |
| A063 | 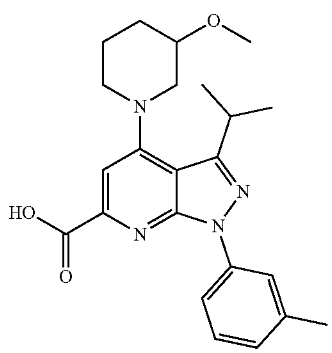 [SMILES: COC1CCCN(c2cc(C(=O)O)nc3c2c(C(C)C)nn3-c2cccc(C)c2)C1] | 3-isopropyl-4-(3-methoxy-1-piperidyl)-1-(m-tolyl)pyrazolo[3,4-b]pyridine-6-carboxylic acid | E088 | J1 | 408 | 409 |
| A064 | 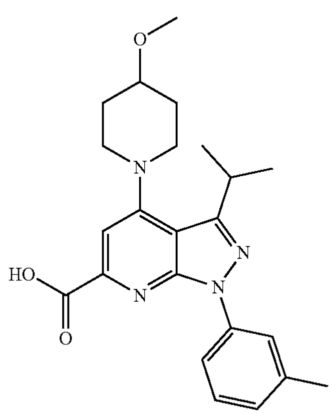 [SMILES: COC1CCN(c2cc(C(=O)O)nc3c2c(C(C)C)nn3-c2cccc(C)c2)CC1] | 3-isopropyl-4-(4-methoxy-1-piperidyl)-1-(m-tolyl)pyrazolo[3,4-b]pyridine-6-carboxylic acid | E048 | J1 | 408 | 409 |

TABLE XIII-continued

List of acids

| Int. | Structure | Name | SM | method | MW | Mes |
|------|-----------|------|-----|--------|-----|-----|
| A065 | 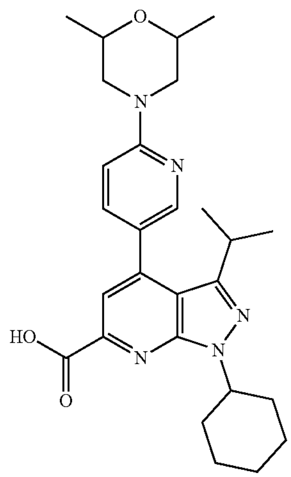 [SMILES: CC1CN(c2ccc(-c3cc(C(=O)O)nc4c3c(C(C)C)nn4C3CCCCC3)cn2)CC(C)O1] | 1-cyclohexyl-4-[6-(2,6-dimethylmorpholin-4-yl)-3-pyridyl]-3-isopropyl-pyrazolo[3,4-b]pyridine-6-carboxylic acid | A250 | J5 Specific example | 477 | 478 |
| A066 | 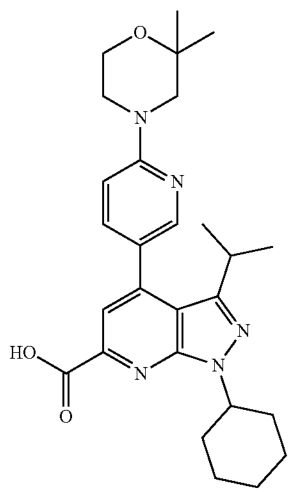 [SMILES: CC(C)c1nn(C2CCCCC2)c2nc(C(=O)O)cc(-c3ccc(N4CCOC(C)(C)C4)nc3)c12] | 1-cyclohexyl-4-[6-(2,2-dimethylmorpholin-4-yl)-3-pyridyl]-3-isopropyl-pyrazolo[3,4-b]pyridine-6-carboxylic acid | A250 | J5 | 477 | 478 |
| A067 | 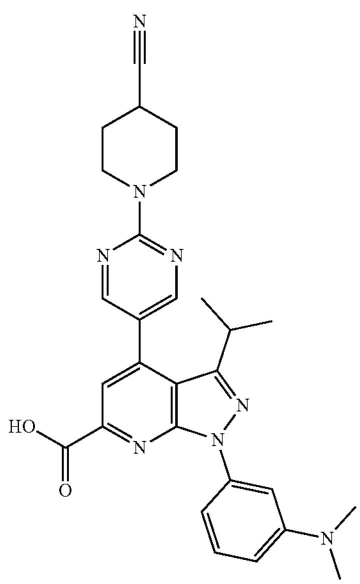 [SMILES: CC(C)c1nn(-c2cccc(N(C)C)c2)c2nc(C(=O)O)cc(-c3cnc(N4CCC(C#N)CC4)nc3)c12] | 4-[2-(4-cyano-1-piperidyl)pyrimidin-5-yl]-1-[3-(dimethylamino)phenyl]-3-isopropyl-pyrazolo[3,4-b]pyridine-6-carboxylic acid | E034 | J1 | 510 | 511 |

TABLE XIII-continued

List of acids

| Int. | Structure | Name | SM | method | MW | Mes |
|------|-----------|------|-----|--------|-----|-----|
| A068 | 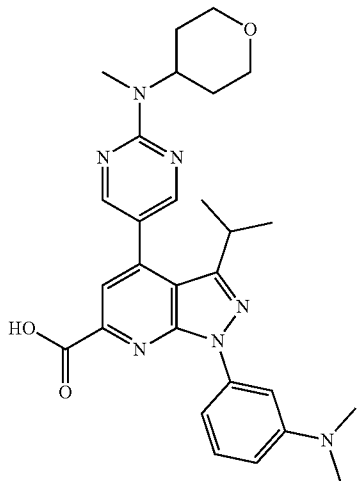 [SMILES: CC(C)c1nn(-c2cccc(N(C)C)c2)c2nc(C(=O)O)cc(-c3cnc(N(C)C4CCOCC4)nc3)c12] | 1-[3-(dimethylamino)phenyl]-3-isopropyl-4-[2-[methyl(tetrahydro-pyran-4-yl)amino]pyrimidin-5-yl]pyrazolo[3,4-b]pyridine-6-carboxylic acid | E032 | J1 | 515 | 516 |
| A069 | 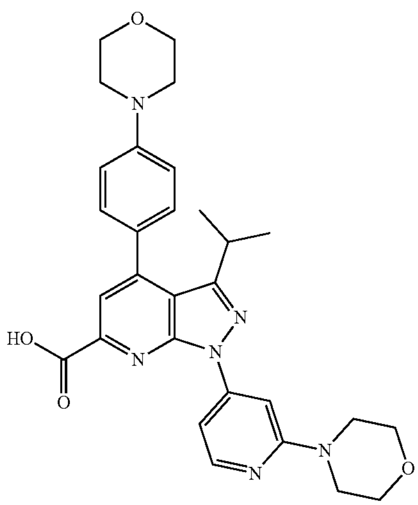 [SMILES: CC(C)c1nn(-c2ccnc(N3CCOCC3)c2)c2nc(C(=O)O)cc(-c3ccc(N4CCOCC4)cc3)c12] | 3-isopropyl-4-(4-morpholinophenyl)-1-(2-morpholino-4-pyridyl)pyrazolo[3,4-b]pyridine-6-carboxylic acid | E066 | J1 | 528 | 529 |
| A070 | 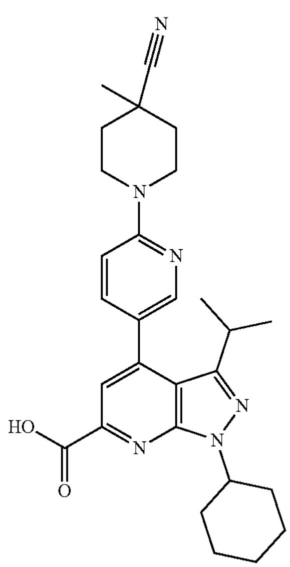 [SMILES: CC(C)c1nn(C2CCCCC2)c2nc(C(=O)O)cc(-c3ccc(N4CCC(C)(C#N)CC4)nc3)c12] | 4-[6-(4-cyano-4-methyl-1-piperidyl)-3-pyridyl]-1-cyclohexyl-3-isopropyl-pyrazolo[3,4-b]pyridine-6-carboxylic acid | A250 | J5 | 486 | 487 |

TABLE XIII-continued

List of acids

| Int. | Structure | Name | SM | method | MW | Mes |
|---|---|---|---|---|---|---|
| A071 | 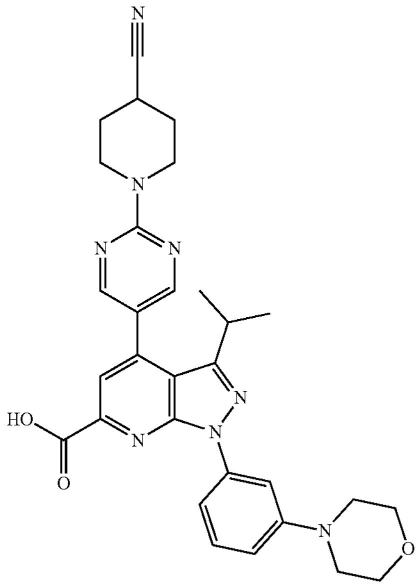 [SMILES: CC(C)c1nn(-c2cccc(N3CCOCC3)c2)c2nc(C(=O)O)cc(-c3cnc(N4CCC(C#N)CC4)nc3)c12] | 4-[2-(4-cyano-1-piperidyl)pyrimidin-5-yl]-3-isopropyl-1-(3-morpholinophenyl)pyrazolo[3,4-b]pyridine-6-carboxylic acid | E037 | J1 | 552 | 553 |
| A072 | 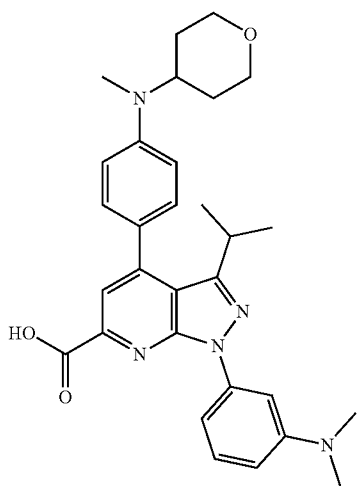 [SMILES: CC(C)c1nn(-c2cccc(N(C)C)c2)c2nc(C(=O)O)cc(-c3ccc(N(C)C4CCOCC4)cc3)c12] | 1-[3-(dimethylamino)phenyl]-3-isopropyl-4-[4-[methyl(tetrahydro-pyran-4-yl)amino]phenyl]pyrazolo[3,4-b]pyridine-6-carboxylic acid | E035 | J1 | 513 | 514 |
| A073 | 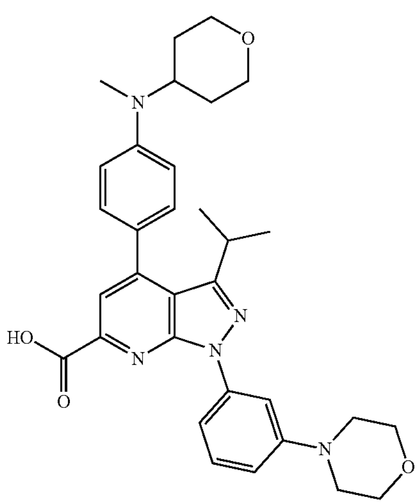 [SMILES: CC(C)c1nn(-c2cccc(N3CCOCC3)c2)c2nc(C(=O)O)cc(-c3ccc(N(C)C4CCOCC4)cc3)c12] | 3-isopropyl-4-[4-[methyl(tetrahydro-pyran-4-yl)amino]phenyl]-1-(3-morpholinophenyl)pyrazolo[3,4-b]pyridine-6-carboxylic acid | E036 | J1 | 555 | 556 |

TABLE XIII-continued

List of acids

| Int. | Structure | Name | SM | method | MW | Mes |
|---|---|---|---|---|---|---|
| A074 | 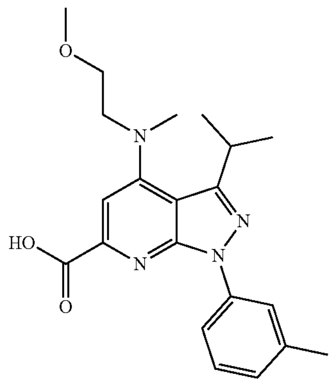 [SMILES: COCCN(C)c1cc(C(=O)O)nc2c1c(C(C)C)nn2-c1cccc(C)c1] | 3-isopropyl-4-[2-methoxyethyl(methyl)amino]-1-(m-tolyl)pyrazolo[3,4-b]pyridine-6-carboxylic acid | E094 | J1 | 382 | 383 |
| A075 | 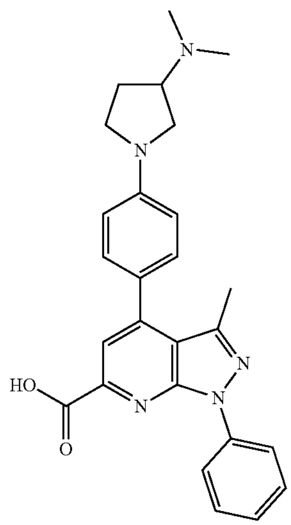 [SMILES: Cc1nn(-c2ccccc2)c2nc(C(=O)O)cc(-c3ccc(N4CCC(N(C)C)C4)cc3)c12] | 4-[4-[3-(dimethylamino)pyrrolidin-1-yl]phenyl]-3-methyl-1-phenyl-pyrazolo[3,4-b]pyridine-6-carboxylic acid | E038 | J1 | 441 | 442 |
| A076 | 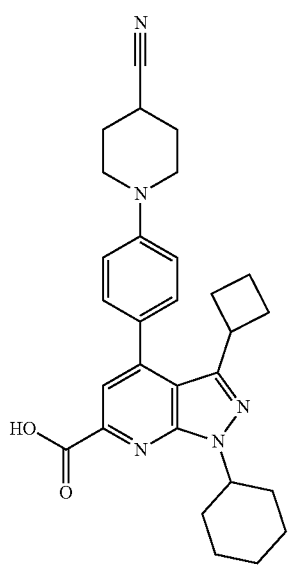 [SMILES: N#CC1CCN(c2ccc(-c3cc(C(=O)O)nc4c3c(C3CCC3)nn4C3CCCCC3)cc2)CC1] | 4-[4-(4-cyano-1-piperidyl)phenyl]-3-cyclobutyl-1-cyclohexyl-pyrazolo[3,4-b]pyridine-6-carboxylic acid | E040 | J1 | 483 | 484 |

TABLE XIII-continued

| Int. | Structure | Name | SM | method | MW | Mes |
|---|---|---|---|---|---|---|
| A077 | 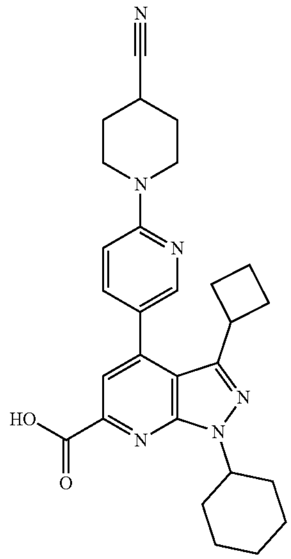 [SMILES: N#CC1CCN(c2ccc(-c3cc(C(=O)O)nc4c3c(C3CCC3)nn4C3CCCCC3)cn2)CC1] | 4-[6-(4-cyano-1-piperidyl)-3-pyridyl]-3-cyclobutyl-1-cyclohexyl-pyrazolo[3,4-b]pyridine-6-carboxylic acid | E041 | J1 | 484 | 485 |
| A078 | 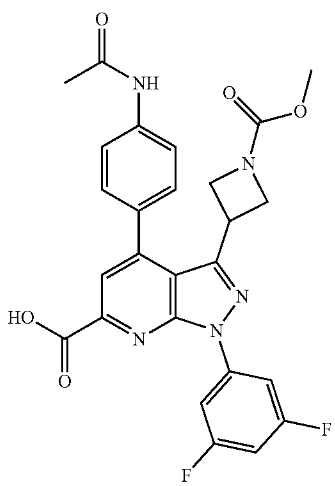 [SMILES: COC(=O)N1CC(c2nn(-c3cc(F)cc(F)c3)c3nc(C(=O)O)cc(-c4ccc(NC(C)=O)cc4)c23)C1] | 4-(4-acetamidophenyl)-1-(3,5-difluorophenyl)-3-(1-methoxycarbonyl azetidin-3-yl)pyrazolo[3,4-b]pyridine-6-carboxylic acid | E042 | J1 | 521 | 522 |
| A079 | 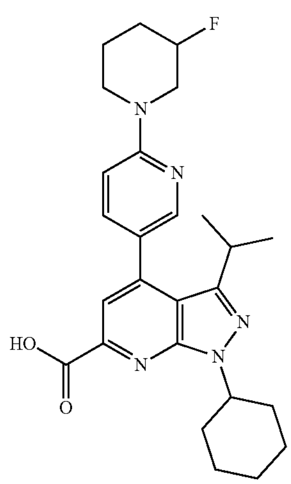 [SMILES: CC(C)c1nn(C2CCCCC2)c2nc(C(=O)O)cc(-c3ccc(N4CCCC(F)C4)nc3)c12] | 1-cyclohexyl-4-[6-(3-fluoro-1-piperidyl)-3-pyridyl]-3-isopropyl-pyrazolo[3,4-b]pyridine-6-carboxylic acid | A250 | J5 | 465 | 466 |

TABLE XIII-continued
List of acids
| Int. | Structure | Name | SM | method | MW | Mes |
|---|---|---|---|---|---|---|
| A080 | 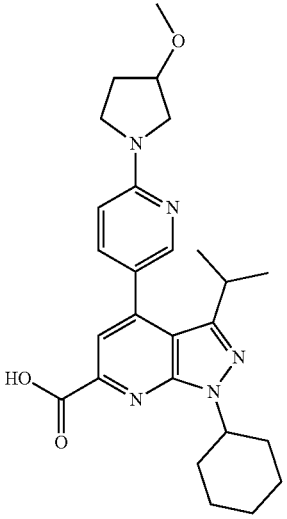 [SMILES: COC1CCN(c2ccc(-c3cc(C(=O)O)nc4c3c(C(C)C)nn4C3CCCCC3)cn2)C1] | 1-cyclohexyl-3-isopropyl-4-[6-(3-methoxypyrrolidin-1-yl)-3-pyridyl]pyrazolo[3,4-b]pyridine-6-carboxylic acid | A250 | J5 | 463 | 464 |
| A081 | 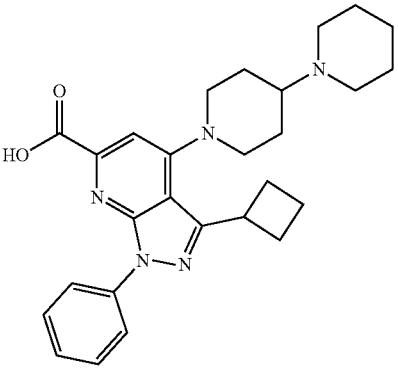 [SMILES: O=C(O)c1cc(N2CCC(N3CCCCC3)CC2)c2c(C3CCC3)nn(-c3ccccc3)c2n1] | 3-cyclobutyl-1-phenyl-4-[4-(1-piperidyl)-1-piperidyl]pyrazolo-[3,4-b]pyridine-6-carboxylic acid | HP10 | J10 Specific example | 459 | 460 |
| A082 | 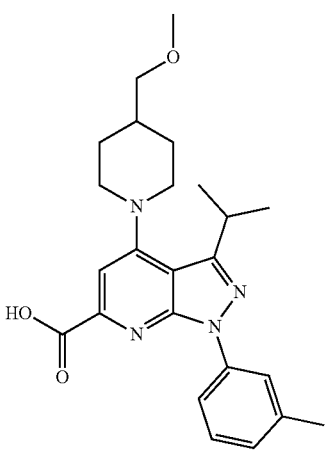 [SMILES: COCC1CCN(c2cc(C(=O)O)nc3c2c(C(C)C)nn3-c2cccc(C)c2)CC1] | 3-isopropyl-4-[4-(methoxymethyl)-1-piperidyl]-1-(m-tolyl)pyrazolo[3,4-b]pyridine-6-carboxylic acid | E082 | J1 | 422 | 423 |

TABLE XIII-continued

| | | List of acids | | | | |
|---|---|---|---|---|---|---|
| Int. | Structure | Name | SM | method | MW | Mes |
| A083 | | 3-isopropyl-4-[4-(2-methoxyethyl)-1-piperidyl]-1-(m-tolyl)pyrazolo[3,4-b]pyridine-6-carboxylic acid | E087 | J1 | 436 | 437 |
| A084 | | 4-[2-(4-cyano-1-piperidyl)pyrimidin-5-yl]-1-cyclohexyl-3-isopropyl-pyrazolo[3,4-b]pyridine-6-carboxylic acid | E049 | J1 | 473 | 474 |
| A085 | | 1-cyclohexyl-3-isopropyl-4-[2-[methyl(tetrahydro-pyran-4-yl)amino]pyrimidin-5-yl]pyrazolo[3,4-b]pyridine-6-carboxylic acid | E051 | J1 | 478 | 479 |

TABLE XIII-continued

List of acids

| Int. | Structure | Name | SM | method | MW | Mes |
|---|---|---|---|---|---|---|
| A086 | 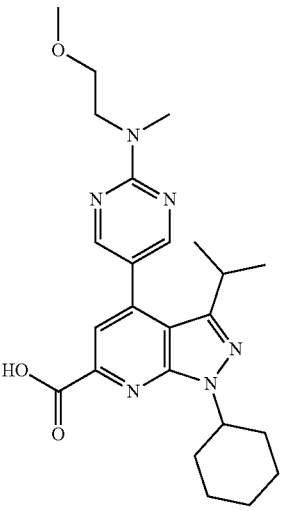 [SMILES: COCCN(C)c1ncc(-c2cc(C(=O)O)nc3c2c(C(C)C)nn3C2CCCCC2)cn1] | 1-cyclohexyl-3-isopropyl-4-[2-[2-methoxyethyl(methyl)amino]pyrimidin-5-yl]pyrazolo[3,4-b]pyridine-6-carboxylic acid | E050 | J1 | 452 | 453 |
| A087 | 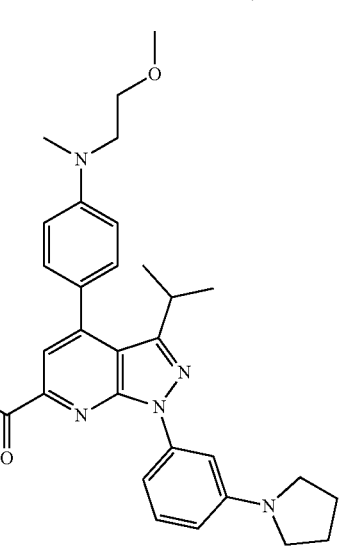 | 3-isopropyl-4-[4-[2-methoxyethyl(methyl)amino]phenyl]-1-(3-pyrrolidin-1-ylphenyl)pyrazolo[3,4-b]pyridine-6-carboxylic acid | E045 | J1 | 513 | 514 |
| A088 | 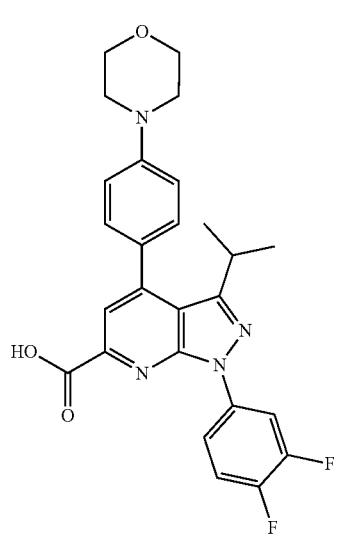 [SMILES: CC(C)c1nn(-c2ccc(F)c(F)c2)c2nc(C(=O)O)cc(-c3ccc(N4CCOCC4)cc3)c12] | 1-(3,4-difluorophenyl)-3-isopropyl-4-(4-morpholinophenyl)pyrazolo[3,4-b]pyridine-6-carboxylic acid | E057 | J1 | 478 | 479 |

TABLE XIII-continued

List of acids

| Int. | Structure | Name | SM | method | MW | Mes |
|---|---|---|---|---|---|---|
| A089 | 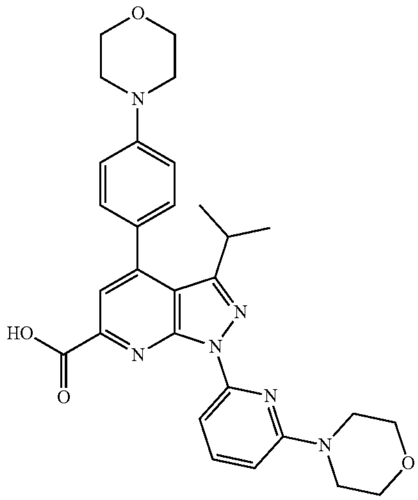 [SMILES: CC(C)c1nn(-c2cccc(N3CCOCC3)n2)c2nc(C(=O)O)cc(-c3ccc(N4CCOCC4)cc3)c12] | 3-isopropyl-4-(4-morpholinophenyl)-1-(6-morpholino-2-pyridyl)pyrazolo[3,4-b]pyridine-6-carboxylic acid | E058 | J1 | 528 | 529 |
| A090 | 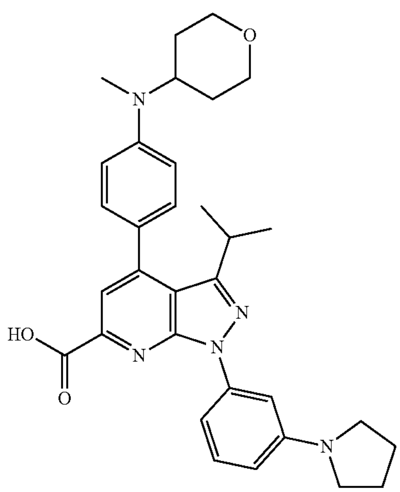 [SMILES: CC(C)c1nn(-c2cccc(N3CCCC3)c2)c2nc(C(=O)O)cc(-c3ccc(N(C)C4CCOCC4)cc3)c12] | 3-isopropyl-4-[4-[methyl(tetrahydro-pyran-4-yl)amino]phenyl]-1-(3-pyrrolidin-1-ylphenyl)pyrazolo[3,4-b]pyridine-6-carboxylic acid | E046 | J1 | 539 | 540 |
| A091 | 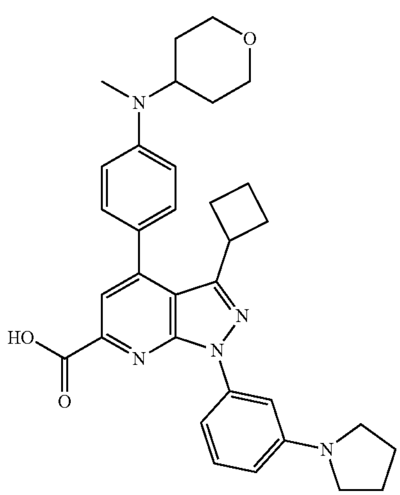 [SMILES: CN(c1ccc(-c2cc(C(=O)O)nc3c2c(C2CCC2)nn3-c2cccc(N3CCCC3)c2)cc1)C1CCOCC1] | 3-cyclobutyl-4-[4-[methyl(tetrahydro-pyran-4-yl)amino]phenyl]-1-(3-pyrrolidin-1-ylphenyl)pyrazolo[3,4-b]pyridine-6-carboxylic acid | E047 | J1 | 551 | 552 |

TABLE XIII-continued

List of acids

| Int. | Structure | Name | SM | method | MW | Mes |
|---|---|---|---|---|---|---|
| A092 | 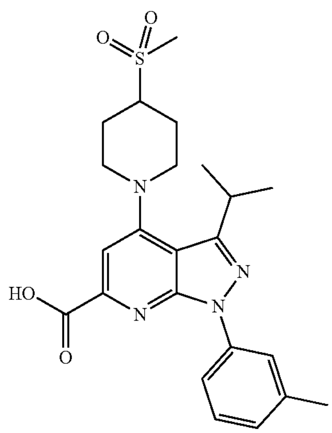 [SMILES: Cc1cccc(-n2nc(C(C)C)c3c(N4CCC(S(C)(=O)=O)CC4)cc(C(=O)O)nc32)c1] | 3-isopropyl-4-(4-methylsulfonyl-1-piperidyl)-1-(m-tolyl)pyrazolo[3,4-b]pyridine-6-carboxylic acid | E089 | J1 | 456 | 457 |
| A093 | 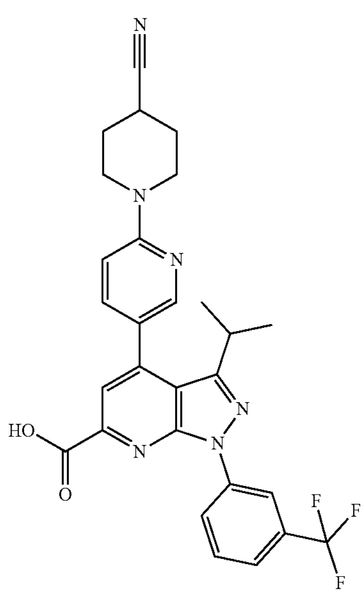 [SMILES: CC(C)c1nn(-c2cccc(C(F)(F)F)c2)c2nc(C(=O)O)cc(-c3ccc(N4CCC(C#N)CC4)nc3)c12] | 4-[6-(4-cyano-1-piperidyl)-3-pyridyl]-3-isopropyl-1-[3-(trifluoromethyl)phenyl]pyrazolo[3,4-b]pyridine-6-carboxylic acid | E052 | J1 | 534 | 535 |

TABLE XIII-continued
| Int. | Structure | Name | SM | method | MW | Mes |
|---|---|---|---|---|---|---|
| A094 | 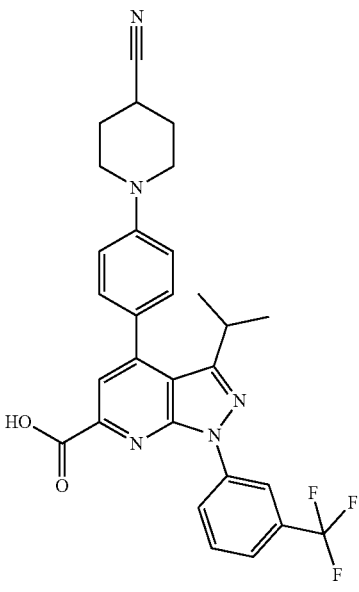 [SMILES: CC(C)c1nn(-c2cccc(C(F)(F)F)c2)c2nc(C(=O)O)cc(-c3ccc(N4CCC(C#N)CC4)cc3)c12] | 4-[4-(4-cyano-1-piperidyl)phenyl]-3-isopropyl-1-[3-(trifluoromethyl)phenyl]pyrazolo[3,4-b]pyridine-6-carboxylic acid | E065 | J1 | 533 | 534 |
| A095 | 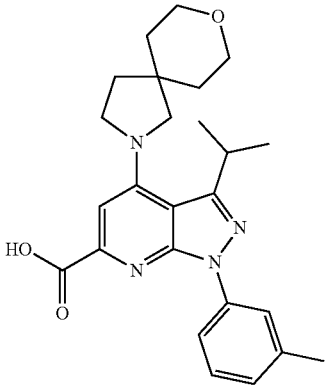 [SMILES: Cc1cccc(-n2nc(C(C)C)c3c(N4CCC5(CCOCC5)C4)cc(C(=O)O)nc32)c1] | 3-isopropyl-1-(m-tolyl)-4-(8-oxa-3-azaspiro[4.5]decan-3-yl)pyrazolo[3,4-b]pyridine-6-carboxylic acid | E095 | J1 | 434 | 435 |
| A096 | 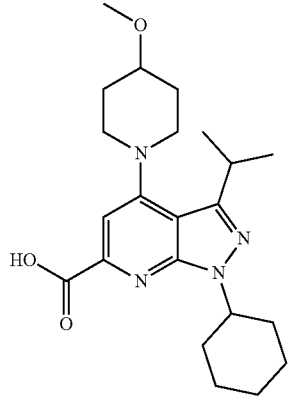 [SMILES: COC1CCN(c2cc(C(=O)O)nc3c2c(C(C)C)nn3C2CCCCC2)CC1] | 1-cyclohexyl-3-isopropyl-4-(4-methoxy-1-piperidyl)pyrazolo[3,4-b]pyridine-6-carboxylic acid | E076 | J1 | 400 | 401 |

TABLE XIII-continued

List of acids

| Int. | Structure | Name | SM | method | MW | Mes |
|---|---|---|---|---|---|---|
| A097 | 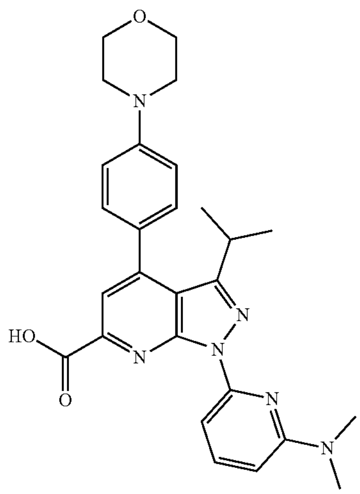 [SMILES: CC(C)c1nn(-c2cccc(N(C)C)n2)c2nc(C(=O)O)cc(-c3ccc(N4CCOCC4)cc3)c12] | 1-[6-(dimethylamino)-2-pyridyl]-3-isopropyl-4-(4-morpholinophenyl)pyrazolo[3,4-b]pyridine-6-carboxylic acid | E053 | J1 | 486 | 487 |
| A098 | 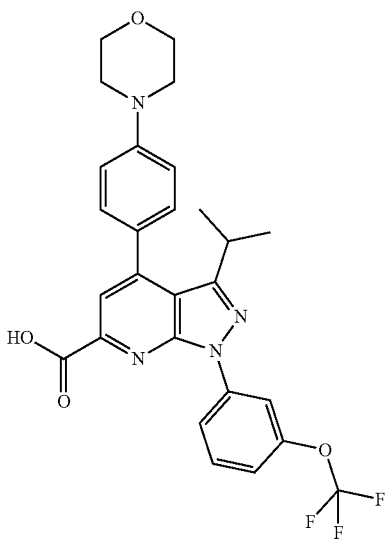 [SMILES: CC(C)c1nn(-c2cccc(OC(F)(F)F)c2)c2nc(C(=O)O)cc(-c3ccc(N4CCOCC4)cc3)c12] | 3-isopropyl-4-(4-morpholinophenyl)-1-[3-(trifluoromethoxy)phenyl]pyrazolo[3,4-b]pyridine-6-carboxylic acid | E054 | J1 | 526 | 527 |
| A099 | 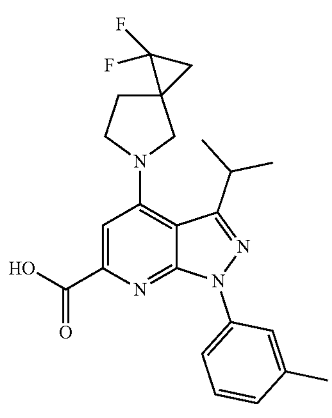 [SMILES: Cc1cccc(-n2nc(C(C)C)c3c(N4CCC5(C4)CC5(F)F)cc(C(=O)O)nc32)c1] | 4-(2,2-difluoro-6-azaspiro[2.4]heptan-6-yl)-3-isopropyl-1-(m-tolyl)pyrazolo[3,4-b]pyridine-6-carboxylic acid | E075 | J1 | 426 | 427 |

TABLE XIII-continued

List of acids

| Int. | Structure | Name | SM | method | MW | Mes |
|---|---|---|---|---|---|---|
| A100 | 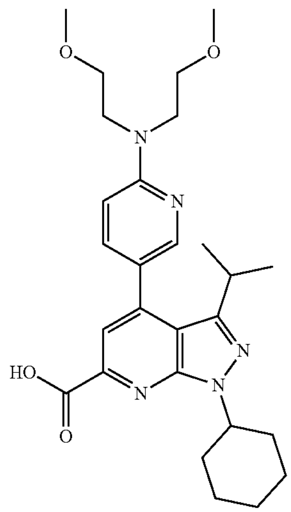 [SMILES: COCCN(CCOC)c1ccc(-c2cc(C(=O)O)nc3c2c(C(C)C)nn3C2CCCCC2)cn1] | 4-[6-[bis(2-methoxyethyl)amino]-3-pyridyl]-1-cyclohexyl-3-isopropyl-pyrazolo[3,4-b]pyridine-6-carboxylic acid | A250 | J5 | 495 | 496 |
| A101 | 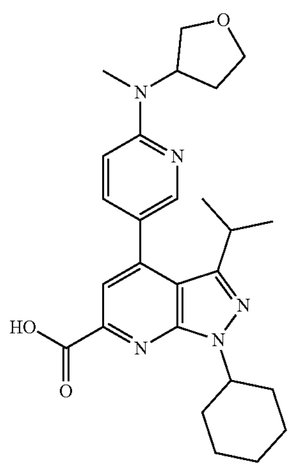 [SMILES: CC(C)c1nn(C2CCCCC2)c2nc(C(=O)O)cc(-c3ccc(N(C)C4CCOC4)nc3)c12] | 1-cyclohexyl-3-isopropyl-4-[6-[methyl(tetrahydrofuran-3-yl)amino]-3-pyridyl]pyrazolo[3,4-b]pyridine-6-carboxylic acid | A250 | J5 | 463 | 464 |
| A102 | 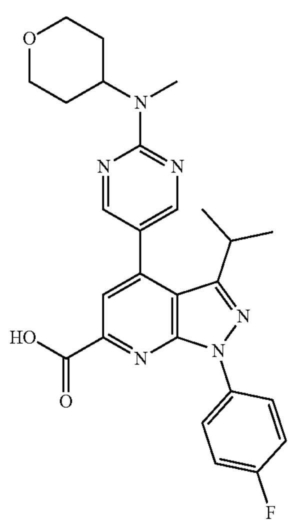 [SMILES: CC(C)c1nn(-c2ccc(F)cc2)c2nc(C(=O)O)cc(-c3cnc(N(C)C4CCOCC4)nc3)c12] | 1-(4-fluorophenyl)-3-isopropyl-4-[2-[methyl(tetrahydropyran-4-yl)amino]pyrimidin-5-yl]pyrazolo[3,4-b]pyridine-6-carboxylic acid | E064 | J1 | 490 | 491 |

TABLE XIII-continued

List of acids

| Int. | Structure | Name | SM | method | MW | Mes |
|---|---|---|---|---|---|---|
| A103 | 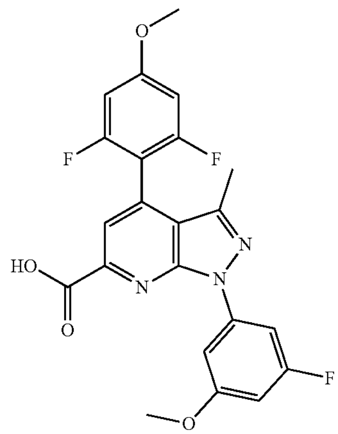 [SMILES: COc1cc(F)cc(-n2nc(C)c3c(-c4c(F)cc(OC)cc4F)cc(C(=O)O)nc32)c1] | 4-(2,6-difluoro-4-methoxy-phenyl)-1-(3-fluoro-5-methoxy-phenyl)-3-methyl-pyrazolo[3,4-b]pyridine-6-carboxylic acid | E059 | J1 | 443 | 444 |
| A104 | 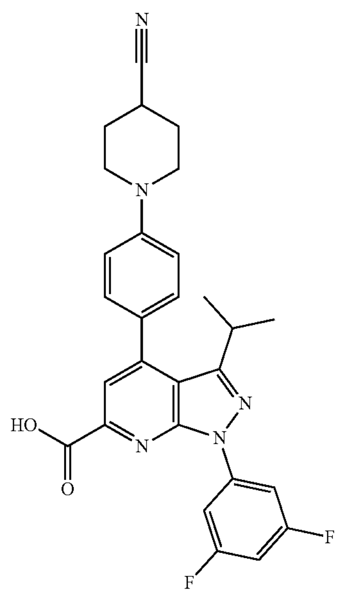 [SMILES: CC(C)c1nn(-c2cc(F)cc(F)c2)c2nc(C(=O)O)cc(-c3ccc(N4CCC(C#N)CC4)cc3)c12] | 4-[4-(4-cyano-1-piperidyl)phenyl]-1-(3,5-difluorophenyl)-3-isopropyl-pyrazolo[3,4-b]pyridine-6-carboxylic acid | E060 | J1 | 501 | 502 |
| A105 | 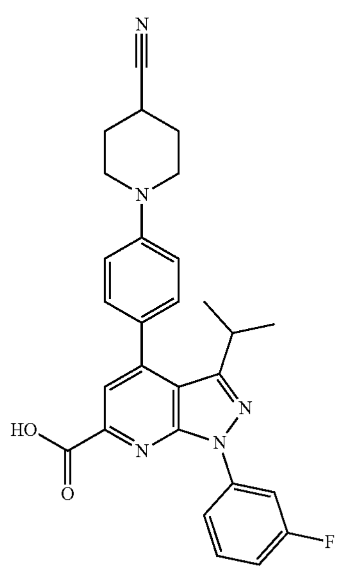 [SMILES: CC(C)c1nn(-c2cccc(F)c2)c2nc(C(=O)O)cc(-c3ccc(N4CCC(C#N)CC4)cc3)c12] | 4-[4-(4-cyano-1-piperidyl)phenyl]-1-(3-fluorophenyl)-3-isopropyl-pyrazolo[3,4-b]pyridine-6-carboxylic acid | E061 | J1 | 483 | 484 |

TABLE XIII-continued

List of acids

| Int. | Structure | Name | SM | method | MW | Mes |
|------|-----------|------|----|--------|----|-----|
| A106 | 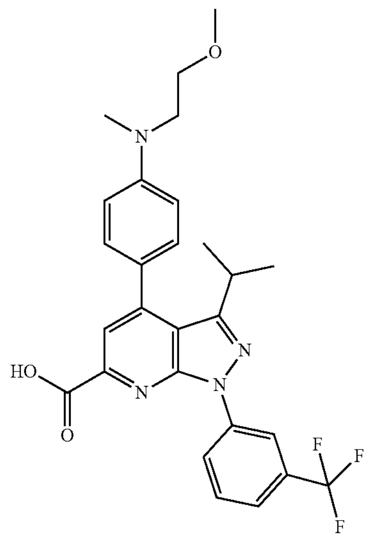 [SMILES: COCCN(C)c1ccc(-c2cc(C(=O)O)nc3c2c(C(C)C)nn3-c2cccc(C(F)(F)F)c2)cc1] | 3-isopropyl-4-[4-[2-methoxyethyl(methyl)amino]phenyl]-1-[3-(trifluoromethyl)phenyl]pyrazolo[3,4-b]pyridine-6-carboxylic acid | E062 | J1 | 512 | 513 |
| A107 | 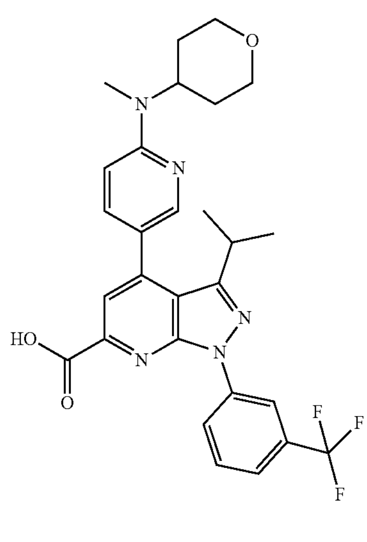 [SMILES: CC(C)c1nn(-c2cccc(C(F)(F)F)c2)c2nc(C(=O)O)cc(-c3ccc(N(C)C4CCOCC4)nc3)c12] | 3-isopropyl-4-[6-[methyl(tetrahydro-pyran-4-yl)amino]-3-pyridyl]-1-[3-(trifluoromethyl)phenyl]pyrazolo[3,4-b]pyridine-6-carboxylic acid | E063 | J1 | 539 | 540 |

TABLE XIII-continued
List of acids
| Int. | Structure | Name | SM | method | MW | Mes |
|---|---|---|---|---|---|---|
| A108 | 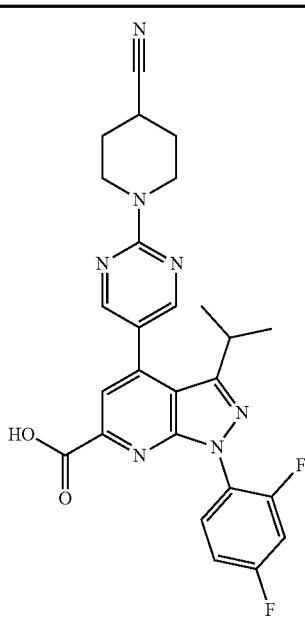 | 4-[2-(4-cyano-1-piperidyl)pyrimidin-5-yl]-1-(2,4-difluorophenyl)-3-isopropyl-pyrazolo[3,4-b]pyridine-6-carboxylic acid | E068 | J1 | 503 | 504 |
| A109 | 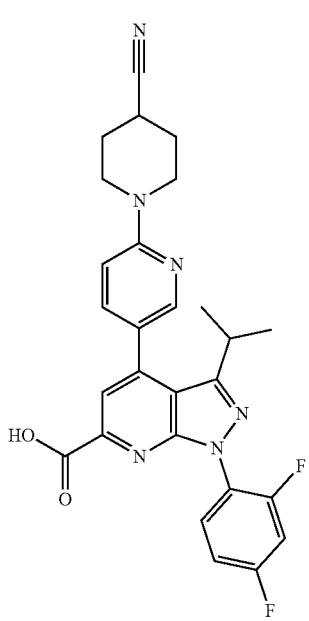 [SMILES: CC(C)c1nn(-c2ccc(F)cc2F)c2nc(C(=O)O)cc(-c3ccc(N4CCC(C#N)CC4)nc3)c12] | 4-[6-(4-cyano-1-piperidyl)-3-pyridyl]-1-(2,4-difluorophenyl)-3-isopropyl-pyrazolo[3,4-b]pyridine-6-carboxylic acid | E069 | J1 | 502 | 503 |

TABLE XIII-continued

List of acids

| Int. | Structure | Name | SM | method | MW | Mes |
|------|-----------|------|----|--------|----|----|
| A110 | 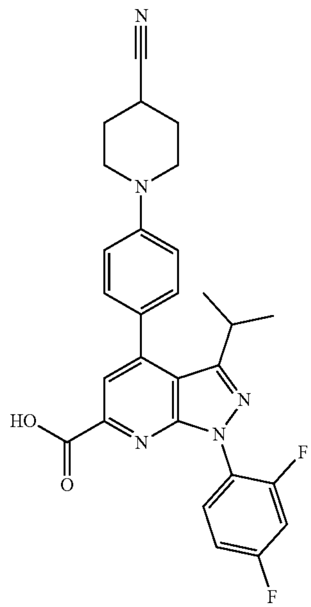 [SMILES: CC(C)c1nn(-c2ccc(F)cc2F)c2nc(C(=O)O)cc(-c3ccc(N4CCC(C#N)CC4)cc3)c12] | 4-[4-(4-cyano-1-piperidyl)phenyl]-1-(2,4-difluorophenyl)-3-isopropyl-pyrazolo[3,4-b]pyridine-6-carboxylic acid | E070 | J1 | 501 | 502 |
| A111 | 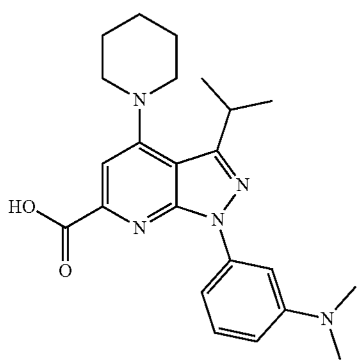 [SMILES: CC(C)c1nn(-c2cccc(N(C)C)c2)c2nc(C(=O)O)cc(N3CCCCC3)c12] | 1-[3-(dimethylamino)phenyl]-3-isopropyl-4-(1-piperidyl)pyrazolo[3,4-b]pyridine-6-carboxylic acid | E083 | J1 | 407 | 408 |
| A112 | 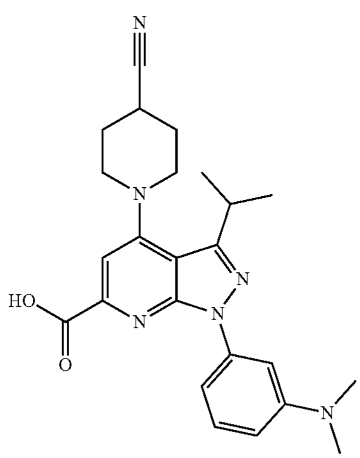 [SMILES: CC(C)c1nn(-c2cccc(N(C)C)c2)c2nc(C(=O)O)cc(N3CCC(C#N)CC3)c12] | 4-(4-cyano-1-piperidyl)-1-[3-(dimethylamino)phenyl]-3-isopropyl-pyrazolo[3,4-b]pyridine-6-carboxylic acid | E086 | J1 | 432 | 433 |

TABLE XIII-continued

List of acids

| Int. | Structure | Name | SM | method | MW | Mes |
|---|---|---|---|---|---|---|
| A113 | 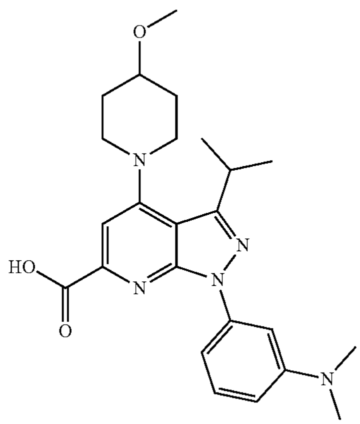 [SMILES: COC1CCN(c2cc(C(=O)O)nc3c2c(C(C)C)nn3-c2cccc(N(C)C)c2)CC1] | 1-[3-(dimethylamino)phenyl]-3-isopropyl-4-(4-methoxy-1-piperidyl)pyrazolo[3,4-b]pyridine-6-carboxylic acid | E081 | J1 | 437 | 438 |
| A114 | 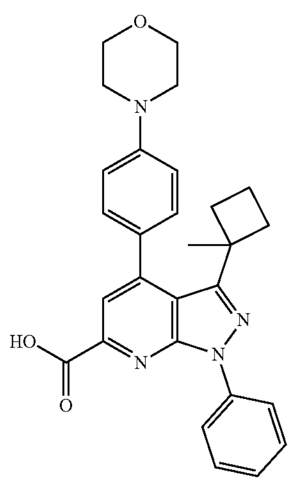 [SMILES: CC1(c2nn(-c3ccccc3)c3nc(C(=O)O)cc(-c4ccc(N5CCOCC5)cc4)c23)CCC1] | 3-(1-methylcyclobutyl)-4-(4-morpholinophenyl)-1-phenyl-pyrazolo[3,4-b]pyridine-6-carboxylic acid | E067 | J1 | 468 | 469 |
| A115 | 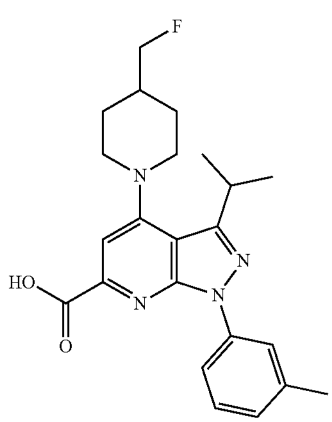 [SMILES: Cc1cccc(-n2nc(C(C)C)c3c(N4CCC(CF)CC4)cc(C(=O)O)nc32)c1] | 4-[4-(fluoromethyl)-1-piperidyl]-3-isopropyl-1-(m-tolyl)pyrazolo[3,4-b]pyridine-6-carboxylic acid | HP16 | J4 | 410 | 411 |

TABLE XIII-continued

List of acids

| Int. | Structure | Name | SM | method | MW | Mes |
|------|-----------|------|----|--------|----|-----|
| A116 | 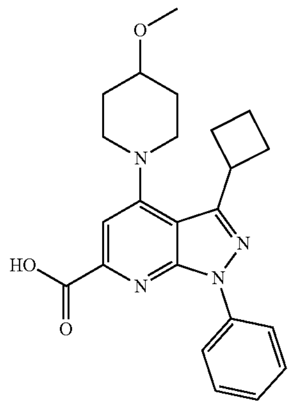 [SMILES: COC1CCN(c2cc(C(=O)O)nc3c2c(C2CCC2)nn3-c2ccccc2)CC1] | 3-cyclobutyl-4-(4-methoxy-1-piperidyl)-1-phenyl-pyrazolo[3,4-b]pyridine-6-carboxylic acid | E071 | J1 | 406 | 407 |
| A117 | 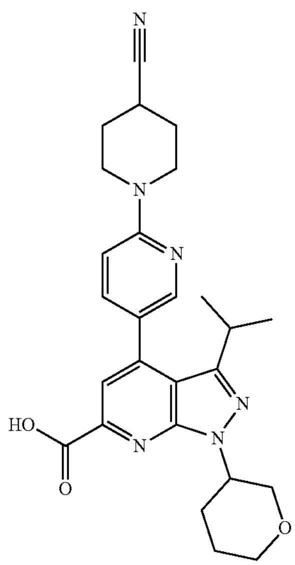 [SMILES: CC(C)c1nn(C2CCCOC2)c2nc(C(=O)O)cc(-c3ccc(N4CCC(C#N)CC4)nc3)c12] | 4-[6-(4-cyano-1-piperidyl)-3-pyridyl]-3-isopropyl-1-tetrahydropyran-3-yl-pyrazolo[3,4-b]pyridine-6-carboxylic acid | E073 | J1 | 474 | 475 |
| A118 | 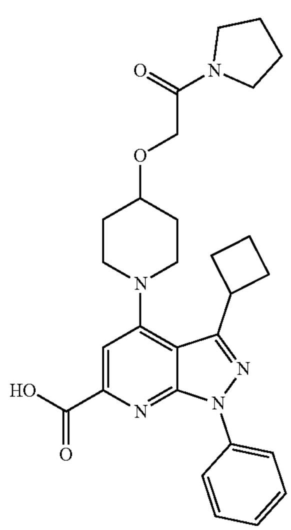 [SMILES: O=C(O)c1cc(N2CCC(OCC(=O)N3CCCC3)CC2)c2c(C3CCC3)nn(-c3ccccc3)c2n1] | 3-cyclobutyl-4-[4-(2-oxo-2-pyrrolidin-1-yl-ethoxy)-1-piperidyl]-1-phenyl-pyrazolo[3,4-b]pyridine-6-carboxylic acid | E080 | J1 | 503 | 504 |

TABLE XIII-continued

List of acids

| Int. | Structure | Name | SM | method | MW | Mes |
|---|---|---|---|---|---|---|
| A119 | 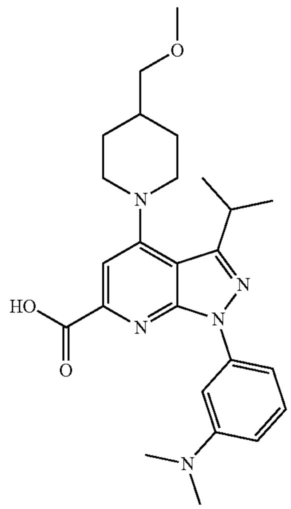 [SMILES: COCC1CCN(c2cc(C(=O)O)nc3c2c(C(C)C)nn3-c2cccc(N(C)C)c2)CC1] | 1-[3-(dimethylamino)phenyl]-3-isopropyl-4-[4-(methoxymethyl)-1-piperidyl]pyrazolo[3,4-b]pyridine-6-carboxylic acid | E072 | J1 | 451 | 452 |
| A120 | 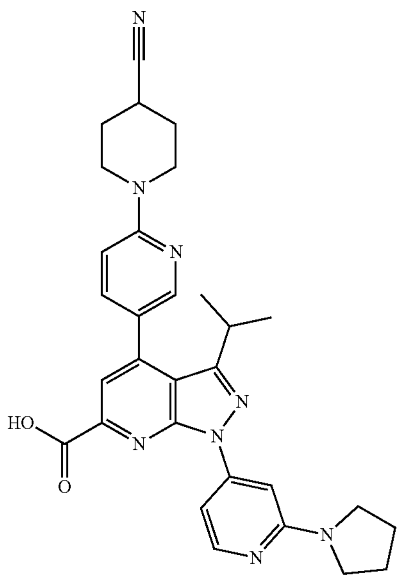 [SMILES: CC(C)c1nn(-c2ccnc(N3CCCC3)c2)c2nc(C(=O)O)cc(-c3ccc(N4CCC(C#N)CC4)nc3)c12] | 4-[6-(4-cyano-1-piperidyl)-3-pyridyl]-3-isopropyl-1-(2-pyrrolidin-1-yl-4-pyridyl)pyrazolo[3,4-b]pyridine-6-carboxylic acid | E084 | J1 | 536 | 537 |
| A121 | 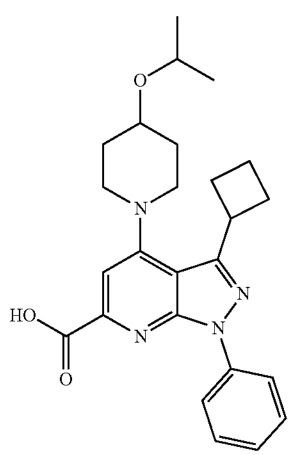 [SMILES: CC(C)OC1CCN(c2cc(C(=O)O)nc3c2c(C2CCC2)nn3-c2ccccc2)CC1] | 3-cyclobutyl-4-(4-isopropoxy-1-piperidyl)-1-phenyl-pyrazolo[3,4-b]pyridine-6-carboxylic acid | E077 | J1 | 434 | 435 |

TABLE XIII-continued

List of acids

| Int. | Structure | Name | SM | method | MW | Mes |
|---|---|---|---|---|---|---|
| A122 | 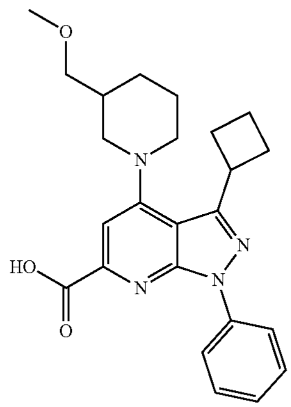 [SMILES: COCC1CCCN(c2cc(C(=O)O)nc3c2c(C2CCC2)nn3-c2ccccc2)C1] | 3-cyclobutyl-4-[3-(methoxymethyl)-1-piperidyl]-1-phenyl-pyrazolo[3,4-b]pyridine-6-carboxylic acid | E079 | J1 | 420 | 421 |
| A123 | 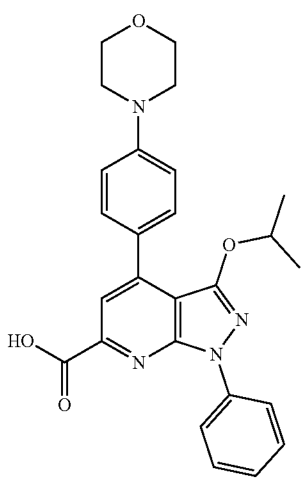 [SMILES: CC(C)Oc1nn(-c2ccccc2)c2nc(C(=O)O)cc(-c3ccc(N4CCOCC4)cc3)c12] | 3-isopropoxy-4-(4-morpholinophenyl)-1-phenyl-pyrazolo[3,4-b]pyridine-6-carboxylic acid | E090 | J1 | 458 | 459 |
| A124 | 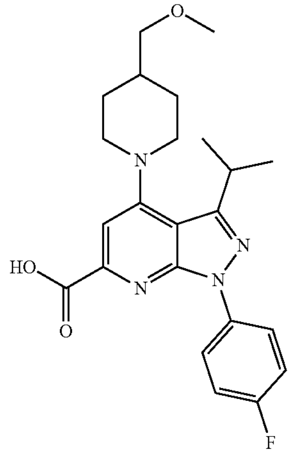 [SMILES: COCC1CCN(c2cc(C(=O)O)nc3c2c(C(C)C)nn3-c2ccc(F)cc2)CC1] | 1-(4-fluorophenyl)-3-isopropyl-4-[4-(methoxymethyl)-1-piperidyl]pyrazolo[3,4-b]pyridine-6-carboxylic acid | E092 | J1 | 426 | 427 |

TABLE XIII-continued

List of acids

| Int. | Structure | Name | SM | method | MW | Mes |
|------|-----------|------|-----|--------|-----|-----|
| A125 | 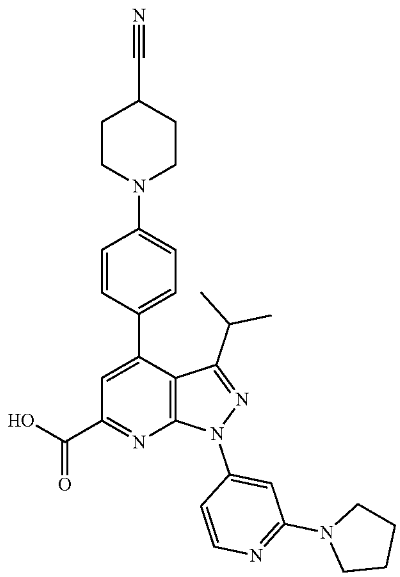 [SMILES: CC(C)c1nn(-c2ccnc(N3CCCC3)c2)c2nc(C(=O)O)cc(-c3ccc(N4CCC(C#N)CC4)cc3)c12] | 4-[4-(4-cyano-1-piperidyl)phenyl]-3-isopropyl-1-(2-pyrrolidin-1-yl-4-pyridyl)pyrazolo[3,4-b]pyridine-6-carboxylic acid | E093 | J1 | 535 | 536 |
| A126 | 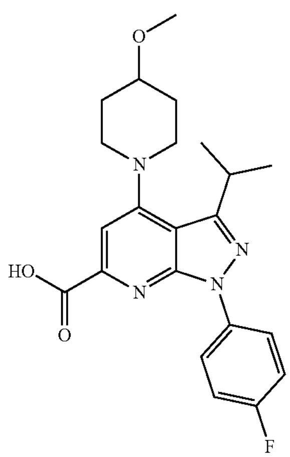 [SMILES: COC1CCN(c2cc(C(=O)O)nc3c2c(C(C)C)nn3-c2ccc(F)cc2)CC1] | 1-(4-fluorophenyl)-3-isopropyl-4-(4-methoxy-1-piperidyl)pyrazolo[3,4-b]pyridine-6-carboxylic acid | E091 | J1 | 412 | 413 |
| A127 | 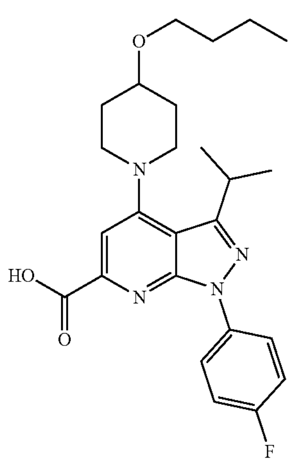 [SMILES: CCCCOC1CCN(c2cc(C(=O)O)nc3c2c(C(C)C)nn3-c2ccc(F)cc2)CC1] | 4-(4-butoxy-1-piperidyl)-1-(4-fluorophenyl)-3-isopropyl-pyrazolo[3,4-b]pyridine-6-carboxylic acid | E096 | J1 | 454 | 455 |

TABLE XIII-continued

List of acids

| Int. | Structure | Name | SM | method | MW | Mes |
|---|---|---|---|---|---|---|
| A128 | 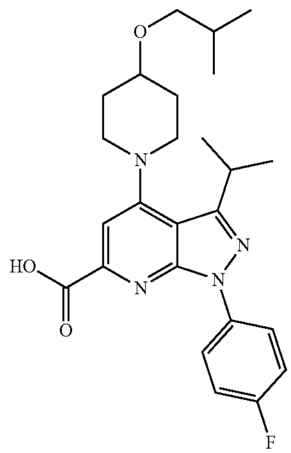 [SMILES: CC(C)COC1CCN(c2cc(C(=O)O)nc3c2c(C(C)C)nn3-c2ccc(F)cc2)CC1] | 1-(4-fluorophenyl)-4-(4-isobutoxy-1-piperidyl)-3-isopropyl-pyrazolo[3,4-b]pyridine-6-carboxylic acid | E098 | J1 | 454 | 455 |
| A129 | 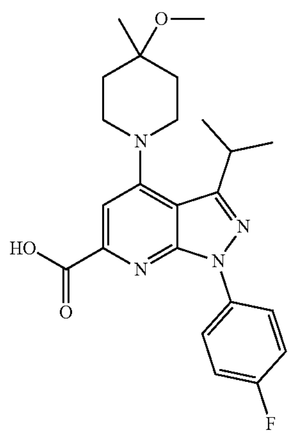 [SMILES: COC1(C)CCN(c2cc(C(=O)O)nc3c2c(C(C)C)nn3-c2ccc(F)cc2)CC1] | 1-(4-fluorophenyl)-3-isopropyl-4-(4-methoxy-4-methyl-1-piperidyl)pyrazolo[3,4-b]pyridine-6-carboxylic acid | E097 | J1 | 426 | 427 |
| A130 | 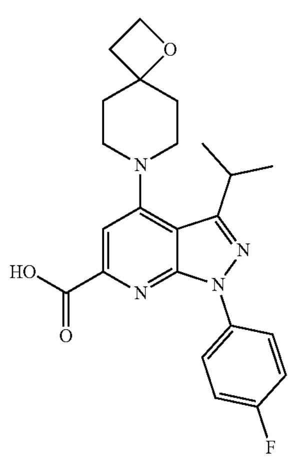 [SMILES: CC(C)c1nn(-c2ccc(F)cc2)c2nc(C(=O)O)cc(N3CCC4(CCO4)CC3)c12] | 1-(4-fluorophenyl)-3-isopropyl-4-(3-oxa-7-azaspiro[3.5]nonan-7-yl)pyrazolo[3,4-b]pyridine-6-carboxylic acid | E099 | J1 | 424 | 425 |

TABLE XIII-continued

| Int. | Structure | Name | SM | method | MW | Mes |
|---|---|---|---|---|---|---|
| A131 | 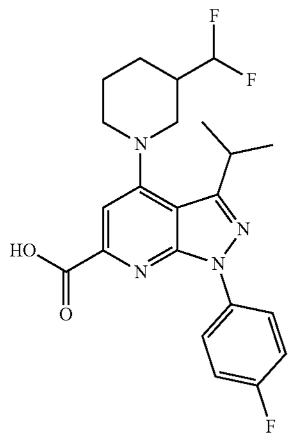 [SMILES: CC(C)c1nn(-c2ccc(F)cc2)c2nc(C(=O)O)cc(N3CCCC(C(F)F)C3)c12] | 4-[3-(difluoromethyl)-1-piperidyl]-1-(4-fluorophenyl)-3-isopropyl-pyrazolo[3,4-b]pyridine-6-carboxylic acid | E100 | J1 | 432 | 433 |
| A132 | 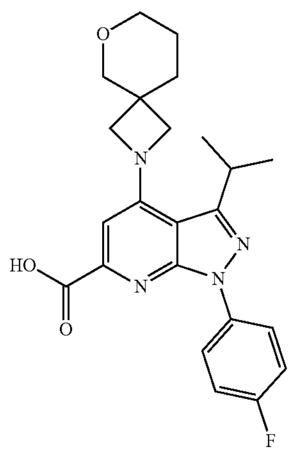 [SMILES: CC(C)c1nn(-c2ccc(F)cc2)c2nc(C(=O)O)cc(N3CC4(CCCOC4)C3)c12] | 1-(4-fluorophenyl)-3-isopropyl-4-(8-oxa-2-azaspiro[3.5]nonan-2-yl)pyrazolo[3,4-b]pyridine-6-carboxylic acid | E101 | J1 | 424 | 425 |
| A133 | 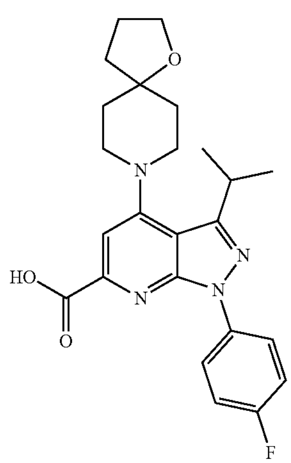 [SMILES: CC(C)c1nn(-c2ccc(F)cc2)c2nc(C(=O)O)cc(N3CCC4(CCCO4)CC3)c12] | 1-(4-fluorophenyl)-3-isopropyl-4-(4-oxa-8-azaspiro[4.5]decan-8-yl)pyrazolo[3,4-b]pyridine-6-carboxylic acid | E102 | J1 | 438 | 439 |

TABLE XIII-continued

List of acids

| Int. | Structure | Name | SM | method | MW | Mes |
|---|---|---|---|---|---|---|
| A134 | 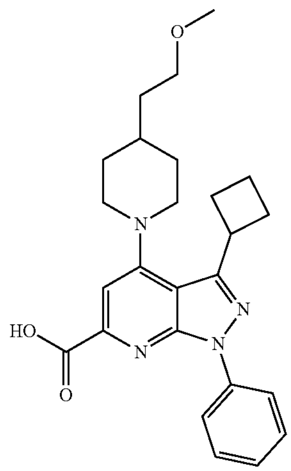 [SMILES: COCCC1CCN(c2cc(C(=O)O)nc3c2c(C2CCC2)nn3-c2ccccc2)CC1] | 3-cyclobutyl-4-[4-(2-methoxyethyl)-1-piperidyl]-1-phenyl-pyrazolo[3,4-b]pyridine-6-carboxylic acid | E104 | J1 | 434 | 435 |
| A135 | 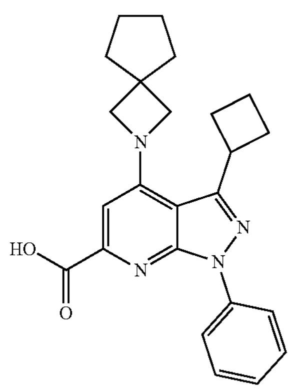 [SMILES: O=C(O)c1cc(N2CC3(CCCC3)C2)c2c(C3CCC3)nn(-c3ccccc3)c2n1] | 4-(2-azaspiro[3.4]octan-2-yl)-3-cyclobutyl-1-phenyl-pyrazolo[3,4-b]pyridine-6-carboxylic acid | E105 | J1 | 402 | 403 |
| A136 | 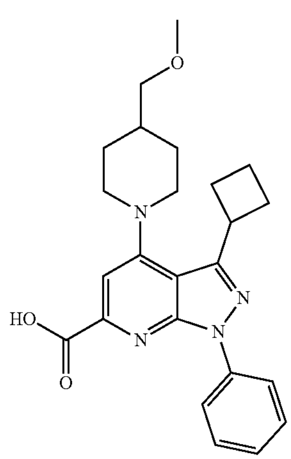 [SMILES: COCC1CCN(c2cc(C(=O)O)nc3c2c(C2CCC2)nn3-c2ccccc2)CC1] | 3-cyclobutyl-4-[4-(methoxymethyl)-1-piperidyl]-1-phenyl-pyrazolo[3,4-b]pyridine-6-carboxylic acid | E106 | J1 | 420 | 421 |

TABLE XIII-continued

List of acids

| Int. | Structure | Name | SM | method | MW | Mes |
|---|---|---|---|---|---|---|
| A137 | 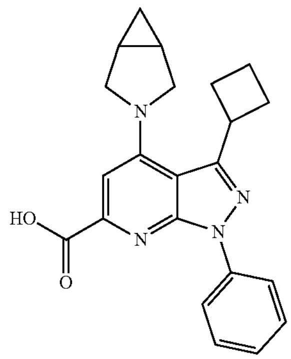 [SMILES: O=C(O)c1cc(N2CC3CC3C2)c2c(C3CCC3)nn(-c3ccccc3)c2n1] | 4-(3-azabicyclo[3.1.0]hexan-3-yl)-3-cyclobutyl-1-phenyl-pyrazolo[3,4-b]pyridine-6-carboxylic acid | E107 | J1 | 374 | 375 |
| A138 | 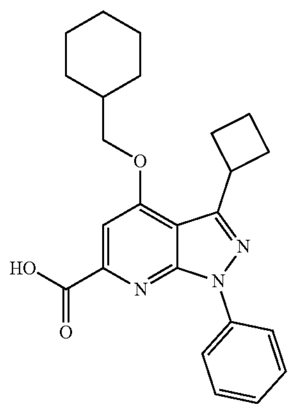 [SMILES: O=C(O)c1cc(OCC2CCCCC2)c2c(C3CCC3)nn(-c3ccccc3)c2n1] | 3-cyclobutyl-4-(cyclohexylmethoxy)-1-phenyl-pyrazolo[3,4-b]pyridine-6-carboxylic acid | HP10 | J3 | 405 | 406 |
| A139 | 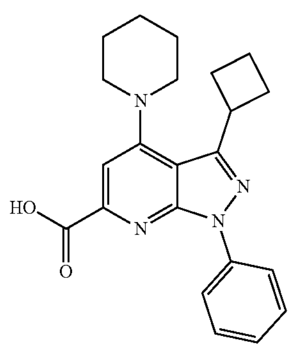 [SMILES: O=C(O)c1cc(N2CCCCC2)c2c(C3CCC3)nn(-c3ccccc3)c2n1] | 3-cyclobutyl-1-phenyl-4-(1-piperidyl)pyrazolo[3,4-b]pyridine-6-carboxylic acid | E103 | J1 | 376 | 377 |
| A140 | 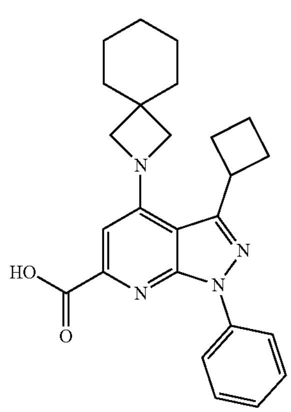 [SMILES: O=C(O)c1cc(N2CC3(CCCCC3)C2)c2c(C3CCC3)nn(-c3ccccc3)c2n1] | 4-(2-azaspiro[3.5]nonan-2-yl)-3-cyclobutyl-1-phenyl-pyrazolo[3,4-b]pyridine-6-carboxylic acid | E115 | J1 | 416 | 417 |

TABLE XIII-continued

List of acids

| Int. | Structure | Name | SM | method | MW | Mes |
|---|---|---|---|---|---|---|
| A141 | 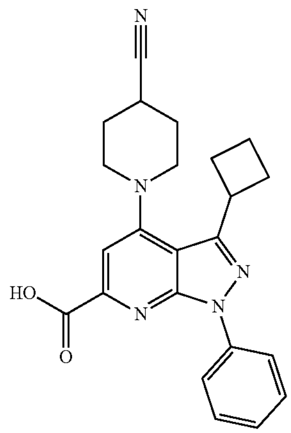 [SMILES: N#CC1CCN(c2cc(C(=O)O)nc3c2c(C2CCC2)nn3-c2ccccc2)CC1] | 4-(4-cyano-1-piperidyl)-3-cyclobutyl-1-phenyl-pyrazolo[3,4-b]pyridine-6-carboxylic acid | E114 | J1 | 401 | 402 |
| A142 | 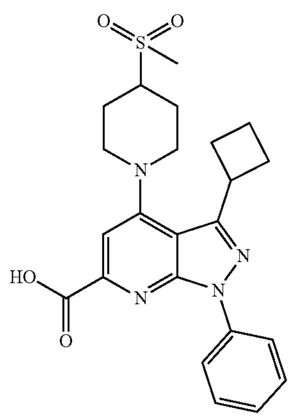 [SMILES: CS(=O)(=O)C1CCN(c2cc(C(=O)O)nc3c2c(C2CCC2)nn3-c2ccccc2)CC1] | 3-cyclobutyl-4-(4-methylsulfonyl-1-piperidyl)-1-phenyl-pyrazolo[3,4-b]pyridine-6-carboxylic acid | E113 | J1 | 454 | 455 |
| A143 | 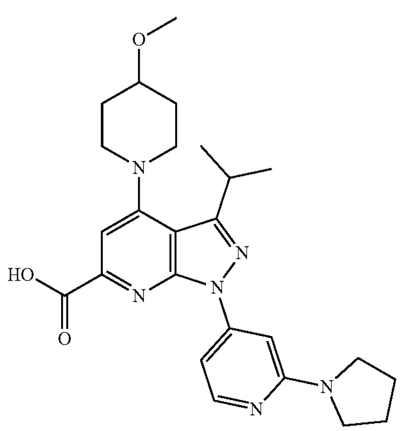 [SMILES: COC1CCN(c2cc(C(=O)O)nc3c2c(C(C)C)nn3-c2ccnc(N3CCCC3)c2)CC1] | 3-isopropyl-4-(4-methoxy-1-piperidyl)-1-(2-pyrrolidin-1-yl-4-pyridyl)pyrazolo[3,4-b]pyridine-6-carboxylic acid | E110 | J1 | 464 | 465 |

TABLE XIII-continued

List of acids

| Int. | Structure | Name | SM | method | MW | Mes |
|---|---|---|---|---|---|---|
| A144 | 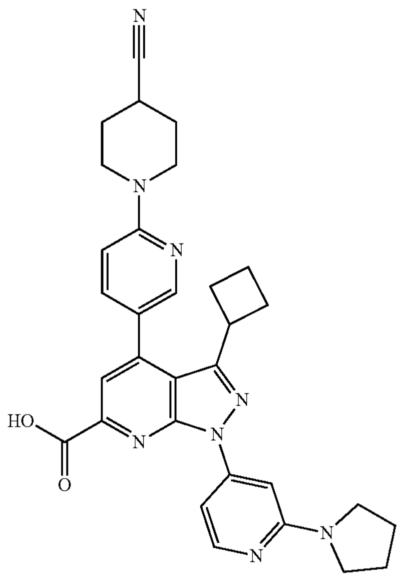 [SMILES: N#CC1CCN(c2ccc(-c3cc(C(=O)O)nc4c3c(C3CCC3)nn4-c3ccnc(N4CCCC4)c3)cn2)CC1] | 4-[6-(4-cyano-1-piperidyl)-3-pyridyl]-3-cyclobutyl-1-(2-pyrrolidin-1-yl-4-pyridyl)pyrazolo[3,4-b]pyridine-6-carboxylic acid | E112 | J1 | 548 | 549 |
| A145 | 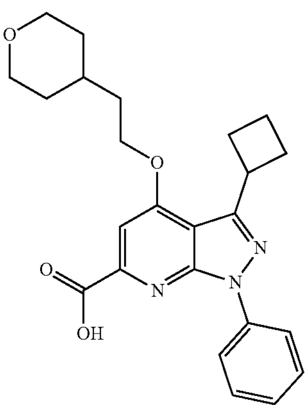 [SMILES: O=C(O)c1cc(OCCC2CCOCC2)c2c(C3CCC3)nn(-c3ccccc3)c2n1] | 3-cyclobutyl-1-phenyl-4-(2-tetrahydropyran-4-ylethoxy)pyrazolo[3,4-b]pyridine-6-carboxylic acid | HP10 | J3 | 421 | 422 |
| A146 | 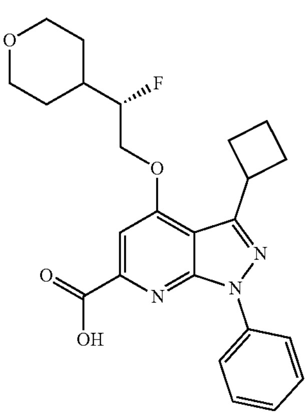 [SMILES: O=C(O)c1cc(OC[C@@H](F)C2CCOCC2)c2c(C3CCC3)nn(-c3ccccc3)c2n1] | 3-cyclobutyl-4-[(2S)-2-fluoro-2-tetrahydropyran-4-yl-ethoxy]-1-phenyl-pyrazolo[3,4-b]pyridine-6-carboxylic acid | HP10, ALC01 | J3 | 439 | 440 |

TABLE XIII-continued

List of acids

| Int. | Structure | Name | SM | method | MW | Mes |
|---|---|---|---|---|---|---|
| A147 | 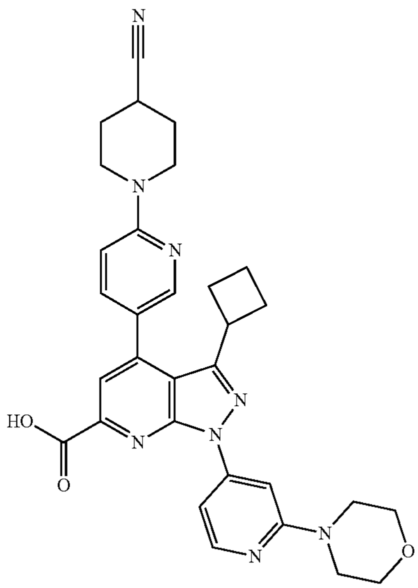 [SMILES: N#CC1CCN(c2ccc(-c3cc(C(=O)O)nc4c3c(C3CCC3)nn4-c3ccnc(N4CCOCC4)c3)cn2)CC1] | 4-[6-(4-cyano-1-piperidyl)-3-pyridyl]-3-cyclobutyl-1-(2-morpholino-4-pyridyl)pyrazolo[3,4-b]pyridine-6-carboxylic acid | E121 | J1 | 564 | 565 |
| A148 | 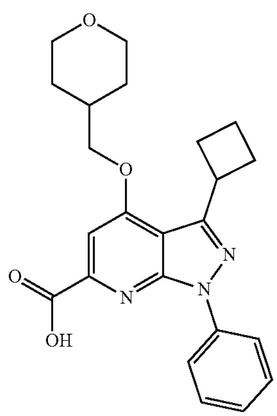 [SMILES: O=C(O)c1cc(OCC2CCOCC2)c2c(C3CCC3)nn(-c3ccccc3)c2n1] | 3-cyclobutyl-1-phenyl-4-(tetrahydropyran-4-ylmethoxy)pyrazolo[3,4-b]pyridine-6-carboxylic acid | HP10 | J3 Specific example | 407 | 408 |
| A149 | 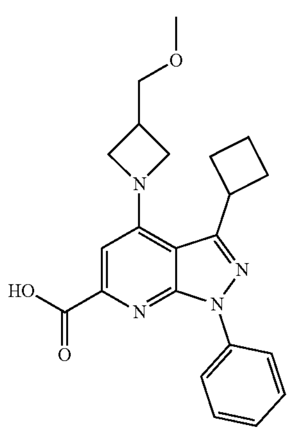 [SMILES: COCC1CN(c2cc(C(=O)O)nc3c2c(C2CCC2)nn3-c2ccccc2)C1] | 3-cyclobutyl-4-[3-(methoxymethyl)azetidin-1-yl]-1-phenyl-pyrazolo[3,4-b]pyridine-6-carboxylic acid | E116 | J1 | 392 | 393 |

TABLE XIII-continued

List of acids

| Int. | Structure | Name | SM | method | MW | Mes |
|---|---|---|---|---|---|---|
| A150 | 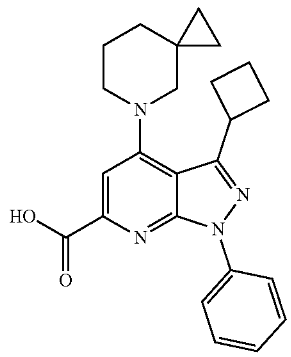 [SMILES: O=C(O)c1cc(N2CCCC3(CC3)C2)c2c(C3CCC3)nn(-c3ccccc3)c2n1] | 4-(7-azaspiro[2.5]octan-7-yl)-3-cyclobutyl-1-phenyl-pyrazolo[3,4-b]pyridine-6-carboxylic acid | E125 | J1 | 402 | 403 |
| A151 | 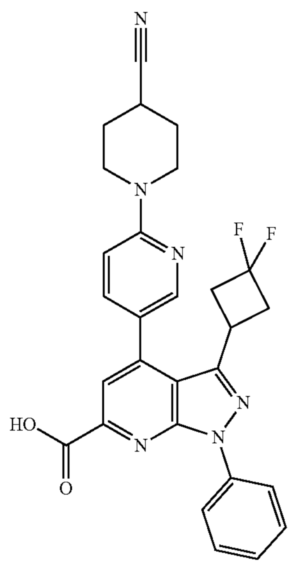 [SMILES: N#CC1CCN(c2ccc(-c3cc(C(=O)O)nc4c3c(C3CC(F)(F)C3)nn4-c3ccccc3)cn2)CC1] | 4-[6-(4-cyano-1-piperidyl)-3-pyridyl]-3-(3,3-difluorocyclobutyl)-1-phenyl-pyrazolo[3,4-b]pyridine-6-carboxylic acid | E118 | J1 | 514 | 515 |
| A152 | 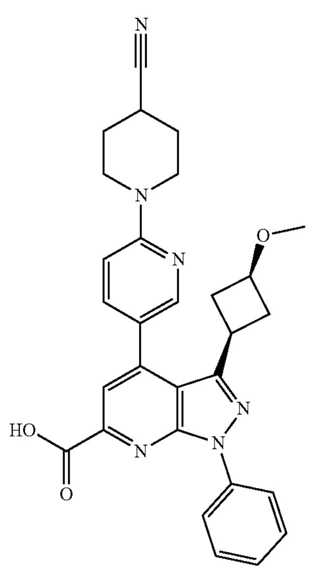 [SMILES: CO[C@H]1C[C@@H](c2nn(-c3ccccc3)c3nc(C(=O)O)cc(-c4ccc(N5CCC(C#N)CC5)nc4)c32)C1] | 4-[6-(4-cyanopiperidin-1-yl)pyridin-3-yl]-3-[(1s,3s)-3-methoxycyclobutyl]-1-phenyl-1H-pyrazolo[3,4-b]pyridine-6-carboxylic acid | E117 | J1 | 508 | 509 |

TABLE XIII-continued

List of acids

| Int. | Structure | Name | SM | method | MW | Mes |
|---|---|---|---|---|---|---|
| A153 | 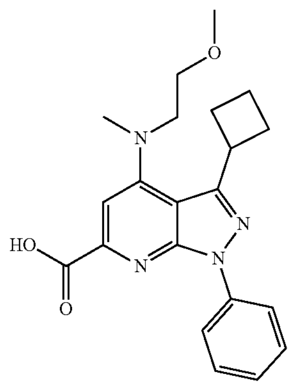 [SMILES: COCCN(C)c1cc(C(=O)O)nc2c1c(C1CCC1)nn2-c1ccccc1] | 3-cyclobutyl-4-[2-methoxyethyl(methyl)amino]-1-phenyl-pyrazolo[3,4-b]pyridine-6-carboxylic acid | E126 | J1 | 380 | 381 |
| A154 | 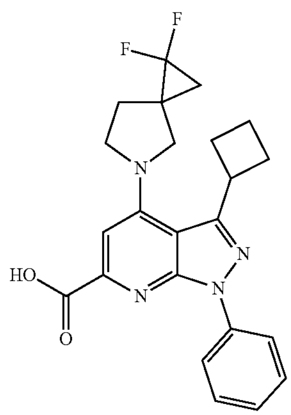 [SMILES: O=C(O)c1cc(N2CCC3(C2)CC3(F)F)c2c(C3CCC3)nn(-c3ccccc3)c2n1] | 3-cyclobutyl-4-(2,2-difluoro-6-azaspiro[2.4]heptan-6-yl)-1-phenyl-pyrazolo[3,4-b]pyridine-6-carboxylic acid | E122 | J1 | 424 | 425 |
| A155 | 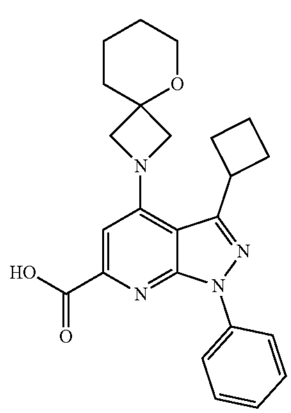 [SMILES: O=C(O)c1cc(N2CC3(CCCCO3)C2)c2c(C3CCC3)nn(-c3ccccc3)c2n1] | 3-cyclobutyl-4-(9-oxa-2-azaspiro[3.5]nonan-2-yl)-1-phenyl-pyrazolo[3,4-b]pyridine-6-carboxylic acid | E123 | J1 | 418 | 419 |

TABLE XIII-continued

| | | List of acids | | | | |
|---|---|---|---|---|---|---|
| Int. | Structure | Name | SM | method | MW | Mes |
| A156 | | 3-cyclobutyl-4-(7-oxa-2-azaspiro[3.5]nonan-2-yl)-1-phenyl-pyrazolo[3,4-b]pyridine-6-carboxylic acid | E124 | J1 | 418 | 419 |
| A157 | | 4-(6-azaspiro[3.3]heptan-6-yl)-3-cyclobutyl-1-phenyl-pyrazolo[3,4-b]pyridine-6-carboxylic acid | E128 | J1 | 388 | 389 |
| A158 | | 4-[4-(benzyloxymethyl)-1-piperidyl]-3-cyclobutyl-1-phenyl-pyrazolo[3,4-b]pyridine-6-carboxylic acid | E127 | J1 | 496 | 497 |

TABLE XIII-continued

List of acids

| Int. | Structure | Name | SM | method | MW | Mes |
|---|---|---|---|---|---|---|
| A159 | 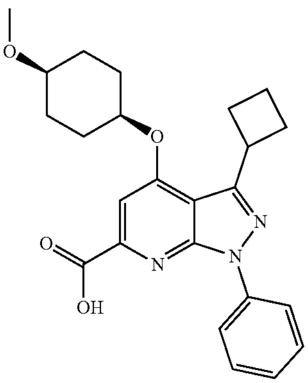 [SMILES: CO[C@H]1CC[C@@H](Oc2cc(C(=O)O)nc3c2c(C2CCC2)nn3-c2ccccc2)CC1] | 3-cyclobutyl-4-{[(1s,4s)-4-methoxycyclohexyl]oxy}-1-phenyl-1H-pyrazolo[3,4-b]pyridine-6-carboxylic acid | HP10 | J3 | 421 | 422 |
| A160 | 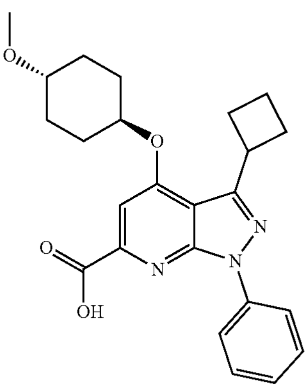 [SMILES: CO[C@H]1CC[C@H](Oc2cc(C(=O)O)nc3c2c(C2CCC2)nn3-c2ccccc2)CC1] | 3-cyclobutyl-4-{[(1r,4r)-4-methoxycyclohexyl]oxy}-1-phenyl-1H-pyrazolo[3,4-b]pyridine-6-carboxylic acid | HP10 | J3 | 421 | 422 |
| A161 | 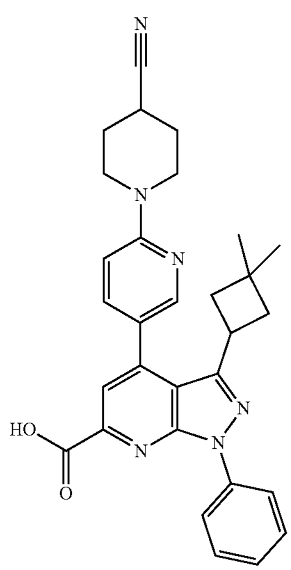 [SMILES: CC1(C)CC(c2nn(-c3ccccc3)c3nc(C(=O)O)cc(-c4ccc(N5CCC(C#N)CC5)nc4)c23)C1] | 4-[6-(4-cyano-1-piperidyl)-3-pyridyl]-3-(3,3-dimethylcyclobutyl)-1-phenyl-pyrazolo[3,4-b]pyridine-6-carboxylic acid | E119 | J1 | 506 | 507 |

TABLE XIII-continued

| | | List of acids | | | | |
|---|---|---|---|---|---|---|
| Int. | Structure | Name | SM | method | MW | Mes |
| A162 | | 1-cyclohexyl-3-isopropyl-4-[4-(methoxymethyl)-1-piperidyl]pyrazolo[3,4-b]pyridine-6-carboxylic acid | E134 | J8 Specific example | 414 | 415 |
| A163 | | 4-[6-(4-cyano-1-piperidyl)-3-pyridyl]-3-(3-fluorocyclobutyl)-1-phenyl-pyrazolo[3,4-b]pyridine-6-carboxylic acid (cis) | A258 | Separation by prep HPLC | 496 | 497 |
| A164 | | 4-[6-(4-cyano-1-piperidyl)-3-pyridyl]-3-(3-fluorocyclobutyl)-1-phenyl-pyrazolo[3,4-b]pyridine-6-carboxylic acid trans | A258 | Separation by prep HPLC | 496 | 497 |

TABLE XIII-continued
| Int. | Structure | Name | SM | method | MW | Mes |
|---|---|---|---|---|---|---|
| A165 | 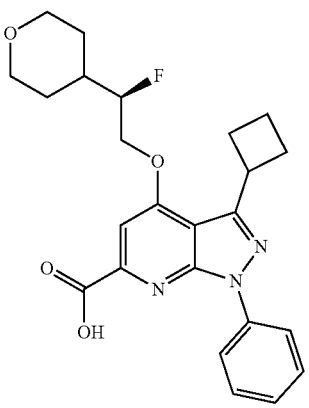 [SMILES: O=C(O)c1cc(OC[C@H](F)C2CCOCC2)c2c(C3CCC3)nn(-c3ccccc3)c2n1] | 3-cyclobutyl-4-[(2R)-2-fluoro-2-tetrahydropyran-4-yl-ethoxy]-1-phenyl-pyrazolo[3,4-b]pyridine-6-carboxylic acid | HP10, ALC02 | J3 | 439 | 440 |
| A166 | 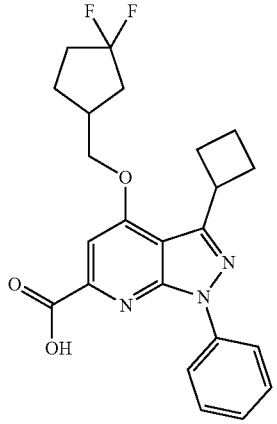 [SMILES: O=C(O)c1cc(OCC2CCC(F)(F)C2)c2c(C3CCC3)nn(-c3ccccc3)c2n1] | 3-cyclobutyl-4-[(3,3-difluorocyclopentyl)methoxy]-1-phenyl-pyrazolo[3,4-b]pyridine-6-carboxylic acid | HP10 | J3 | 427 | 428 |
| A167 | 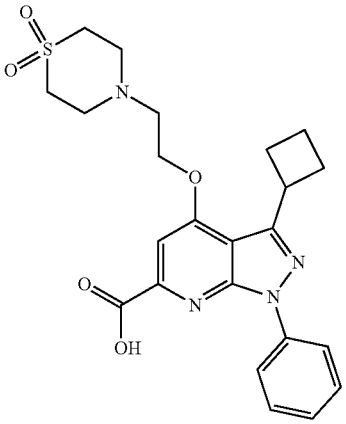 [SMILES: O=C(O)c1cc(OCCN2CCS(=O)(=O)CC2)c2c(C3CCC3)nn(-c3ccccc3)c2n1] | 3-cyclobutyl-4-[2-(1,1-dioxo-1,4-thiazinan-4-yl)ethoxy]-1-phenyl-pyrazolo[3,4-b]pyridine-6-carboxylic acid | HP10 | J3 | 470 | 471 |

TABLE XIII-continued

List of acids

| Int. | Structure | Name | SM | method | MW | Mes |
|---|---|---|---|---|---|---|
| A168 | 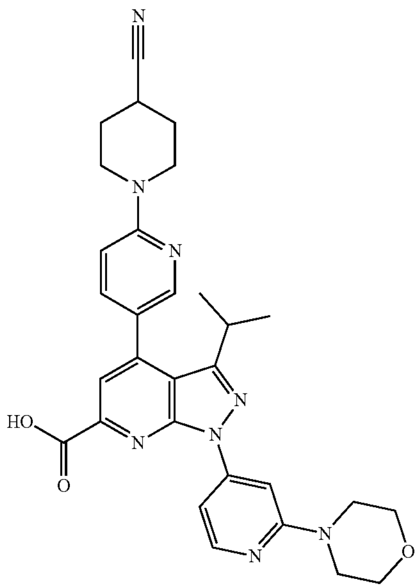 | 4-[6-(4-cyano-1-piperidyl)-3-pyridyl]-3-isopropyl-1-(2-morpholino-4-pyridyl)pyrazolo[3,4-b]pyridine-6-carboxylic acid | E138 | J1 | 552 | 553 |
| A169 | 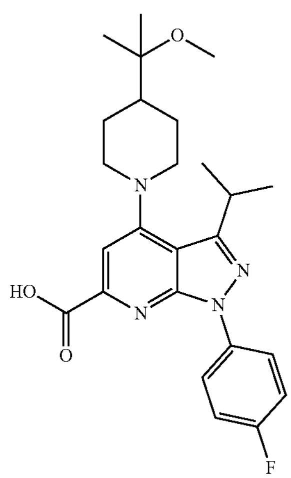 [SMILES: COC(C)(C)C1CCN(c2cc(C(=O)O)nc3c2c(C(C)C)nn3-c2ccc(F)cc2)CC1] | 1-(4-fluorophenyl)-3-isopropyl-4-[4-(1-methoxy-1-methyl-ethyl)-1-piperidyl]pyrazolo[3,4-b]pyridine-6-carboxylic acid | E136 | J8 | 454 | 455 |
| A170 | 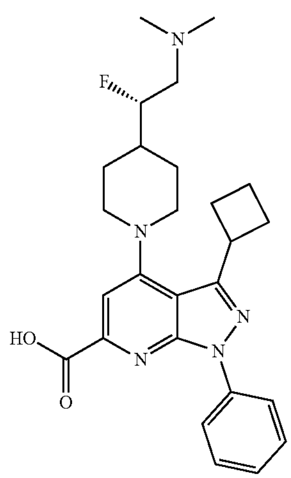 [SMILES: CN(C)C[C@@H](F)C1CCN(c2cc(C(=O)O)nc3c2c(C2CCC2)nn3-c2ccccc2)CC1] | 3-cyclobutyl-4-[4-[(1S)-2-(dimethylamino)-1-fluoro-ethyl]-1-piperidyl]-1-phenyl-pyrazolo[3,4-b]pyridine-6-carboxylic acid | E135 | J1 | 465 | 466 |

TABLE XIII-continued

List of acids

| Int. | Structure | Name | SM | method | MW | Mes |
|---|---|---|---|---|---|---|
| A171 | 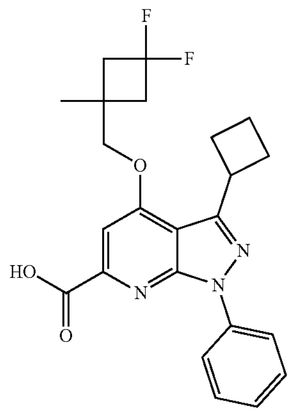 [SMILES: CC1(COc2cc(C(=O)O)nc3c2c(C2CCC2)nn3-c2ccccc2)CC(F)(F)C1] | 3-cyclobutyl-4-[(3,3-difluoro-1-methyl-cyclobutyl)methoxy]-1-phenyl-pyrazolo[3,4-b]pyridine-6-carboxylic acid | HP10 | J3 | 427 | 428 |
| A172 | 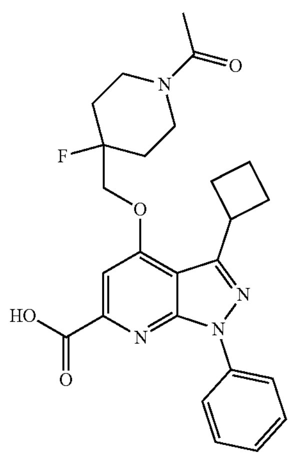 [SMILES: CC(=O)N1CCC(F)(COc2cc(C(=O)O)nc3c2c(C2CCC2)nn3-c2ccccc2)CC1] | 4-[(1-acetyl-4-fluoro-4-piperidyl)methoxy]-3-cyclobutyl-1-phenyl-pyrazolo[3,4-b]pyridine-6-carboxylic acid | HP10 | J3 | 466 | 467 |
| A173 | 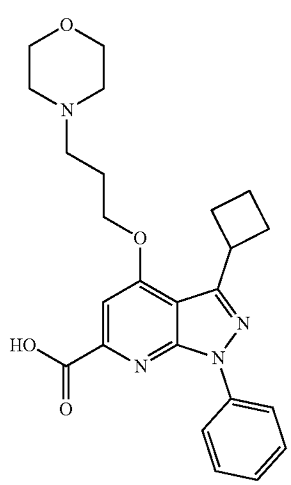 [SMILES: O=C(O)c1cc(OCCCN2CCOCC2)c2c(C3CCC3)nn(-c3ccccc3)c2n1] | 3-cyclobutyl-4-(3-morpholinopropoxy)-1-phenyl-pyrazolo[3,4-b]pyridine-6-carboxylic acid | HP10 | J3 Specific example | 436 | 437 |

TABLE XIII-continued
List of acids
| Int. | Structure | Name | SM | method | MW | Mes |
|---|---|---|---|---|---|---|
| A174 | 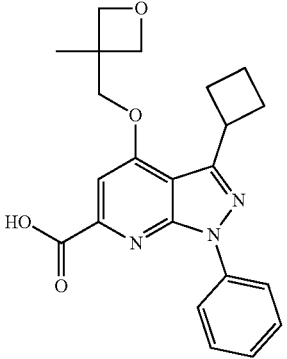 [SMILES: CC1(COc2cc(C(=O)O)nc3c2c(C2CCC2)nn3-c2ccccc2)COC1] | 3-cyclobutyl-4-[(3-methyloxetan-3-yl)methoxy]-1-phenyl-pyrazolo[3,4-b]pyridine-6-carboxylic acid | HP10 | J3 | 393 | 394 |
| A175 | 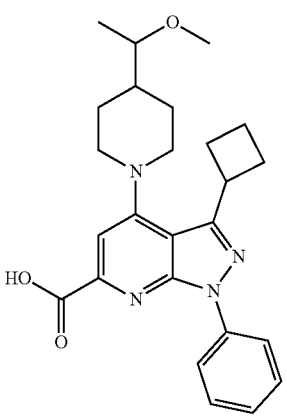 [SMILES: COC(C)C1CCN(c2cc(C(=O)O)nc3c2c(C2CCC2)nn3-c2ccccc2)CC1] | 3-cyclobutyl-4-[4-(1-methoxyethyl)-1-piperidyl]-1-phenyl-pyrazolo[3,4-b]pyridine-6-carboxylic acid | E143 | J8 | 434 | 435 |
| A176 | 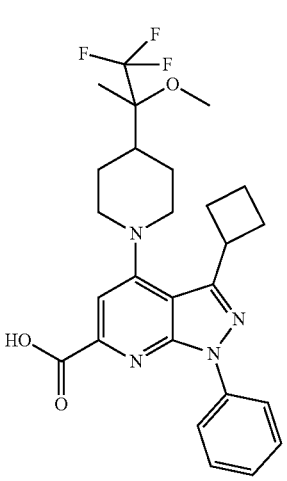 [SMILES: COC(C)(C1CCN(c2cc(C(=O)O)nc3c2c(C2CCC2)nn3-c2ccccc2)CC1)C(F)(F)F] | 3-cyclobutyl-1-phenyl-4-[4-(2,2,2-trifluoro-1-methoxy-1-methyl-ethyl)-1-piperidyl]pyrazolo[3,4-b]pyridine-6-carboxylic acid | E144 | J8 | 502 | 503 |

TABLE XIII-continued

| | | List of acids | | | | |
|---|---|---|---|---|---|---|
| Int. | Structure | Name | SM | method | MW | Mes |
| A177 | | 4-[6-[bis(2-methoxyethyl)amino]-3-pyridyl]-3-cyclobutyl-1-phenyl-pyrazolo[3,4-b]pyridine-6-carboxylic acid | E145 | J1 | 501 | 502 |
| A178 | | 4-[6-[bis(2-methoxyethyl)amino]-3-pyridyl]-3-isopropyl-1-(2-morpholino-4-pyridyl)pyrazolo[3,4-b]pyridine-6-carboxylic acid | E149 | J1 | 575 | 576 |
| A179 | | 3-isopropyl-4-[4-(methoxymethyl)-1-piperidyl]-1-(2-morpholino-4-pyridyl)pyrazolo[3,4-b]pyridine-6-carboxylic acid | E147 | J6 Specific example | 494 | 495 |

TABLE XIII-continued

List of acids

| Int. | Structure | Name | SM | method | MW | Mes |
|---|---|---|---|---|---|---|
| A180 | 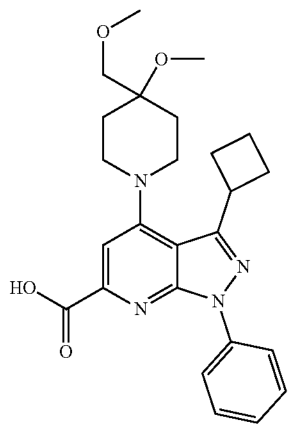 [SMILES: COCC1(OC)CCN(c2cc(C(=O)O)nc3c2c(C2CCC2)nn3-c2ccccc2)CC1] | 3-cyclobutyl-4-[4-methoxy-4-(methoxymethyl)-1-piperidyl]-1-phenyl-pyrazolo[3,4-b]pyridine-6-carboxylic acid | E146 | J8 | 450 | 451 |
| A181 | 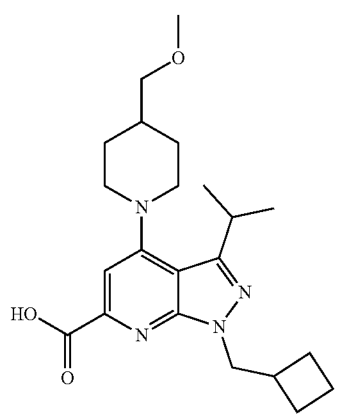 [SMILES: COCC1CCN(c2cc(C(=O)O)nc3c2c(C(C)C)nn3CC2CCC2)CC1] | 1-(cyclobutylmethyl)-3-isopropyl-4-[4-(methoxymethyl)-1-piperidyl]pyrazolo[3,4-b]pyridine-6-carboxylic acid | E154 | J1 | 400 | 401 |
| A182 | 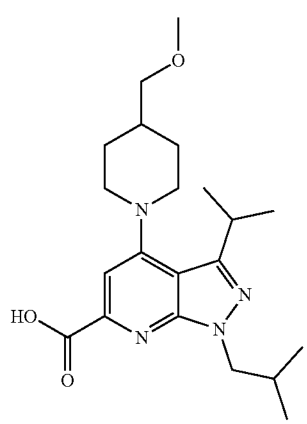 [SMILES: COCC1CCN(c2cc(C(=O)O)nc3c2c(C(C)C)nn3CC(C)C)CC1] | 1-isobutyl-3-isopropyl-4-[4-(methoxymethyl)-1-piperidyl]pyrazolo[3,4-b]pyridine-6-carboxylic acid | E155 | J1 | 388 | 389 |

TABLE XIII-continued

List of acids

| Int. | Structure | Name | SM | method | MW | Mes |
|---|---|---|---|---|---|---|
| A183 | 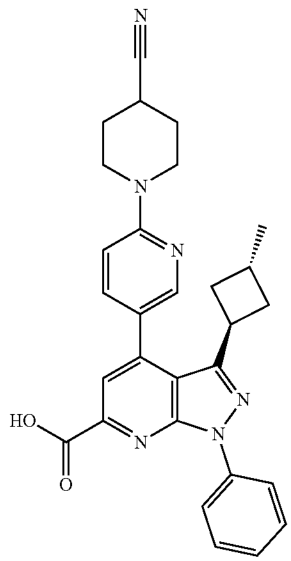 [SMILES: C[C@H]1C[C@H](c2nn(-c3ccccc3)c3nc(C(=O)O)cc(-c4ccc(N5CCC(C#N)CC5)nc4)c32)C1] | 4-[6-(4-cyanopiperidin-1-yl)pyridin-3-yl]-3-[(1r,3r)-3-methylcyclobutyl]-1-phenyl-1H-pyrazolo[3,4-b]pyridine-6-carboxylic acid | E151 | J1 | 492 | 493 |
| A184 | 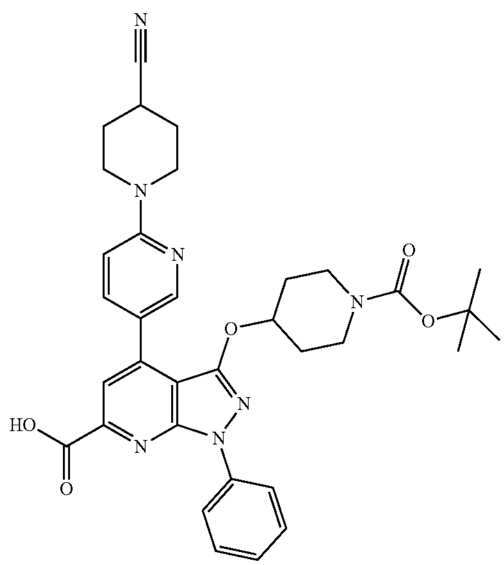 [SMILES: CC(C)(C)OC(=O)N1CCC(Oc2nn(-c3ccccc3)c3nc(C(=O)O)cc(-c4ccc(N5CCC(C#N)CC5)nc4)c23)CC1] | 3-[(1-tert-butoxycarbonyl-4-piperidyl)oxy]-4-[6-(4-cyano-1-piperidyl)-3-pyridyl]-1-phenyl-pyrazolo[3,4-b]pyridine-6-carboxylic acid | E152 | J1 | 623 | 624 |
| A185 | 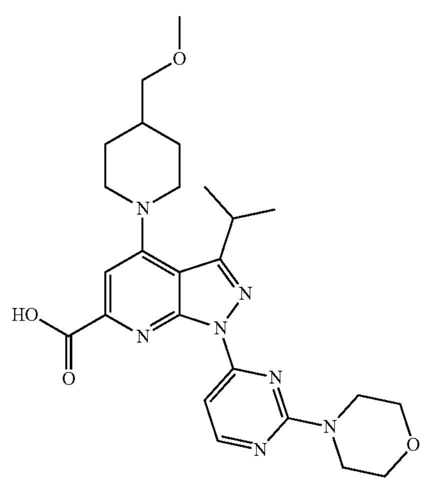 | 3-isopropyl-4-[4-(methoxymethyl)-1-piperidyl]-1-(2-morpholinopyrimidin-4-yl)pyrazolo[3,4-b]pyridine-6-carboxylic acid | E160 | J1 | 495 | 496 |

TABLE XIII-continued
List of acids
| Int. | Structure | Name | SM | method | MW | Mes |
|---|---|---|---|---|---|---|
| A186 | 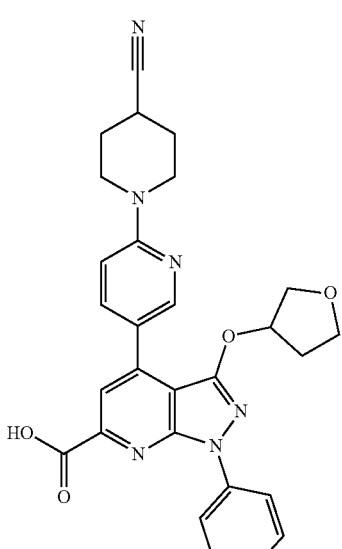 | 4-[6-(4-cyano-1-piperidyl)-3-pyridyl]-1-phenyl-3-tetrahydrofuran-3-yloxy-pyrazolo[3,4-b]pyridine-6-carboxylic acid | E159 | J1 | 510 | 511 |
| A187 | 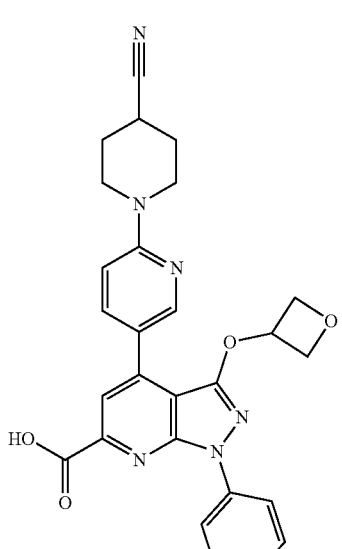 | 4-[6-(4-cyano-1-piperidyl)-3-pyridyl]-3-(oxetan-3-yloxy)-1-phenyl-pyrazolo[3,4-b]pyridine-6-carboxylic acid | E164 | J1 | 496 | 497 |
| A188 | 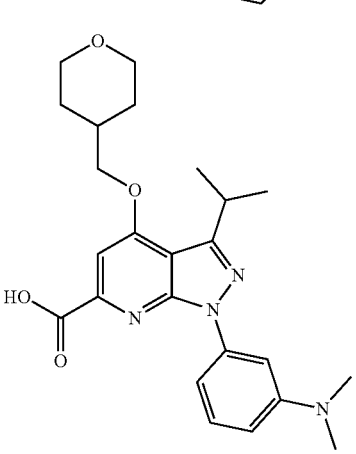 | 1-[3-(dimethylamino)phenyl]-3-isopropyl-4-(tetrahydropyran-4-ylmethoxy)pyrazolo[3,4-b]pyridine-6-carboxylic acid | HP07 | J3 | 438 | 439 |

TABLE XIII-continued

| Int. | Structure | Name | SM | method | MW | Mes |
|------|-----------|------|-----|--------|-----|-----|
| A189 | 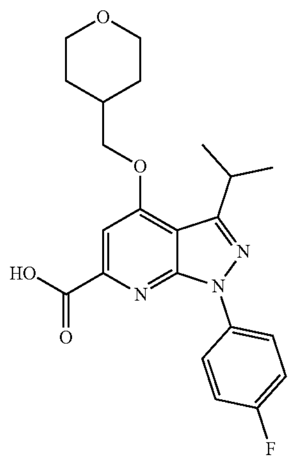 [SMILES: CC(C)c1nn(-c2ccc(F)cc2)c2nc(C(=O)O)cc(OCC3CCOCC3)c12] | 1-(4-fluorophenyl)-3-isopropyl-4-(tetrahydropyran-4-ylmethoxy)pyrazolo[3,4-b]pyridine-6-carboxylic acid | HP11 | J3 | 413 | 414 |
| A190 | 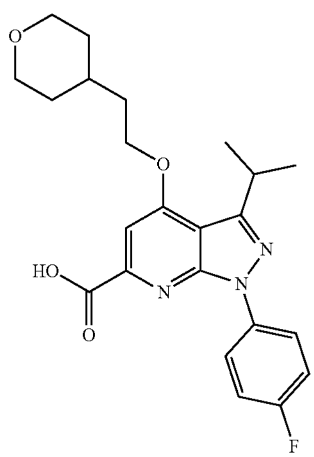 [SMILES: CC(C)c1nn(-c2ccc(F)cc2)c2nc(C(=O)O)cc(OCCC3CCOCC3)c12] | 1-(4-fluorophenyl)-3-isopropyl-4-(2-tetrahydropyran-4-ylethoxy)pyrazolo[3,4-b]pyridine-6-carboxylic acid | HP11 | J3 | 427 | 428 |
| A191 | 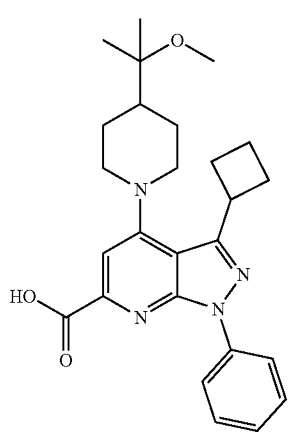 [SMILES: COC(C)(C)C1CCN(c2cc(C(=O)O)nc3c2c(C2CCC2)nn3-c2ccccc2)CC1] | 3-cyclobutyl-4-[4-(1-methoxy-1-methyl-ethyl)-1-piperidyl]-1-phenyl-pyrazolo[3,4-b]pyridine-6-carboxylic acid | E163 | J8 | 448 | 449 |

TABLE XIII-continued

List of acids

| Int. | Structure | Name | SM | method | MW | Mes |
|---|---|---|---|---|---|---|
| A192 | 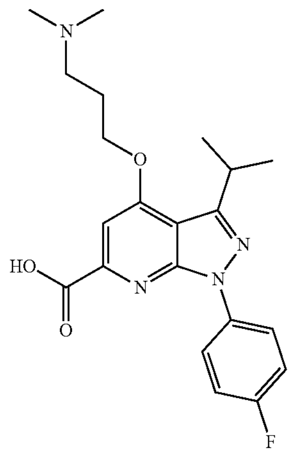 [SMILES: CC(C)c1nn(-c2ccc(F)cc2)c2nc(C(=O)O)cc(OCCCN(C)C)c12] | 4-[3-(dimethylamino)propoxy]-1-(4-fluorophenyl)-3-isopropyl-pyrazolo[3,4-b]pyridine-6-carboxylic acid | HP11 | J3 | 400 | 401 |
| A193 | 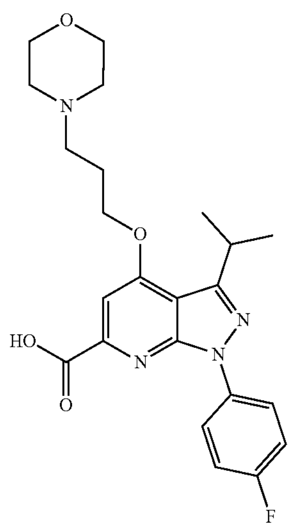 [SMILES: CC(C)c1nn(-c2ccc(F)cc2)c2nc(C(=O)O)cc(OCCCN3CCOCC3)c12] | 1-(4-fluorophenyl)-3-isopropyl-4-(3-morpholinopropoxy)pyrazolo[3,4-b]pyridine-6-carboxylic acid | HP11 | J3 | 442 | 443 |
| A194 | 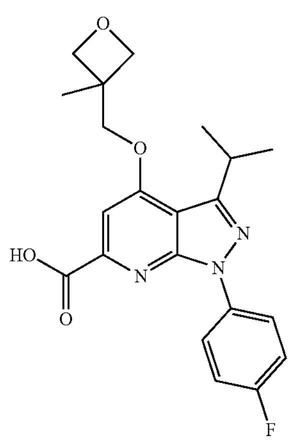 [SMILES: CC(C)c1nn(-c2ccc(F)cc2)c2nc(C(=O)O)cc(OCC3(C)COC3)c12] | 1-(4-fluorophenyl)-3-isopropyl-4-[(3-methyloxetan-3-yl)methoxy]pyrazolo[3,4-b]pyridine-6-carboxylic acid | HP11 | J3 | 399 | 400 |

TABLE XIII-continued

| | | List of acids | | | | |
|---|---|---|---|---|---|---|
| Int. | Structure | Name | SM | method | MW | Mes |
| A195 | | 1-(4-fluorophenyl)-3-isopropyl-4-(tetrahydrofuran-2-ylmethoxy)pyrazolo[3,4-b]pyridine-6-carboxylic acid | HP11 | J3 | 399 | 400 |
| A196 | | 3-cyclobutyl-4-[3-(dimethylamino)propoxy]-1-phenyl-pyrazolo[3,4-b]pyridine-6-carboxylic acid | HP10 | J3 | 394 | 395 |
| A197 | | 3-cyclobutyl-1-phenyl-4-[3-(1-piperidyl)propoxy]pyrazolo[3,4-b]pyridine-6-carboxylic acid | HP10 | J3 | 434 | 435 |

TABLE XIII-continued

List of acids

| Int. | Structure | Name | SM | method | MW | Mes |
|---|---|---|---|---|---|---|
| A198 | 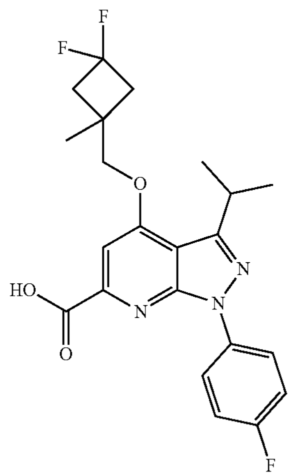 [SMILES: CC(C)c1nn(-c2ccc(F)cc2)c2nc(C(=O)O)cc(OCC3(C)CC(F)(F)C3)c12] | 4-[(3,3-difluoro-1-methyl-cyclobutyl)methoxy]-1-(4-fluorophenyl)-3-isopropyl-pyrazolo[3,4-b]pyridine-6-carboxylic acid | HP11 | J3 | 433 | 434 |
| A199 | 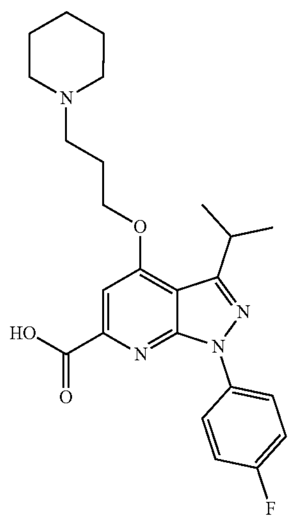 [SMILES: CC(C)c1nn(-c2ccc(F)cc2)c2nc(C(=O)O)cc(OCCCN3CCCCC3)c12] | 1-(4-fluorophenyl)-3-isopropyl-4-[3-(1-piperidyl)propoxy]pyrazolo[3,4-b]pyridine-6-carboxylic acid | HP11 | J3 | 440 | 441 |
| A200 | 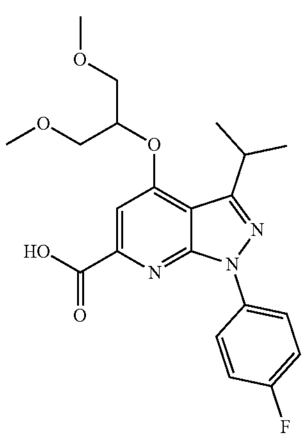 [SMILES: COCC(COC)Oc1cc(C(=O)O)nc2c1c(C(C)C)nn2-c1ccc(F)cc1] | 1-(4-fluorophenyl)-3-isopropyl-4-[2-methoxy-1-(methoxymethyl)ethoxy]pyrazolo[3,4-b]pyridine-6-carboxylic acid | HP11 | J3 | 417 | 418 |

TABLE XIII-continued

List of acids

| Int. | Structure | Name | SM | method | MW | Mes |
|---|---|---|---|---|---|---|
| A201 | 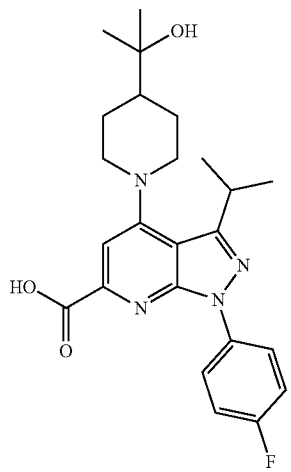 [SMILES: CC(C)c1nn(-c2ccc(F)cc2)c2nc(C(=O)O)cc(N3CCC(C(C)(C)O)CC3)c12] | 1-(4-fluorophenyl)-4-[4-(1-hydroxy-1-methyl-ethyl)-1-piperidyl]-3-isopropyl-pyrazolo[3,4-b]pyridine-6-carboxylic acid | E166 | J1 | 440 | 441 |
| A202 | 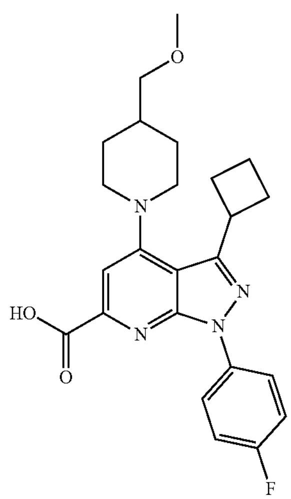 [SMILES: COCC1CCN(c2cc(C(=O)O)nc3c2c(C2CCC2)nn3-c2ccc(F)cc2)CC1] | 3-cyclobutyl-1-(4-fluorophenyl)-4-[4-(methoxymethyl)-1-piperidyl]pyrazolo[3,4-b]pyridine-6-carboxylic acid | E167 | J1 | 438 | 439 |
| A203 | 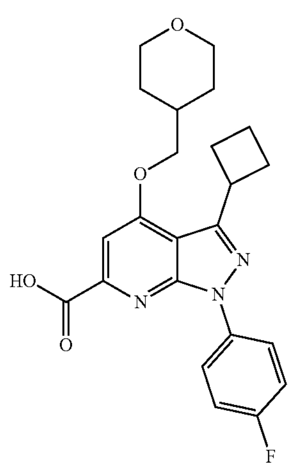 [SMILES: O=C(O)c1cc(OCC2CCOCC2)c2c(C3CCC3)nn(-c3ccc(F)cc3)c2n1] | 3-cyclobutyl-1-(4-fluorophenyl)-4-(tetrahydropyran-4-ylmethoxy)pyrazolo[3,4-d]pyridine-6-carboxylic acid | E171 | J1 | 425 | 426 |

TABLE XIII-continued

| | | List of acids | | | | |
|---|---|---|---|---|---|---|
| Int. | Structure | Name | SM | method | MW | Mes |
| A204 | | 3-cyclobutyl-4-[4-(1-hydroxy-1-methyl-ethyl)-1-piperidyl]-1-phenyl-pyrazolo[3,4-b]pyridine-6-carboxylic acid | E170 | J1 | 434 | 435 |
| A205 | | 4-[4-(dimethylamino)-1-piperidyl]-1-(4-fluorophenyl)-3-isopropyl-pyrazolo[3,4-b]pyridine-6-carboxylic acid | E174 | J1 | 425 | 426 |
| A206 | | 1-(4-fluorophenyl)-3-isopropyl-4-[4-(1-methyl-4-piperidyl)-1-piperidyl]pyrazolo[3,4-b]pyridine-6-carboxylic acid | E175 | J1 | 479 | 480 |

TABLE XIII-continued
List of acids
| Int. | Structure | Name | SM | method | MW | Mes |
|---|---|---|---|---|---|---|
| A207 | 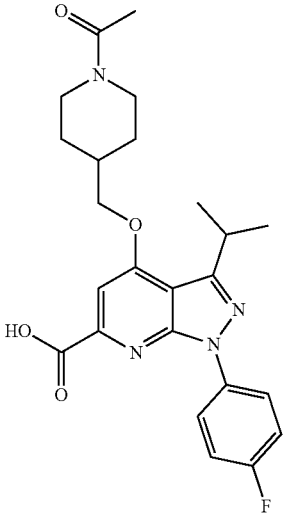 [SMILES: CC(=O)N1CCC(COc2cc(C(=O)O)nc3c2c(C(C)C)nn3-c2ccc(F)cc2)CC1] | 4-[(1-acetyl-4-piperidyl)methoxy]-1-(4-fluorophenyl)-3-isopropyl-pyrazolo[3,4-b]pyridine-6-carboxylic acid | E176 | J1 | 454 | 455 |
| A208 | 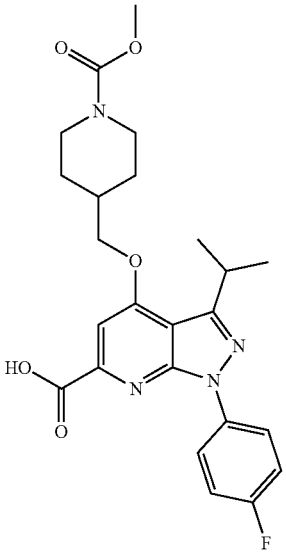 [SMILES: COC(=O)N1CCC(COc2cc(C(=O)O)nc3c2c(C(C)C)nn3-c2ccc(F)cc2)CC1] | 1-(4-fluorophenyl)-3-isopropyl-4-[(1-methoxycarbonyl-4-piperidyl)methoxy]pyrazolo[3,4-b]pyridine-6-carboxylic acid | E178 | J1 | 470 | 471 |
| A209 | 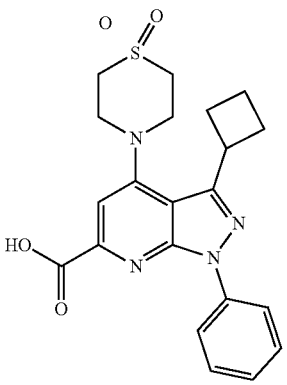 | 3-cyclobutyl-4-(1,1-dioxo-1,4-thiazinan-4-yl)-1-phenyl-pyrazolo[3,4-b]pyridine-6-carboxylic acid | E196 | J1 | 426 | 427 |

TABLE XIII-continued

List of acids

| Int. | Structure | Name | SM | method | MW | Mes |
|---|---|---|---|---|---|---|
| A210 | 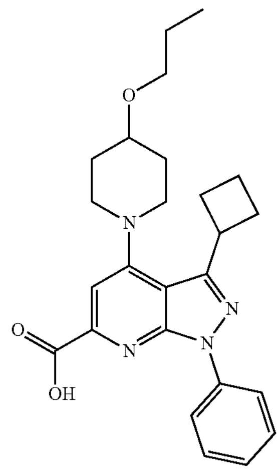 [SMILES: CCCOC1CCN(c2cc(C(=O)O)nc3c2c(C2CCC2)nn3-c2ccccc2)CC1] | 3-cyclobutyl-1-phenyl-4-(4-propoxy-1-piperidyl)pyrazolo[3,4-b]pyridine-6-carboxylic acid | E078 | J1 | 434 | 435 |
| A211 | 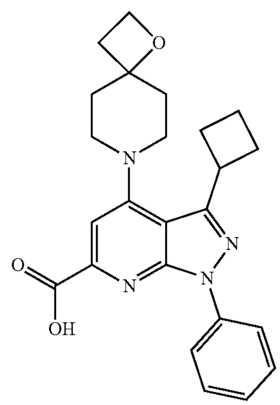 [SMILES: O=C(O)c1cc(N2CCC3(CCO3)CC2)c2c(C3CCC3)nn(-c3ccccc3)c2n1] | 3-cyclobutyl-4-(1-oxa-7-azaspiro[3.5]nonan-7-yl)-1-phenyl-pyrazolo[3,4-b]pyridine-6-carboxylic acid | E085 | J1 | 418 | 419 |
| A212 | 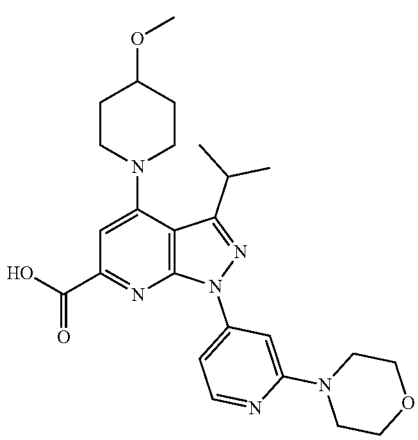 [SMILES: COC1CCN(c2cc(C(=O)O)nc3c2c(C(C)C)nn3-c2ccnc(N3CCOCC3)c2)CC1] | 3-isopropyl-4-(4-methoxy-1-piperidyl)-1-(2-morpholino-4-pyridyl)pyrazolo[3,4-b]pyridine-6-carboxylic acid | A257 Specific example | J7 | 480 | 481 |

TABLE XIII-continued

List of acids

| Int. | Structure | Name | SM | method | MW | Mes |
|------|-----------|------|-----|--------|-----|-----|
| A213 | 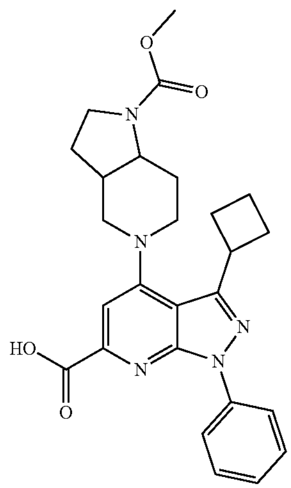 [SMILES: COC(=O)N1CCC2CN(c3cc(C(=O)O)nc4c3c(C3CCC3)nn4-c3ccccc3)CCC21] | 3-cyclobutyl-4-(1-methoxycarbonyl-3,3a,4,6,7,7a-hexahydro-2H-pyrrolo[3,2-c]pyridin-5-yl)-1-phenyl-pyrazolo[3,4-b]pyridine-6-carboxylic acid | E129 | J1 | 476 | 477 |
| A214 | 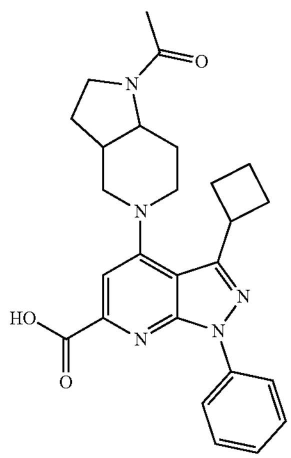 [SMILES: CC(=O)N1CCC2CN(c3cc(C(=O)O)nc4c3c(C3CCC3)nn4-c3ccccc3)CCC21] | 4-(1-acetyl-3,3a,4,6,7,7a-hexahydro-2H-pyrrolo[3,2-c]pyridin-5-yl)-3-cyclobutyl-1-phenyl-pyrazolo[3,4-b]pyridine-6-carboxylic acid | E132 | J1 | 460 | 461 |
| A215 | 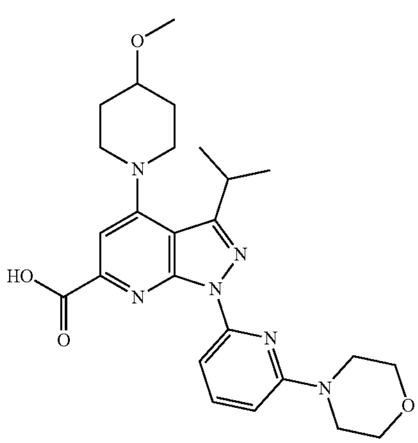 [SMILES: COC1CCN(c2cc(C(=O)O)nc3c2c(C(C)C)nn3-c2cccc(N3CCOCC3)n2)CC1] | 3-isopropyl-4-(4-methoxy-1-piperidyl)-1-(6-morpholino-2-pyridyl)pyrazolo[3,4-b]pyridine-6-carboxylic acid | A259 | J7 | 480 | 481 |

TABLE XIII-continued

List of acids

| Int. | Structure | Name | SM | method | MW | Mes |
|---|---|---|---|---|---|---|
| A216 | 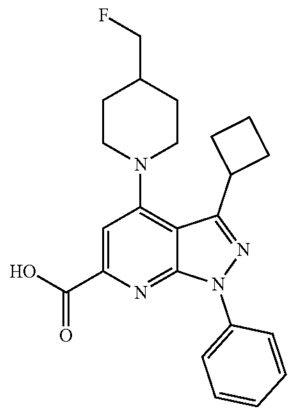 [SMILES: O=C(O)c1cc(N2CCC(CF)CC2)c2c(C3CCC3)nn(-c3ccccc3)c2n1] | 3-cyclobutyl-4-[4-(fluoromethyl)-1-piperidyl]-1-phenyl-pyrazolo[3,4-b]pyridine-6-carboxylic acid | HP10 | J4 Specific example | 408 | 409 |
| A217 | 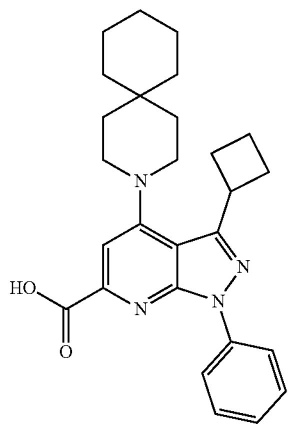 [SMILES: O=C(O)c1cc(N2CCC3(CCCCC3)CC2)c2c(C3CCC3)nn(-c3ccccc3)c2n1] | 4-(3-azaspiro[5.5]undecan-3-yl)-3-cyclobutyl-1-phenyl-pyrazolo[3,4-b]pyridine-6-carboxylic acid | HP10 | J4 | 444 | 445 |
| A218 | 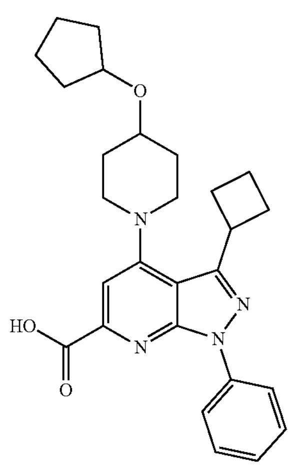 [SMILES: O=C(O)c1cc(N2CCC(OC3CCCC3)CC2)c2c(C3CCC3)nn(-c3ccccc3)c2n1] | 3-cyclobutyl-4-[4-(cyclopentoxy)-1-piperidyl]-1-phenyl-pyrazolo[3,4-b]pyridine-6-carboxylic acid | E139 | J1 | 460 | 461 |

TABLE XIII-continued
| | | List of acids | | | | |
|---|---|---|---|---|---|---|
| Int. | Structure | Name | SM | method | MW | Mes |
| A219 | 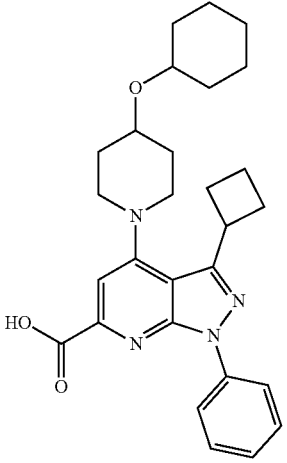 [SMILES: O=C(O)c1cc(N2CCC(OC3CCCCC3)CC2)c2c(C3CCC3)nn(-c3ccccc3)c2n1] | 3-cyclobutyl-4-[4-(cyclohexoxy)-1-piperidyl]-1-phenyl-pyrazolo[3,4-b]pyridine-6-carboxylic acid | E140 | J1 | 474 | 475 |
| A220 | 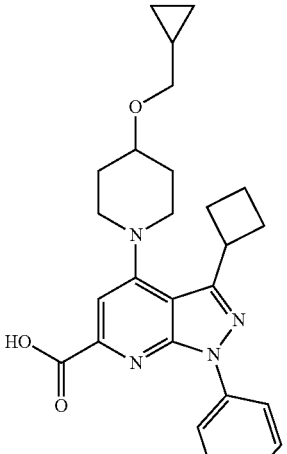 | 3-cyclobutyl-4-[4-(cyclopropylmethoxy)-1-piperidyl]-1-phenyl-pyrazolo[3,4-b]pyridine-6-carboxylic acid | E141 | J1 | 446 | 447 |
| A221 | 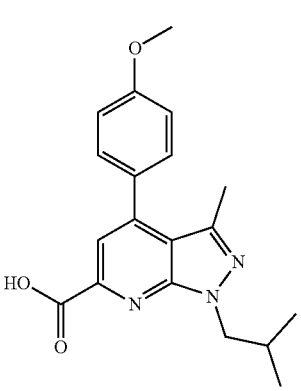 [SMILES: COc1ccc(-c2cc(C(=O)O)nc3c2c(C)nn3CC(C)C)cc1] | 4-(4-methoxyphenyl)-3-methyl-1-(2-methylpropyl)-1H-pyrazolo[3,4-b]pyridine-6-carboxylic acid | ALP06, 3524-36-5 | J2 | 339 | 340 |

TABLE XIII-continued

List of acids

| Int. | Structure | Name | SM | method | MW | Mes |
|---|---|---|---|---|---|---|
| A222 | 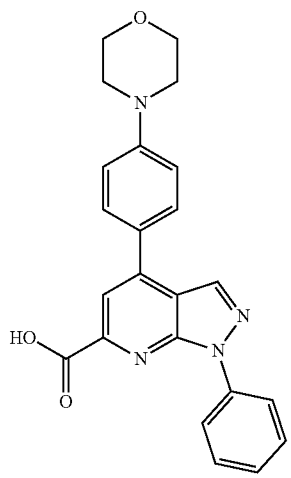 [SMILES: O=C(O)c1cc(-c2ccc(N3CCOCC3)cc2)c2cnn(-c3ccccc3)c2n1] | 4-(4-morpholinophenyl)-1-phenyl-pyrazolo[3,4-b]pyridine-6-carboxylic acid | 127-17-3, 1204-86-0, 826-85-7 | Specific example | 400 | 401 |
| A223 | 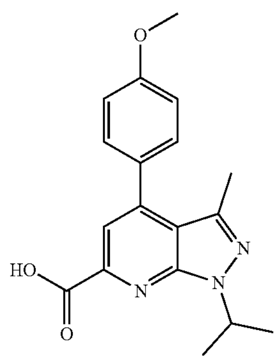 [SMILES: COc1ccc(-c2cc(C(=O)O)nc3c2c(C)nn3C(C)C)cc1] | 1-isopropyl-4-(4-methoxyphenyl)-3-methyl-pyrazolo[3,4-b]pyridine-6-carboxylic acid | ALP06, 1124-16-9 | J2 | 325 | 326 |
| A224 | 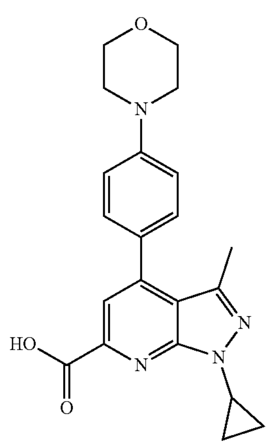 [SMILES: Cc1nn(C2CC2)c2nc(C(=O)O)cc(-c3ccc(N4CCOCC4)cc3)c12] | 1-cyclopropyl-3-methyl-4-(4-morpholinophenyl)pyrazolo[3,4-b]pyridine-6-carboxylic acid | ALP01, AMP15 | J2 | 378 | 379 |

TABLE XIII-continued

List of acids

| Int. | Structure | Name | SM | method | MW | Mes |
|------|-----------|------|-----|--------|-----|-----|
| A225 | 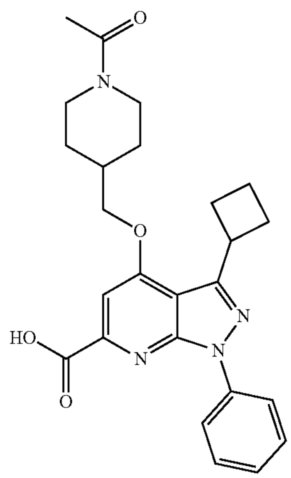 [SMILES: CC(=O)N1CCC(COc2cc(C(=O)O)nc3c2c(C2CCC2)nn3-c2ccccc2)CC1] | 4-[(1-acetyl-4-piperidyl)methoxy]-3-cyclobutyl-1-phenyl-pyrazolo[3,4-b]pyridine-6-carboxylic acid | A261 | J9 Specific example | 448 | 449 |
| A226 | 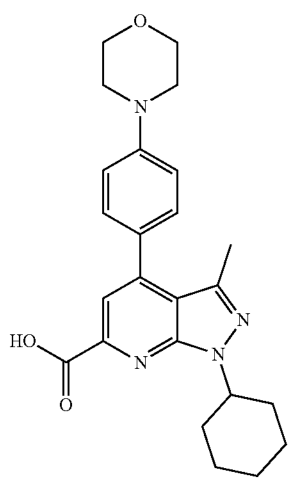 [SMILES: Cc1nn(C2CCCCC2)c2nc(C(=O)O)cc(-c3ccc(N4CCOCC4)cc3)c12] | 1-cyclohexyl-3-methyl-4-(4-morpholinophenyl)pyrazolo[3,4-b]pyridine-6-carboxylic acid | ALP01, 56547-82-1 | J2 | 420 | 421 |
| A227 | 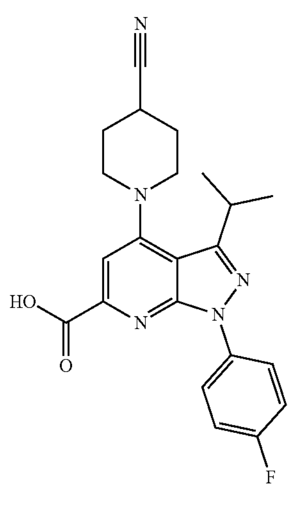 [SMILES: CC(C)c1nn(-c2ccc(F)cc2)c2nc(C(=O)O)cc(N3CCC(C#N)CC3)c12] | 4-(4-cyano-1-piperidyl)-1-(4-fluorophenyl)-3-isopropyl-pyrazolo[3,4-b]pyridine-6-carboxylic acid | E142 | J1 | 407 | 408 |

TABLE XIII-continued

List of acids

| Int. | Structure | Name | SM | method | MW | Mes |
|------|-----------|------|-----|--------|-----|-----|
| A228 | 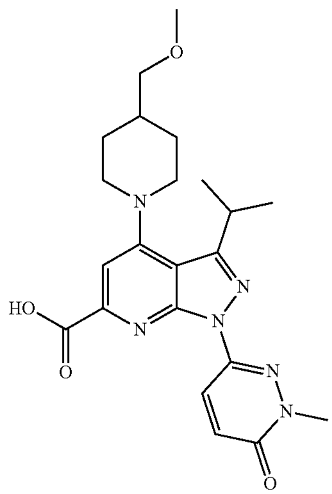 [SMILES: COCC1CCN(c2cc(C(=O)O)nc3c2c(C(C)C)nn3-c2ccc(=O)n(C)n2)CC1] | 3-isopropyl-4-[4-(methoxymethyl)-1-piperidyl]-1-(1-methyl-6-oxo-pyridazin-3-yl)pyrazolo[3,4-b]pyridine-6-carboxylic acid | E157 | J1 | 440 | 441 |
| A229 | 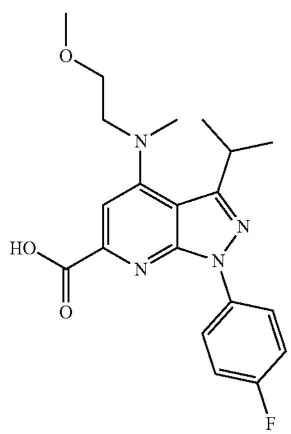 [SMILES: COCCN(C)c1cc(C(=O)O)nc2c1c(C(C)C)nn2-c1ccc(F)cc1] | 1-(4-fluorophenyl)-3-isopropyl-4-[2-methoxyethyl(methyl)amino]pyrazolo[3,4-b]pyridine-6-carboxylic acid | E165 | J1 | 386 | 387 |
| A230 | 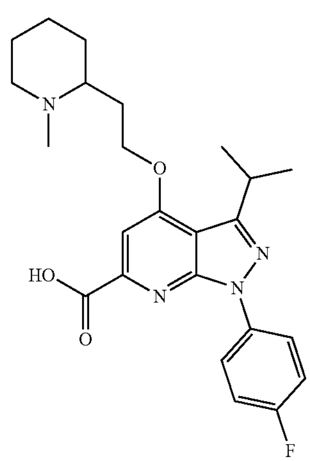 [SMILES: CC(C)c1nn(-c2ccc(F)cc2)c2nc(C(=O)O)cc(OCCC3CCCCN3C)c12] | 1-(4-fluorophenyl)-3-isopropyl-4-[2-(1-methyl-2-piperidyl)ethoxy]pyrazolo[3,4-b]pyridine-6-carboxylic acid | HP11 | J3 | 440 | 441 |

TABLE XIII-continued

List of acids

| Int. | Structure | Name | SM | method | MW | Mes |
|---|---|---|---|---|---|---|
| A231 | 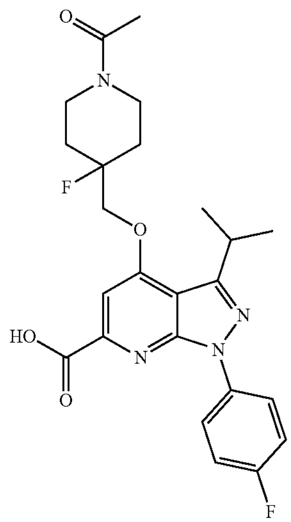 [SMILES: CC(=O)N1CCC(F)(COc2cc(C(=O)O)nc3c2c(C(C)C)nn3-c2ccc(F)cc2)CC1] | 4-[(1-acetyl-4-fluoro-4-piperidyl)methoxy]-1-(4-fluorophenyl)-3-isopropyl-pyrazolo[3,4-b]pyridine-6-carboxylic acid | HP11, ALC03 | J3 | 472 | 473 |
| A232 | 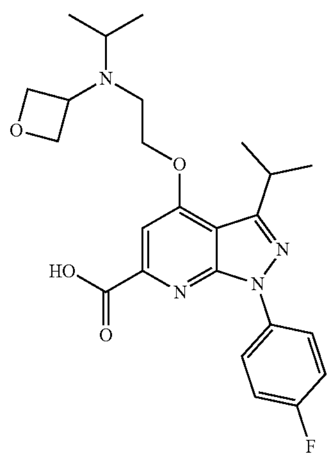 [SMILES: CC(C)c1nn(-c2ccc(F)cc2)c2nc(C(=O)O)cc(OCCN(C(C)C)C3COC3)c12] | 1-(4-fluorophenyl)-3-isopropyl-4-[2-[isopropyl(oxetan-3-yl)amino]ethoxy]pyrazolo[3,4-b]pyridine-6-carboxylic acid | HP11, ALC04 | J3 | 456 | 457 |
| A233 | 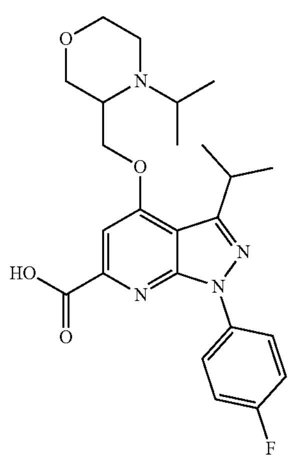 [SMILES: CC(C)c1nn(-c2ccc(F)cc2)c2nc(C(=O)O)cc(OCC3COCCN3C(C)C)c12] | 1-(4-fluorophenyl)-3-isopropyl-4-[(4-isopropylmorpholin-3-yl)methoxy]pyrazolo[3,4-b]pyridine-6-carboxylic acid | HP11, ALC04 (re-arrange-ment) | J3 | 456 | 457 |

TABLE XIII-continued

| | | List of acids | | | | |
|---|---|---|---|---|---|---|
| Int. | Structure | Name | SM | method | MW | Mes |
| A234 | | 4-(1,4-dioxan-2-ylmethoxy)-1-(4-fluorophenyl)-3-isopropyl-pyrazolo[3,4-b]pyridine-6-carboxylic acid | HP11, ALC05 (re-arrange-ment) | J3 | 415 | 416 |
| A235 | | 1-(4-fluorophenyl)-3-isopropyl-4-[2-(oxetan-3-yloxy)ethoxy]pyrazolo[3,4-b]pyridine-6-carboxylic acid | HP11, ALC05 | J3 | 415 | 416 |
| A236 | | 1-(2,6-dimethylpyridin-4-yl)-4-[4-(methoxymethyl)piperidin-1-yl]-3-(propan-2-yl)-1H-pyrazolo[3,4-b]pyridine-6-carboxylic acid | E195 | J1 | 437 | 438 |

TABLE XIII-continued

List of acids

| Int. | Structure | Name | SM | method | MW | Mes |
|------|-----------|------|-----|--------|-----|-----|
| A237 | 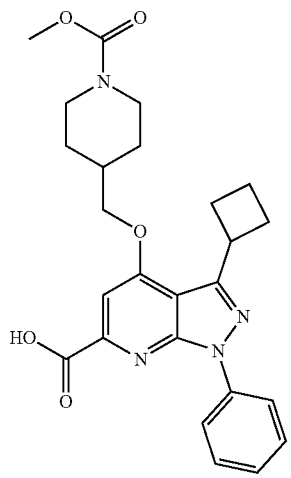 [SMILES: COC(=O)N1CCC(COc2cc(C(=O)O)nc3c2c(C2CCC2)nn3-c2ccccc2)CC1] | 3-cyclobutyl-4-[(1-methoxycarbonyl-4-piperidyl)methoxy]-1-phenyl-pyrazolo[3,4-b]pyridine-6-carboxylic acid | A261 | J9 Specific example | 464 | 465 |
| A238 | 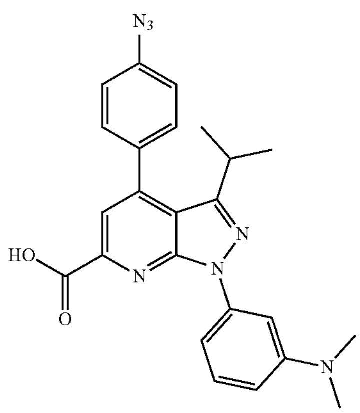 [SMILES: CC(C)c1nn(-c2cccc(N(C)C)c2)c2nc(C(=O)O)cc(-c3ccc(N=[N+]=[N-])cc3)c12] | 4-(4-azidophenyl)-1-[3-(dimethylamino)phenyl]-3-(propan-2-yl)-1H-pyrazolo[3,4-b]pyridine-6-carboxylic acid | E199 | J1 | 441 | 442 |
| A239 | 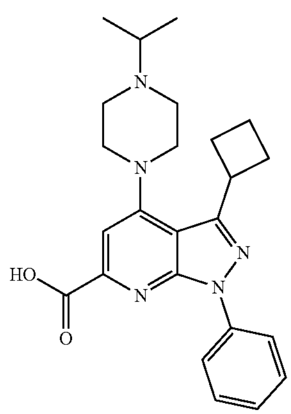 [SMILES: CC(C)N1CCN(c2cc(C(=O)O)nc3c2c(C2CCC2)nn3-c2ccccc2)CC1] | 3-cyclobutyl-4-(4-isopropylpiperazin-1-yl)-1-phenyl-pyrazolo[3,4-b]pyridine-6-carboxylic acid | E158 | J1 | 419 | 420 |

TABLE XIII-continued

List of acids

| Int. | Structure | Name | SM | method | MW | Mes |
|---|---|---|---|---|---|---|
| A240 | 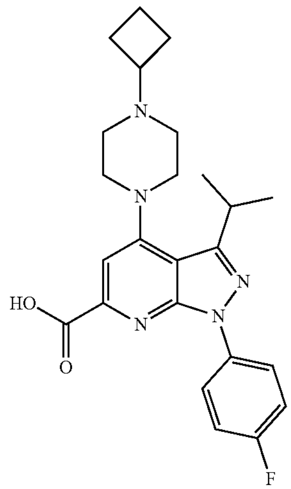 [SMILES: CC(C)c1nn(-c2ccc(F)cc2)c2nc(C(=O)O)cc(N3CCN(C4CCC4)CC3)c12] | 4-(4-cyclobutylpiperazin-1-yl)-1-(4-fluorophenyl)-3-isopropyl-pyrazolo[3,4-b]pyridine-6-carboxylic acid | E162 | J1 | 437 | 438 |
| A241 | 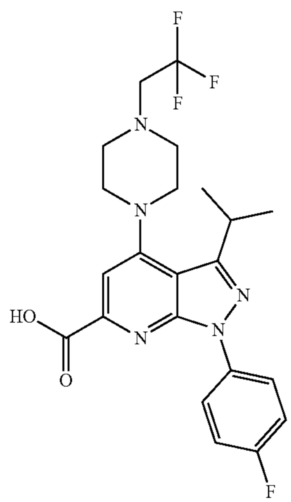 [SMILES: CC(C)c1nn(-c2ccc(F)cc2)c2nc(C(=O)O)cc(N3CCN(CC(F)(F)F)CC3)c12] | 1-(4-fluorophenyl)-3-isopropyl-4-[4-(2,2,2-trifluoroethyl)piperazin-1-yl]pyrazolo[3,4-b]pyridine-6-carboxylic acid | E156 | J1 | 465 | 466 |
| A242 | 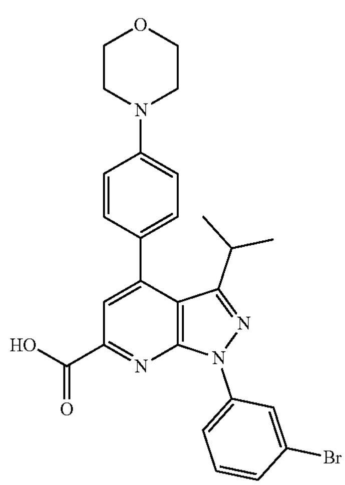 [SMILES: CC(C)c1nn(-c2cccc(Br)c2)c2nc(C(=O)O)cc(-c3ccc(N4CCOCC4)cc3)c12] | 1-(3-bromophenyl)-3-isopropyl-4-(4-morpholinophenyl)pyrazolo[3,4-b]pyridine-6-carboxylic acid | ALP01, AMP05 | J2 | 520-522 | 521-523 |

TABLE XIII-continued

List of acids

| Int. | Structure | Name | SM | method | MW | Mes |
|---|---|---|---|---|---|---|
| A243 | 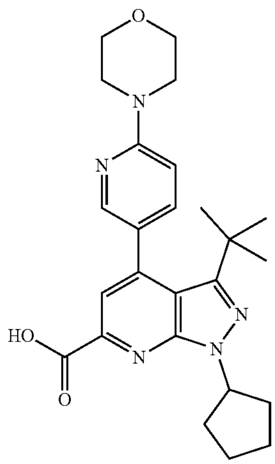 [SMILES: CC(C)(C)c1nn(C2CCCC2)c2nc(C(=O)O)cc(-c3ccc(N4CCOCC4)nc3)c12] | 3-tert-butyl-1-cyclopentyl-4-(6-morpholino-3-pyridyl)pyrazolo[3,4-b]pyridine-6-carboxylic acid | ALP05, AMP37 | J2 | 449 | 450 |
| A244 | 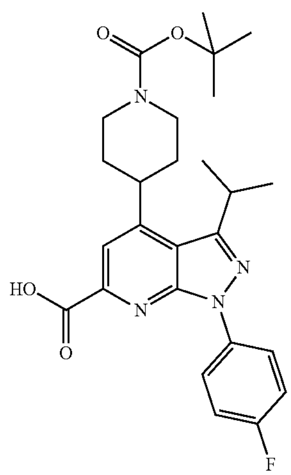 [SMILES: CC(C)c1nn(-c2ccc(F)cc2)c2nc(C(=O)O)cc(C3CCN(C(=O)OC(C)(C)C)CC3)c12] | 4-(1-tert-butoxycarbonyl-4-piperidyl)-1-(4-fluorophenyl)-3-isopropyl-pyrazolo[3,4-b]pyridine-6-carboxylic acid | E197 | J1 | 482 | 483 |
| A245 | 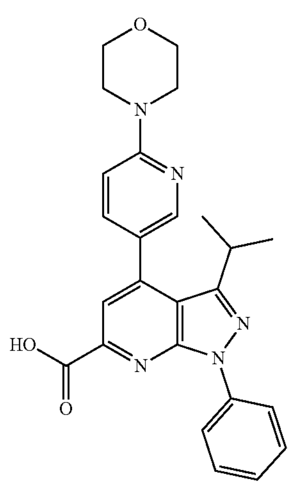 [SMILES: CC(C)c1nn(-c2ccccc2)c2nc(C(=O)O)cc(-c3ccc(N4CCOCC4)nc3)c12] | 3-isopropyl-4-(6-morpholino-3-pyridyl)-1-phenyl-pyrazolo[3,4-b]pyridine-6-carboxylic acid | E007 | J1 | 443 | 444 |

TABLE XIII-continued
List of acids
| Int. | Structure | Name | SM | method | MW | Mes |
|---|---|---|---|---|---|---|
| A246 | 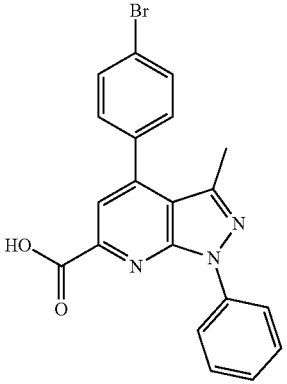 [SMILES: Cc1nn(-c2ccccc2)c2nc(C(=O)O)cc(-c3ccc(Br)cc3)c12] | 4-(4-bromophenyl)-3-methyl-1-phenyl-pyrazolo[3,4-b]pyridine-6-carboxylic acid | ALP19, 1131-18-6 | J2 | 407-409 | 408-410 |
| A247 | 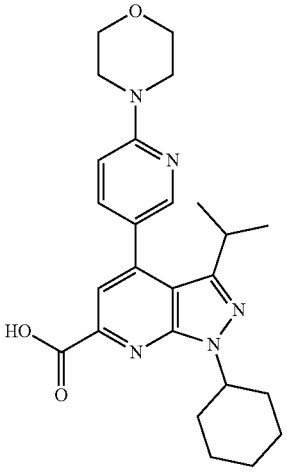 [SMILES: CC(C)c1nn(C2CCCCC2)c2nc(C(=O)O)cc(-c3ccc(N4CCOCC4)nc3)c12] | 1-cyclohexyl-3-isopropyl-4-(6-morpholino-3-pyridyl)pyrazolo[3,4-b]pyridine-6-carboxylic acid | ALP05, AMP23 | J2 | 449 | 450 |
| A248 | 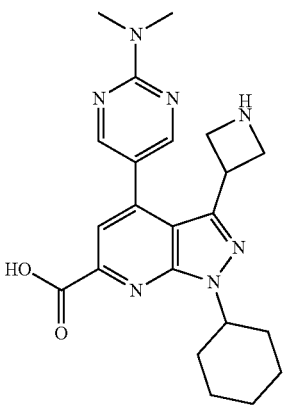 [SMILES: CN(C)c1ncc(-c2cc(C(=O)O)nc3c2c(C2CNC2)nn3C2CCCCC2)cn1] | 3-(azetidin-3-yl)-1-cyclohexyl-4-[2-(dimethylamino)pyrimidin-5-yl]pyrazolo[3,4-b]pyridine-6-carboxylic acid | ALP03, AMP38 | J2 | 421 | 422 |

TABLE XIII-continued

List of acids

| Int. | Structure | Name | SM | method | MW | Mes |
|---|---|---|---|---|---|---|
| A249 | 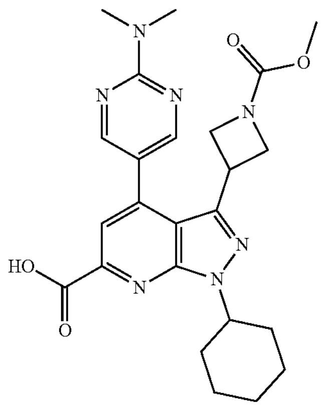 [SMILES: COC(=O)N1CC(c2nn(C3CCCCC3)c3nc(C(=O)O)cc(-c4cnc(N(C)C)nc4)c23)C1] | 1-cyclohexyl-4-[2-(dimethylamino)pyrimidin-5-yl]-3-(1-methoxycarbonylazetidin-3-yl)pyrazolo[3,4-b]pyridine-6-carboxylic acid | A248 | J9 Specific example | 479 | 480 |
| A250 | 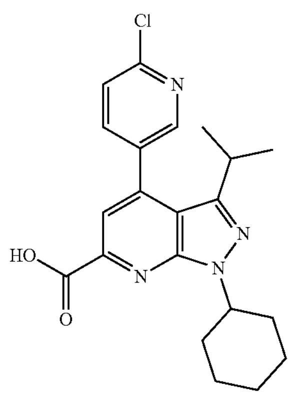 [SMILES: CC(C)c1nn(C2CCCCC2)c2nc(C(=O)O)cc(-c3ccc(Cl)nc3)c12] | 4-(6-chloro-3-pyridyl)-1-cyclohexyl-3-isopropyl-pyrazolo[3,4-b]pyridine-6-carboxylic acid | ALP07, AMP23 | J2 | 398-400 | 399-401 |
| A251 | 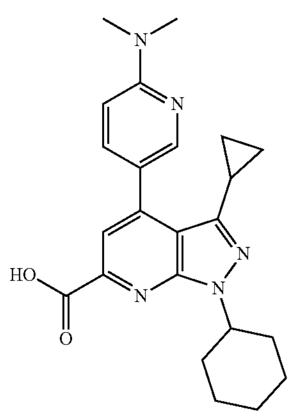 [SMILES: CN(C)c1ccc(-c2cc(C(=O)O)nc3c2c(C2CC2)nn3C2CCCCC2)cn1] | 1-cyclohexyl-3-cyclopropyl-4-[6-(dimethylamino)-3-pyridyl]pyrazolo[3,4-b]pyridine-6-carboxylic acid | E033 | J1 | 405 | 406 |

TABLE XIII-continued

List of acids

| Int. | Structure | Name | SM | method | MW | Mes |
|------|-----------|------|----|--------|----|----|
| A252 | 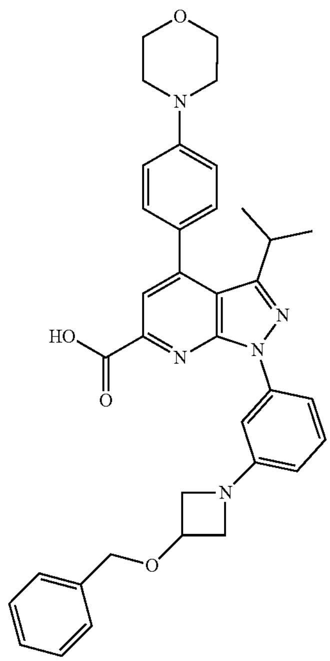 [SMILES: CC(C)c1nn(-c2cccc(N3CC(OCc4ccccc4)C3)c2)c2nc(C(=O)O)cc(-c3ccc(N4CCOCC4)cc3)c12] | 1-[3-(3-benzyloxyazetidin-1-yl)phenyl]-3-isopropyl-4-(4-morpholinophenyl)pyrazolo[3,4-b]pyridine-6-carboxylic acid | A242 | J7 | 603 | 604 |
| A253 | 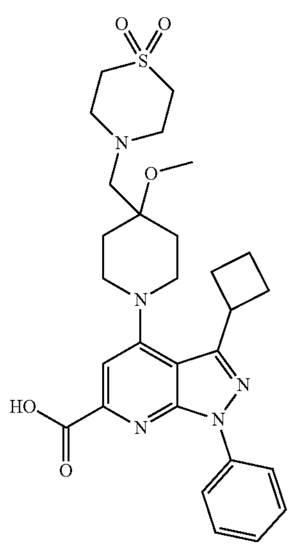 [SMILES: COC1(CN2CCS(=O)(=O)CC2)CCN(c2cc(C(=O)O)nc3c2c(C2CCC2)nn3-c2ccccc2)CC1] | 3-cyclobulyl-4-[4-[(1,1-dioxo-1,4-thiazinan-4-yl)methyl]-4-methoxy-1-piperidyl]-1-phenyl-pyrazolo[3,4-b]pyridine-6-carboxylic acid | E150 | J8 | 553 | 554 |

TABLE XIII-continued

List of acids

| Int. | Structure | Name | SM | method | MW | Mes |
|------|-----------|------|-----|--------|-----|-----|
| A254 | 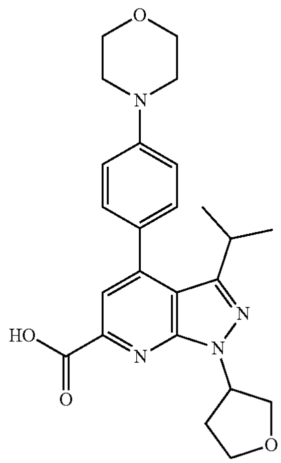 [SMILES: CC(C)c1nn(C2CCOC2)c2nc(C(=O)O)cc(-c3ccc(N4CCOCC4)cc3)c12] | 3-isopropyl-4-(4-morpholinophenyl)-1-tetrahydrofuran-3-yl-pyrazolo[3,4-b]pyridine-6-carboxylic acid | ALP01, AMP27 | J2 | 436 | 437 |
| A255 | 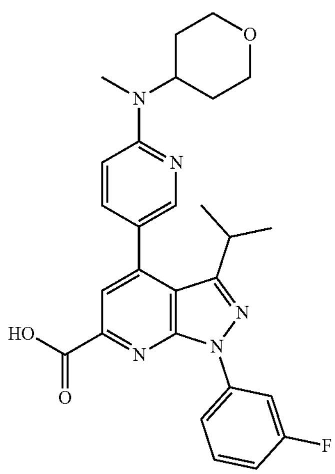 [SMILES: CC(C)c1nn(-c2cccc(F)c2)c2nc(C(=O)O)cc(-c3ccc(N(C)C4CCOCC4)nc3)c12] | 1-(3-fluorophenyl)-3-isopropyl-4-[6-[methyl(tetrahydropyran-4-yl)amino]-3-pyridyl]pyrazolo[3,4-b]pyridine-6-carboxylic acid | E137 | J1 | 489 | 490 |
| A256 | 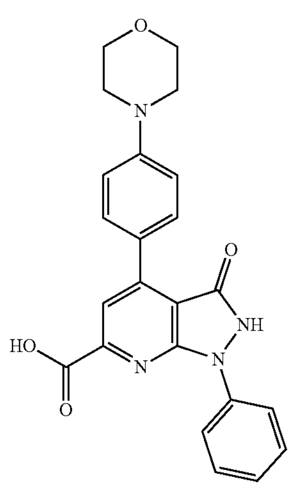 [SMILES: O=C(O)c1cc(-c2ccc(N3CCOCC3)cc2)c2c(=O)[nH]n(-c3ccccc3)c2n1] | 4-(4-morpholinophenyl)-3-oxo-1-phenyl-2H-pyrazolo[3,4-b]pyridine-6-carboxylic acid | ALP01, 70373-98-7 | J2 | 416 | 417 |

TABLE XIII-continued

List of acids

| Int. | Structure | Name | SM | method | MW | Mes |
|------|-----------|------|----|--------|----|----|
| A257 | 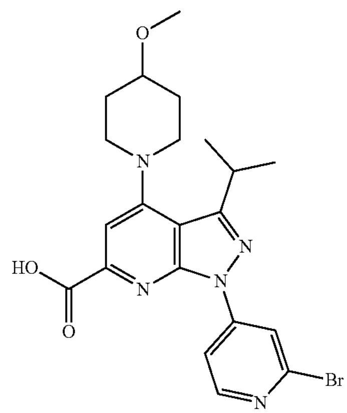 [SMILES: COC1CCN(c2cc(C(=O)O)nc3c2c(C(C)C)nn3-c2ccnc(Br)c2)CC1] | 1-(2-bromo-4-pyridyl)-3-isopropyl-4-(4-methoxy-1-piperidyl)pyrazolo[3,4-b]pyridine-6-carboxylic acid | E108 | J1 | 473-475 | 474-476 |
| A258 | 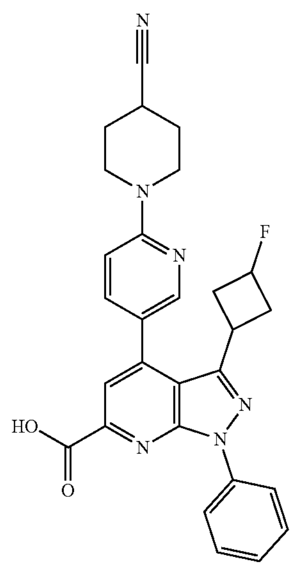 [SMILES: N#CC1CCN(c2ccc(-c3cc(C(=O)O)nc4c3c(C3CC(F)C3)nn4-c3ccccc3)cn2)CC1] | 4-[6-(4-cyano-1-piperidyl)-3-pyridyl]-3-(3-fluorocyclobutyl)-1-phenyl-pyrazolo[3,4-b]pyridine-6-carboxylic acid | E120 | J1 | 496 | 497 |
| A259 | 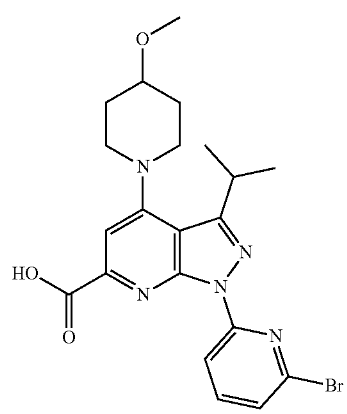 [SMILES: COC1CCN(c2cc(C(=O)O)nc3c2c(C(C)C)nn3-c2cccc(Br)n2)CC1] | 1-(6-bromo-2-pyridyl)-3-isopropyl-4-(4-methoxy-1-piperidyl)pyrazolo[3,4-b]pyridine-6-carboxylic acid | E133 | J1 | 473-475 | 474-476 |

TABLE XIII-continued

List of acids

| Int. | Structure | Name | SM | method | MW | Mes |
|---|---|---|---|---|---|---|
| A260 | 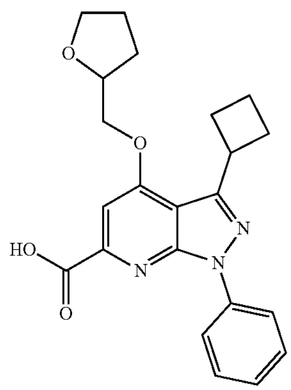 [SMILES: O=C(O)c1cc(OCC2CCCO2)c2c(C3CCC3)nn(-c3ccccc3)c2n1] | 3-cyclobutyl-1-phenyl-4-(tetrahydrofuran-2-ylmethoxy)pyrazolo[3,4-b]pyridine-6-carboxylic acid | HP10 | J3 | 393 | 394 |
| A261 | 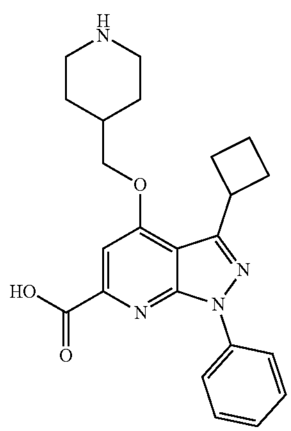 [SMILES: O=C(O)c1cc(OCC2CCNCC2)c2c(C3CCC3)nn(-c3ccccc3)c2n1] | 3-cyclobutyl-1-phenyl-4-(4-piperidylmethoxy)pyrazolo[3,4-b]pyridine-6-carboxylic acid | A262 | I25 | 406 | 407 |
| A262 | 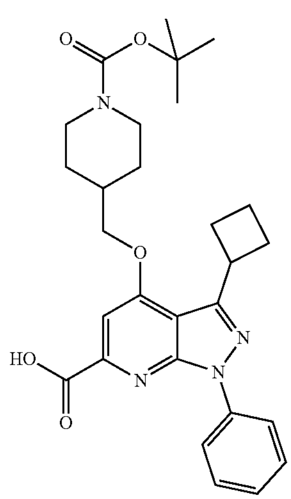 [SMILES: CC(C)(C)OC(=O)N1CCC(COc2cc(C(=O)O)nc3c2c(C2CCC2)nn3-c2ccccc2)CC1] | 4-[(1-tert-butoxycarbonyl-4-piperidyl)methoxy]-3-cyclobutyl-1-phenyl-pyrazolo[3,4-b]pyridine-6-carboxylic acid | HP10 | J3 | 506 | 507 |

TABLE XIII-continued
| Int. | Structure | Name | SM | method | MW | Mes |
|---|---|---|---|---|---|---|
| A263 | 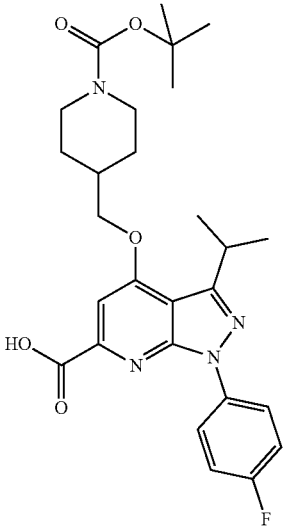 [SMILES: CC(C)c1nn(-c2ccc(F)cc2)c2nc(C(=O)O)cc(OCC3CCN(C(=O)OC(C)(C)C)CC3)c12] | 4-[(1-tert-butoxycarbonyl-4-piperidyl)methoxy]-1-(4-fluorophenyl)-3-isopropyl-pyrazolo[3,4-b]pyridine-6-carboxylic acid | HP11 | J3 | 512 | 513 |
| A264 | 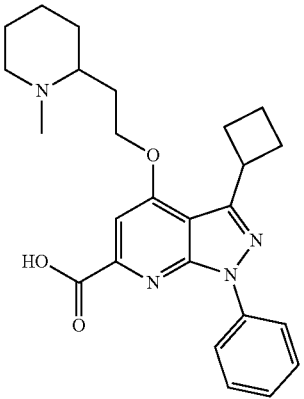 [SMILES: CN1CCCCC1CCOc1cc(C(=O)O)nc2c1c(C1CCC1)nn2-c1ccccc1] | 3-cyclobutyl-4-[2-(1-methyl-2-piperidyl)ethoxy]-1-phenyl-pyrazolo[3,4-b]pyridine-6-carboxylic acid | HP10 | J3 | 434 | 435 |
| A265 | 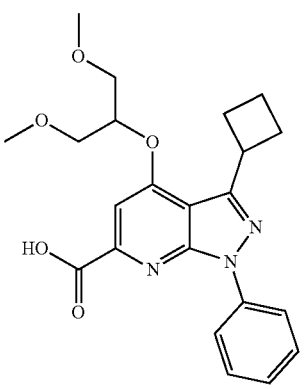 [SMILES: COCC(COC)Oc1cc(C(=O)O)nc2c1c(C1CCC1)nn2-c1ccccc1] | 3-cyclobutyl-4-[2-methoxy-1-(methoxymethyl)ethoxy]-1-phenyl-pyrazolo[3,4-b]pyridine-6-carboxylic acid | HP10 | J3 | 411 | 412 |

TABLE XIII-continued

List of acids

| Int. | Structure | Name | SM | method | MW | Mes |
|------|-----------|------|-----|--------|-----|-----|
| A266 | 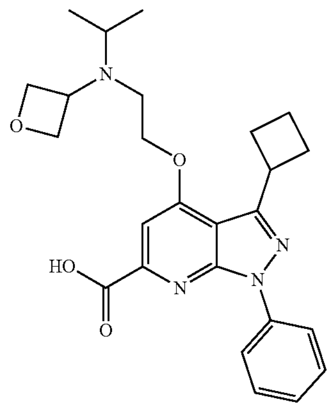 [SMILES: CC(C)N(CCOc1cc(C(=O)O)nc2c1c(C1CCC1)nn2-c1ccccc1)C1COC1] | 3-cyclobutyl-4-[2-[isopropyl(oxetan-3-yl)amino]ethoxy]-1-phenyl-pyrazolo[3,4-b]pyridine-6-carboxylic acid | HP10 | J3 | 450 | 451 |
| A267 | 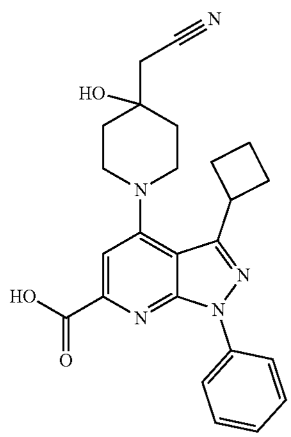 [SMILES: N#CCC1(O)CCN(c2cc(C(=O)O)nc3c2c(C2CCC2)nn3-c2ccccc2)CC1] | 4-[4-(cyanomethyl)-4-hydroxy-1-piperidyl]-3-cyclobutyl-1-phenyl-pyrazolo[3,4-b]pyridine-6-carboxylic acid | E179 | J1 | 431 | 432 |
| A268 | 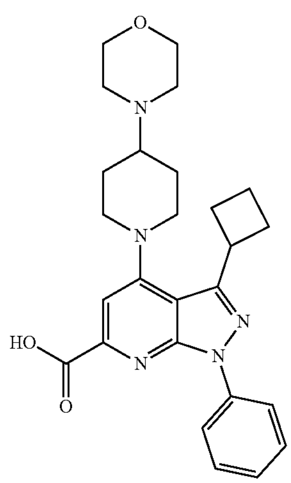 [SMILES: O=C(O)c1cc(N2CCC(N3CCOCC3)CC2)c2c(C3CCC3)nn(-c3ccccc3)c2n1] | 3-cyclobutyl-4-(4-morpholino-1-piperidyl)-1-phenyl-pyrazolo[3,4-b]pyridine-6-carboxylic acid | HP10 | J10 Specific example | 461 | 462 |

TABLE XIII-continued

| Int. | Structure | Name | SM | method | MW | Mes |
|---|---|---|---|---|---|---|
| A269 | 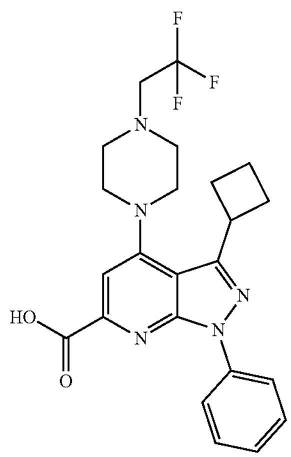 [SMILES: O=C(O)c1cc(N2CCN(CC(F)(F)F)CC2)c2c(C3CCC3)nn(-c3ccccc3)c2n1] | 3-cyclobutyl-1-phenyl-4-[4-(2,2,2-trifluoroethyl)piperazin-1-yl]pyrazolo[3,4-b]pyridine-6-carboxylic acid | E180 | J1 | 459 | 460 |
| A270 | 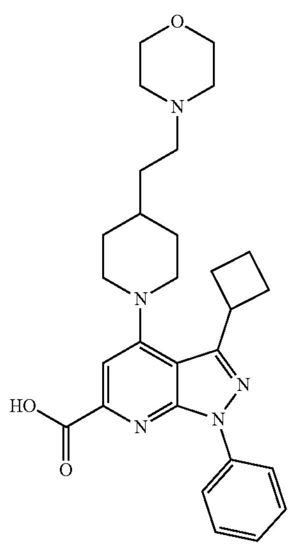 [SMILES: O=C(O)c1cc(N2CCC(CCN3CCOCC3)CC2)c2c(C3CCC3)nn(-c3ccccc3)c2n1] | 3-cyclobutyl-4-[4-(2-morpholinoethyl)-1-piperidyl]-1-phenyl-pyrazolo[3,4-b]pyridine-6-carboxylic acid | HP10 | J10 Specific example | 489 | 490 |
| A271 | 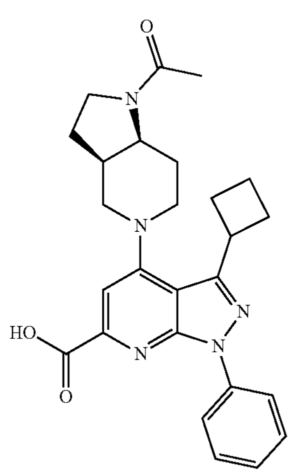 [SMILES: CC(=O)N1CC[C@@H]2CN(c3cc(C(=O)O)nc4c3c(C3CCC3)nn4-c3ccccc3)CC[C@@H]21] | 4-[(3aR,7aS)-1-acetyl-3,3a,4,6,7,7a-hexahydro-2H-pyrrolo[3,2-c]pyridin-5-yl]-3-cyclobutyl-1-phenyl-pyrazolo[3,4-b]pyridine-6-carboxylic acid | HP10 | J10, I25, J9 Specific example | 459 | 458 (ESI-) |

TABLE XIII-continued

List of acids

| Int. | Structure | Name | SM | method | MW | Mes |
|---|---|---|---|---|---|---|
| A272 | 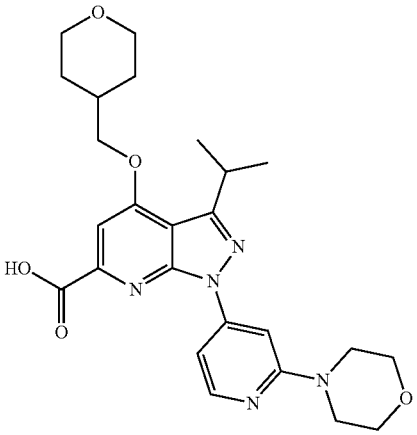 [SMILES: CC(C)c1nn(-c2ccnc(N3CCOCC3)c2)c2nc(C(=O)O)cc(OCC3CCOCC3)c12] | 3-isopropyl-1-(2-morpholino-4-pyridyl)-4-(tetrahydropyran-4-ylmethoxy)pyrazolo[3,4-b]pyridine-6-carboxylic acid | E181 | J6 | 481 | 482 |
| A273 | 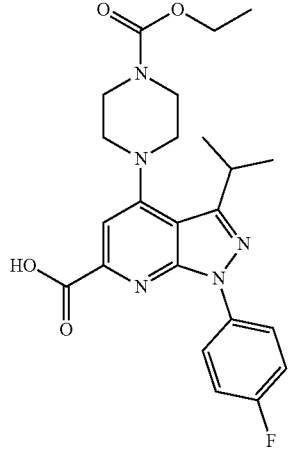 [SMILES: CCOC(=O)N1CCN(c2cc(C(=O)O)nc3c2c(C(C)C)nn3-c2ccc(F)cc2)CC1] | 4-(4-ethoxycarbonyl-piperazin-1-yl)-1-(4-fluorophenyl)-3-isopropyl-pyrazolo[3,4-b]pyridine-6-carboxylic acid | E184 | J1 | 455 | 456 |
| A274 | 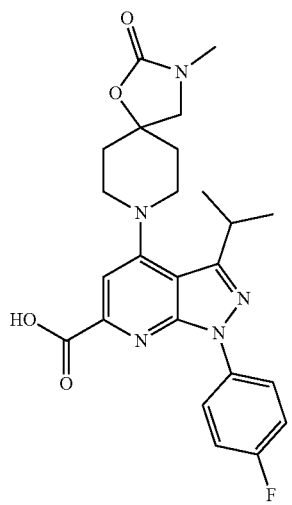 [SMILES: CC(C)c1nn(-c2ccc(F)cc2)c2nc(C(=O)O)cc(N3CCC4(CC3)CN(C)C(=O)O4)c12] | 1-(4-fluorophenyl)-3-isopropyl-4-(3-methyl-2-oxo-1-oxa-3,8-diazaspiro[4.5]decan-8-yl)pyrazolo[3,4-b]pyridine-6-carboxylic acid | E185 | J1 | 467 | 468 |

TABLE XIII-continued

List of acids

| Int. | Structure | Name | SM | method | MW | Mes |
|---|---|---|---|---|---|---|
| A275 | 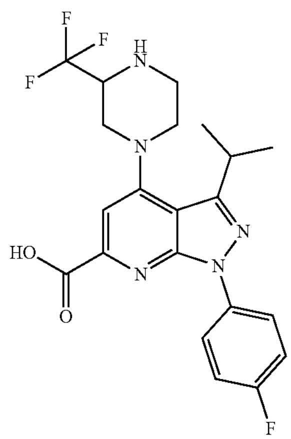 [SMILES: CC(C)c1nn(-c2ccc(F)cc2)c2nc(C(=O)O)cc(N3CCNC(C(F)(F)F)C3)c12] | 1-(4-fluorophenyl)-3-isopropyl-4-[3-(trifluoromethyl)piperazin-1-yl]pyrazolo[3,4-b]pyridine-6-carboxylic acid | E186 | J1 | 451 | 452 |
| A276 | 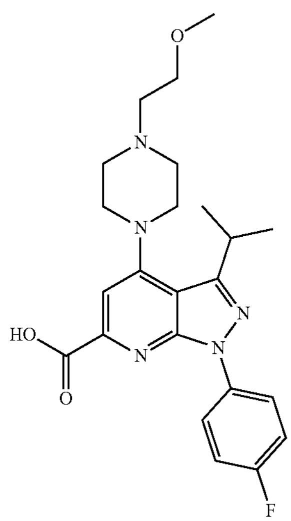 [SMILES: COCCN1CCN(c2cc(C(=O)O)nc3c2c(C(C)C)nn3-c2ccc(F)cc2)CC1] | 1-(4-fluorophenyl)-3-isopropyl-4-[4-(2-methoxyethyl)piperazin-1-yl]pyrazolo[3,4-b]pyridine-6-carboxylic acid | E187 | J1 | 441 | 442 |
| A277 | 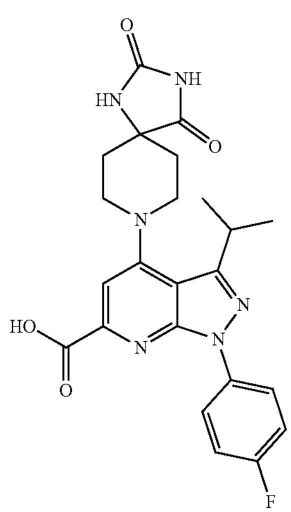 [SMILES: CC(C)c1nn(-c2ccc(F)cc2)c2nc(C(=O)O)cc(N3CCC4(CC3)NC(=O)NC4=O)c12] | 4-(2,4-dioxo-1,3,8-triazaspiro[4.5]decan-8-yl)-1-(4-fluorophenyl)-3-isopropyl-pyrazolo[3,4-b]pyridine-6-carboxylic acid | E188 | J1 | 466 | 467 |

TABLE XIII-continued

List of acids

| Int. | Structure | Name | SM | method | MW | Mes |
|---|---|---|---|---|---|---|
| A278 | 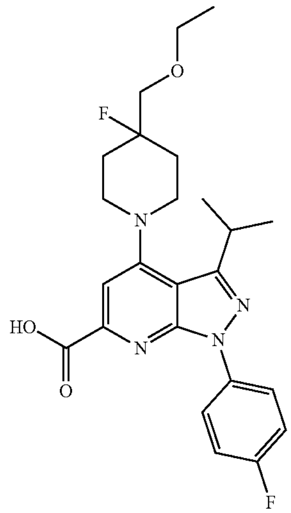 [SMILES: CCOCC1(F)CCN(c2cc(C(=O)O)nc3c2c(C(C)C)nn3-c2ccc(F)cc2)CC1] | 4-[4-(ethoxymethyl)-4-fluoro-1-piperidyl]-1-(4-fluorophenyl)-3-isopropyl-pyrazolo[3,4-b]pyridine-6-carboxylic acid | E189 | J1 | 458 | 459 |
| A279 | 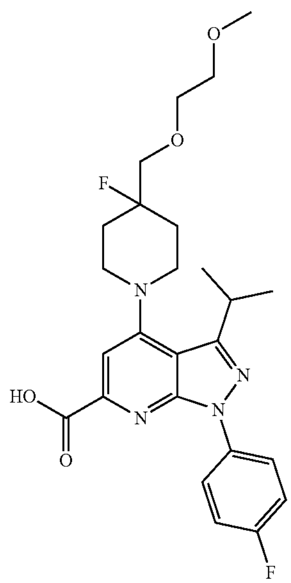 [SMILES: COCCOCC1(F)CCN(c2cc(C(=O)O)nc3c2c(C(C)C)nn3-c2ccc(F)cc2)CC1] | 4-[4-fluoro-4-(2-methoxyethoxy-methyl)-1-piperidyl]-1-(4-fluorophenyl)-3-isopropyl-pyrazolo[3,4-b]pyridine-6-carboxylic acid | E190 | J1 | 488 | 489 |
| A280 | 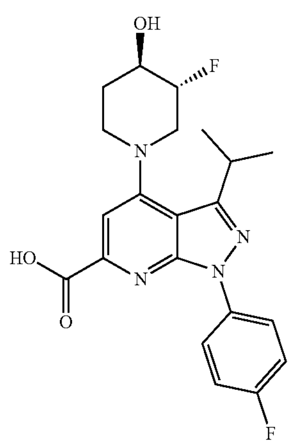 [SMILES: CC(C)c1nn(-c2ccc(F)cc2)c2nc(C(=O)O)cc(N3CC[C@@H](O)[C@H](F)C3)c12] | 4-[(3R,4R)-3-fluoro-4-hydroxy-1-piperidyl]-1-(4-fluorophenyl)-3-isopropyl-pyrazolo[3,4-b]pyridine-6-carboxylic acid | E191 | J1 | 416 | 417 |

TABLE XIII-continued

| | | List of acids | | | | |
|---|---|---|---|---|---|---|
| Int. | Structure | Name | SM | method | MW | Mes |
| A281 | | 4-[4-fluoro-4-(methoxymethyl)-1-piperidyl]-1-(4-fluorophenyl)-3-isopropyl-pyrazolo[3,4-b]pyridine-6-carboxylic acid | E192 | J1 | 444 | 445 |
| A282 | | 4-[3-fluoro-3-(2-methoxyethoxy-methyl)-1-piperidyl]-1-(4-fluorophenyl)-3-isopropyl-pyrazolo[3,4-b]pyridine-6-carboxylic acid | E193 | J1 | 488 | 489 |
| A283 | | 1-(4-fluorophenyl)-3-isopropyl-4-[4-(1-piperidyl)-1-piperidyl]pyrazolo[3,4-b]pyridine-6-carboxylic acid | E194 | J1 | 465 | 466 |

TABLE XIII-continued

List of acids

| Int. | Structure | Name | SM | method | MW | Mes |
|---|---|---|---|---|---|---|
| A284 | 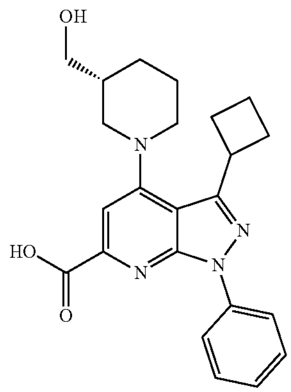 [SMILES: O=C(O)c1cc(N2CCC[C@@H](CO)C2)c2c(C3CCC3)nn(-c3ccccc3)c2n1] | 3-cyclobutyl-4-[(3R)-3-(hydroxymethyl)-1-piperidyl]-1-phenyl-pyrazolo[3,4-b]pyridine-6-carboxylic acid | HP10 | J10 Specific example | 406 | 407 |
| A285 | 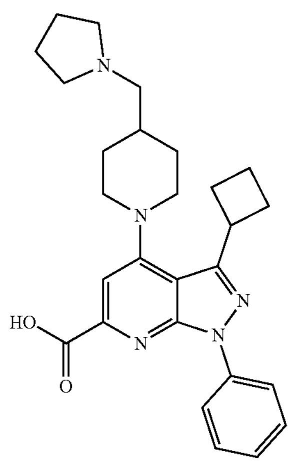 [SMILES: O=C(O)c1cc(N2CCC(CN3CCCC3)CC2)c2c(C3CCC3)nn(-c3ccccc3)c2n1] | 3-cyclobutyl-1-phenyl-4-{4-[(pyrrolidin-1-yl)methyl]piperidin-1-yl}-1H-pyrazolo[3,4-b]pyridine-6-carboxylic acid | E357 | J1, Specific example | 459 | 460 |
| A286 | 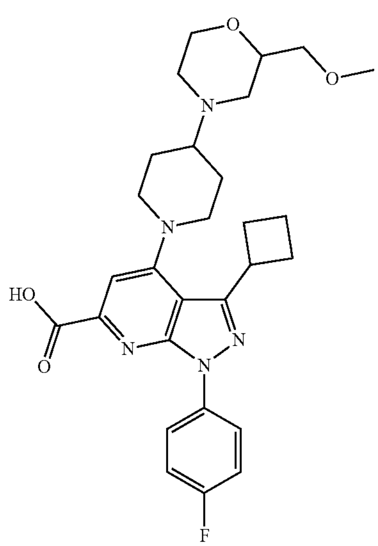 [SMILES: COCC1CN(C2CCN(c3cc(C(=O)O)nc4c3c(C3CCC3)nn4-c3ccc(F)cc3)CC2)CCO1] | 3-cyclobutyl-1-(4-fluorophenyl)-4-{4-[2-(methoxymethyl)morpholin-4-yl]piperidin-1-yl}-1H-pyrazolo[3,4-b]pyridine-6-carboxylic acid | E354 | J1 | 523 | 523 |

TABLE XIII-continued
List of acids
| Int. | Structure | Name | SM | method | MW | Mes |
|---|---|---|---|---|---|---|
| A287 | 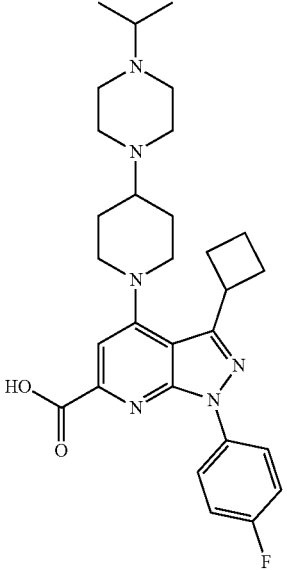 [SMILES: CC(C)N1CCN(C2CCN(c3cc(C(=O)O)nc4c3c(C3CCC3)nn4-c3ccc(F)cc3)CC2)CC1] | 3-cyclobutyl-1-(4-fluorophenyl)-4-{4-[4-(propan-2-yl)piperazin-1-yl]piperidin-1-yl}-1H-pyrazolo[3,4-b]pyridine-6-carboxylic acid | E355 | J1 | 520 | 521 |
| A288 | 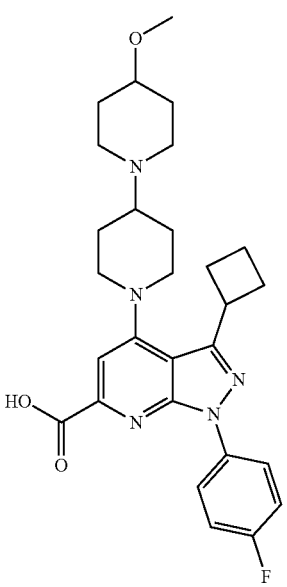 [SMILES: COC1CCN(C2CCN(c3cc(C(=O)O)nc4c3c(C3CCC3)nn4-c3ccc(F)cc3)CC2)CC1] | 3-cyclobutyl-1-(4-fluorophenyl)-4-(4-methoxy[1,4'-bipiperidin]-1'-yl)-1H-pyrazolo[3,4-b]pyridine-6-carboxylic acid | E356 | J1 | 507 | 508 |

TABLE XIII-continued
List of acids
| Int. | Structure | Name | SM | method | MW | Mes |
|---|---|---|---|---|---|---|
| A289 | 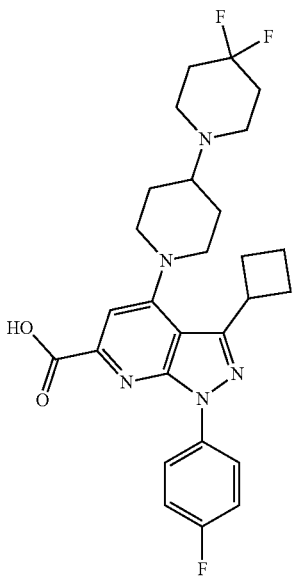 [SMILES: O=C(O)c1cc(N2CCC(N3CCC(F)(F)CC3)CC2)c2c(C3CCC3)nn(-c3ccc(F)cc3)c2n1] | 3-cyclobutyl-4-(4,4-difluoro[1,4'-bipiperidin]-1'-yl)-1-(4-fluorophenyl)-1H-pyrazolo[3,4-b]pyridine-6-carboxylic acid | E358 | J1 | 513 | 514 |
| A290 | 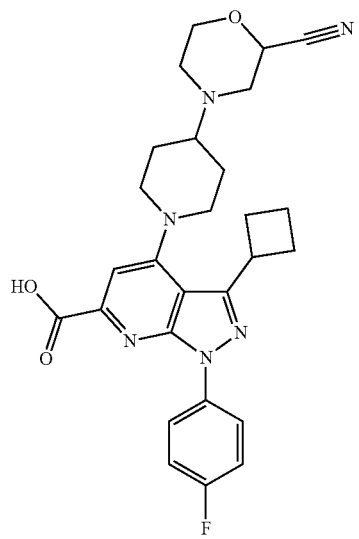 [SMILES: N#CC1CN(C2CCN(c3cc(C(=O)O)nc4c3c(C3CCC3)nn4-c3ccc(F)cc3)CC2)CCO1] | 4-[4-(2-cyanomorpholin-4-yl)piperidin-1-yl]-3-cyclobutyl-1-(4-fluorophenyl)-1H-pyrazolo[3,4-b]pyridine-6-carboxylic acid | E359 | J1 | 505 | 505 |

TABLE XIII-continued
List of acids
| Int. | Structure | Name | SM | method | MW | Mes |
|---|---|---|---|---|---|---|
| A291 | 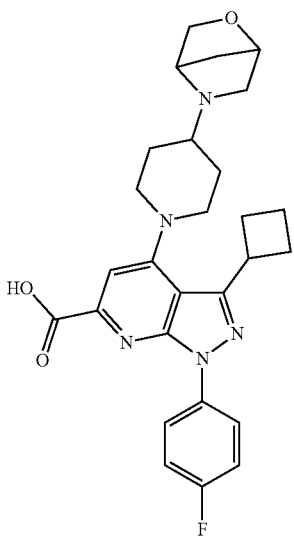 [SMILES: O=C(O)c1cc(N2CCC(N3CC4CC3CO4)CC2)c2c(C3CCC3)nn(-c3ccc(F)cc3)c2n1] | 3-cyclobutyl-1-(4-fluorophenyl)-4-[4-(2-oxa-5-azabicyclo[2.2.1]heptan-5-yl)piperidin-1-yl]-1H-pyrazolo[3,4-b]pyridine-6-carboxylic acid | E360 | J1 | 491 | 492 |
| A292 | 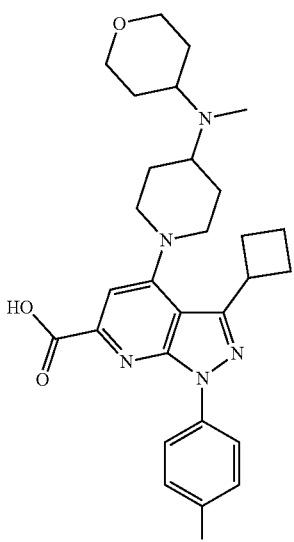 | 3-cyclobutyl-1-(4-fluorophenyl)-4-{4-[methyl(oxan-4-yl)amino]piperidin-1-yl}-1H-pyrazolo[3,4-b]pyridine-6-carboxylic acid | E361 | J1 | 507 | 508 |

TABLE XIII-continued

List of acids

| Int. | Structure | Name | SM | method | MW | Mes |
|------|-----------|------|----|--------|----|----|
| A293 | 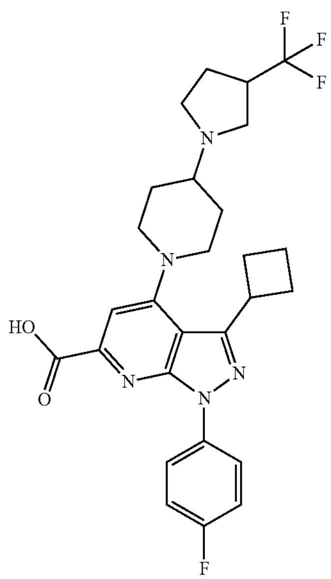 [SMILES: O=C(O)c1cc(N2CCC(N3CCC(C(F)(F)F)C3)CC2)c2c(C3CCC3)nn(-c3ccc(F)cc3)c2n1] | 3-cyclobutyl-1-(4-fluorophenyl)-4-{4-[3-(trifluoromethyl)pyrrolidin-1-yl]piperidin-1-yl}-1H-pyrazolo[3,4-b]pyridine-6-carboxylic acid | E362 | J1 | 531 | 532 |
| A294 | 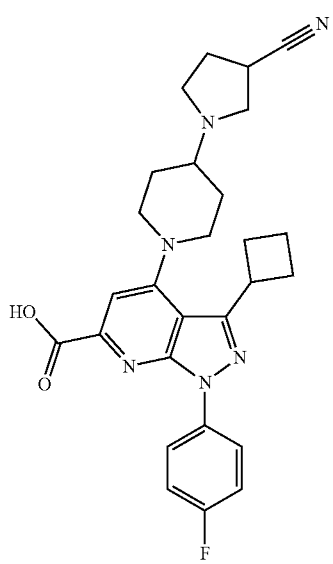 [SMILES: N#CC1CCN(C2CCN(c3cc(C(=O)O)nc4c3c(C3CCC3)nn4-c3ccc(F)cc3)CC2)C1] | 4-[4-(3-cyanopyrrolidin-1-yl)piperidin-1-yl]-3-cyclobutyl-1-(4-fluorophenyl)-1H-pyrazolo[3,4-b]pyridine-6-carboxylic acid | E363 | J1 | 488 | 489 |

TABLE XIII-continued
List of acids
| Int. | Structure | Name | SM | method | MW | Mes |
|---|---|---|---|---|---|---|
| A295 | 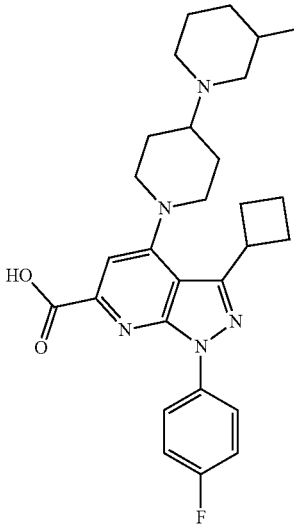 | 4-(3-cyano[1,4'-bipiperidin]-1'-yl)-3-cyclobutyl-1-(4-fluorophenyl)-1H-pyrazolo[3,4-b]pyridine-6-carboxylic acid | E364 | J1 | 502 | 503 |
| A296 | 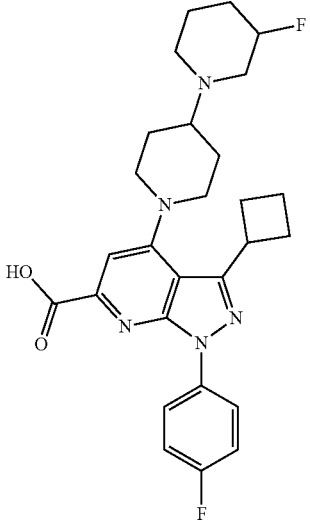 [SMILES: O=C(O)c1cc(N2CCC(N3CCCC(F)C3)CC2)c2c(C3CCC3)nn(-c3ccc(F)cc3)c2n1] | 3-cyclobutyl-4-(3-fluoro[1,4'-bipiperidin]-1'-yl)-1-(4-fluorophenyl)-1H-pyrazolo[3,4-b]pyridine-6-carboxylic acid | E365 | J1 | 495 | 496 |

TABLE XIII-continued
List of acids
| Int. | Structure | Name | SM | method | MW | Mes |
|---|---|---|---|---|---|---|
| A297 | 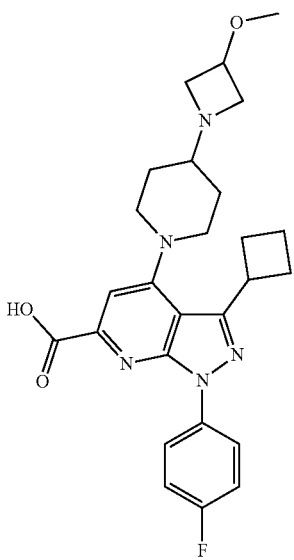 [SMILES: COC1CN(C2CCN(c3cc(C(=O)O)nc4c3c(C3CCC3)nn4-c3ccc(F)cc3)CC2)C1] | 3-cyclobutyl-1-(4-fluorophenyl)-4-[4-(3-methoxyazetidin-1-yl)piperidin-1-yl]-1H-pyrazolo[3,4-b]pyridine-6-carboxylic acid | E366 | J1A | 479 | 480 |
| A298 | 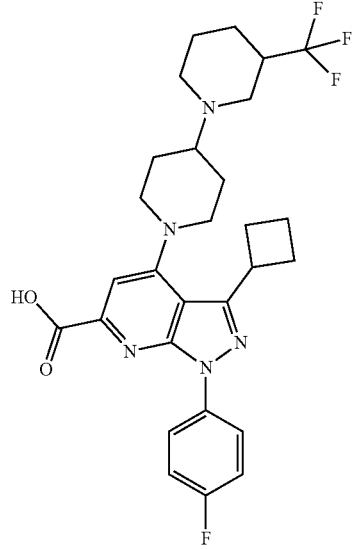 [SMILES: O=C(O)c1cc(N2CCC(N3CCCC(C(F)(F)F)C3)CC2)c2c(C3CCC3)nn(-c3ccc(F)cc3)c2n1] | 3-cyclobutyl-1-(4-fluorophenyl)-4-[3-(trifluoromethyl)[1,4'-bipiperidin]-1'-yl]-1H-pyrazolo[3,4-b]pyridine-6-carboxylic acid | E367 | J1A | 545 | 546 |

… TABLE XIII-continued
List of acids
| Int. | Structure | Name | SM | method | MW | Mes |
|---|---|---|---|---|---|---|
| A299 | 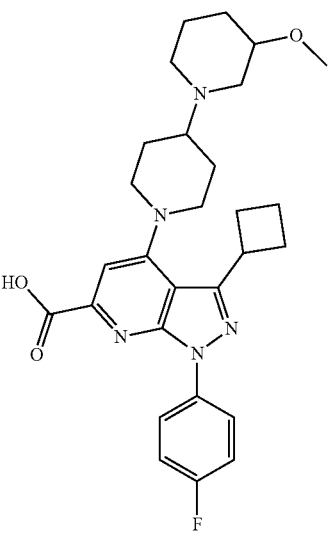 [SMILES: COC1CCCN(C2CCN(c3cc(C(=O)O)nc4c3c(C3CCC3)nn4-c3ccc(F)cc3)CC2)C1] | 3-cyclobutyl-1-(4-fluorophenyl)-4-(3-methoxy[1,4'-bipiperidin]-1'-yl)-1H-pyrazolo[3,4-b]pyridine-6-carboxylic acid | E368 | J1A | 507 | 508 |
| A300 | 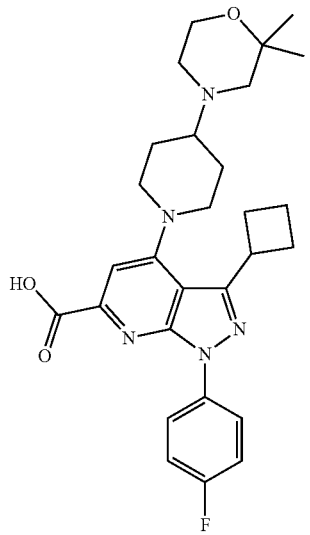 [SMILES: CC1(C)CN(C2CCN(c3cc(C(=O)O)nc4c3c(C3CCC3)nn4-c3ccc(F)cc3)CC2)CCO1] | 3-cyclobutyl-4-[4-(2,2-dimethylmorpholin-4-yl)piperidin-1-yl]-1-(4-fluorophenyl)-1H-pyrazolo[3,4-b]pyridine-6-carboxylic acid | E369 | J1A | 508 | 508 |

TABLE XIII-continued
List of acids
| Int. | Structure | Name | SM | method | MW | Mes |
|---|---|---|---|---|---|---|
| A301 | 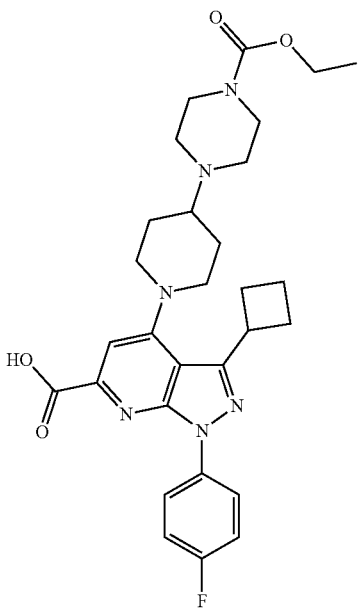 [SMILES: CCOC(=O)N1CCN(C2CCN(c3cc(C(=O)O)nc4c3c(C3CCC3)nn4-c3ccc(F)cc3)CC2)CC1] | 3-cyclobutyl-4-{4-[4-(ethoxycarbonyl)piperazin-1-yl]piperidin-1-yl}-1-(4-fluorophenyl)-1H-pyrazolo[3,4-b]pyridine-6-carboxylic acid | E370 | J1A | 550 | 551 |
| A302 | 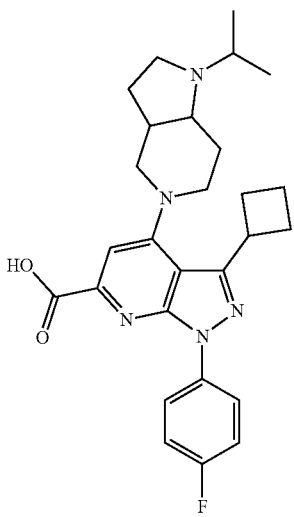 [SMILES: CC(C)N1CCC2CN(c3cc(C(=O)O)nc4c3c(C3CCC3)nn4-c3ccc(F)cc3)CCC21] | 3-cyclobutyl-1-(4-fluorophenyl)-4-[1-(propan-2-yl)octahydro-5H-pyrrolo[3,2-c]pyridin-5-yl]-1H-pyrazolo[3,4-b]pyridine-6-carboxylic acid | E371 | J1 | 477 | 478 |

TABLE XIII-continued

List of acids

| Int. | Structure | Name | SM | method | MW | Mes |
|------|-----------|------|-----|--------|-----|-----|
| A303 | 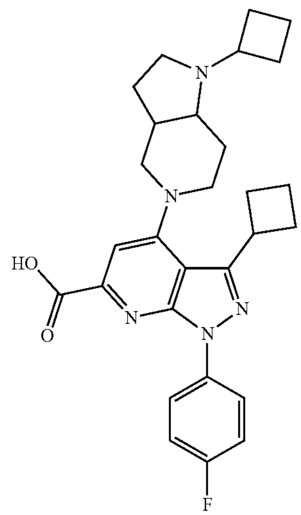 [SMILES: O=C(O)c1cc(N2CCC3C(CCN3C3CCC3)C2)c2c(C3CCC3)nn(-c3ccc(F)cc3)c2n1] | 3-cyclobutyl-4-(1-cyclobutylocta-hydro-5H-pyrrolo[3,2-c]pyridin-5-yl)-1-(4-fluorophenyl)-1H-pyrazolo[3,4-b]pyridine-6-carboxylic acid | E372 | J1 | 489 | 490 |
| A304 | 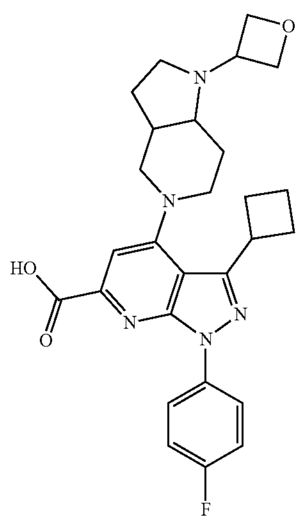 [SMILES: O=C(O)c1cc(N2CCC3C(CCN3C3COC3)C2)c2c(C3CCC3)nn(-c3ccc(F)cc3)c2n1] | 3-cyclobutyl-1-(4-fluorophenyl)-4-[1-(oxetan-3-yl)octahydro-5H-pyrrolo[3,2-c]pyridin-5-yl]-1H-pyrazolo[3,4-b]pyridine-6-carboxylic acid | E373 | J1 | 491 | 492 |
| A305 | 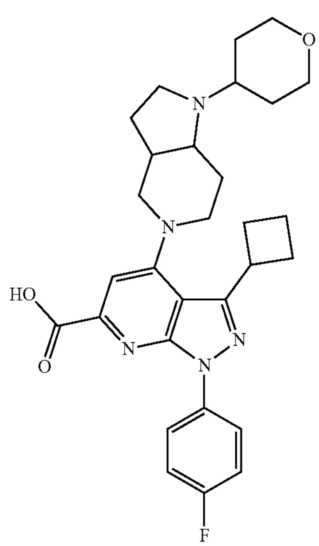 [SMILES: O=C(O)c1cc(N2CCC3C(CCN3C3CCOCC3)C2)c2c(C3CCC3)nn(-c3ccc(F)cc3)c2n1] | 3-cyclobutyl-1-(4-fluorophenyl)-4-[1-(oxan-4-yl)octahydro-5H-pyrrolo[3,2-c]pyridin-5-yl]-1H-pyrazolo[3,4-b]pyridine-6-carboxylic acid | E374 | J1 | 519 | 520 |

TABLE XIII-continued

List of acids

| Int. | Structure | Name | SM | method | MW | Mes |
|---|---|---|---|---|---|---|
| A306 | 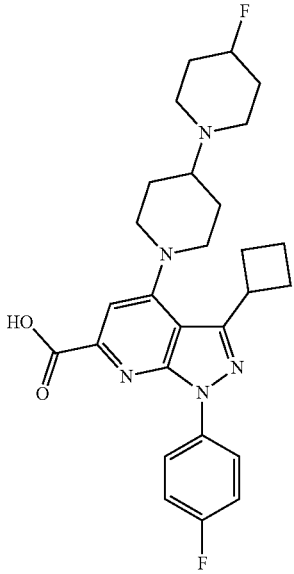 [SMILES: O=C(O)c1cc(N2CCC(N3CCC(F)CC3)CC2)c2c(C3CCC3)nn(-c3ccc(F)cc3)c2n1] | 3-cyclobutyl-4-(4-fluoro[1,4'-bipiperidin]-1'-yl)-1-(4-fluorophenyl)-1H-pyrazolo[3,4-b]pyridine-6-carboxylic acid | E375 | J1 | 495 | 496 |
| A307 | 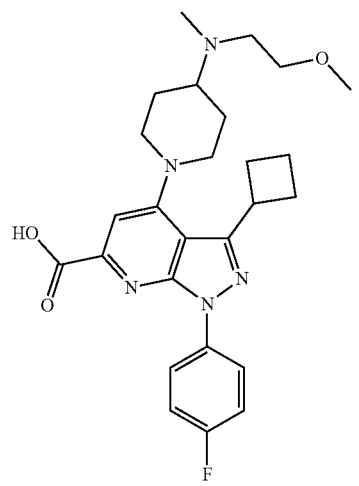 [SMILES: COCCN(C)C1CCN(c2cc(C(=O)O)nc3c2c(C2CCC2)nn3-c2ccc(F)cc2)CC1] | 3-cyclobutyl-1-(4-fluorophenyl)-4-{4-[(2-methoxyethyl)(methyl)amino]piperidin-1-yl}-1H-pyrazolo[3,4-b]pyridine-6-carboxylic acid | E376 | J1A | 481 | 482 |
| A308 | 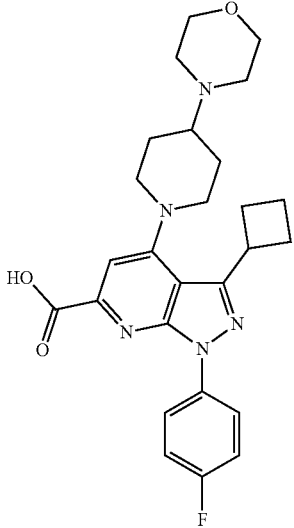 [SMILES: O=C(O)c1cc(N2CCC(N3CCOCC3)CC2)c2c(C3CCC3)nn(-c3ccc(F)cc3)c2n1] | 3-cyclobutyl-1-(4-fluorophenyl)-4-[4-(morpholin-4-yl)piperidin-1-yl]-1H-pyrazolo[3,4-b]pyridine-6-carboxylic acid | E377 | J1 | 479 | 480 |

TABLE XIII-continued

List of acids

| Int. | Structure | Name | SM | method | MW | Mes |
|---|---|---|---|---|---|---|
| A309 | 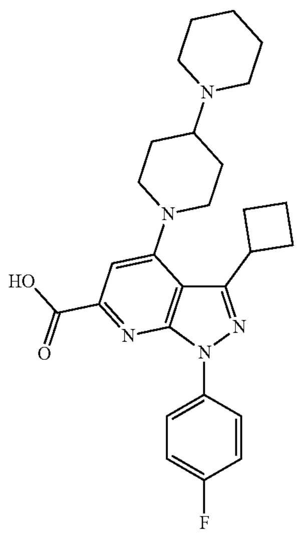 [SMILES: O=C(O)c1cc(N2CCC(N3CCCCC3)CC2)c2c(C3CCC3)nn(-c3ccc(F)cc3)c2n1] | 4-([1,4'-bipiperidin]-1'-yl)-3-cyclobutyl-1-(4-fluorophenyl)-1H-pyrazolo[3,4-b]pyridine-6-carboxylic acid | E378 | J1 | 477 | 478 |
| A310 | 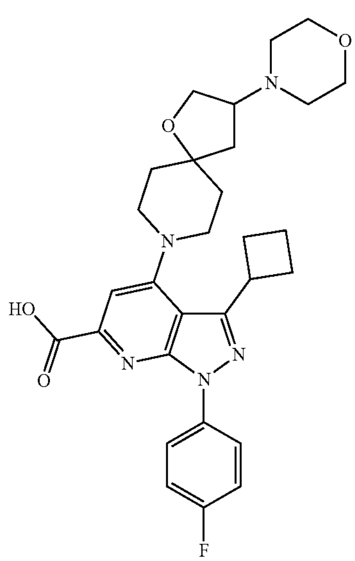 [SMILES: O=C(O)c1cc(N2CCC3(CC2)CC(N2CCOCC2)CO3)c2c(C3CCC3)nn(-c3ccc(F)cc3)c2n1] | 3-cyclobutyl-1-(4-fluorophenyl)-4-[3-(morpholin-4-yl)-1-oxa-8-azaspiro[4.5]decan-8-yl]-1H-pyrazolo[3,4-b]pyridine-6-carboxylic acid | E381 | J1 | 535 | 536 |

TABLE XIII-continued

List of acids

| Int. | Structure | Name | SM | method | MW | Mes |
|------|-----------|------|-----|--------|-----|-----|
| A311 | 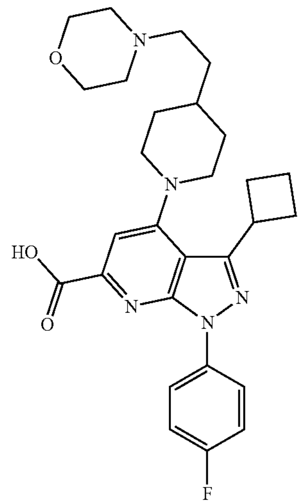 [SMILES: O=C(O)c1cc(N2CCC(CCN3CCOCC3)CC2)c2c(C3CCC3)nn(-c3ccc(F)cc3)c2n1] | 3-cyclobutyl-1-(4-fluorophenyl)-4-{4-[2-(morpholin-4-yl)ethyl]piperidin-1-yl}-1H-pyrazolo[3,4-b]pyridine-6-carboxylic acid | E382 | J1 | 507 | 508 |
| A312 | 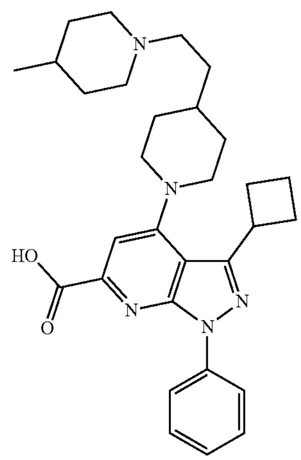 [SMILES: CC1CCN(CCC2CCN(c3cc(C(=O)O)nc4c3c(C3CCC3)nn4-c3ccccc3)CC2)CC1] | 3-cyclobutyl-4-{4-[2-(4-methylpiperidin-1-yl)ethyl]piperidin-1-yl}-1-phenyl-1H-pyrazolo[3,4-b]pyridine-6-carboxylic acid | E383 | J1 | 501 | 502 |
| A313 | 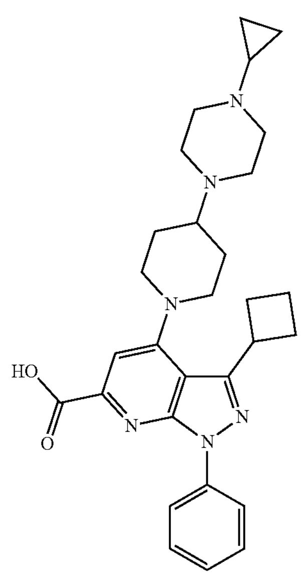 [SMILES: O=C(O)c1cc(N2CCC(N3CCN(C4CC4)CC3)CC2)c2c(C3CCC3)nn(-c3ccccc3)c2n1] | 3-cyclobutyl-4-[4-(4-cyclopropylpiperazin-1-yl)piperidin-1-yl]-1-phenyl-1H-pyrazolo[3,4-b]pyridine-6-carboxylic acid | E384 | J1 | 500 | 501 |

TABLE XIII-continued
| | | List of acids | | | | |
|---|---|---|---|---|---|---|
| Int. | Structure | Name | SM | method | MW | Mes |
| A314 | 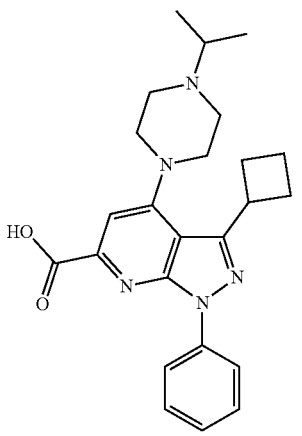 [SMILES: CC(C)N1CCN(c2cc(C(=O)O)nc3c2c(C2CCC2)nn3-c2ccccc2)CC1] | 3-cyclobutyl-1-phenyl-4-[4-(propan-2-yl)piperazin-1-yl]-1H-pyrazolo[3,4-b]pyridine-6-carboxylic acid | E385 | J1 | 419 | 420 |
| A315 | 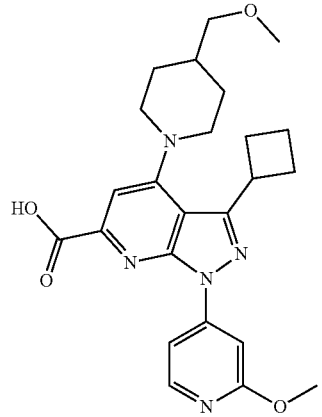 [SMILES: COCC1CCN(c2cc(C(=O)O)nc3c2c(C2CCC2)nn3-c2ccnc(OC)c2)CC1] | 3-cyclobutyl-4-[4-(methoxymethyl)piperidin-1-yl]-1-(2-methoxypyridin-4-yl)-1H-pyrazolo[3,4-b]pyridine-6-carboxylic acid | E388 | J1 | 451 | 452 |
| A316 | 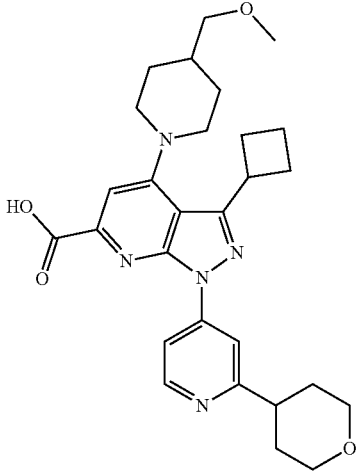 [SMILES: COCC1CCN(c2cc(C(=O)O)nc3c2c(C2CCC2)nn3-c2ccnc(C3CCOCC3)c2)CC1] | 3-cyclobutyl-4-[4-(methoxymethyl)piperidin-1-yl]-1-[2-(oxan-4-yl)pyridin-4-yl]-1H-pyrazolo[3,4-b]pyridine-6-carboxylic acid | E391 | J1A | 505 | 506 |

TABLE XIII-continued

| | | List of acids | | | | |
|---|---|---|---|---|---|---|
| Int. | Structure | Name | SM | method | MW | Mes |
| A317 | | 3-cyclobutyl-1-(2-methoxypyridin-4-yl)-4-[4-(morpholin-4-yl)piperidin-1-yl]-1H-pyrazolo[3,4-b]pyridine-6-carboxylic acid | E394 | J1A | 492 | 493 |
| A318a | | 3-cyclobutyl-1-(3-methylphenyl)-4-[4-(morpholin-4-yl)piperidin-1-yl]-1H-pyrazolo[3,4-b]pyridine-6-carboxylic acid | E395 | J1A Specific example | 475 | 476 |
| A318b | | 3-cyclobutyl-1-(3-methoxyphenyl)-4-[4-(morpholin-4-yl)piperidin-1-yl]-1H-pyrazolo[3,4-b]pyridine-6-carboxylic acid | E396 | J1A | 491 | 492 |

TABLE XIII-continued
| Int. | Structure | Name | SM | method | MW | Mes |
|---|---|---|---|---|---|---|
| A319 | 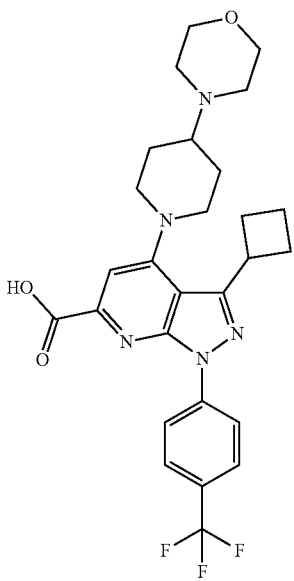 [SMILES: O=C(O)c1cc(N2CCC(N3CCOCC3)CC2)c2c(C3CCC3)nn(-c3ccc(C(F)(F)F)cc3)c2n1] | 3-cyclobutyl-4-[4-(morpholin-4-yl)piperidin-1-yl]-1-[4-(trifluoromethyl)phenyl]-1H-pyrazolo[3,4-b]pyridine-6-carboxylic acid | E397 | J1A | 529 | 530 |
| A320 | 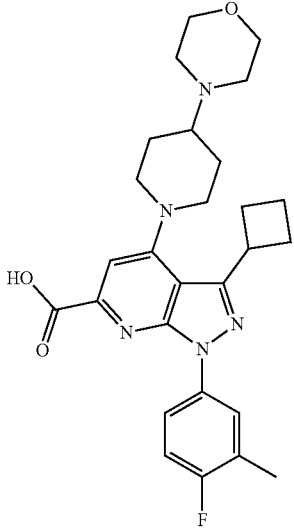 [SMILES: Cc1cc(-n2nc(C3CCC3)c3c(N4CCC(N5CCOCC5)CC4)cc(C(=O)O)nc32)ccc1F] | 3-cyclobutyl-1-(4-fluoro-3-methylphenyl)-4-[4-(morpholin-4-yl)piperidin-1-yl]-1H-pyrazolo[3,4-b]pyridine-6-carboxylic acid | E398 | J1A | 493 | 494 |

TABLE XIII-continued

List of acids

| Int. | Structure | Name | SM | method | MW | Mes |
|---|---|---|---|---|---|---|
| A321 | 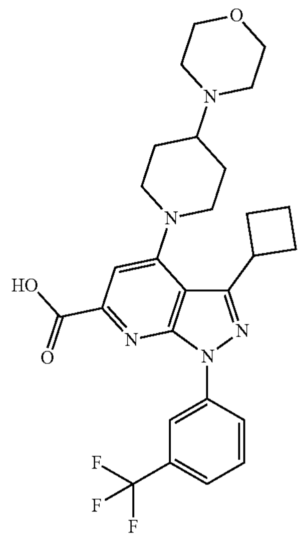 [SMILES: O=C(O)c1cc(N2CCC(N3CCOCC3)CC2)c2c(C3CCC3)nn(-c3cccc(C(F)(F)F)c3)c2n1] | 3-cyclobutyl-4-[4-(morpholin-4-yl)piperidin-1-yl]-1-[3-(trifluoromethyl)phenyl]-1H-pyrazolo[3,4-b]pyridine-6-carboxylic acid | E399 | J1A | 529 | 530 |
| A322 | 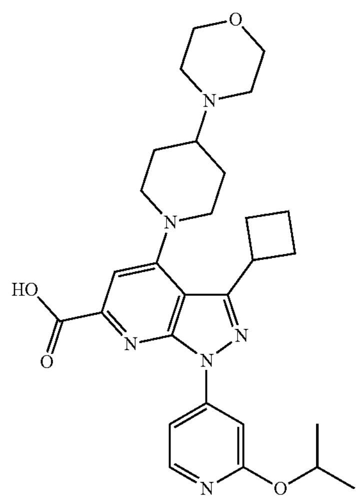 [SMILES: CC(C)Oc1cc(-n2nc(C3CCC3)c3c(N4CCC(N5CCOCC5)CC4)cc(C(=O)O)nc32)ccn1] | 3-cyclobutyl-4-[4-(morpholin-4-yl)piperidin-1-yl]-1-{2-[(propan-2-yl)oxy]pyridin-4-yl}-1H-pyrazolo[3,4-b]pyridine-6-carboxylic acid | E400 | J1A | 520 | 521 |
| A323 | 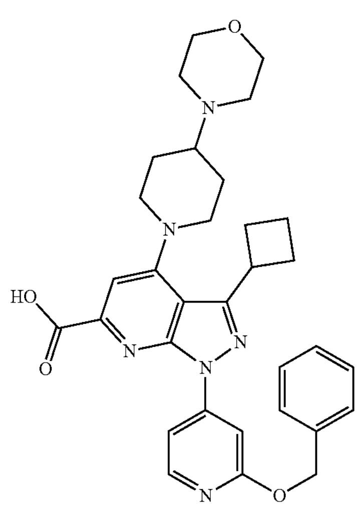 [SMILES: O=C(O)c1cc(N2CCC(N3CCOCC3)CC2)c2c(C3CCC3)nn(-c3ccnc(OCc4ccccc4)c3)c2n1] | 1-[2-(benzyloxy)pyridin-4-yl]-3-cyclobutyl-4-[4-(morpholin-4-yl)piperidin-1-yl]-1H-pyrazolo[3,4-b]pyridine-6-carboxylic acid | E401 | J1A | 568 | 569 |

TABLE XIII-continued

List of acids

| Int. | Structure | Name | SM | method | MW | Mes |
|------|-----------|------|----|--------|----|----|
| A324 | 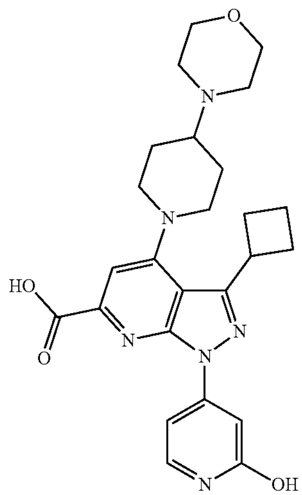 [SMILES: O=C(O)c1cc(N2CCC(N3CCOCC3)CC2)c2c(C3CCC3)nn(-c3ccnc(O)c3)c2n1] | 3-cyclobutyl-1-(2-hydroxypyridin-4-yl)-4-[4-(morpholin-4-yl)piperidin-1-yl]-1H-pyrazolo[3,4-b]pyridine-6-carboxylic acid | E402 | J1A | 478 | 479 |
| A325 | 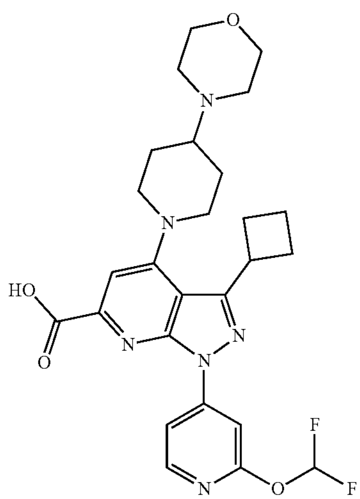 [SMILES: O=C(O)c1cc(N2CCC(N3CCOCC3)CC2)c2c(C3CCC3)nn(-c3ccnc(OC(F)F)c3)c2n1] | 3-cyclobutyl-1-[2-(difluoromethoxy)pyridin-4-yl]-4-[4-(morpholin-4-yl)piperidin-1-yl]-1H-pyrazolo[3,4-b]pyridine-6-carboxylic acid | E403 | J1A | 528 | 529 |
| A326 | 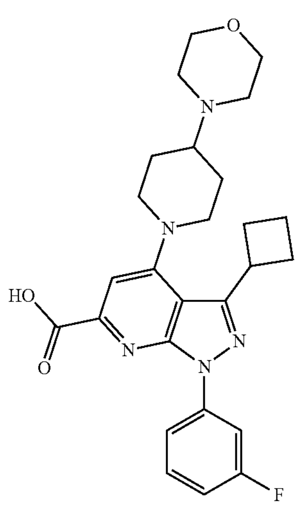 [SMILES: O=C(O)c1cc(N2CCC(N3CCOCC3)CC2)c2c(C3CCC3)nn(-c3cccc(F)c3)c2n1] | 3-cyclobutyl-1-(3-fluorophenyl)-4-[4-(morpholin-4-yl)piperidin-1-yl]-1H-pyrazolo[3,4-b]pyridine-6-carboxylic acid | E404 | J1A | 479 | 480 |

TABLE XIII-continued
List of acids
| Int. | Structure | Name | SM | method | MW | Mes |
|---|---|---|---|---|---|---|
| A327 | 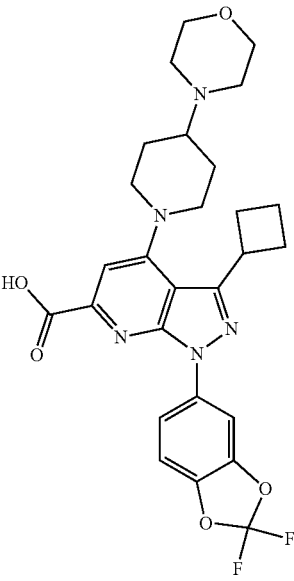 [SMILES: O=C(O)c1cc(N2CCC(N3CCOCC3)CC2)c2c(C3CCC3)nn(-c3ccc4c(c3)OC(F)(F)O4)c2n1] | 3-cyclobutyl-1-(2,2-difluoro-2H-1,3-benzodioxol-5-yl)-4-[4-(morpholin-4-yl)piperidin-1-yl]-1H-pyrazolo[3,4-b]pyridine-6-carboxylic acid | E405 | J1A | 541 | 542 |
| A328 | 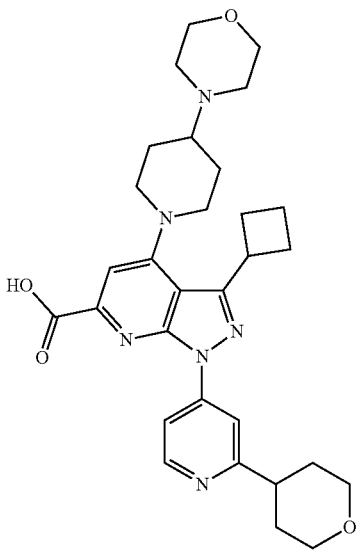 [SMILES: O=C(O)c1cc(N2CCC(N3CCOCC3)CC2)c2c(C3CCC3)nn(-c3ccnc(C4CCOCC4)c3)c2n1] | 3-cyclobutyl-4-[4-(morpholin-4-yl)piperidin-1-yl]-1-[2-(oxan-4-yl)pyridin-4-yl]-1H-pyrazolo[3,4-b]pyridine-6-carboxylic acid | E407 | J1A | 546 | 547 |

TABLE XIII-continued

List of acids

| Int. | Structure | Name | SM | method | MW | Mes |
|---|---|---|---|---|---|---|
| A329 | 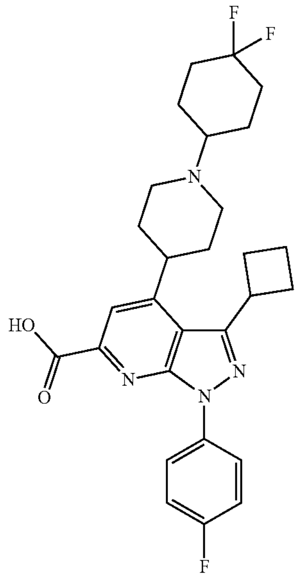 [SMILES: O=C(O)c1cc(C2CCN(C3CCC(F)(F)CC3)CC2)c2c(C3CCC3)nn(-c3ccc(F)cc3)c2n1] | 3-cyclobutyl-4-[1-(4,4-difluorocyclohexyl)piperidin-4-yl]-1-(4-fluorophenyl)-1H-pyrazolo[3,4-b]pyridine-6-carboxylic acid | E414 | J1A | 512 | 513 |
| A330 | 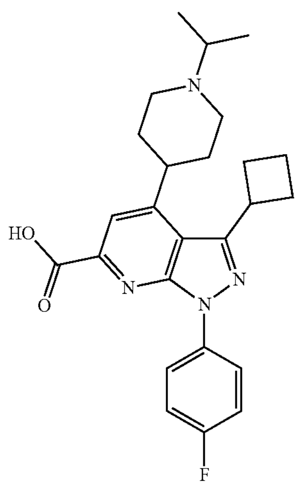 [SMILES: CC(C)N1CCC(c2cc(C(=O)O)nc3c2c(C2CCC2)nn3-c2ccc(F)cc2)CC1] | 3-cyclobutyl-1-(4-fluorophenyl)-4-[1-(propan-2-yl)piperidin-4-yl]-1H-pyrazolo[3,4-b]pyridine-6-carboxylic acid | E415 | J1A | 436 | 437 |
| A331 | 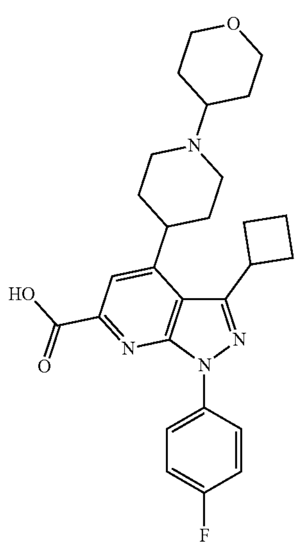 [SMILES: O=C(O)c1cc(C2CCN(C3CCOCC3)CC2)c2c(C3CCC3)nn(-c3ccc(F)cc3)c2n1] | 3-cyclobutyl-1-(4-fluorophenyl)-4-[1-(oxan-4-yl)piperidin-4-yl]-1H-pyrazolo[3,4-b]pyridine-6-carboxylic acid | E416 | J1A | 478 | 479 |

TABLE XIII-continued
| | | List of acids | | | | |
|---|---|---|---|---|---|---|
| Int. | Structure | Name | SM | method | MW | Mes |
| A332 | 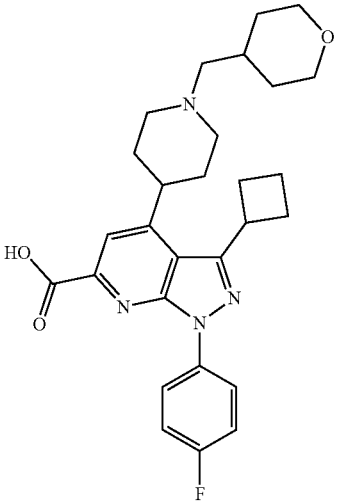 [SMILES: O=C(O)c1cc(C2CCN(CC3CCOCC3)CC2)c2c(C3CCC3)nn(-c3ccc(F)cc3)c2n1] | 3-cyclobutyl-1-(4-fluorophenyl)-4-{1-[(oxan-4-yl)methyl]piperidin-4-yl}-1H-pyrazolo[3,4-b]pyridine-6-carboxylic acid | E417 | J1A | 492 | 493 |
| A333 | 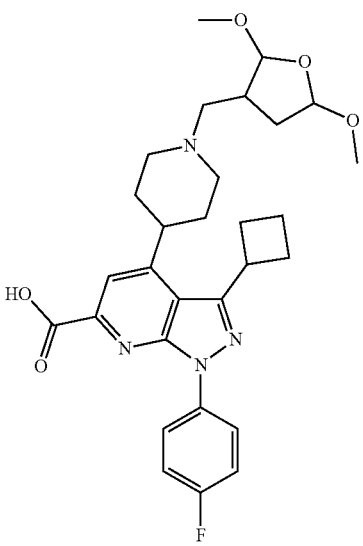 [SMILES: COC1CC(CN2CCC(c3cc(C(=O)O)nc4c3c(C3CCC3)nn4-c3ccc(F)cc3)CC2)C(OC)O1] | 3-cyclobutyl-4-{1-[(2,5-dimethoxyoxolan-3-yl)methyl]piperidin-4-yl}-1-(4-fluorophenyl)-1H-pyrazolo[3,4-b]pyridine-6-carboxylic acid | E418 | J1A | 538 | 539 |

TABLE XIII-continued
List of acids
| Int. | Structure | Name | SM | method | MW | Mes |
|------|-----------|------|----|--------|----|-----|
| A334 | 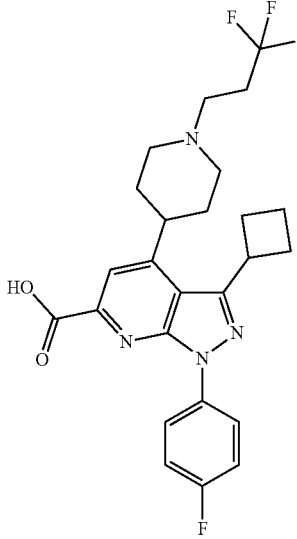 | 3-cyclobutyl-1-(4-fluorophenyl)-4-[1-(3,3,3-trifluoropropyl)piperidin-4-yl]-1H-pyrazolo[3,4-b]pyridine-6-carboxylic acid | E419 | J1A | 490 | 491 |
| A336 | 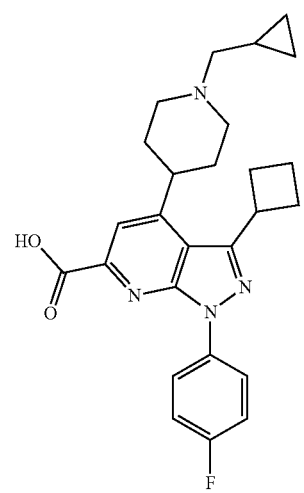 [SMILES: O=C(O)c1cc(C2CCN(CC3CC3)CC2)c2c(C3CCC3)nn(-c3ccc(F)cc3)c2n1] | 3-cyclobutyl-4-[1-(cyclopropylmethyl)piperidin-4-yl]-1-(4-fluorophenyl)-1H-pyrazolo[3,4-b]pyridine-6-carboxylic acid | E421 | J1A | 448 | 449 |

TABLE XIII-continued

List of acids

| Int. | Structure | Name | SM | method | MW | Mes |
|---|---|---|---|---|---|---|
| A337 | 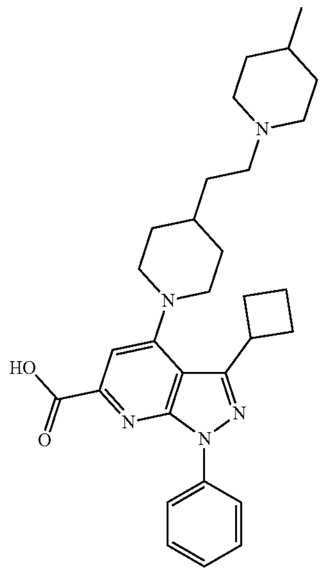 [SMILES: CC1CCN(CCC2CCN(c3cc(C(=O)O)nc4c3c(C3CCC3)nn4-c3ccccc3)CC2)CC1] | 3-cyclobutyl-4-{4-[2-(4-methylpiperidin-1-yl)ethyl]piperidin-1-yl}-1-phenyl-1H-pyrazolo[3,4-b]pyridine-6-carboxylic acid | E412 | J1A | 501 | 502 |
| A338 | 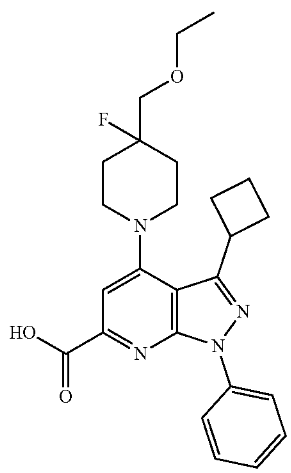 [SMILES: CCOCC1(F)CCN(c2cc(C(=O)O)nc3c2c(C2CCC2)nn3-c2ccccc2)CC1] | 3-cyclobutyl-4-[4-(ethoxymethyl)-4-fluoropiperidin-1-yl]-1-phenyl-1H-pyrazolo[3,4-b]pyridine-6-carboxylic acid | E408 | J1 | 452 | 453 |
| A339 | 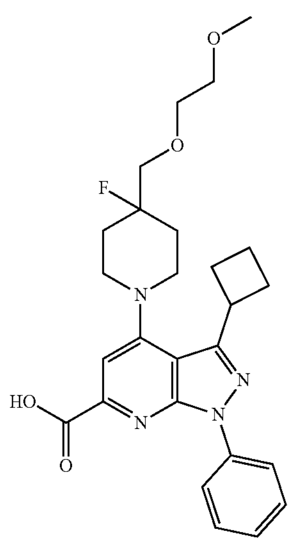 [SMILES: COCCOCC1(F)CCN(c2cc(C(=O)O)nc3c2c(C2CCC2)nn3-c2ccccc2)CC1] | 3-cyclobutyl-4-{4-fluoro-4-[(2-methoxyethoxy)methyl]piperidin-1-yl}-1-phenyl-1H-pyrazolo[3,4-b]pyridine-6-carboxylic acid | E409 | J1 | 482 | 483 |

TABLE XIII-continued

List of acids

| Int. | Structure | Name | SM | method | MW | Mes |
|---|---|---|---|---|---|---|
| A340 | 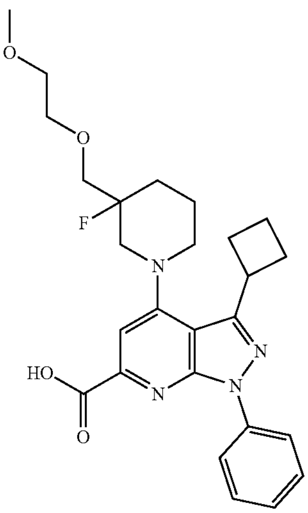 [SMILES: COCCOCC1(F)CCCN(c2cc(C(=O)O)nc3c2c(C2CCC2)nn3-c2ccccc2)C1] | 3-cyclobutyl-4-{3-fluoro-3-[(2-methoxyethoxy)methyl]piperidin-1-yl}-1-phenyl-1H-pyrazolo[3,4-b]pyridine-6-carboxylic acid | E410 | J1 | 482 | 483 |
| A341 | 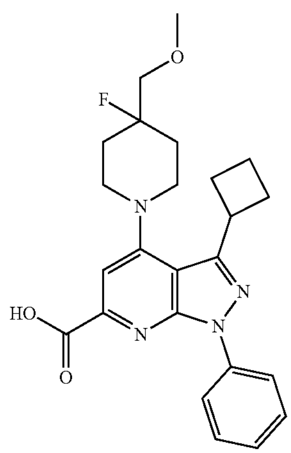 [SMILES: COCC1(F)CCN(c2cc(C(=O)O)nc3c2c(C2CCC2)nn3-c2ccccc2)CC1] | 3-cyclobutyl-4-[4-fluoro-4-(methoxymethyl)piperidin-1-yl]-1-phenyl-1H-pyrazolo[3,4-b]pyridine-6-carboxylic acid | E411 | J1 | 438 | 439 |
| A342 | 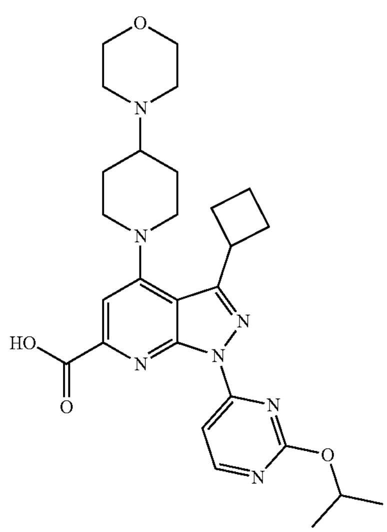 [SMILES: CC(C)Oc1nccc(-n2nc(C3CCC3)c3c(N4CCC(N5CCOCC5)CC4)cc(C(=O)O)nc32)n1] | 3-cyclobutyl-4-[4-(morpholin-4-yl)piperidin-1-yl]-1-{2-[(propan-2-yl)oxy]pyrimidin-4-yl}-1H-pyrazolo[3,4-b]pyridine-6-carboxylic acid | E422 | J11 | 521 | 522 |

TABLE XIII-continued

List of acids

| Int. | Structure | Name | SM | method | MW | Mes |
|---|---|---|---|---|---|---|
| A343 | 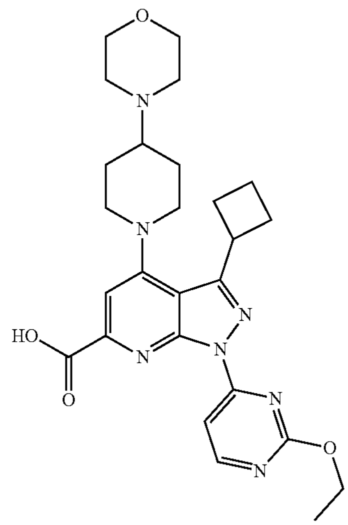 [SMILES: CCOc1nccc(-n2nc(C3CCC3)c3c(N4CCC(N5CCOCC5)CC4)cc(C(=O)O)nc32)n1] | 3-cyclobutyl-1-(2-ethoxypyrimidin-4-yl)-4-[4-(morpholin-4-yl)piperidin-1-yl]-1H-pyrazolo[3,4-b]pyridine-6-carboxylic acid | E422 | J11 Specific example | 507 | 508 |
| A344 | 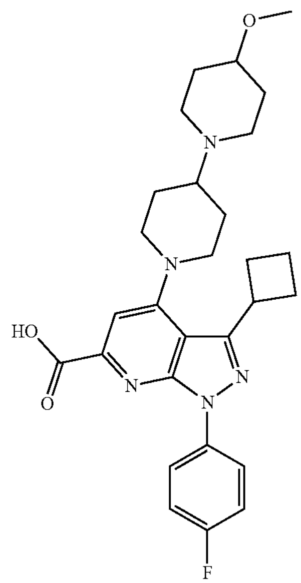 [SMILES: COC1CCN(C2CCN(c3cc(C(=O)O)nc4c3c(C3CCC3)nn4-c3ccc(F)cc3)CC2)CC1] | 3-cyclobutyl-1-(4-fluorophenyl)-4-(4-methoxy[1,4'-bipiperidin]-1'-yl)-1H-pyrazolo[3,4-b]pyridine-6-carboxylic acid | E424 | J1A | 507 | 508 |
| A345 | 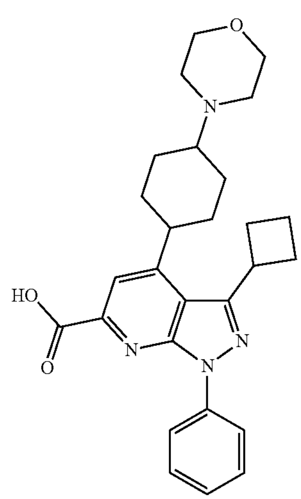 [SMILES: O=C(O)c1cc(C2CCC(N3CCOCC3)CC2)c2c(C3CCC3)nn(-c3ccccc3)c2n1] | 3-cyclobutyl-4-[4-(morpholin-4-yl)cyclohexyl]-1-phenyl-1H-pyrazolo[3,4-b]pyridine-6-carboxylic acid | E433 | J1A | 460 | 461 |

TABLE XIII-continued

List of acids

| Int. | Structure | Name | SM | method | MW | Mes |
|---|---|---|---|---|---|---|
| A346 | 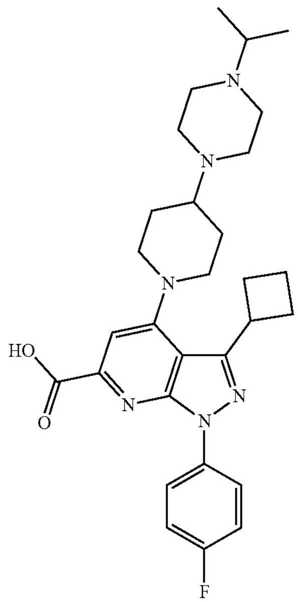 [SMILES: CC(C)N1CCN(C2CCN(c3cc(C(=O)O)nc4c3c(C3CCC3)nn4-c3ccc(F)cc3)CC2)CC1] | 3-cyclobutyl-1-(4-fluorophenyl)-4-{4-[4-(propan-2-yl)piperazin-1-yl]piperidin-1-yl}-1H-pyrazolo[3,4-b]pyridine-6-carboxylic acid | E434 | J1 | 520 | 521 |
| A347 | 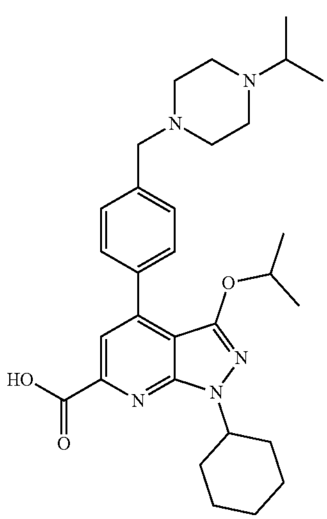 [SMILES: CC(C)Oc1nn(C2CCCCC2)c2nc(C(=O)O)cc(-c3ccc(CN4CCN(C(C)C)CC4)cc3)c12] | 1-cyclohexyl-3-[(propan-2-yl)oxy]-4-(4-{[4-(propan-2-yl)piperazin-1-yl]methyl}phenyl)-1H-pyrazolo[3,4-b]pyridine-6-carboxylic acid | E435 | J1 | 519 | 520 |

TABLE XIII-continued

List of acids

| Int. | Structure | Name | SM | method | MW | Mes |
|---|---|---|---|---|---|---|
| A348 | 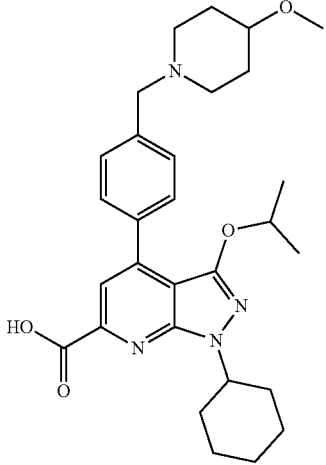 [SMILES: COC1CCN(Cc2ccc(-c3cc(C(=O)O)nc4c3c(OC(C)C)nn4C3CCCCC3)cc2)CC1] | 1-cyclohexyl-4-{4-[(4-methoxypiperidin-1-yl)methyl]phenyl}-3-[(propan-2-yl)oxy]-1H-pyrazolo[3,4-b]pyridine-6-carboxylic acid | E436 | J1 | 506 | 507 |
| A349 | 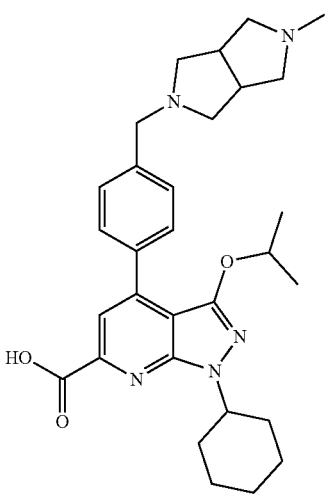 [SMILES: CC(C)Oc1nn(C2CCCCC2)c2nc(C(=O)O)cc(-c3ccc(CN4CC5CN(C)CC5C4)cc3)c12] | 1-cyclohexyl-4-{4-[(5-methylhexahydropyrrolo[3,4-c]pyrrol-2(1H)-yl)methyl]phenyl}-3-[(propan-2-yl)oxy]-1H-pyrazolo[3,4-b]pyridine-6-carboxylic acid | E437 | J1 | 517 | 518 |
| A350 | 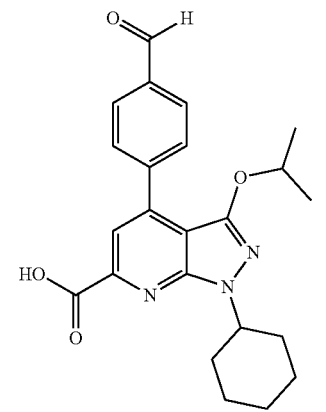 [SMILES: CC(C)Oc1nn(C2CCCCC2)c2nc(C(=O)O)cc(-c3ccc(C=O)cc3)c12] | 1-cyclohexyl-4-(4-formylphenyl)-3-[(propan-2-yl)oxy]-1H-pyrazolo[3,4-b]pyridine-6-carboxylic acid | E425 | J1 | 407 | 408 |

TABLE XIII-continued

List of acids

| Int. | Structure | Name | SM | method | MW | Mes |
|---|---|---|---|---|---|---|
| A351 | 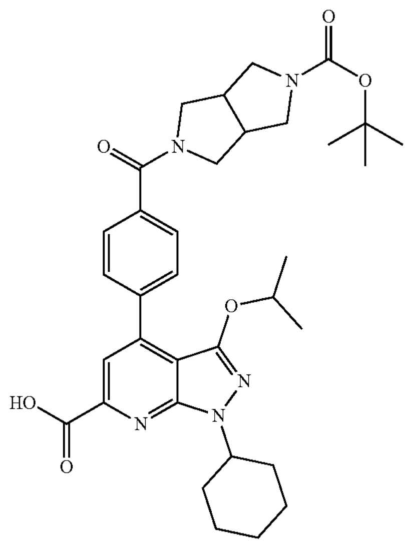 [SMILES: CC(C)Oc1nn(C2CCCCC2)c2nc(C(=O)O)cc(-c3ccc(C(=O)N4CC5CN(C(=O)OC(C)(C)C)CC5C4)cc3)c12] | 4-{4-[5-(tert-butoxycarbonyl)hexahydropyrrolo[3,4-c]pyrrole-2(1H)-carbonyl]phenyl}-1-cyclohexyl-3-[(propan-2-yl)oxy]-1H-pyrazolo[3,4-b]pyridine-6-carboxylic acid | E439 | J1A | 617 | 618 |
| A352 | 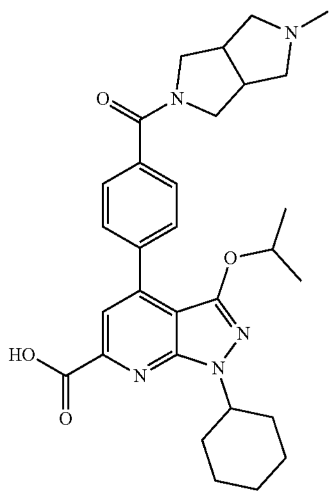 [SMILES: CC(C)Oc1nn(C2CCCCC2)c2nc(C(=O)O)cc(-c3ccc(C(=O)N4CC5CN(C)CC5C4)cc3)c12] | 1-cyclohexyl-4-[4-(5-methylhexahydropyrrolo[3,4-c]pyrrole-2(1H)-carbonyl)phenyl]-3-[(propan-2-yl)oxy]-1H-pyrazolo[3,4-b]pyridine-6-carboxylic acid | E440 | J1A | 531 | 532 |
| A353 | 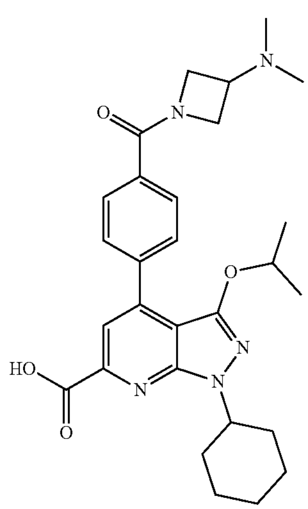 [SMILES: CC(C)Oc1nn(C2CCCCC2)c2nc(C(=O)O)cc(-c3ccc(C(=O)N4CC(N(C)C)C4)cc3)c12] | 1-cyclohexyl-4-{4-[3-(dimethylamino)azetidine-1-carbonyl]phenyl}-3-[(propan-2-yl)oxy]-1H-pyrazolo[3,4-b]pyridine-6-carboxylic acid | E441 | J1A | 505 | 506 |

TABLE XIII-continued

List of acids

| Int. | Structure | Name | SM | method | MW | Mes |
|---|---|---|---|---|---|---|
| A354 | 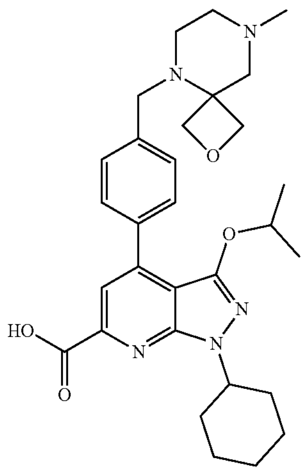 [SMILES: CC(C)Oc1nn(C2CCCCC2)c2nc(C(=O)O)cc(-c3ccc(CN4CCN(C)CC45COC5)cc3)c12] | 1-cyclohexyl-4-{4-[(8-methyl-2-oxa-5,8-diazaspiro[3.5]nonan-5-yl)methyl]phenyl}-3-[(propan-2-yl)oxy]-1H-pyrazolo[3,4-b]pyridine-6-carboxylic acid | E444 | J1A | 533 | 534 |
| A355 | 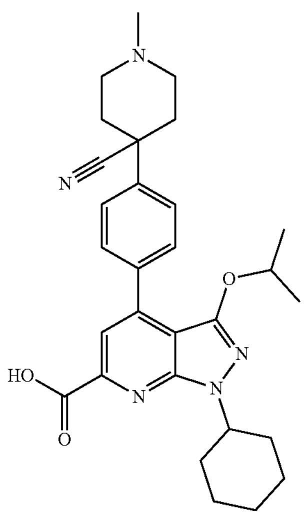 [SMILES: CC(C)Oc1nn(C2CCCCC2)c2nc(C(=O)O)cc(-c3ccc(C4(C#N)CCN(C)CC4)cc3)c12] | 4-[4-(4-cyano-1-methylpiperidin-4-yl)phenyl]-1-cyclohexyl-3-[(propan-2-yl)oxy]-1H-pyrazolo[3,4-b]pyridine-6-carboxylic acid | E445 | J1A | 501 | 502 |
| A356 | 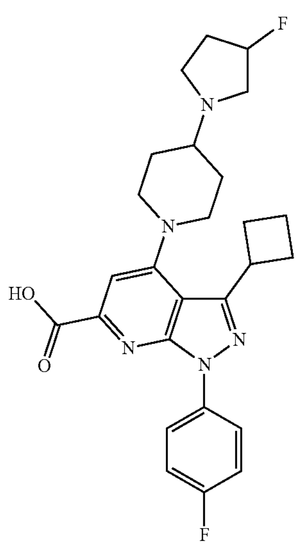 [SMILES: O=C(O)c1cc(N2CCC(N3CCC(F)C3)CC2)c2c(C3CCC3)nn(-c3ccc(F)cc3)c2n1] | 3-cyclobutyl-1-(4-fluorophenyl)-4-[4-(3-fluoropyrrolidin-1-yl)piperidin-1-yl]-1H-pyrazolo[3,4-b]pyridine-6-carboxylic acid | E427 | J1 | 481 | 482 |

TABLE XIII-continued

| | | List of acids | | | | |
|---|---|---|---|---|---|---|
| Int. | Structure | Name | SM | method | MW | Mes |
| A357 | | 4-[4-(3-cyanoazetidin-1-yl)piperidin-1-yl]-3-cyclobutyl-1-(4-fluorophenyl)-1H-pyrazolo[3,4-b]pyridine-6-carboxylic acid | E428 | J1 | 474 | 475 |
| A358 | | 3-cyclobutyl-1-(4-fluorophenyl)-4-[4-(3-methoxypyrrolidin-1-yl)piperidin-1-yl]-1H-pyrazolo[3,4-b]pyridine-6-carboxylic acid | E429 | J1 | 493 | 494 |

TABLE XIII-continued

List of acids

| Int. | Structure | Name | SM | method | MW | Mes |
|---|---|---|---|---|---|---|
| A360 | 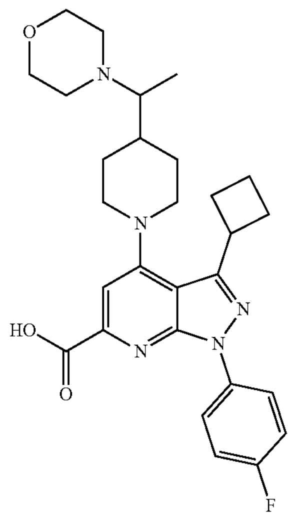 [SMILES: CC(C1CCN(c2cc(C(=O)O)nc3c2c(C2CCC2)nn3-c2ccc(F)cc2)CC1)N1CCOCC1] | 3-cyclobutyl-1-(4-fluorophenyl)-4-{4-[1-(morpholin-4-yl)ethyl]piperidin-1-yl}-1H-pyrazolo[3,4-b]pyridine-6-carboxylic acid | E460 | J1 | 507 | 508 |
| A361 | 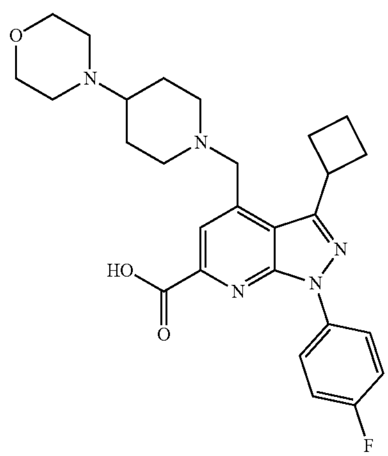 [SMILES: O=C(O)c1cc(CN2CCC(N3CCOCC3)CC2)c2c(C3CCC3)nn(-c3ccc(F)cc3)c2n1] | 3-cyclobutyl-1-(4-fluorophenyl)-4-{[4-(morpholin-4-yl)piperidin-1-yl]methyl}-1H-pyrazolo[3,4-b]pyridine-6-carboxylic acid | HP19 | J13 Specific example | 493 | 494 |
| A362 | 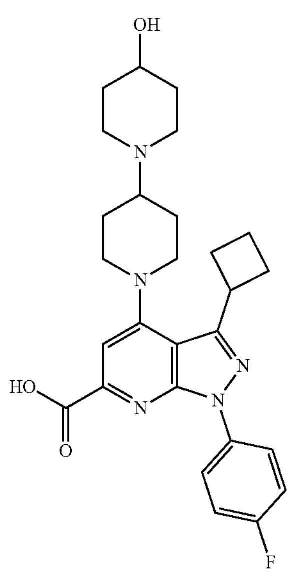 [SMILES: O=C(O)c1cc(N2CCC(N3CCC(O)CC3)CC2)c2c(C3CCC3)nn(-c3ccc(F)cc3)c2n1] | 3-cyclobutyl-1-(4-fluorophenyl)-4-(4-hydroxy[1,4'-bipiperidin]-1'-yl)-1H-pyrazolo[3,4-b]pyridine-6-carboxylic acid | E492 | J1 | 493 | 494 |

TABLE XIII-continued

List of acids

| Int. | Structure | Name | SM | method | MW | Mes |
|---|---|---|---|---|---|---|
| A363 | 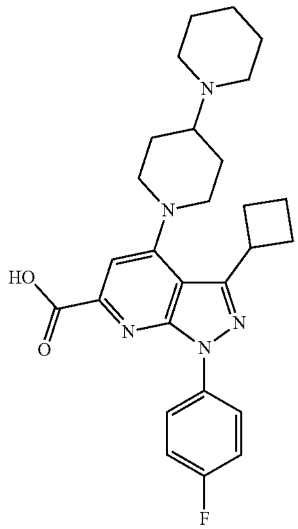 [SMILES: O=C(O)c1cc(N2CCC(N3CCCCC3)CC2)c2c(C3CCC3)nn(-c3ccc(F)cc3)c2n1] | 4-([1,4'-bipiperidin]-1'-yl)-3-cyclobutyl-1-(4-fluorophenyl)-1H-pyrazolo[3,4-b]pyridine-6-carboxylic acid | E493 | J1 | 493 | 494 |
| A364 | 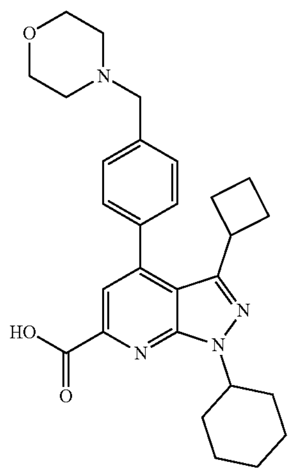 [SMILES: O=C(O)c1cc(-c2ccc(CN3CCOCC3)cc2)c2c(C3CCC3)nn(C3CCCCC3)c2n1] | 3-cyclobutyl-1-cyclohexyl-4-{4-[(morpholin-4-yl)methyl]phenyl}-1H-pyrazolo[3,4-b]pyridine-6-carboxylic acid | HP25, 364794-79-6 | J14 | 474 | 475 |
| A365 | 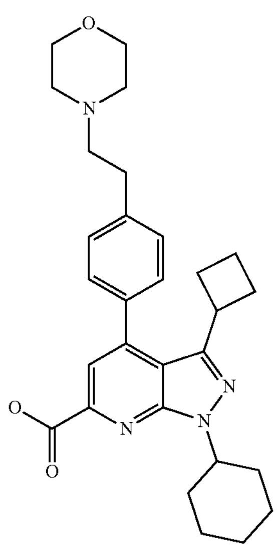 [SMILES: O=C(O)c1cc(-c2ccc(CCN3CCOCC3)cc2)c2c(C3CCC3)nn(C3CCCCC3)c2n1] | 3-cyclobutyl-1-cyclohexyl-4-{4-[2-(morpholin-4-yl)ethyl]phenyl}-1H-pyrazolo[3,4-b]pyridine-6-carboxylic acid | HP25, 1150114-55-8 | J14 | 488 | 489 |

TABLE XIII-continued

List of acids

| Int. | Structure | Name | SM | method | MW | Mes |
|---|---|---|---|---|---|---|
| A366 | 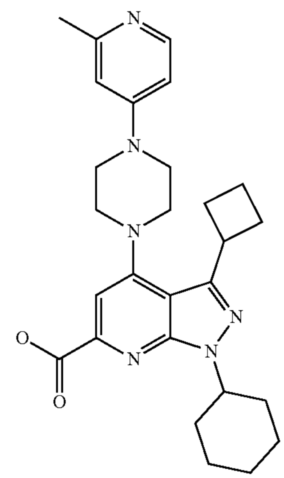 [SMILES: Cc1cc(N2CCN(c3cc(C(=O)O)nc4c3c(C3CCC3)nn4C3CCCCC3)CC2)ccn1] | 3-cyclobutyl-1-cyclohexyl-4-[4-(2-methylpyridin-4-yl)piperazin-1-yl]-1H-pyrazolo[3,4-b]pyridine-6-carboxylic acid | E461 | J1 | 474 | 475 |
| A367 | 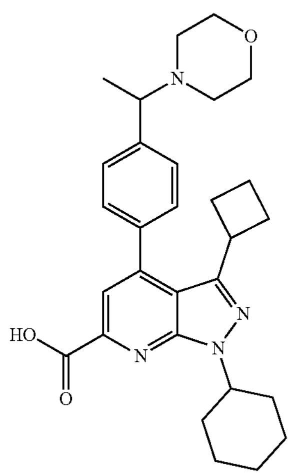 [SMILES: CC(c1ccc(-c2cc(C(=O)O)nc3c2c(C2CCC2)nn3C2CCCCC2)cc1)N1CCOCC1] | 3-cyclobutyl-1-cyclohexyl-4-{4-[1-(morpholin-4-yl)ethyl]phenyl}-1H-pyrazolo[3,4-b]pyridine-6-carboxylic acid | HP25, 1206594-12-8 | J14 | 488 | 489 |
| A368 | 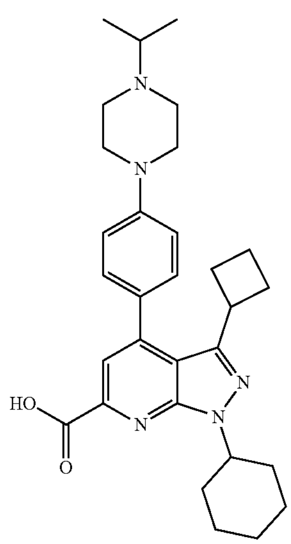 [SMILES: CC(C)N1CCN(c2ccc(-c3cc(C(=O)O)nc4c3c(C3CCC3)nn4C3CCCCC3)cc2)CC1] | 3-cyclobutyl-1-cyclohexyl-4-{4-[4-(propan-2-yl)piperazin-1-yl]phenyl}-1H-pyrazolo[3,4-b]pyridine-6-carboxylic acid | HP25, 1073354-18-3 | J14 | 501 | 502 |

TABLE XIII-continued
List of acids
| Int. | Structure | Name | SM | method | MW | Mes |
|------|-----------|------|-----|--------|-----|-----|
| A369 | 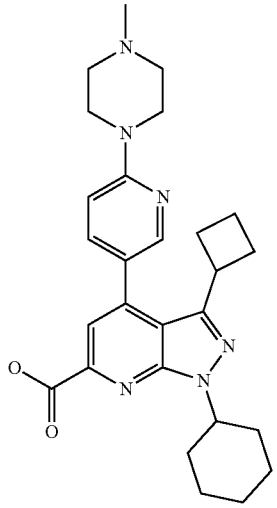 [SMILES: CN1CCN(c2ccc(-c3cc(C(=O)O)nc4c3c(C3CCC3)nn4C3CCCCC3)cn2)CC1] | 3-cyclobutyl-1-cyclohexyl-4-[6-(4-methylpiperazin-1-yl)pyridin-3-yl]-1H-pyrazolo[3,4-b]pyridine-6-carboxylic acid | A407, 109-01-3 | J12 | 474 | 475 |
| A370 | 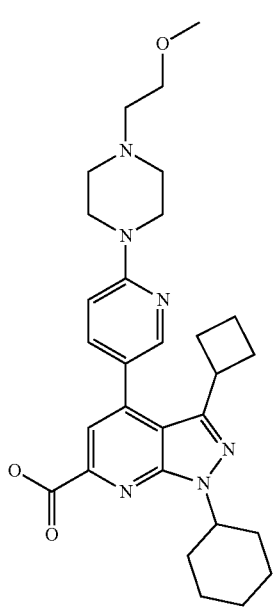 [SMILES: COCCN1CCN(c2ccc(-c3cc(C(=O)O)nc4c3c(C3CCC3)nn4C3CCCCC3)cn2)CC1] | 3-cyclobutyl-1-cyclohexyl-4-{6-[4-(2-methoxyethyl)piperazin-1-yl]pyridin-3-yl}-1H-pyrazolo[3,4-b]pyridine-6-carboxylic acid | A407, 13484-40-7 | J12 | 518 | 519 |

TABLE XIII-continued

List of acids

| Int. | Structure | Name | SM | method | MW | Mes |
|---|---|---|---|---|---|---|
| A371 | 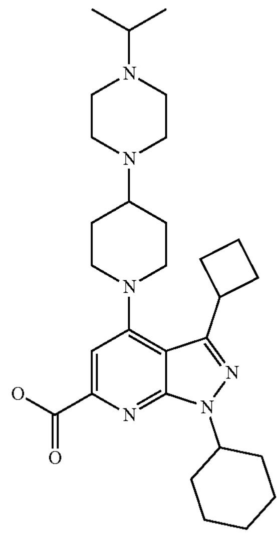 [SMILES: CC(C)N1CCN(C2CCN(c3cc(C(=O)O)nc4c3c(C3CCC3)nn4C3CCCCC3)CC2)CC1] | 3-cyclobutyl-1-cyclohexyl-4-{4-[4-(propan-2-yl)piperazin-1-yl]piperidin-1-yl}-1H-pyrazolo[3,4-b]pyridine-6-carboxylic acid | E462 | J1 | 508 | 509 |
| A372 | 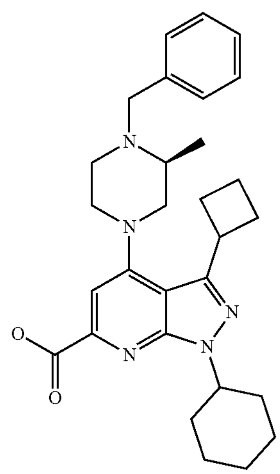 [SMILES: C[C@H]1CN(c2cc(C(=O)O)nc3c2c(C2CCC2)nn3C2CCCCC2)CCN1Cc1ccccc1] | 4-[(3S)-4-benzyl-3-methylpiperazin-1-yl]-3-cyclobutyl-1-cyclohexyl-1H-pyrazolo[3,4-b]pyridine-6-carboxylic acid | E463 | J1 | 487 | 488 |
| A373 | Chiral | 4-[(3R)-4-benzyl-3-methylpiperazin-1-yl]-3-cyclobutyl-1-cyclohexyl-1H-pyrazolo[3,4-b]pyridine-6-carboxylic acid | E464 | J1 | 487 | 488 |

TABLE XIII-continued

List of acids

| Int. | Structure | Name | SM | method | MW | Mes |
|---|---|---|---|---|---|---|
| A374 | 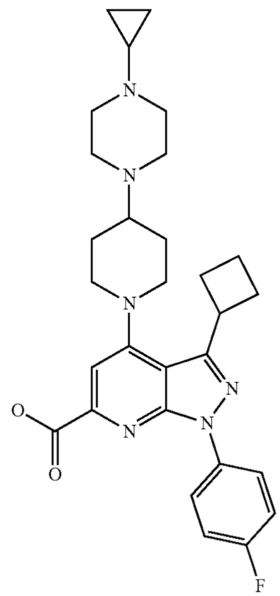 [SMILES: O=C(O)c1cc(N2CCC(N3CCN(C4CC4)CC3)CC2)c2c(C3CCC3)nn(-c3ccc(F)cc3)c2n1] | 3-cyclobutyl-4-[4-(4-cyclopropylpiperazin-1-yl)piperidin-1-yl]-1-(4-fluorophenyl)-1H-pyrazolo[3,4-b]pyridine-6-carboxylic acid | E465 | J1 | 518 | 519 |
| A375 | 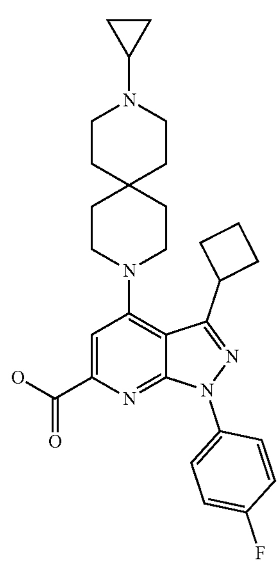 [SMILES: O=C(O)c1cc(N2CCC3(CC2)CCN(C2CC2)CC3)c2c(C3CCC3)nn(-c3ccc(F)cc3)c2n1] | 3-cyclobutyl-4-(9-cyclopropyl-3,9-diazaspiro[5.5]undecan-3-yl)-1-(4-fluorophenyl)-1H-pyrazolo[3,4-b]pyridine-6-carboxylic acid | E466 | J1 | 503 | 504 |

TABLE XIII-continued
List of acids
| Int. | Structure | Name | SM | method | MW | Mes |
|---|---|---|---|---|---|---|
| A376 | 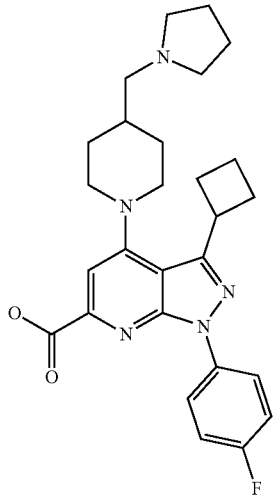 [SMILES: O=C(O)c1cc(N2CCC(CN3CCCC3)CC2)c2c(C3CCC3)nn(-c3ccc(F)cc3)c2n1] | 3-cyclobutyl-1-(4-fluorophenyl)-4-{4-[(pyrrolidin-1-yl)methyl]piperidin-1-yl}-1H-pyrazolo[3,4-b]pyridine-6-carboxylic acid | E467 | J1 | 477 | 478 |
| A377 | 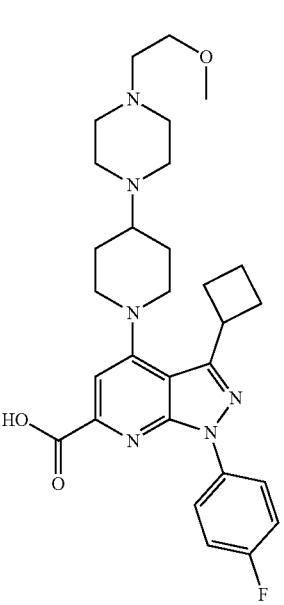 [SMILES: COCCN1CCN(C2CCN(c3cc(C(=O)O)nc4c3c(C3CCC3)nn4-c3ccc(F)cc3)CC2)CC1] | 3-cyclobutyl-1-(4-fluorophenyl)-4-{4-[4-(2-methoxyethyl)piperazin-1-yl]piperidin-1-yl}-1H-pyrazolo[3,4-b]pyridine-6-carboxylic acid | E468 | J1 | 536 | 537 |

TABLE XIII-continued

List of acids

| Int. | Structure | Name | SM | method | MW | Mes |
|---|---|---|---|---|---|---|
| A378 | 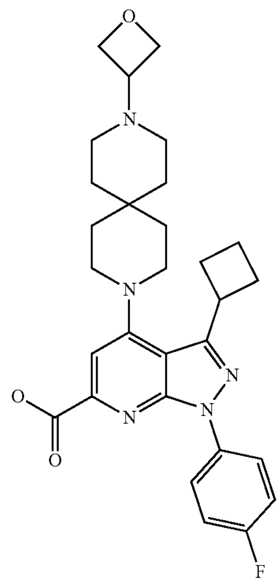 [SMILES: O=C(O)c1cc(N2CCC3(CC2)CCN(C2COC2)CC3)c2c(C3CCC3)nn(-c3ccc(F)cc3)c2n1] | 3-cyclobutyl-1-(4-fluorophenyl)-4-[9-(oxetan-3-yl)-3,9-diazaspiro[5.5]undecan-3-yl]-1H-pyrazolo[3,4-b]pyridine-6-carboxylic acid | E469 | J1 | 519 | 520 |
| A379 | 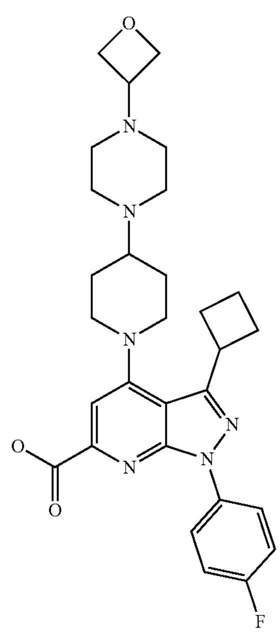 [SMILES: O=C(O)c1cc(N2CCC(N3CCN(C4COC4)CC3)CC2)c2c(C3CCC3)nn(-c3ccc(F)cc3)c2n1] | 3-cyclobutyl-1-(4-fluorophenyl)-4-{4-[4-(oxetan-3-yl)piperazin-1-yl]piperidin-1-yl}-1H-pyrazolo[3,4-b]pyridine-6-carboxylic acid | E470 | J1 | 534 | 535 |

TABLE XIII-continued

List of acids

| Int. | Structure | Name | SM | method | MW | Mes |
|---|---|---|---|---|---|---|
| A380 | 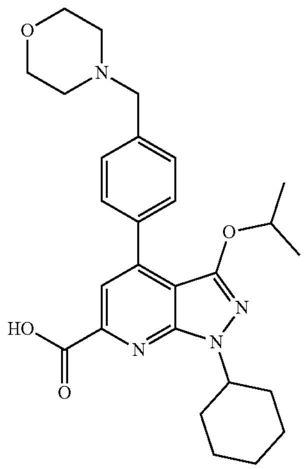 [SMILES: CC(C)Oc1nn(C2CCCCC2)c2nc(C(=O)O)cc(-c3ccc(CN4CCOCC4)cc3)c12] | 1-cyclohexyl-4-{4-[(morpholin-4-yl)methyl]phenyl}-3-[(propan-2-yl)oxy]-1H-pyrazolo[3,4-b]pyridine-6-carboxylic acid | E473 | J1 | 479 | 479 |
| A381 | 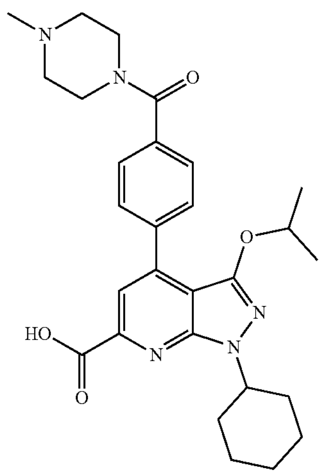 [SMILES: CC(C)Oc1nn(C2CCCCC2)c2nc(C(=O)O)cc(-c3ccc(C(=O)N4CCN(C)CC4)cc3)c12] | 1-cyclohexyl-4-[4-(4-methylpiperazine-1-carbonyl)phenyl]-3-[(propan-2-yl)oxy]-1H-pyrazolo[3,4-b]pyridine-6-carboxylic acid | E474 | J1 | 506 | 506 |
| A382 | 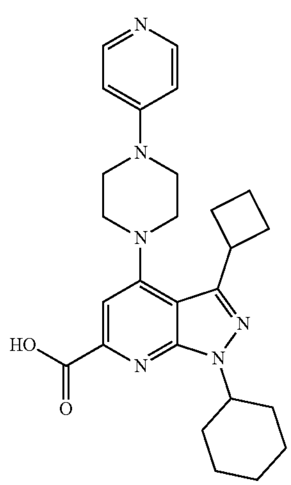 [SMILES: O=C(O)c1cc(N2CCN(c3ccncc3)CC2)c2c(C3CCC3)nn(C3CCCCC3)c2n1] | 3-cyclobutyl-1-cyclohexyl-4-[4-(pyridin-4-yl)piperazin-1-yl]-1H-pyrazolo[3,4-b]pyridine-6-carboxylic acid | E475 | J1 | 461 | 461 |

TABLE XIII-continued

List of acids

| Int. | Structure | Name | SM | method | MW | Mes |
|------|-----------|------|-----|--------|-----|-----|
| A383 | 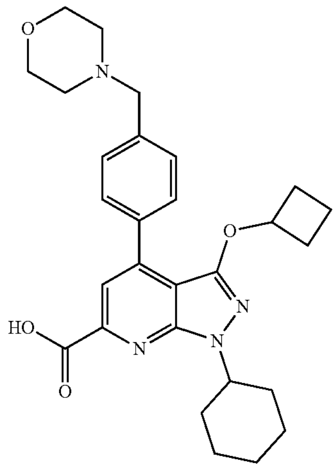 [SMILES: O=C(O)c1cc(-c2ccc(CN3CCOCC3)cc2)c2c(OC3CCC3)nn(C3CCCCC3)c2n1] | 3-(cyclobutyloxy)-1-cyclohexyl-4-{4-[(morpholin-4-yl)methyl]phenyl}-1H-pyrazolo[3,4-b]pyridine-6-carboxylic acid | E476 | J1 | 491 | 491 |
| A384 | 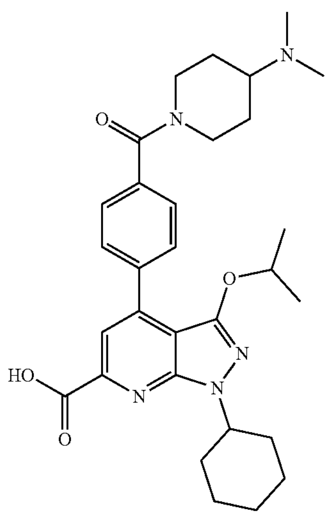 [SMILES: CC(C)Oc1nn(C2CCCCC2)c2nc(C(=O)O)cc(-c3ccc(C(=O)N4CCC(N(C)C)CC4)cc3)c12] | 1-cyclohexyl-4-{4-[4-(dimethylamino)piperidine-1-carbonyl]phenyl}-3-[(propan-2-yl)oxy]-1H-pyrazolo[3,4-b]pyridine-6-carboxylic acid | E477 | J1 | 534 | 535 |
| A385 | 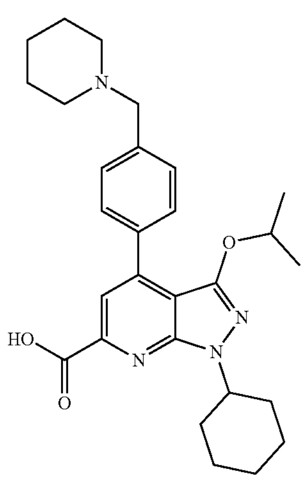 [SMILES: CC(C)Oc1nn(C2CCCCC2)c2nc(C(=O)O)cc(-c3ccc(CN4CCCCC4)cc3)c12] | 1-cyclohexyl-4-{4-[(piperidin-1-yl)methyl]phenyl}-3-[(propan-2-yl)oxy]-1H-pyrazolo[3,4-b]pyridine-6-carboxylic acid | E478 | J1 | 477 | 477 |

TABLE XIII-continued

List of acids

| Int. | Structure | Name | SM | method | MW | Mes |
|---|---|---|---|---|---|---|
| A386 | 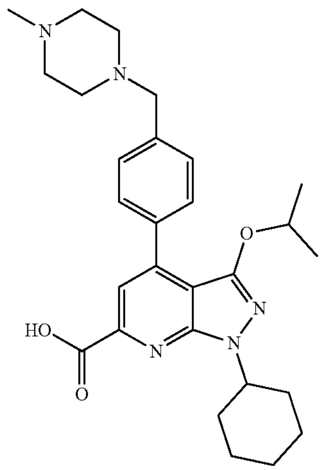 [SMILES: CC(C)Oc1nn(C2CCCCC2)c2nc(C(=O)O)cc(-c3ccc(CN4CCN(C)CC4)cc3)c12] | 1-cyclohexyl-4-{4-[(4-methylpiperazin-1-yl)methyl]phenyl}-3-[(propan-2-yl)oxy]-1H-pyrazolo[3,4-b]pyridine-6-carboxylic acid | E479 | J492 | 492 | 492 |
| A387 | 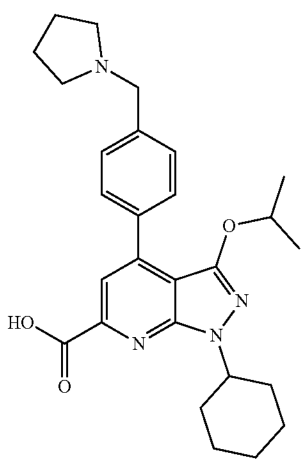 [SMILES: CC(C)Oc1nn(C2CCCCC2)c2nc(C(=O)O)cc(-c3ccc(CN4CCCC4)cc3)c12] | 1-cyclohexyl-3-[(propan-2-yl)oxy]-4-{4-[(pyrrolidin-1-yl)methyl]phenyl}-1H-pyrazolo[3,4-b]pyridine-6-carboxylic acid | E480 | J1 | 463 | 463 |
| A388 | 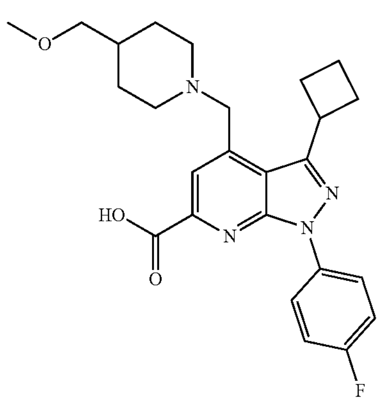 [SMILES: COCC1CCN(Cc2cc(C(=O)O)nc3c2c(C2CCC2)nn3-c2ccc(F)cc2)CC1] | 3-cyclobutyl-1-(4-fluorophenyl)-4-{[4-(methoxymethyl)piperidin-1-yl]methyl}-1H-pyrazolo[3,4-b]pyridine-6-carboxylic acid | E481 | J1 | 453 | 453 |

TABLE XIII-continued

List of acids

| Int. | Structure | Name | SM | method | MW | Mes |
|---|---|---|---|---|---|---|
| A389 | 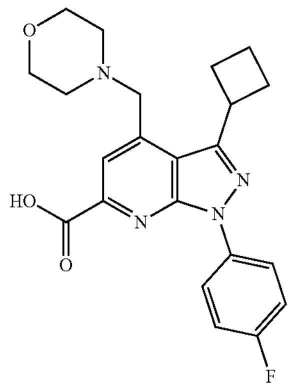 [SMILES: O=C(O)c1cc(CN2CCOCC2)c2c(C3CCC3)nn(-c3ccc(F)cc3)c2n1] | 3-cyclobutyl-1-(4-fluorophenyl)-4-[(morpholin-4-yl)methyl]-1H-pyrazolo[3,4-b]pyridine-6-carboxylic acid | E471 | J1 | 410 | 411 |
| A390 | 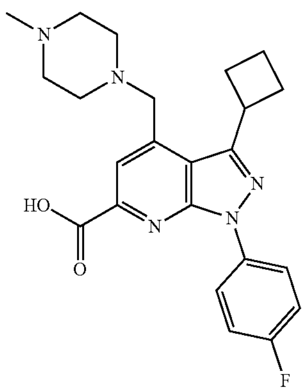 [SMILES: CN1CCN(Cc2cc(C(=O)O)nc3c2c(C2CCC2)nn3-c2ccc(F)cc2)CC1] | 3-cyclobutyl-1-(4-fluorophenyl)-4-[(4-methylpiperazin-1-yl)methyl]-1H-pyrazolo[3,4-b]pyridine-6-carboxylic acid | E472 | J1 | 423 | 424 |
| A391 | 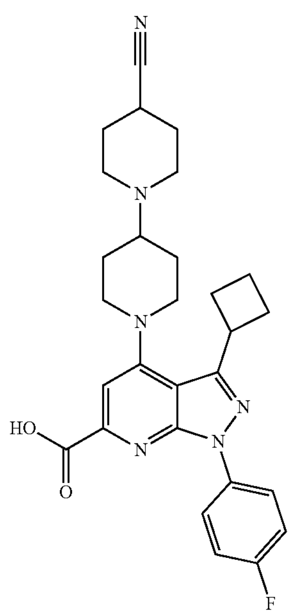 [SMILES: N#CC1CCN(C2CCN(c3cc(C(=O)O)nc4c3c(C3CCC3)nn4-c3ccc(F)cc3)CC2)CC1] | 4-(4-cyano[1,4'-bipiperidin]-1'-yl)-3-cyclobutyl-1-(4-fluorophenyl)-1H-pyrazolo[3,4-b]pyridine-6-carboxylic acid | E485 | J1 | 502 | 503 |

TABLE XIII-continued

List of acids

| Int. | Structure | Name | SM | method | MW | Mes |
|---|---|---|---|---|---|---|
| A392 | 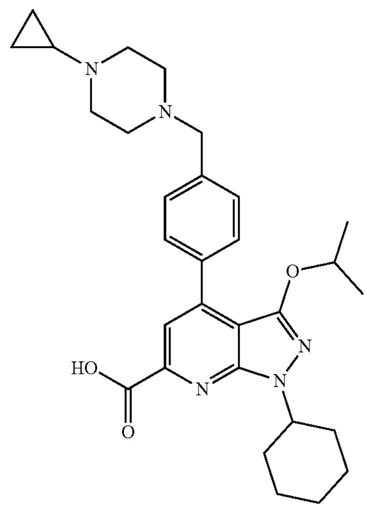 [SMILES: CC(C)Oc1nn(C2CCCCC2)c2nc(C(=O)O)cc(-c3ccc(CN4CCN(C5CC5)CC4)cc3)c12] | 1-cyclohexyl-4-{4-[(4-cyclopropylpiperazin-1-yl)methyl]phenyl}-3-[(propan-2-yl)oxy]-1H-pyrazolo[3,4-b]pyridine-6-carboxylic acid | E482 | J1 | 518 | 518 |
| A393 | 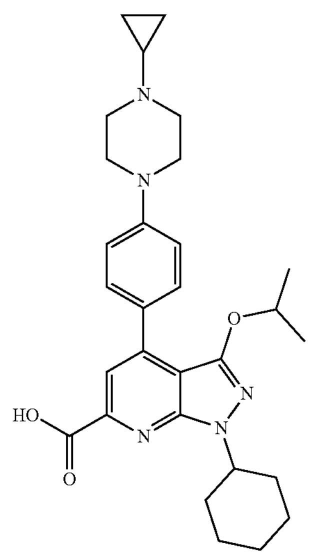 [SMILES: CC(C)Oc1nn(C2CCCCC2)c2nc(C(=O)O)cc(-c3ccc(N4CCN(C5CC5)CC4)cc3)c12] | 1-cyclohexyl-4-[4-(4-cyclopropylpiperazin-1-yl)phenyl]-3-[(propan-2-yl)oxy]-1H-pyrazolo[3,4-b]pyridine-6-carboxylic acid | E484 | J1 | 503 | 504 |
| A394 | 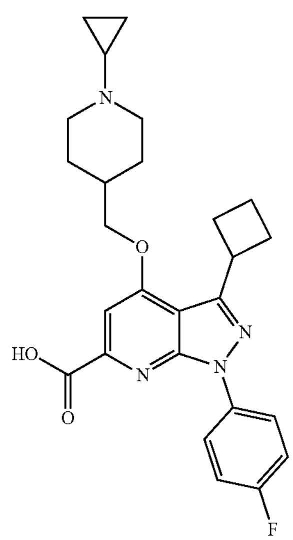 [SMILES: O=C(O)c1cc(OCC2CCN(C3CC3)CC2)c2c(C3CCC3)nn(-c3ccc(F)cc3)c2n1] | 3-cyclobutyl-4-[(1-cyclopropylpiperidin-4-yl)methoxy]-1-(4-fluorophenyl)-1H-pyrazolo[3,4-b]pyridine-6-carboxylic acid | HP26 | J3 | 464 | 465 |

TABLE XIII-continued

| | | List of acids | | | | |
|---|---|---|---|---|---|---|
| Int. | Structure | Name | SM | method | MW | Mes |
| A395 | | 1-cyclohexyl-3-[(propan-2-yl)oxy]-4-{4-[4-(propan-2-yl)piperazin-1-yl]phenyl}-1H-pyrazolo[3,4-b]pyridine-6-carboxylic acid | E483 | J1 | 505 | 506 |
| A396 | | 3-cyclobutyl-1-(4-fluorophenyl)-4-{[1-(oxan-4-yl)piperidin-4-yl]methoxy}-1H-pyrazolo[3,4-b]pyridine-6-carboxylic acid | HP26 ALC08 | J3 | 508 | 509 |

TABLE XIII-continued
List of acids
| Int. | Structure | Name | SM | method | MW | Mes |
|---|---|---|---|---|---|---|
| A397 | 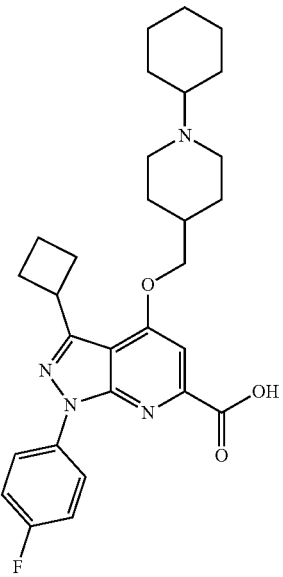 [SMILES: O=C(O)c1cc(OCC2CCN(C3CCCCC3)CC2)c2c(C3CCC3)nn(-c3ccc(F)cc3)c2n1] | 3-cyclobutyl-4-[(1-cyclohexylpiperidin-4-yl)methoxy]-1-(4-fluorophenyl)-1H-pyrazolo[3,4-b]pyridine-6-carboxylic acid | HP26 ALC07 | J3 | 506 | 507 |
| A398 | 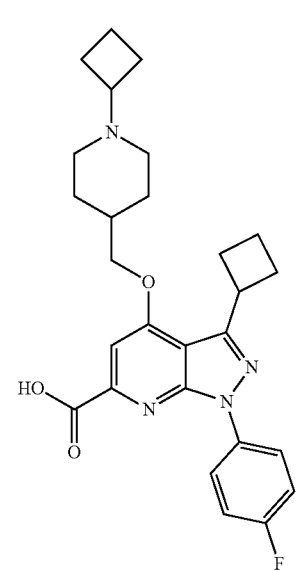 [SMILES: O=C(O)c1cc(OCC2CCN(C3CCC3)CC2)c2c(C3CCC3)nn(-c3ccc(F)cc3)c2n1] | 3-cyclobutyl-4-[(1-cyclobutylpiperidin-4-yl)methoxy]-1-(4-fluorophenyl)-1H-pyrazolo[3,4-b]pyridine-6-carboxylic acid | HP26 ALC06 | J3 | 478 | 479 |

TABLE XIII-continued

List of acids

| Int. | Structure | Name | SM | method | MW | Mes |
|---|---|---|---|---|---|---|
| A399 | 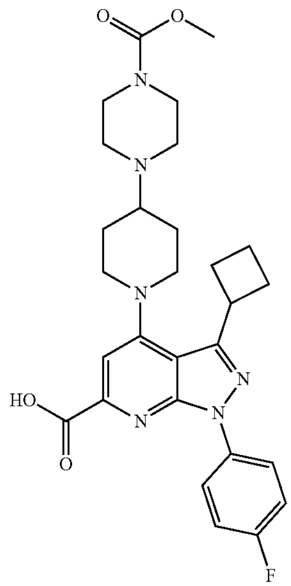 [SMILES: COC(=O)N1CCN(C2CCN(c3cc(C(=O)O)nc4c3c(C3CCC3)nn4-c3ccc(F)cc3)CC2)CC1] | 3-cyclobutyl-1-(4-fluorophenyl)-4-{4-[4-(methoxycarbonyl)piperazin-1-yl]piperidin-1-yl}-1H-pyrazolo[3,4-b]pyridine-6-carboxylic acid | E486 | J1 | 536 | 537 |
| A400 | 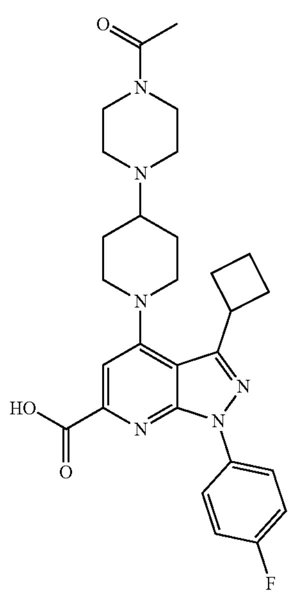 [SMILES: CC(=O)N1CCN(C2CCN(c3cc(C(=O)O)nc4c3c(C3CCC3)nn4-c3ccc(F)cc3)CC2)CC1] | 4-[4-(4-acetylpiperazin-1-yl)piperidin-1-yl]-3-cyclobutyl-1-(4-fluorophenyl)-1H-pyrazolo[3,4-b]pyridine-6-carboxylic acid | E487 | J1 | 520 | 521 |

TABLE XIII-continued

List of acids

| Int. | Structure | Name | SM | method | MW | Mes |
|---|---|---|---|---|---|---|
| A401 | 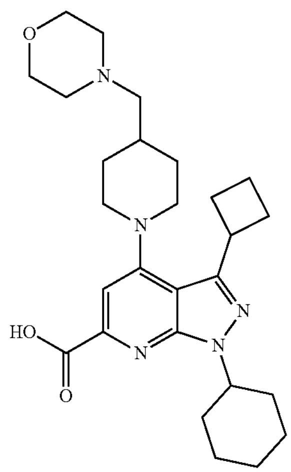 [SMILES: O=C(O)c1cc(N2CCC(CN3CCOCC3)CC2)c2c(C3CCC3)nn(C3CCCCC3)c2n1] | 3-cyclobutyl-1-cyclohexyl-4-{4-[(morpholin-4-yl)methyl]piperidin-1-yl}-1H-pyrazolo[3,4-b]pyridine-6-carboxylic acid | E488 | J1 | 481 | 482 |
| A402 | 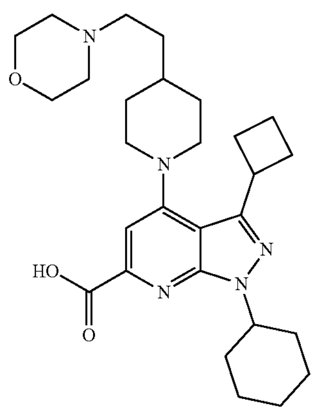 [SMILES: O=C(O)c1cc(N2CCC(CCN3CCOCC3)CC2)c2c(C3CCC3)nn(C3CCCCC3)c2n1] | 3-cyclobutyl-1-cyclohexyl-4-{4-[2-(morpholin-4-yl)ethyl]piperidin-1-yl}-1H-pyrazolo[3,4-b]pyridine-6-carboxylic acid | E489 | J1 | 495 | 496 |
| A403 | 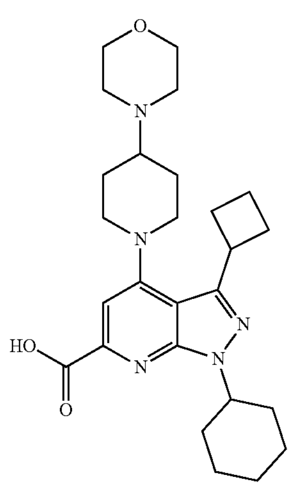 [SMILES: O=C(O)c1cc(N2CCC(N3CCOCC3)CC2)c2c(C3CCC3)nn(C3CCCCC3)c2n1] | 3-cyclobutyl-1-cyclohexyl-4-[4-(morpholin-4-yl)piperidin-1-yl]-1H-pyrazolo[3,4-b]pyridine-6-carboxylic acid | E490 | J1 | 467 | 468 |

TABLE XIII-continued
List of acids
| Int. | Structure | Name | SM | method | MW | Mes |
|------|-----------|------|----|--------|----|-----|
| A404 | 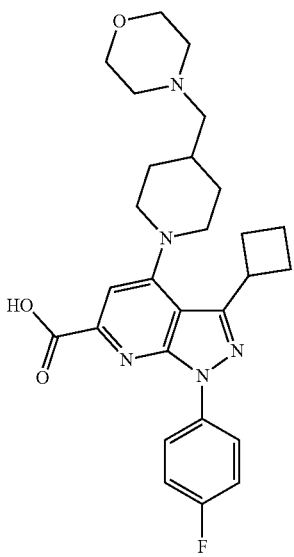 [SMILES: O=C(O)c1cc(N2CCC(CN3CCOCC3)CC2)c2c(C3CCC3)nn(-c3ccc(F)cc3)c2n1] | 3-cyclobutyl-1-(4-fluorophenyl)-4-{4-[(morpholin-4-yl)methyl]piperidin-1-yl}-1H-pyrazolo[3,4-b]pyridine-6-carboxylic acid | E491 | J1 | 493 | 494 |
| A405 | 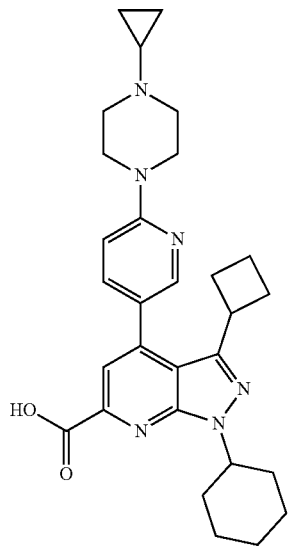 [SMILES: O=C(O)c1cc(-c2ccc(N3CCN(C4CC4)CC3)nc2)c2c(C3CCC3)nn(C3CCCCC3)c2n1] | 3-cyclobutyl-1-cyclohexyl-4-[6-(4-cyclopropylpiperazin-1-yl)pyridin-3-yl]-1H-pyrazolo[3,4-b]pyridine-6-carboxylic acid | A407, 20327-23-5 | J12 Specific example | 500 | 501 |

TABLE XIII-continued

List of acids

| Int. | Structure | Name | SM | method | MW | Mes |
|---|---|---|---|---|---|---|
| A406 | 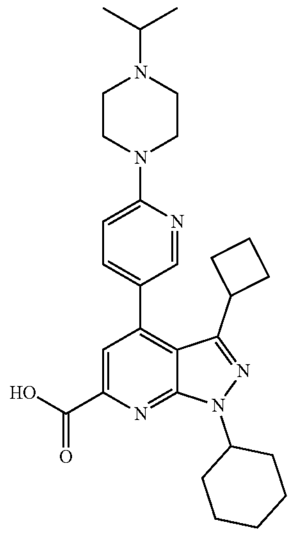 [SMILES: CC(C)N1CCN(c2ccc(-c3cc(C(=O)O)nc4c3c(C3CCC3)nn4C3CCCCC3)cn2)CC1] | 3-cyclobutyl-1-cyclohexyl-4-{6-[4-(propan-2-yl)piperazin-1-yl]pyridin-3-yl}-1H-pyrazolo[3,4-b]pyridine-6-carboxylic acid | A407, 4318-42-7 | J12 | 502 | 503 |
| A407 | 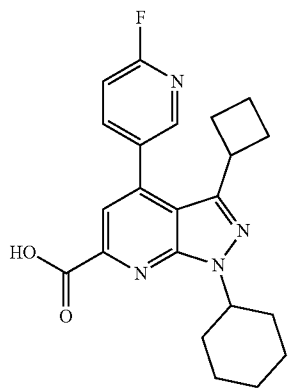 [SMILES: O=C(O)c1cc(-c2ccc(F)nc2)c2c(C3CCC3)nn(C3CCCCC3)c2n1] | 3-cyclobutyl-1-cyclohexyl-4-(6-fluoropyridin-3-yl)-1H-pyrazolo[3,4-b]pyridine-6-carboxylic acid | HP25, 351019-18-6 | J14 | 394 | 395 |
| A408 | 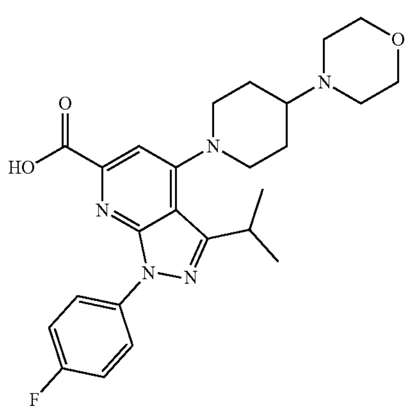 [SMILES: CC(C)c1nn(-c2ccc(F)cc2)c2nc(C(=O)O)cc(N3CCC(N4CCOCC4)CC3)c12] | 1-(4-fluorophenyl)-4-[4-(morpholin-4-yl)piperidin-1-yl]-3-(propan-2-yl)-1H-pyrazolo[3,4-b]pyridine-6-carboxylic acid | HP11, 442563-55-5 | J10 Specific example | 467 | 468 |

TABLE XIII-continued

| | | List of acids | | | | |
|---|---|---|---|---|---|---|
| Int. | Structure | Name | SM | method | MW | Mes |
| A409 | | 3-cyclobutyl-4-[4-(morpholin-4-yl)piperidin-1-yl]-1-phenyl-1H-pyrazolo[3,4-b]pyridine-6-carboxylic acid | HP10 | J10 | 461 | 462 |
| A410 | | 3-cyclobutyl-1-[3-(difluoromethoxy)phenyl]-4-[4-(morpholin-4-yl)piperidin-1-yl]-1H-pyrazolo[3,4-b]pyridine-6-carboxylic acid | E510 | J1 | 527 | 528 |
| A411 | | 1-cyclohexyl-4-(4-{[3-(dimethylamino)azetidin-1-yl]methyl}phenyl)-3-[(propan-2-yl)oxy]-1H-pyrazolo[3,4-b]pyridine-6-carboxylic acid | E426 | J1A | 491 | 492 |

TABLE XIII-continued

List of acids

| Int. | Structure | Name | SM | method | MW | Mes |
|---|---|---|---|---|---|---|
| A412 | 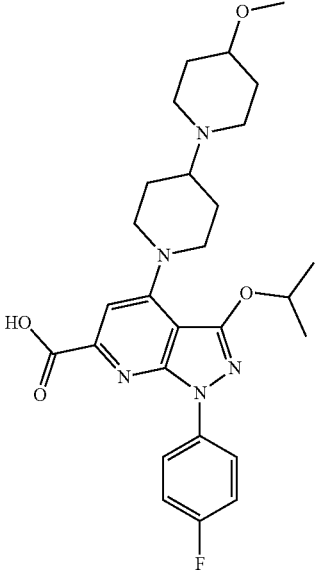 [SMILES: COC1CCN(C2CCN(c3cc(C(=O)O)nc4c3c(OC(C)C)nn4-c3ccc(F)cc3)CC2)CC1] | 1-(4-fluorophenyl)-4-(4-methoxy[1,4'-bipiperidin]-1'-yl)-3-[(propan-2-yl)oxy]-1H-pyrazolo[3,4-b]pyridine-6-carboxylic acid | E511 | J1A | 511 | 512 |
| A413 | 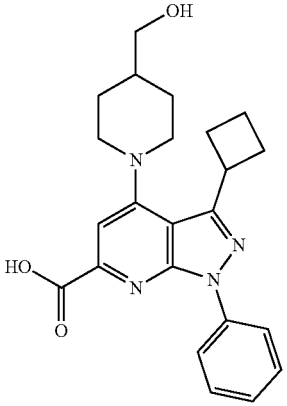 [SMILES: O=C(O)c1cc(N2CCC(CO)CC2)c2c(C3CCC3)nn(-c3ccccc3)c2n1] | 3-cyclobutyl-4-[4-(hydroxymethyl)piperidin-1-yl]-1-phenyl-1H-pyrazolo[3,4-b]pyridine-6-carboxylic acid | HP10 | J10, Specific example | 406 | 407 |
| A414 | 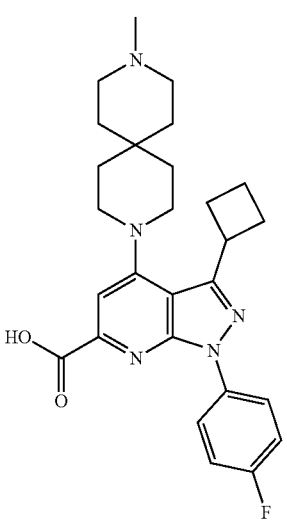 [SMILES: CN1CCC2(CC1)CCN(c1cc(C(=O)O)nc3c1c(C1CCC1)nn3-c1ccc(F)cc1)CC2] | 3-cyclobutyl-1-(4-fluorophenyl)-4-(9-methyl-3,9-diazaspiro[5.5]decan-3-yl)-1H-pyrazolo[3,4-b]pyridine-6-carboxylic acid | E515 | J1 | 477 | 478 |

TABLE XIII-continued

List of acids

| Int. | Structure | Name | SM | method | MW | Mes |
|---|---|---|---|---|---|---|
| A415 | 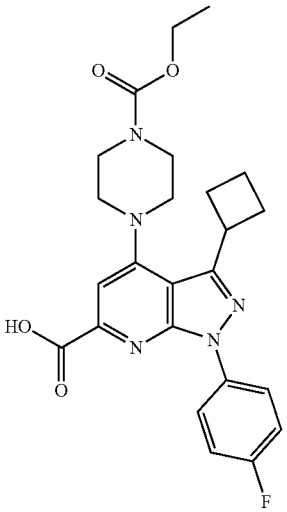 [SMILES: CCOC(=O)N1CCN(c2cc(C(=O)O)nc3c2c(C2CCC2)nn3-c2ccc(F)cc2)CC1] | 3-cyclobutyl-4-[4-(ethoxycarbonyl)piperazin-1-yl]-1-(4-fluorophenyl)-1H-pyrazolo[3,4-b]pyridine-6-carboxylic acid | E516 | J1 | 467 | 468 |
| A416 | 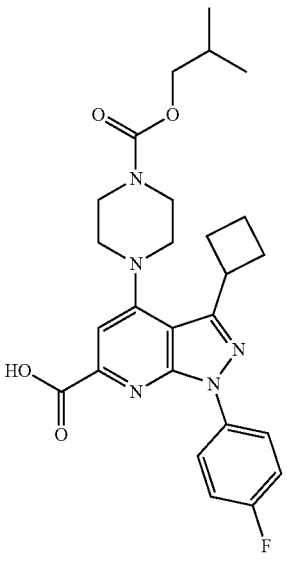 [SMILES: CC(C)COC(=O)N1CCN(c2cc(C(=O)O)nc3c2c(C2CCC2)nn3-c2ccc(F)cc2)CC1] | 3-cyclobutyl-1-(4-fluorophenyl)-4-{4-[(2-methylpropoxy)carbonyl]piperazin-1-yl}-1H-pyrazolo[3,4-b]pyridine-6-carboxylic acid | E517 | J1 | 495 | 496 |

Method X1: Synthesis of Sulfonamide

A procedure similar to that described in J. Org. Chem. (1968) 33(2), 897 is followed: A round bottomed flask is charged with the sulfonyl chloride and diethyl ether (0.06 M), sealed with a septum and cooled in an ice bath. To the cooled solution is slowly added two molar equivalents of a dioxane solution of ammonia (0.5 M), and then the cold bath is removed. After 16 hours, the resulting heterogeneous mixture is filtered through filter paper. Volatiles are removed from the filtrate via rotary evaporation to give the sulfonamide which is used without further purification.

Illustrative Synthesis of S2: Methyl 3-sulfamoylpropanoate

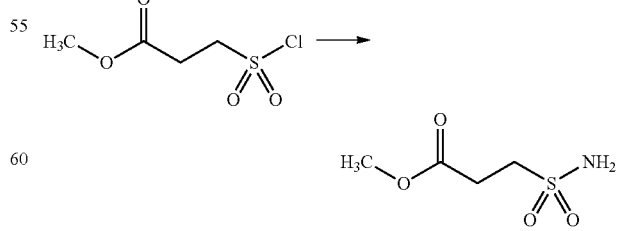

A dioxane solution of ammonia (0.5 M, 10.5 mL, 5.25 mmol, 2.05 equiv) was added at 0° C. to a solution of methyl 3-(chlorosulfonyl)propanoate (CAS: 15441-07-3, 0.476 g, 2.55 mmol) in diethyl ether (10 mL). The reaction mixture was stirred at 0° C. for 1 hour and then 16 hours at RT. The reaction mixture was filtered, and the filtrate was concentrated to give the titled compound which was used without further purification.

Method X2: Synthesis of Sulfonamide

Synthesis of 3-morpholinopropane-1-sulfonamide S10

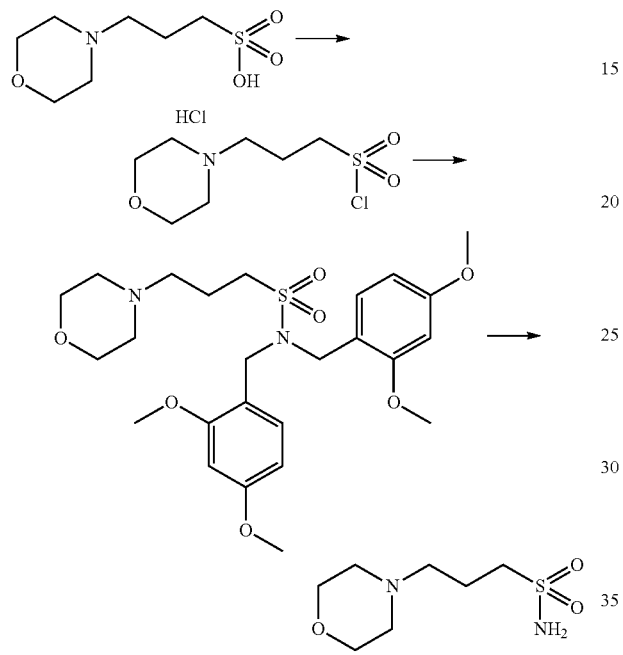

Step 1: 3-(morpholin-4-yl)propane-1-sulfonyl Chloride

3-Morpholinopropanesulfonic acid (CAS: 1132-61-2, 0.63 g, 3.0 mmol) was added to thionyl chloride (4.0 mL, 54.8 mmol, 18 equiv). Dimethylformamide (0.1 mL, 1.2 mmol, 0.4 equiv) was added, and the reaction mixture was stirred at RT for 5 hours. The reaction mixture was diluted with dichloromethane (4 mL) and dropped into heptane. Precipitation occurred, and the supernatant was removed. The residue dissolved in dichloromethane was dropped into pentane. The supernatant was removed, and the solid dried to give 3-morpholinopropanesulfonyl chloride hydrochloride.

Step 2: N,N-bis[(2,4-dimethoxyphenyl)methyl]-3-(morpholin-4-yl)propane-1-sulfonamide Bis(2,4-dimethoxybenzyl)amine (CAS: 20781-23-1, 0.32 g, 1.0 mmol, 1.0 equiv) and potassium carbonate (0.28 g, 2.0 mmol, 2.0 equiv) were added to a solution of 3-morpholinopropanesulfonyl chloride hydrochloride (0.26 g, 1.0 mmol) in acetonitrile (20 mL). The reaction mixture was stirred at RT for 8 hours. The reaction mixture was concentrated and the residue partitioned between water and ethyl acetate. The organic phase was dried over sodium sulfate, filtered and concentrated under reduced pressure. The residue was purified by flash column chromatography eluting with heptane/ethyl acetate (100/0 to 0/100) to give N,N-bis[(2,4-dimethoxyphenyl)methyl]-3-morpholino-propane-1-sulfonamide.

Step 3: 3-(morpholin-4-yl)propane-1-sulfonamide

Trifluoroacetic acid (0.8 mL, 10.4 mmol, 39 equiv) was added to a solution of N,N-bis[(2,4-dimethoxyphenyl)methyl]-3-morpholino-propane-1-sulfonamide (0.135 g, 0.27 mmol) in dichloromethane (4 mL). The reaction mixture was stirred at RT for 16 hours and was added to a saturated aqueous solution of sodium hydrogencarbonate. The mixture was extracted with ethyl acetate and then with a 9:1 mixture of dichloromethane/isopropanol. The organic phases were dried over sodium sulfate, filtered and concentrated under reduced pressure to give the titled compound.

As an alternative preparation of S10, 3-chloropropane-1-sulfonamide (3.15 g, 20.0 mmol), morpholine (1.84, 21.0 mmol), sodium carbonate (4.24 g, 40.0 mmol) and sodium iodide (300 mg, 2.0 mmol) were heated in anhydrous dioxane (70 mL) at 70° C. for a day. The suspension was permitted to cool towards room temperature and then filtered through diatomaceous earth with an MTBE rinse. The filtrate was concentrated and chromatographed on silica (0 to 4% concentrated aqueous $NH_4OH/CH_3CN$) to give the titled compound (1.47 g). $^1H$ NMR (400 MHz, $CDCl_3$) δ ppm 5.41 (s, 2H), 3.70 (t, J=4.7 Hz, 4H), 3.23 (t, J=7.2 Hz, 2H), 2.54-2.43 (m, 6H), 2.10-2.02 (m, 2H); MS (DCI) m/z 209 (M+H)$^+$.

Method X3. Synthesis of Sulfonamide

Synthesis of (2S)-2-(4-methylpiperazine-1-carbonyl)pyrrolidine-1-sulfonamide S11

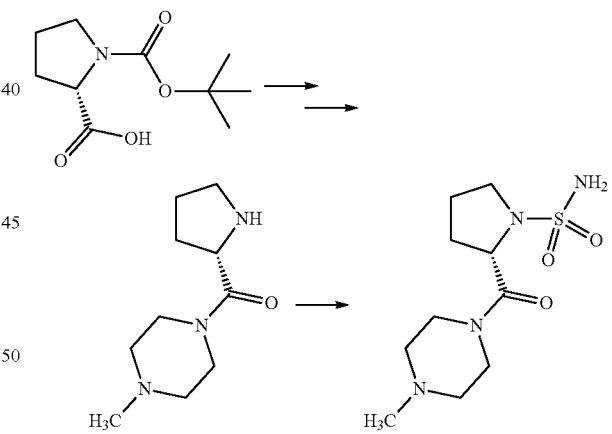

The titled compound may be prepared by the method described in Ebden, et al. PCT Int. Appl. WO2004 011443, example 25, substituting N-methylpiperidine hydrochloride for dimethylamine hydrochloride. To 1-(tert-butoxycarbonyl)-L-proline (5.0 g) in DCM (50 mL) at 5° C. was added dicyclohexylcarbodiimide (5.22 g) and N-hydroxysuccinimide (2.91 g). The mixture was stirred at this temperature for 16 hours. The solid was filtered, and the filtrate cooled to 5° C. To this mixture was added triethylamine (9.80 mL) and N-methylpiperidine hydrochloride (4.7 g). The mixture was stirred at room temperature for 2 days, $H_2O$ (50 mL) was added, and the phases were separated. The organic fraction was washed with saturated sodium carbonate (2×20 mL) and brine (20 mL). This was then dried (MgSO$_4$) and concentrated to dryness to afford tert-butyl (2S)-2-(4-methylpiperazine-1-carbonyl)pyrrolidine-1-carboxylate. This was then treated with 4 M aqueous HCl (20 mL), stirred at room temperature 3 hours, and concentrated in vacuo to dryness. A solution of the residue in dioxane was then treated with 2 grams of triethylamine and 10 grams of sulfamide, and the mixture was heated at reflux for 3 days before cooling. Solids were removed by filtration and washed with methanol. The combined filtrate and washing are concentrated in vacuo, and the residue was purified by column chromatography to give the titled compound.

Method X4. Synthesis of Sulfonamide

Synthesis of 4-(4-methylpiperazine-1-carbonyl)piperidine-1-sulfonamide S12

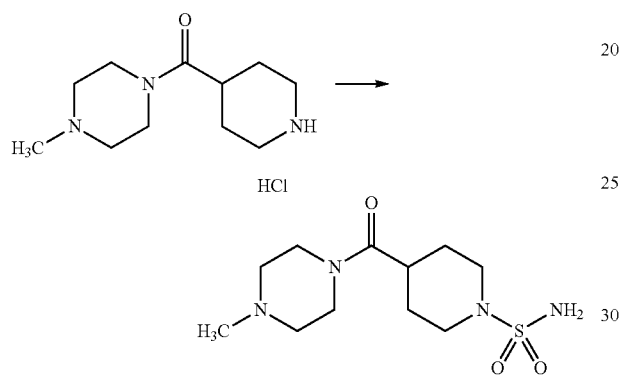

A solution of (4-methylpiperazin-1-yl)(piperidin-4-yl)methanone hydrochloride in dioxane was treated with 5 equivalents of triethylamine and 10 equivalents of sulfamide and heated at reflux for 3 days. The mixture was then cooled and filtered, and the solids were washed with methanol. The filtrate and washings were concentration in vacuo, and the residue was purified by column chromatography to give the titled compound.

Method X4B. Synthesis of Sulfamides

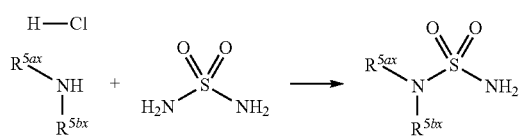

A solution of amine hydrochloride (from 1 to 2 equiv.) in dioxane is treated with triethylamine (from 1.1 to 2.2 equiv), and sulfamide (from 1 to 2 equiv) and refluxed until full conversion is observed. The mixture is then cooled to RT, and the residue is purified by flash column chromatography to give the desired sulfamide derivative.

Illustrative Synthesis of Compound S14

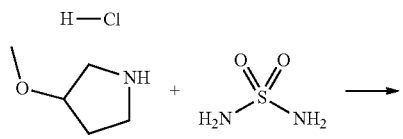

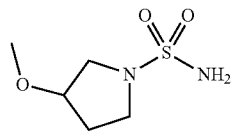

A solution of 3-methoxypyrrolidine hydrochloride ([136725-50-3], 136 mg, 0.98 mmol) in dioxane (2 mL) was treated with triethylamine (0.2 mL, 1.4 mmol) and sulfamide (7803-58-9, 130 mg, 1.3 mmol), and the mixture was refluxed for 16 hours. The mixture was then cooled to RT, and the residue was purified by column chromatography eluted with DCM/MeOH (9/1) to give the titled compound.

Method X5. Synthesis of Sulfamides

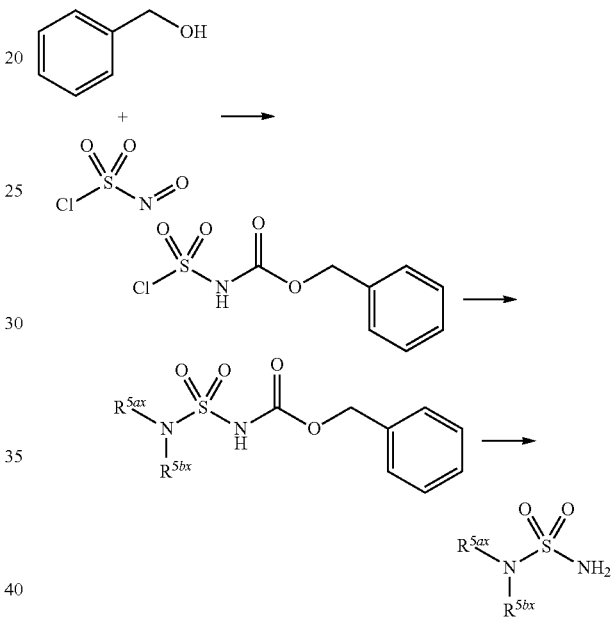

Step 1: Benzyl (chlorosulfonyl)carbamate

A solution of chlorosulfonylisocyanate ([1189-71-5], 1 eq) in anhydrous DCM (2.5 vol.) is cooled down in an ice batch under argon atmosphere. Benzyl alcohol ([100-51-6], 1 eq) is added dropwise over a 15 minutes period. The reaction mixture is stirred for 5 minutes and allowed to warm up to RT. The reaction mixture is worked up when no more starting material remained, by adding n-pentane. The precipitate is filtered, washed with n-pentane, and dried at 40° C. under reduced pressure to give the titled compound.

Step 2: N-Benzyloxycarbonyl Protected Sulfamide

A solution of amine (1 eq) and N,N-diisopropylethylamine (1.2 eq) in anhydrous DCM (10 vol.) is cooled down in an ice bath under an argon atmosphere. The compound from Step 1 (1.2 eq) is added, and after 5 minutes, the solution is allowed to warm up to RT. The reaction mixture is worked up when no more starting material remained, by adding water. The organic phase is diluted, separated, and washed successively with an aqueous 1 M HCl solution and a saturated aqueous solution of NaCl. The organic phase is dried over magnesium sulfate, filtered and concentrated in vacuo. The crude sample is either purified by flash column chromatography or suspended in a mixture of n-heptane/ethyl acetate (9/1), refluxed for 15 minutes, and then left cooling down to RT. The precipitate is collected by filtration, washed with a mixture of n-heptane/ethyl acetate (9/1), and dried at 40° C. under reduced pressure to give the desired N-benzyloxycarbonyl protected sulfamide.

Step 3: N-Deprotected Sulfamide

A solution of N-benzyloxycarbonyl protected sulfamide (1 eq) in THF or MeOH (20 vol.) is degassed with nitrogen. 20% Pd(OH)$_2$ w/w is added, and the reaction mixture is purged with H2. The mixture is stirred at room temperature under a hydrogen atmosphere (balloon) until no more starting material is observed. Additional 20% Pd(OH)$_2$ is added if necessary. The reaction mixture is filtered over a diatomaceous earth pad that is washed with THF or MeOH. The filtrate is concentrated in vacuo. The residue is purified by preparative HPLC or by flash column chromatography or used as such in the next step.

Illustrative Synthesis of Intermediate S15: 4-(methoxymethyl)piperidine-1-sulfonamide

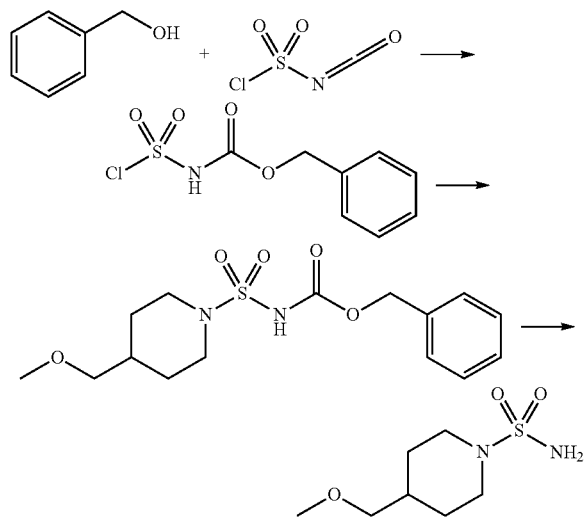

Step 1: Benzyl (chlorosulfonyl)carbamate

A solution of chlorosulfonylisocyanate ([1189-71-5], 8.1 g, 57.4 mmol) in anhydrous DCM (20 mL) was cooled down in an ice bath under an argon atmosphere. Benzyl alcohol ([100-51-6], 5.9 mL, 57.4 mmol) was added dropwise over a 15 minutes period. The reaction mixture was stirred for 5 minutes and allowed to warm up to RT. After 10 minutes, n-pentane (20 mL) was added, and the resulting mixture was stirred at RT for 30 minutes. The precipitate was collected by filtration, washed with n-pentane, and dried at 40° C. under reduced pressure to give the titled compound.

Step 2. Benzyl [4-(methoxymethyl)piperidine-1-sulfonyl]carbamate

A solution of 4-(methoxymethyl)piperidine hydrochloride ([399580-55-3], 1.0 g, 6.0 mmol) and N,N-diisopropylethylamine (2.3 mL, 13.3 mmol) in anhydrous DCM (10 mL) was cooled down in an ice bath under an argon atmosphere. Benzyl (chlorosulfonyl)carbamate from Step 1 (1.8 g, 7.2 mmol) was added and after 5 minutes, and the solution was allowed to warm up to RT. After 3 hours, water (10 mL) and DCM (10 mL) were added, and stirring was continued for 15 minutes. The organic phase was separated, washed successively with an aqueous 1 M HCl solution (2×10 mL), and a saturated aqueous solution of NaCl (10 mL). The organic phase was dried over magnesium sulfate, filtered and concentrated in vacuo. The residue was purified by flash column chromatography eluting with a gradient of DCM/MeOH to give the titled compound.

Step 3: 4-(methoxymethyl)piperidine-1-sulfonamide

A solution of compound from Step 2 (570 mg, 1.8 mmol) in THF (11 mL) was degassed with nitrogen. 20% Pd(OH)$_2$ (w/w, 114 mg) was added, and the reaction mixture was purged with H2. The mixture was stirred for 20 hours at RT under a hydrogen atmosphere (balloon). The reaction mixture was filtered over a diatomaceous earth pad that was washed with THF. The filtrate was concentrated in vacuo to give the titled compound.

TABLE XIV

List of sulfonamides

| Int. | Structure | Name | SM | method | MW | Mes |
|------|-----------|------|-----|--------|-----|-----|
| S1 | 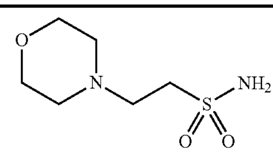 | 2-morpholinoethane-sulfonamide | 103654-84-8 | X1 | 194 | |
| S2 | 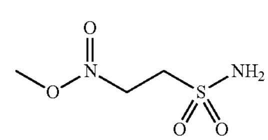 | methyl 3-sulfamoylpropanoate | 15441-07-3 | X1 Specific example | 167 | |
| S3 | 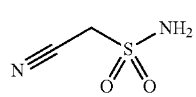 | cyanomethane-sulfonamide | 27869-04-1 | X1 | 120 | |

TABLE XIV-continued

| | | List of sulfonamides | | | | |
|---|---|---|---|---|---|---|
| Int. | Structure | Name | SM | method | MW | Mes |
| S4 | | tetrahydrofuran-3-sulfonamide | 1207346-29-9 | X1 | 151 | |
| S5 | | benzyl N-(2-sulfamoylethyl)carbamate | 52530-50-4 | X1 | 258 | 259 |
| S6 | | methyl 2-sulfamoylacetate | 52530-50-4 | X1 | 153 | |
| S7 | | benzyl 3-sulfamoylpyrrolidine-1-carboxylate | 1035173-74-0 | X1 | 284 | |
| S8 | | tetrahydro-2H-pyran-4-sulfonamide | 1058131-55-7 | X1 | 165 | |
| S9 | | benzyl 4-sulfamoylpiperidine-1-sulfonamide | 287953-54-2 | X1 | 298 | |
| S10 | | 3-morpholinopropane-1-sulfonamide | 1132-61-2 | X2 Specific example | 208 | 209 |
| S11 | | (2S)-2-(4-methylpiperazine-1-carbonyl)pyrrolidine-1-sulfonamide | 15761-39-4 | X3 Specific example | 276 | |

TABLE XIV-continued

List of sulfonamides

| Int. | Structure | Name | SM | method | MW | Mes |
|---|---|---|---|---|---|---|
| S12 | 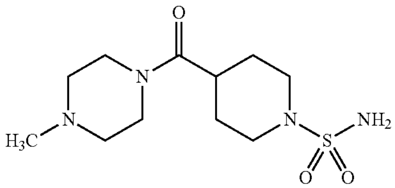 [SMILES: CN1CCN(C(=O)C2CCN(S(N)(=O)=O)CC2)CC1] | 4-(4-methylpiperazine-1-carbonyl)piperidine-1-sulfonamide | 1018826-44-2 | X4 Specific example | 290 | |
| S13 | 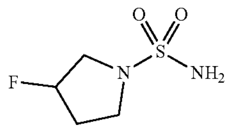 | 3-fluoropyrrolidine-1-sulfonamide | 7803-58-9, 169750-17-8 | X4B | 168 | |
| S14 | 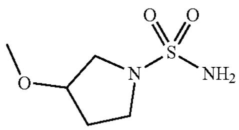 | 3-methoxypyrrolidine-1-sulfonamide | 7803-58-9, 169750-50-3 | X4B Specific example | 180 | |
| S15 | 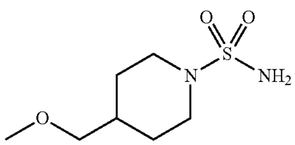 | 4-(methoxymethyl)piperidine-1-sulfonamide | 1189-71-5, 399580-55-3 | X5 Specific example | 208 | |
| S16 | 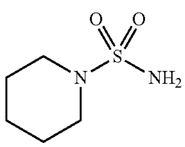 | piperidine-1-sulfonamide | 1189-71-5, 110-89-4 | X5 | 164 | |
| S17 | 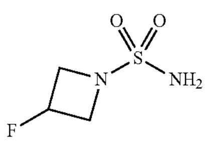 | 3-fluoroazetidine-1-sulfonamide | 1189-71-5, 617718-46-4 | X5 | 154 | |
| S18 | 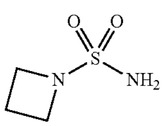 | azetidine-1-sulfonamide | 1189-71-5, 503-29-7 | X5 | 136 | |
| S19 | 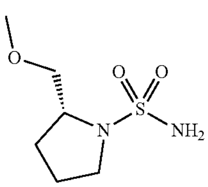 | (2R)-2-(methoxymethyl)pyrrolidine-1-sulfonamide | 1189-71-5, 84025-81-0 | X5 | 194 | |
| S20 | 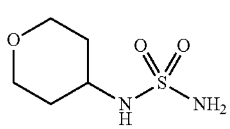 [SMILES: NS(=O)(=O)NC1CCOCC1] | N-oxan-4-ylsulfuric diamide | 1189-71-5, 38041-19-9 | X5 | 180 | |
| S21 | 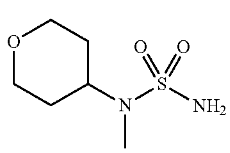 | N-methyl-N-oxan-4-ylsulfuric diamide | 1189-71-5, 220641-87-2 | X5 | 194 | |

TABLE XIV-continued

List of sulfonamides

| Int. | Structure | Name | SM | method | MW | Mes |
|---|---|---|---|---|---|---|
| S22 | 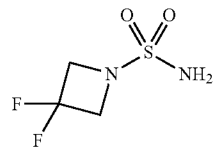 | 3,3-difluoroazetidine-1-sulfonamide | 1189-71-5, 288315-03-7 | X5 | 172 | |
| S23 | 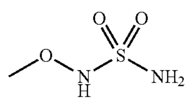 | N-methoxysulfuric diamide | 1189-71-5, 593-56-6 | X5 | 126 | |
| S24 | 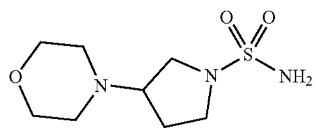 [SMILES: NS(=O)(=O)N1CCC(N2CCOCC2)C1] | 3-(morpholin-4-yl)pyrrolidine-1-sulfonamide | 1189-71-5, 53617-37-1 | X5 | 235 | |
| S25 | 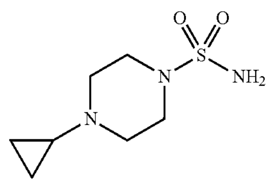 [SMILES: NS(=O)(=O)N1CCN(C2CC2)CC1] | 4-cyclopropylpiperazine-1-sulfonamide | 1189-71-5, 20327-23-5 | X5 | 205 | |
| S26 | 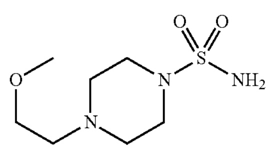 | 4-(2-methoxyethyl)piperazine-1-sulfonamide | 1189-71-5, 13484-40-7 | X5 | 223 | |
| S27 | 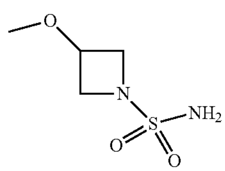 | 3-methoxyazetidine-1-sulfonamide | 1189-71-5, 148644-09-1 | X5 | 166 | |
| S28 | 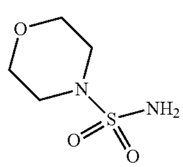 | morpholine-4-sulfonamide | 1189-71-5, 110-91-8 | X5 | 166 | |

Method Y1: Synthesis of Acylsulfonamide and Acylsulfamate from Carboxylic Acid

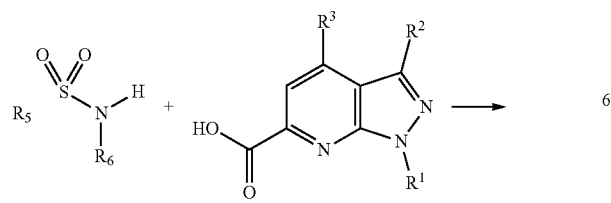

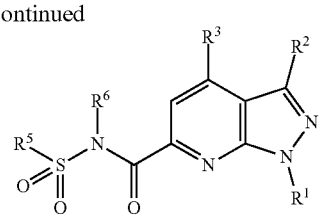

EDC.HCl (CAS 25952-538, 1.0 to 4.0 equiv) is added at RT to a stirring solution of carboxylic acid, sulfonamide or sulfamate (from 1.0 to 4.0 equiv) and 4-(dimethylamino)pyridine (CAS 1122-58-3, from 0.1 to 2.0 equiv) in dichloromethane or/and THF or/and acetone or/and acetonitrile.

The reaction mixture is stirred at RT until full conversion is observed. The reaction mixture can be worked up or the solvent can be evaporated and the residue is purified by precipitation, by flash column chromatography or by preparative HPLC to yield the titled acylsulfonamide or acylsulfamide. To work up the reaction mixture, the solvent can be evaporated, and the residue is then partitioned between dichloromethane and water. The organic phase is successively washed with a saturated aqueous solution of NaHCO$_3$, aqueous 0.5 N HCl and brine. The organic phase is separated, dried over sodium sulfate, filtered and concentrated in vacuo. Alternatively, the reaction mixture may be concentrated without an extractive workup. The residue is purified either by precipitation, by flash column chromatography or by preparative HPLC to yield the titled acylsulfonamide or acylsulfamate.

Alternatively, acylsulfonamides or acylsulfamates can be prepared in the following manner. A solution of the carboxylic acid (1 eq) in dichloromethane, dichloroethane or dimethylformamide can be treated with carbodiimidazole (1-2.5 eq) stirred at ambient temperature to 65° C. for from 0.5-3 hours. Then the sulfonamide or sulfamate (1-3 eq) and optional potassium bis(trimethylsilyl)amide, sodium hydride, or triethylamine followed by 1,8-diazabicycloundec-7-ene (1-3 eq) and optional 4-(dimethylamino)pyridine (1-2 eq) can be added, and the reaction mixture is stirred at 20-60° C. for 2-16 hours. The reaction mixture can then be concentrated and the residue purified.

Illustrative Synthesis of Compound 71: 4-[6-(4-cyanopiperidin-1-yl)pyridin-3-yl]-3-cyclobutyl-N-(methanesulfonyl)-1-phenyl-1H-pyrazolo[3,4-b]pyridine-6-carboxamide

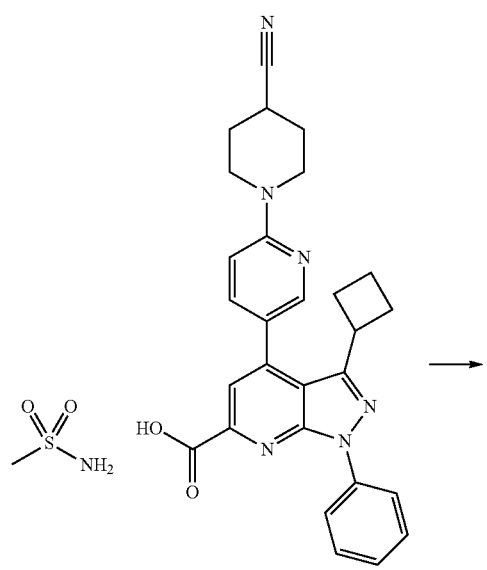

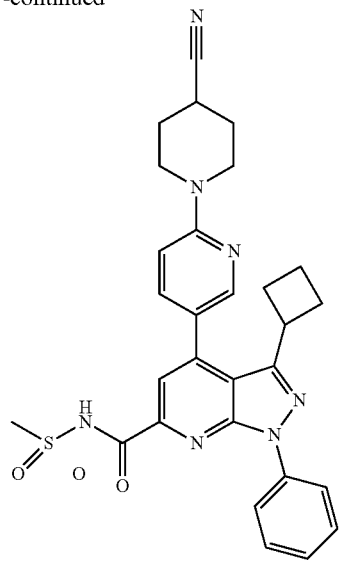

EDC.HCl (CAS 25952-538, 24.6 g, 128.3 mmol) was added at RT to a stirring solution of intermediate A056 (30.7 g, 64.1 mmol), methanesulfonamide (CAS 3144-09-0, 12.2 g, 128.3 mmol) and 4-(dimethylamino) pyridine (CAS 1122-58-3, 3.1 g, 25.7 mmol) in DCM (1 L). The reaction mixture was stirred at RT for 1.5 hours. The solution was diluted with DCM (700 mL), washed successively with a saturated aqueous solution of sodium hydrogencarbonate (500 mL), aqueous 0.5 N HCl (500 mL) and a saturated aqueous solution of NaCl (500 mL). The organic phase was dried over sodium sulfate, filtered and concentrated under reduced pressure. The crude sample was purified by flash column chromatography eluting with DCM/ethyl acetate. The compound was suspended in acetonitrile and refluxed until complete dissolution. The warm solution was poured in hot water (700 mL), and the mixture was refluxed for 2 hours. The reaction volume was reduced to one third under a flow of nitrogen at 80° C. The precipitate was collected by filtration and dried at 40° C. under reduced pressure.

Illustrative Synthesis of Compound 256: 3-cyclobutyl-N-(2-methoxyethanesulfonyl)-4-[4-(methoxymethyl)piperidin-1-yl]-1-phenyl-1H-pyrazolo[3,4-b]pyridine-6-carboxamide

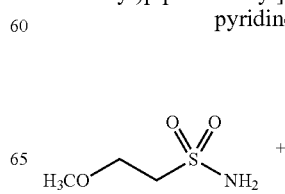

865

-continued

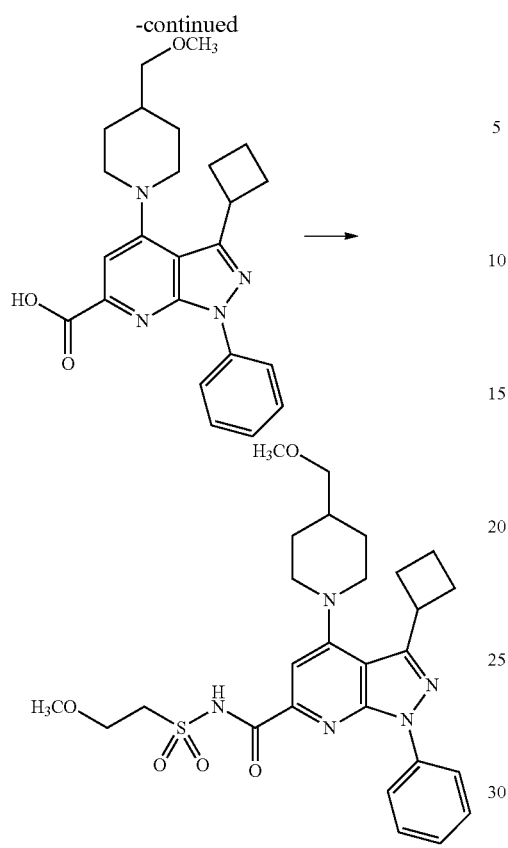

866

To a 4 mL vial charged with stir bar was added 3-cyclobutyl-4-[4-(methoxymethyl)-1-piperidyl]-1-phenyl-pyrazolo[3,4-b]pyridine-6-carboxylic acid (A136, 40 mg, 0.095 mmol) dissolved in 600 μL of dichloroethane followed by carbodiimidazole (34 mg, 0.21 mmol) in 600 μL of dichloroethane. The mixture was stirred at 42° C. for two hours. Then 2-methoxyethanesulfonamide (40 mg, 3 eq, 0.28 mmol) was then added followed by 1,8-diazabicycloundec-7-ene (43 uL, 3 eq, 0.28 mmol). The resultant mixture was heated at 60° C. for 16 hours. After completion of reaction, the reaction mixture was concentrated, dissolved in DMSO, and purified by reverse phase HPLC (C18, 0-100% CH₃CN/water (0.1% TFA)). A gradient of acetonitrile (A) and 0.1% trifluoroacetic acid in water (B) was used, at a flow rate of 50 mL/min (0-0.5 min 10% A, 0.5-6.0 min linear gradient 10-100% A, 6.0-7.0 min 100% A, 7.0-8.0 min linear gradient 100-10% A) to afford the title compound.

Illustrative Synthesis of Compound 328: 3-cyclobutyl-N-(methanesulfonyl)-4-[4-(morpholin-4-yl)piperidin-1-yl]-1-phenyl-1H-pyrazolo[3,4-b]pyridine-6-carboxamide

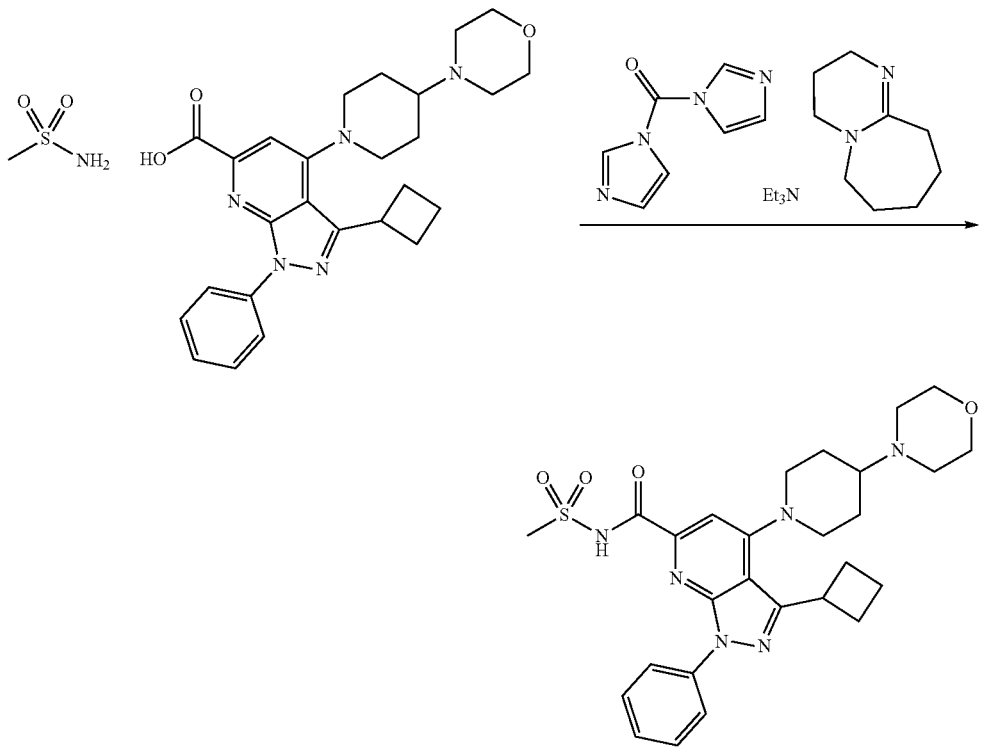

3-Cyclobutyl-4-(4-morpholino-1-piperidyl)-1-phenyl-pyrazolo[3,4-b]pyridine-6-carboxylic acid (A268, 139 mg, 0.30 mmol) and carbonyl diimidazole (73 mg, 0.45 mmol) were stirred in anhydrous DMF (2 mL) at room temperature for 50 minutes. Then methanesulfonamide (57 mg, 0.60 mmol) was added, followed by triethylamine (125 µL, 0.90 mmol), and the suspension was stirred overnight. DBU (45 µL, 0.30 mmol) was added dropwise to the suspension, which was stirred for more than forty minutes before additional DBU (22.5 L, 0.15 mmol) was added, and the solution was heated at 50° C. for more than 4 hours. The reaction mixture was then purified by preparative HPLC on a preparatory Waters® Atlantis® T3 column (30 mm×100 mm) with a 20 to 100% gradient of acetonitrile in 10 mM aqueous ammonium acetate at 40 mL/min to give the titled compound (70 mg).

Illustrative Synthesis of Compound 331: 3-cyclobutyl-N-(methanesulfonyl)-4-{4-[2-(morpholin-4-yl)ethyl]piperidin-1-yl}-1-phenyl-1H-pyrazolo[3,4-b]pyridine-6-carboxamide

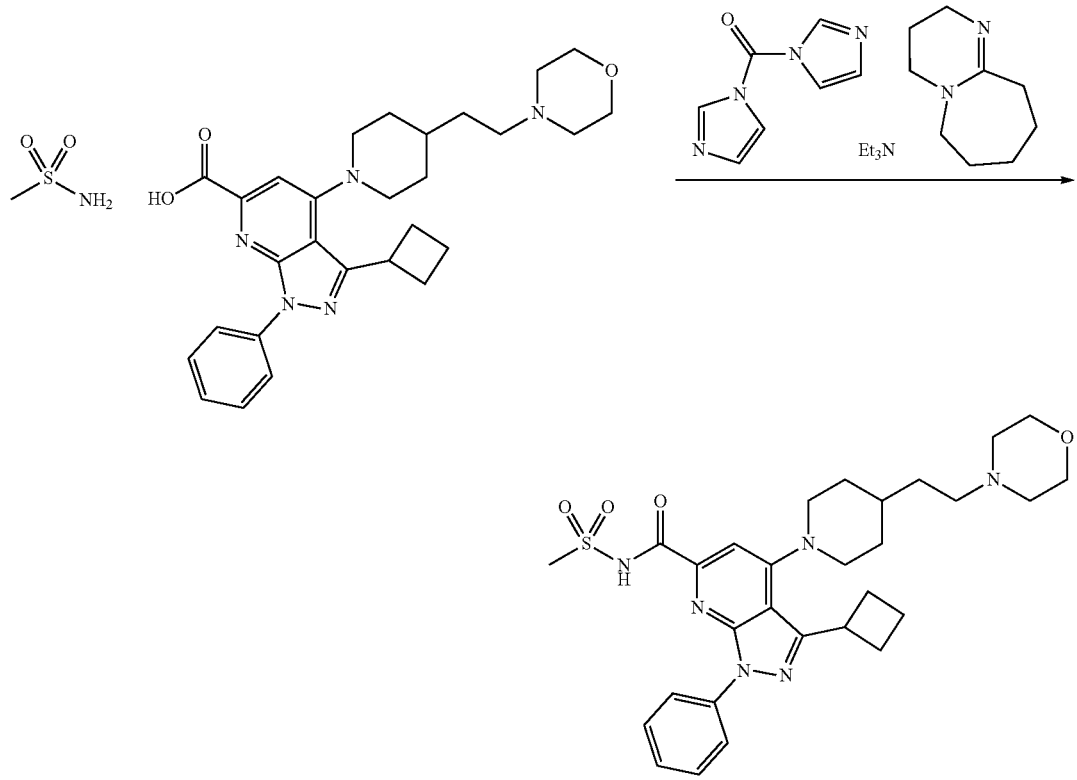

3-Cyclobutyl-4-[4-(2-morpholinoethyl)-1-piperidyl]-1-phenyl-pyrazolo[3,4-b]pyridine-6-carboxylic acid (A270, 118 mg, 0.24 mmol) and carbonyl diimidazole (78 mg, 0.48 mmol) were stirred in anhydrous DMF (1.5 mL) at room temperature for one hour. Then methanesulfonamide (46 mg, 0.48 mmol) and triethylamine (67 µL, 0.48 mmol) were added, followed by slow, dropwise addition of DBU (54 µL, 0.36 mmol). The reaction mixture was stirred for about another 30 minutes, diluted with water (8 mL), concentrated and purified by preparative HPLC on a preparatory Waters® Atlantis® T3 column (30 mm×100 mm) with a 20 to 100% gradient of acetonitrile in 10 mM aqueous ammonium acetate at 40 mL/min to give the titled compound (46 mg).

Illustrative Synthesis of Compound 332: 4-[(3aR,7aS)-1-acetyloctahydro-5H-pyrrolo[3,2-c]pyridin-5-yl]-3-cyclobutyl-N-[3-(morpholin-4-yl)propane-1-sulfonyl]-1-phenyl-1H-pyrazolo[3,4-b]pyridine-6-carboxamide

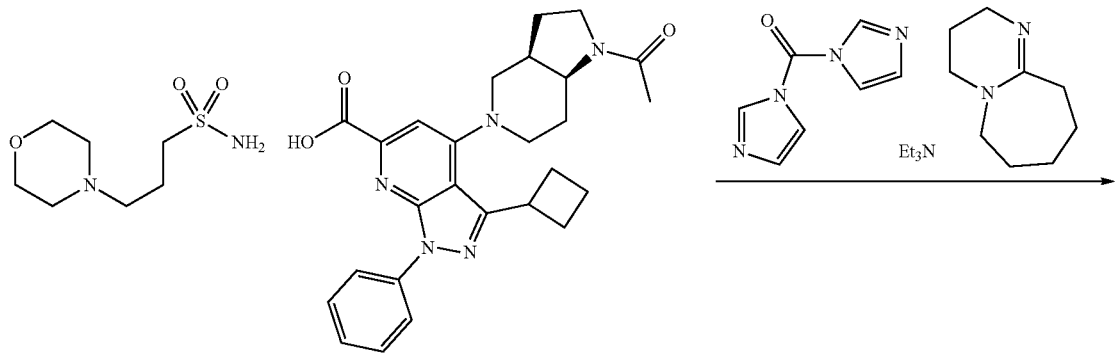

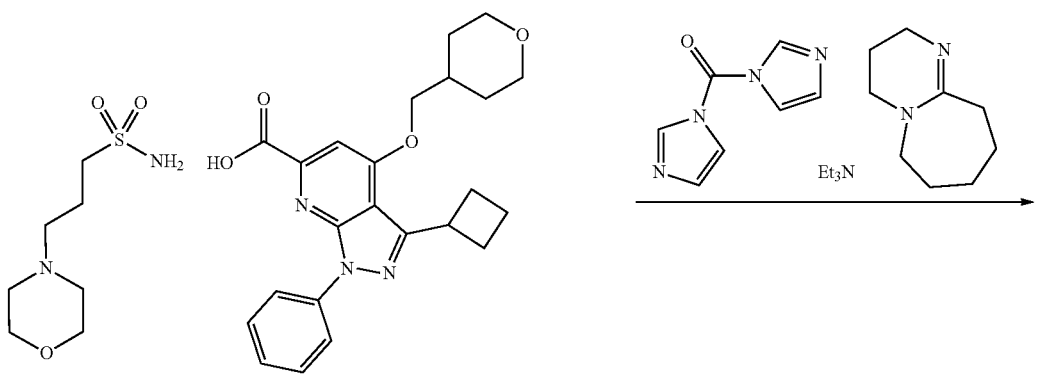

4-[(3aR,7aS)-1-Acetyl-3,3a,4,6,7,7a-hexahydro-2H-pyrrolo[3,2-c]pyridin-5-yl]-3-cyclobutyl-1-phenyl-pyrazolo[3,4-b]pyridine-6-carboxylic acid (A271, <0.5 mmol) and carbonyl diimidazole (243 mg, 1.5 mmol) were stirred in anhydrous DMF (4 mL) at room temperature for an hour. Then triethylamine (210 μL, 1.5 mmol) and a solution of 3-(morpholin-4-yl)propane-1-sulfonamide (S10, 313 mg, 1.5 mmol) in anhydrous acetonitrile (400 μL) were added, followed by slow dropwise addition of DBU (75 μL, 0.50 mmol). The reaction mixture was stirred for an hour, more DBU (45 μL, 0.30 mmol) was added dropwise, and the reaction mixture was stirred another hour before being diluted with water (20 mL), concentrated and purified by preparative HPLC on a preparatory Waters® Atlantis® T3 column (30 mm×100 mm) with a 5 to 100% gradient of acetonitrile in 10 mM aqueous ammonium acetate at 40 mL/min to give the titled compound (74 mg).

Illustrative Synthesis of Compound 347: 3-cyclobutyl-N-[3-(morpholin-4-yl)propane-1-sulfonyl]-4-[(oxan-4-yl)methoxy]-1-phenyl-1H-pyrazolo[3,4-b]pyridine-6-carboxamide

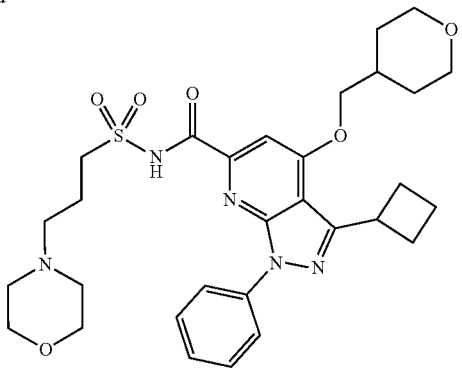

3-Cyclobutyl-1-phenyl-4-(tetrahydropyran-4-ylmethoxy)pyrazolo[3,4-b]pyridine-6-carboxylic acid (A148, 102 mg, 0.25 mmol) and carbonyl diimidazole (61 mg, 0.38 mmol) were stirred in anhydrous DMF (1.6 mL) at room temperature for one hour. Then a solution of 3-(morpholin-4-yl)propane-1-sulfonamide (S10, 104 mg, 0.50 mmol) in DMF (0.4 mL) and triethylamine (70 µL, 0.50 mmol) were added, followed by slow, dropwise addition of DBU (56 µL, 0.37 mmol). The reaction mixture was stirred for another thirty minutes, diluted with water (8 mL), concentrated and purified by preparative HPLC on a Waters® Atlantis® T3 column (30 mm×100 mm) with a 30 to 60% gradient of acetonitrile in 10 mM aqueous ammonium acetate at 50 mL/min to give the titled compound (61 mg).

Illustrative Synthesis of Compound 349: 3-cyclobutyl-4-[(3R)-3-(hydroxymethyl)piperidin-1-yl]-N-(methanesulfonyl)-1-phenyl-1H-pyrazolo[3,4-b]pyridine-6-carboxamide 3-Cyclobutyl-4-[(3R)-3-(hydroxymethyl)piperidin-1-yl]-1-phenyl-1H-pyrazolo[3,4-b]pyridine-6-carboxylic acid (A284, 57 mg, 0.14 mmol) and carbonyl diimidazole (46 mg, 0.28 mmol) were stirred in anhydrous DMF (1.0 mL) at room temperature for about one hour. Then methanesulfonamide (27 mg, 0.28 mmol) and triethylamine (39 µL, 0.28 mmol) were added, followed by slow, dropwise addition of DBU (31.5 µL, 0.21 mmol). The reaction mixture was stirred more than 30 minutes, diluted with water (8 mL), concentrated and purified by preparative HPLC on a Waters® Atlantis® T3 C18 column (30×150 mm) with a 30 to 60% gradient of acetonitrile in 10 mM aqueous ammonium acetate at 50 mL/min to give the titled compound (17 mg).

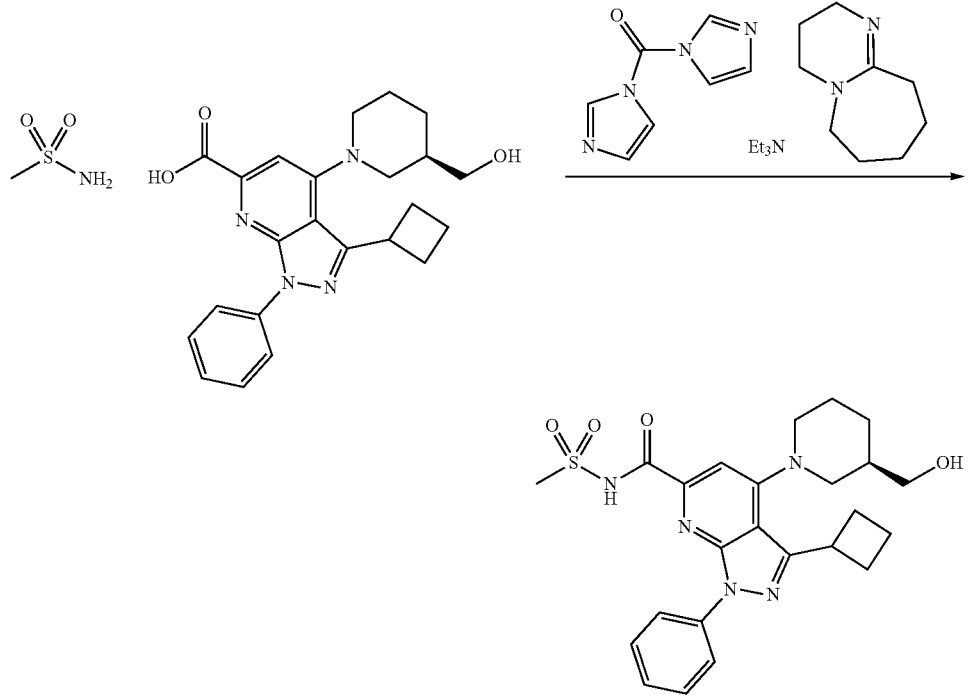

Illustrative Synthesis of Compound 350: 3-cyclobutyl-4-[(3R)-3-(hydroxymethyl)piperidin-1-yl]-N-[3-(morpholin-4-yl)propane-1-sulfonyl]-1-phenyl-1H-pyrazolo[3,4-b]pyridine-6-carboxamide

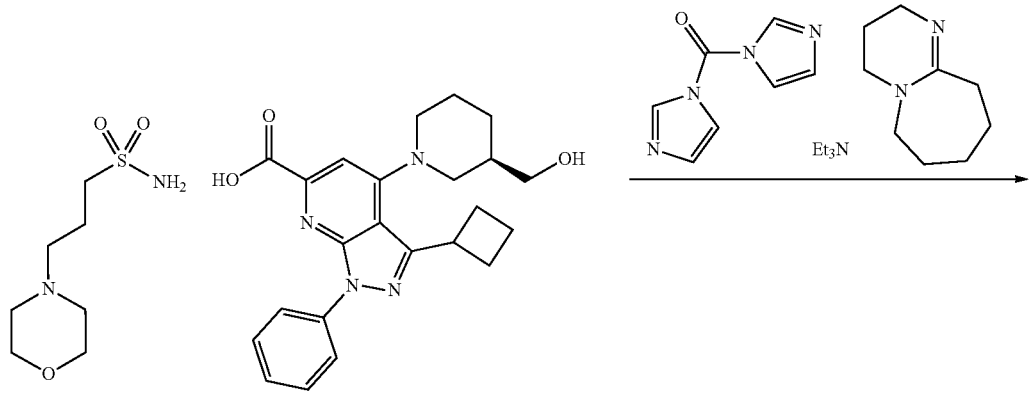

3-Cyclobutyl-4-[(3R)-3-(hydroxymethyl)piperidin-1-yl]-1-phenyl-1H-pyrazolo[3,4-b]pyridine-6-carboxylic acid (A284, 61 mg, 0.15 mmol) and carbonyl diimidazole (49 mg, 0.30 mmol) were stirred in anhydrous DMF (1.0 mL) at room temperature for about one hour. Then a solution of 3-(morpholin-4-yl)propane-1-sulfonamide (S10, 63 mg, 0.30 mmol) in anhydrous acetonitrile (200 µL) and triethylamine (42 µL, 0.30 mmol) were added, followed by slow, dropwise addition of DBU (34 µL, 0.23 mmol). The reaction mixture was stirred for more than 30 minutes, diluted with water (8 mL), concentrated and purified by preparative HPLC on a Waters® Atlantis® T3 C18 column (30×150 mm) with a 40 to 70% gradient of acetonitrile in 10 mM aqueous ammonium acetate at 50 mL/min to the titled compound (30 mg).

Illustrative Synthesis of Compound 365: 4-([1,4'-bipiperidin]-1'-yl)-3-cyclobutyl-N-(methanesulfonyl)-1-phenyl-1H-pyrazolo[3,4-b]pyridine-6-carboxamide

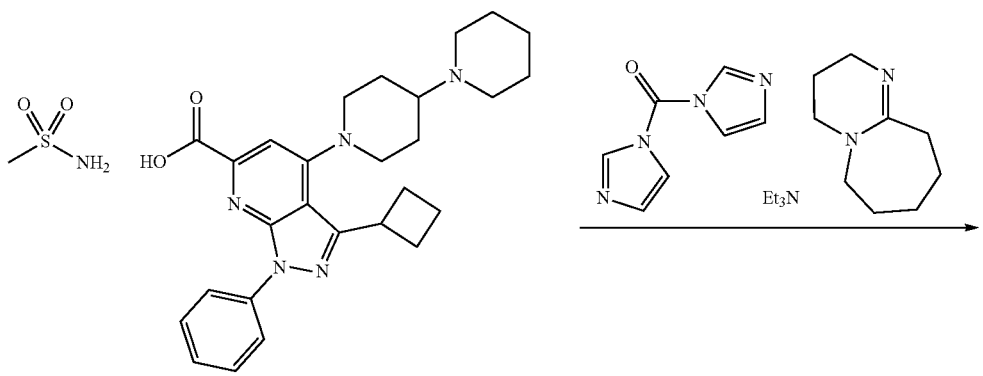

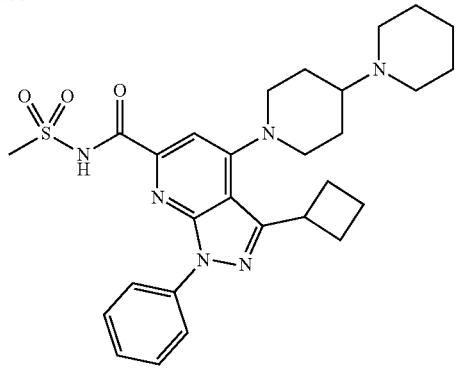

3-Cyclobutyl-1-phenyl-4-[4-(1-piperidyl)-1-piperidyl]pyrazolo[3,4-b]pyridine-6-carboxylic acid (A081, 51 mg, 0.11 mmol) and carbonyl diimidazole (28 mg, 0.17 mmol) were stirred in anhydrous DMF (600 μL) at room temperature for an hour. Then methanesulfonamide (21 mg, 0.22 mmol) and triethylamine (31 μL, 0.22 mmol) were added, followed by DBU (25.5 L, 0.17 mmol). The reaction mixture was stirred 30 minutes at room temperature, diluted with water (5 mL), concentrated and purified by preparative HPLC on a Waters® Sunfire™ C8 column (30×150 mm) with a 30 to 60% gradient of acetonitrile in 10 mM aqueous ammonium acetate at 50 mL/min to give the titled compound (30 mg).

Illustrative Synthesis of Compound 411: 1-(4-fluorophenyl)-N-(methanesulfonyl)-4-[4-(morpholin-4-yl)piperidin-1-yl]-3-(propan-2-yl)-1H-pyrazolo[3,4-b]pyridine-6-carboxamide

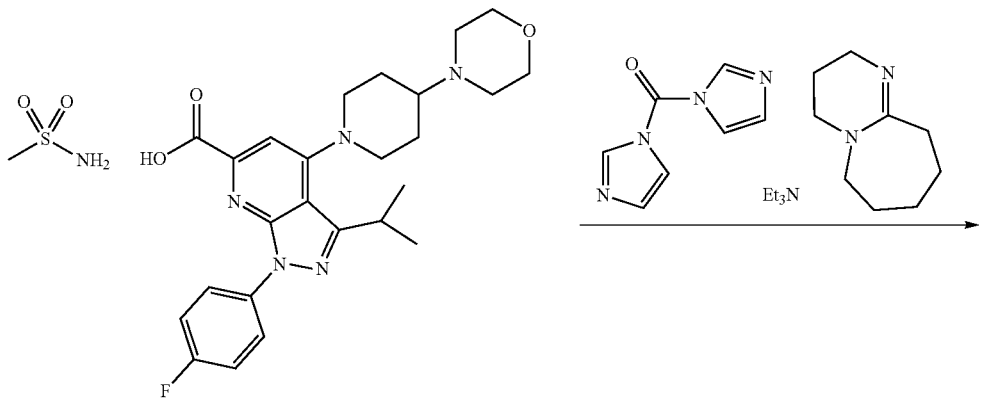

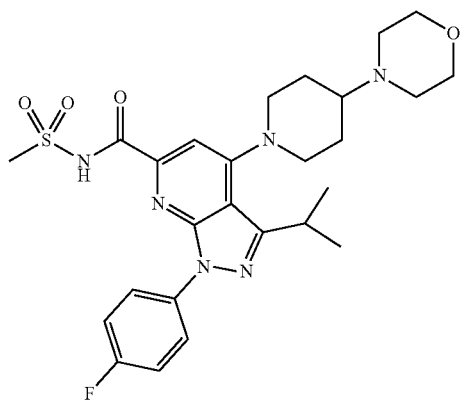

1-(4-Fluorophenyl)-4-[4-(morpholin-4-yl)piperidin-1-yl]-3-(propan-2-yl)-1H-pyrazolo[3,4-b]pyridine-6-carboxylic acid (A408, 70 mg, 0.15 mmol) and carbonyl diimidazole (37 mg, 0.23 mmol) were stirred in anhydrous DMF (800 µL) at room temperature for an hour. Then methanesulfonamide (29 mg, 0.30 mmol) and triethylamine (42 µL, 0.30 mmol) were added, followed by slow addition of DBU (34 µL, 0.23 mmol). The reaction mixture was stirred 30 minutes at room temperature, diluted with methanol and purified by preparative HPLC on a Waters® Sunfire™ C8 column (30×150 mm) with a 30 to 60% gradient of acetonitrile in 10 mM aqueous ammonium acetate to give the titled compound.

Illustrative Synthesis of Compound 413: N-(ethanesulfonyl)-1-(4-fluorophenyl)-4-[4-(morpholin-4-yl)piperidin-1-yl]-3-(propan-2-yl)-1H-pyrazolo[3,4-b]pyridine-6-carboxamide

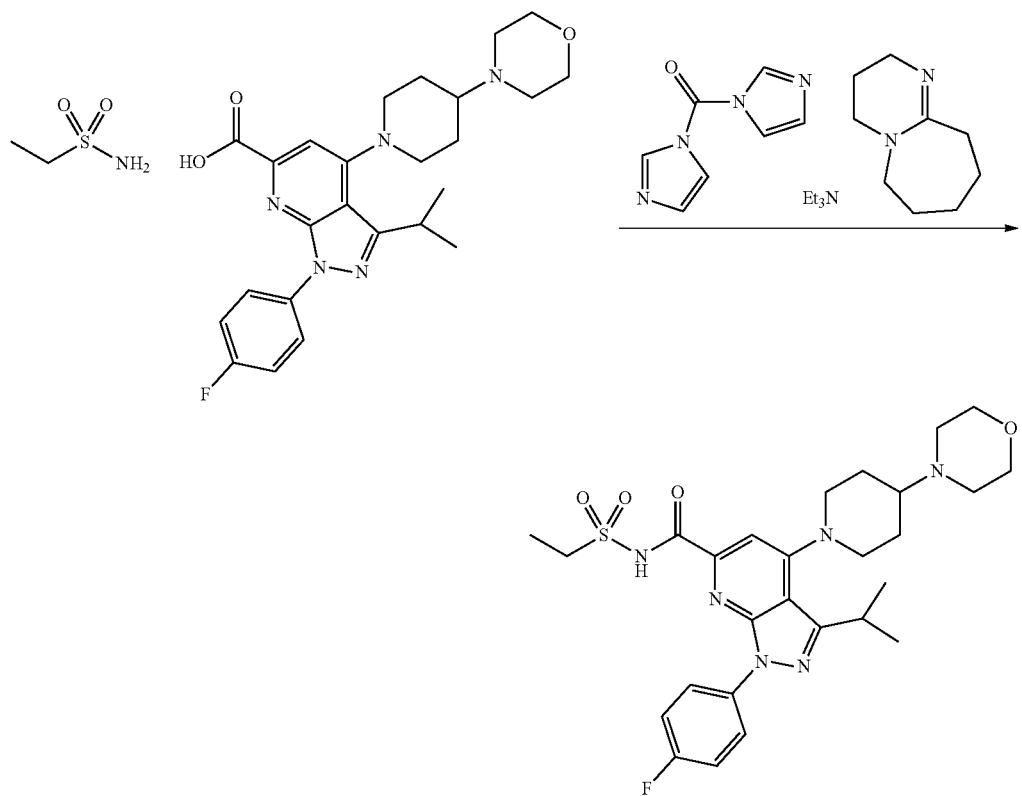

1-(4-Fluorophenyl)-4-[4-(morpholin-4-yl)piperidin-1-yl]-3-(propan-2-yl)-1H-pyrazolo[3,4-b]pyridine-6-carboxylic acid (A408, 70 mg, 0.15 mmol) and carbonyl diimidazole (37 mg, 0.23 mmol) were stirred in anhydrous DMF (800 µL) at room temperature for an hour. Then ethanesulfonamide (33 mg, 0.30 mmol) and triethylamine (42 µL, 0.30 mmol) were added, followed by slow addition of DBU (34 µL, 0.23 mmol). The reaction mixture was stirred 30 minutes at room temperature, diluted with methanol and purified by preparative HPLC on a Waters® Sunfire™ C8 column (30×150 mm) with a 30 to 60% gradient of acetonitrile in 10 mM aqueous ammonium acetate to give the titled compound.

Illustrative Synthesis of Compound 414: N-(cyclopropanesulfonyl)-1-(4-fluorophenyl)-4-[4-(morpholin-4-yl)piperidin-1-yl]-3-(propan-2-yl)-1H-pyrazolo[3,4-b]pyridine-6-carboxamide

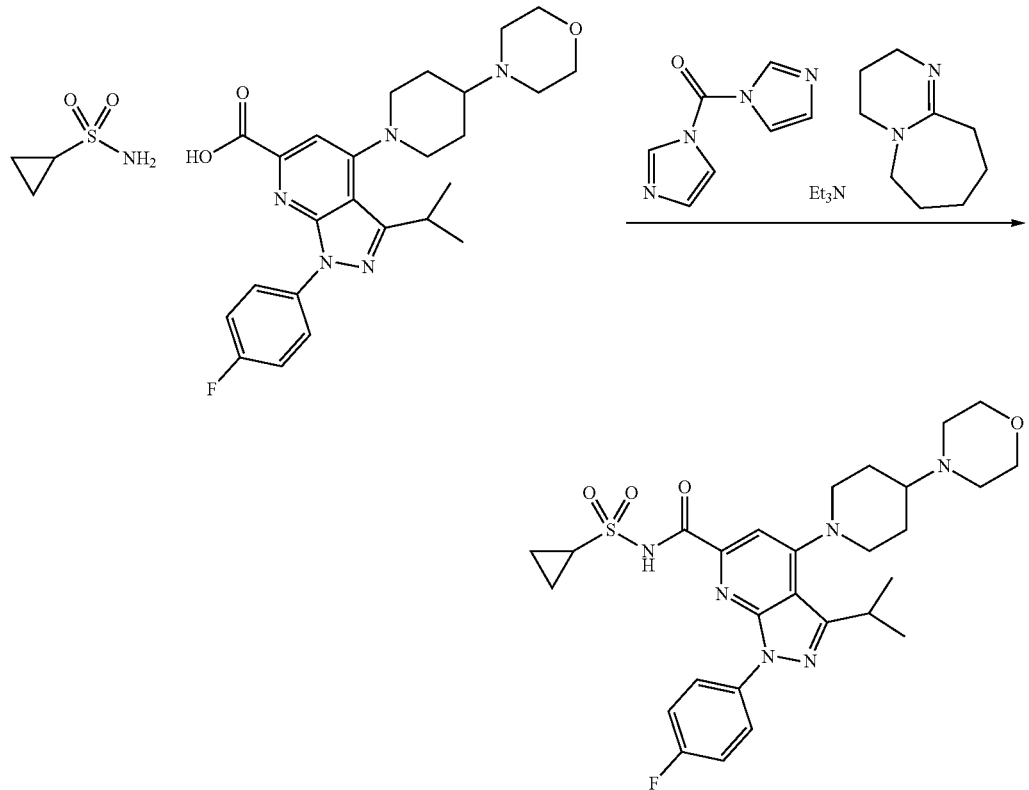

1-(4-Fluorophenyl)-4-[4-(morpholin-4-yl)piperidin-1-yl]-3-(propan-2-yl)-1H-pyrazolo[3,4-b]pyridine-6-carboxylic acid (A408, 70 mg, 0.15 mmol) and carbonyl diimidazole (37 mg, 0.23 mmol) were stirred in anhydrous DMF (800 μL) at room temperature for an hour. Then cyclopropanesulfonamide (36 mg, 0.30 mmol) and triethylamine (42 μL, 0.30 mmol) were added, followed by slow addition of DBU (34 μL, 0.23 mmol). The reaction mixture was stirred 30 minutes at room temperature, diluted with methanol and purified by preparative HPLC on a Waters® Sunfire™ C8 column (30×150 mm) with a 30 to 60% gradient of acetonitrile in 10 mM aqueous ammonium acetate to give the titled compound.

Illustrative Synthesis of Compound 427: 4-([1,4'-bipiperidin]-1'-yl)-3-cyclobutyl-N-(ethanesulfonyl)-1-phenyl-1H-pyrazolo[3,4-b]pyridine-6-carboxamide

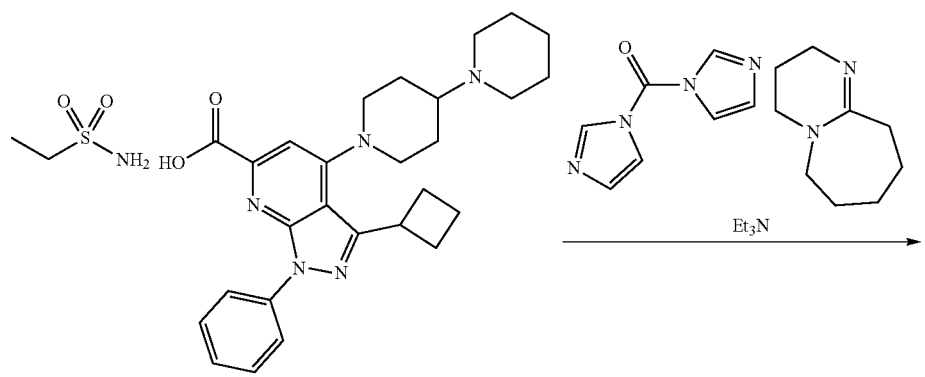

-continued

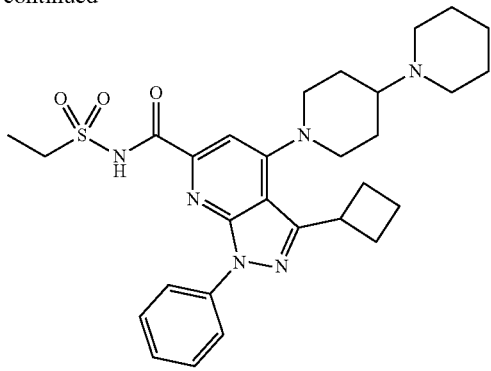

3-Cyclobutyl-1-phenyl-4-[4-(1-piperidyl)-1-piperidyl]pyrazolo[3,4-b]pyridine-6-carboxylic acid (A081, 92 mg, 0.20 mmol) and carbonyl diimidazole (49 mg, 0.30 mmol) were stirred in anhydrous DMF (1.0 mL) at room temperature for 90 minutes. Then ethanesulfonamide (44 mg, 0.40 mmol) and triethylamine (56 µL, 0.40 mmol) were added, followed nearly 15 minutes later by slow addition DBU (45 µL, 0.30 mmol). The reaction mixture was stirred 30 minutes at room temperature, diluted with methanol and purified by preparative HPLC on a Waters® Sunfire™ C8 column (30×150 mm) with a 40 to 70% gradient of acetonitrile in 10 mM aqueous ammonium acetate to give the titled compound.

Illustrative Synthesis of Compound 428: 4-([1,4'-bipiperidin]-1'-yl)-3-cyclobutyl-N-(cyclopropanesulfonyl)-1-phenyl-1H-pyrazolo[3,4-b]pyridine-6-carboxamide 3-Cyclobutyl-1-phenyl-4-[4-(1-piperidyl)-1-piperidyl]pyrazolo[3,4-b]pyridine-6-carboxylic acid (A081, 92 mg, 0.20 mmol) and carbonyl diimidazole (49 mg, 0.30 mmol) were stirred in anhydrous DMF (1.0 mL) at room temperature for 90 minutes. Then cyclopropanesulfonamide (49 mg, 0.40 mmol) and triethylamine (56 µL, 0.40 mmol) were added, followed nearly 15 minutes later by slow addition DBU (45 µL, 0.30 mmol). The reaction mixture was stirred 30 minutes at room temperature, diluted with methanol and purified by preparative HPLC on a Waters® Sunfire™ C8 column (30×150 mm) with a 30 to 60% gradient of acetonitrile in 10 mM aqueous ammonium acetate to give the titled compound.

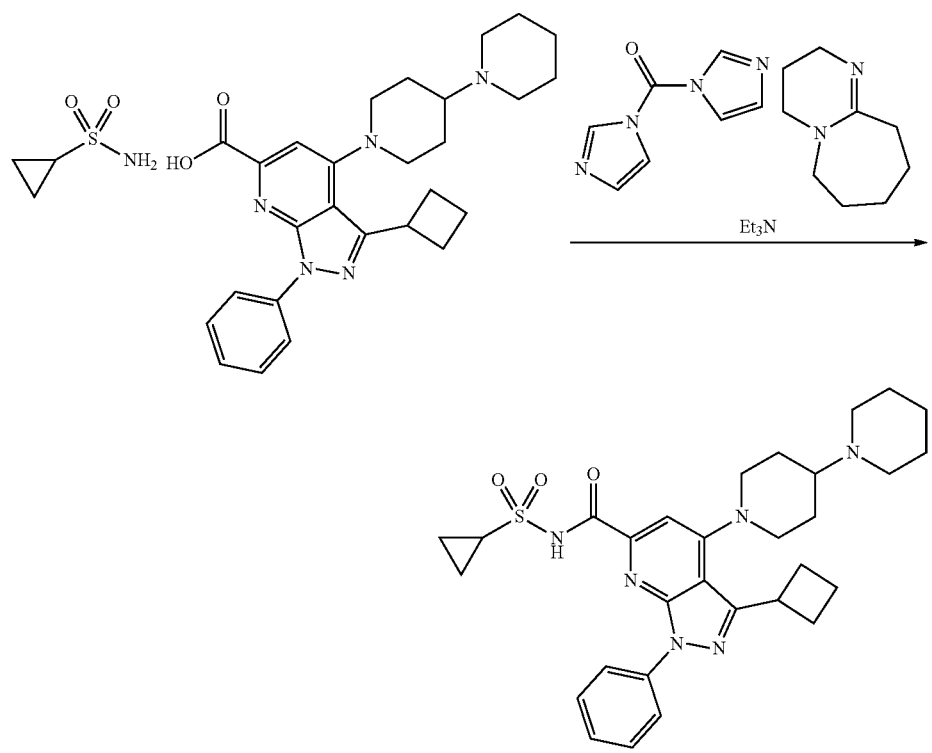

Illustrative Synthesis of Compound 454: 4-([1,4'-bipiperidin]-1'-yl)-3-cyclobutyl-N-[3-(morpholin-4-yl)propane-1-sulfonyl]-1-phenyl-1H-pyrazolo[3,4-b]pyridine-6-carboxamide

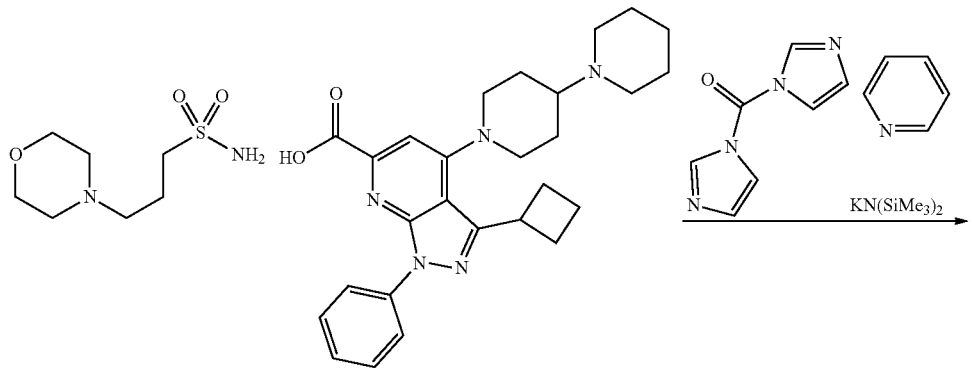

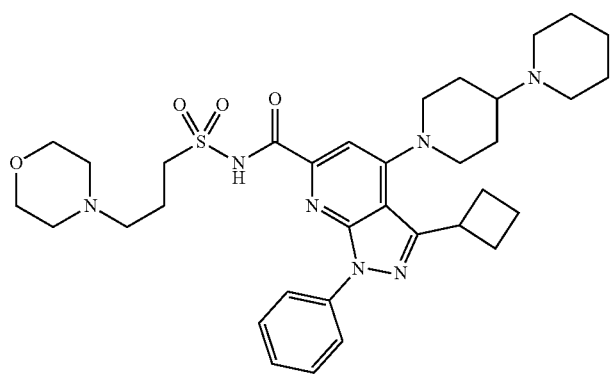

To a suspension of the 3-cyclobutyl-1-phenyl-4-[4-(1-piperidyl)-1-piperidyl]pyrazolo[3,4-b]pyridine-6-carboxylic acid (46 mg, 0.10 mmol, A081) and carbonyl diimidazole (29 mg, 0.18 mmol) in anhydrous DMF (400 µL) was added pyridine (81 µL, 1.0 mmol). The mixture was stirred nearly ten minutes at room temperature and then another 15 minutes at 50° C. before being brought to room temperature. In a separate vial, 3-morpholinopropane-1-sulfonamide (42 mg, 0.20 mmol) under nitrogen was dissolved into anhydrous DMF (400 µL) and treated with 1 M potassium bis(trimethylsilyl)amide in THF (190 µL, 0.19 mmol), stirred ten minutes to give a suspension and then treated dropwise with the contents of the first vial, which were transferred with a DMF (200 µL) rinse. The mixture was stirred at room temperature for three days, diluted with methanol and purified by preparative HPLC on a Waters® Sunfire™ C8 column (30×150 mm) with a 35 to 65% gradient of acetonitrile in 10 mM aqueous ammonium acetate to give the titled compound.

Illustrative Synthesis of Compound 658: 3-cyclobutyl-N-(ethanesulfonyl)-N-methyl-4-[4-(morpholin-4-yl)piperidin-1-yl]-1-phenyl-1H-pyrazolo[3,4-b]pyridine-6-carboxamide

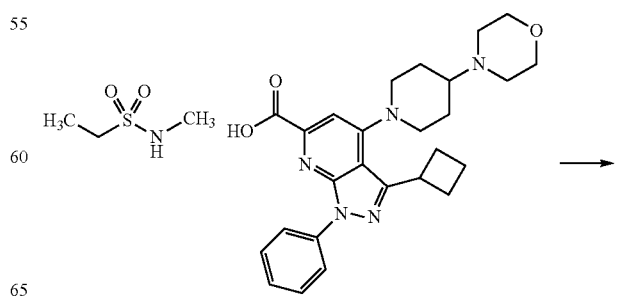

885
-continued

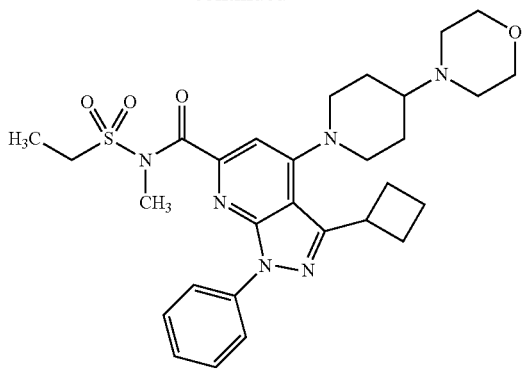

3-Cyclobutyl-4-[4-(morpholin-4-yl)piperidin-1-yl]-1-phenyl-1H-pyrazolo[3,4-b]pyridine-6-carboxylic acid (45 mg, 0.10 mmol, A409) dissolved in dichloromethane (500 μL) was treated with 1-ethyl-3-(3-dimethylaminopropyl) carbodiimide (18 mg, 0.12 mmol) in dichloromethane (500 μL), dimethyl amino pyridine (24 mg, 0.2 mmol) and N-methylethanesulfonamide (13 mg, 0.11 mmol). The mixture was then stirred at room temperature overnight. The mixture was concentrated, and the residue was dissolved DMSO and purified by reverse phase HPLC (C18, 0-100% $CH_3CN$/water (0.1% TFA)). A gradient of acetonitrile (A) and 0.1% trifluoroacetic acid in water (B) was used, at a flow rate of 50 mL/minute (0-0.5 minute 10% A, 0.5-6.0 minutes linear gradient 10-100% A, 6.0-7.0 minutes 100% A, 7.0-8.0 minutes linear gradient 100-10% A) gave the titled compound.

Method Y2: Synthesis of Acylsulfonamide

Synthesis of Compounds 289 & 298: 3-({3-cyclobutyl-4-[4-(methoxymethyl)piperidin-1-yl]-1-phenyl-1H-pyrazolo[3,4-b]pyridine-6-carbonyl}sulfamoyl)propanoic Acid and 3-cyclobutyl-N-[3-(dimethylamino)-3-oxopropane-1-sulfonyl]-4-[4-(methoxymethyl)piperidin-1-yl]-1-phenyl-1H-pyrazolo[3,4-b]pyridine-6-carboxamide

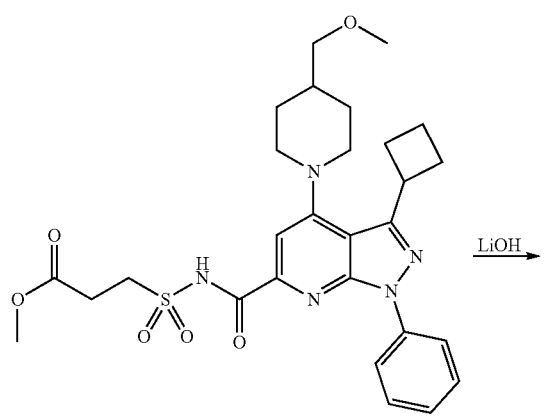

886
-continued

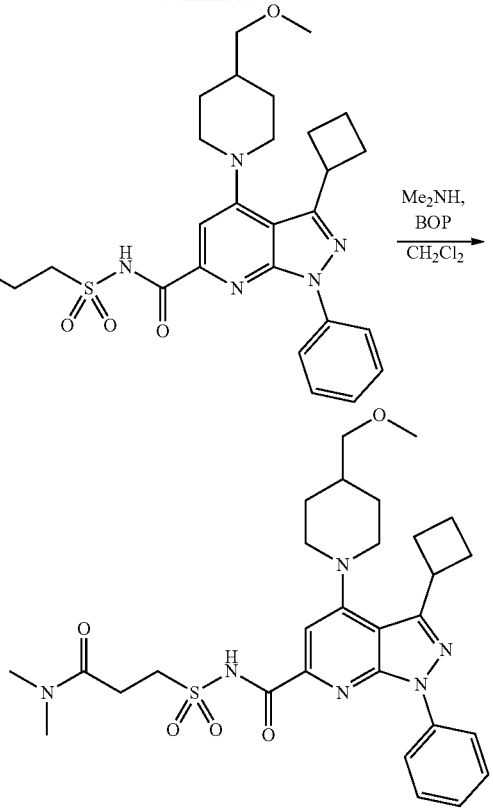

Step 1: 3-({3-cyclobutyl-4-[4-(methoxymethyl)piperidin-1-yl]-1-phenyl-1H-pyrazolo[3,4-b]pyridine-6-carbonyl}sulfamoyl)propanoic Acid A solution of LiOH (0.0189 g, 0.45 mmol, 2.1 equiv) in $H_2O$ (1 mL) was added to a solution of compound 288 (0.123 g, 0.216 mmol) in THF. The reaction mixture was stirred for 30 min and then concentrated. The residue was partitioned between dichloromethane (100 mL) and an aqueous $H_3PO_4$/$NaH_2PO_4$ buffer (1.0 M, pH 2, 100 mL). The organic phase was washed with brine, dried over $MgSO_4$, filtered and concentrated to give compound 289 (carboxylic acid).

Step 2: 3-cyclobutyl-N-[3-(dimethylamino)-3-oxopropane-1-sulfonyl]-4-[4-(methoxymethyl)piperidin-1-yl]-1-phenyl-1H-pyrazolo[3,4-b]pyridine-6-carboxamide BOP (CAS: 56602-33-6, 0.037 g, 0.084 mmol, 1.2 equiv) was added to a solution of compound 289 (0.0378 g, 0.0680 mmol) in dichloromethane (4 mL). After 10 minutes, a THF solution of dimethylamine (2.0 M, 0.25 mL, 0.50 mmol, 7.3 equiv) was added. The reaction mixture was stirred at room temperature for 16 hours. The reaction mixture was charged onto a column of silica gel and eluted with $CH_2Cl_2$/iPrOH (20:1) to yield the titled compound. $^1$H NMR (400 MHz, $CDCl_3$/$CD_3OD$) δ ppm 7.99 (d, J=8.25, 2H), 7.51 (t, J=8.0 Hz, 2H), 7.44 (s, 1H), 7.32 (t, J=7.4, 1H), 3.98 (pent, J=8.4 Hz, 1H), 3.67-3.59 (m, 2H), 3.50 (t, J=6.5 Hz, 2H), 3.40-3.33 (m, 2H), 3.37 (s, 3H), 3.14 (t, J=6.5 Hz, 2H), 2.94-2.84 (m, 2H), 2.6-2.49 (m, 2H), 2.44-2.34 (m, 2H), 2.38 (s, 6H), 2.12-1.79 (m, 5H), 1.60-1.48 (m, 2H)

Method Y3: Synthesis of Acylsulfonamide

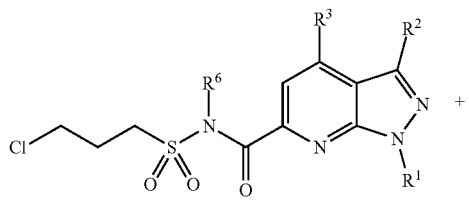

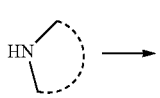

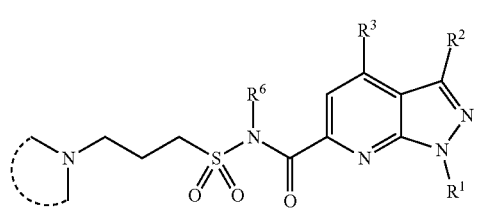

Potassium iodide (0.3 equiv) is added to a solution of alkylchloride in acetonitrile. The amine (15 to 20 equiv) is added, and the vial is sealed. The reaction mixture is stirred at RT or 50° C. for 16 hours. After concentration, the residue is partitioned between water and dichloromethane. The organic phase is washed with brine, dried over MgSO$_4$, filtered and concentrated in vacuo. If necessary, the residue was purified either by precipitation in pentane or by silica gel chromatography.

Illustrative Synthesis of Compound 290: N-[3-(dimethylamino)propane-1-sulfonyl]-1-(4-fluorophenyl)-4-[4-(methoxymethyl)piperidin-1-yl]-3-(propan-2-yl)-1H-pyrazolo[3,4-b]pyridine-6-carboxamide

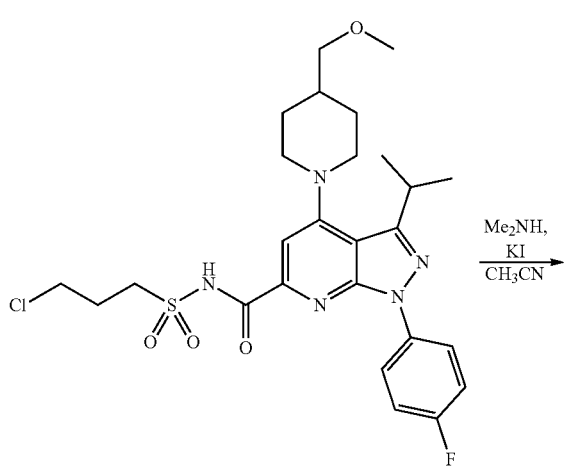

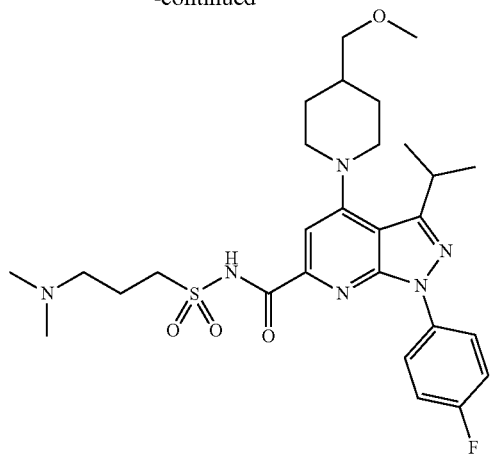

KI (2 mg, 0.012 mmol, 0.3 equiv) was added to a solution of N-(3-chloropropylsulfonyl)-1-(4-fluorophenyl)-3-isopropyl-4-[4-(methoxymethyl)-1-piperidyl]pyrazolo[3,4-b]pyridine-6-carboxamide (AC01, 20 mg, 0.035 mmol) in acetonitrile (3 mL). The vial was sealed, and the reaction mixture was saturated with gaseous dimethylamine. The reaction mixture was stirred at RT for 16 hours. After concentration, the residue was partitioned between water and dichloromethane. The organic phase was washed with brine, dried over MgSO$_4$, filtered and concentrated to give the titled compound.

Method Y4: Synthesis Via Carboxamide

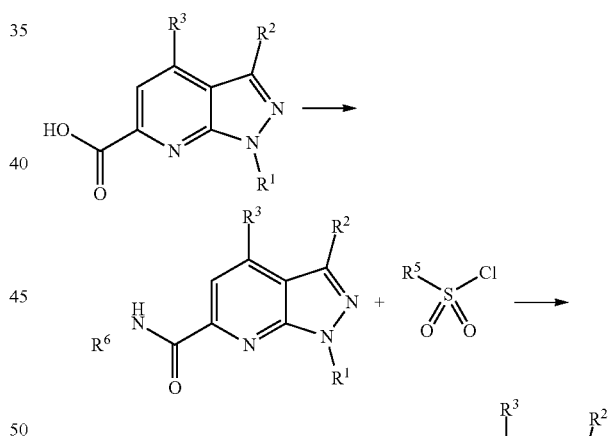

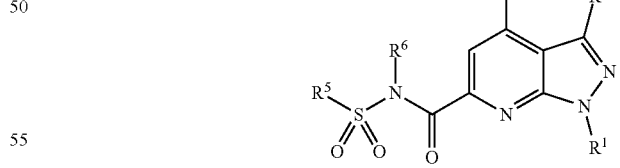

Step 1

Oxalyl chloride (0.40 mL, 4.7 mmol, 9.6 equiv) and a drop of dimethylformamide are added to a solution of carboxylic acid (0.49 mmol) in dichloromethane (2 mL). After effervescence has ceased, the vial is sealed, and the reaction mixture is stirred at room temperature for 1 hour. The reaction mixture is concentrated in vacuo, and to the residue is added a dioxane solution of ammonia (0.5 M, 10.0 mL, 5.0 mmol, 10 equiv). After 1 hour, volatiles are then removed via rotary evaporation. The residue is purified by silica gel chromatography (dichloromethane/ethyl acetate, 4:1) to give the intermediate carboxamide.

Step 2

NaH (60% in mineral oil, 21 equiv to 50 equiv) is added to a solution of carboxamide in dry THF. After effervescence has ceased, sulfonyl chloride (1.4 to 2.0 equiv) is added. The reaction mixture is stirred at room temperature for several hours. An aqueous solution of malate buffer (1.0 M sodium malate/disodium malate, pH 4.5, 4 mL) is slowly added. After 5 minutes, the mixture is combined with chloroform or dichloromethane and stirred. The organic phase is collected and concentrated in vacuo. The residue is purified by preparative HPLC or by flash column chromatography to give the titled compound.

Illustrative Synthesis of Compound 287: 3-cyclobutyl-N-(3,5-dimethyl-1,2-oxazole-4-sulfonyl)-4-[4-(methoxymethyl)piperidin-1-yl]-1-phenyl-1H-pyrazolo[3,4-b]pyridine-6-carboxamide

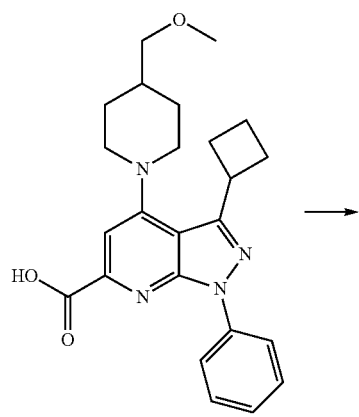

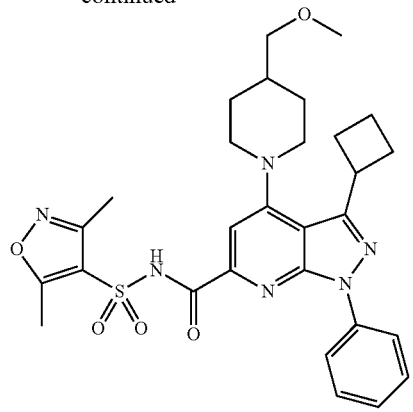

Step 1

Oxalyl chloride (0.40 mL, 4.7 mmol, 9.6 equiv) and a drop of dimethylformamide were added to a solution of A136 (0.207 g, 0.49 mmol) in dichloromethane (2 mL). After effervescence had ceased, the vial was sealed, and the reaction mixture was stirred at room temperature for 1 hour. The reaction mixture was concentrated, and to the residue was added a dioxane solution of ammonia (0.5M, 10.0 mL, 5.0 mmol, 10 equiv). After 1 hour, volatiles were then removed via rotary evaporation. The residue was purified by silica gel chromatography ($CH_2Cl_2$/EtOAc, 4:1) to give 3-cyclobutyl-4-[4-(methoxymethyl)-1-piperidyl]-1-phenyl-pyrazolo[3,4-b]pyridine-6-carboxamide.

Step 2

NaH (60% in mineral oil, 0.080 g, 2.0 mmol, 21 equiv) was added to a solution of 3-cyclobutyl-4-[4-(methoxymethyl)-1-piperidyl]-1-phenyl-pyrazolo[3,4-b]pyridine-6-carboxamide (0.041 g, 0.098 mmol) in dry THF (2 mL). After effervescence has ceased, 3,5-dimethylisoxazole-4-sulfonyl chloride (CAS: 877861-76-2, 0.038 g, 0.19 mmol, 1.9 equiv) was added. The reaction mixture was stirred at room temperature for 16 h. An aqueous solution of malate buffer (1.0 M sodium malate/disodium malate, pH 4.5, 4 mL) was slowly added. After 5 minutes, the mixture was combined with chloroform and agitated. The organic phase was collected and concentrated in vacuo. The residue was purified by preparative HPLC to give the titled compound.

Method Y5: Synthesis of Acylsulfonamide or Acylsulfamide from a Carboxylic Acid Chloride Oxalyl chloride (CAS 79-37-8, 1.5 equiv) and 3 drops of dimethylformamide are added at 0° C. to a solution of carboxylic acid in dichloromethane. After 1 h of stirring at room temperature, additional oxalyl chloride (CAS 79-37-8, 1.5 equiv) is added. After 30 minutes of stirring, the reaction mixture is cooled to 0° C. and sulfonamide (3.0 equiv) followed by triethylamine (2.0 equiv) are added. The reaction mixture is stirred at room temperature for 3 h and then concentrated in vacuo. The residue is partitioned between a saturated aqueous solution of sodium hydrogencarbonate and dichloromethane. The organic phase is dried over MgSO$_4$, filtered and concentrated in vacuo. The residue dissolved in dichloromethane is precipitated by addition to a mixture of diethyl ether/pentane. The solid collected by filtration is purified by silica gel chromatography to give the titled compound.

Alternatively, oxalyl chloride (5-10 equivalents) is added to a mixture of carboxylic acid (1 equiv) in dichloromethane followed by stirring at ambient temperature over 8-24 hours. The reaction mixture is diluted with dichloromethane and concentrated several times followed by drying under vacuum. The carboxylic acid chloride (1 equiv) is then combined with sulfonamide (2 equiv) and triethylamine (2.5-5 equiv) in dichloromethane with stirring at ambient temperature over 1-24 hours. The reaction mixture is concentrated and purified by preparative HPLC.

Illustrative Synthesis of Compound 3: 3-methyl-4-[4-(morpholin-4-yl)phenyl]-1-phenyl-N-(trifluoromethanesulfonyl)-1H-pyrazolo[3,4-b]pyridine-6-carboxamide Oxalyl chloride (CAS 79-37-8, 0.012 mL, 0.15 mmol, 1.5 equiv) and 3 drops of dimethylformamide were added at 0° C. to a solution of A002 (41 mg, 0.1 mmol) in dichloromethane (2 mL). After 1 h of stirring at room temperature, additional oxalyl chloride (CAS 79-37-8, 0.012 mL, 0.15 mmol, 1.5 equiv) was added. After 30 minutes of stirring, the reaction mixture was cooled to 0° C. and trifluoromethanesulfonamide (CAS 421-85-2, 48 mg, 0.3 mmol, 3.0 equiv) followed by triethylamine (0.029 mL, 0.2 mmol, 2.0 equiv) were added. The reaction mixture was stirred at room temperature for 3 h and then concentrated in vacuo. The residue was partitioned between a saturated aqueous solution of sodium hydrogencarbonate and dichloromethane. The organic phase was dried over MgSO$_4$, filtered and concentrated. The residue dissolved in dichloromethane was precipitated by addition to a mixture of diethyl ether/pentane. The solid collected by filtration was purified by silica gel chromatography (heptane/EtOAc 100/0 to 0/100) to give the titled compound.

Illustrative Synthesis of Compound 383: 3-cyclobutyl-N-(morpholine-4-sulfonyl)-4-[4-(morpholin-4-yl)piperidin-1-yl]-1-phenyl-1H-pyrazolo[3,4-b]pyridine-6-carboxamide

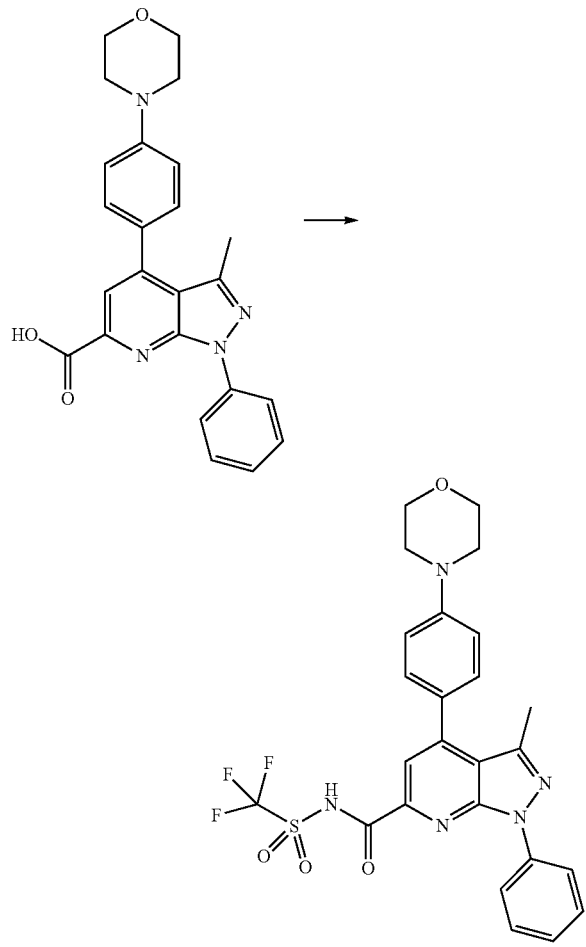

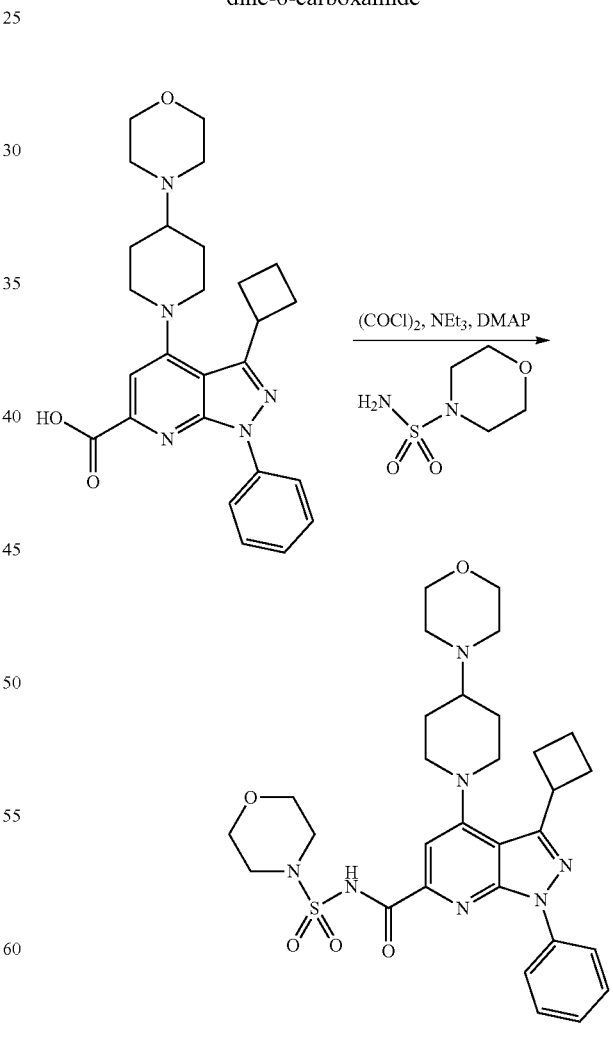

A suspension of 3-cyclobutyl-4-(4-morpholino-1-piperidyl)-1-phenyl-pyrazolo[3,4-b]pyridine-6-carboxylic acid (A268, 0.0511 g, 0.111 mmol) and (COCl)$_2$ (18 μL, 0.206 mmol) in CH$_2$Cl$_2$ (0.40 mL) with catalytic DMF was stirred for 90 minutes, concentrated, and re-dissolved in CH$_2$Cl$_2$ (0.40 mL). To this mixture was added morpholine-4-sulfonamide (0.0213 g, 0.128 mmol), DMAP (0.0141 g, 0.115 mmol), and triethylamine (18 µL, 0.129 mmol), and the mixture was stirred overnight. The reaction mixture was then diluted with saturated NaHCO$_3$, extracted with CH$_2$Cl$_2$, concentrated, and chromatographed on silica gel (25% acetone/CH$_2$Cl$_2$) and re-chromatographed (2.5% CH$_3$OH/CH$_2$Cl$_2$) and precipitated (methanol/methyl tert-butyl ether) to give the titled compound (0.0267 g, 0.044 mmol, 40% yield).

Illustrative Synthesis of Compound 432: 3-cyclobutyl-N-[methyl(propyl)sulfamoyl]-4-[4-(morpholin-4-yl)piperidin-1-yl]-1-phenyl-1H-pyrazolo[3,4-b]pyridine-6-carboxamide

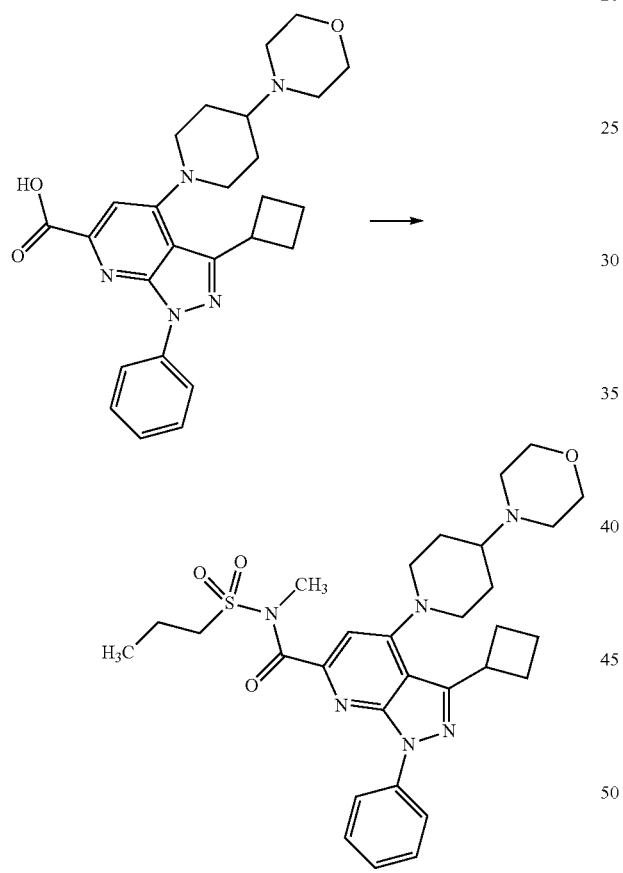

A vial was charged with 3-cyclobutyl-4-[4-(morpholin-4-yl)piperidin-1-yl]-1-phenyl-1H-pyrazolo[3,4-b]pyridine-6-carbonyl chloride (35 mg, 0.08 mmol, prepared as described below for the synthesis of compound 437) dissolved in 500 µL of dichloromethane followed by N-methyl-N-propylsulfonamide (2 eq, 0.15 mmol) in 500 µL of dichloromethane and neat triethylamine (38 µL, 4 eq, 0.32 mmol). The mixture was then stirred at room temperature for one hour. After completion of reaction, the mixture was concentrated, and the residue was dissolved in DMSO and purified by reverse phase HPLC (C18, 0-100% CH$_3$CN/water (0.1% TFA)). A gradient of acetonitrile (A) and 0.1% trifluoroacetic acid in water (B) was used, at a flow rate of 50 mL/minute (0-0.5 minute 10% A, 0.5-6.0 minutes linear gradient 10-100% A, 6.0-7.0 minutes 100% A, 7.0-8.0 minutes linear gradient 100-10% A) to afford the title compound.

Illustrative Synthesis of Compound 437: 3-cyclobutyl-N-(ethanesulfonyl)-4-[4-(morpholin-4-yl)piperidin-1-yl]-1-phenyl-1H-pyrazolo[3,4-b]pyridine-6-carboxamide

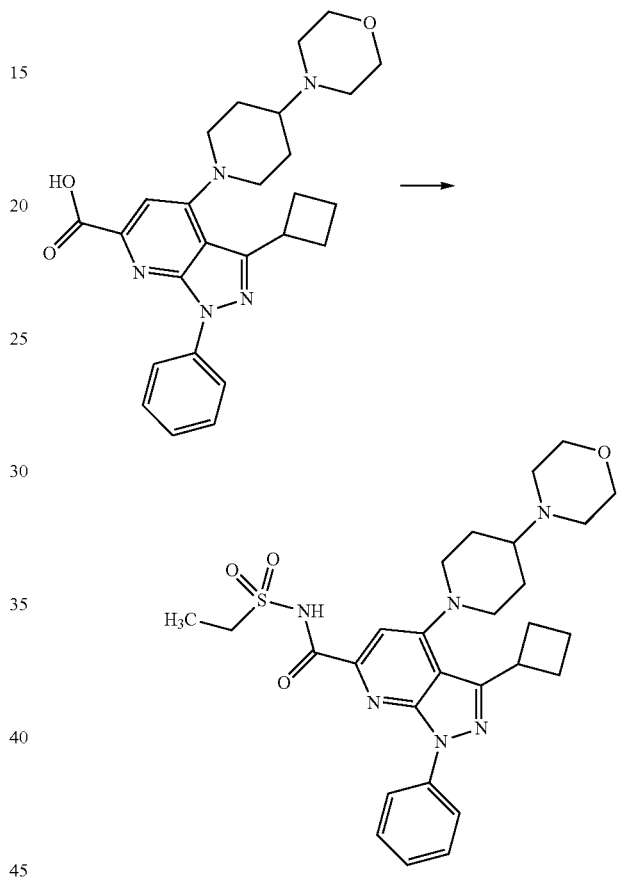

To a suspension of 3-cyclobutyl-4-[4-(morpholin-4-yl)piperidin-1-yl]-1-phenyl-1H-pyrazolo[3,4-b]pyridine-6-carboxylic acid (A409, 0.8117 g, 1.759 mmol) in dichloromethane (10 mL) was added oxalyl chloride (1 mL, 11.4 mmol) dropwise, and the mixture was stirred at RT overnight. The reaction mixture was diluted with more dichloromethane (11 mL) and concentrated under vacuum. This process was repeated two additional times. The resultant yellow solid material, which was kept under vacuum for one hour to give 3-cyclobutyl-4-[4-(morpholin-4-yl)piperidin-1-yl]-1-phenyl-1H-pyrazolo[3,4-b]pyridine-6-carbonyl chloride.

To a suspension of 3-cyclobutyl-4-[4-(morpholin-4-yl)piperidin-1-yl]-1-phenyl-1H-pyrazolo[3,4-b]pyridine-6-carbonyl chloride (0.050 g, 0.104 mmol) in dichloromethane (1.5 mL) was added ethanesulfonamide (0.023 g, 0.208 mmol) and triethylamine (0.051 mL, 0.365 mmol), and the mixture was stirred at RT for overnight. The reaction mixture was concentrated under vacuum and purified by preparative HPLC on a Waters® Sunfire™ C8 column (30×150 mm) with an escalating gradient of acetonitrile in 10 mM aqueous ammonium acetate to the titled compound.

Method Y6: Protecting Group Removal

Protecting groups, known to one of skill in the art can be removed using appropriate procedures known to remove such protecting groups. Specific illustrations for select protecting group removal are provided in the examples below.

Benzyl Ether Removal

Illustrative Synthesis of Compound 366: 3-cyclobutyl-N-(2-hydroxyethanesulfonyl)-4-[4-(methoxymethyl)piperidin-1-yl]-1-phenyl-1H-pyrazolo[3,4-b]pyridine-6-carboxamide Illustrative Synthesis of Compound 105: 1-[3-(3-hydroxyazetidin-1-yl)phenyl]-N-(methanesulfonyl)-4-[4-(morpholin-4-yl)phenyl]-3-(propan-2-yl)-1H-pyrazolo[3,4-b]pyridine-6-carboxamide

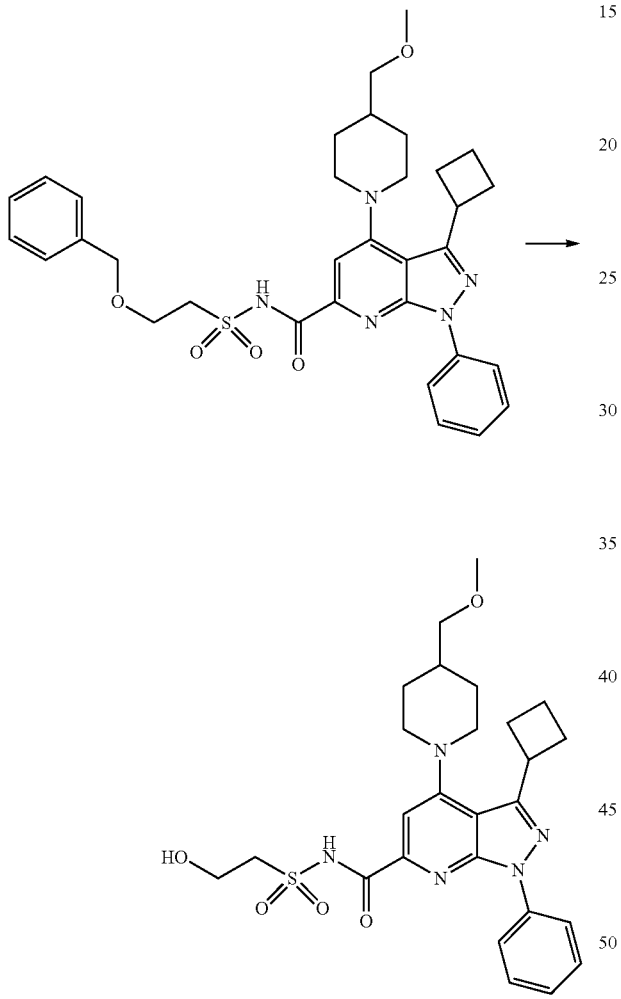

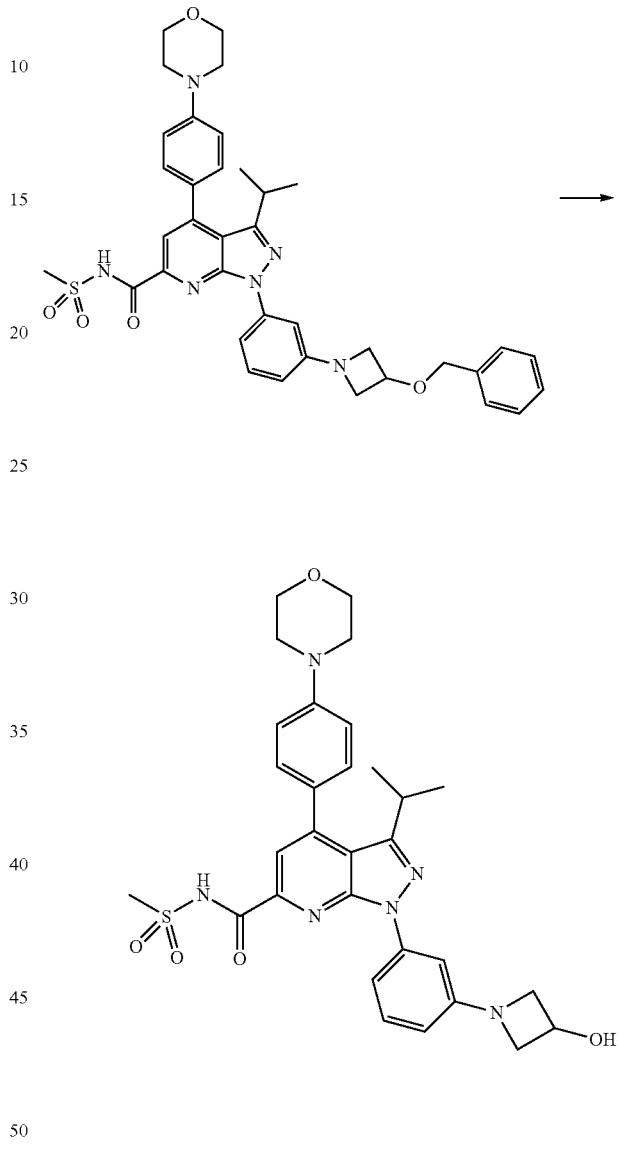

A solution of AC05 (8 mg, 0.013 mmol) in THF (5 mL) was degassed with nitrogen. Palladium hydroxide (2 mg, 25% w/w) was added, and the reaction mixture was stirred under hydrogen atmosphere (balloon) for 3 hours. The reaction mixture was then filtered on Dicalite® diatomaceous earth, and the filtrate was concentrated in vacuo. The residue dissolved in dichloromethane (1 mL) was precipitated by addition to heptane. The collected solid was dried in vacuo to yield the titled compound.

A solution of AC02 (38 mg, 0.06 mmol) in a mixture of EtOH/THF (1/2 mL) was degassed with nitrogen. 10% Pd/C (5 mg) was added. The reaction mixture was degassed with H₂ for 5 min, and then was stirred for 48 hours at room temperature under hydrogen atmosphere (balloon). Additional 10% Pd/C (5 mg) was added, and the reaction mixture was stirred for 18 hours at room temperature under hydrogen atmosphere. The reaction mixture was filtered, and the filtrate was concentrated in vacuo. The residue was purified by preparative HPLC to give the titled compound.

897
Benzyl Carbamate Removal

Illustrative Synthesis of Compound 368: 3-cyclobutyl-4-[4-(methoxymethyl)piperidin-1-yl]-1-phenyl-N-(piperidine-4-sulfonyl)-1H-pyrazolo[3,4-b]pyridine-6-carboxamide

898
Phthalimide Removal

Illustrative Synthesis of Compound 261: N-(2-aminoethanesulfonyl)-3-cyclobutyl-4-[4-(methoxymethyl)piperidin-1-yl]-1-phenyl-1H-pyrazolo[3,4-b]pyridine-6-carboxamide

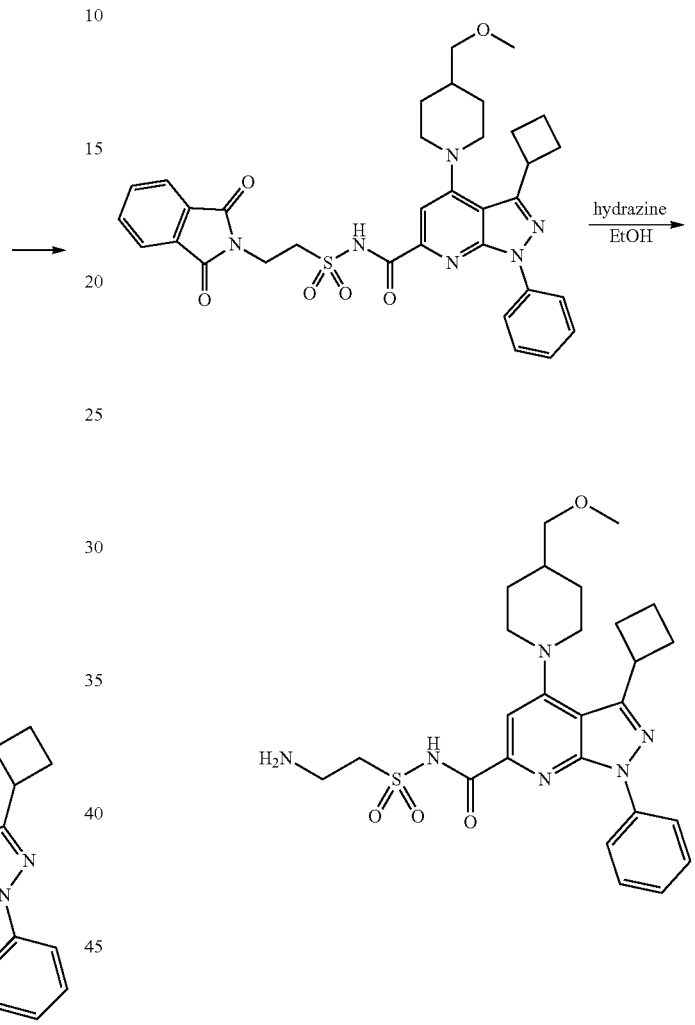

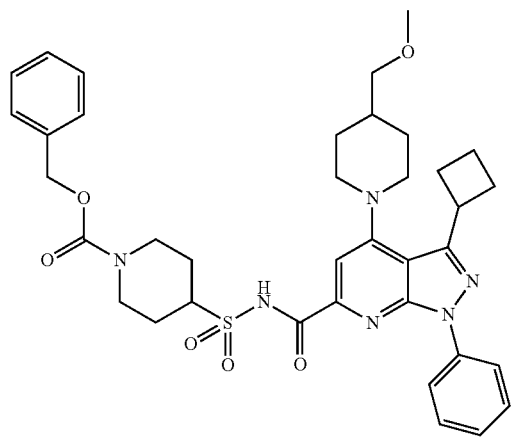

A solution of AC03 (60 mg, 0.09 mmol) in ethanol (10 mL) was degassed with nitrogen. Palladium hydroxide (15 mg, 25% w/w) was added, and the reaction mixture was stirred at RT under hydrogen atmosphere (balloon) for 16 hours. The reaction mixture was filtered, and the cake washed with THF, MeOH and chloroform. The filtrate was concentrated in vacuo. The residue dissolved in dichloromethane was precipitated by addition to a mixture of diethyl ether and pentane. The obtained solid was dried in vacuo to yield the titled compound.

Hydrazine hydrate (50-60% in water, 0.015 mL, 0.2 mmol, 6.7 equiv) was added to a solution of 3-cyclobutyl-N-[2-(1,3-dioxoisoindolin-2-yl)ethylsulfonyl]-4-[4-(methoxymethyl)-1-piperidyl]-1-phenyl-pyrazolo[3,4-b]pyridine-6-carboxamide (compound 260, 20 mg, 0.03 mmol) in ethanol (3 mL). The reaction mixture was refluxed for 3 hours and then concentrated in vacuo. The residue was partitioned between a saturated aqueous solution of sodium hydrogencarbonate and dichloromethane. The organic phase was dried over MgSO₄, filtered and concentrated in vacuo. The residue was purified by silica gel chromatography (dichloromethane/acetone 95/5 to 85/15) to give the titled compound.

899

Tert-Butyl Carbamate Removal

Illustrative Synthesis of Compound 258: 4-[6-(4-cyanopiperidin-1-yl)pyridin-3-yl]-N-(methanesulfonyl)-1-phenyl-3-[(piperidin-4-yl)oxy]-1H-pyrazolo[3,4-b]pyridine-6-carboxamide

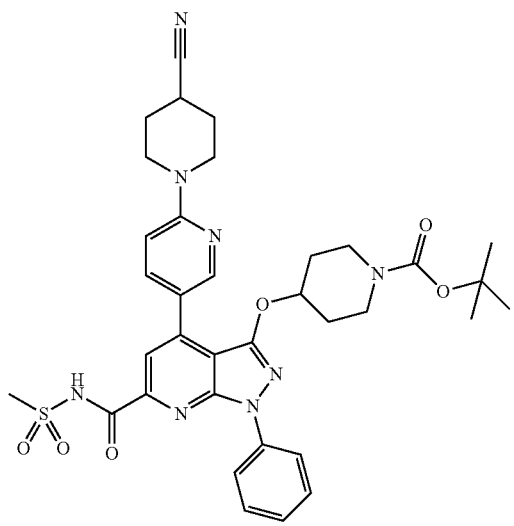

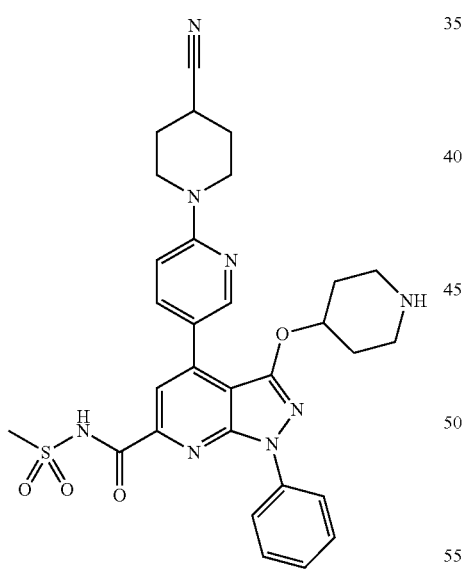

900

Illustrative Synthesis of Compound 631: 1-cyclohexyl-4-[4-(hexahydropyrrolo[3,4-c]pyrrole-2(1H)-carbonyl)phenyl]-N-(methanesulfonyl)-3-[(propan-2-yl)oxy]-1H-pyrazolo[3,4-b]pyridine-6-carboxamide

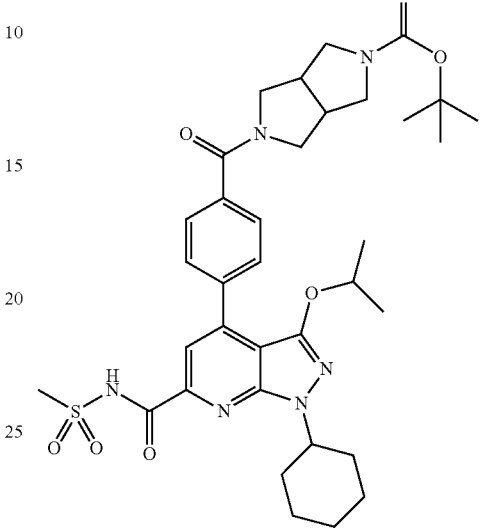

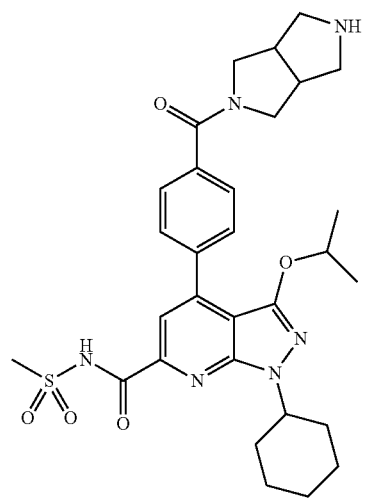

Trifluoroacetic acid (0.1 mL, 1.0 mmol, 23 equiv) was added to a solution of tert-butyl 4-[4-[6-(4-cyano-1-piperidyl)-3-pyridyl]-6-(methylsulfonylcarbamoyl)-1-phenyl-pyrazolo[3,4-b]pyridin-3-yl]oxypiperidine-1-carboxylate (compound 259, 30 mg, 0.043 mmol) in dichloromethane (1 mL). The reaction mixture was stirred at room temperature until completion of the reaction. The reaction mixture was quenched with a saturated solution of sodium bicarbonate. The obtained precipitate was collected by filtration, washed with water and dried to yield the titled compound.

AC15 (18 mg, 26 µmol) was dissolved in dichloromethane (5 mL) and 4 M HCl in dioxane (0.5 mL, 2 mmol) was added. The solution was stirred at room temperature for two hours and then concentrated in vacuo. The residue was suspended in DCM and washed with a phosphate buffer solution (pH 6.2). The organic phase was dried over sodium sulfate, filtered and concentrated under reduced pressure to give the titled compound.

Method Y7: Azide Displacement of Alkyl Halide

Synthesis of Compound 327: 4-(4-azidophenyl)-N-(3-azidopropane-1-sulfonyl)-1-[3-(dimethylamino)phenyl]-3-(propan-2-yl)-1H-pyrazolo[3,4-b]pyridine-6-carboxamide

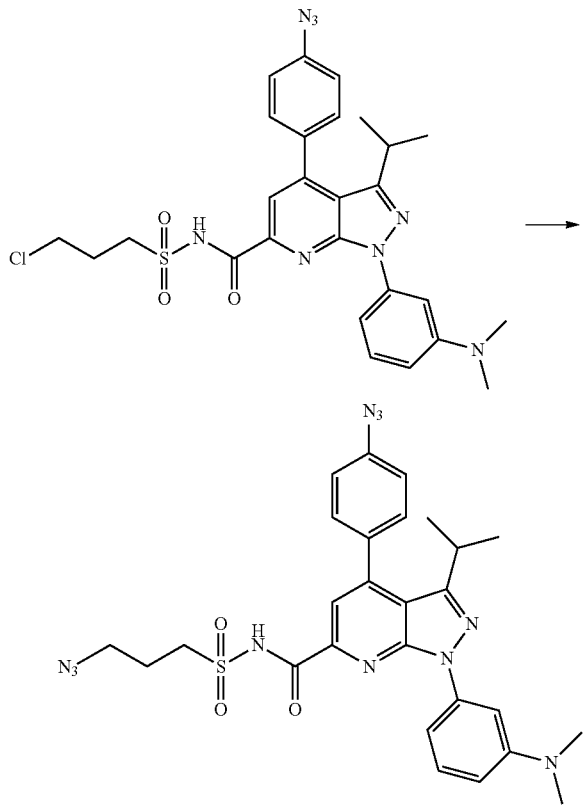

AC06 (160 mg, 0.275 mmol, 1 equiv) in anhydrous DMSO (2 mL) at RT under nitrogen atmosphere was added sodium azide (CAS 26628-22-8, 36 mg, 0.550 mmol, 2.0 equiv). The reaction mixture was stirred at 80° C. for 1 h. Then the reaction mixture was cooled down, diluted with dichloromethane, washed with water and brine, dried over MgSO₄, filtered and concentrated in vacuo. The resulting crude mixture was purified by preparative HPLC to afford the titled compound.

Method Y8: Synthesis of Acylsulfamide

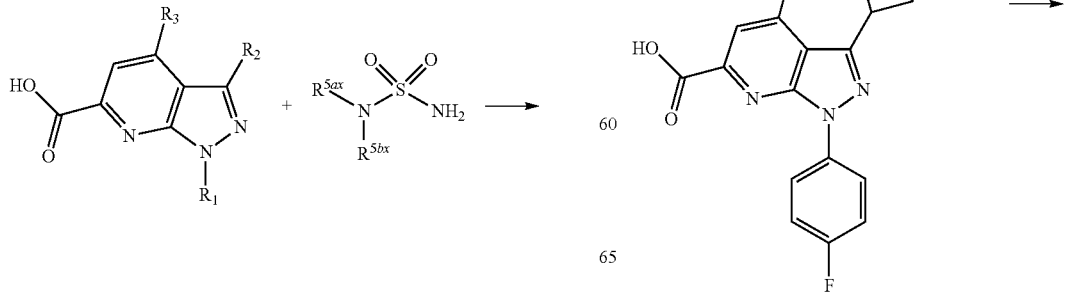

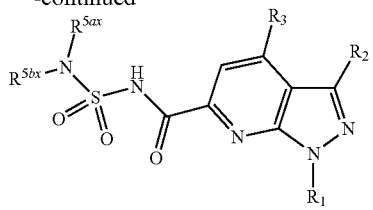

EDC.HCl (CAS 25952-538, 1.0 to 4.0 equiv) is added at RT to a stirring solution of carboxylic acid, sulfamide (from 1 to 4.0 equiv) and 4-(dimethylamino) pyridine (CAS 1122-58-3, from 0.2 to 2 equiv) in dichloromethane or/and THF or/and acetonitrile. The reaction mixture is stirred at RT until complete conversion. The solvent can be evaporated under reduced pressure. The residue can be worked up or purified by preparative HPLC. The work up consists in dissolving the sample in DCM and washing it with water and/or a saturated aqueous solution of NaHCO₃. The organic phase is separated, dried over sodium sulfate, filtered and concentrated in vacuo. The residue is purified either by flash column chromatography or by preparative HPLC to yield the titled compound.

Alternatively, acylsulfamides can be prepared in the following manner. A solution of the carboxylic acid (1 eq) in dichloromethane, dichloroethane or dimethylformamide can be treated with carbodiimidazole (1-2.5 eq) stirred at ambient temperature to 65° C. for 0.5-3 hours. Then the sulfamide (1-3 eq) and optional potassium bis(trimethylsilyl)amide or triethylamine followed by 1,8-diazabicycloundec-7-ene (1-3 eq) and optional 4-(dimethylamino)pyridine (1-2 eq) can be added, and the reaction mixture is stirred at 20-60° C. for 2-16 hours. The reaction mixture can then be concentrated or extractively worked up. The residue can be purified by precipitation, silica gel flash chromatography, or preparative HPLC.

Illustrative Synthesis of Compound 379: 3-cyclobutyl-N-(dimethylsulfamoyl)-1-(4-fluorophenyl)-4-{4-[2-(methoxymethyl)morpholin-4-yl]piperidin-1-yl}-1H-pyrazolo[3,4-b]pyridine-6-carboxamide 903
-continued

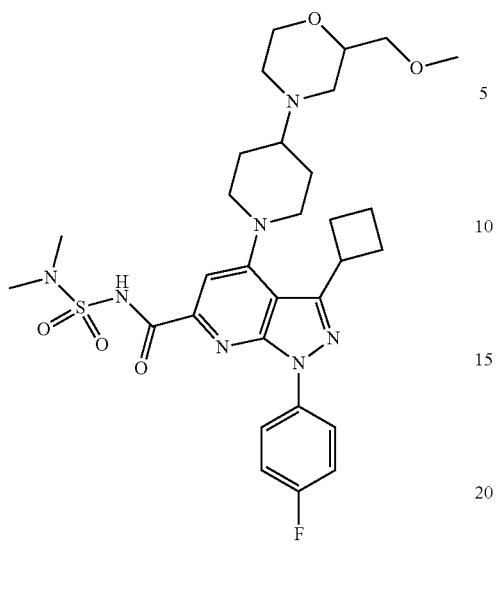

904
-continued

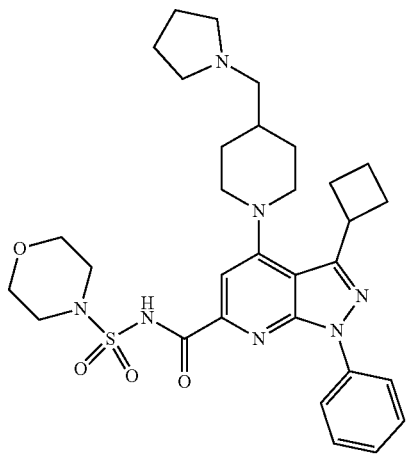

EDC.HCl ([25952-538], 58 mg, 0.46 mmol) was added at RT to a stirred solution of A286 (120 mg, 0.23 mmol), N,N-dimethylsulfamide (58 mg, 0.46 mmol) and 4-(dimethylamino) pyridine (CAS 1122-58-3, 58 mg, 0.46 mmol) in a mixture of dichloromethane/acetonitrile (1:1, 4 mL). The reaction mixture was stirred at RT for 20 hours. The solvent was evaporated at 40° C. under a nitrogen flow. The residue was purified by preparative HPLC to yield the titled compound as formate salt.

Illustrative Synthesis of Compound 380: 3-cyclobutyl-N-(morpholine-4-sulfonyl)-1-phenyl-4-{4-[(pyrrolidin-1-yl)methyl]piperidin-1-yl}-1H-pyrazolo[3,4-b]pyridine-6-carboxamide

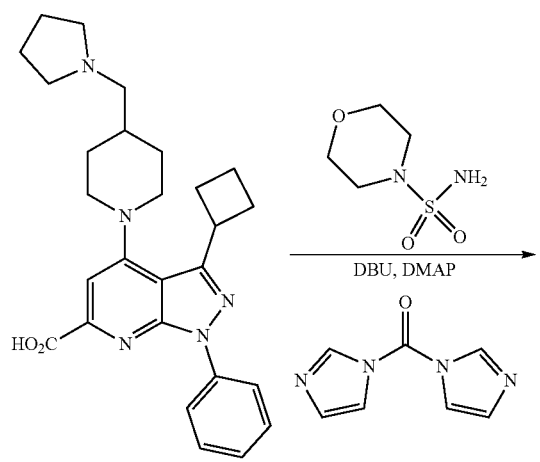

A suspension of 3-cyclobutyl-1-phenyl-4-{4-[(pyrrolidin-1-yl)methyl]piperidin-1-yl}-1H-pyrazolo[3,4-b]pyridine-6-carboxylic acid (A285, 0.1498 g, 0.326 mmol) and carbonyl diimidazole (0.0795 g, 0.490 mmol) in dimethylformamide (DMF) (1.0 mL) was stirred for 2.5 hours, and then morpholine-4-sulfonamide (0.0815 g, 0.490 mmol, [25999-04-6]), DMAP (0.0444 g, 0.363 mmol), and DBU (0.075 mL, 0.498 mmol) were added. The resultant mixture was stirred overnight. The reaction mixture was then diluted with water (10 mL), extracted with dichloromethane (3×8 mL), dried (Na$_2$SO$_4$), and chromatographed (7% CH$_3$OH/CH$_2$Cl$_2$) and triturated (10 volumes methyl tert-butyl ether/5 volumes methanol) to give the titled compound (0.0602 g, 0.099 mmol, 30% yield).

Illustrative Synthesis of Compound 388: 3-cyclobutyl-4-[4-(methoxymethyl)piperidin-1-yl]-1-phenyl-N-[4-(pyrrolidin-1-yl)piperidine-1-sulfonyl]-1H-pyrazolo[3,4-b]pyridine-6-carboxamide

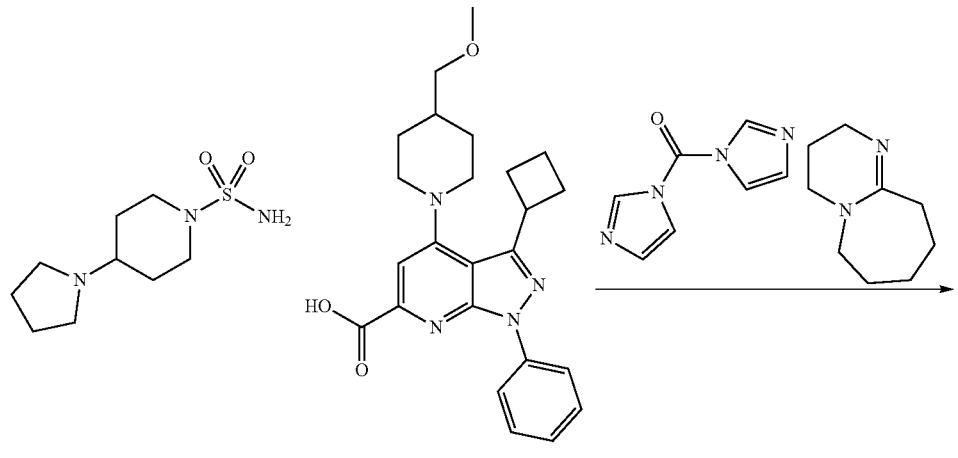

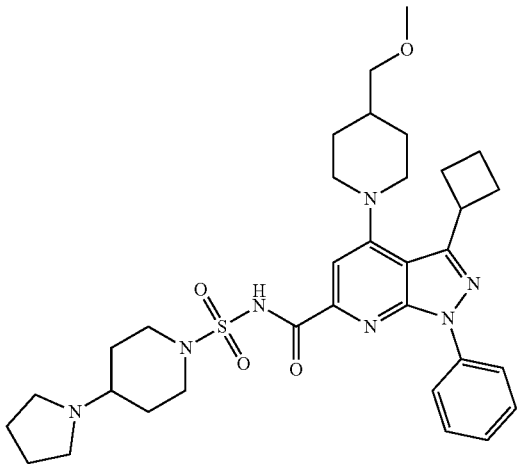

A 4-mL vial was charged with 3-cyclobutyl-4-[4-(methoxymethyl)-1-piperidyl]-1-phenyl-pyrazolo[3,4-b]pyridine-6-carboxylic acid (A136, 35 mg, 0.09 mmol) dissolved in 600 µL of dichloroethane followed by carbonyldiimidazole (27 mg, 0.18 mmol) in 600 µL of dichloroethane, and the mixture was stirred at 40° C. for two hours. To this mixture was then added 4-(pyrrolidin-1-yl)piperidine-1-sulfonamide (40 mg, 3 eq, 0.28 mmol) followed by 1,8-diazabicycloundec-7-ene (42 µL, 3 eq, 0.28 mmol), and the mixture was heated at 60° C. for 16 hours. The mixture was concentrated, and the residue was dissolved in DMSO and purified by reverse phase HPLC (C18, 0-100% CH$_3$CN/water (0.1% TFA)). A gradient of acetonitrile (A) and 0.1% trifluoroacetic acid in water (B) was used, at a flow rate of 50 mL/minute (0-0.5 minute 10% A, 0.5-6.0 minutes linear gradient 10-100% A, 6.0-7.0 minutes 100% A, 7.0-8.0 minutes linear gradient 100-10% A) to afford the title compound.

Illustrative Synthesis of Compound 412: N-(dimethylsulfamoyl)-1-(4-fluorophenyl)-4-[4-(morpholin-4-yl)piperidin-1-yl]-3-(propan-2-yl)-1H-pyrazolo[3,4-b]pyridine-6-carboxamide

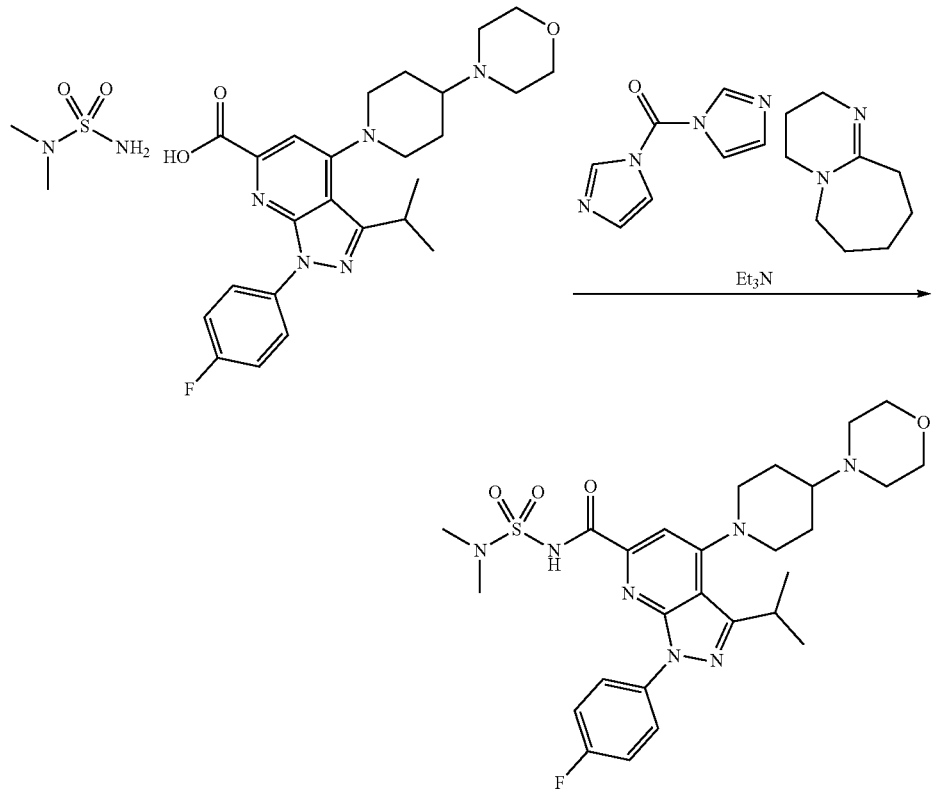

1-(4-Fluorophenyl)-4-[4-(morpholin-4-yl)piperidin-1-yl]-3-(propan-2-yl)-1H-pyrazolo[3,4-b]pyridine-6-carboxylic acid (A408, 70 mg, 0.15 mmol) and carbonyl diimidazole (37 mg, 0.23 mmol) were stirred in anhydrous DMF (800 µL) at room temperature for an hour. Then N,N-dimethylsulfamide (37 mg, 0.30 mmol) and triethylamine (42 µL, 0.30 mmol) were added, followed by slow addition of DBU (34 µL, 0.23 mmol). The reaction mixture was stirred 30 minutes at room temperature, diluted with methanol and purified by preparative HPLC on a Waters® Sunfire™ C8 column (30×150 mm) with a 40 to 70% gradient of acetonitrile in 10 mM aqueous ammonium acetate to give the titled compound.

Illustrative Synthesis of Compound 426: 4-([1,4'-bipiperidin]-1'-yl)-3-cyclobutyl-N-(dimethylsulfamoyl)-1-phenyl-1H-pyrazolo[3,4-b]pyridine-6-carboxamide

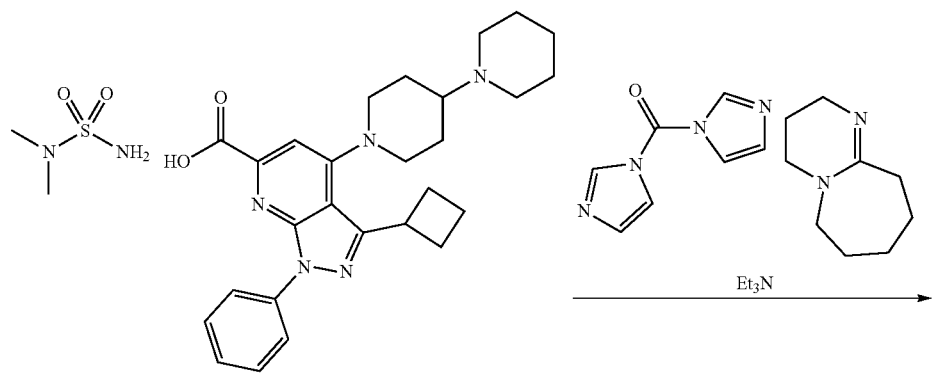

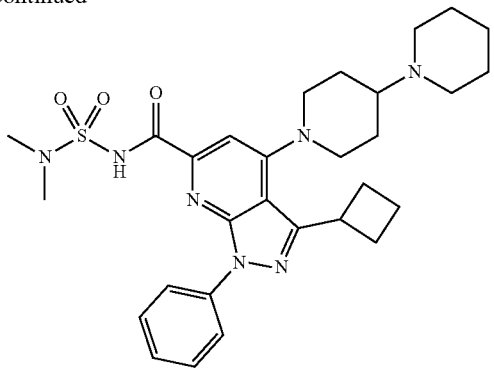

3-Cyclobutyl-1-phenyl-4-[4-(1-piperidyl)-1-piperidyl]pyrazolo[3,4-b]pyridine-6-carboxylic acid (A081, 92 mg, 0.20 mmol) and carbonyl diimidazole (49 mg, 0.30 mmol) were stirred in anhydrous DMF (1.0 mL) at room temperature for 90 minutes. Then N,N-dimethylsulfamide (50 mg, 0.40 mmol) and triethylamine (56 µL, 0.40 mmol) were added, followed nearly 15 minutes later by slow addition DBU (45 µL, 0.30 mmol). The reaction mixture was stirred 30 minutes at room temperature, diluted with methanol and purified by preparative HPLC on a Waters® Sunfire™ C8 column (30×150 mm) with a 30 to 60% gradient of acetonitrile in 10 mM aqueous ammonium acetate to give the titled compound.

Illustrative Synthesis of Compound 652: 3-cyclobutyl-1-[3-(difluoromethoxy)phenyl]-N-(dimethylsulfamoyl)-4-[4-(morpholin-4-yl)piperidin-1-yl]-1H-pyrazolo[3,4-b]pyridine-6-carboxamide

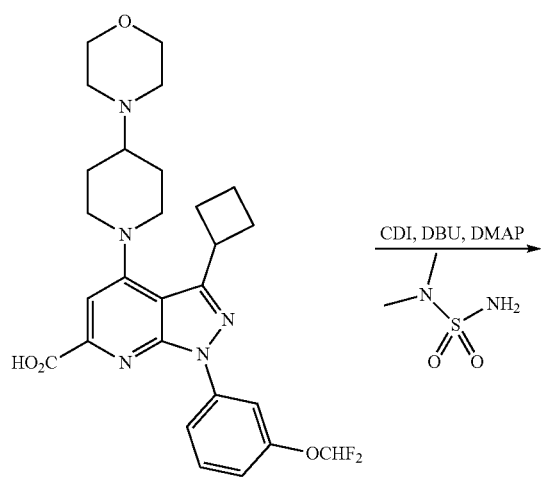

-continued

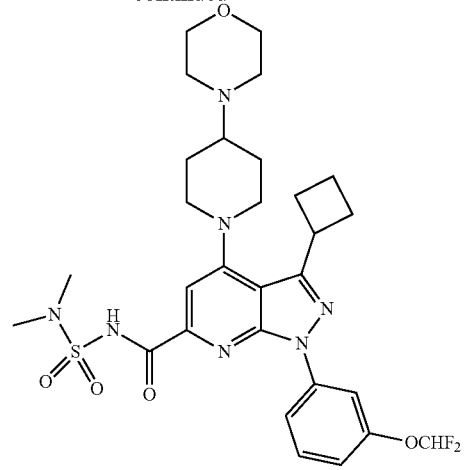

A solution of 3-cyclobutyl-1-[3-(difluoromethoxy)phenyl]-4-[4-(morpholin-4-yl)piperidin-1-yl]-1H-pyrazolo[3,4-b]pyridine-6-carboxylic acid (0.0536 g, 0.102 mmol, A410) and 1,1'-carbonyldiimidazole (0.0253 g, 0.156 mmol) in N,N-dimethylformamide (DMF) (0.40 mL) was stirred at 60° C. for 1 hour. Then N,N-dimethylsulfamide (0.0192 g, 0.155 mmol), DMAP (0.0138 g, 0.113 mmol), and DBU (0.023 mL, 0.153 mmol) were added, and the mixture was stirred for 2.5 hours. The mixture was diluted with water (10 mL), extracted with DCM (4×8 mL), dried (Na₂SO₄), and concentrated. The residue was purified by chromatography on silica gel (0-3% isopropanol/DCM) to give the titled compound Method Y9: De-Benzylation

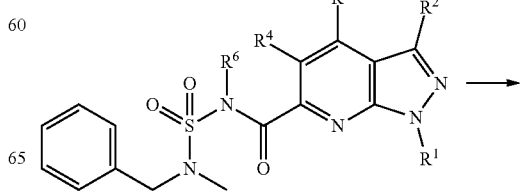

-continued

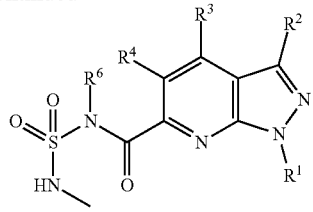

A vial is loaded with benzylated acylsulfonamide (1.0 equiv) and 10% Pd on charcoal (0.1 equiv). The vial is sealed, evacuated and back-filled with N₂ and THF/MeOH 1:1 is added by syringe. The reaction mixture is evacuated and back-filled with H₂ three times, and the reaction mixture is stirred overnight at 50° C. The mixture is filtered on a Pall-Seitz thick paper filter and concentrated in vacuo. The residue is dissolved in MeOH, filtered over a 0.45 µM plug filter and purified by means of semi-preparative HPLC (0.1% TFA in water/CH₃CN). The compound is dissolved in DCM, 4 M HCl in dioxane is added, and the mixture was concentrated in vacuo to afford the debenzylated compound.

Illustrative Synthesis of Compound 517: 3-cyclobutyl-1-(4-fluorophenyl)-N-(methylsulfamoyl)-4-[4-(morpholin-4-yl)piperidin-1-yl]-1H-pyrazolo[3,4-b]pyridine-6-carboxamide

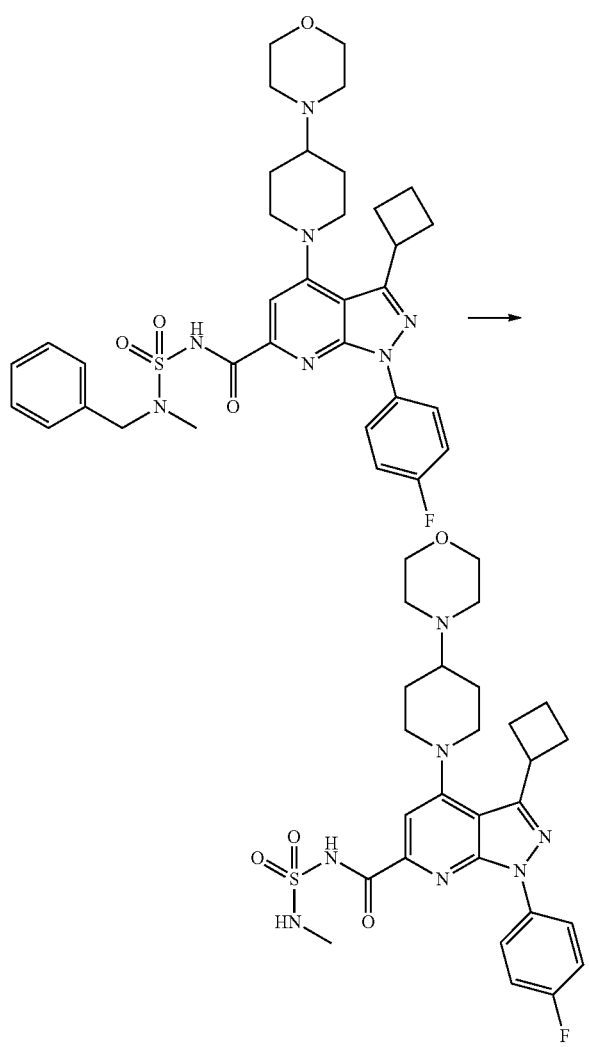

A vial was loaded with N-[benzyl(methyl)sulfamoyl]-3-cyclobutyl-1-(4-fluorophenyl)-4-[4-(morpholin-4-yl)piperidin-1-yl]-1H-pyrazolo[3,4-b]pyridine-6-carboxamide (AC16, 1.0 equiv., 0.151 mmol, 100 mg) and 10% Pd on charcoal (0.1 equiv., 0.015 mmol, 16 mg). The vial was sealed, evacuated and back-filled with N₂, and THF/MeOH 1:1 (2 mL) was added by syringe. The reaction mixture was evacuated and back-filled with H₂ three times, and the reaction mixture was stirred overnight at 50° C. The mixture was filtered on a Pall-Seitz thick paper filter and concentrated in vacuo. The residue was dissolved in MeOH, filtered over a 0.45 µM plug filter and purified by means of semi-preparative HPLC (0.1% TFA in water/CH₃CN). The compound was dissolved in DCM, and then 4 M HCl in dioxane (0.1 mL) was added and the mixture was concentrated in vacuo to afford the titled compound.

Method Y10: Acylsulfonamide N-Alkylation

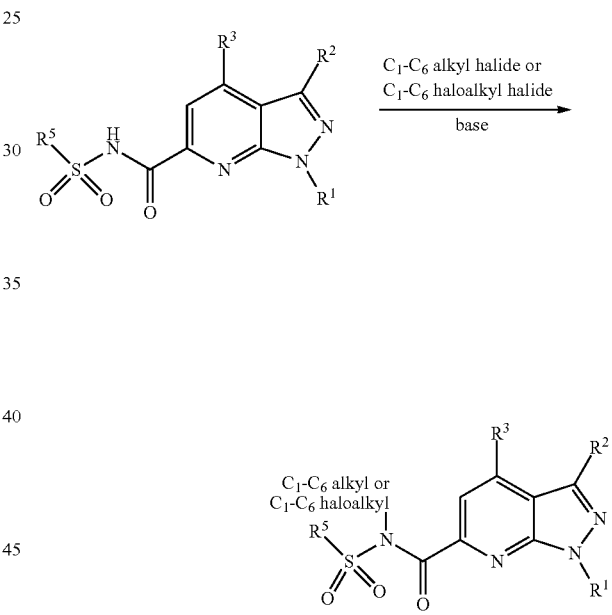

An acylsulfonamide is treated with a $C_1$-$C_6$ alkyl halide or $C_1$-$C_6$ alkyl halide in the presence of a base such as but not limited to sodium bicarbonate or cesium carbonate in acetonitrile or N,N-dimethylformamide or a mixture thereof at room temperature to 70° C. over 8-60 hours. The reaction mixture is optionally quenched with water. The mixture may be optionally extractively worked up and concentrated or simply concentrated. The residue can be purified by precipitation, chromatography on silica gel, or by preparative HPLC to give the N-alkylated acylsulfonamide.

913

Illustrative Synthesis of Compound 656: 3-cyclobutyl-N-(methanesulfonyl)-N-methyl-4-[4-(morpholin-4-yl)piperidin-1-yl]-1-phenyl-1H-pyrazolo[3,4-b]pyridine-6-carboxamide

914

Illustrative Synthesis of Compound 657: 3-cyclobutyl-N-(methanesulfonyl)-4-[4-(methoxymethyl)piperidin-1-yl]-N-methyl-1-phenyl-1H-pyrazolo[3,4-b]pyridine-6-carboxamide

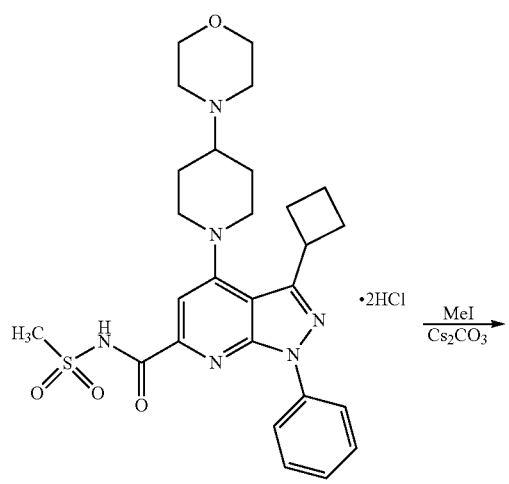

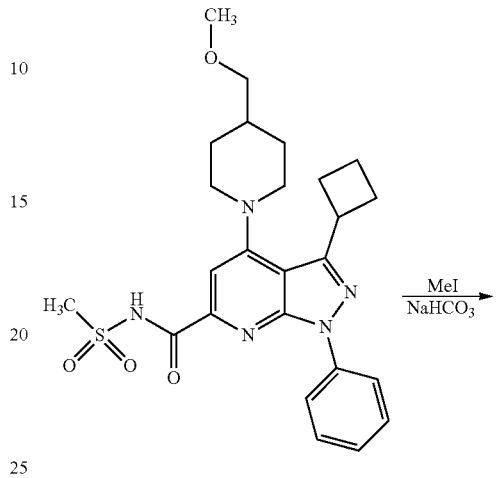

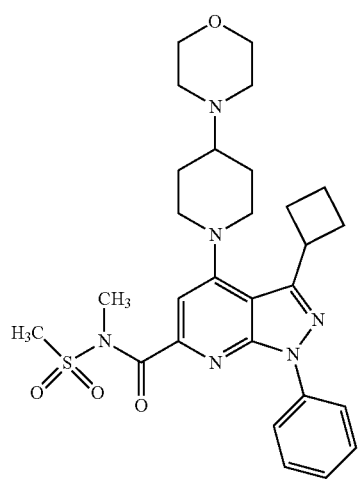

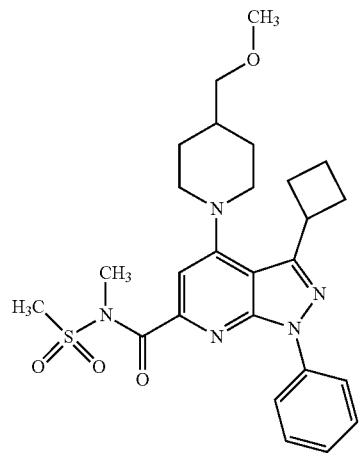

A mixture of 3-cyclobutyl-N-(methanesulfonyl)-4-[4-(morpholin-4-yl)piperidin-1-yl]-1-phenyl-1H-pyrazolo[3,4-b]pyridine-6-carboxamide dihydrochloride (0.0318 g, 0.052 mmol, compound 328), iodomethane (4.86 µl, 0.078 mmol), and $Cs_2CO_3$ (0.0506 g, 0.155 mmol) in N,N-dimethylformamide (DMF) (0.25 mL) was stirred at RT for 1 hour, and at 60° C. overnight. The mixture was then quenched with water, concentrated, and chromatographed on silica gel (5% MeOH/DCM) and re-chromatographed (15-25% acetone/DCM) to give the titled compound.

A mixture of 3-cyclobutyl-N-(methanesulfonyl)-4-[4-(methoxymethyl)piperidin-1-yl]-1-phenyl-1H-pyrazolo[3,4-b]pyridine-6-carboxamide (0.0508 g, 0.102 mmol, compound 185), iodomethane (10 µL, 0.161 mmol), and $NaHCO_3$ (0.0265 g, 0.315 mmol) in acetonitrile (0.40 mL) was stirred at RT overnight. N,N-Dimethylformamide (DMF) (0.20 mL) was added, and the mixture was heated to 60° C. for 5 hours (little reaction). Then, additional iodomethane (10 µL, 0.161 mmol) and $NaHCO_3$ (0.0265 g, 0.315 mmol) were added, and the mixture was stirred at 60° C. overnight. The mixture was diluted with water, extracted with DCM, dried ($Na_2SO_4$), and chromatographed on silica gel (2% EtOAc/DCM) to give the titled compound.

915

Synthesis of Compound 386: N-(2-acetamidoethanesulfonyl)-3-cyclobutyl-4-[4-(methoxymethyl)piperidin-1-yl]-1-phenyl-1H-pyrazolo[3,4-b]pyridine-6-

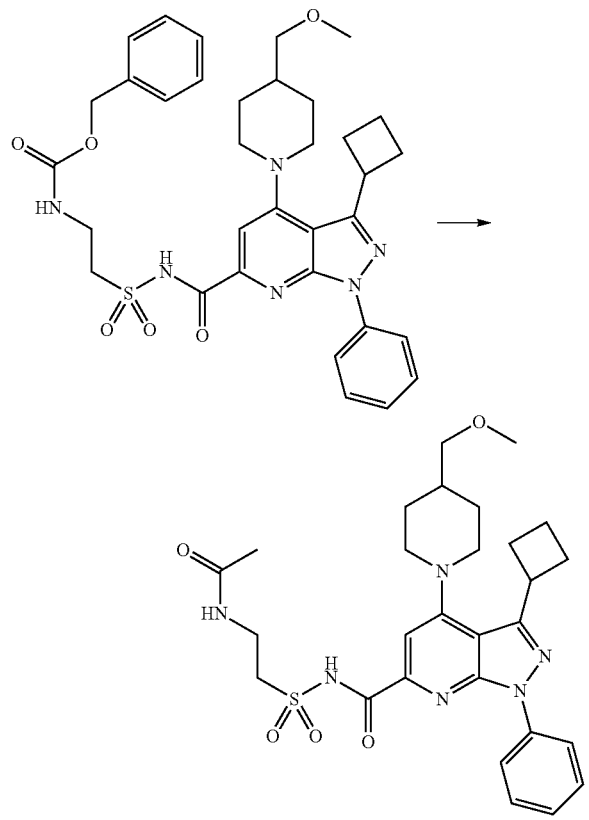

A solution of AC08 (42 mg, 0.06 mmol) in a mixture of THF (6 mL) and acetic anhydride (0.1 mL, 1.0 mmol) was degassed with nitrogen. 10% Pd/C (9 mg, 0.008 mmol) was added and the reaction mixture was purged with H2. The mixture was stirred for 16 hours at RT under a hydrogen atmosphere (balloon). The reaction mixture was filtered over a pad of diatomaceous earth that was then washed with THF. The filtrate was concentrated in vacuo, and the residue was purified by flash column chromatography eluted with DCM/MeOH (20/1) to give the titled compound.

Synthesis of Compound 387: 3-cyclobutyl-4-[4-(methoxymethyl)piperidin-1-yl]-1-phenyl-N-(pyrrolidine-3-sulfonyl)-1H-pyrazolo[3,4-b]pyridine-6-carboxamide

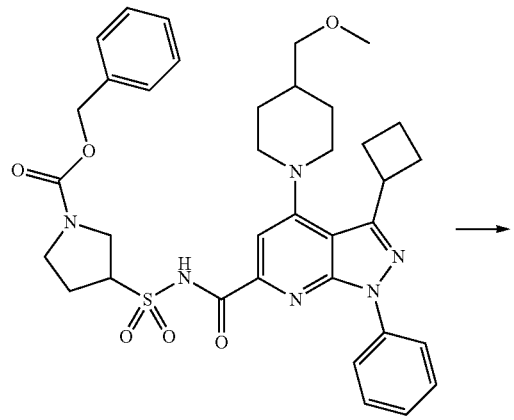

916

-continued

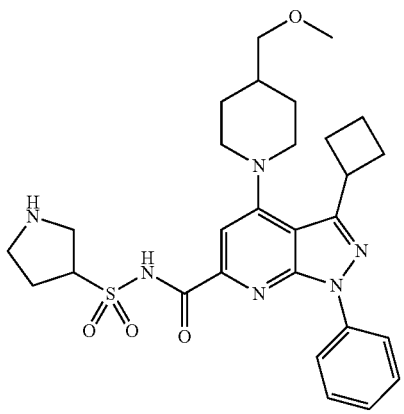

A solution of AC09 (103 mg, 0.15 mmol) in a mixture of THF (8 mL), ethanol (8 mL), acetic acid (1 mL), and aqueous 1 M HCl (1 mL) was degassed with nitrogen. 10% Pd(OH)$_2$ (21 mg, 0.015 mmol) was added, and the reaction mixture was purged with H2. The mixture was stirred for 16 hours at RT under a hydrogen atmosphere (balloon). The reaction mixture was filtered over a pad of diatomaceous earth that was washed with THF. The filtrate and wash were concentrated in vacuo. The residue was partitioned between chloroform (100 mL) and aqueous 1 M NaOH (50 mL). The organic phase was dried over magnesium sulfate, filtered and concentrated under reduced pressure. The residue was purified by silica gel chromatography eluted with DCM/MeOH (20/1) to give the titled compound.

Synthesis of AC10: 3-cyclobutyl-4-[4-(methoxymethyl)piperidin-1-yl]-1-(2-methylpyridin-4-yl)-1H-pyrazolo[3,4-b]pyridine-6-carboxylic Acid

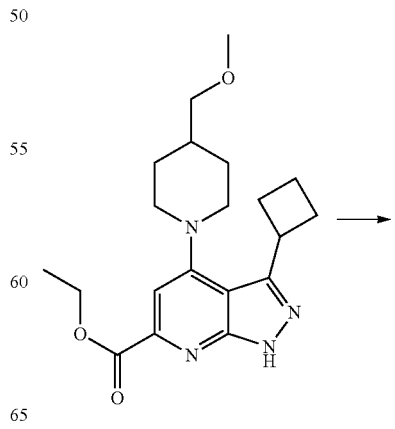

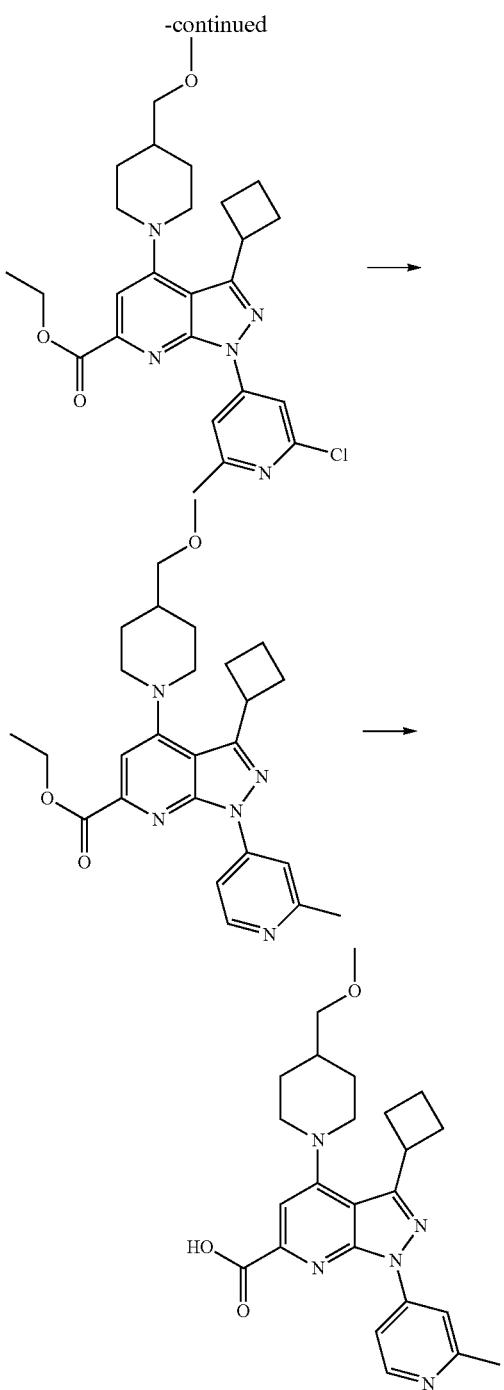

Step 1: Ethyl 1-(2-chloro-6-methylpyridin-4-yl)-3-cyclobutyl-4-[4-(methoxymethyl)piperidin-1-yl]-1H-pyrazolo[3,4-b]pyridine-6-carboxylate To a solution of E168 (64 mg, 0.17 mmol) in dichloromethane (4 mL) at RT was added 2-chloro-6-methylpyridine-4-boronic acid ([1320397-15-6], 43 mg, 0.25 mmol), copper(II) acetate ([142-71-2], 56 mg, 0.31 mmol) and pyridine (66 µL, 0.81 mmol). The reaction mixture was stirred at room temperature under air for 72 hours. The reaction mixture was filtered through a pad of diatomaceous earth. Solids were washed with dichloromethane, and the filtrate was concentrated in vacuo. The resulting residue was purified by flash chromatography on silica gel eluted with ethyl acetate/n-heptane (0/1 to 1/0) to give the titled compound.

Step 2: Ethyl 3-cyclobutyl-4-[4-(methoxymethyl)piperidin-1-yl]-1-(2-methylpyridin-4-yl)-1H-pyrazolo[3,4-b]pyridine-6-carboxylate A solution of the compound from the previous step (50 mg, 0.1 mmol) in ethanol (20 mL) was degassed with nitrogen. 10% Pd/C (5 mg, 0.005 mmol) was added, and the reaction mixture was purged with H2. The mixture was stirred for 16 hours at RT under a hydrogen atmosphere (balloon). The reaction mixture was filtered through a pad of diatomaceous earth that was washed with ethanol. The filtrate was concentrated in vacuo to give the titled compound.

Step 3: 3-cyclobutyl-4-[4-(methoxymethyl)piperidin-1-yl]-1-(2-methylpyridin-4-yl)-1H-pyrazolo[3,4-b]pyridine-6-carboxylic Acid The previous compound (50 mg, 0.1 mmol) was dissolved ethanol (5 mL), and aqueous 1 N sodium hydroxide (0.5 mL, 0.5 mmol) was added at RT. The solution was stirred for 16 hours. A phosphate buffer was added (pH 6.2). The solvent was partially removed under reduced pressure, and the resulting mixture was extracted twice with chloroform. The combined organic phases were dried over magnesium sulfate, filtered and concentrated under reduced pressure to give the titled compound.

Synthesis of AC13: 4-[1-(ethoxycarbonyl)piperidin-4-yl]-1-(4-fluorophenyl)-3-(propan-2-yl)-1H-pyrazolo[3,4-b]pyridine-6-carboxylic Acid

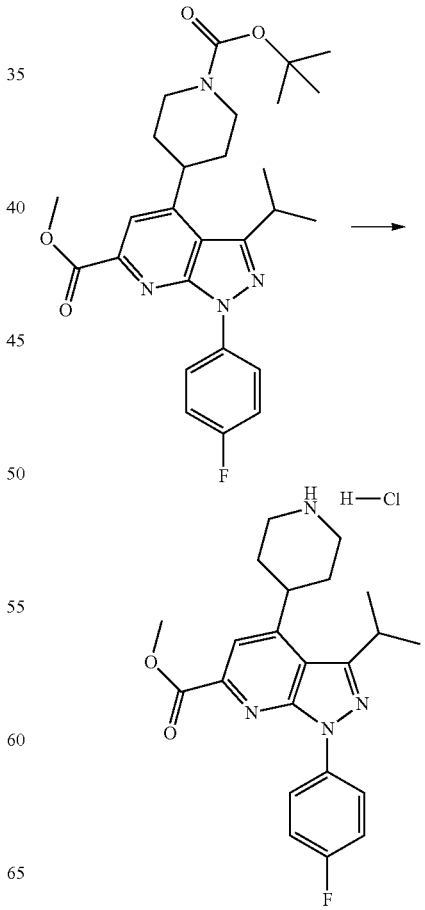

919

-continued

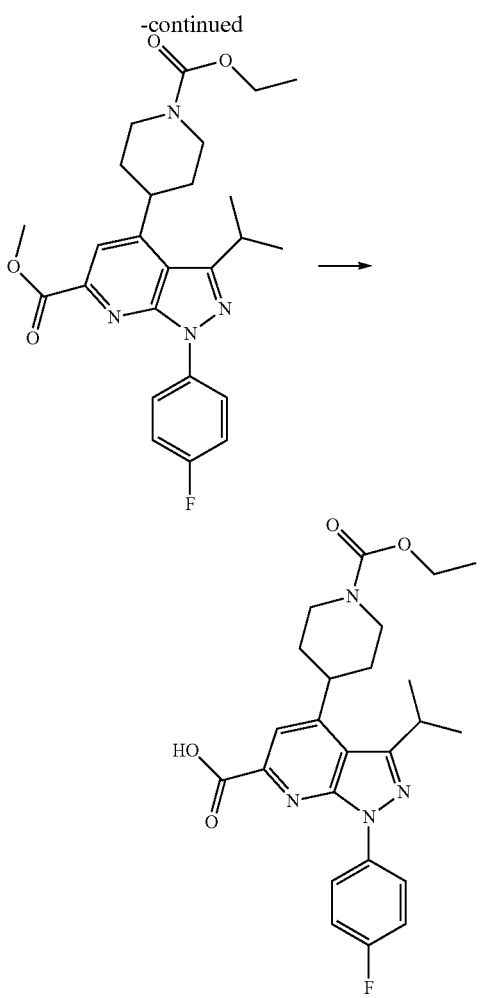

→

Step 1: Methyl 1-(4-fluorophenyl)-4-(piperidin-4-yl)-3-(propan-2-yl)-1H-pyrazolo[3,4-b]pyridine-6-carboxylate Hydrogen Chloride (1/1) HCl Salt E197 (1.7 g, 3.42 mmol) was dissolved into 4 M HCl in dioxane (25.7 mL, 102 mmol), stirred at room temperature for two hours, and then concentrated in vacuo to give the titled compound.

Step 2: Methyl 4-[1-(ethoxycarbonyl)piperidin-4-yl]-1-(4-fluorophenyl)-3-(propan-2-yl)-1H-pyrazolo[3,4-b]pyridine-6-carboxylate Ethyl chloroformate (67 μL, 0.7 mmol) was added dropwise at RT to a stirring solution of the compound from Step 1 (200 mg, 0.42 mmol) and DIPEA (294 μL, 1.7 mmol) in anhydrous DCM (2 mL). The reaction was complete after 2 hours. The reaction solution was diluted with DCM (10 mL) and washed with water (5 mL). The organic phase was dried over sodium sulfate, filtered and concentrated under reduced pressure to give the titled compound.

Step 3: 4-[1-(ethoxycarbonyl)piperidin-4-yl]-1-(4-fluorophenyl)-3-(propan-2-yl)-1H-pyrazolo[3,4-b]pyridine-6-carboxylic Acid The compound from Step 2 (196 mg, 0.42 mmol) was dissolved in THF (5 mL) and aqueous 2 N sodium hydroxide (1.05 mL, 2.1 mmol) was added at RT. The solution was stirred for 20 hours. The resulting mixture was diluted with water (10 mL) and then acidified with aqueous 2 N HCl (1.05 mL). The aqueous phase was extracted twice with DCM. The combined organic phases were dried over sodium sulfate, filtered, and concentrated under reduced pressure to give the titled compound.

TABLE XVa

List of intermediate acylsulfonamides

| Int. | Structure | Name | SM | method | MW | Mes |
|---|---|---|---|---|---|---|
| AC01 | 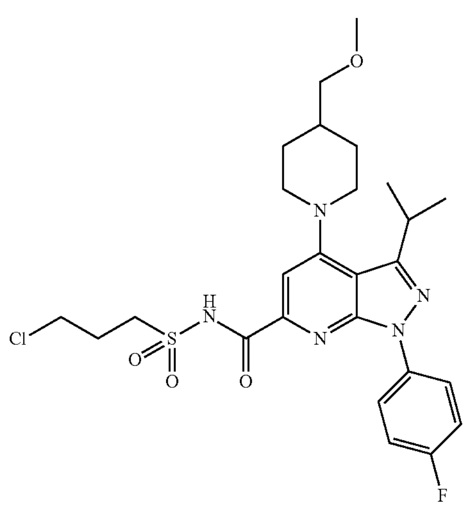 [SMILES: COCC1CCN(c2cc(C(=O)NS(=O)(=O)CCCCl)nc3c2c(C(C)C)nn3-c2ccc(F)cc2)CC1] | N-(3-chloropropane-1-sulfonyl)-1-(4-fluorophenyl)-4-[4-(methoxymethyl)piperidin-1-yl]-3-(propan-2-yl)-1H-pyrazolo[3,4-b]pyridine-6-carboxamide | A124, 35578-28-0 | Y1 | 566 | 567 |

TABLE XVa-continued

List of intermediate acylsulfonamides

| Int. | Structure | Name | SM | method | MW | Mes |
|---|---|---|---|---|---|---|
| AC02 | 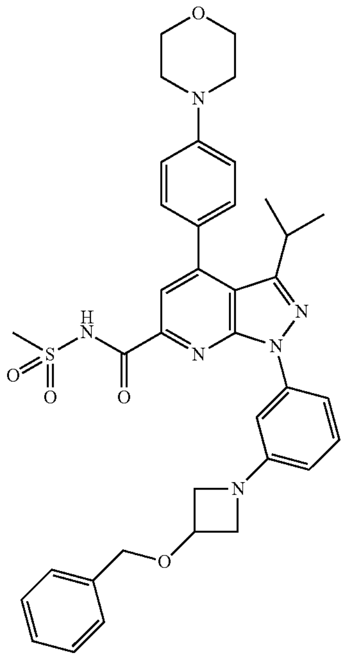 [SMILES: CC(C)c1nn(-c2cccc(N3CC(OCc4ccccc4)C3)c2)c2nc(C(=O)NS(C)(=O)=O)cc(-c3ccc(N4CCOCC4)cc3)c12] | 1-{3-[3-(benzyloxy)azetidin-1-yl]phenyl}-N-(methanesulfonyl)-4-[4-(morpholin-4-yl)phenyl]-3-(propan-2-yl)-1H-pyrazolo[3,4-b]pyridine-6-carboxamide | A252, 3144-09-0 | Y1 | 680 | 681 |
| AC03 | 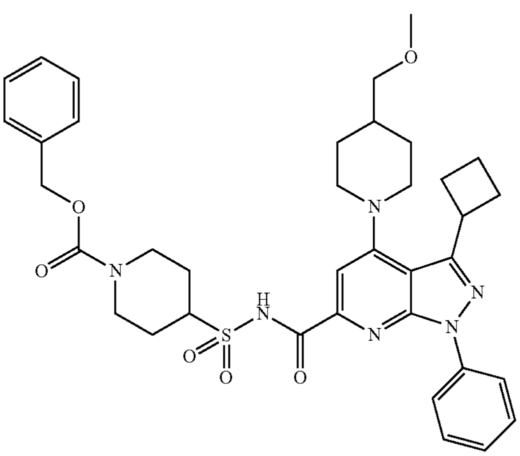 [SMILES: COCC1CCN(c2cc(C(=O)NS(=O)(=O)C3CCN(C(=O)OCc4ccccc4)CC3)nc3c2c(C2CCC2)nn3-c2ccccc2)CC1] | benzyl 4-({3-cyclobutyl-4-[4-methoxymethyl)piperidin-1-yl]-1-phenyl-1H-pyrazolo[3,4-b]pyridine-6-carbonyl}sulfamoyl)piperidine-1-carboxylate | A136, S9 | Y1 | 700 | 701 |
| AC04 | 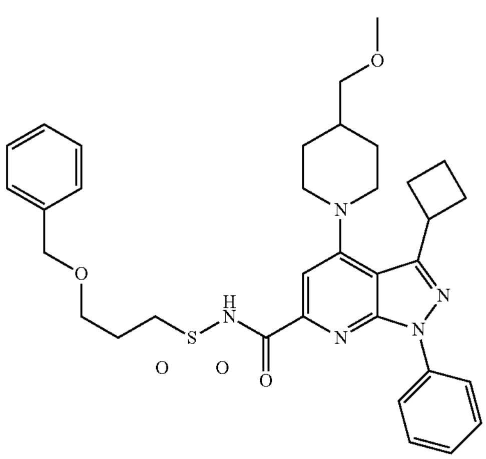 | N-[3-(benzyloxy)propane-1-sulfonyl]-3-cyclobutyl-4-[4-(methoxymethyl)piperidin-1-yl]-1-phenyl-1H-pyrazolo[3,4-b]pyridine-6-carboxamide | A136, 1408646-99-0 | Y1 | 631 | 632 |

TABLE XVa-continued

List of intermediate acylsulfonamides

| Int. | Structure | Name | SM | method | MW | Mes |
|---|---|---|---|---|---|---|
| AC05 | 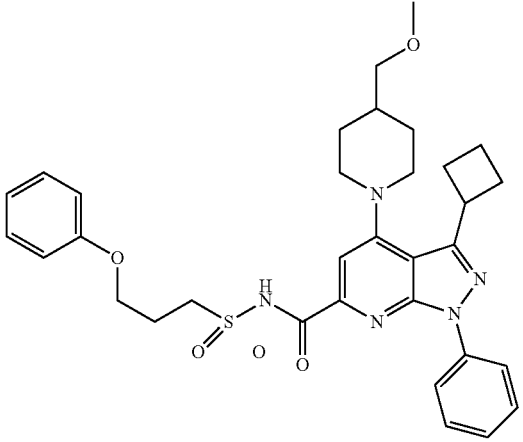 | N-[2-(benzyloxy)ethanesulfonyl]-3-cyclobutyl-4-[4-(methoxymethyl)piperidin-1-yl]-1-phenyl-1H-pyrazolo[3,4-b]pyridine-6-carboxamide | A136, 881407-21-2 | Y1 | 617 | 618 |
| AC06 | 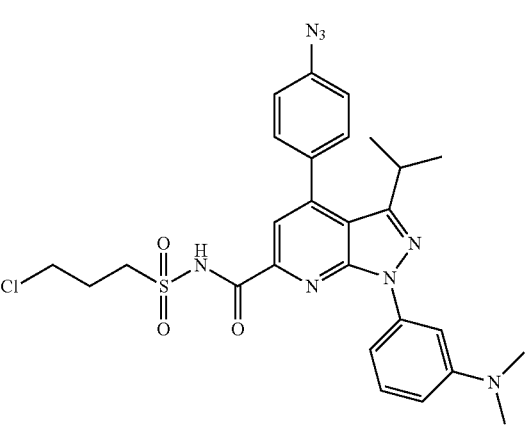 [SMILES: CC(C)c1nn(-c2cccc(N(C)C)c2)c2nc(C(=O)NS(=O)(=O)CCCCl)cc(-c3ccc(N=[N+]=[N-])cc3)c12] | 4-(4-azidophenyl)-N-(3-chloropropane-1-sulfonyl)-1-[3-(dimethylamino)phenyl]-3-(propan-2-yl)-1H-pyrazolo[3,4-b]pyridine-6-carboxamide | A238, 35578-28-0 | Y1 | 580 | 581 |
| AC07 | 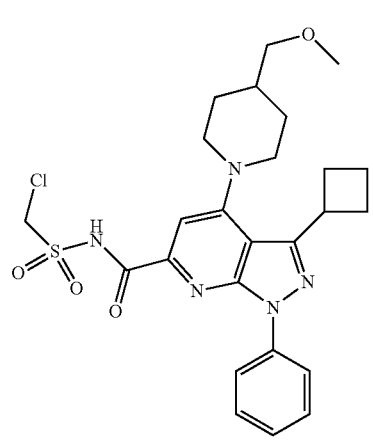 [SMILES: COCC1CCN(c2cc(C(=O)NS(=O)(=O)CCl)nc3c2c(C2CCC2)nn3-c2ccccc2)CC1] | N-(chloromethanesulfonyl)-3-cyclobutyl-4-[4-(methoxymethyl)piperidin-1-yl]-1-phenyl-1H-pyrazolo[3,4-b]pyridine-6-carboxamide | A136 | Y1 | 532-534 | 533-535 |

TABLE XVa-continued

List of intermediate acylsulfonamides

| Int. | Structure | Name | SM | method | MW | Mes |
|---|---|---|---|---|---|---|
| AC08 | 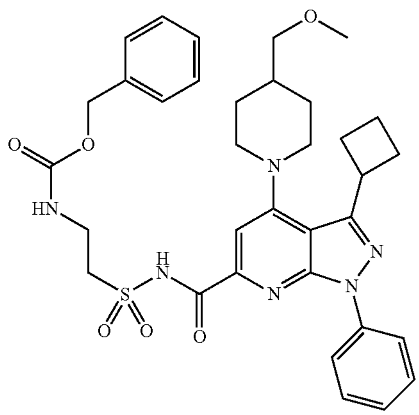 [SMILES: COCC1CCN(c2cc(C(=O)NS(=O)(=O)CCNC(=O)OCc3ccccc3)nc3c2c(C2CCC2)nn3-c2ccccc2)CC1] | benzyl [2-({3-cyclobutyl-4-[4-(methoxymethyl)piperidin-1-yl]-1-phenyl-1H-pyrazolo[3,4-b]pyridine-6-carbonyl}sulfamoyl)ethyl]-carbamate | A136, S5 | Y1 | 660 | 661 |
| AC09 | 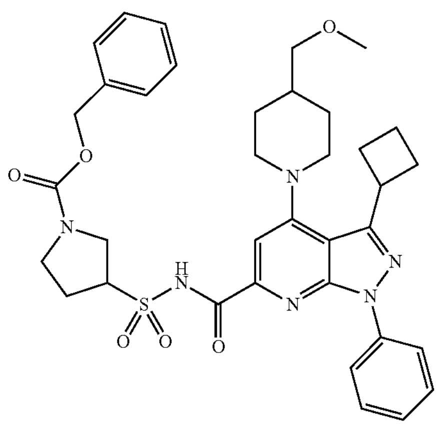 [SMILES: COCC1CCN(c2cc(C(=O)NS(=O)(=O)C3CCN(C(=O)OCc4ccccc4)C3)nc3c2c(C2CCC2)nn3-c2ccccc2)CC1] | benzyl 3-({3-cyclobutyl-4-[4-(methoxymethyl)piperidin-1-yl]-1-phenyl-1H-pyrazolo[3,4-b]pyridine-6-carbonyl}sulfamoyl)-pyrrolidine-1-carboxylate | A136, S7 | Y1 | 686 | 687 |
| AC10 | 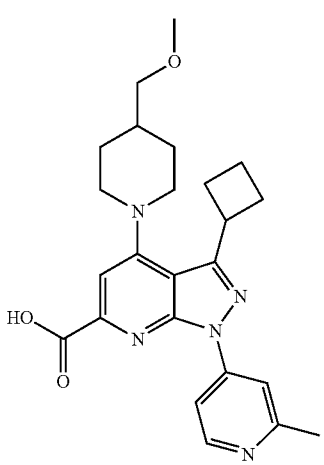 [SMILES: COCC1CCN(c2cc(C(=O)O)nc3c2c(C2CCC2)nn3-c2ccnc(C)c2)CC1] | 3-cyclobutyl-4-[4-(methoxymethyl)piperidin-1-yl]-1-(2-methylpyridin-4-yl)-1H-pyrazolo[3,4-b]pyridine-6-carboxylic acid | E168 | Specific example | 435 | 436 |

TABLE XVa-continued

List of intermediate acylsulfonamides

| Int. | Structure | Name | SM | method | MW | Mes |
|---|---|---|---|---|---|---|
| AC11 | 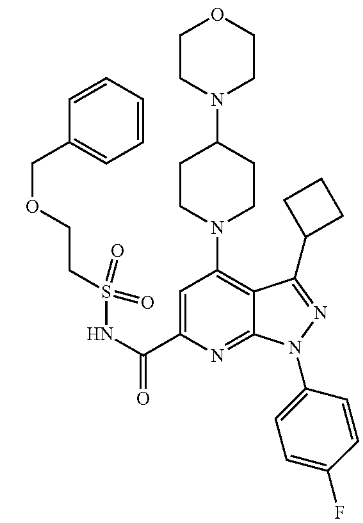 [SMILES: O=C(NS(=O)(=O)CCOCc1ccccc1)c1cc(N2CCC(N3CCOCC3)CC2)c2c(C3CCC3)nn(-c3ccc(F)cc3)c2n1] | N-[2-(benzyloxy)ethanesulfonyl]-3-cyclobutyl-1-(4-fluorophenyl)-4-[4-(morpholin-4-yl)piperidin-1-yl]-1H-pyrazolo[3,4-b]pyridine-6-carboxamide | A308 | Y1 | 676 | 677 |
| AC12 | 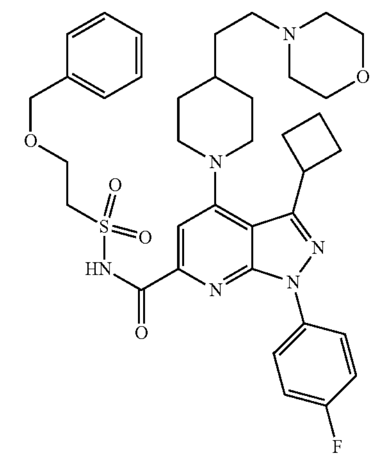 [SMILES: O=C(NS(=O)(=O)CCOCc1ccccc1)c1cc(N2CCC(CCN3CCOCC3)CC2)c2c(C3CCC3)nn(-c3ccc(F)cc3)c2n1] | N-[2-(benzyloxy)ethanesulfonyl]-3-cyclobutyl-1-(4-fluorophenyl)-4-{4-[2-(piperidin-1-yl)ethyl]-piperidin-1-yl}-1H-pyrazolo[3,4-b]pyridine-6-carboxamide | A311 | Y1 | 704 | 705 |
| AC13 | 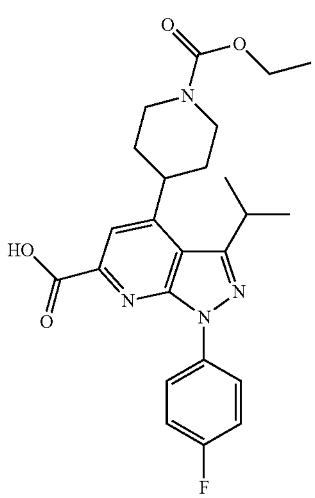 [SMILES: CCOC(=O)N1CCC(c2cc(C(=O)O)nc3c2c(C(C)C)nn3-c2ccc(F)cc2)CC1] | 4-[1-(ethoxycarbonyl)piperidin-4-yl]-1-(4-fluorophenyl)-3-(propan-2-yl)-1H-pyrazolo[3,4-b]pyridine-6-carboxylic acid | E197 | Specific example | 454 | 455 |

TABLE XVa-continued

List of intermediate acylsulfonamides

| Int. | Structure | Name | SM | method | MW | Mes |
|---|---|---|---|---|---|---|
| AC14 | 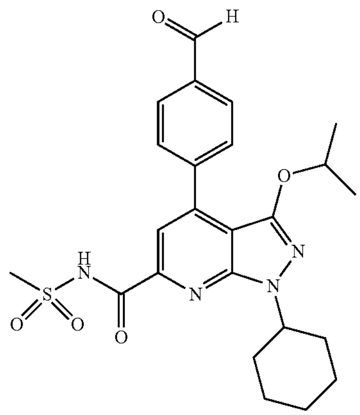 [SMILES: CC(C)Oc1nn(C2CCCCC2)c2nc(C(=O)NS(C)(=O)=O)cc(-c3ccc(C=O)cc3)c12] | 1-cyclohexyl-4-(4-formylphenyl)-N-(methanesulfonyl)-3-[(propan-2-yl)oxy]-1H-pyrazolo[3,4-b]pyridine-6-carboxamide | A350 | Y1 | 484 | 485 |
| AC15 | 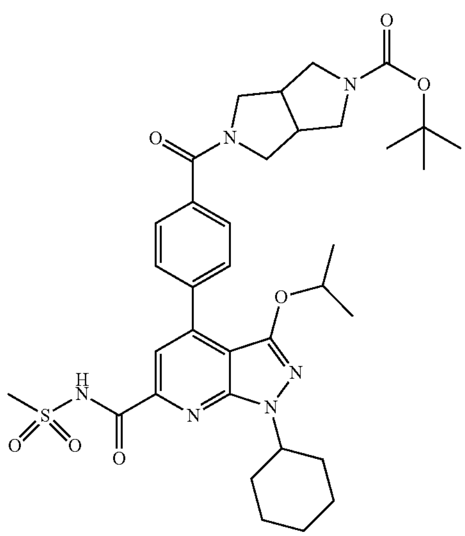 [SMILES: CC(C)Oc1nn(C2CCCCC2)c2nc(C(=O)NS(C)(=O)=O)cc(-c3ccc(C(=O)N4CC5CN(C(=O)OC(C)(C)C)CC5C4)cc3)c12] | tert-butyl 5-(4-{1-cyclohexyl-6-[(methanesulfonyl)carbamoyl]-3-[(propan-2-yl)oxy]-1H-pyrazolo[3,4-b]pyridin-4-yl}benzoyl)hexahydro-pyrrolo[3,4-c]pyrrole-2(1H)-carboxylate | A351 | Y1 | 694 | 695 |
| AC16 | 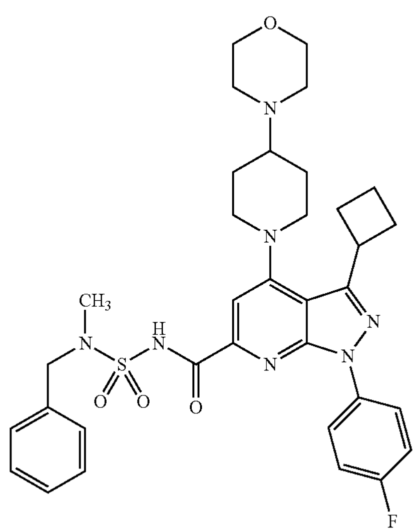 [SMILES: CN(Cc1ccccc1)S(=O)(=O)NC(=O)c1cc(N2CCC(N3CCOCC3)CC2)c2c(C3CCC3)nn(-c3ccc(F)cc3)c2n1] | N-[benzyl(methyl)sulfamoyl]-3-cyclobutyl-1-(4-fluorophenyl)-4-[4-(morpholin-4-yl)piperidin-1-yl]-1H-pyrazolo[3,4-b]pyridine-6-carboxamide | A308, 15205-37-5 | Y8 | 662 | 662 |

TABLE XVa-continued

List of intermediate acylsulfonamides

| Int. | Structure | Name | SM | method | MW | Mes |
|---|---|---|---|---|---|---|
| AC17 | 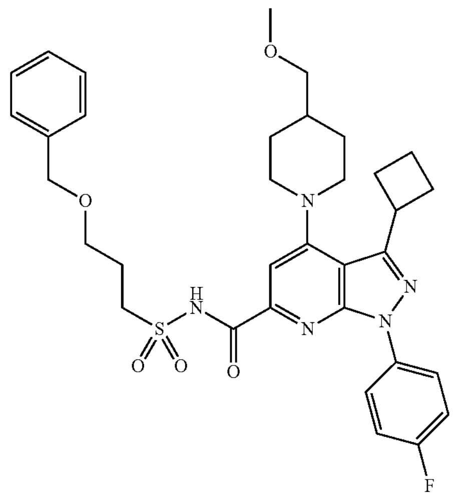 [SMILES: COCC1CCN(c2cc(C(=O)NS(=O)(=O)CCCOCc3ccccc3)nc3c2c(C2CCC2)nn3-c2ccc(F)cc2)CC1] | N-[3-(benzyloxy)propane-1-sulfonyl]-3-cyclobutyl-1-(4-fluorophenyl)-4-[4-(methoxymethyl)piperidin-1-yl]-1H-pyrazolo[3,4-b]pyridine-6-carboxamide | A202, 1408646-99-0 | Y1 | 649 | 650 |

Lengthy table referenced here

US10259810-20190416-T00001

Please refer to the end of the specification for access instructions.

Lengthy table referenced here

US10259810-20190416-T00002

Please refer to the end of the specification for access instructions.

Determination of Biological Activity

Cellular Assays

Measuring CFTR Cell Surface Expression of CFTR-ΔF508 Using PathHunter® U2OS CFTR-ΔF508 Cells The PathHunter® U2OS CFTR-ΔF508 cell assay (DiscoveRx) measures the expression of CFTR-ΔF508 at the plasma membrane. CFTR-ΔF508 has a folding defect leading to absence of protein at the plasma membrane. This assay is used to evaluate the capacity of compounds to increase the expression of CFTR-ΔF508 at the plasma membrane. The CFTR-ΔF508 is tagged with a ProLink™ peptide which can complement with plasma membrane expressed enzyme acceptor protein (EA-MEM). When both the ProLink™ and EA-MEM acceptor are in close proximity, i.e. both are located at the plasma membrane; a functional enzyme is formed of which the activity can be measured. The amount of CFTR-ΔF508 that can be rescued to the plasma membrane is correlated with the amount of functional enzyme that can be measured.

There are several ways to measure the capacity of compounds to rescue CFTR-ΔF508 to the plasma membrane; either compounds are evaluated on their own and the impact on plasma membrane levels is measured or compounds are evaluated in combination with a co-corrector, i.e. a compound that rescues CFTR-ΔF508 to the plasma membrane but rescue can be enhanced by addition of compounds due to a complementary mode of action.

Activity of Compounds in Combination with Co-Corrector:

For this purpose, PathHunter® U2OS CFTR-ΔF508 cells (DiscoveRx; custom made were cultured in AssayComplete™ U2OS Cell Culture medium (DiscoveRx; 92-0018GK3) as per manufacturer's instructions. For compound testing, cells were seeded in white 384-well plates (Greiner; 781080) at five thousand cells/well in 25 μL AssayComplete™ Cell Plating 5 Reagent (DiscoveRx; 93-0563R5A) and incubated overnight at 37° C., 5% $CO_2$. On day two, 5 L of test compounds diluted in Cell Plating 5 Reagent were added to the cells with a final dimethyl sulfoxide (DMSO) concentration of 0.1%. In order to measure synergy with a co-corrector (3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid), 3 μM of co-corrector was added along with test compounds. All cell plates contained 3 μM of co-corrector or DMSO as positive and negative controls, respectively. Cells were incubated with compounds for twenty to twenty-four hours at 37° C., 5% $CO_2$. On day three, plates were placed at room temperature for thirty minutes and then 15 μL of substrate (PathHunter® Flash Detection Kit, DiscoveRx; 93-0247) was added per well. After one hour of incubation at room temperature in the dark, the luminescence signal was measured on a plate reader (Envision®, Perkin Elmer). Raw data were normalized to percentage activity values using the equation: 100× (Sample−Negative control)/(Positive control−Negative Control).

Activity of Compounds for their Intrinsic Corrector Capacity:

For this purpose PathHunter® U2OS CFTR-ΔF508 cells (DiscoveRx; custom made as described above) were cultured in AssayComplete™ U2OS Cell Culture medium (DiscoveRx; 92-0018GK3) as per manufacturer's instructions. For compound testing, cells were seeded in white 384-well plates (Greiner; 781080) at five thousand cells/well in 25 μL AssayComplete™ Cell Plating 5 Reagent (DiscoveRx; 93-0563R5A) and incubated overnight at 37° C., 5%

CO$_2$. On day two, 5 μL of test compounds diluted in Cell Plating 5 Reagent were added to the cells with a final DMSO concentration of 0.1%. All cell plates contained 3 μM corrector (3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) or DMSO as positive and negative controls, respectively. Cells were incubated with compounds for twenty to twenty-four hours at 37° C., 5% CO$_2$. On day three, plates were placed at room temperature for thirty minutes and then 15 L of substrate (PathHunter® Flash Detection Kit, DiscoveRx; 93-0247) was added per well. After one hour of incubation at room temperature in the dark, the luminescence signal was measured on a plate reader (Envision®, Perkin Elmer). Raw data were normalized to percentage activity values using the equation: 100×(Sample−Negative control)/(Positive control−Negative Control).

Activity of Compounds in Presence of Human Serum

To evaluate the impact of plasma protein binding of compounds on their biological activity, the PathHunter® U2OS CFTR-ΔF508 assay was run in the presence of 40% human serum (Sigma; H4522). For this purpose PathHunter® U2OS CFTR-ΔF508 cells (DiscoveRx; custom made) were cultured in AssayComplete™ U2OS Cell Culture medium (DiscoveRx; 92-0018GK3) as per manufacturer's instructions. For compound testing, cells were seeded in white 384-well plates (Greiner; 781080) at five thousand cells/well in 25 μL AssayComplete™ Cell Plating 5 Reagent (DiscoveRx; 93-0563R5A) containing 40% human serum and incubated overnight at 37° C., 5% CO$_2$. On day two, 5 μL of test compounds diluted in Cell Plating 5 Reagent were added to the cells with a final DMSO concentration of 0.1%. All cell plates contained 3 μM corrector (4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) or DMSO as positive and negative controls respectively. Cells were incubated with compounds for twenty to twenty-four hours at 37° C., 5% CO$_2$. On day three, plates were placed at room temperature for thirty minutes, and then 15 L of substrate (PathHunter® Flash Detection Kit, DiscoveRx; 93-0247) was added per well. After one hour of incubation at room temperature in the dark, the luminescence signal was measured on a plate reader (Envision®, Perkin Elmer). Raw data were normalized to percentage activity values using the equation: 100×(Sample−Negative control)/(Positive control−Negative Control).

Activity of Compounds in Presence of Human Serum

To evaluate the impact of plasma protein binding of compounds on their biological activity, the PathHunter® U2OS CFTR-ΔF508 was run in the presence of 40% human serum (Sigma; H4522). For this purpose PathHunter® U2OS CFTR-ΔF508 cells (DiscoveRx; custom made) were cultured in AssayComplete™ U2OS Cell Culture medium (DiscoveRx; 92-0018GK3) as per manufacturer's instructions. For compound testing, cells were seeded in white 384-well plates (Greiner; 781080) at five thousand cells/well in 25 μL AssayComplete™ Cell Plating 5 Reagent (DiscoveRx; 93-0563R5A) and incubated overnight at 37° C., 5% CO$_2$. On day two, the medium was replaced with 25 μL of primary human airway epithelial cell air-liquid interface medium or ALI medium, a 50:50 mixture of DMEM (Dulbecco's Modified Eagle Medium, Invitrogen; 41966-029) and LHC Basal Medium (Invitrogen; 12677-019) with additives as described in Table XVII) and containing 40% human serum. One hour later, 5 μL of test compounds diluted in ALI medium were added to the cells with a final DMSO concentration of 0.1%. All cell plates contained 3 μM corrector (4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) or DMSO as positive and negative controls respectively. Cells were incubated with compounds for twenty to twenty-four hours at 37° C., 5% CO$_2$. On day three, plates were placed at room temperature for thirty minutes and then washed twice with PBS (phosphate buffered saline) followed by the addition of 15 μL of substrate (PathHunter® Flash Detection Kit, DiscoveRx; 93-0247) per well. After one hour of incubation at room temperature in the dark, the luminescence signal was measured on a plate reader (Envision®, Perkin Elmer). Raw data were normalized to percentage activity values using the equation: 100×(Sample−Negative control)/(Positive control−Negative Control).

TABLE XVII

| Ingredient | Final concentration in medium | Provider | Cat# |
|---|---|---|---|
| BSA | 0.5 mg/mL | Sigma | A7638 |
| bovine pituitary extract | 10 μg/mL | Sigma | P1476 |
| Insulin | 0.87 μM | Sigma | I9278 |
| transferrin | 0.125 μM | Sigma | T0665 |
| hydrocortisone | 0.21 μM | Sigma | H0396 |
| triiodothyronine | 0.01 μM | Sigma | T6397 |
| Epinephrine | 0.01 μM | Sigma | E4250 |
| epidermal growth factor | 5 ng/mL | Invitrogen | PHG0313 |
| All-trans retinoic acid | $5 \times 10^{-8}$ M | Sigma | R-2625 |
| o-Phosphoethanolamine | 0.5 μM | Sigma | P-0503 |
| ethanolamine | 0.5 μM | Sigma | E0135 |
| zinc sulfate (ZnSO4•7H2O) | 3.0 μM | Sigma | Z0251 |
| pen/strep | 100 U/mL | Sigma | 15140-122 |
| ferrous sulfate | $1.5 \times 10^{-6}$ M | Sigma | F8048 |
| magnesium chloride hexahydrate | $6 \times 10-4$ | Sigma | M2670 |
| calcium chloride dihydrate | $1.1 \times 10^{-4}$ M | Fluka | 21097 |
| Trace elements: | — | | |
| sodium selenite | 30 nM | Sigma | S5261 |
| manganese chloride tetrahydrate | 1 nM | Sigma | M8054 |
| sodium metasilicate nonahydrate | 500 nM | Sigma | S5904 |
| ammonium molybdate tetrahydrate | 1 nM | Sigma | M1019 |
| ammonium metavanadate | 5 nM | Sigma | 398128 |
| nickel(II)sulfate hexahydrate | 1 nM | Fluka (Sigma) | 72280 (N4882) |
| tin(II) chloride dihydrate | 0.5 nM | Sigma | 243523 |

Measuring CFTR Cell Surface Levels Using HRP-Tagged ΔF508-CFTR Expressing CFBE Cells The HRP-tagged ΔF508-CFTR cell assay measures the expression of CFTR-ΔF508 at the plasma membrane. CFTR-ΔF508 has a folding defect leading to absence of protein at the plasma membrane. This assay is used to evaluate the capacity of compounds to increase the expression of CFTR-ΔF508 at the plasma membrane. The CFTR-ΔF508 is tagged with HRP (horse radish peroxidase enzyme) within the ECL4 (Extracellular loop 4) of CFTR (Phuan, P.-W. et al. Synergy-based small-molecule screen using a human lung epithelial cell line yields ΔF508-CFTR correctors that augment VX-809 maximal efficacy. *Mol. Pharmacol.* 86, 42-51 (2014)). When HRP-tagged ΔF508-CFTR is present at the plasma membrane, the HRP enzyme activity can be measured. The amount of CFTR-ΔF508 that can be rescued to the plasma membrane is correlated with the amount of functional enzyme that can be measured.

There are several ways to measure the capacity of compounds to rescue CFTR-ΔF508 to the plasma membrane;

either compounds are evaluated on their own and the impact on plasma membrane levels is measured or compounds are evaluated in combination with a co-corrector, i.e. a compound that rescues CFTR-ΔF508 to the plasma membrane but rescue can be enhanced by addition of compounds due to a complementary mode of action.

Activity of Compounds in Combination with Co-Corrector:

For this purpose doxycycline-inducible ΔF508-CFTR-HRP expressing CFBE4lo− cells (obtained from Gergely Lukacs, McGill University) were maintained in MEM (Minimum Essential Medium, Gibco; 31095) supplemented with 10% fetal bovine serum (Hyclone; SV30160.03) under puromycin (3 μg/mL) and G418 selection (0.2 mg/mL). For compound testing, cells were seeded at 4000 cells/well in white 384-well plates (Greiner; 781080) in 50 μL of medium containing 0.5 μg/mL doxycycline and incubated for 68 hours at 37° C., 5% $CO_2$. On day four, 10 μL of test compounds diluted in PBS (phosphate buffered saline) were added to the plates at a final DMSO concentration of 0.1%. In order to measure compound synergy with a co-corrector, 3 μM co-corrector (3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid) was added along with test compounds. All compound plates contained negative controls (DMSO) and positive controls (3 μM co-corrector). Cell plates were incubated at 33° C., 5% $CO_2$ for 20 hours. On day five, the cells were washed five times with phosphate-buffered saline, and HRP activity was assayed by the addition of 50 μL/well of HRP substrate (SuperSignal™ West Pico Chemiluminescent Substrate, Thermo Scientific; 34080). After incubation for 15 minutes in the dark, the chemiluminescence was measured using a plate reader (EnVision®, Perkin Elmer). Raw data were normalized to percentage activity values using the equation: 100×(Sample−Negative control)/(Positive control−Negative Control).

TABLE XVIII

Illustrative $EC_{50}$ measured by CFTR cell surface levels using HRP-tagged ΔF508-CFTR expressing CFBE cells in the presence of a co-corrector.

| Compound # | % Activation | $EC_{50}$ (nM) |
| --- | --- | --- |
| 1 | 297.2 | 1186 |
| 2 | 431.5 | 1122 |
| 4 | 405.8 | 297.9 |
| 5 | 362.75 | 371.75 |
| 6 | 387.1 | 510.7 |
| 7 | 420.63 | 554.03 |
| 8 | 441.85 | 853.8 |
| 9 | 335 | 505.05 |
| 10 | 606.5 | 442.65 |
| 11 | 381.33 | 455.35 |
| 12 | 364.15 | 713.8 |
| 13 | 341.75 | 1471 |
| 14 | 335.6 | 1368 |
| 15 | 346.15 | 852.15 |
| 16 | 649.9 | 458.65 |
| 17 | 320 | 1120 |
| 18 | 217.8 | 1110 |
| 19 | 304.05 | 1632.5 |
| 20 | 417.5 | 545.9 |
| 21 | 440.1 | 525.3 |
| 22 | 371.55 | 502.6 |
| 23 | 468.85 | 573.35 |
| 24 | 380.5 | 743.95 |
| 25 | 437.17 | 640.17 |
| 26 | 449.7 | 1548 |
| 27 | 365.2 | 714 |
| 28 | 354.45 | 942.15 |
| 29 | 591.4 | 823.7 |
| 30 | 580.97 | 215.37 |
| 31 | 423.27 | 203.8 |
| 32 | 526 | 234 |
| 33 | 315.6 | 470.95 |
| 34 | 462.55 | 355.9 |
| 35 | 509.7 | 348.4 |
| 36 | 572.93 | 245.77 |
| 37 | 457.25 | 1163.1 |
| 38 | 447.7 | 581.23 |
| 39 | 378.63 | 507.77 |
| 40 | 373.43 | 422.67 |
| 41 | 253.3 | 1141 |
| 42 | 226.3 | 378.5 |
| 43 | 627 | 289.4 |
| 44 | 412.63 | 276.27 |
| 45 | 438.4 | 202.94 |
| 46 | 643.27 | 445.83 |
| 47 | 408.77 | 1604.3 |
| 48 | 417.8 | 1152.5 |
| 49 | 338 | 1996.7 |
| 50 | 300 | 1075.5 |
| 51 | 420.67 | 311.5 |
| 52 | 257.85 | 992.4 |
| 53 | 572.78 | 647.2 |
| 54 | 593.12 | 463.62 |
| 55 | 341.65 | 1047.4 |
| 56 | 336.75 | 838.1 |
| 57 | 440 | 657.2 |
| 58 | 352.5 | 421.8 |
| 59 | 534.8 | 482.5 |
| 60 | 323.63 | 351.47 |
| 61 | 415.3 | 506.2 |
| 62 | 631.2 | 531.8 |
| 63 | 368.48 | 285.56 |
| 64 | 362.45 | 443.65 |
| 65 | 332.05 | 463.55 |
| 66 | 332.85 | 6670 |
| 67 | 371.62 | 241.18 |
| 68 | 456.6 | 847.1 |
| 69 | 362.03 | 403.63 |
| 70 | 342.85 | 409.6 |
| 71 | 447.8 | 263.55 |
| 72 | 400.9 | 5611 |
| 73 | 423.35 | 490.05 |
| 74 | 424.82 | 357.1 |
| 75 | 387.16 | 290.54 |
| 76 | 581.37 | 632.67 |
| 77 | 449.85 | 831.2 |
| 78 | 520.7 | 660.5 |
| 79 | 501.6 | 555 |
| 80 | 457.5 | 389.5 |
| 81 | 646.44 | 253.16 |
| 82 | 535.93 | 383.03 |
| 83 | 567.7 | 424.5 |
| 84 | 468.2 | 408.1 |
| 85 | 570.16 | 232.1 |
| 86 | 489.56 | 255.04 |
| 87 | 623.62 | 456.46 |
| 88 | 546.2 | 412.73 |
| 89 | 609.48 | 396.26 |
| 90 | 384.95 | 388.85 |
| 91 | 619.45 | 890.95 |
| 92 | 367.67 | 278.4 |
| 93 | 456.5 | 270.4 |
| 94 | 421.53 | 341.9 |
| 95 | 611.7 | 649.15 |
| 96 | 707.5 | 473.05 |
| 97 | 692.82 | 277.25 |
| 98 | 360.15 | 393.3 |
| 99 | 601.15 | 336.8 |
| 100 | 340.6 | 3221 |
| 101 | 455.4 | 409.2 |
| 102 | 458.75 | 536.55 |
| 103 | 501.03 | 409.03 |
| 104 | 411.33 | 344.37 |
| 105 | 457.85 | 698.9 |

TABLE XVIII-continued

Illustrative EC$_{50}$ measured by CFTR cell surface levels using HRP-tagged ΔF508-CFTR expressing CFBE cells in the presence of a co-corrector.

| Compound # | % Activation | EC$_{50}$ (nM) |
|---|---|---|
| 106 | 348.1 | 393.95 |
| 107 | 219.4 | 3340 |
| 108 | 428.3 | 509.45 |
| 109 | 571.3 | 634.1 |
| 110 | 665.7 | 336.37 |
| 111 | 596.8 | 377.83 |
| 112 | 472.8 | 884.2 |
| 113 | 455.63 | 235.17 |
| 114 | 277.45 | 951.6 |
| 115 | 389.6 | 664.65 |
| 116 | 438.37 | 630.5 |
| 117 | 417.92 | 200 |
| 118 | 469 | 280 |
| 119 | 389.93 | 331.37 |
| 120 | 351.03 | 347.9 |
| 121 | 368.6 | 281.8 |
| 122 | 405.9 | 280.57 |
| 123 | 365.8 | 238.9 |
| 124 | 447.23 | 312.03 |
| 125 | 520.33 | 463.17 |
| 126 | 487.53 | 322.17 |
| 127 | 449.1 | 251.85 |
| 128 | 529.57 | 251.93 |
| 129 | 307.3 | 790.25 |
| 130 | 496.9 | 540.3 |
| 131 | 465.1 | 580.65 |
| 132 | 417.2 | 881.65 |
| 133 | 417.7 | 335.87 |
| 134 | 435.8 | 236.8 |
| 135 | 512.9 | 373.43 |
| 136 | 428.1 | 72.26 |
| 137 | 339.7 | 638.35 |
| 138 | 433.83 | 235.77 |
| 139 | 335.5 | 764.83 |
| 140 | 377.9 | 380.65 |
| 141 | 414.63 | 221.37 |
| 142 | 376.93 | 78.407 |
| 143 | 217.8 | 833.55 |
| 144 | 674.7 | 242.99 |
| 145 | 271.43 | 636.17 |
| 146 | 357.55 | 96.872 |
| 147 | 363.93 | 99.92 |
| 148 | 448.03 | 169.85 |
| 149 | 299.95 | 259.05 |
| 150 | 380.65 | 318.29 |
| 151 | 387.15 | 108.87 |
| 152 | 409.9 | 107.85 |
| 153 | 290.05 | 130.35 |
| 154 | 447.85 | 203.45 |
| 155 | 555.45 | 229.66 |
| 156 | 636.47 | 360.2 |
| 157 | 542.17 | 358.74 |
| 158 | 512.45 | 266.75 |
| 159 | 270.3 | 483.27 |
| 160 | 490.4 | 201.8 |
| 161 | 574.1 | 354.83 |
| 162 | 331.53 | 304.16 |
| 163 | 342.3 | 111.91 |
| 164 | 492.45 | 387.6 |
| 165 | 534.2 | 884.65 |
| 166 | 408.53 | 309.97 |
| 167 | 429.4 | 81.765 |
| 168 | 581.55 | 409.8 |
| 169 | 519.3 | 284.36 |
| 170 | 425.6 | 721.7 |
| 171 | 289.23 | 312.2 |
| 172 | 462.4 | 207.07 |
| 173 | 183.2 | 432.9 |
| 174 | 545 | 468.45 |
| 175 | 461.1 | 200.23 |
| 176 | 390.43 | 208.64 |
| 177 | 263.9 | 385.45 |
| 178 | 381.73 | 231.52 |
| 179 | 248.85 | 405.85 |
| 180 | 290.53 | 300.17 |
| 181 | 357.93 | 435.4 |
| 182 | 397.6 | 258.1 |
| 183 | 498.57 | 213.78 |
| 184 | 282.7 | 574.4 |
| 185 | 546.7 | 145.09 |
| 186 | 381.87 | 530.53 |
| 187 | 308.87 | 69.253 |
| 188 | 405.37 | 159.6 |
| 189 | 409.6 | 236.27 |
| 190 | 502.4 | 1240.4 |
| 191 | 317.93 | 161.26 |
| 192 | 254.6 | 865.7 |
| 193 | 341.37 | 589.17 |
| 194 | 427.45 | 370.65 |
| 195 | 387.47 | 191.69 |
| 196 | 387.1 | 231.43 |
| 197 | 390.8 | 193.94 |
| 198 | 321.57 | 465.7 |
| 199 | 304.63 | 316.4 |
| 200 | 318.27 | 94.83 |
| 201 | 379.9 | 292.47 |
| 202 | 299.4 | 254.83 |
| 203 | 224.63 | 328.1 |
| 204 | 288.6 | 490.35 |
| 205 | 416.4 | 856 |
| 206 | 387.03 | 890.4 |
| 207 | 284.87 | 174.71 |
| 208 | 419.15 | 363.65 |
| 209 | 393.6 | 230.87 |
| 210 | 390.57 | 173.74 |
| 211 | 288.3 | 292.9 |
| 212 | 290.43 | 324.03 |
| 213 | 469.6 | 336.5 |
| 214 | 250.55 | 383.85 |
| 215 | 569.35 | 47.87 |
| 216 | 456.1 | 299.5 |
| 217 | 418.27 | 257.13 |
| 218 | 476.9 | 238.67 |
| 219 | 524.4 | 230.26 |
| 220 | 389.9 | 207.87 |
| 221 | 492.2 | 77.24 |
| 222 | 247.3 | 1788.2 |
| 223 | 438.2 | 371 |
| 224 | 453.1 | 482 |
| 225 | 427.95 | 578.55 |
| 226 | 392.95 | 386.1 |
| 227 | 378.2 | 307.3 |
| 228 | 395.1 | 334.9 |
| 229 | 418.65 | 366.1 |
| 230 | 440.1 | 179.98 |
| 231 | 329.9 | 518.2 |
| 232 | 199.75 | 1726.5 |
| 233 | 206.57 | 1925.3 |
| 234 | 128.3 | >10000 |
| 235 | 257.55 | 2485 |
| 236 | 497.5 | 93.19 |
| 237 | 264.05 | 222.18 |
| 238 | 347.55 | 218.6 |
| 239 | 431.55 | 1235.2 |
| 240 | 312.8 | 138.7 |
| 241 | 488.15 | 82.165 |
| 242 | 459.15 | 202.77 |
| 243 | 204.1 | 3330 |
| 244 | 290.6 | 413.5 |
| 245 | 460 | 693.6 |
| 246 | 331.65 | 77.25 |
| 247 | 281.7 | 220.67 |
| 248 | 450.6 | 221.44 |
| 249 | 468.15 | 231.26 |
| 250 | 440.4 | 372 |
| 251 | 488.7 | 367 |
| 252 | 310.75 | 1691 |
| 253 | 454.4 | 250.85 |
| 254 | 312.1 | 370 |
| 255 | 365.8 | 3330 |

TABLE XVIII-continued

Illustrative EC$_{50}$ measured by CFTR cell surface levels using HRP-tagged ΔF508-CFTR expressing CFBE cells in the presence of a co-corrector.

| Compound # | % Activation | EC$_{50}$ (nM) |
|---|---|---|
| 256 | 508.63 | 147.3 |
| 257 | 451.25 | 74.3 |
| 258 | 127.1 | >10000 |
| 260 | 664.07 | 129.88 |
| 261 | 129.3 | >10000 |
| 262 | 420.17 | 523.02 |
| 263 | 475.45 | 403.78 |
| 264 | 478.6 | 3330 |
| 265 | 427.8 | 2138 |
| 266 | 328.87 | 230.63 |
| 267 | 433 | 57.095 |
| 268 | 122.05 | >10000 |
| 269 | 275.45 | 97.25 |
| 270 | 327.9 | 730.83 |
| 271 | 260.47 | 1016.5 |
| 272 | 451.2 | 43.33 |
| 273 | 344.05 | 111.1 |
| 274 | 300 | 398.1 |
| 275 | 269.85 | 138 |
| 276 | 417.25 | 42.905 |
| 277 | 355.4 | 127.1 |
| 278 | 388.5 | 88.315 |
| 279 | 530.6 | 227.4 |
| 280 | 323.37 | 1010.2 |
| 281 | 398.47 | 242.33 |
| 282 | 379.95 | 89.015 |
| 283 | 326.85 | 265.5 |
| 284 | 348.7 | 219.8 |
| 285 | 327.57 | 246 |
| 286 | 500.55 | 158.6 |
| 287 | 450.9 | 128.29 |
| 288 | 566.4 | 74.34 |
| 289 | 366.4 | 3330 |
| 290 | 382.2 | 535.7 |
| 291 | 420.07 | 590.9 |
| 292 | 422.55 | 564.7 |
| 293 | 317.1 | 479.7 |
| 294 | 548.45 | 22.065 |
| 295 | 298.07 | 697.2 |
| 296 | 329.13 | 167.8 |
| 297 | 423.43 | 77.2 |
| 298 | 481.2 | 81.025 |
| 299 | 267.2 | 2514.5 |
| 300 | 266.55 | 109.26 |
| 301 | 376.6 | 1136.4 |
| 302 | 401.45 | 1799.6 |
| 303 | 339.95 | 834.25 |
| 304 | 507 | 56.145 |
| 305 | 267 | 2443 |
| 306 | 321.1 | 82.395 |
| 307 | 299.25 | 1278.8 |
| 308 | 328.85 | 2492.5 |
| 309 | 303.6 | 224.05 |
| 310 | 251.5 | 923.65 |
| 311 | 241.35 | 1060.6 |
| 312 | 291.5 | 1882.5 |
| 313 | 319.75 | 1749 |
| 314 | 375.8 | 693.1 |
| 315 | 315.5 | 101.55 |
| 316 | 555.55 | 24.4 |
| 317 | 450.35 | 48.825 |
| 318 | 359.5 | 184.25 |
| 319 | 232 | 979.57 |
| 320 | 590.6 | 82.663 |
| 321 | 314.37 | 496.53 |
| 322 | 342.75 | 61.415 |
| 323 | 292.85 | 372.05 |
| 324 | 259.7 | 1635.4 |
| 325 | 309.8 | 152.6 |
| 326 | 325.3 | 729.7 |
| 327 | 433.9 | 99.9 |
| 328 | 554.2 | 185.7 |
| 329 | 318.4 | 777.1 |
| 330 | 285.4 | 124.3 |
| 331 | 546.05 | 38.185 |
| 332 | 448.25 | 624.3 |
| 336 | 232.42 | 282.15 |
| 337 | 532.3 | 30.55 |
| 338 | 344.25 | 945.55 |
| 339 | 295.5 | 402.1 |
| 340 | 319.2 | 785.8 |
| 341 | 165.4 | 3330 |
| 342 | 336.5 | 207.1 |
| 343 | 356.9 | 566.3 |
| 344 | 374.5 | 1061 |
| 345 | 301.1 | 222.8 |
| 346 | 375.1 | 253.45 |
| 347 | 301.15 | 54.26 |
| 348 | 468.65 | 723.5 |
| 349 | 327.9 | 424.45 |
| 350 | 274.6 | 286.95 |
| 351 | 232.5 | 81.07 |
| 352 | 158.4 | 2778 |
| 353 | 193.45 | 346.44 |
| 354 | 351 | 232.2 |
| 355 | 278.4 | 377.1 |
| 356 | 372 | 48.27 |
| 357 | 229.8 | 129.5 |
| 358 | 242.33 | 89.854 |
| 359 | 236.25 | 298.9 |
| 360 | 182.8 | 100.72 |
| 361 | 204.1 | 181.2 |
| 362 | 195.75 | 413.8 |
| 363 | 415.3 | 116.2 |
| 364 | 575 | 553 |
| 365 | 469.95 | 271.05 |
| 366 | 443.7 | 82.67 |
| 367 | 526.17 | 81.56 |
| 368 | 350.23 | 361 |
| 369 | 444 | 105.88 |
| 370 | 343.2 | 691.05 |
| 371 | 271.9 | 1926.5 |
| 372 | 615.7 | 2560 |
| 373 | 580.5 | 85.76 |
| 374 | 426.05 | 195.67 |
| 375 | 546.75 | 241.45 |
| 376 | 496.8 | 51.61 |
| 377 | 485.55 | 102.74 |
| 378 | 318.6 | 657.55 |
| 379 | 440.55 | 61.09 |
| 380 | 309.17 | 127.16 |
| 381 | 432.09 | 155.99 |
| 382 | 500.01 | 158.29 |
| 383 | 412.20 | 94.26 |
| 384 | 391.35 | 1443 |
| 385 | 393.53 | 64 |
| 386 | 385.05 | 684.75 |
| 387 | 168.9 | 160.7 |
| 388 | 364.5 | 195.93 |
| 389 | 305.1 | 297.3 |
| 390 | 350.17 | 139.8 |
| 391 | 441.15 | 85.535 |
| 392 | 421.4 | 138.66 |
| 393 | 533.65 | 20.77 |
| 394 | 366.87 | 47.877 |
| 395 | 327.95 | 126.69 |
| 396 | 385.8 | 55.037 |
| 397 | 381.8 | 48.963 |
| 398 | 324.03 | 73.623 |
| 399 | 388.77 | 44.157 |
| 400 | 365.43 | 156.83 |
| 401 | 595.1 | 61.98 |
| 402 | 471.42 | 116.35 |
| 403 | 507.35 | 25.628 |
| 404 | 370 | 125.8 |
| 405 | 326.9 | 101.86 |
| 406 | 311.35 | 181.65 |
| 407 | 494.15 | 124.02 |
| 408 | 466.58 | 199.45 |
| 409 | 481.1 | 108.14 |

TABLE XVIII-continued

Illustrative EC$_{50}$ measured by CFTR cell surface levels using HRP-tagged ΔF508-CFTR expressing CFBE cells in the presence of a co-corrector.

| Compound # | % Activation | EC$_{50}$ (nM) |
|---|---|---|
| 410 | 529.58 | 82.442 |
| 411 | 505 | 478.2 |
| 412 | 436.4 | 200.6 |
| 413 | 455.9 | 90.59 |
| 414 | 508.3 | 158.6 |
| 415 | 598 | 69.31 |
| 416 | 458.65 | 64.97 |
| 417 | 539.75 | 91.905 |
| 418 | 512.9 | 220.8 |
| 419 | 505.65 | 277.1 |
| 420 | 486.65 | 209.2 |
| 421 | 512.9 | 124.75 |
| 422 | 434.33 | 204.27 |
| 423 | 376.85 | 108.84 |
| 424 | 453.88 | 92.203 |
| 425 | 462.85 | 166.45 |
| 426 | 385.3 | 82.03 |
| 427 | 419.5 | 162.5 |
| 428 | 434.7 | 77.27 |
| 429 | 422.8 | 205.15 |
| 430 | 383.7 | 89.87 |
| 431 | 568.8 | 47.003 |
| 432 | 514.83 | 65.943 |
| 433 | 563.8 | 49.01 |
| 434 | 470.37 | 59.51 |
| 435 | 474.8 | 82.825 |
| 436 | 568.6 | 71.07 |
| 437 | 563.64 | 155.81 |
| 438 | 541.5 | 380.5 |
| 439 | 374.6 | 381 |
| 440 | 543.55 | 55.44 |
| 441 | 393.27 | 196.47 |
| 442 | 342 | 1110 |
| 443 | 332.5 | 183.9 |
| 444 | 361.3 | 235.1 |
| 445 | 671.25 | 59.11 |
| 446 | 669.9 | 77.435 |
| 447 | 543.1 | 64.69 |
| 448 | 431.1 | 180.75 |
| AC07 | 466.9 | 76.57 |
| 450 | 443.25 | 246.25 |
| 451 | 391 | 2102 |
| 452 | 478.25 | 941.8 |
| 453 | 385.1 | 319 |
| 454 | 430.2 | 639.4 |
| 456 | 457.7 | 93.273 |
| 457 | 508 | 139.41 |
| 458 | 282.8 | 920.4 |
| 459 | 388.87 | 96.053 |
| 460 | 306.75 | 505.05 |
| 461 | 364.1 | 177.2 |
| 462 | 495.1 | 106.85 |
| 463 | 490.6 | 194.5 |
| 464 | 423.3 | 170.38 |
| 465 | 293.15 | 360.35 |
| 466 | 522.47 | 64.097 |
| 467 | 229.15 | 270.35 |
| 468 | 443.05 | 524.2 |
| 469 | 469.4 | 125.4 |
| 470 | 485.5 | 114.8 |
| 471 | 446.07 | 122.4 |
| 472 | 399.79 | 249.47 |
| 473 | 370.7 | 43.935 |
| 474 | 390.2 | 524.45 |
| 475 | 289.95 | 112.32 |
| 476 | 355.65 | 151 |
| 477 | 536.7 | 34.725 |
| 478 | 476.7 | 126.64 |
| 479 | 524.1 | 108.95 |
| 480 | 545.77 | 87.11 |
| 481 | 285.65 | 154.25 |
| 482 | 436.4 | 61.63 |
| 483 | 438.2 | 56.15 |
| 484 | 485.6 | 142.1 |
| 485 | 399.1 | 90.217 |
| 486 | 569 | 180.5 |
| 487 | 404.63 | 68.97 |
| 488 | 488.15 | 682.55 |
| 489 | 280 | 241.2 |
| 490 | 303.9 | 692.6 |
| 491 | 490.9 | 487.8 |
| 492 | 483.4 | 43.91 |
| 493 | 480.78 | 94.585 |
| 494 | 551.8 | 37.085 |
| 495 | 469.08 | 66.152 |
| 496 | 374.65 | 242.9 |
| 497 | 378.25 | 287.65 |
| 498 | 456.3 | 95.12 |
| 499 | 439.6 | 71.165 |
| 500 | 330.05 | 84.215 |
| 501 | 403.55 | 124.3 |
| 502 | 383.8 | 176.9 |
| 503 | 433.2 | 404.7 |
| 504 | 404.8 | 210.05 |
| 505 | 389 | 54.11 |
| 506 | 308.95 | 941.25 |
| 507 | 580.4 | 95.4 |
| 508 | 448.8 | 90.31 |
| 509 | 527.9 | 118.4 |
| 510 | 428.8 | 170.9 |
| 511 | 432.95 | 78.94 |
| 512 | 415.25 | 65.265 |
| 513 | 476.3 | 66.74 |
| 514 | 540.3 | 97.07 |
| 515 | 479.2 | 52.88 |
| 516 | 545.3 | 56.56 |
| 517 | 520.08 | 75.79 |
| 518 | 189.55 | 3125.5 |
| 519 | 252.3 | 1023.3 |
| 520 | 207.1 | 923.7 |
| 521 | 217.3 | 711.5 |
| 522 | 525.66 | 79.788 |
| 523 | 451.33 | 100.04 |
| 524 | 398.75 | 307.55 |
| 525 | 460.3 | 73.968 |
| 526 | 472.58 | 106.56 |
| 527 | 500 | 53.775 |
| 528 | 357.9 | 834.45 |
| 529 | 444.13 | 22.557 |
| 530 | 464.6 | 22.955 |
| 531 | 349.65 | 63.465 |
| 532 | 342.83 | 472.67 |
| 533 | 322.45 | 220.95 |
| 534 | 289.35 | 344.1 |
| 535 | 670.35 | 1251.9 |
| 536 | 341.15 | 280.1 |
| 537 | 417.1 | 50.845 |
| 538 | 427.95 | 357.55 |
| 539 | 429.3 | 38.63 |
| 540 | 443.3 | 102.59 |
| 541 | 457.2 | 114.95 |
| 542 | 320.3 | 216.1 |
| 543 | 336.1 | 139.25 |
| 544 | 344.9 | 1996.4 |
| 545 | 318.7 | 1905.4 |
| 546 | 335.3 | 181.9 |
| 547 | 372.95 | 348.5 |
| 548 | 556.9 | 553.5 |
| 549 | 476.35 | 180.4 |
| 550 | 605.45 | 173.15 |
| 551 | 403.1 | 382.3 |
| 552 | 364.2 | 130.43 |
| 553 | 494.3 | 233.25 |
| 554 | 481 | 56.86 |
| 555 | 432.55 | 104.12 |
| 556 | 595.8 | 136.2 |
| 557 | 474.4 | 116.35 |
| 558 | 571.35 | 106.46 |
| 559 | 291.03 | 154.3 |
| 560 | 544.45 | 66.1 |

TABLE XVIII-continued

Illustrative $EC_{50}$ measured by CFTR cell surface levels using HRP-tagged ΔF508-CFTR expressing CFBE cells in the presence of a co-corrector.

| Compound # | % Activation | $EC_{50}$ (nM) |
|---|---|---|
| 561 | 509.4 | 43.023 |
| 562 | 589.55 | 77.645 |
| 563 | 542.9 | 111.13 |
| 564 | 587.4 | 40.75 |
| 565 | 637.53 | 69.86 |
| 566 | 708.8 | 400.42 |
| 567 | 539.8 | 56.343 |
| 568 | 461 | 46.295 |
| 569 | 436.13 | 88.907 |
| 570 | 412.9 | 208.3 |
| 571 | 487.9 | 77.77 |
| 572 | 412.9 | 225.1 |
| 573 | 467.57 | 58.533 |
| 574 | 283.3 | 541.9 |
| 575 | 361.3 | 87.8 |
| 576 | 443.5 | 54.673 |
| 577 | 379.3 | 104.7 |
| 578 | 462.3 | 107.6 |
| 579 | 420.5 | 318.8 |
| 580 | 387.45 | 52.425 |
| 581 | 191.3 | 760.8 |
| 582 | 245.15 | 271.05 |
| 583 | 480.15 | 47.595 |
| 584 | 337.55 | 272.35 |
| 585 | 509.7 | 247.75 |
| 586 | 618.65 | 37.12 |
| 587 | 504.6 | 398.2 |
| 588 | 571.2 | 29 |
| 589 | 422.95 | 148 |
| 590 | 487.9 | 31.395 |
| 591 | 384 | 1592 |
| 592 | 518.55 | 56.8 |
| 593 | 366.7 | 193.7 |
| 594 | 308.05 | 181.45 |
| 595 | 231.9 | 1430 |
| 596 | 304.8 | 1908 |
| 597 | 433.93 | 110.63 |
| 598 | 153.9 | 10000 |
| 599 | 285.2 | 269.7 |
| 600 | 326.1 | 1618 |
| 601 | 273.9 | 625 |
| 602 | 359.1 | 581.4 |
| 603 | 344.65 | 156.3 |
| 604 | 268.3 | 300 |
| 605 | 395.8 | 723 |
| 606 | 513.7 | 468.6 |
| 607 | 484.3 | 667.1 |
| 608 | 365.7 | 54.765 |
| 609 | 414.2 | 108.91 |
| 610 | 375.5 | 118.72 |
| 611 | 236.7 | 2620 |
| 612 | 320.8 | 3330 |
| 613 | 152.9 | 10000 |
| 614 | 381.35 | 170.65 |
| 615 | 450.85 | 130 |
| 616 | 341.15 | 294.35 |
| 617 | 324.25 | 978.45 |
| 618 | 295.9 | 702.35 |
| 619 | 277.25 | 374.7 |
| 621 | 348.55 | 76.95 |
| 622 | 251.25 | 308.6 |
| 623 | 424.77 | 55.623 |
| 624 | 274.15 | 549.2 |
| 625 | 353.87 | 125.87 |
| 626 | 418.4 | 111.06 |
| 627 | 348.57 | 24.793 |
| 628 | 477.32 | 131.66 |
| 629 | 546.75 | 266.92 |
| 630 | 593.42 | 374.58 |
| 631 | 352.63 | 2986.2 |
| 632 | 466.83 | 153.9 |
| 633 | 400.44 | 206.9 |
| 634 | 439.44 | 78.79 |
| 635 | 449.25 | 73.852 |
| 636 | 388.85 | 434.18 |
| 637 | 413.4 | 971.25 |
| 638 | 606.08 | 95.005 |
| 639 | 464.55 | 74.532 |
| 640 | 416.48 | 107.31 |
| 641 | 443.12 | 46.265 |
| 642 | 430.9 | 97.285 |
| 643 | 445.25 | 496.82 |
| 644 | 529.95 | 160.16 |
| 645 | 384.37 | 244.21 |
| 646 | 447.9 | 259.12 |
| 647 | 337.07 | 112.2 |
| 648 | 288.85 | 110.15 |
| 649 | 231.7 | 152.35 |
| 650 | 592.45 | 96.375 |
| 651 | 532.4 | 127.6 |
| 652 | 499.65 | 24.855 |
| 654 | 347.6 | 114.46 |
| 656 | 289.68 | 71.475 |
| 657 | 270.75 | 196.82 |
| 658 | 270.6 | 148.53 |
| 659 | 290.95 | 130.45 |
| 660 | 172.1 | 235.5 |
| 661 | 227.45 | 135.34 |
| 662 | 346.65 | 104.39 |
| 663 | 206.5 | 102.86 |
| 664 | 230.48 | 172.5 |
| 665 | 271.8 | 100.86 |
| 666 | 266.6 | 121.58 |
| 667 | 225.5 | 85.485 |
| 668 | 307.4 | 257.2 |
| 669 | 394 | 244.4 |
| 670 | 477.6 | 191.3 |
| 671 | 346.1 | 107 |
| 672 | 422.4 | 127.3 |

Activity of Compounds for their Intrinsic Corrector Capacity:

For this purpose doxycycline-inducible ΔF508-CFTR-HRP expressing CFBE4lo– cells (obtained from Gergely Lukacs, McGill University) were maintained in MEM (Gibco; 31095) supplemented with 10% fetal bovine serum (Hyclone; SV30160.03) under puromycin (3 µg/mL) and G418 selection (0.2 mg/mL). For compound testing, cells were seeded at 4000 cells/well in white 384-well plates (Greiner; 781080) in 50 µL medium containing 0.5 µg/mL doxycycline and incubated for 68 hours at 37° C., 5% $CO_2$. On day four, µL test compounds diluted in PBS were added to the plates at a final DMSO concentration of 0.1%. All compound plates contained negative controls (DMSO) and positive controls (3 M corrector, 3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid). Cell plates were incubated at 33° C., 5% $CO_2$ for 20 hours. On day five, the cells were washed five times with phosphate-buffered saline, and HRP activity was assayed by the addition of 50 µL/well of HRP substrate (SuperSignal™ West Pico Chemiluminescent Substrate, Thermo Scientific; 34080). After incubation for 15 minutes in the dark, chemiluminescence was measured using a plate reader (EnVision®, Perkin Elmer). Raw data were normalized to percentage activity values using the equation: 100× (Sample−Negative control)/(Positive control−Negative Control).

TABLE XIX

Illustrative EC$_{50}$ measured by CFTR cell surface levels using HRP-tagged ΔF508-CFTR expressing CFBE cells.

| Compound # | % Activation | EC$_{50}$ (nM) |
|---|---|---|
| 1 | 138.85 | 1628.9 |
| 2 | 226.75 | 1867 |
| 3 | 53.08 | 3340 |
| 4 | 246.7 | 838.35 |
| 5 | 184.6 | 476.6 |
| 6 | 232.1 | 808.3 |
| 7 | 245 | 636 |
| 8 | 270.6 | 899.55 |
| 9 | 143.05 | 785.9 |
| 10 | 418.25 | 572.5 |
| 11 | 164.7 | 556.52 |
| 12 | 161.15 | 1072.5 |
| 13 | 153.85 | 2361 |
| 14 | 148.9 | 1429.5 |
| 15 | 151.65 | 1192.5 |
| 16 | 469.75 | 543.05 |
| 17 | 140.75 | 1225.5 |
| 18 | 64.675 | 2267 |
| 19 | 140.85 | 2652.5 |
| 20 | 210.3 | 669.15 |
| 21 | 264.25 | 685.3 |
| 22 | 161.5 | 731.65 |
| 23 | 287.3 | 883.5 |
| 24 | 193.75 | 887.75 |
| 25 | 247.23 | 996.8 |
| 26 | 202.25 | 1847.5 |
| 27 | 145.5 | 1219 |
| 28 | 149.7 | 1218 |
| 29 | 328.4 | 645.05 |
| 30 | 369.93 | 436.27 |
| 31 | 203.4 | 318.2 |
| 32 | 277.65 | 372.25 |
| 33 | 109 | 2578.5 |
| 34 | 292.95 | 610.75 |
| 35 | 265.23 | 542.1 |
| 36 | 384.57 | 415.9 |
| 37 | 222.85 | 1662 |
| 38 | 182 | 849.97 |
| 39 | 143.4 | 838.2 |
| 40 | 147.1 | 450.97 |
| 41 | 52.497 | 816.53 |
| 42 | 45.225 | 2123 |
| 43 | 379.67 | 299.47 |
| 44 | 203.87 | 404.4 |
| 45 | 210.97 | 326.73 |
| 46 | 457.3 | 706.07 |
| 47 | 169.73 | 1862 |
| 48 | 160.9 | 1195.9 |
| 49 | 115.3 | 2566.7 |
| 50 | 109.8 | 1683.5 |
| 51 | 172.4 | 456.57 |
| 52 | 75.755 | 1153 |
| 53 | 376.8 | 671.1 |
| 54 | 386.92 | 779.92 |
| 55 | 126.75 | 1220.2 |
| 56 | 122.1 | 1177 |
| 57 | 219.65 | 1024.5 |
| 58 | 196.2 | 756.33 |
| 59 | 317.3 | 777.47 |
| 60 | 160.43 | 394.4 |
| 61 | 184.35 | 1003 |
| 62 | 350.85 | 595.75 |
| 63 | 179.68 | 548.28 |
| 64 | 152.75 | 935.35 |
| 65 | 162.33 | 1532.5 |
| 66 | 142.65 | 1861.4 |
| 67 | 181.96 | 361.86 |
| 68 | 253.3 | 1079 |
| 69 | 182.08 | 631.68 |
| 70 | 167.8 | 621.35 |
| 71 | 260.66 | 350 |
| 72 | 232.5 | 2226.5 |
| 73 | 254.1 | 657.45 |
| 74 | 253.38 | 549.12 |
| 75 | 225.82 | 489.92 |
| 76 | 430.87 | 528.07 |
| 77 | 296.45 | 639 |
| 78 | 333.2 | 1878.3 |
| 79 | 280.9 | 1227 |
| 80 | 258.38 | 436.18 |
| 81 | 495.8 | 384.52 |
| 82 | 366.27 | 472.07 |
| 83 | 391.5 | 547.1 |
| 84 | 311.7 | 659.8 |
| 85 | 426.04 | 420.84 |
| 86 | 329.92 | 637.3 |
| 87 | 422.84 | 408.78 |
| 88 | 389.73 | 474.4 |
| 89 | 422.78 | 645.7 |
| 90 | 163.75 | 485.6 |
| 91 | 388.15 | 381.7 |
| 92 | 175.77 | 552.8 |
| 93 | 224.23 | 501.2 |
| 94 | 193.5 | 614.33 |
| 95 | 355.6 | 837.85 |
| 96 | 406.6 | 366.9 |
| 97 | 444.85 | 399.2 |
| 98 | 154 | 555.55 |
| 99 | 414.8 | 409.65 |
| 100 | 113 | 2475 |
| 101 | 254.85 | 838.65 |
| 102 | 233.9 | 897.2 |
| 103 | 263.8 | 535.87 |
| 104 | 239.6 | 496.9 |
| 105 | 258.1 | 908.4 |
| 106 | 162.75 | 525.9 |
| 107 | 64.54 | 3340 |
| 108 | 218.05 | 560.55 |
| 109 | 381.05 | 612.85 |
| 110 | 451.8 | 358.13 |
| 111 | 411.63 | 444.3 |
| 112 | 254.85 | 699.5 |
| 113 | 262.33 | 464.4 |
| 114 | 130.85 | 1136 |
| 115 | 216.05 | 1050 |
| 116 | 295.57 | 957.23 |
| 117 | 281.88 | 332.78 |
| 118 | 289.93 | 397.63 |
| 119 | 188.53 | 519.5 |
| 120 | 169.2 | 553.7 |
| 121 | 159.13 | 652.53 |
| 122 | 184.53 | 469.67 |
| 123 | 153.8 | 428.27 |
| 124 | 288.1 | 544.77 |
| 125 | 369.87 | 988.13 |
| 126 | 309.17 | 597.03 |
| 127 | 301.45 | 517.9 |
| 128 | 357.47 | 515.83 |
| 129 | 187.5 | 1326.5 |
| 130 | 318.25 | 541.35 |
| 131 | 314.35 | 429.85 |
| 132 | 244 | 1270.5 |
| 133 | 222.33 | 412.87 |
| 134 | 229.87 | 465.2 |
| 135 | 299.63 | 695.8 |
| 136 | 262.38 | 154.65 |
| 137 | 131.8 | 1173.2 |
| 138 | 252.9 | 333.73 |
| 139 | 163.83 | 806.07 |
| 140 | 210.3 | 733.5 |
| 141 | 233.07 | 287.2 |
| 142 | 203.17 | 254.9 |
| 143 | 107.15 | 1110 |
| 144 | 531.6 | 416.52 |
| 145 | 112.03 | 1039.4 |
| 146 | 201.23 | 356.08 |
| 147 | 176.47 | 358.63 |
| 148 | 273.33 | 547.73 |
| 149 | 122.3 | 385.75 |
| 150 | 220.98 | 576.45 |

TABLE XIX-continued

Illustrative EC$_{50}$ measured by CFTR cell surface levels using HRP-tagged ΔF508-CFTR expressing CFBE cells.

| Compound # | % Activation | EC$_{50}$ (nM) |
|---|---|---|
| 151 | 228.95 | 346.65 |
| 152 | 242.35 | 357.15 |
| 153 | 146.7 | 354.95 |
| 154 | 275.65 | 532.9 |
| 155 | 439.5 | 454.35 |
| 156 | 411 | 438.63 |
| 157 | 327.8 | 460.03 |
| 158 | 359.1 | 622 |
| 159 | 103.02 | 661.2 |
| 160 | 285.57 | 309.47 |
| 161 | 406.4 | 729.53 |
| 162 | 169 | 445.43 |
| 163 | 175.4 | 441.8 |
| 164 | 295.25 | 594.45 |
| 165 | 373.95 | 1781 |
| 166 | 235.2 | 439.43 |
| 167 | 260.6 | 313.35 |
| 168 | 399.2 | 338.2 |
| 169 | 344.25 | 426.22 |
| 170 | 213.5 | 974.85 |
| 171 | 143.4 | 787.07 |
| 172 | 280.03 | 329.77 |
| 173 | 51.395 | 412.4 |
| 174 | 347.9 | 753.6 |
| 175 | 270.5 | 337.5 |
| 176 | 190.4 | 337.3 |
| 177 | 99.405 | 829.6 |
| 178 | 202.8 | 346.9 |
| 179 | 89.165 | 878.85 |
| 180 | 129.5 | 570.07 |
| 181 | 137.73 | 397.87 |
| 182 | 207.57 | 501.43 |
| 183 | 302 | 389.5 |
| 184 | 95.405 | 719.25 |
| 185 | 331.6 | 241.45 |
| 186 | 209.57 | 616.13 |
| 187 | 160 | 223.43 |
| 188 | 214.93 | 274.5 |
| 189 | 236.2 | 420.6 |
| 190 | 284.8 | 966.55 |
| 191 | 161.23 | 305.6 |
| 192 | 81.49 | 1135 |
| 193 | 175.23 | 1067.5 |
| 194 | 213.75 | 744.5 |
| 195 | 225.2 | 369.7 |
| 196 | 188.47 | 339.43 |
| 197 | 220.2 | 397 |
| 198 | 135.73 | 632.97 |
| 199 | 142.6 | 481.47 |
| 200 | 163.43 | 315.7 |
| 201 | 200.8 | 402.17 |
| 202 | 147.23 | 595.43 |
| 203 | 82.59 | 1015.5 |
| 204 | 117.6 | 977.95 |
| 205 | 208.5 | 955.55 |
| 206 | 169.03 | 1396.1 |
| 207 | 141.93 | 339.73 |
| 208 | 190.55 | 402.45 |
| 209 | 247.6 | 380.97 |
| 210 | 205.57 | 285.6 |
| 211 | 114.4 | 608.15 |
| 212 | 114.63 | 620.9 |
| 213 | 267.5 | 546.25 |
| 214 | 103.6 | 1010.8 |
| 215 | 374.57 | 274.4 |
| 216 | 275.67 | 765.67 |
| 217 | 246.77 | 458.47 |
| 218 | 268.37 | 390.4 |
| 219 | 381.1 | 764.1 |
| 220 | 202.5 | 347.9 |
| 221 | 322.15 | 420.05 |
| 222 | 65.685 | 1423.2 |
| 223 | 258.95 | 469.5 |
| 224 | 228.8 | 544.2 |
| 225 | 215.35 | 456.25 |
| 226 | 206.7 | 445.05 |
| 227 | 216.8 | 448.6 |
| 228 | 217.9 | 489.9 |
| 229 | 174.2 | 414.1 |
| 230 | 243.75 | 406.1 |
| 231 | 162.9 | 939.25 |
| 232 | 71.64 | 1678 |
| 233 | 58.34 | 2438 |
| 234 | 17.89 | >10000 |
| 235 | 102.76 | 3271 |
| 236 | 309.83 | 316.47 |
| 237 | 120 | 453.2 |
| 238 | 159.83 | 600.57 |
| 239 | 184.6 | 999.25 |
| 240 | 176.67 | 376.63 |
| 241 | 261.93 | 366.43 |
| 242 | 242.1 | 282.83 |
| 243 | 78.11 | 3340 |
| 244 | 182.7 | 381.2 |
| 245 | 228 | 495.1 |
| 246 | 112.1 | 371 |
| 247 | 126.8 | 460 |
| 248 | 234.6 | 371 |
| 249 | 187.6 | 371 |
| 250 | 232.7 | 514 |
| 251 | 273.3 | 634 |
| 252 | 115.2 | 396.5 |
| 253 | 174.6 | 675.6 |
| 254 | 117.5 | 399.8 |
| 255 | 122.3 | 1881 |
| 256 | 331.85 | 220.65 |
| 257 | 272.4 | 370 |
| 258 | 8.829 | >10000 |
| 260 | 473.35 | 1868.6 |
| 261 | 26.85 | >10000 |
| 262 | 232.07 | 597.87 |
| 263 | 260.1 | 444.83 |
| 264 | 242.5 | 969.2 |
| 265 | 240.8 | 3330 |
| 266 | 161.5 | 332 |
| 267 | 274.8 | 171.6 |
| 268 | 5.213 | >10000 |
| 269 | 120.6 | 246.4 |
| 270 | 161.5 | 1493 |
| 271 | 63.905 | 1952 |
| 272 | 268.2 | 96.55 |
| 273 | 182.4 | 562.4 |
| 274 | 159.05 | 842.5 |
| 275 | 138.8 | 467.7 |
| 276 | 356.7 | 779.3 |
| 277 | 155.4 | 251.1 |
| 278 | 233.7 | 119.5 |
| 279 | 308.4 | 533.7 |
| 280 | 121.9 | 1007 |
| 281 | 230.15 | 456.5 |
| 282 | 127.8 | 129.3 |
| 283 | 141.2 | 477 |
| 284 | 154.4 | 275.7 |
| 285 | 125.5 | 293.8 |
| 286 | 264 | 326.8 |
| 287 | 204.9 | 183.2 |
| 290 | 200.4 | 617.4 |
| 291 | 219.5 | 3330 |
| 292 | 217.9 | 1057 |
| 293 | 113.3 | 622.2 |
| 294 | 319.6 | 62.24 |
| 295 | 129.6 | 1052 |
| 296 | 154.7 | 396.5 |
| 297 | 193.9 | 99.18 |
| 298 | 312.9 | 282.1 |
| 299 | 81.41 | 3330 |
| 300 | 119.9 | 309.4 |
| 303 | 149.9 | 3330 |
| 304 | 308.2 | 202.9 |
| 306 | 146.7 | 157.7 |

TABLE XIX-continued

Illustrative EC$_{50}$ measured by CFTR cell surface levels using HRP-tagged ΔF508-CFTR expressing CFBE cells.

| Compound # | % Activation | EC$_{50}$ (nM) |
|---|---|---|
| 307 | 172.7 | 3330 |
| 309 | 149 | 444.3 |
| 310 | 66.84 | 691.9 |
| 315 | 154.87 | 218.03 |
| 316 | 380.5 | 182.8 |
| 317 | 269.6 | 93.52 |
| 318 | 183.45 | 411.25 |
| 319 | 34.315 | 297.7 |
| 320 | 376.35 | 309.35 |
| 322 | 158.25 | 128.05 |
| 323 | 144.6 | 1366 |
| 325 | 151.4 | 334.8 |
| 326 | 167.1 | 2384.5 |
| 327 | 239.4 | 145.2 |
| 328 | 380.5 | 2186 |
| 329 | 163.85 | 158.2 |
| 330 | 133.1 | 213.45 |
| 331 | 347.15 | 136.25 |
| 333 | 180 | 82.765 |
| 334 | 121.75 | 167.4 |
| 335 | 171.65 | 149.85 |
| 336 | 107.2 | 419.9 |
| 337 | 404.9 | 133.58 |
| 339 | 142.05 | 1401 |
| 340 | 138.95 | 1392 |
| 346 | 195.8 | 308.2 |
| 347 | 131.4 | 263 |
| 348 | 293.6 | 5969.5 |
| 349 | 161.7 | 512.3 |
| 350 | 104.21 | 357.15 |
| 351 | 50.87 | 73.45 |
| 352 | 27.44 | 5000 |
| 353 | 56.22 | 87.86 |
| 354 | 113.7 | 122.9 |
| 355 | 102.4 | 160.5 |
| 356 | 188.25 | 105.3 |
| 357 | 72.83 | 115.2 |
| 365 | 313 | 1670 |
| 366 | 264 | 297.9 |
| 367 | 364.5 | 311.4 |
| 368 | 185 | 1359 |
| 369 | 292.7 | 100.6 |
| 370 | 172.2 | 1490 |
| 371 | 121.3 | 2744 |
| 373 | 368.2 | 72.97 |
| 374 | 240.7 | 254.3 |
| 375 | 321.6 | 570.9 |
| 376 | 355.7 | 117.4 |
| 377 | 261.3 | 129 |
| 378 | 160 | 1327 |
| 379 | 268.45 | 141.1 |
| 380 | 131.7 | 279.3 |
| 381 | 247.15 | 424.06 |
| 382 | 305.9 | 260.6 |
| 383 | 202.9 | 149.8 |
| 384 | 228 | 2862 |
| 385 | 227.5 | 120.95 |
| 386 | 237.85 | 2116 |
| 387 | 60.58 | 462 |
| 388 | 192.8 | 217.9 |
| 389 | 165 | 556.1 |
| 390 | 188.2 | 176.9 |
| 391 | 247.7 | 77.1 |
| 392 | 240.05 | 150.45 |
| 393 | 423.6 | 51.37 |
| 394 | 194.35 | 99.53 |
| 395 | 209.2 | 473.8 |
| 396 | 222.9 | 121.35 |
| 397 | 234.5 | 154.55 |
| 398 | 173.7 | 181.5 |
| 399 | 237.5 | 72.075 |
| 400 | 180.65 | 163.05 |
| 401 | 400.8 | 104.1 |
| 402 | 303.5 | 312.28 |
| 403 | 389.2 | 30.18 |
| 404 | 181.2 | 185.6 |
| 405 | 160.8 | 190.7 |
| 406 | 125.95 | 240.8 |
| 407 | 331.45 | 496.9 |
| 408 | 272.74 | 689.62 |
| 409 | 245.4 | 154.9 |
| 410 | 337.42 | 212.87 |
| 415 | 365.4 | 165.4 |
| 416 | 288 | 141.9 |
| 417 | 307.45 | 189.7 |
| 418 | 321.3 | 320.9 |
| 419 | 293 | 448.1 |
| 420 | 283.1 | 472 |
| 421 | 308 | 250.1 |
| 422 | 222.8 | 318.5 |
| 423 | 175.55 | 140.1 |
| 424 | 249.25 | 244.25 |
| 425 | 280.2 | 277.1 |
| 426 | 143.7 | 301.6 |
| 429 | 252.1 | 378 |
| 430 | 170.05 | 231.3 |
| 431 | 344.95 | 109.3 |
| 432 | 243.6 | 118.5 |
| 433 | 361.5 | 96.46 |
| 434 | 245.2 | 57.74 |
| 435 | 269.9 | 135.9 |
| 436 | 393.3 | 344 |
| 437 | 353.6 | 257 |
| 438 | 337 | 391.8 |
| 439 | 166.8 | 550 |
| 440 | 334.8 | 129 |
| 441 | 196.1 | 350 |
| 442 | 146.8 | 307.3 |
| 444 | 162.5 | 344.7 |
| 445 | 393.1 | 110.7 |
| 447 | 330.9 | 243.5 |
| 448 | 258.2 | 476.9 |
| AC07 | 268.5 | 139.5 |
| 450 | 253.5 | 617.5 |
| 451 | 184.1 | 1698 |
| 452 | 239.8 | 408.4 |
| 453 | 149.3 | 403 |
| 454 | 168.1 | 1670 |
| 456 | 268.4 | 157.7 |
| 457 | 272.2 | 128.5 |
| 458 | 124.4 | 794.4 |
| 459 | 225.65 | 148.95 |
| 460 | 125.8 | 595.6 |
| 461 | 212.3 | 209.4 |
| 462 | 317.4 | 775.5 |
| 463 | 263.9 | 419.1 |
| 464 | 277.5 | 306.3 |
| 465 | 131.6 | 312.8 |
| 466 | 318.7 | 175.8 |
| 469 | 253.8 | 203.9 |
| 470 | 275.4 | 231.1 |
| 471 | 240.2 | 230.2 |
| 472 | 210.57 | 680.74 |
| 473 | 166.3 | 70.76 |
| 474 | 194.5 | 580.5 |
| 475 | 140.1 | 178.8 |
| 476 | 134.2 | 215 |
| 477 | 341.4 | 117 |
| 478 | 295.4 | 2639 |
| 479 | 305.7 | 196.6 |
| 480 | 322.45 | 135.7 |
| 481 | 114.2 | 278.1 |
| 482 | 214.1 | 88.17 |
| 483 | 212.7 | 84.88 |
| 484 | 216.9 | 124.3 |
| 485 | 218.55 | 155.15 |
| 486 | 332.5 | 467.3 |
| 487 | 203.53 | 174.87 |
| 488 | 246.55 | 655.45 |
| 489 | 99.6 | 141.5 |

TABLE XIX-continued

Illustrative EC$_{50}$ measured by CFTR cell surface levels using HRP-tagged ΔF508-CFTR expressing CFBE cells.

| Compound # | % Activation | EC$_{50}$ (nM) |
|---|---|---|
| 490 | 139.7 | 1546 |
| 491 | 204.5 | 248.3 |
| 492 | 311 | 79.93 |
| 493 | 275.2 | 174.6 |
| 494 | 315.4 | 109.8 |
| 495 | 242.05 | 217.1 |
| 496 | 199.9 | 281.8 |
| 497 | 195.7 | 410.4 |
| 498 | 288.1 | 144.3 |
| 499 | 287.5 | 186.4 |
| 500 | 137.5 | 173.5 |
| 501 | 188.7 | 210.7 |
| 502 | 214.2 | 345.4 |
| 503 | 203.4 | 418.8 |
| 504 | 206.4 | 300.8 |
| 505 | 187.5 | 92.57 |
| 506 | 144.1 | 3330 |
| 507 | 309.4 | 136.8 |
| 508 | 217.5 | 182.2 |
| 509 | 333.2 | 326.6 |
| 510 | 234.9 | 297.6 |
| 511 | 248.55 | 88.31 |
| 512 | 222.27 | 120.97 |
| 513 | 278.5 | 100.5 |
| 514 | 301.4 | 149.8 |
| 515 | 287.1 | 179.2 |
| 516 | 322.7 | 120.2 |
| 517 | 320.5 | 183.95 |
| 518 | 35.86 | 10000 |
| 519 | 114.4 | 3330 |
| 520 | 60 | 1056 |
| 521 | 31.93 | 10000 |
| 522 | 317.9 | 114.21 |
| 523 | 236.53 | 123.6 |
| 524 | 209.35 | 525 |
| 525 | 274.75 | 137.75 |
| 526 | 269.23 | 152.72 |
| 527 | 295.95 | 79.095 |
| 528 | 185.8 | 859.1 |
| 529 | 278.55 | 60.605 |
| 530 | 323.1 | 54.43 |
| 531 | 182.8 | 234.05 |
| 532 | 151.95 | 521.25 |
| 533 | 156.3 | 221.85 |
| 534 | 105 | 240.7 |
| 535 | 385.8 | 389 |
| 536 | 125.1 | 224.8 |
| 537 | 214.5 | 112.2 |
| 538 | 228.9 | 2073 |
| 539 | 234.5 | 71.71 |
| 540 | 248.8 | 123.3 |
| 541 | 231.7 | 444.2 |
| 542 | 153.2 | 266.8 |
| 543 | 115.7 | 238.2 |
| 544 | 135.3 | 3330 |
| 545 | 112.7 | 3330 |
| 546 | 138.05 | 325.2 |
| 548 | 307.2 | 654.3 |
| 549 | 276.9 | 232.9 |
| 550 | 347 | 361 |
| 551 | 197.8 | 763.15 |
| 553 | 293 | 1732 |
| 554 | 269.45 | 108.15 |
| 555 | 235.5 | 358.77 |
| 556 | 386 | 64.67 |
| 557 | 248.5 | 252 |
| 558 | 399.1 | 531.6 |
| 560 | 260.4 | 96.34 |
| 561 | 311.6 | 107.08 |
| 562 | 341.3 | 70.505 |
| 563 | 298.9 | 198.3 |
| 564 | 361.35 | 117.81 |
| 565 | 373.15 | 181.8 |
| 566 | 365.1 | 112.3 |
| 567 | 312.2 | 139.4 |
| 568 | 240.65 | 77.465 |
| 569 | 220.77 | 112.18 |
| 570 | 235.8 | 496.2 |
| 571 | 268.15 | 128.75 |
| 572 | 237.55 | 295.1 |
| 573 | 270.53 | 104.32 |
| 574 | 129.9 | 2756 |
| 575 | 202.65 | 147.4 |
| 576 | 257.15 | 139.41 |
| 577 | 187.15 | 256.6 |
| 578 | 309.25 | 152.15 |
| 579 | 205 | 375.87 |
| 580 | 201.52 | 130.88 |
| 581 | 33.38 | 370 |
| 582 | 75.38 | 370 |
| 583 | 269.7 | 178.2 |
| 584 | 164.3 | 176.7 |
| 585 | 316.6 | 1242 |
| 586 | 331.67 | 52.367 |
| 587 | 277.1 | 234.6 |
| 588 | 366.8 | 125.95 |
| 589 | 193.6 | 199.6 |
| 590 | 290.3 | 86.7 |
| 591 | 189.1 | 795.1 |
| 592 | 300.8 | 182.6 |
| 593 | 157.8 | 189.7 |
| 594 | 135.7 | 518.85 |
| 595 | 58.87 | 1519 |
| 596 | 104.3 | 1381 |
| 597 | 214.3 | 130.2 |
| 598 | 28.03 | 10000 |
| 599 | 88.94 | 331.3 |
| 600 | 126.5 | 1213 |
| 601 | 112 | 2177 |
| 602 | 133.6 | 1177 |
| 603 | 136.2 | 282.7 |
| 604 | 86.51 | 490.4 |
| 605 | 207.5 | 317.5 |
| 606 | 283.8 | 973 |
| 607 | 272.6 | 342 |
| 608 | 194.67 | 103.52 |
| 609 | 202.53 | 249.1 |
| 610 | 182.13 | 185.8 |
| 611 | 77.39 | 3330 |
| 612 | 108.7 | 875.8 |
| 613 | 30.09 | 10000 |
| 614 | 172 | 211.3 |
| 615 | 255.3 | 482.5 |
| 616 | 144.05 | 348.1 |
| 617 | 137.1 | 871.25 |
| 618 | 112.8 | 420.6 |
| 619 | 102.8 | 680.25 |
| 621 | 160.45 | 172.9 |
| 622 | 89.445 | 568.4 |
| 623 | 238.53 | 112.73 |
| 624 | 100.59 | 1203.1 |
| 625 | 182.2 | 222.97 |
| 626 | 206.6 | 150.83 |
| 627 | 162.47 | 82.293 |
| 628 | 283.25 | 425.38 |
| 629 | 337.34 | 517.05 |
| 630 | 339.64 | 738.66 |
| 631 | 122.53 | 3336.7 |
| 632 | 252.75 | 304.4 |
| 633 | 180.46 | 345.2 |
| 634 | 227.46 | 199.84 |
| 635 | 216.38 | 154.84 |
| 636 | 182.7 | 572.78 |
| 637 | 191.88 | 2502.2 |
| 638 | 398.98 | 241.05 |
| 639 | 238.35 | 131.92 |
| 640 | 203.62 | 174.7 |
| 641 | 205.35 | 74.852 |
| 642 | 222 | 234.88 |
| 643 | 181.65 | 505.98 |

TABLE XIX-continued

Illustrative $EC_{50}$ measured by CFTR cell surface levels using HRP-tagged ΔF508-CFTR expressing CFBE cells.

| Compound # | % Activation | $EC_{50}$ (nM) |
|---|---|---|
| 644 | 266.9 | 253.35 |
| 645 | 194.33 | 331.1 |
| 646 | 236.13 | 400.12 |
| 647 | 164.47 | 215.73 |
| 648 | 109.65 | 315.7 |
| 649 | 69.12 | 370 |
| 650 | 385.4 | 115.06 |
| 651 | 317.85 | 205.75 |
| 652 | 289.03 | 84.117 |
| 654 | 73.925 | 5075.4 |
| 656 | 102.63 | 99.61 |
| 657 | 98 | 281.48 |
| 658 | 99.025 | 252.5 |
| 659 | 96.44 | 141.95 |
| 660 | 34.92 | 932 |
| 661 | 67.125 | 154.65 |
| 662 | 134.35 | 123.75 |
| 663 | 57.9 | 234.35 |
| 664 | 70.082 | 277.62 |
| 665 | 101.9 | 259.35 |
| 666 | 99.775 | 255.6 |
| 667 | 75.435 | 208.1 |
| 668 | 89.495 | 384.5 |
| 669 | 334.9 | 211.35 |
| 670 | 399.2 | 276.75 |
| 671 | 252.95 | 273.5 |
| 672 | 362.9 | 330.9 |
| 673 | 423.5 | 288.5 |
| 675 | 398.1 | 315.6 |
| 674 | 389.5 | 155.9 |
| 676 | 251.1 | 251.3 |
| 677 | 458.5 | 170.7 |
| 678 | 345.1 | 220.9 |
| 679 | 476.9 | 131.7 |
| 680 | 351.2 | 339.1 |
| 681 | 366.2 | 172 |
| 682 | 260.8 | 297.2 |
| 683 | 354.9 | 252.9 |
| 684 | 356.9 | 114.6 |
| 685 | 144.3 | 769.9 |

YFP-Halide Influx Assay for the CFTR-ΔF508 Mutation

The YFP halide influx assay measures the functionality of the Cystic Fibrosis Transmembrane Conductance regulator (CFTR) channels in the cystic fibrosis bronchial epithelium cell line CFBE4lo–. The fluorescence of the yellow fluorescent protein (YFP) variant YFP H148Q, I152 L or variant YFP H148Q, I152 L & F47 L is substantially quenched by iodine, a halide that is efficiently transported by CFTR. The assay is thus used to evaluate the effect of corrector compounds on CFTR channel function by measuring the extent of YFP signal quenching. (Galietta, L. J. V., Haggie, P. M., Verkman, A. S., 2001. Green fluorescent protein-based halide indicators with improved chloride and iodide affinities. FEBS Lett. 499, 220-224. doi: 10.1016/S0014-5793(01)02561-3; Nagai, T., Ibata, K., Park, E. S., Kubota, M., Mikoshiba, K., Miyawaki, A., 2002. A variant of yellow fluorescent protein with fast and efficient maturation for cell-biological applications. Nat. Biotechnol. 20, 87-90. doi: 10.1038/nbt0102-87). For this purpose, CFBE4lo– cells were seeded in 96-well plates (6000 CFBE cells/well). One day after seeding, the CFBE cells were transduced with adenoviral vectors that direct the expression of the CFTR ΔF508 mutant and of the YFP reporter. Cells were treated with test compounds for 24 hours at 37° C. to allow trafficking of corrected CFTR to the membrane. The next day the CFTR channels were activated by treatment with the cAMP inducer forskolin (10.67 μM) and potentiator, N-(3-carbamoyl-5,5,7,7-tetramethyl-4,7-dihydro-5H-thieno[2,3-c]pyran-2-yl)-1H-pyrazole-5-carboxamide (0.5 μM), in 1×D-PBS (from Gibco, Cat n#14090-091) for 20 minutes prior to addition of an I⁻ solution (137 mM NaI, 2.7 mM KI, 1.76 mM $KH_2PO_4$, 10.1 mM $Na_2HPO_4$, 5 mM glucose). The potentiator, 3-amino-N-[(2S)-2-hydroxypropyl]-5-{[4-(trifluoromethoxy)phenyl]sulfonyl}pyridine-2-carboxamide, was used in place of N-(3-carbamoyl-5,5,7,7-tetramethyl-4,7-dihydro-5H-thieno[2,3-c]pyran-2-yl)-1H-pyrazole-5-carboxamide in some assays. The I⁻ induced quenching of fluorescence is recorded immediately after injection of I⁻ for 7 seconds. The capacity of a compound to increase number of channels, and therefore overall halide influx is directly correlated with the decrease in fluorescence, and is expressed as (1–(fluorescence after 7 seconds (F)/fluorescence before injection (F0))) and an $EC_{50}$ can be derived from a (1–F/F0) vs compound concentration plot.

TECC Assay

Primary Bronchial Epithelial Cells Protocol

The TECC (Tranepithelial Clamp Circuit, EP-design) assay measures the functionality of the cystic fibrosis Transmembrane Conductance regulator (CFTR) by measuring the short circuit current ($I_{sc}$) generated over the basolateral and apical membrane of lung epithelial cells. In TECC the transepithelial potential PD and transepithelial resistance ($R_t$) are measured in an open circuit and transformed to $I_{eq}$ using Ohm's law. 24 Wells can be measured simultaneously allowing a higher throughput compared to Ussing chambers.

For this purpose, bronchial epithelial cells isolated from CF patients homozygous for the CFTR ΔF508 mutation (hAEC-CF, Epithelix, Geneva, Switzerland; McGill University, Montreal, Qc; Asterand, Detroit, Mich.; University of North Carolina, Chapel Hill, N.C.) are plated on type IV collagen-coated Transwell® supports (Costar). Human airway epithelia are generated by provision of an air-liquid interface for 21 days to form well-differentiated polarized cultures that resemble in vivo pseudo-stratified ciliated epithelium (Fulcher, M. L., Gabriel, S., Burns, K. A., Yankaskas, J. R., Randell, S. H., 2005. Well-differentiated human airway epithelial cell cultures. Methods Mol. Med. 107, 183-206). The differentiated cells are treated with test corrector compound(s) (corrector alone or in combination with co-corrector, 4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid ("acute") or test corrector compounds, co-corrector and potentiator, N-(3-carbamoyl-5,5,7,7-tetramethyl-4,7-dihydro-5H-thieno[2,3-c]pyran-2-yl)-1H-pyrazole-5-carboxamide ("chronic") for 24 hours basolaterally to allow sufficient expression of properly folded CFTR protein on the membrane. All compound plates contained negative controls (DMSO) and positive controls (0.15 μM, 4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid).

For electrophysiological recording of the "acute" experiments, the human airway epithelia are mounted in the TECC heating plate and kept at 37° C. The epithelia are bathed in a NaCl-Ringer solution (120 mM NaCl, 25 mM $NaHCO_3$, 1.2 mM $CaCl_2$, 1.2 mM $MgCl_2$, 0.8 mM $KH_2PO_4$, 0.8 mM $K_2HPO_4$, pH 7.4, 5 mM glucose) on both the basolateral and apical sides. Apical amiloride is used to inhibit the endogenous epithelial sodium channel (ENaC) currents while forskolin is applied on both apical and basolateral side to stimulate CFTR. CFTR activity is measured by addition of forskolin followed by addition of a potentiator, N-(3-carbamoyl-5,5,7,7-tetramethyl-4,7-dihydro-5H-thieno[2,3-c]

pyran-2-yl)-1H-pyrazole-5-carboxamide, on both sides. The potentiator, 3-amino-N-[(2S)-2-hydroxypropyl]-5-{[4-(trifluoromethoxy)phenyl]sulfonyl}pyridine-2-carboxamide, was used in place of N-(3-carbamoyl-5,5,7,7-tetramethyl-4,7-dihydro-5H-thieno[2,3-c]pyran-2-yl)-1H-pyrazole-5-carboxamide in some assays. Measurements are done during a 20 minute timeframe with recordings every 2 minutes. The increase in $I_{eq}$ is used as a measure for the increased CFTR activity, $EC_{50}$ values can be generated by measuring impact of different concentrations of compound on $I_{eq}$ on primary cells, for this purpose each transwell is treated with a different compound concentration for 24 hours. Inhibitor-172, an inhibitor specific for CFTR, is used to test the specificity of the tested compounds. Raw data were normalized to percentage activity values using the equation: 100× (Sample−Negative control)/(Positive control−Negative Control).

TABLE XX

Illustrative acute TECC assay response with and without the presence of a co-corrector.

| Compound # | % Activity at 3 μM (Ieq*) | % Activity at 10 μM (Ieq*) | % Activity at 3 μM with co-corrector (Ieq*) |
|---|---|---|---|
| 10 | 591.84 | | |
| 11 | 351 | | |
| 13 | 74.32 | 174.53 | |
| 104 | | | 102.36 |

*Ieq refers to calculations based on the maximum current.

For electrophysiological recording of the "chronic" experiments, the human airway epithelia are mounted in the TECC heating plate for electrophysiological measurement and kept at 37° C. The epithelia are bathed in a NaCl-Ringer solution (120 mM NaCl, 25 mM NaHCO₃, 1.2 mM CaCl₂, 1.2 mM MgCl₂, 0.8 mM KH₂PO₄, 0.8 mM K₂HPO₄, pH 7.4, 5 mM glucose) on both the basolateral and apical sides. Test compounds (corrector, co-corrector, 4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid, and potentiator, N-(3-carbamoyl-5,5,7,7-tetramethyl-4,7-dihydro-5H-thieno[2,3-c]pyran-2-yl)-1H-pyrazole-5-carboxamide), are re-added to the recording solution prior to measurement. The potentiator, 3-amino-N-[(2S)-2-hydroxypropyl]-5-{[4-(trifluoromethoxy)phenyl]sulfonyl}pyridine-2-carboxamide (1.5 μM), was used in place of N-(3-carbamoyl-5,5,7,7-tetramethyl-4,7-dihydro-5H-thieno[2,3-c]pyran-2-yl)-1H-pyrazole-5-carboxamide in some assays (for Compound numbers >370). Apical amiloride is used to inhibit the endogenous ENaC currents while forskolin is applied on both apical and basolateral side to stimulate CFTR. Measurements are done during a 20 minute timeframe with recordings every 2 minutes. The increase in $I_{eq}$ is used as a measure for the increased CFTR activity, $EC_{50}$ values can be generated by measuring impact of different concentrations of compound on $I_{eq}$ on primary cells, for this purpose each transwell is treated with a different compound concentration. Inhibitor-172, an inhibitor specific for CFTR, is used to test the specificity of the tested compounds. Raw data were normalized to percentage activity values using the equation: 100×(Sample−Negative control)/(Positive control−Negative Control).

TABLE XXI

Illustrative chronic TECC assay response.

| Compound # | % Activity at 1 μM (Ieq*) | EC₅₀ (nM) (Ieq*) | % Activity at 1 μM (AUC**) | % Activity at 3 μM (AUC**) | EC₅₀ (nM) (AUC**) |
|---|---|---|---|---|---|
| 30 | 450 | <30 | | | |
| 34 | 270 | <30 | | | |
| 63 | 325 | 40 | | | |
| 71 | 270 | 19.5 | | | |
| 74 | 240 | <30 | | | |
| 75 | 316 | 30 | | | |
| 80 | 250 | 19.3 | | | |
| 85 | 120 | >1000 | | | |
| 86 | 210 | 30 | | | |
| 87 | 150 | <30 | | | |
| 91 | 250 | <30 | | | |
| 93 | 220 | <30 | | | |
| 95 | 180 | 10 | | | |
| 96 | 310 | <30 | | | |
| 104 | 720 | <30 | | | |
| 110 | 170 | <30 | | | |
| 113 | 310 | 32 | | | |
| 117 | 81 | >1000 | | | |
| 119 | 157 | >1000 | | | |
| 121 | 206 | 74 | | | |
| 128 | 235 | <30 | | | |
| 136 | | | 233.2 | | 23.5 |
| 142 | | | 250 | | <300 |
| 144 | 350 | 12 | | | |
| 146 | 310 | 30 | | | |
| 150 | | 100 | | | |
| 152 | | | 482.77 | | 16 |
| 155 | | | 200 | | 4 |
| 158 | | | 370.9 | | |
| 160 | | | 190 | | 160 |
| 167 | | | 260 | | 32 |
| 168 | | | 282.45 | | 38.2 |
| 169 | | | 210 | | 2.1 |
| 177 | | | 419.90 | | >100 |
| 185 | | | 453 | | 45.4 |
| 187 | | | 180 | | >1000 |
| 188 | | | 257.3 | | |
| 190 | | | 269 | | 51 |
| 193 | | | 317.57 | | |
| 198 | | | 477.39 | | |
| 199 | | | 627.48 | | >1000 |
| 200 | | | 364.3 | | |
| 201 | | | 250 | | <300 |
| 207 | | | 441.31 | | |
| 215 | | | 320 | | 45 |
| 219 | | | 298.20 | | |
| 221 | | | 245.9 | | 40 |
| 226 | | | 530 | | 56 |
| 228 | | | 240 | | 32 |
| 229 | | | 430 | | 20 |
| 230 | | | 265.44 | | 27 |
| 236 | | | 434.22 | | 80 |
| 238 | | | 521.96 | | |
| 240 | | | 288.71 | | 140 |
| 241 | | | 400 | | <10 |
| 242 | | | 308.45 | | 14 |
| 243 | | | 165.81 | | |
| 244 | | | 238.89 | | |
| 245 | | | 628.25 | | |
| 246 | | | 301.36 | | 61 |
| 247 | | | 422.93 | | 81 |
| 248 | | | 275.96 | | |
| 249 | | | 271.29 | | |
| 250 | | | 331.21 | | |
| 251 | | | 336.34 | | |
| 252 | | | 248.51 | | |
| 263 | | | 399.85 | | 77 |
| 267 | | | | | 130 |
| 269 | | | 172.35 | | |
| 270 | | | 250 | | 297 |
| 272 | | | 285.35 | | |
| 273 | | | 197.06 | | |
| 274 | | | 224.99 | | >300 |

TABLE XXI-continued

Illustrative chronic TECC assay response.

| Compound # | % Activity at 1 µM (Ieq*) | EC$_{50}$ (nM) (Ieq*) | % Activity at 1 µM (AUC**) | % Activity at 3 µM (AUC**) | EC$_{50}$ (nM) (AUC**) |
|---|---|---|---|---|---|
| 279 | | | | | 109 |
| 291 | | | 255.92 | | |
| 294 | | | | | 21 |
| 297 | | | 470.97 | | ≤30 |
| 298 | | | 318059 | | |
| 304 | | | 194.54 | | |
| 316 | | | 452.88 | | 45 |
| 317 | | | 311.08 | | 24 |
| 318 | | | 439.94 | | |
| 320 | | | 215.3 | | |
| 322 | | | 440.86 | | |
| 323 | | | 217.91 | | |
| 325 | | | 317.57 | | |
| 328 | | | 531.7 | 423.1 | 96 |
| 331 | | | 537.3 | | 10 |
| 334 | | | | 345.13 | 100 |
| 337 | | | 299.50 | | |
| 340 | | | 216.53 | | |
| 348 | | | 343.24 | | 200 |
| 365 | | | | 521.8 | 200 |
| 366 | | | 427.95 | | |
| 369 | | | 583.16 | | 8.3 |
| 370 | | | | 226.54 | |
| 379 | | | 370 | | 43 |
| 380 | | | | 250 | |
| 381 | | | 441 | | 4105 |
| 382 | | 204.7 | 347 | | 100 |
| 383 | | | 299 | | 2 |
| 385 | | | | | 12.3 |
| 396 | | | 259.4666 | | |
| 397 | | | 251.7766 | | |
| 399 | | | 244.7508 | | |
| 400 | | | 230 | | |
| 402 | | | 345.045 | | 12.1 |
| 404 | | | 433.3333 | | |
| 405 | | | 323.3333 | | |
| 406 | | | 235 | | |
| 407 | | | 310 | | 48.94 |
| 408 | | | 430 | | 21 |
| 409 | | | 420 | | 149.8 |
| 410 | | | 233.3333 | | 1.582 |
| 415 | | | 196.1812 | | 28.4 |
| 416 | | | 288.6036 | | 118.9 |
| 417 | | | 256.6667 | | |
| 418 | | | 196.6667 | | 19.19 |
| 420 | | | 223.3333 | | 0 |
| 421 | | | 193.3333 | | 45.63 |
| 422 | | | 320 | | |
| 423 | | | 365 | | 39.83 |
| 424 | | | | 462.0976 | |
| 429 | | | 180 | | 83.75 |
| 431 | | | 280 | | |
| 440 | | | 696.6667 | | 2.98 |
| 441 | | | 236.6667 | | 205.8 |
| 445 | | | 406.6667 | | |
| 447 | | | 330 | | |
| 448 | | | 116.8948 | | |
| 456 | | | 261.1621 | | |
| 469 | | | 293.3333 | | 108.2 |
| 470 | | | 210 | | |
| 471 | | | 296.6667 | | |
| 472 | | | 181.0865 | | 34.24 |
| 473 | | | 243.3333 | | |
| 474 | | | 226.6667 | | |
| 480 | | | 548.575 | | |
| 484 | | | 380 | | |
| 487 | | | 340 | | |
| 493 | | | 271.4141 | | 370.8 |
| 495 | | | | 262.4635 | |
| 517 | | | | 309.141 | |
| 522 | | | 666.6667 | | 21.95 |
| 523 | | | | 460.2177 | |
| 525 | | | 477.2665 | | 50.35 |
| 526 | | | 400 | | 14.23 |
| 527 | | | 370.693 | | |
| 529 | | | 520 | | 19.11 |
| 530 | | | 326.6667 | | |
| 535 | | | 335.0294 | | |
| 537 | | | | 261.5724 | |
| 541 | | | 320 | | |
| 546 | | | | 282.0317 | |
| 549 | | | 373.3333 | | 242.7 |
| 551 | | | 239.0643 | | |
| 552 | | | 235.2857 | | |
| 555 | | | 296.6667 | | 107 |
| 558 | | | 221.9818 | | 4.74 |
| 559 | | | 231.6378 | | |
| 561 | | | 620 | | |
| 562 | | | 289.8854 | | |
| 569 | | | 1156.667 | | |
| 570 | | | | 377.5594 | |
| 575 | | | 246.6667 | | |
| 576 | | | | 225.798 | |
| 578 | | | 936.6667 | | |
| 583 | | | 613.3333 | | 51.3 |
| 589 | | | 236.6667 | | |
| 590 | | | | 220.4586 | |
| 594 | | | | 320 | |
| 597 | | | 263.3333 | | |
| 599 | | | 116.6667 | | |
| 605 | | | 726.6667 | | |
| 608 | | | | 442.1916 | |
| 609 | | | | 306.6667 | |
| 611 | | | | 176.7495 | |
| 614 | | | | 407.7118 | |
| 621 | | | | 256.6667 | |
| 623 | | | | 433.3333 | |
| 624 | | | | 310 | |
| 625 | | | 403.3333 | | |
| 626 | | | | 387.4854 | |
| 627 | | | | 446.6667 | |
| 628 | | | | 473.0586 | 88.4 |
| 629 | | | | 153.3918 | 6.848 |
| 630 | | | 125.1944 | | 47.07 |
| 631 | | | 156.9645 | | |
| 632 | | | | 237.1158 | 29.28 |
| 633 | | | | | 204.5 |
| 634 | | | | | 137.5 |
| 638 | | | | 341.3493 | 11.24 |
| 645 | | | | 246.4648 | |
| 646 | | | | 276.7167 | 23.45 |
| 647 | | | | 420.0246 | 150.7 |
| 648 | | | 366.0679 | | |
| 649 | | | | 224.5026 | |
| 654 | | | 293.3333 | | |
| 656 | | | | 197.5908 | |
| 657 | | | | 357.6409 | |
| 658 | | | | 260.3278 | |
| 659 | | | | 251.6549 | |

*Ieq refers to calculations based on the maximum current.
**AUC is the full area under the curve upon forskolin stimulation.

Information on protein binding of compounds can be retrieved from incubation of compounds in the presence of 40% human serum. For this purpose the differentiated cells are treated basolaterally with test compounds in medium containing 40% human serum (Sigma; H4522) for 24 hours. For electrophysiological recording, the human airway epithelia are mounted in the TECC heating plate and kept at 37° C. The epithelia are bathed in a NaCl-Ringer solution (120 mM NaCl, 25 mM NaHCO$_3$, 1.2 mM CaCl$_2$, 1.2 mM MgCl$_2$, 0.8 mM KH$_2$PO$_4$, 0.8 mM K$_2$HPO$_4$, pH 7.4, 5 mM glucose) on both the basolateral and apical sides. Test compounds (corrector, co-corrector, 4-[(2R,4R)-4-({[1-(2,2- difluoro-1,3-benzodioxol-5-yl)cyclopropyl]carbonyl}amino)-7-(difluoromethoxy)-3,4-dihydro-2H-chromen-2-yl]benzoic acid, and potentiator, N-(3-carbamoyl-5,5,7,7-tetramethyl-4,7-dihydro-5H-thieno[2,3-c]pyran-2-yl)-1H-pyrazole-5-carboxamide), are re-added to the recording solution prior to measurement. Apical amiloride is used to inhibit the endogenous ENaC currents while forskolin is applied on both apical and basolateral side to stimulate CFTR. Measurements are done during a 20 minute timeframe with recordings every 2 minutes. The increase in $I_{eq}$ is used as a measure for the increased CFTR activity, $EC_{50}$ values can be generated by measuring impact of different concentrations of compound on $I_{eq}$ on primary cells, for this purpose each transwell is treated with a different compound concentration. Inh-172, an inhibitor specific for CFTR, is used to test the specificity of the tested compounds.

It is understood that the foregoing detailed description and accompanying examples are merely illustrative and are not to be taken as limitations upon the scope of the invention, which is defined solely by the appended claims and their equivalents. Various changes and modifications to the described embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

LENGTHY TABLES

The patent contains a lengthy table section. A copy of the table is available in electronic form from the USPTO web site (http://seqdata.uspto.gov/?pageRequest=docDetail&DocID=US10259810B2). An electronic copy of the table will also be available from the USPTO upon request and payment of the fee set forth in 37 CFR 1.19(b)(3).

What is claimed is:

1. A compound, which is

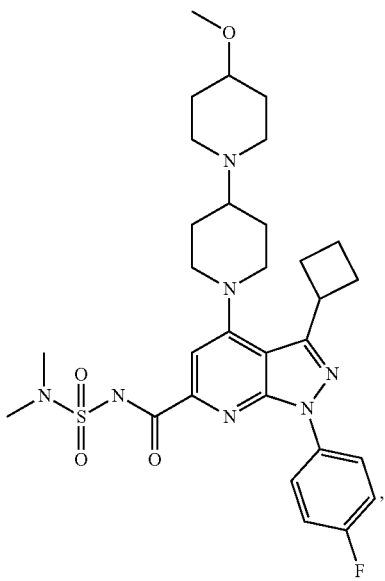 [SMILES: COC1CCN(C2CCN(c3cc(C(=O)NS(=O)(=O)N(C)C)nc4c3c(C3CCC3)nn4-c3ccc(F)cc3)CC2)CC1]

wherein one or more hydrogen atoms are replaced by deuterium; or a pharmaceutically acceptable salt thereof.

2. A pharmaceutical composition comprising a compound of claim 1, or a pharmaceutically acceptable salt thereof, and a potentiator or one or more correctors.

3. The pharmaceutical composition of claim 2, wherein the potentiator is selected from the group consisting of:
Ivacaftor (VX-770, N-(2,4-di-tert-butyl-5-hydroxyphenyl)-4-oxo-1,4-dihydroquinoline-3-carboxamide);
CTP-656;
NVS-QBW251;
FD1860293;
PTI-808;
GLPG1837;
GLPG2451;
2-(2-fluorobenzamido)-5,5,7,7-tetramethyl-5,7-dihydro-4H-thieno[2,3-c]pyran-3-carboxamide;
N-(3-carbamoyl-5,5,7,7-tetramethyl-4,7-dihydro-5H-thieno[2,3-c]pyran-2-yl)-1H-pyrazole-5-carboxamide;
2-(2-hydroxybenzamido)-5,5,7,7-tetramethyl-5,7-dihydro-4H-thieno[2,3-c]pyran-3-carboxamide;
2-(1-hydroxycyclopropanecarboxamido)-5,5,7,7-tetramethyl-5,7-dihydro-4H-thieno[2,3-c]pyran-3-carboxamide;
5,5,7,7-tetramethyl-2-(2-(trifluoromethyl)benzamido)-5,7-dihydro-4H-thieno[2,3-c]pyran-3-carboxamide;
2-(2-hydroxy-2-methylpropanamido)-5,5,7,7-tetramethyl-5,7-dihydro-4H-thieno[2,3-c]pyran-3-carboxamide;
2-(1-(hydroxymethyl)cyclopropanecarboxamido)-5,5,7,7-tetramethyl-5,7-dihydro-4H-thieno[2,3-c]pyran-3-carboxamide;
2-(3-hydroxy-2,2-dimethylpropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-5-methyl-1H-pyrazole-3-carboxamide;
N-(3-carbamoyl-5,5,7,7-tetramethyl-5,7-dihydro-4H-thieno[2,3-c]pyran-2-yl)-5-cyclopropyl-1H-pyrazole-3-carboxamide;
N-(3-carbamoyl-5,5,7,7-tetramethyl-5,7-dihydro-4H-thieno[2,3-c]pyran-2-yl)-5-isopropyl-1H-pyrazole-3-carboxamide;
N-(3-carbamoyl-5,5,7,7-tetramethyl-5,7-dihydro-4H-thieno[2,3-c]pyran-2-yl)-5-(trifluoromethyl)-1H-pyrazole-3-carboxamide;
5-tert-butyl-N-(3-carbamoyl-5,5,7,7-tetramethyl-5,7-dihydro-4H-thieno[2,3-c]pyran-2-yl)-1H-pyrazole-3-carboxamide;

N-(3-carbamoyl-5,5,7,7-tetramethyl-5,7-dihydro-4H-thieno[2,3-c]pyran-2-yl)-5-ethyl-1H-pyrazole-3-carboxamide;
N-(3-carbamoyl-5,5,7,7-tetramethyl-5,7-dihydro-4H-thieno[2,3-c]pyran-2-yl)-3-ethyl-4-methyl-1H-pyrazole-5-carboxamide;
2-(2-hydroxypropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-4-chloro-1H-pyrazole-3-carboxamide;
N-(3-carbamoyl-5,5,7,7-tetramethyl-5,7-dihydro-4H-thieno[2,3-c]pyran-2-yl)-1,4,6,7-tetrahydropyrano[4,3-c]pyrazole-3-carboxamide;
4-bromo-N-(3-carbamoyl-5,5,7,7-tetramethyl-5,7-dihydro-4H-thieno[2,3-c]pyran-2-yl)-1H-pyrazole-3-carboxamide;
N-(3-carbamoyl-5,5,7,7-tetramethyl-5,7-dihydro-4H-thieno[2,3-c]pyran-2-yl)-4-chloro-5-methyl-1H-pyrazole-3-carboxamide;
N-(3-carbamoyl-5,5,7,7-tetramethyl-5,7-dihydro-4H-thieno[2,3-c]pyran-2-yl)-4-methyl-1H-pyrazole-3-carboxamide;
2-(2-hydroxy-3,3-dimethylbutanamido)-5,5,7,7-tetramethyl-5,7-dihydro-4H-thieno[2,3-c]pyran-3-carboxamide;
2-[(2-hydroxy-4-methyl-pentanoyl)amino]-5,5,7,7-tetramethyl-4H-thieno[2,3-c]pyran-3-carboxamide;
5-(2-methoxy-ethoxy)-1H-pyrazole-3-carboxylic acid (3-carbamoyl-5,5,7,7-tetramethyl-4,7-dihydro-5H-thieno[2,3-c]pyran-2-yl)-amide;
N-(3-carbamoyl-5,5,7,7-tetramethyl-4H-thieno[2,3-c]pyran-2-yl)-4-(3-methoxypropyl)-1H-pyrazole-3-carboxamide;
N-(3-carbamoyl-5,5,7,7-tetramethyl-4H-thieno[2,3-c]pyran-2-yl)-4-(2-ethoxyethyl)-1H-pyrazole-3-carboxamide;
2-[[(2S)-2-hydroxy-3,3-dimethyl-butanoyl]amino]-5,5,7,7-tetramethyl-4H-thieno[2,3-c]pyran-3-carboxamide;
2-[[(2R)-2-hydroxy-3,3-dimethyl-butanoyl]amino]-5,5,7,7-tetramethyl-4H-thieno[2,3-c]pyran-3-carboxamide;
2-[(2-hydroxy-2,3,3-trimethyl-butanoyl)amino]-5,5,7,7-tetramethyl-4H-thieno[2,3-c]pyran-3-carboxamide;
[5-[(3-carbamoyl-5,5,7,7-tetramethyl-4H-thieno[2,3-c]pyran-2-yl)carbamoyl]pyrazol-1-yl]methyl dihydrogen phosphate;
[3-[(3-carbamoyl-5,5,7,7-tetramethyl-4H-thieno[2,3-c]pyran-2-yl)carbamoyl]pyrazol-1-yl]methyl dihydrogen phosphate;
N-(3-carbamoyl-5,5,7,7-tetramethyl-4H-thieno[2,3-c]pyran-2-yl)-4-(1,4-dioxan-2-yl)-1H-pyrazole-3-carboxamide;
5,5,7,7-tetramethyl-2-[[(2S)-3,3,3-trifluoro-2-hydroxy-2-methyl-propanoyl]amino]-4H-thieno[2,3-c]pyran-3-carboxamide;
2-[[(2S)-2-hydroxypropanoyl]amino]-5,5,7,7-tetramethyl-4H-thieno[2,3-c]pyran-3-carboxamide;
3-amino-N-(2-hydroxy-2-methylpropyl)-5-{[4-(trifluoromethoxy)phenyl]sulfonyl}pyridine-2-carboxamide;
3-amino-N-[(4-hydroxy-1-methylpiperidin-4-yl)methyl]-5-{[4-(trifluoromethoxy)phenyl]sulfonyl}pyridine-2-carboxamide;
3-amino-N-(3-hydroxy-2,2-dimethylpropyl)-5-{[4-(trifluoromethoxy)phenyl]sulfonyl}pyridine-2-carboxamide;
3-amino-5-[(4-fluorophenyl)sulfonyl]-N-[(1-hydroxycyclopropyl)methyl]pyridine-2-carboxamide;
3-amino-5-[(4-fluorophenyl)sulfonyl]-N-[(2R)-3,3,3-trifluoro-2-hydroxypropyl]pyridine-2-carboxamide;
3-amino-5-[(3-fluorophenyl)sulfonyl]-N-(2-hydroxy-2-methylpropyl)pyridine-2-carboxamide;
3-amino-N-[2-(cyclopropylamino)-2-oxoethyl]-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(azetidin-1-yl)methanone;
(3-amino-5-{[4-(trifluoromethoxy)phenyl]sulfonyl}pyridin-2-yl) [3-(hydroxymethyl)azetidin-1-yl]methanone;
(3-amino-5-{[4-(trifluoromethoxy)phenyl]sulfonyl}pyridin-2-yl)(3-fluoroazetidin-1-yl)methanone;
3-amino-N-[(2R)-2-hydroxy-3-methoxypropyl]-5-{[4-(trifluoromethyl)phenyl]sulfonyl}pyridine-2-carboxamide;
(3-amino-5-{[2-fluoro-4-(trifluoromethoxy)phenyl]sulfonyl}pyridin-2-yl)(3-hydroxyazetidin-1-yl)methanone;
(3-amino-5-{[2-(trifluoromethoxy)phenyl]sulfonyl}pyridin-2-yl)(3,3-difluoroazetidin-1-yl)methanone;
rac-3-amino-N-[(3R,4S)-4-hydroxytetrahydro-2H-pyran-3-yl]-5-{[2-(trifluoromethoxy)phenyl]sulfonyl}pyridine-2-carboxamide;
3-amino-5-[(4,4-difluoropiperidin-1-yl)sulfonyl]-N-(3,3,3-trifluoro-2-hydroxypropyl)pyridine-2-carboxamide;
(3-amino-5-{[2-(trifluoromethoxy)phenyl]sulfonyl}pyridin-2-yl)[3-hydroxy-3-(trifluoromethyl)azetidin-1-yl]methanone;
3-amino-N-(2-hydroxy-4-methylpentyl)-5-{[4-(trifluoromethoxy)phenyl]sulfonyl}pyridine-2-carboxamide;
(3-amino-5-{[4-(trifluoromethyl)phenyl]sulfonyl}pyridin-2-yl)(3-hydroxy-3-methylazetidin-1-yl)methanone;
3-amino-N-(3,3,3-trifluoro-2-hydroxypropyl)-5-{[4-(trifluoromethyl)piperidin-1-yl]sulfonyl}pyridine-2-carboxamide;
3-amino-N-[2-hydroxy-1-(4-methoxyphenyl)ethyl]-5-{[4-(trifluoromethoxy)phenyl]sulfonyl}pyridine-2-carboxamide;
3-amino-5-[(3,3-difluoroazetidin-1-yl)sulfonyl]-N-(3,3,3-trifluoro-2-hydroxypropyl)pyridine-2-carboxamide;
3-amino-5-{[2-fluoro-4-(trifluoromethyl)phenyl]sulfonyl}-N-[(2S)-2-hydroxypropyl]pyridine-2-carboxamide;
3-amino-5-{[2-fluoro-4-(trifluoromethyl)phenyl]sulfonyl}-N-[(2R)-2-hydroxy-3-methoxypropyl]pyridine-2-carboxamide;
3-amino-N-[2-oxo-2-(propan-2-ylamino)ethyl]-5-{[4-(trifluoromethyl)phenyl]sulfonyl}pyridine-2-carboxamide;
(3-amino-5-{[4-(trifluoromethyl)phenyl]sulfonyl}pyridin-2-yl)[3-hydroxy-3-(trifluoromethyl)azetidin-1-yl]methanone;
3-amino-5-{[2-fluoro-4-(trifluoromethyl)phenyl]sulfonyl}-N-[(3R)-tetrahydrofuran-3-ylmethyl]pyridine-2-carboxamide;
(3-amino-5-{[2-fluoro-4-(trifluoromethyl)phenyl]sulfonyl}pyridin-2-yl)[3-hydroxy-3-(trifluoromethyl)azetidin-1-yl]methanone;
3-amino-5-{[2-fluoro-4-(trifluoromethyl)phenyl]sulfonyl}-N-[(3S)-tetrahydrofuran-3-ylmethyl]pyridine-2-carboxamide;

3-amino-5-{[2-fluoro-4-(trifluoromethoxy)phenyl]sulfonyl}-N-[(3S)-tetrahydrofuran-3-ylmethyl]pyridine-2-carboxamide;

3-amino-N-[2-hydroxy-3-(2,2,2-trifluoroethoxy)propyl]-5-{[4-(trifluoromethyl)phenyl]sulfonyl}pyridine-2-carboxamide;

3-amino-N-(3-tert-butoxy-2-hydroxypropyl)-5-{[2-fluoro-4-(trifluoromethyl)phenyl]sulfonyl}pyridine-2-carboxamide;

[3-amino-5-(phenylsulfonyl)pyridin-2-yl][3-hydroxy-3-(trifluoromethyl)azetidin-1-yl]methanone;

{3-amino-5-[(3-fluorophenyl)sulfonyl]pyridin-2-yl}[3-hydroxy-3-(trifluoromethyl)azetidin-1-yl]methanone; and 3-amino-N-[(2S)-2-hydroxypropyl]-5-{[4-(trifluoromethoxy)phenyl]sulfonyl}pyridine-2-carboxamide.

4. The pharmaceutical composition of claim 2, wherein the one or more correctors are selected from the group consisting of:

Lumacaftor (VX-809);

1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661);

PTI-801;
VX-983;
GLPG2665;
VX-152;
VX-440;
FDL169;
FDL3 04;
FD2052160;
FD2035659;

3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-6-methyl-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-6-methoxy-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]cyclohexanecarboxylic acid;

3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-methoxy-3,4-dihydro-2H-chromen-2-yl]cyclohexanecarboxylic acid;

3-[(2R,4R)-4-({[1-(2,2-difluoro-1,3-benzodioxol-5-yl)cyclopropyl]carbonyl}amino)-7-fluoro-3,4-dihydro-2H-chromen-2-yl]benzoic acid;

3-({3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoyl}amino)-1-methylcyclopentanecarboxylic acid;

3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-[(2R)-2,3-dihydroxypropyl]benzamide;

3-[(2R,4R)-4-({[1-(2,2-difluoro-1,3-benzodioxol-5-yl)cyclopropyl]carbonyl}amino)-7-(2-methoxyethoxy)-3,4-dihydro-2H-chromen-2-yl]benzoic acid;

3-[(2R,4R)-7-(benzyloxy)-4-({[1-(2,2-difluoro-1,3-benzodioxol-5-yl)cyclopropyl]carbonyl}amino)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(2-fluoroethoxy)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]cyclohexanecarboxylic acid;

4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-8-fluoro-3,4-dihydro-2H-chromen-2-yl]benzoic acid;

4-[(2R,4R)-4-({[1-(2,2-difluoro-1,3-benzodioxol-5-yl)cyclopropyl]carbonyl}amino)-3,4-dihydro-2H-chromen-2-yl]benzoic acid;

4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;

rac-3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-4-[(2R,4S)-4-({[1-(2,2-difluoro-1,3-benzodioxol-5-yl)cyclopropyl]carbonyl}amino)tetrahydro-2H-pyran-2-yl]benzoic acid;

3-[(2S,4R)-4-({[1-(2,2-difluoro-1,3-benzodioxol-5-yl)cyclopropyl]carbonyl}amino)tetrahydro-2H-pyran-2-yl]benzoic acid;

3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

3-[(2S,4R,6R)-4-({[1-(2,2-difluoro-1,3-benzodioxol-5-yl)cyclopropyl]carbonyl}amino)-6-phenyltetrahydro-2H-pyran-2-yl]benzoic acid;

3-[(2R,4S,6S)-4-({[ 1-(2,2-difluoro-1,3-benzodioxol-5-yl)cyclopropyl]carbonyl}amino)-6-phenyltetrahydro-2H-pyran-2-yl]benzoic acid;

4-[(2R,4S)-4-({[1-(2,2-difluoro-1,3-benzodioxol-5-yl)cyclopropyl]carbonyl}amino)tetrahydro-2H-pyran-2-yl]benzoic acid;

3-cyclobutyl-4-[4-(morpholin-4-yl)piperidin-1-yl]-1-phenyl-1H-pyrazolo[3,4-b]pyridine-6-carboxylic acid;

3-cyclobutyl-1-phenyl-4-{4-[(pyrrolidin-1-yl)methyl]piperidin-1-yl}-1H-pyrazolo[3,4-b]pyridine-6-carboxylic acid;

5-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyrazine-2-carboxylic acid;

6-[(2R,4R)-4-{[(7R)-2,2-difluoro-7-methyl-6,7-dihydro-2H-furo[2,3-f][1,3]benzodioxole-7-carbonyl]amino}-

7-(trifluoromethoxy)-3,4-dihydro-2H-1-benzopyran-2-yl]pyridine-3-carboxylic acid;

trans-4-[(2S,4S)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;

6-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]pyridine-3-carboxylic acid;

trans-4-[(2S,4S)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid;

ethyl trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylate;

cis-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;

trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid;

1-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylic acid;

trans-4-[(2R,4R)-4-{[(5S)-2,2-difluoro-5-methyl-6,7-dihydro-2H,5H-indeno[5,6-d][1,3]dioxole-5-carbonyl]amino}-7-(trifluoromethoxy)-3,4-dihydro-2H-1-benzopyran-2-yl]cyclohexane-1-carboxylic acid;

trans-4-[(2R,4R)-4-{[(5S)-2,2-difluoro-5-methyl-6,7-dihydro-2H,5H-indeno[5,6-d][1,3]dioxole-5-carbonyl]amino}-7-methoxy-3,4-dihydro-2H-1-benzopyran-2-yl]cyclohexane-1-carboxylic acid;

trans-4-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid;

trans-4-[(2R,4R)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid; and trans-4-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid.

5. A pharmaceutical formulation for treating a CFTR mediated disease in a subject comprising a compound of claim 1, or a pharmaceutically acceptable salt thereof, and a therapeutically effective amount of one or two CFTR modulators and one CFTR amplifier.

6. The pharmaceutical formulation of claim 5, wherein the CFTR modulators are either CFTR potentiators or CFTR correctors.

7. The pharmaceutical formulation of claim 6, wherein the CFTR potentiators are selected from the group consisting of Ivacaftor (VX-770), CTP-656, NVS-QBW251, FD1860293, PTI-808, GLPG2451, GLPG1837, and N-(3-carbamoyl-5,5,7,7-tetramethyl-5,7-dihydro-4H-thieno[2,3-c]pyran-2-yl)-1H-pyrazole-5-carboxamide and 3-amino-N-[(2S)-2-hydroxypropyl]-5-{[4-(trifluoromethoxy)phenyl]sulfonyl}pyridine-2-carboxamide.

8. A pharmaceutical composition comprising a compound of 3-cyclobutyl-N-(dimethylsulfamoyl)-1-(4-fluorophenyl)-4-(4-methoxy[1,4'-bipiperidin]-1'-yl)-1H-pyrazolo[3,4-b]pyridine-6-carboxamide, or a pharmaceutically acceptable salt thereof, and a potentiator or one or more correctors.

* * * * *